(12) United States Patent
Bergeron et al.

(10) Patent No.: US 8,163,763 B2
(45) Date of Patent: Apr. 24, 2012

(54) PYRIMIDINE COMPOUNDS, COMPOSITIONS AND METHODS OF USE

(75) Inventors: Philippe Bergeron, San Francisco, CA (US); Frederick Cohen, San Francisco, CA (US); Anthony Estrada, San Carlos, CA (US); Michael F. T. Koehler, Palo Alto, CA (US); Kevin Hon Luen Lau, San Mateo, CA (US); Cuong Ly, Daly City, CA (US); Joseph P. Lyssikatos, Piedmont, CA (US); Daniel Ortwine, San Ramon, CA (US); Zhonghua Pei, Burlingame, CA (US); Xianrui Zhao, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 359 days.

(21) Appl. No.: 12/533,935

(22) Filed: Jul. 31, 2009

(65) Prior Publication Data
US 2010/0069357 A1    Mar. 18, 2010

Related U.S. Application Data

(63) Continuation of application No. 61/085,309, filed on Jul. 31, 2008.

(51) Int. Cl.
A61K 31/519    (2006.01)
C07D 471/04    (2006.01)

(52) U.S. Cl. .................................... 514/264.1; 544/279
(58) Field of Classification Search ............... 514/264.1; 544/279
See application file for complete search history.

(56) References Cited

U.S. PATENT DOCUMENTS

| | | | |
|---|---|---|---|
| 3,248,395 A | 4/1966 | Ohnacker et al. | |
| 5,338,740 A | 8/1994 | Carpino et al. | |
| 5,942,508 A | 8/1999 | Sawa | |
| 6,583,154 B1 | 6/2003 | Norman et al. | |
| 6,608,053 B2 | 8/2003 | Hayakawa et al. | |
| 6,608,056 B1 | 8/2003 | Hayakawa et al. | |
| 6,770,641 B2 | 8/2004 | Hayakawa et al. | |
| 6,800,633 B2 | 10/2004 | Castelhano et al. | |
| 6,838,457 B2 | 1/2005 | Hayakawa et al. | |
| 6,838,559 B2 | 1/2005 | Vaccaro et al. | |
| 7,037,915 B2 | 5/2006 | Hayakawa et al. | |
| 7,091,343 B2 | 8/2006 | Bebbington et al. | |
| 7,105,667 B2 | 9/2006 | Pitts et al. | |
| 7,115,739 B2 | 10/2006 | Bebbington et al. | |
| 7,173,029 B2 | 2/2007 | Hayakawa et al. | |
| 7,208,498 B2 | 4/2007 | Mathvink | |
| 7,223,766 B2 | 5/2007 | Dugar et al. | |
| 7,429,574 B2 | 9/2008 | Castelhano et al. | |
| 7,557,112 B2 * | 7/2009 | Yonetoku et al. ......... | 514/260.1 |
| 2003/0199526 A1 | 10/2003 | Choquette et al. | |
| 2004/0043986 A1 | 3/2004 | Nahra et al. | |
| 2005/0059687 A1 | 3/2005 | Makings et al. | |
| 2005/0153989 A1 | 7/2005 | Grotzfeld et al. | |
| 2005/0187217 A1 | 8/2005 | Wilson et al. | |
| 2005/0277643 A1 | 12/2005 | Kelly et al. | |
| 2006/0128710 A1 | 6/2006 | Lee et al. | |
| 2006/0258658 A1 | 11/2006 | Bebbington et al. | |
| 2007/0037805 A1 | 2/2007 | Hayakawa et al. | |
| 2007/0037834 A1 | 2/2007 | Arai et al. | |
| 2007/0225275 A1 | 9/2007 | Allison et al. | |
| 2008/0039459 A1 | 2/2008 | Folkes et al. | |
| 2008/0070896 A1 | 3/2008 | Yonetoku et al. | |
| 2008/0076758 A1 | 3/2008 | Folkes et al. | |
| 2008/0076768 A1 | 3/2008 | Chuckowree et al. | |
| 2008/0081809 A1 | 4/2008 | Duggan et al. | |
| 2008/0113946 A1 | 5/2008 | Zhang et al. | |
| 2008/0171743 A1 | 7/2008 | Finlay et al. | |
| 2008/0207609 A1 | 8/2008 | Shuttleworth et al. | |
| 2008/0207611 A1 | 8/2008 | Shuttleworth et al. | |
| 2008/0233127 A1 | 9/2008 | Bursavich et al. | |
| 2008/0234262 A1 | 9/2008 | Zask et al. | |
| 2008/0242665 A1 | 10/2008 | Bayliss et al. | |

(Continued)

FOREIGN PATENT DOCUMENTS

FR    2.450 M    3/1963
(Continued)

OTHER PUBLICATIONS

CAS Registry Nos. 1048148-42-0; 1044569-61-0; 1024347-83-8; 860054-79-1; 859869-61-7; 859383-75-8; 859365-67-6; 859132-90-4; 859093-76-8; 858776-44-0; 857669-72-8; 856126-05-1; 855687-17-1; 855135-37-4; 854518-57-3; 854518-54-0; 854487-58-4; 854361-37-8; 854149-34-1; 854065-68-2; 853711-27-0; 101837-80-3.

Kuznetsov, A. Y. et al., "Synthesis of 2-pyridyl-substituted derivatives of 7-benzyl-5,6,7,8-tetra-hydropyrido[3,4-d] pyrimidine" *Chem. Heterocyclic Compounds* 43(10):1320-1324 (2007).

Kuznetsov, A.Y. et al., "Synthesis of 2-pyridyl-substituted derivatives of tetrahydropyridopyrimidines" *Izvestiya Timiryazevskoi Sel'skokhozyaistvennoi Akademii* 4:134-138 (2006).

(Continued)

*Primary Examiner* — Andrew D Kosar
*Assistant Examiner* — Karen Cheng
(74) *Attorney, Agent, or Firm* — Genentech, Inc.

(57) ABSTRACT

Disclosed are compounds of Formula I, including stereoisomers, geometric isomers, tautomers, solvates, metabolites and pharmaceutically acceptable salts thereof, that are useful in modulating PIKK related kinase signaling, e.g., mTOR, and for the treatment of diseases (e.g., cancer) that are mediated at least in part by the dysregulation of the PIKK signaling pathway (e.g., mTOR).

Formula I

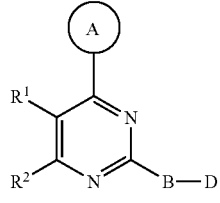

33 Claims, 13 Drawing Sheets

U.S. PATENT DOCUMENTS

| | | |
|---|---|---|
| 2008/0267887 A1 | 10/2008 | Yuan et al. |
| 2008/0269210 A1 | 10/2008 | Castanedo et al. |
| 2009/0042884 A1 | 2/2009 | McDonald et al. |
| 2009/0098086 A1 | 4/2009 | Zask et al. |
| 2009/0118275 A1 | 5/2009 | Castanedo et al. |
| 2009/0131429 A1 | 5/2009 | Shutteleworth |
| 2009/0149458 A1 | 6/2009 | Chen et al. |
| 2009/0156601 A1 | 6/2009 | McDonald et al. |
| 2010/0069357 A1 | 3/2010 | Bergeron et al. |

FOREIGN PATENT DOCUMENTS

| | | |
|---|---|---|
| GB | 2431156 A | 4/2007 |
| JP | 04-224580 | 8/1992 |
| WO | WO 96/40142 | 12/1996 |
| WO | WO 02/22601 | 3/2002 |
| WO | WO 02/22602 | 3/2002 |
| WO | WO 02/22604 | 3/2002 |
| WO | WO 02/22606 | 3/2002 |
| WO | WO 02/088079 | 11/2002 |
| WO | WO 2005/066171 A1 | 7/2005 |
| WO | WO 2006/035061 | 4/2006 |
| WO | WO 2006/067614 | 6/2006 |
| WO | WO 2006/090169 | 8/2006 |
| WO | WO 2006/118598 A1 | 11/2006 |
| WO | WO 2007/080382 A1 | 7/2007 |
| WO | 2007/106503 A2 | 9/2007 |
| WO | WO 2007/122410 | 11/2007 |
| WO | WO 2007/132171 | 11/2007 |
| WO | WO 2008/006025 | 1/2008 |
| WO | WO 2008/023159 A1 | 2/2008 |
| WO | WO 2008/023161 | 2/2008 |
| WO | WO 2008/023161 A1 | 2/2008 |
| WO | WO 2008/032028 A1 | 3/2008 |
| WO | WO 2008/032033 A1 | 3/2008 |
| WO | WO 2008/032036 A1 | 3/2008 |
| WO | WO 2008/032060 A1 | 3/2008 |
| WO | WO 2008/032072 A1 | 3/2008 |
| WO | WO 2008/032086 A1 | 3/2008 |
| WO | WO 2008/032089 A1 | 3/2008 |
| WO | WO 2008/116129 A2 | 9/2008 |
| WO | WO 2008/125833 | 10/2008 |
| WO | WO 2008/125835 | 10/2008 |
| WO | WO 2008/125839 | 10/2008 |
| WO | WO 2008/152387 | 12/2008 |
| WO | WO 2008/152390 | 12/2008 |
| WO | WO 2008/152394 | 12/2008 |
| WO | WO 2009/070524 A1 | 6/2009 |

OTHER PUBLICATIONS

Malagu, K. et al., "The discovery and optimisation of pyrido[2,3,-d]pyrimidine-2,4-diamines as potent and selective inhibitors of mTOR kinase" *Bioorg. Medicinal Chem. Lett.* (doi: 10.1016/j.bmcl.2009.08.038) (2009).

Menear. K.A. et al., "Identification and optimization of novel and selective small molecular weight kinase inhibitors of mTOR" *Bioorg. Medicinal Chem. Lett.* (doi: 10.101006/j.bmcl.2009.08.069) (2009).

Chiang and Abraham, "Targeting the mTOR signaling network in cancer" *Trends in Mol. Med.* 13(10):433-442 (2007).

Guertin and Sabatini, "An expanding role for mTOR in cancer" *Trends in Mol. Med.* 11(8):353-361 (Aug. 2005).

Guertin and Sabatini, "Defining the role of mTOR in cancer" *Cancer Cell* 12:9-22 (Jul. 2007).

Huang and Houghton, "Targeting mTOR signaling for cancer therapy" *Current Opinion in Pharm.* 3:371-377 (2003).

Jacinto and Hall, "TOR signalling in bugs, brain and brawn" *Nature Reviews/Mol. Cell Biol.* 4:117-126 (Feb. 2003).

Richard, D.J. et al., "Incorporation of water-solubilizing groups in pyrazolopyrimidine mTOR inhibitors: discovery of highly potent and selective analogs with improved human microsomal stability" *Bioorg. & Med. Chem. Let.* 19:6830-6835 (2009).

Zask, A. et al., "ATP-competitive inhibitors of the mammalian target of rapamycin: design and synthesis of highly potent and selective pyrazolopyrimidines" *J. Med. Chem. Let.* 52:5013-5016 (2009).

* cited by examiner

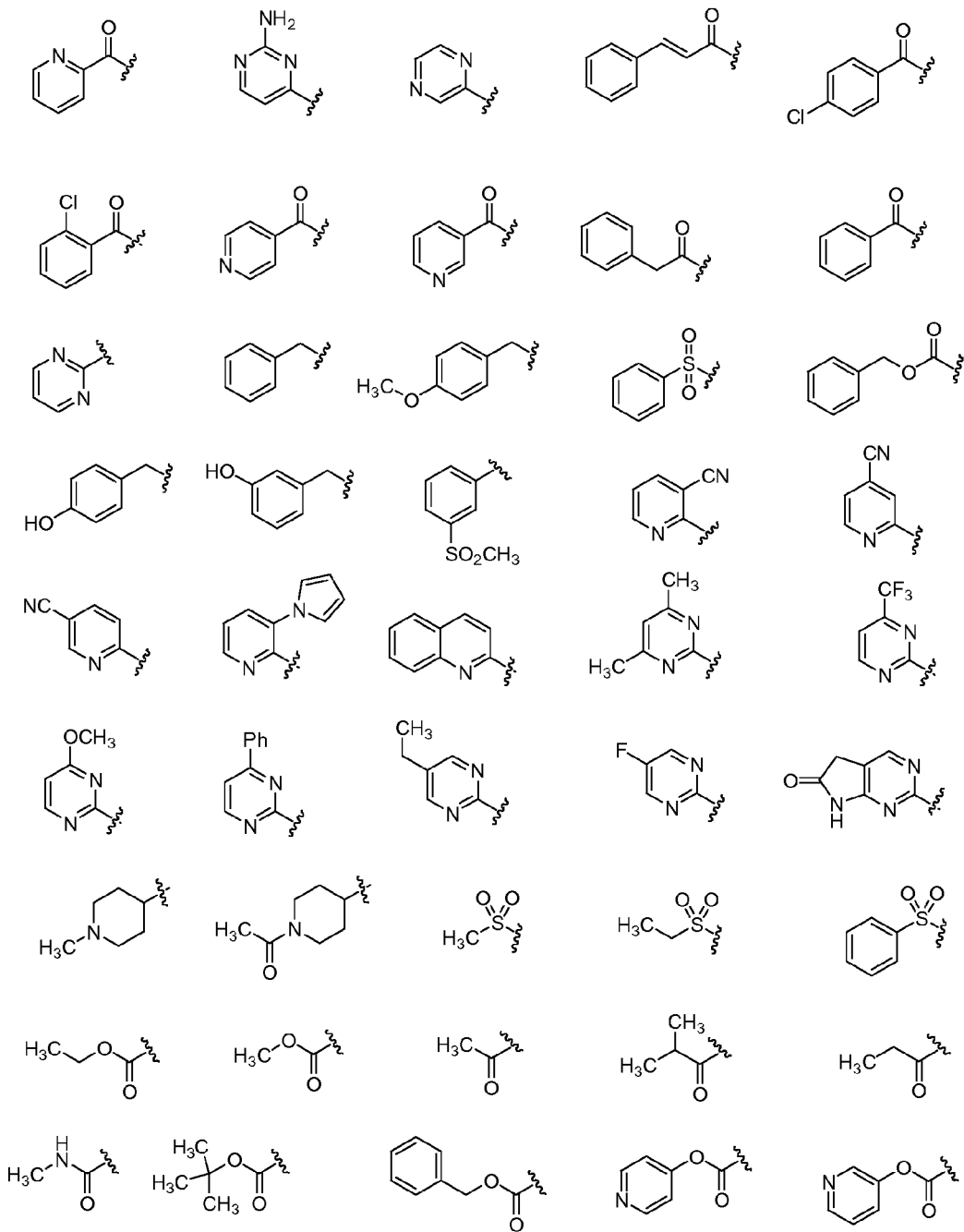
FIG._1A

FIG._1B
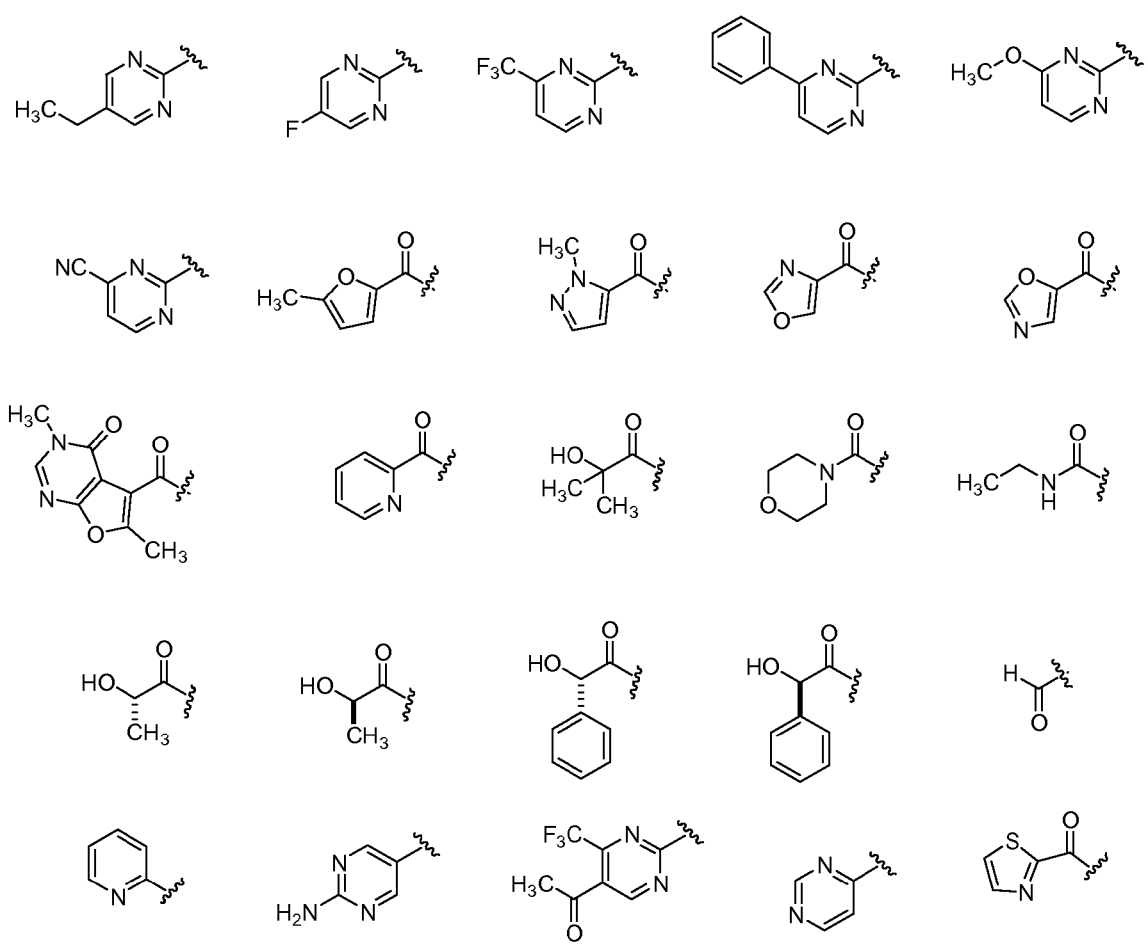

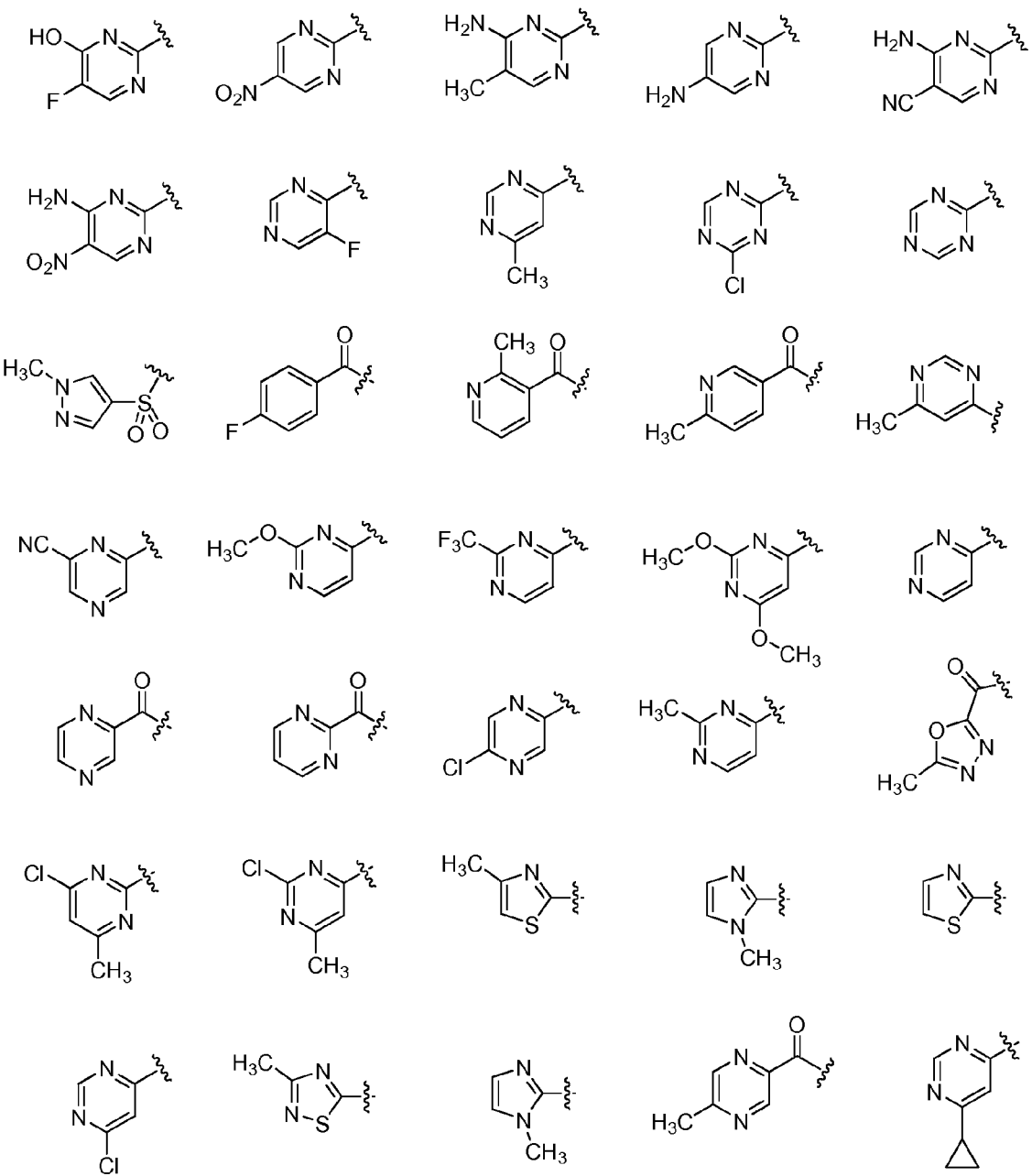
FIG._1C

FIG._1D
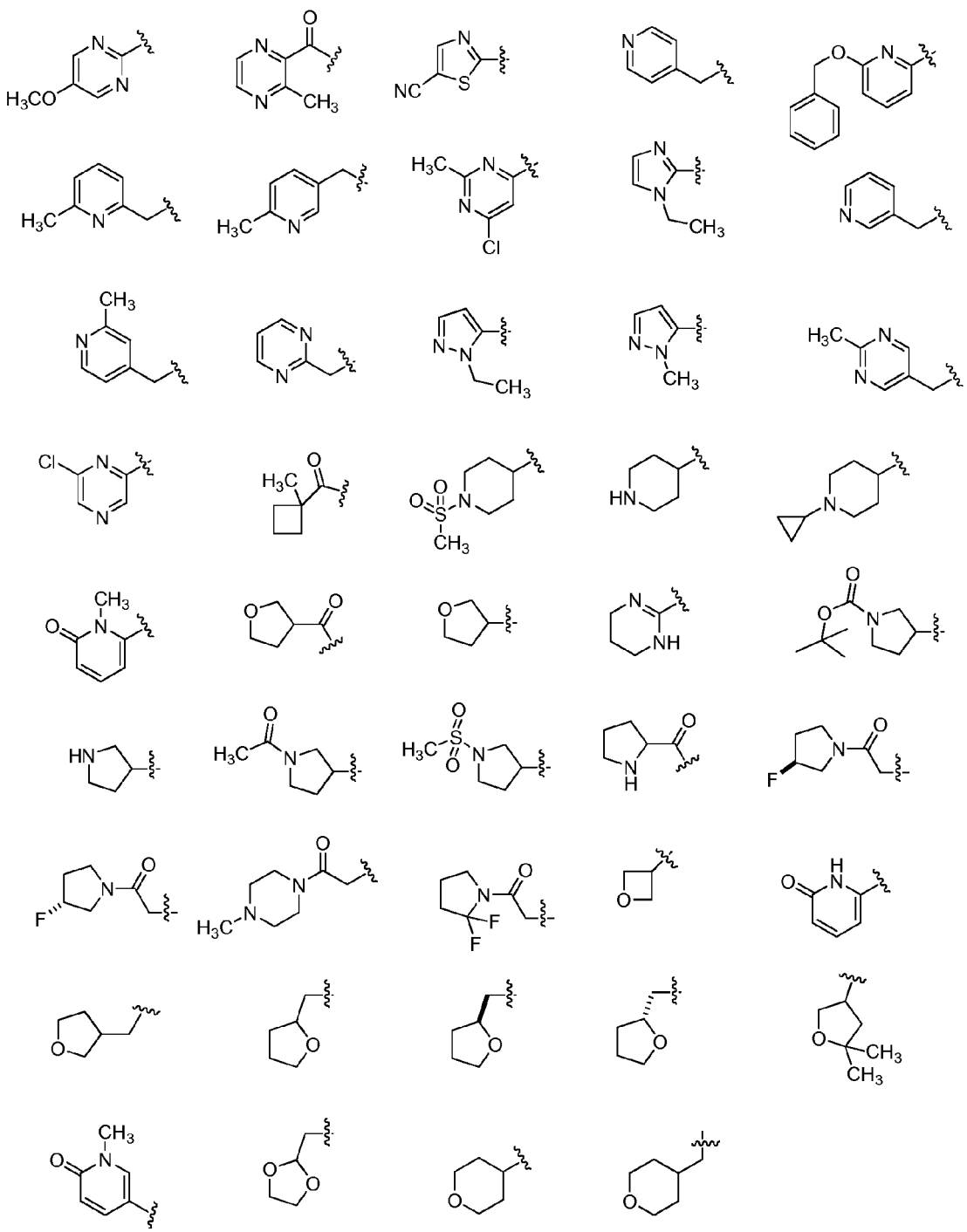

FIG._1E
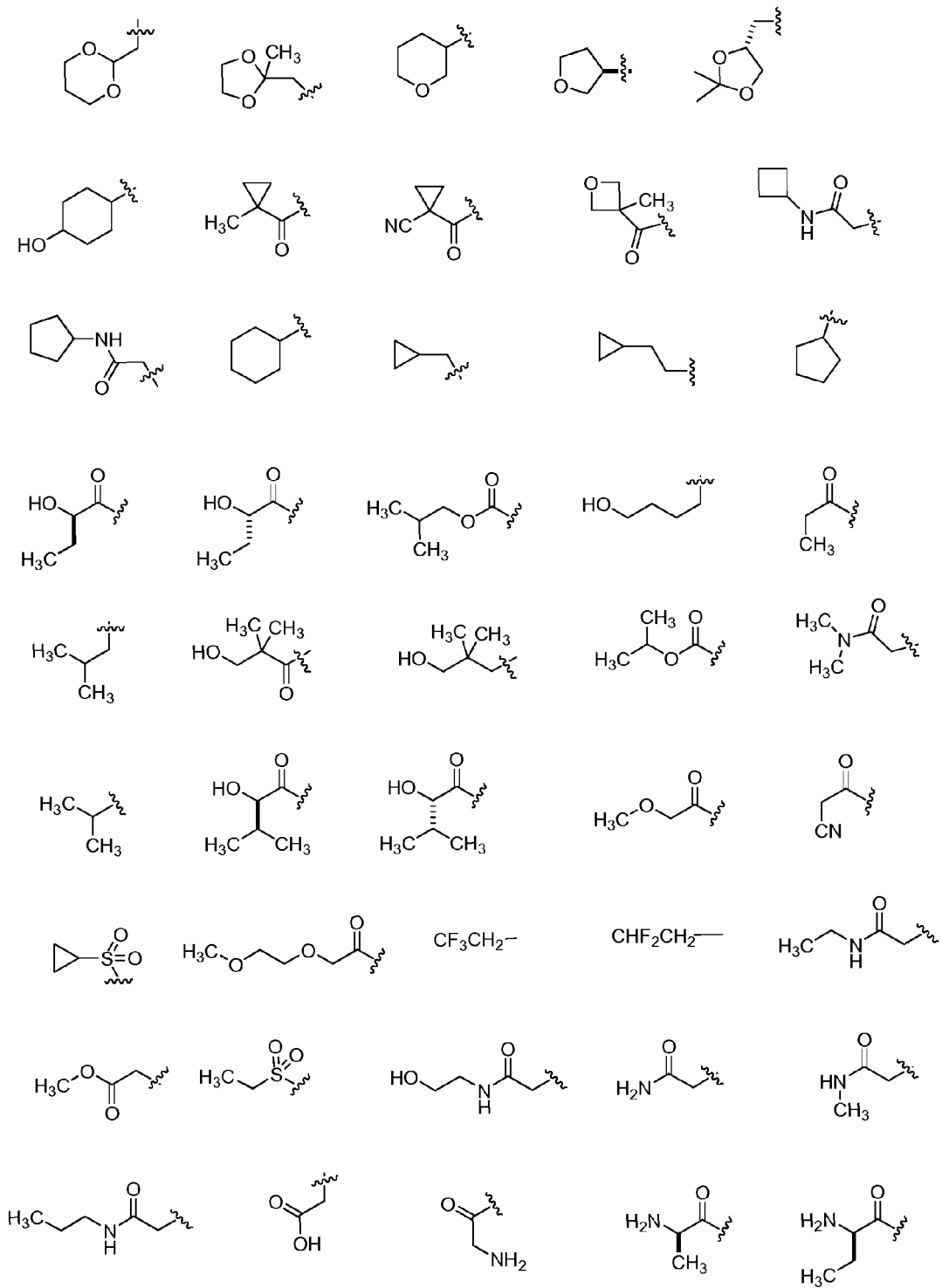

FIG._1F
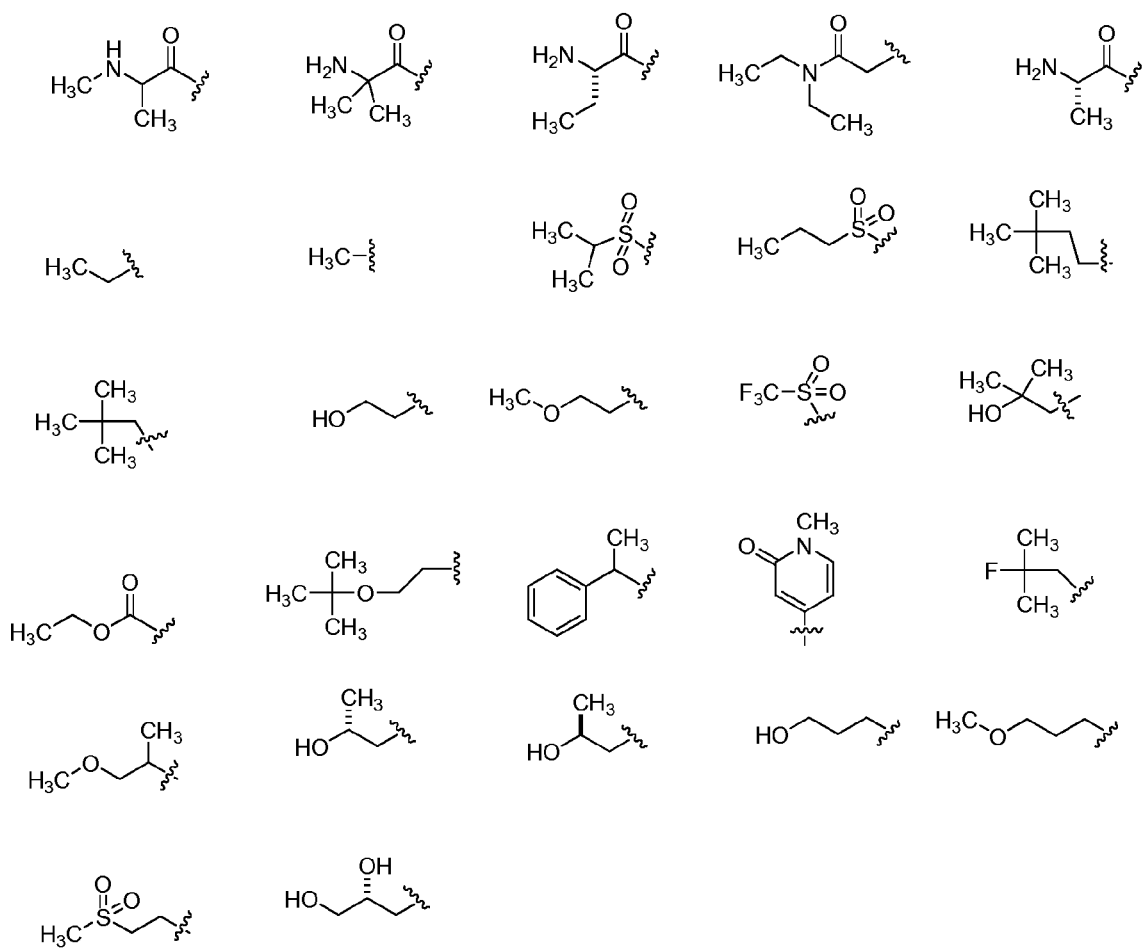

FIG._2A
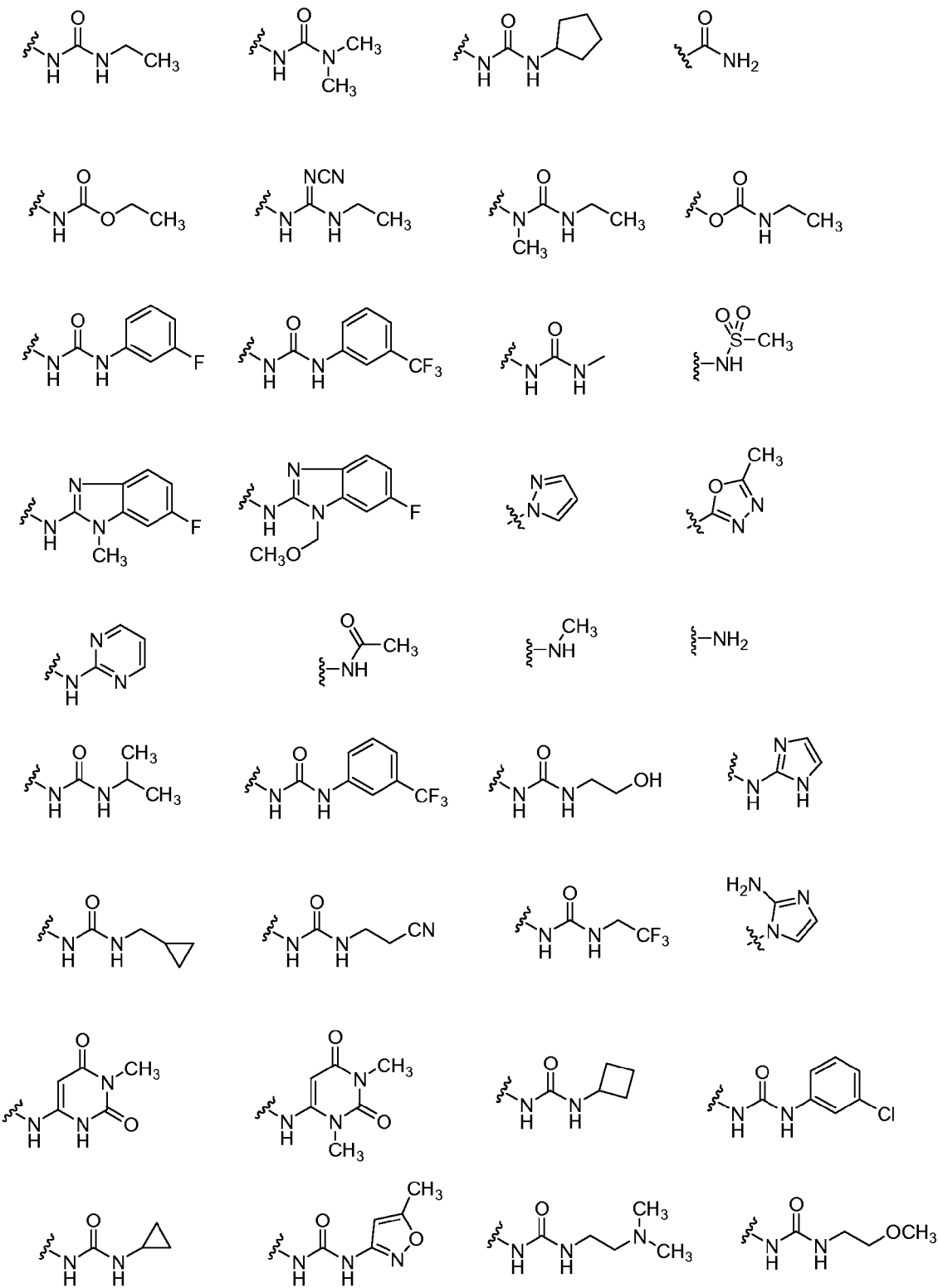

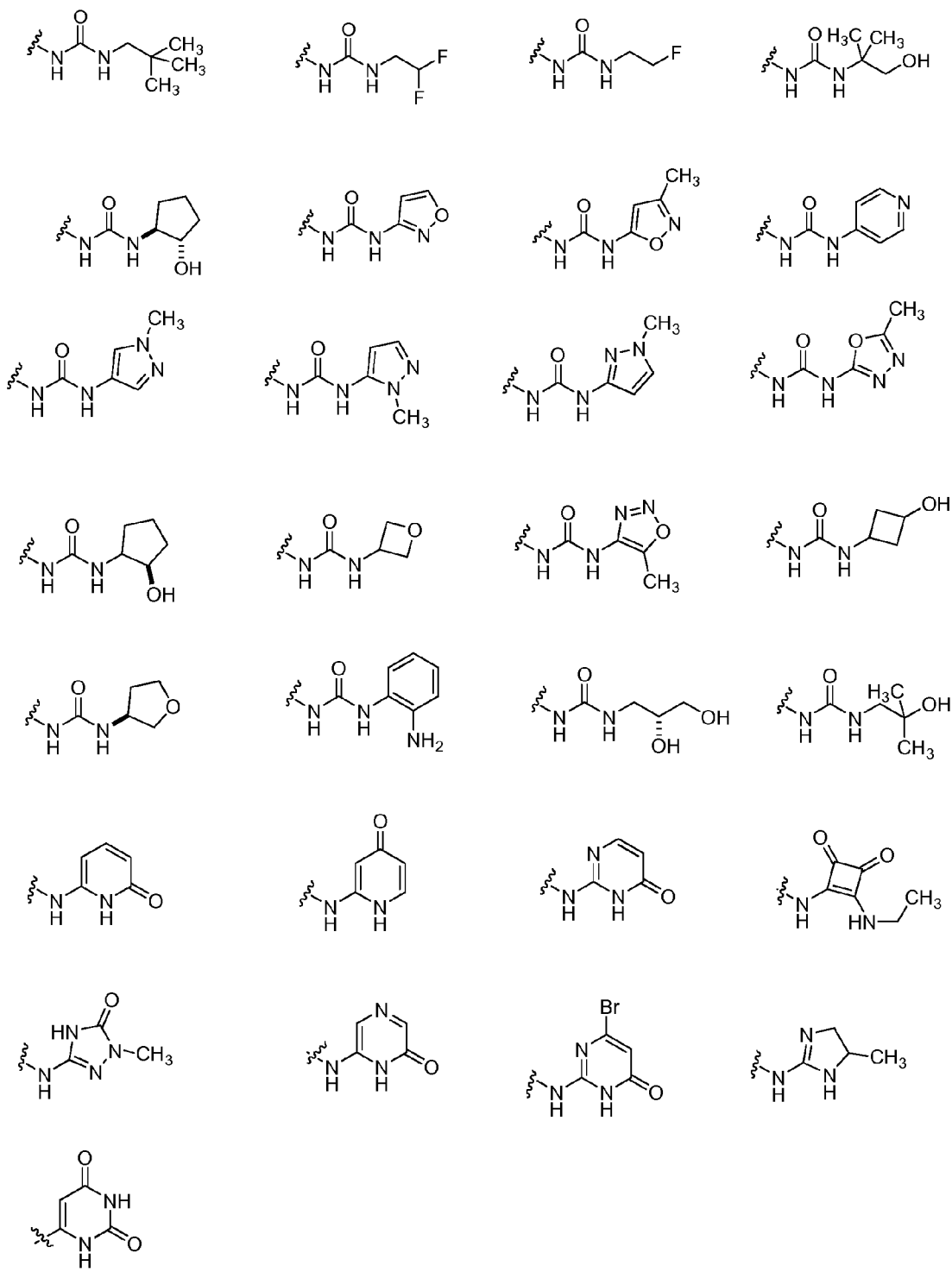
FIG._2B

FIG._3A
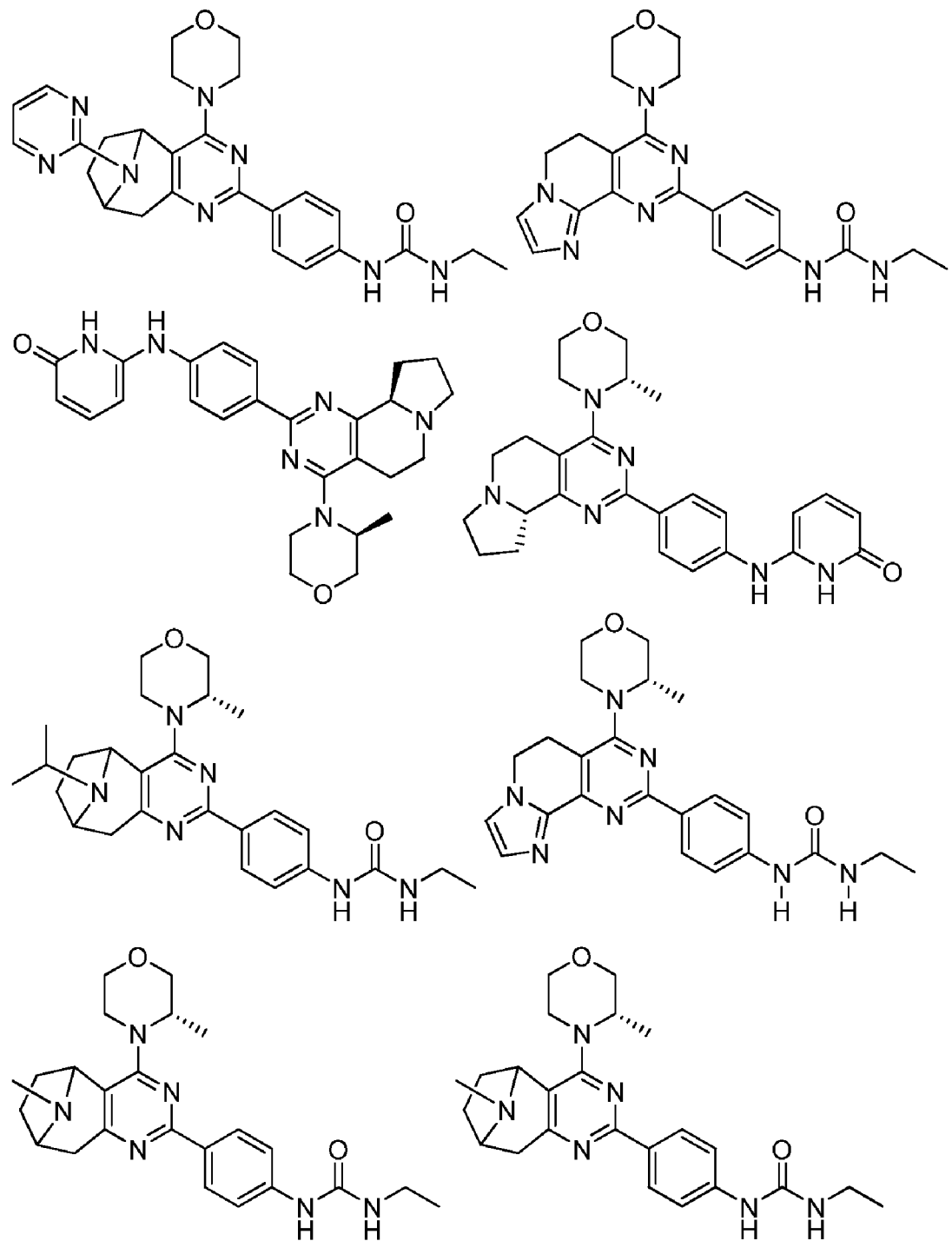

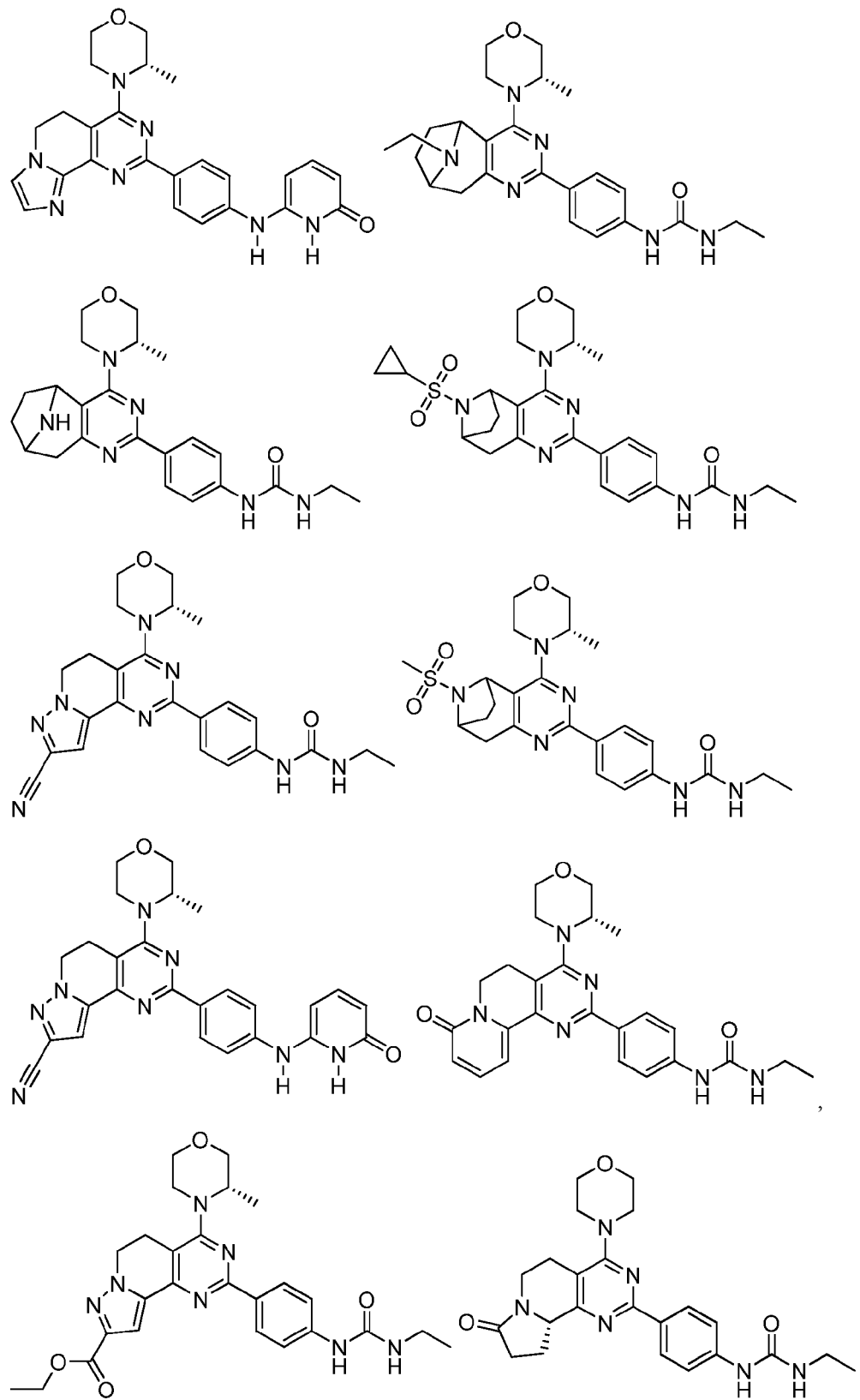
FIG._3B

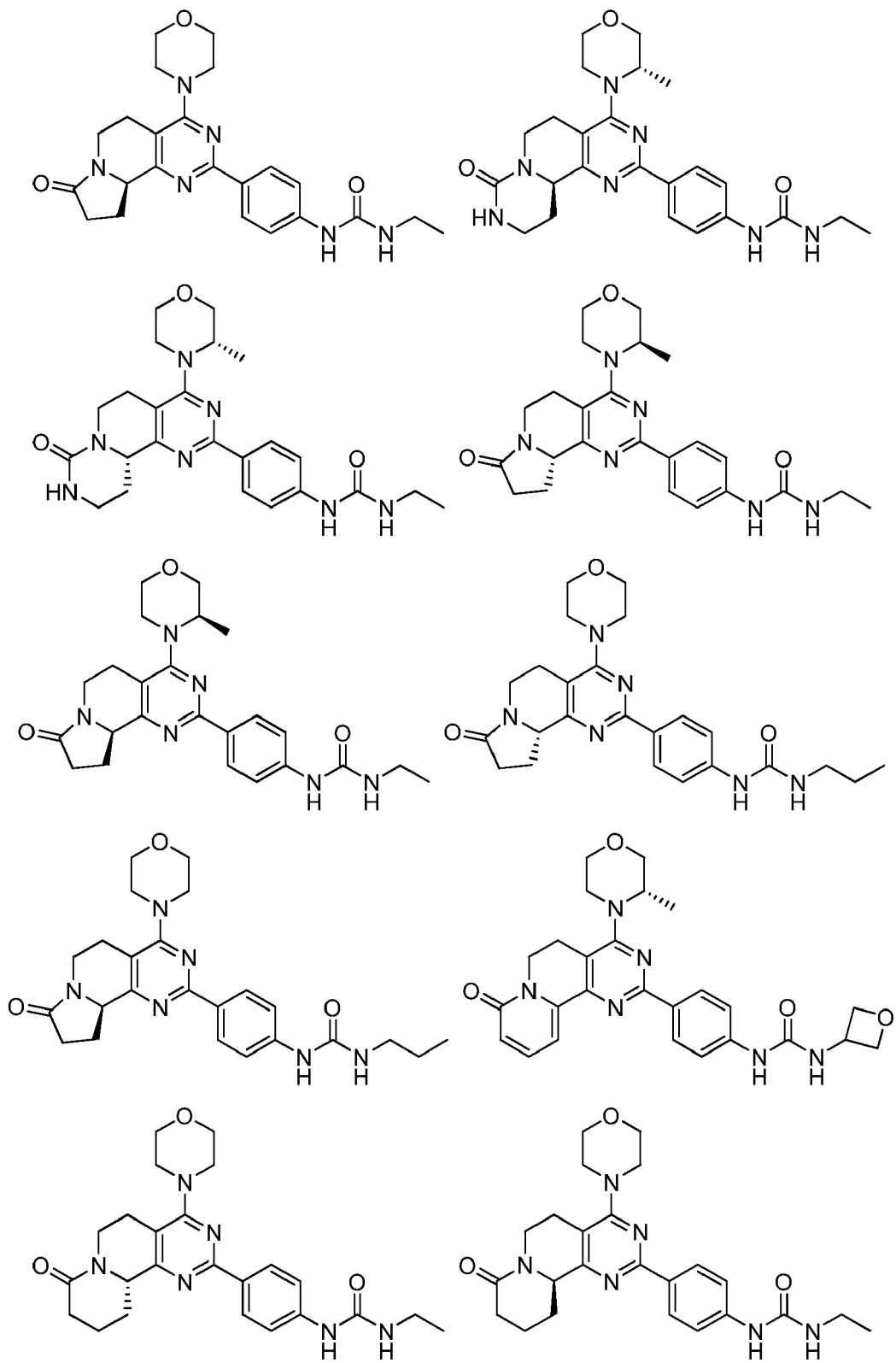
FIG._3C

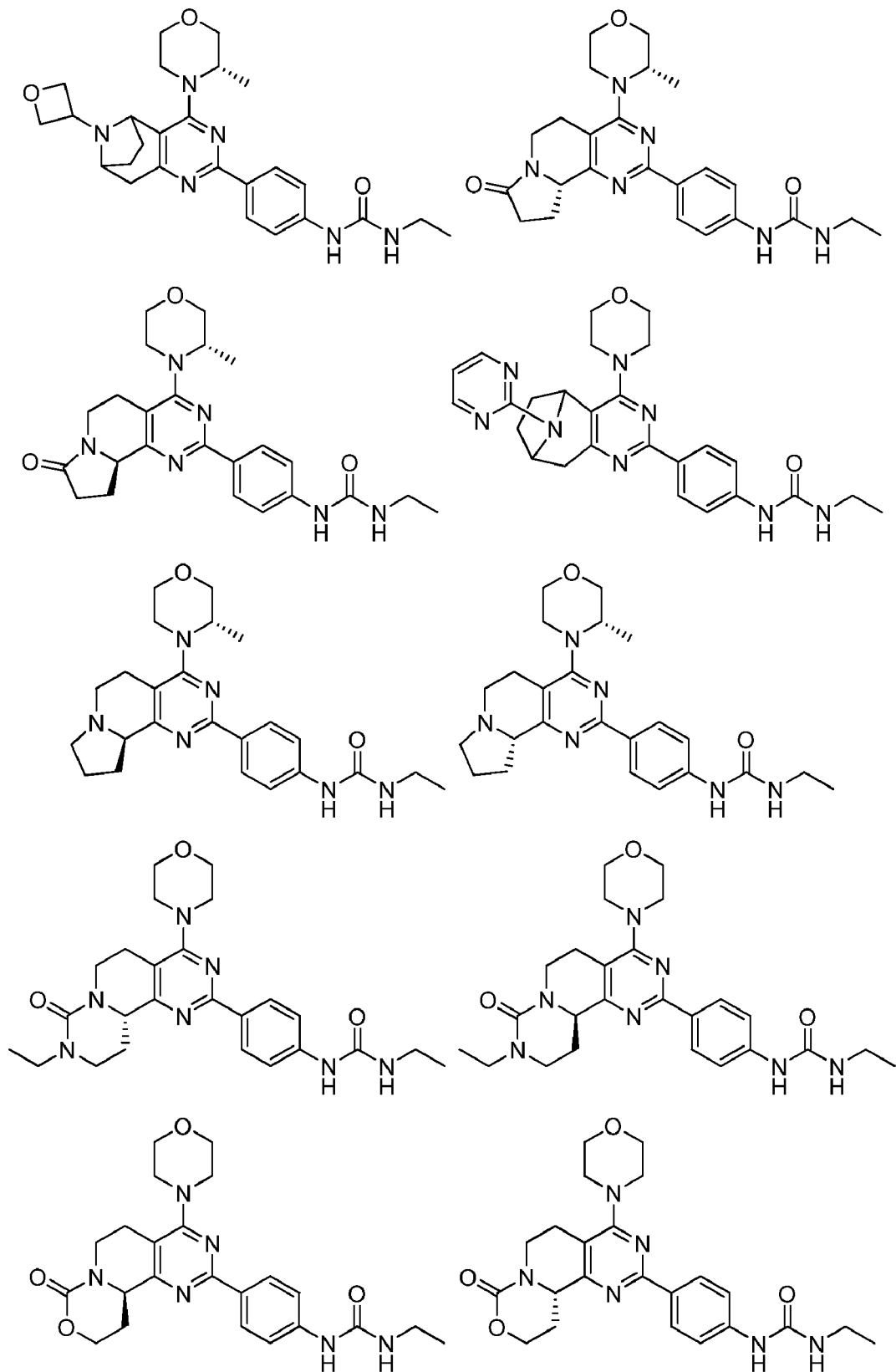
FIG._3D

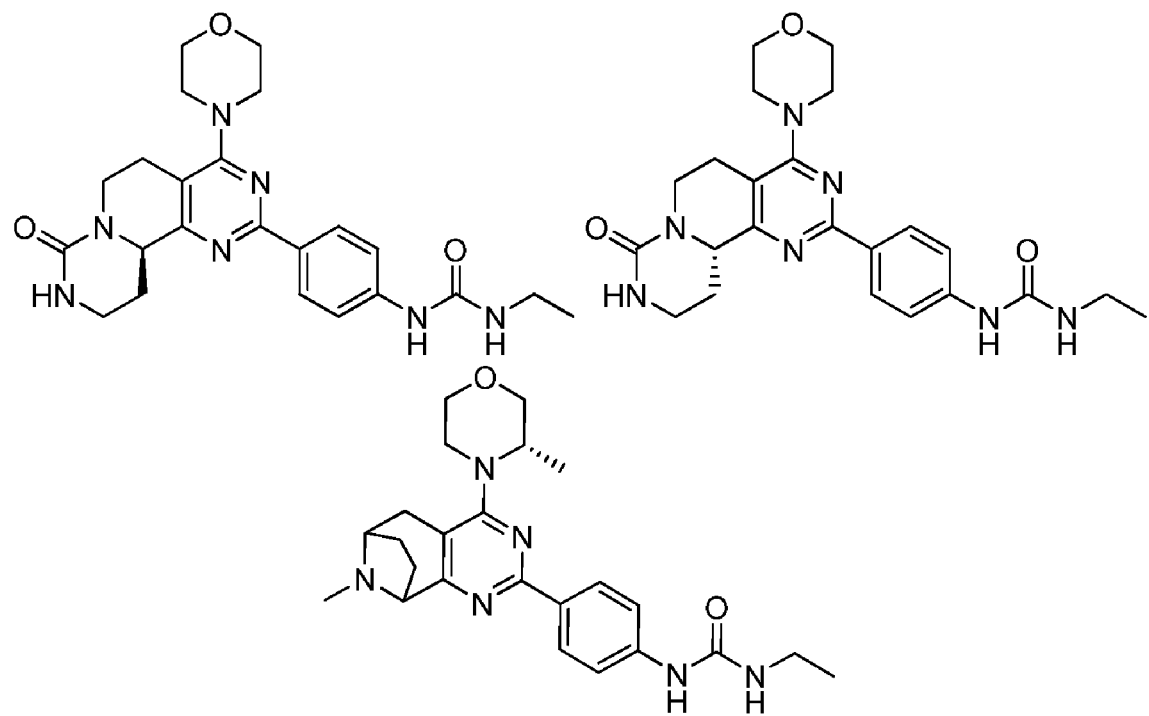
FIG._3E

PYRIMIDINE COMPOUNDS, COMPOSITIONS AND METHODS OF USE

CROSS-REFERENCE TO RELATED APPLICATIONS

This application claims priority to U.S. provisional application No. 61/085,309, filed on Jul. 31, 2008, the contents of which, is incorporated herein by reference for all purposes.

STATEMENT REGARDING FEDERALLY SPONSORED RESEARCH OR DEVELOPMENT

NONE

BACKGROUND OF INVENTION

The mammalian target of rapamycin (mTOR) is a 289 kDa serine/threonine kinase that is considered a member of the phosphoinositide-3-kinase-like kinase (PIKK) family, because it contains a carboxyl terminal kinase domain that has significant sequence homology to the catalytic domain of phosphoinositide 3-kinase (PI3K) lipid kinases. In addition to the catalytic domain at the C-terminus, mTOR kinase also contains a FKBP12-Rapamycin binding (FRB) domain, a putative repressor domain near the C-terminus and up to 20 tandemly-repeated HEAT motifs at the N-terminus as well as a FRAP-ATM-TRRAP (FAT) and FAT C-terminus domain. See, Huang and Houghton, Current Opinion in Pharmacology, 2003, 3, 371-377.) In the literature, mTOR kinase is also referred to as FRAP (FKBP12 and rapamycin associated protein), RAFT1 (rapamycin and FKBP12 target 1), RAPT1 (rapamycin target 1)).

mTOR kinase can be activated by growth factors through the PI3K-Akt pathway or by cellular stresses, such as deprivation of nutrients or hypoxia. The activation of mTOR kinase is thought to play a central role in regulating cell growth and cell survival via a wide range of cellular functions including translation, transcription, mRNA turnover, protein stability, actin cytoskeleton reorganization and autophagy. For a detailed review of mTOR cell signaling biology and potential therapeutic effects of modulating the mTOR signaling interactions, see Sabatini, D. M. and Guertin, D. A. (2005) An Expanding Role for mTOR in Cancer TRENDS in Molecular Medicine, 11, 353-361; Chiang, G. C. and Abraham, R. T. (2007) Targeting the mTOR signaling network in cancer TRENDS 13, 433-442; Jacinto and Hall (2005) Tor signaling in bugs, brain and brawn Nature Reviews Molecular and Cell Biology, 4, 117-126; and Sabatini, D. M. and Guertin, D. A. (2007) Defining the Role of mTOR in Cancer Cancer Cell, 12, 9-22.

Researchers studying mTOR kinase biology have discovered a pathological connection between the dysregulation of mTOR cell signaling and a number of diseases including immunological disorders, cancer, metabolic diseases, cardiovascular diseases and neurological disorders.

For example, there is evidence to show that PI3K-AKT signaling pathway, which lies upstream of mTOR kinase, is frequently overactivated in cancer cells, which subsequently results in the hyperactivation of downstream targets like mTOR kinase. More specifically, the components of the PI3K-AKT pathway that are mutated in different human tumors include, activation mutations of growth factor receptors and the amplification and overexpression of PI3K and AKT. In addition, there is evidence which shows that many tumor types, including glioblastoma, hepatocellular carcinoma, lung carcinoma, melanoma, endometrial carcinomas, and prostate cancer, contain loss-of-function mutations of negative regulators of the PI3K-AKT pathways, such as phosphatases and tensin homolog deleted on chromosome 10 (PTEN) and tuberous sclerosis complex (TSC1/TSC2), which also results in hyperactive signaling of mTOR kinase. The above suggests that inhibitors of mTOR kinase can be effective therapeutics for the treatment of diseases caused, at least in part, by the hyperactivity of the mTOR kinase signalling.

mTOR kinase exists as two physically and functionally distinct signaling complexes (i.e., mTORC1 and mTORC2). mTORC1, also known as the "mTOR-Raptor complex" or the "rapamycin-sensitive complex" because it binds to and is inhibited by the small molecule inhibitor rapamycin. mTORC1 is defined by the presence of the proteins mTOR, Raptor and mLST8. Rapamycin, itself, is a macrolide and was discovered as the first small molecule inhibitor of mTOR kinase. To be biologically active, rapamycin forms a ternary complex with mTOR and FKBP12, which is a cytosolic binding protein collectively called immunophilin. Rapamycin acts to induce the dimerization of mTOR and FKBP12. The formation of rapamycin-FKBP12 complex results in a gain-of-function, because the complex binds directly to mTOR and inhibits the function of mTOR.

A second, more recently discovered mTORC complex, mTORC2, is characterized by the presence of the proteins mTOR, Rictor, Protor-1, mLST8 and mSIN1. mTORC2 is also referred to as the "mTOR-Rictor complex" or the "rapamycin-insensitive" complex because it does not bind to rapamycin.

Both mTOR complexes play important roles in intracellular signaling pathways that affect a cell's growth, and proliferation, and survival. For example, the downstream target proteins of mTORC1 include Ribosomal S6 kinases (e.g., S6K1, S6K2) and eukaryotic initiation factor 4E binding protein (4E-BP1), which are key regulators of protein translation in cells. Also, mTORC2 is responsible for the phosphorylation of AKT (S473); and studies have shown that uncontrolled cell proliferation due to hyperactivation of AKT to be a hallmark of several cancer types.

Currently, several rapamycin analogues are in clinical development for cancer (e.g., Wyeth's CCI-779, Novartis' RAD001 and Ariad Pharmaceuticals' AP23573). Interestingly, the clinical data shows that the rapamycin analogs appear to be effective for certain cancer types, such as mantle-cell lymphoma, endometrial cancer, and renal cell carcinoma.

The discovery of a second mTOR protein complex (mTORC2) that is not inhibited by rapamycin or its analogs suggest that inhibition of mTOR by rapamycin is incomplete and that a direct mTOR kinase inhibitor which can inhibit both mTORC1 and mTORC2 at the catalytic ATP binding site can be more efficacious and have broader anti-tumor activity than rapamycin and its analogs.

Recently, small molecule mTOR inhibitors have disclosed, including in U.S. patent application Ser. Nos. 11/599,663 and 11/657,156 to OSI Pharmaceuticals Inc.; in International Applications WO/2008/023161 and WO/2006/090169 to Kudos Pharmaceuticals; and in International Applications WO/2008/032060, WO/2008/032086, WO/2008032033, WO/2008/032028, WO/2008/032036, WO/2008/032089, WO/2008/032072, WO/2008/031091 to AstraZeneca.

In view of the increased knowledge of the role of mTOR signaling in diseases (e.g., cancer), it is desirable to have small molecule inhibitors of mTOR (including mTORC1 and mTORC2) that can be used to treat diseases wherein aberrant mTOR activity is observed, such as, for example, in cancer. In addition, it can be desirable to have small molecule inhibitors of related enzymes (e.g., PI3K, AKT) that functions upstream or downstream of the mTOR signaling pathway.

SUMMARY OF INVENTION

In one aspect, the invention provides for compounds of Formula I

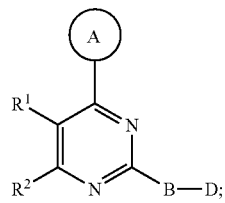

I wherein the variables R¹, R², A, B and D have the meaning as described herein.

In another aspect, the present invention provides for pharmaceutical compositions comprising a compound of Formula I, or a sub-formula thereof as described herein, and a pharmaceutically acceptable carrier, diluent or excipient.

In another aspect, the present invention provides for a method for the treatment of cancers as described herein in a mammal comprising administering to a patient in need thereof a therapeutically acceptable amount of a compound of Formula I or a subformula thereof as described herein.

In another aspect, the present invention provides for method for inhibiting the activity of mTOR kinase in a mammal using compounds of Formula I or a subformula thereof as described herein.

In another aspect, the present invention provides for the use of a compound of Formula I or a subformula thereof as described herein in the preparation of a medicament for the treatment of cancer.

In another aspect, the present invention provides for methods for using compounds of Formula I or subformula thereof, described herein, for the treatment of disease, e.g., cancer, mediated at least in part by the dysregulation of the PIKK signaling pathway (e.g. mTOR kinase signaling).

DESCRIPTION OF THE DRAWINGS

FIG. 1A, FIG. 1B, FIG. 1C, FIG. 1D, FIG. 1E and FIG. 1F illustrate certain particular W groups represented by Formula i.

FIG. 2A and FIG. 2B illustrate certain particular D groups represented in Formula I.

FIG. 3A, FIG. 3B, FIG. 3C, FIG. 3D and FIG. 3E illustrate certain compounds of Formula I.

DETAILED DESCRIPTION OF THE INVENTION

I. Definitions

As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated alkyl radical having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl," "carbocyclic," or "carbocycle" refers to hydrocarbon rings having the indicated number of ring atoms (e.g., $C_{3-6}$ cycloalkyl) and being fully saturated or having no more than one double bond between ring vertices. As used herein, "cycloalkyl," "carbocyclic," or "carbocycle" is also meant to refer to bicyclic, polycyclic and spirocyclic hydrocarbon rings such as, for example, bicyclo[2.2.1]heptane, pinane, bicyclo[2.2.2]octane, adamantane, norborene, spirocyclic $C_{5-12}$ alkane, etc. As used herein, the terms, "alkenyl," "alkynyl," "cycloalkyl,", "carbocycle," and "carbocyclic," are meant to include mono and polyhalogenated variants thereof.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation, and also include mono- and polyhalogenated variants, or combinations thereof. Examples include —$CH_2$—$CH_2$—O—$CH_3$, —$CH_2$—$CH_2$—O—$CF_3$, —$CH_2$—$CH_2$—NH—$CH_3$, —$CH_2$—$CH_2$—N($CH_3$)—$CH_3$, —$CH_2$—S—$CH_2$—$CH_3$, —S(O)—$CH_3$, —$CH_2$—$CH_2$—S($O)_2$—$CH_3$, —CH=CH—O—$CH_3$, —Si($CH_3)_3$, —$CH_2$—CH=N—$OCH_3$, and —CH=CH=N($CH_3$)—$CH_3$. Up to two heteroatoms can be consecutive, such as, for example, —$CH_2$—NH—$OCH_3$ and —$CH_2$—O—Si($CH_3)_3$.

The term "heterocycloalkyl," "heterocyclic," or "heterocycle" refers to a cycloalkane group that contain from one to five heteroatoms selected from N, O, and S, wherein the nitrogen and sulfur atoms are optionally oxidized, and the nitrogen atom(s) are optionally quaternized. Unless otherwise stated, a "heterocycloalkyl," "heterocyclic," or "heterocycle" ring can be a monocyclic, a bicyclic, spirocyclic or a polycylic ring system. Non limiting examples of "heterocycloalkyl," "heterocyclic," or "heterocycle" rings include pyrrolidine, piperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, tropane and the like. A "heterocycloalkyl," "heterocyclic," or "heterocycle" group can be attached to the remainder of the molecule through one or more ring carbons or heteroatoms. A "heterocycloalkyl," "heterocyclic," or "heterocycle" can include mono- and polyhalogenated variants thereof. The compounds of the invention comprise a structure wherein a saturated heterocyclic ring is fused to a pyrimidine ring, which as used herein means that the heterocyclic ring itself that is fused to the pyrimidine core, does not contain any units of unsaturation other than the between the two ring vertices that is share (and fused to) the pyrimidine ring.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. "Haloalkylene" refers to mono and poly halogenated variant of alkylene. "Alkenylene" and "alkynylene" refer to the unsaturated forms of "alkylene" having double or triple bonds, respectively and are also meant to include mono and poly-halogenated variants.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)$CH_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, difluoromethyl, and the like.

The term "aryl" means, unless otherwise stated, a polyunsaturated, typically aromatic, hydrocarbon group, which can be a single ring or multiple rings (up to three rings) which are fused together. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Optional substituents for each of the above noted aryl and heteroaryl ring systems can be selected from the group of acceptable substituents described further below.

As used herein, the term "arylene" generically refers to any aryl that is a divalent radical. For a more specific example, "phenylene" refers to a divalent phenyl ring radical. The terms "1,2-arylene," "1,3-arylene" or "1,4-arylene" refer to geometrical isomers of a particular arylene wherein, two groups attached to an aryl as depicted in a formula are situated in an ortho, meta or para geometrical relationship about the aryl, respectively.

As used herein, the term "heteroarylene" generically refers to any heteroaryl is a divalent radical. For a more specific example, "pyridylene" refers to a divalent pyridyl ring radical. For example, a 2,5-pyridylene refers to a divalent pyridyl ring radical in which the two groups attached to the pyridylene ring as depicted in the formula are attached to the 2- and the 5-position of the pyridine ring.

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl, heteroalkyl and cycloalkyl) can be a variety of groups including, but not limited to, -halogen, —OR', —NR'R", —SR', —SiR'R"R''', —OC(O)R', —C(O)R', —$CO_2$R', —CONR'R", —OC(O)NR'R", —NR"C(O)R', —NR'''C(O)NR'R", —NR"C(O)$_2$R', —NHC($NH_2$)=NH, —NR'C($NH_2$)=NH, —NHC($NH_2$)=NR', —NR'''C(NR'R")=N—CN, —NR'''C(NR'R")=NOR', —NHC($NH_2$)=NR', —S(O)R', —S(O)$_2$R', —S(O)$_2$NR'R", —NR'S(O)$_2$R", —NR"S(O)$_2$NR'R", —CN, —$NO_2$, —($CH_2$)$_{1-4}$—OR', —($CH_2$)$_{1-4}$—NR'R", —($CH_2$)$_{1-4}$—SR', —($CH_2$)$_{1-4}$—SiR'R"R''', —($CH_2$)$_{1-4}$—OC(O)R', —($CH_2$)$_{1-4}$—C(O)R', —($CH_2$)$_{1-4}$—$CO_2$R', —($CH_2$)$_{1-4}$CONR'R", in a number ranging from zero to (2m'+1), where m' is the total number of carbon atoms in such radical. R', R" and R''' each independently refer groups including, for example, hydrogen, unsubstituted $C_{1-6}$ alkyl, unsubstituted heteroalkyl, unsubstituted aryl, aryl substituted with 1-3 halogens, unsubstituted $C_{1-6}$ alkyl, $C_{1-6}$ alkoxy or $C_{1-6}$ thioalkoxy groups, or unsubstituted aryl-$C_{1-4}$ alkyl groups, unsubstituted heteroaryl, substituted heteroaryl, among others. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. Other substituents for alkyl radicals, including heteroalkyl, alkylene, include for example, =O, =NR', =N—OR', =N—CN, =NH, wherein R' include substituents as described above. When a substituent for the alkyl radicals (including those groups often referred to as alkylene, alkenyl, alkynyl, heteroalkyl and cycloalkyl) contains an alkylene linker (e.g., —($CH_2$)$_{1-4}$—NR'R"), the alkylene linker includes halo variants as well. For example, the linker "—($CH_2$)$_{1-4}$—" when used as part of a substituent is meant to include difluoromethylene, 1,2-difluoroethylene, etc.

Similarly, substituents for the aryl and heteroaryl groups are varied and are generally selected from the group including, but not limited to, -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'C(O)NR"R''', —NHC($NH_2$)=NH, —NR'C($NH_2$)=NH, —NHC($NH_2$)=NR', —S(O)R', —S(O)$_2$R', —S(O)$_2$NR'R", —NR'S(O)$_2$R", —$N_3$, perfluoro-$C_{1-4}$ alkoxy, and perfluoro-$C_{1-4}$ alkyl, —($CH_2$)$_{1-4}$—OR', —($CH_2$)$_{1-4}$—NR'R", —($CH_2$)$_{1-4}$—SR', —($CH_2$)$_{1-4}$—SiR'R"R''', —($CH_2$)$_{1-4}$—OC(O)R', —($CH_2$)$_{1-4}$—C(O)R', —($CH_2$)$_{1-4}$—$CO_2$R', —($CH_2$)$_{1-4}$CONR'R", in a number ranging from zero to the total number of open valences on the aromatic ring system; and where R', R" and R''' are independently selected from hydrogen, $C_{1-6}$ alkyl, $C_{3-6}$ cycloalkyl, $C_{2-6}$ alkenyl, $C_{2-6}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms. When a substituent for the aryl or heteroaryl group contains an alkylene linker (e.g., —($CH_2$)$_{1-4}$—NR'R"), the alkylene linker includes halo variants as well. For example, the linker "—($CH_2$)$_{1-4}$—" when used as part of a substituent is meant to include difluoromethylene, 1,2-difluoroethylene, etc.

As used herein, the term "heteroatom" is meant to include oxygen (O), nitrogen (N), sulfur (S) and silicon (Si).

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis $4^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-(($C_{1-6}$)alkanoyloxy)ethyl, 1-methyl-1-(($C_{1-6}$)alkanoyloxy)ethyl, ($C_{1-6}$)alkoxycarbonyloxymethyl, N—($C_{1-6}$)alkoxycarbonylaminomethyl, succinoyl, ($C_{1-6}$)alkanoyl, alpha-amino ($C_{1-4}$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6}$)alkyl$)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^3H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the present invention can also contain unnatural proportions of atomic isotopes at one or more of the atoms that constitute such compounds. For example, the present invention also embraces isotopically-labeled variants of the present invention which are identical to those recited herein, bur the for the fact that one or more atoms are replace by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically labeled compounds of the present invention (e.g., those labeled with $^3$H or $^{14}$C) are useful in compound and/or substrate tissue distribution assays. Tritiated ($^3$H) and carbon-14 ($^{14}$C) isotopes are useful for their ease of preparation and detectability. Further substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting an isotopically labeled reagent for a non-isotopically labeled reagent.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug can prevent growth and/or kill existing cancer cells, it can be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

As used herein, the term "adjunct" relates to the use of active compounds in conjunction with known therapeutic means. Such means include cytotoxic regimes of drugs and/or ionising radiation as used in the treatment of different cancer types. Examples of adjunct chemotherapeutic agents that can be combined with compounds from the invention include, but are not limited to, the following: alkylating agents: nitrogen mustards, mechlorethamine, cyclophosphamide, ifosfamide, melphalan, chlorambucil; Nitrosoureas: carmustine (BCNU), lomustine (CCNU), semustine (methyl-CCNU), ethylenimine/methylmelamine, thriethylenemelamine (TEM), triethylene thiophosphoramide (thiotepa), hexamethylmelamine (HMM, altretamine); Alkyl sufonates: busulfan; Triazines, dacarbazine (DTIC); Antimetabolites: folic acid analogs, methotrexate, trimetrexate, pyrimidine analogs, 5-fluorouracil, fluorodeoxyuridine, gemcitabine, cytosine arabinoside (AraC, cytarabine), 5-azacytidine, 2,2'-difluorodeoxycytidine; Purine analogs: 6-mercaptopurine, 6-thioguanine, azathioprine, 2'-deoxycoformycin (pentostatin, erythrohydroxynonyladenine (EHNA), fludarabine phosphate, 2-Chlorodeoxyadenosine (cladribine, 2-CdA); Topoisomerase I inhibitors: camptothecin, topotecan, irinotecan, rubitecan; Natural products: antimitotic drugs, paclitaxel, vinca alkaloids, vinblastine (VLB), vincristine, vinorelbine, Taxotere, (docetaxel), estramustine, estramustine phosphate; epipodophylotoxins, etoposide, teniposide; Antibiotics: actinomycin D, daunomycin (rubidomycin), doxorubicin (adriamycin), mitoxantrone, idarubicin, bleomycins, plicamycin (mithramycin), mitomycin C, dactinomycin; Enzymes: L-asparaginase, RNAse A; Biological response modifiers: interferon-alpha, IL-2, G-CSF, GM-CSF; Differentiation Agents: retinoic acid derivatives; Radiosensitizers: metronidazole, misonidazole, desmethylmisonidazole, pimonidazole, etanidazole, nimorazole, RSU 1069, E09, RB 6145, SR4233, nicotinamide, 5-bromodeozyuridine, 5-iododeoxyuridine, bromodeoxycytidine; Platinium coordination complexes: cisplatin, carboplatin; Anthracenedione; mitoxantrone, AQ4N Substituted urea; hydroxyurea; Methyl hydrazine derivatives: N-methylhydrazine (MIH), procarbazine; Adrenocortical suppressant: mitotane (o.p-DDD), aminoglutethimide; Cytokines: interferon (alpha, beta, gamma), interleukin; Hormones and antagonists: adrenocorticosteroids/antagonists, prednisone and equivalents, dexamethasone, aminoglutethimide, Progestins, hydroxyprogesterone caproate, medroxyprogesterone acetate, megestrol acetate; Estrogens, diethylstilbestrol, ethynyl estradiol/equivalents, Antiestrogen, tamoxifen, Androgens, testosterone propionate, fluoxymesterone/equivalents, Antiandrogens, flutamide, gonadotropin-releasing hormone analogs, leuprolide; Nonsteroidal antiandrogens, flutamide; EGFR inhibitors; and Proteasome inhibitors. Active compounds can also be used as cell culture additives to inhibit mTOR, for example, in order to sensitize cells to known chemotherapeutic agents or ionising radiation treatments in vitro.

II.A Compounds

In one aspect, the present invention provides for a compound of Formula I

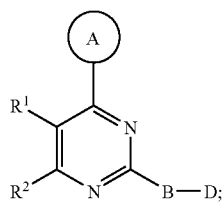

(I)

or a pharmaceutically acceptable salt thereof, wherein in Formula I,

A is a 5- to 8-membered heterocyclic ring having from 1 to 3 heteroatoms independently selected from N, O and S as ring vertices, and having from 0 to 2 double bonds; optionally fused to the heterocyclic ring of A is a 6-membered aryl ring or a 5- to 6-membered heteroaryl ring having from 1 to 3 heteroatoms selected from N, O and S; and wherein the A ring, and if present, the 6-membered aryl ring or the 5- or 6-membered heteroaryl ring fused thereto, is further substituted with from 0 to 5 $R^A$ substituents selected from the group consisting of —C(O)O$R^a$, —C(O)N$R^aR^b$, —N$R^aR^b$, —OC(O)$R^c$, —O$R^a$, —S$R^a$, —S(O)$_2R^c$, —S(O)$R^c$, —$R^c$, —(CH$_2$)$_{1-4}$—N$R^aR^b$, —(CH$_2$)$_{1-4}$—N$R^a$C(O)$R^c$, —(CH$_2$)$_{1-4}$—O$R^a$, —(CH$_2$)$_{1-4}$—S$R^a$, —(CH$_2$)$_{1-4}$—S(O)$_2R^c$, —(CH$_2$)$_{1-4}$—S(O)$R^c$, halogen, F, Cl, Br, I, —NO$_2$, —CN and —N$_3$, wherein $R^a$ and $R^b$ are each independently selected from hydrogen, C$_{1-6}$ alkyl, C$_{1-6}$ haloalkyl, C$_{1-6}$ heteroalkyl, C$_{2-6}$ alkenyl, C$_{2-6}$ alkynyl, C$_{3-6}$ cycloalkyl, phenyl and —(CH$_2$)$_{1-4}$(phenyl), and optionally $R^a$ and $R^b$, together with the nitrogen atom to which each is attached, are combined to form a 3- to 7-membered heterocyclic ring comprising 1 to 2 heteroatoms selected from N, O and S; $R^c$ is selected from C$_{1-6}$ alkyl, C$_{1-6}$ haloalkyl, C$_{2-6}$ alkenyl, C$_{2-6}$ alkynyl, C$_{3-6}$ cycloalkyl, phenyl and —(CH$_2$)$_{1-4}$(phenyl), and any two substituents attached to the same atom in the 5- to 8-membered heterocyclic ring are optionally combined to form a 3- to 5-membered carbocyclic or a 3 to 5-membered heterocyclic ring substituted with 0-3 $R^A$ substituents;

$R^1$ and $R^2$ are combined with the atoms to which they are attached to form a 5- to 8-membered saturated heterocyclic ring comprising —N(W)— as one of the ring vertices, wherein W is represented by Formula i

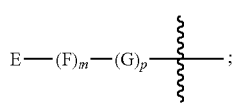

i wherein E is a member selected from the group consisting of hydrogen, C$_{6-10}$ aryl, C$_{5-10}$ heteroaryl, C$_{3-10}$ cycloalkyl, C$_{3-10}$ heterocycloalkyl, C$_{1-6}$ alkyl and C$_{1-6}$ heteroalkyl; and wherein E is independently substituted with from 0 to 5 $R^E$ substituents selected from the group consisting of halogen, F, Cl, Br, I, —N$R^dR^e$, —S$R^d$, —O$R^d$, —C(O)O$R^d$, —C(O)N$R^dR^e$, —C(O)$R^d$, —N$R^d$C(O)$R^e$, —OC(O)$R^f$, —N$R^d$C(O)N$R^dR^e$, —OC(O)N$R^dR^e$, C(=NO$R^d$)N$R^dR^e$, —N$R^d$C(=N—CN)N$R^dR^e$, —N$R^d$S(O)$_2$N$R^dR^e$, —S(O)$_2$ $R^d$, —S(O)$_2$N$R^dR^e$, —$R^f$, —NO$_2$, —N$_3$, =O, —CN, —(CH$_2$)$_{1-4}$—N$R^dR^e$, —(CH$_2$)$_{1-4}$—S$R^d$, —(CH$_2$)$_{1-4}$—O$R^d$, —(CH$_2$)$_{1-4}$—C(O)O$R^d$, —(CH$_2$)$_{1-4}$—C(O)N$R^dR^e$, —(CH$_2$)$_{1-4}$C(O)$R^d$, —(CH$_2$)$_{1-4}$—N$R^d$C(O)$R^e$, —(CH$_2$)$_{1-4}$—OC(O)$R^f$, —(CH$_2$)$_{1-4}$—N$R^d$C(O)N$R^dR^e$, —(CH$_2$)$_{1-4}$—OC(O)N$R^dR^e$, —(CH$_2$)$_{1-4}$—C(=NO$R^d$)N$R^dR^e$, —(CH$_2$)$_{1-4}$—N$R^d$C(=N—CN)N$R^dR^e$, —(CH$_2$)$_{1-4}$—N$R^d$S(O)$_2$N$R^dR^e$, —(CH$_2$)$_{1-4}$—S(O)$_2$ $R^d$, —(CH$_2$)$_{1-4}$—S(O)$_2$N$R^dR^e$, —(CH$_2$)$_{1-4}$—NO$_2$, —(CH$_2$)$_{1-4}$—N$_3$ and —(CH$_2$)$_{1-4}$—CN; wherein $R^d$ and $R^e$ are each independently selected from hydrogen, C$_{1-6}$ alkyl, C$_{1-6}$ haloalkyl, C$_{1-6}$ heteroalkyl, C$_{2-6}$ alkenyl, C$_{2-6}$ alkynyl, C$_{3-7}$ cycloalkyl, C$_{3-7}$ heterocycloalkyl, phenyl and —(CH$_2$)$_{1-4}$-phenyl, and optionally $R^d$ and $R^e$, when attached to the same nitrogen atom are combined to form a 3- to 6-membered heterocyclic ring comprising 1 to 2 heteroatoms selected from N, O and S; $R^f$ is selected from C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ heterocycloalkyl, phenyl and —(CH$_2$)$_{1-4}$-phenyl; and wherein any two substituents located on adjacent atoms, or located on the same atom of E are optionally combined to form a 5- to 6-membered carbocyclic or heterocyclic ring; F is a member selected from the group consisting of C$_{1-6}$ alkylene, C$_{2-6}$ alkenylene, C$_{2-6}$ alkynylene and C$_{1-6}$ heteroalkylene; wherein F is independently substituted with from 0 to 3 $R^F$ substituents selected from the group consisting of halogen, F, Cl, Br, I, —N$R^gR^h$, —S$R^g$, —O$R^g$, —C(O)O$R^g$, —C(O)N$R^gR^h$, —N$R^g$C(O)$R^i$, —OC(O)$R^i$, —N$R^g$C(O)N$R^gR^h$, —OC(O)N$R^gR^h$, N$R^g$S(O)$_2$N$R^gR^h$, —S(O)$_2R^g$, —S(O)$_2$N$R^gR^h$, —$R^i$, —NO$_2$, N$_3$, =O, —CN, —(CH$_2$)$_{1-4}$—N$R^gR^h$, —(CH$_2$)$_{1-4}$—S$R^g$, —(CH$_2$)$_{1-4}$—O$R^g$, —(CH$_2$)$_{1-4}$—C(O)O$R^g$, —(CH$_2$)$_{1-4}$—C(O)N$R^gR^h$, —(CH$_2$)$_{1-4}$—C(O)$R^g$, —(CH$_2$)$_{1-4}$—N$R^g$C(O)$R^h$, —(CH$_2$)$_{1-4}$—C(O)$R^i$, —(CH$_2$)$_{1-4}$—N$R^g$C(O)N$R^gR^h$, —(CH$_2$)$_{1-4}$—OC(O)N$R^g$ $R^h$, —(CH$_2$)$_{1-4}$—N$R^g$S(O)$_2$N$R^gR^h$, —(CH$_2$)$_{1-4}$—S(O)$_2$ $R^g$, —(CH$_2$)$_{1-4}$—S(O)$_2$N$R^gR^h$, —(CH$_2$)$_{1-4}$—NO$_2$, —(CH$_2$)$_{1-4}$—N$_3$ and —(CH$_2$)$_{1-4}$—CN; wherein $R^g$ and $R^h$ are each independently selected from hydrogen, C$_{1-6}$ alkyl, C$_{1-6}$ haloalkyl, C$_{1-6}$ heteroalkyl, C$_{3-7}$ cycloalkyl, C$_{3-7}$ heterocycloalkyl, phenyl and —(CH$_2$)$_{1-4}$-phenyl, and optionally $R^g$ and $R^h$, when attached to the same nitrogen atom are combined to form a 3- to 6-membered heterocyclic ring comprising 1 to 2 heteroatoms selected from N, O and S; $R^i$ is selected from C$_{1-6}$ alkyl, C$_{1-6}$ haloalkyl, C$_{3-7}$ cycloalkyl, C$_{3-7}$ heterocycloalkyl, phenyl and —(CH$_2$)$_{1-4}$-phenyl;

G is a member selected from the group consisting of —C(O)—, —OC(O)—, —NHC(O)—, —NHC(=NOH)—, —S(O)$_{0-2}$— and —NHS(O)$_2$—;

the subscripts m and p are each independently an integer from 0 to 1;

wherein the 5- to 8-membered heterocyclic ring formed by combining $R^1$ and $R^2$ further optionally comprises 1 additional heteroatom selected from the group consisting of N, O and S, and is substituted with from 0 to 5 $R^R$ substituents selected from the group consisting of halogen, F, Cl, Br, I, —N$R^jR^k$, —S$R^j$, —O$R^j$, —C(O)O$R^j$, —C(O)N$R^jR^k$, —NHC(O)$R^j$, —OC(O)$R^j$, —$R^m$, —CN, —(CH$_2$)$_{1-4}$—CN, —(CH$_2$)$_{1-4}$O$R^j$, —(CH$_2$)$_{1-4}$N$R^jR^k$, —(CH$_2$)$_{1-4}$—CO$_2R^j$, —(CH$_2$)$_{1-4}$C(O)N$R^jR^k$, C$_{2-4}$ alkenylene-CO$_2R^j$, C$_{2-4}$ alkenylene-C(O)N$R^jR^k$, =O, =S, and =N—CN, wherein $R^j$ and $R^k$ are each independently selected from hydrogen, C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ heterocycloalkyl, phenyl and —(CH$_2$)$_{1-4}$-(Ph), and $R^j$ and $R^k$, when attached to the same nitrogen atom, are optionally combined to form a 3- to 6-membered heterocyclic ring comprising 1 to 2 heteroatoms selected from N, O and S; and $R^m$ is selected from $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ heterocycloalkyl and —$(CH_2)_{1-4}$-(Ph), and wherein when $R^1$ and $R^2$ are combined to form a monocyclic 5- to 8-membered heterocyclic ring then any two substitutents attached to the same or adjacent atoms in the monocyclic 5- to 8-membered heterocyclic ring are optionally combined to form a 3- to 7-membered cycloalkyl ring, a 3- to 7-membered heterocycloalkyl ring or a 5- to 6-membered heteroaryl ring comprising 1 to 2 heteroatoms selected from N, O and S and is substituted with 0 to 3 $R^R$ substitutents;

B is a member selected from the group consisting of phenylene and 5- to 6-membered heteroarylene, and is substituted with from 0 to 4 $R^B$ substituents selected from halogen, F, Cl, Br, I, —CN, —$N_3$, —$NO_2$, —C(O)OR″, —C(O)NR″R°, —NR″C(O)R°, —NR″C(O)NR″R°, —OR″, —NR″R°, —$(CH_2)_{1-4}$—C(O)OR″, —$(CH_2)_{1-4}$—C(O)NR″R°, —$(CH_2)_{1-4}$—OR″, —$(CH_2)_{1-4}$—NR″R°, —$(CH_2)_{1-4}$—SR$^p$ and R$^p$; wherein R″ and R° are independently selected from hydrogen and $C_{1-6}$ alkyl, $C_{1-6}$ haloalkyl, $C_{1-6}$ heteroalkyl, $C_{2-6}$ alkenyl, $C_{2-6}$ alkynyl, $C_{3-7}$ cycloalkyl, $C_{3-7}$ heterocycloalkyl, phenyl and —$(CH_2)_{1-4}$-(phenyl) or when attached to the same nitrogen atom, R″ and R° are optionally are combined to form a 3- to 6-membered heterocyclic ring comprising 1 to 2 heteroatoms selected from N, O and S; $R^p$ is $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ heterocycloalkyl, phenyl and —$(CH_2)_{1-4}$-(phenyl), wherein any two substituents, not including the D group, located on adjacent atoms of B are optionally combined to form a 5- to 6-membered carbocyclic, heterocyclic, aryl or heteroaryl ring substituted with 0-2 $R^B$ substituents;

D is a member selected from the group consisting of —$NR^3C(O)NR^4R^5$, —$NR^4R^5$, —$C(O)NR^4R^5$, —$OC(O)OR^4$, —$OC(O)NR^4R^5$, —$NR^3C(=N—CN)NR^4R^5$, —$NR^3C(=N—OR^4)NR^4R^5$, —$NR^3C(=N—NR^4)NR^4R^5$, —$NR^3C(O)R^4$, —$NR^3C(O)OR^4$, —$NR^3S(O)_2NR^4R^5$ and —$NR^3S(O)_2R^4$, wherein $R^3$ is selected from the group consisting of hydrogen, $C_{1-6}$ alkyl, $C_{1-6}$ haloalkyl and $C_{2-6}$ alkenyl; $R^4$ and $R^5$ are each independently selected from the group consisting of hydrogen, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ heterocycloalkyl, $C_{6-10}$ aryl and $C_{5-10}$ heteroaryl, and $R^4$ and $R^5$, when attached to the same nitrogen atom, are optionally combined to form a 5- to 7-membered heterocyclic or heteroaryl ring comprising 1 to 3 heteroatoms selected from N, O and S as ring vertices and is substituted with 0-3 $R^D$ substituents; and wherein $R^3$, $R^4$ and $R^5$ are further substituted with from 0 to 3 $R^D$ substituents independently selected from the group consisting of halogen, F, Cl, Br, I, —$NO_2$, —CN, —$NR^qR^r$, —$OR^q$, —$SR^q$, —$C(O)OR^q$, —$C(O)NR^qR^r$, —$NR^qC(O)R^r$, —$NR^qC(O)OR^s$, —$(CH_2)_{1-4}$—$NR^qR^r$, —$(CH_2)_{1-4}$—$OR^q$, —$(CH_2)_{1-4}$—$SR^q$, —$(CH_2)_{1-4}$—$C(O)OR^q$, —$(CH_2)_{1-4}$—$C(O)NR^qR^r$, —$(CH_2)_{1-4}$—$NR^qC(O)R^r$, —$(CH_2)_{1-4}$—$NR^qC(O)OR^r$, —$(CH_2)_{1-4}$—CN, —$(CH_2)_{1-4}$—$NO_2$, —$S(O)R^r$, —$S(O)_2R^r$, =O, and —$R^s$; wherein $R^q$ and $R^r$ is selected from hydrogen, $C_{1-6}$ alkyl, $C_{1-6}$ haloalkyl, $C_{2-6}$ alkenyl, $C_{2-6}$ alkynyl, $C_{1-6}$ heteroalkyl, $C_{3-7}$ cycloalkyl, $C_{3-7}$ heterocycloalkyl, $C_{6-10}$ aryl, $C_{5-10}$ heteroaryl; and $R^s$, at each occurrence, is independently selected from $C_{1-6}$ alkyl, $C_{1-6}$ haloalkyl, $C_{3-7}$ cycloalkyl, $C_{3-7}$ heterocycloalkyl, $C_{6-10}$ aryl and $C_{5-10}$ heteroaryl; and wherein the D group and a substituent located on an adjacent atom of the B ring are optionally combined to form a 5- to 6-membered heterocyclic or heteroaryl ring comprising 1 to 3 heteroatoms selected from N, O and S as ring vertices and is substituted with 0-3 $R^D$ substituents.

In a second embodiment, and for example, within certain aspects of the first embodiment, in Formula I or a subformula thereof, A is a 5- to 8-membered ring and is further substituted with from 0 to 3 $R^A$ substituents selected from the group consisting of —$C(O)R^a$, —$C(O)NR^aR^b$, —$NR^aR^b$, —$OC(O)R^c$, —$OR^a$, —$SR^a$, —$S(O)_2R^c$, —$S(O)R^c$, —$R^c$, —$(CH_2)_{1-4}$—$NR^aR^b$, —$(CH_2)_{1-4}$—$OR^a$, halogen, F, Cl, Br, I, —$NO_2$, —CN and —$N_3$, wherein $R^a$ and $R^b$ are each independently selected from hydrogen, $C_{1-4}$ alkyl, $C_{1-4}$ haloalkyl, $C_{1-4}$ heteroalkyl and $C_{3-6}$ cycloalkyl, and optionally $R^a$ and $R^b$, together with the nitrogen atom to which each is attached, are combined to form a 3- to 6-membered heterocyclic ring; $R^c$ is selected from $C_{1-4}$ alkyl, $C_{1-4}$ haloalkyl, $C_{2-6}$ alkenyl, $C_{2-6}$ alkynyl, $C_{3-6}$ cycloalkyl, phenyl and —$(CH_2)_{1-4}$(phenyl);

B is selected from the group consisting of phenylene, pyridylene, pyrimidylene, pyridazinylene and pyrazinylinle and is substituted with from 0 to 4 $R^B$ substituents selected from halogen, F, Cl, Br, I, —CN, —$N_3$, —$NO_2$, —C(O)OR″, —C(O)NR″R°, —NR″C(O)R°, —NR″C(O)NR″R°, —OR″, —NR″R° and $R^p$; wherein R″ and R° are independently selected from hydrogen and $C_{1-4}$ alkyl, $C_{1-4}$ haloalkyl, $C_{1-4}$ heteroalkyl, $C_{3-7}$ cycloalkyl and $C_{3-7}$ heterocycloalkyl, or when attached to the same nitrogen atom, R″ and R° are optionally are combined to form a 3- to 6-membered ring; $R^p$ is $C_{1-4}$ alkyl, $C_{1-4}$ haloalkyl, $C_{3-7}$ cycloalkyl and $C_{3-7}$ heterocycloalkyl;

D is a member selected from the group consisting of —$NR^3C(O)NR^4R^5$, —$NR^4R^5$, —$C(O)NR^4R^5$, —$OC(O)NR^4R^5$, —$NR^3C(=N—CN)NR^4R^5$, —$NR^3C(O)R^4$, —$NR^3C(O)OR^4$, —$NR^3S(O)_2NR^4R^5$ and —$NR^3S(O)_2R^4$, wherein $R^3$ is selected from the group consisting of hydrogen, $C_{1-6}$ alkyl, $C_{1-6}$ haloalkyl and $C_{2-6}$ alkenyl; $R^4$ and $R^5$ are each independently selected from the group consisting of hydrogen, $C_{1-6}$ alkyl, $C_{1-6}$ haloalkyl, $C_{2-6}$ alkenyl, $C_{2-6}$ alkenyl, $C_{2-6}$ alkynyl, $C_{3-7}$ cycloalkyl, $C_{3-7}$ heterocycloalkyl, $C_{6-10}$ aryl and $C_{5-10}$ heteroaryl, and $R^4$ and $R^5$, when attached to the same nitrogen atom, are optionally combined to form an optionally substituted 5- to 7-membered heterocyclic or heteroaryl ring comprising 1 to 3 heteroatoms selected from N, O and S as ring vertices; and wherein $R^3$, $R^4$ and $R^5$ are further substituted with from 0 to 3 $R^D$ substituents independently selected from the group consisting of halogen, F, Cl, Br, I, —$NO_2$, —CN, —$NR^qR^r$, —$OR^q$, —$SR^q$, —$C(O)OR^q$, —$C(O)NR^qR^r$, —$NR^qC(O)R^r$, —$NR^qC(O)OR^s$, —$(CH_2)_{1-4}$—$NR^qR^r$, —$(CH_2)_{1-4}$—$OR^q$, —$(CH_2)_{1-4}$—$SR^q$, —$(CH_2)_{1-4}$—$C(O)OR^q$, —$(CH_2)_{1-4}$—$C(O)NR^qR^r$, —$(CH_2)_{1-4}$—$NR^qC(O)R^r$, —$(CH_2)_{1-4}$—$NR^qC(O)OR^r$, —$(CH_2)_{1-4}$—CN, —$(CH_2)_{1-4}$—$NO_2$, —$S(O)R^r$, —$S(O)_2R^r$, =O, and —$R^s$; wherein $R^q$ and $R^r$ is selected from hydrogen, $C_{1-4}$ alkyl, $C_{1-4}$ haloalkyl, $C_{2-6}$ alkenyl, $C_{2-6}$ alkynyl, $C_{1-4}$ heteroalkyl, $C_{3-7}$ cycloalkyl, $C_{3-7}$ heterocycloalkyl, $C_{6-10}$ aryl, $C_{5-10}$ heteroaryl; and $R^s$, at each occurrence, is independently selected from $C_{1-4}$ alkyl, $C_{1-4}$ haloalkyl, $C_{3-7}$ cycloalkyl, $C_{3-7}$ heterocycloalkyl, $C_6$ aryl and $C_{5-6}$ heteroaryl; and wherein the D group and a substituent located on an adjacent atom of the B ring are optionally combined to form an optionally substituted 5- to 6-membered heterocyclic or heteroaryl ring comprising 1 to 3 heteroatoms selected from N, O and S as ring vertices.

In a third embodiment, and for example, within certain aspects of the first and second embodiments, in Formula I or a subformula thereof, the A ring is a ring selected from the group consisting of morpholin-4-yl, 3-methyl-morpholin-4-yl, 3-ethyl-morpholin-4-yl, 3-iso-propyl-morpholin-4-yl, 3,3-dimethyl-morpholin-4-yl, 3,4-dihydro-2H-pyran-4-yl, 3,6-dihydro-2H-pyran-4-yl, tetrahydro-2H-pyran-4-yl, 1,4-oxazepan-4-yl, piperidin-1-yl, 2-oxa-5-azabicyclo[2.2.1]heptan-5-yl, 3-oxa-8-azabicyclo[3.2.1]octan-8-yl, 3-isopropyl-morpholin-4-yl, 4-methoxy-piperidin-1-yl and is optionally substituted with from 1 to 2 $R^A$ substituents selected from the group consisting of —C(O)OR$^a$, —C(O)NR$^a$R$^b$, —NR$^a$R$^b$, —OR$^a$, —SR$^a$, —S(O)$_2$R$^c$, —S(O)R$^c$, —R$^c$, halogen, F, Cl, Br, I, —NO$_2$, —CN and —N$_3$, wherein R$^a$ and R$^b$ are each independently selected from hydrogen, C$_{1-6}$ alkyl, C$_{1-6}$ haloalkyl, C$_{1-6}$ heteroalkyl, C$_{2-6}$ alkenyl and C$_{3-6}$ cycloalkyl, wherein optionally R$^a$ and R$^b$, together with the nitrogen atom to which each is attached, are combined to form a 3- to 6-membered ring, and R$^c$ is selected from C$_{1-6}$ alkyl, C$_{1-6}$ haloalkyl, C$_{2-6}$ alkenyl, C$_{3-6}$ cycloalkyl; and B is an optionally substituted group selected from optionally substituted phenylene, pyrimidinylene and pyridylene.

In a fourth embodiment, and for example, within certain aspects of the third embodiment, in Formula I or a subformula thereof, the A ring is optionally substituted with 1 to 2 $R^A$ substituents selected from NR$^a$R$^b$, —OR$^a$ and —R$^c$.

In a fifth embodiment, and for example, within certain aspects of the first, second or third embodiment, in compounds of Formula I or a subformula thereof, the A ring is selected from the group consisting of morpholin-4-yl, 3-methyl-morpholin-4-yl, 3-ethyl-morpholin-4-yl, 3,4-dihydro-2H-pyran-4-yl, 3,6-dihydro-2H-pyran-4-yl, tetrahydro-2H-pyran-4-yl and 1,4-oxazepan-4-yl; and B is an optionally substituted group selected from the group consisting of 1,4-phenylene, 2,5-pyridylene and 2,4-pyridylene.

In a sixth embodiment and for example, within certain aspects of the second and third embodiment, in compounds of Formula I or a subformula thereof, B is an optionally substituted ring selected from the group consisting of 1,4-phenylene, 2,5-pyridylene and 2,4-pyridylene.

In a seventh embodiment, and for example, within certain aspects of the first, second or third embodiment, in Formula I or a subformula thereof, $R^1$ and $R^2$ are combined to form an optionally substituted 5-membered heterocyclic ring comprising the —N(W)— group, wherein the nitrogen atom of —N(W)— is the only heteroatom in said optionally substituted 5-membered heterocyclic ring. Within certain aspects of this seventh embodiment, $R^1$ and $R^2$ are combined to form an optionally substituted pyrrolidine or pyrrolidin-2-one, wherein the nitrogen atom of the pyrrolidine or pyrrolidin-2-one ring is substituted with a W group.

In an eighth embodiment, and for example, within certain aspects of the first, second or third embodiment, in Formula I or a subformula thereof, $R^1$ and $R^2$ are combined to form an optionally substituted 6-membered heterocyclic ring comprising the —N(W)— group, wherein the nitrogen atom of —N(W)— is the only heteroatom in said optionally substituted 6-membered heterocyclic ring. Within certain aspects of the eighth embodiment of Formula I, $R^1$ and $R^2$ are combined to form an optionally substituted piperidine or piperidin-2-one, wherein the nitrogen atom of the piperidine or piperidin-2-one ring is substituted with a W group.

In a ninth embodiment, and for example, within certain aspects of the fortieth embodiment, a compound of Formula I is of a subformula selected from the group consisting of:

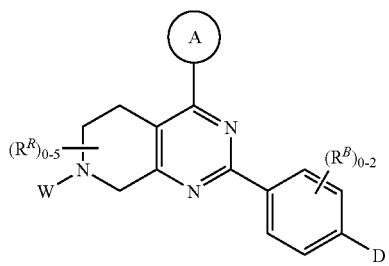

I-A

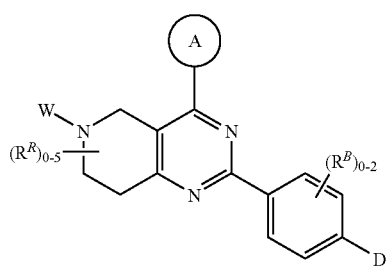

I-B

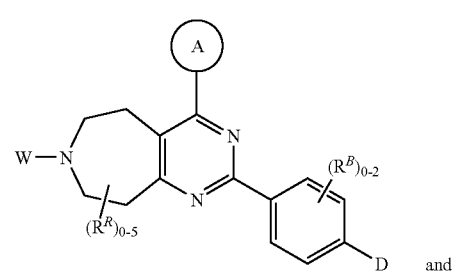

I-C and

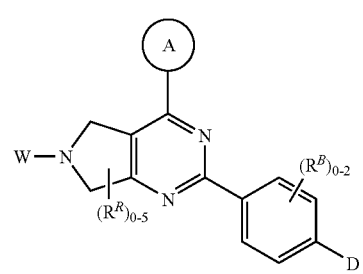

I-D wherein $R^R$ is selected from the group consisting of halogen, F, Cl, Br, I, —R$^m$, —(CH$_2$)$_{1-4}$—CN, —(CH$_2$)$_{1-4}$—CO$_2$R$^j$, —(CH$_2$)$_{1-4}$C(O)NR$^j$R$^k$, —(CH$_2$)$_{1-4}$OR$^j$, —(CH$_2$)$_{1-4}$NR$^j$R$^k$, C$_{2-4}$ alkenylene-CO$_2$R$^j$, C$_{2-4}$ alkenylene-C(O)NR$^j$R$^k$ and =O; and $R^B$ is selected from the group consisting of F, Cl, Br, I, CN, NO$_2$ and R$^p$, wherein R$^p$ is selected form C$_{1-6}$ alkyl, C$_{1-6}$ haloalkyl, C$_{2-6}$ alkenyl and C$_{2-6}$ alkynyl.

In a tenth embodiment, a compound of Formula I is of a subformula selected from the group consisting of
I-E
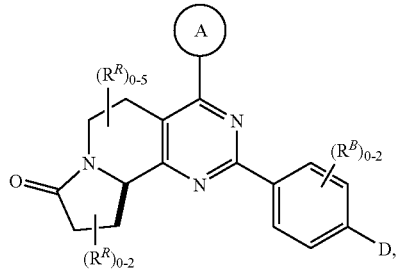
I-F
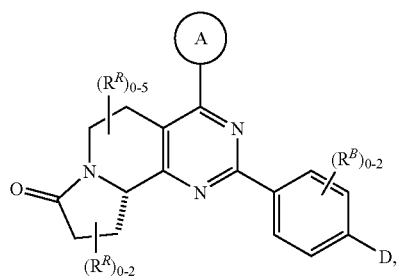
I-G
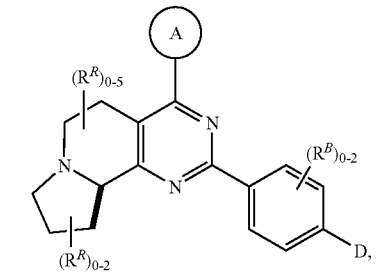
I-H
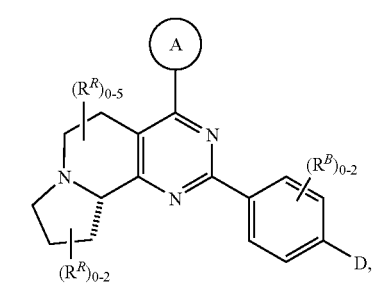
I-I
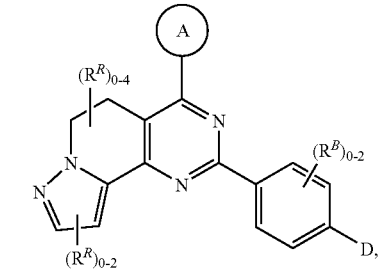
-continued
I-J
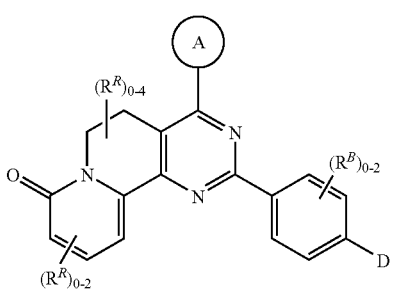
I-K
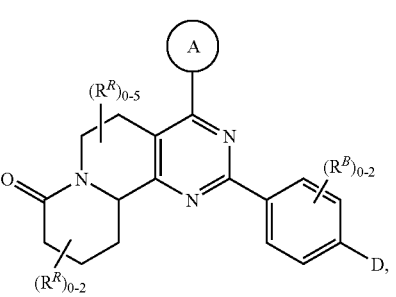
I-L
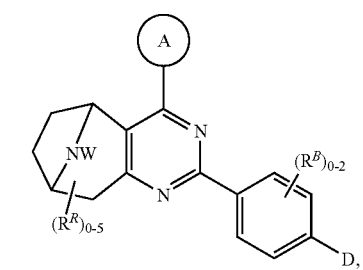
I-M
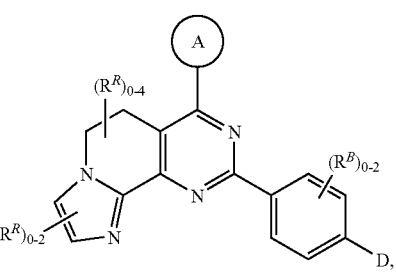
I-N
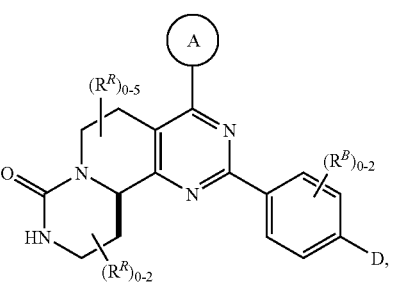

-continued

I-O
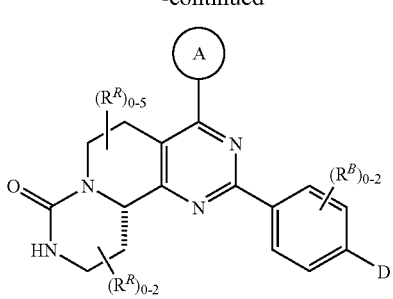

I-P
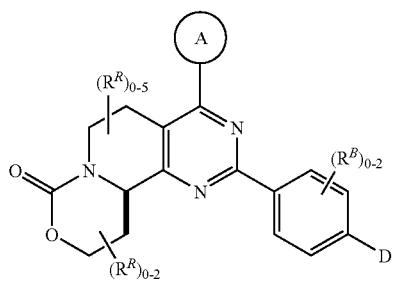

I-Q
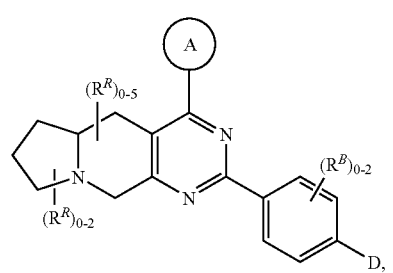

I-R
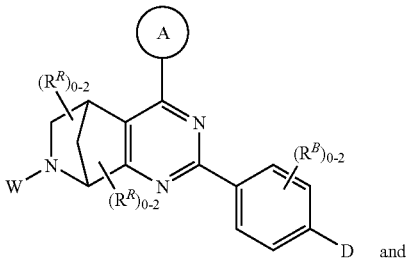

I-S
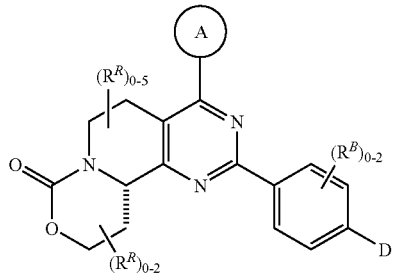

wherein $R^R$ is selected from the group consisting of halogen, F, Cl, Br, I and —$R^m$; and $R^B$ is selected from the group consisting of F, Cl, Br, I, CN, NO$_2$ and $R^p$, wherein $R^p$ is selected form C$_{1-6}$ alkyl, C$_{1-6}$ haloalkyl, C$_{2-6}$ alkenyl and C$_{2-6}$ alkynyl.

In an eleventh embodiment, and for example, within certain aspects of the second, ninth, tenth and thirty-seventh embodiment, in Formula I or a sub-formula thereof, D is selected from the group consisting of —NR$^3$C(O)NR$^4$R$^5$, —NR$^4$R$^5$, —C(O)NR$^4$R$^5$, —NR$^3$C(=N—CN)NR$^4$R$^5$, —NR$^3$C(O)R$^4$, —NR$^3$C(O)OR$^4$, and —NR$^3$S(O)R$^4$.

In a twelfth embodiment, and for example, within certain aspects of the second, ninth, tenth, thirty-seventh and fortieth embodiment, in Formula I or a subformula thereof, D is an optionally substituted group selected from —NR$^3$C(O) NR$^4$R$^5$ and —NR$^4$R$^5$—, wherein R$^3$ is hydrogen; R$^4$ and R$^5$ are each independently an optionally substituted group selected from the group consisting of hydrogen, C$_{1-6}$ alkyl, C$_{1-6}$ heteroalkyl, C$_{1-6}$ haloalkyl, C$_{3-7}$ cycloalkyl, C$_{3-7}$ heterocycloalkyl, C$_{6-10}$ aryl and C$_{5-10}$ heteroaryl, and R$^4$ and R$^5$, when attached to the same nitrogen atom, are optionally combined to form an optionally substituted 5- to 7-membered heterocyclic or heteroaryl ring.

In a thirteenth embodiment and for example, within certain aspects of the twelfth embodiment, in compounds of Formula I or a subformula thereof, D is —NR$^4$R$^5$, wherein R$^4$ is hydrogen or C$_{1-3}$ alkyl, and R$^5$ is a optionally substituted group selected from optionally substituted C$_{6-10}$ aryl, C$_{5-10}$ heteroaryl and C$_{3-7}$ heterocyclylalkyl.

In a fourteenth embodiment, and for example, within a certain aspect of the thirteenth embodiment, in Formula I or a subformula thereof, D is —NR$^4$R$^5$, wherein R$^4$ is hydrogen or C$_{1-3}$ alkyl, and R$^5$ is an optionally substituted C$_{6-10}$ aryl and C$_{5-10}$ heteroaryl.

In a fifteenth embodiment, and for example, within a certain aspect of the thirteenth embodiment, in Formula I or a subformula thereof, D is —NR$^4$R$^5$, wherein R$^4$ is hydrogen or C$_{1-3}$ alkyl and R$^5$ is an optionally substituted group selected from optionally substituted pyrimidine, benzimidazole, imidazole and pyrimidine-2,4(1H,3H)-dione.

In a sixteenth embodiment, and for example, within certain aspects for the thirteenth embodiment, in Formula I or a subformula thereof, D is —NR$^4$R$^5$, wherein R$^4$ is hydrogen or C$_{1-3}$ alkyl, and R$^5$ is an optionally substituted C$_{3-7}$ heterocyclylalkyl selected from the group consisting of:

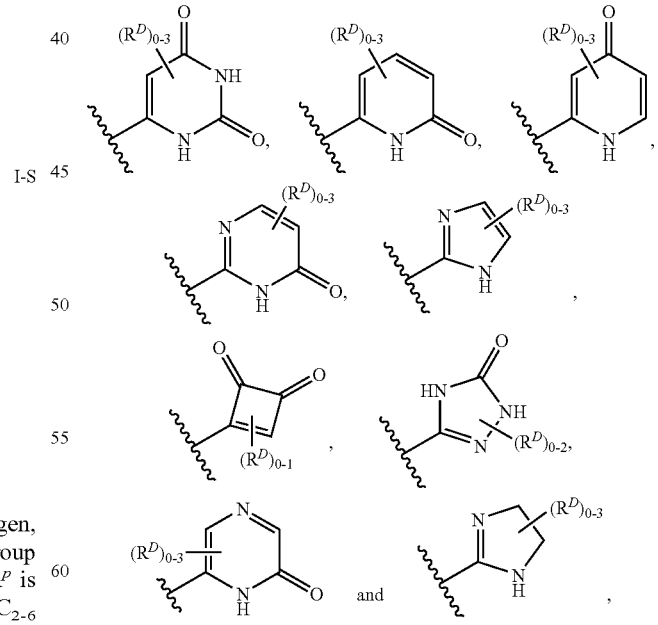

wherein the hydrogen atom attached to one or more nitrogen or carbon ring vertices in the C$_{3-7}$ heterocycloalkyl ring is optionally replace with a R$^D$ substituent selected from the group consisting of F, Cl, Br, I, —NR$^q$R$^r$, —OR$^q$, and R$^s$.

In a seventeenth embodiment, and for example, within certain aspects of the sixteenth embodiment, in compounds of Formula I or a subformula thereof, $R^5$ is selected from the group consisting of:

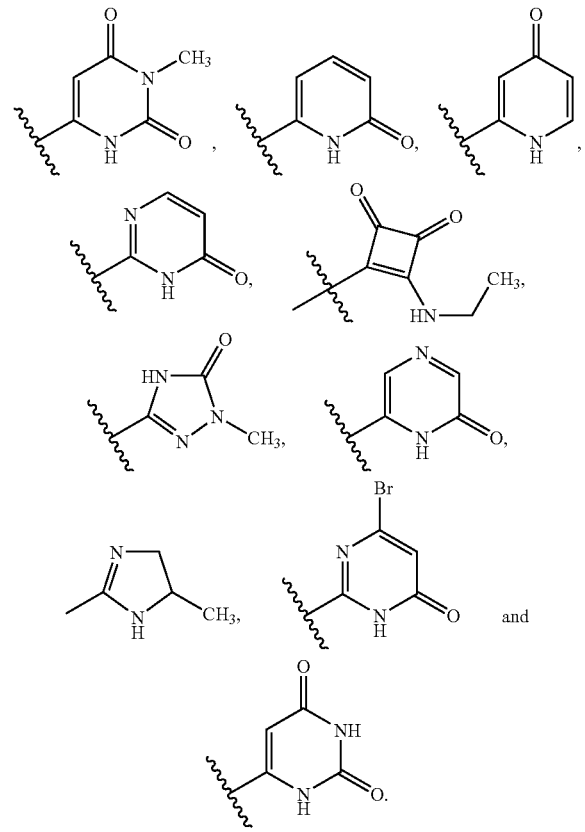

In an eighteenth embodiment, and for example, within certain aspects of the twelfth embodiment, in compounds of Formula I or a subformula thereof, D is —NR⁴R⁵, wherein R⁴ and $R^5$ are combined to form an optionally substituted 5-membered heteroaryl ring selected from the group consisting of pyrrolyl, pyrazolyl, imidazolyl and triazolyl.

In a nineteenth embodiment, and for example, within certain aspects of the twelfth embodiment, in compounds of Formula I or a subformula thereof, D is —NR³C(O)NR⁴R⁵, wherein $R^3$ is hydrogen; $R^4$ and $R^5$ are each independently an optionally substituted group selected from the group consisting of hydrogen, $C_{1-6}$ alkyl, $C_{1-6}$ haloalkyl, $C_{1-6}$ heteroalkyl, $C_{3-7}$ cycloalkyl, $C_{3-7}$ heterocycloalkyl, a 5- to 6-membered heteroaryl, an optionally substituted phenyl.

In a twentieth embodiment, and for example, within certain aspects of the twelfth embodiment, in compounds of Formula I or a subformula thereof, D is —NR³C(O)NR³R⁴, wherein $R^3$ is hydrogen; $R^4$ and $R^5$ are each independently an optionally substituted group selected from the group consisting of hydrogen, $C_{1-6}$ alkyl, $C_{1-6}$ heteroalkyl, $C_{3-7}$ cycloalkyl and $C_{3-7}$ heterocycloalkyl.

In a twenty-first embodiment, and for example, within certain aspects of the twentieth embodiment, in compounds of Formula I or a subformula thereof, one of $R^4$ and $R^5$ is hydrogen.

In a twenty-second embodiment, and for example, within certain aspects of the twentieth or twenty-first embodiment, in compounds of Formula I or a subformula thereof, wherein $R^3$ and $R^4$ are each hydrogen and $R^5$ is an optionally substituted group selected from $C_{1-6}$ alkyl and $C_{1-6}$ haloalkyl.

In a twenty-third embodiment, and for example, within certain aspects of the twenty-second embodiment, in compounds of Formula I or a subformula thereof $R^5$ is selected from the group consisting of

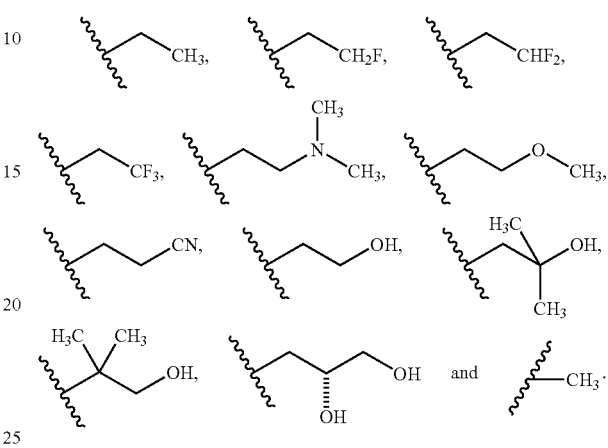

In a twenty-fourth embodiment and within certain aspects of the twenty third embodiment, in compounds of Formula I or a subformula thereof, $R^5$ is ethyl.

In a twenty-fifth embodiment, and for example, within certain aspects of the nineteenth embodiment, in compounds of Formula I or subformula thereof, $R^3$ and $R^4$ are each hydrogen or $C_{1-4}$ alkyl and $R^5$ is an optionally substituted group selected from the group consisting of optionally substituted isoxazol-3-yl, isoxazol-4-yl isoxazol-5-yl, oxazol-2-yl, oxazol-4-yl, oxazol-5-yl, pyrazol-3-yl, pyrazol-4-yl, pyrazol-5-yl, 1,2,3-oxadiazol-4-yl, 1,2,3-oxadiazol-5-yl, 1,3,4-oxadiazol-2-yl, 1,3,4-oxadiazol-5-yl, 2-pyridyl, 3-pyridyl, 4-pyridyl, 5-pyridyl, cyclobutyl, cyclopentyl, cyclohexyl, 2-oxepanyl, 3-oxepanyl, 2-tetrahydrofuranyl, 3-tetrahydrofuranyl and phenyl.

In a twenty-sixth embodiment, and for example, within certain aspects of the twenty-fifth embodiment, in compounds of Formula I or a subformula thereof, $R^5$ is independently substituted with from 0 to 3 substituents selected from F, Cl, Br, I, —CN, —NR$^q$R$^r$ and —OR$^q$.

In a twenty-seventh embodiment, and within certain aspects of the twenty-fifth embodiment, in compounds of Formula I or a subformula thereof, $R^5$ is independently substituted with from 0 to 3 substituents selected from F, Cl, Br, I, —CN, —NR$^q$R$^r$ and —OR$^q$.

In a twenty-eighth embodiment, and within certain aspects of the twenty-fifth embodiment, in compounds of Formula I or a subformula thereof, $R^5$ is selected from the group consisting of

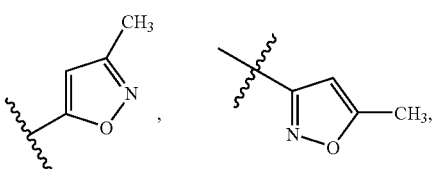

-continued

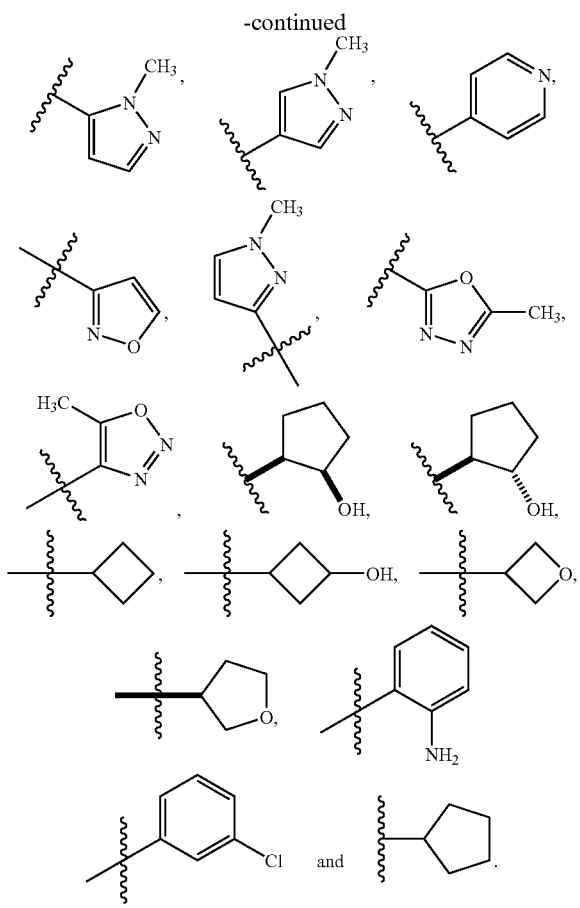

In a twenty-ninth embodiment, and for example, within certain aspects of the first, second, ninth, tenth and thirty-seventh embodiments, in compounds of Formula I or a subformula thereof, E is an optionally substituted group selected from the group consisting of $C_{6-10}$ aryl, $C_{5-10}$ heteroaryl, $C_{3-8}$ heterocycloalkyl, and $C_{3-8}$ cycloalkyl; F is an optionally substituted group selected from the group consisting of $C_{1-4}$ alkylene, $C_{2-4}$ alkenylene, $C_{1-4}$ heteroalkylene, G is selected from the group consisting of —C(O)—, —OC(O)—, —NHC(O)—, —S(O)$_2$—, —NHS(O)$_2$—; and the subscripts m and p are each independently an integer from 0 to 1. Within certain aspects of the twenty-ninth embodiment, the subscripts m and p are each 1. Within certain other aspect of the twenty-ninth embodiment, the subscript m is 0 and the subscript p is 1.

In a thirtieth embodiment, and for example, within certain aspects of the twenty-ninth embodiment, in compounds of Formula I or a subformula thereof, E is an optionally substituted group selected from the group consisting of optionally substituted pyridyl, pyrimidinyl, quinolinyl, pyrazinyl, pyridazinyl, phenyl, pyrrolyl, pyrazolyl, oxazolyl, thiazolyl, piperidinyl, pyrrolidinyl, morpholinyl, furanyl, triazinyl, thiadiazolyl, imidazolyl, cyclobutyl, cyclopropyl, cyclopentyl, cyclohexyl, pyridonyl, tetrahydrofuranyl, tetrahydropyranyl, dioxolanyl, tetrahydropyrimidinyl and tetrahydropyranyl; F is an optionally substituted group selected from the group consisting of $C_{1-4}$ alkylene, $C_{2-4}$ alkenylene, $C_{1-4}$ heteroalkylene, G is selected from the group consisting of —C(O)—, —OC(O)—, —NHC(O)—, —S(O)$_2$—, —NHS(O)$_2$—; and the subscripts m and p are each independently an integer from 0 to 1.

In a thirty-first embodiment, and for example, within certain aspects of the thirtieth embodiment, in compounds of Formula I or a subformula thereof, E is selected from the group consisting of pyridyl, pyrimidinyl, quinolinyl, pyrazinyl, pyridazinyl, phenyl, pyrrolyl, pyrazolyl, oxazolyl, thiazolyl, piperidinyl and pyrrolidinyl and is substituted with from 0 to 3 substitutents selected from —NR$^d$R$^e$, —C(O)R$^d$, —OR$^d$, halogen, —R$^f$ and —CN; F is selected from the group consisting of $C_{1-4}$ alkylene, $C_{2-4}$ alkenylene, $C_{1-4}$ heteroalkylene, and is optionally substituted with —OR$^g$, —NR$^g$R$^h$ and =O; G is selected from the group consisting of —C(O)—, —OC(O)—, —NHC(O)—, —S(O)$_2$—, —NHS(O)$_2$—; and the subscripts m and p are each independently an integer from 0 to 1.

In a thirty-second embodiment, and for example, within certain aspects of the twenty-ninth embodiment, in compounds of Formula I or a subformula thereof, E is an $C_{6-10}$ aryl, $C_{5-10}$ heteroaryl, $C_{3-8}$ heterocycloalkyl, and $C_{3-8}$ cycloalkyl selected from the group consisting of

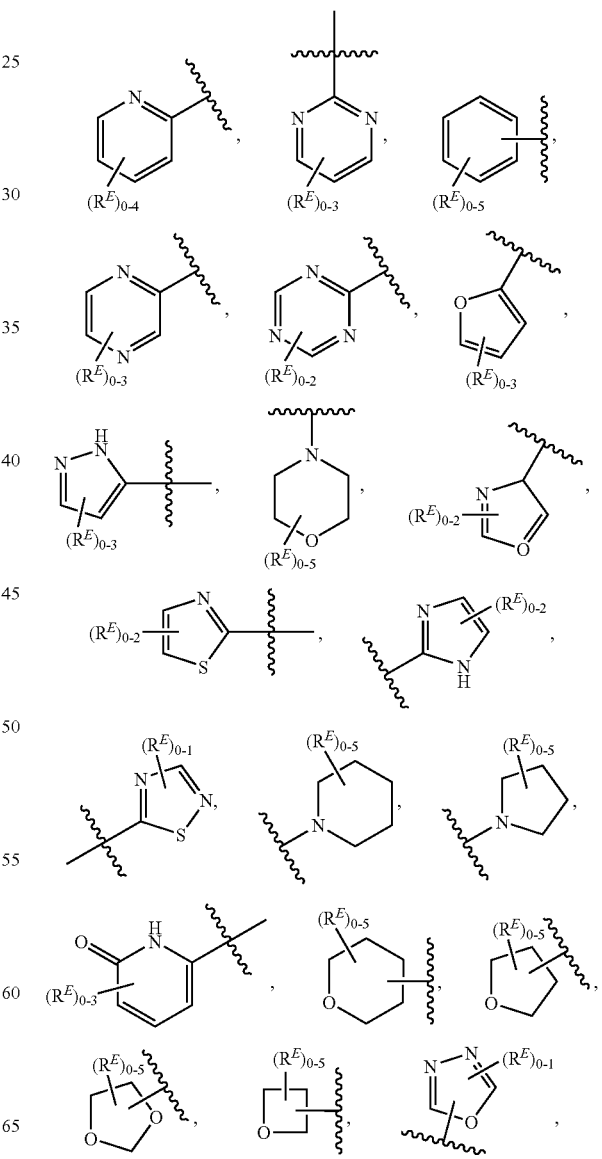

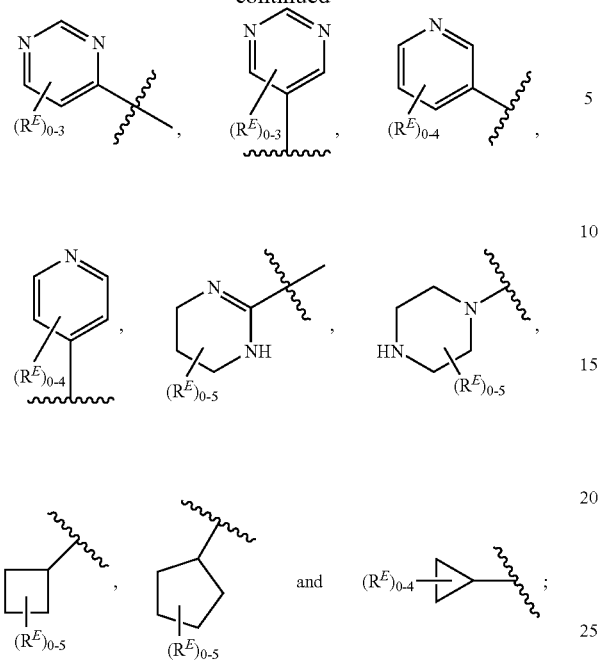

wherein the hydrogen atom attached to one or more nitrogen or carbon ring vertices in the $C_{6-10}$ aryl, $C_{5-10}$ heteroaryl, $C_{3-8}$ heterocycloalkyl, and $C_{3-8}$ cycloalkyl ring is optionally replaced with a $R^E$ substituent.

In a thirty-third embodiment, and for example, within certain aspects of the thirty-second embodiment, in compounds of Formula I or a subformula thereof, E is independently substituted with 0 to 5 with from 0 to 5 substituents selected from the group consisting of —$NR^dR^e$, —$S(O)_2R^d$, —$R^f$, F, Cl, Br, —$C(O)R^d$, —$C(O)OR^d$—$NO_2$, —$OR^d$, and —CN; and F is independently substituted with 0 to 3 substituents selected from =O, —$OR^d$, —$NR^dR^e$ and $R^i$.

In a thirty-fourth embodiment, and for example, within certain aspects of the first, second, ninth and tenth embodiments, in compounds of Formula I or a subformula thereof, E is an optionally substituted group selected from optionally substituted $C_{1-6}$ alkyl and $C_{1-6}$ heteroalkyl; G is —C(O)—, —OC(O)—, —NHC(O)—, —$S(O)_2$— or —$NHS(O)_2$—; and the subscript m is 0 and the subscript p is 1. Within one aspect of the thirty-fourth embodiment, E is optionally substituted group selected from optionally substituted methyl, ethyl, n-propyl, iso-propyl and tert-butyl and G is —C(O)—, —OC(O)—, —NHC(O)—, —$S(O)_2$— or —$NHS(O)_2$—.

In a thirty-fifth embodiment, and for example, within certain aspects of the first, second, ninth, tenth and thirty-seventh embodiments, in compounds of Formula I, W is selected from the group set forth in FIG. 1A, FIG. 1B, FIG. 1C, FIG. 1D, FIG. 1E and FIG. 1F.

In a thirty-sixth embodiment, and for example, within certain aspects of the first, second, ninth, tenth and thirty-seventh embodiments, in compounds of Formula I, D is selected from the group set forth in FIG. 2A and FIG. 2B.

In a thirty-seventh embodiment, and for example, within certain aspects of the first, second and third embodiments of Formula I, compounds of the invention are described by a subformulae selected from the group consisting of:

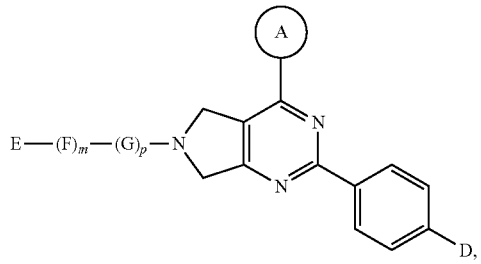

I-a

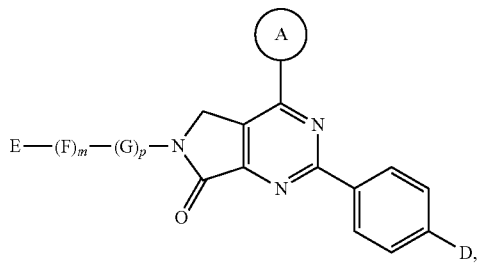

I-b

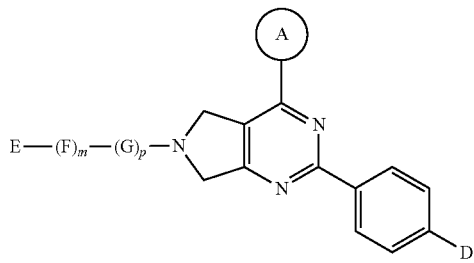

I-c

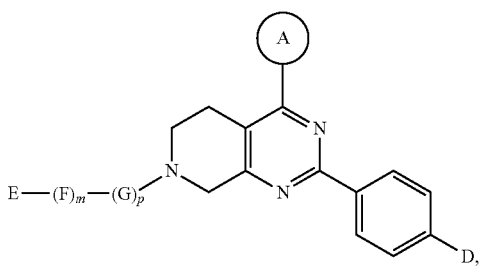

I-d

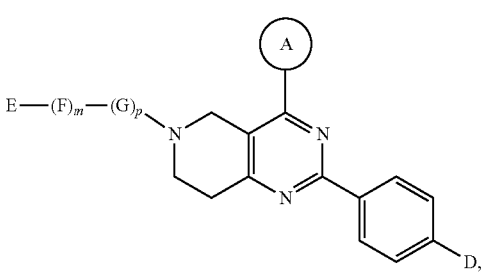

I-e

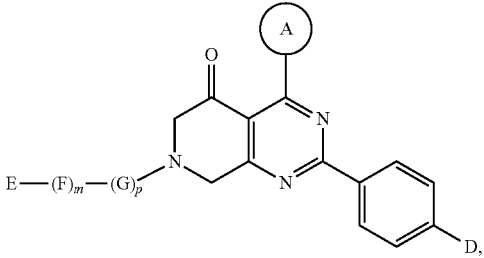

I-f

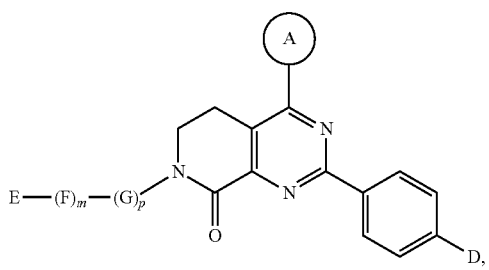

I-g

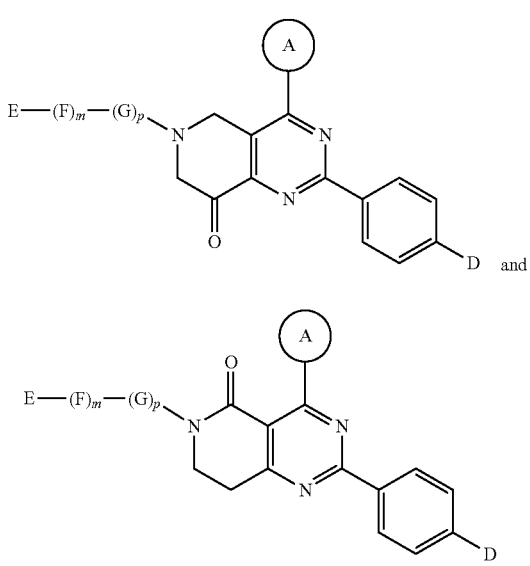

I-h

I-i

In a thirty-eighth embodiment, in compounds of Formula I or a subformula thereof, two substituents located on adjacent atoms of B are combined to form an optionally substituted 5- to 6-membered carbocyclic, heterocyclic, aryl or heteroaryl ring.

In a thirty-ninth embodiment, in compounds of Formula I or a subformula thereof, the D group and a substituent located on an adjacent atom of B are combined to form a 5- to 6-membered heterocyclic or heteroaryl ring. Within certain aspects of the thirty-ninth embodiment, the 5- to 6-membered heterocyclic or heteroaryl ring formed is selected from the group consisting of imidazolidinone, pyrazole, imidazole, pyrrolidinone and pyrimidine. Within another aspect of the thirty-ninth embodiment, the —B-D group in Formula I has the structure selected from the group consisting of:

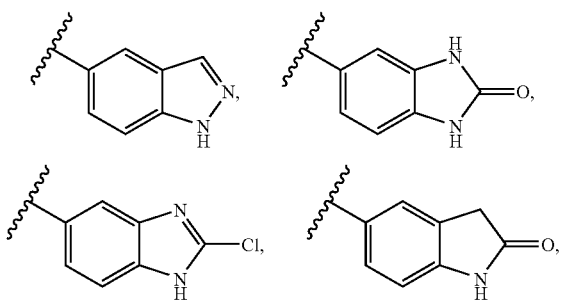

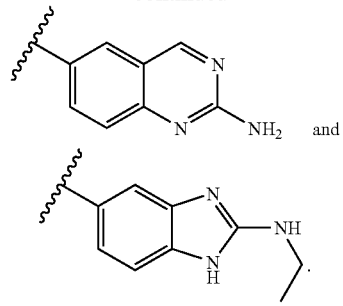

In a fortieth embodiment, of compounds of Formula I,

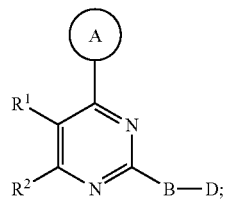

(I)

wherein A is a ring selected from the group consisting of morpholin-4-yl, 3-methyl-morpholin-4-yl, 3-ethyl-morpholin-yl, 3,4-dihydro-2H-pyran-4-yl, 3,6-dihydro-2H-pyran-4-yl, tetrahydro-2H-pyran-4-yl, 1,4-oxazepan-4-yl, piperidin-1-yl, and is optionally substituted with from 1 to 2 $R^A$ substituents selected from the group consisting of —C(O)OR$^a$, —C(O)NR$^a$R$^b$, —NR$^a$R$^b$, —OR$^a$, —SR$^a$, —S(O)$_2$R$^c$, —S(O)R$^c$, —R$^c$, halogen, —NO$_2$, —CN and —N$_3$, wherein R$^a$ and R$^b$ are each independently selected from hydrogen, C$_{1-6}$ alkyl, C$_{1-6}$ haloalkyl, C$_{1-6}$ heteroalkyl, C$_{2-6}$ alkenyl and C$_{3-6}$ cycloalkyl, wherein optionally R$^a$ and R$^b$, together with the nitrogen atom to which each is attached, are combined to form a 3- to 6-membered ring, and R$^c$ is selected from C$_{1-6}$ alkyl, C$_{1-6}$ haloalkyl, C$_{2-6}$ alkenyl, C$_{3-6}$ cycloalkyl. R$^1$ and R$^2$ are combined with the atoms to which they are attached to form an optionally substituted pyrrolidine, piperidine or homopiperidine ring, wherein the nitrogen atom of said pyrrolidine, piperidine or homopiperidine ring is substituted with a W group, wherein W is represented by Formula i

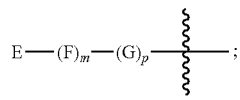

i wherein E is a member selected from consisting of hydrogen, C$_{6-10}$ aryl, C$_{5-10}$ heteroaryl, C$_{3-10}$ cycloalkyl, C$_{3-10}$ heterocycloalkyl, C$_{1-6}$ alkyl and C$_{1-6}$ heteroalkyl; and wherein E is independently substituted with from 0 to 5 R$^E$ substituents selected from the group consisting of halogen, —NR$^d$R$^e$, —SR$^d$, —OR$^d$, —C(O)OR$^d$, —C(O)NR$^d$R$^e$, —C(O)R$^d$, —NR$^d$C(O)R$^e$, —OC(O)R$^f$, —NR$^d$C(O)NR$^d$R$^e$, —OC(O)NR$^d$R$^e$, —C(=NOR$^d$)NR$^d$R$^e$, —NR$^d$C(=N—CN)NR$^d$R$^e$, —NR$^d$S(O)$_2$NR$^d$R$^e$, —S(O)$_2$R$^d$, —S(O)$_2$NR$^d$R$^e$, —R$^f$, —NO$_2$, —N$_3$, =O, —CN, —(CH$_2$)$_{1-4}$—NR$^d$R$^e$, —(CH$_2$)$_{1-4}$—SR$^d$, —(CH$_2$)$_{1-4}$—OR$^d$, —(CH$_2$)$_{1-4}$—C(O)OR$^d$, —(CH$_2$)$_{1-4}$—C(O)NR$^d$R$^e$, —(CH$_2$)$_{1-4}$—C(O)R$^d$, —(CH$_2$)$_{1-4}$—NR$^d$C(O)R$^e$, —(CH$_2$)$_{1-4}$—OC(O)R$^f$, —(CH$_2$)$_{1-4}$—

$NR^dC(O)NR^dR^e$, —$(CH_2)_{1-4}$—$OC(O)NR^dR^e$, —$(CH_2)_{1-4}$—$C(=NOR^d)NR^dR^e$, —$(CH_2)_{1-4}$—$NR^dC(=N-CN)NR^dR^e$, —$(CH_2)_{1-4}$—$NR^dS(O)_2NR^dR^e$, —$(CH_2)_{1-4}$—$S(O)_2R^d$, —$(CH_2)_{1-4}$—$S(O)_2NR^dR^e$, —$(CH_2)_{1-4}$—$NO_2$, —$(CH_2)_{1-4}$—$N_3$ and —$(CH_2)_{1-4}$—CN; wherein $R^d$ and $R^e$ are each independently selected from hydrogen, $C_{1-6}$ alkyl, $C_{1-6}$ haloalkyl, $C_{1-6}$ heteroalkyl, $C_{2-6}$ alkenyl, $C_{2-6}$ alkynyl, $C_{3-7}$ cycloalkyl, $C_{3-7}$ heterocycloalkyl, phenyl and —$(CH_2)_{1-4}$-phenyl, and optionally $R^d$ and $R^e$, when attached to the same nitrogen atom are combined to form a 3- to 6-membered ring; $R^f$ is selected from $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ heterocycloalkyl, phenyl and —$(CH_2)_{1-4}$-phenyl; and wherein any two substituents located on adjacent atoms, or located on the same atom of E are optionally combined to form a 5- to 6-membered carbocyclic or heterocyclic ring. F is a member selected from the group consisting of $C_{1-6}$ alkylene, $C_{2-6}$ alkenylene, $C_{2-6}$ alkynylene and $C_{1-6}$ heteroalkylene; wherein F is independently substituted with from 0 to 3 $R^F$ substituents selected from the group consisting of halogen, —$NR^gR^h$, —$SR^g$, —$OR^g$, —C(O)$OR^g$, —C(O)$NR^gR^h$, —$NR^gC(O)R^i$, —OC(O)$R^i$, —$NR^gC(O)NR^gR^h$, —OC(O)$NR^gR^h$, $NR^gS(O)_2NR^gR^h$, —$S(O)_2R^g$, —$S(O)_2NR^gR^h$, —$R^i$, —$NO_2$, $N_3$, =O, —CN, —$(CH_2)_{1-4}$—$NR^gR^h$, —$(CH_2)_{1-4}$—$SR^g$, —$(CH_2)_{1-4}$—$OR^g$, —$(CH_2)_{1-4}$—C(O)$OR^g$, —$(CH_2)_{1-4}$—C(O)$NR^gR^h$, —$(CH_2)_{1-4}$—C(O)$R^g$, —$(CH_2)_{1-4}$—$NR^gC(O)R^h$, —$(CH_2)_{1-4}$—C(O)$R^i$, —$(CH_2)_{1-4}$—$NR^gC(O)NR^gR^h$, —$(CH_2)_{1-4}$—OC(O)$NR^gR^h$, —$(CH_2)_{1-4}$—$NR^gS(O)_2NR^gR^h$, —$(CH_2)_{1-4}$—$S(O)_2R^g$, —$(CH_2)_{1-4}$—$S(O)_2NR^gR^h$, —$(CH_2)_{1-4}$—$NO_2$, —$(CH_2)_{1-4}$—$N_3$ and —$(CH_2)_{1-4}$—CN; wherein $R^g$ and $R^h$ are each independently selected from hydrogen, $C_{1-6}$ alkyl, $C_{1-6}$ haloalkyl, $C_{1-6}$ heteroalkyl, $C_{3-7}$ cycloalkyl, $C_{3-7}$ heterocycloalkyl, phenyl and —$(CH_2)_{1-4}$-phenyl, and optionally $R^g$ and $R^h$, when attached to the same nitrogen atom are combined to form a 3- to 6-membered ring; $R^i$ is selected from $C_{1-6}$ alkyl, $C_{1-6}$ haloalkyl, $C_{3-7}$ cycloalkyl, $C_{3-7}$ heterocycloalkyl, phenyl and —$(CH_2)_{1-4}$-phenyl. G is a member selected from the group consisting of —C(O)—, —OC(O)—, —NHC(O)—, —NHC(=NOH)—, —$S(O)_2$— and —$NHS(O)_2$—. The subscripts m and p are each independently an integer from 0 to 1. The pyrrolidine, piperidine or homopiperidine ring formed by combining $R^1$ and $R^2$ is further substituted with from 0 to 5 $R^R$ substituents selected from the group consisting of halogen, —$NR^jR^k$, —$SR^j$, —$OR^j$, —C(O)$OR^j$, —C(O)$NR^jR^k$, —$NHC(O)R^j$, —OC(O)$R^j$, —$R^m$, —CN and =O, wherein $R^j$ and $R^k$ are each independently selected from hydrogen, $C_{1-6}$ alkyl, $C_{1-6}$ haloalkyl, $C_{2-6}$ alkenyl, $C_{2-6}$ alkynyl, $C_{3-5}$ cycloalkyl and $C_{3-5}$ heterocycloalkyl, and $R^j$ and $R^k$, when attached to the same nitrogen atom, are optionally combined to form a 3- to 6-membered ring; and $R^m$ is selected from $C_{1-6}$ alkyl, $C_{1-6}$ haloalkyl, $C_{2-6}$ alkenyl, $C_{2-6}$ alkynyl, $C_{3-5}$ cycloalkyl and $C_{3-5}$ heterocycloalkyl. B is selected from the group consisting of phenylene, pyridylene, pyrimidylene, pyridazinylene and pyrazinyline and is substituted with from 0 to 4 $R^B$ substituents selected from halogen, —CN, —$N_3$, —$NO_2$, —C(O)$OR''$, —C(O)$NR''R^o$, —$NR''C(O)R^o$, —$NR''C(O)NR''R^o$, —$OR''$, —$NR''R^o$ and $R^p$; wherein $R''$ and $R^o$ are independently selected from hydrogen and $C_{1-4}$ alkyl, $C_{1-4}$ haloalkyl, $C_{1-4}$ heteroalkyl, $C_{3-7}$ cycloalkyl and $C_{3-7}$ heterocycloalkyl, or when attached to the same nitrogen atom, $R''$ and $R^o$ are optionally are combined to form a 3- to 6-membered ring; $R^p$ is $C_{1-4}$ alkyl, $C_{1-4}$ haloalkyl, $C_{3-7}$ cycloalkyl and $C_{3-7}$ heterocycloalkyl, wherein any two substituents, not including the D group, located on adjacent atoms of B are optionally combined to form a 5- to 6-membered carbocyclic, heterocyclic, aryl or heteroaryl ring. D is a member selected from the group consisting of —$NR^3C(O)NR^4R^5$, —$NR^4R^5$, —C(O)$NR^4R^5$, —OC(O)$OR^4$, —OC(O)$NR^4R^5$, —$NR^3C(=N-CN)NR^4R^5$, —$NR^3C(=N-OR^4)NR^4R^5$, —$NR^3C(=N-NR^4)NR^4R^5$, —$NR^3C(O)R^4$, —$NR^3C(O)OR^4$, —$NR^3S(O)_2 NR^4R^5$ and —$NR^3S(O)_2R^4$, wherein $R^3$ is selected from the group consisting of hydrogen, $C_{1-6}$ alkyl, $C_{1-6}$ haloalkyl and $C_{2-6}$ alkenyl; $R^4$ and $R^5$ are each independently selected from the group consisting of hydrogen, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ heterocycloalkyl, $C_{6-10}$ aryl and $C_{5-10}$ heteroaryl, and $R^4$ and $R^5$, when attached to the same nitrogen atom, are optionally combined to form a 5- to 7-membered heterocyclic or heteroaryl ring; and wherein $R^3$, $R^4$ and $R^5$ are further substituted with from 0 to 3 $R^D$ substituents independently selected from the group consisting of halogen, —$NO_2$, —CN, —$NR^qR^r$, —$OR^q$, —$SR^q$, —C(O)$OR^q$, —C(O)$NR^qR^r$, —$NR^qC(O)R^r$, —$NR^qC(O)OR^s$, —$(CH_2)_{1-4}$—$NR^qR^r$, —$(CH_2)_{1-4}$—$OR^q$, —$(CH_2)_{1-4}$—$SR^q$, —$(CH_2)_{1-4}$—C(O)$OR^q$, —$(CH_2)_{1-4}$—C(O)$NR^qR^r$, —$(CH_2)_{1-4}$—$NR^qC(O)R^r$, —$(CH_2)_{1-4}$—$NR^qC(O)OR^r$, —$(CH_2)_{1-4}$—CN, —$(CH_2)_{1-4}$—$NO_2$, —$S(O)R^r$, —$S(O)_2R^r$, =O, and —$R^s$; wherein $R^q$ and $R^r$ is selected from hydrogen, $C_{1-6}$ alkyl, $C_{1-6}$ haloalkyl, $C_{2-6}$ alkenyl, $C_{2-6}$ alkynyl, $C_{1-6}$ heteroalkyl, $C_{3-7}$ cycloalkyl, $C_{3-7}$ heterocycloalkyl, $C_{6-10}$ aryl, $C_{5-10}$ heteroaryl; and $R^s$, at each occurrence, is independently selected from $C_{1-6}$ alkyl. $C_{1-6}$ haloalkyl, $C_{1-6}$ heteroalkyl, $C_{3-7}$ cycloalkyl, $C_{3-7}$ heterocycloalkyl, $C_{6-10}$ aryl and $C_{5-10}$ heteroaryl; and wherein the D group and a substituent located on an adjacent atom of the B ring are optionally combined to form a 5- to 6-membered heterocyclic or heteroaryl ring. Within certain aspects of this embodiment, if the subscripts m and p are both the integer 0, then E is not $C_{1-6}$ alkyl or $C_{1-6}$ heteroalkyl. Within other aspect of this embodiment, W is selected from the group set forth in FIG. 1A, FIG. 1B, FIG. 1C, FIG. 1D, FIG. 1E and FIG. 1F. Within certain aspects of this embodiment, D is selected from the group consisting of the group set forth in FIG. 2A and FIG. 2B.

In a forty-first embodiment, compounds of Formula I are selected from the group compounds set forth in Table 1 below.

TABLE 1

4-(2-(4-(methylsulfonyl)phenyl)-6,7-dihydro-5H-pyrrolo[3,4-d]pyrimidin-4-yl)morpholine
1-ethyl-3-(4-(4-morpholino-6,7-dihydro-5H-pyrrolo[3,4-d]pyrimidin-2-yl)phenyl)urea
tert-butyl 4-(3,4-dihydro-2H-pyran-4-yl)-2-(pyrimidin-5-yl)-5H-pyrrolo[3,4-d]pyrimidine-6(7H)-carboxylate
1-ethyl-3-(4-(4-morpholino-5,6,7,8-tetrahydropyrido[3,4-d]pyrimidin-2-yl)phenyl)urea
1-ethyl-3-(4-(4-morpholino-5,6,7,8-tetrahydropyrido[4,3-d]pyrimidin-2-yl)phenyl)urea
tert-butyl 2-(pyrimidin-5-yl)-4-(tetrahydro-2H-pyran-4-yl)-5H-pyrrolo[3,4-d]pyrimidine-6(7H)-carboxylate
4-(4-morpholino-7-(pyrimidin-2-yl)-5,6,7,8-tetrahydropyrido[3,4-d]pyrimidin-2-yl)aniline
tert-butyl 2-(2-aminopyrimidin-5-yl)-4-(3,4-dihydro-2H-pyran-4-yl)-5H-pyrrolo[3,4-d]pyrimidine-6(7H)-carboxylate
(S)-1-ethyl-3-(4-(4-(3-methylmorpholino)-5,6,7,8-tetrahydropyrido[4,3-d]pyrimidin-2-yl)phenyl)urea TABLE 1-continued tert-butyl 2-(2-aminopyrimidin-5-yl)-4-(tetrahydro-2H-pyran-4-yl)-5H-pyrrolo[3,4-d]pyrimidine-6(7H)-carboxylate
4-(7-benzyl-4-morpholino-5,6,7,8-tetrahydropyrido[3,4-d]pyrimidin-2-yl)aniline
4-(4-morpholino-6-(pyrimidin-2-yl)-6,7-dihydro-5H-pyrrolo[3,4-d]pyrimidin-2-yl)benzamide
tert-butyl 2-(4-aminophenyl)-4-morpholino-5,6-dihydropyrido[3,4-d]pyrimidine-7(8H)-carboxylate
4-(2-(1H-indazol-5-yl)-7-(pyrimidin-2-yl)-5,6,7,8-tetrahydropyrido[3,4-d]pyrimidin-4-yl)morpholine
N-(3-(4-morpholino-6-(pyrimidin-2-yl)-6,7-dihydro-5H-pyrrolo[3,4-d]pyrimidin-2-yl)phenyl)acetamide
N-(4-(4-morpholino-6-(pyrimidin-2-yl)-6,7-dihydro-5H-pyrrolo[3,4-d]pyrimidin-2-yl)phenyl)acetamide
tert-butyl 2-(4-(methylamino)phenyl)-4-morpholino-5,6-dihydropyrido[3,4-d]pyrimidine-7(8H)-carboxylate
methyl 2-(4-(3-ethylureido)phenyl)-4-morpholino-5H-pyrrolo[3,4-d]pyrimidine-6(7H)-carboxylate
2-(2-aminopyrimidin-5-yl)-6-(4-methoxybenzyl)-4-morpholino-5H-pyrrolo[3,4-d]pyrimidin-7(6H)-one
1-(4-(7-acetyl-4-(1,4-oxazepan-4-yl)-5,6,7,8-tetrahydropyrido[3,4-d]pyrimidin-2-yl)phenyl)-3-ethylurea
N-ethyl-2-(4-(3-ethylureido)phenyl)-4-morpholino-5H-pyrrolo[3,4-d]pyrimidine-6(7H)-carboxamide
ethyl 2-(4-(3-ethylureido)phenyl)-4-morpholino-5H-pyrrolo[3,4-d]pyrimidine-6(7H)-carboxylate
4-(2-(4-(1H-pyrazol-1-yl)phenyl)-7-(pyrimidin-2-yl)-5,6,7,8-tetrahydropyrido[3,4-d]pyrimidin-4-yl)morpholine
N-(4-(6-benzyl-4-morpholino-7-oxo-6,7-dihydro-5H-pyrrolo[3,4-d]pyrimidin-2-yl)phenyl)acetamide
1-ethyl-3-(4-(4-morpholino-6-(pyrimidin-2-yl)-6,7-dihydro-5H-pyrrolo[3,4-d]pyrimidin-2-yl)phenyl)urea
1,1-dimethyl-3-(4-(4-morpholino-6-(pyrimidin-2-yl)-6,7-dihydro-5H-pyrrolo[3,4-d]pyrimidin-2-yl)phenyl)urea
1-ethyl-3-(4-(6-(methylsulfonyl)-4-morpholino-6,7-dihydro-5H-pyrrolo[3,4-d]pyrimidin-2-yl)phenyl)urea
N-(4-(4-morpholino-6-(pyrimidin-2-yl)-6,7-dihydro-5H-pyrrolo[3,4-d]pyrimidin-2-yl)phenyl)methanesulfonamide
(S)-1-ethyl-3-(4-(7-(2-hydroxypropanoyl)-4-morpholino-5,6,7,8-tetrahydropyrido[3,4-d]pyrimidin-2-yl)phenyl)urea
4-(2-(4-(5-methyl-1,3,4-oxadiazol-2-yl)phenyl)-7-(pyrimidin-2-yl)-5,6,7,8-tetrahydropyrido[3,4-d]pyrimidin-4-yl)morpholine
1-(4-(4-(3,6-dihydro-2H-pyran-4-yl)-7-(pyrimidin-2-yl)-5,6,7,8-tetrahydropyrido[3,4-d]pyrimidin-2-yl)phenyl)-3-ethylurea
1-(4-(6-benzyl-4-morpholino-6,7-dihydro-5H-pyrrolo[3,4-d]pyrimidin-2-yl)phenyl)-3-ethylurea
1-ethyl-3-(4-(7-(pyrimidin-2-yl)-4-(tetrahydro-2H-pyran-4-yl)-5,6,7,8-tetrahydropyrido[3,4-d]pyrimidin-2-yl)phenyl)urea
1-ethyl-3-(4-(4-morpholino-6-(pyrazin-2-yl)-5,6,7,8-tetrahydropyrido[4,3-d]pyrimidin-2-yl)phenyl)urea
1-ethyl-3-(4-(4-morpholino-7-(pyrimidin-2-yl)-5,6,7,8-tetrahydropyrido[3,4-d]pyrimidin-2-yl)phenyl)urea
1-(4-(4-(1,4-oxazepan-4-yl)-6-(pyrimidin-2-yl)-6,7-dihydro-5H-pyrrolo[3,4-d]pyrimidin-2-yl)phenyl)-3-ethylurea
1,1-dimethyl-3-(4-(4-morpholino-7-(pyrimidin-2-yl)-5,6,7,8-tetrahydropyrido[3,4-d]pyrimidin-2-yl)phenyl)urea
1-ethyl-3-(4-(4-morpholino-6-(pyrimidin-2-yl)-5,6,7,8-tetrahydropyrido[4,3-d]pyrimidin-2-yl)phenyl)urea
1-ethyl-3-(4-(6-(methylsulfonyl)-4-(1,4-oxazepan-4-yl)-6,7-dihydro-5H-pyrrolo[3,4-d]pyrimidin-2-yl)phenyl)urea
1-(4-(6-(2-aminopyrimidin-4-yl)-4-morpholino-6,7-dihydro-5H-pyrrolo[3,4-d]pyrimidin-2-yl)phenyl)-3-ethylurea
N-(4-(4-morpholino-7-(pyrimidin-2-yl)-5,6,7,8-tetrahydropyrido[3,4-d]pyrimidin-2-yl)phenyl)pyrimidin-2-amine
tert-butyl 2-(4-(3-ethylureido)phenyl)-4-(tetrahydro-2H-pyran-4-yl)-5H-pyrrolo[3,4-d]pyrimidine-6(7H)-carboxylate
tert-butyl 2-(4-(3-ethylureido)phenyl)-4-morpholino-5H-pyrrolo[3,4-d]pyrimidine-6(7H)-carboxylate
1-ethyl-3-(4-(7-(2-hydroxy-2-methylpropanoyl)-4-morpholino-5,6,7,8-tetrahydropyrido[3,4-d]pyrimidin-2-yl)phenyl)urea
(Z)-2-cyano-1-methyl-3-(4-(4-morpholino-7-(pyrimidin-2-yl)-5,6,7,8-tetrahydropyrido[3,4-d]pyrimidin-2-yl)phenyl)guanidine
2-(4-aminophenyl)-6-benzyl-4-morpholino-5H-pyrrolo[3,4-d]pyrimidin-7(6H)-one
1-(4-(6-benzoyl-4-morpholino-6,7-dihydro-5H-pyrrolo[3,4-d]pyrimidin-2-yl)phenyl)-3-ethylurea
1-(4-(7-benzyl-4-morpholino-5,6,7,8-tetrahydropyrido[3,4-d]pyrimidin-2-yl)phenyl)-3-ethylurea
1-(4-(7-benzyl-4-morpholino-5,6,7,8-tetrahydropyrido[3,4-d]pyrimidin-2-yl)phenyl)-3-ethylurea
1-ethyl-3-(4-(6-(3-hydroxybenzyl)-4-morpholino-6,7-dihydro-5H-pyrrolo[3,4-d]pyrimidin-2-yl)phenyl)urea TABLE 1-continued 1-isopropyl-3-(4-(4-morpholino-7-(pyrimidin-2-yl)-5,6,7,8-tetrahydropyrido[3,4-d]pyrimidin-2-yl)phenyl)urea
1-ethyl-3-(4-(6-(3-hydroxybenzyl)-4-morpholino-6,7-dihydro-5H-pyrrolo[3,4-d]pyrimidin-2-yl)phenyl)urea
(S)-1-ethyl-3-(4-(4-(3-methylmorpholino)-6-(pyrazin-2-yl)-5,6,7,8-tetrahydropyrido[4,3-d]pyrimidin-2-yl)phenyl)urea
(S)-1-ethyl-3-(4-(4-(3-methylmorpholino)-6-(pyrimidin-2-yl)-5,6,7,8-tetrahydropyrido[4,3-d]pyrimidin-2-yl)phenyl)urea
1-(4-(4-(1,4-oxazepan-4-yl)-7-(pyrimidin-2-yl)-5,6,7,8-tetrahydropyrido[3,4-d]pyrimidin-2-yl)phenyl)-3-ethylurea
1-(4-(6-(2-aminopyrimidin-4-yl)-4-morpholino-5,6,7,8-tetrahydropyrido[4,3-d]pyrimidin-2-yl)phenyl)-3-ethylurea
1-(4-(7-(2-aminopyrimidin-4-yl)-4-morpholino-5,6,7,8-tetrahydropyrido[3,4-d]pyrimidin-2-yl)phenyl)-3-ethylurea
1-ethyl-3-(4-(4-morpholino-7-(oxazole-4-carbonyl)-5,6,7,8-tetrahydropyrido[3,4-d]pyrimidin-2-yl)phenyl)urea
1-ethyl-3-(4-(4-morpholino-7-(oxazole-5-carbonyl)-5,6,7,8-tetrahydropyrido[3,4-d]pyrimidin-2-yl)phenyl)urea
N-(4-(6-benzyl-4-morpholino-7-oxo-6,7-dihydro-5H-pyrrolo[3,4-d]pyrimidin-2-yl)phenyl)methanesulfonamide
1-ethyl-3-(4-(7-(1-methylpiperidin-4-yl)-4-morpholino-5,6,7,8-tetrahydropyrido[3,4-d]pyrimidin-2-yl)phenyl)urea
tert-butyl 2-(4-(3-ethylureido)phenyl)-4-morpholino-7,8-dihydropyrido[4,3-d]pyrimidine-6(5H)-carboxylate
tert-butyl 2-(4-(3-ethylureido)phenyl)-4-(1,4-oxazepan-4-yl)-5H-pyrrolo[3,4-d]pyrimidine-6(7H)-carboxylate
tert-butyl 2-(4-(3-ethylureido)phenyl)-4-morpholino-5,6-dihydropyrido[3,4-d]pyrimidine-7(8H)-carboxylate
(E)-2-cyano-1-ethyl-3-(4-(4-morpholino-7-(pyrimidin-2-yl)-5,6,7,8-tetrahydropyrido[3,4-d]pyrimidin-2-yl)phenyl)guanidine
1-(4-(7-benzoyl-4-morpholino-5,6,7,8-tetrahydropyrido[3,4-d]pyrimidin-2-yl)phenyl)-3-ethylurea
1-cyclopentyl-3-(4-(4-morpholino-6-(pyrimidin-2-yl)-6,7-dihydro-5H-pyrrolo[3,4-d]pyrimidin-2-yl)phenyl)urea
4-(7-benzoyl-4-morpholino-5,6,7,8-tetrahydropyrido[3,4-d]pyrimidin-2-yl)phenyl ethylcarbamate
ethyl 4-(7-benzoyl-4-morpholino-5,6,7,8-tetrahydropyrido[3,4-d]pyrimidin-2-yl)phenylcarbamate
1-ethyl-3-(4-(4-morpholino-6-picolinoyl-5,6,7,8-tetrahydropyrido[4,3-d]pyrimidin-2-yl)phenyl)urea
1-ethyl-3-(4-(6-isonicotinoyl-4-morpholino-5,6,7,8-tetrahydropyrido[4,3-d]pyrimidin-2-yl)phenyl)urea
1-ethyl-3-(4-(7-isonicotinoyl-4-morpholino-5,6,7,8-tetrahydropyrido[3,4-d]pyrimidin-2-yl)phenyl)urea
1-ethyl-3-(4-(4-morpholino-7-nicotinoyl-5,6,7,8-tetrahydropyrido[3,4-d]pyrimidin-2-yl)phenyl)urea
1-ethyl-3-(4-(4-morpholino-7-picolinoyl-5,6,7,8-tetrahydropyrido[3,4-d]pyrimidin-2-yl)phenyl)urea
1-ethyl-3-(4-(4-morpholino-7-picolinoyl-5,6,7,8-tetrahydropyrido[3,4-d]pyrimidin-2-yl)phenyl)urea
1-ethyl-3-(4-(4-morpholino-6-nicotinoyl-5,6,7,8-tetrahydropyrido[4,3-d]pyrimidin-2-yl)phenyl)urea
1-ethyl-3-(4-(7-(5-ethylpyrimidin-2-yl)-4-morpholino-5,6,7,8-tetrahydropyrido[3,4-d]pyrimidin-2-yl)phenyl)urea
(S)-1-(4-(6-(2-aminopyrimidin-4-yl)-4-(3-methylmorpholino)-5,6,7,8-tetrahydropyrido[4,3-d]pyrimidin-2-yl)phenyl)-3-ethylurea
1-ethyl-3-(4-(7-(1-methyl-1H-pyrazole-5-carbonyl)-4-morpholino-5,6,7,8-tetrahydropyrido[3,4-d]pyrimidin-2-yl)phenyl)urea
1-ethyl-3-(4-(7-(4-methoxypyrimidin-2-yl)-4-morpholino-5,6,7,8-tetrahydropyrido[3,4-d]pyrimidin-2-yl)phenyl)urea
1-ethyl-3-(4-(4-morpholino-7-(thiazole-2-carbonyl)-5,6,7,8-tetrahydropyrido[3,4-d]pyrimidin-2-yl)phenyl)urea
1-(4-(6-(1-acetylpiperidin-4-yl)-4-morpholino-6,7-dihydro-5H-pyrrolo[3,4-d]pyrimidin-2-yl)phenyl)-3-ethylurea
tert-butyl 2-(4-(3-ethylureido)phenyl)-4-(3-oxopiperazin-1-yl)-5,6-dihydropyrido[3,4-d]pyrimidine-7(8H)-carboxylate
1-ethyl-3-(4-(7-(morpholine-4-carbonyl)-4-morpholino-5,6,7,8-tetrahydropyrido[3,4-d]pyrimidin-2-yl)phenyl)urea
tert-butyl 2-(4-(3-ethyl-1-methylureido)phenyl)-4-morpholino-5,6-dihydropyrido[3,4-d]pyrimidine-7(8H)-carboxylate
(S)-tert-butyl 2-(4-(3-ethylureido)phenyl)-4-(3-methylmorpholino)-7,8-dihydropyrido[4,3-d]pyrimidine-6(5H)-carboxylate
1-ethyl-3-(4-(4-morpholino-6-(2-phenylacetyl)-5,6,7,8-tetrahydropyrido[4,3-d]pyrimidin-2-yl)phenyl)urea
1-cyclopentyl-3-(4-(4-morpholino-7-(pyrimidin-2-yl)-5,6,7,8-tetrahydropyrido[3,4-d]pyrimidin-2-yl)phenyl)urea
benzyl 2-(4-(3-ethylureido)phenyl)-4-morpholino-5H-pyrrolo[3,4-d]pyrimidine-6(7H)-carboxylate
1-ethyl-3-(4-(6-(4-methoxybenzyl)-4-morpholino-7-oxo-6,7-dihydro-5H-pyrrolo[3,4-d]pyrimidin-2-yl)phenyl)urea TABLE 1-continued 1-(4-(6-(1-acetylpiperidin-4-yl)-4-(1,4-oxazepan-4-yl)-6,7-dihydro-5H-pyrrolo[3,4-d]pyrimidin-2-yl)phenyl)-3-ethylurea
(E)-1-(4-(6-cinnamoyl-4-morpholino-5,6,7,8-tetrahydropyrido[4,3-d]pyrimidin-2-yl)phenyl)-3-ethylurea
benzyl 2-(4-(3-ethylureido)phenyl)-4-morpholino-5,6-dihydropyrido[3,4-d]pyrimidine-7(8H)-carboxylate
benzyl 2-(4-(3-ethylureido)phenyl)-4-morpholino-5,6-dihydropyrido[3,4-d]pyrimidine-7(8H)-carboxylate
(S)-1-ethyl-3-(4-(7-(2-hydroxy-2-phenylacetyl)-4-morpholino-5,6,7,8-tetrahydropyrido[3,4-d]pyrimidin-2-yl)phenyl)urea
(R)-1-ethyl-3-(4-(7-(2-hydroxy-2-phenylacetyl)-4-morpholino-5,6,7,8-tetrahydropyrido[3,4-d]pyrimidin-2-yl)phenyl)urea
1-methyl-N-(4-(4-morpholino-7-(pyrimidin-2-yl)-5,6,7,8-tetrahydropyrido[3,4-d]pyrimidin-2-yl)phenyl)-1H-benzo[d]imidazol-2-amine
1-(4-(6-(2-chlorobenzoyl)-4-morpholino-5,6,7,8-tetrahydropyrido[4,3-d]pyrimidin-2-yl)phenyl)-3-ethylurea
1-(4-(6-(4-chlorobenzoyl)-4-morpholino-5,6,7,8-tetrahydropyrido[4,3-d]pyrimidin-2-yl)phenyl)-3-ethylurea
1-(4-(4-(1,4-oxazepan-4-yl)-6-(phenylsulfonyl)-6,7-dihydro-5H-pyrrolo[3,4-d]pyrimidin-2-yl)phenyl)-3-ethylurea
1-ethyl-3-(4-(4-morpholino-7-(4-(trifluoromethyl)pyrimidin-2-yl)-5,6,7,8-tetrahydropyrido[3,4-d]pyrimidin-2-yl)phenyl)urea
benzyl 2-(4-(3-ethylureido)phenyl)-4-(1,4-oxazepan-4-yl)-5,6-dihydropyrido[3,4-d]pyrimidine-7(8H)-carboxylate
1-ethyl-3-(4-(4-morpholino-7-(4-phenylpyrimidin-2-yl)-5,6,7,8-tetrahydropyrido[3,4-d]pyrimidin-2-yl)phenyl)urea
1-ethyl-3-(4-(4-morpholino-7-(4-phenylpyrimidin-2-yl)-5,6,7,8-tetrahydropyrido[3,4-d]pyrimidin-2-yl)phenyl)urea
butyl 4-(4-morpholino-7-(4-phenylpyrimidin-2-yl)-5,6,7,8-tetrahydropyrido[3,4-d]pyrimidin-2-yl)phenylcarbamate
butyl 4-(4-morpholino-7-(4-phenylpyrimidin-2-yl)-5,6,7,8-tetrahydropyrido[3,4-d]pyrimidin-2-yl)phenylcarbamate
tert-butyl 4-morpholino-2-(4-(3-(3-(trifluoromethyl)phenyl)ureido)phenyl)-5,6-dihydropyrido[3,4-d]pyrimidine-7(8H)-carboxylate
4-(2-(1H-indazol-5-yl)-7-(pyrimidin-2-yl)-5,6,7,8-tetrahydropyrido[3,4-d]pyrimidin-4-yl)morpholine
tert-butyl 4-morpholino-2-(4-(3-(3-(trifluoromethyl)phenyl)ureido)phenyl)-5,6-dihydropyrido[3,4-d]pyrimidine-7(8H)-carboxylate
tert-butyl 2-(4-(3-ethylureido)phenyl)-4-(2-oxomorpholino)-5,6-dihydropyrido[3,4-d]pyrimidine-7(8H)-carboxylate
1-ethyl-3-(4-(4-(2-methylmorpholino)-7-(thiazole-5-carbonyl)-5,6,7,8-tetrahydropyrido[3,4-d]pyrimidin-2-yl)phenyl)urea
1-(4-(7-(4-cyanopyridin-2-yl)-4-morpholino-5,6,7,8-tetrahydropyrido[3,4-d]pyrimidin-2-yl)phenyl)-3-ethylurea
1-(4-(7-(4,6-dimethylpyrimidin-2-yl)-4-morpholino-5,6,7,8-tetrahydropyrido[3,4-d]pyrimidin-2-yl)phenyl)-3-ethylurea
1-ethyl-3-(4-(7-(5-fluoropyrimidin-2-yl)-4-morpholino-5,6,7,8-tetrahydropyrido[3,4-d]pyrimidin-2-yl)phenyl)urea
1-(4-(7-(4,6-dimethylpyrimidin-2-yl)-4-(1,4-oxazepan-4-yl)-5,6,7,8-tetrahydropyrido[3,4-d]pyrimidin-2-yl)phenyl)-3-ethylurea
1-ethyl-3-(4-(7-(4-methoxypyrimidin-2-yl)-4-(1,4-oxazepan-4-yl)-5,6,7,8-tetrahydropyrido[3,4-d]pyrimidin-2-yl)phenyl)urea
1-(4-(4-(1,4-oxazepan-4-yl)-7-(4-(trifluoromethyl)pyrimidin-2-yl)-5,6,7,8-tetrahydropyrido[3,4-d]pyrimidin-2-yl)phenyl)-3-ethylurea
1-ethyl-3-(4-(7-(5-ethylpyrimidin-2-yl)-4-(1,4-oxazepan-4-yl)-5,6,7,8-tetrahydropyrido[3,4-d]pyrimidin-2-yl)phenyl)urea
1-ethyl-3-(4-(7-(5-fluoropyrimidin-2-yl)-4-(1,4-oxazepan-4-yl)-5,6,7,8-tetrahydropyrido[3,4-d]pyrimidin-2-yl)phenyl)urea
5-(4-morpholino-7-(pyrimidin-2-yl)-5,6,7,8-tetrahydropyrido[3,4-d]pyrimidin-2-yl)-1H-benzo[d]imidazol-2(3H)-one
1-(2-aminophenyl)-3-(4-(4-morpholino-7-(pyrimidin-2-yl)-5,6,7,8-tetrahydropyrido[3,4-d]pyrimidin-2-yl)phenyl)urea
N-(4-(4-morpholino-7-(pyrimidin-2-yl)-5,6,7,8-tetrahydropyrido[3,4-d]pyrimidin-2-yl)phenyl)-1H-benzo[d]imidazol-2-amine
1-(2-hydroxyethyl)-3-(4-(4-morpholino-7-(pyrimidin-2-yl)-5,6,7,8-tetrahydropyrido[3,4-d]pyrimidin-2-yl)phenyl)urea
1-(cyclopropylmethyl)-3-(4-(4-morpholino-7-(pyrimidin-2-yl)-5,6,7,8-tetrahydropyrido[3,4-d]pyrimidin-2-yl)phenyl)urea
1-(2-cyanoethyl)-3-(4-(4-morpholino-7-(pyrimidin-2-yl)-5,6,7,8-tetrahydropyrido[3,4-d]pyrimidin-2-yl)phenyl)urea
1-(4-(4-morpholino-7-(pyrimidin-2-yl)-5,6,7,8-tetrahydropyrido[3,4-d]pyrimidin-2-yl)phenyl)-3-(2,2,2-trifluoroethyl)urea
N-(4-(4-morpholino-7-(pyrimidin-2-yl)-5,6,7,8-tetrahydropyrido[3,4-d]pyrimidin-2-yl)phenyl)-1H-imidazol-2-amine
1-(4-(4-morpholino-7-(pyrimidin-2-yl)-5,6,7,8-tetrahydropyrido[3,4-d]pyrimidin-2-yl)phenyl)-1H-imidazol-2-amine
3-methyl-6-(4-(4-morpholino-7-(pyrimidin-2-yl)-5,6,7,8-tetrahydropyrido[3,4-d]pyrimidin-2-yl)phenylamino)pyrimidine-2,4(1H,3H)-dione
1,3-dimethyl-6-(4-(4-morpholino-7-(pyrimidin-2-yl)-5,6,7,8-tetrahydropyrido[3,4-d]pyrimidin-2-yl)phenylamino)pyrimidine-2,4(1H,3H)-dione TABLE 1-continued 1-cyclobutyl-3-(4-(4-morpholino-7-(pyrimidin-2-yl)-5,6,7,8-tetrahydropyrido[3,4-d]pyrimidin-2-yl)phenyl)urea
1-(4-(7-(3-cyanopyridin-2-yl)-4-morpholino-5,6,7,8-tetrahydropyrido[3,4-d]pyrimidin-2-yl)phenyl)-3-ethylurea
1-(4-(7-(5-cyanopyridin-2-yl)-4-morpholino-5,6,7,8-tetrahydropyrido[3,4-d]pyrimidin-2-yl)phenyl)-3-ethylurea
1-ethyl-3-(4-(4-morpholino-7-(quinolin-2-yl)-5,6,7,8-tetrahydropyrido[3,4-d]pyrimidin-2-yl)phenyl)urea
1-ethyl-3-(4-(7-formyl-4-morpholino-5,6,7,8-tetrahydropyrido[3,4-d]pyrimidin-2-yl)phenyl)urea
1-(4-(7-acetyl-4-morpholino-5,6,7,8-tetrahydropyrido[3,4-d]pyrimidin-2-yl)phenyl)-3-ethylurea
1-ethyl-3-(4-(4-morpholino-7-propionyl-5,6,7,8-tetrahydropyrido[3,4-d]pyrimidin-2-yl)phenyl)urea
1-ethyl-3-(4-(7-isobutyryl-4-morpholino-5,6,7,8-tetrahydropyrido[3,4-d]pyrimidin-2-yl)phenyl)urea
1-ethyl-3-(4-(7-(methylsulfonyl)-4-morpholino-5,6,7,8-tetrahydropyrido[3,4-d]pyrimidin-2-yl)phenyl)urea
1-ethyl-3-(4-(7-(ethylsulfonyl)-4-morpholino-5,6,7,8-tetrahydropyrido[3,4-d]pyrimidin-2-yl)phenyl)urea
1-ethyl-3-(4-(4-morpholino-7-(phenylsulfonyl)-5,6,7,8-tetrahydropyrido[3,4-d]pyrimidin-2-yl)phenyl)urea
methyl 2-(4-(3-ethylureido)phenyl)-4-morpholino-5,6-dihydropyrido[3,4-d]pyrimidine-7(8H)-carboxylate
tert-butyl 2-(4-(3-ethylureido)phenyl)-4-morpholino-5,6-dihydropyrido[3,4-d]pyrimidine-7(8H)-carboxylate
(S)-tert-butyl 2-(4-(3-ethylureido)phenyl)-4-(3-methylmorpholino)-5,6-dihydropyrido[3,4-d]pyrimidine-7(8H)-carboxylate
(S)-1-ethyl-3-(4-(4-(3-methylmorpholino)-5,6,7,8-tetrahydropyrido[3,4-d]pyrimidin-2-yl)phenyl)urea
(S)-1-ethyl-3-(4-(4-(3-methylmorpholino)-7-(pyrimidin-2-yl)-5,6,7,8-tetrahydropyrido[3,4-d]pyrimidin-2-yl)phenyl)urea
1-cyclopropyl-3-(4-(4-morpholino-7-(pyrimidin-2-yl)-5,6,7,8-tetrahydropyrido[3,4-d]pyrimidin-2-yl)phenyl)urea
6-(4-(4-morpholino-7-(pyrimidin-2-yl)-5,6,7,8-tetrahydropyrido[3,4-d]pyrimidin-2-yl)phenylamino)pyrimidine-2,4(1H,3H)-dione
1-ethyl-3-(4-(4-morpholino-7-(pyridin-2-yl)-5,6,7,8-tetrahydropyrido[3,4-d]pyrimidin-2-yl)phenyl)urea
1-(5-methylisoxazol-3-yl)-3-(4-(4-morpholino-7-(pyrimidin-2-yl)-5,6,7,8-tetrahydropyrido[3,4-d]pyrimidin-2-yl)phenyl)urea
(S)-1-(4-(7-(2-aminopyrimidin-4-yl)-4-(3-methylmorpholino)-5,6,7,8-tetrahydropyrido[3,4-d]pyrimidin-2-yl)phenyl)-3-ethylurea
4-(2-(2-chloro-1H-benzo[d]imidazol-5-yl)-7-(pyrimidin-2-yl)-5,6,7,8-tetrahydropyrido[3,4-d]pyrimidin-4-yl)morpholine
5-(4-morpholino-7-(pyrimidin-2-yl)-5,6,7,8-tetrahydropyrido[3,4-d]pyrimidin-2-yl)indolin-2-one
1-(2-(dimethylamino)ethyl)-3-(4-(4-morpholino-7-(pyrimidin-2-yl)-5,6,7,8-tetrahydropyrido[3,4-d]pyrimidin-2-yl)phenyl)urea
1-(2-methoxyethyl)-3-(4-(4-morpholino-7-(pyrimidin-2-yl)-5,6,7,8-tetrahydropyrido[3,4-d]pyrimidin-2-yl)phenyl)urea
1-(4-(4-morpholino-7-(pyrimidin-2-yl)-5,6,7,8-tetrahydropyrido[3,4-d]pyrimidin-2-yl)phenyl)-3-neopentylurea
1-(2,2-difluoroethyl)-3-(4-(4-morpholino-7-(pyrimidin-2-yl)-5,6,7,8-tetrahydropyrido[3,4-d]pyrimidin-2-yl)phenyl)urea
1-(2-fluoroethyl)-3-(4-(4-morpholino-7-(pyrimidin-2-yl)-5,6,7,8-tetrahydropyrido[3,4-d]pyrimidin-2-yl)phenyl)urea
methyl 2-(2-(4-(3-ethylureido)phenyl)-4-morpholino-5,6-dihydropyrido[3,4-d]pyrimidin-7(8H)-yl)-4-(trifluoromethyl)pyrimidine-5-carboxylate
1-ethyl-3-(4-(4-morpholino-8-oxo-5,6,7,8-tetrahydropyrido[3,4-d]pyrimidin-2-yl)phenyl)urea
6-(7-benzyl-4-morpholino-5,6,7,8-tetrahydropyrido[3,4-d]pyrimidin-2-yl)quinazolin-2-amine
1-ethyl-3-(2-fluoro-4-(4-morpholino-7-(pyrimidin-2-yl)-5,6,7,8-tetrahydropyrido[3,4-d]pyrimidin-2-yl)phenyl)urea
(S)-1-ethyl-3-(4-(7-(2-hydroxy-2-methylpropanoyl)-4-(3-methylmorpholino)-5,6,7,8-tetrahydropyrido[3,4-d]pyrimidin-2-yl)phenyl)urea
(S)-1-ethyl-3-(4-(7-(1-methyl-1H-pyrazole-5-carbonyl)-4-(3-methylmorpholino)-5,6,7,8-tetrahydropyrido[3,4-d]pyrimidin-2-yl)phenyl)urea
(S)-1-ethyl-3-(4-(4-(3-methylmorpholino)-7-nicotinoyl-5,6,7,8-tetrahydropyrido[3,4-d]pyrimidin-2-yl)phenyl)urea
(S)-1-ethyl-3-(4-(4-(3-methylmorpholino)-7-(thiazole-2-carbonyl)-5,6,7,8-tetrahydropyrido[3,4-d]pyrimidin-2-yl)phenyl)urea
1-(1-hydroxy-2-methylpropan-2-yl)-3-(4-(4-morpholino-7-(pyrimidin-2-yl)-5,6,7,8-tetrahydropyrido[3,4-d]pyrimidin-2-yl)phenyl)urea
1-((1S,2S)-2-hydroxycyclopentyl)-3-(4-(4-morpholino-7-(pyrimidin-2-yl)-5,6,7,8-tetrahydropyrido[3,4-d]pyrimidin-2-yl)phenyl)urea
1-(4-(6-benzyl-4-morpholino-5,6,7,8-tetrahydropyrido[4,3-d]pyrimidin-2-yl)phenyl)-3-(1-methyl-2,6-dioxo-1,2,3,6-tetrahydropyrimidin-4-yl)urea
1-(3-methylisoxazol-5-yl)-3-(4-(4-morpholino-7-(pyrimidin-2-yl)-5,6,7,8-tetrahydropyrido[3,4-d]pyrimidin-2-yl)phenyl)urea TABLE 1-continued 1-(isoxazol-3-yl)-3-(4-(4-morpholino-7-(pyrimidin-2-yl)-5,6,7,8-tetrahydropyrido[3,4-d]pyrimidin-2-yl)phenyl)urea
N-ethyl-5-(4-morpholino-7-(pyrimidin-2-yl)-5,6,7,8-tetrahydropyrido[3,4-d]pyrimidin-2-yl)-1H-benzo[d]imidazol-2-amine
(S)-1-(4-(7-(1-acetylpiperidin-4-yl)-4-(3-methylmorpholino)-5,6,7,8-tetrahydropyrido[3,4-d]pyrimidin-2-yl)phenyl)-3-ethylurea
(S)-1-ethyl-3-(4-(4-(3-methylmorpholino)-7-(1-methylpiperidin-4-yl)-5,6,7,8-tetrahydropyrido[3,4-d]pyrimidin-2-yl)phenyl)urea
(S)-6-(4-(7-benzyl-4-(3-methylmorpholino)-5,6,7,8-tetrahydropyrido[3,4-d]pyrimidin-2-yl)phenylamino)-3-methylpyrimidine-2,4(1H,3H)-dione
(R)-tert-butyl 2-(4-(3-ethylureido)phenyl)-4-(3-methylmorpholino)-5,6-dihydropyrido[3,4-d]pyrimidine-7(8H)-carboxylate
(R)-1-ethyl-3-(4-(4-(3-methylmorpholino)-5,6,7,8-tetrahydropyrido[3,4-d]pyrimidin-2-yl)phenyl)urea
(R)-1-ethyl-3-(4-(7-(2-hydroxy-2-methylpropanoyl)-4-(3-methylmorpholino)-5,6,7,8-tetrahydropyrido[3,4-d]pyrimidin-2-yl)phenyl)urea
(R)-1-ethyl-3-(4-(4-(3-methylmorpholino)-7-nicotinoyl-5,6,7,8-tetrahydropyrido[3,4-d]pyrimidin-2-yl)phenyl)urea
(R)-1-ethyl-3-(4-(4-(3-methylmorpholino)-7-(thiazole-2-carbonyl)-5,6,7,8-tetrahydropyrido[3,4-d]pyrimidin-2-yl)phenyl)urea
(R)-1-ethyl-3-(4-(4-(3-methylmorpholino)-7-(pyrimidin-2-yl)-5,6,7,8-tetrahydropyrido[3,4-d]pyrimidin-2-yl)phenyl)urea
(S)-tert-butyl 4-(3-ethylmorpholino)-2-(4-(3-ethylureido)phenyl)-5,6-dihydropyrido[3,4-d]pyrimidine-7(8H)-carboxylate
(R)-1-ethyl-3-(4-(4-(3-methylmorpholino)-7-(pyrimidin-4-yl)-5,6,7,8-tetrahydropyrido[3,4-d]pyrimidin-2-yl)phenyl)urea
(S)-tert-butyl 2-(4-(1-methyl-2,6-dioxo-1,2,3,6-tetrahydropyrimidin-4-ylamino)phenyl)-4-(3-methylmorpholino)-5,6-dihydropyrido[3,4-d]pyrimidine-7(8H)-carboxylate
(S)-1-(4-(7-(3-cyanopyridin-2-yl)-4-(3-methylmorpholino)-5,6,7,8-tetrahydropyrido[3,4-d]pyrimidin-2-yl)phenyl)-3-ethylurea
(S)-1-(4-(7-acetyl-4-(3-methylmorpholino)-5,6,7,8-tetrahydropyrido[3,4-d]pyrimidin-2-yl)phenyl)-3-ethylurea
(S)-1-ethyl-3-(4-(4-(3-methylmorpholino)-7-propionyl-5,6,7,8-tetrahydropyrido[3,4-d]pyrimidin-2-yl)phenyl)urea
(S)-1-ethyl-3-(4-(7-formyl-4-(3-methylmorpholino)-5,6,7,8-tetrahydropyrido[3,4-d]pyrimidin-2-yl)phenyl)urea
(R)-1-ethyl-3-(4-(6-(2-hydroxy-2-methylpropanoyl)-4-(3-methylmorpholino)-5,6,7,8-tetrahydropyrido[4,3-d]pyrimidin-2-yl)phenyl)urea
(R)-1-ethyl-3-(4-(4-(3-methylmorpholino)-6-nicotinoyl-5,6,7,8-tetrahydropyrido[4,3-d]pyrimidin-2-yl)phenyl)urea
(R)-tert-butyl 2-(4-(3-ethylureido)phenyl)-4-(3-methylmorpholino)-7,8-dihydropyrido[4,3-d]pyrimidine-6(5H)-carboxylate
(R)-1-ethyl-3-(4-(4-(3-methylmorpholino)-5,6,7,8-tetrahydropyrido[4,3-d]pyrimidin-2-yl)phenyl)urea
1-(4-(4-morpholino-7-(pyrimidin-2-yl)-5,6,7,8-tetrahydropyrido[3,4-d]pyrimidin-2-yl)phenyl)-3-(pyridin-4-yl)urea
(R)-1-ethyl-3-(5-(4-(3-methylmorpholino)-7-(pyrimidin-2-yl)-5,6,7,8-tetrahydropyrido[3,4-d]pyrimidin-2-yl)pyridin-2-yl)urea
tert-butyl 2-(2-aminopyrimidin-5-yl)-4-morpholino-5,6-dihydropyrido[3,4-d]pyrimidine-7(8H)-carboxylate
(S)-tert-butyl 2-(4-(3-(2,2-difluoroethyl)ureido)phenyl)-4-(3-methylmorpholino)-7,8-dihydropyrido[4,3-d]pyrimidine-6(5H)-carboxylate
(S)-tert-butyl 2-(4-(3-(2-hydroxyethyl)ureido)phenyl)-4-(3-methylmorpholino)-7,8-dihydropyrido[4,3-d]pyrimidine-6(5H)-carboxylate
1-(4-(7-benzyl-4-morpholino-6,7,8,9-tetrahydro-5H-pyrimido[5,4-d]azepin-2-yl)phenyl)-3-ethylurea
(S)-1-ethyl-3-(4-(7-(1-methyl-1H-pyrazole-5-carbonyl)-4-(3-methylmorpholino)-5,6,7,8-tetrahydropyrido[3,4-d]pyrimidin-2-yl)phenyl)urea
methyl 2-(2-(4-(3-ethylureido)phenyl)-4-morpholino-5,6-dihydropyrido[3,4-d]pyrimidin-7(8H)-yl)-6-methylpyrimidine-4-carboxylate
2-(2-(4-(3-ethylureido)phenyl)-4-morpholino-5,6-dihydropyrido[3,4-d]pyrimidin-7(8H)-yl)-6-methylpyrimidine-4-carboxylic acid
1-ethyl-3-(4-(4-morpholino-7-(4-morpholinopyrimidin-2-yl)-5,6,7,8-tetrahydropyrido[3,4-d]pyrimidin-2-yl)phenyl)urea
1-(4-(7-(4,6-dimethoxypyrimidin-2-yl)-4-morpholino-5,6,7,8-tetrahydropyrido[3,4-d]pyrimidin-2-yl)phenyl)-3-ethylurea
2-(2-(4-(3-ethylureido)phenyl)-4-morpholino-5,6-dihydropyrido[3,4-d]pyrimidin-7(8H)-yl)-4-(trifluoromethyl)pyrimidine-5-carboxylic acid
2-(2-(4-(3-ethylureido)phenyl)-4-morpholino-5,6-dihydropyrido[3,4-d]pyrimidin-7(8H)-yl)-4-(trifluoromethyl)pyrimidine-5-carboxylic acid
1-(4-(7-(1-cyclopropylpiperidin-4-yl)-4-morpholino-5,6,7,8-tetrahydropyrido[3,4-d]pyrimidin-2-yl)phenyl)-3-ethylurea In a forty-second embodiment, compounds of Formula I are selected from the group compounds set forth in Table 2 below.

TABLE 2

6-(4-(4-morpholino-7-(pyrimidin-2-yl)-5,6,7,8-tetrahydropyrido[3,4-d]pyrimidin-2-yl)phenylamino)pyridin-2(1H)-one
(S)-1-(4-(7-(4-cyanopyridin-2-yl)-4-(3-methylmorpholino)-5,6,7,8-tetrahydropyrido[3,4-d]pyrimidin-2-yl)phenyl)-3-ethylurea
(S)-1-(4-(7-(5-cyanopyridin-2-yl)-4-(3-methylmorpholino)-5,6,7,8-tetrahydropyrido[3,4-d]pyrimidin-2-yl)phenyl)-3-ethylurea
(S)-1-(4-(7-(4,6-dimethylpyrimidin-2-yl)-4-(3-methylmorpholino)-5,6,7,8-tetrahydropyrido[3,4-d]pyrimidin-2-yl)phenyl)-3-ethylurea
(S)-1-ethyl-3-(4-(7-(5-ethylpyrimidin-2-yl)-4-(3-methylmorpholino)-5,6,7,8-tetrahydropyrido[3,4-d]pyrimidin-2-yl)phenyl)urea
6-(4-(4-morpholino-7-(pyrimidin-2-yl)-5,6,7,8-tetrahydropyrido[3,4-d]pyrimidin-2-yl)phenylamino)pyridin-2(1H)-one
1-ethyl-3-(4-(4-morpholino-7-(5-nitropyrimidin-2-yl)-5,6,7,8-tetrahydropyrido[3,4-d]pyrimidin-2-yl)phenyl)urea
1-(4-(7-(4-amino-5-cyanopyrimidin-2-yl)-4-morpholino-5,6,7,8-tetrahydropyrido[3,4-d]pyrimidin-2-yl)phenyl)-3-ethylurea
1-ethyl-3-(4-(7-(4-hydroxycyclohexyl)-4-morpholino-5,6,7,8-tetrahydropyrido[3,4-d]pyrimidin-2-yl)phenyl)urea
(S)-3-methyl-6-(4-(4-(3-methylmorpholino)-7-(pyrimidin-2-yl)-5,6,7,8-tetrahydropyrido[3,4-d]pyrimidin-2-yl)phenylamino)pyrimidine-2,4(1H,3H)-dione
(S)-6-(4-(7-(2-hydroxy-2-methylpropanoyl)-4-(3-methylmorpholino)-5,6,7,8-tetrahydropyrido[3,4-d]pyrimidin-2-yl)phenylamino)-3-methylpyrimidine-2,4(1H,3H)-dione
(S)-3-methyl-6-(4-(4-(3-methylmorpholino)-7-(thiazole-2-carbonyl)-5,6,7,8-tetrahydropyrido[3,4-d]pyrimidin-2-yl)phenylamino)pyrimidine-2,4(1H,3H)-dione
(S)-1-(2,2-difluoroethyl)-3-(4-(4-(3-methylmorpholino)-5,6,7,8-tetrahydropyrido[4,3-d]pyrimidin-2-yl)phenyl)urea
(S)-1-cyclobutyl-3-(4-(4-(3-methylmorpholino)-5,6,7,8-tetrahydropyrido[4,3-d]pyrimidin-2-yl)phenyl)urea
(S)-1-ethyl-3-(4-(4-(3-methylmorpholino)-8-oxo-5,6,7,8-tetrahydropyrido[3,4-d]pyrimidin-2-yl)phenyl)urea
(S)-1-cyclobutyl-3-(4-(4-(3-methylmorpholino)-6-(thiazole-2-carbonyl)-5,6,7,8-tetrahydropyrido[4,3-d]pyrimidin-2-yl)phenyl)urea
(S)-1-cyclobutyl-3-(4-(4-(3-methylmorpholino)-6-nicotinoyl-5,6,7,8-tetrahydropyrido[4,3-d]pyrimidin-2-yl)phenyl)urea
(S)-1-cyclobutyl-3-(4-(4-(3-methylmorpholino)-6-(oxazole-5-carbonyl)-5,6,7,8-tetrahydropyrido[4,3-d]pyrimidin-2-yl)phenyl)urea
(S)-1-cyclobutyl-3-(4-(6-(2-hydroxy-2-methylpropanoyl)-4-(3-methylmorpholino)-5,6,7,8-tetrahydropyrido[4,3-d]pyrimidin-2-yl)phenyl)urea
(S)-1-(4-(6-(2-hydroxy-2-methylpropanoyl)-4-(3-methylmorpholino)-5,6,7,8-tetrahydropyrido[4,3-d]pyrimidin-2-yl)phenyl)-3-(2-hydroxyethyl)urea
(S)-1-cyclobutyl-3-(4-(4-(3-methylmorpholino)-6-(pyrimidin-2-yl)-5,6,7,8-tetrahydropyrido[4,3-d]pyrimidin-2-yl)phenyl)urea
(S)-1-(2-hydroxyethyl)-3-(4-(4-(3-methylmorpholino)-6-(pyrimidin-2-yl)-5,6,7,8-tetrahydropyrido[4,3-d]pyrimidin-2-yl)phenyl)urea
2-(4-(4-morpholino-7-(pyrimidin-2-yl)-5,6,7,8-tetrahydropyrido[3,4-d]pyrimidin-2-yl)phenylamino)pyridin-4(1H)-one
1-((1S,2R)-2-hydroxycyclopentyl)-3-(4-(4-morpholino-7-(pyrimidin-2-yl)-5,6,7,8-tetrahydropyrido[3,4-d]pyrimidin-2-yl)phenyl)urea
tert-butyl 2-(4-(3-ethylureido)phenyl)-4-(pyridin-4-yl)-5,6-dihydropyrido[3,4-d]pyrimidine-7(8H)-carboxylate
1-ethyl-3-(4-(7-(3-methyloxetane-3-carbonyl)-4-morpholino-5,6,7,8-tetrahydropyrido[3,4-d]pyrimidin-2-yl)phenyl)urea
2-(4-(4-morpholino-7-(pyrimidin-2-yl)-5,6,7,8-tetrahydropyrido[3,4-d]pyrimidin-2-yl)phenylamino)pyrimidin-4(3H)-one
(R)-1-ethyl-3-(4-(4-(3-methylmorpholino)-6-(thiazole-2-carbonyl)-5,6,7,8-tetrahydropyrido[4,3-d]pyrimidin-2-yl)phenyl)urea
(R)-1-ethyl-3-(4-(4-(3-methylmorpholino)-6-(pyrimidin-2-yl)-5,6,7,8-tetrahydropyrido[4,3-d]pyrimidin-2-yl)phenyl)urea
1-ethyl-3-(4-(4-morpholino-7-(pyrimidin-2-yl)-6,7,8,9-tetrahydro-5H-pyrimido[4,5-d]azepin-2-yl)phenyl)urea
(S)-1-ethyl-3-(4-(4-(3-methylmorpholino)-7-(pyrimidin-2-yl)-6,7,8,9-tetrahydro-5H-pyrimido[4,5-d]azepin-2-yl)phenyl)urea
1-(4-(4-(1,4-oxazepan-4-yl)-7-(pyrimidin-2-yl)-6,7,8,9-tetrahydro-5H-pyrimido[4,5-d]azepin-2-yl)phenyl)-3-ethylurea
(S)-3-methyl-6-(4-(4-(3-methylmorpholino)-5,6,7,8-tetrahydropyrido[3,4-d]pyrimidin-2-yl)phenylamino)pyrimidine-2,4(1H,3H)-dione
(S)-2-(2-(4-(3-ethylureido)phenyl)-4-(3-methylmorpholino)-5,6-dihydropyrido[3,4-d]pyrimidin-7(8H)-yl)-N,N-dimethylacetamide
(S)-1-ethyl-3-(4-(4-(3-methylmorpholino)-7-(methylsulfonyl)-5,6,7,8-tetrahydropyrido[3,4-d]pyrimidin-2-yl)phenyl)urea
(S)-methyl 2-(4-(3-ethylureido)phenyl)-4-(3-methylmorpholino)-5,6-dihydropyrido[3,4-d]pyrimidine-7(8H)-carboxylate
(S)-ethyl 2-(4-(3-ethylureido)phenyl)-4-(3-methylmorpholino)-5,6-dihydropyrido[3,4-d]pyrimidine-7(8H)-carboxylate TABLE 2-continued (S)-1-ethyl-3-(4-(4-(3-ethylmorpholino)-7-(pyrimidin-2-yl)-5,6,7,8-tetrahydropyrido[3,4-d]pyrimidin-2-yl)phenyl)urea
1-(3-hydroxycyclobutyl)-3-(4-(4-morpholino-7-(pyrimidin-2-yl)-5,6,7,8-tetrahydropyrido[3,4-d]pyrimidin-2-yl)phenyl)urea
1-ethyl-3-(4-(7-(5-fluoro-4-hydroxypyrimidin-2-yl)-4-morpholino-5,6,7,8-tetrahydropyrido[3,4-d]pyrimidin-2-yl)phenyl)urea
1-(4-(7-(5-aminopyrimidin-2-yl)-4-morpholino-5,6,7,8-tetrahydropyrido[3,4-d]pyrimidin-2-yl)phenyl)-3-ethylurea
1-(4-(7-(4-amino-5-nitropyrimidin-2-yl)-4-morpholino-5,6,7,8-tetrahydropyrido[3,4-d]pyrimidin-2-yl)phenyl)-3-ethylurea
(S)-3-(ethylamino)-4-(4-(4-(3-methylmorpholino)-7-(pyrimidin-2-yl)-5,6,7,8-tetrahydropyrido[3,4-d]pyrimidin-2-yl)phenylamino)cyclobut-3-ene-1,2-dione
(S)-1-(2-cyanoethyl)-3-(4-(4-(3-methylmorpholino)-7-(pyrimidin-2-yl)-5,6,7,8-tetrahydropyrido[3,4-d]pyrimidin-2-yl)phenyl)urea
(S)-1-(2-hydroxyethyl)-3-(4-(4-(3-methylmorpholino)-7-(pyrimidin-2-yl)-5,6,7,8-tetrahydropyrido[3,4-d]pyrimidin-2-yl)phenyl)urea
(S)-1-cyclobutyl-3-(4-(4-(3-methylmorpholino)-7-(pyrimidin-2-yl)-5,6,7,8-tetrahydropyrido[3,4-d]pyrimidin-2-yl)phenyl)urea
(S)-1-(2,2-difluoroethyl)-3-(4-(4-(3-methylmorpholino)-7-(pyrimidin-2-yl)-5,6,7,8-tetrahydropyrido[3,4-d]pyrimidin-2-yl)phenyl)urea
(S)-1-(2-fluoroethyl)-3-(4-(4-(3-methylmorpholino)-7-(pyrimidin-2-yl)-5,6,7,8-tetrahydropyrido[3,4-d]pyrimidin-2-yl)phenyl)urea
(S)-1-(2,2-difluoroethyl)-3-(4-(4-(3-methylmorpholino)-6-(thiazole-2-carbonyl)-5,6,7,8-tetrahydropyrido[4,3-d]pyrimidin-2-yl)phenyl)urea
(S)-1-(2,2-difluoroethyl)-3-(4-(4-(3-methylmorpholino)-6-(pyrimidin-2-yl)-5,6,7,8-tetrahydropyrido[4,3-d]pyrimidin-2-yl)phenyl)urea
(S)-1-ethyl-3-(4-(4-(3-methylmorpholino)-7-(pyrazin-2-yl)-5,6,7,8-tetrahydropyrido[3,4-d]pyrimidin-2-yl)phenyl)urea
(S)-1-ethyl-3-(4-(4-(3-methylmorpholino)-7-(2-morpholino-2-oxoethyl)-5,6,7,8-tetrahydropyrido[3,4-d]pyrimidin-2-yl)phenyl)urea
1-(4-(7-(4-amino-5-methylpyrimidin-2-yl)-4-morpholino-5,6,7,8-tetrahydropyrido[3,4-d]pyrimidin-2-yl)phenyl)-3-ethylurea
1-ethyl-3-(4-(7-(1-(methylsulfonyl)piperidin-4-yl)-4-morpholino-5,6,7,8-tetrahydropyrido[3,4-d]pyrimidin-2-yl)phenyl)urea
1-ethyl-3-(4-(4-morpholino-7-(piperidin-4-yl)-5,6,7,8-tetrahydropyrido[3,4-d]pyrimidin-2-yl)phenyl)urea
(S)-1-cyclobutyl-3-(4-(4-(3-methylmorpholino)-5,6,7,8-tetrahydropyrido[3,4-d]pyrimidin-2-yl)phenyl)urea
1-((1S,2S)-2-hydroxycyclopentyl)-3-(4-(4-((S)-3-methylmorpholino)-5,6,7,8-tetrahydropyrido[3,4-d]pyrimidin-2-yl)phenyl)urea
(S)-1-(2,2-difluoroethyl)-3-(4-(4-(3-methylmorpholino)-5,6,7,8-tetrahydropyrido[3,4-d]pyrimidin-2-yl)phenyl)urea
1-(4-(7-(2-hydroxy-2-methylpropanoyl)-4-((S)-3-methylmorpholino)-5,6,7,8-tetrahydropyrido[3,4-d]pyrimidin-2-yl)phenyl)-3-((1S,2S)-2-hydroxycyclopentyl)urea
(S)-1-(2,2-difluoroethyl)-3-(4-(7-(2-hydroxy-2-methylpropanoyl)-4-(3-methylmorpholino)-5,6,7,8-tetrahydropyrido[3,4-d]pyrimidin-2-yl)phenyl)urea
(S)-1-(2-fluoroethyl)-3-(4-(7-(2-hydroxy-2-methylpropanoyl)-4-(3-methylmorpholino)-5,6,7,8-tetrahydropyrido[3,4-d]pyrimidin-2-yl)phenyl)urea
1-((1S,2S)-2-hydroxycyclopentyl)-3-(4-(4-((S)-3-methylmorpholino)-5,6,7,8-tetrahydropyrido[3,4-d]pyrimidin-2-yl)phenyl)urea
(S)-1-(2,2-difluoroethyl)-3-(4-(4-(3-methylmorpholino)-5,6,7,8-tetrahydropyrido[3,4-d]pyrimidin-2-yl)phenyl)urea
1-(4-(7-(2-hydroxy-2-methylpropanoyl)-4-((S)-3-methylmorpholino)-5,6,7,8-tetrahydropyrido[3,4-d]pyrimidin-2-yl)phenyl)-3-((1S,2S)-2-hydroxycyclopentyl)urea
(S)-1-(2,2-difluoroethyl)-3-(4-(7-(2-hydroxy-2-methylpropanoyl)-4-(3-methylmorpholino)-5,6,7,8-tetrahydropyrido[3,4-d]pyrimidin-2-yl)phenyl)urea
(S)-1-(2-fluoroethyl)-3-(4-(7-(2-hydroxy-2-methylpropanoyl)-4-(3-methylmorpholino)-5,6,7,8-tetrahydropyrido[3,4-d]pyrimidin-2-yl)phenyl)urea
(S)-1-cyclobutyl-3-(4-(7-(2-hydroxy-2-methylpropanoyl)-4-(3-methylmorpholino)-5,6,7,8-tetrahydropyrido[3,4-d]pyrimidin-2-yl)phenyl)urea
(S)-1-(2-fluoroethyl)-3-(4-(4-(3-methylmorpholino)-7-nicotinoyl-5,6,7,8-tetrahydropyrido[3,4-d]pyrimidin-2-yl)phenyl)urea
1-((1S,2S)-2-hydroxycyclopentyl)-3-(4-(4-((S)-3-methylmorpholino)-7-nicotinoyl-5,6,7,8-tetrahydropyrido[3,4-d]pyrimidin-2-yl)phenyl)urea
(S)-1-(2,2-difluoroethyl)-3-(4-(4-(3-methylmorpholino)-7-nicotinoyl-5,6,7,8-tetrahydropyrido[3,4-d]pyrimidin-2-yl)phenyl)urea
(S)-1-(2-cyanoethyl)-3-(4-(4-(3-methylmorpholino)-7-nicotinoyl-5,6,7,8-tetrahydropyrido[3,4-d]pyrimidin-2-yl)phenyl)urea
(S)-1-cyclobutyl-3-(4-(4-(3-methylmorpholino)-7-nicotinoyl-5,6,7,8-tetrahydropyrido[3,4-d]pyrimidin-2-yl)phenyl)urea
(S)-1-cyclobutyl-3-(4-(4-(3-methylmorpholino)-7-(pyrazin-2-yl)-5,6,7,8-tetrahydropyrido[3,4-d]pyrimidin-2-yl)phenyl)urea
1-(4-(4-((S)-3-methylmorpholino)-7-(pyrazin-2-yl)-5,6,7,8-tetrahydropyrido[3,4-d]pyrimidin-2-yl)phenyl)-3-((S)-tetrahydrofuran-3-yl)urea
(S)-1-ethyl-3-(4-(7-(5-fluoropyrimidin-4-yl)-4-(3-methylmorpholino)-5,6,7,8-tetrahydropyrido[3,4-d]pyrimidin-2-yl)phenyl)urea
(S)-1-(2-fluoroethyl)-3-(4-(4-(3-methylmorpholino)-7-(pyrazin-2-yl)-5,6,7,8-tetrahydropyrido[3,4-d]pyrimidin-2-yl)phenyl)urea
(S)-2-(4-(4-(3-methylmorpholino)-5,6,7,8-tetrahydropyrido[3,4-d]pyrimidin-2-yl)phenylamino)pyrimidin-4(3H)-one TABLE 2-continued 1-ethyl-3-(4-(4-morpholino-7-(pyrimidin-4-yl)-5,6,7,8-tetrahydropyrido[3,4-d]pyrimidin-2-yl)phenyl)urea
(S)-1-(3-methylisoxazol-5-yl)-3-(4-(3-methylmorpholino)-7-(pyrazin-2-yl)-5,6,7,8-tetrahydropyrido[3,4-d]pyrimidin-2-yl)phenyl)urea
(S)-isopropyl 2-(4-(3-ethylureido)phenyl)-4-(3-methylmorpholino)-5,6-dihydropyrido[3,4-d]pyrimidine-7(8H)-carboxylate
(S)-isobutyl 2-(4-(3-ethylureido)phenyl)-4-(3-methylmorpholino)-5,6-dihydropyrido[3,4-d]pyrimidine-7(8H)-carboxylate
(S)-1-ethyl-3-(4-(4-(3-methylmorpholino)-7-(3-methyloxetane-3-carbonyl)-5,6,7,8-tetrahydropyrido[3,4-d]pyrimidin-2-yl)phenyl)urea
(S)-1-ethyl-3-(4-(4-(3-methylmorpholino)-7-(tetrahydrofuran-3-carbonyl)-5,6,7,8-tetrahydropyrido[3,4-d]pyrimidin-2-yl)phenyl)urea
(S)-1-ethyl-3-(4-(4-(3-methylmorpholino)-7-(tetrahydrofuran-2-carbonyl)-5,6,7,8-tetrahydropyrido[3,4-d]pyrimidin-2-yl)phenyl)urea
(S)-1-ethyl-3-(4-(7-(4-hydroxybutyl)-4-(3-methylmorpholino)-6,7,8,9-tetrahydro-5H-pyrimido[5,4-d]azepin-2-yl)phenyl)urea
(S)-1-ethyl-3-(4-(4-(3-methylmorpholino)-6,7,8,9-tetrahydro-5H-pyrimido[5,4-d]azepin-2-yl)phenyl)urea
(S)-1-(4-(7-formyl-4-(3-methylmorpholino)-5,6,7,8-tetrahydropyrido[3,4-d]pyrimidin-2-yl)phenyl)-3-(2-hydroxyethyl)urea
(S)-1-(4-(7-formyl-4-(3-methylmorpholino)-5,6,7,8-tetrahydropyrido[3,4-d]pyrimidin-2-yl)phenyl)-3-(2,2,2-trifluoroethyl)urea
(S)-1-(4-(7-acetyl-4-(3-methylmorpholino)-5,6,7,8-tetrahydropyrido[3,4-d]pyrimidin-2-yl)phenyl)-3-(2-hydroxyethyl)urea
(S)-1-(4-(7-acetyl-4-(3-methylmorpholino)-5,6,7,8-tetrahydropyrido[3,4-d]pyrimidin-2-yl)phenyl)-3-(2,2,2-trifluoroethyl)urea
(S)-1-(2-hydroxyethyl)-3-(4-(4-(3-methylmorpholino)-7-propionyl-5,6,7,8-tetrahydropyrido[3,4-d]pyrimidin-2-yl)phenyl)urea
(S)-1-(4-(4-(3-methylmorpholino)-7-propionyl-5,6,7,8-tetrahydropyrido[3,4-d]pyrimidin-2-yl)phenyl)-3-(2,2,2-trifluoroethyl)urea
(S)-1-(isoxazol-3-yl)-3-(4-(4-(3-methylmorpholino)-7-(pyrimidin-2-yl)-5,6,7,8-tetrahydropyrido[3,4-d]pyrimidin-2-yl)phenyl)urea
(S)-1-(1-methyl-1H-pyrazol-5-yl)-3-(4-(4-(3-methylmorpholino)-7-nicotinoyl-5,6,7,8-tetrahydropyrido[3,4-d]pyrimidin-2-yl)phenyl)urea
(S)-2-(4-(4-(3-methylmorpholino)-7-nicotinoyl-5,6,7,8-tetrahydropyrido[3,4-d]pyrimidin-2-yl)phenylamino)pyrimidin-4(3H)-one
(S)-1-methyl-3-(4-(4-(3-methylmorpholino)-7-(pyrimidin-2-yl)-5,6,7,8-tetrahydropyrido[3,4-d]pyrimidin-2-yl)phenylamino)-1H-1,2,4-triazol-5-(4H)-one
(S)-6-(4-(4-(3-methylmorpholino)-7-nicotinoyl-5,6,7,8-tetrahydropyrido[3,4-d]pyrimidin-2-yl)phenylamino)pyridin-2(1H)-one
(S)-6-(4-(4-(3-methylmorpholino)-5,6,7,8-tetrahydropyrido[3,4-d]pyrimidin-2-yl)phenylamino)pyridin-2(1H)-one
(S)-tert-butyl 4-(3-ethylmorpholino)-2-(4-(3-(2-hydroxyethyl)ureido)phenyl)-5,6-dihydropyrido[3,4-d]pyrimidine-7(8H)-carboxylate
(S)-1-ethyl-3-(4-(4-(3-methylmorpholino)-7-(6-methylpyrimidin-4-yl)-5,6,7,8-tetrahydropyrido[3,4-d]pyrimidin-2-yl)phenyl)urea
(S)-1-ethyl-3-(4-(7-(5-fluoropyrimidin-2-yl)-4-(3-methylmorpholino)-5,6,7,8-tetrahydropyrido[3,4-d]pyrimidin-2-yl)phenyl)urea
(S)-1-ethyl-3-(4-(4-(3-methylmorpholino)-7-(4-(trifluoromethyl)pyrimidin-2-yl)-5,6,7,8-tetrahydropyrido[3,4-d]pyrimidin-2-yl)phenyl)urea
(S)-1-ethyl-3-(4-(7-(4-methoxypyrimidin-2-yl)-4-(3-methylmorpholino)-5,6,7,8-tetrahydropyrido[3,4-d]pyrimidin-2-yl)phenyl)urea
(S)-1-(2-hydroxyethyl)-3-(4-(4-(3-methylmorpholino)-7-(pyrimidin-4-yl)-5,6,7,8-tetrahydropyrido[3,4-d]pyrimidin-2-yl)phenyl)urea
(S)-1-(2-cyanoethyl)-3-(4-(4-(3-methylmorpholino)-7-(pyrimidin-4-yl)-5,6,7,8-tetrahydropyrido[3,4-d]pyrimidin-2-yl)phenyl)urea
(S)-1-cyclobutyl-3-(4-(4-(3-methylmorpholino)-7-(pyrimidin-4-yl)-5,6,7,8-tetrahydropyrido[3,4-d]pyrimidin-2-yl)phenyl)urea
(S)-1-(isoxazol-3-yl)-3-(4-(4-(3-methylmorpholino)-7-(pyrimidin-4-yl)-5,6,7,8-tetrahydropyrido[3,4-d]pyrimidin-2-yl)phenyl)urea
(S)-tert-butyl 2-(4-(3-ethylureido)phenyl)-4-(3-isopropylmorpholino)-5,6-dihydropyrido[3,4-d]pyrimidine-7(8H)-carboxylate
(S)-1-(4-(4-(3-ethylmorpholino)-5,6,7,8-tetrahydropyrido[3,4-d]pyrimidin-2-yl)phenyl)-3-(2-hydroxyethyl)urea
(S)-2-(4-(7-(2-hydroxy-2-methylpropanoyl)-4-(3-methylmorpholino)-5,6,7,8-tetrahydropyrido[3,4-d]pyrimidin-2-yl)phenylamino)pyrimidin-4(3H)-one
(S)-2-(4-(4-(3-methylmorpholino)-7-(1,4,5,6-tetrahydropyrimidin-2-yl)-5,6,7,8-tetrahydropyrido[3,4-d]pyrimidin-2-yl)phenylamino)pyrimidin-4(3H)-one
(S)-1-(1-methyl-1H-pyrazol-5-yl)-3-(4-(4-(3-methylmorpholino)-7-(pyrimidin-2-yl)-5,6,7,8-tetrahydropyrido[3,4-d]pyrimidin-2-yl)phenyl)urea
(S)-1-(3-methylisoxazol-5-yl)-3-(4-(4-(3-methylmorpholino)-7-(pyrimidin-2-yl)-5,6,7,8-tetrahydropyrido[3,4-d]pyrimidin-2-yl)phenyl)urea
(S)-1-(1-methyl-1H-pyrazol-3-yl)-3-(4-(4-(3-methylmorpholino)-7-(pyrimidin-2-yl)-5,6,7,8-tetrahydropyrido[3,4-d]pyrimidin-2-yl)phenyl)urea
(S)-1-(4-(4-(3-ethylmorpholino)-7-(pyrimidin-2-yl)-5,6,7,8-tetrahydropyrido[3,4-d]pyrimidin-2-yl)phenyl)-3-(2-hydroxyethyl)urea
(S)-1-(4-(7-(2-hydroxy-2-methylpropanoyl)-4-(3-methylmorpholino)-5,6,7,8-tetrahydropyrido[3,4-d]pyrimidin-2-yl)phenyl)-3-(1-methyl-1H-pyrazol-5-yl)urea
(S)-1-(4-(7-(2-hydroxy-2-methylpropanoyl)-4-(3-methylmorpholino)-5,6,7,8-tetrahydropyrido[3,4-d]pyrimidin-2-yl)phenyl)-3-(3-methylisoxazol-5-yl)urea

TABLE 2-continued (S)-1-(4-(7-(2-hydroxy-2-methylpropanoyl)-4-(3-methylmorpholino)-5,6,7,8-tetrahydropyrido[3,4-d]pyrimidin-2-yl)phenyl)-3-(1-methyl-1H-pyrazol-3-yl)urea
(S)-1-(4-(7-(2-hydroxy-2-methylpropanoyl)-4-(3-methylmorpholino)-5,6,7,8-tetrahydropyrido[3,4-d]pyrimidin-2-yl)phenyl)-3-(isoxazol-3-yl)urea
(S)-1-(4-(7-(4-chloro-1,3,5-triazin-2-yl)-4-(3-methylmorpholino)-5,6,7,8-tetrahydropyrido[3,4-d]pyrimidin-2-yl)phenyl)-3-ethylurea
(S)-1-ethyl-3-(4-(4-(3-methylmorpholino)-7-(1,3,5-triazin-2-yl)-5,6,7,8-tetrahydropyrido[3,4-d]pyrimidin-2-yl)phenyl)urea
(S)-1-ethyl-3-(4-(7-isopropyl-4-(3-methylmorpholino)-5,6,7,8-tetrahydropyrido[3,4-d]pyrimidin-2-yl)phenyl)urea
(S)-1-ethyl-3-(4-(7-isobutyl-4-(3-methylmorpholino)-5,6,7,8-tetrahydropyrido[3,4-d]pyrimidin-2-yl)phenyl)urea
tert-butyl 3-(2-(4-(3-ethylureido)phenyl)-4-((S)-3-methylmorpholino)-5,6-dihydropyrido[3,4-d]pyrimidin-7(8H)-yl)pyrrolidine-1-carboxylate
1-ethyl-3-(4-(4-((S)-3-methylmorpholino)-7-(pyrrolidin-3-yl)-5,6,7,8-tetrahydropyrido[3,4-d]pyrimidin-2-yl)phenyl)urea
(S)-1-ethyl-3-(4-(7-methyl-4-(3-methylmorpholino)-8-oxo-5,6,7,8-tetrahydropyrido[3,4-d]pyrimidin-2-yl)phenyl)urea
1-ethyl-3-(4-(7-(1-methyl-1H-pyrazol-4-ylsulfonyl)-4-morpholino-5,6,7,8-tetrahydropyrido[3,4-d]pyrimidin-2-yl)phenyl)urea
(S)-1-ethyl-3-(2-methyl-4-(4-(3-methylmorpholino)-7-(pyrimidin-2-yl)-5,6,7,8-tetrahydropyrido[3,4-d]pyrimidin-2-yl)phenyl)urea
1-ethyl-3-(4-(4-morpholino-7-pivaloyl-5,6,7,8-tetrahydropyrido[3,4-d]pyrimidin-2-yl)phenyl)urea
(S)-2-(4-(4-(3-methylmorpholino)-7-(pyrimidin-2-yl)-5,6,7,8-tetrahydropyrido[3,4-d]pyrimidin-2-yl)phenylamino)pyrimidin-4(3H)-one
1-ethyl-3-(4-(7-(4-fluorobenzoyl)-4-morpholino-5,6,7,8-tetrahydropyrido[3,4-d]pyrimidin-2-yl)phenyl)urea
1-(4-(7-(4-chlorobenzoyl)-4-morpholino-5,6,7,8-tetrahydropyrido[3,4-d]pyrimidin-2-yl)phenyl)-3-ethylurea
1-ethyl-3-(4-(7-(2-methylnicotinoyl)-4-morpholino-5,6,7,8-tetrahydropyrido[3,4-d]pyrimidin-2-yl)phenyl)urea
1-ethyl-3-(4-(7-(6-methylnicotinoyl)-4-morpholino-5,6,7,8-tetrahydropyrido[3,4-d]pyrimidin-2-yl)phenyl)urea
(S)-1-ethyl-3-(4-(4-(3-methylmorpholino)-6-(6-methylpyrimidin-4-yl)-5,6,7,8-tetrahydropyrido[4,3-d]pyrimidin-2-yl)phenyl)urea
(S)-isopropyl 2-(4-(3-ethylureido)phenyl)-4-(3-methylmorpholino)-7,8-dihydropyrido[4,3-d]pyrimidine-6(5H)-carboxylate
(S)-isobutyl 2-(4-(3-ethylureido)phenyl)-4-(3-methylmorpholino)-7,8-dihydropyrido[4,3-d]pyrimidine-6(5H)-carboxylate
isopropyl 2-(4-(3-ethylureido)phenyl)-4-morpholino-5,6-dihydropyrido[3,4-d]pyrimidine-7(8H)-carboxylate
isobutyl 2-(4-(3-ethylureido)phenyl)-4-morpholino-5,6-dihydropyrido[3,4-d]pyrimidine-7(8H)-carboxylate
1-ethyl-3-(4-(7-(6-methylpyrimidin-4-yl)-4-morpholino-5,6,7,8-tetrahydropyrido[3,4-d]pyrimidin-2-yl)phenyl)urea
(S)-1-ethyl-3-(4-(7-(1-methylcyclopropanecarbonyl)-4-(3-methylmorpholino)-5,6,7,8-tetrahydropyrido[3,4-d]pyrimidin-2-yl)phenyl)urea
(S)-1-(4-(7-(1-cyanocyclopropanecarbonyl)-4-(3-methylmorpholino)-5,6,7,8-tetrahydropyrido[3,4-d]pyrimidin-2-yl)phenyl)-3-ethylurea
(S)-1-ethyl-3-(4-(7-(3-hydroxy-2,2-dimethylpropanoyl)-4-(3-methylmorpholino)-5,6,7,8-tetrahydropyrido[3,4-d]pyrimidin-2-yl)phenyl)urea
(S)-1-ethyl-3-(4-(4-(3-methylmorpholino)-6-(3-methyloxetane-3-carbonyl)-5,6,7,8-tetrahydropyrido[4,3-d]pyrimidin-2-yl)phenyl)urea
1-(4-(7-(6-cyanopyrazin-2-yl)-4-morpholino-5,6,7,8-tetrahydropyrido[3,4-d]pyrimidin-2-yl)phenyl)-3-ethylurea
1-(4-(7-(1-acetylpyrrolidin-3-yl)-4-((S)-3-methylmorpholino)-5,6,7,8-tetrahydropyrido[3,4-d]pyrimidin-2-yl)phenyl)-3-ethylurea
1-ethyl-3-(4-(4-((S)-3-methylmorpholino)-7-(1-(methylsulfonyl)pyrrolidin-3-yl)-5,6,7,8-tetrahydropyrido[3,4-d]pyrimidin-2-yl)phenyl)urea
(S)-1-(4-(7-(1-cyclopropylpiperidin-4-yl)-4-(3-methylmorpholino)-5,6,7,8-tetrahydropyrido[3,4-d]pyrimidin-2-yl)phenyl)-3-ethylurea
(S)-1-ethyl-3-(4-(4-(3-methylmorpholino)-7-(tetrahydro-2H-pyran-4-yl)-5,6,7,8-tetrahydropyrido[3,4-d]pyrimidin-2-yl)phenyl)urea
1-ethyl-3-(4-(7-((R)-2-hydroxypropanoyl)-4-((S)-3-methylmorpholino)-5,6,7,8-tetrahydropyrido[3,4-d]pyrimidin-2-yl)phenyl)urea
1-ethyl-3-(4-(7-((R)-2-hydroxybutanoyl)-4-((S)-3-methylmorpholino)-5,6,7,8-tetrahydropyrido[3,4-d]pyrimidin-2-yl)phenyl)urea
1-ethyl-3-(4-(4-((S)-3-methylmorpholino)-7-(1-(methylsulfonyl)pyrrolidin-3-yl)-5,6,7,8-tetrahydropyrido[3,4-d]pyrimidin-2-yl)phenyl)urea
(S)-1-(4-(7-(1-cyclopropylpiperidin-4-yl)-4-(3-methylmorpholino)-5,6,7,8-tetrahydropyrido[3,4-d]pyrimidin-2-yl)phenyl)-3-ethylurea
(S)-1-ethyl-3-(4-(4-(3-methylmorpholino)-7-(tetrahydro-2H-pyran-4-yl)-5,6,7,8-tetrahydropyrido[3,4-d]pyrimidin-2-yl)phenyl)urea
1-ethyl-3-(4-(7-((R)-2-hydroxypropanoyl)-4-((S)-3-methylmorpholino)-5,6,7,8-tetrahydropyrido[3,4-d]pyrimidin-2-yl)phenyl)urea
1-ethyl-3-(4-(7-((R)-2-hydroxybutanoyl)-4-((S)-3-methylmorpholino)-5,6,7,8-tetrahydropyrido[3,4-d]pyrimidin-2-yl)phenyl)urea
(S)-1-methyl-3-(4-(4-(3-methylmorpholino)-7-(pyrimidin-2-yl)-5,6,7,8-tetrahydropyrido[3,4-d]pyrimidin-2-yl)phenyl)urea

TABLE 2-continued 1-ethyl-3-(4-(7-((S)-2-hydroxypropanoyl)-4-((S)-3-methylmorpholino)-5,6,7,8-tetrahydropyrido[3,4-d]pyrimidin-2-yl)phenyl)urea
1-ethyl-3-(4-(7-((S)-2-hydroxybutanoyl)-4-((S)-3-methylmorpholino)-5,6,7,8-tetrahydropyrido[3,4-d]pyrimidin-2-yl)phenyl)urea
1-(4-(7-(6-chloropyrazin-2-yl)-4-morpholino-5,6,7,8-tetrahydropyrido[3,4-d]pyrimidin-2-yl)phenyl)-3-ethylurea
(S)-1-ethyl-3-(4-(7-isopropyl-4-(3-methylmorpholino)-8-oxo-5,6,7,8-tetrahydropyrido[3,4-d]pyrimidin-2-yl)phenyl)urea
(S)-1-ethyl-3-(4-(7-(2-methoxypyrimidin-4-yl)-4-(3-methylmorpholino)-5,6,7,8-tetrahydropyrido[3,4-d]pyrimidin-2-yl)phenyl)urea
(S)-1-ethyl-3-(4-(4-(3-methylmorpholino)-7-(2-(trifluoromethyl)pyrimidin-4-yl)-5,6,7,8-tetrahydropyrido[3,4-d]pyrimidin-2-yl)phenyl)urea
(S)-1-(4-(7-(2,6-dimethoxypyrimidin-4-yl)-4-(3-methylmorpholino)-5,6,7,8-tetrahydropyrido[3,4-d]pyrimidin-2-yl)phenyl)-3-ethylurea
1-(4-(7-(3-cyanopyrazin-2-yl)-4-morpholino-5,6,7,8-tetrahydropyrido[3,4-d]pyrimidin-2-yl)phenyl)-3-ethylurea
1-ethyl-3-(4-(7-((R)-2-hydroxy-3-methylbutanoyl)-4-((S)-3-methylmorpholino)-5,6,7,8-tetrahydropyrido[3,4-d]pyrimidin-2-yl)phenyl)urea
(S)-1-methyl-3-(4-(4-(3-methylmorpholino)-7-(pyrimidin-4-yl)-5,6,7,8-tetrahydropyrido[3,4-d]pyrimidin-2-yl)phenyl)urea
1-(4-(7-(3-chloropyrazin-2-yl)-4-morpholino-5,6,7,8-tetrahydropyrido[3,4-d]pyrimidin-2-yl)phenyl)-3-ethylurea
1-ethyl-3-(4-(4-morpholino-7-(pyrazine-2-carbonyl)-5,6,7,8-tetrahydropyrido[3,4-d]pyrimidin-2-yl)phenyl)urea
(S)-1-(5-methyl-1,3,4-oxadiazol-2-yl)-3-(4-(4-(3-methylmorpholino)-7-(pyrimidin-2-yl)-5,6,7,8-tetrahydropyrido[3,4-d]pyrimidin-2-yl)phenyl)urea
1-ethyl-3-(4-(7-((S)-2-hydroxy-3-methylbutanoyl)-4-((S)-3-methylmorpholino)-5,6,7,8-tetrahydropyrido[3,4-d]pyrimidin-2-yl)phenyl)urea
(S)-1-ethyl-3-(4-(7-(2-methoxyacetyl)-4-(3-methylmorpholino)-5,6,7,8-tetrahydropyrido[3,4-d]pyrimidin-2-yl)phenyl)urea
(S)-1-(4-(7-(2-cyanoacetyl)-4-(3-methylmorpholino)-5,6,7,8-tetrahydropyrido[3,4-d]pyrimidin-2-yl)phenyl)-3-ethylurea
(S)-1-(4-(6-acetyl-4-(3-methylmorpholino)-5,6,7,8-tetrahydropyrido[4,3-d]pyrimidin-2-yl)phenyl)-3-ethylurea
(S)-1-ethyl-3-(4-(4-(3-methylmorpholino)-6-(methylsulfonyl)-5,6,7,8-tetrahydropyrido[4,3-d]pyrimidin-2-yl)phenyl)urea
(S)-1-(4-(6-(cyclopropylsulfonyl)-4-(3-methylmorpholino)-5,6,7,8-tetrahydropyrido[4,3-d]pyrimidin-2-yl)phenyl)-3-ethylurea
(S)-1-ethyl-3-(4-(6-(2-methoxyacetyl)-4-(3-methylmorpholino)-5,6,7,8-tetrahydropyrido[4,3-d]pyrimidin-2-yl)phenyl)urea
(S)-6-(4-(7-(2-hydroxy-2-methylpropanoyl)-4-(3-methylmorpholino)-5,6,7,8-tetrahydropyrido[3,4-d]pyrimidin-2-yl)phenylamino)pyridin-2(1H)-one
1-ethyl-3-(4-(4-morpholino-7-(pyrimidine-2-carbonyl)-5,6,7,8-tetrahydropyrido[3,4-d]pyrimidin-2-yl)phenyl)urea
(S)-1-(4-(6-(2-cyanoacetyl)-4-(3-methylmorpholino)-5,6,7,8-tetrahydropyrido[4,3-d]pyrimidin-2-yl)phenyl)-3-ethylurea
(S)-1-methyl-3-(4-(4-(3-methylmorpholino)-7-(6-methylpyrimidin-4-yl)-5,6,7,8-tetrahydropyrido[3,4-d]pyrimidin-2-yl)phenyl)urea
(S)-1-(1-methyl-1H-pyrazol-4-yl)-3-(4-(4-(3-methylmorpholino)-7-(pyrimidin-2-yl)-5,6,7,8-tetrahydropyrido[3,4-d]pyrimidin-2-yl)phenyl)urea
(S)-6-(4-(4-(3-methylmorpholino)-7-nicotinoyl-5,6,7,8-tetrahydropyrido[3,4-d]pyrimidin-2-yl)phenylamino)pyrazin-2(1H)-one
(S)-6-(4-(4-(3-methylmorpholino)-7-nicotinoyl-5,6,7,8-tetrahydropyrido[3,4-d]pyrimidin-2-yl)phenylamino)pyrazin-2(1H)-one
1-ethyl-3-(4-(7-(2-((S)-3-fluoropyrrolidin-1-yl)-2-oxoethyl)-4-((S)-3-methylmorpholino)-5,6,7,8-tetrahydropyrido[3,4-d]pyrimidin-2-yl)phenyl)urea
(S)-tert-butyl 2-(4-(4-ethylureido)phenyl)-4-(3-(hydroxymethyl)morpholino)-5,6-dihydropyrido[3,4-d]pyrimidine-7(8H)-carboxylate
1-ethyl-3-(4-(7-(2-((R)-3-fluoropyrrolidin-1-yl)-2-oxoethyl)-4-((S)-3-methylmorpholino)-5,6,7,8-tetrahydropyrido[3,4-d]pyrimidin-2-yl)phenyl)urea
(S)-1-ethyl-3-(4-(4-(3-methylmorpholino)-6-(methylsulfonyl)-6,7-dihydro-5H-pyrrolo[3,4-d]pyrimidin-2-yl)phenyl)urea
1-(4-(7-(3-chloropyrazine-2-carbonyl)-4-morpholino-5,6,7,8-tetrahydropyrido[3,4-d]pyrimidin-2-yl)phenyl)-3-ethylurea
(S)-1-ethyl-3-(4-(7-(2-(2-methoxyethoxy)acetyl)-4-(3-methylmorpholino)-5,6,7,8-tetrahydropyrido[3,4-d]pyrimidin-2-yl)phenyl)urea
(S)-1-ethyl-3-(4-(6-(2-(2-methoxyethoxy)acetyl)-4-(3-methylmorpholino)-5,6,7,8-tetrahydropyrido[4,3-d]pyrimidin-2-yl)phenyl)urea
(S)-1-ethyl-3-(4-(7-(5-methyl-1,3,4-oxadiazole-2-carbonyl)-4-(3-methylmorpholino)-5,6,7,8-tetrahydropyrido[3,4-d]pyrimidin-2-yl)phenyl)urea
(S)-6-(4-(4-(3-methylmorpholino)-7-(2,2,2-trifluoroethyl)-5,6,7,8-tetrahydropyrido[3,4-d]pyrimidin-2-yl)phenylamino)pyridin-2(1H)-one
(S)-1-ethyl-3-(4-(6-(ethylsulfonyl)-4-(3-methylmorpholino)-6,7-dihydro-5H-pyrrolo[3,4-d]pyrimidin-2-yl)phenyl)urea
(S)-N-ethyl-2-(2-(4-(3-ethylureido)phenyl)-4-(3-methylmorpholino)-5,6-dihydropyrido[3,4-d]pyrimidin-7(8H)-yl)acetamide
(S)-methyl 2-(2-(4-(3-ethylureido)phenyl)-4-(3-methylmorpholino)-5,6-dihydropyrido[3,4-d]pyrimidin-7(8H)-yl)acetate
(S)-2-(2-(4-(3-ethylureido)phenyl)-4-(3-methylmorpholino)-5,6-dihydropyrido[3,4-d]pyrimidin-7(8H)-yl)-N-(2-hydroxyethyl)acetamide TABLE 2-continued 1-(4-(7-(5-chloropyrazin-2-yl)-4-morpholino-5,6,7,8-tetrahydropyrido[3,4-d]pyrimidin-2-yl)phenyl)-3-ethylurea
(S)-tert-butyl 2-(4-(3-ethylureido)phenyl)-8,8-dimethyl-4-(3-methylmorpholino)-5,6-dihydropyrido[3,4-d]pyrimidine-7(8H)-carboxylate
1-ethyl-3-(4-(4-morpholino-7-(2,2,2-trifluoroethyl)-5,6,7,8-tetrahydropyrido[3,4-d]pyrimidin-2-yl)phenyl)urea
tert-butyl 2-(4-(3-ethylureido)phenyl)-8-methyl-4-((S)-3-methylmorpholino)-5,6-dihydropyrido[3,4-d]pyrimidine-7(8H)-carboxylate
(S)-1-(4-(6-(cyclopropylsulfonyl)-4-(3-methylmorpholino)-6,7-dihydro-5H-pyrrolo[3,4-d]pyrimidin-2-yl)phenyl)-3-ethylurea
(S)-1-ethyl-3-(4-(4-(3-methylmorpholino)-7-(2-methylpyrimidin-4-yl)-5,6,7,8-tetrahydropyrido[3,4-d]pyrimidin-2-yl)phenyl)urea
(S)-1-ethyl-3-(4-(4-(3-methylmorpholino)-6-(2-methylpyrimidin-4-yl)-5,6,7,8-tetrahydropyrido[4,3-d]pyrimidin-2-yl)phenyl)urea
1-(4-(7-(4-chloro-6-methylpyrimidin-2-yl)-4-morpholino-5,6,7,8-tetrahydropyrido[3,4-d]pyrimidin-2-yl)phenyl)-3-ethylurea
1-(4-(7-(2-chloro-6-methylpyrimidin-4-yl)-4-morpholino-5,6,7,8-tetrahydropyrido[3,4-d]pyrimidin-2-yl)phenyl)-3-ethylurea
tert-butyl 2-(4-(3-ethylureido)phenyl)-8-methyl-4-morpholino-5,6-dihydropyrido[3,4-d]pyrimidine-7(8H)-carboxylate
(S)-1-(4-(8,8-dimethyl-4-(3-methylmorpholino)-5,6,7,8-tetrahydropyrido[3,4-d]pyrimidin-2-yl)phenyl)-3-ethylurea
(R)-tert-butyl 2-(4-(3-ethylureido)phenyl)-8-methyl-4-((S)-3-methylmorpholino)-5,6-dihydropyrido[3,4-d]pyrimidine-7(8H)-carboxylate
(S)-tert-butyl 2-(4-(3-ethylureido)phenyl)-8-methyl-4-((S)-3-methylmorpholino)-5,6-dihydropyrido[3,4-d]pyrimidine-7(8H)-carboxylate
(S)-2-(2-(4-(3-ethylureido)phenyl)-4-(3-methylmorpholino)-5,6-dihydropyrido[3,4-d]pyrimidin-7(8H)-yl)acetamide
(S)-2-(2-(4-(3-ethylureido)phenyl)-4-(3-methylmorpholino)-5,6-dihydropyrido[3,4-d]pyrimidin-7(8H)-yl)-N-methylacetamide
(S)-2-(2-(4-(3-ethylureido)phenyl)-4-(3-methylmorpholino)-5,6-dihydropyrido[3,4-d]pyrimidin-7(8H)-yl)-N-propylacetamide
(S)-N-cyclobutyl-2-(2-(4-(3-ethylureido)phenyl)-4-(3-methylmorpholino)-5,6-dihydropyrido[3,4-d]pyrimidin-7(8H)-yl)acetamide
(S)-N-cyclopentyl-2-(2-(4-(3-ethylureido)phenyl)-4-(3-methylmorpholino)-5,6-dihydropyrido[3,4-d]pyrimidin-7(8H)-yl)acetamide
(S)-1-ethyl-3-(4-(4-(3-methylmorpholino)-7-(2-oxo-2-(pyrrolidin-1-yl)ethyl)-5,6,7,8-tetrahydropyrido[3,4-d]pyrimidin-2-yl)phenyl)urea
(S)-2-(2-(4-(3-ethylureido)phenyl)-4-(3-methylmorpholino)-5,6-dihydropyrido[3,4-d]pyrimidin-7(8H)-yl)acetic acid
(S)-1-(4-(7-(2-aminoacetyl)-4-(3-methylmorpholino)-5,6,7,8-tetrahydropyrido[3,4-d]pyrimidin-2-yl)phenyl)-3-ethylurea
1-(4-(7-((R)-2-aminopropanoyl)-4-((S)-3-methylmorpholino)-5,6,7,8-tetrahydropyrido[3,4-d]pyrimidin-2-yl)phenyl)-3-ethylurea
1-(4-(7-((R)-2-aminobutanoyl)-4-((S)-3-methylmorpholino)-5,6,7,8-tetrahydropyrido[3,4-d]pyrimidin-2-yl)phenyl)-3-ethylurea
1-ethyl-3-(4-(4-((S)-3-methylmorpholino)-7-(pyrrolidine-2-carbonyl)-5,6,7,8-tetrahydropyrido[3,4-d]pyrimidin-2-yl)phenyl)urea
1-ethyl-3-(4-(7-(2-(methylamino)propanoyl)-4-((S)-3-methylmorpholino)-5,6,7,8-tetrahydropyrido[3,4-d]pyrimidin-2-yl)phenyl)urea
(S)-1-(4-(7-(2-amino-2-methylpropanoyl)-4-(3-methylmorpholino)-5,6,7,8-tetrahydropyrido[3,4-d]pyrimidin-2-yl)phenyl)-3-ethylurea
(S)-2-(4-(4-(3-methylmorpholino)-7-(6-methylpyrimidin-4-yl)-5,6,7,8-tetrahydropyrido[3,4-d]pyrimidin-2-yl)phenylamino)pyrimidin-4(3H)-one
(S)-6-bromo-2-(4-(4-(3-ethylmorpholino)-7-(pyrimidin-2-yl)-5,6,7,8-tetrahydropyrido[3,4-d]pyrimidin-2-yl)phenylamino)pyrimidin-4(3H)-one
(S)-1-methyl-3-(4-(4-(3-methylmorpholino)-7-(6-methylpyrimidin-4-yl)-5,6,7,8-tetrahydropyrido[3,4-d]pyrimidin-2-yl)phenylamino)-1H-1,2,4-triazol-5-(4H)-one
1-(4-(7-((S)-2-aminobutanoyl)-4-((S)-3-methylmorpholino)-5,6,7,8-tetrahydropyrido[3,4-d]pyrimidin-2-yl)phenyl)-3-ethylurea
(S,E)-2-cyano-1-ethyl-3-(4-(4-(3-methylmorpholino)-7-(pyrimidin-2-yl)-5,6,7,8-tetrahydropyrido[3,4-d]pyrimidin-2-yl)phenyl)guanidine
1-ethyl-3-(4-((S)-8-methyl-4-((S)-3-methylmorpholino)-5,6,7,8-tetrahydropyrido[3,4-d]pyrimidin-2-yl)phenyl)urea
tert-butyl 2-(4-(3-ethylureido)phenyl)-8,8-dimethyl-4-morpholino-5,6-dihydropyrido[3,4-d]pyrimidine-7(8H)-carboxylate
1-(4-(7-((S)-2-aminopropanoyl)-4-((S)-3-methylmorpholino)-5,6,7,8-tetrahydropyrido[3,4-d]pyrimidin-2-yl)phenyl)-3-ethylurea
(S)-6-(4-(4-(3-methylmorpholino)-6-(methylsulfonyl)-6,7-dihydro-5H-pyrrolo[3,4-d]pyrimidin-2-yl)phenylamino)pyridin-2(1H)-one
(S)-2-(4-(4-(3-ethylmorpholino)-7-(pyrimidin-2-yl)-5,6,7,8-tetrahydropyrido[3,4-d]pyrimidin-2-yl)phenylamino)pyrimidin-4(3H)-one
1-ethyl-3-(4-((S)-8-methyl-4-((S)-3-methylmorpholino)-7-(pyrimidin-2-yl)-5,6,7,8-tetrahydropyrido[3,4-d]pyrimidin-2-yl)phenyl)urea
1-ethyl-3-(4-(7-(1-methyl-1H-imidazol-2-yl)-4-morpholino-5,6,7,8-tetrahydropyrido[3,4-d]pyrimidin-2-yl)phenyl)urea
(S)-6-(4-(4-(3-methylmorpholino)-7-(6-methylpyrimidin-4-yl)-5,6,7,8-tetrahydropyrido[3,4-d]pyrimidin-2-yl)phenylamino)pyridin-2(1H)-one
(S)-1-(4-(7-(cyclopropylsulfonyl)-4-(3-methylmorpholino)-5,6,7,8-tetrahydropyrido[3,4-d]pyrimidin-2-yl)phenyl)-3-ethylurea

TABLE 2-continued 1-(4-(4-morpholino-7-(pyrimidin-2-yl)-5,6,7,8-tetrahydropyrido[3,4-d]pyrimidin-2-yl)phenyl)urea
(S)-1-ethyl-3-(4-(4-(3-methylmorpholino)-7-(2-(4-methylpiperazin-1-yl)-2-oxoethyl)-5,6,7,8-tetrahydropyrido[3,4-d]pyrimidin-2-yl)phenyl)urea
(S)-1-ethyl-3-(4-(7-ethyl-4-(3-methylmorpholino)-8-oxo-5,6,7,8-tetrahydropyrido[3,4-d]pyrimidin-2-yl)phenyl)urea
1-ethyl-3-(4-(8-methyl-4-morpholino-7-(pyrimidin-2-yl)-5,6,7,8-tetrahydropyrido[3,4-d]pyrimidin-2-yl)phenyl)urea
(R)-1-ethyl-3-(4-(4-(3-methylmorpholino)-6-(methylsulfonyl)-6,7-dihydro-5H-pyrrolo[3,4-d]pyrimidin-2-yl)phenyl)urea
(S)-2-(4-(4-(3-methylmorpholino)-6-(methylsulfonyl)-6,7-dihydro-5H-pyrrolo[3,4-d]pyrimidin-2-yl)phenylamino)pyrimidin-4(3H)-one
(S)-6-(4-(7-acetyl-4-(3-methylmorpholino)-5,6,7,8-tetrahydropyrido[3,4-d]pyrimidin-2-yl)phenylamino)pyridin-2(1H)-one
(S)-N,N-diethyl-2-(2-(4-(3-ethylureido)phenyl)-4-(3-methylmorpholino)-5,6-dihydropyrido[3,4-d]pyrimidin-7(8H)-yl)acetamide
(S)-1-(4-(7-(2-(3,3-difluoropyrrolidin-1-yl)-2-oxoethyl)-4-(3-methylmorpholino)-5,6,7,8-tetrahydropyrido[3,4-d]pyrimidin-2-yl)phenyl)-3-ethylurea
(S)-1-(4-(4-(3-methylmorpholino)-7-(pyrimidin-2-yl)-5,6,7,8-tetrahydropyrido[3,4-d]pyrimidin-2-yl)phenyl)urea
(S)-6-(4-(7-isopropyl-4-(3-methylmorpholino)-5,6,7,8-tetrahydropyrido[3,4-d]pyrimidin-2-yl)phenylamino)pyridin-2(1H)-one
(S)-6-(4-(4-(3-methylmorpholino)-6-(6-methylpyrimidin-4-yl)-5,6,7,8-tetrahydropyrido[4,3-d]pyrimidin-2-yl)phenylamino)pyridin-2(1H)-one
(S)-tert-butyl 8-allyl-2-(4-(3-ethylureido)phenyl)-4-((S)-3-methylmorpholino)-5,6-dihydropyrido[3,4-d]pyrimidine-7(8H)-carboxylate
(R)-tert-butyl 8-allyl-2-(4-(3-ethylureido)phenyl)-4-((S)-3-methylmorpholino)-5,6-dihydropyrido[3,4-d]pyrimidine-7(8H)-carboxylate
(S)-1-ethyl-3-(5-(4-(3-methylmorpholino)-7-(pyrimidin-2-yl)-5,6,7,8-tetrahydropyrido[3,4-d]pyrimidin-2-yl)pyridin-2-yl)urea
(S)-1-ethyl-3-(5-(4-(3-methylmorpholino)-7-(6-methylpyrimidin-4-yl)-5,6,7,8-tetrahydropyrido[3,4-d]pyrimidin-2-yl)pyridin-2-yl)urea
(S)-2-(5-(4-(3-methylmorpholino)-7-(6-methylpyrimidin-4-yl)-5,6,7,8-tetrahydropyrido[3,4-d]pyrimidin-2-yl)pyridin-2-ylamino)pyrimidin-4(3H)-one
(S)-6-(5-(4-(3-methylmorpholino)-7-(6-methylpyrimidin-4-yl)-5,6,7,8-tetrahydropyrido[3,4-d]pyrimidin-2-yl)pyridin-2-ylamino)pyridin-2(1H)-one
(S)-tert-butyl 2-(4-(2-amino-5-methyl-1H-imidazol-1-yl)phenyl)-4-(3-methylmorpholino)-5,6-dihydropyrido[3,4-d]pyrimidine-7(8H)-carboxylate
(S)-1-(4-(4-(3-ethylmorpholino)-7-(pyrimidin-2-yl)-5,6,7,8-tetrahydropyrido[3,4-d]pyrimidin-2-yl)phenyl)-3-(isoxazol-3-yl)urea
(S)-1-(4-(4-(3-ethylmorpholino)-7-(pyrimidin-2-yl)-5,6,7,8-tetrahydropyrido[3,4-d]pyrimidin-2-yl)phenyl)-3-(5-methyl-1,2,3-oxadiazol-4-yl)urea
(S)-2-(4-(4-(3-methylmorpholino)-6-(6-methylpyrimidin-4-yl)-5,6,7,8-tetrahydropyrido[4,3-d]pyrimidin-2-yl)phenylamino)pyrimidin-4(3H)-one
1-ethyl-3-(4-(7-(1-methylcyclopropanecarbonyl)-4-morpholino-5,6,7,8-tetrahydropyrido[3,4-d]pyrimidin-2-yl)phenyl)urea
1-(4-(7-(1-cyanocyclopropanecarbonyl)-4-morpholino-5,6,7,8-tetrahydropyrido[3,4-d]pyrimidin-2-yl)phenyl)-3-ethylurea
(S)-1-(4-(4-(3-ethylmorpholino)-7-(pyrimidin-2-yl)-5,6,7,8-tetrahydropyrido[3,4-d]pyrimidin-2-yl)phenyl)-3-(oxetan-3-yl)urea
(S)-6-(5-(7-methyl-4-(3-methylmorpholino)-5,6,7,8-tetrahydropyrido[3,4-d]pyrimidin-2-yl)pyridin-2-ylamino)pyridin-2(1H)-one
(S)-6-(5-(7-methyl-4-(3-methylmorpholino)-5,6,7,8-tetrahydropyrido[3,4-d]pyrimidin-2-yl)pyridin-2-ylamino)pyridin-2(1H)-one
(S)-6-(5-(7-methyl-4-(3-methylmorpholino)-5,6,7,8-tetrahydropyrido[3,4-d]pyrimidin-2-yl)pyridin-2-ylamino)pyridin-2(1H)-one
1-ethyl-3-(4-((S)-4-((S)-3-methylmorpholino)-8-oxo-5,6,8,9,10,10a-hexahydropyrimido[5,4-g]indolizin-2-yl)phenyl)urea
(S)-1-ethyl-3-(4-(4-(3-methylmorpholino)-7-(thiazol-2-yl)-5,6,7,8-tetrahydropyrido[3,4-d]pyrimidin-2-yl)phenyl)urea
(S)-1-(4-(7-cyclopentyl-4-(3-methylmorpholino)-5,6,7,8-tetrahydropyrido[3,4-d]pyrimidin-2-yl)phenyl)-3-ethylurea
(S)-1-ethyl-3-(4-(4-(3-methylmorpholino)-7-(4-methylthiazol-2-yl)-5,6,7,8-tetrahydropyrido[3,4-d]pyrimidin-2-yl)phenyl)urea
(S)-1-ethyl-3-(4-(4-(3-ethylmorpholino)-7-methyl-8-oxo-5,6,7,8-tetrahydropyrido[3,4-d]pyrimidin-2-yl)phenyl)urea
(S)-1-(4-(7-cyclohexyl-4-(3-methylmorpholino)-5,6,7,8-tetrahydropyrido[3,4-d]pyrimidin-2-yl)phenyl)-3-ethylurea
(S)-1-(4-(7-(6-chloropyrimidin-4-yl)-4-(3-methylmorpholino)-5,6,7,8-tetrahydropyrido[3,4-d]pyrimidin-2-yl)phenyl)-3-ethylurea
(S)-1-ethyl-3-(4-(4-(3-methylmorpholino)-7-(6-methylpyrimidin-4-yl)-6,7,8,9-tetrahydro-5H-pyrimido[5,4-d]azepin-2-yl)phenyl)urea
(S)-1-ethyl-3-(4-(4-(3-methylmorpholino)-7-(2-methylpyrimidin-4-yl)-6,7,8,9-tetrahydro-5H-pyrimido[5,4-d]azepin-2-yl)phenyl)urea
(S)-1-isopropyl-3-(4-(4-(3-methylmorpholino)-7-(pyrimidin-2-yl)-5,6,7,8-tetrahydropyrido[3,4-d]pyrimidin-2-yl)phenyl)urea
1-ethyl-3-(4-(7-(2-methylpyrimidin-4-yl)-4-morpholino-5,6,7,8-tetrahydropyrido[3,4-d]pyrimidin-2-yl)phenyl)urea
(S)-1-ethyl-3-(4-(4-(3-methylmorpholino)-7-(2,2,2-trifluoroethyl)-5,6,7,8-tetrahydropyrido[3,4-d]pyrimidin-2-yl)phenyl)urea TABLE 2-continued 1-(4-(4-((1S,4S)-2-oxa-5-azabicyclo[2.2.1]heptan-5-yl)-7-(pyrimidin-2-yl)-5,6,7,8-tetrahydropyrido[3,4-d]pyrimidin-2-yl)phenyl)-3-ethylurea
(S)-1-ethyl-3-(4-(4-(3-methylmorpholino)-7-(pyrazine-2-carbonyl)-5,6,7,8-tetrahydropyrido[3,4-d]pyrimidin-2-yl)phenyl)urea
(S)-6-(5-(7-isopropyl-4-(3-methylmorpholino)-5,6,7,8-tetrahydropyrido[3,4-d]pyrimidin-2-yl)pyridin-2-ylamino)pyridin-2(1H)-one
1-ethyl-3-(4-(7-(3-methyl-1,2,4-thiadiazol-5-yl)-4-morpholino-5,6,7,8-tetrahydropyrido[3,4-d]pyrimidin-2-yl)phenyl)urea
(S)-1-ethyl-3-(4-(7-(1-methyl-1H-imidazol-2-yl)-4-(3-methylmorpholino)-5,6,7,8-tetrahydropyrido[3,4-d]pyrimidin-2-yl)phenyl)urea
1-ethyl-3-(4-(7-(5-methylpyrazine-2-carbonyl)-4-morpholino-5,6,7,8-tetrahydropyrido[3,4-d]pyrimidin-2-yl)phenyl)urea
1-(4-(7-(6-cyclopropylpyrimidin-4-yl)-4-morpholino-5,6,7,8-tetrahydropyrido[3,4-d]pyrimidin-2-yl)phenyl)-3-ethylurea
(S)-1-ethyl-3-(4-(4-(3-methylmorpholino)-7-(methylsulfonyl)-6,7,8,9-tetrahydro-5H-pyrimido[5,4-d]azepin-2-yl)phenyl)urea
1-ethyl-3-(4-(7-(1-methyl-6-oxo-1,6-dihydropyridin-2-yl)-4-morpholino-5,6,7,8-tetrahydropyrido[3,4-d]pyrimidin-2-yl)phenyl)urea
(S)-1-ethyl-3-(4-(4-(3-methylmorpholino)-7-(5-methylpyrimidin-2-yl)-5,6,7,8-tetrahydropyrido[3,4-d]pyrimidin-2-yl)phenyl)urea
1-(4-(4-((1S,4S)-2-oxa-5-azabicyclo[2.2.1]heptan-5-yl)-7-(6-methylpyrimidin-4-yl)-5,6,7,8-tetrahydropyrido[3,4-d]pyrimidin-2-yl)phenyl)-3-ethylurea
1-(4-(4-((1S,4S)-2-oxa-5-azabicyclo[2.2.1]heptan-5-yl)-7-(5-fluoropyrimidin-2-yl)-5,6,7,8-tetrahydropyrido[3,4-d]pyrimidin-2-yl)phenyl)-3-ethylurea
1-(4-(4-((1S,4S)-2-oxa-5-azabicyclo[2.2.1]heptan-5-yl)-7-(2-methylpyrimidin-4-yl)-5,6,7,8-tetrahydropyrido[3,4-d]pyrimidin-2-yl)phenyl)-3-ethylurea
1-ethyl-3-(4-(7-(3-methylpyrazine-2-carbonyl)-4-morpholino-5,6,7,8-tetrahydropyrido[3,4-d]pyrimidin-2-yl)phenyl)urea
(S)-1-cyclobutyl-3-(4-(4-(3-ethylmorpholino)-7-(2-methylpyrimidin-4-yl)-5,6,7,8-tetrahydropyrido[3,4-d]pyrimidin-2-yl)phenyl)urea
(S)-1-ethyl-3-(4-(4-(3-ethylmorpholino)-7-(5-fluoropyrimidin-2-yl)-5,6,7,8-tetrahydropyrido[3,4-d]pyrimidin-2-yl)phenyl)urea
(S)-1-ethyl-3-(4-(4-(3-methylmorpholino)-7-(oxetan-3-yl)-5,6,7,8-tetrahydropyrido[3,4-d]pyrimidin-2-yl)phenyl)urea
(S)-1-ethyl-3-(4-(7-(ethylsulfonyl)-4-(3-methylmorpholino)-5,6,7,8-tetrahydropyrido[3,4-d]pyrimidin-2-yl)phenyl)urea
(S)-1-ethyl-3-(4-(7-(isopropylsulfonyl)-4-(3-methylmorpholino)-5,6,7,8-tetrahydropyrido[3,4-d]pyrimidin-2-yl)phenyl)urea
(S)-1-ethyl-3-(4-(7-methyl-4-(3-methylmorpholino)-5,6,7,8-tetrahydropyrido[3,4-d]pyrimidin-2-yl)phenyl)urea
(S)-1-ethyl-3-(4-(7-(5-methyl-1,3,4-oxadiazol-2-yl)-4-(3-methylmorpholino)-5,6,7,8-tetrahydropyrido[3,4-d]pyrimidin-2-yl)phenyl)urea
(S)-1-(4-(7-(5-cyanothiazol-2-yl)-4-(3-methylmorpholino)-5,6,7,8-tetrahydropyrido[3,4-d]pyrimidin-2-yl)phenyl)-3-ethylurea
1-ethyl-3-(4-(4-((S)-3-methylmorpholino)-7-(tetrahydrofuran-3-yl)-5,6,7,8-tetrahydropyrido[3,4-d]pyrimidin-2-yl)phenyl)urea
(S)-1-ethyl-3-(4-(7-(isobutylsulfonyl)-4-(3-methylmorpholino)-5,6,7,8-tetrahydropyrido[3,4-d]pyrimidin-2-yl)phenyl)urea
(S)-1-ethyl-3-(4-(4-(3-methylmorpholino)-6-(2-methylpyrimidin-4-yl)-6,7-dihydro-5H-pyrrolo[3,4-d]pyrimidin-2-yl)phenyl)urea
(S)-1-ethyl-3-(4-(6-(5-fluoropyrimidin-2-yl)-4-(3-methylmorpholino)-6,7-dihydro-5H-pyrrolo[3,4-d]pyrimidin-2-yl)phenyl)urea
(S)-1-ethyl-3-(4-(7-(3-methyl-1,2,4-thiadiazol-5-yl)-4-(3-methylmorpholino)-5,6,7,8-tetrahydropyrido[3,4-d]pyrimidin-2-yl)phenyl)urea
(S)-6-(4-(7-(1-methyl-1H-imidazol-2-yl)-4-(3-methylmorpholino)-5,6,7,8-tetrahydropyrido[3,4-d]pyrimidin-2-yl)phenylamino)pyridin-2(1H)-one
(S)-1-ethyl-3-(4-(4-(3-ethylmorpholino)-7-(2,2,2-trifluoroethyl)-5,6,7,8-tetrahydropyrido[3,4-d]pyrimidin-2-yl)phenyl)urea
(S)-1-(4-(7-(cyclopropylmethyl)-4-(3-methylmorpholino)-5,6,7,8-tetrahydropyrido[3,4-d]pyrimidin-2-yl)phenyl)-3-ethylurea
(S)-1-ethyl-3-(4-(4-(3-methylmorpholino)-6-(6-methylpyrimidin-4-yl)-6,7-dihydro-5H-pyrrolo[3,4-d]pyrimidin-2-yl)phenyl)urea
(S)-1-ethyl-3-(4-(4-(3-methylmorpholino)-7-(pyridin-4-ylmethyl)-5,6,7,8-tetrahydropyrido[3,4-d]pyrimidin-2-yl)phenyl)urea
(S)-1-ethyl-3-(4-(7-ethyl-4-(3-ethylmorpholino)-8-oxo-5,6,7,8-tetrahydropyrido[3,4-d]pyrimidin-2-yl)phenyl)urea
(S)-1-ethyl-3-(4-(7-(3-hydroxy-2,2-dimethylpropyl)-4-(3-methylmorpholino)-5,6,7,8-tetrahydropyrido[3,4-d]pyrimidin-2-yl)phenyl)urea
(S)-7-ethyl-4-(3-ethylmorpholino)-2-(4-(6-oxo-1,6-dihydropyridin-2-ylamino)phenyl)-6,7-dihydropyrido[3,4-d]pyrimidin-8(5H)-one
1-(4-((R)-7-acetyl-8-methyl-4-((S)-3-methylmorpholino)-5,6,7,8-tetrahydropyrido[3,4-d]pyrimidin-2-yl)phenyl)-3-ethylurea
1-ethyl-3-(4-((R)-4-((S)-3-methylmorpholino)-5,6,8,9,10,a10-hexahydropyrimido[5,4-g]indolizin-2-yl)phenyl)urea
1-ethyl-3-(4-((S)-4-((S)-3-methylmorpholino)-5,6,8,9,10,a10-hexahydropyrimido[5,4-g]indolizin-2-yl)phenyl)urea
1-ethyl-3-(4-((R)-7-ethyl-8-methyl-4-((S)-3-methylmorpholino)-5,6,7,8-tetrahydropyrido[3,4-d]pyrimidin-2-yl)phenyl)urea
1-ethyl-3-(4-((S)-7-ethyl-8-methyl-4-((S)-3-methylmorpholino)-5,6,7,8-tetrahydropyrido[3,4-d]pyrimidin-2-yl)phenyl)urea TABLE 2-continued 1-(4-((R)-7,8-dimethyl-4-((S)-3-methylmorpholino)-5,6,7,8-tetrahydropyrido[3,4-d]pyrimidin-2-yl)phenyl)-3-ethylurea
1-(4-((S)-7,8-dimethyl-4-((S)-3-methylmorpholino)-5,6,7,8-tetrahydropyrido[3,4-d]pyrimidin-2-yl)phenyl)-3-ethylurea
(S)-1-ethyl-3-(4-(7-ethyl-4-(3-methylmorpholino)-5,6,7,8-tetrahydropyrido[3,4-d]pyrimidin-2-yl)phenyl)urea
(S)-1-ethyl-3-(4-(4-(3-methylmorpholino)-7-(propylsulfonyl)-5,6,7,8-tetrahydropyrido[3,4-d]pyrimidin-2-yl)phenyl)urea
(R)-1-ethyl-3-(4-(8-methyl-7-(2-methylpyrimidin-4-yl)-4-morpholino-5,6,7,8-tetrahydropyrido[3,4-d]pyrimidin-2-yl)phenyl)urea
(S)-1-ethyl-3-(4-(8-methyl-7-(2-methylpyrimidin-4-yl)-4-morpholino-5,6,7,8-tetrahydropyrido[3,4-d]pyrimidin-2-yl)phenyl)urea
1-ethyl-3-(4-(8-methyl-7-(2-methylpyrimidin-4-yl)-4-morpholino-5,6,7,8-tetrahydropyrido[3,4-d]pyrimidin-2-yl)phenyl)urea
(S)-1-ethyl-3-(4-(7-(1-methyl-6-oxo-1,6-dihydropyridin-2-yl)-4-(3-methylmorpholino)-5,6,7,8-tetrahydropyrido[3,4-d]pyrimidin-2-yl)phenyl)urea
1-(4-(7-(6-(benzyloxy)pyridin-2-yl)-4-morpholino-5,6,7,8-tetrahydropyrido[3,4-d]pyrimidin-2-yl)phenyl)-3-ethylurea
(S)-1-ethyl-3-(4-(4-(3-methylmorpholino)-6-(trifluoromethylsulfonyl)-6,7-dihydro-5H-pyrrolo[3,4-d]pyrimidin-2-yl)phenyl)urea
(S)-1-(4-(7-(3,3-dimethylbutyl)-4-(3-methylmorpholino)-5,6,7,8-tetrahydropyrido[3,4-d]pyrimidin-2-yl)phenyl)-3-ethylurea
(S)-1-(4-(7-(5-fluoropyrimidin-2-yl)-4-(3-methylmorpholino)-5,6,7,8-tetrahydropyrido[3,4-d]pyrimidin-2-yl)phenyl)-3-methylurea
(S)-1-(4-(7-(6-chloro-2-methylpyrimidin-4-yl)-4-(3-methylmorpholino)-5,6,7,8-tetrahydropyrido[3,4-d]pyrimidin-2-yl)phenyl)-3-methylurea
1-ethyl-3-(4-(4-morpholino-7-(6-oxo-1,6-dihydropyridin-2-yl)-5,6,7,8-tetrahydropyrido[3,4-d]pyrimidin-2-yl)phenyl)urea
1-ethyl-3-(4-(4-((S)-3-methylmorpholino)-7-((tetrahydrofuran-3-yl)methyl)-5,6,7,8-tetrahydropyrido[3,4-d]pyrimidin-2-yl)phenyl)urea
(S)-1-ethyl-3-(4-(6-(1-methyl-1H-imidazol-2-yl)-4-(3-methylmorpholino)-6,7-dihydro-5H-pyrrolo[3,4-d]pyrimidin-2-yl)phenyl)urea
1-(4-((S)-7-acetyl-8-methyl-4-((S)-3-methylmorpholino)-5,6,7,8-tetrahydropyrido[3,4-d]pyrimidin-2-yl)phenyl)-3-ethylurea
(S)-1-ethyl-3-(4-(4-(3-methylmorpholino)-7-((6-methylpyridin-2-yl)methyl)-5,6,7,8-tetrahydropyrido[3,4-d]pyrimidin-2-yl)phenyl)urea
(S)-1-methyl-3-(4-(4-(3-methylmorpholino)-7-(2-methylpyrimidin-4-yl)-5,6,7,8-tetrahydropyrido[3,4-d]pyrimidin-2-yl)phenyl)urea
6-(4-((R)-4-((S)-3-methylmorpholino)-5,6,8,9,10,10a-hexahydropyrimido[5,4-g]indolizin-2-yl)phenylamino)pyridin-2(1H)-one
6-(4-((S)-4-((S)-3-methylmorpholino)-5,6,8,9,10,10a-hexahydropyrimido[5,4-g]indolizin-2-yl)phenylamino)pyridin-2(1H)-one
1-(4-((R)-8-allyl-4-((S)-3-methylmorpholino)-5,6,7,8-tetrahydropyrido[3,4-d]pyrimidin-2-yl)phenyl)-3-ethylurea
1-(4-((S)-8-allyl-4-((S)-3-methylmorpholino)-5,6,7,8-tetrahydropyrido[3,4-d]pyrimidin-2-yl)phenyl)-3-ethylurea
1-(4-((R)-7-acetyl-8-allyl-4-((S)-3-methylmorpholino)-5,6,7,8-tetrahydropyrido[3,4-d]pyrimidin-2-yl)phenyl)-3-ethylurea
1-(4-((S)-7-acetyl-8-allyl-4-((S)-3-methylmorpholino)-5,6,7,8-tetrahydropyrido[3,4-d]pyrimidin-2-yl)phenyl)-3-ethylurea
1-ethyl-3-(4-(4-((S)-3-methylmorpholino)-7-(((R)-tetrahydrofuran-3-yl)methyl)-5,6,7,8-tetrahydropyrido[3,4-d]pyrimidin-2-yl)phenyl)urea
(S)-1-ethyl-3-(4-(4-(3-methylmorpholino)-7-((6-methylpyridin-3-yl)methyl)-5,6,7,8-tetrahydropyrido[3,4-d]pyrimidin-2-yl)phenyl)urea
(S)-4-(3-methylmorpholino)-2-(4-(6-oxo-1,6-dihydropyridin-2-ylamino)phenyl)-5,6-dihydropyrido[3,4-d]pyrimidine-7(8H)-carbaldehyde
(S)-6-(4-(7-ethyl-4-(3-methylmorpholino)-5,6,7,8-tetrahydropyrido[3,4-d]pyrimidin-2-yl)phenylamino)pyridin-2(1H)-one
(S)-6-(4-(7-ethyl-4-(3-methylmorpholino)-5,6,7,8-tetrahydropyrido[3,4-d]pyrimidin-2-yl)phenylamino)pyridin-2(1H)-one
1-ethyl-3-(4-(4-((S)-3-methylmorpholino)-7-((tetrahydrofuran-2-yl)methyl)-5,6,7,8-tetrahydropyrido[3,4-d]pyrimidin-2-yl)phenyl)urea
(S)—N-ethyl-4-(3-methylmorpholino)-2-(4-(6-oxo-1,6-dihydropyridin-2-ylamino)phenyl)-5,6-dihydropyrido[3,4-d]pyrimidine-7(8H)-carboxamide
(S)-1-ethyl-3-(4-(7-(1-ethyl-1H-imidazol-2-yl)-4-(3-methylmorpholino)-5,6,7,8-tetrahydropyrido[3,4-d]pyrimidin-2-yl)phenyl)urea
(S)-1-ethyl-3-(4-(4-(3-methylmorpholino)-7-(trifluoromethylsulfonyl)-5,6,7,8-tetrahydropyrido[3,4-d]pyrimidin-2-yl)phenyl)urea
1-ethyl-3-(4-(4-((S)-3-methylmorpholino)-7-(((S)-tetrahydrofuran-2-yl)methyl)-5,6,7,8-tetrahydropyrido[3,4-d]pyrimidin-2-yl)phenyl)urea
1-ethyl-3-(4-(4-((S)-3-methylmorpholino)-7-(((R)-tetrahydrofuran-2-yl)methyl)-5,6,7,8-tetrahydropyrido[3,4-d]pyrimidin-2-yl)phenyl)urea
(S)-1-ethyl-3-(4-(4-(3-methylmorpholino)-7-neopentyl-5,6,7,8-tetrahydropyrido[3,4-d]pyrimidin-2-yl)phenyl)urea
(S)-6-(4-(7-(1-ethyl-1H-imidazol-2-yl)-4-(3-methylmorpholino)-5,6,7,8-tetrahydropyrido[3,4-d]pyrimidin-2-yl)phenylamino)pyridin-2(1H)-one
(S)-tert-butyl 2-(2-aminopyrimidin-5-yl)-4-(3-methylmorpholino)-5,6-dihydropyrido[3,4-d]pyrimidine-7(8H)-carboxylate
(S)-5-(4-(3-methylmorpholino)-7-(2-methylpyrimidin-4-yl)-5,6,7,8-tetrahydropyrido[3,4-d]pyrimidin-2-yl)pyrimidin-2-amine

TABLE 2-continued (S)-5-(7-(5-fluoropyrimidin-2-yl)-4-(3-methylmorpholino)-5,6,7,8-tetrahydropyrido[3,4-d]pyrimidin-2-yl)pyrimidin-2-amine
(S)-5-(7-isopropyl-4-(3-methylmorpholino)-5,6,7,8-tetrahydropyrido[3,4-d]pyrimidin-2-yl)pyrimidin-2-amine
(S)-2-(4-(7-isopropyl-4-(3-methylmorpholino)-5,6,7,8-tetrahydropyrido[3,4-d]pyrimidin-2-yl)phenylamino)pyrimidin-4(3H)-one
(S)-1-ethyl-3-(4-(4-(3-methylmorpholino)-8-oxo-6,8-dihydro-5H-pyrimido[4,5-a]quinolizin-2-yl)phenyl)urea
1-ethyl-3-(4-(7-(5-fluoropyrimidin-2-yl)-4-(4-methoxypiperidin-1-yl)-5,6,7,8-tetrahydropyrido[3,4-d]pyrimidin-2-yl)phenyl)urea
(S)-2-(4-(7-ethyl-4-(3-methylmorpholino)-5,6,7,8-tetrahydropyrido[3,4-d]pyrimidin-2-yl)phenylamino)pyrimidin-4(3H)-one
1-ethyl-3-(4-(7-(1-methyl-6-oxo-1,6-dihydropyridin-3-yl)-4-morpholino-5,6,7,8-tetrahydropyrido[3,4-d]pyrimidin-2-yl)phenyl)urea
(S)-6-(4-(4-(3-methylmorpholino)-7-(2-methylpyrimidin-4-yl)-5,6,7,8-tetrahydropyrido[3,4-d]pyrimidin-2-yl)phenylamino)pyridin-2(1H)-one
(S)-6-(4-(7-(5-fluoropyrimidin-2-yl)-4-(3-methylmorpholino)-5,6,7,8-tetrahydropyrido[3,4-d]pyrimidin-2-yl)phenylamino)pyridin-2(1H)-one
(S)-6-(4-(7-(2-hydroxyethyl)-4-(3-methylmorpholino)-5,6,7,8-tetrahydropyrido[3,4-d]pyrimidin-2-yl)phenylamino)pyridin-2(1H)-one
(S)-1-ethyl-3-(4-(4-(3-methylmorpholino)-7-(pyridin-3-ylmethyl)-5,6,7,8-tetrahydropyrido[3,4-d]pyrimidin-2-yl)phenyl)urea
(S)-1-(4-(7-((1,3-dioxolan-2-yl)methyl)-4-(3-methylmorpholino)-5,6,7,8-tetrahydropyrido[3,4-d]pyrimidin-2-yl)phenyl)-3-ethylurea
(S)-1-ethyl-3-(4-(4-(3-ethylmorpholino)-5,6,7,8-tetrahydropyrido[3,4-d]pyrimidin-2-yl)phenyl)urea
(S)-1-ethyl-3-(4-(4-(3-ethylmorpholino)-7-isopropyl-5,6,7,8-tetrahydropyrido[3,4-d]pyrimidin-2-yl)phenyl)urea
(S)-1-(4-(7-acetyl-4-(3-ethylmorpholino)-5,6,7,8-tetrahydropyrido[3,4-d]pyrimidin-2-yl)phenyl)-3-ethylurea
(S)-1-ethyl-3-(4-(4-(3-ethylmorpholino)-7-formyl-5,6,7,8-tetrahydropyrido[3,4-d]pyrimidin-2-yl)phenyl)urea
(S)-1-ethyl-3-(4-(4-(3-ethylmorpholino)-7-(oxetan-3-yl)-5,6,7,8-tetrahydropyrido[3,4-d]pyrimidin-2-yl)phenyl)urea
1-ethyl-3-(4-(7-(2-methoxyethyl)-4-morpholino-5,6,7,8-tetrahydropyrido[3,4-d]pyrimidin-2-yl)phenyl)urea
(S)-1-ethyl-3-(4-(7-(2-methoxyethyl)-4-(3-methylmorpholino)-5,6,7,8-tetrahydropyrido[3,4-d]pyrimidin-2-yl)phenyl)urea
(S)-1-ethyl-3-(4-(4-(3-methylmorpholino)-7-((2-methylpyridin-4-yl)methyl)-5,6,7,8-tetrahydropyrido[3,4-d]pyrimidin-2-yl)phenyl)urea
(S)-1-(4-(7-ethyl-4-(3-ethylmorpholino)-8-oxo-5,6,7,8-tetrahydropyrido[3,4-d]pyrimidin-2-yl)phenyl)-3-(isoxazol-3-yl)urea
(S)-1-ethyl-3-(4-(4-(3-ethylmorpholino)-7-(methylsulfonyl)-5,6,7,8-tetrahydropyrido[3,4-d]pyrimidin-2-yl)phenyl)urea
(S)-6-(4-(7-(2-methoxyethyl)-4-(3-methylmorpholino)-5,6,7,8-tetrahydropyrido[3,4-d]pyrimidin-2-yl)phenylamino)pyridin-2(1H)-one
1-(4-(7-(5,5-dimethyltetrahydrofuran-3-yl)-4-((S)-3-methylmorpholino)-5,6,7,8-tetrahydropyrido[3,4-d]pyrimidin-2-yl)phenyl)-3-ethylurea
1-(4-(7-(5,5-dimethyltetrahydrofuran-3-yl)-4-((S)-3-methylmorpholino)-5,6,7,8-tetrahydropyrido[3,4-d]pyrimidin-2-yl)phenyl)-3-ethylurea
(S)-1-ethyl-3-(4-(7-ethyl-4-(3-ethylmorpholino)-5,6,7,8-tetrahydropyrido[3,4-d]pyrimidin-2-yl)phenyl)urea
(S)-1-ethyl-3-(4-(4-(3-ethylmorpholino)-7-(trifluoromethylsulfonyl)-5,6,7,8-tetrahydropyrido[3,4-d]pyrimidin-2-yl)phenyl)urea
(S)-1-ethyl-3-(4-(6-ethyl-7,7-dimethyl-4-(3-methylmorpholino)-6,7-dihydro-5H-pyrrolo[3,4-d]pyrimidin-2-yl)phenyl)urea
(S)-1-ethyl-3-(4-(6-ethyl-7,7-dimethyl-4-(3-methylmorpholino)-6,7-dihydro-5H-pyrrolo[3,4-d]pyrimidin-2-yl)phenyl)urea
(S)-tert-butyl 8-(cyanomethyl)-2-(4-(3-ethylureido)phenyl)-4-((S)-3-methylmorpholino)-5,6-dihydropyrido[3,4-d]pyrimidine-7(8H)-carboxylate
(S)-1-ethyl-3-(4-(4-(3-methylmorpholino)-6-(oxetan-3-yl)-5,6,7,8-tetrahydropyrido[4,3-d]pyrimidin-2-yl)phenyl)urea
tert-butyl 8-(2-aminoethyl)-2-(4-(3-ethylureido)phenyl)-4-((S)-3-methylmorpholino)-5,6-dihydropyrido[3,4-d]pyrimidine-7(8H)-carboxylate
(S)-1-ethyl-3-(4-(4-(3-ethylmorpholino)-7-(tetrahydro-2H-pyran-4-yl)-5,6,7,8-tetrahydropyrido[3,4-d]pyrimidin-2-yl)phenyl)urea
(S)-1-ethyl-3-(4-(7-(2-hydroxy-2-methylpropyl)-4-(3-methylmorpholino)-5,6,7,8-tetrahydropyrido[3,4-d]pyrimidin-2-yl)phenyl)urea
(S)-1-ethyl-3-(4-(4-(3-methylmorpholino)-7-(pyrimidin-2-ylmethyl)-5,6,7,8-tetrahydropyrido[3,4-d]pyrimidin-2-yl)phenyl)urea
(S)-1-(4-(7-(2,2-difluoroethyl)-4-(3-methylmorpholino)-5,6,7,8-tetrahydropyrido[3,4-d]pyrimidin-2-yl)phenyl)-3-ethylurea
(S)-tert-butyl 4-(3-methylmorpholino)-2-(4-(3-oxetan-3-ylureido)phenyl)-5,6-dihydropyrido[3,4-d]pyrimidine-7(8H)-carboxylate
5-methyl-N-(4-(4-morpholino-7-(pyrimidin-2-yl)-5,6,7,8-tetrahydropyrido[3,4-d]pyrimidin-2-yl)phenyl)-4,5-dihydro-1H-imidazol-2-amine
(S)-1-ethyl-3-(4-(4-morpholino-8-oxo-5,6,8,9,10,10a-hexahydropyrimido[5,4-g]indolizin-2-yl)phenyl)urea
(R)-1-ethyl-3-(4-(4-morpholino-8-oxo-5,6,8,9,10,10a-hexahydropyrimido[5,4-g]indolizin-2-yl)phenyl)urea TABLE 2-continued (S)-1-(4-(7-(2-tert-butoxyethyl)-4-(3-methylmorpholino)-5,6,7,8-tetrahydropyrido[3,4-d]pyrimidin-2-yl)phenyl)-3-ethylurea
1-ethyl-3-(4-((S)-4-((R)-3-methylmorpholino)-8-oxo-5,6,8,9,10,10a-hexahydropyrimido[5,4-g]indolizin-2-yl)phenyl)urea
1-ethyl-3-(4-((R)-4-((R)-3-methylmorpholino)-8-oxo-5,6,8,9,10,10a-hexahydropyrimido[5,4-g]indolizin-2-yl)phenyl)urea
(S)-tert-butyl 2-(4-(3-ethylureido)-1H-pyrazol-1-yl)-4-(3-methylmorpholino)-5,6-dihydropyrido[3,4-d]pyrimidine-7(8H)-carboxylate
1-ethyl-3-(4-(4-((S)-3-methylmorpholino)-7-(1-(pyridin-3-yl)ethyl)-5,6,7,8-tetrahydropyrido[3,4-d]pyrimidin-2-yl)phenyl)urea
1-ethyl-3-(4-(7-(2-methoxyethyl)-8-methyl-4-morpholino-5,6,7,8-tetrahydropyrido[3,4-d]pyrimidin-2-yl)phenyl)urea
(S)-1-(isoxazol-3-yl)-3-(4-(7-methyl-4-(3-methylmorpholino)-5,6,7,8-tetrahydropyrido[3,4-d]pyrimidin-2-yl)phenyl)urea
(S)-1-(4-(7-ethyl-4-(3-methylmorpholino)-5,6,7,8-tetrahydropyrido[3,4-d]pyrimidin-2-yl)phenyl)-3-(isoxazol-3-yl)urea
(S)-1-(1-methyl-1H-pyrazol-4-yl)-3-(4-(7-methyl-4-(3-methylmorpholino)-5,6,7,8-tetrahydropyrido[3,4-d]pyrimidin-2-yl)phenyl)urea
(S)-1-(5-methyl-1,3,4-oxadiazol-2-yl)-3-(4-(7-methyl-4-(3-methylmorpholino)-5,6,7,8-tetrahydropyrido[3,4-d]pyrimidin-2-yl)phenyl)urea
(S)-1-(4-(7-ethyl-4-(3-methylmorpholino)-5,6,7,8-tetrahydropyrido[3,4-d]pyrimidin-2-yl)phenyl)-3-(1-methyl-1H-pyrazol-4-yl)urea
(S)-1-(4-(7-ethyl-4-(3-methylmorpholino)-5,6,7,8-tetrahydropyrido[3,4-d]pyrimidin-2-yl)phenyl)-3-(5-methyl-1,3,4-oxadiazol-2-yl)urea
(S)-tert-butyl 4-(3-methylmorpholino)-2-(2-oxo-1,2-dihydroquinolin-6-yl)-5,6-dihydropyrido[3,4-d]pyrimidine-7(8H)-carboxylate
(S)-6-(7-isopropyl-4-(3-methylmorpholino)-5,6,7,8-tetrahydropyrido[3,4-d]pyrimidin-2-yl)quinolin-2(1H)-one
(S)-1-ethyl-3-(4-(4-(3-methylmorpholino)-7-((tetrahydro-2H-pyran-4-yl)methyl)-5,6,7,8-tetrahydropyrido[3,4-d]pyrimidin-2-yl)phenyl)urea
1-(4-((S)-8-(cyanomethyl)-4-((S)-3-methylmorpholino)-5,6,7,8-tetrahydropyrido[3,4-d]pyrimidin-2-yl)phenyl)-3-ethylurea
1-(4-((R)-8-(cyanomethyl)-4-((S)-3-methylmorpholino)-5,6,7,8-tetrahydropyrido[3,4-d]pyrimidin-2-yl)phenyl)-3-ethylurea
1-(4-((R)-8-(cyanomethyl)-7-ethyl-4-((S)-3-methylmorpholino)-5,6,7,8-tetrahydropyrido[3,4-d]pyrimidin-2-yl)phenyl)-3-ethylurea
1-(4-((S)-8-(cyanomethyl)-7-ethyl-4-((S)-3-methylmorpholino)-5,6,7,8-tetrahydropyrido[3,4-d]pyrimidin-2-yl)phenyl)-3-ethylurea
(S)-1-ethyl-3-(4-(7-(2-methoxyethyl)-8-methyl-4-morpholino-5,6,7,8-tetrahydropyrido[3,4-d]pyrimidin-2-yl)phenyl)urea
(R)-1-ethyl-3-(4-(7-(2-methoxyethyl)-8-methyl-4-morpholino-5,6,7,8-tetrahydropyrido[3,4-d]pyrimidin-2-yl)phenyl)urea
(R)-1-ethyl-3-(4-(7-(2-methoxyethyl)-8-methyl-4-morpholino-5,6,7,8-tetrahydropyrido[3,4-d]pyrimidin-2-yl)phenyl)urea
(S)-1-(4-(7-(2-cyclopropylethyl)-4-(3-methylmorpholino)-5,6,7,8-tetrahydropyrido[3,4-d]pyrimidin-2-yl)phenyl)-3-ethylurea
(S)-1-(4-(4-morpholino-8-oxo-5,6,8,9,10,10a-hexahydropyrimido[5,4-g]indolizin-2-yl)phenyl)-3-propylurea
(R)-1-(4-(4-morpholino-8-oxo-5,6,8,9,10,10a-hexahydropyrimido[5,4-g]indolizin-2-yl)phenyl)-3-propylurea
1-(4-((R)-8-(cyanomethyl)-7-isopropyl-4-((S)-3-methylmorpholino)-5,6,7,8-tetrahydropyrido[3,4-d]pyrimidin-2-yl)phenyl)-3-ethylurea
1-(4-((S)-8-(cyanomethyl)-7-isopropyl-4-((S)-3-methylmorpholino)-5,6,7,8-tetrahydropyrido[3,4-d]pyrimidin-2-yl)phenyl)-3-ethylurea
(S)-1-ethyl-3-(4-(7-(1-methyl-2-oxo-1,2-dihydropyridin-4-yl)-4-(3-methylmorpholino)-5,6,7,8-tetrahydropyrido[3,4-d]pyrimidin-2-yl)phenyl)urea
(S)-1-(4-(7-isopropyl-4-(3-methylmorpholino)-5,6,7,8-tetrahydropyrido[3,4-d]pyrimidin-2-yl)phenyl)-3-(1-methyl-1H-pyrazol-4-yl)urea
(S)-1-(4-(7-isopropyl-4-(3-methylmorpholino)-5,6,7,8-tetrahydropyrido[3,4-d]pyrimidin-2-yl)phenyl)-3-(5-methyl-1,3,4-oxadiazol-2-yl)urea
(S)-1-(4-(7-isopropyl-4-(3-methylmorpholino)-5,6,7,8-tetrahydropyrido[3,4-d]pyrimidin-2-yl)phenyl)-3-(5-methylisoxazol-3-yl)urea
(S)-1-(4-(4-(3-methylmorpholino)-8-oxo-6,8-dihydro-5H-pyrimido[4,5-a]quinolizin-2-yl)phenyl)-3-(oxetan-3-yl)urea
(S,E)-tert-butyl 8-(4-ethoxy-4-oxobut-2-enyl)-2-(4-(3-ethylureido)phenyl)-4-morpholino-5,6-dihydropyrido[3,4-d]pyrimidine-7(8H)-carboxylate
(R,E)-tert-butyl 8-(4-ethoxy-4-oxobut-2-enyl)-2-(4-(3-ethylureido)phenyl)-4-morpholino-5,6-dihydropyrido[3,4-d]pyrimidine-7(8H)-carboxylate
(S)-tert-butyl 8-(4-ethoxy-4-oxobutyl)-2-(4-(3-ethylureido)phenyl)-4-morpholino-5,6-dihydropyrido[3,4-d]pyrimidine-7(8H)-carboxylate
(R)-tert-butyl 8-(4-ethoxy-4-oxobutyl)-2-(4-(3-ethylureido)phenyl)-4-morpholino-5,6-dihydropyrido[3,4-d]pyrimidine-7(8H)-carboxylate
(S)-1-(4-(7-((1,3-dioxan-2-yl)methyl)-4-(3-methylmorpholino)-5,6,7,8-tetrahydropyrido[3,4-d]pyrimidin-2-yl)phenyl)-3-ethylurea
1-(4-(7-((1,3-dioxolan-2-yl)methyl)-8-methyl-4-morpholino-5,6,7,8-tetrahydropyrido[3,4-d]pyrimidin-2-yl)phenyl)-3-ethylurea
(S)-1-ethyl-3-(4-(7-(2-fluoro-2-methylpropyl)-4-(3-methylmorpholino)-5,6,7,8-tetrahydropyrido[3,4-d]pyrimidin-2-yl)phenyl)urea
(S)-1-ethyl-3-(4-(4-(3-methylmorpholino)-7-((2-methylpyrimidin-5-yl)methyl)-5,6,7,8-tetrahydropyrido[3,4-d]pyrimidin-2-yl)phenyl)urea TABLE 2-continued (S)-1-ethyl-3-(4-(7-((1-methyl-1H-pyrazol-5-yl)methyl)-4-(3-methylmorpholino)-5,6,7,8-tetrahydropyrido[3,4-d]pyrimidin-2-yl)phenyl)urea
(S)-1-(4-(7-isopropyl-4-(3-methylmorpholino)-5,6,7,8-tetrahydropyrido[3,4-d]pyrimidin-2-yl)phenyl)-3-(isoxazol-3-yl)urea
(S)-1-(4-(7-(5-fluoropyrimidin-2-yl)-4-(3-methylmorpholino)-5,6,7,8-tetrahydropyrido[3,4-d]pyrimidin-2-yl)phenyl)-3-(isoxazol-3-yl)urea
(S)-tert-butyl 2-(3-(hydroxymethyl)-4-methoxyphenyl)-4-(3-methylmorpholino)-5,6-dihydropyrido[3,4-d]pyrimidine-7(8H)-carboxylate
(S)-1-(4-(7-methyl-4-(3-methylmorpholino)-5,6,7,8-tetrahydropyrido[3,4-d]pyrimidin-2-yl)phenyl)-3-(5-methylisoxazol-3-yl)urea
(S)-1-(4-(7-ethyl-4-(3-methylmorpholino)-5,6,7,8-tetrahydropyrido[3,4-d]pyrimidin-2-yl)phenyl)-3-(5-methylisoxazol-3-yl)urea
1-ethyl-3-(4-(7-(1-methoxypropan-2-yl)-4-((S)-3-methylmorpholino)-5,6,7,8-tetrahydropyrido[3,4-d]pyrimidin-2-yl)phenyl)urea
(S)-1-ethyl-3-(4-(4-morpholino-8-oxo-6,8,9,10,11,11a-hexahydro-5H-pyrimido[4,5-a]quinolizin-2-yl)phenyl)urea
(R)-1-ethyl-3-(4-(4-morpholino-8-oxo-6,8,9,10,11,11a-hexahydro-5H-pyrimido[4,5-a]quinolizin-2-yl)phenyl)urea
1-ethyl-3-(4-(4-((S)-3-methylmorpholino)-7-(tetrahydro-2H-pyran-3-yl)-5,6,7,8-tetrahydropyrido[3,4-d]pyrimidin-2-yl)phenyl)urea
1-ethyl-3-(4-(4-((S)-3-methylmorpholino)-7-(tetrahydro-2H-pyran-3-yl)-5,6,7,8-tetrahydropyrido[3,4-d]pyrimidin-2-yl)phenyl)urea
1-(4-(4-(3,3-dimethylmorpholino)-7-(2-methoxyethyl)-5,6,7,8-tetrahydropyrido[3,4-d]pyrimidin-2-yl)phenyl)-3-ethylurea
(S)-tert-butyl 2-(4-(1H-imidazol-2-ylamino)phenyl)-4-(3-methylmorpholino)-5,6-dihydropyrido[3,4-d]pyrimidine-7(8H)-carboxylate
(S)-1-ethyl-3-(4-(7-((1-ethyl-1H-pyrazol-5-yl)methyl)-4-(3-methylmorpholino)-5,6,7,8-tetrahydropyrido[3,4-d]pyrimidin-2-yl)phenyl)urea
1-ethyl-3-(4-(7-((R)-2-hydroxypropyl)-4-((S)-3-methylmorpholino)-5,6,7,8-tetrahydropyrido[3,4-d]pyrimidin-2-yl)phenyl)urea
(S)-1-(4-(7-(2-ethoxyethyl)-4-(3-methylmorpholino)-5,6,7,8-tetrahydropyrido[3,4-d]pyrimidin-2-yl)phenyl)-3-ethylurea
(S)-1-ethyl-3-(4-(7-(3-hydroxy-3-methylbutyl)-4-(3-methylmorpholino)-5,6,7,8-tetrahydropyrido[3,4-d]pyrimidin-2-yl)phenyl)urea
1-ethyl-3-(4-(7-((S)-2-hydroxypropyl)-4-((S)-3-methylmorpholino)-5,6,7,8-tetrahydropyrido[3,4-d]pyrimidin-2-yl)phenyl)urea
1-ethyl-3-(4-(4-((S)-3-methylmorpholino)-7-((R)-tetrahydrofuran-3-yl)-5,6,7,8-tetrahydropyrido[3,4-d]pyrimidin-2-yl)phenyl)urea
1-(4-(7-(((R)-2,2-dimethyl-1,3-dioxolan-4-yl)methyl)-4-((S)-3-methylmorpholino)-5,6,7,8-tetrahydropyrido[3,4-d]pyrimidin-2-yl)phenyl)-3-ethylurea
(S)-tert-butyl 8-(cyanomethyl)-2-(4-(3-ethylureido)phenyl)-4-morpholino-5,6-dihydropyrido[3,4-d]pyrimidine-7(8H)-carboxylate
(R)-tert-butyl 8-(cyanomethyl)-2-(4-(3-ethylureido)phenyl)-4-morpholino-5,6-dihydropyrido[3,4-d]pyrimidine-7(8H)-carboxylate
(S)-1-ethyl-3-(4-(7-((2-methyl-1,3-dioxolan-2-yl)methyl)-4-(3-methylmorpholino)-5,6,7,8-tetrahydropyrido[3,4-d]pyrimidin-2-yl)phenyl)urea
(S)-1-ethyl-3-(4-(7-(2-hydroxyethyl)-4-(3-methylmorpholino)-5,6,7,8-tetrahydropyrido[3,4-d]pyrimidin-2-yl)phenyl)urea
(S)-1-ethyl-3-(4-(7-(3-hydroxypropyl)-4-(3-methylmorpholino)-5,6,7,8-tetrahydropyrido[3,4-d]pyrimidin-2-yl)phenyl)urea
(S)-1-ethyl-3-(4-(7-(3-methoxypropyl)-4-(3-methylmorpholino)-5,6,7,8-tetrahydropyrido[3,4-d]pyrimidin-2-yl)phenyl)urea
(R)-1-(4-(7-((1,3-dioxolan-2-yl)methyl)-8-methyl-4-morpholino-5,6,7,8-tetrahydropyrido[3,4-d]pyrimidin-2-yl)phenyl)-3-ethylurea
(S)-1-(4-(7-((1,3-dioxolan-2-yl)methyl)-8-methyl-4-morpholino-5,6,7,8-tetrahydropyrido[3,4-d]pyrimidin-2-yl)phenyl)-3-ethylurea
(S)-4-(2-(1H-indol-5-yl)-5,6,7,8-tetrahydropyrido[3,4-d]pyrimidin-4-yl)-3-methylmorpholine
(S)-1-ethyl-3-(4-(4-(3-methylmorpholino)-7-(2-(methylsulfonyl)ethyl)-5,6,7,8-tetrahydropyrido[3,4-d]pyrimidin-2-yl)phenyl)urea
(S)-1-(4-(4-morpholino-8-oxo-5,6,8,9,10,10a-hexahydropyrimido[5,4-g]indolizin-2-yl)phenyl)-3-(oxetan-3-yl)urea
(R)-1-(4-(4-morpholino-8-oxo-5,6,8,9,10,10a-hexahydropyrimido[5,4-g]indolizin-2-yl)phenyl)-3-(oxetan-3-yl)urea
(S)-1-(4-(4-(3-methylmorpholino)-7-(6-methylpyrimidin-4-yl)-5,6,7,8-tetrahydropyrido[3,4-d]pyrimidin-2-yl)phenyl)-3-(oxetan-3-yl)urea
1-(4-(4-((1R,5S)-3-oxa-8-azabicyclo[3.2.1]octan-8-yl)-7-(oxetan-3-yl)-5,6,7,8-tetrahydropyrido[3,4-d]pyrimidin-2-yl)phenyl)-3-ethylurea
(S)-1-ethyl-3-(4-(4-(3-methylmorpholino)-7-(1-(pyridin-3-ylmethyl)piperidin-4-yl)-5,6,7,8-tetrahydropyrido[3,4-d]pyrimidin-2-yl)phenyl)urea
(S)-1-(4-(7-(2-cyanoethyl)-4-(3-methylmorpholino)-5,6,7,8-tetrahydropyrido[3,4-d]pyrimidin-2-yl)phenyl)-3-ethylurea
(S)-tert-butyl 2-(1H-indol-5-yl)-4-(3-methylmorpholino)-5,6-dihydropyrido[3,4-d]pyrimidine-7(8H)-carboxylate
1-ethyl-3-(4-(7-(2-methoxypyrimidin-4-yl)-4-morpholino-5,6,7,8-tetrahydropyrido[3,4-d]pyrimidin-2-yl)phenyl)urea
1-ethyl-3-(4-(4-morpholino-7-(oxetan-3-yl)-5,6,7,8-tetrahydropyrido[3,4-d]pyrimidin-2-yl)phenyl)urea
1-(4-(7-((R)-2,3-dihydroxypropyl)-4-((S)-3-methylmorpholino)-5,6,7,8-tetrahydropyrido[3,4-d]pyrimidin-2-yl)phenyl)-3-ethylurea

TABLE 2-continued 1-(4-(4-((1R,5S)-3-oxa-8-azabicyclo[3.2.1]octan-8-yl)-7-(6-methylpyrimidin-4-yl)-5,6,7,8-tetrahydropyrido[3,4-d]pyrimidin-2-yl)phenyl)-3-ethylurea
(S)—N-(4-(7-isopropyl-4-(3-methylmorpholino)-5,6,7,8-tetrahydropyrido[3,4-d]pyrimidin-2-yl)phenyl)-1H-imidazol-2-amine
(S)—N-(4-(4-(3-methylmorpholino)-7-(oxetan-3-yl)-5,6,7,8-tetrahydropyrido[3,4-d]pyrimidin-2-yl)phenyl)-1H-imidazol-2-amine
(S)-1-ethyl-3-(4-(7-(3-fluoropropyl)-4-(3-methylmorpholino)-5,6,7,8-tetrahydropyrido[3,4-d]pyrimidin-2-yl)phenyl)urea
(S)-methyl 3-(2-(4-(3-ethylureido)phenyl)-4-(3-methylmorpholino)-5,6-dihydropyrido[3,4-d]pyrimidin-7(8H)-yl)propanoate
1-(4-(4-((1R,5S)-8-oxa-3-azabicyclo[3.2.1]octan-3-yl)-7-(pyrimidin-2-yl)-5,6,7,8-tetrahydropyrido[3,4-d]pyrimidin-2-yl)phenyl)-3-ethylurea
1-(4-(4-((1R,5S)-8-oxa-3-azabicyclo[3.2.1]octan-3-yl)-7-(6-methylpyrimidin-4-yl)-5,6,7,8-tetrahydropyrido[3,4-d]pyrimidin-2-yl)phenyl)-3-ethylurea
1-(4-(4-((1R,5S)-8-oxa-3-azabicyclo[3.2.1]octan-3-yl)-7-(oxetan-3-yl)-5,6,7,8-tetrahydropyrido[3,4-d]pyrimidin-2-yl)phenyl)-3-ethylurea
1-(4-(4-((1R,5S)-8-oxa-3-azabicyclo[3.2.1]octan-3-yl)-7-isopropyl-5,6,7,8-tetrahydropyrido[3,4-d]pyrimidin-2-yl)phenyl)-3-ethylurea
1-ethyl-3-(4-(8-methyl-4-morpholino-7-(oxetan-3-yl)-5,6,7,8-tetrahydropyrido[3,4-d]pyrimidin-2-yl)phenyl)urea
(S)-1-ethyl-3-(4-(8-methyl-4-morpholino-7-(oxetan-3-yl)-5,6,7,8-tetrahydropyrido[3,4-d]pyrimidin-2-yl)phenyl)urea
(R)-1-ethyl-3-(4-(8-methyl-4-morpholino-7-(oxetan-3-yl)-5,6,7,8-tetrahydropyrido[3,4-d]pyrimidin-2-yl)phenyl)urea
1-ethyl-3-(4-(4-(2-methylmorpholino)-7-(oxetan-3-yl)-5,6,7,8-tetrahydropyrido[3,4-d]pyrimidin-2-yl)phenyl)urea
tert-butyl 4-((1R,5S)-8-oxa-3-azabicyclo[3.2.1]octan-3-yl)-2-(4-(3-ethylureido)phenyl)-5,6-dihydropyrido[3,4-d]pyrimidine-7(8H)-carboxylate
(S)-4-(2-(1H-indol-5-yl)-7-(1-(pyridin-3-ylmethyl)piperidin-4-yl)-5,6,7,8-tetrahydropyrido[3,4-d]pyrimidin-4-yl)-3-methylmorpholine
1-(4-(4-((1R,5S)-3-oxa-8-azabicyclo[3.2.1]octan-8-yl)-7-isopropyl-5,6,7,8-tetrahydropyrido[3,4-d]pyrimidin-2-yl)phenyl)-3-ethylurea
1-ethyl-3-(4-(4'-morpholino-6',8'-dihydro-5'H-spiro[oxetane-3,7'-pyrido[4,3-d]pyrimidine]-2'-yl)phenyl)urea
allyl 2'-(4-(3-ethylureido)phenyl)-4'-morpholino-5'H-spiro[oxetane-3,7'-pyrido[4,3-d]pyrimidine]-6'(8'H)-carboxylate
1-ethyl-3-(4-(6'-methyl-4'-morpholino-6',8'-dihydro-5'H-spiro[oxetane-3,7'-pyrido[4,3-d]pyrimidine]-2'-yl)phenyl)urea
(S)-1-(4-(7-(6-chloro-2-methylpyrimidin-4-yl)-4-(3-methylmorpholino)-5,6,7,8-tetrahydropyrido[3,4-d]pyrimidin-2-yl)phenyl)-3-(isoxazol-3-yl)urea
(S)-1-(4-(7-(2-chloro-6-methylpyrimidin-4-yl)-4-(3-methylmorpholino)-5,6,7,8-tetrahydropyrido[3,4-d]pyrimidin-2-yl)phenyl)-3-(isoxazol-3-yl)urea
(S)-1-ethyl-3-(4-(4-(3-methylmorpholino)-7-((3-methyloxetan-3-yl)methyl)-5,6,7,8-tetrahydropyrido[3,4-d]pyrimidin-2-yl)phenyl)urea
(S)-tert-butyl 2-(4-(3-ethylureido)phenyl)-8-(2-hydroxyethyl)-4-morpholino-5,6-dihydropyrido[3,4-d]pyrimidine-7(8H)-carboxylate
(S)-tert-butyl 2-(4-(3-ethylureido)phenyl)-8-(2-hydroxyethyl)-4-morpholino-5,6-dihydropyrido[3,4-d]pyrimidine-7(8H)-carboxylate
(R)-tert-butyl 2-(4-(3-ethylureido)phenyl)-8-(2-hydroxyethyl)-4-morpholino-5,6-dihydropyrido[3,4-d]pyrimidine-7(8H)-carboxylate
(S)-1-ethyl-3-(4-(8-(2-hydroxyethyl)-4-morpholino-5,6,7,8-tetrahydropyrido[3,4-d]pyrimidin-2-yl)phenyl)urea
(R)-1-ethyl-3-(4-(8-(2-hydroxyethyl)-4-morpholino-5,6,7,8-tetrahydropyrido[3,4-d]pyrimidin-2-yl)phenyl)urea
(S)-1-(4-(7-(2-(dimethylamino)pyrimidin-4-yl)-4-(3-methylmorpholino)-5,6,7,8-tetrahydropyrido[3,4-d]pyrimidin-2-yl)phenyl)-3-ethylurea
(S)-1-(4-(7-(2,6-dimethoxypyrimidin-4-yl)-8-methyl-4-morpholino-5,6,7,8-tetrahydropyrido[3,4-d]pyrimidin-2-yl)phenyl)-3-ethylurea
(R)-1-(4-(7-(2,6-dimethoxypyrimidin-4-yl)-8-methyl-4-morpholino-5,6,7,8-tetrahydropyrido[3,4-d]pyrimidin-2-yl)phenyl)-3-ethylurea
(S)-1-(4-(7-(2-chloro-6-methylpyrimidin-4-yl)-8-methyl-4-morpholino-5,6,7,8-tetrahydropyrido[3,4-d]pyrimidin-2-yl)phenyl)-3-ethylurea
(R)-1-(4-(7-(2-chloro-6-methylpyrimidin-4-yl)-8-methyl-4-morpholino-5,6,7,8-tetrahydropyrido[3,4-d]pyrimidin-2-yl)phenyl)-3-ethylurea
1-(4-(7-(2,6-dimethylpyrimidin-4-yl)-4-morpholino-5,6,7,8-tetrahydropyrido[3,4-d]pyrimidin-2-yl)phenyl)-3-ethylurea
(R)-1-(4-(7-(2,6-dimethylpyrimidin-4-yl)-8-methyl-4-morpholino-5,6,7,8-tetrahydropyrido[3,4-d]pyrimidin-2-yl)phenyl)-3-ethylurea
(S)-1-(4-(7-(2,6-dimethylpyrimidin-4-yl)-8-methyl-4-morpholino-5,6,7,8-tetrahydropyrido[3,4-d]pyrimidin-2-yl)phenyl)-3-ethylurea
(S)-1-(4-(7-(4-chloro-6-methylpyrimidin-2-yl)-8-methyl-4-morpholino-5,6,7,8-tetrahydropyrido[3,4-d]pyrimidin-2-yl)phenyl)-3-ethylurea
(R)-1-(4-(7-(4-chloro-6-methylpyrimidin-2-yl)-8-methyl-4-morpholino-5,6,7,8-tetrahydropyrido[3,4-d]pyrimidin-2-yl)phenyl)-3-ethylurea
(S)-1-(isoxazol-3-yl)-3-(4-(4-(3-methylmorpholino)-7-(2-methylpyrimidin-4-yl)-5,6,7,8-tetrahydropyrido[3,4-d]pyrimidin-2-yl)phenyl)urea
(S)-1-isopropyl-3-(4-(4-(3-methylmorpholino)-7-(oxetan-3-yl)-5,6,7,8-tetrahydropyrido[3,4-d]pyrimidin-2-yl)phenyl)urea
(S)-1-(3-fluoropropyl)-3-(4-(4-(3-methylmorpholino)-7-(oxetan-3-yl)-5,6,7,8-tetrahydropyrido[3,4-d]pyrimidin-2-yl)phenyl)urea TABLE 2-continued (S)-1-(isoxazol-3-yl)-3-(4-(4-(3-methylmorpholino)-7-(oxetan-3-yl)-5,6,7,8-tetrahydropyrido[3,4-d]pyrimidin-2-yl)phenyl)urea
(S)-1-ethyl-3-(4-(8-(2-hydroxyethyl)-7-(2-methylpyrimidin-4-yl)-4-morpholino-5,6,7,8-tetrahydropyrido[3,4-d]pyrimidin-2-yl)phenyl)urea
(R)-1-ethyl-3-(4-(8-(2-hydroxyethyl)-7-(2-methylpyrimidin-4-yl)-4-morpholino-5,6,7,8-tetrahydropyrido[3,4-d]pyrimidin-2-yl)phenyl)urea
(S)-1-ethyl-3-(4-(8-(2-hydroxyethyl)-7-(2-methoxyethyl)-4-morpholino-5,6,7,8-tetrahydropyrido[3,4-d]pyrimidin-2-yl)phenyl)urea
(R)-1-ethyl-3-(4-(8-(2-hydroxyethyl)-7-(2-methoxyethyl)-4-morpholino-5,6,7,8-tetrahydropyrido[3,4-d]pyrimidin-2-yl)phenyl)urea
1-ethyl-3-(4-(8-(2-hydroxyethyl)-7-(6-methylpyrimidin-4-yl)-4-morpholino-5,6,7,8-tetrahydropyrido[3,4-d]pyrimidin-2-yl)phenyl)urea
1-(isoxazol-3-yl)-3-(4-(4'-morpholino-6',8'-dihydro-5'H-spiro[oxetane-3,7'-pyrido[4,3-d]pyrimidine]-2'-yl)phenyl)urea
(S)-1-ethyl-3-(4-(8-methyl-7-(6-methylpyrimidin-4-yl)-4-morpholino-5,6,7,8-tetrahydropyrido[3,4-d]pyrimidin-2-yl)phenyl)urea
(R)-1-ethyl-3-(4-(8-methyl-7-(6-methylpyrimidin-4-yl)-4-morpholino-5,6,7,8-tetrahydropyrido[3,4-d]pyrimidin-2-yl)phenyl)urea
(S)-1-ethyl-3-(4-(7-(5-fluoropyrimidin-2-yl)-8-methyl-4-morpholino-5,6,7,8-tetrahydropyrido[3,4-d]pyrimidin-2-yl)phenyl)urea
(R)-1-ethyl-3-(4-(7-(5-fluoropyrimidin-2-yl)-8-methyl-4-morpholino-5,6,7,8-tetrahydropyrido[3,4-d]pyrimidin-2-yl)phenyl)urea
(S)-1-(5-methyl-1,3,4-oxadiazol-2-yl)-3-(4-(4-(3-methylmorpholino)-7-(oxetan-3-yl)-5,6,7,8-tetrahydropyrido[3,4-d]pyrimidin-2-yl)phenyl)urea
(S)-1-(5-methylisoxazol-3-yl)-3-(4-(4-(3-methylmorpholino)-7-(oxetan-3-yl)-5,6,7,8-tetrahydropyrido[3,4-d]pyrimidin-2-yl)phenyl)urea
(S)-1-(1-methyl-1H-pyrazol-4-yl)-3-(4-(4-(3-methylmorpholino)-7-(oxetan-3-yl)-5,6,7,8-tetrahydropyrido[3,4-d]pyrimidin-2-yl)phenyl)urea
1-ethyl-3-(4-(6'-ethyl-4'-morpholino-6',8'-dihydro-5'H-spiro[oxetane-3,7'-pyrido[4,3-d]pyrimidine]-2'-yl)phenyl)urea
1-(isoxazol-3-yl)-3-(4-(6'-methyl-4'-morpholino-6',8'-dihydro-5'H-spiro[oxetane-3,7'-pyrido[4,3-d]pyrimidine]-2'-yl)phenyl)urea
(S)-1-ethyl-3-(4-(8-methyl-4-morpholino-7-(pyrimidin-2-ylmethyl)-5,6,7,8-tetrahydropyrido[3,4-d]pyrimidin-2-yl)phenyl)urea
(R)-1-ethyl-3-(4-(8-methyl-4-morpholino-7-(pyrimidin-2-ylmethyl)-5,6,7,8-tetrahydropyrido[3,4-d]pyrimidin-2-yl)phenyl)urea
(R)-1-(4-(7-(5-cyanopyridin-2-yl)-8-methyl-4-morpholino-5,6,7,8-tetrahydropyrido[3,4-d]pyrimidin-2-yl)phenyl)-3-ethylurea
1-ethyl-3-(4-(4-((S)-3-methylmorpholino)-7-((S)-tetrahydrofuran-3-yl)-5,6,7,8-tetrahydropyrido[3,4-d]pyrimidin-2-yl)phenyl)urea
1-ethyl-3-(4-(4-((S)-3-methylmorpholino)-7-((S)-tetrahydrofuran-3-yl)-5,6,7,8-tetrahydropyrido[3,4-d]pyrimidin-2-yl)phenyl)urea
(S)-1-ethyl-3-(4-(4-(3-methylmorpholino)-7-(3-oxocyclohex-1-enyl)-5,6,7,8-tetrahydropyrido[3,4-d]pyrimidin-2-yl)phenyl)urea
(S)-1-ethyl-3-(4-(4-(3-methylmorpholino)-7-(6-methylpyridazin-3-yl)-5,6,7,8-tetrahydropyrido[3,4-d]pyrimidin-2-yl)phenyl)urea
(S)-1-(4-(4-(3-methylmorpholino)-7-(oxetan-3-yl)-5,6,7,8-tetrahydropyrido[3,4-d]pyrimidin-2-yl)phenyl)-3-(oxetan-3-yl)urea
1-ethyl-3-(4-(4-(2-(methoxymethyl)morpholino)-7-methyl-5,6,7,8-tetrahydropyrido[3,4-d]pyrimidin-2-yl)phenyl)urea
(S)-1-(4-(7-(2,6-dimethylpyrimidin-4-yl)-4-(3-methylmorpholino)-5,6,7,8-tetrahydropyrido[3,4-d]pyrimidin-2-yl)phenyl)-3-ethylurea
(S)-1-ethyl-3-(4-(7-(1-methylazetidin-3-yl)-4-(3-methylmorpholino)-5,6,7,8-tetrahydropyrido[3,4-d]pyrimidin-2-yl)phenyl)urea
(S)-1-ethyl-3-(4-(7-(1-methyl-6-oxo-1,6-dihydropyridin-3-yl)-4-(3-methylmorpholino)-5,6,7,8-tetrahydropyrido[3,4-d]pyrimidin-2-yl)phenyl)urea
(S)-1-ethyl-3-(4-(4-(3-methylmorpholino)-7-(3-oxocyclopent-1-enyl)-5,6,7,8-tetrahydropyrido[3,4-d]pyrimidin-2-yl)phenyl)urea
1-ethyl-3-(4-(7-((S)-2-methoxypropyl)-4-((S)-3-methylmorpholino)-5,6,7,8-tetrahydropyrido[3,4-d]pyrimidin-2-yl)phenyl)urea
(S)-1-methyl-3-(4-(4-(3-methylmorpholino)-7-(oxetan-3-yl)-5,6,7,8-tetrahydropyrido[3,4-d]pyrimidin-2-yl)phenyl)urea
(S)-1-ethyl-3-(4-(4-(3-methylmorpholino)-7-(5-oxo-2,5-dihydrofuran-3-yl)-5,6,7,8-tetrahydropyrido[3,4-d]pyrimidin-2-yl)phenyl)urea
(R)-tert-butyl 8-ethyl-2-(4-(3-ethylureido)phenyl)-4-morpholino-5,6-dihydropyrido[3,4-d]pyrimidine-7(8H)-carboxylate
(S)-tert-butyl 8-ethyl-2-(4-(3-ethylureido)phenyl)-4-morpholino-5,6-dihydropyrido[3,4-d]pyrimidine-7(8H)-carboxylate
(S)-1-ethyl-3-(4-(4-(3-methylmorpholino)-7-(pyridazin-3-yl)-5,6,7,8-tetrahydropyrido[3,4-d]pyrimidin-2-yl)phenyl)urea
(S)-1-(4-(7-(6-chloropyridazin-3-yl)-4-(3-methylmorpholino)-5,6,7,8-tetrahydropyrido[3,4-d]pyrimidin-2-yl)phenyl)-3-ethylurea
(S)-1-(4-(7-(azetidin-3-yl)-4-(3-methylmorpholino)-5,6,7,8-tetrahydropyrido[3,4-d]pyrimidin-2-yl)phenyl)-3-ethylurea
(S)-1-(3,4-difluorophenyl)-3-(4-(4-(3-methylmorpholino)-7-(oxetan-3-yl)-5,6,7,8-tetrahydropyrido[3,4-d]pyrimidin-2-yl)phenyl)urea TABLE 2-continued (S)-1-ethyl-3-(4-(7-(6-methoxypyridazin-3-yl)-4-(3-methylmorpholino)-5,6,7,8-
tetrahydropyrido[3,4-d]pyrimidin-2-yl)phenyl)urea
(S)-1-(isoxazol-3-yl)-3-(4-(4-(3-methylmorpholino)-7-(6-methylpyrimidin-4-yl)-5,6,7,8-
tetrahydropyrido[3,4-d]pyrimidin-2-yl)phenyl)urea In a forty-third embodiment, compounds of the invention are selected from the group set forth in FIG. 3A, FIG. 3B, FIG. 3C, FIG. 3D and FIG. 3E.

In a forty-fourth embodiment, and within certain aspects of the first, second, third or ninth embodiment, the A ring is a ring selected from the group consisting of morpholin-4-yl, 3-(S)-methyl-morpholin-4-yl, 3-(S)-ethyl-morpholin-4-yl.

The various combinations the embodiments of the recited members (e.g, $R^1$, $R^2$, A, B and D) in Formula I described above, are provided for illustrative purposes only, i.e., to illustrate certain sub-genuses of compounds of the invention, and is not meant to excludes other combinations. In fact, other combination of the embodiments of the recited members of Formula I (e.g., $R^1$, $R^2$, A, B and D) described above would be recognized by a skilled artisan and are also within the scope of the present invention.

Also falling within the scope of this invention are the in vivo metabolic products of Formula I described herein or any subgenus (e.g., Formula I-a to Formula I-I; and Formula I-A to Formula I-S) or species thereof. The invention includes metabolites of compounds of Formula I, including compounds produced by a process comprising contacting a compound of this invention with a mammal for a period of time sufficient to yield a metabolic product thereof.

Also falling with in the scope of the invention, are pharmaceutically acceptable prodrugs of compounds of Formula I described herein or any subgenus (e.g., Formula I-a to Formula I-I; and Formula I-A to Formula I-S) or species thereof.

II.B Synthesis of Compounds

As shown in the Examples section below, there are a variety of synthetic routes by which a skilled artisan can prepare compounds and intermediates of the present invention. Schemes 1 illustrate several methods for the preparation of compounds of the invention. In each of the Schemes described below, P or P' each represents a protecting group, Q is a heteroatom, X is a leaving group, such as a halogen, (H)Ar is an aryl or heteroaryl group that is optionally substituted with non-interfering substitutents, HAr is a heteroaryl group that is optionally substituted with non-interfering substituents, the subscript n, at each occurrence, is independently an integer from 0 to 2, and non-interfering substitutents are provided as —R, —R', —R" and —R''', in which —R and —R' are combined to form a heterocyclic ring comprising an oxygen atom; or any two R groups are combined to form a ring.

Scheme 1 illustrates the synthesis of compounds of the invention in which Suzuki-cross coupling conditions can used to mediate the coupling of pyrimidine 1b to an aryl boronate ester/boronic acid to produce 2-aryl substituted pyrimidine derivatives 1c. For a detailed review of Suzuki coupling procedures, see Suzuki, A. J. Organometallic Chem. 1999, 576, 147-168. Deprotection of 1c to remove an amino protecting group (P) will provide the secondary amine product 1d, which can be subsequently used in a nucleophilic substitution reaction with HAr—X, in the presence of a weak base, e.g., Hunig's base, triethylamine, pyridine, $K_2CO_3$) to provide compound 1e.

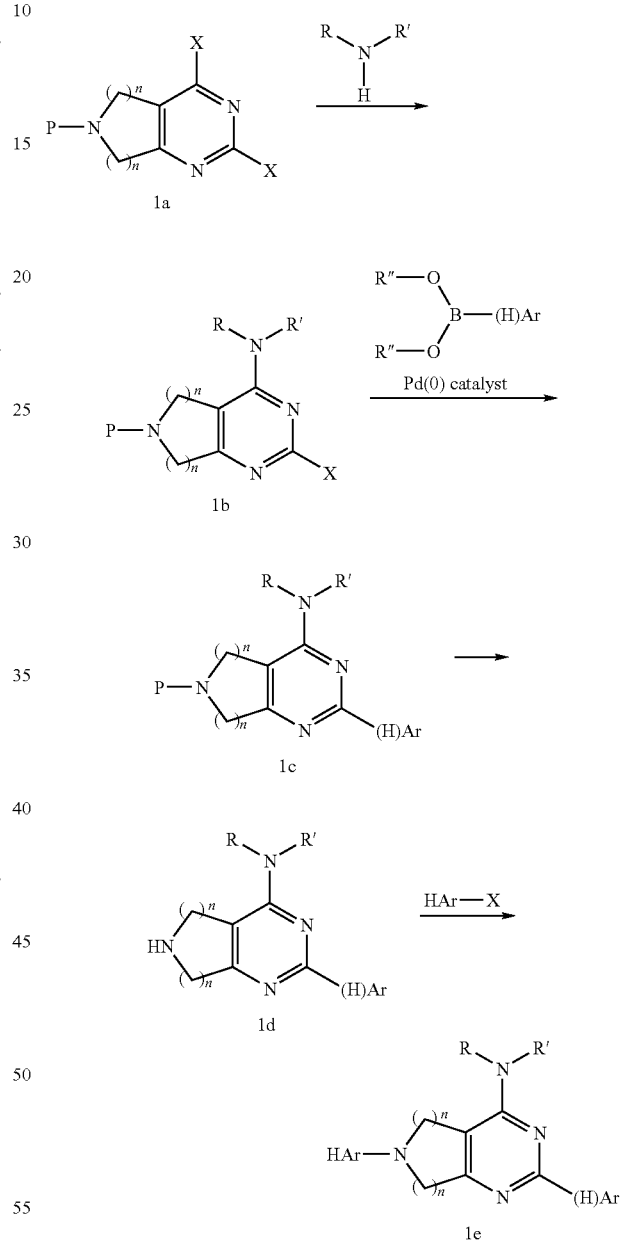

Scheme 2 illustrates several methods to substitute on the secondary nitrogen atom of 1d. For example, reaction of 1d with an acyl halide in the presence of a weak base, such as triethylamine, will provide the amide product $1e^1$; reaction of 1d with an chloroformate derivative in the presence of a base, will provide carbamate $1e^2$; reaction of 1d will an aldehyde under reactive alkylation conditions will provide tertiary amine $1e^3$, reaction of 1d with R''''—X, wherein X is a leaving group will provide the product $1e^4$.

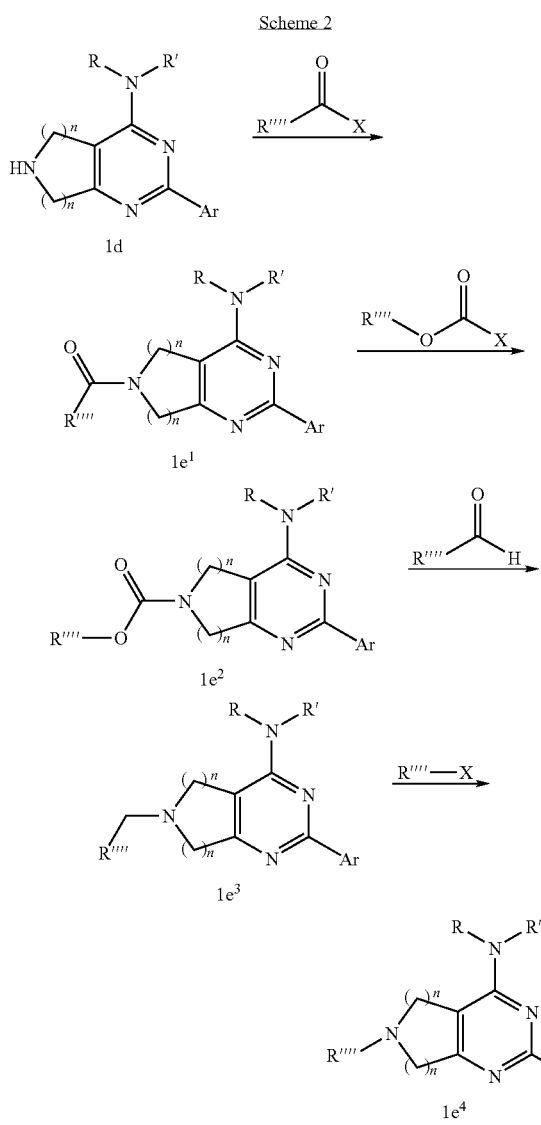

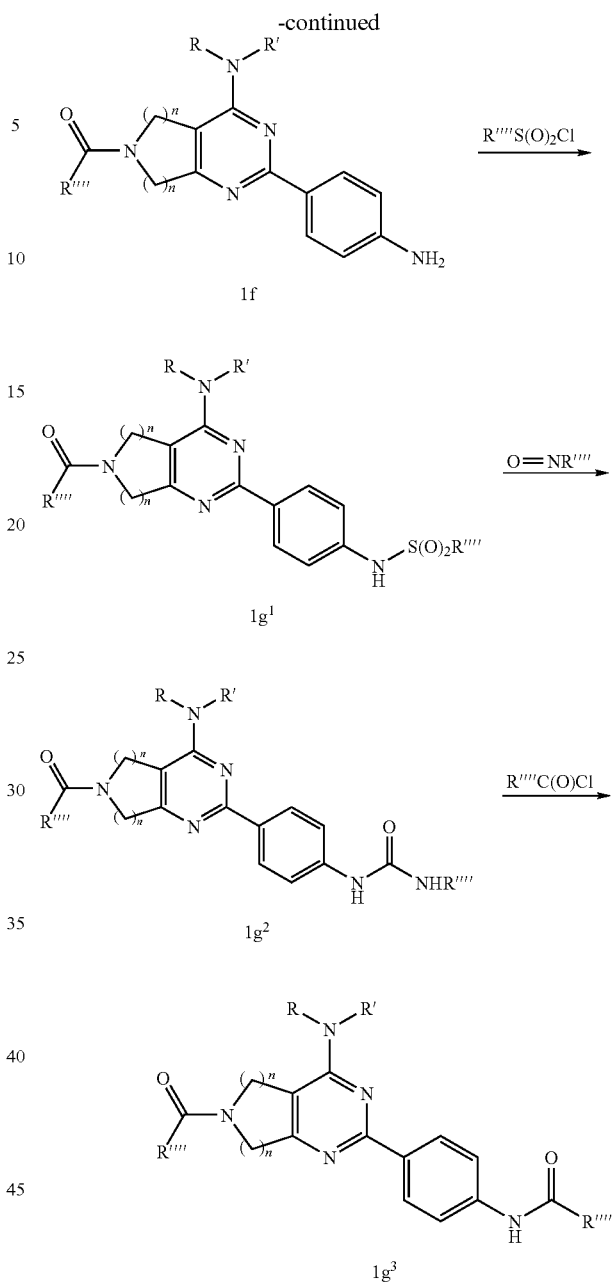

Scheme 3 illustrates several methods to derivative the Ar group located off the 2-position of the pyrimidine ring. As shown herein, hydrogenation of a nitro compound 1e⁴ will provide a free primary amine derivative 1f. Compound 1f can then react with various electrophile, e.g., sulfonyl chloride, isocyanates, acyl halides, respectively, to provide the corresponding, sulfonamide $1g^1$, urea, $1g^2$ and amide $1g^3$.

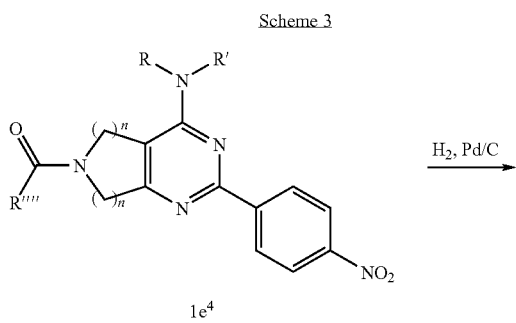

Scheme 4 illustrates a method for preparing N-heterocyclic fused pyrimidines intermediates useful to prepare compounds of the invention. In Scheme 4, a N-heterocyclic beta-ketoester was can be condensed with urea to form the pyrimidine-dione ring product 1i ring. Compound 1i can be converted to the dichloro product 1j upon treatment with a chlorinating agent such as, for example, POCl₃. Displacement of the chloride group on compound 1j with a N-heterocyclic amine can produce compound 1k. In Scheme 4, two occurrences of a R group on a reactant/product are optionally combined to be a ring. Thus, for example, in certain compounds represented by compound 1h, two R groups can be combined to form a ring. Therefore compound 1h also represents bicyclic and spirocyclic variants of compound 1h. Compound 1k can be further elaborated in to other compounds of the invention by processes described in Schemes 1, 2, and 3 and in the Examples herein.

Scheme 4

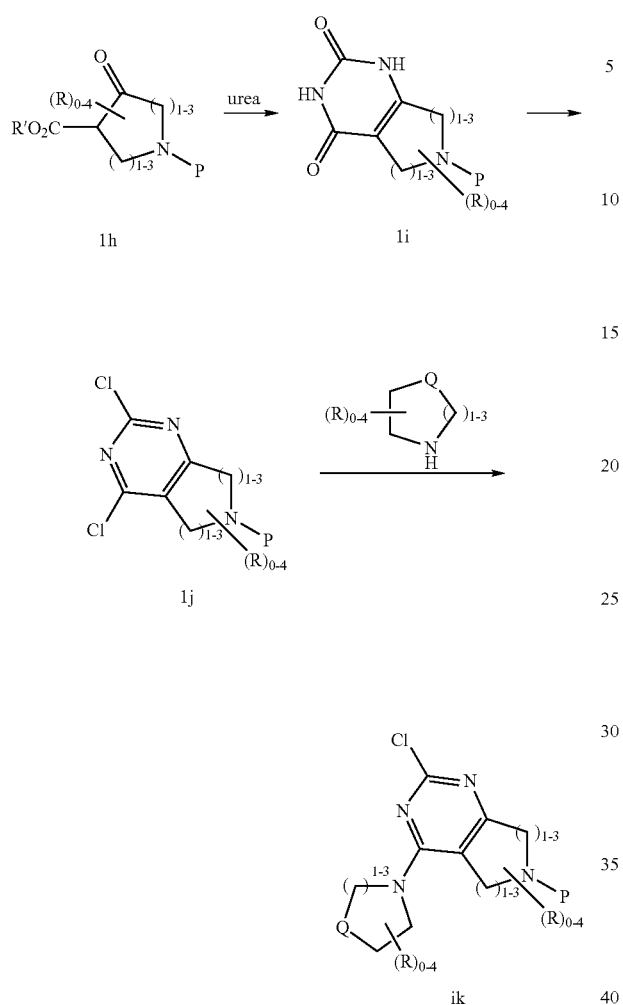

Scheme 5 illustrates a method to prepare certain N-heterocylic fused pyridine intermediates useful for preparing compounds of the invention. The carbonyl group of diketo-ester compounds 11 can be condensed with ammonia (e.g., from ammonium formate) for produce compound 1m, which can be reacted with diazotized using sodium nitrate to produce the dihydroxypyrimidine product 1o. Chlorination of compound 1o using, for example POCl₃, can produce the N-heterocyclic fused pyrimidine product 1p. In Scheme 5, two occurrences of a R group on a reactant/product are optionally combined to be a ring. Thus, for example, in certain compounds represented by compound 11, two R groups can be combined to form a ring. Therefore compound 11 also represents bicyclic and spirocyclic variants of compound 11.

Scheme 5

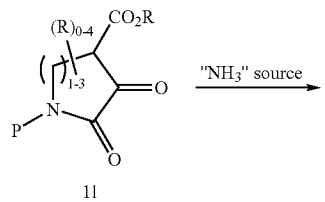

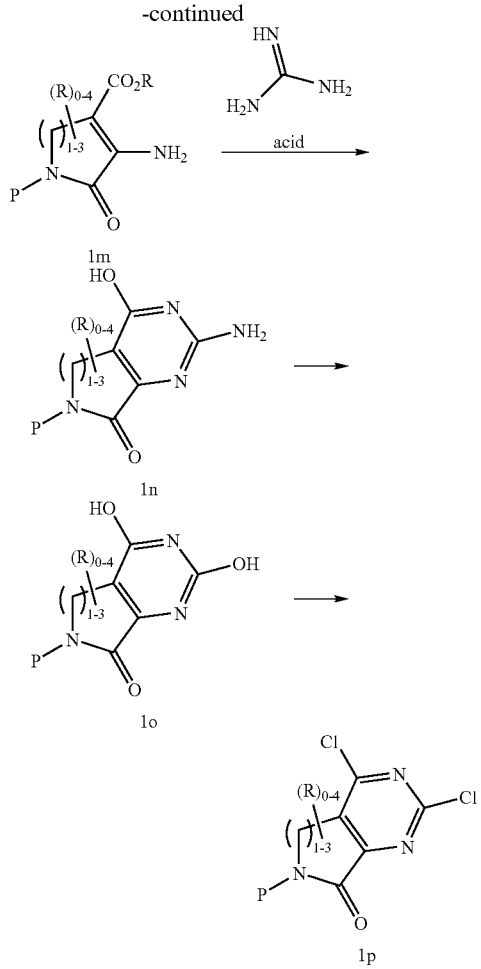

As shown in Scheme 6, N-heterocyclic fused pyrimide product 1p can also be prepare by direct benylic oxidation of compound 1j, using a suitable oxidant such as sodium periodate.

Scheme 6

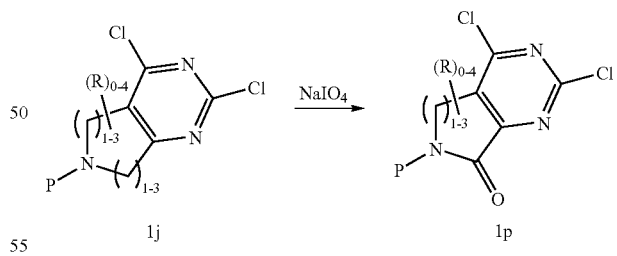

Scheme 7 illustrates a synthetic method for preparing N-heterocyclic fused pyrimidines of the invention. As outlined herein, an aryl or heteroaryl cyanide 1q can be reacted with ammonia to produce the aryl or heteroaryl amidine compound 1r which can then be condensed with beta-ketoester 1h to produce the 2-aryl or 2-heteroaryl pyrimidinone product 1s which can be chlorinated to produce compound 1t. Displacement of the chloride group on 1t with a heterocyclic amine will provide for the 4-N-heterocyclic substituted products, i.e., compound 1u. In Scheme 7, two occurrences of a R group on a reactant/product are optionally combined to be a ring.

Thus, for example, in certain compounds represented by compound 1h, two R groups can be combined to form a ring. Therefore compound 1h also represents bicyclic and spirocyclic variants of compound 1h.

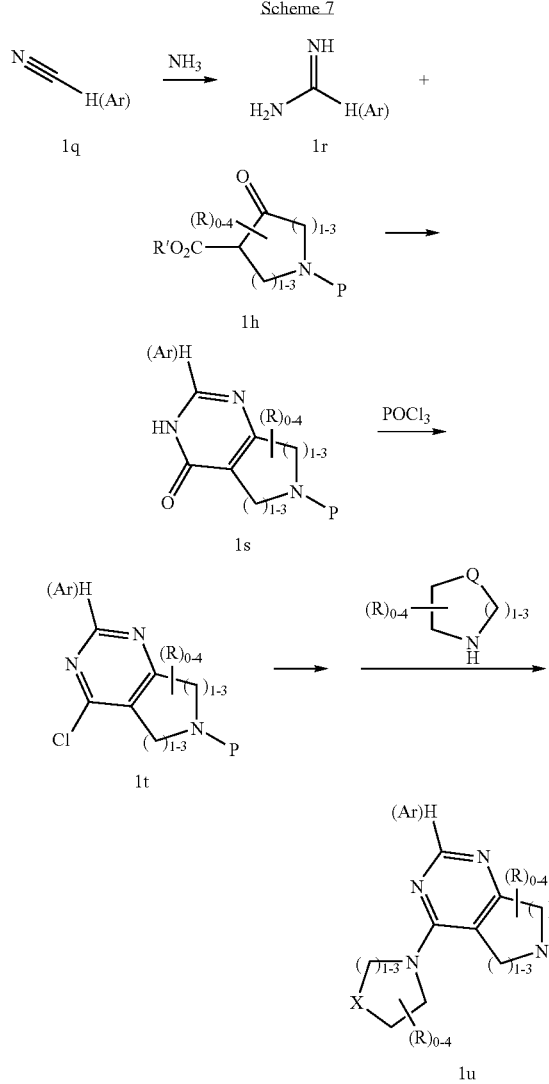

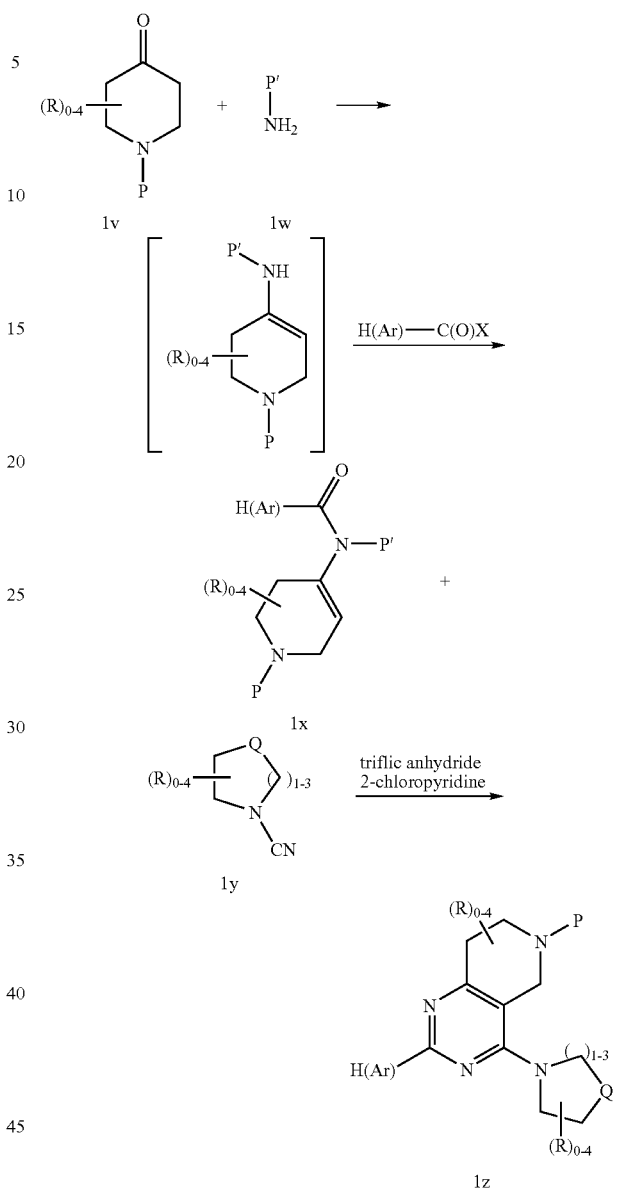

As shown in Scheme 8, N-heterocyclic fused pyrimidine compounds of the invention can be prepared a modified procedure described by Movassaghi and Hill, J. Am. Chem. Soc., 2006, 128 (44), 14254-14255, in which a ketone, such as piperidone 1v is reacted with the protected amine P′—NH$_2$ to form an enamine intermediate that is acylated with an aryl or heteroaryl acylating reagent, such as for example, a para-nitro benzoyl chloride to form the acyl-enamine 1x. Compound 1x can be reacted with a N-cyano-heterocyclic compound 1y in the presence of triflic anhydride and 2-chloropyridine to for the N-heterocyclic fused pyrimidine product 1z. In Scheme 8, two occurrences of a R group on a reactant/product are optionally combined to be a ring. Thus, for example, in certain compounds represented by compound 1v or 1y, two R groups if present on 1v or 1y can be combined to form a ring. Therefore compound 1v and 1y also represents bicyclic and spirocyclic variants of compound 1v and 1y.

III Pharmaceutical Compositions

In addition to one or more of the compounds provided above (or stereoisomers, geometric isomers, tautomers, solvates, metabolites or pharmaceutically acceptable salts, or prodrugs thereof), compositions for modulating mTOR activity in humans and animals will typically contain a pharmaceutical carrier, diluent or excipient.

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention (e.g., a compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S) in association with a pharmaceutically acceptable carrier, diluent or excipient.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

The pharmaceutical composition (or formulation) for application can be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container can also include a tamper-proof assemblage to prevent indiscreet access to the contents of the package. In addition, the container has deposited thereon a label that describes the contents of the container. The label can also include appropriate warnings.

Pharmaceutical formulations of a compound of the present invention can be prepared for various routes and types of administration. For example, a compound of the invention (e.g., a compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S) having the desired degree of purity can optionally be mixed with pharmaceutically acceptable diluents, carriers, excipients or stabilizers (see, Remington: The Science and Practice of Pharmacy: Remington the Science and Practice of Pharmacy (2005) $21^{st}$ Edition, Lippincott Williams & Wilkins, Philadelphia, Pa.), in the form of a lyophilized formulation, milled powder, or an aqueous solution. Formulation can be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but can range from about 3 to about 8. Formulation in an acetate buffer at pH 5 is a suitable embodiment.

A compound of this invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S) for use herein is preferably sterile. In particular, formulations to be used for in vivo administration must be sterile. Such sterilization is readily accomplished by filtration through sterile filtration membranes.

A compound of the invention ordinarily can be stored as a solid composition, a lyophilized formulation or as an aqueous solution.

A pharmaceutical composition of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of an inhibitor compound of the invention administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). An active pharmaceutical ingredient of the invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) 21$^{st}$ Edition, Lippincott Williams & Wilkins, and Philadelphia, Pa.

Sustained-release preparations of a compound of the invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S) can be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773, 919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) 21$^{st}$ Edition, Lippincott Williams & Wilkins, Philadelphia, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of the invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base.

If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of a compound of the invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

A pharmaceutical composition of a compound of the invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment or prophylaxis disorders as described below.

Formulations suitable for vaginal administration can be presented as pessaries, tampons, creams, gels, pastes, foams or spray formulations containing in addition to the active ingredient such carriers as are known in the art to be appropriate.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S) as above defined together with a veterinary carrier therefore. Veterinary carriers are materials useful for the purpose of administering the composition and can be solid, liquid or gaseous materials which are otherwise inert or acceptable in the veterinary art and are compatible with the active ingredient. These veterinary compositions can be administered parenterally, orally or by any other desired route.

IV Methods of Use

In another aspect, the present invention provides for a compound of the invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S), or a stereoisomer, geometric isomer, tautomer, solvate, metabolite, or pharmaceutically acceptable salt, prodrug thereof that inhibits the activity of mTOR kinase. In one embodiment, a compound of the invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S), or a stereoisomer, geometric isomer, tautomer, solvate, metabolite, or pharmaceutically acceptable salt, prodrug thereof inhibits the activity of mTORC1 and mTORC2. In another embodiment, a compound of the invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P and I-Q), or a stereoisomer, geometric isomer, tautomer, solvate, metabolite, or pharmaceutically acceptable salt, prodrug thereof, inhibits the activity of mTORC1. In another embodiment, a compound of the invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S), or a stereoisomer, geometric isomer, tautomer, solvate, metabolite, or pharmaceutically acceptable salt, prodrug thereof, inhibits the activity of mTORC2. In each of the above embodiment, in one particular aspect, a compound of the invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S), or stereoisomer, geometric isomer, tautomer, solvate, metabolite, or pharmaceutically acceptable salt, or prodrug thereof, is formulated as a pharmaceutical composition.

The present invention further provides for a method of inhibiting the activity of mTOR in a cell, comprising contacting said cell with an effective amount of an active compound of the invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S), or a stereoisomer, geometric isomer, tautomer, solvate, metabolite, or pharmaceutically acceptable salt or prodrug thereof. Such a method can be practiced in vitro or in vivo.

A compound of the present invention, or stereoisomer, geometric isomer, tautomer, solvate, metabolite, or pharmaceutically acceptable salt, prodrug thereof, is useful for treating diseases, conditions and/or disorders including, but not limited to, those characterized by over expression of PIKK kinases, e.g. mTOR kinase. Accordingly, another aspect of this invention includes methods of treating diseases or conditions that can be treated by inhibiting mTOR kinase. In one embodiment, the method comprises administering to a mammal in need thereof a therapeutically effective amount of a compound of the invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S), or a stereoisomer, geometric isomer, tautomer, solvate, metabolite, or pharmaceutically acceptable salt or prodrug thereof. In the above embodiment, in one particular aspect, a compound of the invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S), or stereoisomer, geometric isomer, tautomer, solvate, metabolite, or pharmaceutically acceptable salt, prodrug thereof, is formulated as a pharmaceutical composition.

The compounds of the invention can be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds can be administered by intralesional administration, including perfusing or otherwise contacting the graft with the inhibitor before transplantation. It will be appreciated that the preferred route can vary with for example the condition of the recipient. Where the compound is administered orally, it can be formulated as a pill, capsule, tablet, etc. with a pharmaceutically acceptable carrier or excipient. Where the compound is administered parenterally, it can be formulated with a pharmaceutically acceptable parenteral vehicle and in a unit dosage injectable form, as detailed below.

A dose to treat human patients can range from about 10 mg to about 1000 mg of a Formula I compound. A typical dose can be about 100 mg to about 300 mg of the compound. A dose can be administered once a day (QID), twice per day (BID), or more frequently, depending on the pharmacokinetic and pharmacodynamic properties, including absorption, distribution, metabolism, and excretion of the particular compound. In addition, toxicity factors can influence the dosage and administration regimen. When administered orally, the pill, capsule, or tablet can be ingested daily or less frequently for a specified period of time. The regimen can be repeated for a number of cycles of therapy.

Diseases and conditions treatable according to the methods of this invention include, but are not limited to, cancer, stroke, diabetes, hepatomegaly, cardiovascular disease, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders in a patient. In one embodiment, a human patient is treated with a compound of a compound of the invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-Q, I-R and I-S) and a pharmaceutically acceptable carrier, adjuvant, or vehicle, wherein a compound of the invention is present in an amount to detectably inhibit mTOR kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Cardiovascular diseases which can be treated according to the methods of this invention include, but are not limited to, restenosis, cardiomegaly, atherosclerosis, myocardial infarction, and congestive heart failure.

Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

Inflammatory diseases which can be treated according to the methods of this invention include, but are not limited to, rheumatoid arthritis, psoriasis, contact dermatitis, and delayed hypersensitivity reactions.

Another aspect of this invention provides a compound of the invention, or stereoisomer, geometric isomer, tautomer, solvate, metabolite, or pharmaceutically acceptable salt, or prodrug thereof, in the treatment of the diseases or conditions described herein in a mammal, for example, a human, suffering from such disease or condition.

In one embodiment, this invention provides a compound of the invention, or stereoisomer, geometric isomer, tautomer, solvate, metabolite, or pharmaceutically acceptable salt, or prodrug thereof, in the treatment of cancer in a mammal comprising administering to a patient in need thereof a therapeutically acceptable amount of a compound of claim 1 wherein said cancer is selected from the group consisting of breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

In certain aspects of the above embodiment, cancer is selected from breast, NSCLC, small cell carcinoma, liver carcinoma, lymphoid disorders, sarcoma, colon-rectum, rectum, ovary, kidney, and leukemia.

Also provided is the use of a compound of this invention, or stereoisomer, geometric isomer, tautomer, solvate, metabolite, or pharmaceutically acceptable salt, or prodrug thereof, in the preparation of a medicament for the treatment of the diseases and conditions described herein in a warm-blooded animal, such as a mammal, for example a human, suffering from such disorder (e.g, cancer, neurodegenerative disease, cardiovasucular disease, inflammatory disease, described herein).

A method of inhibiting the activity of mTOR kinase in a mammal comprising administering to the mammal a therapeutically acceptable amount of a compound of Formula I or a sub-formula thereof.

In one embodiment, a compound of the invention (e.g., compound of Formula I, I-a, I-b, I-c, I-d, I-e, I-f, I-g, I-i, I-A, I-B, I-C, I-D, I-E, I-F, I-G, I-H, I-I, I-J, I-K, I-L, I-M, I-N, I-O, I-P, I-Q, I-R and I-S), or stereoisomer, geometric isomer, tautomer, solvate, metabolite, or pharmaceutically acceptable salt, prodrug thereof, is used as an anticancer agent or as an adjunct agent for the treatment of cancer in a combination therapy. One of ordinary skill in the art is readily able to determine whether or not a candidate compound treats a cancerous condition for any particular cell type, either alone or in combination. Within certain aspects of this embodiment, compounds of the invention are used in adjunct with other therapies, including conventional surgery, radiotherapy and chemotherapy, for the treatment of cancer.

Such chemotherapy can include one or more of the following categories of anti-cancer agents: (a) other antiproliferative/antineoplastic drugs and combinations thereof, as used in medical oncology, such as alkylating agents (for example cis-platin, oxaliplatin, 5 carboplatin, cyclophosphamide, nitrogen mustard, melphalan, chlorambucil, busulphan, improsulfan, piposulfan, temozolamide and nitrosoureas); antimetabolites (for example gemcitabine and antifolates such as fluoropyrimidines like 5 fluorouracil and tegafur, raltitrexed, methotrexate, cytosine arabinoside, hydroxyurea, and fludarabine); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin); (b) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5-alpha-reductase such as finasteride; (c) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661), and metalloproteinase inhibitors like marimastat, inhibitors of urokinase plasminogen activator receptor function or antibodies to Heparanase); (d) inhibitors of growth factor function: for example such inhibitors include growth factor antibodies and growth factor receptor antibodies (for example the anti erbB2 antibody trastuzumab [Herceptin™], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp 11-29), Avastin®; such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amme (gefitinib, ZD1 839), N-(3-ethynylphenyl)-6,7-bis (2-methoxyethoxy)quinazolin-4-amine (erlotinib (Tarceva®), OSI 774) and 6-acrylamido-N-(3-chloro-4-fluorophenyl)-7-(3-morpholinopropoxy)-quinazolin-4-amme (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through PI3K (GDC-0941, GDC0980), MEK (e.g. PD 325901, GDC-0973) AKT and/or mTOR kinase (rapamycin), inhibitors of the hepatocyte growth factor family, c-kit inhibitors, abl kinase inhibitors, IGF receptor (insulin-like growth factor) kinase inhibitors; aurora kinase inhibitors (for example AZDI 152, PH739358, VX-680, MLN8054, R763, MP235, MP529, VX-528 AND AX39459) and cyclin dependent kinase inhibitors such as CDK2 and/or CDK4 inhibitors; (e) vascular damaging agents such as Combretastatin A4 and compounds disclosed in International Patent Applications WO 99/02166, WO 00/40529, WO 00/41669, WO 01/92224, WO 02/04434 and WO 02/08213; (g) antisense therapies, for example those which are directed to the targets listed above, such as ISIS 2503, an anti-ras antisense; (h) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; (i) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies; (j) proteosome inhibitors, such as Velcade®; and (k) Bcl-2 family protein inhibitors (e.g., ABT-263, ABT-737, obatoclax).

The combination therapy can be administered as a simultaneous or sequential regimen. When administered sequentially, the combination can be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and can be lowered due to the combined action (synergy) of the newly identified agent and other chemotherapeutic agents or treatments.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

V Examples

These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

The chemical reactions in the Examples described can be readily adapted to prepare a number of other mTOR inhibitors of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention. Accordingly, the following examples are provided to illustrate but not limit the invention.

In the Examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Certain reactions were carried out using a standard microwave reactor commercially available from Biotage Corporation or CEM Corporation. Column chromatography was conducted on a Biotage system (Manufacturer: Dyax Corporation) having a silica gel column or on a silica SEP PAK® cartridge (Waters); or alternatively column chromatography was carried out using on an ISCO chromatography system (Manufacturer: Teledyne ISCO) having a silica gel column. $^1$H NMR spectra were recorded on a Varian instrument operating at 400 MHz. $^1$H NMR spectra were obtained in deuterated CDCl$_3$, d$_6$-DMSO, CH$_3$OD or d$_6$-acetone solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz). When possible, product formation in the reaction mixtures were monitored by LC/MS was performed either on an Agilent 1200 Series LC coupled to a 6140 quadrupole mass spectrometer using a Supelco Ascentis Express C18 column with a linear gradient of 5%-95% acetonitrile/water (with 0.1% trifluoroacetic acid in each mobile phase) within 1.4 minutes and held at 95% for 0.3 minute, or on a PE Sciex API 150 EX using a Phenomenex DNYC monolithic C18 column with a linear gradient of 5%-95% acetonitrile/water (with 0.1% trifluoroacetic acid in each mobile phase) within 5 minutes and held at 95% for 1 minute. All abbreviations used to described reagents, reaction conditions, or equipment used are consistent with the definitions set forth in the "List of standard abbreviations and acronyms" published yearly by the Journal of Organic Chemistry (an American Chemical Society journal). Certain abbreviations used in the Examples have the following meaning unless otherwise indicated: MeOH=Methanol, DMSO=dimethylsulfoxide, LDA=lithium diisopropylamide, MsCl=mesyl chloride, Hex=hexane(s), EtOAc or EA=ethyl acetate, DCM=dichloromethane, RT or r.t.=room temperature, Boc=tert-butyoxycarbonyl, DMF=dimethylformamide, (RP)HPLC=(reverse phase) high pressure liquid chromatography, EDC=-Ethyl-3-(3-dimethylaminopropyl)-carbodiimide, HOBT=hydroxybenzotriazole, DIPEA=diisopropylethylamine, HATU=O-(7-Azabenzotriazole-1-yl)-N,N,N'N'-tetramethyluronium hexafluorophosphate, TFA=trifluoroacetic acid, AcOH=acetic acid, Hep or Hept=heptane, IPA=isopropyl alcohol, PyBOP=benzotriazol-1-yl-oxytripyrrolidinophosphonium hexafluorophosphate, SFC=supercritical fluid chromatography, Example 1

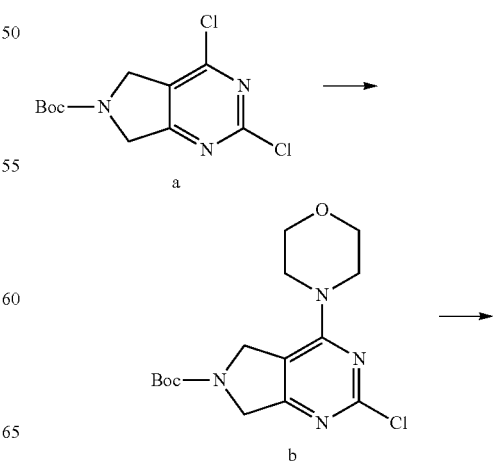

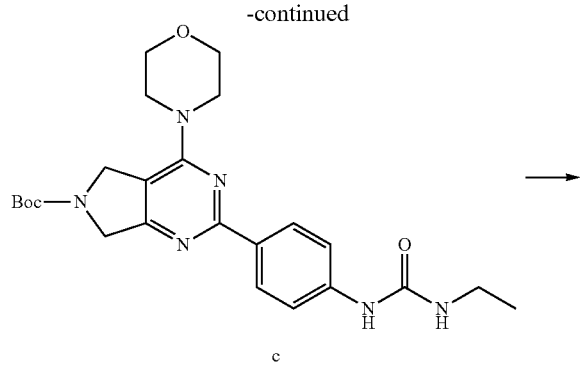

c added and the resulting mixture was concentrated in vacuo. The resulting residue was azeotroped with toluene two more times. Methanol and methylene chloride (4 mL each) were added to the resulting residue, then PS-carbonate (2.5-3.5 mmol N/gram resin, 1.45 g) was added. The mixture was stirred at room temperature until the pH reached >7 (~1 hr). The mixture was filtered, the resin was washed with methanol and dichloromethane. The filtrate was concentrated to provide 1-ethyl-3-(4-(4-morpholino-6,7-dihydro-5H-pyrrolo[3,4-d]pyrimidin-2-yl)phenyl)urea as a free amine, which was used in the next step. An aliquot was purified by reverse-phase HPLC to give the pure desired product: $^1$H NMR (400 MHz, DMSO) δ 9.57 (s, 1H), 8.75 (s, 1H), 8.19 (d, J=8.9, 2H), 7.50 (d, J=8.9, 2H), 6.38-6.08 (m, 1H), 4.71 (s, 2H), 4.38 (s, 2H), 3.72 (s, 8H), 3.24-3.03 (m, 2H), 1.06 (t, J=7.2, 3H); LC-MS: m/z=+369 (M+H)$^+$.

Example 2

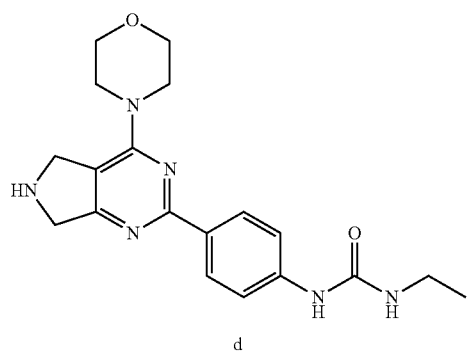

d

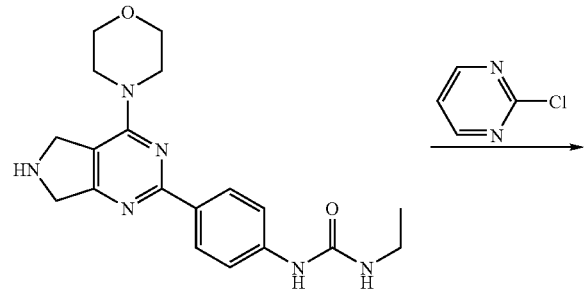

d

Step 1—Synthesis of b: To a mixture of tert-butyl 2,4-dichloro-5H-pyrrolo[3,4-d]pyrimidine-6(7H)-carboxylate (1.2 g, 4.1 mmol) and i-Pr$_2$NEt (1.4 mL, 8.3 mmol) in isopropanol (8 mL) was added morphorline (0.430 mL, 5.0 mmol). The mixture was stirred at room temperature until the reaction was done (~1 hr). The mixture was concentrated in vacuo and the resulting residue was purified by flash column chromatography (40% EA/Hex) to give tert-butyl 2-chloro-4-morpholino-5H-pyrrolo[3,4-d]pyrimidine-6(7H)-carboxylate (b) (1.378 g, 98%).

Step 2—Synthesis of c: Compound b (0.366 mmol), (4-ethylureido)phenylboronic acid pinacol ester (0.439 mmol), tetrakis(triphenylphosphine)palladium (0.022 mmol), 1 M aq. KOAc (0.55 mL), 1 M aq. Na$_2$CO$_3$ (0.55 mL) and MeCN (2 mL) were mixed in a microwave reaction tube. The mixture was heated in a microwave reactor at 120° C. for 25 min. The mixture was extracted with EtOAc (3×) and the combined organic extract was concentrated. The resulting residue was purified by flash column chromatography (40% EA/Hex) to give tert-butyl 2-(4-(3-ethylureido)phenyl)-4-morpholino-5H-pyrrolo[3,4-d]pyrimidine-6(7H)-carboxylate (c) (149 mg, 83%): $^1$H NMR (500 MHz, CDCl3) δ 8.28 (d, J=8.7, 2H), 7.38 (d, J=8.8, 2H), 7.10 (d, J=8.6, 1H), 6.81 (d, J=8.8, 1H), 4.78 (s, 2H), 4.57 (s, 2H), 3.93-3.59 (m, 8H), 3.36-3.29 (m, 2H), 1.53 (s, 9H), 1.17 (t, J=7.2, 3H); LC-MS: m/z=+469 (M+H)$^+$.

Step 3—Synthesis of d: tert-butyl 2-(4-(3-ethylureido)phenyl)-4-morpholino-5H-pyrrolo[3,4-d]pyrimidine-6(7H)-carboxylate (c, 1.74 mmol) was dissolved in dichloromethane (5 mL), then TFA (3 mL) was added. The mixture was stirred at room temperature for 2 hours. Isopropanol and toluene were

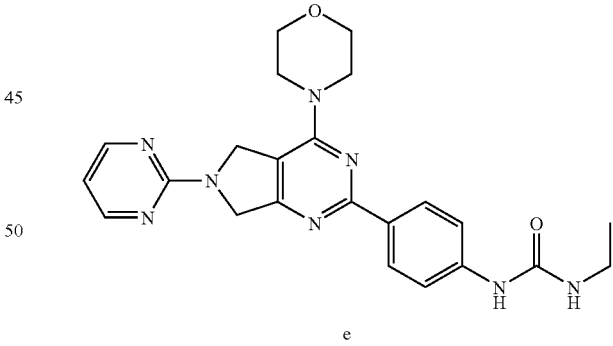

e

Synthesis of compound e: 1-Ethyl-3-(4-(4-morpholino-6,7-dihydro-5H-pyrrolo[3,4-d]pyrimidin-2-yl)phenyl)urea (d, 0.15 mmol), chloropyrimidine (0.21 mmol) and i-Pr$_2$NEt (0.6 mmol) were mixed in DMF (0.6 mL) in a microwave reaction tube. The mixture was heated to 120° C. and stirred for 15 min. After cooling to room temperature, the mixture was diluted with DMF. The resulting mixture was purified by reverse-phase HPLC to give 1-ethyl-3-(4-(4-morpholino-6-(pyrimidin-2-yl)-6,7-dihydro-5H-pyrrolo[3,4-d]pyrimidin-2-yl)phenyl)urea (e): $^1$H NMR (500 MHz, DMSO) δ 8.71 (s, 1H), 8.47 (d, J=4.8, 2H), 8.21 (d, J=8.8, 2H), 7.51 (d, J=8.8, 2H), 6.77 (t, J=2.5, 1H), 6.18 (m, 1H), 4.99 (s, 2H), 4.68 (s, 2H), 3.78 (m, 8H), 3.20-3.15 (m, 2H), 1.26 (t, J=6.9, 3H); LC-MS: m/z=+447 (M+H)⁺.

6.46 (m, 1H), 6.24-6.16 (m, 1H), 4.73 (s, 2H), 4.45 (s, 2H), 3.76 (m, 8H), 3.13 (m, 4H), 1.07 (q, J=7.2, 6H); LC-MS: m/z=+440 (M+H)⁺.

Example 3

Example 5

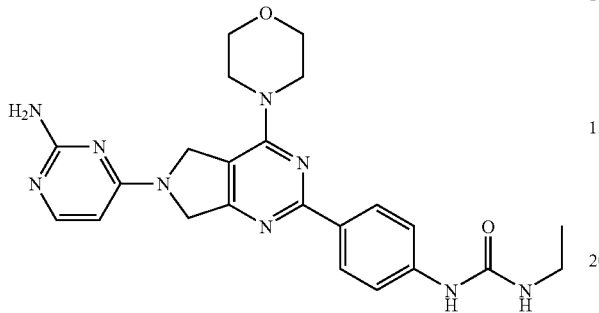

ee

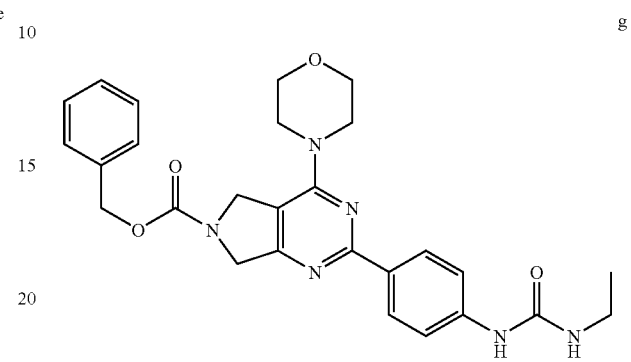

g

Synthesis of 1-(4-(6-(2-aminopyrimidin-4-yl)-4-morpholino-6,7-dihydro-5H-pyrrolo[3,4-d]pyrimidin-2-yl)phenyl)-3-ethylurea (ee): The title compound was prepared by the procedure described in Example 2, by substituting chloropyrimidine with 2-amino-4-chloropyrimidine: $^1$H NMR (500 MHz, DMSO) δ 8.71 (s, 1H), 8.21 (dd, J=3.9, 8.8, 2H), 7.94 (t, J=7.5, 2H), 7.49 (dd, J=2.1, 8.7, 1H), 6.67-6.34 (m, 1H), 6.25-6.17 (m, 1H), 5.06 (s, 2H), 4.86-4.65 (m, 2H), 3.76 (m, 8H), 3.24-3.04 (m, 3H), 1.06 (t, J=7.2, 3H). LC-MS: m/z=+462 (M+H)⁺.

Synthesis of g: To the mixture of 1-ethyl-3-(4-(4-morpholino-6,7-dihydro-5H-pyrrolo[3,4-d]pyrimidin-2-yl)phenyl)urea (d, 0.095 mmol), i-PrN₂Et (0.19 mmol) and DMF (0.4 mL) was added benzyl chloroformate (0.15 mmol) at room temperature. After the reaction was done, the mixture was diluted with DMF and purified by reverse-phase HPLC to give the title compound: $^1$H NMR (500 MHz, DMSO) δ 8.73 (s, 1H), 8.24-8.13 (m, 2H), 7.50 (d, J=8.6, 2H), 7.46-7.37 (m, 4H), 7.37-7.31 (m, 1H), 6.20 (m, 1H), 5.20 (d, J=5.6, 2H), 4.88 (d, J=31.4, 2H), 4.56 (d, J=41.6, 3H), 3.82-3.69 (m, 8H), 3.12 (m, 3H), 1.06 (t, J=7.2, 3H); LC-MS: m/z=+503 (M+H)⁺.

Example 4

Example 6

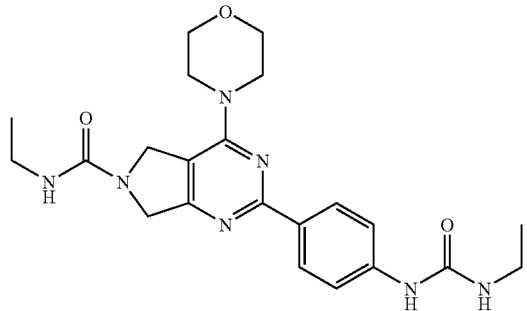

f

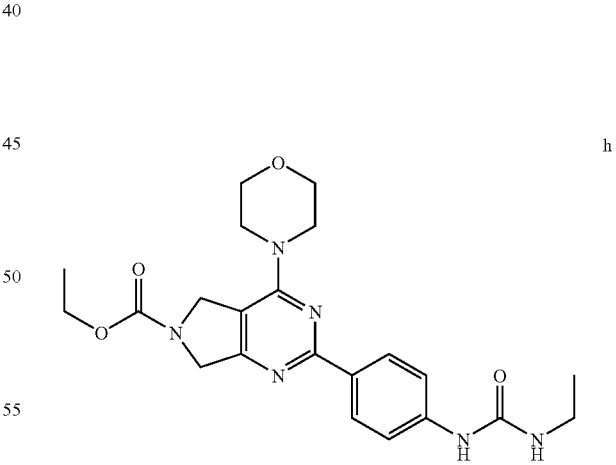

h

Synthesis of f: 1-Ethyl-3-(4-(4-morpholino-6,7-dihydro-5H-pyrrolo[3,4-d]pyrimidin-2-yl)phenyl)urea (d, 0.095 mmol) was dissolved in DMF (0.5 mL) then ethylisocynate (0.19 mmol) was added. The mixture was stirred at room temperature until the reaction was complete. The mixture was diluted with DMF and then purified by reverse-phase HPLC to give the title compound: $^1$H NMR (500 MHz, DMSO) δ 8.75 (s, 1H), 8.18 (d, J=8.9, 2H), 7.51 (d, J=8.8, 2H), 6.54-

Synthesis of h: Compound h was prepared according to the procedure described in Example 5 by substituting benzyl chloroformate with ethyl chloroformate: $^1$H NMR (500 MHz, DMSO) δ 8.73 (s, 1H), 8.18 (d, J=6.7, 2H), 7.49 (d, J=8.8, 2H), 6.26-6.15 (m, 1H), 4.82 (d, J=13.9, 2H), 4.50 (d, J=15.2, 2H), 4.21-4.07 (m, 2H), 3.80-3.69 (m, 8H), 3.19-3.06 (m, 2H), 1.25 (t, J=7.0, 3H), 1.06 (t, J=7.2, 3H); LC-MS: m/z=+441 (M+H)+.

Example 7

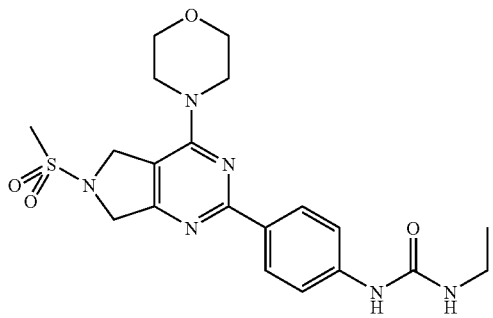

i

Synthesis of compound i: Compound i was prepared according to the procedure described in Example 5 by substituting benzyl chloroformate with methylsulfonyl chloride: $^1$H NMR (400 MHz, DMSO) δ 8.69 (s, 1H), 8.18 (d, J=8.7, 2H), 7.49 (d, J=8.8, 2H), 6.19 (br s, 1H), 4.84 (s, 2H), 4.51 (s, 2H), 4.04-3.76 (m, 8H), 3.20-3.08 (m, 2H), 3.06 (s, 3H), 1.06 (t, J=7.2, 3H); LC-MS: m/z=+447 (M+H)+.

Example 8 j

HO
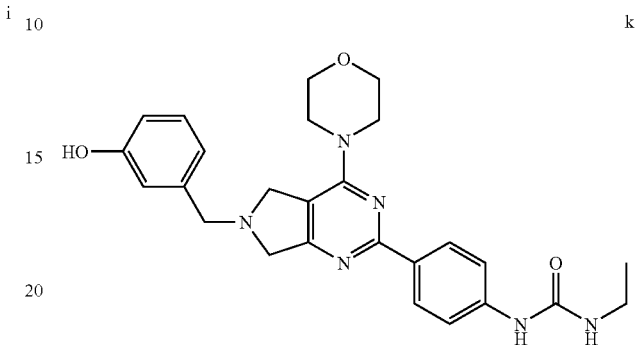

Synthesis of j: 1-Ethyl-3-(4-(4-morpholino-6,7-dihydro-5H-pyrrolo[3,4-d]pyrimidin-2-yl)phenyl)urea (d, 0.13 mmol) and 4-hydroxybenzaldehyde (0.21 mmol) were mixed in 1,2-dichloroethane (0.4 mL). The mixture was stirred at 70° C. for 25 minutes, then NaH(OAc)3 (0.54 mmol) was added. The mixture was stirred at 70° C. for 1 h. The mixture was taken up in a mixture of water (~0.1 mL) and DMF (~0.4 mL) and purified by reverse-phase HPLC to give compound j: $^1$H NMR (500 MHz, DMSO) δ 8.71 (s, 1H), 8.19 (d, J=8.7, 2H), 7.50 (d, J=8.8, 2H), 7.41 (d, J=8.4, 2H), 6.85 (d, J=8.0, 2H), 6.22 (m, 1H), 5.07-4.72 (m, 2H), 4.66-4.31 (m, 4H), 3.79-3.67 (m, 8H), 3.22-3.02 (m, 2H), 1.07 (t, J=7.1, 3H); LC-MS: m/z=+475 (M+H)−.

Example 9 k

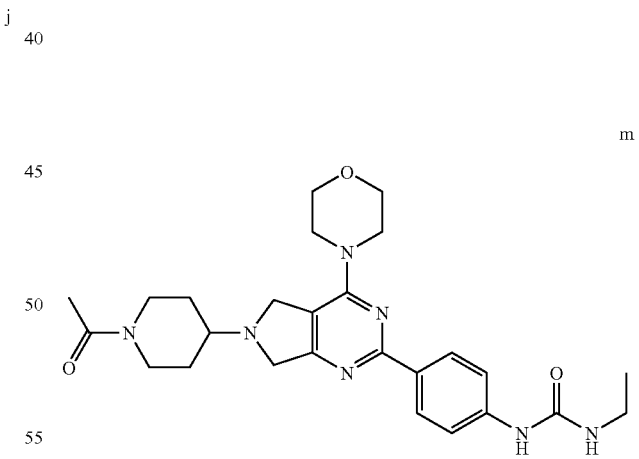

Synthesis of k: Compound k was synthesized according to the procedure described in Example 8 by substituting 4-hydroxybenzaldehyde with 3-hydroxybenzaldehyde: $^1$H NMR (500 MHz, DMSO) δ 8.72 (s, 1H), 8.19 (d, J=8.5, 2H), 7.50 (d, J=8.4, 2H), 7.34-7.25 (m, 1H), 7.06-6.94 (m, 2H), 6.93-6.82 (m, 1H), 6.22 (m, 1H), 4.97-4.75 (m, 2H), 4.58-4.39 (m, 3H), 3.81-3.66 (m, 8H), 3.18-3.10 (m, 2H), 1.08 (d, J=7.0, 3H); LC-MS: m/z=+475 (M+H)+.

Example 10 m

Synthesis of m: Compound m was synthesized according to the procedure described in Example 8 by substituting 4-hydroxybenzaldehyde with N-acylpiperidone: $^1$H NMR (400 MHz, DMSO) δ 8.73 (s, 1H), 8.19 (d, J=8.8, 2H), 7.50 (d, J=8.8, 2H), 6.22 (s, 1H), 4.99-4.74 (s, 2H), 4.61 (s, 2H), 4.56-4.47 (m, 1H), 4.00-3.88 (m, 2H), 3.81-3.63 (m, 8H), 3.12 (m, 3H), 2.72-2.53 (m, 1H), 2.28-2.11 (m, 2H), 2.04 (s, 3H), 1.75-1.25 (m, 2H), 1.06 (t, J=7.2, 3H); LC-MS: m/z=+494 (M+H)⁺.

Example 11

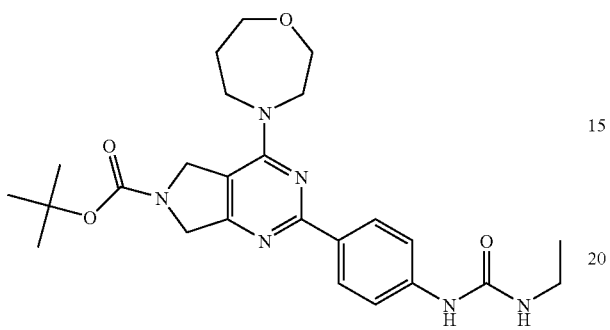

Synthesis of n: Compound n was synthesized according to the sequence of Example 1 by substituting morpholine with homomorpholine in step 1: ¹H NMR (500 MHz, DMSO) δ 8.67 (s, 1H), 8.17 (d, J=8.6, 2H), 7.48 (d, J=8.7, 2H), 6.18 (s, 1H), 4.74 (s, 2H), 4.43 (s, 2H), 3.87-3.64 (m, 6H), 3.64 (s, 2H), 3.19-3.05 (m, 2H), 1.93 (s, 2H), 1.47 (s, 9H), 1.06 (t, J=7.2, 3H); LC-MS: m/z=+483 (M+H)⁻.

Example 12

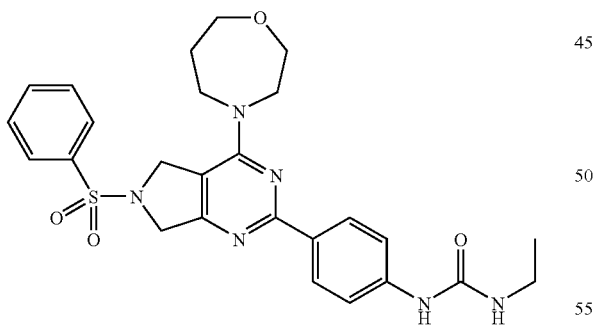

Synthesis of o: Compound o was synthesized according to the procedure described in Example 5 by using phenysulfonyl chloride instead of benzylchloroformate: ¹H NMR (400 MHz, DMSO) δ 8.64 (s, 1H), 8.09 (d, J=8.8, 2H), 7.95 (d, J=7.3, 2H), 7.70 (m, 1H), 7.63 (d, J=7.8, 2H), 7.45 (d, J=8.8, 2H), 6.31-6.02 (m, 1H), 4.78 (s, 2H), 4.44 (s, 2H), 3.83-3.7 (m, 7H), 3.11 (m, 2H), 1.96-1.81 (m, 2H), 1.05 (t, J=7.2, 3H); LC-MS: m/z=+553 (M+H)⁺.

Example 13

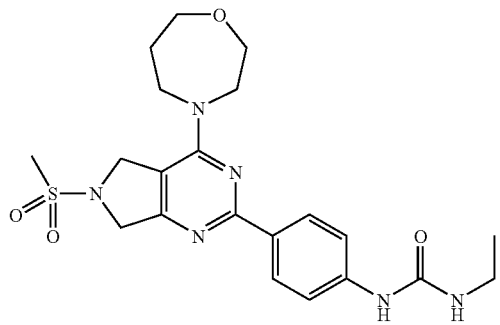

Synthesis of p: Compound p was synthesized according to the procedure described in Example 5 by using methanesulfonyl chloride instead of benzylchloroformate: ¹H NMR (400 MHz, DMSO) δ 8.68 (s, 1H), 8.16 (d, J=8.8, 2H), 7.49 (d, J=8.8, 2H), 6.18 (m, 1H), 4.82 (s, 2H), 4.51 (s, 2H), 3.89-3.75 (m, 7H), 3.21-3.10 (m, 2H), 3.06 (s, 3H), 1.74 (m, 2H), 1.06 (t, J=7.2, 3H); LC-MS: m/z=+461 (M+H)⁺.

Example 14

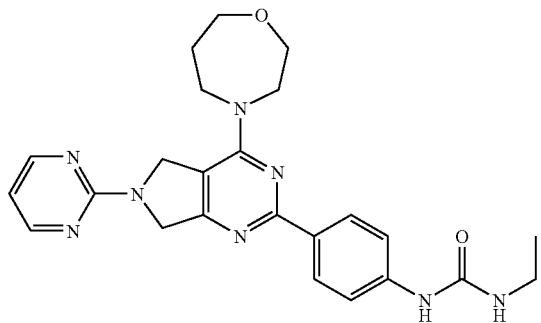

Synthesis of q: Compound q was synthesized following the procedures outlined in Examples 1, 2 and 11 to provide compound g: ¹H NMR (400 MHz, DMSO) δ 8.70 (s, 1H), 8.46 (d, J=4.7, 2H), 8.20 (d, J=8.8, 2H), 7.49 (d, J=8.8, 2H), 6.75 (t, J=4.8, 1H), 6.22 (m, 1H), 4.98 (s, 2H), 4.66 (s, 2H), 3.3.93-3.8

(m, 6H), 3.72-3.62 (m, 2H), 3.19-3.07 (m, 2H), 2.09-1.83 (m, 2H), 1.06 (t, J=7.2, 3H); LC-MS: m/z=+461 (M+H)+.

Example 15

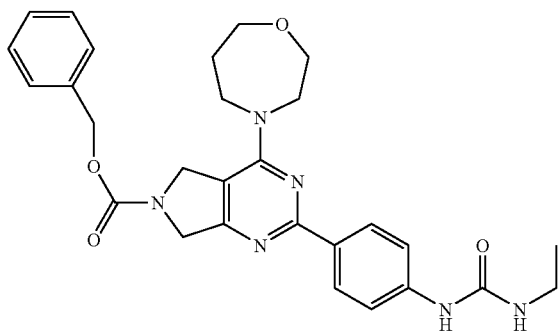
r

Synthesis of r: Compound r was prepared generally according the procedures outlined in Examples 1, 5 and 11 to provide compound r: $^1$H NMR (500 MHz, DMSO) δ 8.70 (s, 1H), 8.24-8.11 (m, 2H), 7.48 (d, J=8.8, 2H), 7.46-7.31 (m, 5H), 6.21 (s, 1H), 5.19 (d, J=6.1, 2H), 4.86 (d, J=37.2, 2H), 4.54 (d, J=42.2, 2H), 3.94-3.72 (m, 6H), 3.71-3.58 (m, 2H), 3.19-3.05 (m, 2H), 2.00-1.85 (m, 2H), 1.06 (t, J=7.2, 3H); LC-MS: m/z=+517 (M+H)+.

Example 16

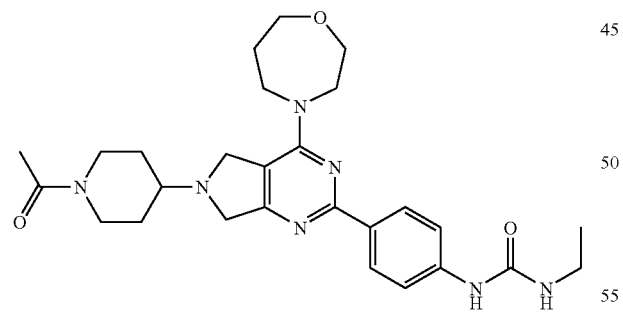
s

Synthesis of s: Compound s was synthesized generally according to the procedures outlined in Examples 1, 8 and 11 to provide compound s: $^1$H NMR (400 MHz, DMSO) δ 8.71 (s, 1H), 8.17 (d, J=8.8, 2H), 7.50 (d, J=8.8, 2H), 6.22 (s, 1H), 4.86-4.59 (m, 5H), 4.01-3.67 (m, 14H), 3.12 (m, 3H), 2.77-2.53 (m, 1H), 2.30-2.12 (m, 1H), 1.92 (m, 2H), 1.75-1.27 (m, 2H), 1.06 (t, J=7.2, 3H); LC-MS: m/z=+508 (M+H)+.

Example 17

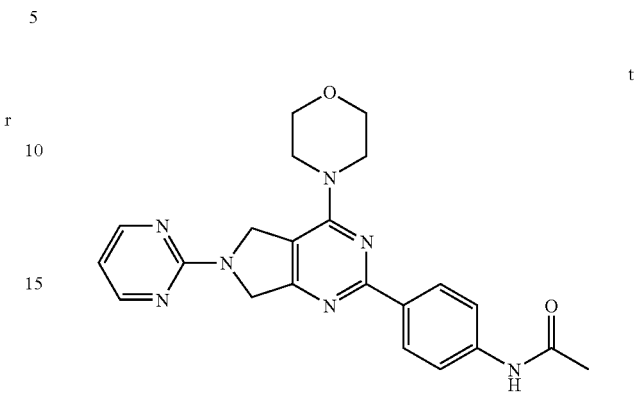
t

Synthesis of t: Compound t was synthesized using procedures described in Examples 1 and 2 except that 4-acetamidophenyl boronic acid pinacol ester was used instead of (4-ethylureido)phenylboronic acid pinacol ester in step 2 of Example 1: LC-MS m/z=+418 (M+H)+.

Example 18

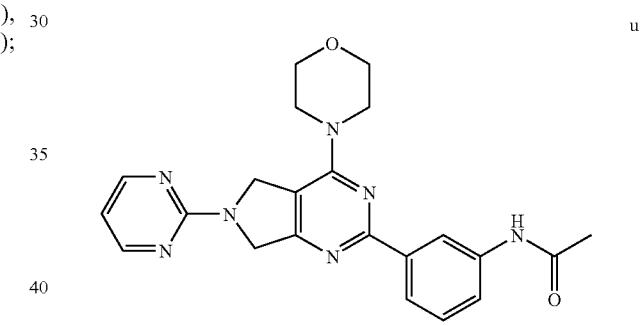
u

Synthesis of compound u: Compound was synthesized using the same described in Examples 1 and 2 except that 3-acetamidophenyl boronic acid, pinacol ester was used instead of (4-ethylureido)phenylboronic acid pinacol ester in step 2 of Example 1.

Example 19

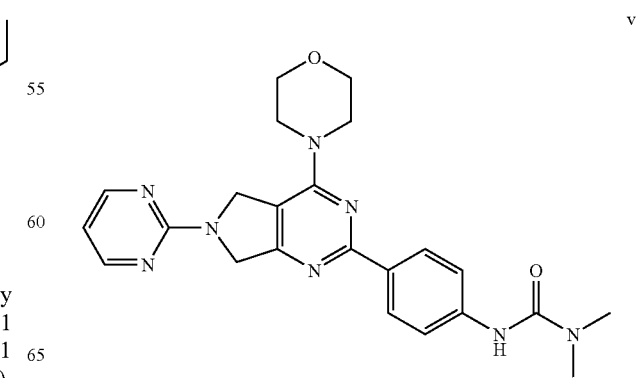
v

Synthesis of v: Compound v was synthesized using the procedure as described in Examples 1 and 2 except that 4-(3-dimethylureido)phenylboronic acid, pinacol ester was used instead of (4-ethylureido)phenylboronic acid pinacol ester in step 2 of Example 1.

Example 20

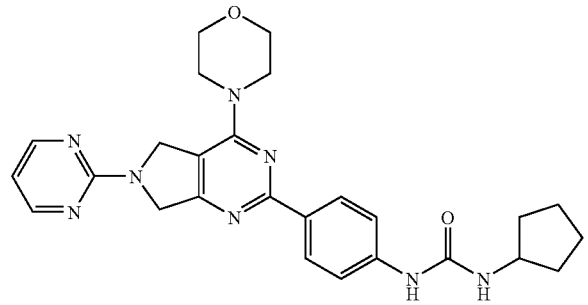

w

Synthesis of w: Compound w was synthesized using the same procedure as described for Examples 1 and 2 except that 4-(3-cyclopentylureido)phenylboronic acid pinacol ester was used instead of (4-ethylureido)phenylboronic acid pinacol ester in step 2 of Example 1.

Example 21

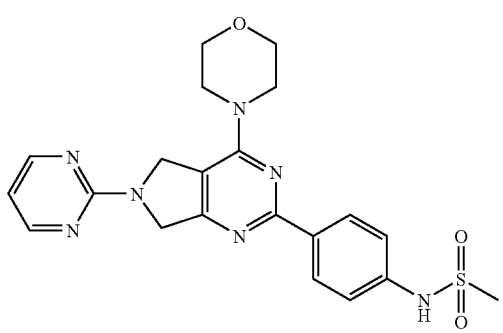

x

Synthesis of x: Compound x was synthesized using the procedures as described in Examples 1 and 2 except that 4-methanesulfonamidephenyl boronic acid pinacol ester was used instead of (4-ethylureido)phenylboronic acid pinacol ester in step 2 of Example 1.

Example 22

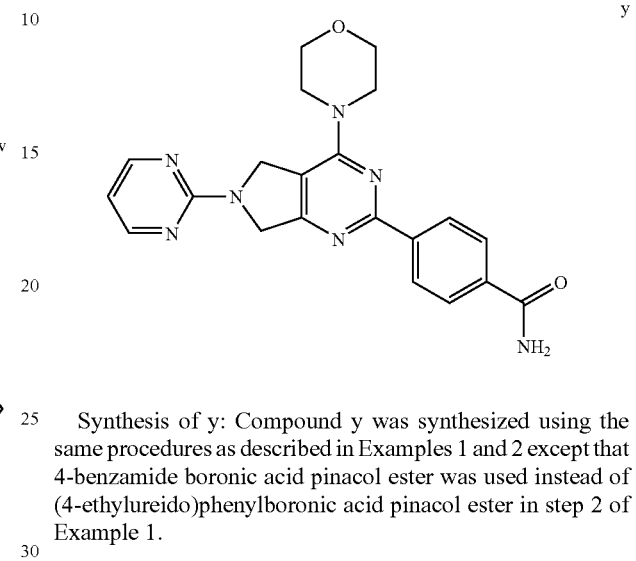

y

Synthesis of y: Compound y was synthesized using the same procedures as described in Examples 1 and 2 except that 4-benzamide boronic acid pinacol ester was used instead of (4-ethylureido)phenylboronic acid pinacol ester in step 2 of Example 1.

Example 23

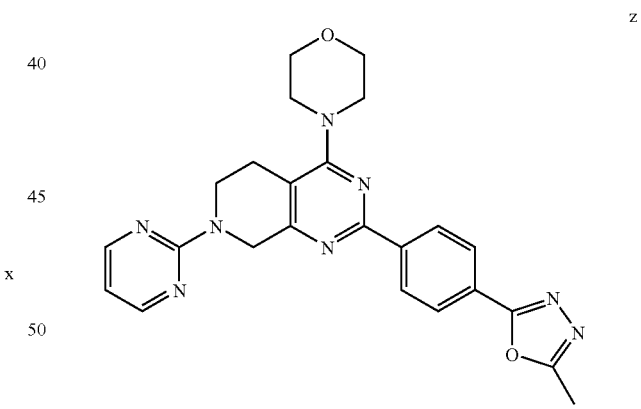

z

Synthesis of z: Compound z was prepared generally following the procedures described in Examples 1 and 2 except that tert-butyl 2,4-dichloro-5,6-dihydropyrido[3,4-d]pyrimidine-7(8H)-carboxylate was used instead of tert-butyl 2,4-dichloro-5H-pyrrolo[3,4-d]pyrimidine-6(7H)-carboxylate in step 1 of Example 1, and 4-(5-methyl-1,3,4-oxadiazol-2-yl)phenylboronic acid was used instead of (4-ethylureido)phenylboronic acid pinacol ester and in step 2: $^1$H NMR (400 MHz, DMSO) δ 8.54 (d, J=8.4, 2H), 8.44 (d, J=4.7, 2H), 8.09 (d, J=8.4, 2H), 6.70 (t, J=4.7, 1H), 4.87 (s, 2H), 4.01 (t, J=5.3, 2H), 3.75 (d, J=4.6, 4H), 3.54 (d, J=4.4, 4H), 2.80 (s, 2H), 2.61 (s, 3H); LC/MS-m/z+457 (M+H)+.

J=4.7, 1H), 4.86 (s, 2H), 4.00 (s, 2H), 3.76 (s, 4H), 3.51 (s, 4H), 2.78 (s, 2H); LC/MS-m/z+415 (M+H)+.

Example 24

Example 26

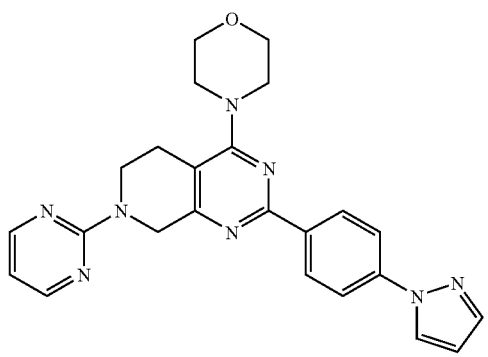

aa

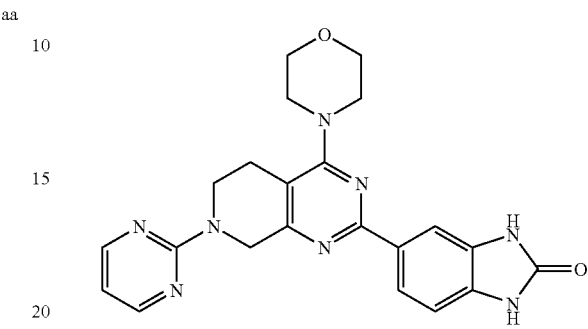

ac

Synthesis of aa: Compound aa was synthesized using the generally following the procedures described in Examples 1 and 2 except that tert-butyl 2,4-dichloro-5,6-dihydropyrido[3,4-d]pyrimidine-7(8H)-carboxylate was used instead of tert-butyl 2,4-dichloro-5H-pyrrolo[3,4-d]pyrimidine-6(7H)-carboxylate in step 1 of Example 1, and 4-(1H-pyrazol-1-yl)phenylboronic acid was used instead of (4-ethylureido)phenylboronic acid pinacol ester in step 2 of Example 1: ¹H NMR (400 MHz, DMSO) δ 8.58 (d, J=2.5, 1H), 8.45 (dd, J=3.7, 6.7, 4H), 7.96 (d, J=8.7, 2H), 7.80 (d, J=1.5, 1H), 6.70 (t, J=4.7, 1H), 6.60-6.57 (m, 1H), 4.86 (s, 2H), 4.00 (t, J=5.3, 2H), 3.78-3.73 (m, 4H), 3.52 (d, J=4.5, 4H), 2.78 (s, 2H); LC/MS-m/z+441 (M+H)+.

Synthesis of ac: Compound ac was synthesized using the generally following the procedures described in Examples 1 and 2 except that tert-butyl 2,4-dichloro-5,6-dihydropyrido[3,4-d]pyrimidine-7(8H)-carboxylate was used instead of tert-butyl 2,4-dichloro-5H-pyrrolo[3,4-d]pyrimidine-6(7H)-carboxylate in step 1 of Example 1, and 5-(4,4,5,5-tetramethyl-1,3,2-dioxaborolan-2-yl)-1H-benzo[d]imidazol-2(3H)-one was used instead of (4-ethylureido)phenylboronic acid pinacol ester in step 2 of Example 1: ¹H NMR (400 MHz, DMSO) δ 10.79 (s, 1H), 10.69 (s, 1H), 8.44 (d, J=4.7, 2H), 8.05 (d, J=8.2, 1H), 7.93 (s, 1H), 7.00 (d, J=8.2, 1H), 6.70 (t, J=4.7, 1H), 4.83 (s, 2H), 3.99 (s, 2H), 3.75 (s, 4H), 3.48 (s, 4H), 2.76 (s, 2H); LC/MS-m/z+431 (M+H)+.

Example 25

Example 27

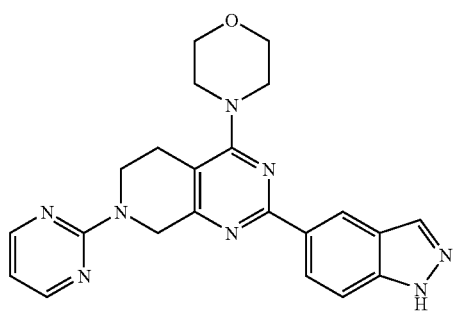

ab

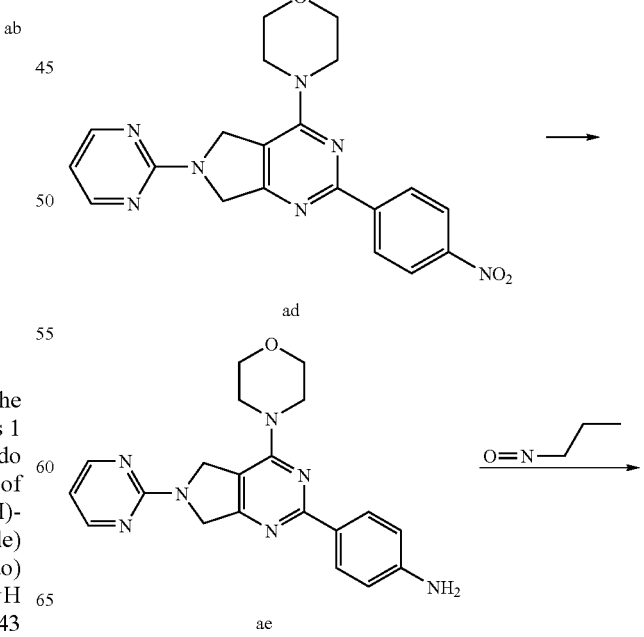

Synthesis of ab: Compound ab was synthesized using the generally following the procedures described in Examples 1 and 2 except that tert-butyl 2,4-dichloro-5,6-dihydropyrido[3,4-d]pyrimidine-7(8H)-carboxylate was used instead of tert-butyl 2,4-dichloro-5H-pyrrolo[3,4-d]pyrimidine-6(7H)-carboxylate in step 1 of Example 1, and 5-(1H-indazole)boronic acid pinacol ester was used instead of (4-ethylureido)phenylboronic acid pinacol ester in step 2 of Example 1: ¹H NMR (400 MHz, DMSO) δ 13.16 (s, 1H), 8.80 (s, 1H), 8.43 (dd, J=6.8, 14.4, 3H), 8.20 (s, 1H), 7.60 (d, J=8.8, 1H), 6.70 (t,

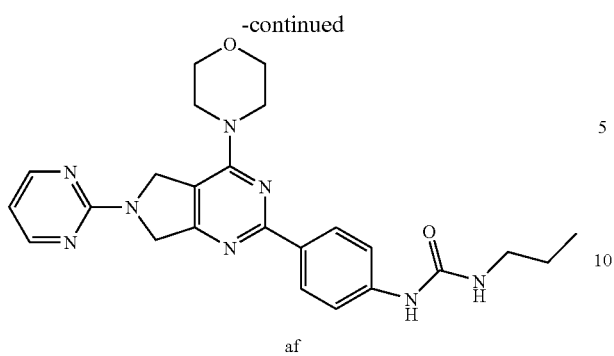

af

Step 1—Synthesis of ad: Compound ad was synthesized using the same procedure described in Example 1 except that 4-nitrophenyl boronic acid, pinacol ester was used instead of (4-ethylureido)phenylboronic acid pinacol ester in step 2 of Example 1.

Step 2—Synthesis of ae: To a suspension of 4-(2-(4-nitrophenyl)-6-(pyrimidin-2-yl)-6,7-dihydro-5H-pyrrolo[3,4-d]pyrimidin-4-yl)morpholine (ad)(336 mg, 0.8 mmol) and SnCl$_2$ dihydrate (900 mg, 4.0 mmol) in EtOH (10 mL) was heated at 100° C. for 2 h. Solvent was removed in vacuo, diluted with H$_2$O, basified with 1 N NaOH, added 10% MeOH/DCM (50 mL), stirred for 1 h. The layers were separated. The organic was extracted again with 10% MeOH/DCM (2×50 mL). The combined organic were dried over Magnesium sulfate, filtered, concentrated in vacuo to give 310 mg (100%) of the desired product ae as yellow solid.

Step 3—Synthesis of af: A mixture of aniline ae (70 mg, 0.2 mmol), propyl isocyanate (34 μL, 0.36 mmol), and DIPEA (63 μL, 0.36 mmol) in DMF (1 mL) was stirred at rt for 1 h. Two equivalents of (34 μL) propyl isocyanate was added, the mixture was heated at 100° C. overnight. The crude product was purified by reverse-phase chromatography to give 36 mg (40%) of desired product as an off-white solid: $^1$H NMR (400 MHz, DMSO) δ 8.63 (s, 1H), 8.43 (d, J=4.7, 2H), 8.21 (d, J=8.7, 2H), 6.69 (t, J=4.7, 1H), 6.20 (t, J=5.6, 1H), 4.81 (s, 2H), 3.98 (s, 2H), 3.73 (d, J=4.4, 4H), 3.47 (d, J=4.3, 4H), 3.06 (dd, J=6.7, 12.9, 2H), 2.75 (s, 2H), 1.45 (dd, J=7.2, 14.4, 2H), 0.89 (t, J=7.4, 3H); LC/MS-m/z+475 (M+H)+.

Example 28 ag

Synthesis of ag: Compound ag was synthesized using the generally following the procedures described in Examples 1 and 27 except that tert-butyl 2,4-dichloro-5,6-dihydropyrido[3,4-d]pyrimidine-7(8H)-carboxylate was used instead of tert-butyl 2,4-dichloro-5H-pyrrolo[3,4-d]pyrimidine-6(7H)-carboxylate in step 1 of Example 1, and n-propyl isocynate was substituted with isopropyl isocyanate in step 3 of Example 27: $^1$H NMR (400 MHz, DMSO) δ 8.51 (s, 1H), 8.43 (d, J=4.7, 2H), 8.21 (d, J=8.7, 2H), 7.47 (d, J=8.7, 2H), 6.69 (t, J=4.7, 1H), 6.06 (d, J=7.5, 1H), 4.81 (s, 2H), 3.98 (s, 2H), 3.81-3.70 (m, 5H), 3.47 (s, 4H), 2.75 (s, 2H), 1.11 (d, J=6.5, 6H); LC/MS-m/z+475 (M+H)+.

Example 29

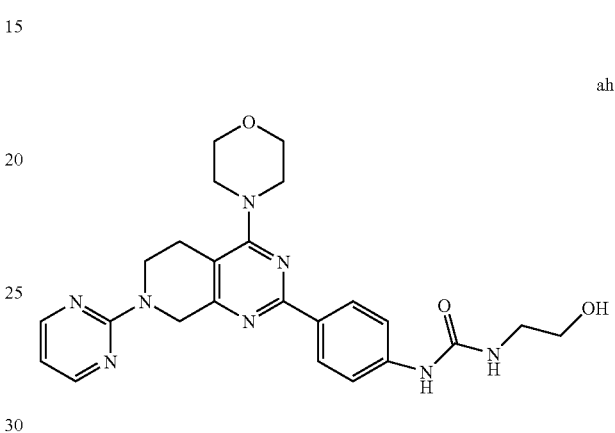

ah

Synthesis of ah: A suspension of 4-(4-morpholino-6-(pyrimidin-2-yl)-5,6,7,8-tetrahydropyrido[4,3-d]pyrimidin-2-yl)aniline (50 mg, 0.1 mmol), 4-nitrophenyl chloroformate (20 mg, 0.1 mmol), and DIPEA (40 μL, 0.2 mmol) in DCM was stirred at rt overnight. Ethanolamine (50 μL, 0.8 mmol) was added to the reaction mixture, stirred for 1.5 h. The precipitated solid was filtered, and purified by column chromatography (ISCO, 12 g column, 5% MeOH/DCM (+2% TEA)) to give 31 mg (50%) of compound ah as an off-white solid: $^1$H NMR (500 MHz, DMSO) δ 8.81 (s, 1H), 8.44 (d, J=4.7, 2H), 8.22 (d, J=8.8, 2H), 7.49 (d, J=8.8, 2H), 6.70 (t, J=4.7, 1H), 6.27 (t, J=5.6, 1H), 4.81 (s, 2H), 4.77 (t, J=5.1, 1H), 3.98 (s, 2H), 3.73 (d, J=4.6, 4H), 3.46 (dd, J=5.6, 11.1, 6H), 3.17 (q, J=5.6, 2H), 2.75 (s, 2H). Mass found-m/z+477 (M+H)+.

Example 30

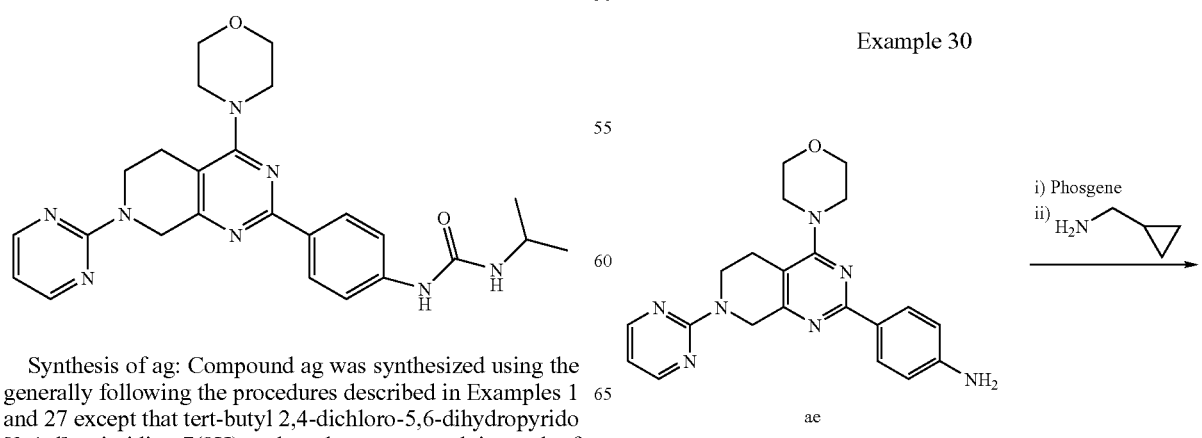

ae

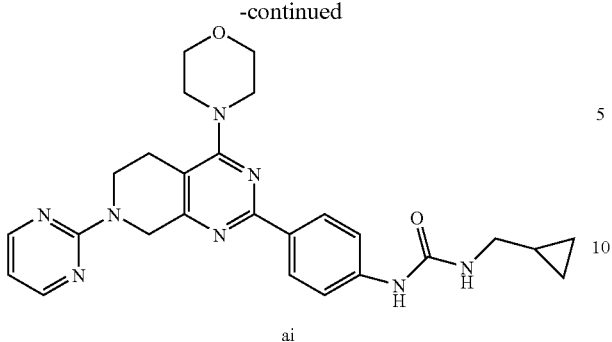

ai

Synthesis of ai: Phosgene (20% in toluene, 75 µL) was added to a mixture of 4-(4-morpholino-6-(pyrimidin-2-yl)-5,6,7,8-tetrahydropyrido[4,3-d]pyrimidin-2-yl)aniline (50 mg, 0.1 mmol) and DIPEA (20 µL, 0.14 mmol) in 1,4-dioxane (1.0 mL). The reaction mixture was heated at 50° C. for 45 min. Upon cooling, cyclopropylmethylamine (66 µL, 0.77 mmol) was added to the reaction mixture and the resultant mixture was stirred for 1.5 h. The precipitated solid was filtered, washed with small amount of DCM. The solid was triturated with small amount of H$_2$O, filtered, dried to give 43 mg (70%) of compound ai as an off-white solid: $^1$H NMR (400 MHz, DMSO) δ 8.70 (s, 1H), 8.44 (d, J=4.7, 2H), 8.22 (d, J=8.8, 2H), 7.49 (d, J=8.8, 2H), 6.70 (t, J=4.7, 1H), 6.28 (t, J=5.6, 1H), 4.81 (s, 2H), 3.98 (s, 2H), 3.74 (s, 4H), 3.47 (s, 4H), 2.99 (t, J=6.2, 2H), 2.75 (s, 2H), 0.95 (s, 1H), 0.47-0.40 (m, 2H), 0.19 (q, J=4.8, 2H); LC/MS Mass found-m/z+487 (M+H)+.

Example 31

3.47 (s, 4H), 3.39-3.35 (m, 2H), 2.71 (dd, J=9.4, 15.8, 4H). Mass found-m/z+486 (M+H)+.

Example 32

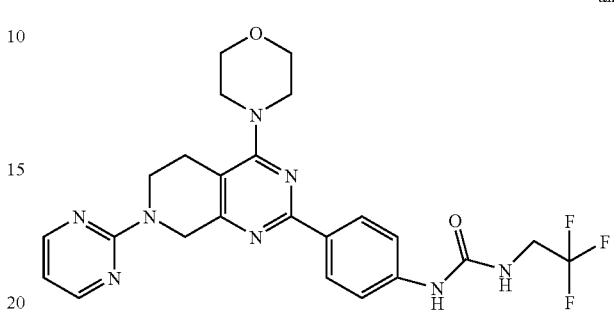

ak

Synthesis of ak: Compound ak was synthesized by using 2,2,2-trifluoroethylamine instead of cyclopropylmethylamine according to the procedure described in Example 30: $^1$H NMR (400 MHz, DMSO) δ 9.02 (s, 1H), 8.44 (d, J=4.7, 2H), 8.25 (d, J=8.8, 2H), 7.52 (d, J=8.8, 2H), 6.83 (s, 1H), 6.70 (t, J=4.7, 1H), 4.82 (s, 2H), 3.96 (dd, J=6.3, 16.5, 4H), 3.74 (s, 4H), 3.47 (s, 4H), 2.75 (s, 2H); LC-MS-m/z+515 (M+H)+.

Example 33

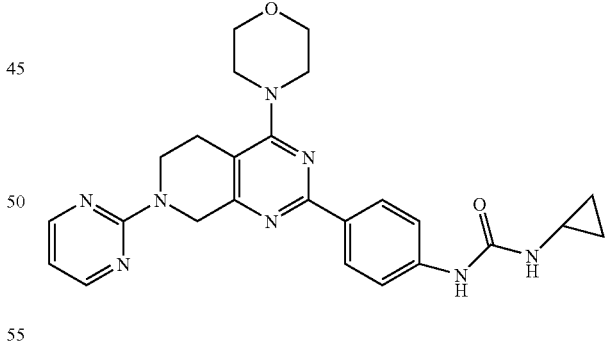

am

Synthesis of am: Compound am was synthesized by using aminocyclopropane instead of cyclopropylmethylamine according to the procedure described in Example 30: $^1$H NMR (400 MHz, DMSO) δ 8.56 (s, 1H), 8.44 (d, J=4.7, 2H), 8.22 (d, J=8.8, 2H), 7.51 (d, J=8.8, 2H), 6.70 (t, J=4.7, 1H), 6.46 (d, J=2.3, 1H), 4.81 (s, 2H), 3.98 (t, J=5.1, 2H), 3.73 (d, aj Synthesis of aj: Compound aj was synthesized following the procedure described in Example 30 except that β-cyanoethylamine was used instead of cyclopropylmethylamine: $^1$H NMR (400 MHz, DMSO) δ 8.94 (s, 1H), 8.44 (d, J=4.7, 2H), 8.23 (d, J=8.8, 2H), 7.52 (d, J=8.8, 2H), 6.70 (t, J=4.7, 1H), 6.54 (t, J=5.9, 1H), 4.82 (s, 2H), 3.98 (s, 2H), 3.74 (s, 4H), J=4.4, 4H), 3.47 (d, J=4.1, 4H), 2.74 (d, J=6.7, 2H), 2.58-2.53 (m, 1H), 0.68-0.61 (m, 2H), 0.44-0.39 (m, 2H); LC-MS-m/z+473 (M+H)+.

Example 34 an

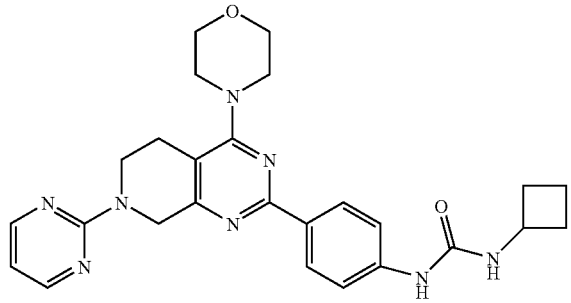

Synthesis of an: Compound an was synthesized by using aminocyclobutane instead of cyclopropylmethylamine according to the procedure described in Example 30: $^1$H NMR (400 MHz, DMSO) δ 8.57 (s, 1H), 8.44 (d, J=4.7, 2H), 8.21 (d, J=8.8, 2H), 7.47 (d, J=8.8, 2H), 6.70 (t, J=4.7, 1H), 6.48 (d, J=8.1, 1H), 4.81 (s, 2H), 4.14 (dd, J=8.2, 16.3, 1H), 3.98 (s, 2H), 3.73 (s, 4H), 3.57 (s, 2H), 3.46 (s, 4H), 2.75 (s, 2H), 2.20 (d, J=8.4, 2H), 1.91-1.79 (m, 2H), 1.62 (d, J=6.7, 2H); LC-MS-m/z+487 (M+H)+.

Example 35

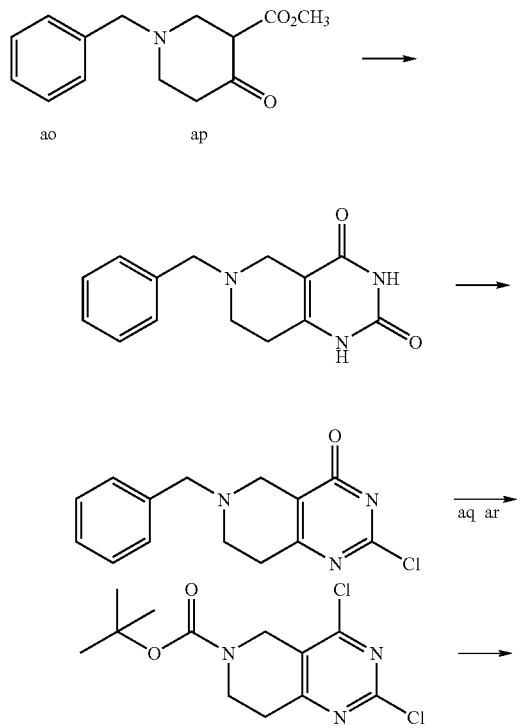

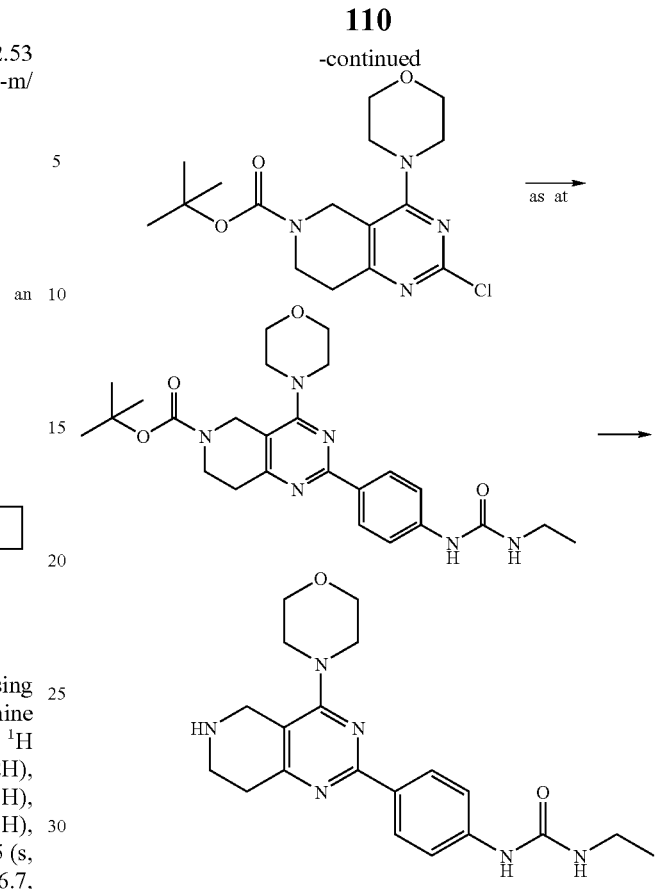

Synthesis of ao—Step 1: Methyl 1-benzyl-4-oxo-3-piperidinecarboxylate (20.194 g, 71.168 mmol) and urea (9.031 g, 150.4 mmol) were dissolved in methanol (150 mL). 4.63 M of sodium methoxide in methanol (46 mL) was added dropwise. Then the reaction was heated to reflux under nitrogen for 96 h. The reaction was cooled to 0° C. and filtered to give a white solid. This was stirred vigorously for 30 minutes with 50 ml water, then cooled to 0° C. and filtered to give 6-benzylhexahydropyrido[4,3-d]pyrimidine-2,4(1H,3H)-dione (ao) as a white solid (11.77 g, 45.7 mmol) which was dried under high vacuum overnight and then used without further purification: $^1$H NMR (D$_6$-DMSO, 400 MHz) δ 7.47-7.07 (m, 5H), 3.56 (s, 2H), 2.96 (s, 2H), 2.51 (t, 4H), 2.27 (t, J=5.6, 2H).

Synthesis of ap—Step 2: The above dione (ao) (16.95 g, 65.88 mmol) was added to phosphoryl chloride (1.00E2 mL, 1070 mmol) in a 500 ml round bottom flask equipped with a stir bar and the solution was refluxed 3 h under nitrogen. After the reaction was done, the reaction mixture was concentrated using a rotovevaporator to remove the volatiles, and the resultant residue was poured into 250 ml ice. To this mixture was then added 3M NaOH to pH 10. The mixture was then extracted with CH$_2$Cl$_2$ (3×150 ml). The combined organics was dried over Magnesium sulfate, filtered and concentrated to provide a tan-colored oil. The crude material was dissolved in dichloromethane and adsorbed onto silica gel. This material was purified by column chromatography (120 g column, with a gradient of 0% to 50% ethyl acetate in hexanes) to provide 6-benzyl-2,4-dichloro-5,6,7,8-tetrahydropyrido[4,3-d]pyrimidine (ap) as a pale solid (14.63 g, 49.7 mmol): $^1$H NMR (CDCl$_3$, 400 MHz) δ 7.41-7.27 (m, 5H), 3.77 (s, 2H), 3.62 (s, 2H), 2.99 (t, J=5.8, 2H), 2.81 (t, J=5.8, 2 H).

Synthesis of aq—Step 3: The above dichloride (ap) (1.84 g, 6.25 mmol) was dissolved in methylene chloride (40 mL) in a round bottom flask equipped with a stir bar and the resultant solution was cooled to 0° C. α-chloroethyl chloroformate (0.810 mL, 7.50 mmol) was added slowly to the reaction mixture and the reaction mixture stirred at 0° C. for 15 minutes. The reaction mixture was warmed to rt, and then refluxed for 1 h. LC-MS analysis of the reaction mixture showed clean conversion to the intermediate carbamate. The reaction mixture was concentrated using a rotovevaporator to remove volatiles. The resultant residue was redissolved in 20 mL MeOH, and heated to reflux for 30 min. The reaction mixture was concentrated again using a rotoevaporator to provide the crude intermediate, the free amine, as confirmed by LC-MS analysis.

This crude product was dissolved in 50 ml of dry DCM, and to it was added 3.1 g tetraalkylammonium carbonate polymer-bound (2.5-3.5 mmol N/g) and di-tert-butyldicarbonate (2.45 g, 11.2 mmol). The resultant mixture was stirred at rt for 1 h. The reaction mixture was filtered to remove the resin, then adsorbed onto silica gel. The crude product was purified by flashed chromatography (12 g column, 0-30% EtOAc in hexanes) to provide tert-butyl 2,4-dichloro-7,8-dihydropyrido[4,3-d]pyrimidine-6(5H)-carboxylate (aq) as a clear oil, which slowly crystallized (1.68 g, 5.52 mmol): $^1$H NMR (CDCl$_3$, 400 MHz) δ 4.56 (s, 2H), 3.75 (t, J=5.9, 2H), 2.97 (t, J=5.8, 2H), 1.50 (s, 9H).

Synthesis of ar—Step 4: tert-butyl 2-chloro-4-morpholino-7,8-dihydropyrido[4,3-d]pyrimidine-6(5H)-carboxylate (ar) was synthesized using the procedure described in Step 1 of Example 1: $^1$H NMR (D$_6$-DMSO, 400 MHz) δ 4.37 (s, 2H), 3.67 (m, 4H), 3.47 (m, 6H), 2.63 (t, J=5.2, 2H), 1.43 (s, 9H).

Synthesis of as—Step 5: tert-butyl 2-(4-(3-ethylureido)phenyl)-4-morpholino-7,8-dihydropyrido[4,3-d]pyrimidine-6(5H)-carboxylate (as) was prepared following the procedure described in step 2 of Example 1: $^1$H NMR (D$_6$-DMSO, 400 MHz) δ 8.67 (s, 1H), 8.19 (d, J=8.7, 2H), 7.48 (d, J=8.8, 2H), 6.18 (t, J=5.5, 1H), 4.42 (s, 2H), 3.78-3.70 (m, J=4.6, 4H), 3.67 (t, J=6.2, 2H), 3.44-3.36 (m, J=4.5, 4H), 3.17-3.05 (m, 2H), 2.85 (t, J=6.2, 2H), 1.41 (s, 9H), 1.06 (t, J=7.2, 3H).

Synthesis of at: Compound at was synthesized using the general procedure described in step 3 of Example 1: $^1$H NMR (D$_6$-DMSO, 400 MHz) δ 8.38 (s, 1H), 8.17 (d, J=8.7, 2H), 7.44 (d, J=8.7, 2H), 6.01 (s, 1H), 3.78-3.66 (m, J=3.7, 8.6, 6H), 3.44-3.33 (m, 4H), 3.20-3.08 (m, J=6.4, 13.5, 2H), 2.74 (t, J=6.0, 2H), 1.07 (t, J=7.2, 3H).

$^1$H NMR (D$_6$-DMSO, 400 MHz) δ 8.41 (s, 1H), 8.15 (d, J=8.7, 2H), 7.45 (d, J=8.8, 2H), 7.30-7.08 (m, 5 H), 6.06-5.97 (m, 1H), 4.54 (s, 2H), 3.90-3.65 (m, J=19.9, 8H), 3.49 (br s, 4H), 3.07 (q, 2H), 2.86 (t, 2H), 1.07 (t, J=7.2, 3H).

Example 38

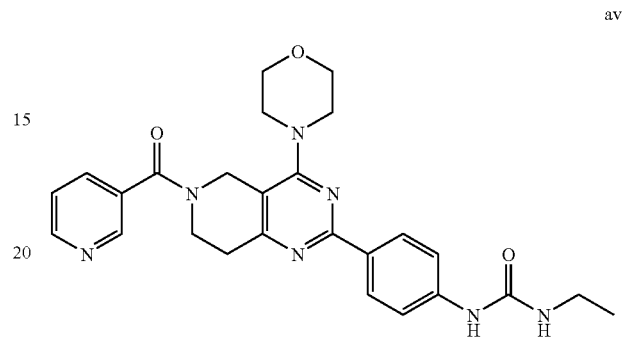

av

Synthesis of av: Compound av was synthesized following the procedure described in Example 5 by reacting 1-ethyl-3-(4-(4-morpholino-5,6,7,8-tetrahydropyrido[4,3-d]pyrimidin-2-yl)phenyl)urea (at) with nicotinyl chloride hydrochloride: $^1$H NMR (D$_6$-DMSO, 400 MHz) δ 8.67 (dd, J=1.6, 4.8, 1H), 8.63 (d, 1H), 8.42 (s, 1H), 8.19 (d, J=8.8, 2H), 7.84 (d, J=7.8, 1H), 7.50-7.42 (m, J=6.3, 3H), 6.08-5.96 (m, 1H), 4.62 (s, 2H), 3.89-3.72 (m, 3H), 3.68 (s, 4H), 3.39 (s, 4H), 3.23-3.07 (m, 4H), 2.95 (t, J=6.3, 2H), 1.07 (t, J=7.2, 3H); LC-MS: m/z=+488 (M+H)$^+$.

Example 39

Example 36

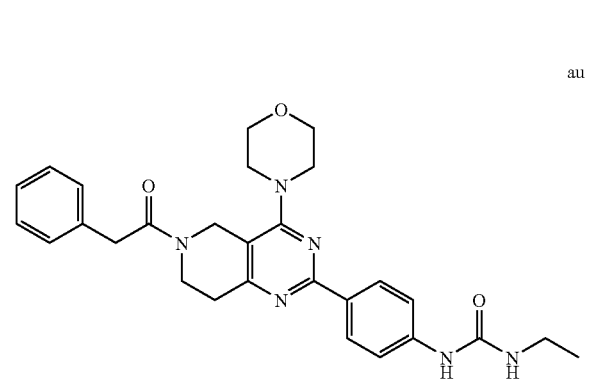

au

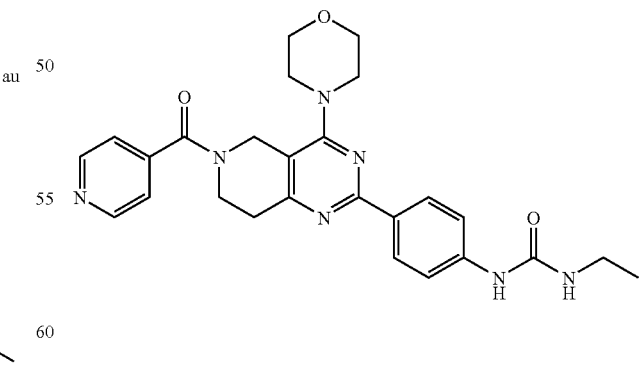

aw

Synthesis of au: Compound au was synthesized using the general procedure described in Example 5 by reacting 1-ethyl-3-(4-(4-morpholino-5,6,7,8-tetrahydropyrido[4,3-d]pyrimidin-2-yl)phenyl)urea (at) with phenylacetyl chloride:

Synthesis of aw: Compound aw was synthesized using the procedure described in Example 5 by reacting 1-ethyl-3-(4-(4-morpholino-5,6,7,8-tetrahydropyrido[4,3-d]pyrimidin-2- yl)phenyl)urea (at) with isonicotinoyl chloride hydrochloride: LC-MS m/z=+488.3 (M+H)+.

Example 40

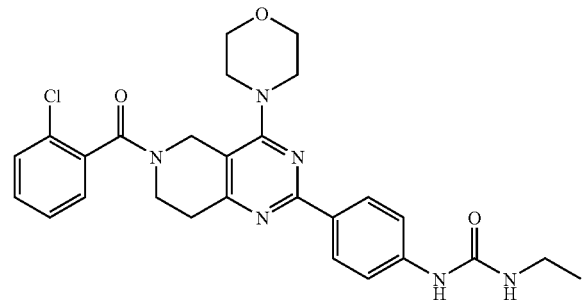

ax

Synthesis of ax: Compound ax was synthesized following the procedure described in Example 5 by reacting 1-ethyl-3-(4-(4-morpholino-5,6,7,8-tetrahydropyrido[4,3-d]pyrimidin-2-yl)phenyl)urea (at) with 2-chlorobenzoyl chloride: $^1$H NMR (D$_6$-DMSO, 400 MHz) δ 8.42 (s, 1H), 8.18 (d, J=8.7, 2H), 7.57-7.26 (m, 6H), 6.02 (s, 1H), 4.83-4.65 (m, 1H), 4.29-4.14 (m, 1H), 4.07-3.90 (m, 1H), 3.88-3.71 (m, 3H), 3.60-3.34 (m, 5H), 3.24-3.07 (m, J=6.4, 13.5, 4H), 2.92-2.78 (m, 1H), 1.07 (t, J=7.2, 3H); LC-MS m/z=+521.2 (M+H)+.

Example 41

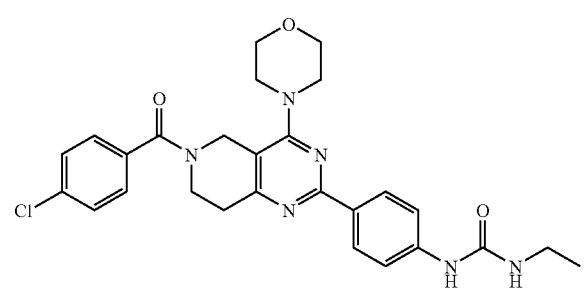

ay

Synthesis of ay: Compound ay was synthesized using the procedure described in Example 5 by reacting 1-ethyl-3-(4-(4-morpholino-5,6,7,8-tetrahydropyrido[4,3-d]pyrimidin-2-yl)phenyl)urea with 4-chlorobenzoic acid chloride: $^1$H NMR (D$_6$-DMSO, 400 MHz) δ 8.42 (s, 1H), 8.19 (d, J=8.6, 2H), 7.55-7.36 (m, 6H), 6.07-5.96 (m, 1H), 4.59 (s, 2H), 3.78 (s, 3H), 3.68 (s, 4H), 3.39 (s, 4H), 3.23-3.08 (m, 4H), 2.93 (t, J=6.2, 2H), 1.07 (t, J=7.1, 3H); LC-MS: m/z=+521.2 (M+H)+.

Example 42

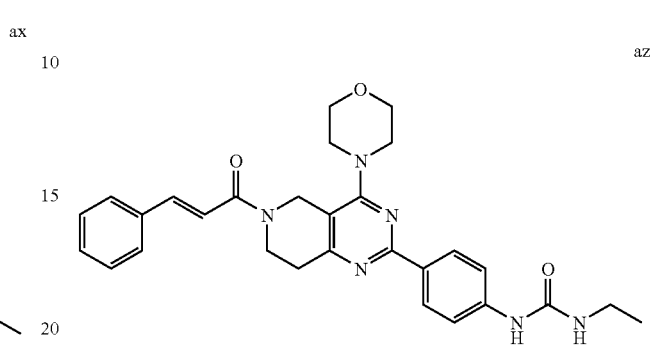

az

Synthesis of az: Compound az was synthesized using the procedure described in Example 5 by reacting 1-ethyl-3-(4-(4-morpholino-5,6,7,8-tetrahydropyrido[4,3-d]pyrimidin-2-yl)phenyl)urea (at) with 3-phenyl-2-propenoyl chloride: $^1$H NMR (D$_6$-DMSO, 400 MHz) δ 8.41 (s, 1H), 8.18 (d, J=8.7, 2H), 7.67 (d, J=6.7, 2H), 7.51-7.31 (m, 6H), 7.22 (d, J=15.5, 1H), 6.06-5.96 (m, 1H), 4.69 (s, 2H), 4.05-3.92 (m, 2H), 3.84-3.70 (m, 4H), 3.53-3.42 (m, 4H), 3.20-3.06 (m, 3H), 2.98-2.90 (m, 2H), 1.07 (t, J=7.2, 3H); LC-MS m/z=+513.3 (M+H)+.

Example 43

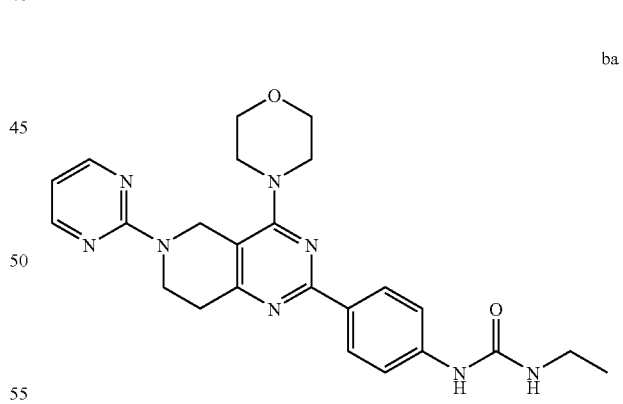

ba

Synthesis of ba: Compound ba was synthesized using the procedure described in Example 2 by reacting 1-ethyl-3-(4-(4-morpholino-5,6,7,8-tetrahydropyrido[4,3-d]pyrimidin-2-yl)phenyl)urea (at) with 2-chloropyrimidine: $^1$H NMR (D$_6$-DMSO, 400 MHz) δ 8.64 (s, 1H), 8.40 (d, J=4.7, 2H), 8.18 (d, J=8.7, 2H), 7.47 (d, J=8.8, 2H), 6.66 (t, J=4.7, 1H), 6.15 (t, J=5.6, 1H), 4.85 (s, 2H), 4.10 (t, J=6.2, 2H), 3.83-3.72 (m, 4H), 3.52-3.42 (m, 4H), 3.18-3.04 (m, 2H), 2.92 (t, J=6.1, 2H), 1.06 (t, J=7.2, 3H); LC-MS m/z=+461.3 (M+J)+.

(m, 4H), 3.50-3.41 (m, J=4.3, 4H), 3.16-3.05 (m, 2H), 2.91 (t, J=6.1, 2H), 1.06 (t, J=7.2, 3H).

Example 44

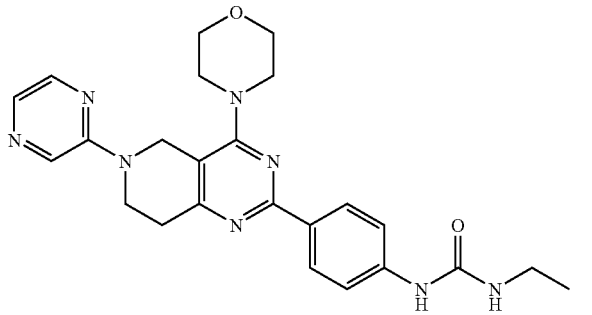

bb

Synthesis of bb: Compound bb was synthesized using the procedure described in Example 2 by reacting 1-ethyl-3-(4-(4-morpholino-5,6,7,8-tetrahydropyrido[4,3-d]pyrimidin-2-yl)phenyl)urea (at) with 2-chloropyrazine: ¹H NMR (D₆-DMSO, 400 MHz) δ 8.64 (s, 1H), 8.42 (s, 1H), 8.18 (d, J=8.7, 2H), 8.11 (s, 1H), 7.85 (d, J=2.6, 1H), 7.47 (d, J=8.7, 2H), 6.16 (t, J=5.6, 1H), 4.70 (s, 2H), 3.98 (t, J=6.2, 2H), 3.86-3.72 (m, 5H), 3.52-3.41 (m, 4H), 3.19-3.05 (m, 2H), 2.97 (t, J=6.1, 2H), 1.06 (t, J=7.2, 3H): LC-MS m/z=+461.3 (M+H)+.

Example 45

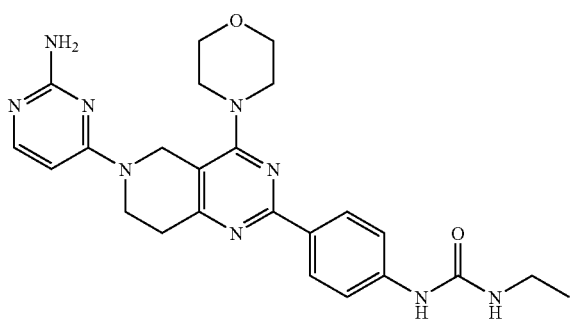

bc

Synthesis of bc: Compound bc was synthesized using the procedure described in Example 2 by reacting 1-ethyl-3-(4-(4-morpholino-5,6,7,8-tetrahydropyrido[4,3-d]pyrimidin-2-yl)phenyl)urea (at) with 2-amino-4-chloropyrimidine: LC-MS m/z=+476.2 (M+H); ¹H NMR (D₆-DMSO, 400 MHz) δ 8.63 (s, 1H), 8.18 (d, J=8.7, 2H), 7.80 (d, J=6.0, 1H), 7.47 (d, J=8.7, 2H), 6.15 (t, J=5.5, 1H), 6.10 (d, J=6.0, 1H), 6.02 (s, 2H), 4.64 (s, 2H), 3.93-3.81 (m, J=10.7, 16.7, 3H), 3.82-3.74

Example 46

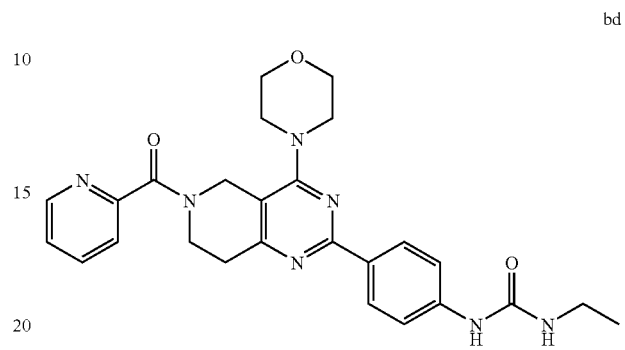

bd

Synthesis of bd: Compound bd was synthesized using general procedure described in Example 5 by reacting 1-ethyl-3-(4-(4-morpholino-5,6,7,8-tetrahydropyrido[4,3-d]pyrimidin-2-yl)phenyl)urea (at) with picolinoyl chloride hydrochloride: LC-MS: m/z=+488.3 (M+H)+; ¹H NMR (D₆-DMSO, 400 MHz) δ 8.69-8.58 (m, 2H), 8.19 (t, J=7.7, 2H), 7.95 (t, J=7.7, 1H), 7.62 (d, J=7.8, 1H), 7.57-7.43 (m, 3H), 6.16 (t, J=5.5, 1H), 4.69 (d, J=42.1, 2H), 4.06 (q, J=5.3, 1H), 4.03-3.95 (m, 1H), 3.85-3.70 (m, 4H), 3.51 (d, J=23.6, 4H), 3.28-3.22 (m, 15H), 3.20-3.05 (m, 4H), 3.03-2.89 (m, 2H), 1.06 (t, J=7.2, 3H).

Example 47

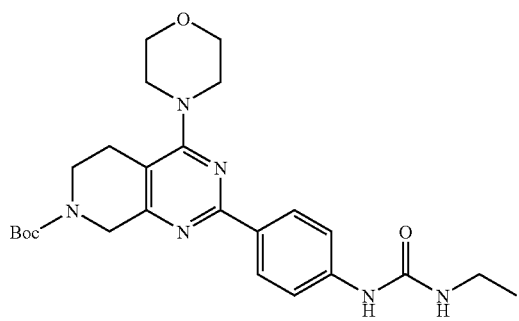

be

Synthesis of be: Compound be was synthesized using the procedure described in steps 1 and 2 of Example 1 by using tert-butyl 2,4-dichloro-5,6-dihydropyrido[3,4-d]pyrimidine-7(8H)-carboxylate instead of tert-butyl 2,4-dichloro-5H-pyrrolo[3,4-d]pyrimidine-6(7H)-carboxylate in step 1: LC-MS: m/z=+483 (M+H)+; ¹H NMR (D₆-DMSO, 400 MHz) δ 8.63 (s, 1H), 8.18 (d, J=8.7, 2H), 7.48 (d, J=8.8, 2H), 6.14 (s, 1H), 4.46 (s, 2H), 3.90 (s, 1H), 3.73 (s, 4H), 3.49 (d, J=22.0, 6H), 3.18-3.06 (m, 2H), 2.66 (s, 2H), 1.46 (s, 9H), 1.09-1.03 (m, 8H).

Example 48

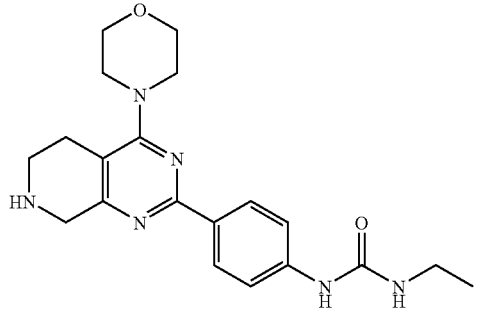

bf

Synthesis of bf: Compound bf was synthesized using the general procedure described in step 3 of Example 1: LC-MS: m/z=+383 (M+H)+; $^1$H NMR (D$_6$-DMSO, 400 MHz) δ 8.66 (s, 1H), 8.18 (d, J=8.8, 2H), 7.47 (d, J=8.8, 2H), 6.17 (t, J=5.6, 1 H), 3.86 (s, 2H), 3.77-3.70 (m, 4H), 3.47-3.40 (m, 4H), 3.15-3.06 (m, 2H), 2.93-2.85 (m, 2H), 2.62-2.56 (m, 2H), 1.06 (t, J=7.2, 3H).

Example 49

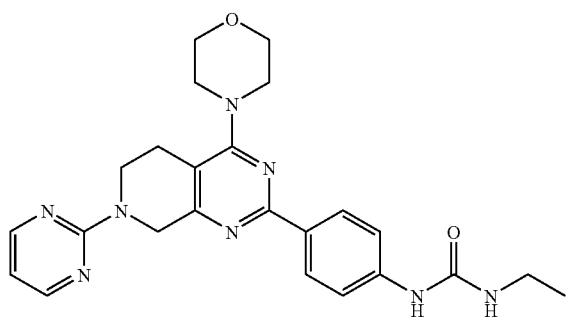

bg

Synthesis of bg: Compound bg was synthesized using general procedure described in Example 2 by reacting 1-ethyl-3-(4-(4-morpholino-5,6,7,8-tetrahydropyrido[3,4-d]pyrimidin-2-yl)phenyl)urea with 2-chloropyrimidine: LC-MS: m/z=+461 (M+H)+; $^1$H NMR (D$_6$-DMSO, 400 MHz) δ 8.64 (s, 1H), 8.43 (d, J=4.7, 2H), 8.21 (d, J=8.7, 2H), 7.49 (d, J=8.8, 2H), 6.69 (t, J=4.7, 1H), 6.16 (t, J=5.5, 1H), 4.81 (s, 2H), 3.98 (s, 2H), 3.73 (d, J=4.5, 4H), 3.47 (d, J=4.4, 4H), 3.19-3.02 (m, 2H), 2.75 (s, 2H), 1.06 (t, J=7.2, 3H).

Example 50

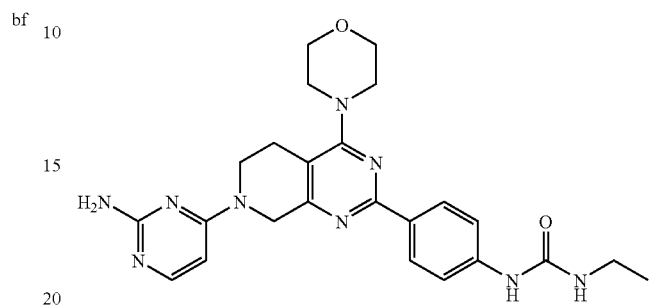

bh

Synthesis of bh: Compound bh was synthesized using the general procedure described in Example 2 by reacting 1-ethyl-3-(4-(4-morpholino-5,6,7,8-tetrahydropyrido[3,4-d]pyrimidin-2-yl)phenyl)urea with 2-amino-4-chloropyrimidine: LC-MS: m/z=+476 (M+H)+; $^1$H NMR (400 MHz, D$_6$-DMSO) δ 12.08-11.82 (m, 1H), 8.67 (s, 1H), 8.19 (s, 2H), 7.91-7.84 (m, 1H), 7.50 (d, J=8.8, 2H), 6.75-6.60 (m, 1H), 6.24-6.12 (m, 1H), 4.95 (s, 2H), 4.13-3.82 (m, 4H), 3.12 (s, 3H), 2.86-2.74 (m, 2H), 1.06 (t, J=7.2, 3H).

Example 51

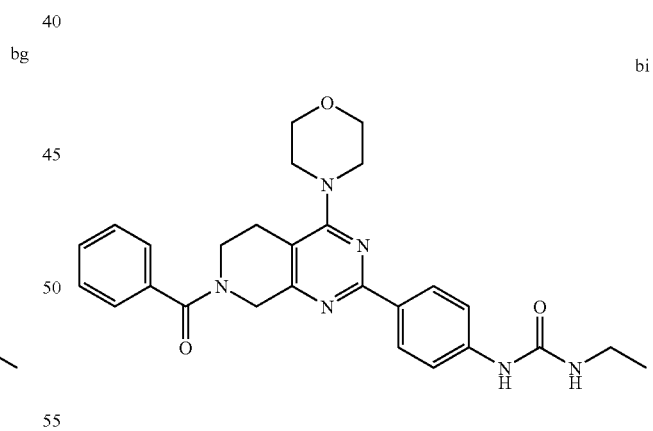

bi

Synthesis of bi: Compound bi was synthesized using general procedure described in Example 5 by reacting 1-ethyl-3-(4-(4-morpholino-5,6,7,8-tetrahydropyrido[3,4-d]pyrimidin-2-yl)phenyl)urea with benzoyl chloride: LC-MS m/z=+487.2 (M+H)+; $^1$H NMR (400 MHz, D$_6$-DMSO) δ 10.12-9.97 (m, J=23.6, 2H), 9.35 (s, 1H), 9.09 (s, 1H), 7.62 (d, J=9.0, 1H), 6.97 (d, J=8.7, 2H), 5.69 (s, 1H), 3.40-3.24 (m, J=6.3, 13.6, 7H), 3.17 (s, 1H), 3.04-2.91 (m, 1H), 1.20 (t, J=7.2, 3H), 0.97 (t, J=7.2, 2H).

Example 52

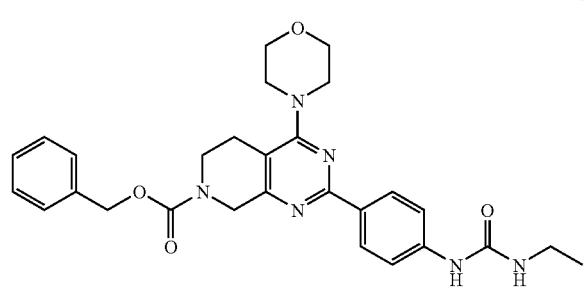

bj

Synthesis of bj: Compound bj was synthesized using the general procedure described in Example 5 by reacting 1-ethyl-3-(4-(4-morpholino-5,6,7,8-tetrahydropyrido[3,4-d]pyrimidin-2-yl)phenyl)urea with benzyl chloroformate: LC/MS m/z=+517 (M+H)+; $^1$H NMR (400 MHz, $D_6$-DMSO) δ 8.68 (s, 1H), 8.19 (d, J=7.8, 2H), 7.48 (d, J=8.0, 2H), 7.44-7.31 (m, 5H), 6.17 (d, J=5.5, 1H), 5.16 (s, 2H), 4.55 (d, J=23.3, 2H), 3.73 (br s, 4H), 3.65-3.53 (m, 2H), 3.49 (br s, 4H), 3.16-3.05 (m, 2H), 2.74-2.66 (m, 2H), 1.06 (t, J=7.2, 3H).

Example 53 bk

Synthesis of bk: Compound bk was synthesized using the general procedure described in Example 5 by reacting 1-ethyl-3-(4-(4-morpholino-5,6,7,8-tetrahydropyrido[3,4-d]pyrimidin-2-yl)phenyl)urea with picolinoyl chloride hydrochloride: LC-MS m/z=+488 (M+H)+; $^1$H NMR (400 MHz, $D_6$-DMSO) δ 9.06-8.87 (m, 1H), 8.71-8.61 (m, 1H), 8.20 (d, J=8.7, 1H), 8.11 (d, J=8.7, 1H), 8.03-7.92 (m, J=7.8, 1H), 7.71 (d, J=7.7, 1 H), 7.63-7.46 (m, J=8.5, 3H), 6.45 (br s, 1H), 4.83 (d, J=22.3, 2H), 3.89-3.80 (m, 2H), 3.23 (t, 2H), 2.94-2.70 (m, 2H), 1.14-0.97 (m, 3H).

Example 54

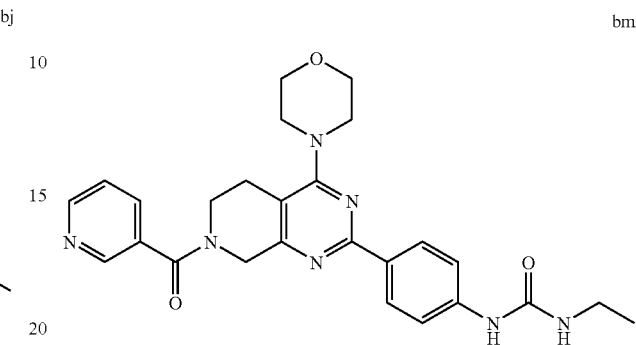

bm

Synthesis of bm: Compound bm was synthesized using the general procedure described in Example 5 by reacting 1-ethyl-3-(4-(4-morpholino-5,6,7,8-tetrahydropyrido[3,4-d]pyrimidin-2-yl)phenyl)urea with nicotinoyl chloride hydrochloride: LC-MS m/z=+488 (M+H)+; $^1$H NMR (400 MHz, $D_6$-DMSO) δ 8.89-8.48 (m, J=15.9, 19.2, 4H), 8.40-8.05 (m, 3H), 7.97 (d, J=7.8, 1H), 7.68-7.27 (m, J=5.1, 7.7, 4H), 6.16 (s, 1H), 4.91-4.38 (m, 3H), 3.92 (s, 1H), 3.73 (s, 6H), 3.58-3.44 (m, 7H), 3.17-3.05 (m, 3H), 2.87-2.69 (m, 3H), 1.06 (t, J=7.1, 4H).

Example 55

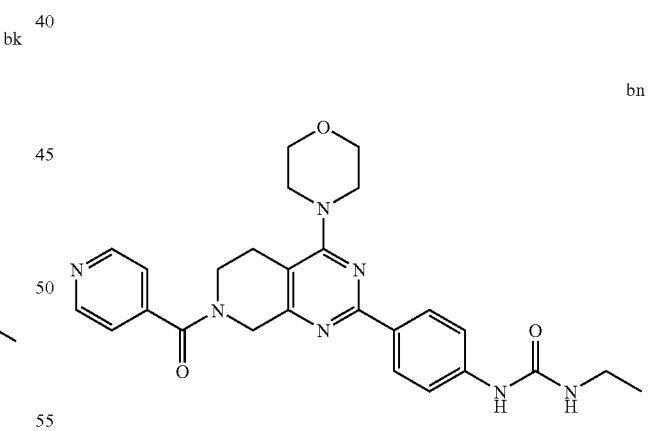

bn

Synthesis of bn: Compound bn was synthesized using the general procedure described in Example 5 by reacting 1-ethyl-3-(4-(4-morpholino-5,6,7,8-tetrahydropyrido[3,4-d]pyrimidin-2-yl)phenyl)urea with isonicotinoyl chloride hydrochloride: LC-MS: m/z=+488 (M+H)+; $^1$H NMR (400 MHz, $D_6$-DMSO) δ 8.96-8.84 (m, 1H), 8.80 (s, 2 H), 8.25-8.03 (m, 2H), 7.65 (d, J=5.8, 2H), 7.59-7.43 (m, 2H), 6.38 (br s, 1H), 4.81 (s, 1H), 4.85-4.45 (m, 1H), 3.88-3.57 (m, J=33.2, 9H), 3.51-3.40 (m, 2H), 3.18-3.04 (m, 2 H), 2.86-2.74 (m, 2H), 1.12 (t, J=7.0, 3H).

Example 56

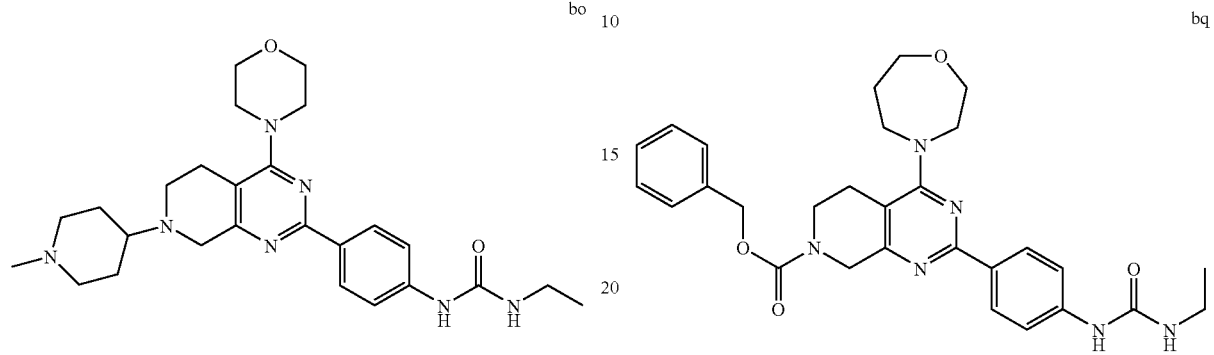

bo

Synthesis of bo: Compound bo was synthesized according to general procedure described in Example 8 by reacting 1-ethyl-3-(4-(4-morpholino-5,6,7,8-tetrahydropyrido[3,4-d]pyrimidin-2-yl)phenyl)urea with N-methylpiperidone: LC-MS: m/z=+480 (M+H)+.

Example 57 bp

Synthesis of bp: Compound bp was prepared following the procedure described in Examples 1 and 5 with the modification that homomorpholine instead of morpholine was used in step 1 of Example 1 and acetyl chloride was used instead of benzylchloroformate in Example 5: $^1$H NMR (400 MHz, DMSO) δ 8.61 (s, 1H), 8.16 (d, J=7.3, 2H), 7.47 (d, J=7.8, 2H), 6.15 (s, 1H), 4.55 (d, J=32.6, 2H), 3.80 (d, J=2.6, 6H), 3.73-3.54 (m, 4H), 3.20-3.04 (m, 2H), 2.80 (s, 1H), 2.68 (s, 1H), 2.11 (s, 3H), 1.98 (s, 2H), 1.06 (t, J=7.2, 3H); LC-MS: m/z=+439 (M+H)+.

Example 58

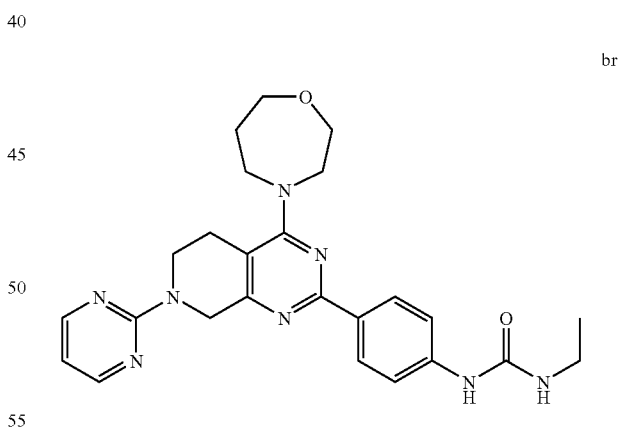

bq

Synthesis of bq: Compound bq was synthesized as described in Example 57: $^1$H NMR (400 MHz, DMSO) δ 8.60 (s, 1H), 8.14 (d, J=8.6, 2H), 7.64-7.19 (m, 7H), 6.14 (t, J=5.5, 1H), 5.14 (s, 2H), 4.50 (s, 2H), 3.77 (m, 6H), 3.69-3.62 (m, 2H), 3.58 (s, 2H), 3.19-2.95 (m, 2H), 2.73 (s, 2H), 1.96 (m, 2H), 1.05 (t, J=7.2, 3H); LC-MS: m/z=+531 (M+H)+.

Example 59 br

Synthesis of br: Compound br was synthesized as described in Example 57: $^1$H NMR (400 MHz, DMSO) δ 8.62 (s, 1H), 8.43 (d, J=4.7, 2H), 8.18 (d, J=8.7, 2H), 7.67-7.51 (m, 2H), 7.48 (d, J=8.7, 2H), 6.68 (t, J=4.7, 1H), 6.16 (t, J=5.5, 1 H), 4.78 (s, 2H), 3.96 (m, 2H), 3.78 (m, 6H), 3.66 (t, J=5.5, 2H), 3.20-3.06 (m, 2H), 2.73 (m, 2H), 1.99 (m, 2H), 1.06 (t, J=7.2, 3H); LC-MS: m/z=+475 (M+H)+.

3.48-3.33 (m, 2H), 3.17-2.93 (m, 4H), 2.73 (t, J=6.0, 2H), 1.21 (d, J=6.6, 3H), 1.06 (t, J=7.2, 3H).

Example 60

Example 62

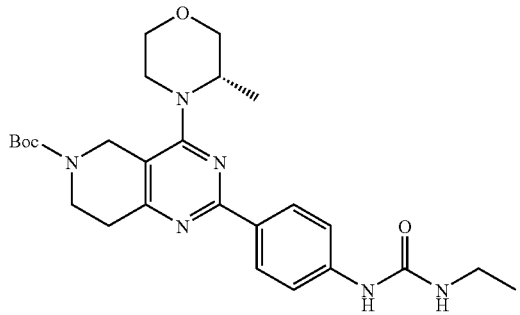

bs

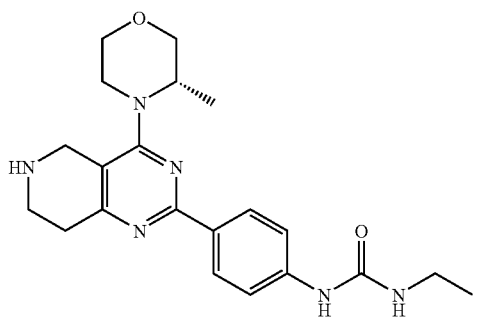

bu

Synthesis of bs: Compound bs was synthesized following the procedure described in steps 1 and 2 of Example 1 with the modification that tert-butyl 2,4-dichloro-7,8-dihydropyrido[4,3-d]pyrimidine-6(5H)-carboxylate was reacted with 3S-3-methylmorpholine in step 1: LC-MS: m/z=+497 (M+H)+; $^1$H NMR (D$_6$-DMSO, 400 MHz) δ 8.66 (s, 1H), 8.18 (d, J=8.8, 2H), 7.48 (d, J=8.8, 2H), 6.18 (s, 1H), 4.47 (d, J=16.0, 1H), 4.38 (d, 1H), 3.88 (d, J=11.4, 2H), 3.76-3.35 (m, 7H), 3.19-3.03 (m, 2H), 2.85 (t, J=6.2, 2H), 1.41 (s, 9H), 1.25 (d, J=6.2, 3H), 1.06 (t, J=7.2, 3H).

Synthesis of bu: Compound bu was synthesized following using the general procedure described in Example 2 by reacting (S)-1-ethyl-3-(4-(4-(3-methylmorpholino)-5,6,7,8-tetrahydropyrido[4,3-d]pyrimidin-2-yl)phenyl)urea (bt) with 2-chloropyrimidine: LC-MS: m/z=+475.3 (M+H)+; $^1$H NMR (D$_6$-DMSO, 400 MHz) δ 8.66 (s, 1H), 8.40 (d, J=4.7, 2H), 8.17 (d, J=8.7, 2H), 7.47 (d, J=8.8, 2H), 6.65 (t, J=4.7, 1H), 6.18 (t, J=5.5, 1H), 4.93 (d, J=16.1, 1H), 4.75 (d, J=16.1, 1H), 4.25-4.12 (m, 1H), 4.06-3.95 (m, 2H), 3.90 (d, J=11.3, 1H), 3.79-3.60 (m, 3H), 3.58-3.41 (m, 2H), 3.17-3.05 (m, 2H), 2.93 (t, J=6.1, 2H), 1.27 (d, J=6.6, 3H), 1.06 (t, J=7.2, 3H).

Example 61

Example 63 bt bv

Synthesis of bt: Compound bt was synthesized from compound bs by the procedure described in step 3 of Example 1: LC-MS: m/z=+397 (M+H)+; $^1$H NMR (D$_6$-DMSO, 400 MHz) δ 8.63 (s, 1H), 8.17 (d, J=8.7, 2H), 7.46 (d, J=8.7, 2H), 6.17 (t, J=5.5, 1H), 3.97-3.80 (m, 2H), 3.75-3.52 (m, 5H), Synthesis of bv: Compound bv was synthesized using the procedure described in Example 2 by reacting (S)-1-ethyl-3-(4-(4-(3-methylmorpholino)-5,6,7,8-tetrahydropyrido[4,3-d]pyrimidin-2-yl)phenyl)urea (bt) with 2-amino-4-chloropyrimidine: LC-MS: m/z=+490 (M+H)+; $^1$H NMR (D$_6$-DMSO, 400 MHz) δ 8.65 (s, 1H), 8.17 (d, J=8.7, 2H), 7.80 (d, J=6.0, 1H), 7.47 (d, J=8.8, 2H), 6.17 (t, J=5.5, 1H), 6.09 (d, J=6.0, 1H), 6.00 (s, 2H), 4.69 (d, J=15.9, 1H), 4.57 (d, J=16.1, 1H), 4.05-3.95 (m, 1 H), 3.94-3.87 (m, 2H), 3.85-3.39 (m, 7H), 3.18-3.04 (m, 2H), 2.91 (s, 2H), 1.29 (d, J=6.6, 3H), 1.06 (t, J=7.2, 3H).

Example 64

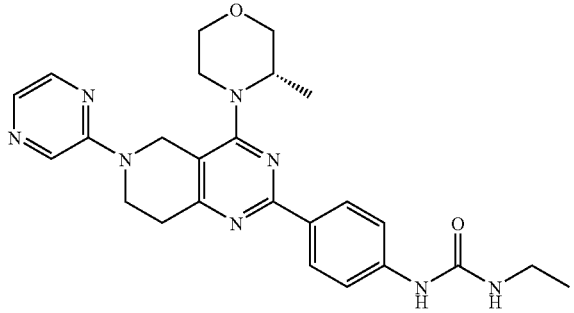

bw

Synthesis of bw: Compound bw was synthesized using the general procedure described in Example 2 by reacting (S)-1-ethyl-3-(4-(4-(3-methylmorpholino)-5,6,7,8-tetrahydropyrido[4,3-d]pyrimidin-2-yl)phenyl)urea (bt) with 2-chloropyrazine: LC-MS: m/z=+475 (M+H)+; $^1$H NMR (D$_6$-DMSO, 400 MHz) δ 8.65 (s, 1H), 8.41 (s, 1H), 8.17 (d, J=8.7, 2H), 7.85 (d, J=2.6, 1H), 7.47 (d, J=8.8, 2H), 6.17 (t, J=5.5, 1H), 4.76 (d, J=16.1, 1H), 4.61 (d, J=16.1, 1H), 4.08-3.98 (m, 2H), 3.96-3.84 (m, 3H), 3.78 (d, J=8.6, 1H), 3.66 (t, J=9.8, 3H), 3.56-3.42 (m, 3H), 3.17-3.05 (m, 2H), 2.97 (t, J=6.1, 2 H), 1.27 (d, J=6.6, 4H), 1.06 (t, J=7.2, 3H).

Example 65

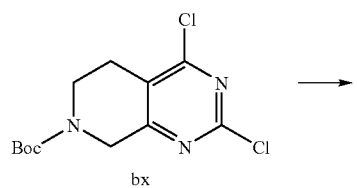

bx

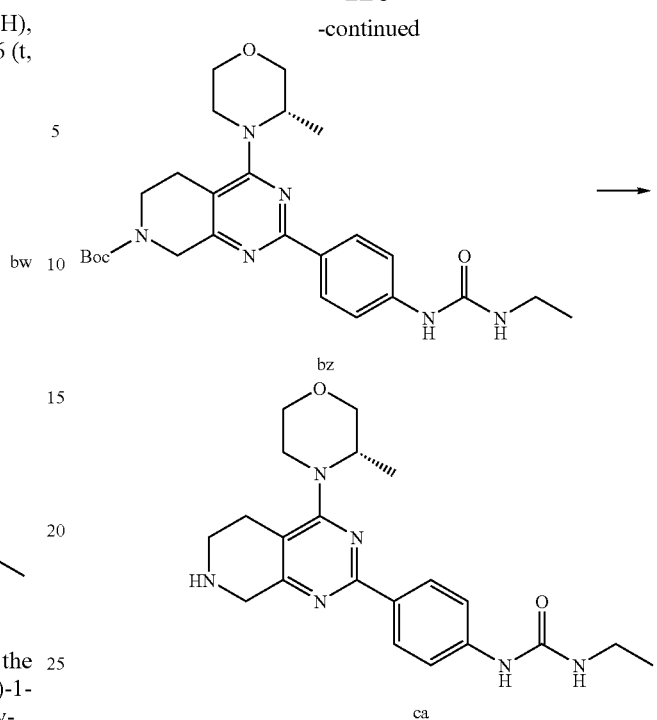

Synthesis of bz—Step 1: Compound bz was synthesized following the procedure described in steps 1 and 2 of Example 1 by reacting tert-butyl 2,4-dichloro-5,6-dihydropyrido[3,4-d]pyrimidine-7(8H)-carboxylate (bx) with 3S-3-methylmorpholine to form compound by in step 1: LC-MS: m/z=+497 (M+H)+; $^1$H NMR (D$_6$-DMSO, 400 MHz) δ 8.64 (s, 1H), 8.17 (d, J=8.7, 2H), 7.48 (d, J=8.7, 2H), 6.15 (t, 1H), 4.55-4.31 (m, 2H), 4.17-4.03 (m, 1H), 3.87 (d, J=11.4, 1H), 3.74-3.53 (m, 5H), 3.49-3.33 (m, 2H), 3.17-3.05 (m, 2H), 2.71-2.60 (m, 2H), 1.46 (s, 9H), 1.25 (d, J=6.6, 3H), 1.06 (t, J=7.2, 3H).

Synthesis of ca: Compound ca was synthesized by general procedure described in step 3 of Example 1: LC-MS: m/z=+ 397 (M+H)+; $^1$H NMR (D$_6$-DMSO, 400 MHz) δ 8.68 (s, 1H), 8.15 (d, J=8.7, 2H), 7.47 (d, J=8.7, 2H), 6.22 (t, 1H), 4.13-4.01 (m, 1H), 3.91-3.48 (m, 8H), 3.45-3.35 (m, 1H), 3.17-3.04 (m, 2H), 2.97-2.86 (m, 1H), 2.85-2.75 (m, 1H), 2.61-2.52 (m, 3H), 1.22 (d, J=6.6, 3H), 1.06 (t, J=7.2, 3H).

Example 66

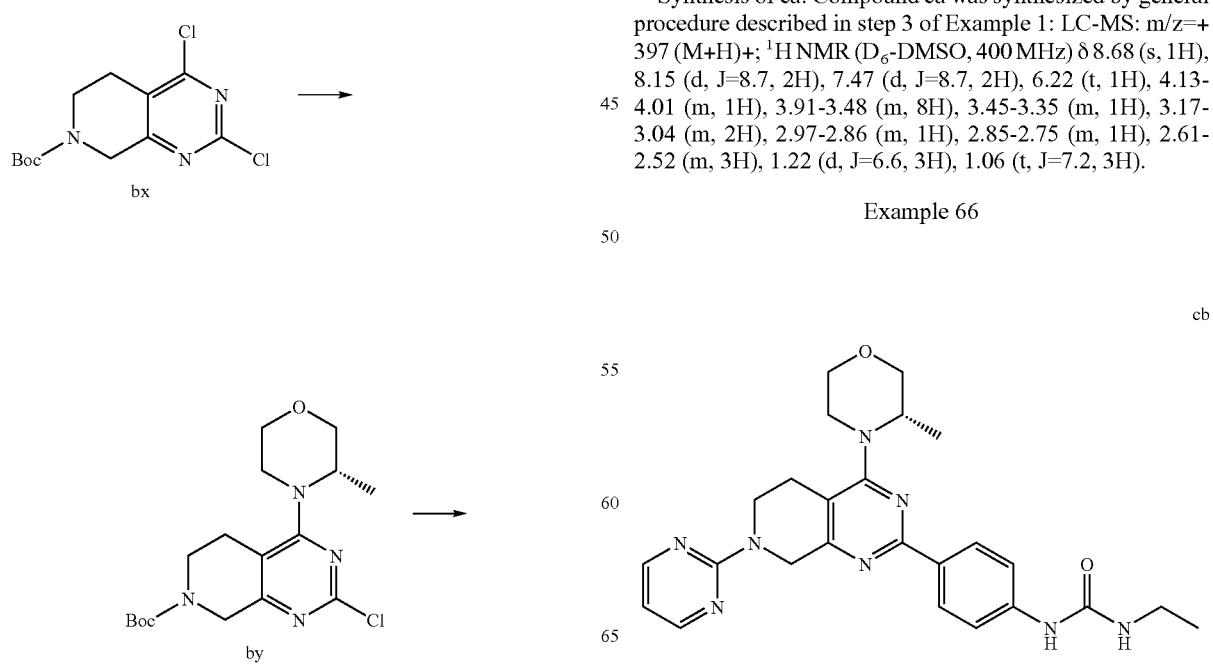

Synthesis of cb: Compound ca was synthesized using the general procedure described in Example 2 by reacting (S)-1-ethyl-3-(4-(4-(3-methylmorpholino)-5,6,7,8-tetrahydropyrido[3,4-d]pyrimidin-2-yl)phenyl)urea (ca) with 2-chloropyrimidine: LC-MS: m/z=+475 (M+H)+; $^1$H NMR (D$_6$-DMSO, 400 MHz) δ 8.68 (s, 1H), 8.44 (d, J=4.7, 2H), 8.20 (d, J=8.8, 2H), 7.49 (d, J=8.8, 2H), 6.69 (t, J=4.7, 1H), 6.19 (t, J=5.6, 1H), 4.90 (d, J=18.7, 1H), 4.73 (d, J=18.7, 1H), 4.19-4.06 (m, 2H), 3.94-3.76 (m, 2H), 3.74-3.54 (m, 4H), 3.50-3.36 (m, 1H), 3.17-3.06 (m, 2H), 2.80-2.68 (m, 2H), 1.25 (d, J=6.6, 3H), 1.06 (t, J=7.2, 3H).

Example 67

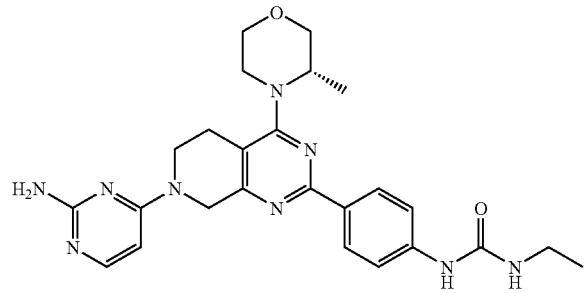

cc

Synthesis of cc: Compound cc was synthesized using general procedure described in Example 2 by reacting (S)-1-ethyl-3-(4-(4-(3-methylmorpholino)-5,6,7,8-tetrahydropyrido[3,4-d]pyrimidin-2-yl)phenyl)urea (ca) with 2-amino-4-chloropyrimidine: LC-MS: m/z=+490 (M+H)+; $^1$H NMR (D$_6$-DMSO, 400 MHz) δ 8.68 (s, 1H), 8.19 (d, J=8.8, 2H), 7.82 (d, J=6.0, 1H), 7.49 (d, J=8.8, 2H), 6.22-6.12 (m, 2H), 6.09 (s, 2H), 4.71 (d, 1H), 4.59 (d, J=18.3, 1H), 4.10 (s, 1H), 3.87 (d, J=11.2, 2H), 3.76-3.51 (m, 6H), 3.49-3.37 (m, 1H), 3.18-3.03 (m, 2H), 2.70 (s, 2H), 1.25 (d, J=6.6, 3H), 1.06 (t, J=7.2, 3H).

Example 68

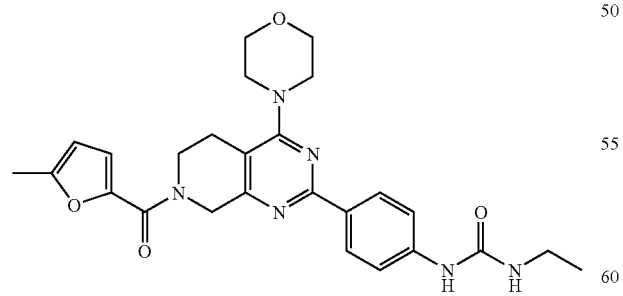

cd

Synthesis of cd: Compound cd was synthesized generally following the synthetic procedures described in Examples 1, 2 and 5: LC-MS: m/z=+491 (M+H)+; $^1$H NMR (400 MHz, DMSO) δ 8.65 (s, 1H), 8.19 (d, J=8.7, 2H), 7.48 (d, J=8.8, 2H), 7.03 (d, J=3.3, 1H), 6.30 (s, 1H), 6.16 (s, 1H), 4.95-4.60 (m, 2H), 3.86 (s, 2H), 3.74 (s, 4H), 3.49 (s, 4H), 3.18-3.05 (m, 2H), 2.78 (s, 2H), 2.37 (s, 3H), 1.06 (t, J=7.2, 3H).

Example 69

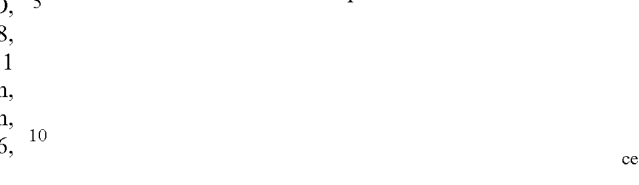

ce

Synthesis of ce: Compound ce was synthesized generally following the synthetic procedures described in Examples 1, 2 and 5: LC-MS: m/z=+478 (M+H)+; $^1$H NMR (400 MHz, DMSO) δ 8.66 (s, 1H), 8.61 (s, 1H), 8.20 (d, J=8.6, 2H), 7.86 (s, 1H), 7.48 (d, J=8.7, 2H), 6.17 (s, 1H), 5.02-4.54 (m, 2H), 3.85 (s, 2H), 3.74 (s, 4H), 3.49 (s, 4H), 3.19-3.04 (m, 2H), 2.94-2.70 (m, 2H), 1.06 (t, J=7.2, 3H).

Example 70

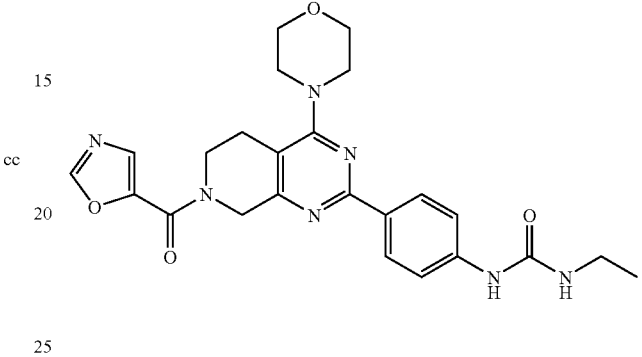

cf

Synthesis of cf: Compound cf was synthesized generally following the synthetic procedures described in Examples 1, 2 and 5: LC-MS: m/z=+478 (M+H)+; $^1$H NMR (400 MHz, DMSO) δ 8.66 (d, J=4.3, 2H), 8.57 (s, 1H), 8.19 (s, 2H), 7.48 (d, J=8.5, 2H), 6.17 (s, 1H), 5.18-5.02 (m, 1H), 4.70 (s, 1H), 4.16-3.98 (m, 1H), 3.89-3.77 (m, 1H), 3.73 (s, 4H), 3.48 (s, 4H), 3.18-3.04 (m, 2H), 2.80 (s, 2H), 1.06 (t, J=7.2, 3H).

Example 71

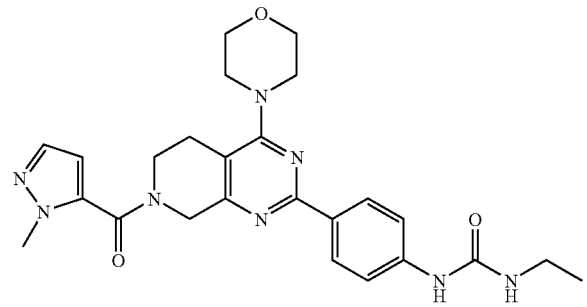

cg

Synthesis of cg: Compound cg was synthesized generally following the synthetic procedures described in Examples 1, 2 and 5: LC-MS m/z=+491 (M+H)+; $^1$H NMR (400 MHz, DMSO) δ 8.67 (s, 1H), 8.20 (s, 2H), 7.51 (m, 3H), 6.67 (s, 1H), 6.18 (s, 1H), 4.70 (s, 2H), 3.81 (m, 9H), 3.49 (s, 4H), 3.12 (s, 2H), 2.80 (s, 2H), 1.06 (t, J=7.1, 3H).

Example 72

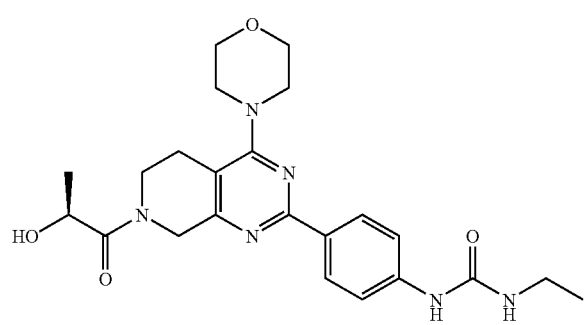

ch

Synthesis of ch: Compound ch was synthesized generally following the synthetic procedures described in Examples 1, 2 and 5: LC-MS: m/z=455 (M+H)+; $^1$H NMR (400 MHz, DMSO) δ 8.71 (s, 1H), 8.19 (d, J=8.7, 2H), 7.48 (d, J=8.7, 2H), 6.65-6.49 (m, 1H), 6.22 (s, 1H), 5.08 (s, 1H), 4.89-4.63 (m, 1H), 4.55 (s, 2H), 3.73 (m, 5H), 3.48 (m, 4H), 3.18-3.05 (m, 2H), 2.75 (s, 1H), 2.70-2.59 (m, 1H), 1.26 (d, J=6.5, 3H), 1.06 (t, J=7.2, 3H).

Example 73

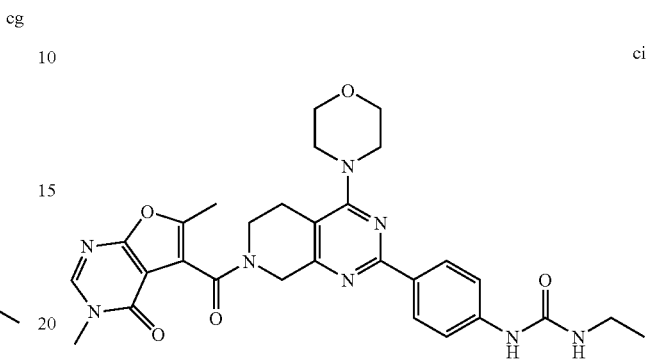

ci

Synthesis of ci: Compound ci was synthesized generally following the synthetic procedures described in Examples 1, 2 and 5: LC-MS: m/z=573 (M+H)+; $^1$H NMR (400 MHz, DMSO) δ 8.67 (d, J=12.3, 1H), 8.45 (d, J=5.8, 1H), 8.22 (d, J=8.7, 1H), 8.10 (d, J=8.7, 1H), 7.50 (d, J=8.7, 1H), 7.43 (d, J=8.7, 1H), 6.19 (s, 1H), 4.91-4.60 (m, 1H), 4.59-4.35 (m, 1H), 4.28-3.98 (m, 1H), 3.71 (s, 4H), 3.47 (m, 8H), 3.15 (m, 2H), 2.91-2.57 (m, 2H), 2.38 (d, J=9.5, 3H), 1.06 (q, J=7.3, 3H).

Example 74

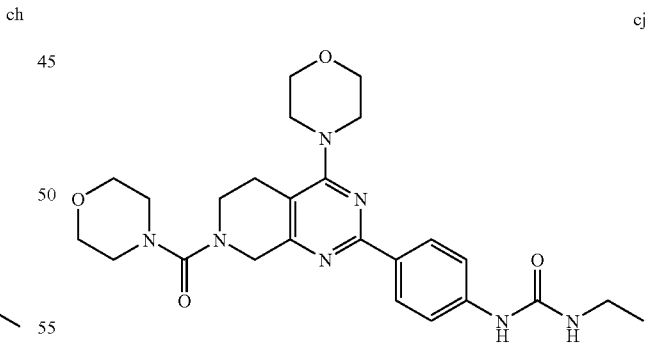

cj

Synthesis of cj: Compound cj was synthesized generally following the synthetic procedures described in Examples 1, 2 and 5: LC-MS: m/z=+496 (M+H)+; $^1$H NMR (400 MHz, DMSO) δ 8.64 (s, 1H), 8.18 (d, J=8.7, 2H), 7.48 (d, J=8.8, 2H), 6.16 (t, J=5.6, 1H), 4.36 (s, 2H), 3.73 (s, 4H), 3.62 (s, 4H), 3.47 (s, 4H), 3.38 (s, 2H), 3.22 (s, 4H), 3.11 (dd, J=7.0, 12.9, 2H), 2.72 (s, 2H), 1.06 (t, J=7.2, 3H).

J=8.6, 3H), 6.70 (t, J=4.7, 1H), 4.83 (s, 2H), 3.99 (s, 2H), 3.73 (d, J=4.5, 4H), 3.50 (d, J=4.5, 4H), 3.28 (m, 2H), 2.77 (s, 2H), 1.12 (t, J=7.1, 3H).

Example 75

Example 76

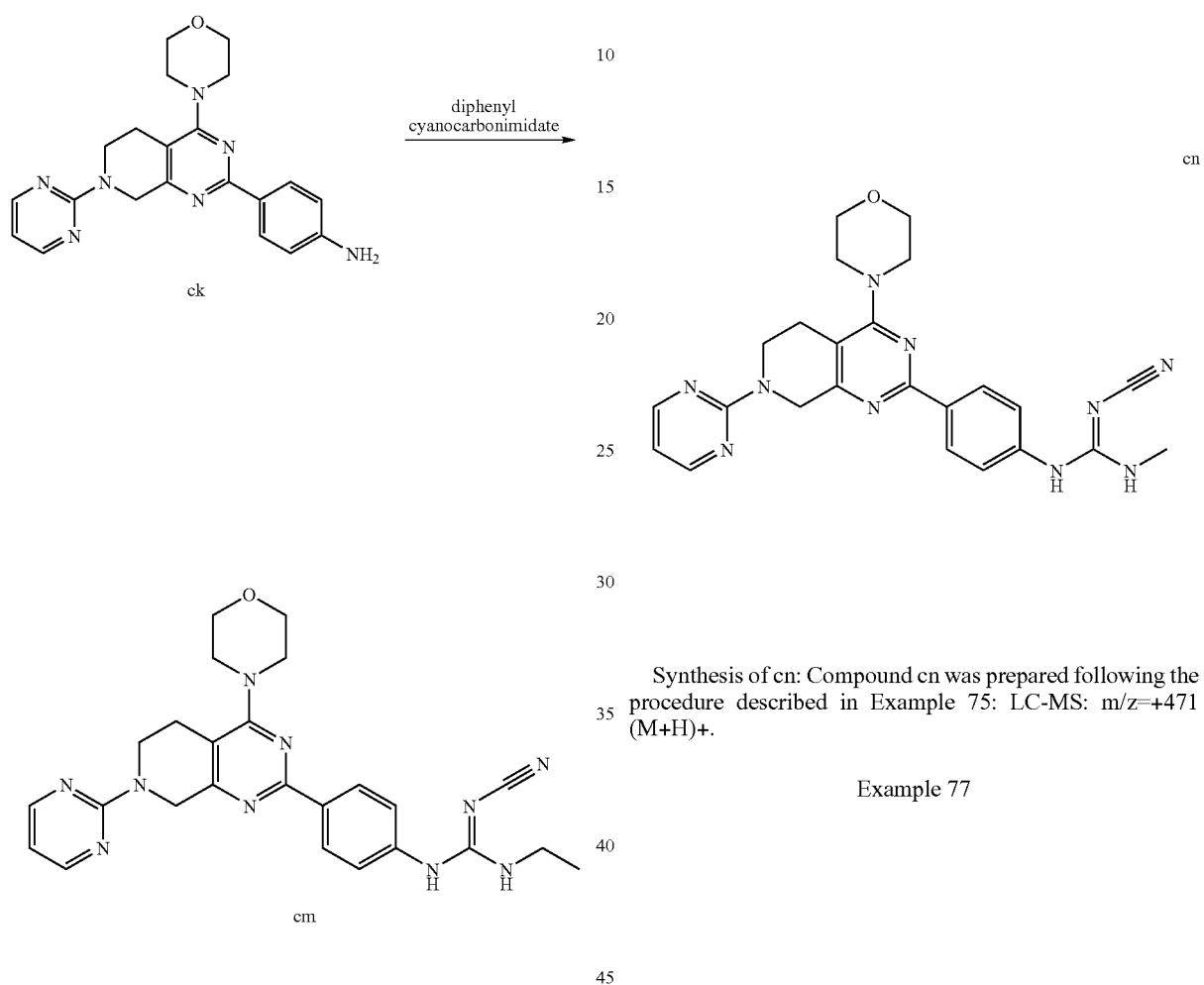

Synthesis of cn: Compound cn was prepared following the procedure described in Example 75: LC-MS: m/z=+471 (M+H)+.

Example 77

Synthesis of cm: 2-(p-Aminophenyl)-4-morpholine-7-(2-pyrimidine)-5,6,7,8-tetrahydropyrido[3,4-d]pyrimidine (ck) (0.0460 g, 0.118 mmol), diphenyl cyanocarbonimidate (0.0391 g, 0.164 mmol), and isopropyl alcohol (3.80 mL) were combined, heated at 90° C. and stirred for 5 hours. Isopropyl alcohol (0.354 mL) was added and the mixture was stirred overnight at 90° C. Additional diphenyl cyanocarbonimidate (0.0414 g, 0.174 mmol) was added and the mixture was stirred at 90° C. overnight. The mixture was cooled to room temperature and then ethylamine hydrochloride (0.292 g, 3.58 mmol) was added followed by N,N-diisopropylethylamine (0.823 mL, 4.72 mmol). The mixture was heated at 50° C. and stirred for 3 days. The volatiles were evaporated and the residue was chromatographed through silica gel (4 g, 0-10% MeOH in dichloromethane) and then purified by HPLC to provide the desired product cm (0.0077 g, 13%): LC-MS: m/z=+485 (M+H)+; $^1$H NMR (400 MHz, DMSO) δ 9.10 (s, 1H), 8.44 (d, J=4.7, 2H), 8.30 (d, J=8.6, 2H), 7.35 (d, Synthesis of co: Compound co was prepared following the procedures described in Examples 1 and 2: LC-MS: m/z=+468 (M+H)+; $^1$H NMR (400 MHz, DMSO) δ 9.85 (s, 1H), 8.53 (d, J=4.8, 2H), 8.44 (d, J=4.7, 2H), 8.27 (d, J=8.8, 2H), 7.89 (d, J=8.8, 2H), 6.89 (t, J=4.8, 1H), 6.69 (t, J=4.7, 1H), 4.83 (s, 2H), 3.99 (s, 2H), 3.74 (s, 4H), 3.49 (s, 4H), 2.76 (s, 2H).

Example 78

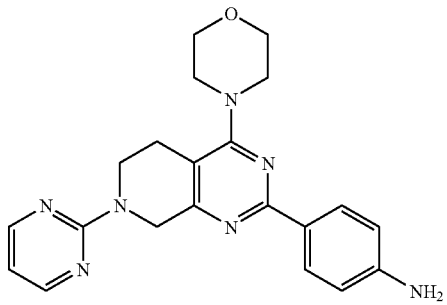

cp

Synthesis of cp: Compound cp was prepared generally following the procedures described in steps 1 and 2 of Example 27: LC-MS: m/z=+390 (M+H)+; $^1$H NMR (400 MHz, DMSO) δ 8.43 (d, J=4.7, 2H), 8.05 (d, J=8.6, 2H), 6.68 (t, J=4.7, 1H), 6.60 (d, J=8.6, 2H), 5.51 (s, 2H), 4.77 (s, 2H), 3.97 (t, J=5.3, 2H), 3.81-3.66 (m, 4H), 3.43 (d, J=4.4, 4H), 2.72 (s, 2H).

Example 79

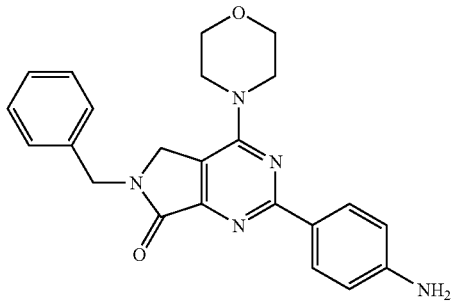

cq

Synthesis of cq: Compound cq was synthesized as described below: LC-MS: m/z=+402 (M+H)+; $^1$H NMR (500 MHz, DMSO) δ 8.13 (d, J=8.6, 2H), 7.37 (d, J=6.7, 2H), 7.31 (d, J=7.0, 3H), 6.69 (d, J=8.5, 2H), 4.76 (s, 2H), 4.64 (s, 2H), 3.73 (m, 10H).

Step 1: Synthesis of Ethyl 1-benzyl-4,5-dioxopyrrolidine-3-carboxylate (cs)

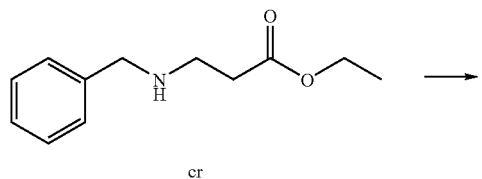

cr

-continued

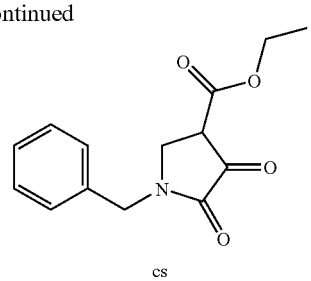

cs

21% Sodium ethoxide in ethanol (21:79, sodium ethoxide: ethanol, 56.0 mL) was added dropwise to a mixture of ethyl-beta-benzylaminopropionate (22.178 g, 0.10700 mol) and diethyl oxalate (15.0 mL, 0.110 mol). The reaction mixture was stirred at room temperature for 1 hour. The reaction mixture was concentrated and then water (about 200 mL) was added. The mixture was stirred for 5 min and then 1M HCl was added until pH 1. The mixture was vacuum filtered. The solids were collected and dried in vacuo overnight, and then crystallized from ethanol to give the desired product (20.946 g, 75%).

Step 2: Synthesis of ethyl 4-amino-1-benzyl-5-oxo-2,5-dihydro-1H-pyrrole-3-carboxylate (ct)

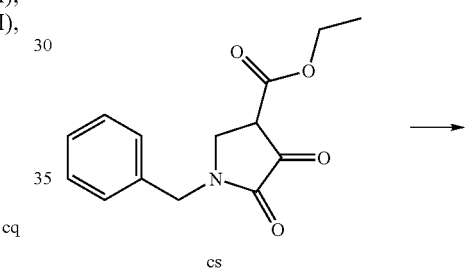

cs

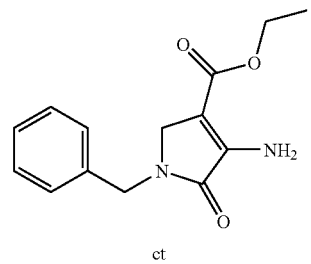

ct

The above ester (20.946 g, 0.080169 mol), ammonium formate (10.192 g, 0.16163 mol), and ethanol (100.0 mL) were combined and then stirred at 78° C. for 3 days. The reaction mixture was evaporated, filtered through a plug of silica gel using EtOAc as the solvent. The filtrate was evaporated and the resulting solid was crystallized from ethanol to compound ct (15.975 g, 76%).

Step 3: Synthesis of 2-amino-6-benzyl-4-hydroxy-5H-pyrrolo[3,4-d]pyrimidin-7(6H)-one (cu)

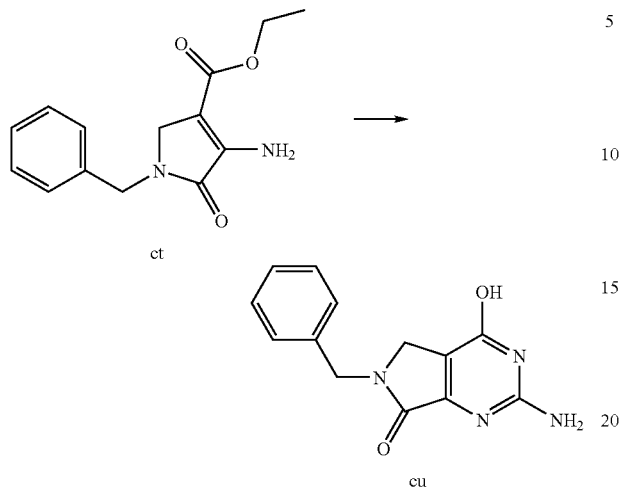

21% Sodium ethoxide in ethanol (21:79, sodium ethoxide: ethanol, 135.18 mL) was added to guanidine hydrochloride (29.492 g, 0.30871 mol) in ethanol (306.75 mL, 5.2536 mol) followed by amine ct. The reaction mixture was then stirred at 78° C. for 3 days. The reaction mixture was concentrated then water (325 mL) was added. The mixture was stirred until everything became dissolved. Acetic acid was added dropwise until pH 5. The mixture was then vacuum filtered. The filtrate was triturated with hot DMF then cooled to room temperature and vacuum filtered to give the desired product cu (8.721 g, 55%).

Step 4: Synthesis of 6-benzyl-2,4-dihydroxy-5H-pyrrolo[3,4-d]pyrimidin-7(6H)-one (cv)

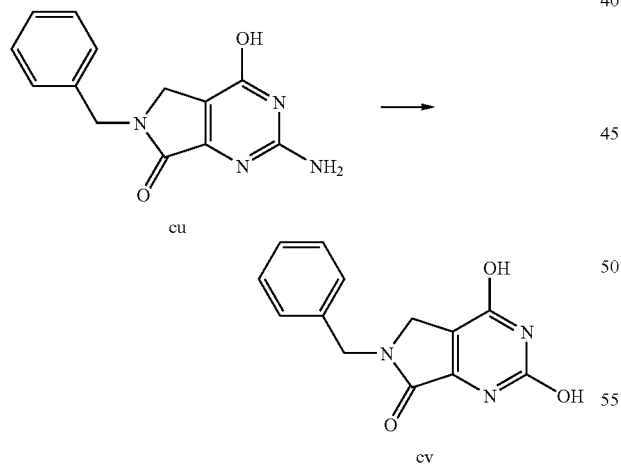

2-amino-6-benzyl-4-hydroxy-5H-pyrrolo[3,4-d]pyrimidin-7(6H)-one (8.721 g, 0.03403 mol) and water (510.7 mL, 28.35 mol) were mixed and the mixture was heated at 100° C. Conc. HCl was added slowly until the sample dissolved. The mixture was cooled at 90° C. then sodium nitrite (7.044 g, 0.1021 mol) in water (68.05 mL, 3.778 mol) was added dropwise. The reaction mixture was stirred at 90° C. for 1 hour then vacuum filtered hot to provide the product cv (3.187 g, 36%).

Step 5: Synthesis of 6-benzyl-2,4-dichloro-5H-pyrrolo[3,4-d]pyrimidin-7(6H)-one (cw)

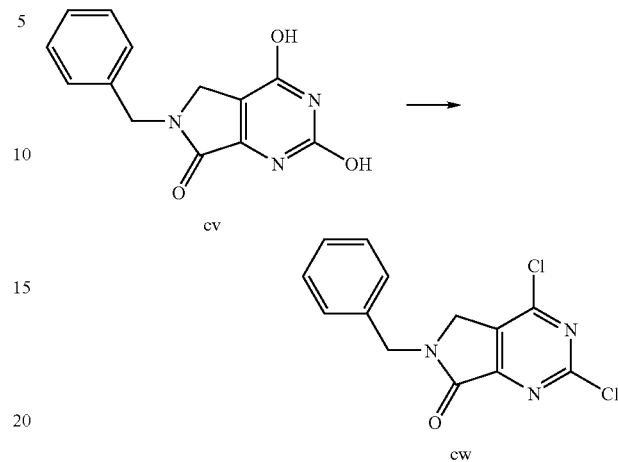

6-benzyl-2,4-dihydroxy-5H-pyrrolo[3,4-d]pyrimidin-7(6H)-one (cv) (0.569 g, 0.00221 mol), phosphoryl chloride (8.50 mL, 0.0912 mol), and N,N-diethylaniline (0.530 mL, 0.00333 mol) were combined and the mixture was heated at 106° C. and stirred overnight. The reaction mixture was poured into ice, extracted 3 times with $CH_2Cl_2$. The combined organic extract was dried over Magnesium sulfate, filtered and concentrated. The resulting residue was chromatographed through silica gel (80 g, 0-50% EtOAc in hexanes) to give the compound cw (0.405 g, 62%).

Step 6: Synthesis of 6-benzyl-2-chloro-4-morpholino-5H-pyrrolo[3,4-d]pyrimidin-7(6H)-one (cx)

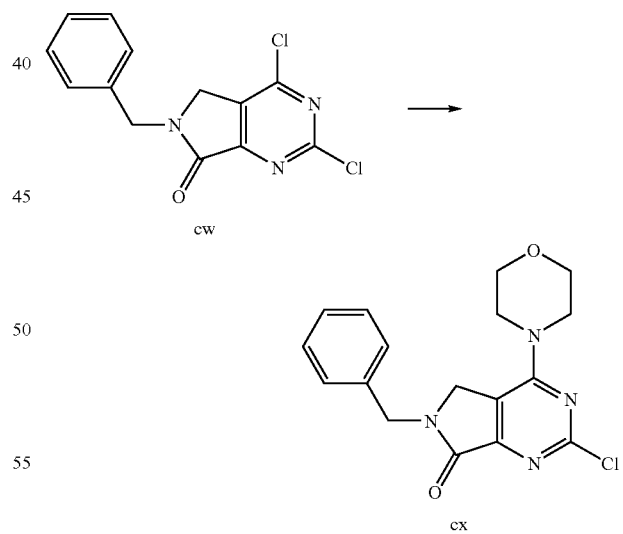

6-benzyl-2,4-dichloro-5H-pyrrolo[3,4-d]pyrimidin-7(6H)-one (cw) (0.125 g, 0.000425 mol), isopropyl alcohol (2.90 mL), N,N-diisopropylethylamine (0.150 mL, 0.861 mmol) and morpholine (0.0556 mL, 0.638 mmol) were mixed and the mixture was stirred for 30 minutes. The reaction mixture was concentrated. The resulting residue was chromatographed through silica gel (40 g, 0-5% MeOH in dichloromethane) to give the compound cx (0.126 g, 86%).

Step 7: Synthesis of 6-benzyl-4-morpholino-2-(4-nitrophenyl)-5H-pyrrolo[3,4-d]pyrimidin-7(6H)-one (cy)

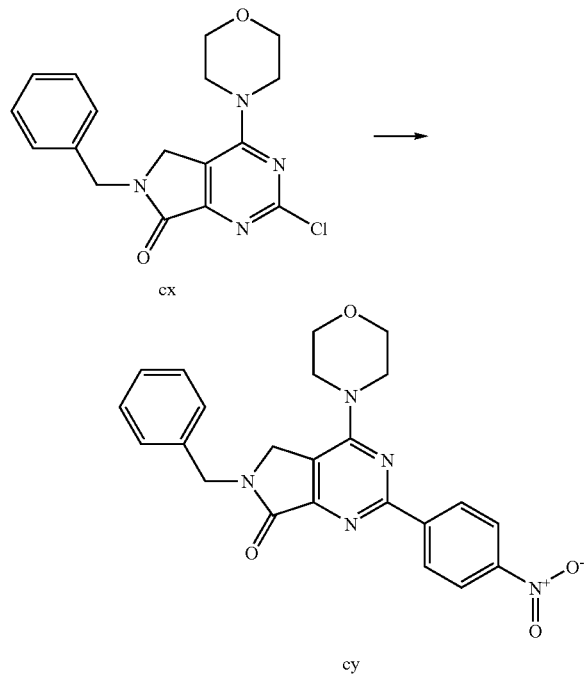

4-Nitrophenylboronic acid, pinacol ester (0.136 g, 0.546 mmol), tetrakis(triphenylphosphine)palladium(0) (0.046 g, 0.040 mmol), sodium carbonate (0.0720 g, 0.000679 mol), and potassium acetate (0.0660 g, 0.672 mmol) were combined, nitrogen purged three times. Compound cx (0.153 g, 0.444 mmol) in dry acetonitrile (2.30 mL) was added followed by deoxygenated water (1.20 mL). The reaction was microwaved on 300 watts, 120° C. for 15 minutes using a Biotage microwave reactor. The reaction mixture was diluted with $CH_2Cl_2$ and $H_2O$, extracted three times with $CH_2Cl_2$. The combined organic extract was dried over Magnesium sulfate, filtered and concentrated. The resulting residue was chromatographed through silica gel (12 g, 0-5% MeOH in dichloromethane). The fractions was concentrated and triturated with hot EtOH then cooled to room temperature, filtered, and washed with 10% MeOH in dichloromethane to give compound cy (0.049 g, 26%).

Step 8: Synthesis of 6-benzyl-4-morpholino-2-(4-aminophenyl)-5H-pyrrolo[3,4-d]pyrimidin-7(6H)-one (cz)

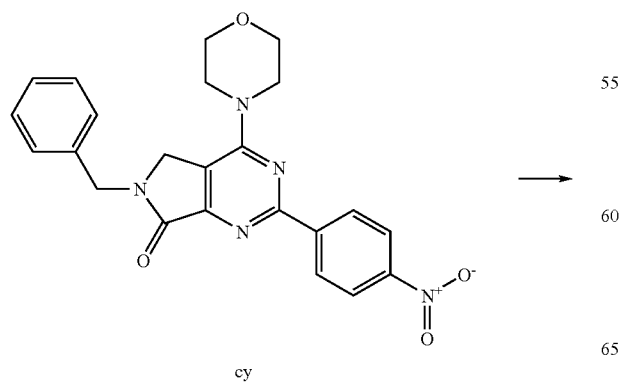

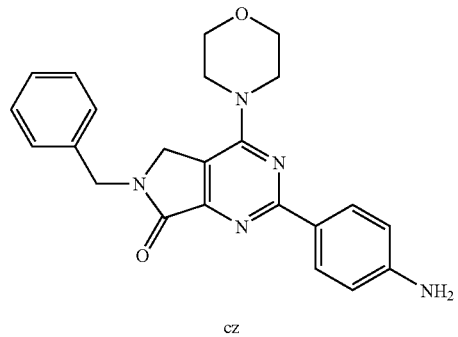

6-benzyl-4-morpholino-2-(4-nitrophenyl)-5H-pyrrolo[3,4-d]pyrimidin-7(6H)-one (cy) (0.112 g, 0.260 mmol), stannous chloride dihydrate (0.310 g, 1.36 mmol) and ethanol (2.00 mL) were combined and stirred at 80° C. for 1 hour. The mixture was diluted with $H_2O$ and 10% MeOH in dichloromethane, extracted 3 times with 10% MeOH in dichloromethane. The combined organic extract was dried over Magnesium sulfate and concentrated to give compound cz (0.083 g, 80%): LC-MS: m/z=+434 (M+H)+; $^1$H NMR (400 MHz, DMSO) δ 9.10 (s, 2H), 7.24 (d, J=8.6, 2H), 7.14 (s, 2H), 6.91 (d, J=8.6, 2H), 4.64 (d, J=27.1, 4H), 3.80-3.60 (m, 11H).

Example 80

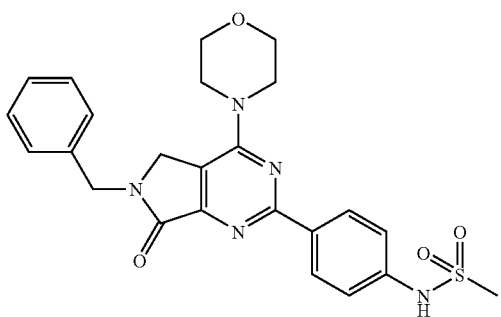

Synthesis of compound da: Compound da was synthesized using general procedure described in Example 5 by reacting 2-(4-aminophenyl)-6-benzyl-4-morpholino-5H-pyrrolo[3,4-d]pyrimidin-7(6H)-one (cz) with methanesulfonyl chloride: LC-MS: m/z=480 (M+H)+; $^1$H NMR (400 MHz, DMSO) δ

8.34 (d, J=8.8, 1H), 7.67-7.50 (m, 4H), 7.41-7.25 (m, 4H), 4.76 (s, 1H), 4.67 (s, 1H), 3.74 (d, J=10.1, 4H), 3.06 (s, 2H), 2.56-2.45 (m, 7H).

Example 81

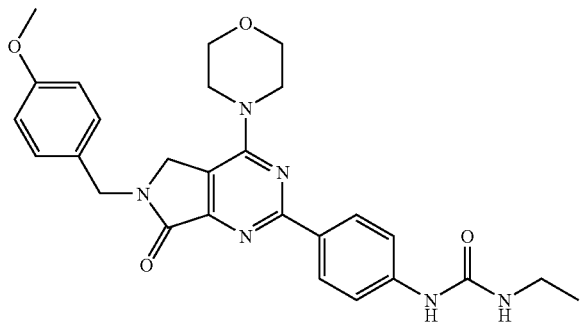

Synthesis of db: Compound db was synthesized by the general procedure described in step 3 of Example 27 by reacting 6-benzyl-4-morpholino-2-(4-aminophenyl)-5H-pyrrolo[3,4-d]pyrimidin-7(6H)-one (cz) with ethyl isocyanate: LC-MS: m/z=+503 (M+H)+; $^1$H NMR (400 MHz, DMSO) δ 8.69 (s, 1H), 8.25 (d, J=8.8, 2H), 7.50 (d, J=8.8, 2H), 7.25 (d, J=8.6, 2H), 6.92 (d, J=8.6, 2H), 6.19 (s, 1H), 4.68 (s, 2H), 4.61 (s, 2H), 3.73 (d, J=5.6, 11H), 3.19-3.05 (m, 2H), 1.07 (t, J=7.2, 3H).

Example 82

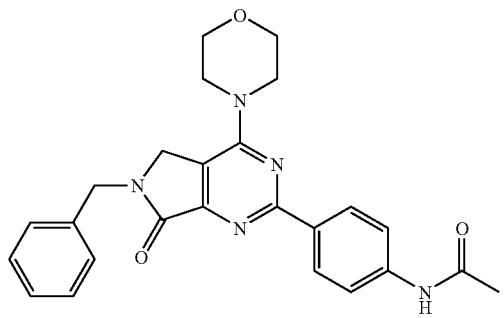

Synthesis of dc: Compound dc was synthesized using the procedure described in Example 5 by reacting 6-benzyl-4-morpholino-2-(4-aminophenyl)-5H-pyrrolo[3,4-d]pyrimidin-7(6H)-one (cz) with acetyl chloride: LC-MS: m/z=+444 (M+H)+; $^1$H NMR (400 MHz, DMSO) δ 10.12 (s, 1H), 8.32 (d, J=8.7, 2H), 7.70 (d, J=8.7, 2H), 7.41-7.33 (m, 2H), 7.30 (d, J=7.3, 3H), 4.76 (s, 2H), 4.66 (s, 2H), 3.74 (m, 8H), 2.07 (d, J=2.9, 3H).

Example 83

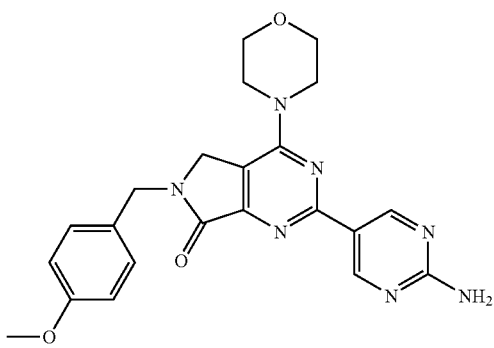

Step 1: Synthesis of 2-chloro-6-(4-methoxybenzyl)-4-morpholino-5H-pyrrolo[3,4-d]pyrimidin-7(6H)-one Synthesis of 2-chloro-6-(4-methoxybenzyl)-4-morpholino-5H-pyrrolo[3,4-d]pyrimidin-7(6H)-one was synthesized by following procedures as described in steps 1 to 6 of example 79 except that ethyl 1-(4-methoxybenzyl)-4,5-dioxopyrrolidine-3-carboxylate was used instead of ethyl 1-benzyl-4,5-dioxopyrrolidine-3-carboxylate in step 1.

Step 2: Synthesis of dd: Compound dd was synthesized using the general procedure described in step 2 of Example 1 by reacting 2-chloro-6-(4-methoxybenzyl)-4-morpholino-5H-pyrrolo[3,4-d]pyrimidin-7(6H)-one with 2-aminopyrimidin-5-ylboronic acid.

Example 84

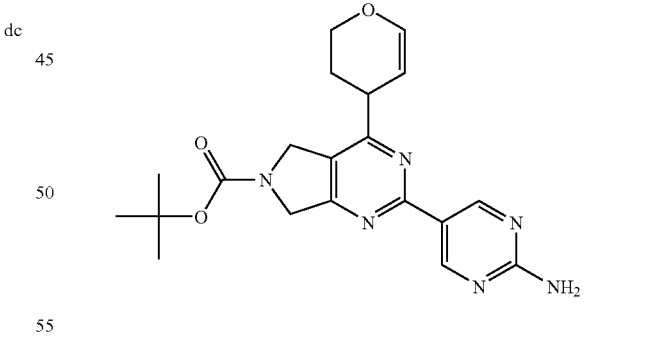

Step 1: Synthesis of tributyl(3,6-dihydro-2H-pyran-4-yl)stannane (dg)

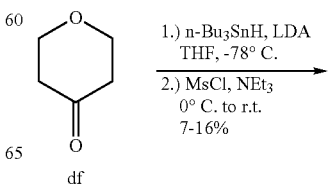

-continued

In a round-bottomed flask, 2.5M of n-butyllithium in hexane (6.77 mL, 17.0 mmol) was added to a solution of N,N-diisopropylamine (2.39 mL, 17.1 mmol) in tetrahydrofuran (80 mL) at 0° C. The reaction was stirred for 10 minutes and tri-n-butyltin hydride (4.18 mL, 15.5 mmol) was added. The resulting mixture was stirred for 10 minutes at 0° C. The reaction was then cooled to −78° C. and tetrahydro-4H-pyran-4-one (1.4 mL, 15.0 mmol) was added. The resulting mixture was stirred for 15 min and triethylamine (15.9 mL, 114 mmol) and methanesulfonyl chloride (4.77 mL, 61.6 mmol) were added. The mixture was stirred while allowed to warm up to room temperature and then stirred for an additional 30 minutes. The mixture was then diluted with 300 mL of hexane and washed with 3×100 mL of acetonitrile. The hexane phase was then concentrated on silica gel and purified by flash chromatography (100% Hex to 25% EtOAc/Hex, 40 g column) to afford the stannate dg as a colourless oil (955 mg, 17%): $^1$H NMR (500 MHz, CDCl3) δ 5.95-5.65 (m, 1H), 4.26-4.07 (m, 2H), 3.79 (t, J=5.3, 2H), 2.29 (dt, J=2.6, 7.7, 2H), 1.55-1.44 (m, 6H), 1.38-1.24 (m, 8H), 0.98-0.83 (m, 21H).

Step 2: Synthesis of tert-butyl 2-chloro-4-(3,6-dihydro-2H-pyran-4-yl)-5H-pyrrolo[3,4-d]pyrimidine-6(7H)-carboxylate (di)

-continued

A microwave flask was charged with the tin reagent dg (197 mg, 0.53 mmol), t-butyl-2,4-dichloro-5H-pyrrolo-[3,4-d]pyrimidine-6(7H)-carboxylate (dh) (150 mg, 0.52 mmol) and tetrakis(triphenylphosphine)palladium (60 mg, 0.05 mmol). The reaction was microwaved at 130° C. for 20 minutes. The reaction mixture was concentrated on silica gel and purified by flash chromatography (100% Hex to 80% EtOAc/Hex, 12 g column) to afford 115 mg (66%) of the desired product (di) as a white solid: $^1$H NMR (500 MHz, CDCl3) δ 6.58 (d, J=29.4, 1H), 4.80 (d, J=26.6, 2H), 4.72-4.56 (m, 2H), 4.49-4.29 (m, 2H), 3.92 (dt, J=5.3, 10.7, 2H), 2.66 (d, J=1.6, 2H), 1.53 (d, J=6.8, 9H); LC-MS: m/z=+340/338 (M+H)+.

Step 3: Synthesis of tert-butyl 2-(2-aminopyrimidin-5-yl)-4-(3,4-dihydro-2H-pyran-4-yl)-5H-pyrrolo[3,4-d]pyrimidine-6(7H)-carboxylate (de). Compound de was synthesized according to general procedure described in step 2 of Example 1 by reacting tert-butyl 2-chloro-4-(3,6-dihydro-2H-pyran-4-yl)-5,6-dihydropyrido[3,4-d]pyrimidine-7(8H)-carboxylate with 2-aminopyrimidin-5-ylboronic acid. LC-MS: m/z=397 (M+H)+.

Example 85

Synthesis of dj: Compound dj was synthesized according to general procedure described in step 2 of Example 1 by reacting tert-butyl 2-chloro-4-(3,6-dihydro-2H-pyran-4-yl)-5,6-dihydropyrido[3,4-d]pyrimidine-7(8H)-carboxylate with (4-ethylureido)phenylboronic acid pinacol ester: $^1$H NMR (500 MHz, DMSO) δ 8.70 (s, 1H), 8.27 (s, 2H), 7.54 (d, J=8.8, 2H), 6.18 (s, 1H), 4.81-4.49 (m, 4H), 3.98 (s, 2H), 3.14

(s, 2H), 3.06-2.87 (m, 1H), 1.93 (s, 2H), 1.76 (s, 2H), 1.08 (t, J=7.2, 3H); LC-MS: m/z=+468 (M+H)+.

Example 86

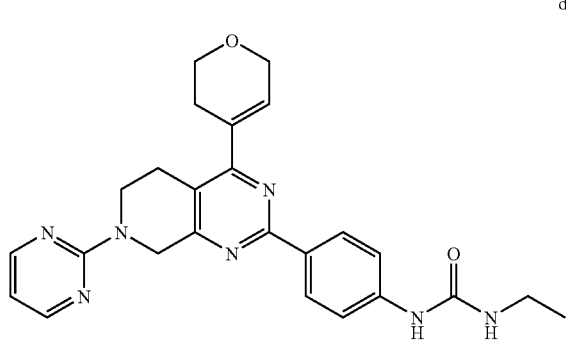

Synthesis of dk: Compound dk was synthesized according to sequence of step 2 of Example 1 by reacting tert-butyl 2-chloro-4-(3,6-dihydro-2H-pyran-4-yl)-5,6-dihydropyrido[3,4-d]pyrimidine-7(8H)-carboxylate with (4-ethylureido)phenylboronic acid pinacol ester: ¹H NMR (400 MHz, DMSO) δ 8.80 (s, 1H), 8.45 (d, J=4.7, 2H), 8.26 (d, J=8.8, 2H), 7.53 (d, J=8.8, 2H), 6.71 (t, J=4.7, 1H), 6.28 (s, 2H), 4.94 (s, 2H), 4.27 (s, 2H), 4.04 (s, 2H), 3.87 (t, J=5.4, 2H), 3.21-3.05 (m, 3H), 2.96 (s, 2H), 2.60 (s, 2H), 1.06 (t, J=7.2, 3H); LC-MS: m/z=+458 (M+H)+.

Example 87

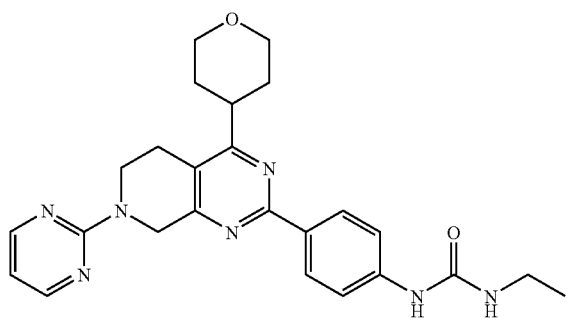

Synthesis of dm: Olefin dk (65 mg, 0.14 mmol) was dissolved in ethanol (5 mL, 80 mmol). 10% Palladium on carbon (15 mg) was added and the mixture was stirred under an atmospheric hydrogen at room temperature overnight. Additional palladium on carbon (915 mg) was added the mixture was hydrogenated for another overnight. The mixture was filtered and the filtrate was concentrated. The resulting residue was purified by HPLC to give the desired product dm: ¹H NMR (400 MHz, DMSO) δ 8.72 (s, 1H), 8.44 (t, J=4.5, 2H), 8.28 (d, J=8.8, 2H), 7.55 (t, J=13.6, 3H), 6.70 (t, J=4.7, 1H), 6.19 (t, J=5.5, 1 H), 4.93 (d, J=7.7, 2H), 4.11 (d, J=5.7, 2H), 3.96 (s, 2H), 3.49 (t, J=11.1, 2H), 3.24-3.03 (m, 3H), 2.92 (s, 2H), 1.94 (d, J=8.7, 2H), 1.65 (d, J=11.6, 2H), 1.07 (t, J=7.2, 3H); LC/MS: m/z=+460 (M+H)+.

Example 88

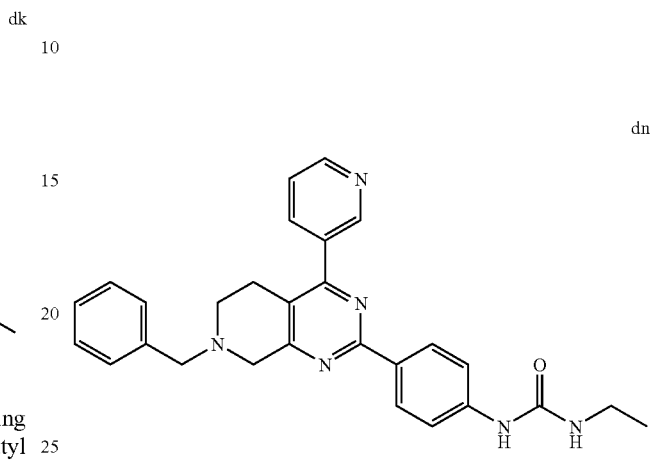

Synthesis of dn: Compound dn was synthesized according to the procedure described in Example 1 by using 7-benzyl-2,4-dichloro-5,6,7,8-tetrahydropyrido[3,4-d]pyrimidine in step 1 and pyridin-3-ylboronic acid in step 2: LC-MS: m/z=+465 (M+H)+.

Example 89

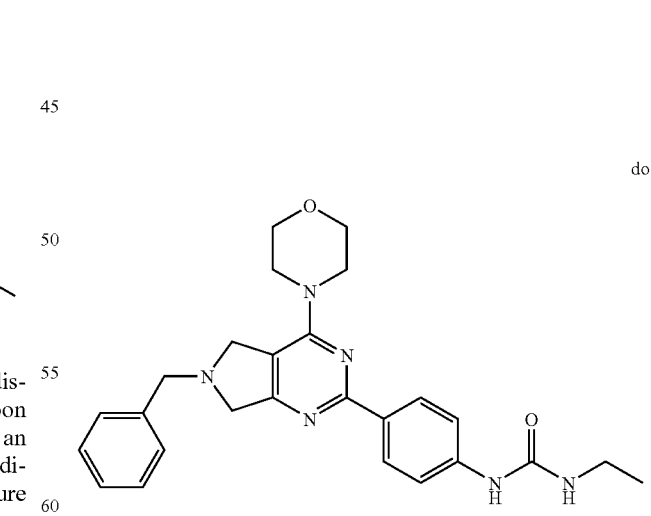

Synthesis of do: Compound do was synthesized according to the procedure described in Example 1 by using 6-benzyl- 2,4-dichloro-6,7-dihydro-5H-pyrrolo[3,4-d]pyrimidine in step 1 of Example 1: LC-MS: m/z=+459 (M+H)+.

Example 90

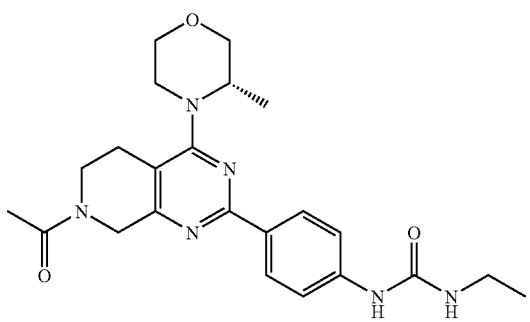
(dp)

Synthesis of (S)-1-(4-(7-acetyl-4-(3-methylmorpholino)-5,6,7,8-tetrahydropyrido[3,4-d]pyrimidin-2-yl)phenyl)-3-ethylurea (dp): Compound dp was prepared according to the procedure described in Example 5 by reacting (S)-1-ethyl-3-(4-(4-(3-methylmorpholino)-5,6,7,8-tetrahydropyrido[3,4-d]pyrimidin-2-yl)phenyl)urea with acetyl chloride. LC-MS: m/z=+439 (M+H)+.

Example 91

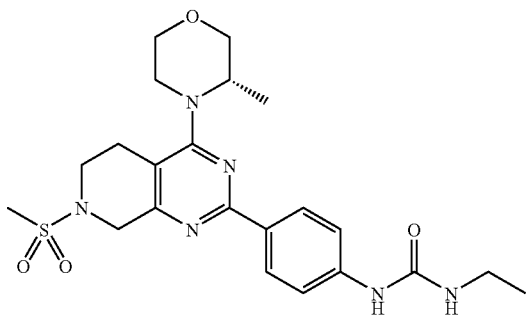
(dq)

Synthesis of (S)-1-ethyl-3-(4-(4-(3-methylmorpholino)-7-(methylsulfonyl)-5,6,7,8-tetrahydropyrido[3,4-d]pyrimidin-2-yl)phenyl)urea (dq) was prepared according to the procedure described in Example 5 by reacting (S)-1-ethyl-3-(4-(4-(3-methylmorpholino)-5,6,7,8-tetrahydropyrido[3,4-d]pyrimidin-2-yl)phenyl)urea with methanesulfonyl chloride. LC-MS: m/z=+475 (M+H)−.

Example 92

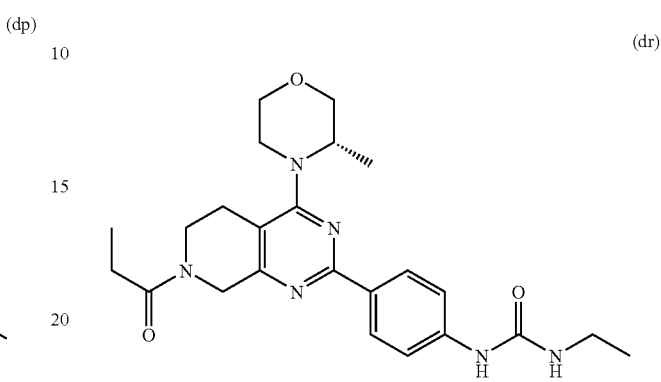
(dr)

Synthesis of (S)-1-(4-(7-acetyl-4-(3-methylmorpholino)-5,6,7,8-tetrahydropyrido[3,4-d]pyrimidin-2-yl)phenyl)-3-ethylurea (dr): Compound dr was prepared according to the procedure described in Example 5 by reacting (S)-1-ethyl-3-(4-(4-(3-methylmorpholino)-5,6,7,8-tetrahydropyrido[3,4-d]pyrimidin-2-yl)phenyl)urea with propionyl chloride. LC-MS: m/z=+439 (M+H)+.

Example 93

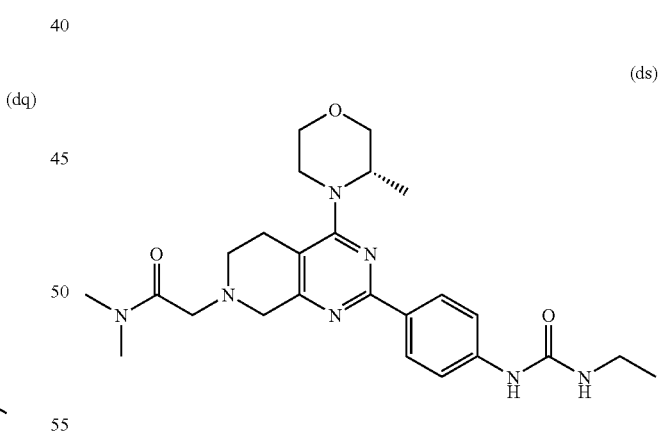
(ds)

Synthesis of (S)-2-(2-(4-(3-ethylureido)phenyl)-4-(3-methylmorpholino)-5,6-dihydropyrido[3,4-d]pyrimidin-7(8H)-yl)-N,N-dimethylacetamide (ds): (S)-1-ethyl-3-(4-(4-(3-methylmorpholino)-5,6,7,8-tetrahydropyrido[3,4-d]pyrimidin-2-yl)phenyl)urea (0.086 mmol), N,N-diisopropylaethylamine (0.26 mmol), potassium iodide (0.06 mmol) were mixed in DMF (0.4 mL), then 2-chloro-N,N-dimethylacetamide was added. The mixture was stirred at room temperature for ~3 h and the product was purified by reverse-phase HPLC to give the desired product. LC-MS: m/z=+482 (M+H)⁺.

Example 94

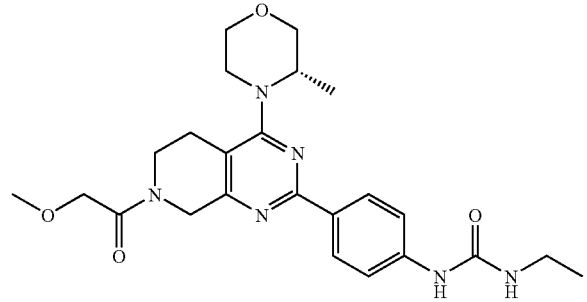
(dt)

Synthesis of (S)-1-ethyl-3-(4-(7-(2-methoxyacetyl)-4-(3-methylmorpholino)-5,6,7,8-tetrahydropyrido[3,4-d]pyrimidin-2-yl)phenyl)urea (dt): Compound dt was prepared according to the procedure described in Example 5 by reacting (S)-1-ethyl-3-(4-(4-(3-methylmorpholino)-5,6,7,8-tetrahydropyrido[3,4-d]pyrimidin-2-yl)phenyl)urea with 2-methoxyacetyl chloride. LC-MS: m/z=+469 (M+H)⁻.

Example 95

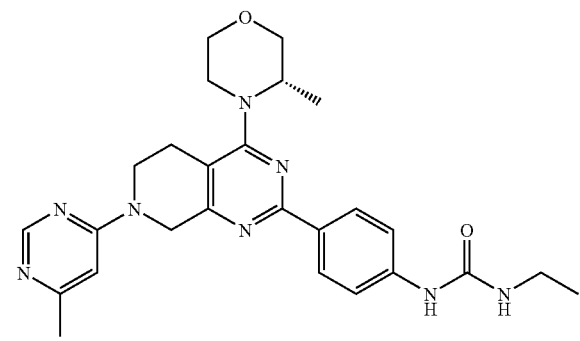
(du)

Synthesis of (S)-1-ethyl-3-(4-(4-(3-methylmorpholino)-7-(6-methylpyrimidin-4-yl)-5,6,7,8-tetrahydropyrido[3,4-d]pyrimidin-2-yl)phenyl)urea (du): Compound du was prepared according to the procedure described in Example 2 by reacting (S)-1-ethyl-3-(4-(4-(3-methylmorpholino)-5,6,7,8-tetrahydropyrido[3,4-d]pyrimidin-2-yl)phenyl)urea with 6-methyl-4-chloropyrimidin. LC-MS: m/z=+489 (M+H)⁺.

Example 96

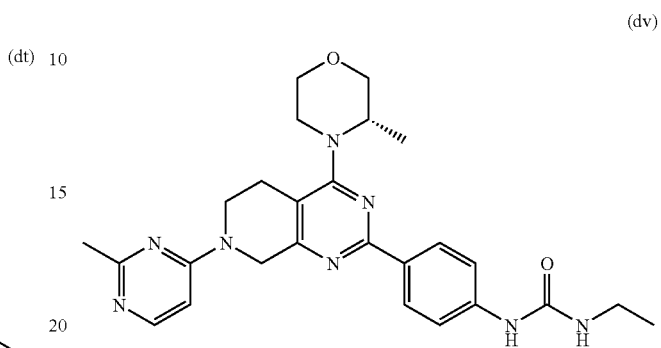
(dv)

Synthesis of (S)-1-ethyl-3-(4-(4-(3-methylmorpholino)-7-(2-methylpyrimidin-4-yl)-5,6,7,8-tetrahydropyrido[3,4-d]pyrimidin-2-yl)phenyl)urea (dv): Compound (dv) was prepared according to the procedure described in Example 2 by reacting (S)-1-ethyl-3-(4-(4-(3-methylmorpholino)-5,6,7,8-tetrahydropyrido[3,4-d]pyrimidin-2-yl)phenyl)urea with 2-methyl-4-chloropyrimidin. LC-MS: m/z=+489 (M+H)⁺.

Example 97

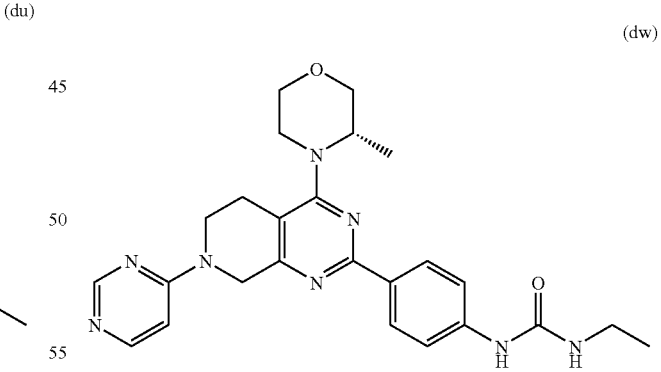
(dw)

Synthesis of (S)-1-ethyl-3-(4-(4-(3-methylmorpholino)-7-(pyrimidin-4-yl)-5,6,7,8-tetrahydropyrido[3,4-d]pyrimidin-2-yl)phenyl)urea (dw): Compound (dw) was prepared according to the procedure described in Example 2 by reacting (S)-1-ethyl-3-(4-(4-(3-methylmorpholino)-5,6,7,8-tetrahydropyrido[3,4-d]pyrimidin-2-yl)phenyl)urea with 4-chloropyrimidine. LC-MS: m/z=+475 (M+H)⁻.

Example 98

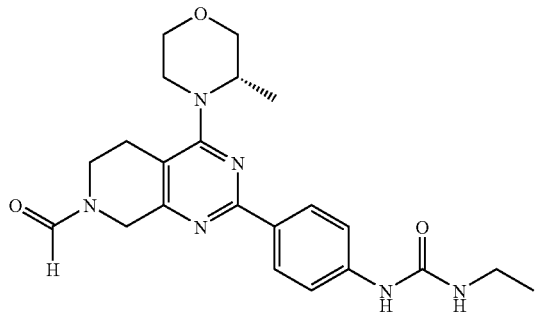

(dx)

Synthesis of (S)-1-ethyl-3-(4-(7-formyl-4-(3-methylmorpholino)-5,6,7,8-tetrahydropyrido[3,4-d]pyrimidin-2-yl)phenyl)urea (dx): Compound dx was prepared according to the procedure described in Example 213 by reacting (S)-1-ethyl-3-(4-(4-(3-methylmorpholino)-5,6,7,8-tetrahydropyrido[3,4-d]pyrimidin-2-yl)phenyl)urea with formic acid. LC-MS: m/z=+425 (M+H)⁺.

Example 99

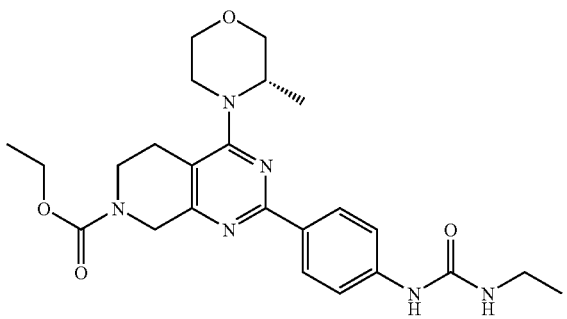

(dy)

Synthesis of (S)-ethyl 2-(4-(3-ethylureido)phenyl)-4-(3-methylmorpholino)-5,6-dihydropyrido[3,4-d]pyrimidine-7(8H)-carboxylate (dy): Compound dy was prepared according to the procedure described in Example 5 by reacting (S)-1-ethyl-3-(4-(4-(3-methylmorpholino)-5,6,7,8-tetrahydropyrido[3,4-d]pyrimidin-2-yl)phenyl)urea with ethyl chloroformate. LC-MS: m/z=+469 (M+H)⁺.

Example 100

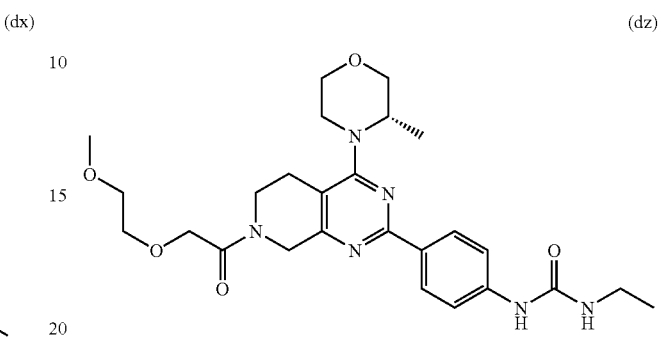

(dz)

Synthesis of (S)-1-ethyl-3-(4-(7-(2-(2-methoxyethoxy)acetyl)-4-(3-methylmorpholino)-5,6,7,8-tetrahydropyrido[3,4-d]pyrimidin-2-yl)phenyl)urea (dz): Compound dz was prepared according to the procedure described in Example 5 by reacting (S)-1-ethyl-3-(4-(4-(3-methylmorpholino)-5,6,7,8-tetrahydropyrido[3,4-d]pyrimidin-2-yl)phenyl)urea with 2-(2-methoxyethoxy)acetyl chloride. LC-MS: m/z=+513 (M+H)⁺.

Example 101

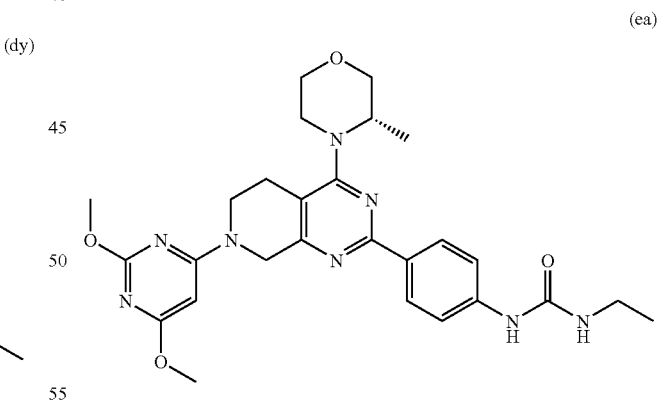

(ea)

Synthesis of (S)-1-(4-(7-(2,6-dimethoxypyrimidin-4-yl)-4-(3-methylmorpholino)-5,6,7,8-tetrahydropyrido[3,4-d]pyrimidin-2-yl)phenyl)-3-ethylurea (ea): Compound ea was prepared according to the procedure described in Example 2 by reacting (S)-1-ethyl-3-(4-(4-(3-methylmorpholino)-5,6,7, 8-tetrahydropyrido[3,4-d]pyrimidin-2-yl)phenyl)urea with 2,6-dimethoxy-4-chloropyrimidine. LC-MS: m/z=+535 (M+H)⁺.

Example 102

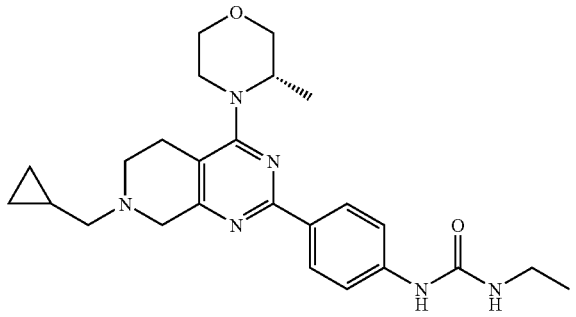

(eb)

Synthesis of (S)-1-(4-(7-(cyclopropylmethyl)-4-(3-methylmorpholino)-5,6,7,8-tetrahydropyrido[3,4-d]pyrimidin-2-yl)phenyl)-3-ethylurea (eb): Compound eb was synthesized according to the procedure described in Example 8 reacting (S)-1-ethyl-3-(4-(4-(3-methylmorpholino)-5,6,7,8-tetrahydropyrido[3,4-d]pyrimidin-2-yl)phenyl)urea with cyclopropylaldehyde. LC-MS: m/z=+451 (M+H)⁺.

Example 103

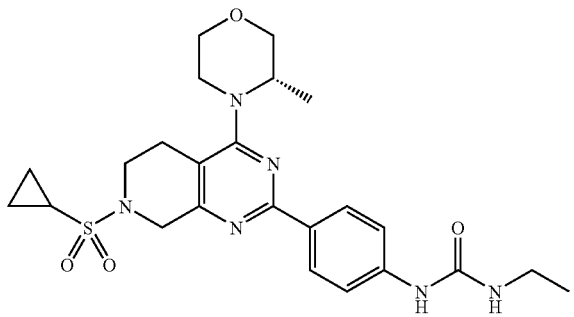

(ec)

Synthesis of (S)-1-(4-(7-(cyclopropylsulfonyl)-4-(3-methylmorpholino)-5,6,7,8-tetrahydropyrido[3,4-d]pyrimidin-2-yl)phenyl)-3-ethylurea (ec): Compound ec was prepared according to the procedure described in Example 5 by reacting (S)-1-ethyl-3-(4-(4-(3-methylmorpholino)-5,6,7,8-tetrahydropyrido[3,4-d]pyrimidin-2-yl)phenyl)urea with cyclopropylsulfonyl chloride. LC-MS: m/z=+501 (M+H)⁺.

Example 104

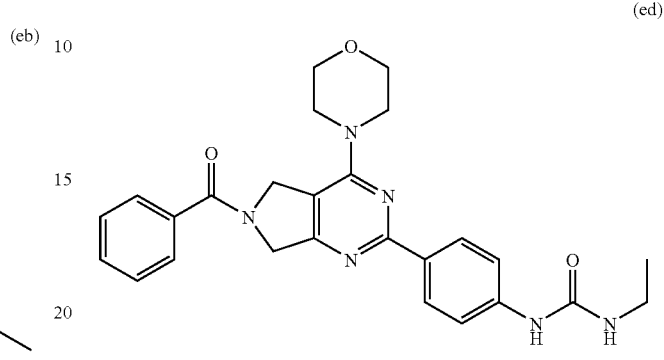

(ed)

Synthesis of 1-(4-(6-benzoyl-4-morpholino-6,7-dihydro-5H-pyrrolo[3,4-d]pyrimidin-2-yl)phenyl)-3-ethylurea (ed): Compound ed was prepared according to the procedure described in Example 5 by reacting 1-ethyl-3-(4-(4-morpholino-6,7-dihydro-5H-pyrrolo[3,4-d]pyrimidin-2-yl)phenyl)urea with benzoyl chloride. LC-MS: m/z=+501 (M+H)⁺.

Example 105

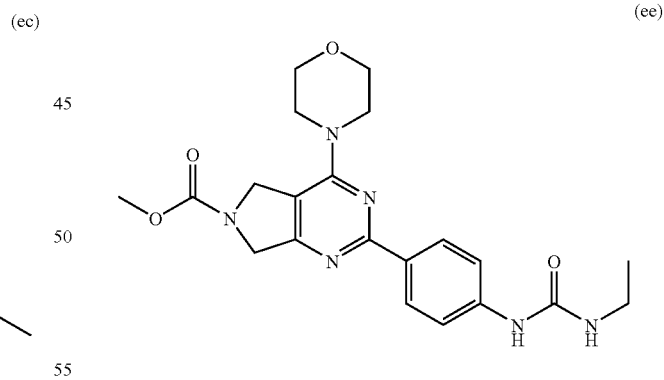

(ee)

Synthesis of Methyl 2-(4-(3-ethylureido)phenyl)-4-morpholino-5H-pyrrolo[3,4-d]pyrimidine-6(7H)-carboxylate (ee): Compound ee was prepared according to the procedure described in Example 5 by reacting 1-ethyl-3-(4-(4-mor-

Example 106

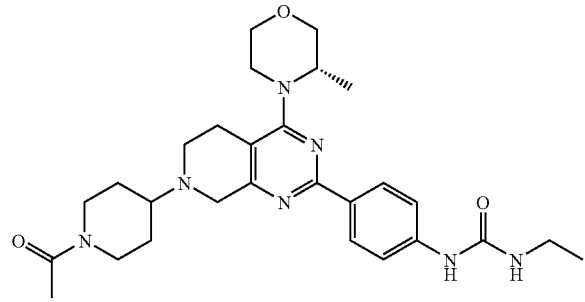

(ef)

Synthesis of (S)-1-(4-(7-(1-acetylpiperidin-4-yl)-4-(3-methylmorpholino)-5,6,7,8-tetrahydropyrido[3,4-d]pyrimidin-2-yl)phenyl)-3-ethylurea (ef): Compound ef was synthesized according to the procedure described in Example 8 reacting (S)-1-ethyl-3-(4-(4-(3-methylmorpholino)-5,6,7,8-tetrahydropyrido[3,4-d]pyrimidin-2-yl)phenyl)urea with 1-acetylpiperidin-4-one. LC-MS: m/z=+522 (M+H)⁺.

Example 107

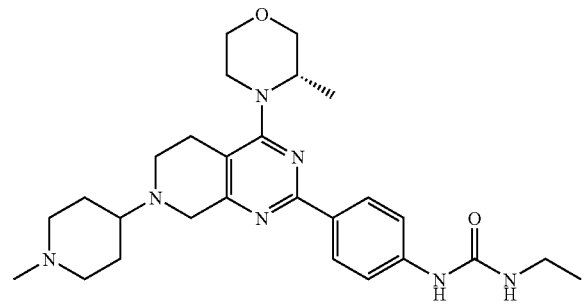

(eg)

Synthesis of (S)-1-ethyl-3-(4-(4-(3-methylmorpholino)-7-(1-methylpiperidin-4-yl)-5,6,7,8-tetrahydropyrido[3,4-d]pyrimidin-2-yl)phenyl)urea (eg): Compound eg was synthesized according to the procedure described in Example 8 reacting (S)-1-ethyl-3-(4-(4-(3-methylmorpholino)-5,6,7,8-tetrahydropyrido[3,4-d]pyrimidin-2-yl)phenyl)urea with 1-methylpiperidin-4-one. LC-MS: m/z=+494 (M+H)⁺.

Example 108

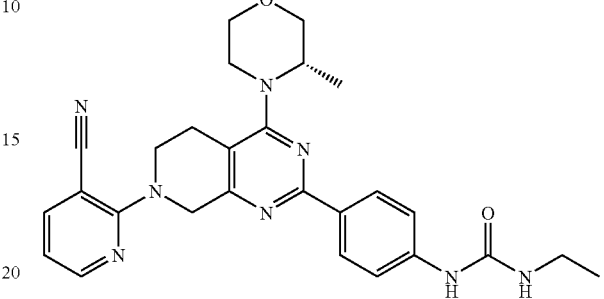

(eh)

Synthesis of (S)-1-(4-(7-(3-cyanopyridin-2-yl)-4-(3-methylmorpholino)-5,6,7,8-tetrahydropyrido[3,4-d]pyrimidin-2-yl)phenyl)-3-ethylurea (eh): Compound eh was prepared according to the procedure described in Example 2 by reacting (S)-1-ethyl-3-(4-(4-(3-methylmorpholino)-5,6,7,8-tetrahydropyrido[3,4-d]pyrimidin-2-yl)phenyl)urea with 3-cyano-2-chloropyridine. LC-MS: m/z=+499 (M+H)⁻.

Example 109

(ei)

Synthesis of (S)-1-(4-(7-(4-cyanopyridin-2-yl)-4-(3-methylmorpholino)-5,6,7,8-tetrahydropyrido[3,4-d]pyrimidin-2-yl)phenyl)-3-ethylurea (ei): Compound ei was prepared according to the procedure described in Example 2 by reacting (S)-1-ethyl-3-(4-(4-(3-methylmorpholino)-5,6,7,8-tetrahydropyrido[3,4-d]pyrimidin-2-yl)phenyl)urea with 4-cyano-2-chloropyridin. LC-MS: m/z=+499 (M+H)⁺.

Example 110

(ej)

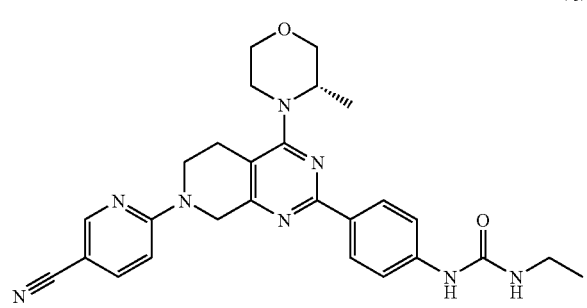

Synthesis of (S)-1-(4-(7-(5-cyanopyridin-2-yl)-4-(3-methylmorpholino)-5,6,7,8-tetrahydropyrido[3,4-d]pyrimidin-2-yl)phenyl)-3-ethylurea (ej): Compound ej was prepared according to the procedure described in Example 2 by reacting (S)-1-ethyl-3-(4-(4-(3-methylmorpholino)-5,6,7,8-tetrahydropyrido[3,4-d]pyrimidin-2-yl)phenyl)urea with 5-cyano-2-chloropyridine. LC-MS: m/z=+499 (M+H)⁻.

Example 111

(ek)

Synthesis of (S)-1-(4-(7-(4,6-dimethylpyrimidin-2-yl)-4-(3-methylmorpholino)-5,6,7,8-tetrahydropyrido[3,4-d]pyrimidin-2-yl)phenyl)-3-ethylurea (ek): Compound ek was prepared according to the procedure described in Example 2 by reacting (S)-1-ethyl-3-(4-(4-(3-methylmorpholino)-5,6,7,8-tetrahydropyrido[3,4-d]pyrimidin-2-yl)phenyl)urea with 4,6-dimethyl-2-chloropyridine. LC-MS: m/z=+503 (M+H)⁺.

Example 112

(el)

Synthesis of (S)-1-ethyl-3-(4-(7-(5-ethylpyrimidin-2-yl)-4-(3-methylmorpholino)-5,6,7,8-tetrahydropyrido[3,4-d]pyrimidin-2-yl)phenyl)urea (el): Compound el was prepared according to the procedure described in Example 2 by reacting (S)-1-ethyl-3-(4-(4-(3-methylmorpholino)-5,6,7,8-tetrahydropyrido[3,4-d]pyrimidin-2-yl)phenyl)urea with 4-ethyl-2-chloropyridine. LC-MS: m/z=+499 (M+H)⁻.

Example 113

(em)

Synthesis of (S)-methyl 2-(4-(3-ethylureido)phenyl)-4-(3-methylmorpholino)-5,6-dihydropyrido[3,4-d]pyrimidine-7(8H)-carboxylate (em): Compound em was prepared according to the procedure described in Example 5 by reacting (S)-1-ethyl-3-(4-(4-(3-methylmorpholino)-5,6,7,8-tetrahy-

Example 114

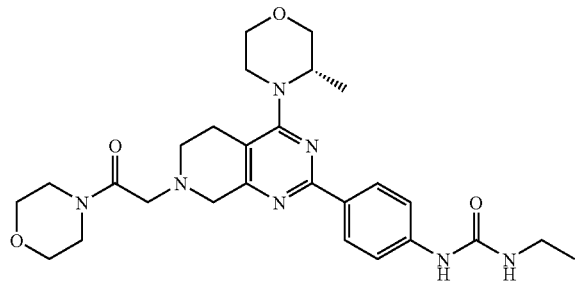

Synthesis of (S)-1-ethyl-3-(4-(4-(3-methylmorpholino)-7-(2-morpholino-2-oxoethyl)-5,6,7,8-tetrahydropyrido[3,4-d]pyrimidin-2-yl)phenyl)urea (en): Compound en was prepared according to the procedure described in Example 93 by reacting (S)-1-ethyl-3-(4-(4-(3-methylmorpholino)-5,6,7,8-tetrahydropyrido[3,4-d]pyrimidin-2-yl)phenyl)urea with morpholine-4-carbonyl chloride. LC-MS: m/z=+482 (M+H)$^+$.

Example 115

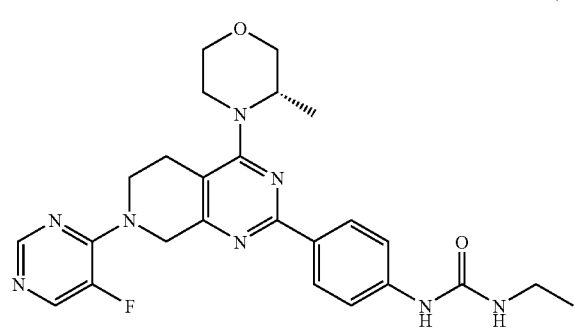

Synthesis of (S)-1-ethyl-3-(4-(7-(5-fluoropyrimidin-4-yl)-4-(3-methylmorpholino)-5,6,7,8-tetrahydropyrido[3,4-d]pyrimidin-2-yl)phenyl)urea (eo): Compound eo was prepared according to the procedure described in Example 2 by reacting (S)-1-ethyl-3-(4-(4-(3-methylmorpholino)-5,6,7,8-tet-rahydropyrido[3,4-d]pyrimidin-2-yl)phenyl)urea with 5-fluoro-4-chloropyridine. LC-MS: m/z=+493 (M+H)$^-$.

Example 116

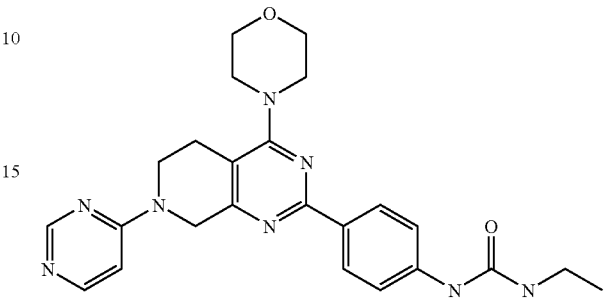

Synthesis of 1-ethyl-3-(4-(4-morpholino-7-(pyrimidin-4-yl)-5,6,7,8-tetrahydropyrido[3,4-d]pyrimidin-2-yl)phenyl)urea (ep): Compound ep was prepared according to the procedure described in Example 2 by reacting 1-ethyl-3-(4-(4-morpholino-5,6,7,8-tetrahydropyrido[3,4-d]pyrimidin-2-yl)phenyl)urea with 4-chloropyridine. LC-MS: m/z=+461 (M+H)$^-$.

Example 117

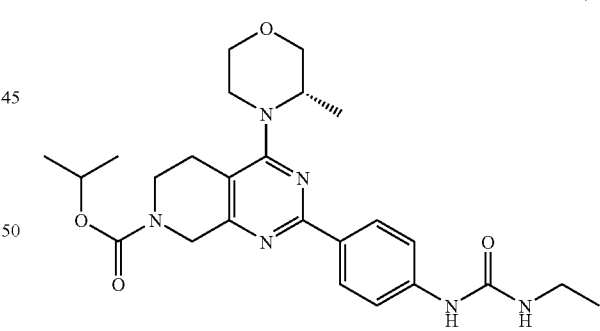

Synthesis of (S)-isopropyl 2-(4-(3-ethylureido)phenyl)-4-(3-methylmorpholino)-5,6-dihydropyrido[3,4-d]pyrimidine-7(8H)-carboxylate (eq): Compound eq was prepared according to the procedure described in Example 5 by reacting (S)-1-ethyl-3-(4-(4-(3-methylmorpholino)-5,6,7,8-tetrahydropyrido[3,4-d]pyrimidin-2-yl)phenyl)urea with isopropyl chloroformate. LC-MS: m/z=+483 (M+H)$^+$.

Example 118

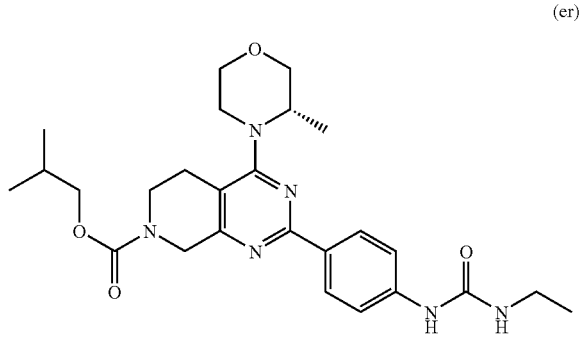

(er)

Synthesis of (S)-isobutyl 2-(4-(3-ethylureido)phenyl)-4-(3-methylmorpholino)-5,6-dihydropyrido[3,4-d]pyrimidine-7(8H)-carboxylate (er): Compound er was prepared according to the procedure described in Example 5 by reacting (S)-1-ethyl-3-(4-(4-(3-methylmorpholino)-5,6,7,8-tetrahydropyrido[3,4-d]pyrimidin-2-yl)phenyl)urea with isobutyl chloroformate. LC-MS: m/z=+497 (M+H)$^+$.

Example 119

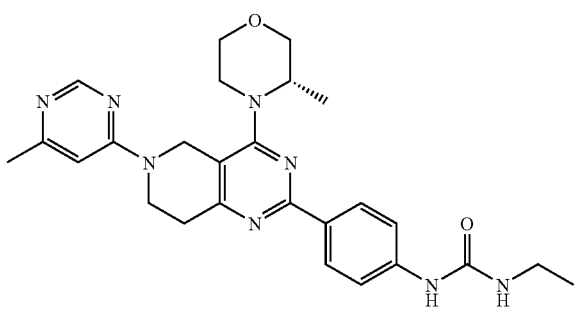

(es)

Synthesis of (S)-1-ethyl-3-(4-(4-(3-methylmorpholino)-6-(6-methylpyrimidin-4-yl)-5,6,7,8-tetrahydropyrido[4,3-d]pyrimidin-2-yl)phenyl)urea (es): Compound es was prepared according to the procedure described in Example 2 by reacting (S)-1-ethyl-3-(4-(4-(3-methylmorpholino)-5,6,7,8-tetrahydropyrido[4,3-d]pyrimidin-2-yl)phenyl)urea with 6-methyl-4-chloropyridine. LC-MS: m/z=+489 (M+H)$^+$.

Example 120

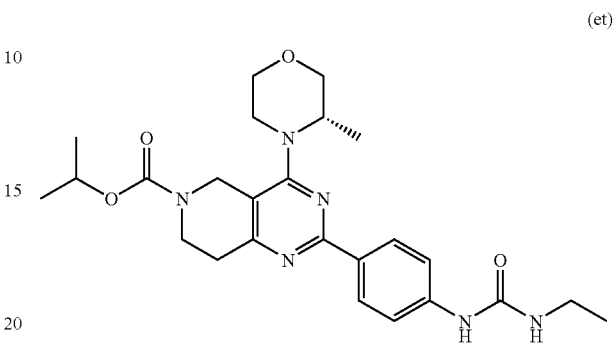

(et)

Synthesis of (S)-isopropyl 2-(4-(3-ethylureido)phenyl)-4-(3-methylmorpholino)-7,8-dihydropyrido[4,3-d]pyrimidine-6(5H)-carboxylate (et): Compound et was prepared according to the procedure described in Example 5 by reacting (S)-1-ethyl-3-(4-(4-(3-methylmorpholino)-5,6,7,8-tetrahydropyrido[4,3-d]pyrimidin-2-yl)phenyl)urea with isopropyl chloroformate. LC-MS: m/z=+483 (M+H)$^+$.

Example 121

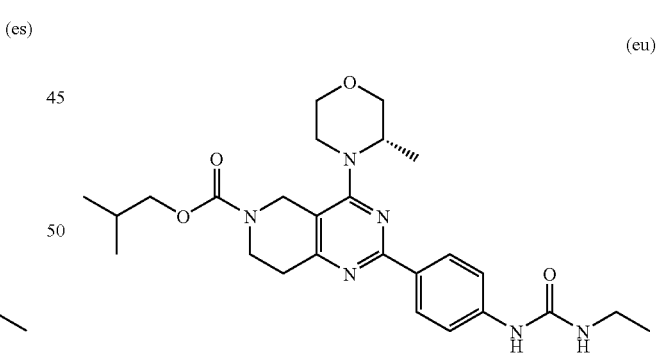

(eu)

Synthesis of (S)-isobutyl 2-(4-(3-ethylureido)phenyl)-4-(3-methylmorpholino)-7,8-dihydropyrido[4,3-d]pyrimidine-6(5H)-carboxylate (eu): Compound eu was prepared according to the procedure described in Example 5 by reacting (S)-1-ethyl-3-(4-(4-(3-methylmorpholino)-5,6,7,8-tetrahydropyrido[4,3-d]pyrimidin-2-yl)phenyl)urea with isobutyl chloroformate. LC-MS: m/z=+497 (M+H)⁺.

Example 122

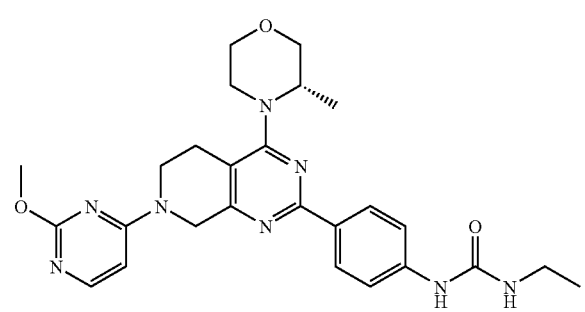

(ev)

Synthesis of (S)-1-ethyl-3-(4-(7-(2-methoxypyrimidin-4-yl)-4-(3-methylmorpholino)-5,6,7,8-tetrahydropyrido[3,4-d]pyrimidin-2-yl)phenyl)urea (ev): Compound ev was prepared according to the procedure described in Example 2 by reacting (S)-1-ethyl-3-(4-(4-(3-methylmorpholino)-5,6,7,8-tetrahydropyrido[3,4-d]pyrimidin-2-yl)phenyl)urea with 2-methoxy-4-chloropyridine. LC-MS: m/z=+505 (M+H)⁺.

Example 123 pholino)-5,6,7,8-tetrahydropyrido[3,4-d]pyrimidin-2-yl)phenyl)urea with 2-trifluoromethyl-4-chloropyridine. LC-MS: m/z=+543 (M+H)⁺.

Example 124

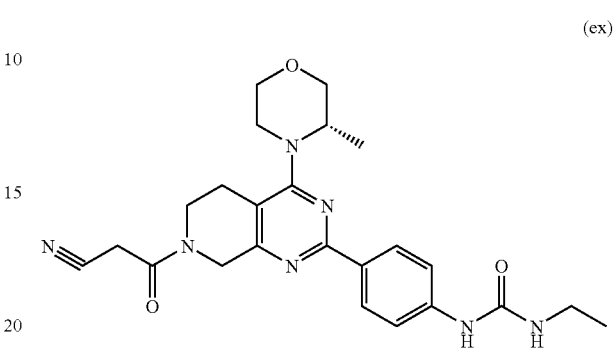

(ex)

Synthesis of (S)-1-(4-(7-(2-cyanoacetyl)-4-(3-methylmorpholino)-5,6,7,8-tetrahydropyrido[3,4-d]pyrimidin-2-yl)phenyl)-3-ethylurea (ex): Compound ex was prepared according to the procedure described in Example 5 by reacting (S)-1-ethyl-3-(4-(4-(3-methylmorpholino)-5,6,7,8-tetrahydropyrido[3,4-d]pyrimidin-2-yl)phenyl)urea with 2-cyanoacetyl chloride. LC-MS: m/z=+464 (M+H)⁺.

Example 125

(ew)

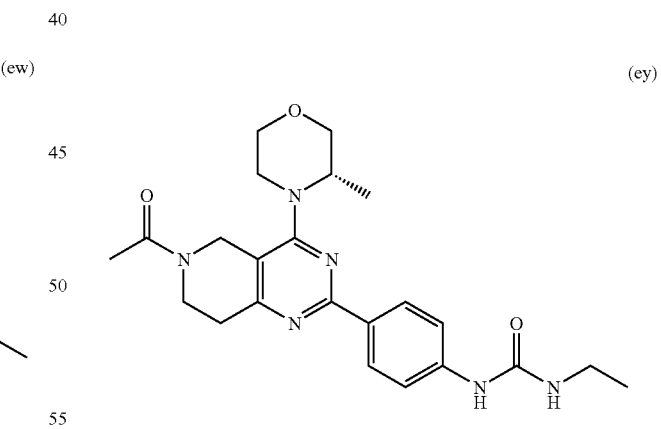

(ey)

Synthesis of (S)-1-ethyl-3-(4-(4-(3-methylmorpholino)-7-(2-(trifluoromethyl)pyrimidin-4-yl)-5,6,7,8-tetrahydropyrido[3,4-d]pyrimidin-2-yl)phenyl)urea (ew): Compound ew was prepared according to the procedure described in Example 2 by reacting (S)-1-ethyl-3-(4-(4-(3-methylmor- Synthesis of (S)-1-(4-(6-acetyl-4-(3-methylmorpholino)-5,6,7,8-tetrahydropyrido[4,3-d]pyrimidin-2-yl)phenyl)-3-ethylurea (ey): Compound ey was prepared according to the procedure described in Example 5 by reacting (S)-1-ethyl-3-

(4-(4-(3-methylmorpholino)-5,6,7,8-tetrahydropyrido[4,3-d]pyrimidin-2-yl)phenyl)urea with acetyl chloride. LC-MS: m/z=+439 (M+H)+.

Example 126

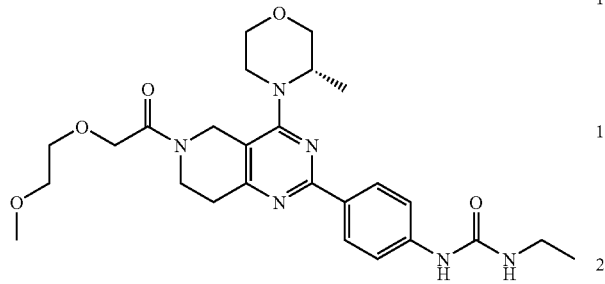
(ez)

Synthesis of (S)-1-ethyl-3-(4-(6-(2-(2-methoxyethoxy)acetyl)-4-(3-methylmorpholino)-5,6,7,8-tetrahydropyrido[4,3-d]pyrimidin-2-yl)phenyl)urea (ez): Compound ez was prepared according to the procedure described in Example 5 by reacting (S)-1-ethyl-3-(4-(4-(3-methylmorpholino)-5,6,7,8-tetrahydropyrido[4,3-d]pyrimidin-2-yl)phenyl)urea with 2-(2-methoxyethoxy)acetyl chloride. LC-MS: m/z=+513 (M+H)+.

Example 127

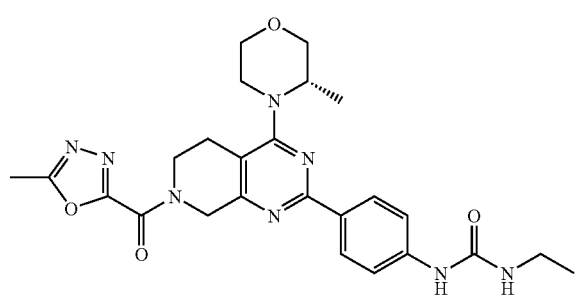
(fa)

Synthesis of (S)-1-ethyl-3-(4-(7-(5-methyl-1,3,4-oxadiazole-2-carbonyl)-4-(3-methylmorpholino)-5,6,7,8-tetrahydropyrido[3,4-d]pyrimidin-2-yl)phenyl)urea (fa): Compound fa was prepared according to the procedure described in Example 213 by reacting (S)-1-ethyl-3-(4-(4-(3-methylmorpholino)-5,6,7,8-tetrahydropyrido[3,4-d]pyrimidin-2-yl)phenyl)urea with 5-methyl-1,3,4-oxadiazole-2-carboxylic acid. LC-MS: m/z=+507 (M+H)+.

Example 128

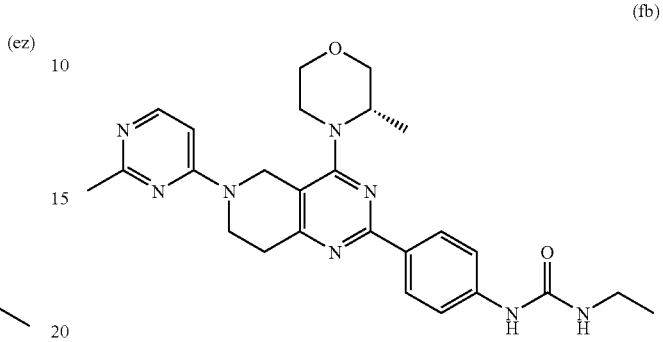
(fb)

Synthesis of (S)-1-ethyl-3-(4-(4-(3-methylmorpholino)-6-(2-methylpyrimidin-4-yl)-5,6,7,8-tetrahydropyrido[4,3-d]pyrimidin-2-yl)phenyl)urea (fb): Compound fb was prepared according to the procedure described in Example 2 by reacting (S)-1-ethyl-3-(4-(4-(3-methylmorpholino)-5,6,7,8-tetrahydropyrido[4,3-d]pyrimidin-2-yl)phenyl)urea with 2-methyl-4-chloropyridine. LC-MS: m/z=+489 (M+H)+.

Example 129

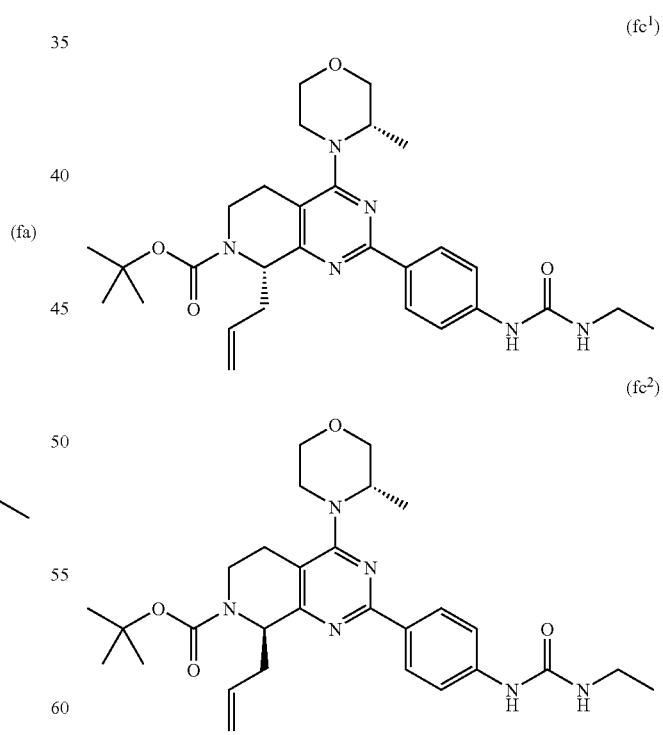
(fc1)

(fc2)

Synthesis of (S)-tert-butyl 8-allyl-2-(4-(3-ethylureido)phenyl)-4-((S)-3-methylmorpholino)-5,6-dihydropyrido[3,4-d]pyrimidine-7(8H)-carboxylate (fc1); and (R)-tert-butyl 8-allyl-2-(4-(3-ethylureido)phenyl)-4-((S)-3-methylmorpholino)-5,6-dihydropyrido[3,4-d]pyrimidine-7(8H)-carboxylate (fc²): Compounds fc¹ and fc² were prepared according to the procedure described in Example 2 step 2 by reacting tert-butyl 8-allyl-2-chloro-4-((S)-3-methylmorpholino)-5,6-dihydropyrido[3,4-d]pyrimidine-7(8H)-carboxylate with (4-ethylureido)phenylboronic acid pinacol ester. The diastereoisomers were separated by chrial column chromatography. LC-MS: m/z=+537 (M+H)⁺.

Example 130

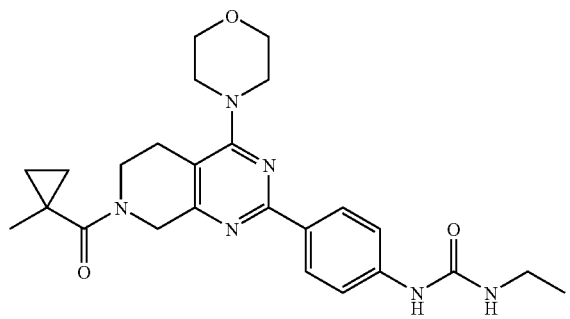
(fd)

Synthesis of 1-ethyl-3-(4-(7-(1-methylcyclopropanecarbonyl)-4-morpholino-5,6,7,8-tetrahydropyrido[3,4-d]pyrimidin-2-yl)phenyl)urea (fd): Compound fd was prepared according to the procedure described in Example 213 by reacting 1-ethyl-3-(4-(4-morpholino-5,6,7,8-tetrahydropyrido[3,4-d]pyrimidin-2-yl)phenyl)urea with 1-methylcyclopropanecarboxylic acid. LC-MS: m/z=+465 (M+H)⁺.

Example 131

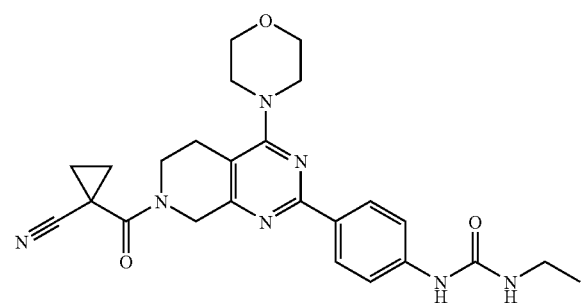
(fe)

Synthesis of 1-(4-(7-(1-cyanocyclopropanecarbonyl)-4-morpholino-5,6,7,8-tetrahydropyrido[3,4-d]pyrimidin-2-yl)phenyl)-3-ethylurea (fe): Compound fe was prepared according to the procedure described in Example 213 by reacting 1-ethyl-3-(4-(4-morpholino-5,6,7,8-tetrahydropyrido[3,4-d]pyrimidin-2-yl)phenyl)urea with 1-cyanocyclopropanecarboxylic acid. LC-MS: m/z=+476 (M+H)⁻.

Example 132

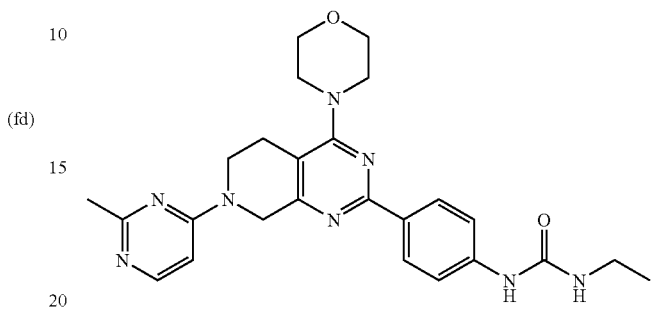
(ff)

Synthesis of 1-ethyl-3-(4-(7-(2-methylpyrimidin-4-yl)-4-morpholino-5,6,7,8-tetrahydropyrido[3,4-d]pyrimidin-2-yl)phenyl)urea (ff): Compound ff was prepared according to the procedure described in Example 2 by reacting 1-ethyl-3-(4-(4-morpholino-5,6,7,8-tetrahydropyrido[3,4-d]pyrimidin-2-yl)phenyl)urea with 2-methyl-4-chloropyridine. LC-MS: m/z=+475 (M+H)⁺.

Example 133

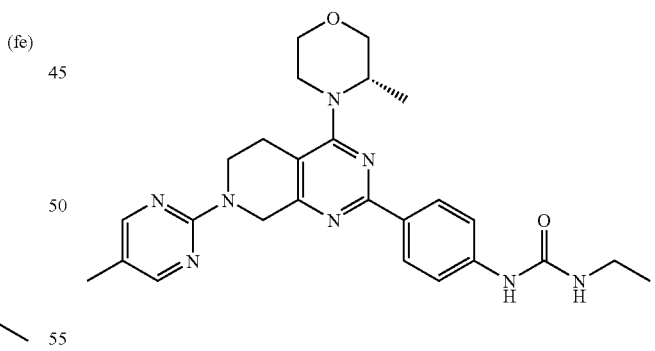
(fg)

Synthesis of (S)-1-ethyl-3-(4-(4-(3-methylmorpholino)-7-(5-methylpyrimidin-2-yl)-5,6,7,8-tetrahydropyrido[3,4-d]pyrimidin-2-yl)phenyl)urea (fg): Compound fg was prepared according to the procedure described in Example 2 by reacting (S)-1-ethyl-3-(4-(4-(3-methylmorpholino)-5,6,7,8-tetrahydropyrido[3,4-d]pyrimidin-2-yl)phenyl)urea with 5-methyl-2-chloropyridine. LC-MS: m/z=+489 (M+H)+.

Example 134

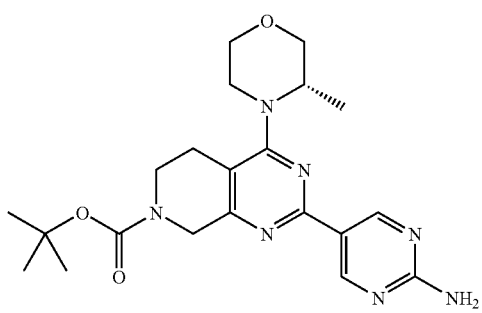

(fh)

Synthesis of (S)-tert-butyl 2-(2-aminopyrimidin-5-yl)-4-(3-methylmorpholino)-5,6-dihydropyrido[3,4-d]pyrimidine-7(8H)-carboxylate (fh): Compound fh was prepared according to the procedure described in Example 2 step 2 by reacting tert-butyl 8-allyl-2-chloro-4-((S)-3-methylmorpholino)-5,6-dihydropyrido[3,4-d]pyrimidine-7(8H)-carboxylate with 5-(4,4,5,5-tetramethyl-1,3,2-dioxaborolan-2-yl)pyrimidin-2-amine. LC-MS: m/z=+428 (M+H)+.

Example 135

(fi)

Synthesis of (S)-5-(4-(3-methylmorpholino)-7-(2-methylpyrimidin-4-yl)-5,6,7,8-tetrahydropyrido[3,4-d]pyrimidin-2-yl)pyrimidin-2-amine (fi): Compound fi was prepared according to the procedure described in Example 2 by reacting (S)-5-(4-(3-methylmorpholino)-5,6,7,8-tetrahydropyrido[3,4-d]pyrimidin-2-yl)pyrimidin-2-amine with 2-methyl-4-chloropyridin. LC-MS: m/z=+420 (M+H)+.

Example 136

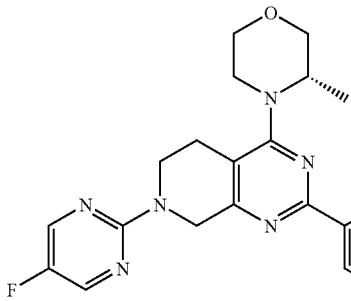

(fj)

Synthesis of (S)-5-(7-(5-fluoropyrimidin-2-yl)-4-(3-methylmorpholino)-5,6,7,8-tetrahydropyrido[3,4-d]pyrimidin-2-yl)pyrimidin-2-amine (fj): Compound fj was prepared according to the procedure described in Example 2 by reacting (S)-5-(4-(3-methylmorpholino)-5,6,7,8-tetrahydropyrido[3,4-d]pyrimidin-2-yl)pyrimidin-2-amine with 2-methyl-4-chloropyridine. LC-MS: m/z=+424 (M+H)+.

Example 137

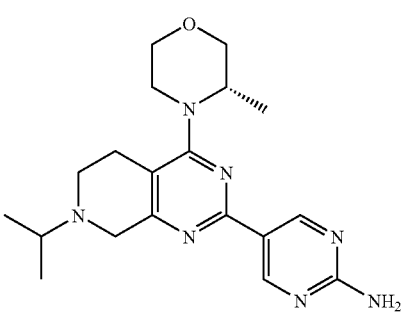

(fk)

Synthesis of (S)-5-(7-isopropyl-4-(3-methylmorpholino)-5,6,7,8-tetrahydropyrido[3,4-d]pyrimidin-2-yl)pyrimidin-2-amine (fk): Compound fk was prepared according to the procedure described in Example 2 by reacting (S)-5-(4-(3- methylmorpholino)-5,6,7,8-tetrahydropyrido[3,4-d]pyrimidin-2-yl)pyrimidin-2-amine with isopropylbromide. LC-MS: m/z=+370 (M+H)⁻.

Example 138

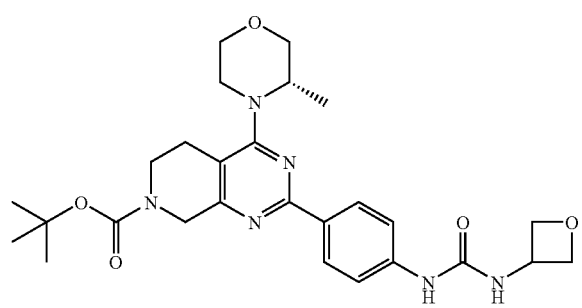

(fl)

Synthesis of (S)-tert-butyl 4-(3-methylmorpholino)-2-(4-(3-oxetan-3-ylureido)phenyl)-5,6-dihydropyrido[3,4-d]pyrimidine-7(8H)-carboxylate (fl): Compound fl was prepared according to the procedure described in Example 30 by reacting (S)-tert-butyl 2-(4-aminophenyl)-4-(3-methylmorpholino)-5,6-dihydropyrido[3,4-d]pyrimidine-7(8H)-carboxylate with oxetan-3-amine. LC-MS: m/z=+525 (M+H)⁺.

Example 139

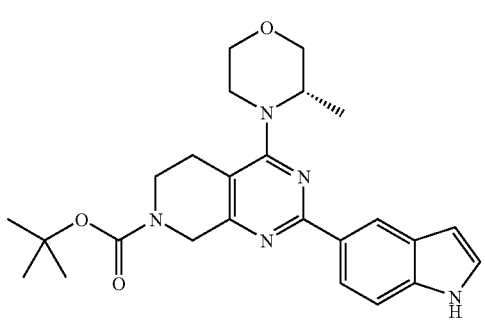

(fm)

Synthesis of (S)-tert-butyl 2-(1H-indol-5-yl)-4-(3-methylmorpholino)-5,6-dihydropyrido[3,4-d]pyrimidine-7(8H)-carboxylate (fm): Compound fm was prepared according to the procedure described in Example 2 step 2 by reacting tert-butyl 8-allyl-2-chloro-4-((S)-3-methylmorpholino)-5,6-dihydropyrido[3,4-d]pyrimidine-7(8H)-carboxylate with 1H-indol-5-ylboronic acid. LC-MS: m/z=+450 (M+H)⁻.

Example 140

(fn)

Synthesis of 1-ethyl-3-(4-(7-(2-methoxypyrimidin-4-yl)-4-morpholino-5,6,7,8-tetrahydropyrido[3,4-d]pyrimidin-2-yl)phenyl)urea (fn): Compound fn was prepared according to the procedure described in Example 2 by reacting 1-ethyl-3-(4-(4-morpholino-5,6,7,8-tetrahydropyrido[3,4-d]pyrimidin-2-yl)phenyl)urea with 2-methoxy-4-chloropyridine. LC-MS: m/z=+491 (M+H)⁺.

Example 141

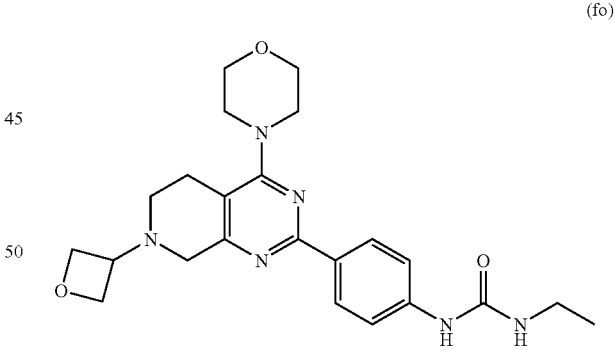

(fo)

Synthesis of 1-ethyl-3-(4-(4-morpholino-7-(oxetan-3-yl)-5,6,7,8-tetrahydropyrido[3,4-d]pyrimidin-2-yl)phenyl)urea (fo): Compound fo was prepared according to the procedure described in Example 8 by reacting 1-ethyl-3-(4-(4-morpholino-5,6,7,8-tetrahydropyrido[3,4-d]pyrimidin-2-yl)phenyl)urea with oxetan-3-one. LC-MS: m/z=+439 (M+H)+.

Example 142

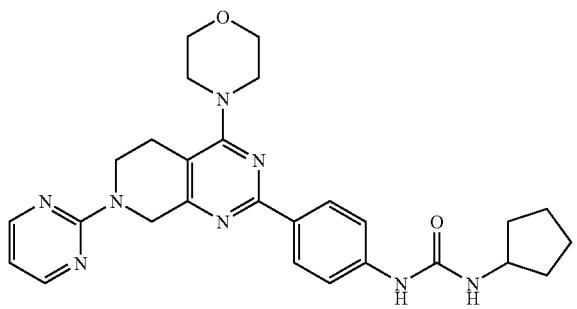

(fp)

Synthesis of 1-cyclopentyl-3-(4-(4-morpholino-7-(pyrimidin-2-yl)-5,6,7,8-tetrahydropyrido[3,4-d]pyrimidin-2-yl)phenyl)urea (fp): Compound fp was prepared generally following the procedures described in Examples 1 and 2 except that tert-butyl 2,4-dichloro-5,6-dihydropyrido[3,4-d]pyrimidine-7(8H)-carboxylate was used instead of tert-butyl 2,4-dichloro-5H-pyrrolo[3,4-d]pyrimidine-6(7H)-carboxylate in step 1 of Example 1, and 1-cyclopentyl-3-(4-(4,4,5,5-tetramethyl-1,3,2-dioxaborolan-2-yl)phenyl)urea was used instead of (4-ethylureido)phenylboronic acid pinacol ester in step 2: LC/MS-m/z+501.3 (M+H)+.

Example 143

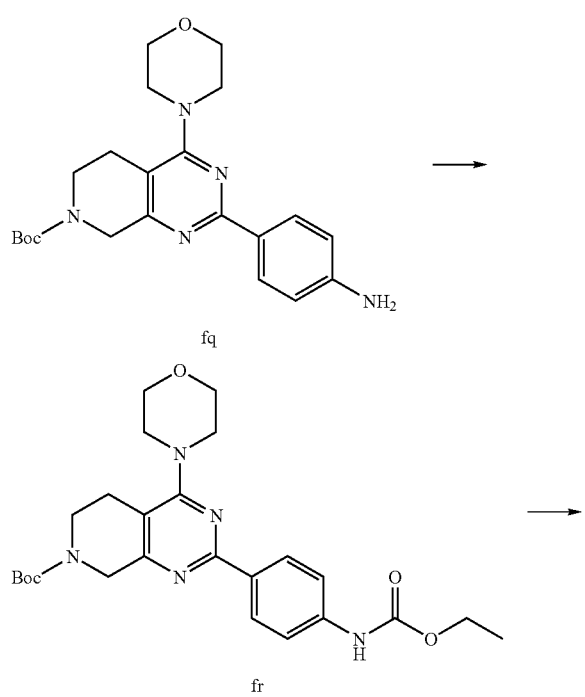

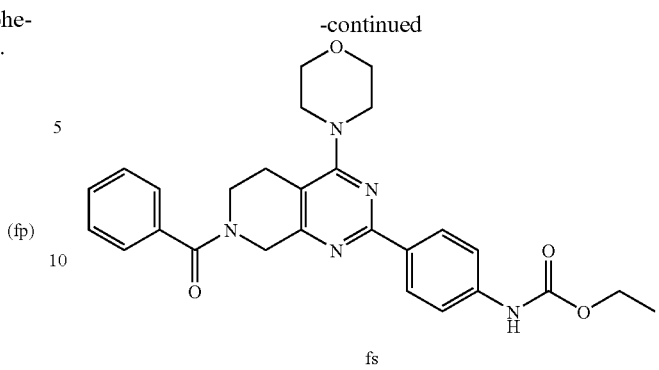

fs

Synthesis of Compound fs:

Step 1—Synthesis of fr: Compound fq (see Example 145) (180 mg, 0.44 mmol) was dissolved in tetrahydrofuran (3.00 mL, 37.0 mmol). N,N-diisopropylethylamine (2.00E2 uL, 1.15 mmol) was added, then ethyl chloroformate (85 uL, 0.89 mmol) in a single portion. The reaction was stirred at RT for 1 h, then allowed to stir overnight at RT. The crude material was rotovaped onto silica gel, then subjected to column chromatography using a 4 g column, with a gradient of 0% to 50% ethyl acetate in hexanes. The product containing fractions were combined and evaporated under reduced pressure to give the desired material (fr): $^1$H NMR (400 MHz, CDCl3) δ 8.33 (d, J=8.7, 2H), 7.46 (d, J=8.6, 2H), 6.79 (s, 1H), 4.60 (s, 2H), 4.24 (q, J=7.1, 2H), 3.89-3.80 (m, 4H), 3.61 (t, J=5.2, 2H), 3.55-3.46 (m, 4 H), 2.73-2.63 (m, 2H), 1.51 (s, 9H), 1.32 (t, J=7.1, 3H).

Step 2—Synthesis of compound fs: Compound fr (149 mg, 0.308 mmol) was dissolved in methylene chloride (2.0 mL, 31 mmol) and trifluoroacetic acid (0.50 mL, 6.5 mmol) was added in a single portion. The volatile materials were removed by rotoevaporation and the resultant residue (oil) was washed with Et$_2$O, which produced a white solid precipitate. The precipitate was filtered off, then dissolved in CH$_2$Cl$_2$ and MeOH and stirred with 0.16 g PS-carbonate resin (2.5-3.6 mmol N/g) for 1 h at RT. The resin was filtered off and washed with CH$_2$Cl$_2$. The filtrate was then concentrated to a white solid, which was used without further purification. The crude material was placed in a reaction vial and methylene chloride (1.5 mL, 23 mmol) and N,N-diisopropylethylamine (160 uL, 0.92 mmol) were added, then benzoyl chloride (50.0 uL, 0.431 mmol). The reaction was stirred at RT for 1.5 h. The reaction was quenched with 5 ml water and the layers separated. The aqueous phase was extracted with additional CH$_2$Cl$_2$ (3×5 ml), the organics were combined and the volatiles were removed under reduced pressure to give a tan solid. This solid was triturated with 0.5 ml DMF, filtered and washed with a small amount of water. This gave a pure white powder product fs: $^1$H NMR (400 MHz, DMSO) δ 9.80 (s, 1H), 8.34-8.08 (m, J=32.8 Hz, 2H), 7.62-7.44 (m, 7H), 4.79-4.44 (m, J=74.2 Hz, 2H), 4.14 (q, J=6.6 Hz, 2H), 3.91-3.78

(m, 1H), 3.77-3.68 (m, 4H), 3.57-3.43 (m, 5H), 2.81-2.73 (m, 2H), 1.25 (t, J=7.0 Hz, 3H). LC-MS: m/z=+488.3 (M+H)+.

Example 144

(ft)

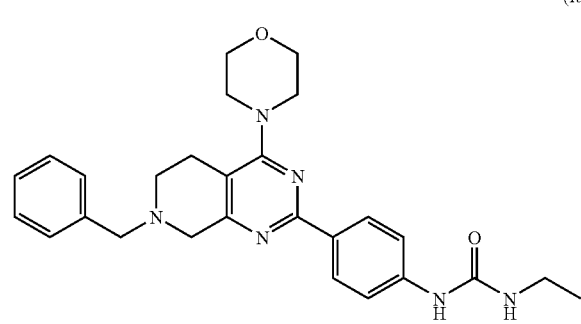

Synthesis of 1-(4-(7-benzyl-4-morpholino-5,6,7,8-tetrahydropyrido[3,4-d]pyrimidin-2-yl)phenyl)-3-ethylurea (ft): Compound ft was prepared generally following the procedures described in Example 35 except that methyl 1-benzyl-3-oxopiperidine-4-carboxylate was used instead of methyl 1-benzyl-4-oxo-3-piperidinecarboxylate in step 1 of Example 35, and step 3 was omitted (so that the N-benzyl group was not exchanged for a N-Boc): LC/MS-m/z+473.3 (M+H)+.

Example 145

(fq)

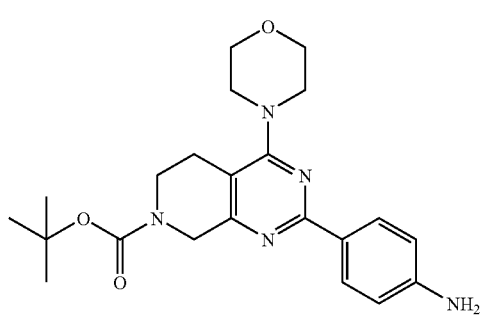

Synthesis of tert-butyl 2-(4-aminophenyl)-4-morpholino-5,6-dihydropyrido[3,4-d]pyrimidine-7(8H)-carboxylate (fq): Compound fq was prepared generally following the procedures described in Example 1 and 2 except that tert-butyl 2,4-dichloro-5,6-dihydropyrido[3,4-d]pyrimidine-7(8H)-carboxylate was used instead of tert-butyl 2,4-dichloro-5H-pyrrolo[3,4-d]pyrimidine-6(7H)-carboxylate in step 1 and 4-(4,4,5,5-tetramethyl-1,3,2-dioxaborolan-2-yl)aniline was used instead of (4-ethylureido)phenylboronic acid pinacol ester in step 2. LC/MS-m/z+412.3 (M+H)+.

Example 146

(fu)

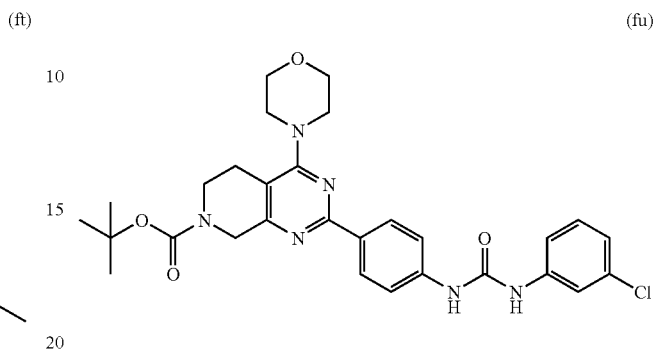

Synthesis of tert-butyl 2-(4-(3-(3-chlorophenyl)ureido)phenyl)-4-morpholino-5,6-dihydropyrido[3,4-d]pyrimidine-7(8H)-carboxylate (fu): Compound fu was prepared generally following the procedures described in Example 143 except that 1-chloro-3-isocyanatobenzene was used instead of ethyl chloroformate in step 1. LC/MS-m/z+565.3 (M+H)+.

Example 147

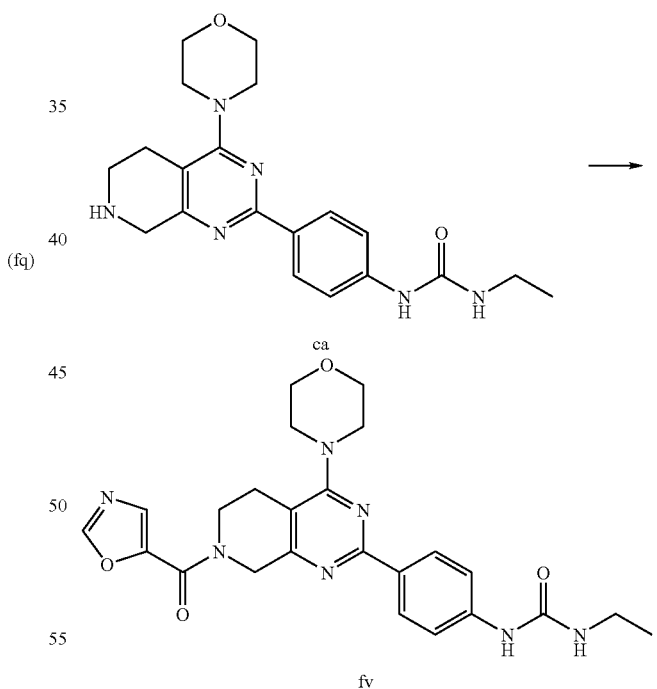

Synthesis of 1-ethyl-3-(4-(4-morpholino-7-(oxazole-5-carbonyl)-5,6,7,8-tetrahydropyrido[3,4-d]pyrimidin-2-yl)phenyl)urea (fv): (S)-1-ethyl-3-(4-(4-(3-methylmorpholino)-5,6,7,8-tetrahydropyrido[3,4-d]pyrimidin-2-yl)phenyl)urea (71 mg, 0.18 mmol) and N,N-diisopropylethylamine (6.0E1 uL, 0.34 mmol) were dissolved in N,N-Dimethylformamide (1.0 mL, 13 mmol). Oxazole-5-carboxylic acid (30.0 mg, 0.265 mmol) 1-hydroxybenzotriazole (27.8 mg, 0.206 mmol) and N-(3-dimethylaminopropyl)-N'-ethylcarbodiimide hydrochloride (49.9 mg, 0.260 mmol) were weighed out into a vial, and the solution of the amines was added, then the reaction stirred overnight. The resultant precipitate was removed by filtration and washed with H₂O. The resulting solid was purified by reverse phase HPLC: ¹H NMR (400 MHz, DMSO) δ 8.68 (s, 1H), 8.63 (s, 1H), 8.19 (d, J=8.4 Hz, 2H), 7.88 (s, 1H), 7.49 (d, J=8.7 Hz, 2H), 6.18 (t, J=5.5 Hz, 1H), 4.98-4.54 (m, 2H), 4.19-4.07 (m, 1H), 4.00-3.54 (m, 7H), 3.48-3.37 (m, 1H), 3.15-3.08 (m, 2H), 2.92-2.65 (m, 2H), 1.26 (d, J=6.6 Hz, 3H), 1.06 (t, J=7.2 Hz, 3H) LC-MS: m/z=+492.2 (M+H)⁺.

Example 148

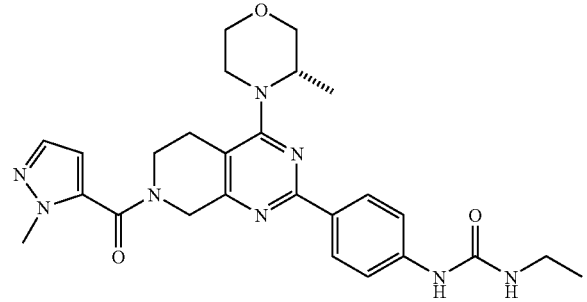

(fw)

Synthesis of (S)-1-ethyl-3-(4-(7-(1-methyl-1H-pyrazole-5-carbonyl)-4-(3-methylmorpholino)-5,6,7,8-tetrahydropyrido[3,4-d]pyrimidin-2-yl)phenyl)urea (fw): Compound fw was prepared generally following the procedures described in Example 147 except that 1-methyl-1H-pyrazole-5-carboxylic acid was used instead of oxazole-5-carboxylic acid. LC/MS-m/z+505.3 (M+H)+.

Example 149

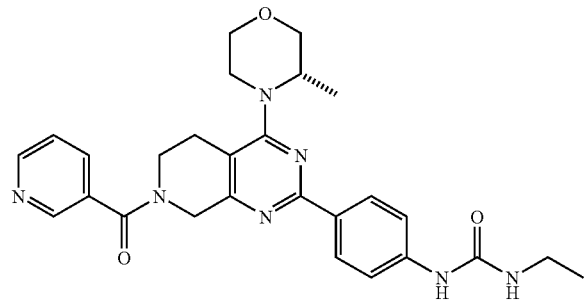

(fx)

Synthesis of (S)-1-ethyl-3-(4-(4-(3-methylmorpholino)-7-nicotinoyl-5,6,7,8-tetrahydropyrido[3,4-d]pyrimidin-2-yl)phenyl)urea (fx): Compound fx was prepared generally following the procedures described in Example 147 except that nicotinyl chloride hydrochloride was used instead of oxazole-5-carboxylic acid, 1-hydroxybenzotriazole and N-(3-dimethylaminopropyl)-N'-ethylcarbodiimide hydrochloride. LC/MS-m/z+502.3 (M+H)+.

Example 150

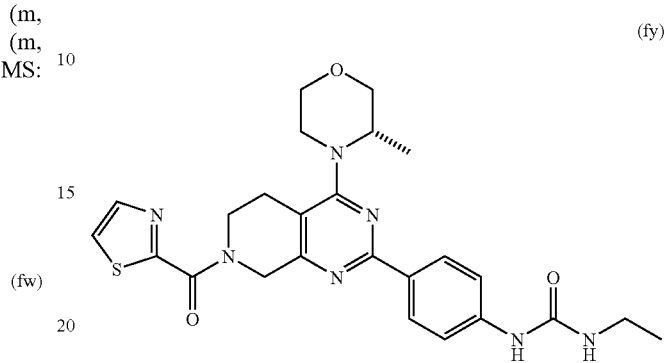

(fy)

Synthesis of (S)-1-ethyl-3-(4-(4-(3-methylmorpholino)-7-(thiazole-2-carbonyl)-5,6,7,8-tetrahydropyrido[3,4-d]pyrimidin-2-yl)phenyl)urea (fy): Compound fy was prepared generally following the procedures described in Example 147 except that 1,3-thiazole-2-carbonyl chloride was used instead of oxazole-5-carboxylic acid, 1-hydroxybenzotriazole and N-(3-dimethylaminopropyl)-N'-ethylcarbodiimide hydrochloride. LC/MS-m/z+502.3 (M+H)+.

Example 151

(fz)

Synthesis of (R)-tert-butyl 2-(4-(3-ethylureido)phenyl)-4-(3-methylmorpholino)-5,6-dihydropyrido[3,4-d]pyrimidine-7(8H)-carboxylate (fz): Compound fz was prepared generally following the procedures described in Example 1 except that tert-butyl 2,4-dichloro-5,6-dihydropyrido[3,4-d]pyrimidine-7(8H)-carboxylate was used instead of tert-butyl 2,4-dichloro-5H-pyrrolo[3,4-d]pyrimidine-6(7H)-carboxylate and 3R-3-methylmorpholine was used instead of morpholine in step 1 of Example 1: LC/MS-m/z+497.3 (M+H)+.

Example 152

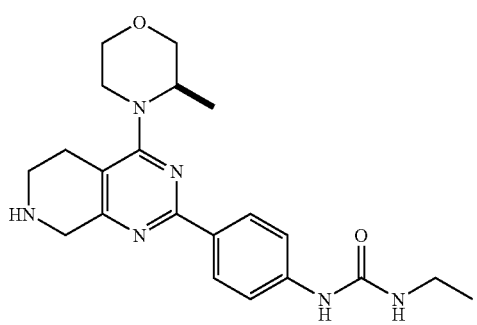
(ga)

Synthesis of (R)-1-ethyl-3-(4-(4-(3-methylmorpholino)-5,6,7,8-tetrahydropyrido[3,4-d]pyrimidin-2-yl)phenyl)urea (ga): Compound ga was prepared generally following the procedures described in Example 1 except that tert-butyl 2,4-dichloro-5,6-dihydropyrido[3,4-d]pyrimidine-7(8H)-carboxylate was used instead of tert-butyl 2,4-dichloro-5H-pyrrolo[3,4-d]pyrimidine-6(7H)-carboxylate and 3R-3-methylmorpholine was used instead of morpholine in step 1 of Example 1: LC/MS-m/z+397.3 (M+H)+.

Example 153

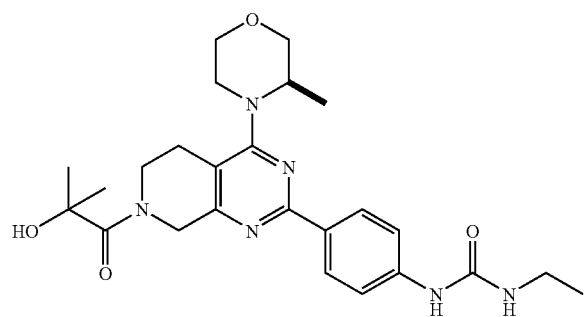
(gb)

Synthesis of (R)-1-ethyl-3-(4-(7-(2-hydroxy-2-methylpropanoyl)-4-(3-methylmorpholino)-5,6,7,8-tetrahydropyrido[3,4-d]pyrimidin-2-yl)phenyl)urea (gb): Compound gb was prepared generally following the procedures described in Examples 1 and 147 except that tert-butyl 2,4-dichloro-5,6-dihydropyrido[3,4-d]pyrimidine-7(8H)-carboxylate was used instead of tert-butyl 2,4-dichloro-5H-pyrrolo[3,4-d]pyrimidine-6(7H)-carboxylate and 3R-3-methylmorpholine was used instead of morpholine in step 1 of Example 1. Additionally, 2-hydroxyisobutyric acid was used instead of oxazole-5-carboxylic acid in Example 147: LC/MS-m/z+483.3 (M+H)+.

Example 154

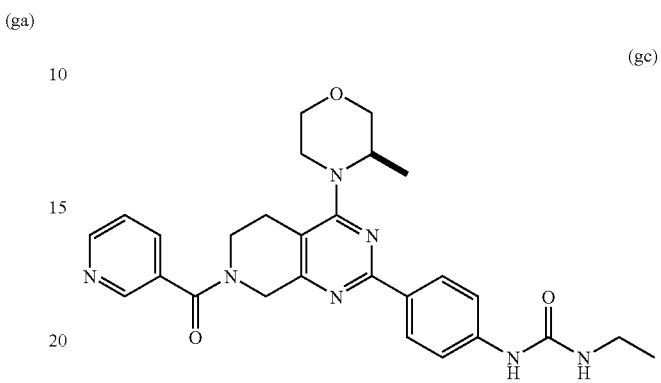
(gc)

Synthesis of (R)-1-ethyl-3-(4-(4-(3-methylmorpholino)-7-nicotinoyl-5,6,7,8-tetrahydropyrido[3,4-d]pyrimidin-2-yl)phenyl)urea (gc): Compound gc was prepared generally following the procedures described in Examples 1 and 147 except that tert-butyl 2,4-dichloro-5,6-dihydropyrido[3,4-d]pyrimidine-7(8H)-carboxylate was used instead of tert-butyl 2,4-dichloro-5H-pyrrolo[3,4-d]pyrimidine-6(7H)-carboxylate and 3R-3-methylmorpholine was used instead of morpholine in step 1 of Example 1. Additionally, nicotinyl chloride hydrochloride was used instead of oxazole-5-carboxylic acid, 1-hydroxybenzotriazole and N-(3-dimethylaminopropyl)-N'-ethylcarbodiimide hydrochloride in Example 159: LC/MS-m/z+502.3 (M+H)+.

Example 155

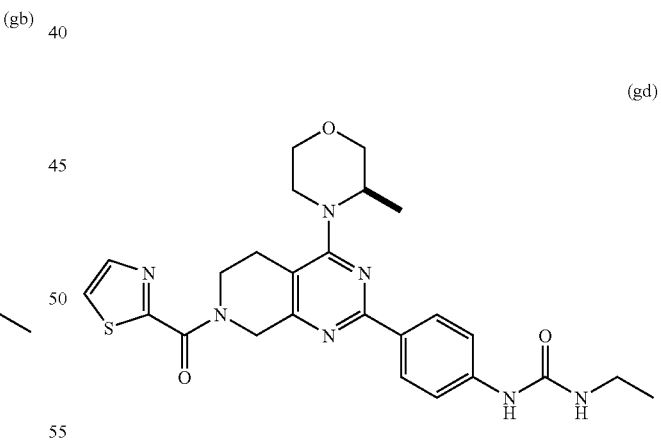
(gd)

Synthesis of (R)-1-ethyl-3-(4-(4-(3-methylmorpholino)-7-(thiazole-2-carbonyl)-5,6,7,8-tetrahydropyrido[3,4-d]pyrimidin-2-yl)phenyl)urea (gd): Compound gd was prepared generally following the procedures described in Examples 1 and 147 except that tert-butyl 2,4-dichloro-5,6-dihydropyrido[3,4-d]pyrimidine-7(8H)-carboxylate was used instead of tert-butyl 2,4-dichloro-5H-pyrrolo[3,4-d]pyrimidine-6(7H)-carboxylate and 3R-3-methylmorpholine was used instead of morpholine in step 1 of Example 1. Additionally, 1,3-thiazole-2-carbonyl chloride was used instead of oxazole-5-carboxylic acid, 1-hydroxybenzotriazole and

Example 156

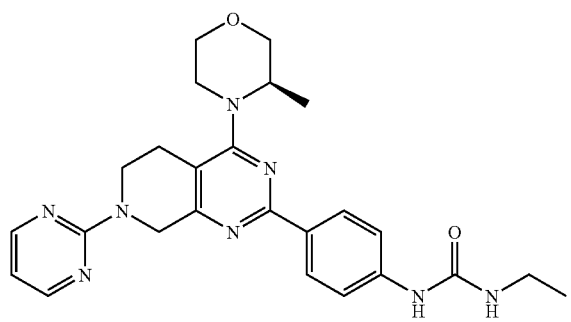
(ge)

Synthesis of (R)-1-ethyl-3-(4-(4-(3-methylmorpholino)-7-(pyrimidin-2-yl)-5,6,7,8-tetrahydropyrido[3,4-d]pyrimidin-2-yl)phenyl)urea (ge): Compound ge was prepared generally following the procedures described in Examples 1 and 2 except that tert-butyl 2,4-dichloro-5,6-dihydropyrido[3,4-d]pyrimidine-7(8H)-carboxylate was used instead of tert-butyl 2,4-dichloro-5H-pyrrolo[3,4-d]pyrimidine-6(7H)-carboxylate and 3R-3-methylmorpholine was used instead of morpholine in step 1 of Example 1: LC/MS-m/z+475.3 (M+H)+.

Example 157

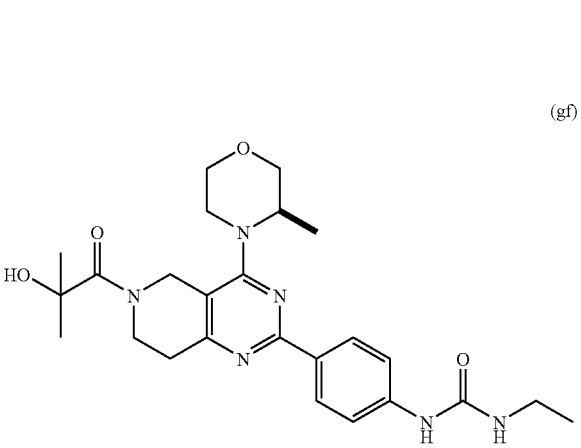
(gf)

Synthesis of (R)-1-ethyl-3-(4-(6-(2-hydroxy-2-methylpropanoyl)-4-(3-methylmorpholino)-5,6,7,8-tetrahydropyrido[4,3-d]pyrimidin-2-yl)phenyl)urea (gf): Compound gf was prepared generally following the procedures described in Examples 35 and 147 except that 3R-3-methylmorpholine was used instead of morpholine in step 4 of Example 35. Additionally, 2-hydroxyisobutyric acid was used instead of oxazole-5-carboxylic acid in Example 147: LC/MS-m/z+ 483.3 (M+H)+.

Example 158

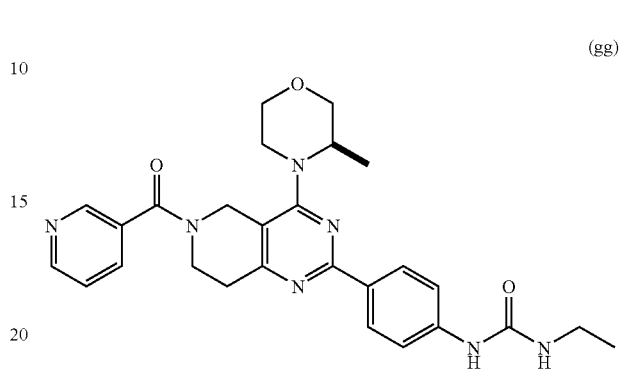
(gg)

Synthesis of (R)-1-ethyl-3-(4-(4-(3-methylmorpholino)-6-nicotinoyl-5,6,7,8-tetrahydropyrido[4,3-d]pyrimidin-2-yl)phenyl)urea: Compound gg was prepared generally following the procedures described in Examples 35 and 147 except that 3R-3-methylmorpholine was used instead of morpholine in step 4 of Example 35. Additionally, 2-hydroxyisobutyric acid was used instead of nicotinyl chloride hydrochloride was used instead of oxazole-5-carboxylic acid, 1-hydroxybenzotriazole and N-(3-dimethylaminopropyl)-N'-ethylcarbodiimide hydrochloride in Example 147: LC/MS-m/z+502.3 (M+H)+.

Example 159

(gh)

Synthesis of (R)-tert-butyl 2-(4-(3-ethylureido)phenyl)-4-(3-methylmorpholino)-7,8-dihydropyrido[4,3-d]pyrimidine-6(5H)-carboxylate (gh): Compound gh was prepared generally following the procedures described in Example 35 except that 3R-3-methylmorpholine was used instead of morpholine in step 4: LC/MS-m/z+497.3 (M+H)+.

Example 160

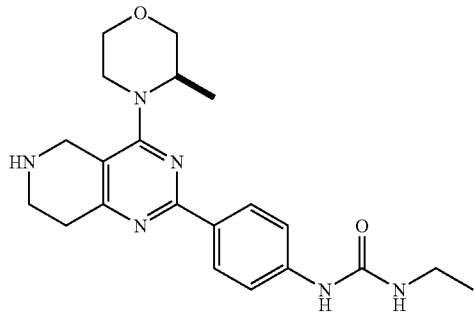

(gi)

Synthesis of (R)-1-ethyl-3-(4-(4-(3-methylmorpholino)-5,6,7,8-tetrahydropyrido[4,3-d]pyrimidin-2-yl)phenyl)urea (gi): Compound gi was prepared generally following the procedures described in Example 35 except that 3R-3-methylmorpholine was used instead of morpholine in step 4: LC/MS-m/z+397.2 (M+H)+.

Example 161

(gj)

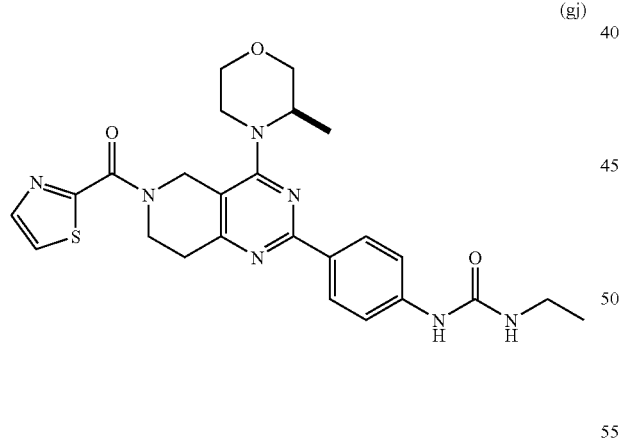

Synthesis of (R)-1-ethyl-3-(4-(4-(3-methylmorpholino)-6-(thiazole-2-carbonyl)-5,6,7,8-tetrahydropyrido[4,3-d]pyrimidin-2-yl)phenyl)urea (gj): Compound u was prepared generally following the procedures described in Examples 35 and 147 except that 3R-3-methylmorpholine was used instead of morpholine in step 4 of Example 35. Additionally, 1,3-thiazole-2-carbonyl chloride was used instead of oxazole-5-carboxylic acid, 1-hydroxybenzotriazole and N-(3-dimethylaminopropyl)-N'-ethylcarbodiimide hydrochloride in Example 147: LC/MS-m/z+508.2 (M+H)+.

Example 162

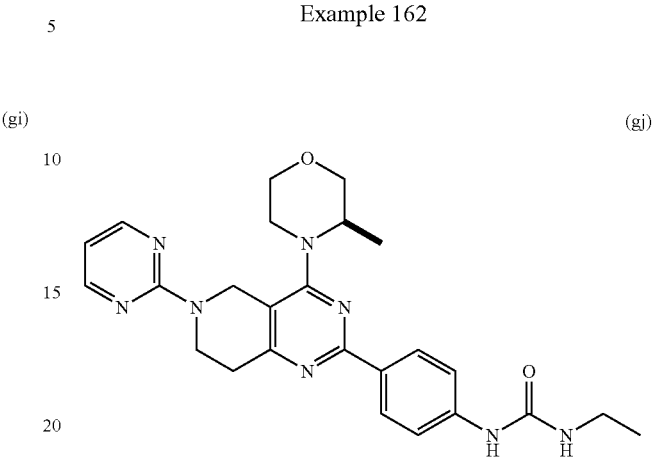

(gj)

Synthesis of (R)-1-ethyl-3-(4-(4-(3-methylmorpholino)-6-(pyrimidin-2-yl)-5,6,7,8-tetrahydropyrido[4,3-d]pyrimidin-2-yl)phenyl)urea (gj): Compound gj was prepared generally following the procedures described in Examples 35 and 2 except that 3R-3-methylmorpholine was used instead of morpholine in step 4 of Example 35: LC/MS-m/z+475.2 (M+H)+.

Example 163

(gk)

Synthesis of (S)-1-ethyl-3-(4-(4-(3-methylmorpholino)-7-(pyrazin-2-yl)-5,6,7,8-tetrahydropyrido[3,4-d]pyrimidin-2-yl)phenyl)urea (gk): Compound gk was prepared generally following the procedures described in Examples 65 and 66 except that 2-chloropyrazine was used instead of 2-chloropyrimidine in Example 66 and the reaction was performed for 2 h at 130° C.: LC/MS-m/z+475.2 (M+H)+.

Example 164

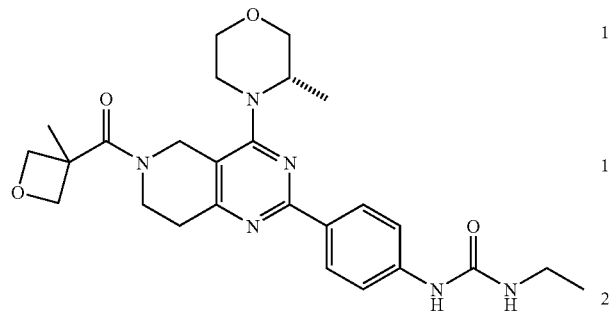

(gl)

Synthesis of (S)-1-ethyl-3-(4-(4-(3-methylmorpholino)-6-(3-methyloxetane-3-carbonyl)-5,6,7,8-tetrahydropyrido[4,3-d]pyrimidin-2-yl)phenyl)urea (gl): Compound gl was prepared generally following the procedures described in Examples 35 and 147 except that 3-methyloxetane-3-carboxylic acid was used instead of oxazole-5-carboxylic acid, and O-(7-Azabenzotriazol-1-yl)-N,N,N',N'-tetramethyluronium hexafluorophosphate was used instead of 1-hydroxybenzotriazole and N-(3-dimethylaminopropyl)-N'-ethylcarbodiimide hydrochloride in Example 147: LC/MS-m/z+ 495.3 (M+H)+.

Example 165

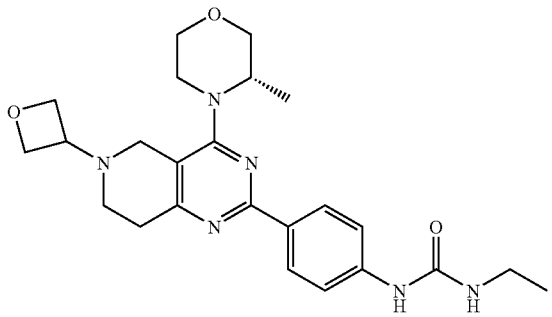

(gm)

Synthesis of (S)-1-ethyl-3-(4-(4-(3-methylmorpholino)-6-(oxetan-3-yl)-5,6,7,8-tetrahydropyrido[4,3-d]pyrimidin-2-yl)phenyl)urea (gm): Compound gm was prepared generally following the procedures described in Examples 35 and 8 except that oxetan-3-one was used instead of 4-hydroxybenzaldehyde in Example 8: LC/MS-m/z+453.2 (M+H)+.

Example 166

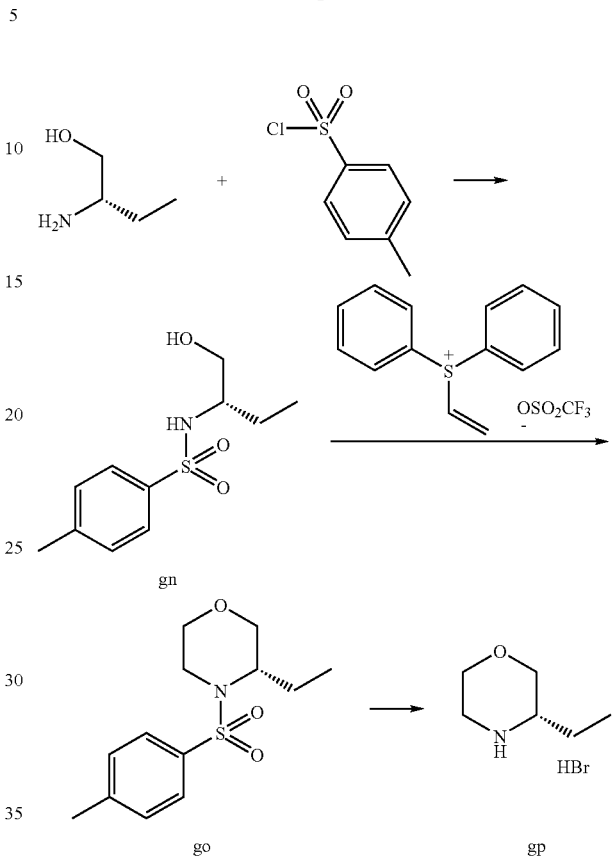

Synthesis of (S)-3-ethylmorpholine hydrobromide (gp)

Step 1—(S)—N-(1-hydroxybutan-2-yl)-4-methylbenzenesulfonamide (gn): (2S)-2-Aminobutan-1-ol (2.1 mL, 22 mmol) and triethylamine (3.8 mL, 27 mmol) were dissolved in methylene chloride (30 mL, 500 mmol) and the solution was stirred at 0° C. for 5 minutes. Then, p-toluenesulfonyl chloride (4.3 g, 22 mmol) was added and the reaction mixture was stirred and permitted to warm to room temperature. The reaction was quenched with water and the phases were separated. The aqueous phase was extracted with 1×50 mL of DCM. The combined organic phases were washed with 1N HCl (50 mL), sat. NaHCO3 (50 mL) and brine (50 mL), dried with Magnesium sulfate, filtered and concentrated to give a white solid. The crude material was crystallized in ether/hexane to give (S)—N-(1-hydroxybutan-2-yl)-4-ethylbenzenesulfonamide as a white solid: $^1$H NMR (400 MHz, DMSO) δ 7.69 (d, J=8.2 Hz, 2H), 7.38 (t, J=9.0 Hz, 3H), 4.62 (t, J=5.6 Hz, 1H), 3.24 (dd, J=10.3, 5.2 Hz, 1H), 3.18-3.02 (m, 1H), 2.92 (dd, J=7.9, 4.2 Hz, 1H), 1.61-1.39 (m, 1H), 1.19 (dd, J=14.5, 7.1 Hz, 1H), 0.63 (t, J=7.4 Hz, 3H); LC-MS: m/z=244 (M+H).

Step 2—(S)-3-ethyl-4-tosylmorpholine (go): Compound gn (800 mg, 3 mmol) was dissolved in dichloromethane (20 mL) and triethylamine (0.92 mL, 6.6 mmol) was added. The mixture was stirred at 0° C. for 10 minutes. Diphenyl(vinyl) sulfonium trifluoromethanesulfonate (1.25 g, 3.45 mmol), dissolved in dichloromethane (10 mL) was added dropwise over 5 minutes. The mixture was stirred while allowed to warm up to room temperature overnight. Saturated aqueous NH₄Cl was added and the phases were separated. The aqueous phase was extracted with 2×30 mL of DCM. The combined organic phases were dried with Magnesium sulfate and filtered. The filtrate was concentrated on silica gel and purified by flash chromatography (100% Hex to 60% EtOAc/Hex) to give (S)-3-ethyl-4-tosylmorpholine (go) as a white solid: ¹H NMR (400 MHz, CDCl₃) δ 7.71 (d, J=8.3 Hz, 2H), 7.30 (t, J=8.3 Hz, 2H), 3.77-3.60 (m, 3H), 3.60-3.44 (m, 2H), 3.44-3.19 (m, 3H), 2.43 (s, 3H), 1.67 (dtd, J=28.6, 14.0, 7.4 Hz, 2H), 1.31-1.12 (m, 2H), 0.97-0.84 (m, 3H); LC-MS: m/z=270 (M+H).

Step 3—(S)-3-ethylmorpholine hydrobromide (gp): Compound go (220 mg, 0.82 mmol) and phenol (150 mg, 1.6 mmol) were dissolved in 4.1 M of hydrogen bromide in acetic acid (2.4 mL) and the solution was stirred at room temperature overnight. The reaction mixture was poured into ether and the precipitated solid was collected by filtration and washed with ether to provide (S)-3-ethylmorpholine hydrobromide (gp) as a white solid: ¹H NMR (400 MHz, CDCl₃) δ 3.77-3.60 (m, 3H), 3.60-3.44 (m, 2H), 3.44-3.19 (m, 3H), 1.67 (dtd, J=28.6, 14.0, 7.4 Hz, 2H), 1.31-1.12 (m, 2H), 0.97-0.84 (m, 3H).

Example 167

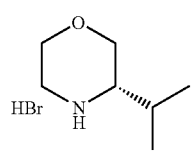

(gq)

Synthesis of (S)-3-isopropylmorpholine hydrobromide (gq): Compound gq was prepared according to the procedure described in Example 166 but using (S)-2-amino-3-methylbutan-1-ol instead of (2S)-2-Aminobutan-1-ol in step 1 of Example 166: LC-MS: m/z=+130 (M+H)⁺.

Example 167

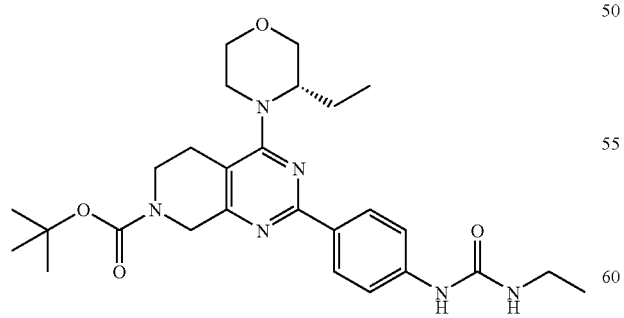

(gr)

Synthesis of (S)-tert-butyl 4-(3-ethylmorpholino)-2-(4-(3-ethylureido)phenyl)-5,6-dihydropyrido[3,4-d]pyrimidine-7(8H)-carboxylate (gr): Compound gr was synthesized using the general procedure described in Example 65 but using (S)-3-ethylmorpholine hydrobromide in step 1 of Example 65 instead of morpholine: LC-MS: m/z=+511 (M+H)⁺.

Example 168

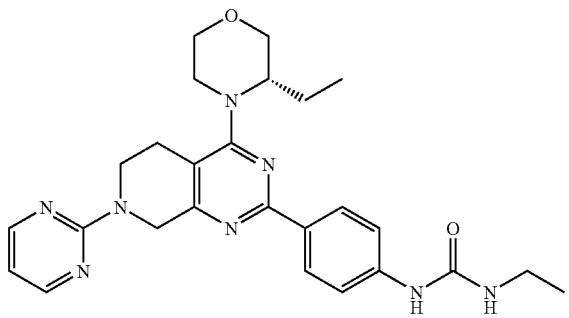

(gs)

Synthesis of (S)-1-ethyl-3-(4-(4-(3-ethylmorpholino)-7-(pyrimidin-2-yl)-5,6,7,8-tetrahydropyrido[3,4-d]pyrimidin-2-yl)phenyl)urea (gs): Compound gs was synthesized using the general procedure described in Example 2 by reacting (S)-1-ethyl-3-(4-(4-(3-ethylmorpholino)-5,6,7,8-tetrahydropyrido[3,4-d]pyrimidin-2-yl)phenyl)urea with 2-chloropyrimidine: LC-MS: m/z=+489 (M+H)⁺.

Example 169

(gt)

Synthesis of (S)-tert-butyl 4-(3-ethylmorpholino)-2-(4-(3-(2-hydroxyethyl)ureido)phenyl)-5,6-dihydropyrido[3,4-d]pyrimidine-7(8H)-carboxylate (gt): Compound gt was synthesized using the general procedure described in Example 30 except that ethanolamine was used instead of cyclopropylmethylamine: LC-MS: m/z=+527 (M+H)⁺.

Example 170

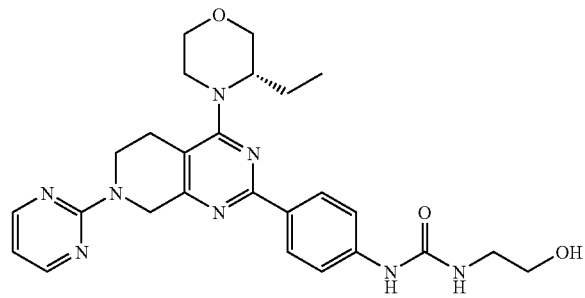
(gu)

Synthesis of (S)-1-(4-(4-(3-ethylmorpholino)-7-(pyrimidin-2-yl)-5,6,7,8-tetrahydropyrido[3,4-d]pyrimidin-2-yl)phenyl)-3-(2-hydroxyethyl)urea (gu): Compound gu was synthesized using the general procedure described in Example 30 except that ethanolamine was used instead of cyclopropylmethylamine: LC-MS: m/z=+505 (M+H)⁺.

Example 171

(gv)

Synthesis of (S)-1-(4-(4-(3-ethylmorpholino)-7-(pyrimidin-2-yl)-5,6,7,8-tetrahydropyrido[3,4-d]pyrimidin-2-yl)phenyl)-3-(isoxazol-3-yl)urea (gv): Compound gv was synthesized using the general procedure described in Example 30 except that isoxazol-3-amine was used instead of cyclopropylmethylamine: LC-MS: m/z=+528 (M+H)⁺.

Example 172

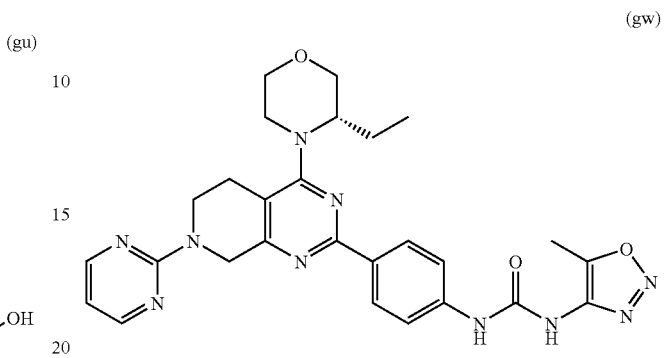
(gw)

Synthesis of (S)-1-(4-(4-(3-ethylmorpholino)-7-(pyrimidin-2-yl)-5,6,7,8-tetrahydropyrido[3,4-d]pyrimidin-2-yl)phenyl)-3-(5-methyl-1,2,3-oxadiazol-4-yl)urea (gw): Compound gw was synthesized using the general procedure described in Example 30 except that 5-methyl-1,2,3-oxadiazol-4-amine was used instead of cyclopropylmethylamine: LC-MS: m/z=+528 (M+H)⁻.

Example 173

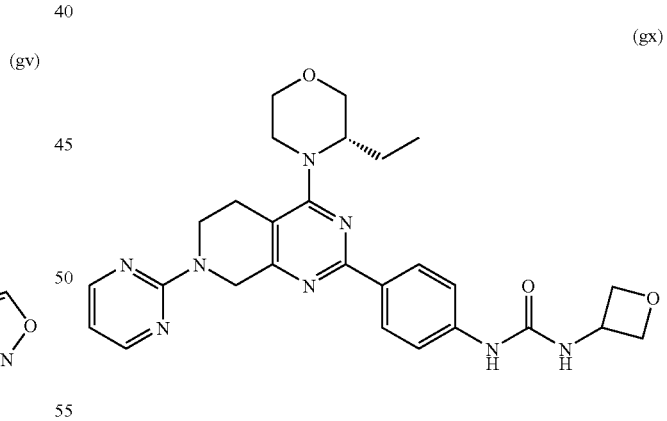
(gx)

Synthesis of (S)-1-(4-(4-(3-ethylmorpholino)-7-(pyrimidin-2-yl)-5,6,7,8-tetrahydropyrido[3,4-d]pyrimidin-2-yl)phenyl)-3-(oxetan-3-yl)urea (gx): Compound gx was synthesized using the general procedure described in Example 30 except that oxetan-3-amine was used instead of cyclopropylmethylamine: LC-MS: m/z=+517 (M+H)⁻.

Example 174

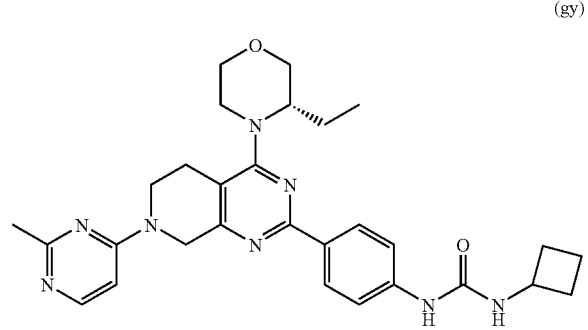

(gy)

Synthesis of (S)-1-cyclobutyl-3-(4-(4-(3-ethylmorpholino)-7-(2-methylpyrimidin-4-yl)-5,6,7,8-tetrahydropyrido[3,4-d]pyrimidin-2-yl)phenyl)urea (gy): Compound gy was synthesized using the general procedure described in Example 2 and Example 30 except that 4-chloro-2-methylpyrimidine was used instead of 2-chloropyrimidine in Example 2 and cyclobutanamine was used instead of cyclopropylmethylamine in Example 30: LC-MS: m/z=+529 (M+H)⁺.

Example 175

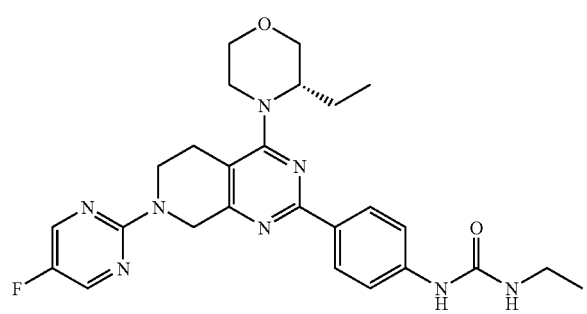

(gz)

Synthesis of (S)-1-ethyl-3-(4-(4-(3-ethylmorpholino)-7-(5-fluoropyrimidin-2-yl)-5,6,7,8-tetrahydropyrido[3,4-d]pyrimidin-2-yl)phenyl)urea (gz): Compound gz was synthesized using the general procedure described in Example 2 and Example 30 except that 2-chloro-5-fluoropyrimidine was used instead of 2-chloropyrimidine in Example 2 and ethylamine was used instead of cyclopropylmethylamine in Example 30: LC-MS: m/z=+507 (M+H)⁺.

Example 176

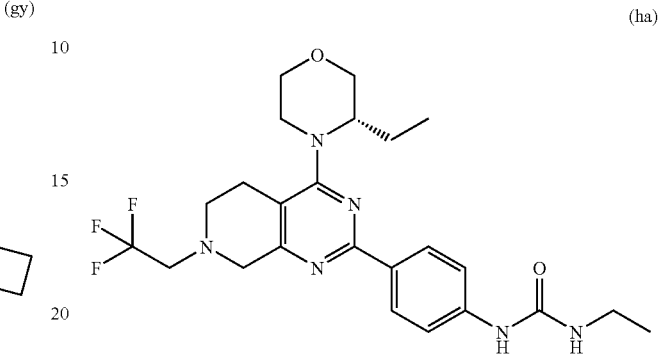

(ha)

Synthesis of (S)-1-ethyl-3-(4-(4-(3-ethylmorpholino)-7-(2,2,2-trifluoroethyl)-5,6,7,8-tetrahydropyrido[3,4-d]pyrimidin-2-yl)phenyl)urea (ha): Compound ha was synthesized using the general procedure described in Example 5 but by reacting (S)-1-ethyl-3-(4-(4-(3-ethylmorpholino)-5,6,7,8-tetrahydropyrido[3,4-d]pyrimidin-2-yl)phenyl)urea with 1,1,1-trifluoro-2-iodoethane instead of benzyl chloroformate: LC-MS: m/z=+493 (M+H)⁻.

Example 177

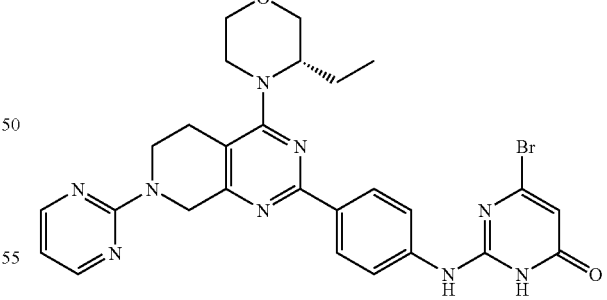

(hb)

Synthesis of (S)-6-bromo-2-(4-(4-(3-ethylmorpholino)-7-(pyrimidin-2-yl)-5,6,7,8-tetrahydropyrido[3,4-d]pyrimidin-2-yl)phenylamino)pyrimidin-4(3H)-one (hb): Compound hb was prepared using the general procedure described in Examples 2, 216 and 218: LC-MS: m/z=+591 (M+H)⁺.

Example 178

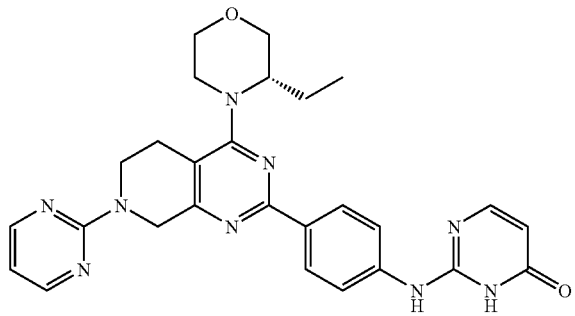

(hc)

Synthesis of (S)-2-(4-(4-(3-ethylmorpholino)-7-(pyrimidin-2-yl)-5,6,7,8-tetrahydropyrido[3,4-d]pyrimidin-2-yl)phenylamino)pyrimidin-4(3H)-one (hc): Compound hc was prepared using the general procedure described in Examples 2, 216 and 218: LC-MS: m/z=+512 (M+H)⁺.

Example 179

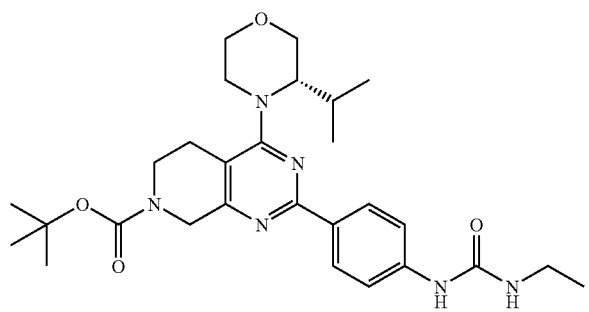

(hd)

Synthesis of (S)-tert-butyl 2-(4-(3-ethylureido)phenyl)-4-(3-isopropylmorpholino)-5,6-dihydropyrido[3,4-d]pyrimidine-7(8H)-carboxylate (hd): Compound hd was synthesized using the general procedure described in Example 65 but using (S)-3-isopropylmorpholine hydrobromide (ca) (see, Example 167) in step 1 of Example 65 instead of morpholine: LC-MS: m/z=+525 (M+H)⁻.

Example 180

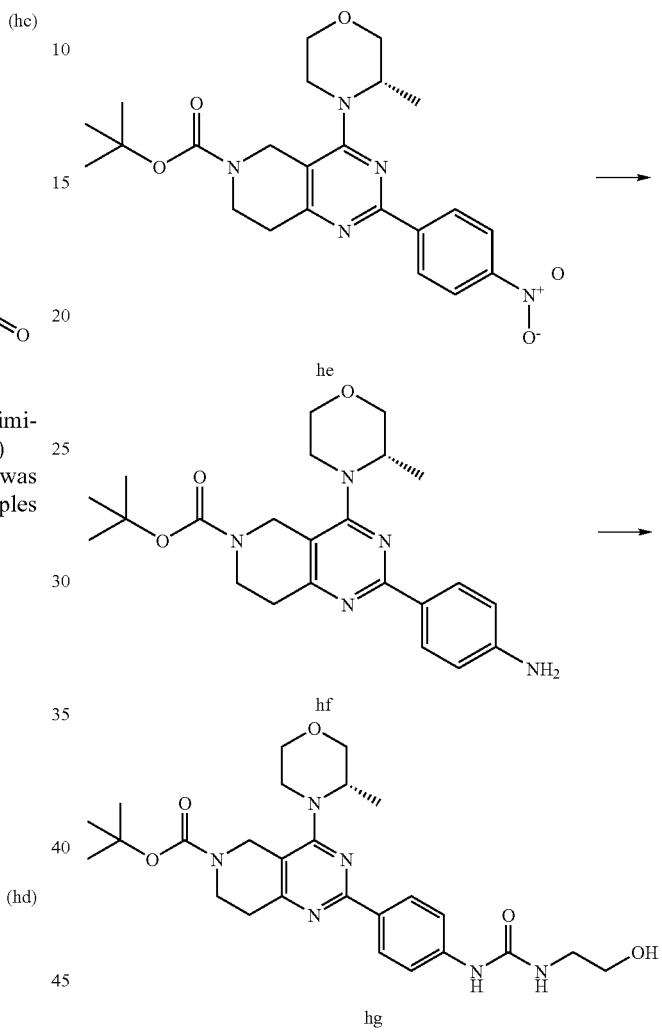

Synthesis of (S)-tert-butyl 2-(4-(3-(2-hydroxyethyl)ureido)phenyl)-4-(3-methylmorpholino)-7,8-dihydropyrido[4,3-d]pyrimidine-6(5H)-carboxylate (hg)

Step 1—(S)-tert-butyl 4-(3-methylmorpholino)-2-(4-nitrophenyl)-7,8-dihydropyrido[4,3-d]pyrimidine-6(5H)-carboxylate (he): Compound he was synthesized using the same procedure described in Example 1 except that 4-nitrophenyl boronic acid, pinacol ester was used instead of (4-ethylureido)phenylboronic acid pinacol ester in step 2 of Example 1.

Step 2—(S)-tert-butyl 2-(4-aminophenyl)-4-(3-methylmorpholino)-7,8-dihydropyrido[4,3-d]pyrimidine-6(5H)-carboxylate (hf): Compound hf was prepared using the general procedure described in step 2 of Example 29 except that (S)-tert-butyl 4-(3-methylmorpholino)-2-(4-nitrophenyl)-7,8-dihydropyrido[4,3-d]pyrimidine-6(5H)-carboxylate was used.

Step 3—(S)-tert-butyl 2-(4-(3-(2-hydroxyethyl)ureido)phenyl)-4-(3-methylmorpholino)-7,8-dihydropyrido[4,3-d]pyrimidine-6(5H)-carboxylate (hg): Compound hg was prepared using the general procedure in Example 30 except that ethanolamine was used instead of cyclopropylmethylamine: LC/MS: m/z=+513 (M+H)+.

Example 181

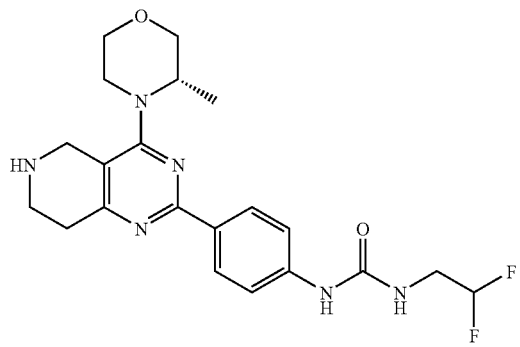

(hi)

Synthesis of (S)-1-(2,2-difluoroethyl)-3-(4-(4-(3-methylmorpholino)-5,6,7,8-tetrahydropyrido[4,3-d]pyrimidin-2-yl)phenyl)urea (hi): Compound hi was synthesized using the general procedure described in Example 30 except that 2,2-difluoroethylamine was used instead of cyclopropylmethylamine, and using the procedure described in step 3 of Example 1: LC-MS: m/z=+433 (M+H)+.

Example 182

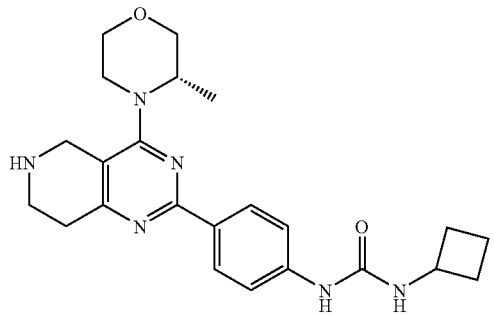

(hj)

Synthesis of (S)-1-cyclobutyl-3-(4-(4-(3-methylmorpholino)-5,6,7,8-tetrahydropyrido[4,3-d]pyrimidin-2-yl)phenyl)urea (hj): Compound hj was synthesized using the general procedure described in Example 30 except that cyclobutanamine was used instead of cyclopropylmethylamine, and using the procedure described in step 3 of Example 1: LC-MS: m/z=+423 (M+H)−.

Example 183

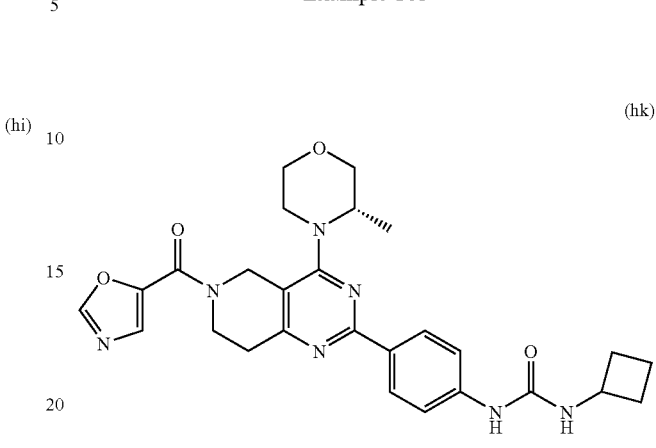

(hk)

Synthesis of (S)-1-cyclobutyl-3-(4-(4-(3-methylmorpholino)-6-(oxazole-5-carbonyl)-5,6,7,8-tetrahydropyrido[4,3-d]pyrimidin-2-yl)phenyl)urea (hk): Compound hk was synthesized using the general procedures outlined in Examples 1, 5, 27 and 30: LC-MS: m/z=+518 (M+H)+.

Example 184

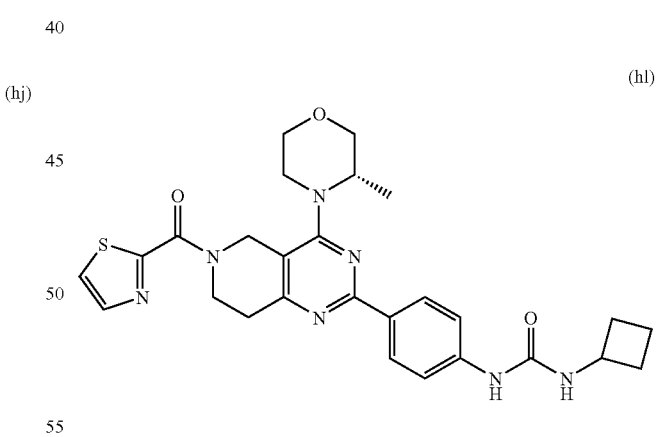

(hl)

Synthesis of (S)-1-cyclobutyl-3-(4-(4-(3-methylmorpholino)-6-(thiazole-2-carbonyl)-5,6,7,8-tetrahydropyrido[4,3-d]pyrimidin-2-yl)phenyl)urea (hl): Compound hl was Example 185

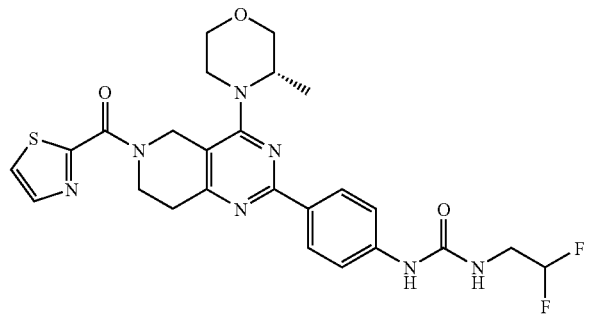

(hm)

Synthesis of (S)-1-(2,2-difluoroethyl)-3-(4-(4-(3-methylmorpholino)-6-(thiazole-2-carbonyl)-5,6,7,8-tetrahydropyrido[4,3-d]pyrimidin-2-yl)phenyl)urea (hm): Compound hm was synthesized using the general procedures outlined in Examples 1, 5, 27 and 30: LC-MS: m/z=+544 (M+H)$^+$.

Example 186

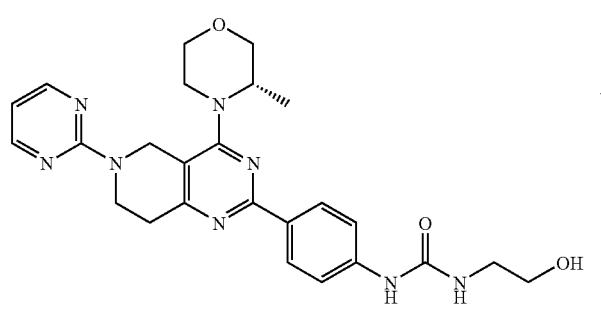

(hn)

Synthesis of (S)-1-(2-hydroxyethyl)-3-(4-(4-(3-methylmorpholino)-6-(pyrimidin-2-yl)-5,6,7,8-tetrahydropyrido[4,3-d]pyrimidin-2-yl)phenyl)urea (hn): Compound hn was synthesized using the general procedures outlined in Examples 1, 2, 27 and 30: LC-MS: m/z=+491 (M+H)$^+$.

Example 187

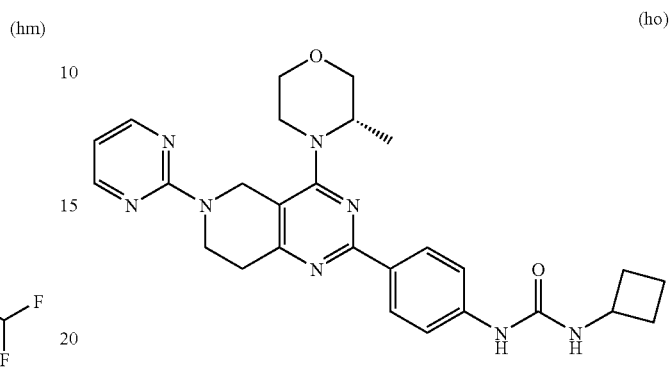

(ho)

Synthesis of (S)-1-cyclobutyl-3-(4-(4-(3-methylmorpholino)-6-(pyrimidin-2-yl)-5,6,7,8-tetrahydropyrido[4,3-d]pyrimidin-2-yl)phenyl)urea (ho): Compound ho was synthesized using the general procedures outlined in Examples 1, 2, 27 and 30: LC-MS: m/z=+501 (M+H)$^+$.

Example 188

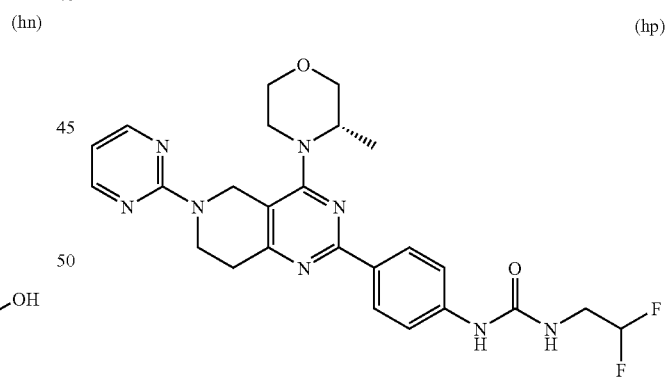

(hp)

Synthesis of (S)-1-(2,2-difluoroethyl)-3-(4-(4-(3-methylmorpholino)-6-(pyrimidin-2-yl)-5,6,7,8-tetrahydropyrido[4,3-d]pyrimidin-2-yl)phenyl)urea (hp): Compound hp was synthesized using the general procedures outlined in Examples 1, 2, 27 and 30: LC-MS: m/z=+511 (M+H)+.

Example 189

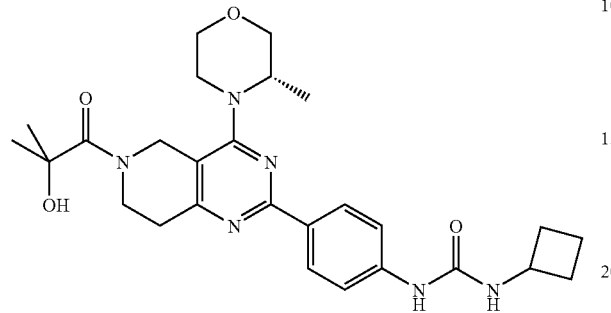

(hq)

Synthesis of (S)-1-cyclobutyl-3-(4-(6-(2-hydroxy-2-methylpropanoyl)-4-(3-methylmorpholino)-5,6,7,8-tetrahydropyrido[4,3-d]pyrimidin-2-yl)phenyl)urea (hq): Compound hq was prepared generally following the procedures described in Examples 1, 27 and 30 and 147 except that (S)-1-cyclobutyl-3-(4-(4-(3-methylmorpholino)-5,6,7,8-tetrahydropyrido[4,3-d]pyrimidin-2-yl)phenyl)urea was used instead of tert-butyl 2,4-dichloro-5H-pyrrolo[3,4-d]pyrimidine-6(7H)-carboxylate and 3S-3-methylmorpholine was used instead of morpholine in step 1 of Example 1. Additionally, 2-hydroxyisobutyric acid was used instead of oxazole-5-carboxylic acid in Example 147: LC/MS-m/z+509 (M+H)+.

Example 190

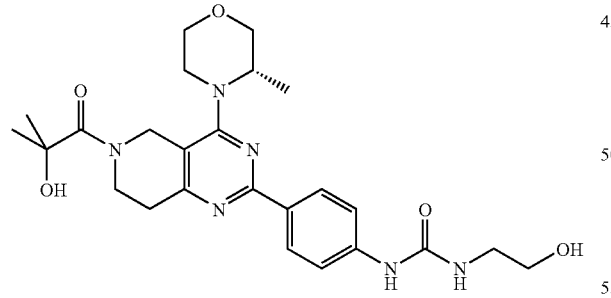

(hr)

Synthesis of (S)-1-(4-(6-(2-hydroxy-2-methylpropanoyl)-4-(3-methylmorpholino)-5,6,7,8-tetrahydropyrido[4,3-d]pyrimidin-2-yl)phenyl)-3-(2-hydroxyethyl)urea (hr): Compound hr was prepared generally following the procedures described in Examples 1, 27 and 30 and 147 except that (S)-1-(2-hydroxyethyl)-3-(4-(4-(3-methylmorpholino)-5,6,7,8-tetrahydropyrido[4,3-d]pyrimidin-2-yl)phenyl)urea was used instead of tert-butyl 2,4-dichloro-5H-pyrrolo[3,4-d]pyrimidine-6(7H)-carboxylate and 3S-3-methylmorpholine was used instead of morpholine in step 1 of Example 1. Additionally, 2-hydroxyisobutyric acid was used instead of oxazole-5-carboxylic acid in Example 147: LC/MS-m/z+499 (M+H)+.

Example 191

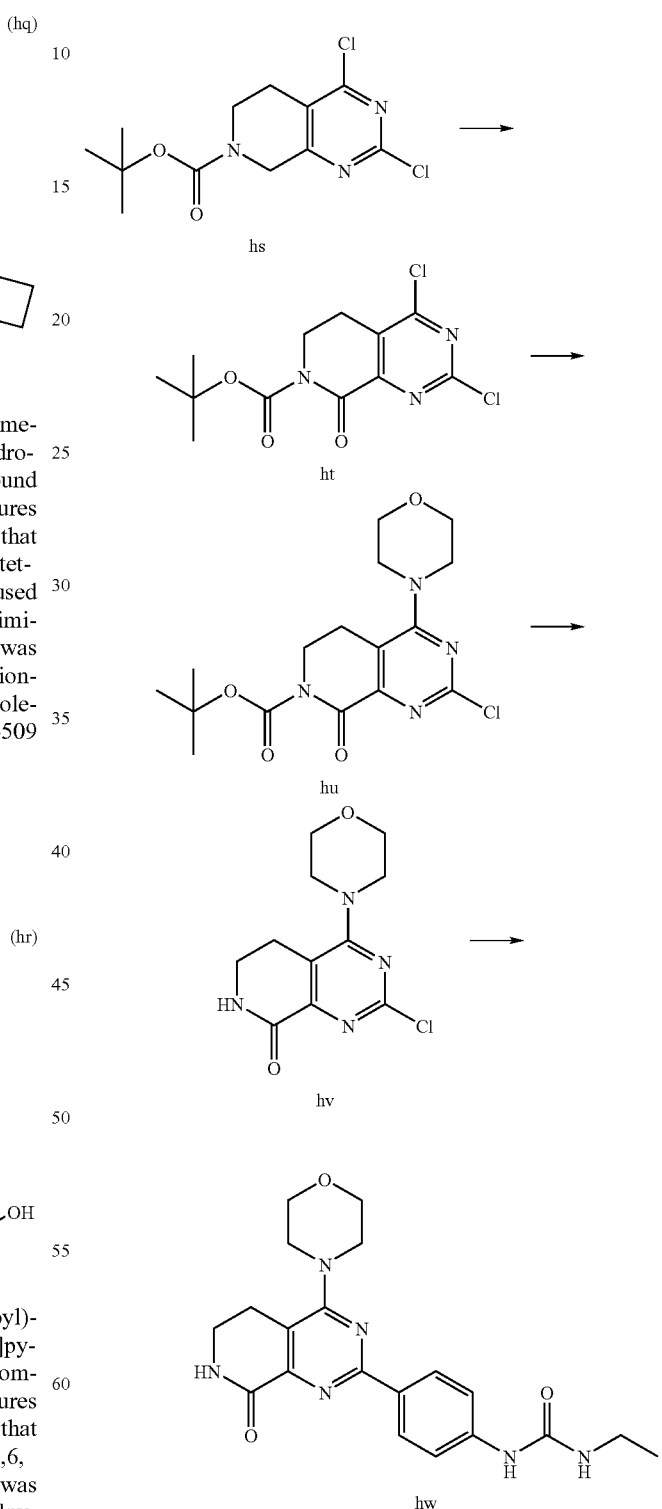

Synthesis of 1-ethyl-3-(4-(4-morpholino-8-oxo-5,6,7,8-tetrahydropyrido[3,4-d]pyrimidin-2-yl)phenyl)urea (hw)

Step 1—To tert-butyl 2,4-dichloro-8-oxo-5,6-dihydropyrido[3,4-d]pyrimidine-7(8H)-carboxylate (ht): t-butyl 2,4-dichloro-5,6-dihydropyrido-[3,4-d]pyrimidine-7(8H)-carboxylate (hs, 1.5 g, 4.9 mmol), dissolved in ethyl acetate (40 mL, 500 mmol), was added to a mixture of ruthenium tetroxide (1.0E2 mg, 0.64 mmol) and 0.47 M of Sodium periodate in Water (49 mL). The mixture was stirred vigorously at room temperature overnight. The reaction was then partitioned between water and EtOAc. The aqueous phase was extracted with EtOAc. The combined organic phases were dried with Magnesium sulfate, filtered, concentrated on silica gel and purified by flash chromatography (100% hex to 100% EtOAc) to give compound ht as a white solid: $^1$H NMR (400 MHz, CDCl$_3$) δ 4.14-4.00 (m, 1H), 3.16-3.05 (m, 1H), 1.57 (d, J=3.1 Hz, 5H); LC-MS: m/z=+319 (M+H)$^+$.

Step 2—tert-butyl 2-chloro-4-morpholino-8-oxo-5,6-dihydropyrido[3,4-d]pyrimidine-7(8H)-carboxylate (hu): tert-butyl 2,4-dichloro-8-oxo-5,6-dihydropyrido[3,4-d]pyrimidine-7(8H)-carboxylate (ht) (500 mg, 2 mmol) was dissolved in DMF (60 mL, 700 mmol), and to this solution was added N,N-diisopropylethylamine (550 uL, 3.1 mmol) was added, followed by Morpholine (160 uL, 1.9 mmol) in a single portion at 0° C. The resultant solution was stirred and permitted to warm to RT overnight. Water was added and the aqueous phase was extratcted with 2×50 mL of EtOAc. The combined organic phases were dried with Magnesium sulfate, filtered and concentrated to give a pale yellow solid: $^1$H NMR (400 MHz, CDCl$_3$) δ 3.93 (s, 2H), 3.86-3.74 (m, 4H), 3.65-3.55 (m, 3H), 2.83 (s, 2H), 1.56 (d, J=3.4 Hz, 12H); LC-MS: m/z=+370 (M+H)$^-$.

Step 3—2-chloro-4-morpholino-6,7-dihydropyrido[3,4-d]pyrimidin-8(5H)-one (hv): tert-butyl 2-chloro-4-morpholino-8-oxo-5,6-dihydropyrido[3,4-d]pyrimidine-7(8H)-carboxylate (hu) (310 mg, 0.84 mmol) was dissolved in 4 M of hydrogen chloride in 1,4-Dioxane (21 mL). The mixture was stirred at room temperature for 30 minutes then concentrated to provide the product as a white solid that was used without purification: LC-MS: m/z=+270 (M+H)$^+$.

Step 4—1-ethyl-3-(4-(4-morpholino-8-oxo-5,6,7,8-tetrahydropyrido[3,4-d]pyrimidin-2-yl)phenyl)urea (hw): 2-chloro-4-morpholino-6,7-dihydropyrido[3,4-d]pyrimidin-8(5H)-one (hv) (200 mg, 0.5 mmol), [4-Ethylureido)phenyl]boronic acid, pinacol ester (189 mg, 0.651 mmol) and Tetrakis(triphenylphosphine)palladium (63 mg, 0.054 mmol) were weighed into a microwave vial. Acetonitrile (1.2 mL), 1.00 M of Sodium carbonate in Water (0.6 mL) and 1.00 M of Potassium acetate in Water (0.6 mL) were added and the mixture heated to 110° C. for 15 min. Water was added and the aqueous phase was extracted with 2×20 mL of ethyl acetate. The combined organic phases were dried with Magnesium sulfate, filtered and concentrated and purified by reverse phase HPLC to provide compound hw: $^1$H NMR (400 MHz, DMSO) δ 8.70 (s, 1H), 8.28 (s, 1H), 8.22 (d, J=8.8 Hz, 2H), 7.50 (d, J=8.8 Hz, 2H), 6.22 (dd, J=11.9, 6.4 Hz, 1H), 3.81-3.68 (m, 4H), 3.56-3.43 (m, 4H), 3.20-3.04 (m, 2H), 2.81 (t, J=6.2 Hz, 2H), 1.06 (t, J=7.2 Hz, 3H); LC-MS: m/z=+397 (M+H)$^+$.

Example 192

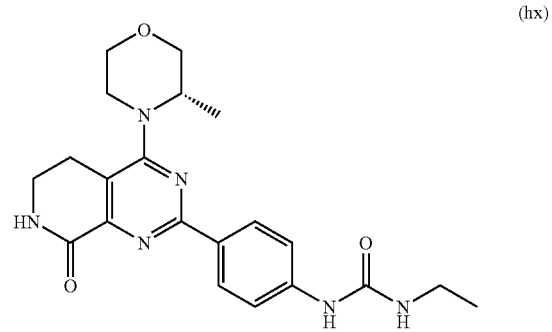

(S)-1-ethyl-3-(4-(4-(3-methylmorpholino)-8-oxo-5,6,7,8-tetrahydropyrido[3,4-d]pyrimidin-2-yl)phenyl)urea (hx): Compound hx was synthesized using the general procedures described in Example 191 except that 3S-3-methylmorpholine was used instead of morpholine in step 2: LC-MS: m/z=+411 (M+H)$^+$.

Example 193

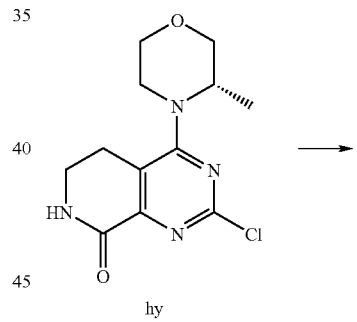

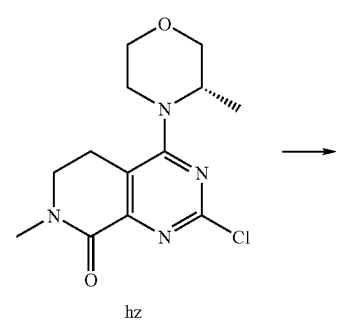

-continued

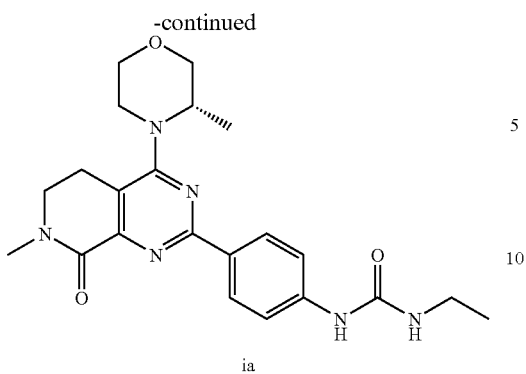

Synthesis of (S)-1-ethyl-3-(4-(7-methyl-4-(3-methylmorpholino)-8-oxo-5,6,7,8-tetrahydropyrido[3,4-d]pyrimidin-2-yl)phenyl)urea (ia)

Step 1—(S)-2-chloro-7-methyl-4-(3-methylmorpholino)-6,7-dihydropyrido[3,4-d]pyrimidin-8(5H)-one (hz): (S)-2-chloro-4-(3-methylmorpholino)-6,7-dihydropyrido[3,4-d]pyrimidin-8(5H)-one (hy) (80 mg, 0.2 mmol) was dissolved in N,N-dimethylformamide (2 mL) and to the reaction mixture was added cesium carbonate (100 mg, 0.4 mmol). The resultant mixture was stirred at 50° C. under an atmosphere of Nitrogen for 30 minutes then methyl iodide (16 uL, 0.26 mmol) was added and the reaction was stirred at 50° C. overnight. The reaction mixture was cooled to rt. Water was added ant the aqueous phase was extracted with 3×20 mL of DCM. The combined organic phases were dried with Magnesium sulfate, filtered and concentrated on silica gel. The crude product was purified by flash chromatography (100% DCM to 10% MeOH/DCM) to give compound hz: LC-MS: m/z=+384 (M+H)$^+$.

Step 2—(S)-1-ethyl-3-(4-(7-methyl-4-(3-methylmorpholino)-8-oxo-5,6,7,8-tetrahydropyrido[3,4-d]pyrimidin-2-yl)phenyl)urea (ia): Compound ia was prepared following a similar procedure as described in Step 2 of Example 1, with the exception that compound hz was used instead of tert-butyl 2-chloro-4-morpholino-5H-pyrrolo[3,4-d]pyrimidine-6(7H)-carboxylate (b). LC-MS: m/z=425 (M+H)+.

Example 194

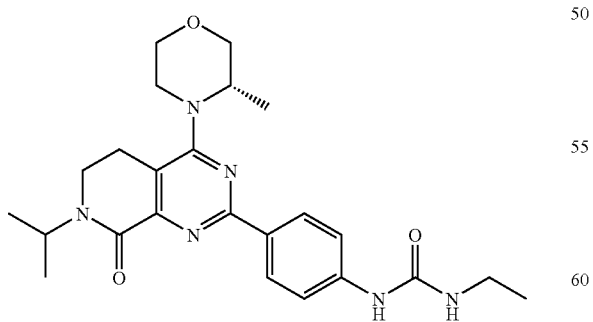

Synthesis of (S)-1-ethyl-3-(4-(7-isopropyl-4-(3-methylmorpholino)-8-oxo-5,6,7,8-tetrahydropyrido[3,4-d]pyrimidin-2-yl)phenyl)urea (ib): Compound ib was synthesized using the general procedure described in Example 193 except that 2-iodopropane was used instead of iodomethane in step 1: LC-MS: m/z=+453 (M+H)$^+$.

Example 195

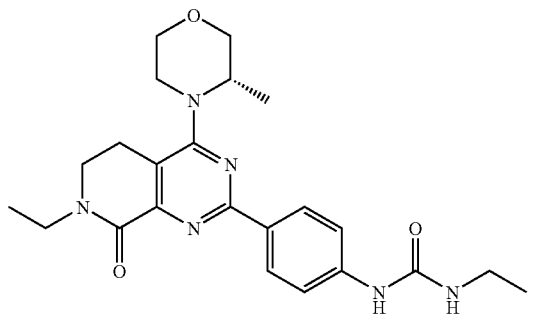

Synthesis of (S)-1-ethyl-3-(4-(7-ethyl-4-(3-methylmorpholino)-8-oxo-5,6,7,8-tetrahydropyrido[3,4-d]pyrimidin-2-yl)phenyl)urea (ic): Compound ic was synthesized using the general procedure described in Example 193 except that iodoethane was used instead of iodomethane in step 1: LC-MS: m/z=+439 (M+H)$^+$.

Example 196

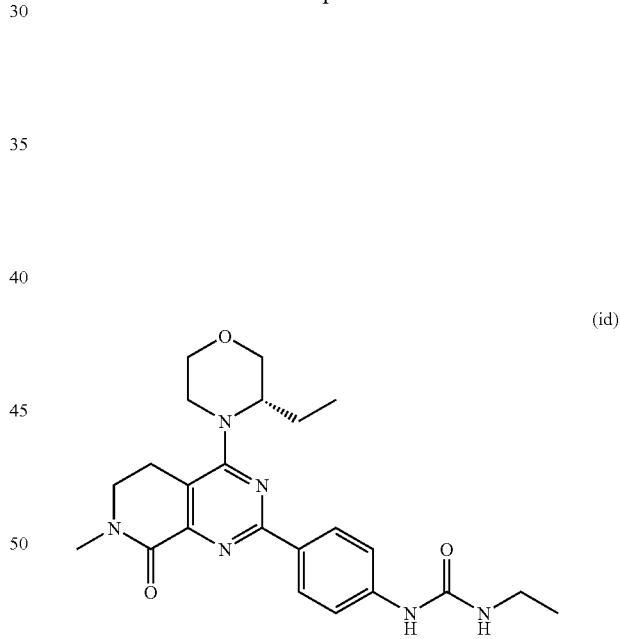

Synthesis of (S)-1-ethyl-3-(4-(4-(3-ethylmorpholino)-7-methyl-8-oxo-5,6,7,8-tetrahydropyrido[3,4-d]pyrimidin-2-yl)phenyl)urea (id): Compound id was synthesized using the general procedure described in Examples 191 and 193 except Example 197

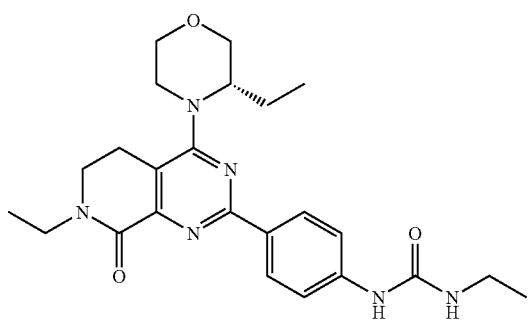

(ie)

Synthesis of (S)-1-ethyl-3-(4-(7-ethyl-4-(3-ethylmorpholino)-8-oxo-5,6,7,8-tetrahydropyrido[3,4-d]pyrimidin-2-yl)phenyl)urea (ie): Compound ie was synthesized using the general procedure described in Examples 191 and 193 except that 3S-3-ethylmorpholine was used instead of morpholine in step 2 of Example 193 and iodoethane was used instead of iodomethane in step 1 of Example 193: LC-MS: m/z=+453 (M+H)⁺.

Example 198

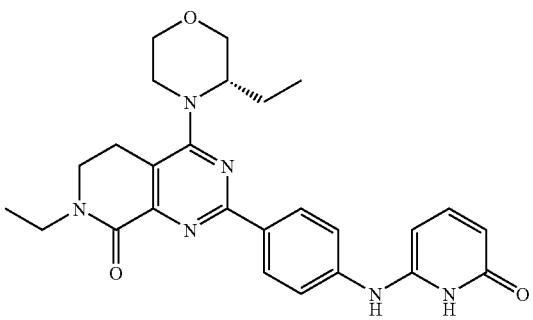

(if)

Synthesis of (S)-7-ethyl-4-(3-ethylmorpholino)-2-(4-(6-oxo-1,6-dihydropyridin-2-ylamino)phenyl)-6,7-dihydropyrido[3,4-d]pyrimidin-8(5H)-one (if): Compound if was synthesized using the general procedure described in Examples 191, 201 and 193 except that 3S-3-ethylmorpholine was used instead of morpholine in step 2 of Example 191 and iodoethane was used instead of iodomethane in step 1 of Example 193: LC-MS: m/z=+475 (M+H)⁺.

Example 199

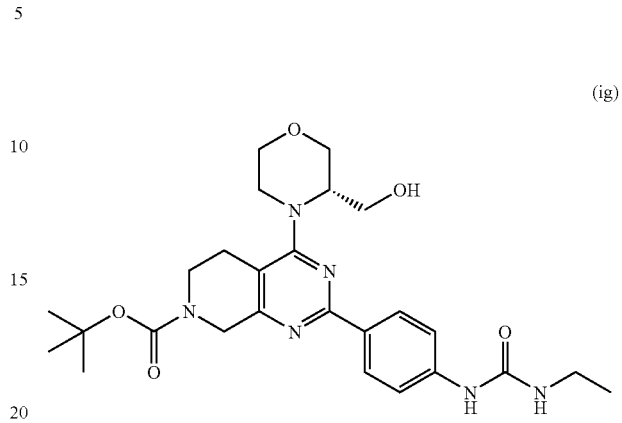

(ig)

Synthesis of (S)-tert-butyl 2-(4-(3-ethylureido)phenyl)-4-(3-(hydroxymethyl)morpholino)-5,6-dihydropyrido[3,4-d]pyrimidine-7(8H)-carboxylate (ig): Compound ig was synthesized using the general procedure described in Example 65 except that 3S-3-hydroxymethylmorpholine hydrochloride was used instead of 3S-3-methylmorpholine in step 1: LC-MS: m/z=+513 (M+H)⁺.

Example 200

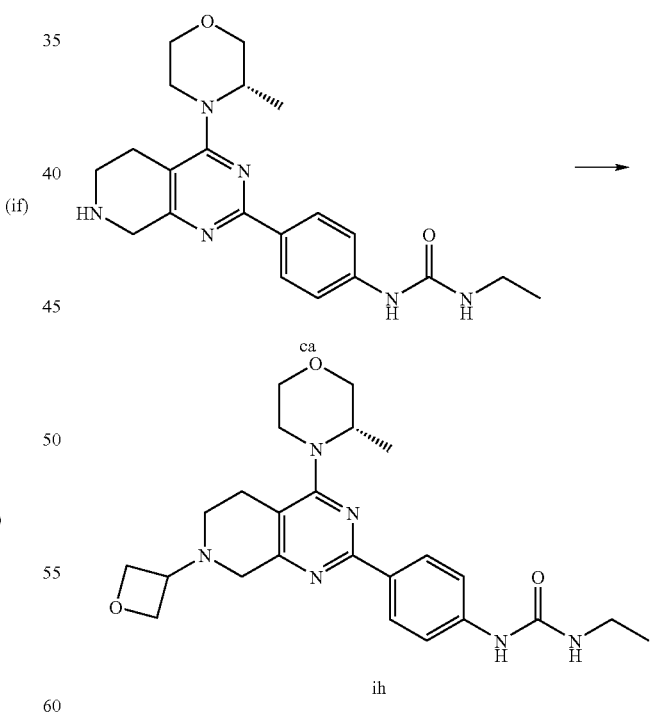

Synthesis of (S)-1-ethyl-3-(4-(4-(3-methylmorpholino)-7-(oxetan-3-yl)-5,6,7,8-tetrahydropyrido[3,4-d]pyrimidin-2-yl)phenyl)urea (ih): A mixture of (S)-1-ethyl-3-(4-(4-(3-methylmorpholino)-5,6,7,8-tetrahydropyrido[3,4-d]pyrimidin-2-yl)phenyl)urea (ca) (1.0 g, 2.5 mmol), 3-oxetanone (0.91 mL, 13 mmol) and sodium triacetoxyborohydride (1.7 g, 8.1 mmol) in 1,2-dichloroethane (25 mL, 320 mmol) was stirred at 70° C. under N₂ for 3 h. The mixture was then cooled down and poured in diluted NaHCO₃. The organic and aqueous phases were separated. The aqueous phase was extracted with 2×50 mL of DCM. The combined organic phases were dried with Magnesium sulfate, filtered and concentrated. The crude solid was purified by flash chromatography (100% DCM to 5% MeOH/DCM) to provide product ih as a pale yellow solid: ¹H NMR (400 MHz, DMSO) δ 8.61 (s, 1H), 8.15 (d, J=8.7 Hz, 2H), 7.46 (d, J=8.7 Hz, 2H), 6.15 (s, 1H), 4.64 (t, J=6.5 Hz, 2H), 4.55 (d, J=5.9 Hz, 2H), 4.13 (d, J=6.7 Hz, 1H), 3.87 (d, J=11.4 Hz, 1H), 3.62 (dd, J=34.1, 22.2 Hz, 6H), 3.43 (d, J=16.1 Hz, 2H), 3.20-3.04 (m, 2H), 2.69 (d, J=4.6 Hz, 3H), 1.24 (d, J=6.6 Hz, 3H), 1.06 (t, J=7.2 Hz, 3H); LC-MS: m/z=+453 (M+H)⁺.

Example 201

(ii)

Synthesis of 1-(4-(4-((1R,5S)-8-oxa-3-azabicyclo[3.2.1]octan-3-yl)-5,6,7,8-tetrahydropyrido[3,4-d]pyrimidin-2-yl)phenyl)-3-ethylurea (ii): Compound ii was synthesized using the general procedures described in Example 65 and 200 except that (1R,5S)-8-oxa-3-azabicyclo[3.2.1]octane hydrochloride was used instead of 3S-3-methylmorpholine in step 1 of Example 65: LC-MS: m/z=+465 (M+H)⁺.

Example 202

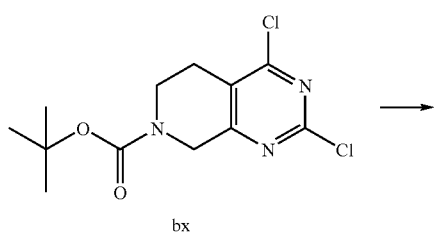

bx

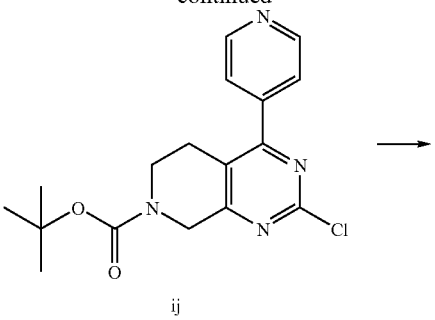

ij ik

Synthesis of tert-butyl 2-(4-(3-ethylureido)phenyl)-4-(pyridin-4-yl)-5,6-dihydropyrido[3,4-d]pyrimidine-7(8H)-carboxylate (ik)

Step 1—tert-butyl 2-chloro-4-(pyridin-4-yl)-5,6-dihydropyrido[3,4-d]pyrimidine-7(8H)-carboxylate (ij): 4-(Tributylstannyl)pyridine (247 mg, 0.671 mmol), t-butyl 2,4-dichloro-5,6-dihydropyrido-[3,4-d]pyrimidine-7(8H)-carboxylate (bx) (200 mg, 0.6 mmol) and tetrakis(triphenylphosphine) palladium(0) (76 mg, 0.066 mmol) were dissolved in 1,4-Dioxane (7 mL). The reaction was microwaved at 130° C. for 20 minutes The reaction mixture was concentrated on silica gel and purified by flash chromatography (100% Hex to 80% EtOAc/Hex) to give compound ij as a white solid: LC/MS: m/z=+347.8 (M+H)⁺.

Step 2—tert-butyl 2-(4-(3-ethylureido)phenyl)-4-(pyridin-4-yl)-5,6-dihydropyrido[3,4-d]pyrimidine-7(8H)-carboxylate (ik): Tert-butyl 2-chloro-4-(pyridin-4-yl)-5,6-dihydropyrido[3,4-d]pyrimidine-7(8H)-carboxylate (ij) (77 mg, 0.22 mmol), [4-ethylureido)phenyl]boronic acid, pinacol ester (77 mg, 0.26 mmol) and tetrakis(triphenylphosphine) palladium(0) (26 mg, 0.022 mmol) were weighed into a microwave vial. Acetonitrile (0.5 mL), 1.00 M of Sodium carbonate in Water (0.2 mL) and 1.00 M of Potassium acetate in Water (0.2 mL) were added to the reaction vial and the mixture was heated to 110° C. for 15 min. The resultant mixture was diluted with 15 ml of water and extracted with EtOAc (3×15 ml). The combined organic layers were dried with Magnesium sulfate, filtered, concentrated onto silica gel and purified by flash chromatography (100% DCM to 15% MeOH/DCM) to give compound ik as a yellow solid: ¹H NMR (400 MHz, DMSO) δ 8.76 (dd, J=4.4, 1.6 Hz, 2H), 8.72 (s, 1H), 8.27 (d, J=8.8 Hz, 2H), 7.74 (dd, J=4.4, 1.6 Hz, 2H), 7.53 (d, J=8.8 Hz, 2H), 6.18 (t, J=5.6 Hz, 1H), 4.66 (s, 2H), 3.58 (s, 2H), 3.12 (s, 2H), 2.85 (s, 2H), 1.06 (t, J=7.2 Hz, 3H); LCMS: m/z=+475 (M+H)⁺.

Example 203

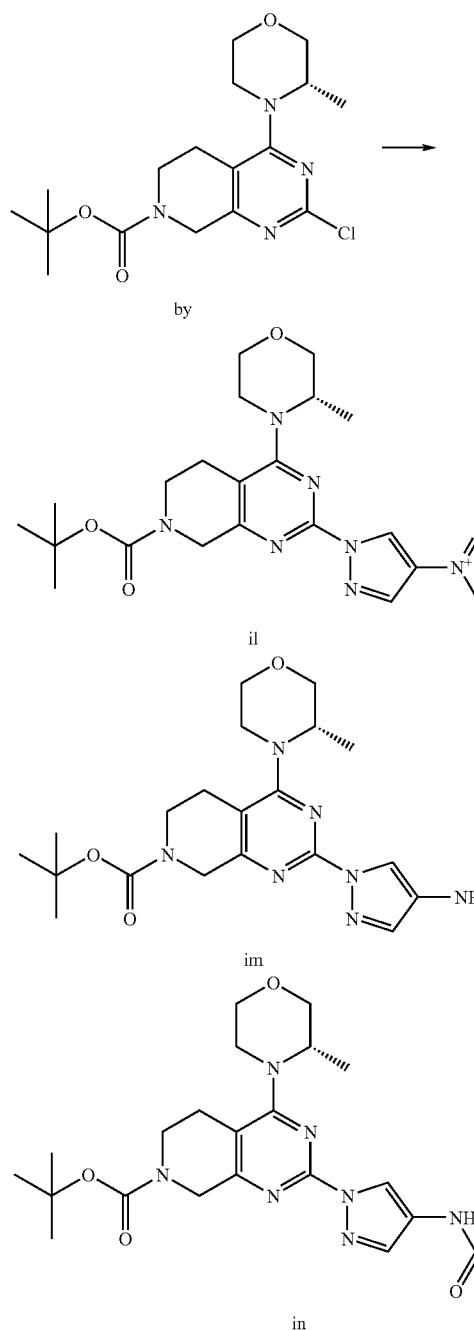

Synthesis of (S)-tert-butyl 2-(4-(3-ethylureido)-1H-pyrazol-1-yl)-4-(3-methylmorpholino)-5,6-dihydropyrido[3,4-d]pyrimidine-7(8H)-carboxylate (in)

Step 1—(S)-tert-butyl 4-(3-methylmorpholino)-2-(4-nitro-1H-pyrazol-1-yl)-5,6-dihydropyrido[3,4-d]pyrimidine-7(8H)-carboxylate (il): (S)-tert-butyl 2-chloro-4-(3-methylmorpholino)-5,6-dihydropyrido[3,4-d]pyrimidine-7(8H)-carboxylate (by) (150 mg, 0.41 mmol) and 4-nitro-1H-pyrazole (69 mg, 0.61 mmol) were dissolved in toluene (2.0 mL). To this mixture was added potassium carbonate (110 mg, 0.81 mmol). The resultant mixture was heated at 140° C. for 20 min in the microwave, and then quenched with the addition of Water. The precipitated solid was collected by filtration, washed with water and dried overnight under vacuum to give compound il as a white solid that was used for next step without purification: LCMS: m/z=+446 (M+H)⁺.

Step 2—(S)-tert-butyl 2-(4-amino-1H-pyrazol-1-yl)-4-(3-methylmorpholino)-5,6-dihydropyrido[3,4-d]pyrimidine-7(8H)-carboxylate (im): A microwave vial was charged with (S)-tert-butyl-4-(3-methylmorpholino)-2-(4-nitro-1H-pyrazol-1-yl)-5,6-dihydropyrido[3,4-d]pyrimidine-7(8H)-carboxylate (il) (150 mg, 0.34 mmol), iron (188 mg, 3.37 mmol), ammonium chloride (72.0 mg, 1.35 mmol) in ethanol (0.3 mL) and water (1.0 mL). The mixture was heated at 80° C. for 10 minutes. The mixture was poured on saturated NaHCO₃ and the aqueous phase was extracted with DCM (2×20 mL). The combined organic phases were dried with Magnesium sulfate, filtered and concentrated to give the desired compound im as a pale yellow solid that was used for next step without purification: LCMS: m/z=+416 (M+H)⁺.

Step 3—(S)-tert-butyl 2-(4-(3-ethylureido)-1H-pyrazol-1-yl)-4-(3-methylmorpholino)-5,6-dihydropyrido[3,4-d]pyrimidine-7(8H)-carboxylate (in): (S)-tert-butyl 2-(4-amino-1H-pyrazol-1-yl)-4-(3-methylmorpholino)-5,6-dihydropyrido[3,4-d]pyrimidine-7(8H)-carboxylate (im) (125 mg, 0.301 mmol) and ethyl isocyanate (140 uL, 1.8 mmol) were dissolved in N,N-Dimethylformamide (3 mL) and the mixture was stirred at 75° C. for 1 h. The crude product was purified by reverse phase HPLC to give compound "in" as a white solid: ¹H NMR (400 MHz, DMSO) δ 8.47 (s, 1H), 8.37 (s, 1H), 7.66 (s, 1H), 6.18 (t, J=5.4 Hz, 1H), 4.43 (q, J=18.5 Hz, 2H), 4.18 (s, 1H), 3.87 (d, J=11.1 Hz, 1H), 3.77-3.50 (m, 6H), 3.51-3.36 (m, 3H), 3.18-3.01 (m, 2H), 2.66 (d, J=4.0 Hz, 2H), 1.27 (d, J=6.6 Hz, 4H), 1.04 (s, 3H); LCMS: m/z=+487 (M+H)⁺.

Example 204

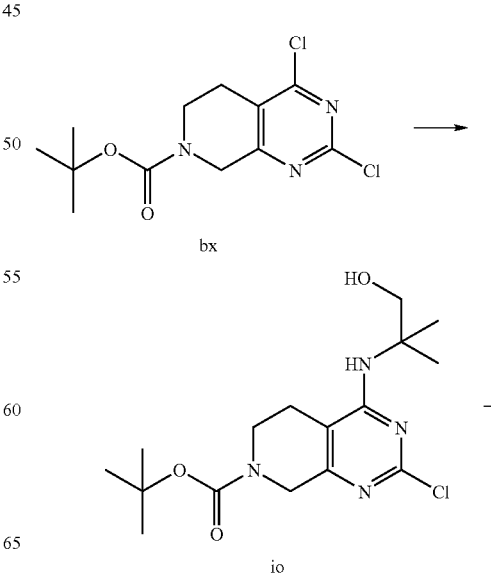

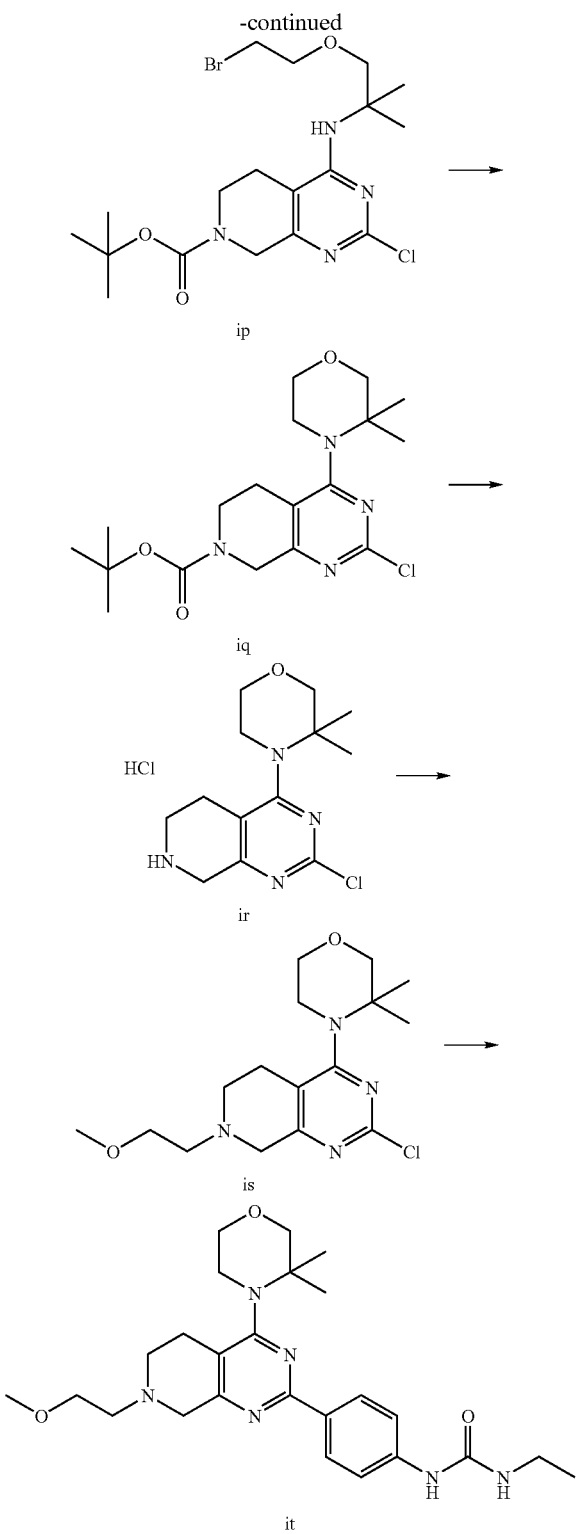

Synthesis of Compound it:

Step 1—tert-butyl 2-chloro-4-(1-hydroxy-2-methylpropan-2-ylamino)-5,6-dihydropyrido[3,4-d]pyrimidine-7(8H)-carboxylate (io): t-butyl 2,4-dichloro-5,6-dihydropyrido-[3,4-d]pyrimidine-7(8H)-carboxylate (bx) (2.0 g, 6.6 mmol) was dissolved in N,N-Dimethylformamide (40 mL). N,N-Diisopropylethylamine (2.3 mL, 13 mmol) was added, followed by 2-Amino-2-methyl-1-propanol (530 uL, 9.9 mmol). The mixture was stirred at room temperature overnight. To the reaction mixture was added water, and the aqueous phase was extracted with 2×20 mL of DCM. The combined organic phases were dried with Magnesium sulfate, filtered and concentrated on silica gel. Purification by flash chromatography (100% Heptane to 100% EtOAc) gave compound io as a yellow solid: $^1$H NMR (400 MHz, CDCl$_3$) δ 8.02 (s, 1H), 4.42 (d, J=11.6 Hz, 2H), 3.71 (t, J=5.9 Hz, 3H), 2.92 (d, J=29.0 Hz, 6H), 1.47 (dd, J=17.8, 11.7 Hz, 12H); LCMS: m/z=+357.8 (M+H)$^+$.

Step 2—tert-butyl 4-(1-(2-bromoethoxy)-2-methylpropan-2-ylamino)-2-chloro-5,6-dihydropyrido[3,4-d]pyrimidine-7(8H)-carboxylate (ip): tert-butyl 2-chloro-4-(1-hydroxy-2-methylpropan-2-ylamino)-5,6-dihydropyrido[3,4-d]pyrimidine-7(8H)-carboxylate (io) (1.1 g, 3.1 mmol) was dissolved in DCM and to the reaction mixture was added NaH in oil (6:4, Sodium hydride:Mineral Oil, 925 mg) at 0° C. The resultant mixture was stirred for 5 minutes at 0° C., then (2-bromoethyl)diphenylsulfonium trifluoromethanesulfonate (5.1 g, 12 mmol) was added thereto. The reaction was stirred at 0° C. for 2 h and then warm up to room temperature and stirred at room temperature for 2 h and then to reflux for 6 h. The reaction mixture was cooled and quenched with saturated ammonium chloride. The phases were separated. The aqueous phase was extracted with DCM. The combined organic phases were dried with Magnesium sulfate, filtered and concentrated on silica gel, and purified by flash chromatography (100% Hep to 70% EtOAc/Hep) gave compound ip as a white solid: $^1$H NMR (400 MHz, CDCl$_3$) δ 4.41 (s, 2H), 3.81 (t, J=5.6 Hz, 2H), 3.68 (t, J=5.6 Hz, 2H), 3.57 (s, 2H), 3.49 (t, J=5.5 Hz, 2H), 2.38 (t, J=5.4 Hz, 2H), 1.59-1.42 (m, 15H); LCMS: m/z=+364.8 (M+H)$^+$.

Step 3—tert-butyl 2-chloro-4-(3,3-dimethylmorpholino)-5,6-dihydropyrido[3,4-d]pyrimidine-7(8H)-carboxylate (iq): Tert-butyl 4-(1-(2-bromoethoxy)-2-methylpropan-2-ylamino)-2-chloro-5,6-dihydropyrido[3,4-d]pyrimidine-7(8H)-carboxylate (ip) (680 mg, 1.5 mmol) was dissolved in N-methylpyrrolidinone (2 mL) and Sodium iodide (22 mg, 0.15 mmol) was added. The reaction mixture was stirred for 5 min then to it was added NaH in Oil (6:4, Sodium hydride:Mineral Oil, 120 mg). The resultant mixture was stirred at 90° C. for 4 h then cooled down to r.t. Water was added to the reaction mixture and the aqueous phase was extracted with 2×25 mL of DCM. The combined organic phases were dried with Magnesium sulfate, filtered, concentrated on silica gel, and purified by flash chromatography (100% Hep to 100% EtOAc) to provide compound iq as a white solid: LCMS: m/z=+383.8 (M+H)$^+$.

Step 4—4-(2-chloro-5,6,7,8-tetrahydropyrido[3,4-d]pyrimidin-4-yl)-3,3-dimethylmorpholine hydrochloride (ir): tert-butyl 2-chloro-4-(3,3-dimethylmorpholino)-5,6-dihydropyrido[3,4-d]pyrimidine-7(8H)-carboxylate (iq) (230 mg, 0.60 mmol) was dissolved in 4 M of Hydrogen chloride in 1,4-Dioxane (7.51 mL) and the solution was stirred at room temperature for 30 min. The solution was then concentrated to give compound ir as a yellow solid that was used without purification: LCMS: m/z=+283.8 (M+H)$^+$.

Step 5—4-(2-chloro-7-(2-methoxyethyl)-5,6,7,8-tetrahydropyrido[3,4-d]pyrimidin-4-yl)-3,3-dimethylmorpholine (is): 4-(2-chloro-5,6,7,8-tetrahydropyrido[3,4-d]pyrimidin-4-yl)-3,3-dimethylmorpholine hydrochloride (ir) (238 mg, 0.746 mmol) was dissolved in N-methylpyrrolidinone (1.5 mL, 15 mmol) and N,N-Diisopropylethylamine (390 uL, 2.2 mmol) was added, followed by ethane, 1-bromo-2-methoxy (1.40E2 uL, 1.49 mmol). The reaction mixture was stirred at 65° C. overnight then cooled down to r.t. Water was added to the reaction solution and the aqueous phase was extracted with 3×20 mL of DCM. The combined organic phases were dried with Magnesium sulfate, filtered and concentrated to give compound "is" that was used without purification: LCMS: m/z=+341.8 (M+H)$^+$.

Step 6—1-(4-(4-(3,3-dimethylmorpholino)-7-(2-methoxyethyl)-5,6,7,8-tetrahydropyrido[3,4-d]pyrimidin-2-yl)phenyl)-3-ethylurea (it): 4-(2-chloro-7-(2-methoxyethyl)-5,6,7,8-tetrahydropyrido[3,4-d]pyrimidin-4-yl)-3,3-dimethylmorpholine (is) (200 mg, 0.6 mmol), [4-ethylureido)phenyl]boronic acid, pinacol ester (2.0E2 mg, 0.70 mmol) and Tetrakis(triphenylphosphine)palladium(0) (68 mg, 0.059 mmol) were weighed into a microwave vial. To the reaction vial was added Acetonitrile (1 mL), 1.00 M of Sodium carbonate in Water (0.6 mL) and 1.00 M of Potassium acetate in Water (0.6 mL), and the resultant the mixture was heated to 110° C. for 15 min. The reaction mixture was quenched with Water and the aqueous phase was extracted with 2×20 mL of DCM. The combined organic phases were dried with Magnesium sulfate, filtered and concentrated on silica gel. Purification by flash chromatography (100% DCM to 10% MeOH/DCM) gave compound "it" as a white solid: $^1$H NMR (400 MHz, DMSO) δ 8.63 (s, 1H), 8.15 (d, J=8.7 Hz, 2 H), 7.50 (d, J=8.7 Hz, 2H), 6.18 (s, 1H), 3.73 (d, J=4.2 Hz, 2H), 3.63 (s, 2H), 3.54 (t, J=5.6 Hz, 2H), 3.12 (t, J=6.2 Hz, 4H), 2.81-2.55 (m, 6H), 1.45 (s, 6H), 1.06 (t, J=7.2 Hz, 3H); LCMS: m/z=+469 (M+H)$^+$.

Example 205

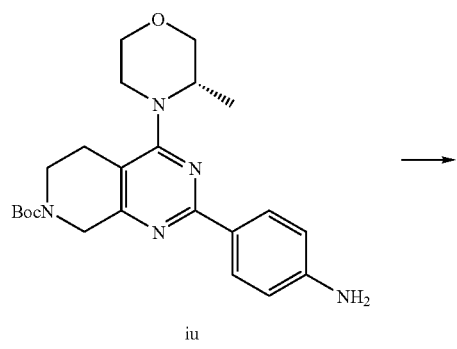

iu

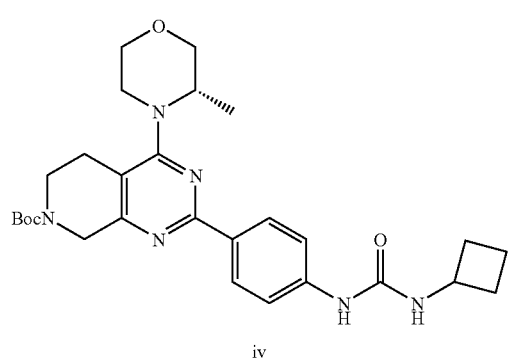

iv

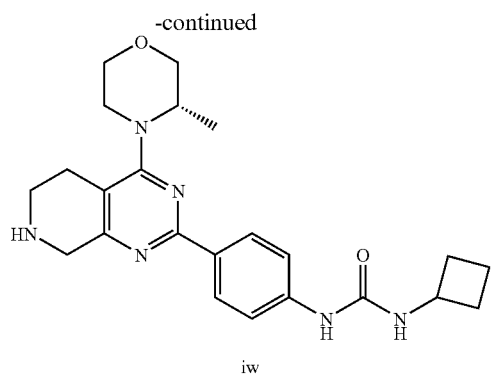

iw

Synthesis of Compound iw:

Step 1—(S)-tert-butyl 2-(4-(3-cyclobutylureido)phenyl)-4-(3-methylmorpholino)-5,6-dihydropyrido[3,4-d]pyrimidine-7(8H)-carboxylate (iv): The title compound was prepared by the procedure of Example 30 substituting (S)-tert-butyl 2-(4-aminophenyl)-4-(3-methylmorpholino)-5,6-dihydropyrido[3,4-d]pyrimidine-7(8H)-carboxylate (iu) for 4-(4-morpholino-6-(pyrimidin-2-yl)-5,6,7,8-tetrahydropyrido[4,3-d]pyrimidin-2-yl)aniline and substituting cyclobutyl amine for cyclopropylmethylamine amine in Example 30. LC-MS: m/z=+524 (M+H)+.

Step 2—Synthesis of (S)-1-cyclobutyl-3-(4-(4-(3-methylmorpholino)-5,6,7,8-tetrahydropyrido[3,4-d]pyrimidin-2-yl)phenyl)urea (iw). The title compound iw was prepared by the procedure of step 3 in Example 1. LC-MS: m/z=+424 (M+H)+.

Example 206

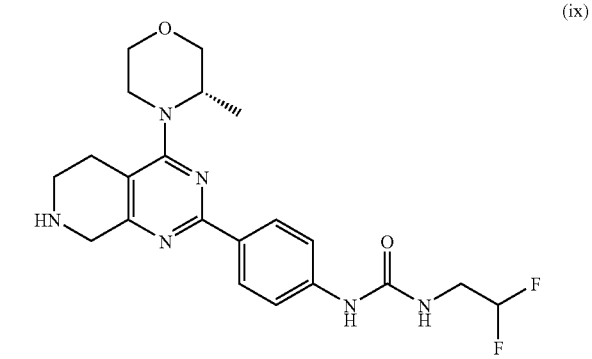

(ix)

Synthesis of (S)-1-(2,2-difluoroethyl)-3-(4-(4-(3-methylmorpholino)-5,6,7,8-tetrahydropyrido[3,4-d]pyrimidin-2-yl)phenyl)urea (ix): Compound ix was prepared by the pro-

Example 207

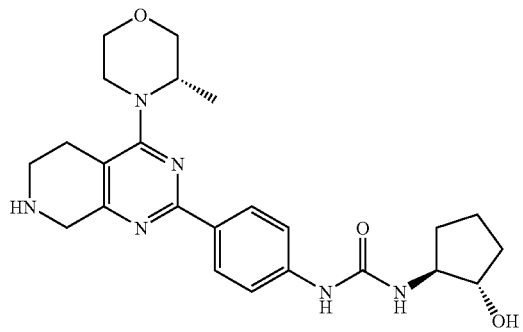

(iy)

Synthesis of 1-((1S,2S)-2-hydroxycyclopentyl)-3-(4-(4-((S)-3-methylmorpholino)-5,6,7,8-tetrahydropyrido[3,4-d]pyrimidin-2-yl)phenyl)urea (iy): Compound iy was prepared by the procedure of Example 205 substituting (1S,2S)-2-aminocyclopentanol for cyclobutyl amine. LC-MS: m/z=+433 (M+H)+.

cedure of Example 205 substituting difluoroethyl amine for cyclobutyl amine. LC-MS: m/z=+433 (M+H)+.

Example 208

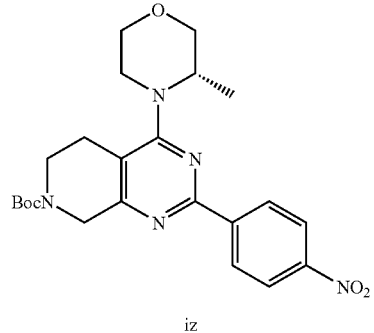

iz

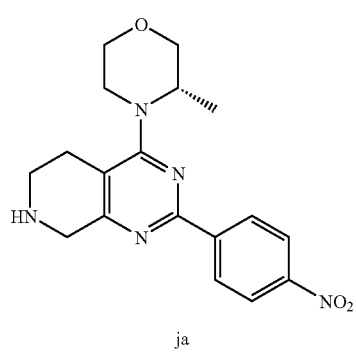

ja

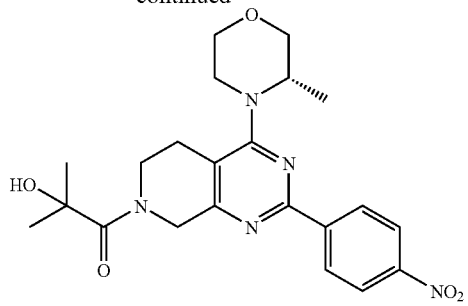

jb

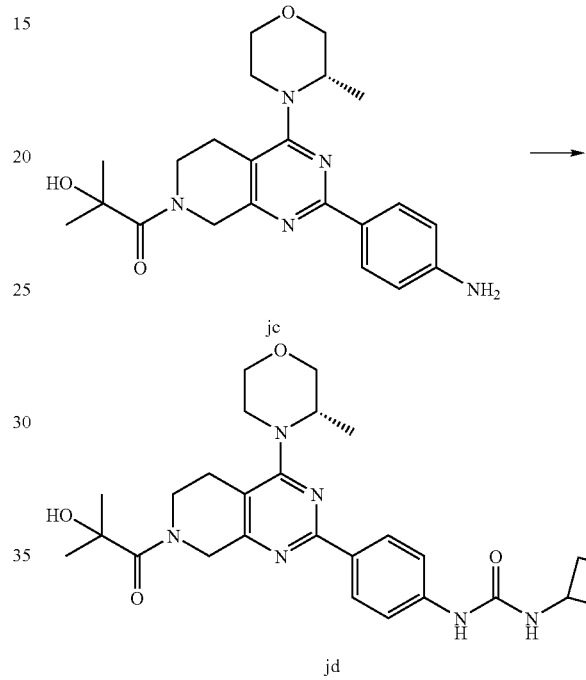

jc jd

Synthesis of Compound jd:

Step 1—Synthesis of (S)-tert-butyl 4-(3-methylmorpholino)-2-(4-nitrophenyl)-5,6-dihydropyrido[3,4-d]pyrimidine-7(8H)-carboxylate (iz): The title compound iz was prepared by the general procedure in Example 1, except that 4-nitrophenyl boronic acid, pinacol ester was used instead of (4-ethylureido)phenylboronic acid pinacol ester in step 2 of Example 1. LC-MS: m/z=+456.

Step 2—Synthesis of (S)-3-methyl-4-(2-(4-nitrophenyl)-5,6,7,8-tetrahydropyrido[3,4-d]pyrimidin-4-yl)morpholine hydrochloride (ja): A solution of HCl in dioxane (4.0 M, 50 mL) was added to compound iz (3.30 g, 7.24 mmol), and the mixture stirred for 2 h. To the reaction solution was added Ether (100 mL) and the precipitate was collected by filtration, rinsed with ether, and dried under high vacuum to afford 2.74 g (90%) of the title compound ja as a colorless solid: $^1$H NMR (400 MHz, MeOD) δ 8.67-8.49 (m, 2H), 8.41-8.24 (m, 2H), 4.48-4.32 (m, 3H), 4.00 (d, J=11.0 Hz, 1H), 3.96-3.68 (m, 5H), 3.59-3.41 (m, 2H), 3.13-2.90 (m, 2H), 1.42 (t, J=15.2 Hz, 3H); LC-MS: m/z=+356.

Step 3—Synthesis of (S)-2-hydroxy-2-methyl-1-(4-(3-methylmorpholino)-2-(4-nitrophenyl)-5,6-dihydropyrido[3,4-d]pyrimidin-7(8H)-yl)propan-1-one (jb): The product ja from Step 2 (212 mg, 0.54 mmol) was treated with 2-hydroxy isobutryic acid (112 mg, 1.08 mmol), HOBT (150 mg, 1.08 mmol), EDC (210 mg, 1.08 mmol), and DIPEA (0.47 mL, 2.7 mmol) in DMF (4.0 mL) for 18 h. The mixture was concentrated under reduced pressure and the residue diluted with ethyl acetate (30 mL) and washed with 1 N NaOH (3×10 mL). The combined aqueous phases were extracted with ethyl acetate (1×10 mL). The combined organic phases were washed with saturated NH$_4$Cl (3×5 mL). The combined aqueous phases were extracted with ethyl acetate (1×5 mL). The combined organic phases were dried with Na$_2$SO$_4$, filtered and concentrated to afford 266 mg (94%) of the title compound jb as an oil: $^1$H NMR (400 MHz, CDCl$_3$) δ 8.55 (d, J=8.9 Hz, 2H), 8.29 (d, J=8.9 Hz, 2H), 4.97 (d, J=18.6 Hz, 1H), 4.81 (d, J=17.0 Hz, 1H), 4.05-3.91 (m, 2H), 3.88-3.48 (m, 8 H), 2.85-2.64 (m, 2H), 1.69-1.50 (m, 11H), 1.37 (d, J=9.2 Hz, 3H); LC-MS: m/z=+442.

Step 4—Synthesis of (S)-1-(2-(4-aminophenyl)-4-(3-methylmorpholino)-5,6-dihydropyrido[3,4-d]pyrimidin-7(8H)-yl)-2-hydroxy-2-methylpropan-1-one (jc). A mixture of the product jb from Step 3 (210 mg, 0.46 mmol), 10% palladium on carbon (50 mg), and methanol (15 mL) in a flask was evacuated under vacuum and backfilled with H$_2$ (3×), and then stirred vigorously under 1 atm of H$_2$ for 3 h. The mixture was filtered through a 0.45 μM filter, then concentrated to afford 194 mg of the title compound jc with 90% purity (90% yield), which was used directly in the next step without purification. LC-MS: m/z=+426.

Step 5—Synthesis of (S)-1-cyclobutyl-3-(4-(7-(2-hydroxy-2-methylpropanoyl)-4-(3-methylmorpholino)-5,6,7,8-tetrahydropyrido[3,4-d]pyrimidin-2-yl)phenyl)urea (jd). The compound jd was prepared following the general procedure of Example 30, substituting the product of step 4 (compound jc) for 4-(4-morpholino-6-(pyrimidin-2-yl)-5,6,7,8-tetrahydropyrido[4,3-d]pyrimidin-2-yl)aniline, and cyclobutyl amine for cyclopropylmethylamine. LC-MS: m/z=+510.

Example 209

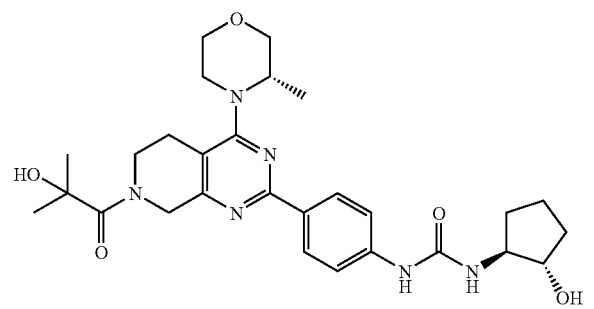

(je)

Synthesis of 1-(4-(7-(2-hydroxy-2-methylpropanoyl)-4-((S)-3-methylmorpholino)-5,6,7,8-tetrahydropyrido[3,4-d]pyrimidin-2-yl)phenyl)-3-((1S,2S)-2-hydroxycyclopentyl)urea (je): Compound je was prepared by the general procedure of Example 208, substituting 1S,2S)-2-aminocyclopentanol for cyclobutyl amine. LC-MS: m/z=+539 (M+H)+.

Example 210

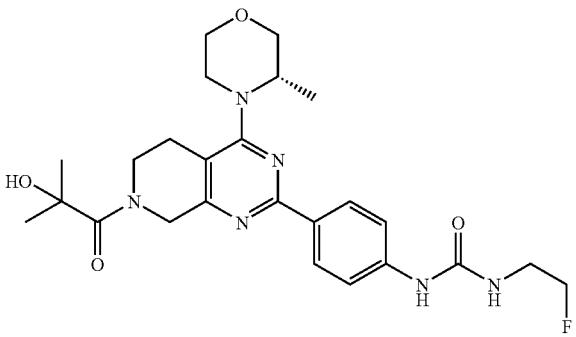

(jf)

Synthesis of (S)-1-(2-fluoroethyl)-3-(4-(7-(2-hydroxy-2-methylpropanoyl)-4-(3-methylmorpholino)-5,6,7,8-tetrahydropyrido[3,4-d]pyrimidin-2-yl)phenyl)urea (jf): Compound jf was prepared by the general procedure of Example 208, substituting 2-fluoroethyl amine for cyclobutyl amine. LC-MS: m/z=+501 (M+H)+.

Example 211

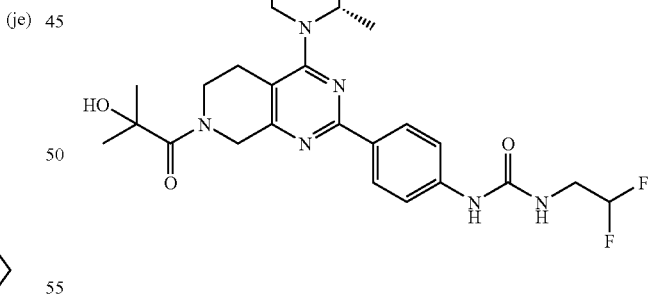

Synthesis of (S)-1-(2,2-difluoroethyl)-3-(4-(7-(2-hydroxy-2-methylpropanoyl)-4-(3-methylmorpholino)-5,6,7,8-tetrahydropyrido[3,4-d]pyrimidin-2-yl)phenyl)urea (jg): Compound jg was prepared by the general procedure of Example 208, substituting 2-fluoroethyl amine for cyclobutyl amine. LC-MS: m/z=+519 (M+H)+.

Example 212

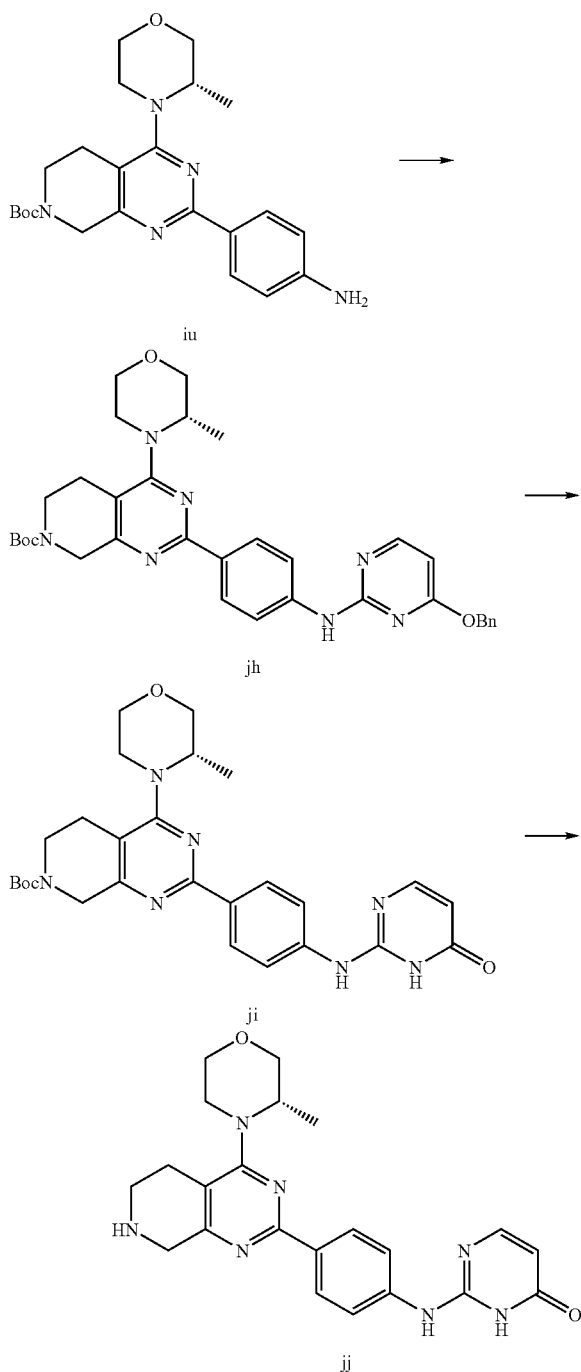

Synthesis of Compound jj:

Step 1—Synthesis of (S)-tert-butyl 2-(4-(4-(benzyloxy)pyrimidin-2-ylamino)phenyl)-4-(3-methylmorpholino)-5,6-dihydropyrido[3,4-d]pyrimidine-7(8H)-carboxylate (jh): A mixture of compound iu (100 mg, 0.24 mmol), 4-(benzyloxy)-2-chloropyrimidine (57 mg, 0.26 mmol), PdDBA$_2$ (7 mg, 0.012 mmol), sodium tert-butoxide (32 mg, 0.32 mmol), 2-Dicyclohexylphosphino-2'-(N,N-dimethylamino)biphenyl (6 mg, 0.015 mmol) in toluene (2.4 mL) was purged with N$_2$ for 5 minutes, then heated at 120° C. for 20 min in a μWave reactor. The resulting dark mixture was filtered through cotton, concentrated onto Celite, and the residue chromatographed: ISCO 12 g (silica gel) column 0-30% ethyl acetate in DCM to afford 105 mg (70%) of the title compound jh as a yellow solid: $^1$H NMR (500 MHz, CDCl$_3$) δ 8.35 (d, J=8.6 Hz, 2H), 8.19 (d, J=5.7 Hz, 1H), 7.69 (d, J=8.5 Hz, 2H), 7.54-7.29 (m, 5H), 6.29 (d, J=5.7 Hz, 1H), 5.42 (s, 2H), 4.69 (d, J=18.1Hz, 1H), 4.53 (d, J=18.5 Hz, 1H), 4.06 (t, J=6.6 Hz, 1H), 3.96 (d, J=11.3 Hz, 1H), 3.89-3.67 (m, 4H), 3.63-3.50 (m, 2H), 3.50-3.37 (m, 1H), 2.68 (s, 2H), 1.51 (s, 9H), 1.33 (d, J=6.8 Hz, 3 H); LC-MS: m/z=610 (M+H)+.

Step 2—Synthesis of (S)-tert-butyl 4-(3-methylmorpholino)-2-(4-(6-oxo-1,6-dihydropyrimidin-2-ylamino)phenyl)-5,6-dihydropyrido[3,4-d]pyrimidine-7(8H)-carboxylate (ji). A flask containing a mixture of the product jh from Step 1 (105 mg, 0.17 mmol), 20% Pd(OH)$_2$ on carbon (40 mg), acetic acid (0.25 mL) and THF (5 mL) was evacuated and refilled with H$_2$ (3x), then stirred vigorously under 1 atm of H$_2$ for 18 h. The mixture was filtered through Celite, then concentrated to afford 94 mg (84%) of the title compound ji: $^1$H NMR (400 MHz, CDCl$_3$) δ 8.38 (d, J=8.2 Hz, 2H), 7.72 (s, 2H), 5.97 (d, J=6.0 Hz, 1H), 4.68 (d, J=18.2 Hz, 1H), 4.56 (d, J=18.5 Hz, 1H), 4.07 (s, 1H), 3.98-3.87 (m, 1H), 3.87-3.36 (m, 8H), 2.77-2.42 (m, 2H), 1.64-1.45 (m, 9H), 1.34 (dd, J=6.1 Hz, 3 H), 1.29 (d, J=15.6 Hz, 5H); LC-MS: m/z=+520 (M+H)+.

Step 3—Synthesis of (S)-2-(4-(4-(3-methylmorpholino)-5,6,7,8-tetrahydropyrido[3,4-d]pyrimidin-2-yl)phenylamino)pyrimidin-4(3H)-one (jj). The title compound jj was prepared by the procedure of step 3 in Example 1. LC-MS: m/z=+420 (M+H)+.

Example 213

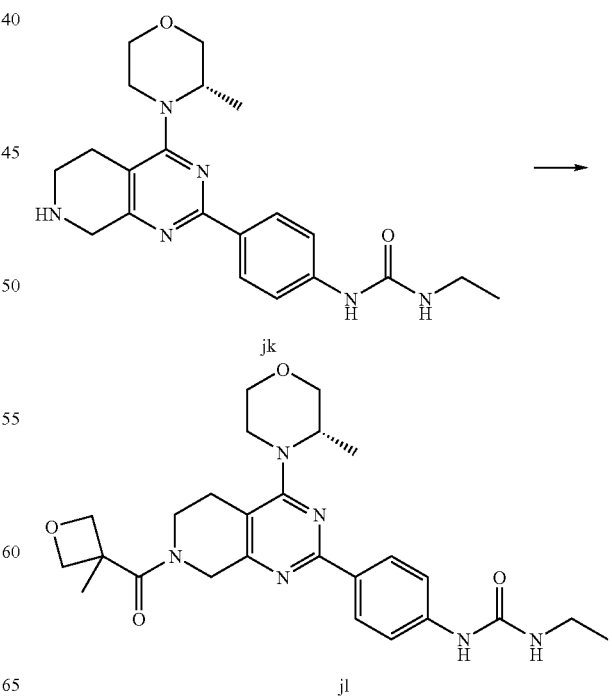

Synthesis of (S)-1-ethyl-3-(4-(4-(3-methylmorpholino)-7-(3-methyloxetane-3-carbonyl)-5,6,7,8-tetrahydropyrido[3,4-d]pyrimidin-2-yl)phenyl)urea (jl) A mixture of (S)-1-ethyl-3-(4-(4-(3-methylmorpholino)-5,6,7,8-tetrahydropyrido[3,4-d]pyrimidin-2-yl)phenyl)urea (jk).HCl (111 mg, 0.26 mmol), 3-methyloxetane-3-carboxylic acid (36 mg, 0.31 mmol), HATU (195 mg, 0.51 mmol), DIPEA (0.25 mL, 1.28 mmol) and DMF (1.5 mL) was stirred at rt for 12 h. The mixture was partitioned between ethyl acetate (10 mL) and 1 N HCl (10 ml). The phases were separated and the aqueous phase was extracted with ethyl acetate (2×5 mL). The combined organic phases were washed with 1 N NaOH (2×4 mL), dried over Na₂SO₄, filtered and concentrated. The residue was purified by HPLC to afford 21 mg of the title compound jl as a colorless solid. LC-MS: m/z=+495 (M+H)+.

Example 214

(jm)

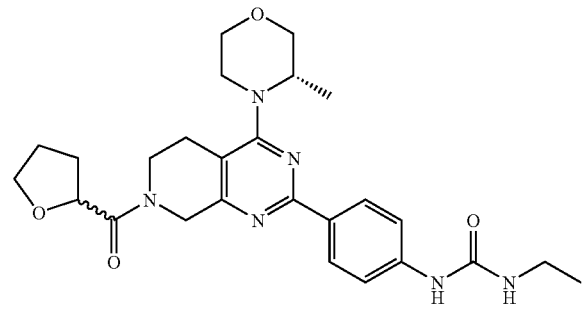

Synthesis of (S)-1-ethyl-3-(4-(4-(3-methylmorpholino)-7-(tetrahydrofuran-2-carbonyl)-5,6,7,8-tetrahydropyrido[3,4-d]pyrimidin-2-yl)phenyl)urea (jm): The title compound jm was prepared by the procedure described in Example 213, substituting tetrahydrofuran-2-carboxylic acid for 3-methyloxetane-3-carboxylic acid. LC-MS: m/z=+495 (M+H)+.

Example 215

(jn)

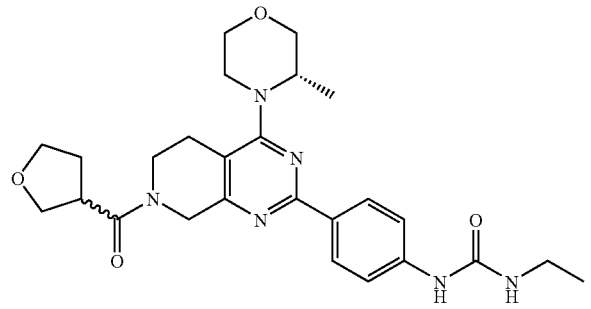

Synthesis of (S)-1-ethyl-3-(4-(4-(3-methylmorpholino)-7-(tetrahydrofuran-3-carbonyl)-5,6,7,8-tetrahydropyrido[3,4-d]pyrimidin-2-yl)phenyl)urea (jn). The title compound jn was prepared by the procedure of Example 213, substituting tetrahydrofuran-3-carboxylic acid for 3-methyloxetane-3-carboxylic acid. LC-MS: m/z=+495 (M+H)+.

Example 216

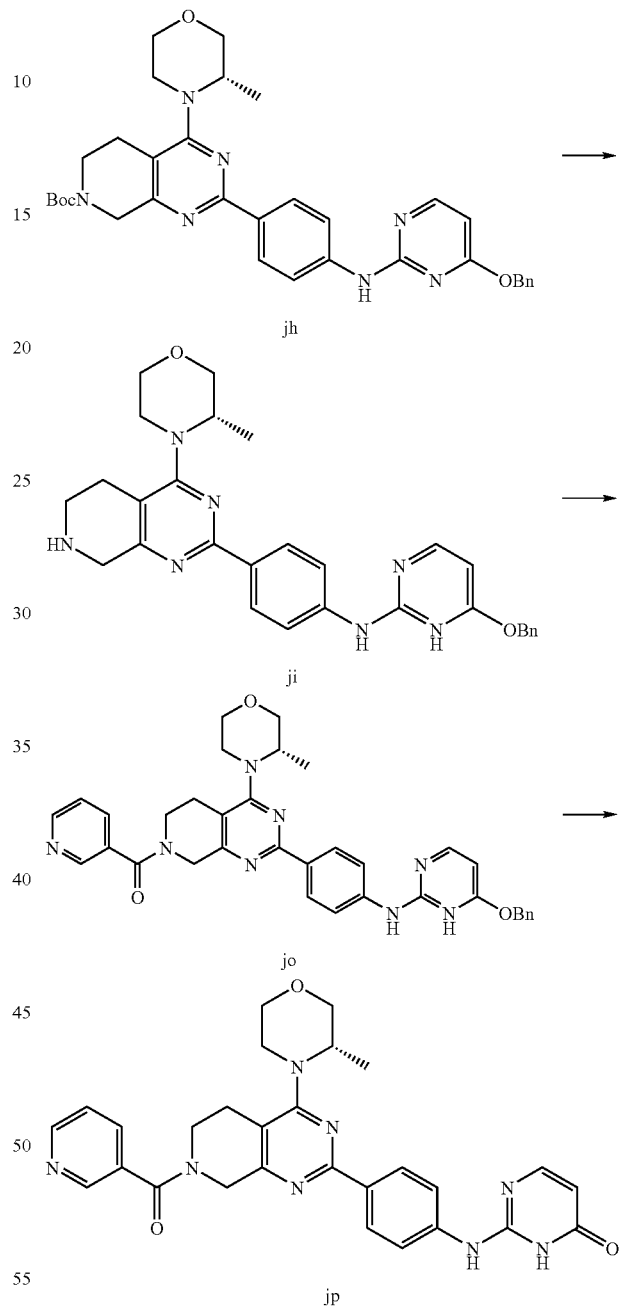

Step 1—Synthesis of (S)-4-(benzyloxy)-N-(4-(4-(3-methylmorpholino)-5,6,7,8-tetrahydropyrido[3,4-d]pyrimidin-2-yl)phenyl)pyrimidin-2-amine hydrochloride (ji): A solution of (S)-tert-butyl 2-(4-(4-(benzyloxy)pyrimidin-2-ylamino)phenyl)-4-(3-methylmorpholino)-5,6-dihydropyrido[3,4-d]pyrimidine-7(8H)-carboxylate (jh) (prepared in Example 212) (260 mg, 0.36 mmol) in MeOH (3.0 mL) was treated with 4.0 M HCl in dioxane (3.0 mL) for 1 h. The solution was concentrated to afford the title compound ji as an off-white solid. LC-MS: m/z=+510 (M+H)+.

221

Step 2—Synthesis of (S)-(2-(4-(4-(benzyloxy)pyrimidin-2-ylamino)phenyl)-4-(3-methylmorpholino)-5,6-dihydropyrido[3,4-d]pyrimidin-7(8H)-yl)(pyridin-3-yl)methanone (jo). A solution of the product ji of step 1 (100 mg, 0.18 mmol) DIPEA (0.13 mL, 0.73 mmol), and DCM (1.2 mL) was treated with nicotinoyl chloride hydrochloride (40 mg, 2.2 mmol) for 3 h. The solution was diluted with DCM (20 mL), washed with 0.1 N HCl (3×5 mL). The combined aqueous phases were extracted with DCM (1×5 mL). The combined organic phases were dried over $Na_2SO_4$, filtered and concentrated to afford 94 mg (84%) of the title compound jo as a solid: LC-MS: m/z=+615 (M+H)+.

Step 3—Synthesis of (S)-2-(4-(4-(3-methylmorpholino)-7-nicotinoyl-5,6,7,8-tetrahydropyrido[3,4-d]pyrimidin-2-yl)phenylamino)pyrimidin-4(3H)-one (jp): The title compound jp was prepared by the general procedure of Example 212, Step 2. LC-MS: m/z=+525 (M+H)+.

Example 217

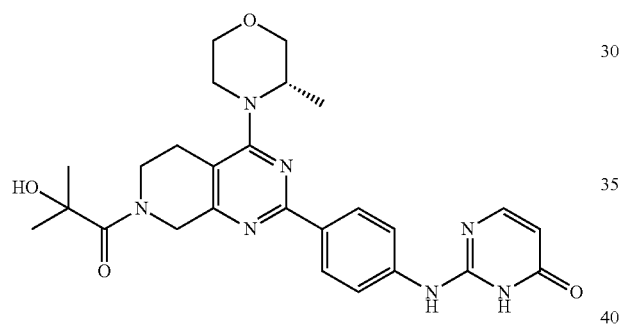

(jq)

Synthesis of (S)-2-(4-(7-(2-hydroxy-2-methylpropanoyl)-4-(3-methylmorpholino)-5,6,7,8-tetrahydropyrido[3,4-d]pyrimidin-2-yl)phenylamino)pyrimidin-4(3H)-one (jq): The title compound jq was prepared by the general procedure of Example 208, Step 3 and Example 212, Step 2. LC-MS: m/z=+506 (M+H)+.

Example 218

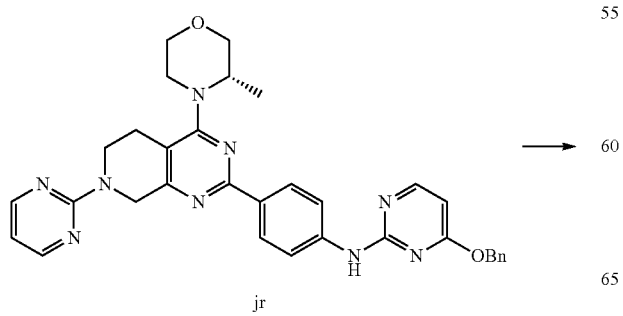

jr

222

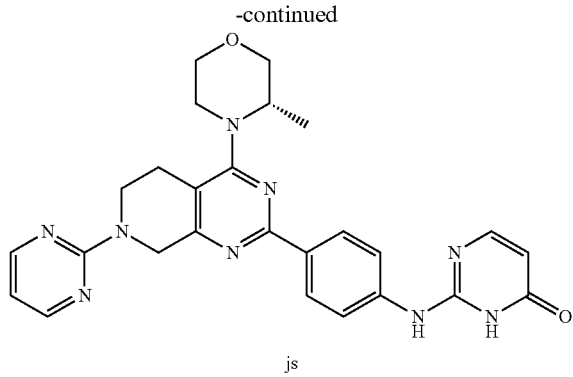

js

Synthesis (S)-2-(4-(4-(3-methylmorpholino)-7-(pyrimidin-2-yl)-5,6,7,8-tetrahydropyrido[3,4-d]pyrimidin-2-yl)phenylamino)pyrimidin-4(3H)-one (j s): A solution of (S)-4-(benzyloxy)-N-(4-(4-(3-methylmorpholino)-7-(pyrimidin-2-yl)-5,6,7,8-tetrahydropyrido[3,4-d]pyrimidin-2-yl)phenyl)pyrimidin-2-amine (jr) 50 mg (0.08 mmol) in AcOH (0.5 mL) was treated with 33% HBr in AcOH (0.5 mL) for 3h. The solution was concentrated under reduced pressure and the residue purified by reverse phase HPLC (RPHPLC) to afford the title compound js: LC-MS: m/z=+498 (M+H)+.

Example 219

(jt)

Synthesis of (S)-2-(4-(4-(3-methylmorpholino)-7-(1,4,5,6-tetrahydropyrimidin-2-yl)-5,6,7,8-tetrahydropyrido[3,4-d]pyrimidin-2-yl)phenylamino)pyrimidin-4(3H)-one (jt):

The title compound jt was prepared by the procedure of Example 216, Step 3, except that the reaction was run for 2 d. LC-MS: m/z=+502 (M+H)+.

Example 220

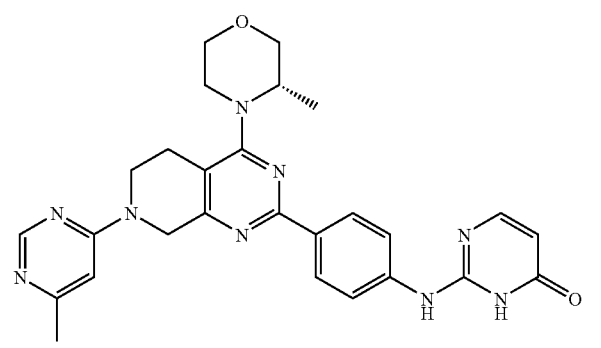

(ju)

Synthesis of (S)-2-(4-(4-(3-methylmorpholino)-7-(6-methylpyrimidin-4-yl)-5,6,7,8-tetrahydropyrido[3,4-d]pyrimidin-2-yl)phenylamino)pyrimidin-4(3H)-one (ju): The title compound ju was prepared by the general procedures of Example 2, Example 206, step 1, and Example 218: LC-MS: m/z=+512 (M+H)+.

Example 221

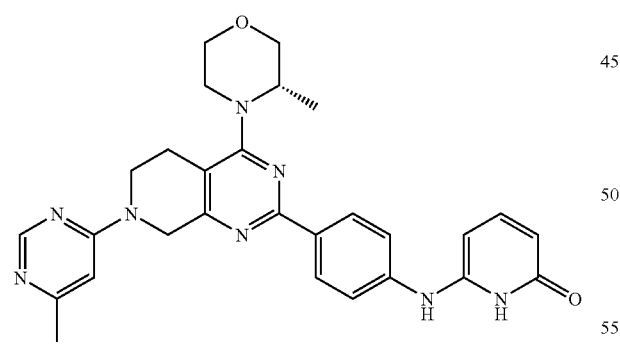

(jv)

Synthesis of (S)-6-(4-(4-(3-methylmorpholino)-7-(6-methylpyrimidin-4-yl)-5,6,7,8-tetrahydropyrido[3,4-d]pyrimidin-2-yl)phenylamino)pyridin-2(1H)-one (jv). The title compound jv was prepared by the general procedure of Example 220: LC-MS: m/z=+511 (M+H)+.

Example 222

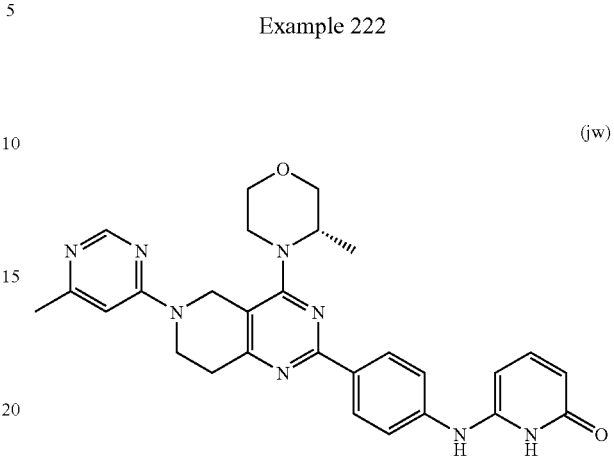

(jw)

Synthesis of (S)-6-(4-(4-(3-methylmorpholino)-6-(6-methylpyrimidin-4-yl)-5,6,7,8-tetrahydropyrido[4,3-d]pyrimidin-2-yl)phenylamino)pyridin-2(1H)-one (jw): The title compound jw was prepared by the general procedure of Example 220: LC-MS: m/z=+511 (M+H)+.

Example 223

(jx)

Synthesis of (S)-2-(4-(4-(3-methylmorpholino)-6-(6-methylpyrimidin-4-yl)-5,6,7,8-tetrahydropyrido[4,3-d]pyrimidin-2-yl)phenylamino)pyrimidin-4(3H)-one (jx): The title compound jx was prepared by the procedure of Example 220. LC-MS: m/z=+512 (M+H)+.

3H), 2.49 (s, 2H), 1.32 (t, J=6.2 Hz, 3H), 1.24-1.06 (m, 3H), 0.95 (s, 6H); LC-MS: m/z=+483 (M+H)+.

Example 224

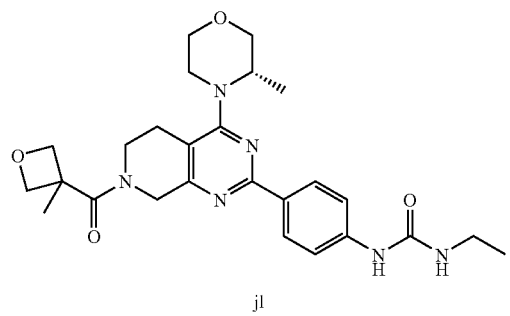

jl

Example 225

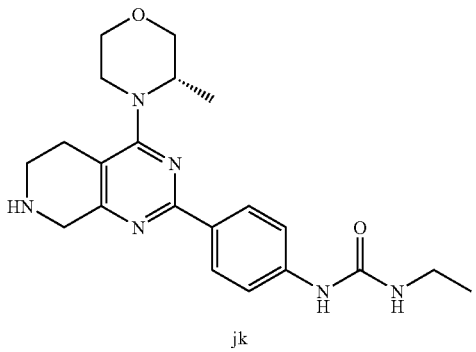

jk

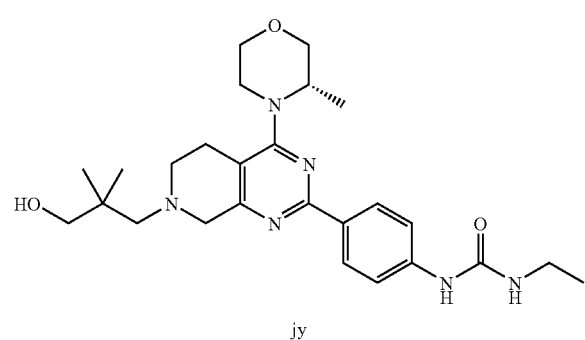

jy

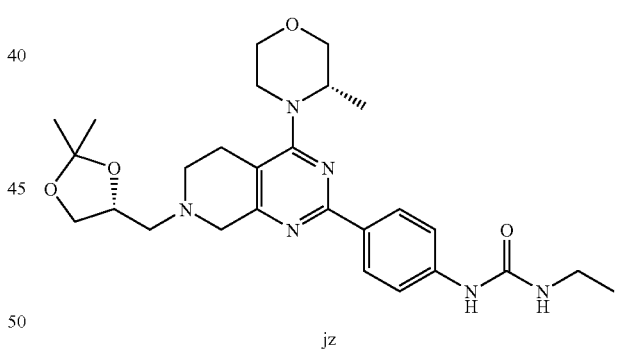

jz

Synthesis of (S)-1-ethyl-3-(4-(7-(3-hydroxy-2,2-dimethylpropyl)-4-(3-methylmorpholino)-5,6,7,8-tetrahydropyrido[3,4-d]pyrimidin-2-yl)phenyl)urea (jm): A solution of (S)-1-ethyl-3-(4-(4-(3-methylmorpholino)-7-(3-methyloxetane-3-carbonyl)-5,6,7,8-tetrahydropyrido[3,4-d]pyrimidin-2-yl)phenyl)urea (jl) (Example 213) (30 mg, 0.061 mmol), borane (0.5 mL of 1.0 M in THF, 0.5 mmol) and THF (1.5 mL) was heated at reflux for 7 h. Further borane (0.3 mL of 1.0 M in THF, 0.3 mmol) was added, and the solution heated at reflux for 15 h. After cooling to rt, sat. NaHCO₃ (1 mL) and 3% aq hydrogen peroxide (1 mL) were added and the mixture stirred vigorously for 3 h. The mixture was diluted with 1 N NaOH (20 ml) and extracted with ethyl acetate (3×10 mL). The combined organic phases were washed with brine (1×10 mL) dried over Na₂SO₄, filtered and concentrated. The residue was purified by RP-HPLC to afford 8 mg (26%) of the title compound as a colorless solid: ¹H NMR (400 MHz, MeOD) δ 8.23-8.09 (m, 2H), 7.53-7.36 (m, 2H), 4.29-4.08 (m, 1H), 3.93 (d, J=11.1Hz, 1H), 3.86-3.61 (m, 6H), 3.58-3.45 (m, 1H), 3.24 (q, J=7.2 Hz, 2H), 2.94-2.77 (m, 1H), 2.77-2.68 (m, Synthesis of 1-(4-(7-(((R)-2,2-dimethyl-1,3-dioxolan-4-yl)methyl)-4-((S)-3-methylmorpholino)-5,6,7,8-tetrahydropyrido[3,4-d]pyrimidin-2-yl)phenyl)-3-ethylurea (jz): A solution of (S)-1-ethyl-3-(4-(4-(3-methylmorpholino)-5,6,7,8-tetrahydropyrido[3,4-d]pyrimidin-2-yl)phenyl)urea hydrochloride (jk) (270 mg, 0.69 mmol), (S)-(2,2-dimethyl-1,3-dioxolan-4-yl)methyl 4-methylbenzenesulfonate (377 mg, 132 mmol), sodium iodide (104 mg, 0.69 mmol), DIPEA (0.48 mL, 2.8 mmol), and DMF (1.0 mL) was heated at 110° C. for 22 h. The mixture was partitioned between ethyl acetate and sat. NaHCO₃. The phases were separated, and the aqueous layer extracted with ethyl acetate (2×). The combined organic phases were dried over Na₂SO₄, filtered and concentrated onto Celite, and the residue chromatographed: ISCO 12 g column 0-20% IPA in DCM to afford 228 mg (64%) of the title compound jz as an off-white solid: LC-MS: m/z=+511 (M+H)+.

Example 226

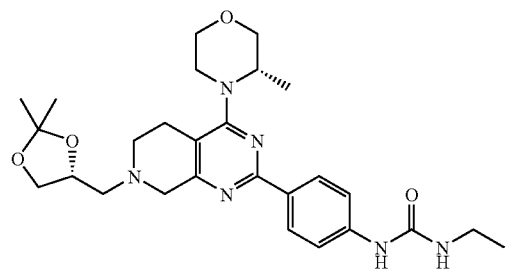

jz

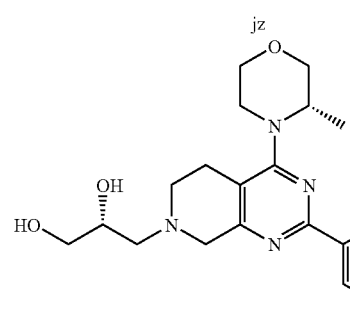

ka

Synthesis of 1-(4-(7-((R)-2,3-dihydroxypropyl)-4-((S)-3-methylmorpholino)-5,6,7,8-tetrahydropyrido[3,4-d]pyrimidin-2-yl)phenyl)-3-ethylurea (ka): A solution of 1-(4-(7-(((R)-2,2-dimethyl-1,3-dioxolan-4-yl)methyl)-4-((S)-3-methylmorpholino)-5,6,7,8-tetrahydropyrido[3,4-d]pyrimidin-2-yl)phenyl)-3-ethylurea (jz) (50 mg, 0.10 mmol), 1 N HCl (0.20 mL, 0.2 mmol) and water (0.5 mL) was maintained at rt for 24 h. The mixture was purified by RPHPLC to afford 28 mg (60%) of the title compound ka as a colorless solid: LC-MS: m/z=+471 (M+H)+.

Example 227

(kb)

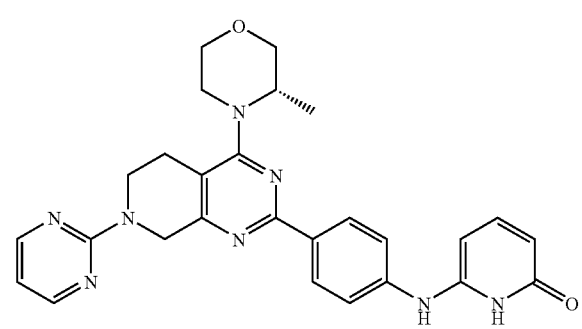

Synthesis of (S)-6-(4-(4-(3-methylmorpholino)-7-(pyrimidin-2-yl)-5,6,7,8-tetrahydropyrido[3,4-d]pyrimidin-2-yl) phenylamino)pyridin-2(1H)-one (kb). The title kb compound was prepared by the general procedure of Example 218: LC-MS: m/z=+497 (M+H)+.

Example 228

(kc)

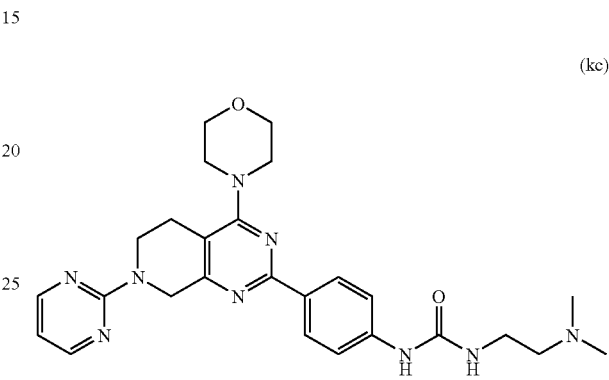

Synthesis of 1-(2-(dimethylamino)ethyl)-3-(4-(4-morpholino-7-(pyrimidin-2-yl)-5,6,7,8-tetrahydropyrido[3,4-d]pyrimidin-2-yl)phenyl)urea (kc). The title compound kc was prepared by the general procedure of Example 30 substituting N,N-dimethyl-1,2-ethanediamine for cyclopropylmethylamine amine. LC-MS: m/z=+504 (M+H)+.

Example 229

(kd)

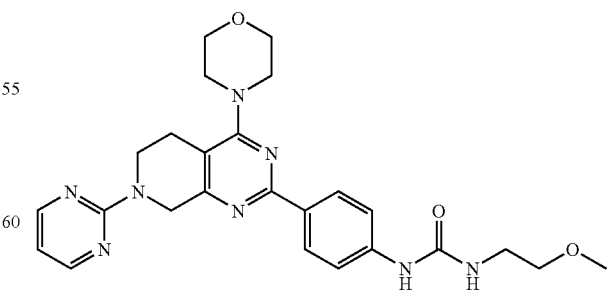

Synthesis of 1-(2-methoxyethyl)-3-(4-(4-morpholino-7-(pyrimidin-2-yl)-5,6,7,8-tetrahydropyrido[3,4-d]pyrimidin-2-yl)phenyl)urea (kd): The title compound kd was prepared by the general procedure of Example 30 substituting 2-methoxyethylamine for cyclopropylmethylamine. LC-MS: m/z=+491 (M+H)+.

Example 230


Synthesis of 1-(2-hydroxy-2-methylpropyl)-3-(4-(4-morpholino-7-(pyrimidin-2-yl)-5,6,7,8-tetrahydropyrido[3,4-d]pyrimidin-2-yl)phenyl)urea (ke): The title compound ke was prepared by the general procedure of Example 30 substituting 1-amino-2-methylpropan-2-ol for cyclopropylmethylamine. LC-MS: m/z=+505 (M+H)+.

Example 231

Synthesis of 1-(2,2-difluoroethyl)-3-(4-(4-morpholino-7-(pyrimidin-2-yl)-5,6,7,8-tetrahydropyrido[3,4-d]pyrimidin-2-yl)phenyl)urea (kf): The title compound kf was prepared by the general procedure of Example 30 substituting 2,2-difluoroethylamine for cyclopropylmethylamine. LC-MS: m/z=+497 (M+H)+.

Example 232

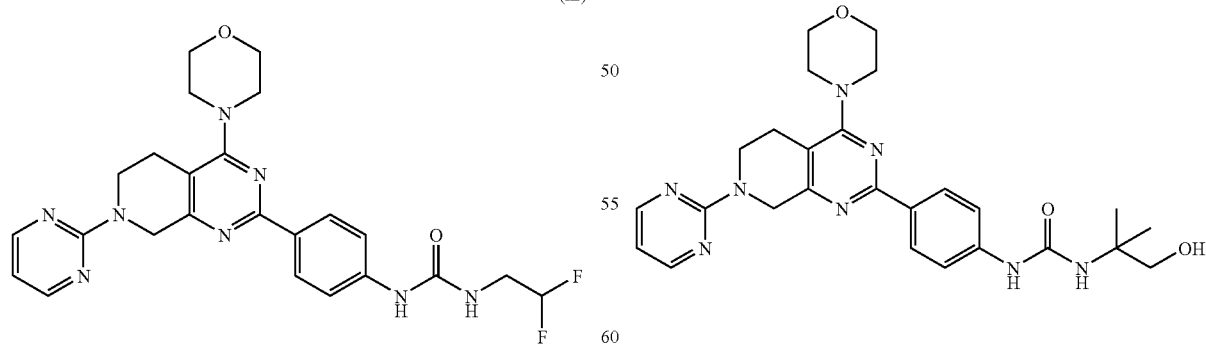

Synthesis of 1-(2-fluoroethyl)-3-(4-(4-morpholino-7-(pyrimidin-2-yl)-5,6,7,8-tetrahydropyrido[3,4-d]pyrimidin-2-yl)phenyl)urea (kg): The title compound kg was prepared by the general procedure of Example 30 substituting 2-fluoroethylamine hydrochloride for cyclopropylmethylamine. LC-MS: m/z=+479 (M+H)+.

Example 233

Synthesis of 1-(1-hydroxy-2-methylpropan-2-yl)-3-(4-(4-morpholino-7-(pyrimidin-2-yl)-5,6,7,8-tetrahydropyrido[3,4-d]pyrimidin-2-yl)phenyl)urea (kh): The title compound kh was prepared by the general procedure of Example 30 substituting 2-amino-2-methyl-1-propanol for cyclopropylmethylamine. LC-MS: m/z=+505 (M+H)+.

Example 234

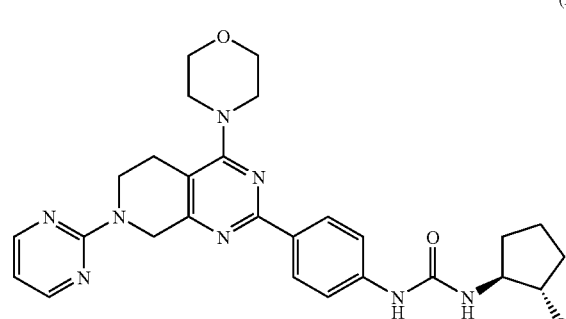
(ki)

Synthesis of 1-((iS,2S)-2-hydroxycyclopentyl)-3-(4-(4-morpholino-7-(pyrimidin-2-yl)-5,6,7,8-tetrahydropyrido[3,4-d]pyrimidin-2-yl)phenyl)urea (ki): The title compound ki was prepared by the general procedure of Example 30 substituting (1S,2S)-trans-2-aminocyclopentanol hydrochloride for cyclopropylmethylamine. LC-MS: m/z=+517 (M+H)+.

Example 235

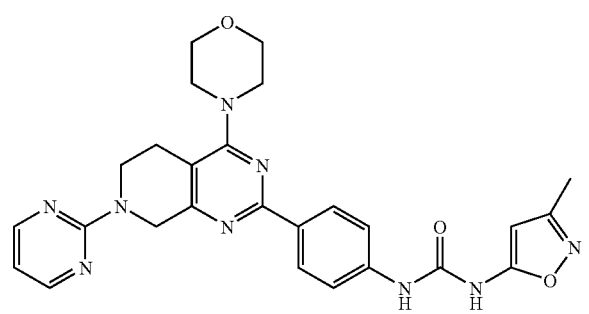
(kk)

Synthesis of 1-(3-methylisoxazol-5-yl)-3-(4-(4-morpholino-7-(pyrimidin-2-yl)-5,6,7,8-tetrahydropyrido[3,4-d]pyrimidin-2-yl)phenyl)urea (kk). The title compound kk was prepared by the general procedure of Example 30 substituting 3-methylisoxazol-5-amine for cyclopropylmethylamine. LC-MS: m/z=+514 (M+H)+.

Example 236

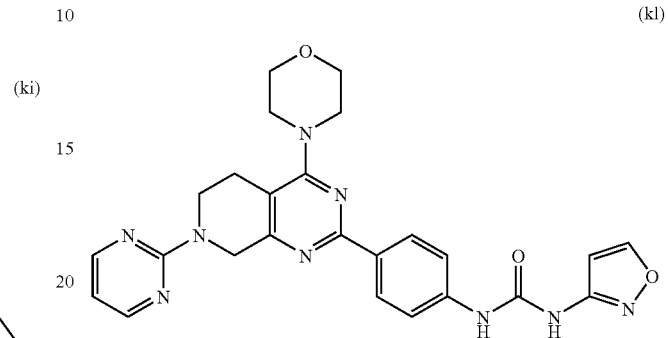
(kl)

Synthesis of 1-(isoxazol-3-yl)-3-(4-(4-morpholino-7-(pyrimidin-2-yl)-5,6,7,8-tetrahydropyrido[3,4-d]pyrimidin-2-yl)phenyl)urea (kl): The title compound kl was prepared by the general procedure of Example 30 substituting isoxazol-3-amine for cyclopropylmethylamine. LC-MS: m/z=+500 (M+H)+.

Example 237

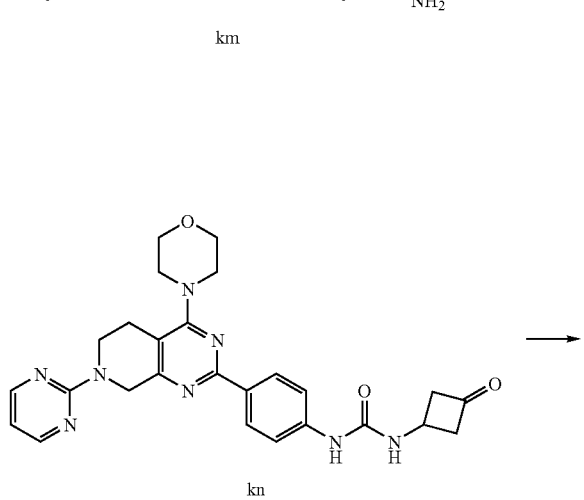

-continued

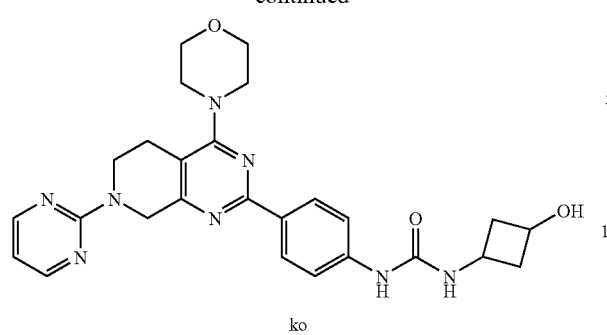

ko

Step 1—Synthesis of 1-(4-(4-morpholino-7-(pyrimidin-2-yl)-5,6,7,8-tetrahydropyrido[3,4-d]pyrimidin-2-yl)phenyl)-3-(3-oxocyclobutyl)urea (kn). The title compound kn was prepared by the general procedure of Example 30 substituting azetidin-3-one hydrochloride for cyclopropylmethylamine. LC-MS: m/z=+501 (M+H)+.

Step 2—Synthesis of 1-(3-hydroxycyclobutyl)-3-(4-(4-morpholino-7-(pyrimidin-2-yl)-5,6,7,8-tetrahydropyrido[3,4-d]pyrimidin-2-yl)phenyl)urea (ko). To a solution of compound kn (100 mg, 0.2 mmol) in MeOH (2 mL) was added NaBH$_4$ (15 mg, 0.4 mmol) in portions. After 1.5 hr at rt, additional NaBH$_4$ (15 mg) was added the resultant solution was stirred at rt overnight. More NaBH$_4$ (15 mg) was added to the reaction mixture. After 4 hrs, it was quenched by dropwise addition of acetone. It was concentrated in vacuo and purified by RP-HPLC to afford the title compound ko. 1H NMR (400 MHz, DMSO) δ 8.58 (s, 1H), 8.44 (d, J=4.7, 2H), 8.21 (d, J=8.8, 2H), 7.47 (d, J=8.8, 2H), 6.69 (t, J=4.7, 1 H), 6.43 (d, J=7.8, 1H), 5.05 (d, J=5.7, 1H), 4.81 (s, 2H), 3.98 (t, J=5.2, 2H), 3.83-3.70 (m, 5H), 3.64 (dd, J=15.1, 7.5, 1H), 3.47 (d, J=4.3, 4H), 2.75 (t, J=5.0, 2H), 2.55 (ddd, J=15.7, 7.0, 2.8, 2H), 1.68 (ddd, J=17.1, 8.8, 2.8, 2H). LC-MS: m/z=+503 (M+H)+.

Example 238

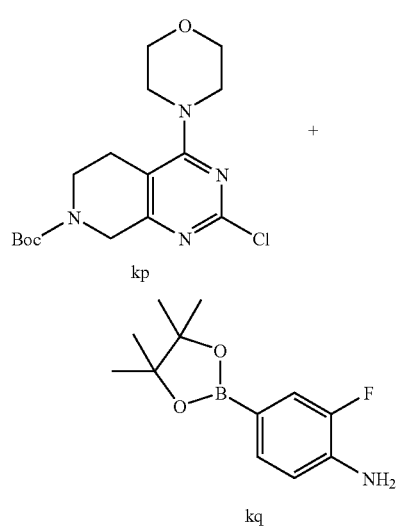

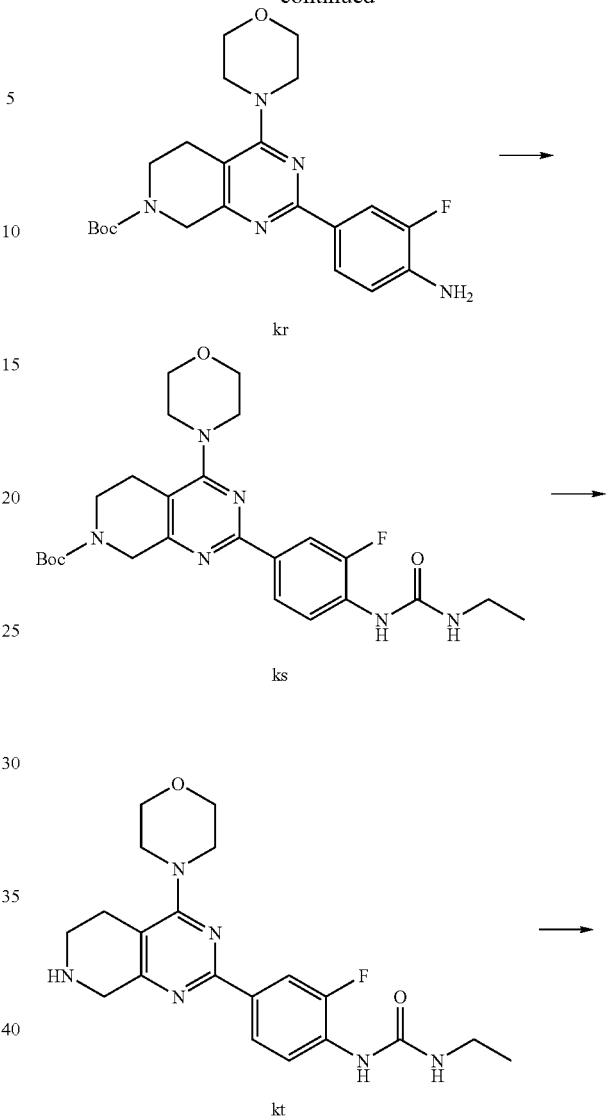

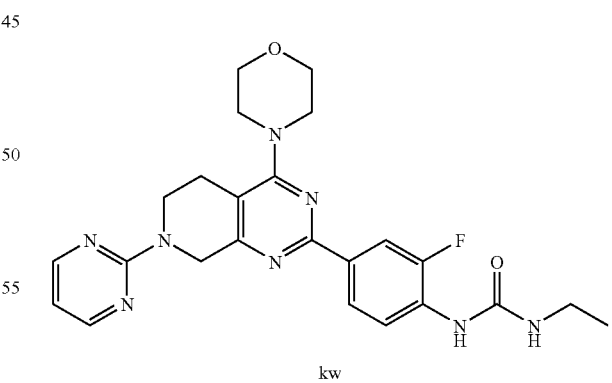

Synthesis of 2-fluoro-4-(4,4,5,5-tetramethyl-1,3,2-dioxaborolan-2-yl)aniline (kq): To a mixture of 4-bromo-2-fluoroaniline (570 mg, 3.0 mmol), bispinacol ester boronate (1.14 g, 4.5 mmol), PdCl$_2$(dppf) CH$_2$Cl$_2$ adduct (245 mg, 0.3 mmol), and KOAc (883 mg, 9.0 mmol) in DMSO (10 mL) was purged with N$_2$ for 5 min. It was then heated at 80° C. for 7 hrs. After cooled, the mixture was diluted with H$_2$O (30 mL)

and EtOAc (30 mL). The mixture was filtered through a short pad of Celite. The layers were separated and the aqueous layer was re-extracted with EtOAc (30 mL). The combined EtOAc were washed with brine, dried over Magnesium sulfate, filtered, concentrated onto Celite, and chromatographed: ISCO 12 g column 1-10% ethyl acetate in hexane to afford 785 mg (100%) of the title compound as an off white solid. 1H NMR (400 MHz, DMSO) δ 7.18 (dd, J=7.9, 1.2, 1H), 7.13 (dd, J=12.1, 1.0, 1H), 6.71 (dt, J=12.1, 6.1, 1H), 5.58 (s, 2H), 1.25 (s, 12H). LC-MS: m/z=+238 (M+H)+.

Step 1—Synthesis of tert-butyl 2-(4-amino-3-fluorophenyl)-4-morpholino-5,6-dihydropyrido[3,4-d]pyrimidine-7(8H)-carboxylate (kr): The title compound kr was prepared by following the general procedure in Example 1, Step 2, substituting tert-butyl 2-chloro-4-morpholino-5,6-dihydropyrido[3,4-d]pyrimidine-7(8H)-carboxylate (kp) for tert-butyl 2-chloro-4-morpholino-5H-pyrrolo[3,4-d]pyrimidine-6(7H)-carboxylate and 2-fluoro-4-(4,4,5,5-tetramethyl-1,3,2-dioxaborolan-2-yl)aniline (kq) for (4-ethylureido)phenylboronic acid pinacol ester. 1H NMR (400 MHz, DMSO) δ 7.91-7.83 (m, 2H), 6.79 (t, J=8.8, 1H), 5.63 (s, 2H), 4.43 (s, 2H), 3.74-3.70 (m, 4H), 3.50 (s, 2H), 3.44 (d, J=4.4, 4H), 2.64 (s, 2H), 1.45 (s, 9H). LC-MS: m/z=+430 (M+H)+.

Step 2—Synthesis of tert-butyl 2-(4-(3-ethylureido)-3-fluorophenyl)-4-morpholino-5,6-dihydropyrido[3,4-d]pyrimidine-7(8H)-carboxylate (ks). A mixture of the tert-butyl 2-(4-amino-3-fluorophenyl)-4-morpholino-5,6-dihydropyrido[3,4-d]pyrimidine-7(8H)-carboxylate (kr) from Step 1 (200 mg, 0.5 mmol), ethyl isocyanate (55 μL, 0.7 mmol), and DIPEA (122 μL, 0.7 mmol) in DMF (3 mL) was heated at 100° C. for overnight. Additional ethyl isocyanate (55 μL) was added and the reaction was continued heating at 40° C. overnight. The solvent was removed in vacuo, and chromatographed using an ISCO silica gel column, 25 g column 0-20% EtOAc in DCM to afford 107 mg (40%) of the title compound ks. 1H NMR (400 MHz, CDCl3) δ 8.24-8.11 (m, 2H), 8.09-8.00 (m, 1H), 6.88 (d, J=3.1, 1H), 5.13 (t, J=5.4, 1H), 4.59 (s, 2H), 3.87-3.81 (m, 4H), 3.61 (t, J=5.3, 2H), 3.52-3.46 (m, 4H), 3.37-3.29 (m, 2H), 2.67 (t, J=4.9, 2H), 1.51 (s, 9H), 1.21-1.16 (m, 3 H). LC-MS: m/z=+501 (M+H)+.

Step 3—Synthesis of 1-ethyl-3-(2-fluoro-4-(4-morpholino-5,6,7,8-tetrahydropyrido[3,4-d]pyrimidin-2-yl)phenyl)urea (kt): The title kt compound was prepared by following the general procedure in Example 1, Step 3. It was used as crude (without further purification. LC-MS: m/z=+401 (M+H)+.

Step 4—Synthesis of 1-ethyl-3-(2-fluoro-4-(4-morpholino-7-(pyrimidin-2-yl)-5,6,7,8-tetrahydropyrido[3,4-d]pyrimidin-2-yl)phenyl)urea (kw). To a mixture of 1-ethyl-3-(2-fluoro-4-(4-morpholino-5,6,7,8-tetrahydropyrido[3,4-d]pyrimidin-2-yl)phenyl)urea (kt) (83 mg, 0.2 mmol), 2-chloropyrimidine (47 mg, 0.4 mmol), and DIPEA (110 μL, 0.6 mmol) in DMF (1.5 mL) was heated at 100° C. for overnight. It was purified by RP-HPLC to afford the title compound kw. 1H NMR (500 MHz, DMSO) δ 8.43 (d, J=4.7, 3H), 8.27 (s, 1H), 8.05 (dd, J=20.4, 10.9, 2H), 6.69 (t, J=4.7, 2H), 4.82 (s, 2H), 3.98 (s, 2H), 3.74 (s, 4H), 3.49 (s, 4H), 3.18-3.11 (m, 2H), 2.76 (s, 2H), 1.07 (t, J=7.2, 3H). LC-MS: m/z=+479 (M+H)+.

Example 239

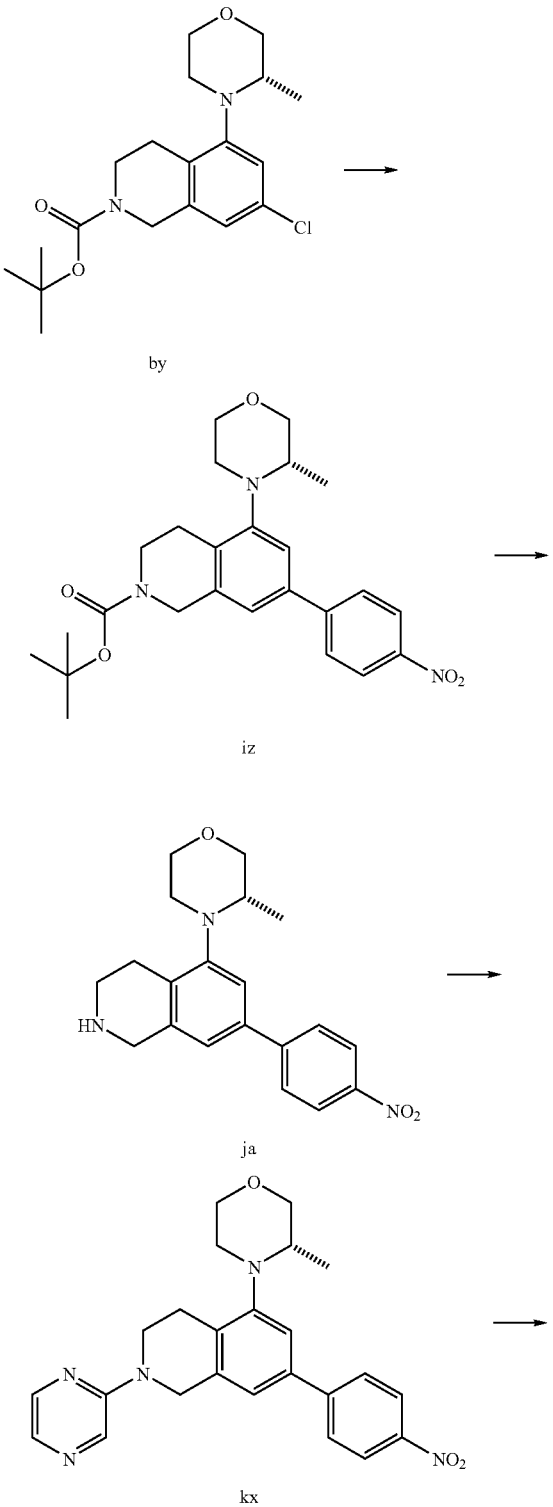

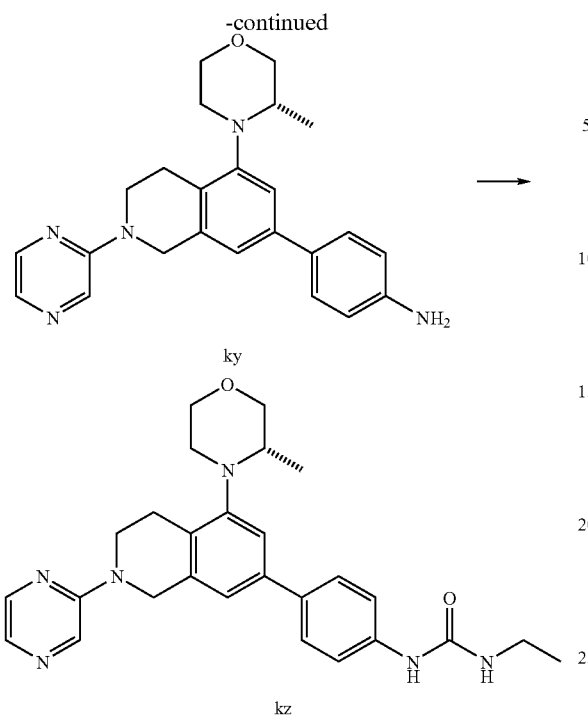

ky kz

Step 1—Synthesis of (S)-tert-butyl 4-(3-methylmorpholino)-2-(4-nitrophenyl)-5,6-dihydropyrido[3,4-d]pyrimidine-7(8H)-carboxylate (iz). The title compound iz prepared by following the general procedure in Example 1, Step 2, substituting (S)-tert-butyl 2-chloro-4-(3-methylmorpholino)-5,6-dihydropyrido[3,4-d]pyrimidine-7(8H)-carboxylate (by) for tert-butyl 2-chloro-4-morpholino-5H-pyrrolo[3,4-d]pyrimidine-6(7H)-carboxylate and 4,4,5,5-tetramethyl-2-(4-nitrophenyl)-1,3,2-dioxaborolane for (4-ethylureido)phenylboronic acid pinacol ester. LC-MS: m/z=+456 (M+H)+.

Step 2—Synthesis of (S)-3-methyl-4-(2-(4-nitrophenyl)-5,6,7,8-tetrahydropyrido[3,4-d]pyrimidin-4-yl)morpholine (ja). (S)-tert-butyl 4-(3-methylmorpholino)-2-(4-nitrophenyl)-5,6-dihydropyrido[3,4-d]pyrimidine-7(8H)-carboxylate (iz) (2.0 g, 4.4 mmol) was treated with TFA/DCM (1:1, 30 mL) at rt for 1.5 hrs. Solvent was removed in vacuo. The residue was redissolved in DCM (150 mL), washed with 10% aq. NaHCO3. The basic aqueous layer was extracted again with DCM (150 mL). The combined DCM were concentrated in vacuo then high vac to afford 1.62 g (100%) dark colored solid. LC-MS: m/z=+356 (M+H)+.

Step 3—Synthesis of (S)-3-methyl-4-(2-(4-nitrophenyl)-7-(pyrazin-2-yl)-5,6,7,8-tetrahydropyrido[3,4-d]pyrimidin-4-yl)morpholine (kx). The title compound kx prepared by following the general procedure in Example 238, Step 4, substituting 2-chloropyrazine for 2-chloropyrimidine. LC-MS: m/z=+434 (M+H)+.

Step 4—Synthesis of (S)-4-(4-(3-methylmorpholino)-7-(pyrazin-2-yl)-5,6,7,8-tetrahydropyrido[3,4-d]pyrimidin-2-yl)aniline (ky). A mixture of (S)-3-methyl-4-(2-(4-nitrophenyl)-7-(pyrazin-2-yl)-5,6,7,8-tetrahydropyrido[3,4-d]pyrimidin-4-yl)morpholine (kx) (395 mg, 0.9 mmol) and SnCl2 dihydrate (1.04 g, 4.5 mmol) in EtOH (15 mL) was heated at 95° C. for 1.5 hrs. The reaction mixture was cooled, concentrated in vacuo. The crude residue was suspended in H2O (100 mL), basified with 1 N aq. NaOH, stirred in 10% MeOH/DCM (100 mL) for 45 min. The organic phase was isolated and the aqueous layer was extracted with 10% MeOH/DCM (100 mL). The combined organic phases were dried over Magnesium sulfate, filtered, concentrated in vacuo to afford 300 mg (82%) of yellow solid. LC-MS: m/z=+404 (M+H)+.

Step 5—Synthesis of (S)-1-cyclobutyl-3-(4-(4-(3-methylmorpholino)-7-(pyrazin-2-yl)-5,6,7,8-tetrahydropyrido[3,4-d]pyrimidin-2-yl)phenyl)urea (kz). The title compound kz was prepared by the general procedure of Example 30 substituting aminocyclobutane for cyclopropylmethylamine. LC-MS: m/z=+501 (M+H)+.

Example 240

(la)

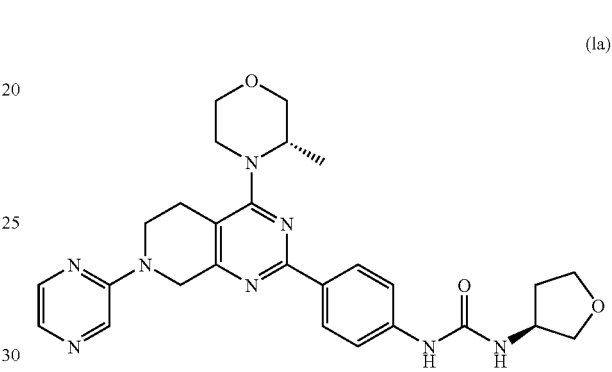

Synthesis of 1-(4-(4-((S)-3-methylmorpholino)-7-(pyrazin-2-yl)-5,6,7,8-tetrahydropyrido[3,4-d]pyrimidin-2-yl)phenyl)-3-((S)-tetrahydrofuran-3-yl)urea (la): The title compound la was prepared by the general procedure of Example 30 substituting (S)-tetrahydrofuran-3-amine toluene-4-sulfonate for cyclopropylmethylamine. LC-MS: m/z=+517 (M+H)+.

Example 241

(lb)

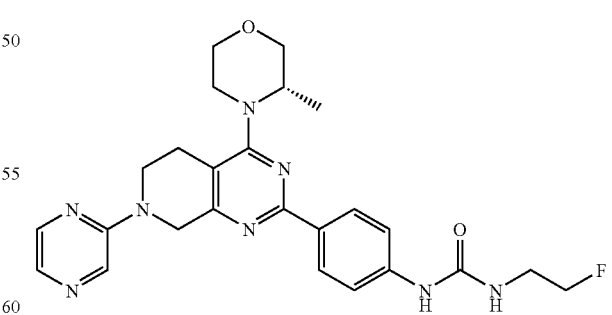

Synthesis of (S)-1-(2-fluoroethyl)-3-(4-(4-(3-methylmorpholino)-7-(pyrazin-2-yl)-5,6,7,8-tetrahydropyrido[3,4-d]pyrimidin-2-yl)phenyl)urea (lb): The title compound lb was prepared by the general procedure of Example 30 substituting 2-fluoethylamine hydrochloride for cyclopropylmethylamine. LC-MS: m/z=+493 (M+H)+.

Example 242

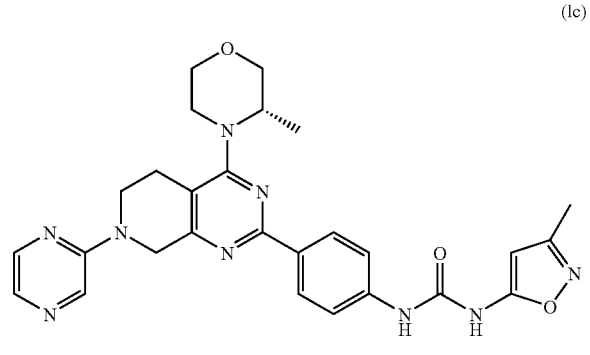

Synthesis of (S)-1-(3-methylisoxazol-5-yl)-3-(4-(4-(3-methylmorpholino)-7-(pyrazin-2-yl)-5,6,7,8-tetrahydropyrido[3,4-d]pyrimidin-2-yl)phenyl)urea (lc): The title compound lc was prepared by the general procedure of Example 30 substituting 5-amino-3-methylisoxazole for cyclopropylmethylamine. LC-MS: m/z=+528 (M+H)+.

Example 243

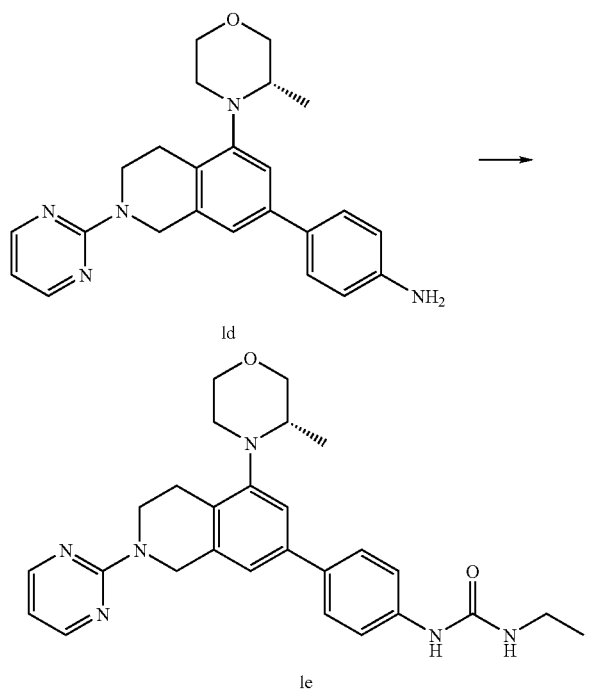

Synthesis of (S)-1-(1-methyl-1H-pyrazol-5-yl)-3-(4-(4-(3-methylmorpholino)-7-(pyrimidin-2-yl)-5,6,7,8-tetrahydropyrido[3,4-d]pyrimidin-2-yl)phenyl)urea (le). The title compound was prepared by the general procedure of Example 30 substituting (S)-4-(4-(3-methylmorpholino)-7-(pyrimidin-2-yl)-5,6,7,8-tetrahydropyrido[3,4-d]pyrimidin-2-yl)aniline (ld) for 4-(4-morpholino-7-(pyrimidin-2-yl)-5,6, 7,8-tetrahydropyrido[4,3-d]pyrimidin-2-yl)aniline and 5-amino-1-methyl-1H-pyrazole for cyclopropylmethylamine. LC-MS: m/z=+527 (M+H)+.

Example 244

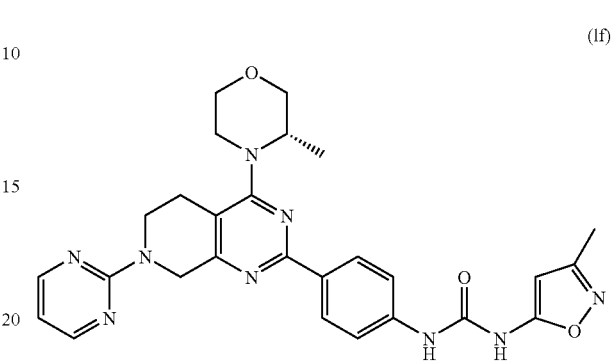

Synthesis of (S)-1-(3-methylisoxazol-5-yl)-3-(4-(4-(3-methylmorpholino)-7-(pyrimidin-2-yl)-5,6,7,8-tetrahydropyrido[3,4-d]pyrimidin-2-yl)phenyl)urea (lf). The title compound lf was prepared by the general procedure of Example 30 substituting (S)-4-(4-(3-methylmorpholino)-7-(pyrimidin-2-yl)-5,6,7,8-tetrahydropyrido[3,4-d]pyrimidin-2-yl)aniline for 4-(4-morpholino-7-(pyrimidin-2-yl)-5,6,7,8-tetrahydropyrido[4,3-d]pyrimidin-2-yl)aniline and 5-amino-3-methylisoxazole for cyclopropylmethylamine. LC-MS: m/z=+528 (M+H)+.

Example 245

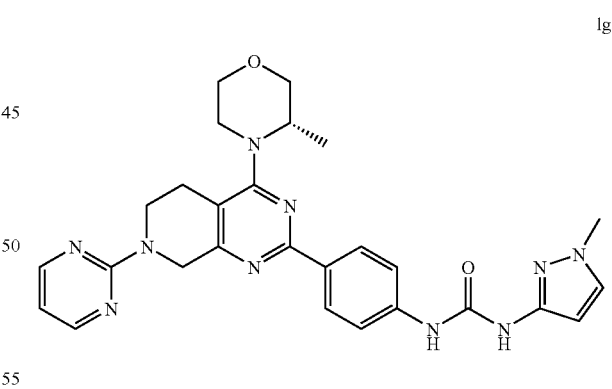

Synthesis of (S)-1-(1-methyl-1H-pyrazol-3-yl)-3-(4-(4-(3-methylmorpholino)-7-(pyrimidin-2-yl)-5,6,7,8-tetrahydropyrido[3,4-d]pyrimidin-2-yl)phenyl)urea (lg): The title compound lg was prepared by the general procedure of Example 30 substituting (S)-4-(4-(3-methylmorpholino)-7-(pyrimidin-2-yl)-5,6,7,8-tetrahydropyrido[3,4-d]pyrimidin-2-yl)aniline for 4-(4-morpholino-7-(pyrimidin-2-yl)-5,6,7,8-tetrahydropyrido[4,3-d]pyrimidin-2-yl)aniline and 1-methyl-1H-pyrazole-3-amine for cyclopropylmethylamine. LC-MS: m/z=+527 (M+H)+.

Example 246

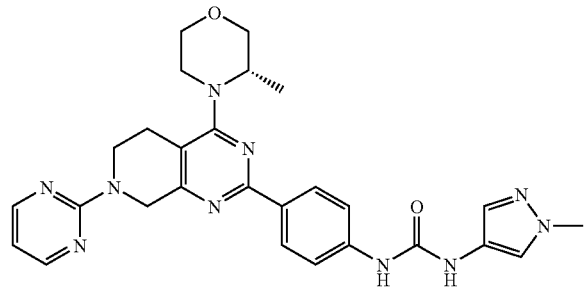

(lh)

Synthesis of (S)-1-(1-methyl-1H-pyrazol-4-yl)-3-(4-(4-(3-methylmorpholino)-7-(pyrimidin-2-yl)-5,6,7,8-tetrahydropyrido[3,4-d]pyrimidin-2-yl)phenyl)urea (lh): The title compound lh was prepared by the general procedure of Example 30 substituting (S)-4-(4-(3-methylmorpholino)-7-(pyrimidin-2-yl)-5,6,7,8-tetrahydropyrido[3,4-d]pyrimidin-2-yl)aniline for 4-(4-morpholino-7-(pyrimidin-2-yl)-5,6,7,8-tetrahydropyrido[4,3-d]pyrimidin-2-yl)aniline and 1-methyl-1H-pyrazol-4-amine for cyclopropylmethylamine. LC-MS: m/z=+527 (M+H)+.

Example 247

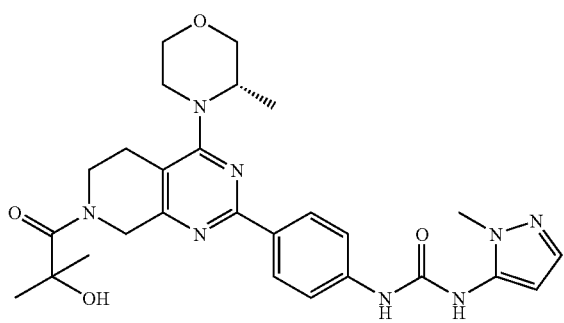

(li)

Synthesis of (S)-1-(4-(7-(2-hydroxy-2-methylpropanoyl)-4-(3-methylmorpholino)-5,6,7,8-tetrahydropyrido[3,4-d]pyrimidin-2-yl)phenyl)-3-(1-methyl-1H-pyrazol-5-yl)urea (li): Compound li was prepared by the general procedure of Example 208, substituting 5-amino-1-methyl-1H-pyrazole for cyclobutyl amine. LC-MS: m/z=+535 (M+H)+.

Example 248

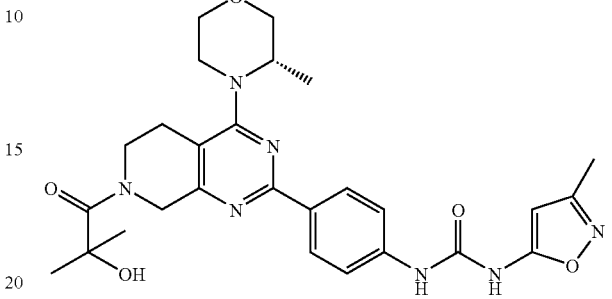

(lj)

Synthesis of (S)-1-(4-(7-(2-hydroxy-2-methylpropanoyl)-4-(3-methylmorpholino)-5,6,7,8-tetrahydropyrido[3,4-d]pyrimidin-2-yl)phenyl)-3-(3-methylisoxazol-5-yl)urea (lj): Compound lj was prepared by the general procedure of Example 208, substituting 5-amino-3-methylisoxazole for cyclobutyl amine. LC-MS: m/z=+536 (M+H)+.

Example 249

(lm)

Synthesis of (S)-1-(4-(7-(2-hydroxy-2-methylpropanoyl)-4-(3-methylmorpholino)-5,6,7,8-tetrahydropyrido[3,4-d]pyrimidin-2-yl)phenyl)-3-(1-methyl-1H-pyrazol-3-yl)urea (lm): Compound lm was prepared by the general procedure of Example 208, substituting 1-methyl-1H-pyrazole-3-amine for cyclobutyl amine. LC-MS: m/z=+535 (M+H)+.

Example 250

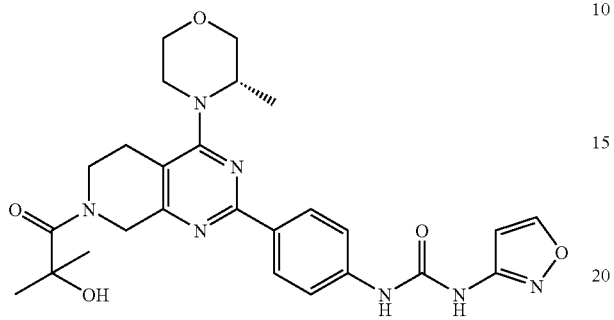
(ln)

Synthesis of (S)-1-(4-(7-(2-hydroxy-2-methylpropanoyl)-4-(3-methylmorpholino)-5,6,7,8-tetrahydropyrido[3,4-d]pyrimidin-2-yl)phenyl)-3-(isoxazol-3-yl)urea (ln). Compound ln was prepared by the general procedure of Example 208, substituting 3-aminoisoxazole for cyclobutyl amine. LC-MS: m/z=+522 (M+H)+.

Example 251

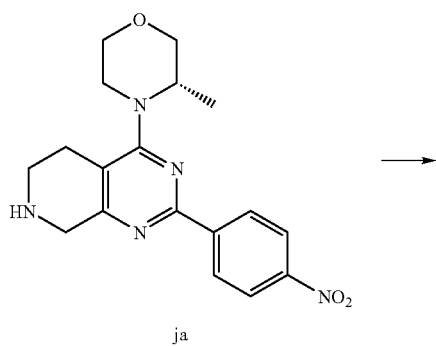
ja

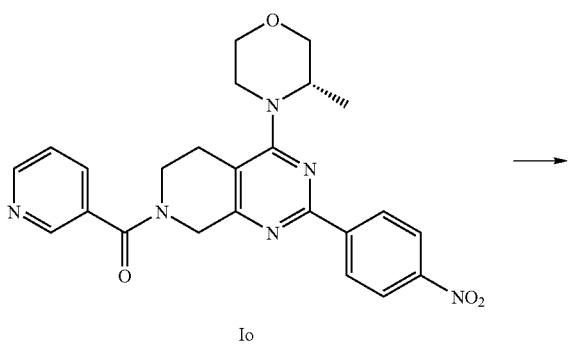
Io

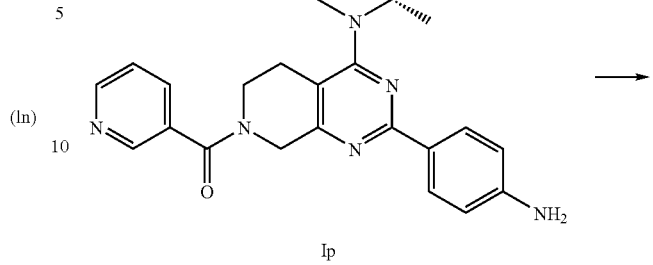
Ip

Iq

Synthesis of (S)-1-(1-methyl-1H-pyrazol-5-yl)-3-(4-(4-(3-methylmorpholino)-7-nicotinoyl-5,6,7,8-tetrahydropyrido[3,4-d]pyrimidin-2-yl)phenyl)urea (Iq)

Step 1—Synthesis of (S)-(4-(3-methylmorpholino)-2-(4-nitrophenyl)-5,6-dihydropyrido[3,4-d]pyrimidin-7(8H)-yl)(pyridin-3-yl)methanone (Io): Compound Ib was prepared by the general procedure of Example 216, step 2, substituting (S)-3-methyl-4-(2-(4-nitrophenyl)-5,6,7,8-tetrahydropyrido[3,4-d]pyrimidin-4-yl)morpholine (ja) for (S)-4-(benzyloxy)-N-(4-(4-(3-methylmorpholino)-5,6,7,8-tetrahydropyrido[3,4-d]pyrimidin-2-yl)phenyl)pyrimidin-2-amine hydrochloride. LC-MS: m/z=+461 (M+H)+.

Step 2—Synthesis of (S)-(2-(4-aminophenyl)-4-(3-methylmorpholino)-5,6-dihydropyrido[3,4-d]pyrimidin-7(8H)-yl)(pyridin-3-yl)methanone (Ip): Compound Ip was prepared by the general procedure of Example 239, step 4. LC-MS: m/z=+431 (M+H)+.

Step 3—Synthesis of (S)-1-(1-methyl-1H-pyrazol-5-yl)-3-(4-(4-(3-methylmorpholino)-7-nicotinoyl-5,6,7,8-tetrahydropyrido[3,4-d]pyrimidin-2-yl)phenyl)urea (Iq): The title compound lq was prepared by the general procedure of Example 30 using 5-amino-1-methyl-1H-pyrazole. LC-MS: m/z=+554 (M+H)+.

Example 252

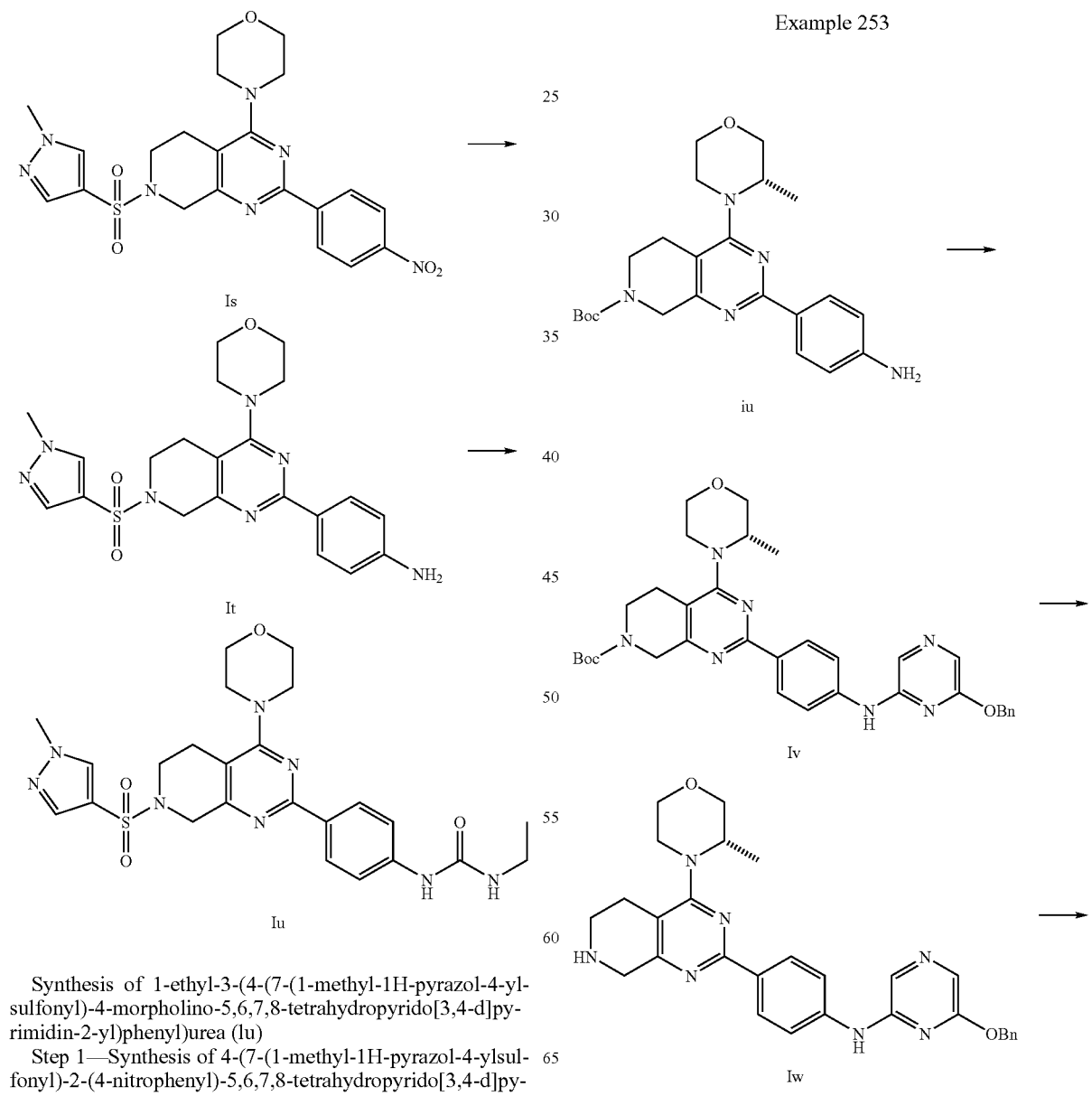

Synthesis of 1-ethyl-3-(4-(7-(1-methyl-1H-pyrazol-4-yl-sulfonyl)-4-morpholino-5,6,7,8-tetrahydropyrido[3,4-d]pyrimidin-2-yl)phenyl)urea (lu)

Step 1—Synthesis of 4-(7-(1-methyl-1H-pyrazol-4-ylsulfonyl)-2-(4-nitrophenyl)-5,6,7,8-tetrahydropyrido[3,4-d]pyrimidin-4-yl)morpholine (ls): Compound is was prepared by the general procedure of Example 216, step 2, substituting (S)-3-methyl-4-(2-(4-nitrophenyl)-5,6,7,8-tetrahydropyrido[3,4-d]pyrimidin-4-yl)morpholine (lr) for (S)-4-(benzyloxy)-N-(4-(4-(3-methylmorpholino)-5,6,7,8-tetrahydropyrido[3,4-d]pyrimidin-2-yl)phenyl)pyrimidin-2-amine hydrochloride and 1-methyl-1H-pyrazole-4-sulfonyl chloride for nicotinoyl chloride hydrochloride LC-MS: m/z=+486 (M+H)+.

Step 2—Synthesis of 4-(7-(1-methyl-1H-pyrazol-4-ylsulfonyl)-4-morpholino-5,6,7,8-tetrahydropyrido[3,4-d]pyrimidin-2-yl)aniline (lt): Compound it was prepared by the general procedure of Example 239, step 4. LC-MS: m/z=+456 (M+H)+.

Step 3—Synthesis of 1-ethyl-3-(4-(7-(1-methyl-1H-pyrazol-4-ylsulfonyl)-4-morpholino-5,6,7,8-tetrahydropyrido[3,4-d]pyrimidin-2-yl)phenyl)urea (lu): The title compound lu was prepared by the general procedure of Example 238, step 2. LC-MS: m/z=+527 (M+H)+.

Example 253

-continued

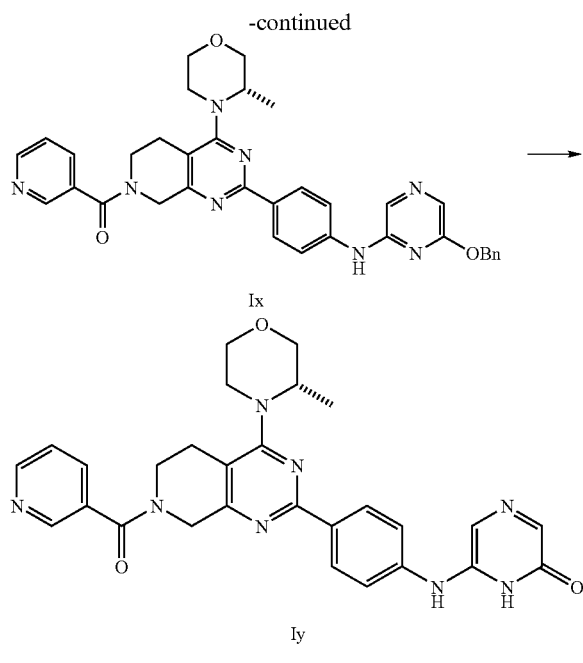

Synthesis of (S)-6-(4-(4-(3-methylmorpholino)-7-nicotinoyl-5,6,7,8-tetrahydropyrido[3,4-d]pyrimidin-2-yl)phenylamino)pyrazin-2(1H)-one (ly)

Step 1—Synthesis of (S)-tert-butyl 2-(4-(6-(benzyloxy) pyrazin-2-ylamino)phenyl)-4-(3-methylmorpholino)-5,6-dihydropyrido[3,4-d]pyrimidine-7(8H)-carboxylate (lv). Compound lv was prepared by the general procedure of Example 212, step 1, by substituting 6-chloro-2-(benzyloxy) pyrazine for 4-(benzyloxy)-2-chloropyrimidine. LC-MS: m/z=+610 (M+H)+.

Step 2—Synthesis of (S)-6-(benzyloxy)-N-(4-(4-(3-methylmorpholino)-5,6,7,8-tetrahydropyrido[3,4-d]pyrimidin-2-yl)phenyl)pyrazin-2-amine (lw). (S)-tert-butyl 2-(4-(6-(benzyloxy)pyrazin-2-ylamino)phenyl)-4-(3-methylmorpholino)-5,6-dihydropyrido[3,4-d]pyrimidine-7(8H)-carboxylate (lv) from step 1 (568 mg, 0.9 mmol) was treated with 4 N HCl/dioxane (10 mL) at rt for 1.5 hrs. The reaction mixture was diluted with ether, stirred for 15 min. The precipitates were filtered, washed with ether, and dried to afford 530 mg (100%) of compound lw as a HCl salt. LC-MS: m/z=+511 (M+H)+.

Step 3—Synthesis of (S)-(2-(4-(6-(benzyloxy)pyrazin-2-ylamino)phenyl)-4-(3-methylmorpholino)-5,6-dihydropyrido[3,4-d]pyrimidin-7(8H)-yl)(pyridin-3-yl)methanone (lx). Compound lx was prepared by the general procedure of Example 251, Step 1, Substituting (S)-6-(benzyloxy)-N-(4-(4-(3-methylmorpholino)-5,6,7,8-tetrahydropyrido[3,4-d] pyrimidin-2-yl)phenyl)pyrazin-2-amine (lw) for (S)-3-methyl-4-(2-(4-nitrophenyl)-5,6,7,8-tetrahydropyrido[3,4-d] pyrimidin-4-yl)morpholine. LC-MS: m/z=+615 (M+H)+.

Step 4—Synthesis of (S)-6-(4-(4-(3-methylmorpholino)-7-nicotinoyl-5,6,7,8-tetrahydropyrido[3,4-d]pyrimidin-2-yl) phenylamino)pyrazin-2(1H)-one (ly): (S)-(2-(4-(6-(benzyloxy)pyrazin-2-ylamino)phenyl)-4-(3-methylmorpholino)-5,6-dihydropyrido[3,4-d]pyrimidin-7(8H)-yl)(pyridin-3-yl) methanone (lx) from step 3 (50 mg, 0.08 mmol) was dissolved in AcOH (0.75 mL). To this solution was added 33% HBr/AcOH (0.55 mL, 3.0 mmol), stirred at rt overnight. It was diluted with MeOH, concentrated in vacuo, purified by RP-HPLC to afford 17 mg (40%) of the title compound ly. LC-MS: m/z=+525 (M+H)+.

Example 254

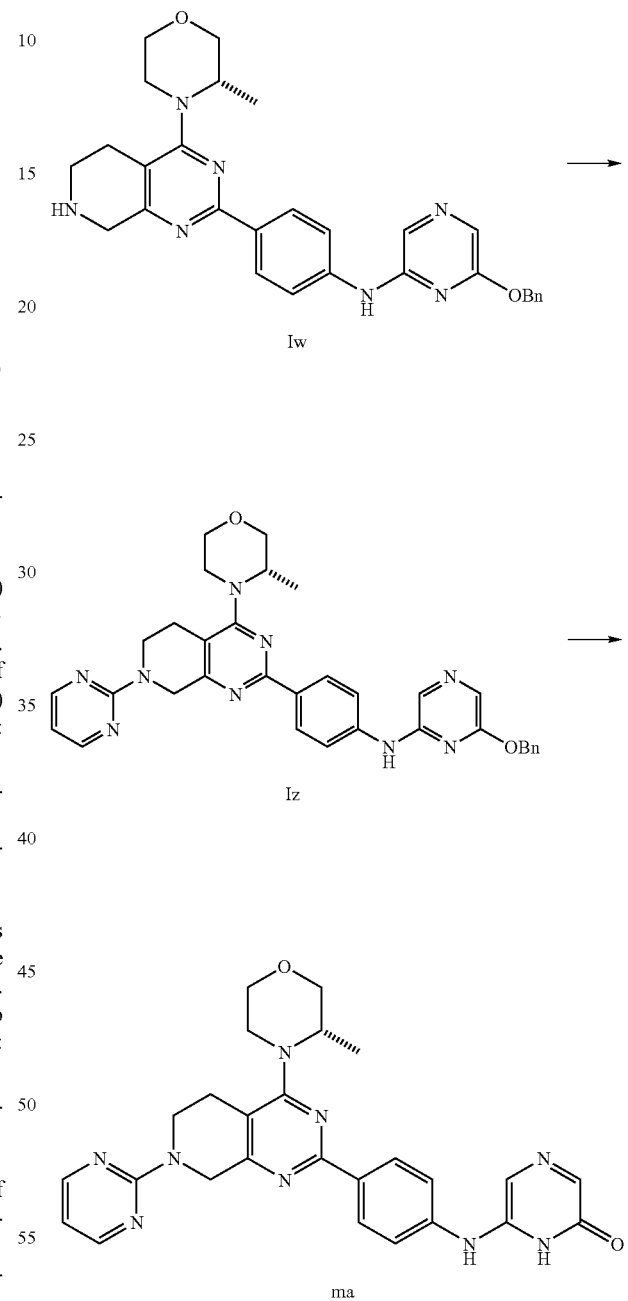

Step 1—Synthesis of (S)-6-(benzyloxy)-N-(4-(4-(3-methylmorpholino)-7-(pyrimidin-2-yl)-5,6,7,8-tetrahydropyrido [3,4-d]pyrimidin-2-yl)phenyl)pyrazin-2-amine (lz): Compound lz was prepared by the general procedure in Example 238, Step 4. LC-MS: m/z=+588 (M+H)+.

Step 2—Synthesis of (S)-6-(4-(4-(3-methylmorpholino)-7-(pyrimidin-2-yl)-5,6,7,8-tetrahydropyrido[3,4-d]pyrimidin-2-yl)phenylamino)pyrazin-2(1H)-one (ma): The title compound ma was prepared by the general procedure of Example 253, step 4. LC-MS: m/z=+498 (M+H)+.

Example 255

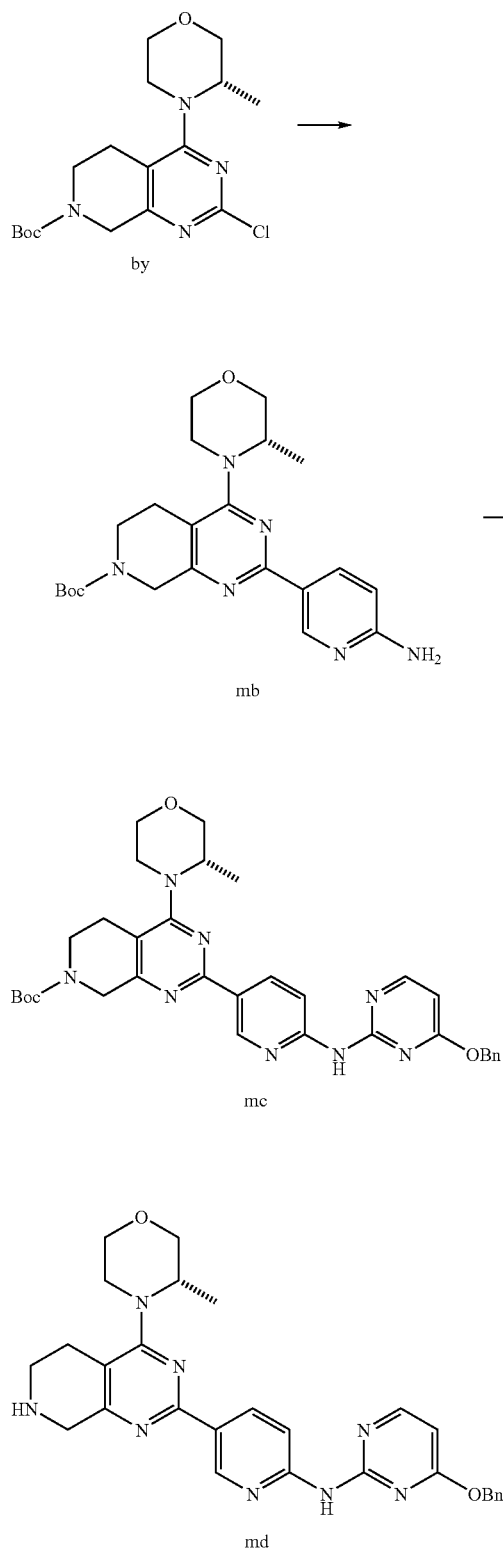

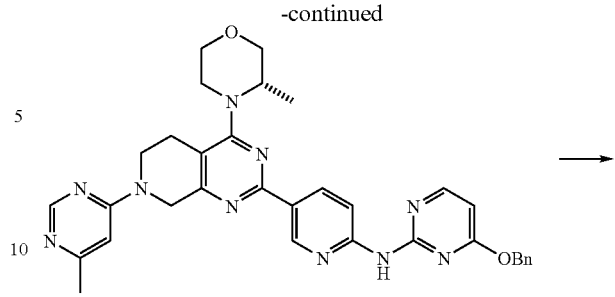

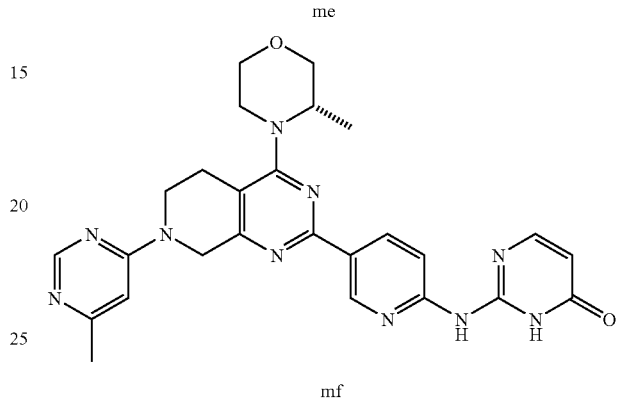

Synthesis of (S)-6-(4-(4-(3-methylmorpholino)-7-(6-methylpyrimidin-4-yl)-5,6,7,8-tetrahydropyrido[3,4-d]pyrimidin-2-yl)phenylamino)pyrazin-2(1H)-one (mf)

Step 1—Synthesis of (S)-tert-butyl 2-(6-aminopyridin-3-yl)-4-(3-methylmorpholino)-5,6-dihydropyrido[3,4-d]pyrimidine-7(8H)-carboxylate (mb): The title compound mb was prepared by following the general procedure in Example 1, Step 2, substituting (S)-tert-butyl 2-chloro-4-(3-methylmorpholino)-5,6-dihydropyrido[3,4-d]pyrimidine-7(8H)-carboxylate for tert-butyl 2-chloro-4-morpholino-5H-pyrrolo[3,4-d]pyrimidine-6(7H)-carboxylate and 2-aminopyridine-5-boronic acid, pinacol ester for (4-ethylureido)phenylboronic acid pinacol ester. $^1$H NMR (500 MHz, DMSO) δ 8.85 (d, J=2.1, 1H), 8.19 (dd, J=8.7, 2.3, 1H), 6.48 (d, J=8.7, 1H), 6.39 (s, 2H), 4.44 (t, J=27.5, 2H), 4.08 (d, J=6.9, 1H), 3.86 (d, J=11.7, 1H), 3.67 (d, J=2.7, 1H), 3.60 (dd, J=11.8, 3.7, 4H), 3.45-3.39 (m, 2H), 2.63 (s, 2H), 1.44 (d, J=8.7, 9H), 1.24 (d, J=6.7, 3H). LC-MS: m/z=+427 (M+H)+.

Step 2—Synthesis of (S)-tert-butyl 2-(6-(4-(benzyloxy)pyrimidin-2-ylamino)pyridin-3-yl)-4-(3-methylmorpholino)-5,6-dihydropyrido[3,4-d]pyrimidine-7(8H)-carboxylate (mc). Prepared by the general procedure of Example 253, step 1, substituting (S)-tert-butyl 2-(6-aminopyridin-3-yl)-4-(3-methylmorpholino)-5,6-dihydropyrido[3,4-d]pyrimidine-7(8H)-carboxylate for (S)-tert-butyl 2-(4-aminophenyl)-4-(3-methylmorpholino)-5,6-dihydropyrido[3,4-d]pyrimidine-7(8H)-carboxylate and 4-(benzyloxy)-2-chloropyrimidine for 6-chloro-2-(benzyloxy)pyrazine. LC-MS: m/z=+611 (M+H)+.

Step 3—Synthesis of (S)-4-(benzyloxy)-N-(5-(4-(3-methylmorpholino)-5,6,7,8-tetrahydropyrido[3,4-d]pyrimidin-2-yl)pyridin-2-yl)pyrimidin-2-amine (md). Compound md was prepared by the general procedure of Example 253, step 2 to afford a HCl salt of compound md. LC-MS: m/z=+511 (M+H)+.

Step 4—Synthesis of (S)-4-(benzyloxy)-N-(5-(4-(3-methylmorpholino)-7-(6-methylpyrimidin-4-yl)-5,6,7,8-tetrahydropyrido[3,4-d]pyrimidin-2-yl)pyridin-2-yl)pyrimidin-2- amine (me): Compound me was prepared by following the general procedure in Example Example 238, Step 4, substituting 4-chloro-6-methylpyrimidine for 2-chloropyrimidine. LC-MS: m/z=+603 (M+H)+.

Step 5—Synthesis of (S)-6-(4-(4-(3-methylmorpholino)-7-(6-methylpyrimidin-4-yl)-5,6,7,8-tetrahydropyrido[3,4-d]pyrimidin-2-yl)phenylamino)pyrazin-2(1H)-one (mf). The title compound mf was prepared by the general procedure of Example 253, step 4. LC-MS: m/z=+513 (M+H)+.

Example 256

(mg)

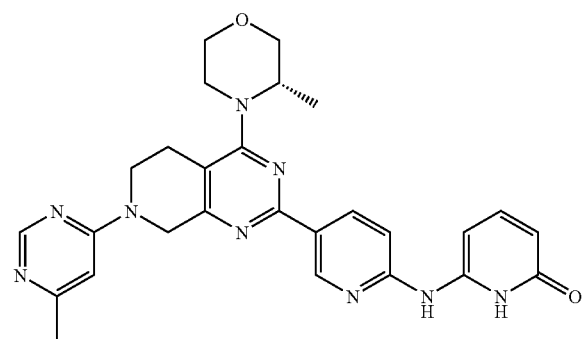

Synthesis of (S)-6-(5-(4-(3-methylmorpholino)-7-(6-methylpyrimidin-4-yl)-5,6,7,8-tetrahydropyrido[3,4-d]pyrimidin-2-yl)pyridin-2-ylamino)pyridin-2(1H)-one (mg). The title compound mg was prepared by the general procedure of Example 255 by substituting 2-(benzyloxy)-6-bromopyridine for 4-(benzyloxy)-2-chloropyrimidine. LC-MS: m/z=+512 (M+H)+.

Example 257

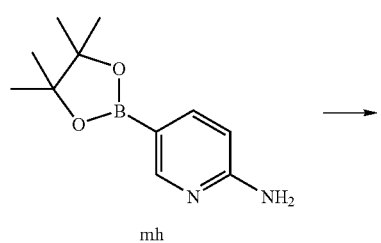

mh

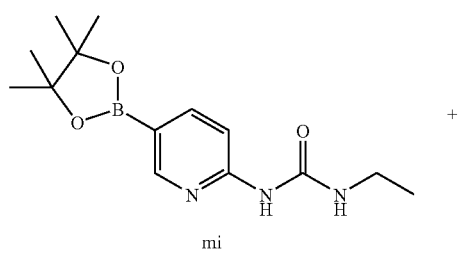

mi

-continued

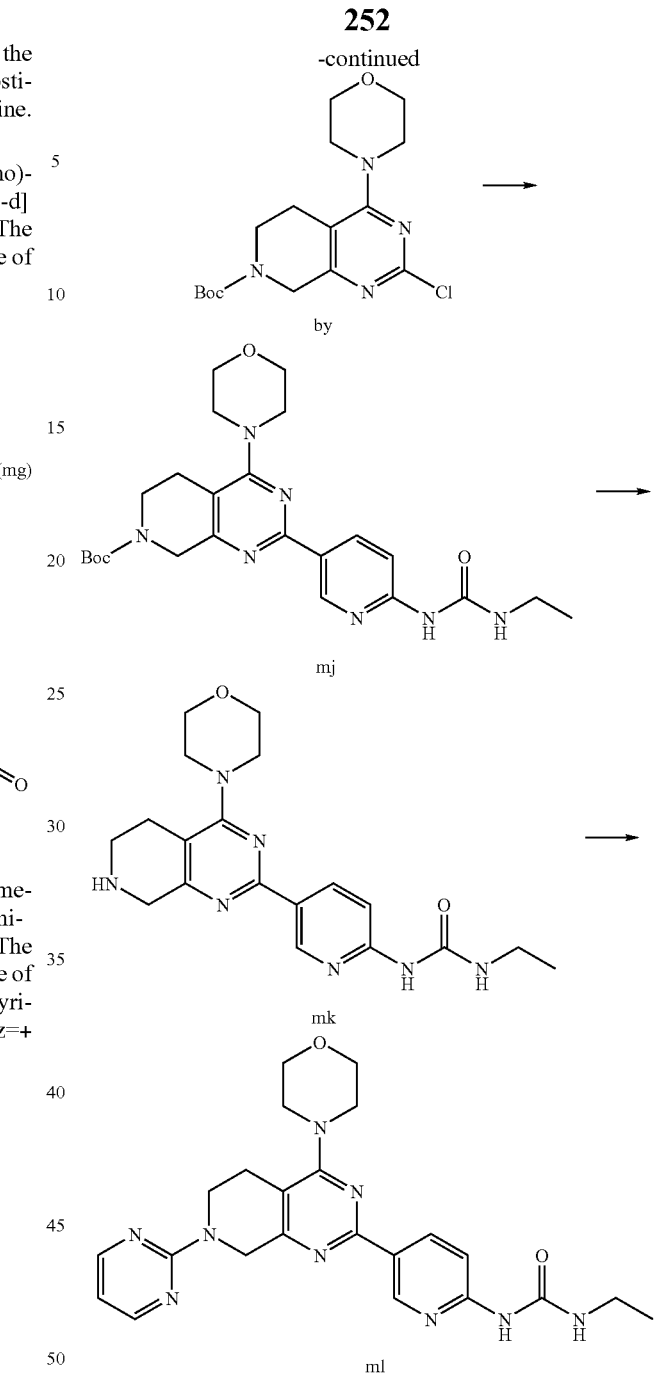

Synthesis of (S)-1-ethyl-3-(5-(4-(3-methylmorpholino)-7-(pyrimidin-2-yl)-5,6,7,8-tetrahydropyrido[3,4-d]pyrimidin-2-yl)pyridin-2-yl)urea (ml)

Step 1—Synthesis of 1-ethyl-3-(5-(4,4,5,5-tetramethyl-1,3,2-dioxaborolan-2-yl)pyridin-2-yl)urea (mi): A mixture of 5-(4,4,5,5-tetramethyl-1,3,2-dioxaborolan-2-yl)pyridin-2-amine (mh) (500 mg, 2 mmol) and ethyl isocyanate (200 μL, 2.5 mmol) in DCM (20 mL) was stirred at rt overnight. Additional ethyl isocyanate (400 μL) was added, stirred for another 24 hrs. The reaction mixture was concentrated onto Celite, and chromatographed using an ISCO silica gel column, 12 g column, 0-5% MeOH/DCM to afford 475 mg (70%) of white solid as the product mi. $^{1}$H NMR (400 MHz, CDCl3) δ 9.38 (s, 1H), 8.55 (d, J=1.0, 1H), 7.91 (dd, J=8.2, 1.8, 1H), 7.46 (s, 1H), 6.65 (d, J=8.3, 1H), 3.41 (qd, J=7.2, 5.6, 2H), 1.33 (s, 12H), 1.24 (dd, J=8.2, 6.3, 3H). LC-MS: m/z=+292 (M+H)+.

Step 2—Synthesis of (S)-tert-butyl 2-(6-(3-ethylureido)pyridin-3-yl)-4-(3-methylmorpholino)-5,6-dihydropyrido[3,4-d]pyrimidine-7(8H)-carboxylate (mj). Compound mj was prepared by the general procedure of Example 255, step 1, by substituting 1-ethyl-3-(5-(4,4,5,5-tetramethyl-1,3,2-dioxaborolan-2-yl)pyridin-2-yl)urea (mi) for 5-(4,4,5,5-tetramethyl-1,3,2-dioxaborolan-2-yl)pyridin-2-amine. 1H NMR (400 MHz, CDCl3) δ 9.43 (s, 1H), 9.18 (d, J=2.0, 1H), 8.52 (dd, J=8.6, 2.1, 1H), 7.73 (s, 1H), 6.76 (d, J=8.6, 1H), 4.66 (d, J=18.7, 1H), 4.52 (d, J=18.7, 1H), 4.12-4.03 (m, 1H), 3.95 (s, 1H), 3.85-3.68 (m, 4H), 3.65-3.51 (m, 2H), 3.51-3.39 (m, 3H), 2.68 (s, 2H), 1.52 (s, 9H), 1.35 (d, J=6.7, 3H), 1.27 (dd, J=11.8, 4.5, 3H). LC-MS: m/z=+498 (M+H)+.

Step 3—Synthesis of (S)-1-ethyl-3-(5-(4-(3-methylmorpholino)-5,6,7,8-tetrahydropyrido[3,4-d]pyrimidin-2-yl)pyridin-2-yl)urea (mk). Product mj from Step 2 was treated with 4 N HCl/dioxane (10 mL) at rt for 1 hr. It was diluted with ether. The precipitate was filtered off, washed with ether, and dried under high vacuum to afford 210 mg (100%) yellow solid compound mk as a HCl salt. It was used as crude material without further purification. LC-MS: m/z=+399 (M+H)+.

Step 4—Synthesis of (S)-1-ethyl-3-(5-(4-(3-methylmorpholino)-7-(pyrimidin-2-yl)-5,6,7,8-tetrahydropyrido[3,4-d]pyrimidin-2-yl)pyridin-2-yl)urea (ml). The title compound ml was prepared by the general procedure of Example 255, step 4, and using 2-chloropyrimidine. 1H NMR (400 MHz, DMSO) δ 9.43 (s, 1H), 9.10 (d, J=1.9, 1H), 8.49 (dd, J=8.8, 2.3, 1H), 8.44 (d, J=4.7, 2H), 8.14 (s, 1H), 7.46 (d, J=8.8, 1H), 6.70 (t, J=4.7, 1H), 4.89 (d, J=18.8, 1H), 4.75 (d, J=18.8, 1H), 4.20-4.07 (m, 2H), 3.85 (dd, J=16.3, 8.0, 2H), 3.73-3.66 (m, 2H), 3.64-3.56 (m, 2H), 3.46-3.38 (m, 1H), 3.25-3.17 (m, 2H), 2.75 (s, 2H), 1.26 (d, J=6.6, 3H), 1.14-1.10 (m, 3H). LC-MS: m/z=+476 (M+H)+.

Example 258

(mm)

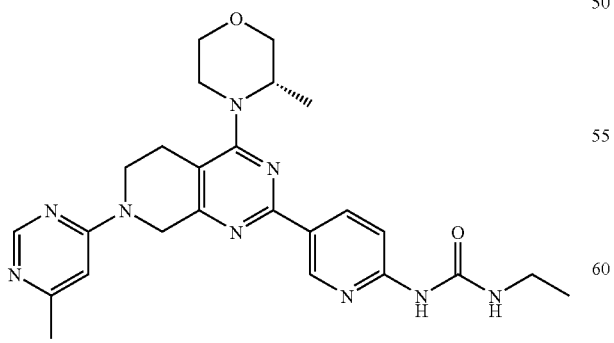

Synthesis of (S)-1-ethyl-3-(5-(4-(3-methylmorpholino)-7-(6-methylpyrimidin-4-yl)-5,6,7,8-tetrahydropyrido[3,4-d]pyrimidin-2-yl)pyridin-2-yl)urea (mm): Compound mm was prepared by the general procedure of Example 257 using 4-chloro-6-methylpyrimidine. LC-MS: m/z=+490 (M+H)+.

Example 259

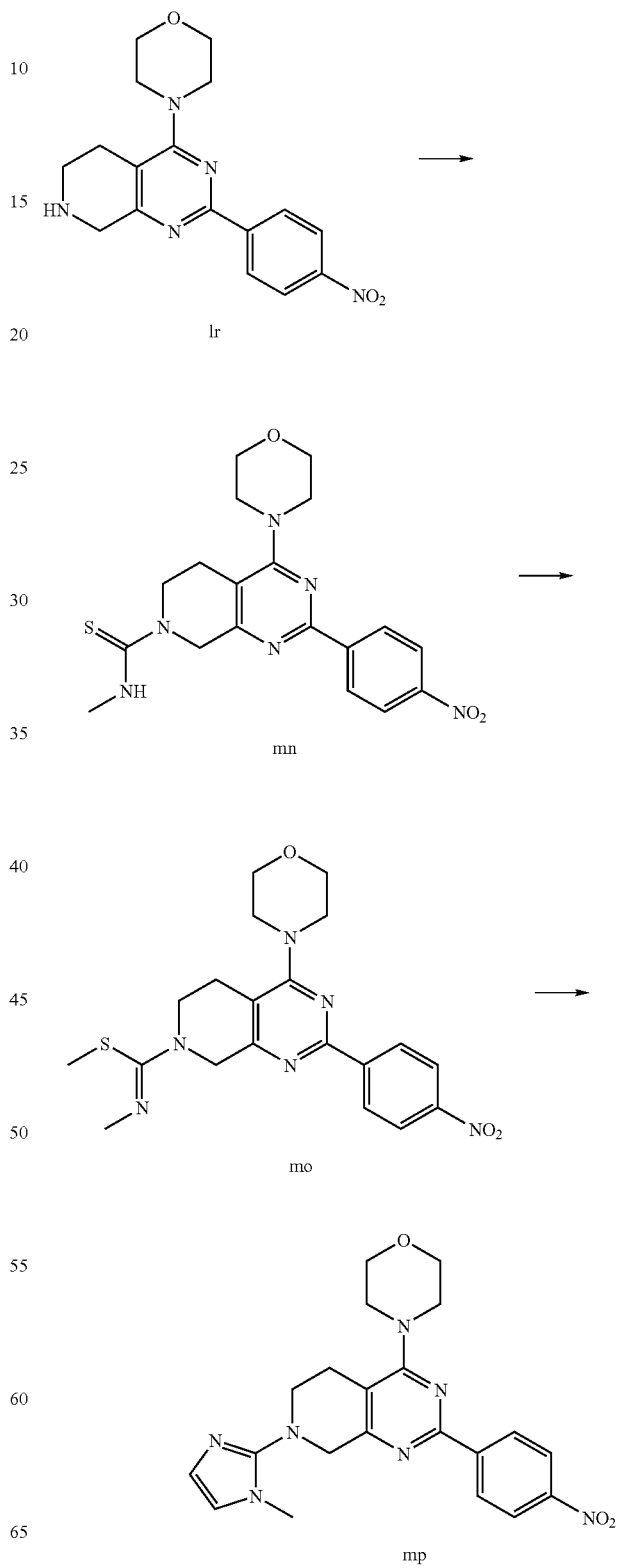

lr mn mo mp

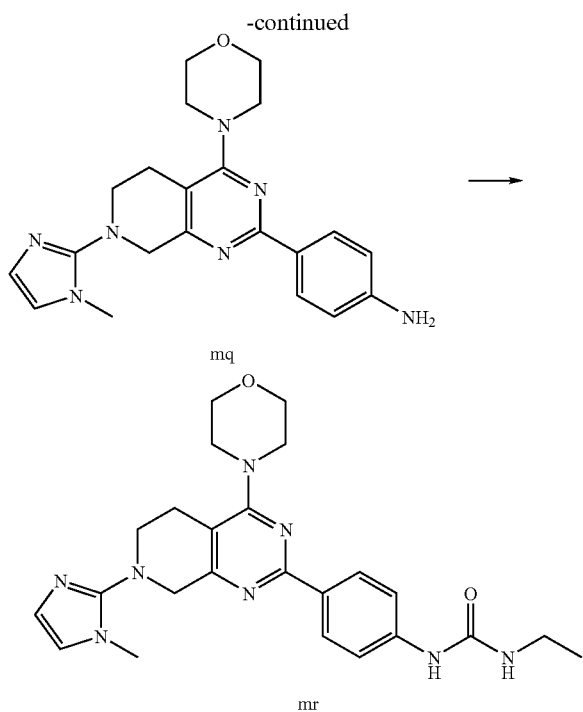

Synthesis of 1-ethyl-3-(4-(7-(1-methyl-1H-imidazol-2-yl)-4-morpholino-5,6,7,8-tetrahydropyrido[3,4-d]pyrimidin-2-yl)phenyl)urea (mr)

Step 1—Synthesis of N-methyl-4-morpholino-2-(4-nitrophenyl)-5,6-dihydropyrido[3,4-d]pyrimidine-7(8H)-carbothioamide (mn): To a solution of 4-(2-(4-nitrophenyl)-5,6,7,8-tetrahydropyrido[3,4-d]pyrimidin-4-yl)morpholine (lr) (486 mg, 1.4 mmol) in DMF (15 mL) was added dropwise a solution of isothiocyanatomethane (208 mg, 2.8 mmol) in DMF (3 mL) at rt. After 3.5 hrs, LCMS showed reaction proceeded slowly. Additional isothiocyanatomethane (104 mg) was added. It was stirred at rt for 48 hrs. It was diluted with H$_2$O. The solid was filtered off, washed with H$_2$O, dried to afford 443 mg (75%) desired compound mn as a light yellow solid. $^1$H NMR (500 MHz, DMSO) δ 8.58-8.53 (m, 2H), 8.38-8.33 (m, 2H), 7.93 (d, J=4.2, 1H), 4.91 (s, 2H), 4.04 (t, J=5.1, 2H), 3.77-3.72 (m, 4H), 3.59-3.54 (m, 4H), 2.96 (d, J=4.1, 3H), 2.76 (t, J=5.1, 2H). LC-MS: m/z=+415 (M+H)+.

Step 2—Synthesis of (E)-methyl N-methyl-4-morpholino-2-(4-nitrophenyl)-5,6-dihydropyrido[3,4-d]pyrimidine-7(8H)-carbimidothioate hydroiodide (mo). Compound mn from step 1 (443 mg, 1.1 mmol) was suspended in DMF (8 mL). To this suspension was added dropwise a solution of methyl iodide (166 µL, 2.7 mmol) in DMF (2 mL). The resulting mixture was stirred at rt for 18 hrs. DMF was removed in vacuo. The residue was triturated in H$_2$O. The solid was filtered off, washed with H$_2$O, and dried under high vacuum to afford 568 mg (95%) of desired compound mo as a HI salt. $^1$H NMR (400 MHz, DMSO) ä 8.55 (d, J=9.0, 2H), 8.37 (d, J=9.0, 2H), 4.89 (s, 2H), 4.00 (s, 2H), 3.76 (d, J=4.5, 4H), 3.60 (d, J=4.4, 4H), 3.21 (s, 3H), 2.93 (s, 2H), 2.66 (s, 3H). LC-MS: m/z=+429 (M+H)+.

Step 3—Synthesis of 4-(7-(1-methyl-1H-imidazol-2-yl)-2-(4-nitrophenyl)-5,6,7,8-tetrahydropyrido[3,4-d]pyrimidin-4-yl)morpholine (mp): To a solution of product mo from step 2 (260 mg, 0.5 mmol) in pyridine (3 mL) was added dropwise 2,2-diethoxyethanamine (82 µL, 0.6 mmol) at rt. The resulting solution was heated at 115° C. for 3.5 hrs. After the reaction mixture cooled, it was concentrated in vacuo. The residue was treated with 2 N aqueous HCl (2.5 mL), and heated to reflux for 1 hr. The reaction solution was then cooled, and diluted with H$_2$O, made basic with sat. aq. NaHCO$_3$, extracted with EtOAc (3×10 mL). The combined organics were dried over Magnesium sulfate, filtered, concentrated onto Celite, and chromatographed (ISCO, 12 g column, 0-5% MeOH/EtOAc) to afford 113 mg (57%) of desired compound mp as a yellow solid. $^1$H NMR (400 MHz, CDCl3) δ 8.59-8.53 (m, 2H), 8.32-8.26 (m, 2H), 6.83 (d, J=1.4, 1H), 6.74 (d, J=1.4, 1H), 4.38 (s, 2H), 3.91-3.85 (m, 4H), 3.62-3.56 (m, 7H), 3.38 (t, J=5.4, 2H), 2.90-2.84 (m, 2H). LC-MS: m/z=+422 (M+H)+.

Step 4—Synthesis of 4-(7-(1-methyl-1H-imidazol-2-yl)-4-morpholino-5,6,7,8-tetrahydropyrido[3,4-d]pyrimidin-2-yl)aniline (mq): Compound mq was prepared by the general procedure of Example 239, step 4. 1H NMR (400 MHz, DMSO) ä 8.03 (d, J=8.6, 2H), 6.93 (d, J=1.3, 1H), 6.63 (d, J=1.3, 1H), 6.59 (d, J=8.7, 2H), 5.54 (s, 2H), 4.17 (s, 2H), 3.77-3.72 (m, 4H), 3.53 (s, 3H), 3.45 (d, J=4.2, 4H), 3.18 (t, J=5.0, 2H), 2.78 (d, J=4.9, 2H). LC-MS: m/z=+392 (M+H)+.

Step 5—Synthesis of 1-ethyl-3-(4-(7-(1-methyl-1H-imidazol-2-yl)-4-morpholino-5,6,7,8-tetrahydropyrido[3,4-d]pyrimidin-2-yl)phenyl)urea (mr). The title compound was prepared by the general procedure of Example 238, step 2. 1H NMR (400 MHz, DMSO) δ 8.66 (s, 1H), 8.19 (d, J=8.8, 2H), 7.48 (d, J=8.8, 2H), 6.93 (d, J=1.3, 1H), 6.63 (d, J=1.4, 1H), 6.17 (t, J=5.6, 1H), 4.21 (s, 2H), 3.78-3.73 (m, 4H), 3.54 (s, 3H), 3.49 (d, J=4.4, 4H), 3.20 (t, J=5.1, 2H), 3.16-3.08 (m, 2H), 2.81 (d, J=4.8, 2H), 1.06 (t, J=7.2, 3H). LC-MS: m/z=+463 (M+H)+.

Example 260

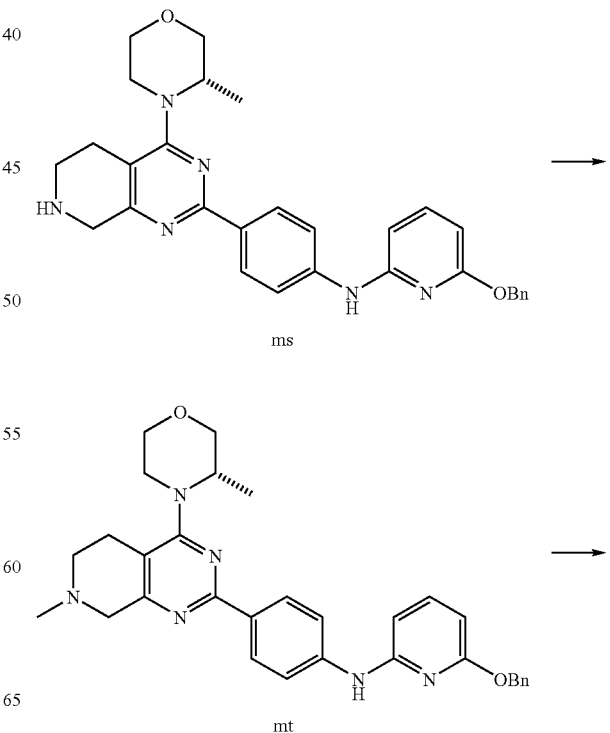

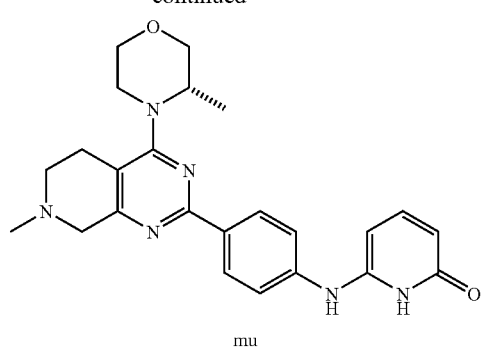

mu

Synthesis of (S)-6-(4-(7-methyl-4-(3-methylmorpholino)-5,6,7,8-tetrahydropyrido[3,4-d]pyrimidin-2-yl)phenylamino)pyridin-2(1H)-one (mu)

Step 1—Synthesis of (S)-6-(benzyloxy)-N-(4-(7-methyl-4-(3-methylmorpholino)-5,6,7,8-tetrahydropyrido[3,4-d]pyrimidin-2-yl)phenyl)pyridin-2-amine (mt): (S)-6-(benzyloxy)-N-(4-(4-(3-methylmorpholino)-5,6,7,8-tetrahydropyrido[3,4-d]pyrimidin-2-yl)phenyl)pyridin-2-amine (ms) (100 mg, 0.2 mmol) was dissolved in DMF (2 mL) and DIPEA (159 μL, 0.9 mmol)). To this solution was added MeI (14 μL, 0.2 mmol) at rt. The resulting solution was stirred at rt for 4 hrs. It was diluted with H$_2$O, extracted with EtOAc (2×10 mL). The combined organics were washed with brine, dried over Magnesium sulfate, filtered, concentrated in vacuo to afford 100 mg (100%) of the title compound mt. LC-MS: m/z=+524 (M+H)+.

Step 2—Synthesis of (S)-6-(4-(7-methyl-4-(3-methylmorpholino)-5,6,7,8-tetrahydropyrido[3,4-d]pyrimidin-2-yl)phenylamino)pyridin-2(1H)-one (mu): To a solution of product mt from step 1 (100 mg, 0.2 mmol) in CHCl$_3$ (2 mL) was added dropwise methanesulfonic acid (470 μL, 7.2 mmol) at rt. After 3 hrs, additional methansulfonic acid (225 μL) was added, stirred at rt overnight. It was diluted with H$_2$O, quenched with sat. NaHCO$_3$, extracted with DCM (2×10 mL). The combined DCM extracts were dried over Magnesium sulfate, filtered, concentrated in vacuo, and purified by RP-HPLC to afford 12.3 mg (10%) of the title compound mu. LC-MS: m/z=+434 (M+H)+.

Example 261

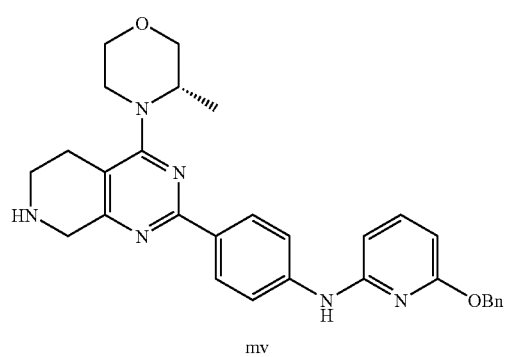

mv

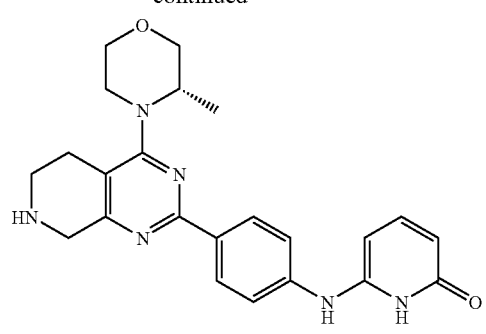

mw

Synthesis of (S)-6-(4-(4-(3-methylmorpholino)-5,6,7,8-tetrahydropyrido[3,4-d]pyrimidin-2-yl)phenylamino)pyridin-2(1H)-one (mw): Compound mw was prepared by the general procedure of Example 260, step 2. LC-MS: m/z=+420 (M+H)+.

Example 262

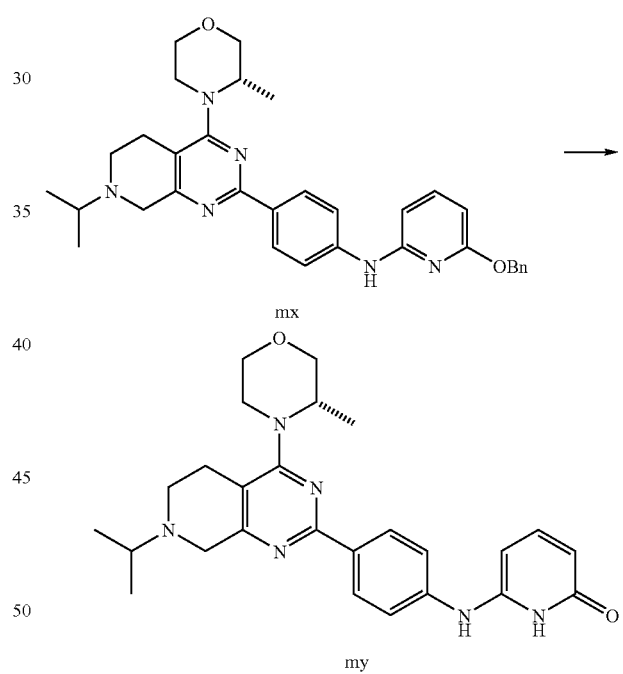

mx my

Synthesis of (S)-6-(4-(7-isopropyl-4-(3-methylmorpholino)-5,6,7,8-tetrahydropyrido[3,4-d]pyrimidin-2-yl)phenylamino)pyridin-2(1H)-one (my)

Step 1—Synthesis of (S)-6-(benzyloxy)-N-(4-(7-isopropyl-4-(3-methylmorpholino)-5,6,7,8-tetrahydropyrido[3,4-d]pyrimidin-2-yl)phenyl)pyridin-2-amine (mx). Compound mx was prepared by the general procedure of Example 260, step 1, and using isopropopyl iodide instead of methyl iodide. LC-MS: m/z=+552 (M+H)+.

Step 2—Synthesis of (S)-6-(4-(7-isopropyl-4-(3-methylmorpholino)-5,6,7,8-tetrahydropyrido[3,4-d]pyrimidin-2-yl)phenylamino)pyridin-2(1H)-one (my): Compound my was prepared by the general procedure of Example 253, step 4. LC-MS: m/z=+462 (M+H)+.

Example 263

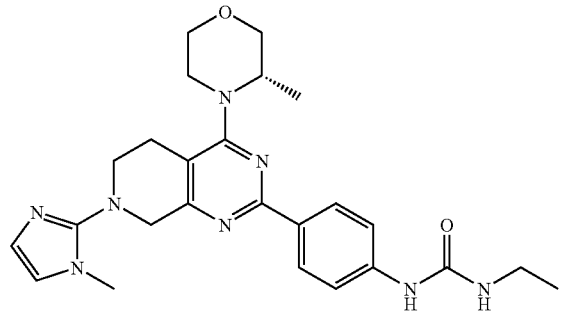

(mz)

Synthesis of (S)-1-ethyl-3-(4-(7-(1-methyl-1H-imidazol-2-yl)-4-(3-methylmorpholino)-5,6,7,8-tetrahydropyrido[3,4-d]pyrimidin-2-yl)phenyl)urea (mz): Compound mz was prepared by the general procedure of Example 259 substituting (S)-3-methylmorpholine for morpholine. LC-MS: m/z=+477 (M+H)+.

Example 264

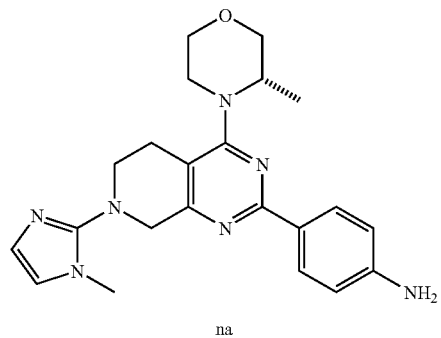

na

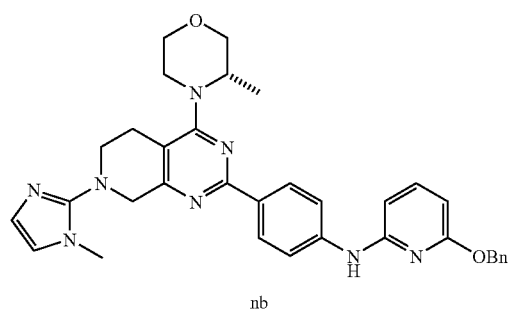

nb

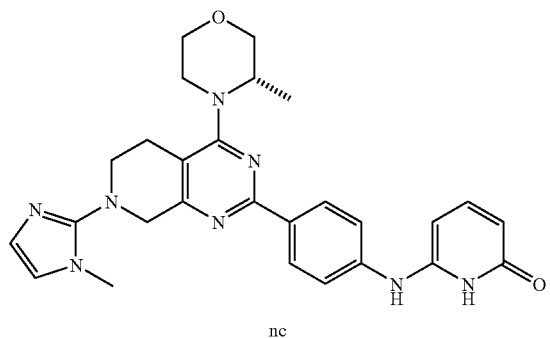

nc

Synthesis of (S)-6-(4-(7-(1-methyl-1H-imidazol-2-yl)-4-(3-methylmorpholino)-5,6,7,8-tetrahydropyrido[3,4-d]pyrimidin-2-yl)phenylamino)pyridin-2(1H)-one (nc)

Step 1—Synthesis of (S)-6-(benzyloxy)-N-(4-(7-(1-methyl-1H-imidazol-2-yl)-4-(3-methylmorpholino)-5,6,7,8-tetrahydropyrido[3,4-d]pyrimidin-2-yl)phenyl)pyridin-2-amine (nb). Compound nb was prepared by the general procedure of Example 255, step 2, and using (S)-4-(7-(1-methyl-1H-imidazol-2-yl)-4-(3-methylmorpholino)-5,6,7,8-tetrahydropyrido[3,4-d]pyrimidin-2-yl)aniline from Example 263 and 2-bromo-6-benzyloxypyridine. LC-MS: m/z=+589 (M+H)+.

Step 2—Synthesis of (S)-6-(4-(7-(1-methyl-1H-imidazol-2-yl)-4-(3-methylmorpholino)-5,6,7,8-tetrahydropyrido[3,4-d]pyrimidin-2-yl)phenylamino)pyridin-2(1H)-one (nc). Compound nc was prepared by the general procedure of Example 253 step 4. LC-MS: m/z=+499 (M+H)+.

Example 265

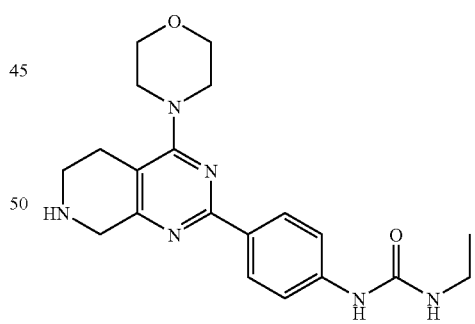

bf

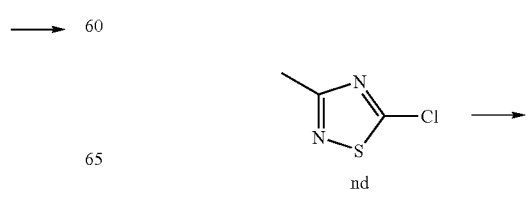

nd

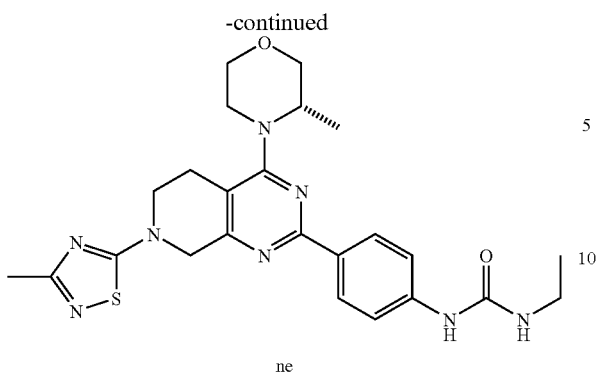

ne

Synthesis of 1-ethyl-3-(4-(7-(3-methyl-1,2,4-thiadiazol-5-yl)-4-morpholino-5,6,7,8-tetrahydropyrido[3,4-d]pyrimidin-2-yl)phenyl)urea (ne)

Step 1—Synthesis of 5-chloro-3-methyl-1,2,4-thiadiazole (nd): To a mixture of acetamidine hydrochloride (1 g, 10 mmol) and trichloromethyl hypochlorothioite (1.2 mL, 10 mmol) in DCM (10 mL) was cooled to −5° C., 6 N aq. NaOH (8.8 mL, 50 mmol) was added dropwise. The resulting mixture was stirred at 0° C. for 30 min and then allowed to warm to rt. The biphasic was separated, and the aqueous was extracted with DCM. The combined DCM were washed with brine, dried over Magnesium sulfate, filtered, concentrated in vacuo to give a semi oil material, 948 mg (66%). The crude product nd was used immediately without further purification.

Step 2—Synthesis of 1-ethyl-3-(4-(7-(3-methyl-1,2,4-thiadiazol-5-yl)-4-morpholino-5,6,7,8-tetrahydropyrido[3,4-d]pyrimidin-2-yl)phenyl)urea (ne). To a mixture of 1-ethyl-3-(4-(4-morpholino-5,6,7,8-tetrahydropyrido[3,4-d]pyrimidin-2-yl)phenyl)urea (bf) (100 mg, 0.3 mmol) and 5-chloro-3-methyl-1,2,4-thiadiazole (nd) (200 mg, 1 mmol) in DIPEA (200 μL, 1 mmol) and EtOH (2 mL) was heated at 80° C. overnight. It was concentrated in vacuo and purified by RP-HPLC to afford 7 mg (6%) of the title compound ne. 1H NMR (400 MHz, DMSO) δ 8.66 (d, J=10.1, 1H), 8.19 (t, J=9.4, 2H), 7.48 (t, J=9.4, 2H), 6.17 (s, 1H), 4.57 (d, J=9.5, 2H), 3.73 (s, 6H), 3.46 (s, 4H), 3.11 (s, 2H), 2.83 (s, 2H), 2.66 (s, 2H), 2.32 (d, J=10.3, 3H), 1.08-1.00 (m, 3H). LC-MS: m/z=+481 (M+H)+.

Example 266

(nf)

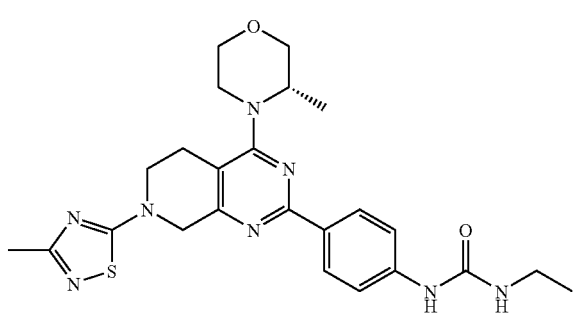

Synthesis of (S)-1-ethyl-3-(4-(7-(3-methyl-1,2,4-thiadiazol-5-yl)-4-(3-methylmorpholino)-5,6,7,8-tetrahydropyrido[3,4-d]pyrimidin-2-yl)phenyl)urea (nf): Compound nf was prepared by the general procedure of Example 264. LC-MS: m/z=+495 (M+H)+.

Example 267

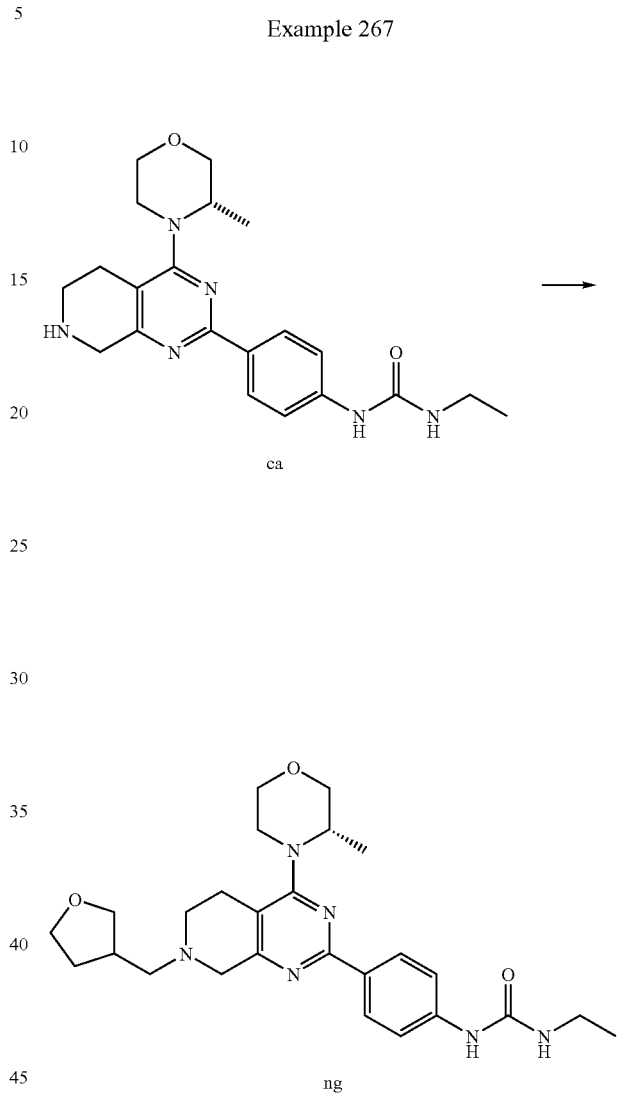

Synthesis of 1-ethyl-3-(4-(4-((S)-3-methylmorpholino)-7-((tetrahydrofuran-3-yl)methyl)-5,6,7,8-tetrahydropyrido[3,4-d]pyrimidin-2-yl)phenyl)urea (ng). To a suspension of (S)-1-ethyl-3-(4-(4-(3-methylmorpholino)-5,6,7,8-tetrahydropyrido[3,4-d]pyrimidin-2-yl)phenyl)urea hydrochloride (ca) (174 mg, 0.4 mmol) and tetrahydrofuran-3-carbaldehyde (55 μL, 0.6 mmol) in THF (3 mL) was added Na(OAc)$_3$BH in portions. After 2 hrs, more aldehyde (18 μL) and borohydride (71 mg) were added, and the resultant mixture was stirred for 1 h. The reaction mixture was quenched by addition of MeOH and few drops of AcOH, and concentrated in vacuo. The crude solid was redissolved in H$_2$O, extracted with EtOAc (4×10 mL). The combined EtOAc were dried over Magnesium sulfate, filtered, and purified by RP-HPLC to afford 110 mg (57%) of compound ng as a yellow solid. 1H NMR (400 MHz, DMSO) δ 8.65 (s, 1H), 8.15 (d, J=8.8, 2H), 7.47 (d, J=8.8, 2H), 6.16 (t, J=5.5, 1H), 4.13 (d, J=6.6, 1H), 3.87 (d, J=11.3, 1H), 3.80-3.39 (m, 12H), 3.16-3.07 (m, 2H), 2.75-2.64 (m, 3H), 2.55 (d, J=8.6, 1H), 2.46 (d, J=7.4, 2H), 1.98 (td, J=12.7, 7.7, 1H), 1.57 (td, J=13.5, 7.1, 1H), 1.24 (d, J=6.6, 3H), 1.06 (t, J=7.2, 3H). LC-MS: m/z=+481 (M+H)+.

Example 268

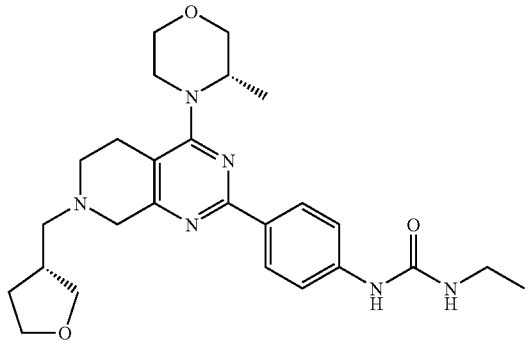

(ng[1])

Synthesis of 1-ethyl-3-(4-(4-((S)-3-methylmorpholino)-7-(((R)-tetrahydrofuran-3-yl)methyl)-5,6,7,8-tetrahydropyrido[3,4-d]pyrimidin-2-yl)phenyl)urea (ng[1]). The title compound ng[1] was obtained by the separation of product ng in Example 267 with chiral column. LC-MS: m/z=+481 (M+H)+.

Example 269

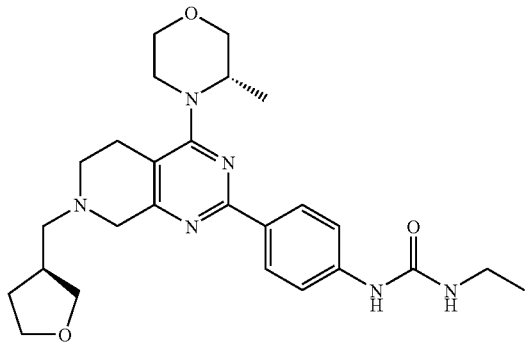

(ng[2])

1-ethyl-3-(4-(4-((S)-3-methylmorpholino)-7-(((S)-tetrahydrofuran-3-yl)methyl)-5,6,7,8-tetrahydropyrido[3,4-d]pyrimidin-2-yl)phenyl)urea (ng[2]). The title compound ng[2] was obtained by the separation of product ni in Example 267 with chiral column. LC-MS: m/z=+481 (M+H)+.

Example 270

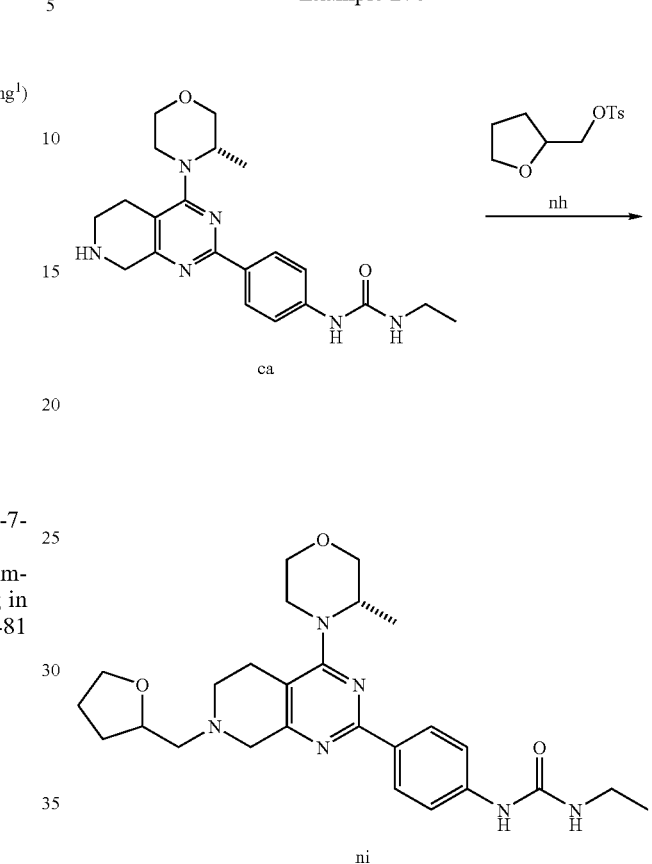

Synthesis of 1-ethyl-3-(4-(4-((S)-3-methylmorpholino)-7-((tetrahydrofuran-2-yl)methyl)-5,6,7,8-tetrahydropyrido[3,4-d]pyrimidin-2-yl)phenyl)urea (ni)

Step 1—Synthesis of (tetrahydrofuran-2-yl)methyl 4-methylbenzenesulfonate (nh): To a solution of (tetrahydrofuran-2-yl)methanol (1 mL, 10 mmol) in TEA (2.1 mL, 15 mmol) and DCM (20 mL) was added p-toluenesulfonyl chloride slowly at rt. The resulting clear solution was stirred at rt overnight. It was diluted with DCM (30 mL), washed with 0.5 N HCl, 10% NaHCO$_3$, dried over Magnesium sulfate, filtered, concentrated in vacuo, and chromatographed: ISCO, 40 g column, 0-20% EtOAc/heptane to give 2.4 g (90%) of compound nh as a clear oil. 1H NMR (400 MHz, CDCl3) δ 7.80 (d, J=8.3, 2H), 7.34 (d, J=8.1, 2H), 4.13-4.05 (m, 1H), 4.04-3.96 (m, 2H), 3.83-3.69 (m, 2H), 2.44 (d, J=7.3, 3H), 2.02-1.93 (m, 1H), 1.92-1.82 (m, 2H), 1.67 (ddd, J=20.8, 11.5, 6.7, 1H). LC-MS: m/z=+257 (M+H)+.

Step 2—Synthesis of 1-ethyl-3-(4-(4-((S)-3-methylmorpholino)-7-((tetrahydrofuran-2-yl)methyl)-5,6,7,8-tetrahydropyrido[3,4-d]pyrimidin-2-yl)phenyl)urea (ni). Compound ni was prepared by the general procedure of N-alkylation in Example 265. $^1$H NMR (400 MHz, DMSO) δ 8.63 (s, 1H), 8.16 (d, J=8.7, 2H), 7.47 (d, J=8.7, 2H), 6.16 (t, J=5.5, 1H), 4.13 (d, J=6.5, 1H), 4.05 (dd, J=12.4, 6.0, 1H), 3.88 (d, J=11.3, 1H), 3.78 (dt, J=9.8, 5.0, 2H), 3.73-3.55 (m, 6H), 3.41 (t, J=12.0, 1H), 3.17-3.08 (m, 2H), 2.86-2.79 (m, 1H), 2.74 (d, J=10.3, 1H), 2.70-2.55 (m, 5H), 1.98 (dt, J=11.9, 7.4, 1H), 1.88-1.76 (m, 2H), 1.55 (td, J=16.2, 7.8, 1H), 1.24 (d, J=5.1, 3H), 1.07 (t, J=7.2, 3H). LC-MS: m/z=+481 (M+H)+.

Example 271

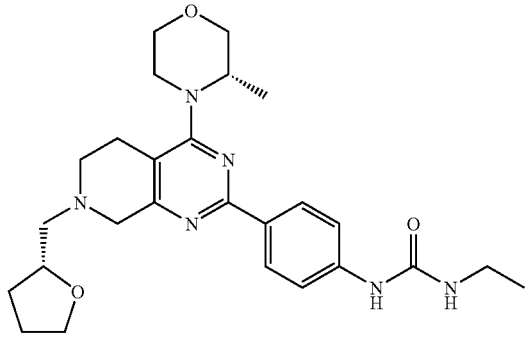

(ni$^1$)

Synthesis of 1-ethyl-3-(4-(4-((S)-3-methylmorpholino)-7-(((R)-tetrahydrofuran-2-yl)methyl)-5,6,7,8-tetrahydropyrido[3,4-d]pyrimidin-2-yl)phenyl)urea (ni$^1$): The title compound ni$^1$ was obtained by the separation of product ni in Example 270 with chiral column. LC-MS: m/z=+481 (M+H)+.

Example 272

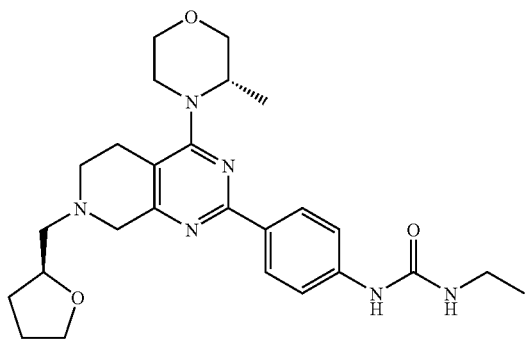

(ni$^2$)

Synthesis of 1-ethyl-3-(4-(4-((S)-3-methylmorpholino)-7-(((S)-tetrahydrofuran-2-yl)methyl)-5,6,7,8-tetrahydropyrido[3,4-d]pyrimidin-2-yl)phenyl)urea (ni$^2$). The title compound ni$^2$ was obtained by the separation of product ni in Example 270 with chiral column. LC-MS: m/z=+481 (M+H)+.

Example 273

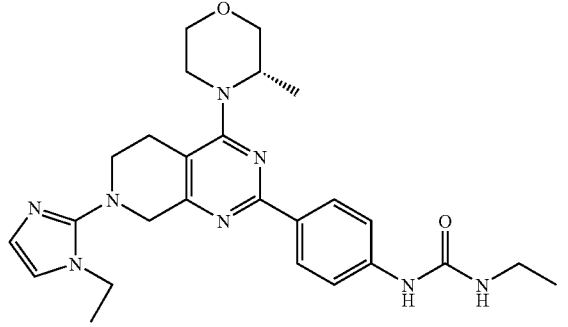

(nj)

Synthesis of (S)-1-ethyl-3-(4-(7-(1-ethyl-1H-imidazol-2-yl)-4-(3-methylmorpholino)-5,6,7,8-tetrahydropyrido[3,4-d]pyrimidin-2-yl)phenyl)urea (nj): Compound nj was prepared by the general procedure of Example 236 by substituting isothiocyanatoethane for isothiocyanatomethane. LC-MS: m/z=+491 (M+H)+.

Example 274

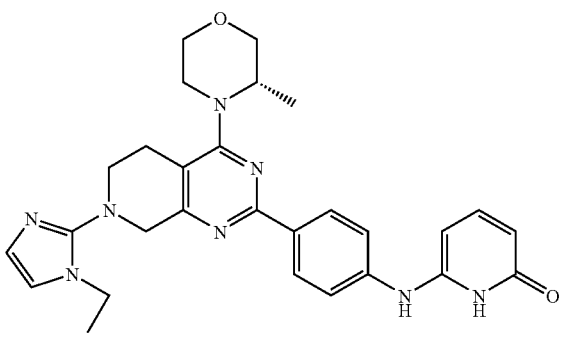

(nk)

Synthesis of (S)-6-(4-(7-(1-ethyl-1H-imidazol-2-yl)-4-(3-methylmorpholino)-5,6,7,8-tetrahydropyrido[3,4-d]pyrimidin-2-yl)phenylamino)pyridin-2(1H)-one (nk): Compound nk was prepared by the general procedure of Example 264, by substituting isothiocyanatoethane for isothiocyanatomethane. LC-MS: m/z=+513 (M+H)+.

Example 275

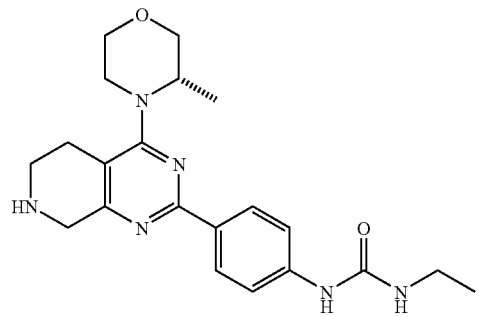

ca

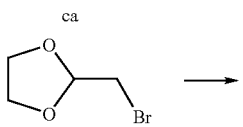

nl

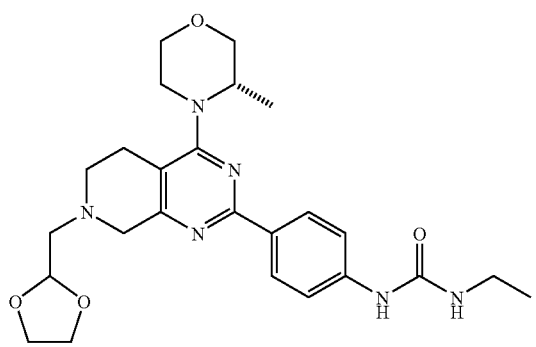

nm

Synthesis of (S)-1-(4-(7-((1,3-dioxolan-2-yl)methyl)-4-(3-methylmorpholino)-5,6,7,8-tetrahydropyrido[3,4-d]pyrimidin-2-yl)phenyl)-3-ethylurea (nm): The title compound nm was prepared by the general procedure of Example 225. LC-MS: m/z=+483 (M+H)+.

Example 276

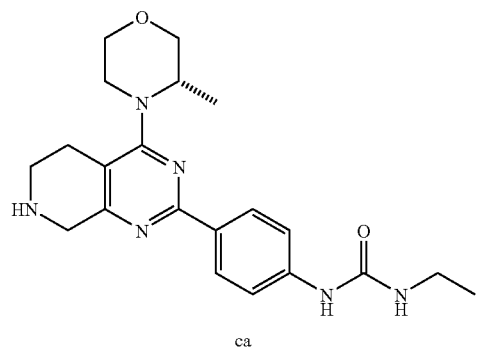

ca

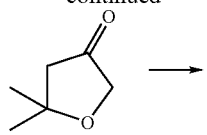

nn

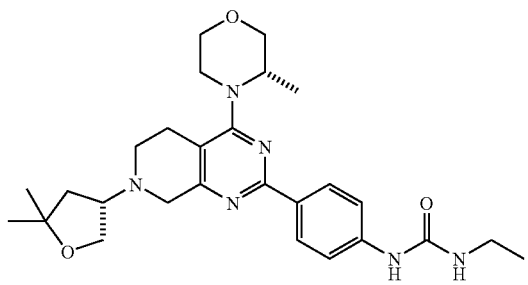

no¹

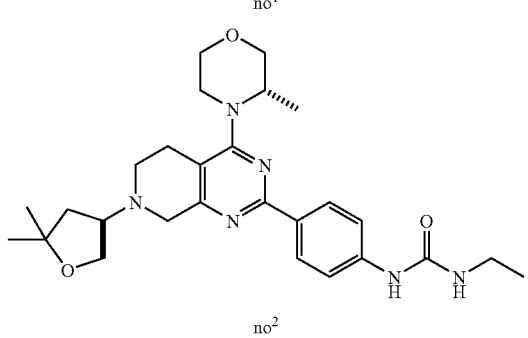

no²

Synthesis of 1-(4-(7-((S)-5,5-dimethyltetrahydrofuran-3-yl)-4-((S)-3-methylmorpholino)-5,6,7,8-tetrahydropyrido[3,4-d]pyrimidin-2-yl)phenyl)-3-ethylurea (no¹); and 1-(4-(7-((R)-5,5-dimethyltetrahydrofuran-3-yl)-4-((S)-3-methylmorpholino)-5,6,7,8-tetrahydropyrido[3,4-d]pyrimidin-2-yl)phenyl)-3-ethylurea (no²): Compounds no¹ and no² were prepared by the general procedure of Example 267, by substituting 5,5-dimethyldihydrofuran-3(2H)-one for tetrahydrofuran-3-carbaldehyde, then followed by chiral separation to afford products no¹ and no². LC-MS: m/z=+495 (M+H)+.

Example 277

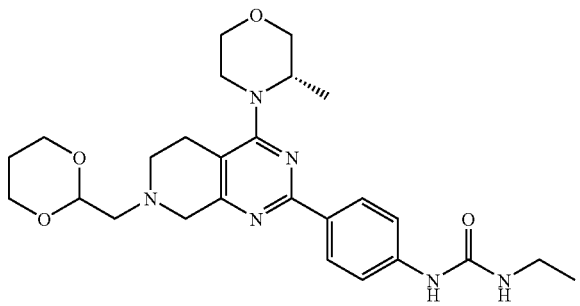

np

Synthesis of (S)-1-(4-(7-((1,3-dioxan-2-yl)methyl)-4-(3-methylmorpholino)-5,6,7,8-tetrahydropyrido[3,4-d]pyrimidin-2-yl)phenyl)-3-ethylurea (np): Compound np was prepared by the general procedure of Example 225 by substituting 2-(chloromethyl)-1,3-dioxane for (S)-(2,2-dimethyl-1,3-dioxolan-4-yl)methyl 4-methylbenzenesulfonate. LC-MS: m/z=+497 (M+H)+.

general procedure of Example 276 to afford products nr[1] and nr[2]: LC-MS: m/z=+481 (M+H)+.

Example 278

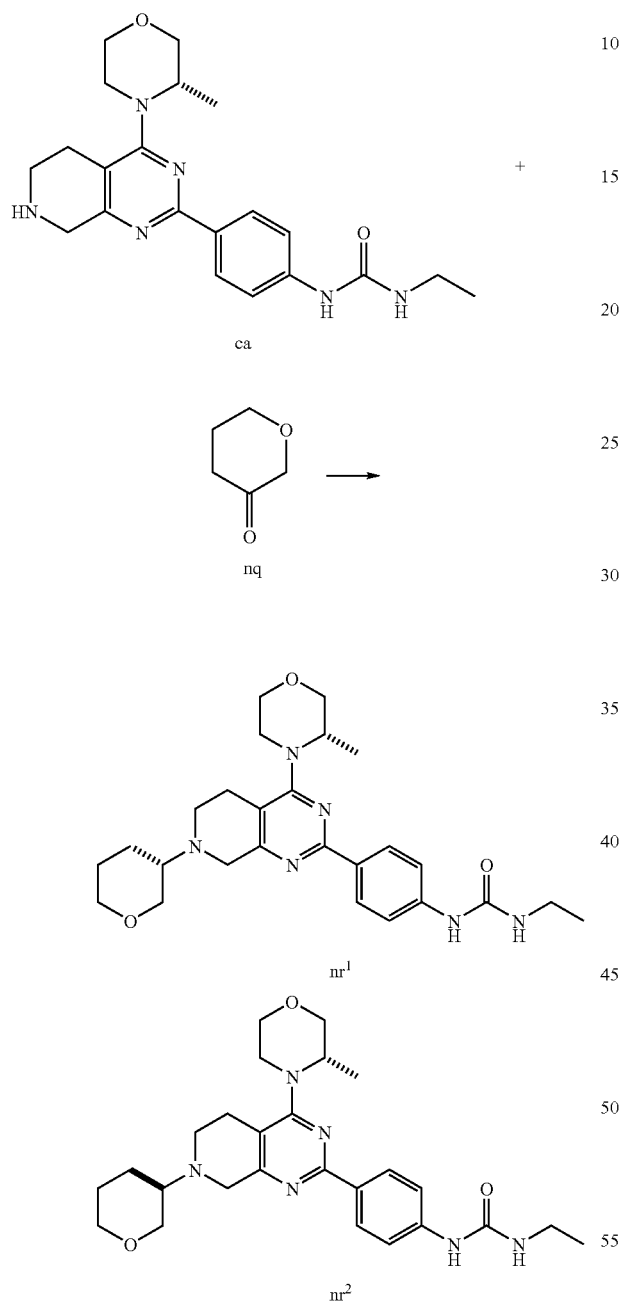

Example 279

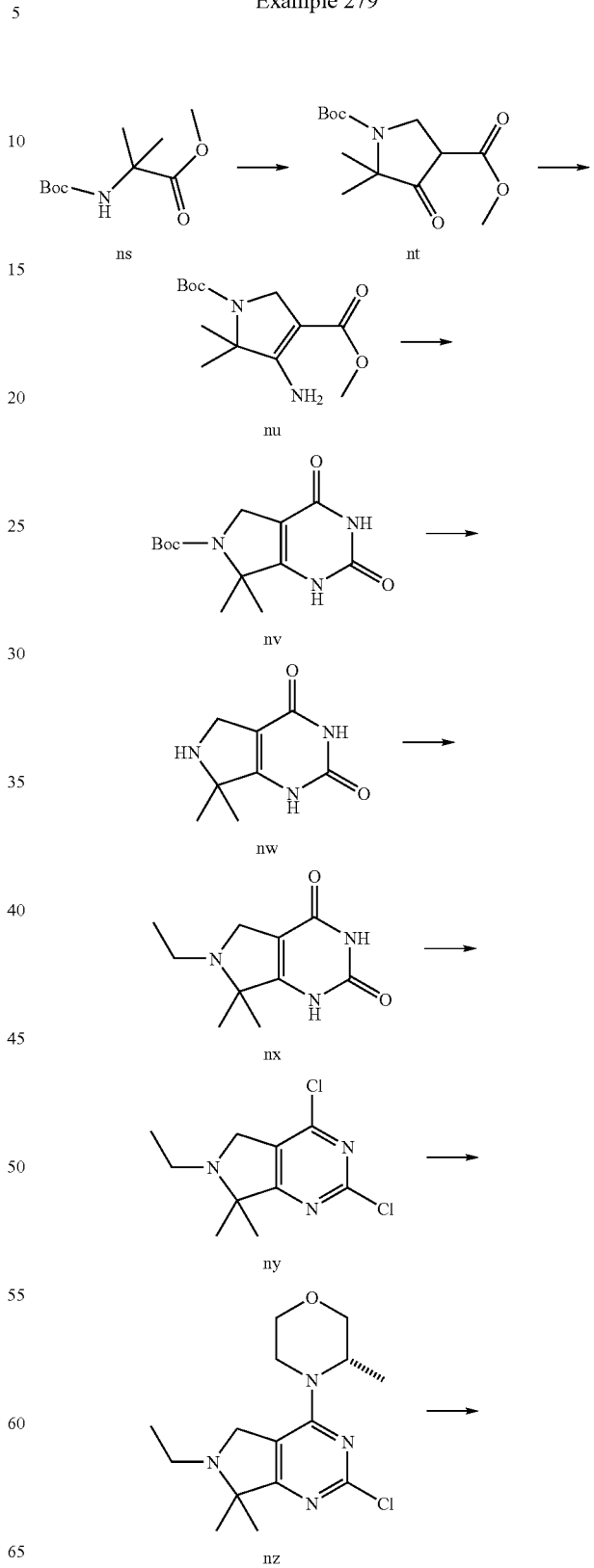

Synthesis of 1-ethyl-3-(4-(4-((S)-3-methylmorpholino)-7-((S)-tetrahydro-2H-pyran-3-yl)-5,6,7,8-tetrahydropyrido[3,4-d]pyrimidin-2-yl)phenyl)urea (nr[1]); and 1-ethyl-3-(4-(4-((S)-3-methylmorpholino)-7-((R)-tetrahydro-2H-pyran-3-yl)-5,6,7,8-tetrahydropyrido[3,4-d]pyrimidin-2-yl)phenyl) urea (nr[2]). Compounds nr[1] and nr[2] were prepared by the

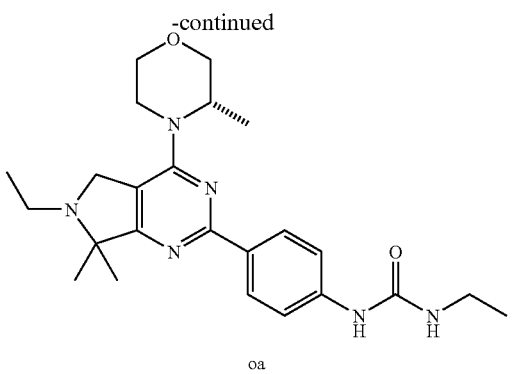

Synthesis of (S)-1-ethyl-3-(4-(6-ethyl-7,7-dimethyl-4-(3-methylmorpholino)-6,7-dihydro-5H-pyrrolo[3,4-d]pyrimidin-2-yl)phenyl)urea (oa)

Step 1—Synthesis of 1-tert-butyl 3-methyl 5,5-dimethyl-4-oxopyrrolidine-1,3-dicarboxylate (nt). To a solution of methyl 2-(tert-butoxycarbonylamino)-2-methylpropanoate (ns) (6.5 g, 30.1 mmol) and methyl acrylate (3.0 mL, 33.2 mmol) in THF (75 mL) was added potassium tert-butoxide (4.1 g, 36.2 mmol) portionwise under ice-water bath temperature. The resulting mixture was warmed to rt and stirred for 24 hrs. Heptane was added to the mixture and the solid was collected by filtration, washed with ether, dried. The crude solid was partitioned in 3% aqueous AcOH and ether, and separated. The aqueous layer was again extracted with ether twice. The combined organics were dried over Magnesium sulfate, filtered, concentrated in vacuo to give the desired compound nt as clear pale yellow oil, which was used without further purification. LC-MS: m/z=+272 (M+H)+.

Step 2—Synthesis of 1-tert-butyl 3-methyl 4-amino-5,5-dimethyl-1H-pyrrole-1,3(2H,5H)-dicarboxylate (nu). Compound nt from step 1 (841 mg, 3.1 mmol) was treated with ammonium acetate (2.4 g, 31 mmol) in MeOH (10 mL) at 85° C. for overnight. The solvent was removed in vacuo, and the crude residue was diluted with EtOAc, washed with 10% NaHCO₃, water, and brine. The organic phase was dried over Magnesium sulfate, filtered, and concentrated in vacuo to give 588 mg (70%) of crude product nu as an off white solid. It was carried on without further purification. LC-MS: m/z=+271 (M+H)+.

Step 3—Synthesis of tert-butyl 7,7-dimethyl-2,4-dioxo-3,4,5,7-tetrahydro-1H-pyrrolo[3,4-d]pyrimidine-6(2H)-carboxylate (nv). A solution of compound nu (586 mg, 2.2 mmol) and pyridine (700 µL, 8.7 mmol) in DCM (15 mL) under N₂ and at 0° C. was added dropwise a 20% phosgene/toluene solution (1.7 mL, 3.2 mmol). The reaction was kept at 0° C. for 30 min and 3 hrs at rt. It was cooled with ice bath, aqueous NH₄OH (9 mL, 65 mmol) was added slowly. The resultant mixture was heated at 70° C. for 48 hrs. It was diluted with water, extracted with DCM twice. The aqueous layer was freeze dried to afford 203 mg (33%) of crude compound nv as a cream solid, which was carried on without further purification. LC-MS: m/z=+282 (M+H)+.

Step 4—Synthesis of 7,7-dimethyl-6,7-dihydro-1H-pyrrolo[3,4-d]pyrimidine-2,4(3H,5H)-dione (nw). Compound nv was treated with 4 N HCl/dioxane to afford compound nw as a HCL salt. LC-MS: m/z=+182 (M+H)+.

Step 5—Synthesis of 6-ethyl-7,7-dimethyl-6,7-dihydro-1H-pyrrolo[3,4-d]pyrimidine-2,4(3H,5H)-dione (nx). Compound nx was prepared by the general procedure of Example 267 using acetaldehyde. LC-MS: m/z=+210 (M+H)+.

Step 6 to 8—Synthesis of (S)-1-ethyl-3-(4-(6-ethyl-7,7-dimethyl-4-(3-methylmorpholino)-6,7-dihydro-5H-pyrrolo[3,4-d]pyrimidin-2-yl)phenyl)urea (oa). Compound oa was prepared starting from compound nx by the general procedure of Example 35, step 2-5. 1H NMR (400 MHz, DMSO) δ 8.63 (s, 1H), 8.19 (d, J=8.7, 2H), 7.46 (d, J=8.7, 2H), 6.14 (t, J=5.5, 1H), 4.44 (s, 1H), 4.10-4.00 (m, 2H), 3.92 (d, J=12.4, 2H), 3.69 (dd, J=26.7, 10.0, 2H), 3.51 (t, J=10.6, 1H), 3.36 (d, J=6.2, 1H), 3.16-3.08 (m, 2H), 2.68 (d, J=7.3, 2H), 1.26 (d, J=6.7, 3H), 1.20 (d, J=4.5, 6H), 1.13 (t, J=7.1, 3H), 1.06 (t, J=7.2, 3H). LC-MS: m/z=+439 (M+H)+.

Example 280

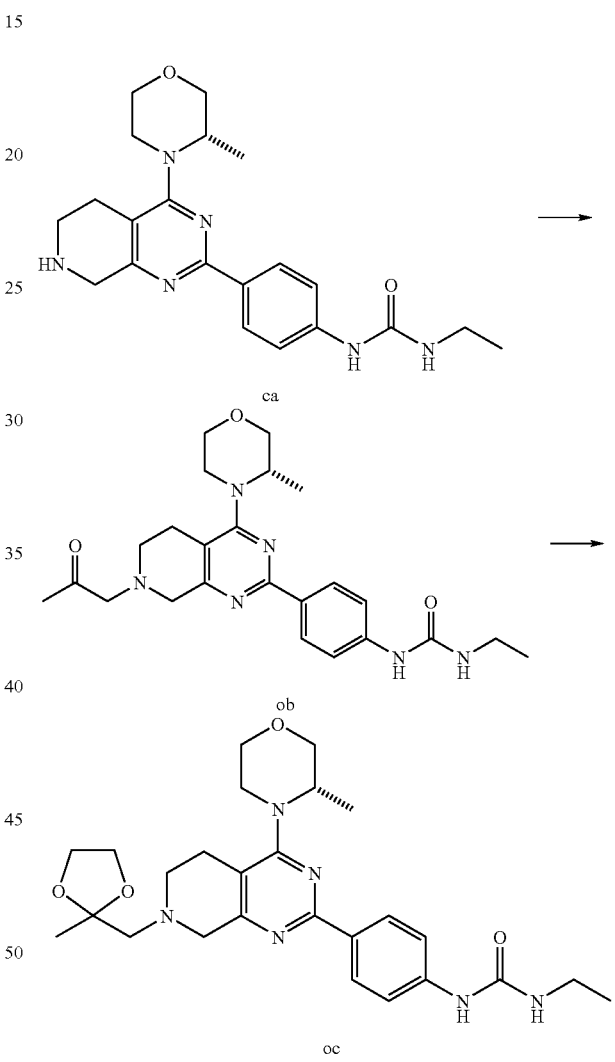

Synthesis of (S)-1-ethyl-3-(4-(7-((2-methyl-1,3-dioxolan-2-yl)methyl)-4-(3-methylmorpholino)-5,6,7,8-tetrahydropyrido[3,4-d]pyrimidin-2-yl)phenyl)urea (oc)

Step 1—Synthesis of (S)-1-ethyl-3-(4-(4-(3-methylmorpholino)-7-(2-oxopropyl)-5,6,7,8-tetrahydropyrido[3,4-d]pyrimidin-2-yl)phenyl)urea (ob): Compound ob was prepared by the general procedure of Example 225 substituting chloroacetone for (S)-(2,2-dimethyl-1,3-dioxolan-4-yl)methyl 4-methylbenzenesulfonate. 1H NMR (500 MHz, CDCl3) δ 8.29 (d, J=8.7, 2H), 7.36 (d, J=8.7, 2H), 6.57 (s, 1H), 4.86 (t, J=5.4, 1H), 4.08 (dd, J=8.5, 4.9, 1H), 3.94 (d, J=11.2, 1H), 3.87-3.79 (m, 2H), 3.75-3.66 (m, 3H), 3.59 (s, 1H), 3.52 (ddd, J=13.7, 10.8, 3.2, 1H), 3.44 (s, 2H), 3.34-3.28 (m, 2H), 2.84-2.72 (m, 3H), 2.65 (ddd, J=11.8, 7.6, 4.1, 1H), 2.22 (s, 3H), 1.31 (d, J=6.7, 3H), 1.16 (t, J=7.2, 3H). LC-MS: m/z=+453 (M+H)+.

Step 2—Synthesis of (S)-1-ethyl-3-(4-(7-((2-methyl-1,3-dioxolan-2-yl)methyl)-4-(3-methylmorpholino)-5,6,7,8-tetrahydropyrido[3,4-d]pyrimidin-2-yl)phenyl)urea (oc). A mixture of compound ob (500 mg, 1 mmol), 1,2-ethanediol (500 µL, 9 mmol), and naphthalene-2-sulfonic acid (70 mg, 0.3 mmol) in toluene (5 mL) in a capped vial was heated in an oil bath at 110° C. for overnight. The crude mixture was concentrated onto Celite, chromatographed: ISCO, 25 g column, 0-5% IPA/DCM to give desired (C), which was again purified by RP-HPLC. 1H NMR (400 MHz, DMSO) δ 8.67 (s, 1H), 8.15 (d, J=8.7, 2H), 7.47 (d, J=8.8, 2H), 6.18 (t, J=5.6, 1H), 4.13 (d, J=6.8, 1H), 3.91 (d, J=3.1, 5H), 3.72 (t, J=15.5, 2H), 3.66-3.55 (m, 4H), 3.45-3.36 (m, 2H), 3.11 (dd, J=13.4, 6.5, 2H), 2.81 (d, J=5.4, 1H), 2.66 (s, 2H), 2.58 (s, 2H), 1.34 (s, 3H), 1.24 (d, J=6.6, 3H), 1.06 (t, J=7.2, 3H). LC-MS: m/z=+497 (M+H)+.

Example 281

(od)

Synthesis of 1-((1S,2R)-2-hydroxycyclopentyl)-3-(4-(4-morpholino-7-(pyrimidin-2-yl)-5,6,7,8-tetrahydropyrido[3,4-d]pyrimidin-2-yl)phenyl)urea (od). The title compound od was prepared by the general procedure of Example 30 substituting (1R,2S)-2-aminocyclopentanol for cyclopropylmethylamine. LC-MS: m/z=+517 (M+H)+.

Example 282

(oe)

Synthesis of 1-(4-(4-morpholino-7-(pyrimidin-2-yl)-5,6,7,8-tetrahydropyrido[3,4-d]pyrimidin-2-yl)phenyl)-3-(pyridin-4-yl)urea (oe): The title compound (oe) was prepared by the general procedure of Example 30 substituting pyridin-4-amine for cyclopropylmethylamine. LC-MS: m/z=+510 (M+H)+.

Example 283

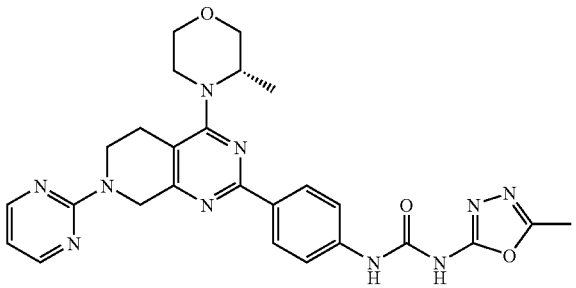

(of)

Synthesis of (S)-1-(5-methyl-1,3,4-oxadiazol-2-yl)-3-(4-(4-(3-methylmorpholino)-7-(pyrimidin-2-yl)-5,6,7,8-tetrahydropyrido[3,4-d]pyrimidin-2-yl)phenyl)urea (of). The title compound "of" was prepared by the general procedure of Example 30 substituting (S)-4-(4-(3-methylmorpholino)-7-(pyrimidin-2-yl)-5,6,7,8-tetrahydropyrido[3,4-d]pyrimidin-2-yl)aniline for 4-(4-morpholino-6-(pyrimidin-2-yl)-5,6,7,8-tetrahydropyrido[4,3-d]pyrimidin-2-yl)aniline and 5-methyl-1,3,4-oxadiazol-2-amine for cyclopropylmethylamine. LC-MS: m/z=+529 (M+H)+.

Example 284

Synthesis of benzyl 2,4-dichloro-8,9-dihydro-5H-pyrimido[4,5-d]azepine-7(6H)-carboxylate (oj)

Step 1—Synthesis of 1-benzyl 4-ethyl 5-oxoazepane-1,4-dicarboxylate (oh): To a solution of benzyl 4-oxopiperidine- 1-carboxylate (og) (1.0 eq) in dry diethyl ether was added ethyl diazoacetate (1.3 eq) in ether and boron trifluoride etherate (2.0 eq) simultaneously by a syringe pump (speed: 4.0 mL/hr) at −30° C. under $N_2$. The reaction solution was stirred at −30° C. for another 1 hour after addition, and was allowed to warm up to room temperature slowly. The organic solution was washed by 30% KOH solution, water, and brine until the final pH of the solution was pH~7. The organic phase was dried by Magnesium sulfate, evaporated, and purified by chromatography on silica gel column to give the desired product oh (50% yield) as colorless oil: $^1$H NMR (400 MHz, $CD_3OD$) δ 7.31 (m, 5H), 4.15 (m, 2H), 3.74-3.50 (m, 2H), 2.74 (m, 6H), 2.03 (m, 2H), 1.23 (t, J=7.1, 3H); LC-MS m/z=276 (M+H).

Step 2—Synthesis of benzyl 2,4-dioxo-3,4,5,6,8,9-hexahydro-1H-pyrimido[4,5-d]azepine-7(2H)-carboxylate (oi): To a solution of 1-benzyl 4-ethyl 5-oxoazepane-1,4-dicarboxylate (oh) (2.00 g, 6.26 mmol) and urea (0.752 g, 12.5 mmol) in methanol (12 mL) was added 4.37 M of sodium methoxide in methanol (2.87 mL) dropwise at room temperature, and the yellow solution was heated to reflux under $N_2$ for 1 h, then at 50° C. overnight. The purification of the crude product on silica gel column gave the desired product oi (634 mg, 32% yield) as white solid: $^1$H NMR (400 MHz, $CD_3OD$) δ 7.45-7.21 (m, 5H), 5.11 (s, 2H), 3.70-3.33 (m, 4H), 2.69-2.52 (m, 2H), 2.41-2.27 (m, 2H); LC-MS m/z=316 (M+H).

Step 3—Synthesis of benzyl 2,4-dichloro-8,9-dihydro-5H-pyrimido[4,5-d]azepine-7(6H)-carboxylate (oj): To a suspension solution of benzyl 2,4-dioxo-3,4,5,6,8,9-hexahydro-1H-pyrimido[4,5-d]azepine-7(2H)-carboxylate (oi) (265 mg, 0.840 mmol) and 4-Dimethylaminopyridine (76.1 mg, 0.623 mmol) in 1,4-Dioxane (1.6 mL) was added Phosphoryl chloride (0.801 mL, 8.59 mmol) at room temperature, and the solution was stirred at 40° C. for overnight, followed by ice-water quench. The extraction was done with dichloromethane at pH~8, and the organic layer was washed by water and brine, dried over Magnesium sulfate, and evaporated. The purification of the crude product by silica gel column gave product oj (191 mg, 65% yield) as white solid: $^1$H NMR (400 MHz, $CDCl_3$) δ 7.37 (m, 5H), 5.18 (s, 2H), 3.71 (m, 4H), 3.14 (m, 4H); LC-MS m/z=352 (M+H).

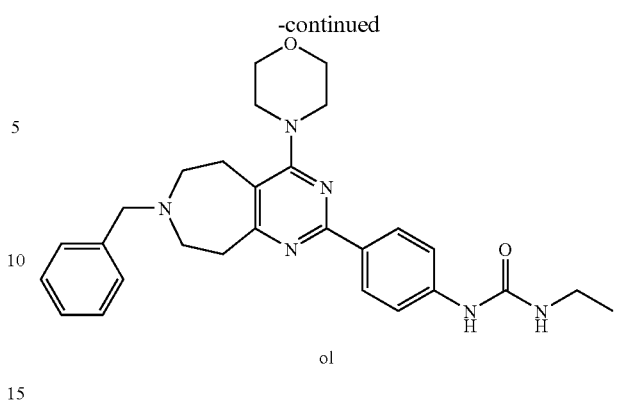

Synthesis of 1-(4-(7-benzyl-4-morpholino-6,7,8,9-tetrahydro-5H-pyrimido[5,4-d]azepin-2-yl)phenyl)-3-ethylurea (ol)

Step 1—Synthesis of 4-(7-benzyl-2-chloro-6,7,8,9-tetrahydro-5H-pyrimido[5,4-d]azepin-4-yl)morpholine (ok): The compound ok was prepared following the general procedure in Step 1 of Example 1, substituting tert-butyl 2,4-dichloro-5H-pyrrolo[3,4-d]pyrimidine-6(7H)-carboxylate for 7-Benzyl-2,4-dichloro-6,7,8,9-tetrahydro-5H-pyrimido [4,5-d]azepine (rk). Title compound ok (59% yield) was obtained as white powder: $^1$H NMR (400 MHz, $CDCl_3$) δ 7.38-7.24 (m, 5H), 3.84-3.70 (m, 4H), 3.63 (s, 2H), 3.35-3.23 (m, 4H), 3.04 (m, 2H), 2.81-2.73 (m, 2H), 2.69 (m, 2H), 2.60 (m, 2H); LC-MS m/z=359 (M+H).

Step 2—Synthesis of 1-(4-(7-benzyl-4-morpholino-6,7,8,9-tetrahydro-5H-pyrimido[5,4-d]azepin-2-yl)phenyl)-3-ethylurea (ol): The compound (ol) was prepared following the general procedure in Step 2 of Example 1, substituting tert-butyl 2-chloro-4-morpholino-5H-pyrrolo[3,4-d]pyrimidine-6(7H)-carboxylate for 4-(7-benzyl-2-chloro-6,7,8,9-tetrahydro-5H-pyrimido[5,4-d]azepin-4-yl)morpholine. The desired product ol (51% yield) was obtained as white solid: $^1$H NMR (400 MHz, DMSO) δ 8.67 (s, 1H), 8.19 (d, J=8.8, 2H), 7.47 (d, J=8.8, 2H), 7.39-7.30 (m, 4H), 7.26 (m, 1H), 6.17 (t, J=5.6, 1H), 3.72 (m, 4H), 3.62 (s, 2H), 3.24 (m, 4H), 3.17-3.07 (m, 2H), 3.02 (m, 2H), 2.79 (m, 2H), 2.65 (m, 2H), 2.56 (m, 2H), 1.06 (t, J=7.2, 3H); LC-MS m/z=487 (M+H).

Example 285

Example 286

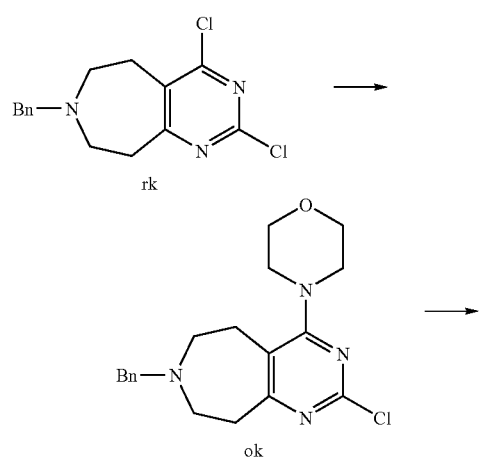

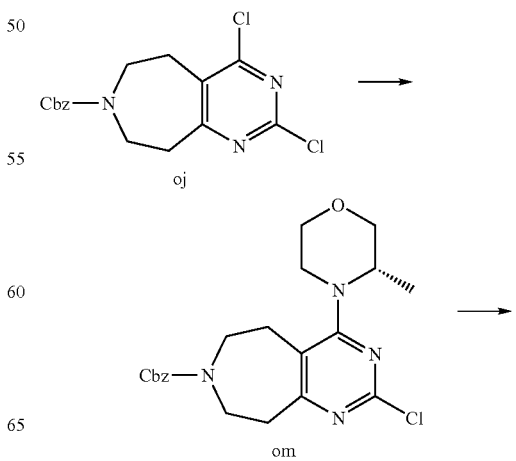

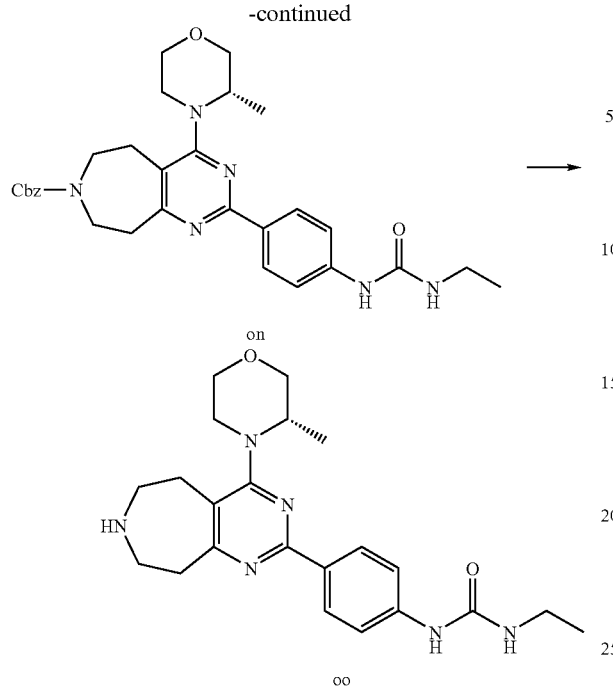

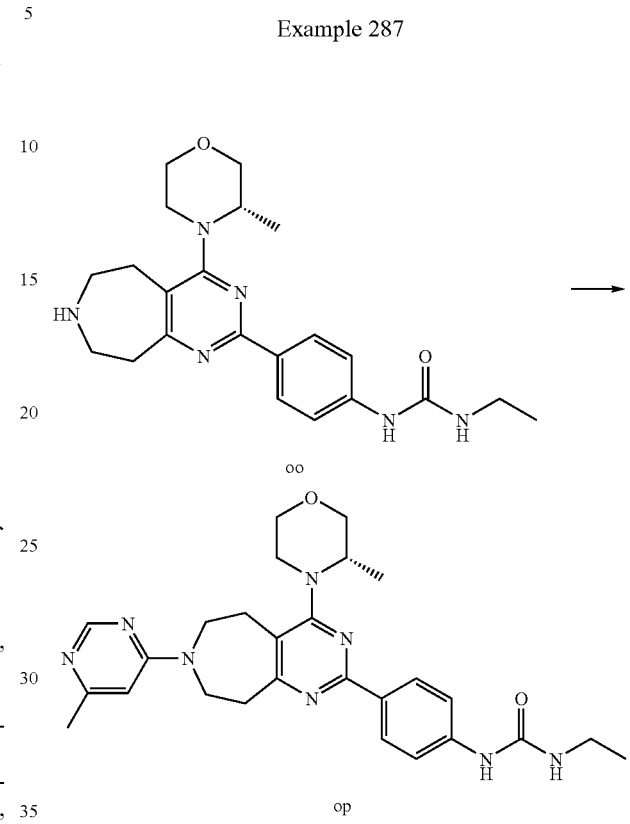

Synthesis of (S)-1-ethyl-3-(4-(4-(3-methylmorpholino)-6,7,8,9-tetrahydro-5H-pyrimido[5,4-d]azepin-2-yl)phenyl)urea (oo)

Step 1—Synthesis of (S)-benzyl 2-chloro-4-(3-methylmorpholino)-8,9-dihydro-5H-pyrimido[5,4-d]azepine-7(6H)-carboxylate (om): Benzyl 2,4-dichloro-8,9-dihydro-5H-pyrimido[5,4-d]azepine-7(6H)-carboxylate (oj) (143 mg, 0.406 mmol) and S-3-methylmorpholine (48.6 mg, 0.480 mmol) were dissolved in Dimethyl sulfoxide (1.60 mL) and N,N-Diisopropylethylamine (0.14 mL, 0.80 mmol) was added. The mixture was stirred at 50° C. for overnight. After removal of volatiles from the reaction mixture, the crude residue was purified by chromatography on silica gel column, which gave the title compound om (96.2 mg, 74% yield based on conversion) as white solid: $^1$H NMR (400 MHz, CDCl$_3$) δ 7.41-7.29 (m, 5H), 5.19 (s, 2H), 3.92-3.14 (m, 11H), 3.03 (m, 2H), 2.78 (m, 2H), 1.32-1.16 (d, J=7.2 Hz, 3H); LC-MS m/z=417 (M+H).

Step 2—Synthesis of (S)-benzyl 2-(4-(3-ethylureido)phenyl)-4-(3-methylmorpholino)-8,9-dihydro-5H-pyrimido[5,4-d]azepine-7(6H)-carboxylate (on): The compound "on" was prepared following the general procedure of the step 2 in Example 285, substituting 4-(7-benzyl-2-chloro-6,7,8,9-tetrahydro-5H-pyrimido[5,4-d]azepin-4-yl)morpholine for (S)-benzyl 2-chloro-4-(3-methylmorpholino)-8,9-dihydro-5H-pyrimido[5,4-d]azepine-7(6H)-carboxylate: LC-MS m/z=545 (M+H).

Step 3—Synthesis of (S)-1-ethyl-3-(4-(4-(3-methylmorpholino)-6,7,8,9-tetrahydro-5H-pyrimido[5,4-d]azepin-2-yl)phenyl)urea (oo). To a solution of (S)-benzyl 2-(4-(3-ethylureido)phenyl)-4-(3-methylmorpholino)-8,9-dihydro-5H-pyrimido[5,4-d]azepine-7(6H)-carboxylate (on) (61 mg, 0.11 mmol) in Tetrahydrofuran (16.0 mL) and Acetic acid (1.0 mL) was added 20% Palladium hydroxide on carbon (63 mg). The reaction solution was purged with hydrogen three times, and stirred overnight at room temperature under 1 atm of H$_2$. After filtration and purification, the desired product oo (29 mg, 63% yield) was obtained as white powder: $^1$H NMR (400 MHz, CDCl$_3$) δ 8.36 (d, J=8.2, 2H), 7.36 (d, J=8.3, 2H), 6.29 (s, 1H), 4.68 (m, 1H), 3.34 (m, 18H), 1.19 (m, 6H); LC-MS m/z=411 (M+H).

Example 287

Synthesis of (S)-1-ethyl-3-(4-(4-(3-methylmorpholino)-7-(6-methylpyrimidin-4-yl)-6,7,8,9-tetrahydro-5H-pyrimido[5,4-d]azepin-2-yl)phenyl)urea (op): The compound op was prepared following the general procedure in Example 2, substituting 1-ethyl-3-(4-(4-morpholino-6,7-dihydro-5H-pyrrolo[3,4-d]pyrimidin-2-yl)phenyl)urea with (S)-1-ethyl-3-(4-(4-(3-methylmorpholino)-6,7,8,9-tetrahydro-5H-pyrimido[5,4-d]azepin-2-yl)phenyl)urea and substituting 2-Chloropyrimidine with 4-Chloro-6-methylpyrimidine. The desired product op (36% yield) was obtained as white powder: $^1$H NMR (500 MHz, DMSO) δ 8.70 (s, 1H), 8.42 (s, 1H), 8.20 (d, J=8.8 Hz, 2H), 7.49 (d, J=8.8 Hz, 2H), 6.80 (s, 1H), 6.19 (t, J=5.5 Hz, 1H), 4.10-3.62 (m, 9H), 3.52 (dd, J=11.0, 3.6 Hz, 1H), 3.21-3.02 (m, 5H), 2.88 (m, 2H), 2.28 (s, 3H), 1.12 (d, J=6.4 Hz, 3H), 1.06 (t, J=7.2 Hz, 3H); LC-MS m/z=503 (M+H).

Example 288

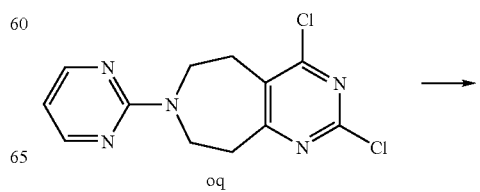

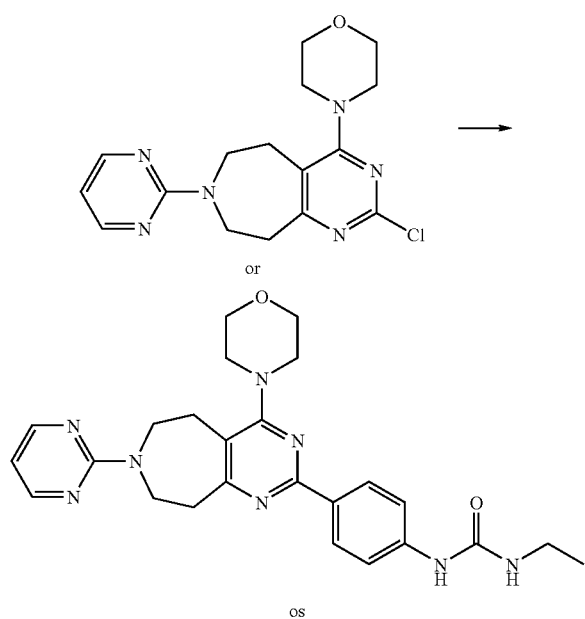

os

Synthesis of 1-ethyl-3-(4-(4-morpholino-7-(pyrimidin-2-yl)-6,7,8,9-tetrahydro-5H-pyrimido[4,5-d]azepin-2-yl)phenyl)urea (os)

Step 1—Synthesis of 4-(2-chloro-7-(pyrimidin-2-yl)-6,7,8,9-tetrahydro-5H-pyrimido[4,5-d]azepin-4-yl)morpholine (or). The compound "or" was prepared following the general procedure in Step 1 of Example 285, substituting 7-Benzyl-2,4-dichloro-6,7,8,9-tetrahydro-5H-pyrimido[4,5-d]azepine for 2,4-dichloro-7-(pyrimidin-2-yl)-6,7,8,9-tetrahydro-5H-pyrimido[4,5-d]azepine: LC-MS m/z=347 (M+H).

Step 2—Synthesis of 1-ethyl-3-(4-(4-morpholino-7-(pyrimidin-2-yl)-6,7,8,9-tetrahydro-5H-pyrimido[4,5-d]azepin-2-yl)phenyl)urea (os): The compound os was prepared following the general procedure in Step 2 of Example 285, substituting 4-(7-benzyl-2-chloro-6,7,8,9-tetrahydro-5H-pyrimido[5,4-d]azepin-4-yl)morpholine for 4-(2-chloro-7-(pyrimidin-2-yl)-6,7,8,9-tetrahydro-5H-pyrimido[4,5-d]azepin-4-yl)morpholine (or): LC-MS m/z=475 (M+H).

Example 289

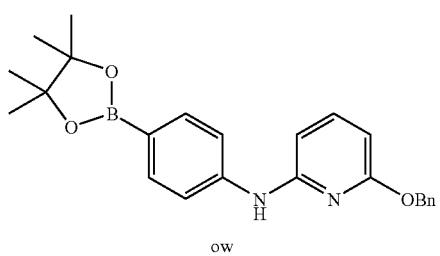

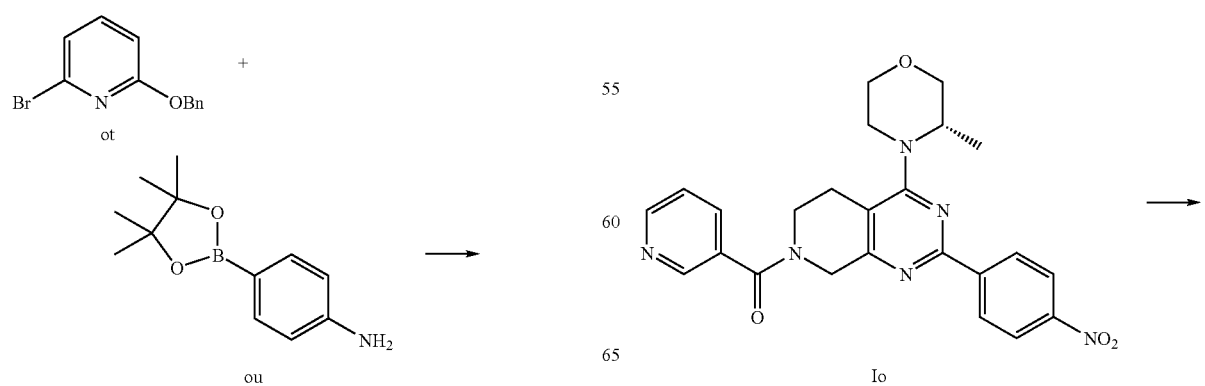

ou

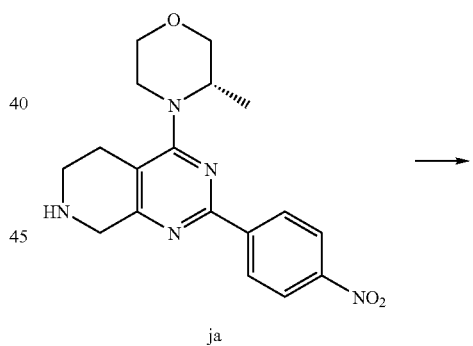

ow

Synthesis of 6-(benzyloxy)-N-(4-(4,4,5,5-tetramethyl-1,3,2-dioxaborolan-2-yl)phenyl)pyridin-2-amine (ow): Sodium tert-butoxide (556 mg, 5.78 mmol), 2-Dicyclohexylphosphino-2'-(N,N-dimethylamino)biphenyl (98 mg, 0.25 mmol), Bis(dibenzylideneacetone)palladium(0) (96 mg, 0.17 mmol), 4-(4,4,5,5-tetramethyl-1,3,2-dioxaborolan-2-yl)aniline (ou) (1.00 g, 4.57 mmol) and 2-Bromo-6-benzyloxypyridine (ot) (1.10 g, 4.15 mmol) were mixed in tert-Butyl alcohol (20 mL), which was purged by nitrogen for a few minutes. The dark orange mixture was microwaved at 120° C. for 15 minutes, and the reaction was quenched by 10% citric acid (aqueous). After purification on silica gel column, the desired product ow (1.08 g 65% yield) was obtained as slightly brown solid: $^1$H NMR (400 MHz, CDCl$_3$) δ 7.75 (d, J=8.4 Hz, 2H), 7.49-7.41 (m, 3H), 7.41-7.34 (m, 4H), 7.34-7.27 (m, 1H), 6.46 (s, 1H), 6.44 (d, J=7.9 Hz, 1H), 6.30 (d, J=7.9 Hz, 1H), 5.37 (s, 2H), 1.34 (s, 12H); LC-MS m/z=403 (M+H).

Example 290 ja lo

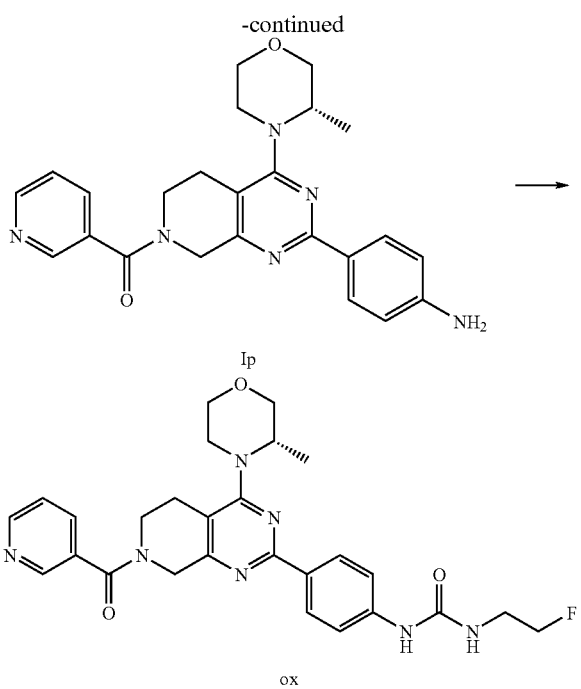

(S)-1-(2-fluoroethyl)-3-(4-(4-(3-methylmorpholino)-7-nicotinoyl-5,6,7,8-tetrahydropyrido[3,4-d]pyrimidin-2-yl)phenyl)urea (ox)

Step 1—Synthesis of (S)-(4-(3-methylmorpholino)-2-(4-nitrophenyl)-5,6-dihydropyrido[3,4-d]pyrimidin-7(8H)-yl)(pyridin-3-yl)methanone (lo). To a yellow suspension solution of (S)-3-methyl-4-(2-(4-nitrophenyl)-5,6,7,8-tetrahydropyrido[3,4-d]pyrimidin-4-yl)morpholine (ja) (101 mg, 0.258 mmol) and 4-Dimethylaminopyridine (5.0 mg, 0.041 mmol) in 1,4-Dioxane (1.2 mL), Acetonitrile (1.2 mL) and N,N-Diisopropylethylamine (0.20 mL, 1.1 mmol) was added nicotinyl chloride hydrochloride (55.1 mg, 0.309 mmol). The reaction was stirred overnight at room temperature and quenched with NaHCO$_3$, followed by extraction with chloroform. The organic layer was evaporated to dryness, and the residue was purified by chromatography, which gave the desired product lo (112 mg, 94% yield) as yellow solid: $^1$H NMR (400 MHz, CDCl$_3$) δ 8.81 (s, 1H), 8.74 (d, J=3.8 Hz, 1H), 8.39 (m, 2H), 8.24 (d, J=6.4 Hz, 2H), 7.99-7.80 (m, 1H), 7.43 (dd, J=7.4, 5.0 Hz, 1H), 5.21-4.51 (m, 2H), 4.26-3.44 (m, 9H), 2.83 (bs, 2H), 1.40 (d, J=6.8 Hz, 3H); LC-MS m/z=461 (M+H).

Step 2—Synthesis of (S)-(2-(4-aminophenyl)-4-(3-methylmorpholino)-5,6-dihydropyrido[3,4-d]pyrimidin-7(8H)-yl)(pyridin-3-yl)methanone (lp). Stannous chloride, dihydrate (495 mg, 2.17 mmol) and (S)-(4-(3-methylmorpholino)-2-(4-nitrophenyl)-5,6-dihydropyrido[3,4-d]pyrimidin-7(8H)-yl)(pyridin-3-yl)methanone (lo) (201 mg, 0.435 mmol) and were mixed in Ethanol (7.0 mL). The flask was kept at 100° C. for 2 h. After evaporation of ethanol, the yellow solid residue was diluted with chloroform and NaHCO3 (aq), and the mixture was stirred at room temperature for 20 min. After separation and extraction, the organic layers were combined and washed by brine to pH 7. The removal of the solvent gave yellow solid lp (210 mg), which was applied in the next step without further purification: $^1$H NMR (400 MHz, CDCl$_3$) δ 8.79 (s, 1H), 8.71 (d, J=3.6 Hz, 1H), 8.19 (m, 2H), 7.92-7.78 (m, 1H), 7.49-7.30 (m, 1H), 6.69 (bs, 2H), 5.11-4.50 (m, 2H), 4.19-3.38 (m, 11H), 2.75 (m, 2H), 1.33 (d, J=7.6 Hz, 3H); LC-MS m/z=431 (M+H).

Step 3—(S)-1-(2-fluoroethyl)-3-(4-(4-(3-methylmorpholino)-7-nicotinoyl-5,6,7,8-tetrahydropyrido[3,4-d]pyrimidin-2-yl)phenyl)urea (ox). To a suspension solution of (S)-(2-(4-aminophenyl)-4-(3-methylmorpholino)-5,6-dihydropyrido[3,4-d]pyrimidin-7(8H)-yl)(pyridin-3-yl)methanone (lp) (60.0 mg, 0.116 mmol) and Triethylamine (0.018 mL, 0.13 mmol) in 1,4-Dioxane (0.90 mL) was added 1.90 M of Phosgene in toluene (0.14 mL), and the mixture was stirred for 2 h at room temperature, then at 50° C. for 45 min. 2-fluoroethylamine hydrochloride (57.6 mg, 0.578 mmol) and Triethylamine (0.10 mL, 0.72 mmol) were added into the reaction mixture, and stirred at room temperature for 4 h. The reaction was quenched with NaHCO$_3$ (aq) and extracted with CHCl$_3$. Purification of the crude product gave the desired product ox (22.8 mg, 37.9% yield) as slightly yellow powder: $^1$H NMR (400 MHz, DMSO) δ 8.81 (s, 1H), 8.74 (d, J=1.6 Hz, 1H), 8.70 (dd, J=4.8, 1.6 Hz, 1H), 8.17 (m, 2H), 7.97 (dt, J=7.8, 1.8 Hz, 1H), 7.58-7.37 (m, 3H), 6.45 (s, 1H), 4.89-4.47 (m, 3H), 4.40 (m, 1H), 4.15 (m, 1H), 4.02-3.82 (m, 1H), 3.80-3.34 (m, 9H), 2.78 (bs, 2H), 1.27 (d, J=6.6 Hz, 3H); LC-MS m/z=520 (M+H).

Example 291

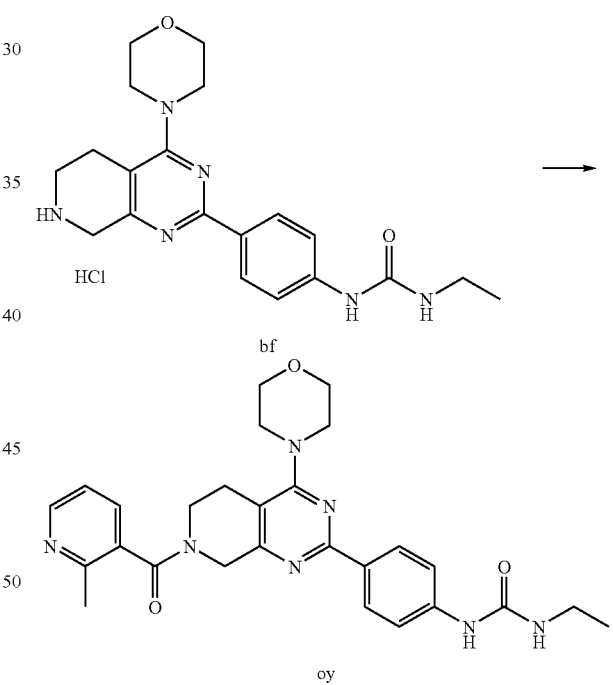

Synthesis of 1-ethyl-3-(4-(7-(2-methylnicotinoyl)-4-morpholino-5,6,7,8-tetrahydropyrido[3,4-d]pyrimidin-2-yl)phenyl)urea (oy): The compound oy was obtained following the general procedure in Example 213, substituting 3-methyloxetane-3-carboxylic acid for 2-methylnicotinic acid and substituting (S)-1-ethyl-3-(4-(4-(3-methylmorpholino)-5,6,7,8-tetrahydropyrido[3,4-d]pyrimidin-2-yl)phenyl)urea hydrochloride salt (jk) for 1-ethyl-3-(4-(4-morpholino-5,6,7,8-tetrahydropyrido[3,4-d]pyrimidin-2-yl)phenyl)urea hydrochloride salt (bf). The desired product oy (74 mg, 58% yield) was obtained as white solid: $^1$H NMR (400 MHz, DMSO) δ 8.64 (s, 1H), 8.20 (m, 2H), 7.42 (m, 2H), 6.15 (m, 1H), 4.61 (m, 2H), 3.82 (m, 1H), 3.73 (m, 4H), 3.49 (m, 5H), 3.20-3.04 (m, 2H), 2.76 (m, 2H), 2.53 (s, 3H, overlapping with DMSO peak), 1.06 (t, J=7.1 Hz, 3H); LC-MS m/z=502 (M+H).

Example 292

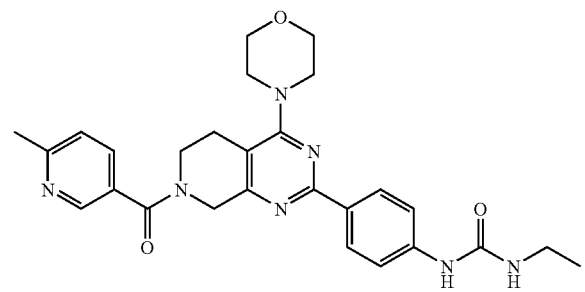

(oz)

Synthesis of 1-ethyl-3-(4-(7-(6-methylnicotinoyl)-4-morpholino-5,6,7,8-tetrahydropyrido[3,4-d]pyrimidin-2-yl)phenyl)urea (oz): The compound oz was prepared following the general procedure in Example 291, substituting 6-Methylnicotinic acid for 2-Methylnicotinic acid: LC-MS m/z=502 (M+H).

Example 294

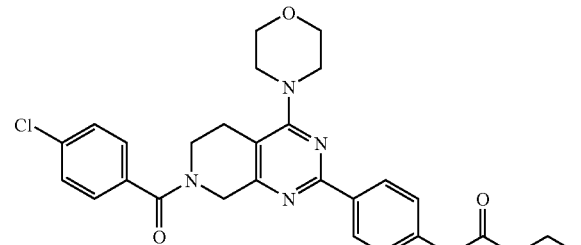

(pa)

Synthesis of 1-(4-(7-(4-chlorobenzoyl)-4-morpholino-5,6,7,8-tetrahydropyrido[3,4-d]pyrimidin-2-yl)phenyl)-3-ethylurea (pa): The compound pa was prepared following the general procedure described in Example 5 by reacting 1-ethyl-3-(4-(4-morpholino-5,6,7,8-tetrahydropyrido[3,4-d]pyrimidin-2-yl)phenyl)urea hydrochloride salt with 4-Chlorobenzoic acid chloride: LC-MS m/z=521 (M+H).

Example 295

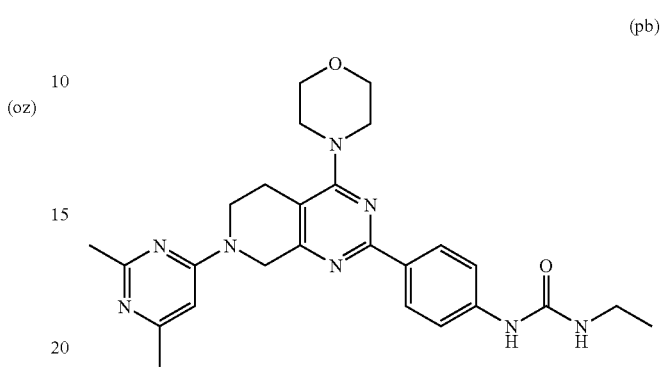

(pb)

Synthesis of 1-(4-(7-(2,6-dimethylpyrimidin-4-yl)-4-morpholino-5,6,7,8-tetrahydropyrido[3,4-d]pyrimidin-2-yl)phenyl)-3-ethylurea (pb): The compound pb was prepared following the general procedure described in Example 287 by reacting 1-ethyl-3-(4-(4-morpholino-5,6,7,8-tetrahydropyrido[3,4-d]pyrimidin-2-yl)phenyl)urea hydrochloride salt with 2-chloro-4,6-dimethylpyrimidine: LC-MS m/z=489 (M+H).

Example 296

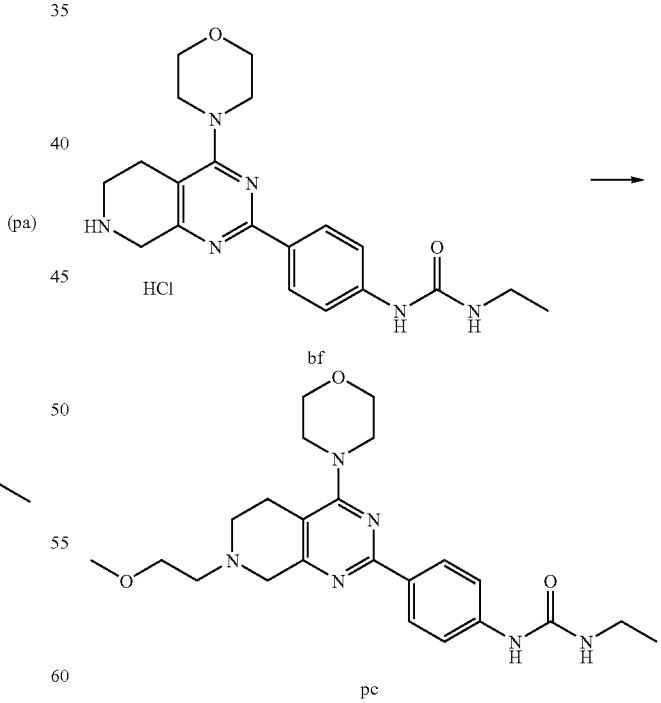

Synthesis of 1-ethyl-3-(4-(7-(2-methoxyethyl)-4-morpholino-5,6,7,8-tetrahydropyrido[3,4-d]pyrimidin-2-yl)phenyl)urea (pc). To a solution of 1-ethyl-3-(4-(4-morpholino-5,6,7,8-tetrahydropyrido[3,4-d]pyrimidin-2-yl)phenyl)urea, hydrochloride salt (bf) (51 mg, 0.13 mmol) in N,N-Diisopropylethylamine (7.0E1 uL, 0.40 mmol) and N-Methylpyrrolidinone (0.80 mL, 8.3 mmol) was added 1-Bromo-2-methoxyethane (3.01 uL, 0.32 mmol) at room temperature. The reaction was microwaved at 80° C. for 30 minutes. After purification, 30.6 mg white powder pc (52% yield) was obtained: $^1$H NMR (400 MHz, DMSO) δ 8.63 (s, 1H), 8.16 (d, J=8.7 Hz, 2H), 7.46 (d, J=8.7 Hz, 2H), 6.15 (t, J=5.5 Hz, 1H), 3.72 (m, 4H), 3.62 (s, 2H), 3.54 (t, J=5.6 Hz, 2H), 3.47 (m, 4H), 3.28 (s, 3H), 3.18-3.05 (m, 2H), 2.73-2.62 (m, 6H), 1.06 (t, J=7.2 Hz, 3H); LC-MS m/z=441 (M+H).

Example 297

(pd)

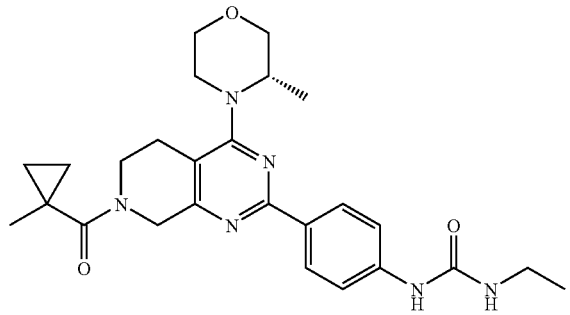

Synthesis of (S)-1-ethyl-3-(4-(7-(1-methylcyclopropanecarbonyl)-4-(3-methylmorpholino)-5,6,7,8-tetrahydropyrido[3,4-d]pyrimidin-2-yl)phenyl)urea (pd): The compound pd was prepared following the general procedure in Example 213, substituting 3-methyloxetane-3-carboxylic acid for 1-Methylcyclopropanecarboxylic acid: LC-MS m/z=479 (M+H).

Example 298

(pe)

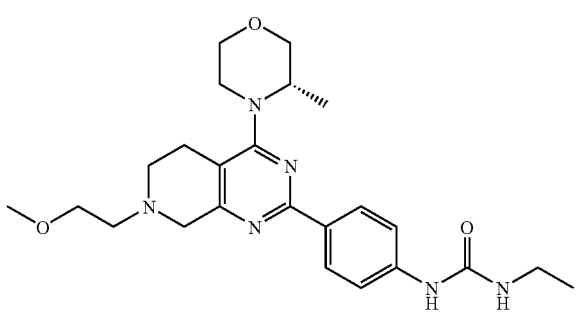

Synthesis of (S)-1-ethyl-3-(4-(7-(2-methoxyethyl)-4-(3-methylmorpholino)-5,6,7,8-tetrahydropyrido[3,4-d]pyrimidin-2-yl)phenyl)urea (pe): The compound pe was prepared following the general procedure in Example 296, substituting 1-ethyl-3-(4-(4-morpholino-5,6,7,8-tetrahydropyrido[3,4-d]pyrimidin-2-yl)phenyl)urea hydrochloride salt for (S)-1-ethyl-3-(4-(4-(3-methylmorpholino)-5,6,7,8-tetrahydropyrido[3,4-d]pyrimidin-2-yl)phenyl)urea hydrochloride salt: LC-MS m/z=455 (M+H).

Example 299

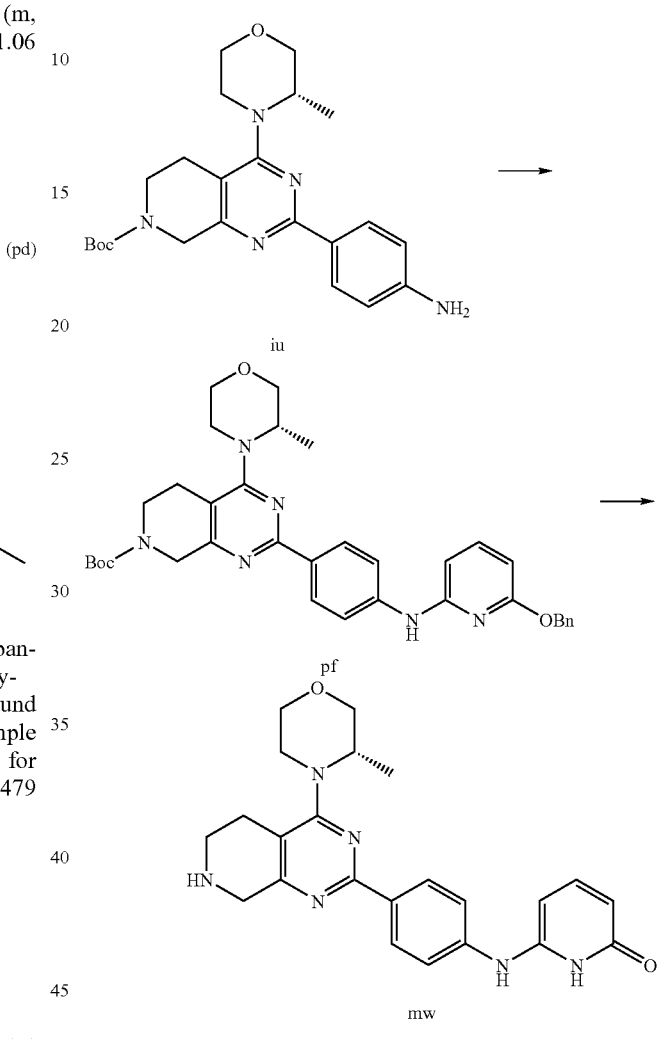

Step 1—Synthesis of (S)-tert-butyl 2-(4-(6-(benzyloxy)pyridin-2-ylamino)phenyl)-4-(3-methylmorpholino)-5,6-dihydropyrido[3,4-d]pyrimidine-7(8H)-carboxylate (pf): The compound pf was obtained following the general procedure in Step 1 of Example 212, substituting 4-(benzyloxy)-2-chloropyrimidine for 2-(benzyloxy)-6-bromopyridine: LC-MS m/z=609 (M+H).

Step 2—Synthesis of (S)-6-(4-(4-(3-methylmorpholino)-5,6,7,8-tetrahydropyrido[3,4-d]pyrimidin-2-yl)phenylamino)pyridin-2(1H)-one (mw). To a solution of (S)-tert-butyl 2-(4-(6-(benzyloxy)pyridin-2-ylamino)phenyl)-4-(3-methylmorpholino)-5,6-dihydropyrido[3,4-d]pyrimidine-7(8H)-carboxylate (pf) (57 mg, 0.094 mmol) in Methylene chloride (3.0 mL) was added 1.0 M of Boron tribromide in Methylene chloride (0.47 mL) at 0° C., which generated yellow precipitates immediately. The reaction was kept at 0° C. for 1 h, then at room temperature for 4 h. The reaction was quenched by MeOH, followed by evaporation of all volatile components. The yellow residue was purified to give the desired product (18.4 mg, 47% yield) as yellow solid: ¹H NMR (400 MHz, DMSO) δ 9.01 (s, 1H), 8.20 (d, J=9.2 Hz, 2H), 7.72 (d, J=9.2 Hz, 2H), 7.41 (t, J=7.9 Hz, 1H), 6.29 (d, J=7.8 Hz, 1H), 5.99 (d, J=7.9 Hz, 1H), 4.19-3.50 (m, 9H), 3.47-3.38 (m, 2H), 3.00-2.77 (m, 2H), 2.58 (m, 1H), 1.38-1.15 (d, J=7.2 Hz, 3H); LC-MS m/z=419 (M+H).

Example 300

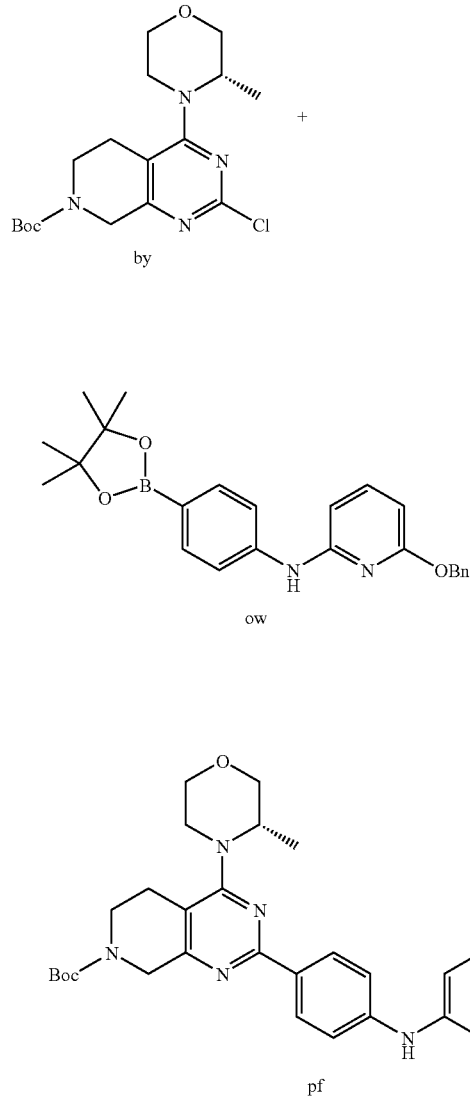

Synthesis of (S)-tert-butyl 2-(4-(6-(benzyloxy)pyridin-2-ylamino)phenyl)-4-(3-methylmorpholino)-5,6-dihydropyrido[3,4-d]pyrimidine-7(8H)-carboxylate (pf). To a mixture of (S)-tert-butyl 2-chloro-4-(3-methylmorpholino)-5,6-dihydropyrido[3,4-d]pyrimidine-7(8H)-carboxylate (by) (54 mg, 0.15 mmol), 6-(benzyloxy)-N-(4-(4,4,5,5-tetramethyl-1,3,2-dioxaborolan-2-yl)phenyl)pyridin-2-amine (ow) (prepared in Example 289, 61 mg, 0.15 mmol), Tetrakis(triphenylphosphine)palladium(0) (11.7 mg, 0.0101 mmol), Potassium carbonate (26.8 mg, 0.194 mmol) and Potassium acetate (19.9 mg, 0.203 mmol) was added Acetonitrile (0.56 mL) and Water (0.23 mL) under N₂. The reaction was microwaved at 120° C. for 20 minutes. After evaporation of solvents, the residue was purified on a silica gel column to give the desired product (80 mg, 90% yield) as slightly brown powder. The ¹H-NMR, TLC and LC-MS were identical to the one in Example 299.

Example 301

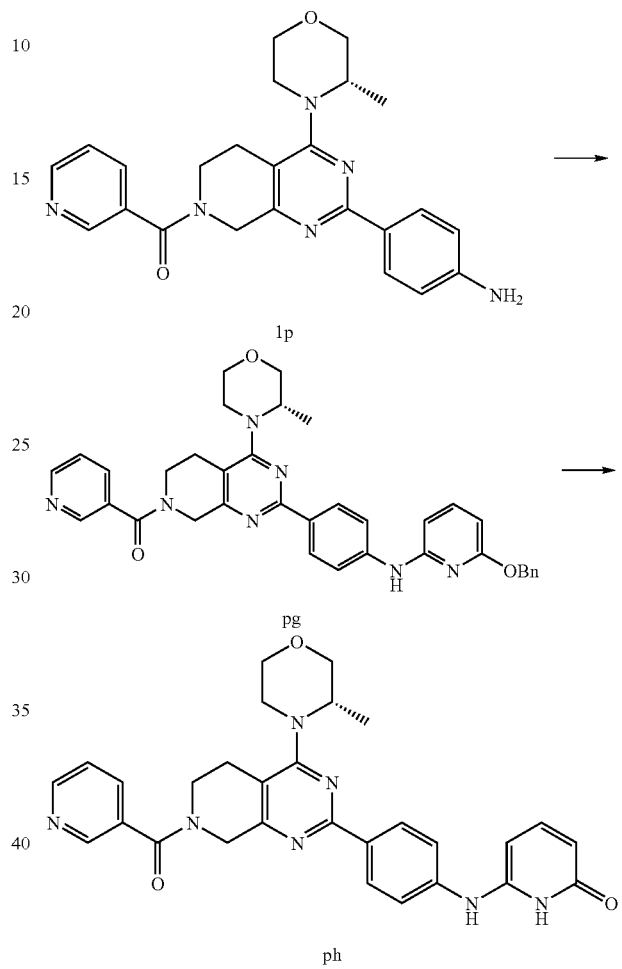

Synthesis of (S)-6-(4-(4-(3-methylmorpholino)-7-nicotinoyl-5,6,7,8-tetrahydropyrido[3,4-d]pyrimidin-2-yl)phenylamino)pyridin-2(1H)-one (ph)

Step 1—Synthesis of (S)-(2-(4-(6-(benzyloxy)pyridin-2-ylamino)phenyl)-4-(3-methylmorpholino)-5,6-dihydropyrido[3,4-d]pyrimidin-7(8H)-yl)(pyridin-3-yl)methanone (pg): The compound pg was obtained following the general procedure in Step 1 of Example 212, substituting 4-(benzyloxy)-2-chloropyrimidine for 2-(benzyloxy)-6-bromopyridine and substituting (S)-tert-butyl 2-(4-aminophenyl)-4-(3-methylmorpholino)-5,6-dihydropyrido[3,4-d]pyrimidine-7(8H)-carboxylate for (S)-(2-(4-aminophenyl)-4-(3-methylmorpholino)-5,6-dihydropyrido[3,4-d]pyrimidin-7(8H)-yl)(pyridin-3-yl)methanone: LC-MS m/z=614 (M+H).

Step 2—Synthesis of (S)-6-(4-(4-(3-methylmorpholino)-7-nicotinoyl-5,6,7,8-tetrahydropyrido[3,4-d]pyrimidin-2-yl)phenylamino)pyridin-2(1H)-one (ph): The compound ph was prepared following the general procedure in Step 2 of Example 212, substituting (S)-tert-butyl 2-(4-(4-(benzyloxy)pyrimidin-2-ylamino)phenyl)-4-(3-methylmorpholino)-5,6-dihydropyrido[3,4-d]pyrimidine-7(8H)-carboxylate for (S)-

(2-(4-(6-(benzyloxy)pyridin-2-ylamino)phenyl)-4-(3-methylmorpholino)-5,6-dihydropyrido[3,4-d]pyrimidin-7(8H)-yl)(pyridin-3-yl)methanone (pg): LC-MS m/z=524 (M+H).

Example 302

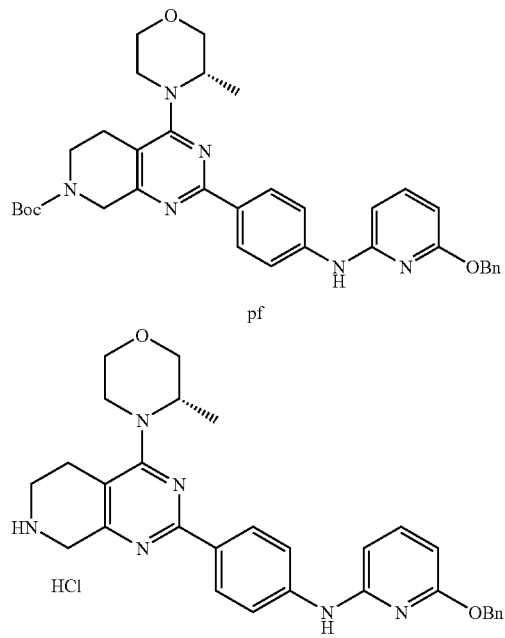

Synthesis of (S)-6-(4-(7-(2-hydroxy-2-methylpropanoyl)-4-(3-methylmorpholino)-5,6,7,8-tetrahydropyrido[3,4-d]pyrimidin-2-yl)phenylamino)pyridin-2(1H)-one (pj)

Step 1—Synthesis of (S)-6-(benzyloxy)-N-(4-(4-(3-methylmorpholino)-5,6,7,8-tetrahydropyrido[3,4-d]pyrimidin-2-yl)phenyl)pyridin-2-amine hydrochloride salt (ms). The compound was prepared following the general procedure in Step 2 of Example 205, substituting (S)-tert-butyl 2-(4-(3-cyclobutylureido)phenyl)-4-(3-methylmorpholino)-5,6-dihydropyrido[3,4-d]pyrimidine-7(8H)-carboxylate for (S)-tert-butyl 2-(4-(6-(benzyloxy)pyridin-2-ylamino)phenyl)-4-(3-methylmorpholino)-5,6-dihydropyrido[3,4-d]pyrimidine-7(8H)-carboxylate (pf): LC-MS m/z=509 (M+H).

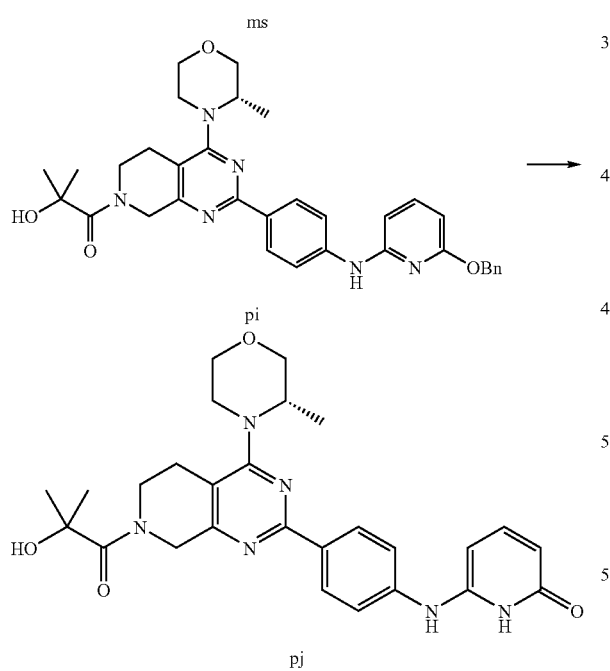

Step 2—Synthesis of (S)-1-(2-(4-(6-(benzyloxy)pyridin-2-ylamino)phenyl)-4-(3-methylmorpholino)-5,6-dihydropyrido[3,4-d]pyrimidin-7(8H)-yl)-2-hydroxy-2-methylpropan-1-one (pi). The compound pi was prepared following the general procedure in Step 3 of Example 208, substituting (S)-3-methyl-4-(2-(4-nitrophenyl)-5,6,7,8-tetrahydropyrido[3,4-d]pyrimidin-4-yl)morpholine hydrochloride for (S)-6-(benzyloxy)-N-(4-(4-(3-methylmorpholino)-5,6,7,8-tetrahydropyrido[3,4-d]pyrimidin-2-yl)phenyl)pyridin-2-amine hydrochloride (ms): LC-MS m/z=595 (M+H).

Step 3—Synthesis of (S)-6-(4-(7-(2-hydroxy-2-methylpropanoyl)-4-(3-methylmorpholino)-5,6,7,8-tetrahydropyrido[3,4-d]pyrimidin-2-yl)phenylamino)pyridin-2(1H)-one (pj): The compound pj was prepared following the general procedure in Step 2 of Example 299, substituting (S)-tert-butyl 2-(4-(6-(benzyloxy)pyridin-2-ylamino)phenyl)-4-(3-methylmorpholino)-5,6-dihydropyrido[3,4-d]pyrimidine-7(8H)-carboxylate for (S)-1-(2-(4-(6-(benzyloxy)pyridin-2-ylamino)phenyl)-4-(3-methylmorpholino)-5,6-dihydropyrido[3,4-d]pyrimidin-7(8H)-yl)-2-hydroxy-2-methylpropan-1-one (pi): LC-MS m/z=505 (M+H).

Example 303

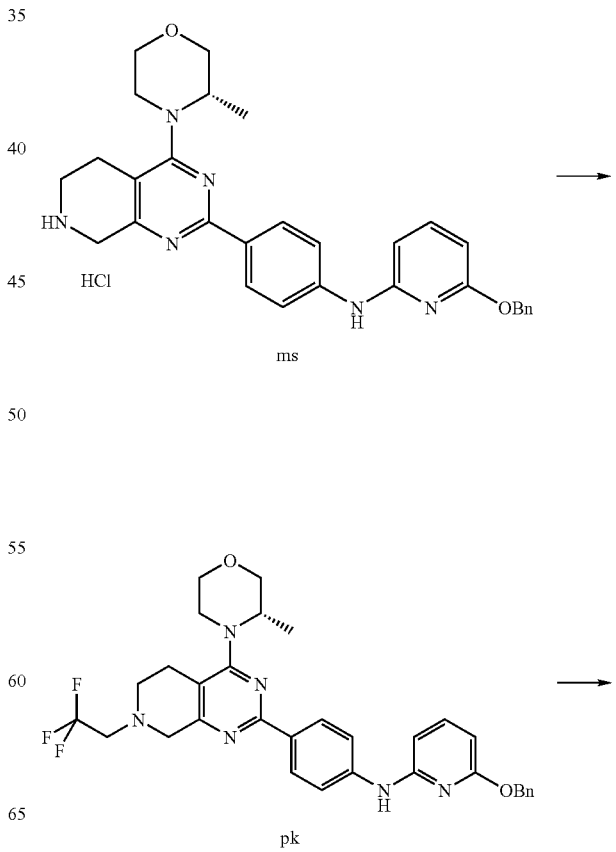

-continued

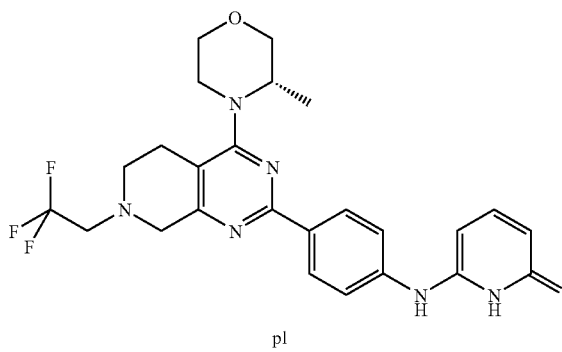

pl

Synthesis of (S)-6-(4-(4-(3-methylmorpholino)-7-(2,2,2-trifluoroethyl)-5,6,7,8-tetrahydropyrido[3,4-d]pyrimidin-2-yl)phenylamino)pyridin-2(1H)-one (pl)

Step 1—Synthesis of (S)-6-(benzyloxy)-N-(4-(4-(3-methylmorpholino)-7-(2,2,2-trifluoroethyl)-5,6,7,8-tetrahydropyrido[3,4-d]pyrimidin-2-yl)phenyl)pyridin-2-amine (pk). To a solution of (S)-6-(benzyloxy)-N-(4-(4-(3-methylmorpholino)-5,6,7,8-tetrahydropyrido[3,4-d]pyrimidin-2-yl)phenyl)pyridin-2-amine hydrochloride salt (ms) (51 mg, 0.094 mmol) in Acetonitrile (1.0 mL) and N,N-Diisopropylethylamine (0.10 mL, 0.57 mmol) was added trifluoroethanol triflate (0.020 mL, 0.14 mmol) at room temperature, and the reaction mixture was microwaved at 140° C. for 30 minutes, followed by the addition of a second portion of Trifluoroethanol triflate (0.030 mL, 0.21 mmol). The resultant reaction mixture was microwaved at 140° C. for 20 minutes. The reaction mixture was diluted with Ethyl acetate, and washed by NaHCO$_3$, water, and brine till pH 7. The orange organic solution was evaporated after dried over Magnesium sulfate. The residue was purified on a silica gel column to give the desired product (pk) (61 mg, 110% yield) as yellow powder: $^1$H NMR (500 MHz, CDCl$_3$) δ 8.30 (d, J=8.4 Hz, 2H), 7.46 (m, 5H), 7.39 (t, J=7.5 Hz, 2H), 7.32 (t, J=7.2 Hz, 1H), 6.55 (s, 1H), 6.45 (d, J=7.8 Hz, 1H), 6.31 (d, J=7.9 Hz, 1H), 5.38 (s, 2H), 4.11 (m, 1H), 4.06-3.80 (m, 4H), 3.80-3.47 (m, 4H), 3.20 (q, J=9.4 Hz, 2H), 3.05-2.95 (m, 1H), 2.86 (m, 1H), 2.82-2.68 (m, 2H), 1.33 (d, J=6.6 Hz, 3H); LC-MS m/z=591 (M+H).

Step 2—Synthesis of (S)-6-(4-(4-(3-methylmorpholino)-7-(2,2,2-trifluoroethyl)-5,6,7,8-tetrahydropyrido[3,4-d]pyrimidin-2-yl)phenylamino)pyridin-2(1H)-one (pl). The compound pl was prepared following the general procedure in Example 218, substituting (S)-4-(benzyloxy)-N-(4-(4-(3-methylmorpholino)-7-(pyrimidin-2-yl)-5,6,7,8-tetrahydropyrido[3,4-d]pyrimidin-2-yl)phenyl)pyrimidin-2-amine for (S)-6-(benzyloxy)-N-(4-(4-(3-methylmorpholino)-7-(2,2,2-trifluoroethyl)-5,6,7,8-tetrahydropyrido[3,4-d]pyrimidin-2-yl)phenyl)pyridin-2-amine: LC-MS m/z=501 (M+H).

Example 304

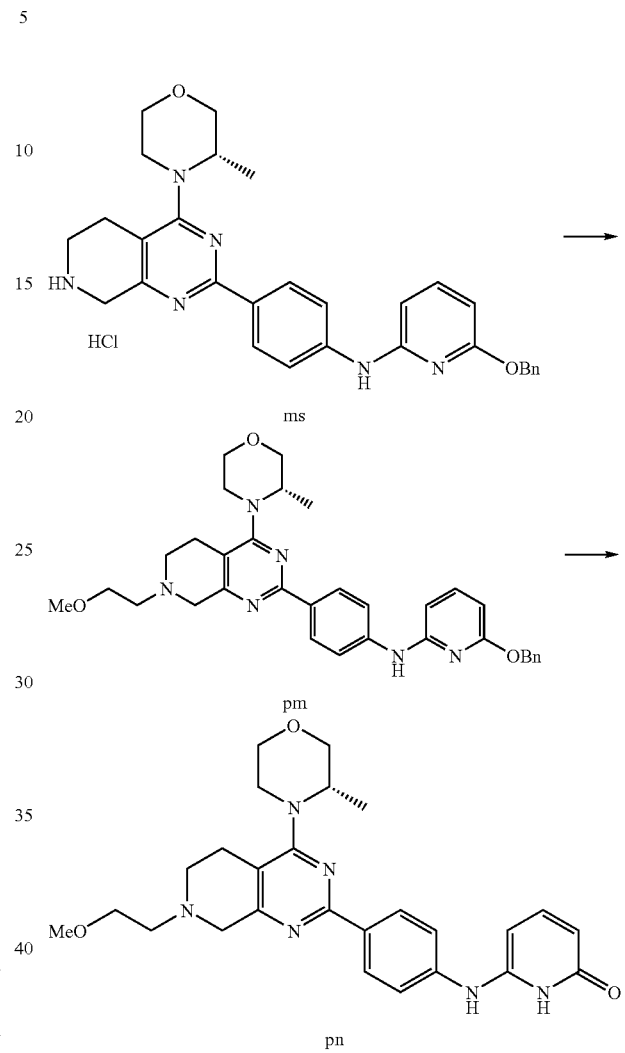

Synthesis of (S)-6-(4-(7-(2-methoxyethyl)-4-(3-methylmorpholino)-5,6,7,8-tetrahydropyrido[3,4-d]pyrimidin-2-yl)phenylamino)pyridin-2(1H)-one (pn)

Step 1—Synthesis of (S)-6-(benzyloxy)-N-(4-(7-(2-methoxyethyl)-4-(3-methylmorpholino)-5,6,7,8-tetrahydropyrido[3,4-d]pyrimidin-2-yl)phenyl)pyridin-2-amine (pm): The compound pm was prepared following the general procedure in Example 296, substituting 1-ethyl-3-(4-(4-morpholino-5,6,7,8-tetrahydropyrido[3,4-d]pyrimidin-2-yl)phenyl)urea, hydrochloride salt for (S)-6-(benzyloxy)-N-(4-(4-(3-methylmorpholino)-5,6,7,8-tetrahydropyrido[3,4-d]pyrimidin-2-yl)phenyl)pyridin-2-amine hydrochloride salt (ms): LC-MS m/z=567 (M+H).

Step 2—Synthesis of (S)-6-(4-(7-(2-methoxyethyl)-4-(3-methylmorpholino)-5,6,7,8-tetrahydropyrido[3,4-d]pyrimidin-2-yl)phenylamino)pyridin-2(1H)-one (pn): To a solution of (S)-6-(benzyloxy)-N-(4-(7-(2-methoxyethyl)-4-(3-methylmorpholino)-5,6,7,8-tetrahydropyrido[3,4-d]pyrimidin-2-yl)phenyl)pyridin-2-amine (pm) (91 mg, 0.16 mmol) in Methanol (20.0 mL) and Ethyl acetate (10.0 mL) was added Lindlar's Catalyst (22 mg) and 20% Pd(OH)$_2$ on carbon (30 mg). The reaction mixture was purged with H$_2$ and the reaction suspension was stirred at room temperature overnight under 1 atm H$_2$. The reaction mixture was then filted and the filtrate was removed by evaporation. The crude product was purified to give the desired product pn (37.9 mg, 50% yield) as grey powder: $^1$H NMR (400 MHz, DMSO) δ 10.19 (bs, 1H), 9.02 (bs, 1H), 8.18 (d, J=8.7 Hz, 2H), 7.74 (bs, 2H), 7.41 (t, J=7.9 Hz, 1H), 6.30 (s, 1H), 6.00 (d, J=7.8 Hz, 1H), 4.13 (m, 1H), 3.88 (d, J=10.5 Hz, 1H), 3.78-3.34 (m, 9H), 3.28 (s, 3H), 2.84-2.55 (m, 6H), 1.24 (d, J=6.6 Hz, 3H); LC-MS m/z=477 (M+H).

Example 305

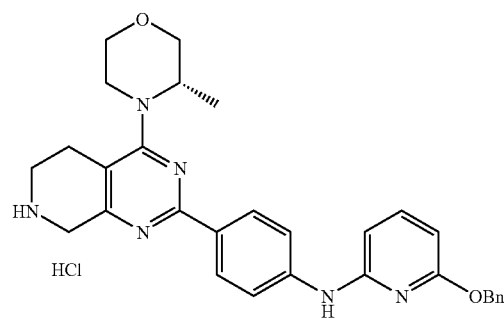

ms

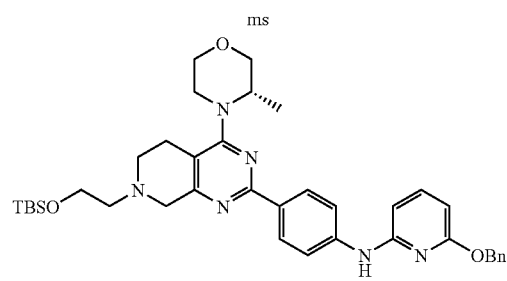

po

Synthesis of (S)-6-(4-(7-(2-hydroxyethyl)-4-(3-methyl-morpholino)-5,6,7,8-tetrahydropyrido[3,4-d]pyrimidin-2-yl)phenylamino)pyridin-2(1H)-one (pq)

Step 1—Synthesis of (S)-6-(benzyloxy)-N-(4-(7-(2-(tert-butyldimethylsilyloxy)ethyl)-4-(3-methylmorpholino)-5,6,7,8-tetrahydropyrido[3,4-d]pyrimidin-2-yl)phenyl)pyridin-2-amine (po): The compound po was prepared following the general procedure in Example 296, substituting 1-ethyl-3-(4-(4-morpholino-5,6,7,8-tetrahydropyrido[3,4-d]pyrimidin-2-yl)phenyl)urea, hydrochloride salt for (S)-6-(benzyloxy)-N-(4-(4-(3-methylmorpholino)-5,6,7,8-tetrahydropyrido[3,4-d]pyrimidin-2-yl)phenyl)pyridin-2-amine hydrochloride salt (ms) and substituting 1-bromo-2-methoxyethane for (2-bromoethoxy)(tert-butyl)dimethylsilane: LC-MS m/z=667 (M+H).

Step 2—Synthesis of (S)-2-(2-(4-(6-(benzyloxy)pyridin-2-ylamino)phenyl)-4-(3-methylmorpholino)-5,6-dihydropyrido[3,4-d]pyrimidin-7(8H)-yl)ethanol (pp): To a solution of (S)-6-(benzyloxy)-N-(4-(7-(2-(tert-butyldimethylsilyloxy)ethyl)-4-(3-methylmorpholino)-5,6,7,8-tetrahydropyrido[3,4-d]pyrimidin-2-yl)phenyl)pyridin-2-amine (po) (413 mg, 0.619 mmol) in Methylene chloride (9.0 mL) and Methanol (4.0 mL) was added 4.0 M of Hydrogen chloride in 1,4-Dioxane (4.50 mL), and the yellow solution was stirred at room temperature for 2.5 h. The evaporation of the volatiles from the reaction mixture gave yellow solid pp, which was washed twice by ether. The crude product pp was used without further purification: LC-MS m/z=553 (M+H).

Step 3—Synthesis of (S)-6-(4-(7-(2-hydroxyethyl)-4-(3-methylmorpholino)-5,6,7,8-tetrahydropyrido[3,4-d]pyrimidin-2-yl)phenylamino)pyridin-2(1H)-one (pq): The compound pq was prepared following the general procedure in Step 2 of Example 304, substituting (S)-6-(benzyloxy)-N-(4-(7-(2-methoxyethyl)-4-(3-methylmorpholino)-5,6,7,8-tetrahydropyrido[3,4-d]pyrimidin-2-yl)phenyl)pyridin-2-amine for (S)-2-(2-(4-(6-(benzyloxy)pyridin-2-ylamino)phenyl)-4-(3-methylmorpholino)-5,6-dihydropyrido[3,4-d]pyrimidin-7(8H)-yl)ethanol (pp): LC-MS m/z=463 (M+H).

Example 306

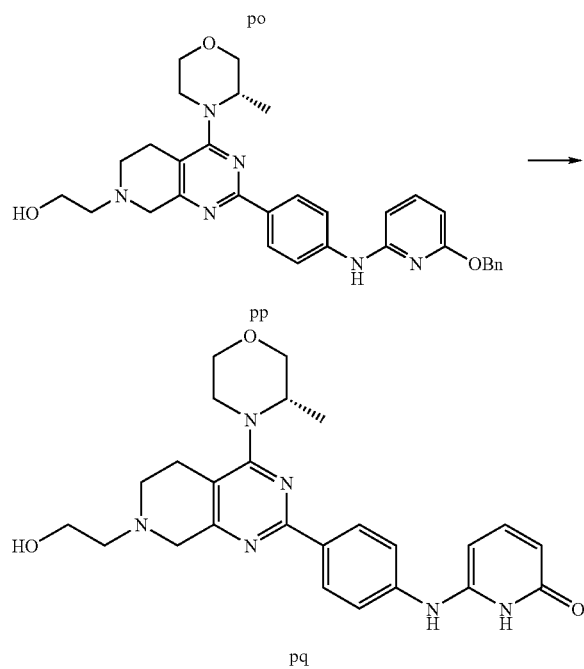

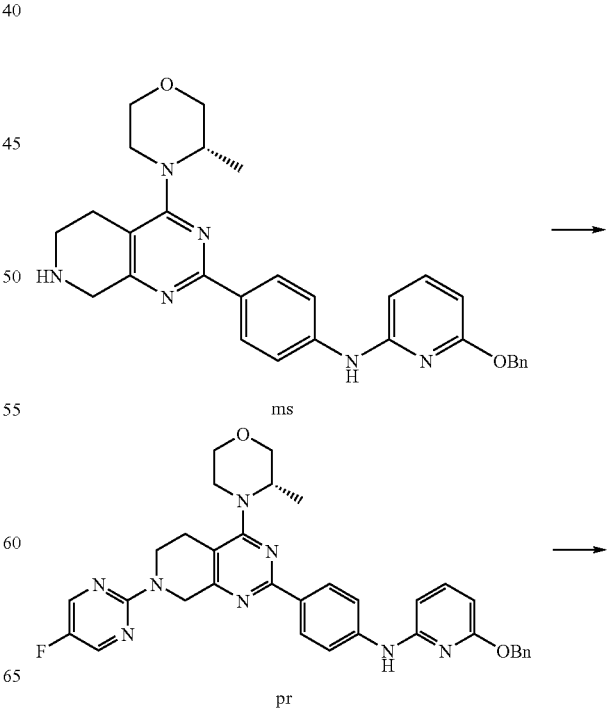

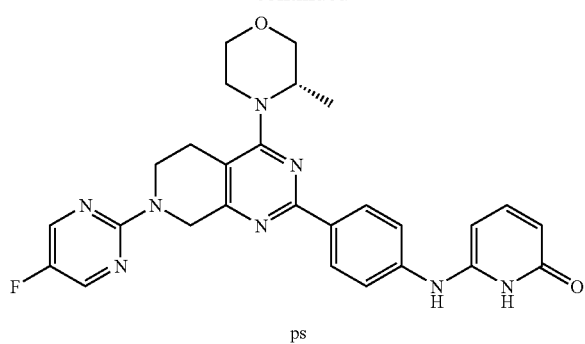

ps

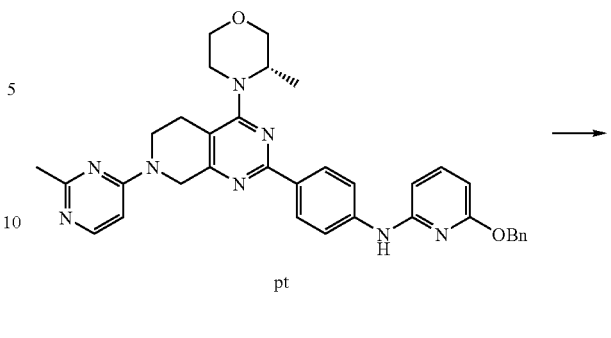

pt

Synthesis of (S)-6-(4-(7-(5-fluoropyrimidin-2-yl)-4-(3-methylmorpholino)-5,6,7,8-tetrahydropyrido[3,4-d]pyrimidin-2-yl)phenylamino)pyridin-2(1H)-one (ps)

Step 1—Synthesis of (S)-6-(benzyloxy)-N-(4-(7-(5-fluoropyrimidin-2-yl)-4-(3-methylmorpholino)-5,6,7,8-tetrahydropyrido[3,4-d]pyrimidin-2-yl)phenyl)pyridin-2-amine (pr): The compound pr was prepared following the general procedure in Example 287, substituting (S)-1-ethyl-3-(4-(4-(3-methylmorpholino)-6,7,8,9-tetrahydro-5H-pyrimido[5,4-d]azepin-2-yl)phenyl)urea for (S)-6-(benzyloxy)-N-(4-(4-(3-methylmorpholino)-5,6,7,8-tetrahydropyrido[3,4-d]pyrimidin-2-yl)phenyl)pyridin-2-amine (ms) and substituting 4-Chloro-6-methylpyrimidine for 2-Chloro-4-fluoropyrimidine: LC-MS m/z=605 (M+H).

Step 2—Synthesis of (S)-6-(4-(7-(5-fluoropyrimidin-2-yl)-4-(3-methylmorpholino)-5,6,7,8-tetrahydropyrido[3,4-d]pyrimidin-2-yl)phenylamino)pyridin-2(1H)-one (ps). The compound ps was prepared following the general procedure in Step 2 of Example 304, substituting (S)-6-(benzyloxy)-N-(4-(7-(2-methoxyethyl)-4-(3-methylmorpholino)-5,6,7,8-tetrahydropyrido[3,4-d]pyrimidin-2-yl)phenyl)pyridin-2-amine for (S)-6-(benzyloxy)-N-(4-(7-(5-fluoropyrimidin-2-yl)-4-(3-methylmorpholino)-5,6,7,8-tetrahydropyrido[3,4-d]pyrimidin-2-yl)phenyl)pyridin-2-amine (pr): LC-MS m/z=515 (M+H).

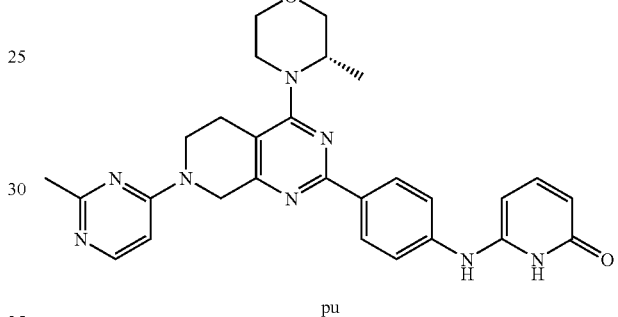

pu

Synthesis of (S)-6-(4-(4-(3-methylmorpholino)-7-(2-methylpyrimidin-4-yl)-5,6,7,8-tetrahydropyrido[3,4-d]pyrimidin-2-yl)phenylamino)pyridin-2(1H)-one (pu): Compound pu was prepared through the intermediate compounds (S)-6-(benzyloxy)-N-(4-(4-(3-methylmorpholino)-7-(2-methylpyrimidin-4-yl)-5,6,7,8-tetrahydropyrido[3,4-d]pyrimidin-2-yl)phenyl)pyridin-2-amine (pt) and compound ms, according to the procedures outlined in Example 306: LC-MS m/z=511 (M+H).

Example 307

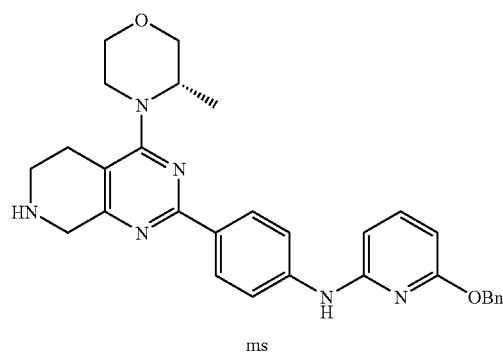

ms

Example 308

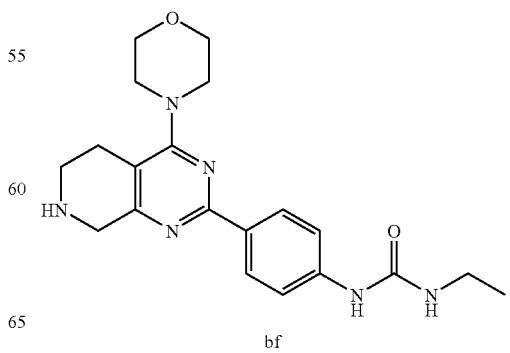

bf

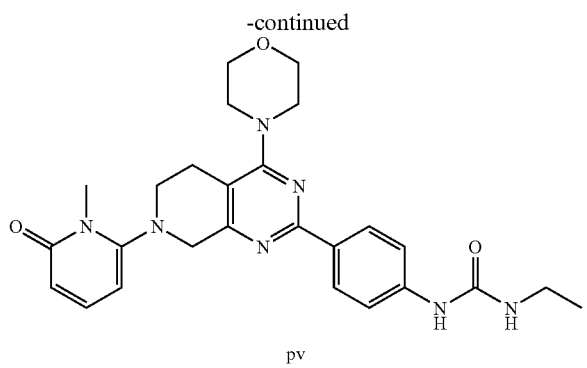

pv

Synthesis of 1-ethyl-3-(4-(7-(1-methyl-6-oxo-1,6-dihydropyridin-2-yl)-4-morpholino-5,6,7,8-tetrahydropyrido[3,4-d]pyrimidin-2-yl)phenyl)urea (pv): To a solution of 1-ethyl-3-(4-(4-morpholino-5,6,7,8-tetrahydropyrido[3,4-d]pyrimidin-2-yl)phenyl)urea (bf) (115 mg, 0.300 mmol) in N,N-Dimethylformamide (2.00 mL) and N,N-Diisopropylethylamine (0.104 mL, 0.600 mmol) was added 6-chloror-1-methylpyridin-2(1H)-one (129 mg, 0.90 mmol) at room temperature. The reaction was kept at 140° C. overnight, followed by RPHPLC purification. The desired product pv (6.4 mg, 4.4% yield) was obtained as white powder: $^1$H NMR (400 MHz, DMSO) δ 8.64 (s, 1H), 8.19 (d, J=8.8 Hz, 2H), 7.48 (d, J=8.8 Hz, 2H), 7.38 (m, 1H), 6.19-6.10 (m, 2H), 6.01 (d, J=6.6 Hz, 1H), 4.15 (s, 2H), 3.80-3.71 (m, 4H), 3.53 (m, 4H), 3.48 (s, 3H), 3.24-3.06 (m, 4H), 2.86 (s, 2H), 1.06 (t, J=7.2 Hz, 3H); LC-MS m/z=490 (M+H).

Example 309

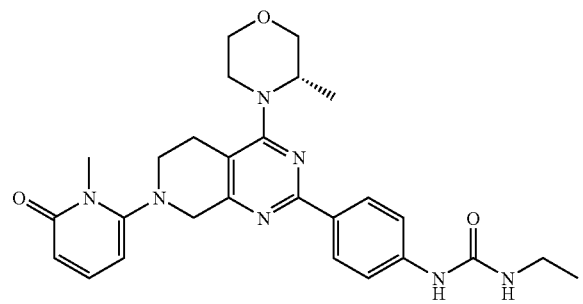

(pw)

Synthesis of (S)-1-ethyl-3-(4-(7-(1-methyl-6-oxo-1,6-dihydropyridin-2-yl)-4-(3-methylmorpholino)-5,6,7,8-tetrahydropyrido[3,4-d]pyrimidin-2-yl)phenyl)urea (pw): The compound was prepared following the general procedure in Example 308, substituting 1-ethyl-3-(4-(4-morpholino-5,6,7,8-tetrahydropyrido[3,4-d]pyrimidin-2-yl)phenyl)urea for (S)-1-ethyl-3-(4-(4-(3-methylmorpholino)-5,6,7,8-tetrahydropyrido[3,4-d]pyrimidin-2-yl)phenyl)urea: LC-MS m/z=504 (M+H).

Example 310

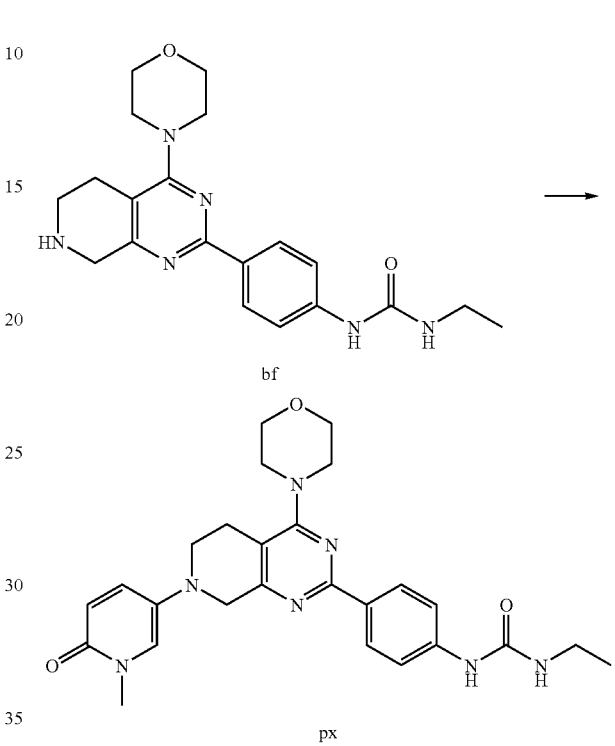

Synthesis of 1-ethyl-3-(4-(7-(1-methyl-6-oxo-1,6-dihydropyridin-3-yl)-4-morpholino-5,6,7,8-tetrahydropyrido[3,4-d]pyrimidin-2-yl)phenyl)urea (px). The compound was prepared following the general procedure in Example 289, substituting 4-(4,4,5,5-tetramethyl-1,3,2-dioxaborolan-2-yl)aniline for 1-ethyl-3-(4-(4-morpholino-5,6,7,8-tetrahydropyrido[3,4-d]pyrimidin-2-yl)phenyl)urea and substituting 2-Bromo-6-benzyloxypyridine for 5-bromo-1-methylpyridin-2(1H)-one: LC-MS m/z=490 (M+H).

Example 311

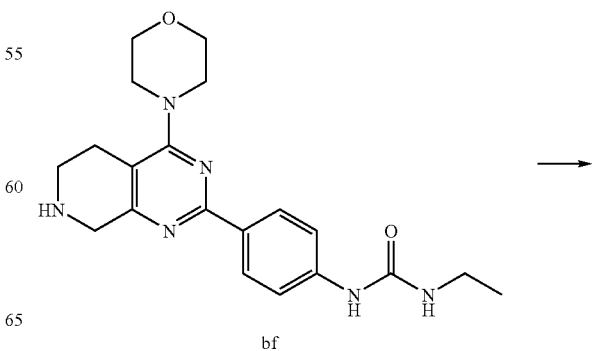

bf

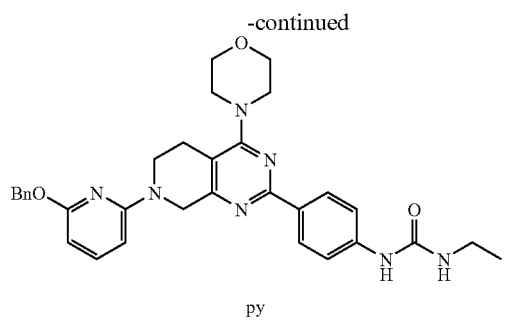

py

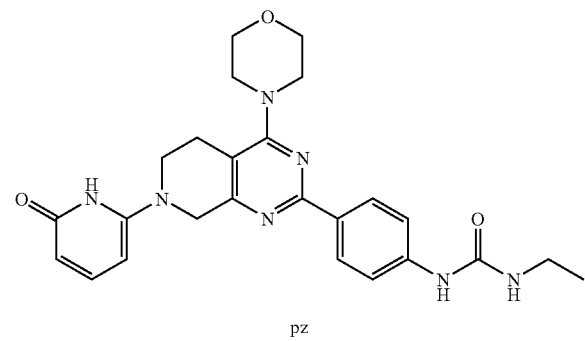

pz

Synthesis of 1-ethyl-3-(4-(4-morpholino-7-(6-oxo-1,6-dihydropyridin-2-yl)-5,6,7,8-tetrahydropyrido[3,4-d]pyrimidin-2-yl)phenyl)urea (pz)

Step 1—Synthesis of 1-(4-(7-(6-(benzyloxy)pyridin-2-yl)-4-morpholino-5,6,7,8-tetrahydropyrido[3,4-d]pyrimidin-2-yl)phenyl)-3-ethylurea (py). The compound py was prepared following the general procedure in Example 289, substituting 4-(4,4,5,5-tetramethyl-1,3,2-dioxaborolan-2-yl)aniline for 1-ethyl-3-(4-(4-morpholino-5,6,7,8-tetrahydropyrido[3,4-d]pyrimidin-2-yl)phenyl)urea: LC-MS m/z=566 (M+H).

Step 2—Synthesis of 1-ethyl-3-(4-(4-morpholino-7-(6-oxo-1,6-dihydropyridin-2-yl)-5,6,7,8-tetrahydropyrido[3,4-d]pyrimidin-2-yl)phenyl)urea (pz). Compound pz was prepared following the general procedure in Step 2 of Example 304, substituting (S)-6-(benzyloxy)-N-(4-(7-(2-methoxyethyl)-4-(3-methylmorpholino)-5,6,7,8-tetrahydropyrido[3,4-d]pyrimidin-2-yl)phenyl)pyridin-2-amine for 1-(4-(7-(6-(benzyloxy)pyridin-2-yl)-4-morpholino-5,6,7,8-tetrahydropyrido[3,4-d]pyrimidin-2-yl)phenyl)-3-ethylurea: LC-MS m/z=476 (M+H).

Example 312

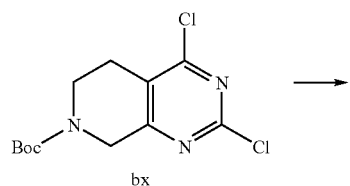

bx

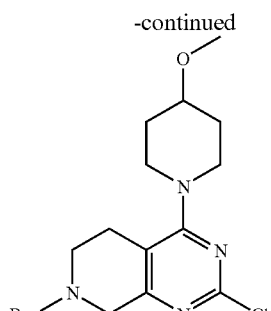

qa

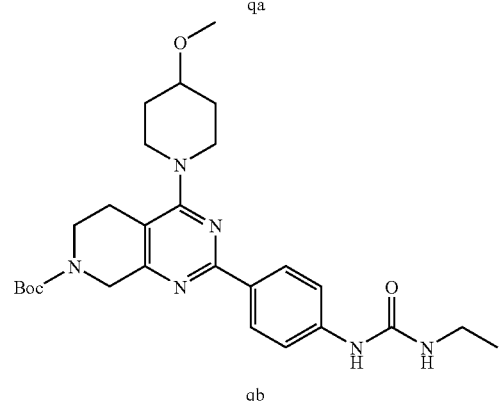

qb

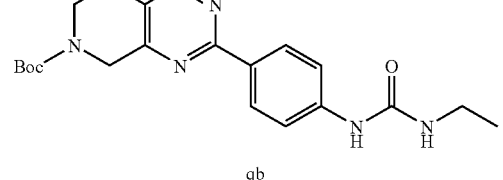

qc

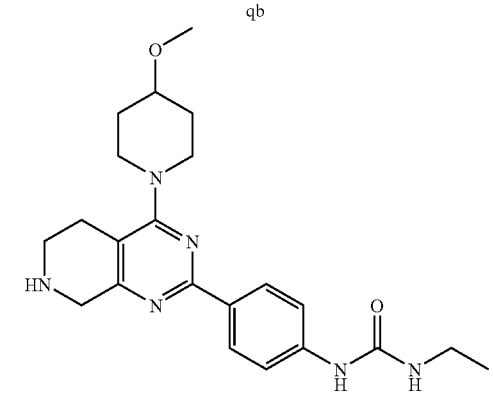

qd

Synthesis of 1-ethyl-3-(4-(4-(4-methoxypiperidin-1-yl)-7-(pyrimidin-2-yl)-5,6,7,8-tetrahydropyrido[3,4-d]pyrimidin-2-yl)phenyl)urea (qd)

Step 1—Synthesis of tert-butyl 2-chloro-4-(4-methoxypiperidin-1-yl)-5,6-dihydropyrido[3,4-d]pyrimidine-7(8H)-carboxylate (qa). Compound qa was prepared following the general procedure in Step 1 of Example 285, substituting 7-Benzyl-2,4-dichloro-6,7,8,9-tetrahydro-5H-pyrimido[4,5-d]azepine for tert-butyl 2,4-dichloro-5,6-dihydropyrido[3,4-d]pyrimidine-7(8H)-carboxylate and substituting Morpholine for 4-methoxypiperidine: LC-MS m/z=383 (M+H).

Step 2—Synthesis of tert-butyl 2-(4-(3-ethylureido)phenyl)-4-(4-methoxypiperidin-1-yl)-5,6-dihydropyrido[3,4-d]pyrimidine-7(8H)-carboxylate (qb). The compound qb was prepared following the general procedure in Step 2 of Example 285, substituting 4-(7-benzyl-2-chloro-6,7,8,9-tetrahydro-5H-pyrimido[5,4-d]azepin-4-yl)morpholine for tert-butyl 2-chloro-4-(4-methoxypiperidin-1-yl)-5,6-dihydropyrido[3,4-d]pyrimidine-7(8H)-carboxylate (qa): LC-MS m/z=511 (M+H).

Step 3—Synthesis of 1-ethyl-3-(4-(4-(4-methoxypiperidin-1-yl)-5,6,7,8-tetrahydropyrido[3,4-d]pyrimidin-2-yl)phenyl)urea (qc). The compound qc was prepared following the general procedure in Step 2 of Example 205, substituting (S)-tert-butyl 2-(4-(3-cyclobutylureido)phenyl)-4-(3-methylmorpholino)-5,6-dihydropyrido[3,4-d]pyrimidine-7(8H)-carboxylate for tert-butyl 2-(4-(3-ethylureido)phenyl)-4-(4-methoxypiperidin-1-yl)-5,6-dihydropyrido[3,4-d]pyrimidine-7(8H)-carboxylate (qb): LC-MS m/z=411 (M+H).

Step 4—Synthesis of 1-ethyl-3-(4-(4-(4-methoxypiperidin-1-yl)-7-(pyrimidin-2-yl)-5,6,7,8-tetrahydropyrido[3,4-d]pyrimidin-2-yl)phenyl)urea (qd). The compound was prepared following the general procedure in Example 287, substituting (S)-1-ethyl-3-(4-(4-(3-methylmorpholino)-6,7,8,9-tetrahydro-5H-pyrimido[5,4-d]azepin-2-yl)phenyl)urea for 1-ethyl-3-(4-(4-(4-methoxypiperidin-1-yl)-5,6,7,8-tetrahydropyrido[3,4-d]pyrimidin-2-yl)phenyl)urea (qc) and substituting 4-Chloro-6-methylpyrimidine for 2-Chloropyrimidine: LC-MS m/z=489 (M+H).

Example 313

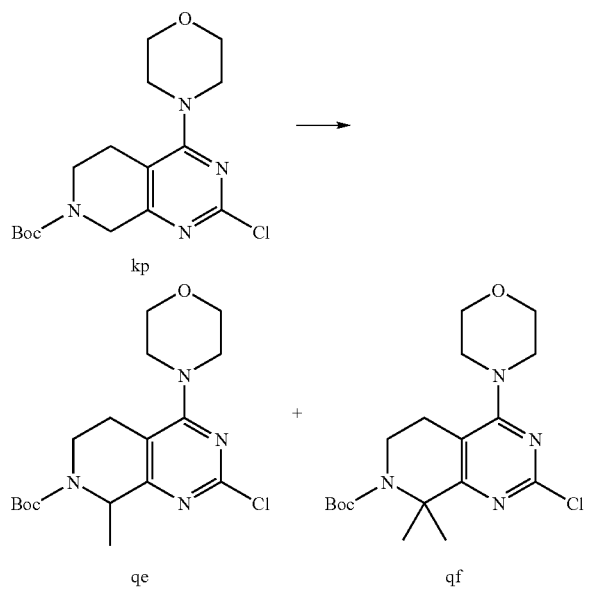

Synthesis of tert-butyl 2-chloro-8-methyl-4-morpholino-5,6-dihydropyrido[3,4-d]pyrimidine-7(8H)-carboxylate (qe) and tert-butyl 2-chloro-8,8-dimethyl-4-morpholino-5,6-dihydropyrido[3,4-d]pyrimidine-7(8H)-carboxylate (qf). To a solution of tert-butyl 2-chloro-4-morpholino-5,6-dihydropyrido[3,4-d]pyrimidine-7(8H)-carboxylate (dp) (501 mg, 1.41 mmol) in Tetrahydrofuran (14 mL) was added 1.7 M of tert-Butyllithium in Pentane (1.1 mL) at −78° C., which resulted orange color solution. The reaction was kept at −78° C. for 40 min before Methyl iodide (0.44 mL, 7.1 mmol) was injected. The solution was kept at −78° C. for another 40 min before quenching with water. The mixture was diluted by Dichloromethane, which was washed by water and brine till pH 7. After evaporation, the residue was purified on a silica gel column. Tert-butyl 2-chloro-8-methyl-4-morpholino-5,6-dihydropyrido[3,4-d]pyrimidine-7(8H)-carboxylate (qe) (452 mg, 87% yield) was obtained as white solid: $^1$H NMR (500 MHz, CDCl$_3$) δ 5.02 (bs, 1H), 4.26 (bs, 1H), 3.91-3.79 (m, 2H), 3.79-3.67 (m, 2H), 3.61 (m, 2H), 3.36 (m, 2H), 2.89 (bs, 1H), 2.75 (bs, 1H), 2.46 (d, J=15.0 Hz, 1H), 1.50 (d, J=7.0 Hz, 3H), 1.48 (s, 9H); LC-MS m/z=369 (M+H). Tert-butyl 2-chloro-8,8-dimethyl-4-morpholino-5,6-dihydropyrido[3,4-d]pyrimidine-7(8H)-carboxylate (qf) (44 mg, 8% yield) was obtained as white solid: $^1$H NMR (400 MHz, CDCl$_3$) δ 3.87-3.73 (m, 4H), 3.60-3.52 (m, 2H), 3.52-3.42 (m, 4H), 2.65-2.56 (m, 2H), 1.74 (s, 6H), 1.50 (s, 9H); LC-MS m/z=383 (M+H).

Example 314

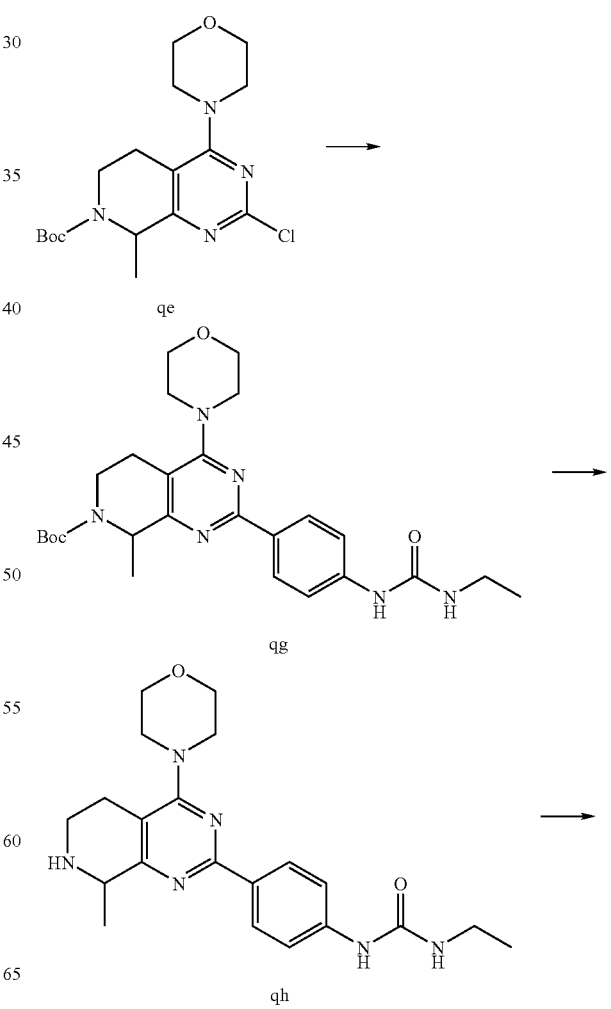

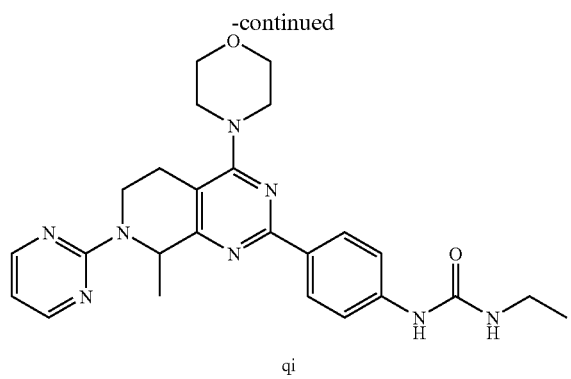

qi

Synthesis of 1-ethyl-3-(4-(8-methyl-4-morpholino-7-(pyrimidin-2-yl)-5,6,7,8-tetrahydropyrido[3,4-d]pyrimidin-2-yl)phenyl)urea (qi)

Step 1—Synthesis of tert-butyl 2-(4-(3-ethylureido)phenyl)-8-methyl-4-morpholino-5,6-dihydropyrido[3,4-d]pyrimidine-7(8H)-carboxylate (qg). The compound qg was prepared following the general procedure in Step 2 of Example 285, substituting 4-(7-benzyl-2-chloro-6,7,8,9-tetrahydro-5H-pyrimido[5,4-d]azepin-4-yl)morpholine for tert-butyl 2-chloro-8-methyl-4-morpholino-5,6-dihydropyrido[3,4-d]pyrimidine-7(8H)-carboxylate (qe): LC-MS m/z=497 (M+H).

Step 2—Synthesis of 1-ethyl-3-(4-(8-methyl-4-morpholino-5,6,7,8-tetrahydropyrido[3,4-d]pyrimidin-2-yl)phenyl)urea hydrochloride salt (qh). The compound qh was prepared following the general procedure in Step 2 of Example 201, substituting (S)-tert-butyl 2-(4-(3-cyclobutylureido)phenyl)-4-(3-methylmorpholino)-5,6-dihydropyrido[3,4-d]pyrimidine-7(8H)-carboxylate for tert-butyl 2-(4-(3-ethylureido)phenyl)-8-methyl-4-morpholino-5,6-dihydropyrido[3,4-d]pyrimidine-7(8H)-carboxylate (qg): LC-MS m/z=397 (M+H).

Step 3—Synthesis of 1-ethyl-3-(4-(8-methyl-4-morpholino-7-(pyrimidin-2-yl)-5,6,7,8-tetrahydropyrido[3,4-d]pyrimidin-2-yl)phenyl)urea (qi). The compound qi was prepared following the general procedure in Example 287, substituting (S)-1-ethyl-3-(4-(4-(3-methylmorpholino)-6,7,8,9-tetrahydro-5H-pyrimido[5,4-d]azepin-2-yl)phenyl)urea for 1-ethyl-3-(4-(8-methyl-4-morpholino-5,6,7,8-tetrahydropyrido[3,4-d]pyrimidin-2-yl)phenyl)urea hydrochloride salt (qh) and substituting 4-Chloro-6-methylpyrimidine for 2-Chloropyrimidine: LC-MS m/z=475 (M+H). The two enantiomers were separated by chiral HPLC.

Example 315

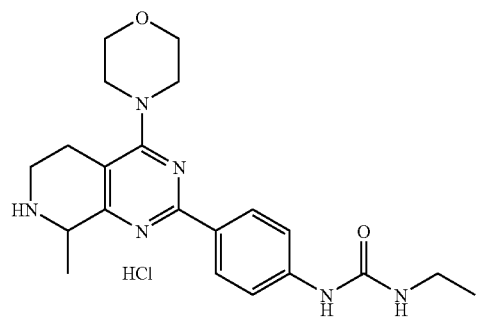

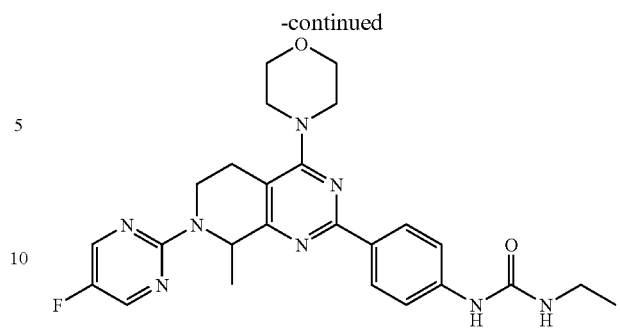

Synthesis of 1-ethyl-3-(4-(7-(5-fluoropyrimidin-2-yl)-8-methyl-4-morpholino-5,6,7,8-tetrahydropyrido[3,4-d]pyrimidin-2-yl)phenyl)urea (qj). The compound qj was prepared following the general procedure in Step 3 of Example 314, substituting 2-Chloropyrimidine for 2-chloro-5-fluoropyrimidine: LC-MS m/z=493 (M+H).

Example 316

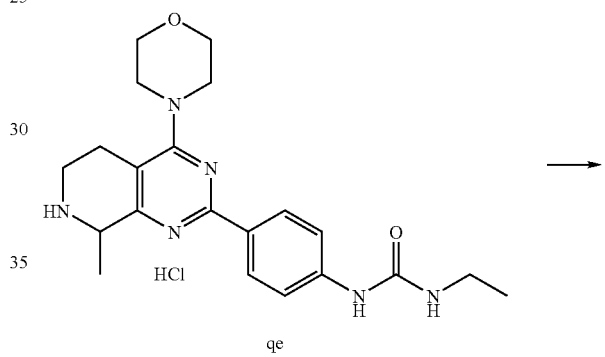

qe

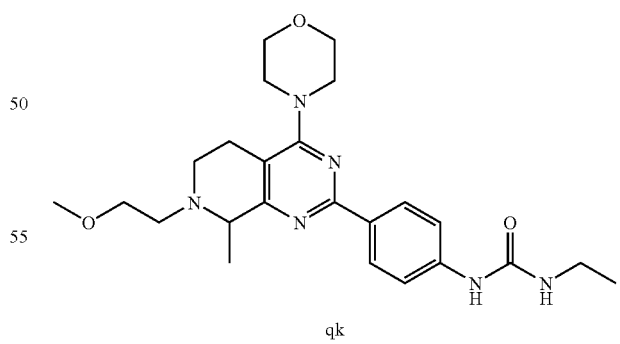

qk

Synthesis of 1-ethyl-3-(4-(7-(2-methoxyethyl)-8-methyl-4-morpholino-5,6,7,8-tetrahydropyrido[3,4-d]pyrimidin-2-yl)phenyl)urea (qk): The compound qk was prepared following the general procedure in Example 296, substituting 1-ethyl-3-(4-(4-morpholino-5,6,7,8-tetrahydropyrido[3,4-d]pyrimidin-2-yl)phenyl)urea hydrochloride salt for 1-ethyl-3-(4-(8-methyl-4-morpholino-5,6,7,8-tetrahydropyrido[3,4-d]

pyrimidin-2-yl)phenyl)urea hydrochloride salt (qe). The two enantiomers were separated by chiral HPLC: LC-MS m/z=455 (M+H).

Example 317

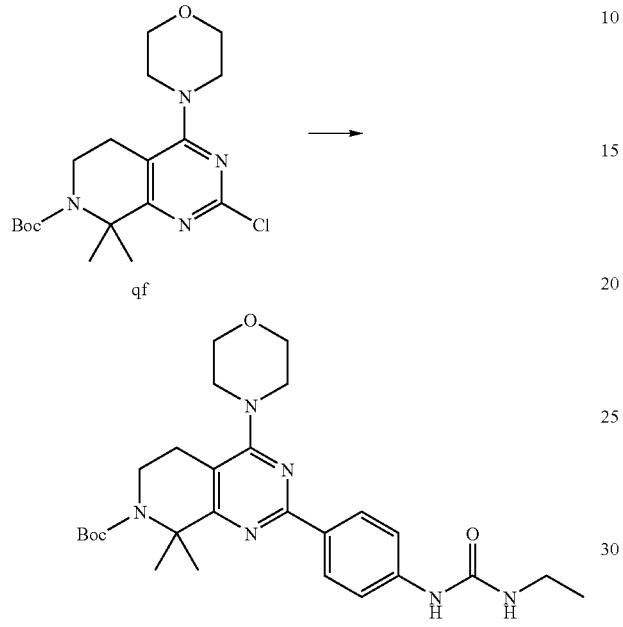

Synthesis of tert-butyl 2-(4-(3-ethylureido)phenyl)-8,8-dimethyl-4-morpholino-5,6-dihydropyrido[3,4-d]pyrimidine-7(8H)-carboxylate (ql): The compound was prepared following the general procedure in Step 2 of Example 285, substituting 4-(7-benzyl-2-chloro-6,7,8,9-tetrahydro-5H-pyrimido[5,4-d]azepin-4-yl)morpholine for tert-butyl 2-chloro-8,8-dimethyl-4-morpholino-5,6-dihydropyrido[3,4-d]pyrimidine-7(8H)-carboxylate (qf): LC-MS m/z=511 (M+H).

Example 318

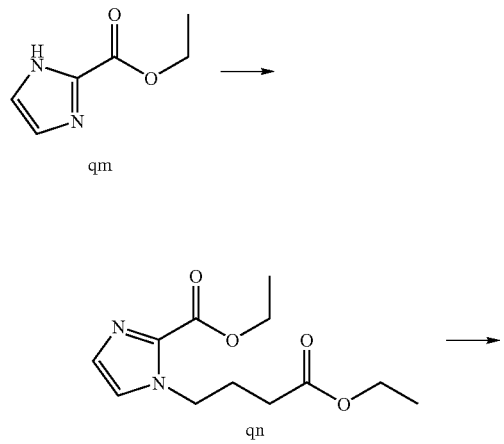

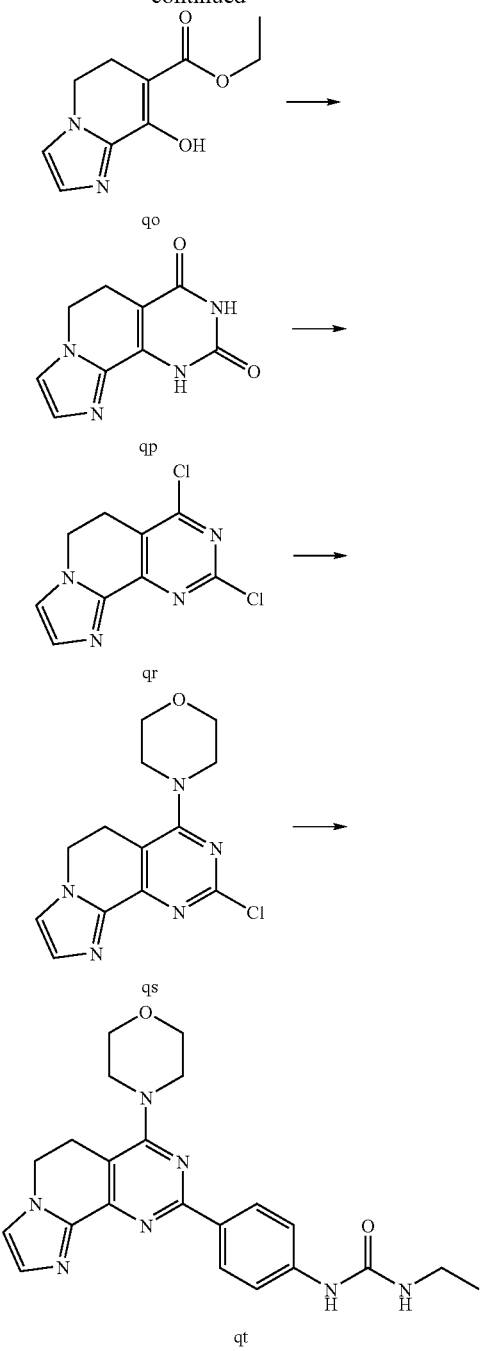

Synthesis of Compound qt

Step 1—Synthesis of ethyl 1-(4-ethoxy-4-oxobutyl)-1H-imidazole-2-carboxylate (qn). To a solution of Ethyl imidazole-2-carboxylate (qm) (290 mg, 2.0 mmol) and Ethyl 4-bromobutyrate (0.35 mL, 2.4 mmol) in N,N-Dimethylformamide (4.0 mL) was added Potassium carbonate (330 mg, 2.4 mmol), and the mixture was kept at 100° C. overnight. After removal of DMF, the residue was diluted by ethyl acetate, which was washed by water and brine until pH 7. The organic layer was dried over Magnesium sulfate and evaporated to dryness, and the residue was purified by chromatography on silica gel column, which gave the desired product qn (472 mg, 93% yield) as colorless sticky oil: $^1$H NMR (400 MHz, CDCl$_3$) δ 7.16 (s, 1H), 7.09 (s, 1H), 4.48 (t, J=7.1 Hz, 2H), 4.45-4.35 (q, J=7.1 Hz, 2H), 4.14 (q, J=7.1 Hz, 2H), 2.33 (t, J=7.2 Hz, 2H), 2.14 (p, J=7.1 Hz, 2H), 1.43 (t, J=7.1 Hz, 3H), 1.26 (t, J=7.1 Hz, 3H); LC-MS m/z=255 (M+H).

Step 2—Synthesis of ethyl 8-hydroxy-5,6-dihydroimidazo [1,2-a]pyridine-7-carboxylate (qo). To a suspension solution of Sodium hydride (26.7 mg, 1.11 mmol) in Tetrahydrofuran (11 mL) was added a solution of ethyl 1-(4-ethoxy-4-oxobutyl)-1H-imidazole-2-carboxylate (qn) (237 mg, 0.932 mmol) in Tetrahydrofuran (11 mL, 140 mmol) at room temperature. A few drops of absolute ethanol were added to the reaction mixture, and the mixture was kept stirring overnight. The reaction was quenched with HOAc and $H_2O$, followed by addition of $NaHCO_3$ to pH—7. The reaction mixture was concentrated in vacuo and the crude residue was diluted with Ethyl acetate, which was washed with water and brine, dried over Magnesium sulfate, and evaporated to give the crude product qo (120 mg, 62% yield). The crude was directly used in next step: LC-MS m/z=209 (M+H).

Step 3—Synthesis of compound qp: Ammonium acetate (781 mg, 10.1 mmol) and ethyl 8-hydroxy-5,6-dihydroimidazo[1,2-a]pyridine-7-carboxylate (qo) (211 mg, 1.01 mmol) were dissolved in Methanol (3.0 mL), and the transparent slightly yellow solution was stirred overnight at 85° C. The methanol solvent was removed from the reaction mixture, and the residue was diluted by Ethyl acetate, which was washed by $NaHCO_3$, water, and brine. After evaporation of the organic phase, the crude powder (190 mg, 8.02 mmol, 90% yield, LC-MS m/z=208 (M+H)) was dissolved in Pyridine (0.30 mL, 3.67 mmol) and Methylene chloride (6.6 mL), followed by addition of 2.25 M of Phosgene in Toluene (0.61 mL) at 0° C. under $N_2$. After the reaction was stirred at 0° C. for 30 min and at room temperature for 3 h, 15.3 M of Ammonium hydroxide in Water (3.6 mL) was added at 0° C., and the reaction mixture turned into a brown suspension. The reaction mixture was stirred at 0° C. for another 30 min and room temperature for 2 h, and heated at 80° C. for overnight. All volatile materials from the reaction mixture were removed under reduced pressure, and the crude yellow powder product qp was used in the next step without further purification: LC-MS m/z=205 (M+H).

Step 4—Synthesis of qr. The crude yellow powder qp (5.00 g, 6.11 mmol) was mixed with 1,4-Dioxane (2.9 mL) and Phosphoryl chloride (35 mL, 374 mmol). The reaction solution was microwaved at 150° C. for 30 minutes. The resultant brown suspension solution was quenched in KOH-ice to pH 8-9. The aqueous layer was extracted by $CHCl_3$, and the organic layer was washed by water and brine to pH 7, and was dried by Magnesium sulfate. After evaporation of the organic layer, the crude residue was purified by chromatography on silica gel column, which gave the desired product qr (812 mg, 42% yield for three steps) as white solid was obtained: $^1$H NMR (500 MHz, $CDCl_3$) δ 7.38 (s, 1H), 7.13 (s, 1H), 4.35 (t, J=7.1 Hz, 2H), 3.33 (t, J=7.1 Hz, 2H); LC-MS m/z=241 (M+H).

Step 5—Synthesis of qs. The compound qs was synthesized following the general procedure in Step 1 of Example 285, substituting 7-Benzyl-2,4-dichloro-6,7,8,9-tetrahydro-5H-pyrimido[4,5-d]azepine for qr: LC-MS m/z=292 (M+H).

Step 6—Synthesis of qt. The compound was synthesized following the general procedure in Step 2 of Example 285 substituting 4-(7-benzyl-2-chloro-6,7,8,9-tetrahydro-5H-pyrimido[5,4-d]azepin-4-yl)morpholine for compound qs: LC-MS m/z=420 (M+H).

Example 319

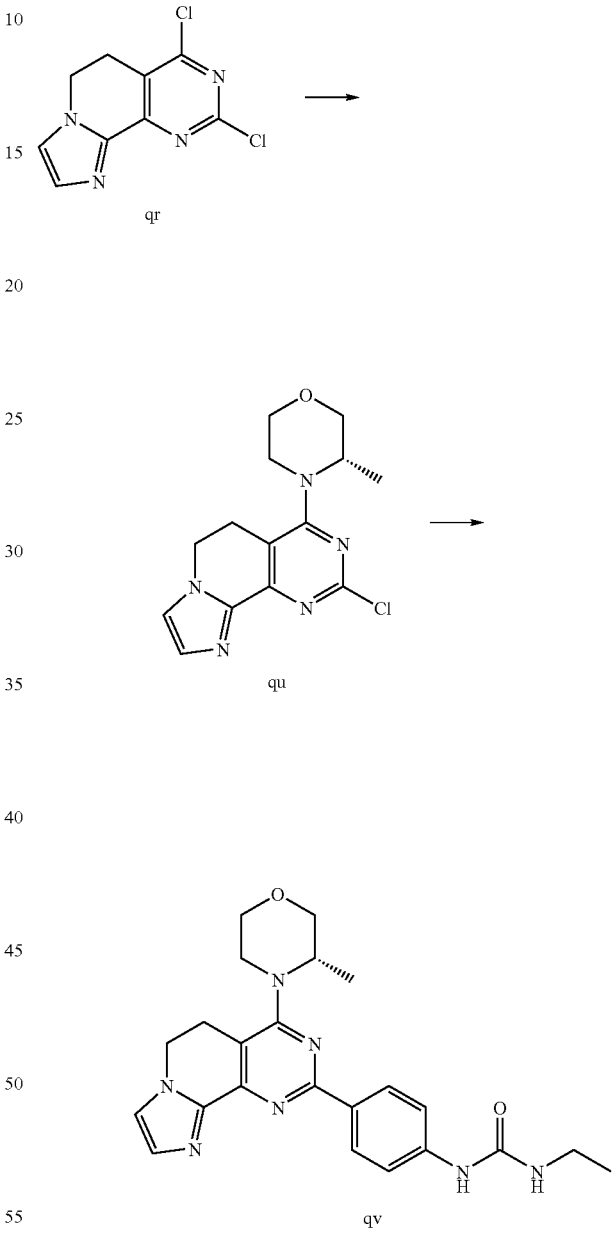

Synthesis of Compound qv

Step 1—Synthesis of qu. The compound qu was prepared following the general procedure in Step 1 of Example 286, substituting Benzyl 2,4-dichloro-8,9-dihydro-5H-pyrimido [5,4-d]azepine-7(6H)-carboxylate for compound qr: LC-MS m/z=306 (M+H).

Step 2—Synthesis of qv. The compound qv was synthesized following the general procedure in Step 2 of Example 285, substituting 4-(7-benzyl-2-chloro-6,7,8,9-tetrahydro-5H-pyrimido[5,4-d]azepin-4-yl)morpholine for qu: LC-MS m/z=434 (M+H).

Example 320

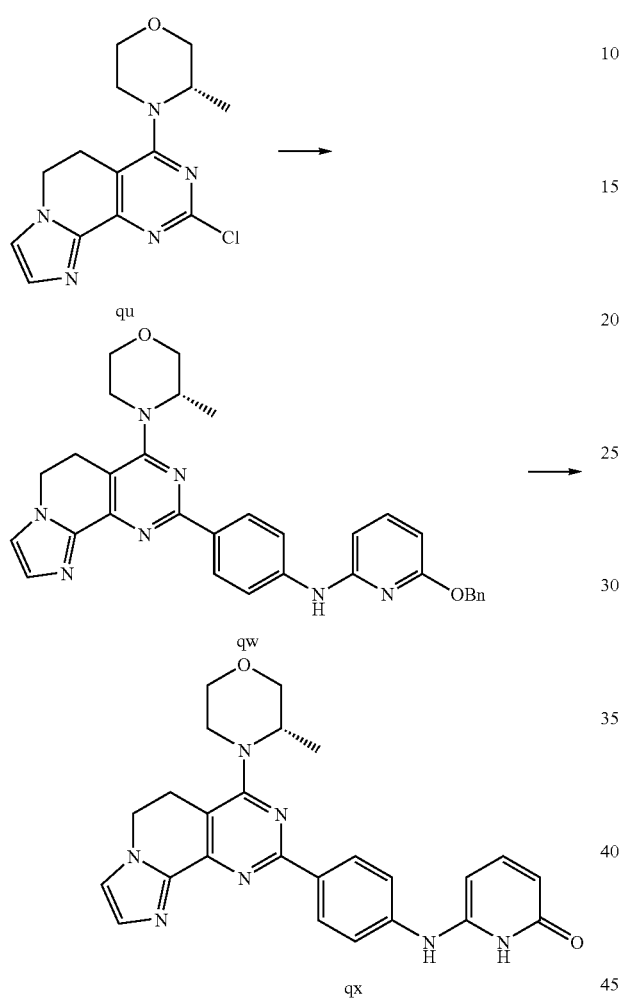

qu qw qx

Synthesis of Compound qx

Step 1—Synthesis of qw. The compound qw was prepared following the general procedure in Example 300, substituting (S)-tert-butyl 2-chloro-4-(3-methylmorpholino)-5,6-dihydropyrido[3,4-d]pyrimidine-7(8H)-carboxylate for qu. The desired product qw (56% yield) was obtained as slightly yellow powder: $^1$H NMR (500 MHz, CDCl$_3$) δ 8.52 (d, J=8.7 Hz, 2H), 7.48 (d, J=8.6 Hz, 4H), 7.45 (t, J=7.9 Hz, 1H), 7.38 (t, J=7.5 Hz, 2H), 7.32 (d, J=7.4 Hz, 1H), 7.30 (s, 1H), 7.01 (s, 1H), 6.73 (s, 1H), 6.45 (t, J=8.7 Hz, 1H), 6.30 (d, J=7.9 Hz, 1H), 5.39 (s, 2H), 4.25-4.02 (m, 2H), 3.98-3.74 (m, 4H), 3.71-3.62 (m, 1H), 3.57-3.40 (m, 2H), 3.12-2.94 (m, 2H), 1.31 (d, J=6.0 Hz, 3H); LC-MS m/z=546 (M+H).

Step 2—Synthesis of qx. The compound qx was prepared following the general procedure in Example 304, substituting (S)-6-(benzyloxy)-N-(4-(7-(2-methoxyethyl)-4-(3-methylmorpholino)-5,6,7,8-tetrahydropyrido[3,4-d]pyrimidin-2-yl)phenyl)pyridin-2-amine for qw. The desired product qx (66% yield) was obtained as grey powder: $^1$H NMR (500 MHz, DMSO) δ 10.34 (s, 1H), 9.24 (s, 1H), 8.38 (d, J=8.8 Hz, 2H), 7.92 (bs, 2H), 7.63-7.40 (m, 2H), 7.25 (s, 1H), 6.43 (s, 1H), 6.11 (s, 1H), 4.42-4.18 (m, 2H), 4.09 (m, 1H), 3.99 (d, J=11.3 Hz, 1H), 3.86 (d, J=9.0 Hz, 1H), 3.81-3.66 (m, 2H), 3.64-3.52 (m, 2H), 3.15 (t, J=6.8 Hz, 2H), 1.36 (d, J=6.6 Hz, 3H); LC-MS m/z=456 (M+H).

Example 321

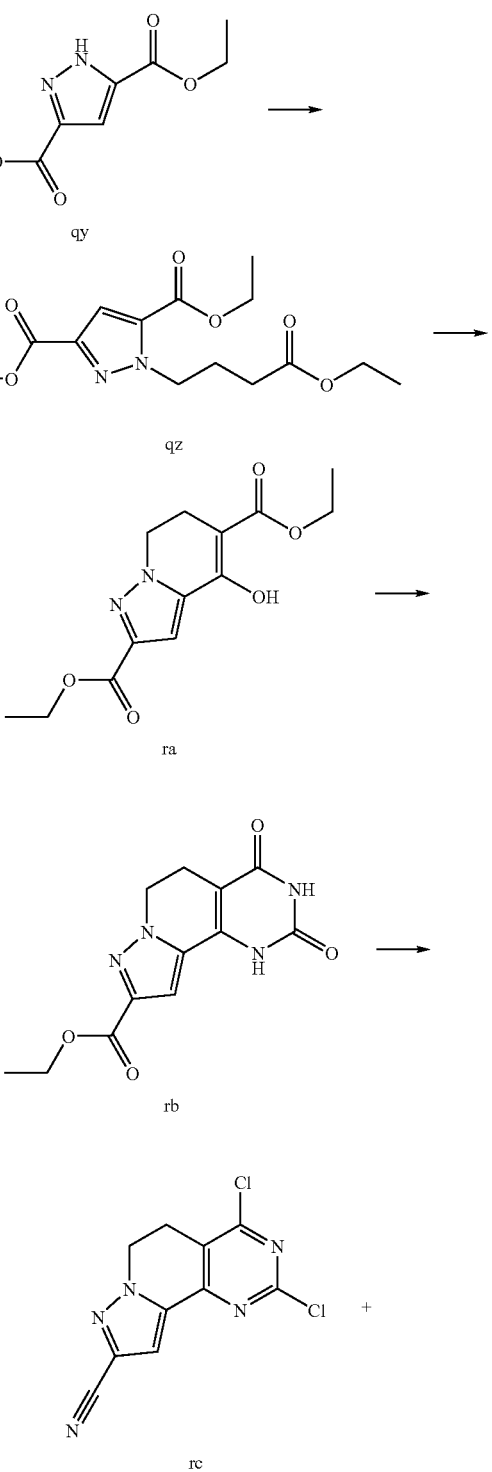

qy qz ra rb rc

311
-continued

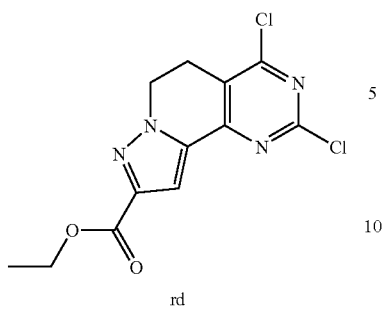

rd

Synthesis of Compounds Synthesis of rc and rd

Step 1—Synthesis of diethyl 1-(4-ethoxy-4-oxobutyl)-1H-pyrazole-3,5-dicarboxylate (qz): The compound qz was prepared following the general procedure in Step 1 of Example 318, substituting Ethyl imidazole-2-carboxylate for diethyl 1H-pyrazole-3,5-dicarboxylate (qy): LC-MS m/z=327 (M+H).

Step 2—Synthesis of diethyl 4-hydroxy-6,7-dihydropyrazolo[1,5-a]pyridine-2,5-dicarboxylate (ra): The title compound ra was prepared following the general procedure in Step 2 of Example 318, substituting ethyl 1-(4-ethoxy-4-oxobutyl)-1H-imidazole-2-carboxylate for diethyl 1-(4-ethoxy-4-oxobutyl)-1H-pyrazole-3,5-dicarboxylate (qz): LC-MS m/z=281 (M+H).

Step 3—Synthesis of rb: The title compound rb was prepared following the general procedure in Step 3 of Example 318, substituting ethyl 8-hydroxy-5,6-dihydroimidazo[1,2-a]pyridine-7-carboxylate for diethyl 4-hydroxy-6,7-dihydropyrazolo[1,5-a]pyridine-2,5-dicarboxylate (ra): LC-MS m/z=277 (M+H).

Step 4—Synthesis of rc and rd. The compounds rc and rd were prepared following the general procedure in Step 4 of Example 318, substituting compound qp for compound rb: LC-MS m/z=266 and 313 (M+H), respectively.

Example 322

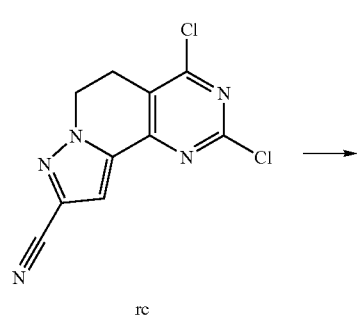

rc

312
-continued

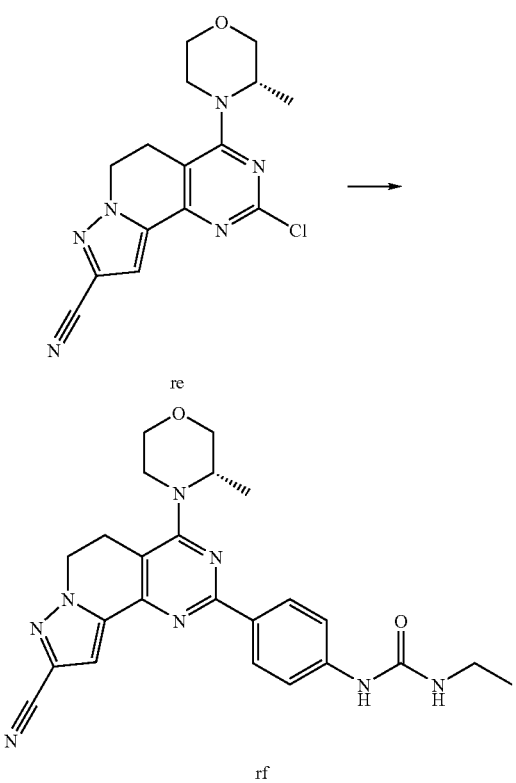

Synthesis of Compound rf

Step 1—Synthesis of re: The compound re was prepared following the general procedure in Step 1 of Example 286, substituting Benzyl 2,4-dichloro-8,9-dihydro-5H-pyrimido[5,4-d]azepine-7(6H)-carboxylate for compound rc: LC-MS m/z=331 (M+H).

Step 2—Synthesis of rf: The compound rf was synthesized following the general procedure in Step 2 of Example 285, substituting 4-(7-benzyl-2-chloro-6,7,8,9-tetrahydro-5H-pyrimido[5,4-d]azepin-4-yl)morpholine for compound re: LC-MS m/z=459 (M+H).

Example 323

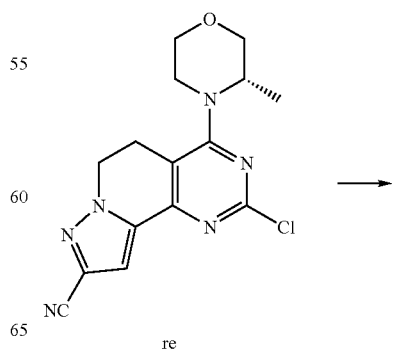

re

-continued

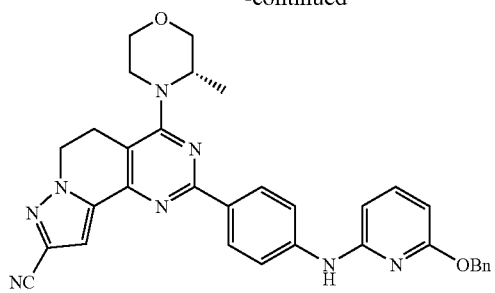

rg

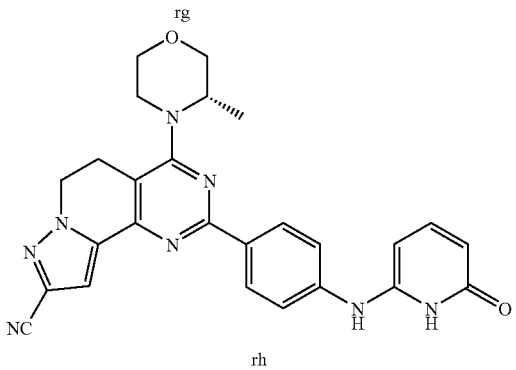

rh

Synthesis of Compound rh

Step 1—Synthesis of rg: The compound rg was prepared following the general procedure in Step 1 of Example 320, substituting compound qu for compound re: LC-MS m/z=571 (M+H).

Step 2—Synthesis of rh: The compound rh was prepared following the general procedure in Step 2 of Example 320, substituting compound qw for compound rg: LC-MS m/z=481 (M+H).

Example 324

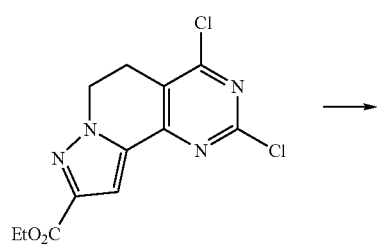

rd

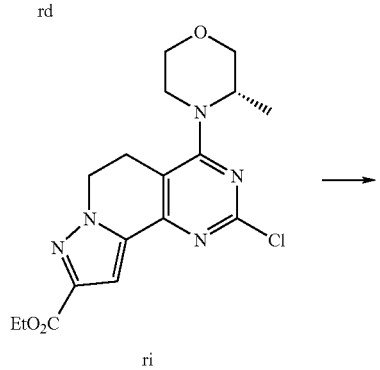

ri

-continued

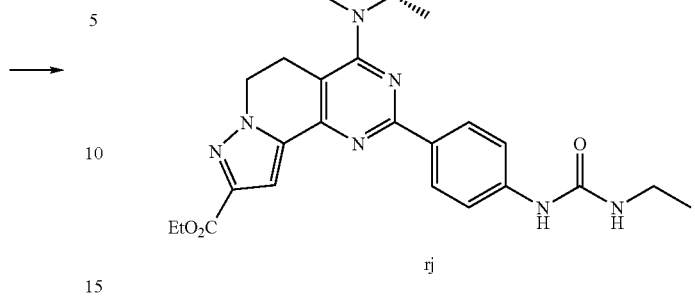

rj

Step 1—Synthesis of ri: The compound ri was prepared following the general procedure in Step 1 of Example 286, substituting Benzyl 2,4-dichloro-8,9-dihydro-5H-pyrimido [5,4-d]azepine-7(6H)-carboxylate for compound rd: LC-MS m/z=378 (M+H).

Step 2—Synthesis of ij. The compound ij was synthesized following the general procedure in Step 2 of Example 285, substituting 4-(7-benzyl-2-chloro-6,7,8,9-tetrahydro-5H-pyrimido[5,4-d]azepin-4-yl)morpholine for compound ri: LC-MS m/z=506 (M+H).

Example 325

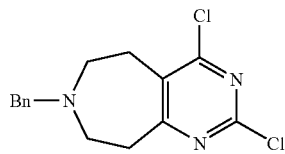

rk

Synthesis of 7-benzyl-2,4-dichloro-6,7,8,9-tetrahydro-5H-pyrimido[4,5-d]azepine (rk): The compound rk was prepared following the general procedure described in Example 284 by using 1-benzylpiperidin-4-one as the starting material instead of benzyl 4-oxopiperidine-1-carboxylate (og): LC-MS m/z=308 (M+H).

Example 326

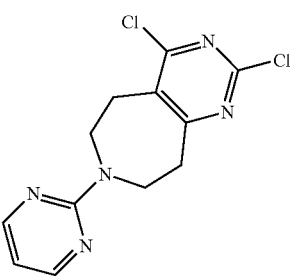

oq

Synthesis of 2,4-Dichloro-7-(pyrimidin-2-yl)-6,7,8,9-tetrahydro-5H-pyrimido[4,5-d]azepine (oq). The compound was prepared following the general procedure described in Example 284 by using 1-(pyrimidin-2-yl)piperidin-4-one as the starting material instead of Ethyl 1-benzyl-5-oxoazepane-4-carboxylate: LC-MS m/z=296 (M+H).

Example 327

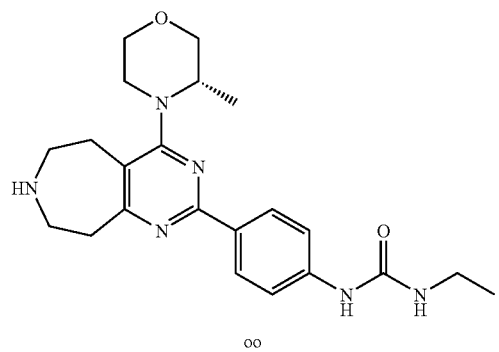

oo

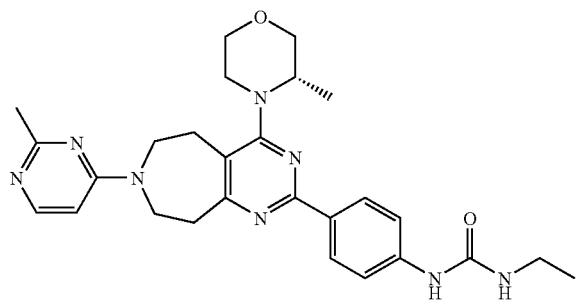

rm

Synthesis of (S)-1-ethyl-3-(4-(4-(3-methylmorpholino)-7-(2-methylpyrimidin-4-yl)-6,7,8,9-tetrahydro-5H-pyrimido[5,4-d]azepin-2-yl)phenyl)urea (rm): The compound rm was prepared following the general procedure in Example 287, substituting 4-Chloro-6-methylpyrimidine for 4-Chloro-2-methylpyrimidine: LC-MS m/z=503 (M+H).

Example 328

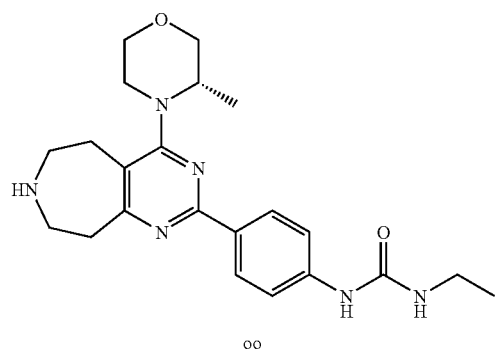

oo

-continued

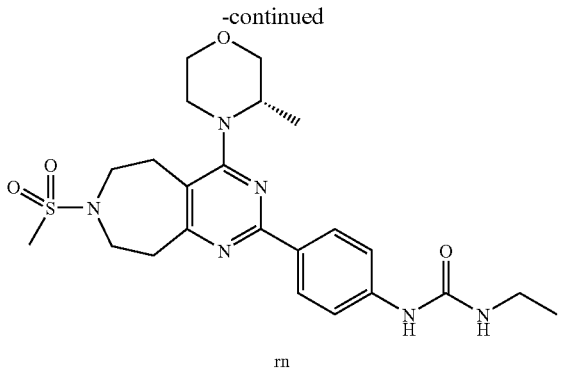

rn

Synthesis of (S)-1-ethyl-3-(4-(4-(3-methylmorpholino)-7-(methylsulfonyl)-6,7,8,9-tetrahydro-5H-pyrimido[5,4-d]azepin-2-yl)phenyl)urea (rn): To a suspension solution of (S)-1-ethyl-3-(4-(4-(3-methylmorpholino)-6,7,8,9-tetrahydro-5H-pyrimido[5,4-d]azepin-2-yl)phenyl)urea (oo) (99.9 mg, 0.243 mmol) in Chloroform (1.0 mL) and 1,4-Dioxane (3.0 mL, 38 mmol) was added N,N-Diisopropylethylamine (0.127 mL, 0.730 mmol) and Methanesulfonyl chloride (0.0226 mL, 0.292 mmol) at 0° C. After 1 min, a clear solution was observed, and the reaction was stirred at room temperature overnight. The reaction mixture was quenched by the addition of MeOH, the volatiles were removed. The crude residue was purified to provide the desired product rn (43.6 mg, 37% yield) as white powder: $^1$H NMR (400 MHz, DMSO) δ 8.64 (s, 1H), 8.20 (d, J=8.8 Hz, 2H), 7.49 (d, J=8.8 Hz, 2H), 6.16 (t, J=5.5 Hz, 1H), 3.89-3.60 (m, 4H), 3.41 (m, 6H), 3.24-3.05 (m, 5H), 2.98-2.85 (m, 5H, containing a singlet at 2.90 ppm for 3H), 1.15 (d, J=6.4 Hz, 3H), 1.06 (t, J=7.2 Hz, 3H); LC-MS m/z=489 (M+H).

Example 329

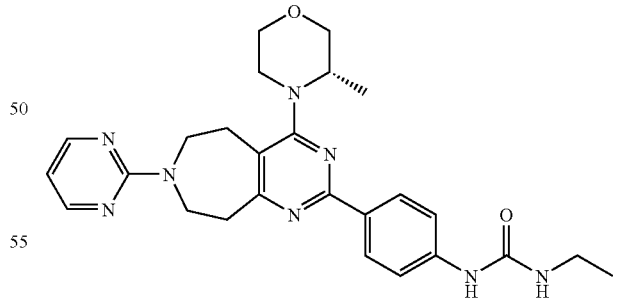

ro

Synthesis of (S)-1-ethyl-3-(4-(4-(3-methylmorpholino)-7-(pyrimidin-2-yl)-6,7,8,9-tetrahydro-5H-pyrimido[4,5-d]azepin-2-yl)phenyl)urea (rp): The compound rp was prepared following the general procedure in Example 288, using compound oq and substituting morpholine for (S)-3-methylmorpholine: LC-MS m/z=489 (M+H).

Example 330

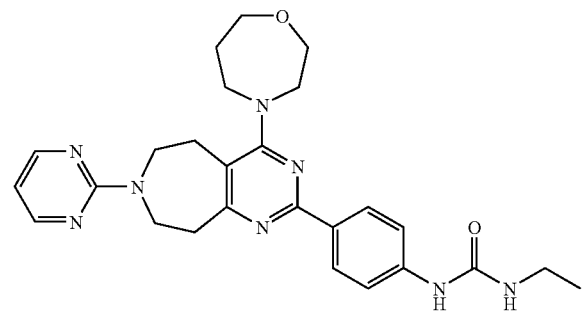

(rp)

Synthesis of 1-(4-(4-(1,4-oxazepan-4-yl)-7-(pyrimidin-2-yl)-6,7,8,9-tetrahydro-5H-pyrimido[4,5-d]azepin-2-yl)phenyl)-3-ethylurea (rp). The compound was prepared following the general procedure in Example 288, using compound oq and substituting morpholine for 1,4-oxazepane: LC-MS m/z=489 (M+H).

Example 331

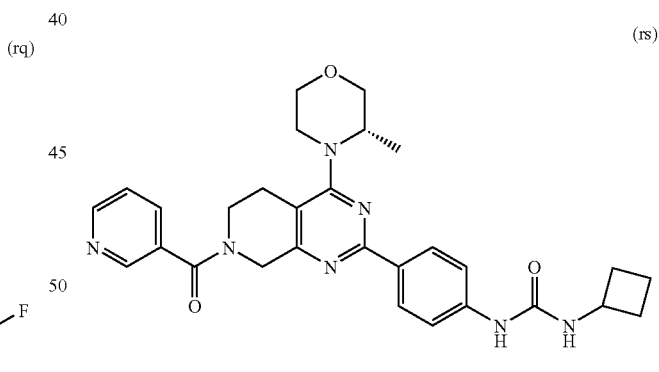

(rq)

Synthesis of (S)-1-(2,2-difluoroethyl)-3-(4-(4-(3-methylmorpholino)-7-nicotinoyl-5,6,7,8-tetrahydropyrido[3,4-d]pyrimidin-2-yl)phenyl)urea (rq): The compound rq was prepared following the general procedure in Step 3 of Example 290, substituting 2-fluoroethylamine hydrochloride for 2,2-difluoroethylamine: LC-MS m/z=538 (M+H).

Example 332

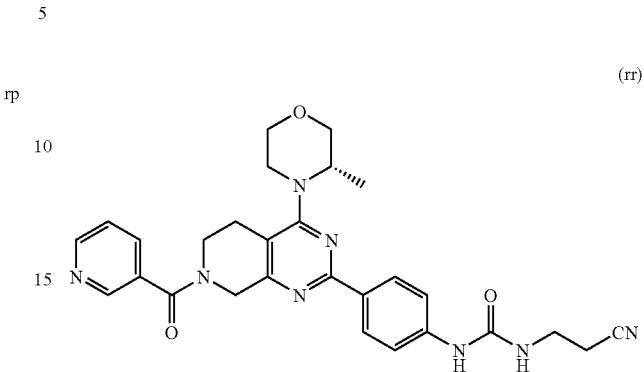

(rr)

Synthesis of (S)-1-(2-cyanoethyl)-3-(4-(4-(3-methylmorpholino)-7-nicotinoyl-5,6,7,8-tetrahydropyrido[3,4-d]pyrimidin-2-yl)phenyl)urea (rr): The compound rr was prepared following the general procedure in Step 3 of Example 290, substituting 2-fluoroethylamine hydrochloride for β-Cyanoethylamine: LC-MS m/z=527 (M+H).

Example 333

(rs)

Synthesis of (S)-1-cyclobutyl-3-(4-(4-(3-methylmorpholino)-7-nicotinoyl-5,6,7,8-tetrahydropyrido[3,4-d]pyrimidin-2-yl)phenyl)urea (rs): The compound rs was prepared following the general procedure in Step 3 of Example 290, substituting 2-fluoroethylamine hydrochloride for aminocyclobutane: LC-MS m/z=528 (M+H).

Example 334

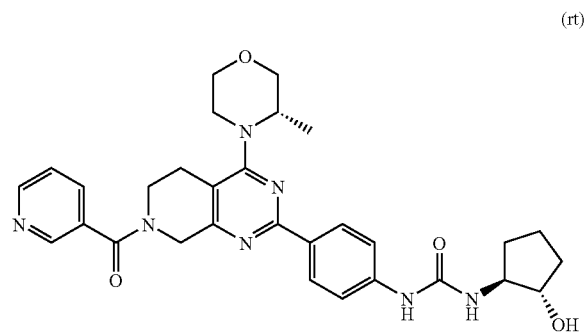

(rt)

Synthesis of 1-((1S,2S)-2-hydroxycyclopentyl)-3-(4-(4-((S)-3-methylmorpholino)-7-nicotinoyl-5,6,7,8-tetrahydropyrido[3,4-d]pyrimidin-2-yl)phenyl)urea (rt): The compound rt was prepared following the general procedure in Step 3 of Example 290, substituting 2-fluoroethylamine hydrochloride for (1S,2S)-trans-2-aminocyclopentanol hydrochloride: LC-MS m/z=558 (M+H).

Example 335

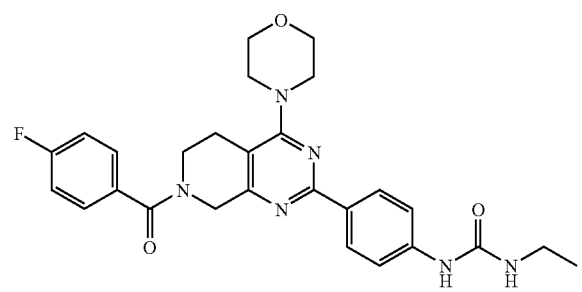

(ru)

Synthesis of 1-ethyl-3-(4-(7-(4-fluorobenzoyl)-4-morpholino-5,6,7,8-tetrahydropyrido[3,4-d]pyrimidin-2-yl)phenyl)urea (ru): The compound ru was prepared following the general procedure described in Example 5 by reacting 1-ethyl-3-(4-(4-morpholino-5,6,7,8-tetrahydropyrido[3,4-d]pyrimidin-2-yl)phenyl)urea hydrochloride salt with 4-Fluorobenzoic acid chloride: LC-MS m/z=505 (M+H).

Example 336

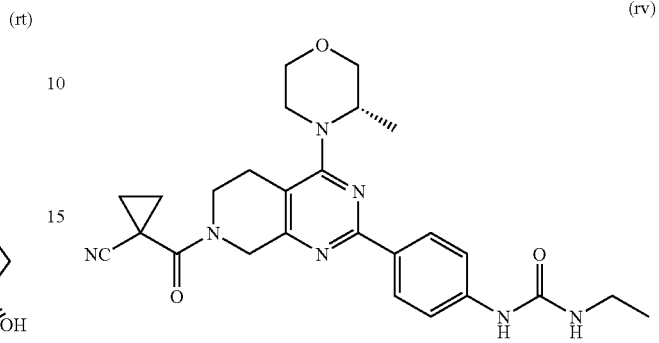

(rv)

Synthesis of (S)-1-(4-(7-(1-cyanocyclopropanecarbonyl)-4-(3-methylmorpholino)-5,6,7,8-tetrahydropyrido[3,4-d]pyrimidin-2-yl)phenyl)-3-ethylurea (rv): The compound rv was prepared following the general procedure in Example 213, substituting 3-methyloxetane-3-carboxylic acid for 1-Cyano-1-cyclopropanecarboxylic acid: LC-MS m/z=490 (M+H).

Example 337

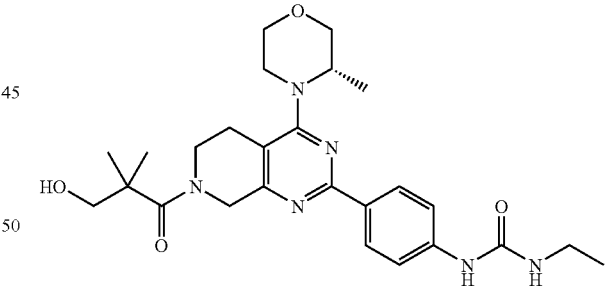

(rw)

Synthesis of (S)-1-ethyl-3-(4-(7-(3-hydroxy-2,2-dimethylpropanoyl)-4-(3-methylmorpholino)-5,6,7,8-tetrahydropyrido[3,4-d]pyrimidin-2-yl)phenyl)urea (rw): The compound rw was prepared following the general procedure in Example 213, substituting 3-methyloxetane-3-carboxylic acid for Hydroxypivalic acid: LC-MS m/z=497 (M+H).

Example 338

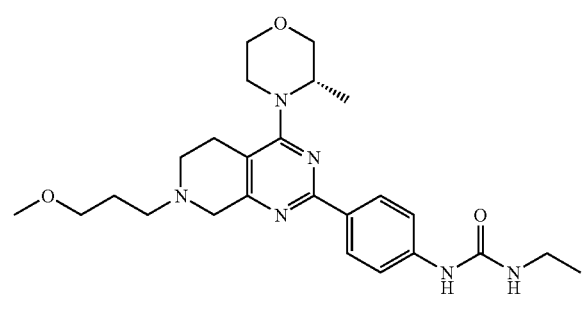

(rx)

Synthesis of (S)-1-ethyl-3-(4-(7-(3-methoxypropyl)-4-(3-methylmorpholino)-5,6,7,8-tetrahydropyrido[3,4-d]pyrimidin-2-yl)phenyl)urea (rx): The compound rx was prepared following the general procedure in Example 296, substituting 1-ethyl-3-(4-(4-morpholino-5,6,7,8-tetrahydropyrido[3,4-d]pyrimidin-2-yl)phenyl)urea hydrochloride salt for (S)-1-ethyl-3-(4-(4-(3-methylmorpholino)-5,6,7,8-tetrahydropyrido[3,4-d]pyrimidin-2-yl)phenyl)urea hydrochloride salt and substituting 1-bromo-2-methoxyethane for 1-bromo-3-methoxypropane: LC-MS m/z=469 (M+H).

Example 339

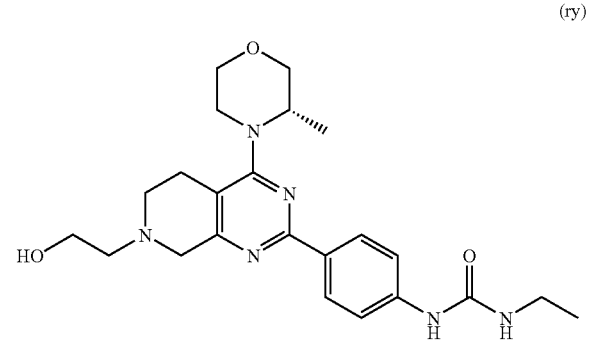

(ry)

Synthesis of (S)-1-ethyl-3-(4-(7-(2-hydroxyethyl)-4-(3-methylmorpholino)-5,6,7,8-tetrahydropyrido[3,4-d]pyrimidin-2-yl)phenyl)urea (ry): To a suspension of (S)-1-ethyl-3-(4-(4-(3-methylmorpholino)-5,6,7,8-tetrahydropyrido[3,4-d]pyrimidin-2-yl)phenyl)urea (301 mg, 0.759 mmol) in Acetonitrile (1.3 mL), N-Methylpyrrolidinone (0.44 mL) and N,N-Diisopropylethylamine (0.40 mL, 2.3 mmol) was added (2-Bromoethoxy)-tert-butyldimethylsilane (0.82 mL, 3.8 mmol), and the reaction was kept at 50° C. overnight. LC-MS showed the reaction was completed (desired peak m/z=555 (M+H)). The yellow solution was evaporated to dryness as much as possible, followed by dilution in Methylene chloride (6.0 mL) and Methanol (3.0 mL). Then, 4.0 M of Hydrogen chloride in 1,4-Dioxane (5.7 mL) was added, and the yellow solution was stirred at room temperature for 2.5 h. The solvents were removed and the residue was purified to give the final product ry (174.4 mg, 52% yield after two steps) as off-white powder: $^1$H NMR (400 MHz, DMSO) δ 8.65 (s, 1H), 8.15 (d, J=8.8 Hz, 2H), 7.47 (d, J=8.7 Hz, 2H), 6.18 (t, J=5.5 Hz, 1H), 4.48 (m, 1H), 4.12 (m, 1H), 3.87 (d, J=10.6 Hz, 1H), 3.75-3.48 (m, 8H), 3.40 (t, J=11.3 Hz, 1H), 3.17-3.04 (m, 2H), 2.80-2.53 (m, 6H), 1.22 (d, J=6.6 Hz, 3H), 1.06 (t, J=7.2 Hz, 3H); LC-MS m/z=441 (M+H).

Example 340

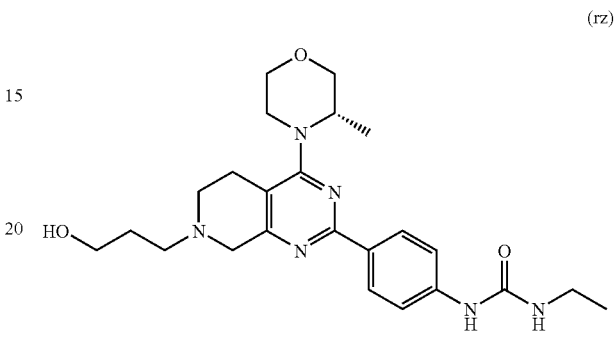

(rz)

Synthesis of (S)-1-ethyl-3-(4-(7-(3-hydroxypropyl)-4-(3-methylmorpholino)-5,6,7,8-tetrahydropyrido[3,4-d]pyrimidin-2-yl)phenyl)urea (rz): The compound rz was prepared in as generally described in Example 339 using (2-Bromopropoxy)-tert-butyldimethylsilane: LC-MS m/z=455 (M+H).

Example 341

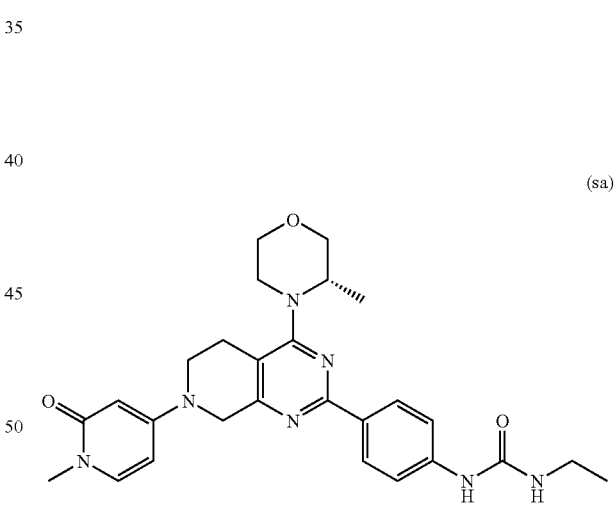

(sa)

Synthesis of (S)-1-ethyl-3-(4-(7-(1-methyl-2-oxo-1,2-dihydropyridin-4-yl)-4-(3-methylmorpholino)-5,6,7,8-tetrahydropyrido[3,4-d]pyrimidin-2-yl)phenyl)urea (sa). The compound was prepared following the general procedure in Example 308, substituting 1-ethyl-3-(4-(4-morpholino-5,6,7,8-tetrahydropyrido[3,4-d]pyrimidin-2-yl)phenyl)urea for (S)-1-ethyl-3-(4-(4-(3-methylmorpholino)-5,6,7,8-tetrahydropyrido[3,4-d]pyrimidin-2-yl)phenyl)urea and substitut-

Example 342

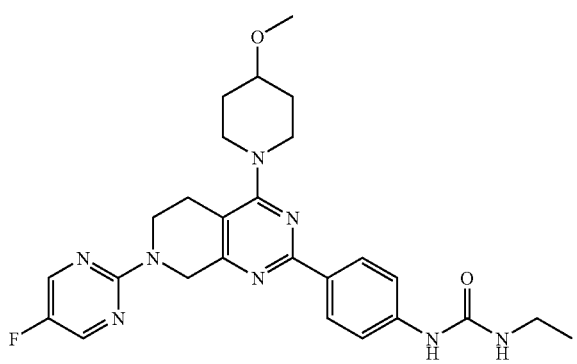
(sb)

Synthesis of 1-ethyl-3-(4-(7-(5-fluoropyrimidin-2-yl)-4-(4-methoxypiperidin-1-yl)-5,6,7,8-tetrahydropyrido[3,4-d]pyrimidin-2-yl)phenyl)urea (sb): The compound was prepared following the general procedure in Example 287, substituting (S)-1-ethyl-3-(4-(4-(3-methylmorpholino)-6,7,8,9-tetrahydro-5H-pyrimido[5,4-d]azepin-2-yl)phenyl)urea for 1-ethyl-3-(4-(4-(4-methoxypiperidin-1-yl)-5,6,7,8-tetrahydropyrido[3,4-d]pyrimidin-2-yl)phenyl)urea and substituting 4-Chloro-6-methylpyrimidine for 2-Chloro-5-fluoropyrimidine: LC-MS m/z=507 (M+H).

Example 343

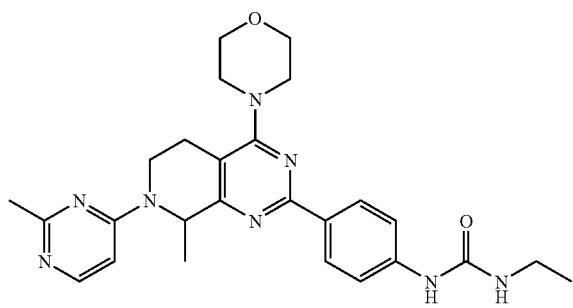
(sc)

Synthesis of 1-ethyl-3-(4-(8-methyl-7-(2-methylpyrimidin-4-yl)-4-morpholino-5,6,7,8-tetrahydropyrido[3,4-d]pyrimidin-2-yl)phenyl)urea (sc): The compound sc was prepared following the general procedure in Step 3 of Example 314, substituting 2-Chloropyrimidine for 4-chloro-2-methylpyrimidine: LC-MS m/z=489 (M+H).

Example 344

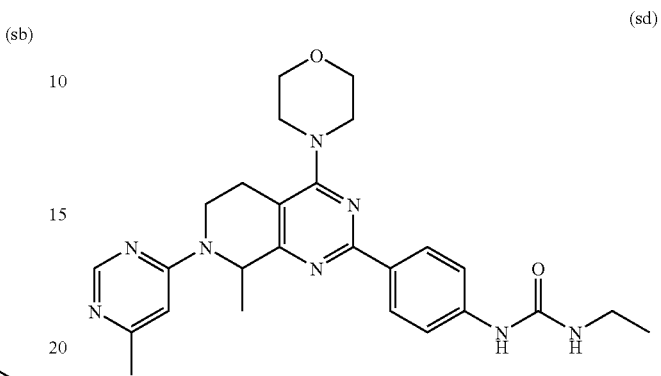
(sd)

Synthesis of 1-ethyl-3-(4-(8-methyl-7-(6-methylpyrimidin-4-yl)-4-morpholino-5,6,7,8-tetrahydropyrido[3,4-d]pyrimidin-2-yl)phenyl)urea (sd): The compound sd was prepared following the general procedure in Step 3 of Example 314, substituting 2-Chloropyrimidine for 4-chloro-6-methylpyrimidine: LC-MS m/z=489 (M+H).

Example 345

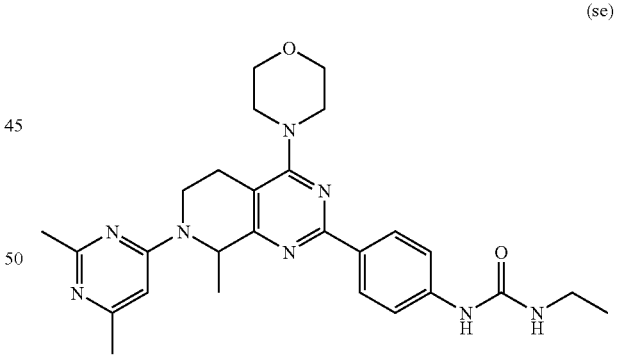
(se)

Synthesis of 1-(4-(7-(2,6-dimethylpyrimidin-4-yl)-8-methyl-4-morpholino-5,6,7,8-tetrahydropyrido[3,4-d]pyrimidin-2-yl)phenyl)-3-ethylurea (se): The compound se was prepared following the general procedure in Step 3 of Example

Example 346

(sf)

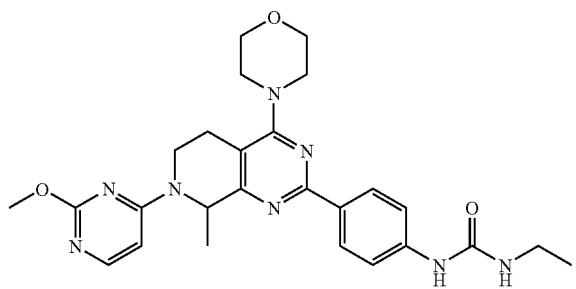

Synthesis of 1-ethyl-3-(4-(7-(2-methoxypyrimidin-4-yl)-8-methyl-4-morpholino-5,6,7,8-tetrahydropyrido[3,4-d]pyrimidin-2-yl)phenyl)urea (sf): The compound sf was prepared following the general procedure in Step 3 of Example 314, substituting 2-Chloropyrimidine for 4-chloro-2-methoxypyrimidine: LC-MS m/z=505 (M+H).

Example 347

(sg)

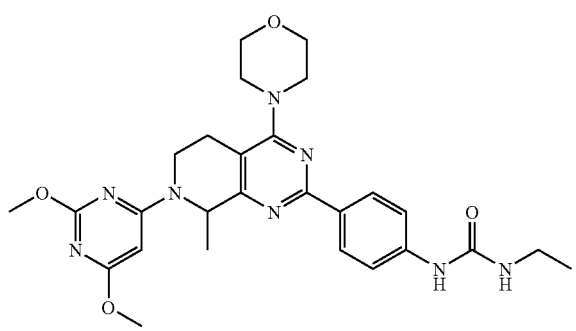

Synthesis of 1-(4-(7-(2,6-dimethoxypyrimidin-4-yl)-8-methyl-4-morpholino-5,6,7,8-tetrahydropyrido[3,4-d]pyrimidin-2-yl)phenyl)-3-ethylurea (sg): The compound sg was prepared following the general procedure in Step 3 of Example 314, substituting 2-Chloropyrimidine for 4-chloro-2,6-dimethoxypyrimidine: LC-MS m/z=535 (M+H).

Example 348

(sh)

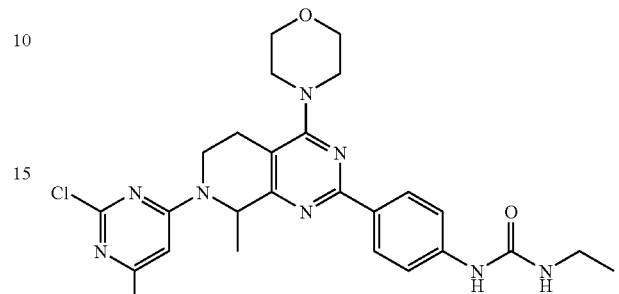

Synthesis of 1-(4-(7-(2-chloro-6-methylpyrimidin-4-yl)-8-methyl-4-morpholino-5,6,7,8-tetrahydropyrido[3,4-d]pyrimidin-2-yl)phenyl)-3-ethylurea (sh): The compound sh was prepared following the general procedure in Step 3 of Example 314, substituting 2-Chloropyrimidine for 2,4-dichloro-6-methylpyrimidine: LC-MS m/z=523 (M+H).

Example 349

(si)

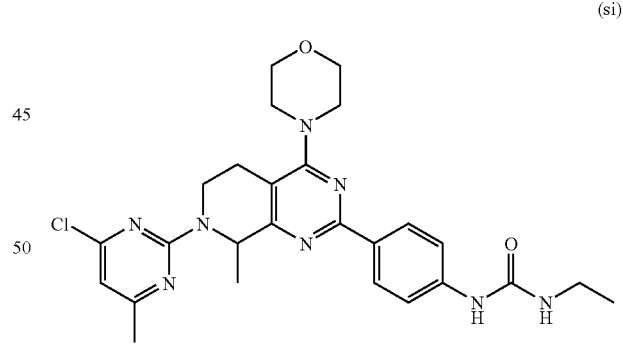

Synthesis of 1-(4-(7-(4-chloro-6-methylpyrimidin-2-yl)-8-methyl-4-morpholino-5,6,7,8-tetrahydropyrido[3,4-d]pyrimidin-2-yl)phenyl)-3-ethylurea (si): The compound si was prepared following the general procedure in Step 3 of Example 314, substituting 2-Chloropyrimidine for 2,4-dichloro-6-methylpyrimidine: LC-MS m/z=523 (M+H).

Example 350

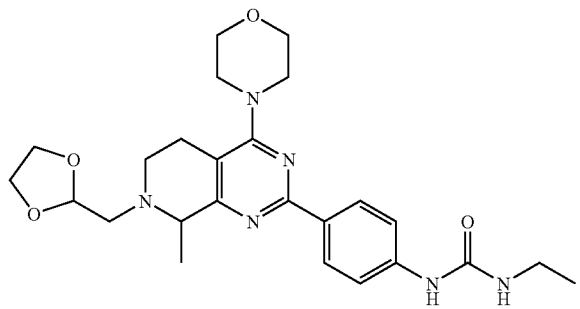

(sj)

Synthesis of 1-(4-(7-((1,3-dioxolan-2-yl)methyl)-8-methyl-4-morpholino-5,6,7,8-tetrahydropyrido[3,4-d]pyrimidin-2-yl)phenyl)-3-ethylurea (sj): The compound sj was prepared following the general procedure in Example 296, substituting 1-ethyl-3-(4-(4-morpholino-5,6,7,8-tetrahydropyrido[3,4-d]pyrimidin-2-yl)phenyl)urea hydrochloride salt for 1-ethyl-3-(4-(8-methyl-4-morpholino-5,6,7,8-tetrahydropyrido[3,4-d]pyrimidin-2-yl)phenyl)urea hydrochloride salt and substituting 1-bromo-2-methoxyethane for 2-(bromomethyl)-1,3-dioxolane. For this reaction, a catalytic amount Sodium iodide was also added: LC-MS m/z=483 (M+H).

Example 351

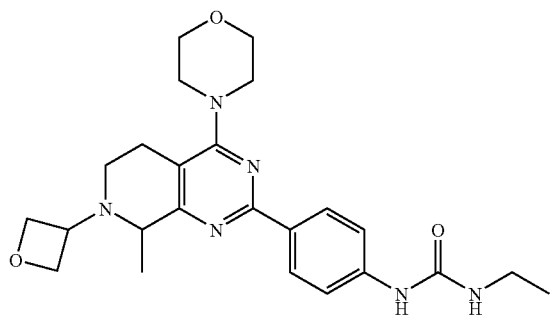

(sk)

Synthesis of 1-ethyl-3-(4-(8-methyl-4-morpholino-7-(oxetan-3-yl)-5,6,7,8-tetrahydropyrido[3,4-d]pyrimidin-2-yl)phenyl)urea (sk): 3-oxetanone (0.38 mL, 5.2 mmol) and 1-ethyl-3-(4-(8-methyl-4-morpholino-5,6,7,8-tetrahydropyrido[3,4-d]pyrimidin-2-yl)phenyl)urea hydrochloride salt (451 mg, 1.04 mmol) were mixed in 1,2-Dichloroethane (6.2 mL) and N,N-Diisopropylethylamine (0.73 mL, 4.2 mmol). The reaction was stirred at 70° C. for 1 h and at 80° C. for 30 minutes. Sodium triacetoxyborohydride (0.71 g, 3.3 mmol) was added to the reaction, and the mixture was stirred at 80° C. for 30 minutes. The reaction mixture was quenched with NaHCO$_3$ and water, which was extracted by CHCl$_3$. The organic layers were combined, washed by water and brine (final pH ~9), dried over Magnesium sulfate and evaporated. The residue was purified to give the desired product sk (269 mg, 57% yield) as white powder: $^1$H NMR (400 MHz, DMSO) δ 8.62 (s, 1H), 8.18 (d, J=8.8 Hz, 2H), 7.47 (d, J=8.8 Hz, 2H), 6.14 (t, J=5.5 Hz, 1H), 4.62 (m, 3H), 4.53 (t, J=6.2 Hz, 1H), 4.04 (p, J=6.7 Hz, 1H), 3.81-3.64 (m, 5H), 3.54-3.35 (m, 4H), 3.17-3.03 (m, 2H), 2.67 (m, 4H), 1.29 (d, J=6.8 Hz, 3H), 1.06 (t, J=7.2 Hz, 3H); LC-MS m/z=453 (M+H).

Example 352

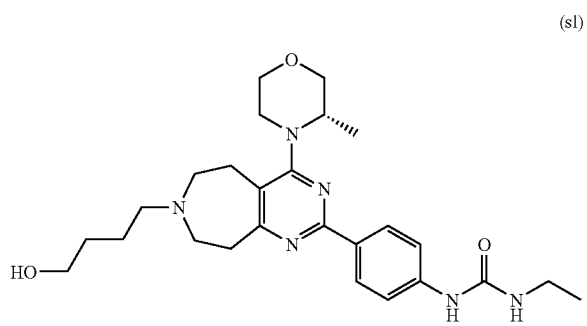

(sl)

Synthesis of (S)-1-ethyl-3-(4-(7-(4-hydroxybutyl)-4-(3-methylmorpholino)-6,7,8,9-tetrahydro-5H-pyrimido[5,4-d]azepin-2-yl)phenyl)urea (sl): During the synthesis of S)-1-ethyl-3-(4-(4-(3-methylmorpholino)-6,7,8,9-tetrahydro-5H-pyrimido[5,4-d]azepin-2-yl)phenyl)urea (Step 3 of Example 286), the title compound sl (a white powder) was obtained as a by-product due to the oxidation of THF during long-term storage: $^1$H NMR (400 MHz, CDCl$_3$) δ 8.35 (d, J=8.6 Hz, 2H), 7.36 (d, J=8.7 Hz, 2H), 6.33 (s, 1H), 4.62 (m, 1H), 3.89-3.55 (m, 6H), 3.39-3.15 (m, 5H), 2.98-2.52 (m, 7H), 1.74 (m, 8H), 1.33-1.02 (m, 6H); LC-MS m/z=483 (M+H).

Example 353

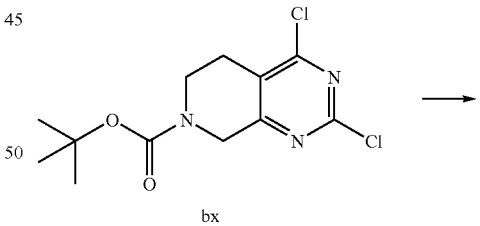

bx

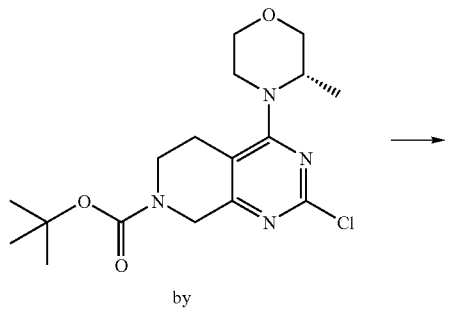

by

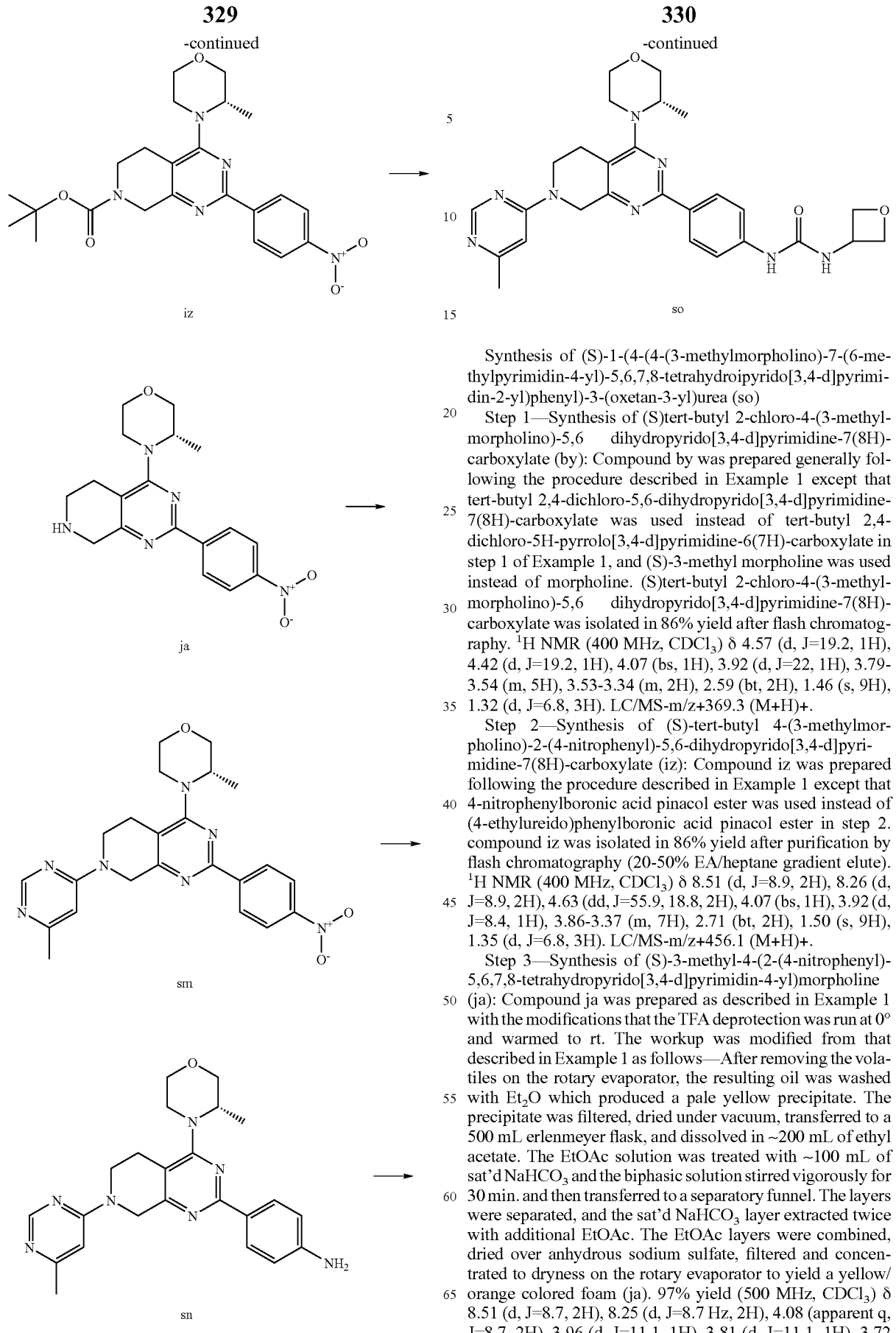

Synthesis of (S)-1-(4-(4-(3-methylmorpholino)-7-(6-methylpyrimidin-4-yl)-5,6,7,8-tetrahydroipyrido[3,4-d]pyrimidin-2-yl)phenyl)-3-(oxetan-3-yl)urea (so)

Step 1—Synthesis of (S)tert-butyl 2-chloro-4-(3-methylmorpholino)-5,6 dihydropyrido[3,4-d]pyrimidine-7(8H)-carboxylate (by): Compound by was prepared generally following the procedure described in Example 1 except that tert-butyl 2,4-dichloro-5,6-dihydropyrido[3,4-d]pyrimidine-7(8H)-carboxylate was used instead of tert-butyl 2,4-dichloro-5H-pyrrolo[3,4-d]pyrimidine-6(7H)-carboxylate in step 1 of Example 1, and (S)-3-methyl morpholine was used instead of morpholine. (S)tert-butyl 2-chloro-4-(3-methylmorpholino)-5,6 dihydropyrido[3,4-d]pyrimidine-7(8H)-carboxylate was isolated in 86% yield after flash chromatography. $^1$H NMR (400 MHz, CDCl$_3$) δ 4.57 (d, J=19.2, 1H), 4.42 (d, J=19.2, 1H), 4.07 (bs, 1H), 3.92 (d, J=22, 1H), 3.79-3.54 (m, 5H), 3.53-3.34 (m, 2H), 2.59 (bt, 2H), 1.46 (s, 9H), 1.32 (d, J=6.8, 3H). LC/MS-m/z+369.3 (M+H)+.

Step 2—Synthesis of (S)-tert-butyl 4-(3-methylmorpholino)-2-(4-nitrophenyl)-5,6-dihydropyrido[3,4-d]pyrimidine-7(8H)-carboxylate (iz): Compound iz was prepared following the procedure described in Example 1 except that 4-nitrophenylboronic acid pinacol ester was used instead of (4-ethylureido)phenylboronic acid pinacol ester in step 2. compound iz was isolated in 86% yield after purification by flash chromatography (20-50% EA/heptane gradient elute). $^1$H NMR (400 MHz, CDCl$_3$) δ 8.51 (d, J=8.9, 2H), 8.26 (d, J=8.9, 2H), 4.63 (dd, J=55.9, 18.8, 2H), 4.07 (bs, 1H), 3.92 (d, J=8.4, 1H), 3.86-3.37 (m, 7H), 2.71 (bt, 2H), 1.50 (s, 9H), 1.35 (d, J=6.8, 3H). LC/MS-m/z+456.1 (M+H)+.

Step 3—Synthesis of (S)-3-methyl-4-(2-(4-nitrophenyl)-5,6,7,8-tetrahydropyrido[3,4-d]pyrimidin-4-yl)morpholine (ja): Compound ja was prepared as described in Example 1 with the modifications that the TFA deprotection was run at 0° and warmed to rt. The workup was modified from that described in Example 1 as follows—After removing the volatiles on the rotary evaporator, the resulting oil was washed with Et$_2$O which produced a pale yellow precipitate. The precipitate was filtered, dried under vacuum, transferred to a 500 mL erlenmeyer flask, and dissolved in ~200 mL of ethyl acetate. The EtOAc solution was treated with ~100 mL of sat'd NaHCO$_3$ and the biphasic solution stirred vigorously for 30 min. and then transferred to a separatory funnel. The layers were separated, and the sat'd NaHCO$_3$ layer extracted twice with additional EtOAc. The EtOAc layers were combined, dried over anhydrous sodium sulfate, filtered and concentrated to dryness on the rotary evaporator to yield a yellow/orange colored foam (ja). 97% yield (500 MHz, CDCl$_3$) δ 8.51 (d, J=8.7, 2H), 8.25 (d, J=8.7 Hz, 2H), 4.08 (apparent q, J=8.7, 2H), 3.96 (d, J=11.1, 1H), 3.81 (d, J=11.1, 1H), 3.72

(dt, J=18.4, 6.2 2H), 3.55 (m, 2H), 3.15 (m, 1H), 3.08-2.96 (m, 1H), 2.66 (bt, 3H), 1.36 (d, J=6.8, 3H). LC/MS-m/z+ 356.1 (M+H)+.

Step 4—Synthesis of (S)-3-methyl-4-(7-(6-methylpyrimidin-4-yl)-2-(4-nitrophenyl)-5,6,7,8-tetrahydropyrido[3,4-d]pyrimidin-4-yl)morpholine (sm): Compound sm was prepared generally as in Example 2 except that (S)-3-methyl-4-(2-(4-nitrophenyl)-5,6,7,8-tetrahydropyrido[3,4-d]pyrimidin-4-yl)morpholine (1.0 equiv) was mixed in DMF (5.0 mL) with 4-chloro-6-methylpyrimidine (1.2 equiv), sodium carbonate (3.24 equiv) and heated to 80° for 8 h. Upon cooling to room temperature, a solid mass formed which was washed with H₂O, collected by filtration, and dried under vacuum. The solids were transferred to a 125 mL Erlenmeyer flask, dissolved in ethyl acetate (~75 mL), transferred to a 125 mL separatory funnel, washed 1× with water, 1× with brine, dried (Na₂SO₄), filtered and concentrated to give a light yellow powder which was dried further under vacuum. The crude material sm was used in the next reaction. LC/MS-m/z+448.4 (M+H)+.

Step 5—Synthesis of (S)-4-(4-(3-methylmorpholino)-7-(6-methylpyrimidin-4-yl)-5,6,7,8-tetrahydropyrido[3,4-d]pyrimidin-2-yl) aniline (sn): Compound sn was prepared by suspending (S)-3-methyl-4-(7-(6-methylpyrimidin-4-yl)-2-(4-nitrophenyl)-5,6,7,8-tetrahydropyrido[3,4-d]pyrimidin-4-yl)morpholine (130 mg, 0.29 mmol) in ethanol (0.35 mL)/water (0.79 mL) and treating with ammonium chloride (62 mg, 4.0 equiv) and iron powder (−325 mesh, 81 mg, 5.0 equiv. The 14/20 round bottomed flask was equipped with a stir bar and reflux condenser and placed in a pre-heated 80° C. oil bath. The reaction mixture heated to 80° C. and stirred. The dark slurry was vigorously stirred at 80° C. for 1 h and 15 min when an aliquot was removed and analyzed by LCMS to indicate complete conversion of starting material to the product sn. The reaction was concentrated to remove the ethanol, diluted with dichloromethane and a small amount of methanol, sonicated for ~5 min. and filtered through a pad of Celite. The Celite pad was rinsed with dichloromethane and a small amount of methanol. The filtrate was treated with saturated aqueous sodium bicarbonate solution, transferred to a separatory funnel and layers separated. The aqueous layer was extracted additionally (2×) with ethyl acetate, the organic extracts combined, dried (Magnesium sulfate), and filtered through a pad of Celite. The solvents were removed on a rotary evaporater, the crude residue dissolved in a small amount of dichloromethane and placed under high vacuum resulting in formation of a solid which was further dried under high vacuum. 120 mg of crude product sn (100%) was obtained and used without further purification. ¹H NMR (400 MHz, CDCl₃) δ 8.54 (s, 1H), 8.24 (d, J=8.7 Hz, 2H), 6.70 (d, J=8.7 Hz, 2H), 6.48 (s, 1H), 4.64 (dt, J=29.9, 22.3, 2H), 4.26-3.39 (m, 11H), 2.72 (m, 2H), 2.39 (s, 3H), 1.32 (d, J=6.8, 3H). LC/MS-m/z+418.5 (M+H)+.

Step 6—Synthesis of (S)-1-(4-(4-(3-methylmorpholino)-7-(6-methylpyrimidin-4-yl)-5,6,7,8-tetrahydropyrido[3,4-d]pyrimidin-2-yl)phenyl)-3-(oxetan-3-yl)urea (so): Compound so was prepared by dissolving the aniline intermediate (59 mg, 0.14 mmol) in anhydrous 1,2 dichloroethane (3.0 mL, 0.05M), treating with triethylamine (69 uL, 3.5 equiv), cooling to 0° and adding triphosgene (42 mg, 1.0 equiv) in one portion. The reaction mixture turned from orange to a dark reddish color upon addition of triphosgene. After 5 min at 0° C., the flask was equipped with a reflux condensor, placed in a pre-heated oil bath at 70° C., stirred at 70° C. for 1 h and then cooled to room temperature. 3-oxetanamine HCL (93 mg, 4.7 equiv) was placed in a 20 mL scintillation vial and converted to its free base by treatment with DMF (0.5 mL), DIPEA (0.2 mL) and sonicating for ~5 min. The DMF/DIPEA/oxetane solution was drawn up into a pasteur pipette, added in one portion to the red colored reaction mixture, and the reaction mixture stirred at room temperature for 21 h. LCMS indicated the oxetane urea had formed. The reaction mixture was diluted with ~50 mL of ethyl acetate, transferred to a 125 mL separatory funnel and washed with water(emulsion formed). The layers slowly separated and the aqueous layer was re-extracted with ethyl acetate (2×15 mL). The ethyl acetate extracts were combined, washed 1× with brine, filtered through a 30 mL 30F fritted filter funnel to remove some reddish insoluble solids and concentrated to dryness. Purification by RP HPLC yielded 5.4 mg of compound so (100% purity, ultraviolet absorption at 254 nM). ¹H NMR (400 MHz, CDCl₃) δ 8.76 (s, 1H), 8.45 (s, 1H), 8.22 (d, J=8.8 Hz, 2H), 7.50 (d, J=8.8 Hz, 2H), 6.97 (d, J=6.6 Hz, 1H), 6.86 (s, 1H) 4.92-4.57 (m, 5H), 4.45 (t, J=5.8 Hz, 2H), 4.23-3.83 (m, 3H), 3.84-3.51 (m, 5H), 3.43 (t, J=11.2 Hz, 1H), 2.70 (bt, 2H), 2.33 (s, 3H), 1.26 (d, J=6.8, 3H). LC/MS-m/z+517.3 (M+H)+.

Example 354

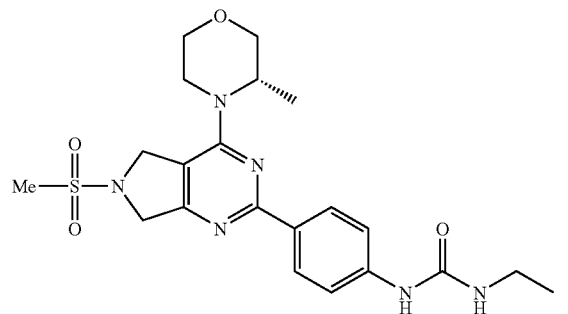

(sp)

Synthesis of (S)-1-ethyl-3-(4-(4-(3-methylmorpholino)-6-(methylsulfonyl)-6,7-dihydro-5H-pyrrolo[3,4-d]pyrimidin-2-yl)phenyl)urea (sp): The title compound sp was prepared by the procedures described in Examples 1 and 2, by substituting morpholine with (S)-3-methylmorpholine in Example 1 and chloropyrimidine with methanesulfonyl chloride in Example 2: LC-MS: m/z=+461 (M+H)⁻.

Example 355

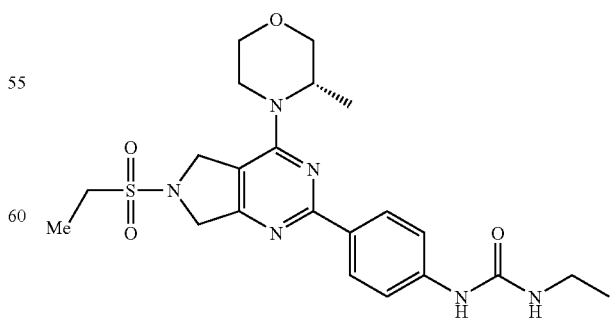

(sq)

Synthesis of (S)-1-ethyl-3-(4-(6-(ethylsulfonyl)-4-(3-methylmorpholino)-6,7-dihydro-5H-pyrrolo[3,4-d]pyrimidin- 2-yl)phenyl)urea (sq): The title compound sq was prepared by the procedures described in Examples 1 and 2, by substituting morpholine with (S)-3-methylmorpholine in Example 1 and chloropyrimidine with ethanesulfonyl chloride in Example 2: LC-MS: m/z=+475 (M+H)+.

Example 356

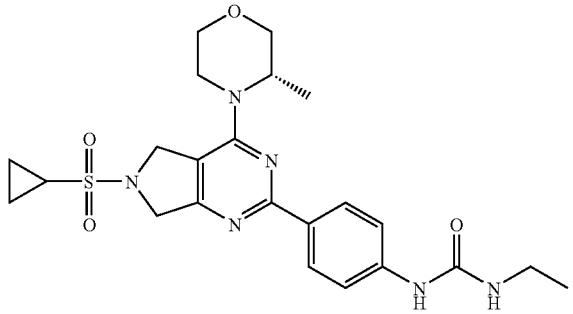

(sr)

Synthesis of (S)-1-(4-(6-(cyclopropylsulfonyl)-4-(3-methylmorpholino)-6,7-dihydro-5H-pyrrolo[3,4-d]pyrimidin-2-yl)phenyl)-3-ethylurea (sr): The title compound sr was prepared by the procedures described in Examples 1 and 2, by substituting morpholine with (S)-3-methylmorpholine in Example 1 and chloropyrimidine with cyclopropanesulfonyl chloride in Example 2: LC-MS: m/z=+487 (M+H)+.

Example 357

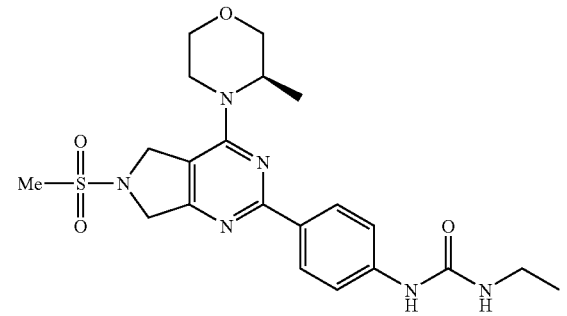

(st)

Synthesis of (R)-1-ethyl-3-(4-(4-(3-methylmorpholino)-6-(methylsulfonyl)-6,7-dihydro-5H-pyrrolo[3,4-d]pyrimidin-2-yl)phenyl)urea (st): The title compound st was prepared by the procedures described in Examples 1 and 2, by substituting morpholine with (R)-3-methylmorpholine in Example 1 and chloropyrimidine with methanesulfonyl chloride in Example 2: LC-MS: m/z=+461 (M+H)−.

Example 358

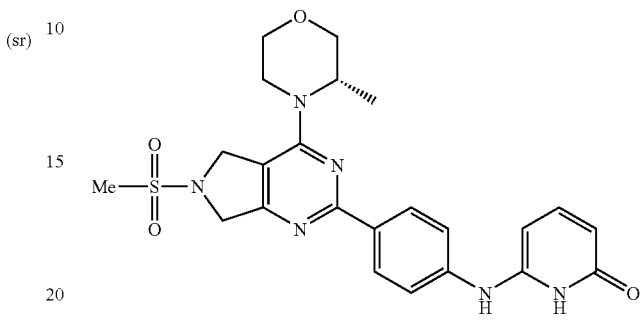

(su)

Synthesis of (S)-6-(4-(4-(3-methylmorpholino)-6-(methylsulfonyl)-6,7-dihydro-5H-pyrrolo[3,4-d]pyrimidin-2-yl)phenylamino)pyridin-2(1H)-one (su): The title compound su was prepared by the procedures described in Examples 1, 2, steps 1 and 2 of Example 27, and steps 1 and 2 of Example 212 by substituting morpholine with (S)-3-methylmorpholine in Example 1 and chloropyrimidine with methanesulfonyl chloride in Example 2: LC-MS: m/z=+483 (M+H)+.

Example 359

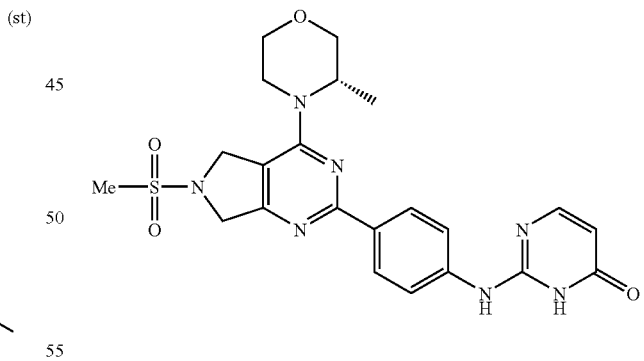

(sv)

Synthesis of (S)-2-(4-(4-(3-methylmorpholino)-6-(methylsulfonyl)-6,7-dihydro-5H-pyrrolo[3,4-d]pyrimidin-2-yl)phenylamino)pyrimidin-4(3H)-one (sv): The title compound sv was prepared by the procedures described in Examples 1, 2, steps 1 and 2 of Example 27, and steps 1 and 2 of Example 212 by substituting morpholine with (S)-3-methylmorpholine in Example 1 and chloropyrimidine with methanesulfonyl chloride in Example 2: LC-MS: m/z=+484 (M+H)$^+$.

Example 360

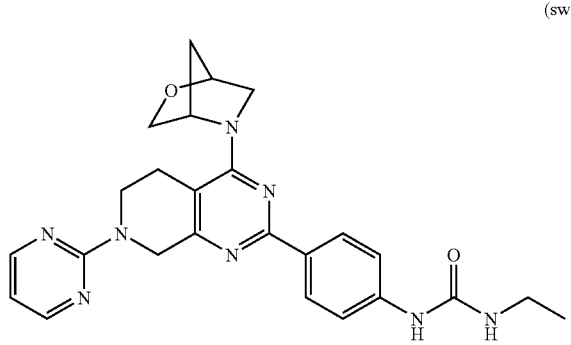

(sw)

Synthesis of 1-(4-(4-((1S,4S)-2-oxa-5-azabicyclo[2.2.1]heptan-5-yl)-7-(pyrimidin-2-yl)-5,6,7,8-tetrahydropyrido[3,4-d]pyrimidin-2-yl)phenyl)-3-ethylurea (sw): The title compound sw was prepared by the procedures described in Examples 1 and 2, by substituting tert-butyl 2,4-dichloro-5H-pyrrolo[3,4-d]pyrimidine-6(7H)-carboxylate with tert-butyl 2,4-dichloro-5,6-dihydropyrido[3,4-d]pyrimidine-7(8H)-carboxylate and morpholine with (1S,4S)-2-oxa-5-azoniabicyclo[2.2.1]heptane chloride in Example 1: LC-MS: m/z=+473 (M+H)$^+$.

Example 361

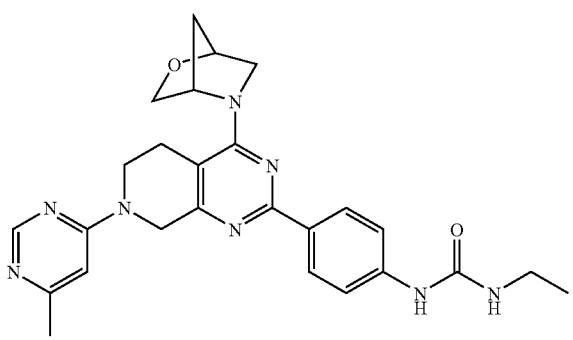

(sx)

Synthesis of 1-(4-(4-((1S,4S)-2-oxa-5-azabicyclo[2.2.1]heptan-5-yl)-7-(6-methylpyrimidin-4-yl)-5,6,7,8-tetrahydropyrido[3,4-d]pyrimidin-2-yl)phenyl)-3-ethylurea (sx): The title compound sx was prepared by the procedures described in Examples 1 and 2, by substituting tert-butyl 2,4-dichloro-5H-pyrrolo[3,4-d]pyrimidine-6(7H)-carboxylate with tert-butyl 2,4-dichloro-5,6-dihydropyrido[3,4-d]pyrimidine-7(8H)-carboxylate and morpholine with (1S,4S)-2-oxa-5-azoniabicyclo[2.2.1]heptane chloride in Example 1 and chloropyrimidine with 4-chloro-6-methylpyrimidine in Example 2: LC-MS: m/z=+487 (M+H)$^+$.

Example 362

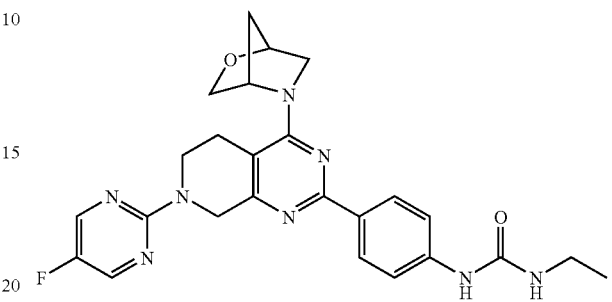

(sy)

Synthesis of 1-(4-(4-((1S,4S)-2-oxa-5-azabicyclo[2.2.1]heptan-5-yl)-7-(5-fluoropyrimidin-2-yl)-5,6,7,8-tetrahydropyrido[3,4-d]pyrimidin-2-yl)phenyl)-3-ethylurea (sy): The title compound sy was prepared by the procedures described in Examples 1 and 2, by substituting tert-butyl 2,4-dichloro-5H-pyrrolo[3,4-d]pyrimidine-6(7H)-carboxylate with tert-butyl 2,4-dichloro-5,6-dihydropyrido[3,4-d]pyrimidine-7(8H)-carboxylate and morpholine with (1S,4S)-2-oxa-5-azoniabicyclo[2.2.1]heptane chloride in Example 1 and chloropyrimidine with 2-chloro-5-fluoropyrimidine in Example 2: LC-MS: m/z=+491 (M+H)$^+$.

Example 363

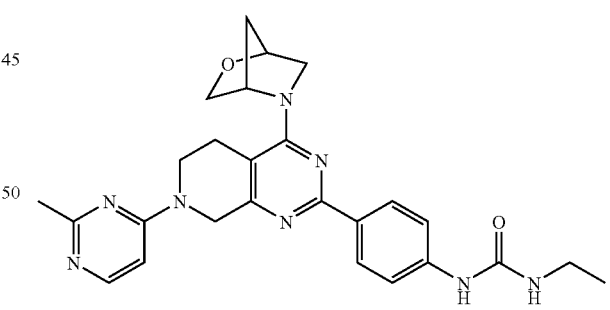

(sz)

Synthesis of 1-(4-(4-((1S,4S)-2-oxa-5-azabicyclo[2.2.1]heptan-5-yl)-7-(2-methylpyrimidin-4-yl)-5,6,7,8-tetrahydropyrido[3,4-d]pyrimidin-2-yl)phenyl)-3-ethylurea (sz): The title compound sz was prepared by the procedures described in Examples 1 and 2, by substituting tert-butyl 2,4-dichloro-5H-pyrrolo[3,4-d]pyrimidine-6(7H)-carboxylate with tert-butyl 2,4-dichloro-5,6-dihydropyrido[3,4-d]pyrimidine-7(8H)-carboxylate and morpholine with (1S,4S)-2-oxa-5-azoniabicyclo[2.2.1]heptane chloride in Example 1

Example 364

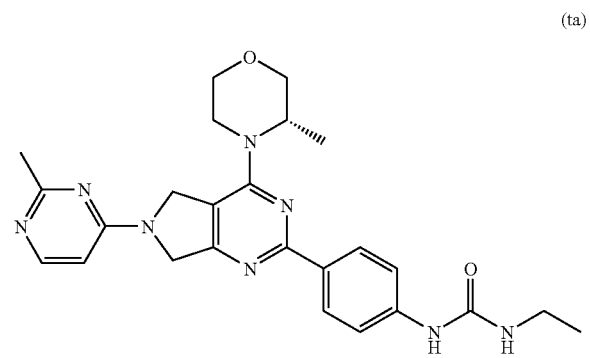

(ta)

Synthesis of (S)-1-ethyl-3-(4-(4-(3-methylmorpholino)-6-(2-methylpyrimidin-4-yl)-6,7-dihydro-5H-pyrrolo[3,4-d]pyrimidin-2-yl)phenyl)urea (ta): The title compound ta was prepared by the procedures described in Examples 1 and 2, by substituting morpholine with (S)-3-methylmorpholine in Example 1 and chloropyrimidine with 4-chloro-2-methylpyrimidine in Example 2: LC-MS: m/z=+475 (M+H)⁻.

Example 365

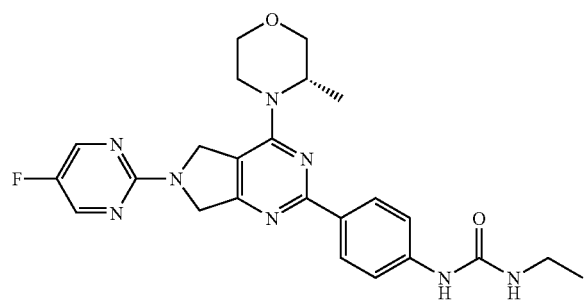

(tb)

Synthesis of (S)-1-ethyl-3-(4-(6-(5-fluoropyrimidin-2-yl)-4-(3-methylmorpholino)-6,7-dihydro-5H-pyrrolo[3,4-d]pyrimidin-2-yl)phenyl)urea (tb): The title compound tb was prepared by the procedures described in Examples 1 and 2, by substituting morpholine with (S)-3-methylmorpholine in Example 1 and chloropyrimidine with 2-chloro-5-fluoropyrimidine in Example 2: LC-MS: m/z=+479 (M+H)⁺.

Example 366

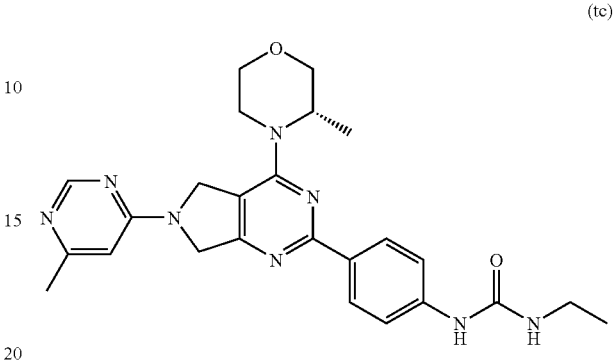

(tc)

Synthesis of (S)-1-ethyl-3-(4-(4-(3-methylmorpholino)-6-(6-methylpyrimidin-4-yl)-6,7-dihydro-5H-pyrrolo[3,4-d]pyrimidin-2-yl)phenyl)urea (tc): The title compound tc was prepared by the procedures described in Examples 1 and 2, by substituting morpholine with (S)-3-methylmorpholine in Example 1 and chloropyrimidine with 4-chloro-6-methylpyrimidine in Example 2: LC-MS: m/z=+475 (M+H)⁻.

Example 367

(td)

Synthesis of (S)-1-ethyl-3-(4-(4-(3-methylmorpholino)-6-(trifluoromethylsulfonyl)-6,7-dihydro-5H-pyrrolo[3,4-d]pyrimidin-2-yl)phenyl)urea (td): The title compound td was prepared by the procedures described in Examples 1 and 2, by substituting morpholine with (S)-3-methylmorpholine in Example 1 and chloropyrimidine with trifluoromethanesulfonyl chloride in Example 2: LC-MS: m/z=+515 (M+H)+.

Example 368

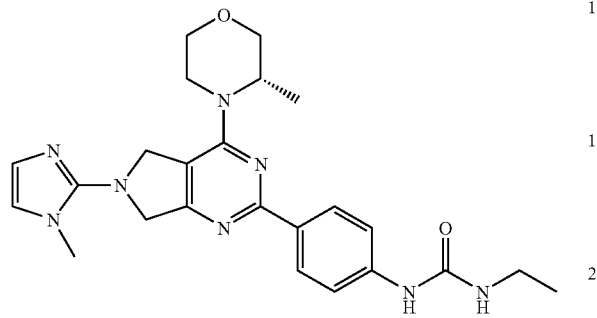

Synthesis of (S)-1-ethyl-3-(4-(6-(1-methyl-1H-imidazol-2-yl)-4-(3-methylmorpholino)-6,7-dihydro-5H-pyrrolo[3,4-d]pyrimidin-2-yl)phenyl)urea (te): The title compound was prepared by the procedures described in Example 1, steps 1-5 of Example 259, and steps 1 and 2 of Example 27, by substituting morpholine with (S)-3-methylmorpholine in Example 1, (S)-3-methyl-4-(2-(4-nitrophenyl)-5,6,7,8-tetrahydropyrido[3,4-d]pyrimidin-4-yl)morpholine with (S)-3-methyl-4-(2-(4-nitrophenyl)-6,7-dihydro-5H-pyrrolo[3,4-d]pyrimidin-4-yl)morpholine in step 1 of Example 259, and propyl isocyanate with ethyl isocyanate in step 2 of Example 27, and: LC-MS: m/z=+463 (M+H)+.

Example 369

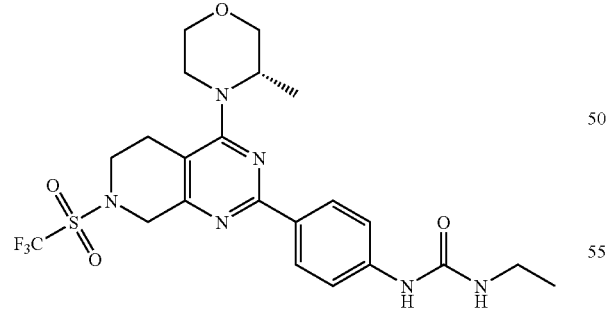

Synthesis of (S)-1-ethyl-3-(4-(4-(3-methylmorpholino)-7-(trifluoromethylsulfonyl)-5,6,7,8-tetrahydropyrido[3,4-d]pyrimidin-2-yl)phenyl)urea (tf): The title compound tf was prepared by the procedures described in Examples 1 and 2, by substituting tert-butyl 2,4-dichloro-5H-pyrrolo[3,4-d]pyrimidine-6(7H)-carboxylate with tert-butyl 2,4-dichloro-5,6-dihydropyrido[3,4-d]pyrimidine-7(8H)-carboxylate and morpholine with (S)-3-methylmorpholine in Example 1 and chloropyrimidine with trifluoromethanesulfonyl chloride in Example 2: LC-MS: m/z=+529 (M+H)+.

Example 370

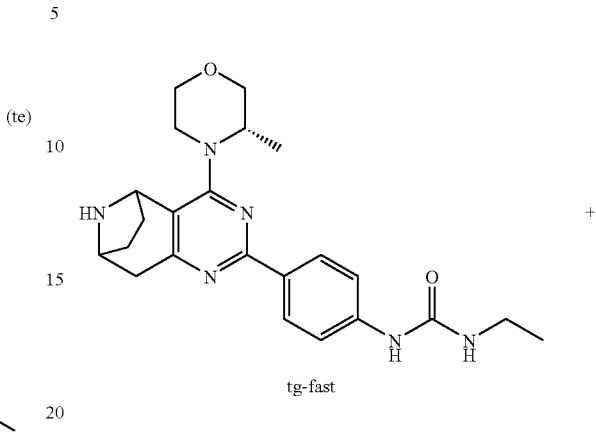

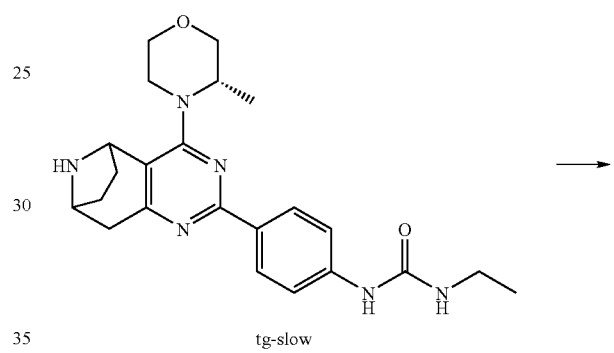

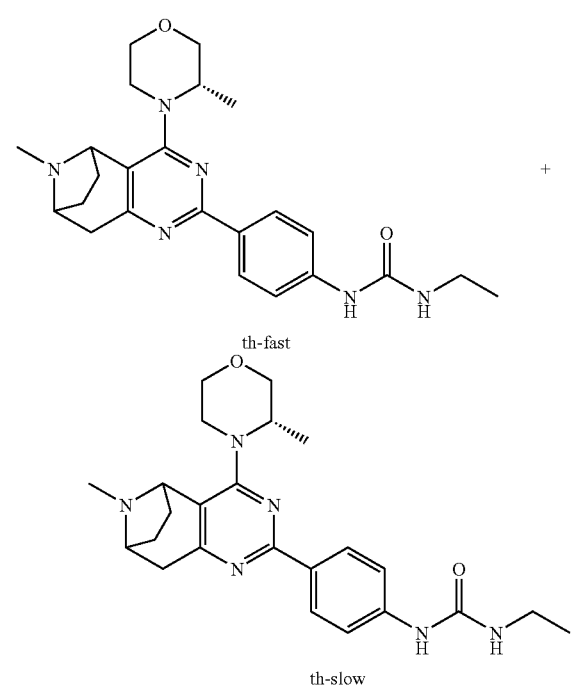

Step 1—Synthesis of compounds tg-fast and tg-slow: The compounds tg-fast and tg-slow were prepared by a modified procedure described that is described in J. Am. Chem. Soc., 2006, 128 (44), 14254-14255, and by the procedures described in Example 208, using allyl 3-(N-(4-methoxybenzyl)-4-nitrobenzamido)-8-azabicyclo[3.2.1]oct-2-ene-8-carboxylate and (S)-3-methylmorpholine-4-carbonitrile to produce crude N-allyloxycarbonyl ethyl urea product intermediates (not shown) (400 mg, 0.90 mmol) which were dissolved in THF (4.0 mL) was added Pd(PPh$_3$)$_4$ (100 mg, 0.09 mmol) and morpholine (4.0 mL, 40 mmol) at 0° C. After stirring for 15 min at 0° C., the mixture was diluted with CH$_2$Cl$_2$ (5 mL) and aqueous 5% HCl solution until acidic. After separation, the aqueous phase is basified with saturated aqueous NaHCO$_3$ solution and extracted with CHCl$_3$ (4×). The combined organic extract was then dried (Na$_2$SO$_4$), filtered and concentrated. The residue was purified and separated by reverse-phase HPLC to give the pure desired products tg-fast and tg-slow, whose absolute stereochemistry has yet to be assigned: (tg-fast, faster eluting isomer): $^1$H NMR (400 MHz, CDCl$_3$) δ 8.29 (d, J=8.6, 2H), 7.34 (d, J=8.6, 2H), 6.37 (s, 1H), 4.71 (s, 1H), 4.46 (d, J=5.8, 1H), 3.97 (s, 4H), 3.71 (s, 2H), 3.62-3.54 (m, 1H), 3.39 (d, J=13.3, 1H), 3.31 (s, 2H), 3.20 (dd, J=18.1, 5.5, 1H), 2.81 (s, 1H), 2.35-2.19 (m, 2H), 2.03 (s, 1H), 1.78 (dd, J=15.3, 6.4, 1H), 1.17 (t, J=7.5, 6H); LC-MS: m/z=+423 (M+H)$^+$; (tg-slow, slower eluting isomer): $^1$H NMR (400 MHz, CDCl$_3$) δ 8.29 (d, J=8.6, 2H), 7.34 (d, J=8.6, 2H), 6.26 (s, 1H), 4.65 (s, 1H), 4.34 (d, J=5.8, 1H), 4.09-4.01 (m, 1H), 4.00-3.83 (m, 3H), 3.79-3.72 (m, 2H), 3.67 (dd, J=11.3, 2.5, 1H), 3.45 (ddd, J=13.6, 10.0, 3.5, 1H), 3.38-3.28 (m, 2H), 3.17 (dd, J=18.4, 4.9, 1H), 2.76 (s, 1H), 2.31-2.14 (m, 2H), 2.01 (t, J=9.1, 1H), 1.79-1.70 (m, 1H), 1.47 (d, J=6.6, 3H), 1.17 (t, J=7.2, 3H); LC-MS: m/z=+423 (M+H)$^+$.

Step 2—Synthesis of compounds th-fast and th-slow: To the diastereomeric mixture of secondary amines tg-fast and tg-slow dissolved in CH$_3$CN (7.96 mL) was added sodium cyanoborohydride (151 mg, 2.41 mmol) and after stirring for 5 min at room temperature, aqueous formaldehyde (0.30 mL, 4.0 mmol, 37% w/w) was added. The mixture was stirred vigorously for 6 h, quenched with glacial acetic acid (0.40 mL), concentrated, washed with 1 N NaOH and extracted with EtOAc (3×). The combined organic extract was then dried (Na$_2$SO$_4$), filtered and concentrated. The residue was purified and separated by reverse-phase HPLC to give the pure desired products (af+ag), whose absolute stereochemistry has yet to be assigned: (th-fast, faster eluting isomer): $^1$H NMR (400 MHz, DMSO) δ 8.60 (s, 1H), 8.15 (d, J=8.8, 2H), 7.46 (d, J=8.8, 2H), 6.15 (t, J=5.7, 1H), 3.97 (d, J=6.5, 1H), 3.87-3.80 (m, 2H), 3.76-3.55 (m, 4H), 3.43-3.33 (m, 3H), 3.16-3.00 (m, 3H), 2.30 (dd, J=11.9, 5.9, 1H), 2.19 (s, 4H), 1.84 (t, J=10.8, 1H), 1.62 (d, J=12.8, 1H), 1.36 (d, J=6.6, 3H), 1.06 (t, J=7.2, 3H); LC-MS: m/z=+437 (M+H)$^+$; (th-slow, slower eluting isomer): $^1$H NMR (400 MHz, DMSO) δ 8.65 (s, 1H), 8.16 (d, J=8.8, 2H), 7.46 (d, J=8.8, 2H), 6.16 (t, J=5.6, 1H), 4.01-3.82 (m, 4H), 3.65-3.55 (m, 2H), 3.34 (s, 4H), 3.16-3.01 (m, 3H), 2.33 (td, J=11.9, 5.8, 1H), 2.16 (s, 4H), 1.85-1.76 (m, 1H), 1.69-1.61 (m, 1H), 1.09-1.02 (m, 6H); LC-MS: m/z=+437 (M+H)$^+$.

Example 371

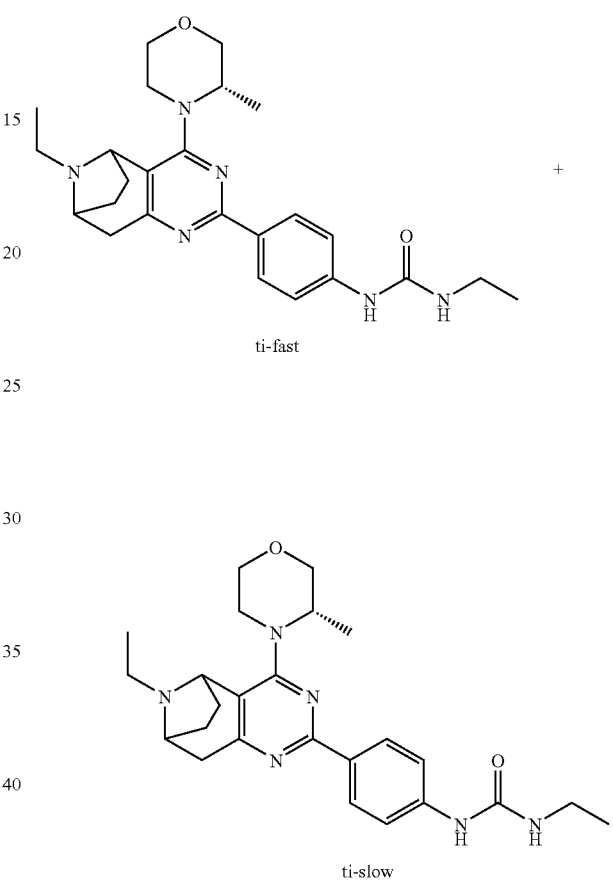

ti-fast ti-slow

Synthesis of compounds ti-fast and ti-slow: The compounds ti-fast and ti-slow were prepared by the procedures described in Example 370, by substituting formaldehyde with acetaldehyde in step 2: LC-MS: m/z=+451 (M+H)$^+$.

Example 372

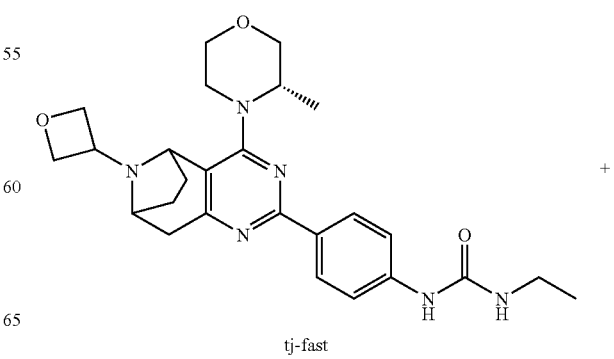

tj-fast

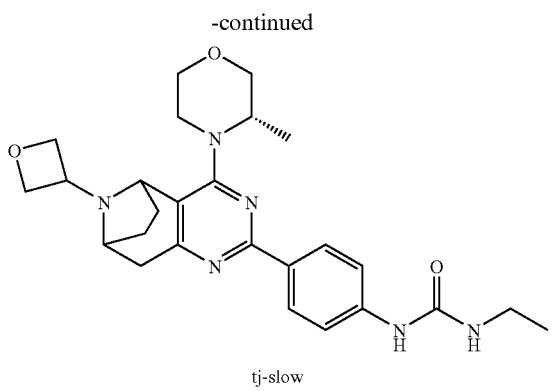

tj-slow

Synthesis of compounds tj-fast and tj-slow: The compounds tj-fast and tj-slow were prepared by the procedures described in Example 370, by substituting formaldehyde with oxetan-3-one in step 2: LC-MS: m/z=+479 (M+H)⁻.

Example 373

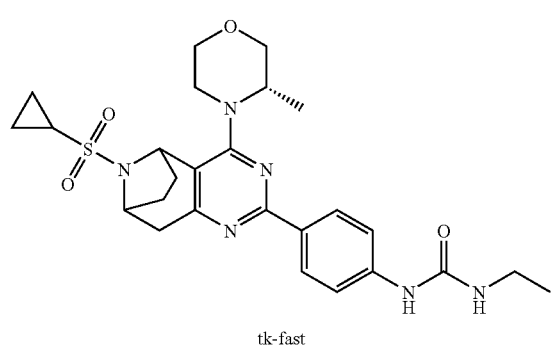

tk-fast

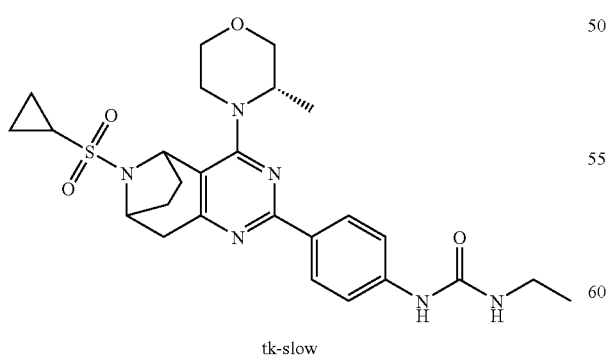

tk-slow

Synthesis of compounds tk-fast and tk-slow: The compounds tk-fast and tk-slow were prepared by the procedures described in Step 1 of Example 370, and as described in Example 2 by substituting chloropyrimidine with cyclopropanesulfonyl chloride: LC-MS: m/z=+527 (M+H)⁻.

Example 374

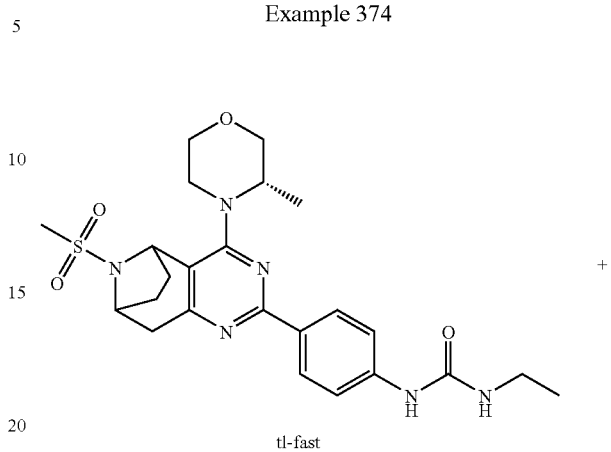

tl-fast

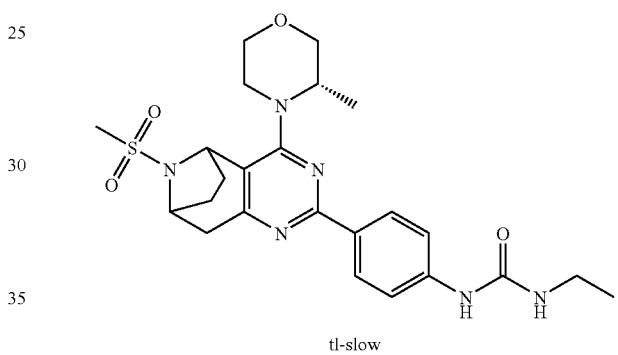

tl-slow

Synthesis of compounds tl-fast and tl-slow: The compounds tl-fast and tl-slow were prepared by the procedures described in Example 370, and as described in Example 2 by by substituting chloropyrimidine with methanesulfonyl chloride: LC-MS: m/z=+501 (M+H)⁺.

Example 375

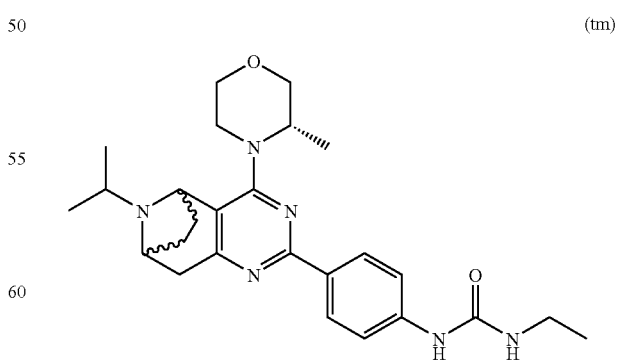

(tm)

Synthesis of compound tm: The compound tm was prepared by the procedures described in Example 370, and as described in Example 2 by substituting chloropyrimidine with 2-iodopropane in Example 2. The final product was isolated as a 1:1 mixture of diastereomers: LC-MS: m/z=+465 (M+H).

Example 376

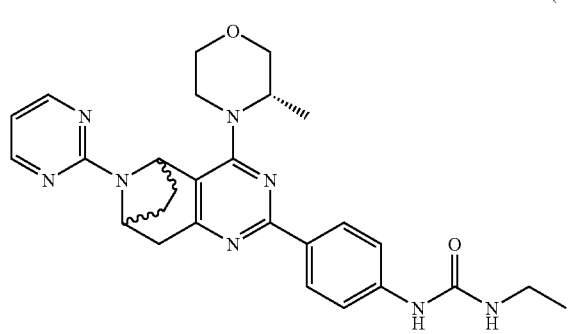
(tn)

Synthesis of compound tn: The compound tn was prepared by the procedures described in Example 370, and in Example 2. The final product was isolated as a 1:1 mixture of diastereomers: LC-MS: m/z=+501 (M+H)$^+$.

Example 377

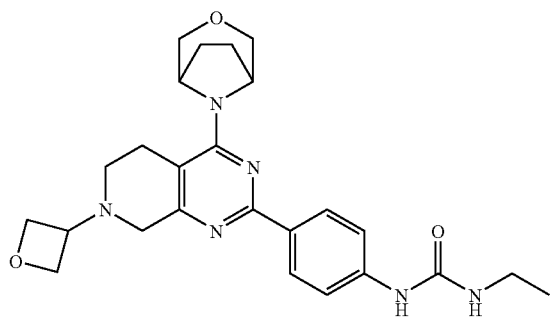
(tp)

Synthesis of 1-(4-(4-((1R,5S)-3-oxa-8-azabicyclo[3.2.1] octan-8-yl)-7-(oxetan-3-yl)-5,6,7,8-tetrahydropyrido[3,4-d] pyrimidin-2-yl)phenyl)-3-ethylurea (tp): The title compound (tp) was prepared by the procedures described in Examples 1 and 2, by substituting tert-butyl 2,4-dichloro-5H-pyrrolo[3,4-d]pyrimidine-6(7H)-carboxylate with tert-butyl 2,4-dichloro-5,6-dihydropyrido[3,4-d]pyrimidine-7(8H)-carboxylate and morpholine with 3-oxa-8-azabicyclo[3.2.1] octane hydrochloride in Example 1 and formaldehyde with oxetan-3-one in step 2 of Example 370: LC-MS: m/z=+465 (M+H)$^+$.

Example 378

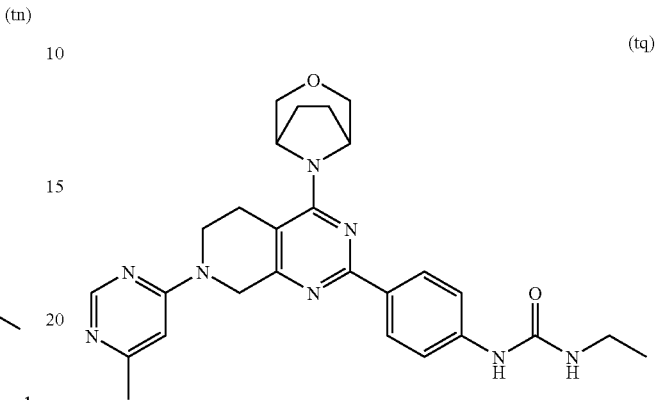
(tq)

Synthesis of 1-(4-(4-((1R,5S)-3-oxa-8-azabicyclo[3.2.1] octan-8-yl)-7-(6-methylpyrimidin-4-yl)-5,6,7,8-tetrahydropyrido[3,4-d]pyrimidin-2-yl)phenyl)-3-ethylurea (tq): The compound was tq prepared by the procedures described in Examples 1 and 2, by substituting tert-butyl 2,4-dichloro-5H-pyrrolo[3,4-d]pyrimidine-6(7H)-carboxylate with tert-butyl 2,4-dichloro-5,6-dihydropyrido[3,4-d]pyrimidine-7(8H)-carboxylate and morpholine with 3-oxa-8-azabicyclo[3.2.1] octane hydrochloride in Example 1 and and by substituting chloropyrimidine with 4-chloro-6-methylpyrimidine in Example 2: LC-MS: m/z=+501 (M+H)$^+$.

Example 379

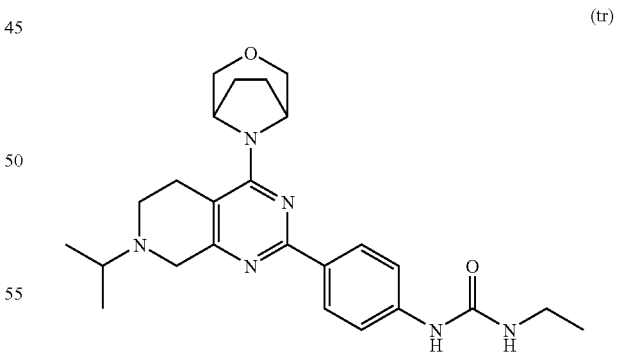
(tr)

Synthesis of 1-(4-(4-((1R,5S)-3-oxa-8-azabicyclo[3.2.1] octan-8-yl)-7-isopropyl-5,6,7,8-tetrahydropyrido[3,4-d]pyrimidin-2-yl)phenyl)-3-ethylurea (tr): The title compound tr was prepared by the procedures described in Examples 1 and 2, by substituting tert-butyl 2,4-dichloro-5H-pyrrolo[3,4-d]pyrimidine-6(7H)-carboxylate with tert-butyl 2,4-dichloro-5,6-dihydropyrido[3,4-d]pyrimidine-7(8H)-carboxylate and morpholine with 3-oxa-8-azabicyclo[3.2.1]octane hydro-

Example 380

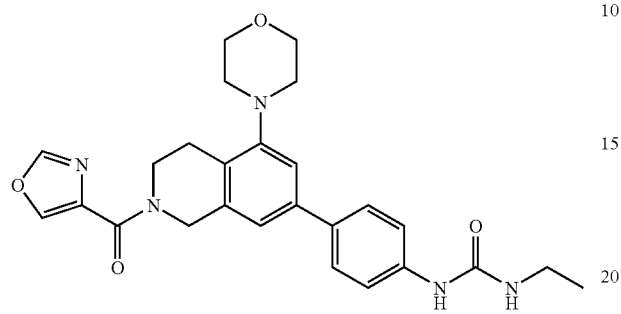

(ts)

Synthesis of 1-ethyl-3-(4-(5-morpholino-2-(oxazole-4-carbonyl)-1,2,3,4-tetrahydroisoquinolin-7-yl)phenyl)urea (ts): To (Oxazole-4-carboxylic acid (0.0106 g, 0.0000937 mol) in dry N,N-Dimethylformamide (0.460 mL, 0.00594 mol) was added 1-Hydroxybenzotriazole (0.0125 g, 0.0000925 mol) followed by N-(3-Dimethylaminopropyl)-N'-ethylcarbodiimide hydrochloride (0.0184 g, 0.0000960 mol) then followed by N,N-Diisopropylethylamine (0.0286 mL, 0.000164 mol) and then followed by 1-ethyl-3-(4-(4-morpholino-5,6,7,8-tetrahydropyrido[3,4-d]pyrimidin-2-yl)phenyl)urea (0.0242 g, 0.0000633 mol). The reaction mixture was stirred overnight. The reaction solution was concentrated and purified by HPLC. $^1$H NMR (400 MHz, DMSO) δ 8.71 (d, J=14.3, 2H), 8.59 (d, J=1.0, 1H), 8.20 (t, J=9.1, 2H), 7.49 (d, J=7.4, 2H), 6.22 (t, J=5.5, 1H), 5.10 (s, 1H), 4.70 (s, 1H), 4.08 (s, 1H), 3.81 (s, 1H), 3.73 (d, J=4.3, 4H), 3.49 (d, J=4.3, 4H), 3.18-3.05 (m, 2H), 2.77 (d, J=26.3, 2H), 1.06 (t, J=7.2, 3H). LC/MS-m/z+478.2 (M+H)+.

Example 381

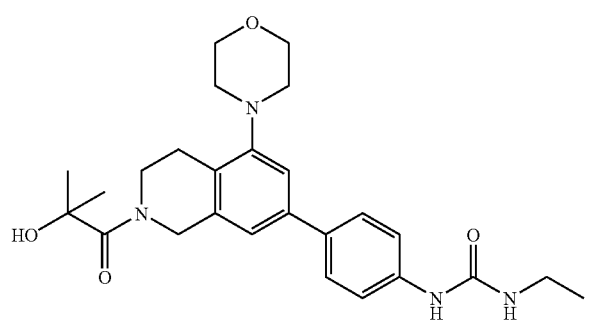

(tu)

1-ethyl-3-(4-(2-(2-hydroxy-2-methylpropanoyl)-5-morpholino-1,2,3,4-tetrahydroisoquinolin-7-yl)phenyl)urea (tu): (2-hydroxyisobutyric acid (0.0388 g, 0.000373 mol) 1-ethyl-3-(4-(4-morpholino-5,6,7,8-tetrahydropyrido[3,4-d]pyrimidin-2-yl)phenyl)urea (0.100 g, 0.000261 mol) 1-Hydroxybenzotriazole (0.0513 g, 0.000380 mol) and N,N-Dimethylformamide (1.80 mL, 0.0232 mol) were combined, stirred for 5 minutes, and then to the mixture N-(3-Dimethylaminopropyl)-N'-ethylcarbodiimide hydrochloride (0.0727 g, 0.000379 mol) was added followed by N,N-Diisopropylethylamine (0.1140 mL, 0.0006545 mol). The reaction mixture was stirred overnight. The reaction mixture was concentrated, chromatographed through silica gel (12 g, 0-5% MeOH in dichloromethane), and purified by HPLC. $^1$H NMR (400 MHz, DMSO) δ 8.68 (s, 1H), 8.19 (d, J=8.8, 2H), 7.48 (d, J=8.8, 2H), 6.17 (t, J=5.6, 1H), 5.57 (s, 1H), 5.16 (s, 1H), 4.54 (s, 1H), 4.09 (s, 1H), 3.70 (d, J=32.5, 5H), 3.48 (d, J=4.1, 4H), 3.17-3.05 (m, 2H), 2.70 (d, J=24.2, 2H), 1.37 (s, 6H), 1.12-0.99 (m, 3H). LC/MS-m/z+469.3 (M+H)+.

Example 382

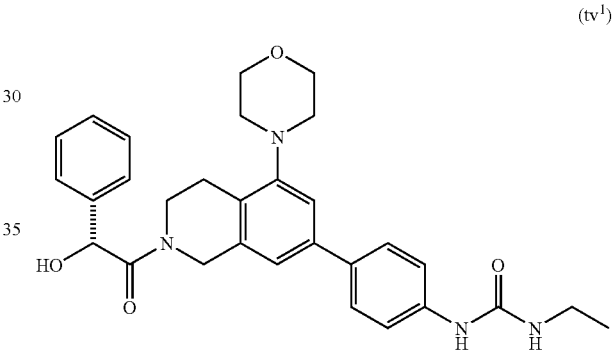

(tv$^1$)

(R)-1-ethyl-3-(4-(2-(2-hydroxy-2-phenylacetyl)-5-morpholino-1,2,3,4-tetrahydroisoquinolin-7-yl)phenyl)urea (tv): (R)-2-hydroxy-2-phenylacetic acid (0.0137 g, 0.0000900 mol) 1-ethyl-3-(4-(4-morpholino-5,6,7,8-tetrahydropyrido[3,4-d]pyrimidin-2-yl)phenyl)urea (0.0251 g, 0.0000656 mol) 1-Hydroxybenzotriazole (0.0133 g, 0.0000984 mol) and N,N-Dimethylformamide (0.46 mL, 0.0059 mol) were combined, stirred for 5 minutes, and to this reaction mixture N-(3-Dimethylaminopropyl)-N'-ethylcarbodiimide hydrochloride (0.0177 g, 0.0000923 mol) was added followed by N,N-Diisopropylethylamine (0.0286 mL, 0.000164 mol). The reaction mixture was stirred overnight and concentrated and purified by HPLC. $^1$H NMR (400 MHz, DMSO) δ 8.70 (s, 1H), 8.16 (dd, J=15.3, 8.7, 2H), 7.51-7.24 (m, 7H), 6.19 (t, J=5.5, 1H), 5.83 (d, J=27.0, 1H), 5.52 (s, 1H), 4.77-4.34 (m, 2H), 3.69 (t, J=11.3, 4H), 3.65-3.39 (m, 4H), 3.16-3.05 (m, 2H), 2.72-2.56 (m, 1H), 2.30 (dd, J=17.9, 9.1, 1H), 1.05 (t, J=7.2, 3H). LC/MS-m/z+517.3 (M+H)+.

Example 383

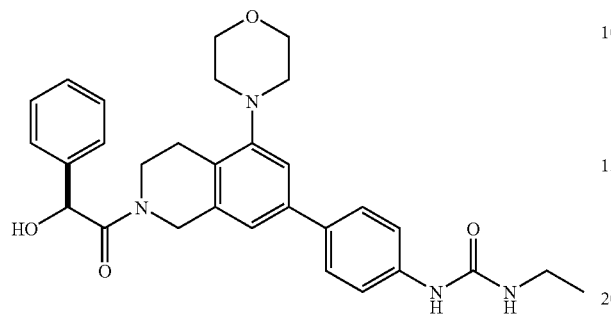
(tv²)

(S)-1-ethyl-3-(4-(2-(2-hydroxy-2-phenylacetyl)-5-morpholino-1,2,3,4-tetrahydroisoquinolin-7-yl)phenyl)urea (tv²): (S)-2-hydroxy-2-phenylacetic acid (0.0143 g, 0.0000940 mol) 1-ethyl-3-(4-(4-morpholino-5,6,7,8-tetrahydropyrido[3,4-d]pyrimidin-2-yl)phenyl)urea (0.0252 g, 0.0000659 mol) 1-Hydroxybenzotriazole (0.0127 g, 0.0000940 mol) and N,N-Dimethylformamide (0.46 mL, 0.0059 mol) were combined, and stirred for 5 minutes. To the reaction mixture was added N-(3-Dimethylaminopropyl)-N'-ethylcarbodiimide hydrochloride (0.0175 g, 0.0000915 mol) followed by N,N-Diisopropylethylamine (0.0286 mL, 0.000164 mol) and the resultant solution was stirred overnight. The reaction solution was concentrated and purified by HPLC. ¹H NMR (400 MHz, DMSO) δ 8.70 (s, 1H), 8.16 (dd, J=15.3, 8.7, 2H), 7.51-7.23 (m, 7H), 6.19 (t, J=5.6, 1H), 5.83 (d, J=30.5, 1H), 5.53 (d, J=8.0, 1H), 4.78-4.33 (m, 2H), 3.71 (d, J=3.7, 4H), 3.65-3.41 (m, 4H), 3.17-3.05 (m, 2H), 2.73-2.56 (m, 1H), 2.30 (dd, J=18.0, 9.0, 1H), 1.05 (t, J=7.2, 3H). LC/MS-m/z+517.3 (M+H)+.

Example 384

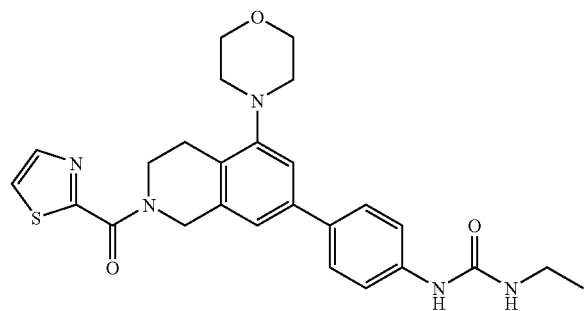
(tw)

Synthesis of 1-ethyl-3-(4-(5-morpholino-2-(thiazole-2-carbonyl)-1,2,3,4-tetrahydroisoquinolin-7-yl)phenyl)urea (tw): To 1-ethyl-3-(4-(4-morpholino-5,6,7,8-tetrahydropyrido[3,4-d]pyrimidin-2-yl)phenyl)urea (0.101 g, 0.000264 mol) in dry N,N-Dimethylformamide (1.80 mL, 0.0232 mol) was added dry Pyridine (0.111 mL, 0.00137 mol) followed by 1,3-thiazole-2-carbonyl chloride (0.0818 g, 0.000554 mol). The reaction solution was stirred overnight. The sample was concentrated, chromatographed through silica gel (12 g, 0-10% MeOH in dichloromethane) and purified by HPLC. ¹H NMR (400 MHz, DMSO) δ 8.71 (s, 1H), 8.20 (t, J=8.5, 2H), 8.11 (q, J=2.9, 2H), 7.49 (dd, J=8.7, 4.7, 2H), 6.19 (d, J=2.9, 1H), 5.48 (s, 1H), 4.77 (s, 1H), 4.48 (s, 1H), 3.87 (d, J=4.9, 1H), 3.80-3.68 (m, 4H), 3.49 (d, J=4.1, 4H), 3.12 (p, J=6.6, 2H), 2.82 (d, J=23.8, 2H), 1.06 (t, J=7.1, 3H). LC/MS-m/z+ 494.2 (M+H)+

Example 385

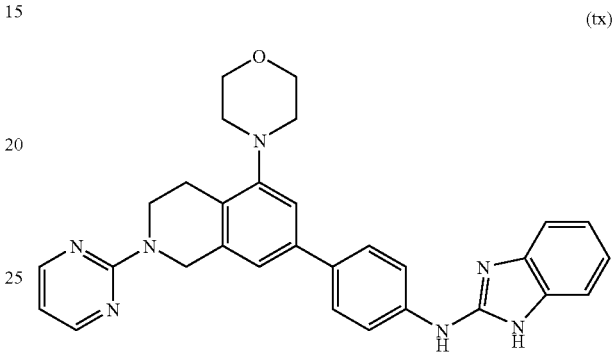
(tx)

Synthesis of N-(4-(5-morpholino-2-(pyrimidin-2-yl)-1,2,3,4-tetrahydroisoquinolin-7-yl)phenyl)-1H-benzo[d]imidazol-2-amine (tx)

Step 1—Synthesis of 1-(2-aminophenyl)-3-(4-(4-morpholino-7-(pyrimidin-2-yl)-5,6,7,8-tetrahydropyrido[3,4-d]pyrimidin-2-yl)phenyl)thiourea: To 4-(4-morpholino-7-(pyrimidin-2-yl)-5,6,7,8-tetrahydropyrido[3,4-d]pyrimidin-2-yl)aniline (0.099 g, 0.00025 mol) in Chloroform (0.940 mL, 0.0117 mol) was added an equal volume of sat NaHCO₃ was added Carbonothioic dichloride (0.030 mL, 0.00039 mol) in Chloroform (0.240 mL, 0.00300 mol) and the reaction mixture was stirred for 1 hour then the layers were allowed to separate. The chloroform layer was washed twice with saturated NaCl, dried over Magnesium sulfate, filtered, and concentrated. To this crude mixture was added dry Methylene chloride (5.00 mL, 0.0780 mol) followed by 1,2-Benzenediamine (0.0275 g, 0.000254 mol). The sample was stirred for 30 minutes, but no product was formed. To the reaction mixture was added dry Methanol (5.00 mL, 0.123 mol) and the resultant solution was stirred overnight which produced the product as evidence by LC-MS mass peak. The crude reaction mixture was concentrated, chromatographed through silica gel (4 g, 0-5% MeOH in dichloromethane, and purified by HPLC. ¹H NMR (500 MHz, DMSO) δ 9.84 (s, 1H), 9.20 (s, 1H), 8.44 (d, J=4.7, 2H), 8.28 (d, J=8.7, 2H), 7.69 (d, J=8.6, 2H), 7.11 (dd, J=7.8, 1.3, 1H), 6.97 (t, J=7.4, 1H), 6.75 (d, J=8.0, 1H), 6.70 (t, J=4.7, 1H), 6.57 (t, J=7.5, 1H), 4.95 (s, 2H), 4.83 (s, 2H), 3.99 (t, J=5.3, 2H), 3.78-3.69 (m, 4H), 3.54-3.47 (m, 4H), 2.77 (d, J=4.9, 2H). LC/MS-m/z+540.2 (M+H)+

Step 2—Synthesis of compound tw: 1-(2-aminophenyl)-3-(4-(4-morpholino-7-(pyrimidin-2-yl)-5,6,7,8-tetrahydropyrido[3,4-d]pyrimidin-2-yl)phenyl)thiourea (0.053 g, 0.000098 mol), yellow Mercury(II) oxide (0.0450 g, 0.000208 mol), Octasulfur (0.0061 g, 0.000024 mol), and Ethanol (2.00 mL, 0.0342 mol) were combined, then heated at 78° C. for 2 hours, then filtered through celite, and concentrated. Mercury(II) oxide (0.0658 g, 0.000304 mol) Octasulfur (0.0111 g, 0.0000433 mol) and Ethanol (2.00 mL, 0.0342 mol) were added once again to the sample, heated at 78° C. for 1 hour, filtered through celite, concentrated to provide the desired product, which was purified by HPLC. $^1$H NMR (400 MHz, DMSO) δ 9.81 (s, 1H), 8.45 (d, J=4.3, 2H), 8.32 (d, J=8.2, 2H), 8.16 (s, 1H), 7.87 (d, J=8.3, 2H), 7.35 (d, J=21.2, 2H), 7.01 (s, 2H), 6.70 (s, 1H), 4.84 (s, 2H), 4.00 (s, 2H), 3.75 (s, 4H), 3.49 (s, 4H), 2.76 (s, 2H). LC/MS-m/z+506.3 (M+H)+

Example 386

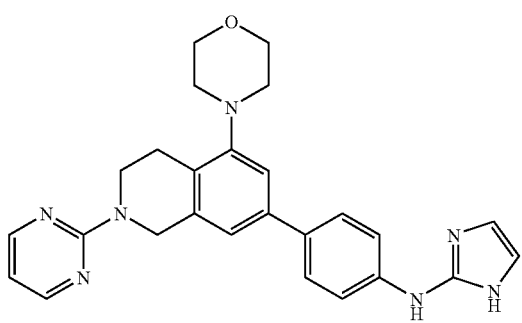

(ty)

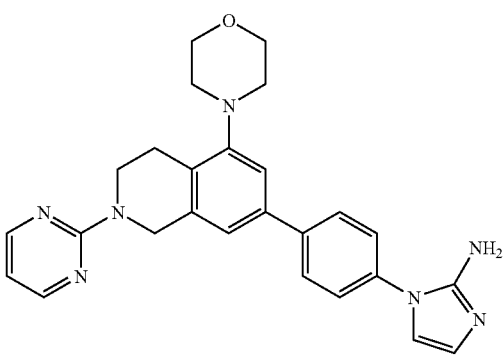

(tz)

Synthesis of N-(4-(4-morpholino-7-(pyrimidin-2-yl)-5,6,7,8-tetrahydropyrido[3,4-d]pyrimidin-2-yl)phenyl)-1H-imidazol-2-amine (ty); and 1-(4-(4-morpholino-7-(pyrimidin-2-yl)-5,6,7,8-tetrahydropyrido[3,4-d]pyrimidin-2-yl)phenyl)-1H-imidazol-2-amine (tz)

Step 1—Synthesis of 1-(4-(4-morpholino-7-(pyrimidin-2-yl)-5,6,7,8-tetrahydropyrido[3,4-d]pyrimidin-2-yl)phenyl)thiourea: To 4-(4-morpholino-7-(pyrimidin-2-yl)-5,6,7,8-tetrahydropyrido[3,4-d]pyrimidin-2-yl)aniline (0.0968 g, 0.000248 mol) in Chloroform (0.940 mL, 0.0117 mol) was added an equal volume of sat NaHCO3 and Carbonothioic dichloride (0.030 mL, 0.00039 mol) in Chloroform (0.240 mL, 0.00300 mol). The resultant solution was stirred for 30 minutes then the layers were allowed to separate. The chloroform layer was washed twice with sat NaCl, dried over Magnesium sulfate, filtered, and concentrated. To the crude residue was added dry Methanol (3.00 mL, 0.0740 mol) followed by 7.0 M of Ammonia in Methanol (0.110 mL). The resultant solution was stirred for 3 hours followed by the addition of more dry Methylene chloride (3.00 mL, 0.0468 mol) and 7.0 M of Ammonia in Methanol (0.110 mL). The reaction mixture was stirred overnight. The next morning 7.0 M of Ammonia in Methanol (0.110 mL) and dry Methylene chloride (3.00 mL, 0.0468 mol) was added to the reaction mixture and the resultant solution was stirred for 3 hours. The sample was vacuum filtered and the solid was washed with dichloromethane. $^1$H NMR (400 MHz, DMSO) δ 8.44 (d, J=4.7, 2H), 8.29 (d, J=8.6, 2H), 7.58 (d, J=8.6, 2H), 6.70 (t, J=4.7, 1H), 4.83 (s, 2H), 3.99 (t, J=5.2, 2H), 3.73 (d, J=4.3, 4H), 3.50 (d, J=4.4, 4H), 2.77 (s, 2H). LC/MS-m/z+449/2 (M+H)+.

Step 2—Synthesis of Methyl 4-(4-morpholino-7-(pyrimidin-2-yl)-5,6,7,8-tetrahydropyrido[3,4-d]pyrimidin-2-yl)phenylcarbamimidothioate: 1-(4-(4-morpholino-7-(pyrimidin-2-yl)-5,6,7,8-tetrahydropyrido[3,4-d]pyrimidin-2-yl)phenyl)thiourea (0.0696 g, 0.000155 mol) in dry Methanol (2.00 mL, 0.0494 mol) was added Methyl iodide (0.01110 mL, 0.0001783 mol and the resultant mixture was stirred for 30 minutes. To the reaction mixture was added Acetone (2.00 g, 0.0344 mol) and the mixture was stirred overnight. To the reaction mixture was added more Methyl iodide (0.01110 mL, 0.0001783 mol) and the reaction solution was heated at 40° C. and stirred for 2 days, followed by further addition of Methyl iodide (0.330 mL, 0.00530 mol). The reaction solution was stirred at 40° C. for 1 more hour. The reaction solution was concentrated and was chromatographed on silica gel (4 g, 0-10% MeOH in dichloromethane). $^1$H NMR (400 MHz, CDCl$_3$) δ 8.43 (t, J=7.5, 2H), 8.37 (d, J=4.7, 2H), 7.22 (d, J=8.1, 2H), 6.55 (t, J=4.7, 1H), 4.98 (s, 2H), 4.06 (t, J=5.3, 2H), 3.88-3.82 (m, 4H), 3.55-3.50 (m, 4H), 2.78 (t, J=5.1, 2H), 2.62 (s, 3H). LC/MS-m/z+463.3 (M+H)+.

Step 3—Synthesis of compounds ty and tz:
Methyl 4-(4-morpholino-7-(pyrimidin-2-yl)-5,6,7,8-tetrahydropyrido[3,4-d]pyrimidin-2-yl)phenylcarbamimidothioate (0.070 g, 0.00015 mol) in 1-Propanol (5.00 mL, 0.0669 mol) was added Ethanamine, 2,2-diethoxy- (0.0664 mL, 0.000454 mol) heated at 97° C. for 2 hours. At this time, an additional portion of Ethanamine, 2,2-diethoxy- (0.0222 mL, 0.000152 mol) was added to the reaction mixture and stirred for 1 hour at 97° C. After this time, an additional portion of Ethanamine, 2,2-diethoxy- (0.0222 mL, 0.000152 mol) was added to the reaction mixture and heated at 97° C. for 6 hours. The reaction mixture was concentrated and dried in vacuo overnight. The crude product was cooled at 0° C. and then added 10.0 M of Hydrogen chloride in Water (2.00 mL), allowed to warm slowly to room temperature, stirred for 6 hours, then poured into ice, and to the ice solution was added saturated NaHCO$_3$ until the pH was approximately 9. The aqueous solution was extracted three times with 10% MeOH in dichloromethane, dried over Magnesium sulfate, filtered, and concentrated to provide the crude product which was chromatographed through silica gel (4 g, 0-10% MeOH in dichloromethane), and further purified by HPLC. 1-(4-(4-morpholino-(pyrimidin-2-yl)-5,6,7,8-tetrahydropyrido[3,4-d]pyrimidin-2-yl)phenyl)-1H-imidazol-2-amine (tz) $^1$H NMR (400 MHz, DMSO) δ 8.44 (t, J=6.7, 3H), 8.23 (s, 1H), 7.58 (d, J=8.7, 2H), 6.93 (d, J=1.5, 1H), 6.71 (t, J=4.7, 1H), 6.59 (d, J=1.5, 1H), 5.52 (s, 2H), 4.86 (s, 2H), 4.00 (t, J=5.1, 2H), 3.74 (d, J=4.5, 4H), 3.52 (d, J=4.4, 4H), 2.79 (s, 2H). LC/MS-m/z+456.2 (M+H)+; and N-(4-(4-morpholino-7-

(pyrimidin-2-yl)-5,6,7,8-tetrahydropyrido[3,4-d]pyrimidin-2-yl)phenyl)-1H-imidazol-2-amine (ty) LC/MS-m/z+456.2 (M+H)+.

Example 387

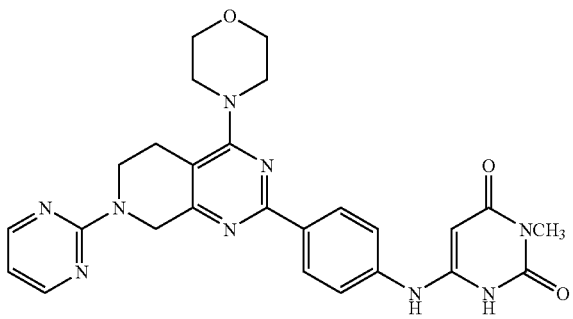

(ua)

Synthesis of 3-methyl-6-(4-(4-morpholino-7-(pyrimidin-2-yl)-5,6,7,8-tetrahydropyrido[3,4-d]pyrimidin-2-yl)phenylamino)pyrimidine-2,4(1H,3H)-dione (ua): 4-(4-morpholino-7-(pyrimidin-2-yl)-5,6,7,8-tetrahydropyrido[3,4-d]pyrimidin-2-yl)aniline (0.0183 g, 0.0000470 mol) 6-chloro-3-methylpyrimidine-2,4(1H,3H)-dione (0.0080 g, 0.000050 mol) N,N-Diethylaniline (0.0163 mL, 0.000103 mol) and Acetic acid (0.0040 mL, 0.000070 mol) were combined, and the reaction mixture was heated at 190° C. for 30 minutes. The crude product was chromatographed through silica gel (4 g, 0-10% MeOH in dichloromethane) and purified by HPLC. $^1$H NMR (400 MHz, DMSO) δ 11.19 (s, 1H), 9.04 (s, 1H), 8.44 (d, J=4.7, 2H), 8.34 (t, J=6.8, 2H), 7.33 (d, J=8.6, 2H), 6.70 (t, J=4.7, 1H), 5.04 (s, 1H), 4.83 (s, 2H), 3.99 (t, J=5.0, 2H), 3.73 (d, J=4.4, 4H), 3.50 (d, J=4.2, 4H), 3.09 (s, 3H), 2.76 (s, 2H). LC/MS-m/z+514.2 (M+H)+

Example 388

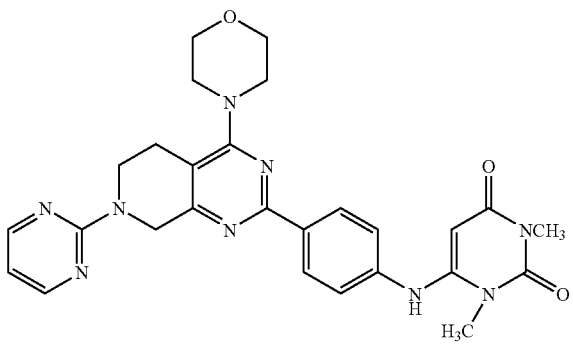

(ub)

Synthesis of 1,3-dimethyl-6-(4-(4-morpholino-7-(pyrimidin-2-yl)-5,6,7,8-tetrahydropyrido[3,4-d]pyrimidin-2-yl)phenylamino)pyrimidine-2,4(1H,3H)-dione (ub): 4-(4-morpholino-7-(pyrimidin-2-yl)-5,6,7,8-tetrahydropyrido[3,4-d]pyrimidin-2-yl)aniline (0.0587 g, 0.000151 mol) 6-chloro-1,3-dimethylpyrimidine-2,4(1H,3H)-dione (0.0287 g, 0.000164 mol) N,N-Diethylaniline (0.0480 mL, 0.000301 mol) and Acetic acid (0.01200 mL, 0.0002110 mol) were combined, and the reaction mixture was heated at 190° C. for 3.5 hours. The reaction solution was chromatographed through silica gel (4 g, 0-10% MeOH in dichloromethane) and purified by HPLC. $^1$H NMR (400 MHz, DMSO) δ 8.68 (s, 1H), 8.45 (d, J=4.7, 2H), 8.38 (d, J=8.6, 2H), 7.34 (d, J=8.6, 2H), 6.70 (t, J=4.7, 1H), 4.86 (d, J=11.7, 3H), 4.00 (t, J=5.1, 2H), 3.74 (d, J=4.4, 4H), 3.51 (d, J=4.2, 4H), 3.45 (s, 3H), 3.13 (s, 3H), 2.77 (s, 2H). LC/MS-m/z+528.2 (M+H)+

Example 389

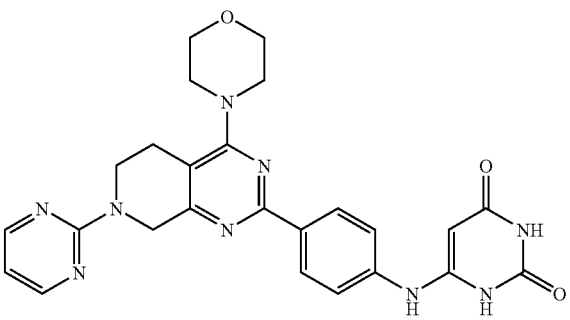

(uc)

Synthesis of 6-(4-(4-morpholino-7-(pyrimidin-2-yl)-5,6,7,8-tetrahydropyrido[3,4-d]pyrimidin-2-yl)phenylamino)pyrimidine-2,4(1H,3H)-dione (uc): 4-(4-Morpholino-7-(pyrimidin-2-yl)-5,6,7,8-tetrahydropyrido[3,4-d]pyrimidin-2-yl)aniline (0.0626 g, 0.000161 mol) 6-Chlorouracil (0.0243 g, 0.000166 mol) N,N-Diethylaniline (0.0512 mL, 0.000322 mol) and Acetic acid (0.01280 mL, 0.0002251 mol) were combined, and the reaction solution was heated at 190° C. for 30 minutes. The reaction solution was chromatographed through silica gel (4 g, 0-10% MeOH in dichloromethane). The combined fractions were concentrated and the resulting material was slurried in DMF, filtered, concentrated, and purified by HPLC. $^1$H NMR (400 MHz, DMSO) δ 10.37 (s, 1H), 9.21 (s, 1H), 8.44 (d, J=4.7, 2H), 8.33 (d, J=8.7, 2H), 7.32 (d, J=8.6, 2H), 6.70 (t, J=4.7, 1H), 6.62 (s, 1H), 4.89 (s, 1H), 4.84 (s, 2H), 3.99 (t, J=5.0, 2H), 3.73 (d, J=4.3, 4H), 3.50 (d, J=4.2, 4H), 2.77 (s, 2H). LC/MS-m/z+500.2 (M+H)+

Example 390

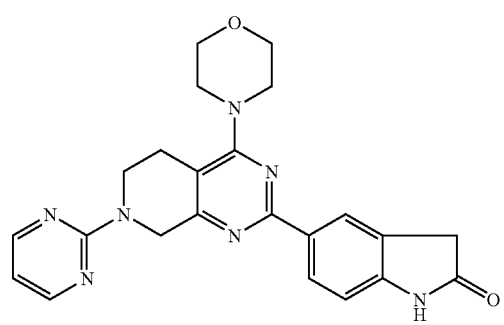

(ud)

Synthesis of 5-(4-morpholino-7-(pyrimidin-2-yl)-5,6,7,8-tetrahydropyrido[3,4-d]pyrimidin-2-yl)indolin-2-one (ud)

Step 1—Synthesis of Tert-butyl 4-morpholino-2-(2-oxoindolin-5-yl)-5,6-dihydropyrido[3,4-d]pyrimidine-7(8H)-carboxylate: 5-(4,4,5,5-tetramethyl-1,3,2-dioxaborolan-2-yl)indolin-2-one (0.133 g, 0.000513 mol), Tetrakis(triphenylphosphine)palladium(0) (0.0380 g, 0.0000329 mol) Sodium carbonate (0.073 g, 0.00069 mol) and Potassium acetate (0.094 g, 0.00096 mol) were combined, and the reaction solution was nitrogen purged three times. To the reaction solution was added tert-butyl 2-chloro-4-morpholino-5,6-dihydropyrido[3,4-d]pyrimidine-7(8H)-carboxylate (0.150 g, 0.000423 mol) in dry Acetonitrile (2.00 mL, 0.0383 mol) followed by deoxygenated Water (1.20 mL, 0.0666 mol), and the resultant mixture was microwaved on 300 watts, 120° C. for 30 minutes on a Biotage microwave and then heated at 90° C. overnight in an oil bath. The reaction solution was diluted with $H_2O$, extracted three times with 10% MeOH in dichloromethane, dried over Magnesium sulfate, filtered, concentrated, chromatographed through silica gel (40 g, 0-5% MeOH in dichloromethane). The material was used in the next step without further purification. LC/MS-m/z+452.2 (M+H)+

Step 2—Synthesis of 5-(4-Morpholino-5,6,7,8-tetrahydropyrido[3,4-d]pyrimidin-2-yl)indolin-2-one: Tert-butyl 4-morpholino-2-(2-oxoindolin-5-yl)-5,6-dihydropyrido[3,4-d]pyrimidine-7(8H)-carboxylate (0.142 g, 0.000314 mol) and 4.0 M of Hydrogen chloride in 1,4-Dioxane (2.3 mL) were combined and shaken for 2 hours then concentrated and dried in vacuo overnight. The crude material was diluted with sat NaHCO3 and extracted 6 times with 10% MeOH in dichloromethane, dried over Magnesium sulfate, filtered, concentrated. The resultant material was used in the next step without further purification. LC/MS-m/z+352.2 (M+H)+

Step 3—Synthesis of compound ud: 5-(4-Morpholino-5,6,7,8-tetrahydropyrido[3,4-d]pyrimidin-2-yl)indolin-2-one (0.083 g, 0.24 mmol), 2-Chloropyrimidine (0.0406 g, 0.354 mmol), N,N-Dimethylformamide (4.00 mL, 51.6 mmol) and N,N-Diisopropylethylamine (0.164 mL, 0.945 mmol) were combined and reaction mixture was microwaved on 300 watts, 120° C. for 30 minutes on a CEM microwave, and vacuum filtered. $^1$H NMR (400 MHz, DMSO) δ 10.60 (s, 1H), 8.44 (d, J=4.7, 2H), 8.24 (d, J=8.2, 1H), 8.20 (s, 1H), 6.92 (t, J=10.8, 1H), 6.70 (t, J=4.7, 1H), 4.82 (s, 2H), 3.98 (t, J=5.2, 2H), 3.77-3.69 (m, 4H), 3.57 (s, 2H), 3.47 (d, J=4.4, 4H), 2.75 (dd, J=8.8, 3.8, 2H). LC/MS-m/z+430.2 (M+H)+.

Example 391

(ue)

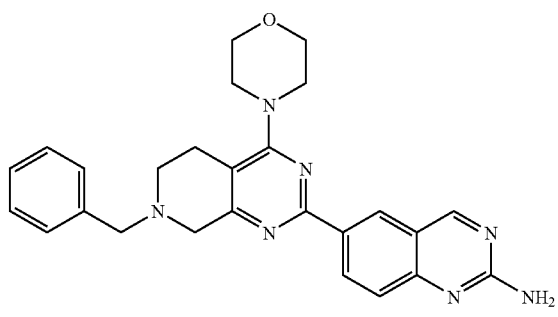

Synthesis of 6-(7-benzyl-4-morpholino-5,6,7,8-tetrahydropyrido[3,4-d]pyrimidin-2-yl)quinazolin-2-amine (ue)

Step 1—Synthesis of di-tert-butyl(6-bromoquinazolin-2-imino)dicarboxylate

6-Bromoquinazolin-2-amine (0.492 g, 0.00220 mol), Di-tert-Butyldicarbonate (2.4513 g, 0.011232 mol), and 4-Dimethylaminopyridine (0.0151 g, 0.000124 mol) were combined and the resultant mixture was heated with a heat gun until it was homogeneous. The sample was chromatographed through silica gel (80 g, 0-20% EtOAc in hexanes) and used in the next step without further purification. $^1$H NMR (400 MHz, CDCl$_3$) δ 9.35 (s, 1H), 8.14 (d, J=2.0, 1H), 8.00 (dd, J=9.0, 2.1, 1H), 7.91 (d, J=9.0, 1H), 1.48-1.39 (m, 24H). LC/MS-m/z+426.0 (M+H)+.

Step 2—Synthesis of di-tert-butyl(6-(4,4,5,5-tetramethyl-1,3,2-dioxaborolan-2-yl)quinazolin-2-imino)dicarboxylate: Tris(dibenzylideneacetone)dipalladium(0) (0.0100 g, 0.0000109 mol) and (2-Biphenyl)dicyclohexylphosphine (0.0120 g, 0.0000342 mol) were combined, and the reaction solution was nitrogen purged three times, and to it was added dry 1,4-Dioxane (1.40 mL, 0.0179 mol) and the resultant solution was stirred at room temperature for 10 minutes. The bromide intermediate from step 1 (0.218 g, 0.000514 mol) Bispinacol ester boronate (0.1580 g, 0.0006222 mol) and Potassium acetate (0.0880 g, 0.000897 mol) were combined in a different flask, which was nitrogen purged three times. To this reaction mixture was then added 1,4-Dioxane (1.40 mL, 0.0179 mol). The palladium mixture was then added to the bromide solution via syringe, and the resultant mixture was heated at 80° C., and stirred overnight. The reaction mixture was filtered through celite, concentrated, and was chromatographed through silica gel (12 g, 0-20% EtOAc in hexanes) to provide the desired product. LC/MS-m/z+472.2 (M+H)+

Step 3—Synthesis of compound ue: The boronate ester from step 2 (0.0440 g, 0.0000933 mol) Tetrakis(triphenylphosphine)palladium(0) (0.0288 g, 0.0000249 mol) Sodium carbonate (0.0125 g, 0.000118 mol) and Potassium acetate (0.0199 g, 0.000203 mol) were combined, and the resultant solution was nitrogen purged three times. To the reaction mixture was added 4-(7-benzyl-2-chloro-5,6,7,8-tetrahydropyrido[3,4-d]pyrimidin-4-yl)morpholine (0.0275 g, 0.0000797 mol) in dry Acetonitrile (0.370 mL, 0.00708 mol) followed by deoxygenated Water (0.210 mL, 0.0116 mol) and the resulting solution was microwaved on 300 watts, 150° C. for 15 minutes on the Biotage microwave. The reaction solution was diluted with $H_2O$, extracted three times with 10% MeOH in dichloromethane, dried over Magnesium sulfate, filtered, concentrated, and chromatographed through silica gel (4 g, 0-10% MeOH in dichloromethane). The sample was slurried in DMF, filtered, concentrated, and purified by HPLC. $^1$H NMR (500 MHz, DMSO) δ 9.23 (s, 1H), 8.70 (d, J=1.8, 1H), 8.57 (dd, J=8.9, 1.9, 1H), 7.95 (s, 1H), 7.45 (d, J=8.8, 1H), 7.42-7.35 (m, 3H), 7.30 (t, J=7.2, 1H), 6.94 (s, 2H), 3.77-3.65 (m, 6H), 3.59-3.51 (m, 5H), 2.89 (s, 1H), 2.73 (s, 2H), 2.68 (d, J=4.9, 2H). LC/MS-m/z+454.2 (M+H)+

Example 392

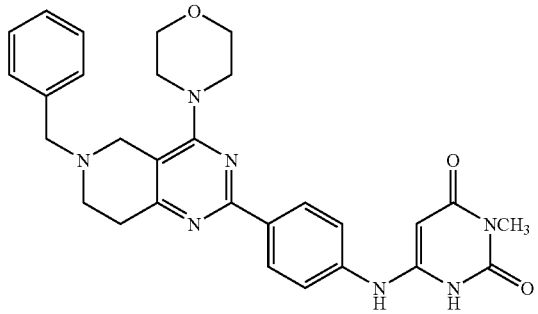

(uf)

Synthesis of 6-(4-(6-benzyl-4-morpholino-5,6,7,8-tetrahydropyrido[4,3-d]pyrimidin-2-yl)phenylamino)-3-methylpyrimidine-2,4(1H,3H)-dione (uf): 4-(6-Benzyl-4-morpholino-5,6,7,8-tetrahydropyrido[4,3-d]pyrimidin-2-yl) aniline (0.0379 g, 0.0000944 mol) Palladium(II) acetate (0.0038 g, 0.000017 mol) Cesium Carbonate (0.0697 g, 0.000214 mol) 4,5-bis(diphenylphosphino)-9,9-dimethylxanthene (0.0208 g, 0.0000359 mol), and 6-chloro-3-methylpyrimidine-2,4(1H,3H)-dione (0.0239 g, 0.000149 mol) were combined, and the reaction mixture was nitrogen purged three times, followed by the addition of dry 1,4-Dioxane (0.700 mL, 0.00897 mol). The reaction solution was microwaved on 300 watts, 160° C. for 40 minutes on a CEM microwave. The reaction mixture was concentrated, chromatographed through silica gel (0-10% MeOH in dichloromethane), and purified by HPLC. ¹H NMR (500 MHz, DMSO) δ 8.83 (s, 1H), 8.30 (d, J=8.6, 2H), 8.23 (s, 1H), 7.35 (d, J=4.4, 4H), 7.29 (dd, J=8.6, 4.5, 3H), 6.49 (s, 1H), 5.02 (s, 1H), 3.67 (dd, J=11.3, 7.1, 6H), 3.44 (s, 2H), 3.40-3.36 (m, 4H), 3.08 (s, 3H), 2.86 (d, J=5.7, 2H), 2.78 (t, J=5.8, 2H). LC/MS-m/z+526.3 (M+H)+.

Example 393

1,3,2-dioxaborolan-2-yl)-1H-benzo[d]imidazol-2(3H)-one (0.270 g, 0.00104 mol), Tetrakis(triphenylphosphine)palladium(0) (0.0716 g, 0.0000620 mol) Sodium carbonate (0.140 g, 0.00132 mol) and Potassium acetate (0.155 g, 0.00158 mol) were combined, and the reaction mixture was nitrogen purged three times, followed by the addition of tert-butyl 2-chloro-4-morpholino-5,6-dihydropyrido[3,4-d]pyrimidine-7(8H)-carboxylate (0.300 g, 0.000845 mol) in dry Acetonitrile (6.50 mL, 0.124 mol) and deoxygenated Water (3.60 mL, 0.200 mol). The reaction was microwaved on 300 watts, 120° C. for 15 minutes on the Biotage microwave then heated at 90° C. in an oil bath and stirred overnight. The reaction solution was diluted with H₂O and dichloromethane during with a solid formed. The sample was filtered through a Buchner funnel and the aqueous layer was extracted three times with dichloromethane. The solid was combined with the organic extracts, dried over Magnesium sulfate, filtered, concentrated and chromatographed through silica gel (40 g, 0-10% MeOH in dichloromethane). The resultant material was used in the next step without further purification. LC/MS-m/z+453.3 (M+H)+.

Step 2—Synthesis of 5-(4-morpholino-5,6,7,8-tetrahydropyrido[3,4-d]pyrimidin-2-yl)-1H-benzo[d]imidazol-2(3H)-one: Tert-butyl 4-morpholino-2-(2-oxo-2,3-dihydro-1H-benzo[d]imidazol-5-yl)-5,6-dihydropyrido[3,4-d]pyrimidine-7(8H)-carboxylate (0.382 g, 0.000844 mol) and 4.0 M of Hydrogen chloride in 1,4-Dioxane (6.50 mL) were combined and shaken for 2 hours. The reaction mixture was diluted with sat NaHCO₃ and 10% MeOH in dichloromethane and the aqueous layer was extracted 6 times with 10% MeOH in dichloromethane, dried over Magnesium sulfate, filtered, concentrated. The resulting material was used in the next step without further purification.

Step 3—Synthesis of compound ug: 5-(4-morpholino-5,6,7,8-tetrahydropyrido[3,4-d]pyrimidin-2-yl)-1H-benzo[d]imidazol-2(3H)-one (0.297 g, 0.843 mmol), 2-Chloropyrimidine (0.145 g, 1.27 mmol), N,N-Dimethylformamide (10.0 mL, 129 mmol) and N,N-Diisopropylethylamine (0.588 mL, 3.38 mmol) were combined. The reaction solution was microwaved on 300 watts, 120° C. for 30 minutes on a CEM microwave. The reaction solution was filtered and washed with dichloromethane. LC/MS-m/z+431.2 (M+H)+

Example 394

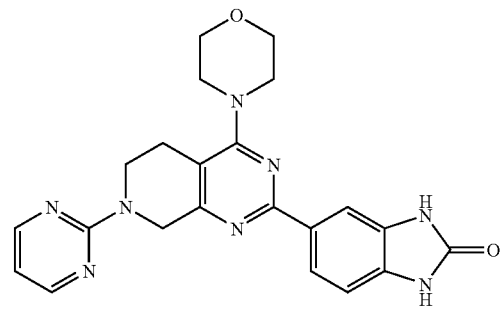

(ug)

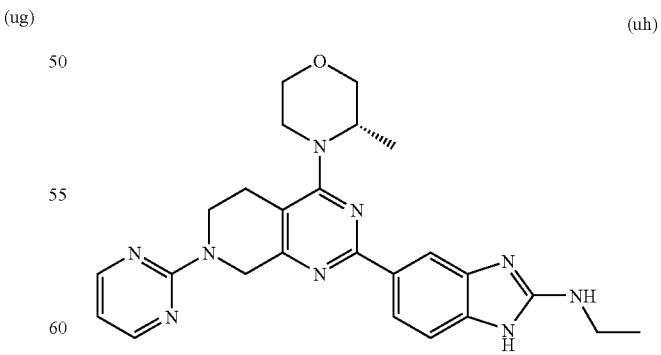

(uh)

Synthesis of 5-(4-morpholino-7-(pyrimidin-2-yl)-5,6,7,8-tetrahydropyrido[3,4-d]pyrimidin-2-yl)-1H-benzo[d]imidazol-2(3H)-one (ug)

Step 1—Synthesis of Tert-butyl 4-morpholino-2-(2-oxo-2,3-dihydro-1H-benzo[d]imidazol-5-yl)-5,6-dihydropyrido[3,4-d]pyrimidine-7(8H)-carboxylate: 5-(4,4,5,5-tetramethyl- Synthesis of N-ethyl-5-(4-morpholino-7-(pyrimidin-2-yl)-5,6,7,8-tetrahydropyrido[3,4-d]pyrimidin-2-yl)-1H-benzo[d]imidazol-2-amine (uh)

Step 1—Synthesis of 4-(2-(2-chloro-1H-benzo[d]imidazol-5-yl)-7-(pyrimidin-2-yl)-5,6,7,8-tetrahydropyrido[3,4- d]pyrimidin-4-yl)morpholine: 5-(4-morpholino-7-(pyrimidin-2-yl)-5,6,7,8-tetrahydropyrido[3,4-d]pyrimidin-2-yl)-1H-benzo[d]imidazol-2(3H)-one (0.225 g, 0.000523 mol) and Phosphoryl chloride (2.30 mL, 0.0247 mol) were combined, heated at 106° C. overnight. The reaction solution was cooled to room temperature, concentrated, added ice, added 5M NaOH until pH13, extracted three times with 10% MeOH in dichloromethane, dried over Magnesium sulfate, filtered, concentrated, and chromatographed through silica gel (4 g, 0-10% MeOH in dichloromethane). LC/MS-m/z+449.2 (M+H)+

Step 2—Synthesis of compound uh: 4-(2-(2-chloro-1H-benzo[d]imidazol-5-yl)-7-(pyrimidin-2-yl)-5,6,7,8-tetrahydropyrido[3,4-d]pyrimidin-4-yl)morpholine (0.054 g, 0.00012 mol) and Ethylamine Hydrochloride (0.4678 g, 0.005737 mol) were combined then added Ethanol (0.320 mL, 0.00548 mol) followed by N,N-Diisopropylethylamine (2.40 mL, 0.0138 mol). The reaction mixture was heated at 160° C. and stirred overnight. The reaction mixture was concentrated, chromatographed through silica gel (4 g, 0-10% MeOH in dichloromethane) and purified by HPLC. $^1$H NMR (400 MHz, DMSO) δ 8.44 (d, J=4.7, 2H), 8.34 (s, 1H), 8.14 (d, J=1.3, 1H), 8.04-7.97 (m, 1H), 7.15 (d, J=8.3, 1H), 6.80 (s, 1H), 6.69 (t, J=4.7, 1H), 4.82 (s, 2H), 3.99 (t, J=5.2, 2H), 3.80-3.72 (m, 4H), 3.48 (d, J=4.4, 4H), 3.38-3.27 (m, 2H), 2.76 (d, J=5.0, 2H), 1.19 (t, J=7.1, 3H). LC/MS-m/z+458.3 (M+H)+

Example 395

(ui)

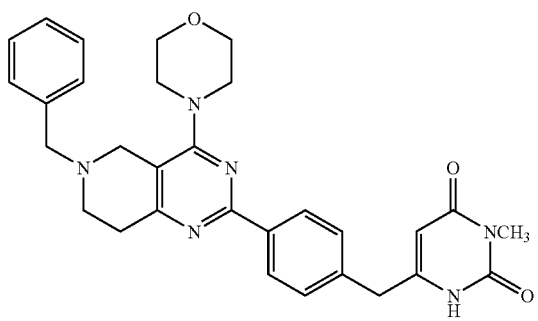

Synthesis of 6-(4-(6-benzyl-4-morpholino-5,6,7,8-tetrahydropyrido[4,3-d]pyrimidin-2-yl)phenylamino)-3-methylpyrimidine-2,4(1H,3H)-dione (ui): 4-(7-Benzyl-4-morpholino-5,6,7,8-tetrahydropyrido[3,4-d]pyrimidin-2-yl) aniline (0.0500 g, 0.000124 mol) Palladium(II) acetate (0.0043 g, 0.000019 mol) Cesium Carbonate (0.0921 g, 0.000283 mol) 4,5-bis(diphenylphosphino)-9,9-dimethylxanthene (0.0255 g, 0.0000441 mol) and 6-chloro-3-methylpyrimidine-2,4(1H,3H)-dione (0.0321 g, 0.000200 mol) were combined, nitrogen purged three times, added dry 1,4-Dioxane (0.88 mL, 0.011 mol) The reaction was microwaved on 300 watts, 120° C. for 160 minutes on a CEM microwave. The reaction mixture was purified by HPLC. $^1$H NMR (400 MHz, DMSO) δ 10.36 (s, 1H), 8.53 (s, 1H), 8.27 (d, J=8.7, 2H), 7.42-7.34 (m, 4H), 7.28 (dd, J=15.1, 7.8, 3H), 5.01 (s, 1H), 3.72 (dd, J=9.7, 5.0, 6H), 3.55 (s, 2H), 3.50 (d, J=4.4, 4H), 3.08 (s, 3H), 2.68 (dd, J=18.0, 4.8, 4H). LC/MS-m/z+ 528.3 (M+H)+

Example 396

(uj)

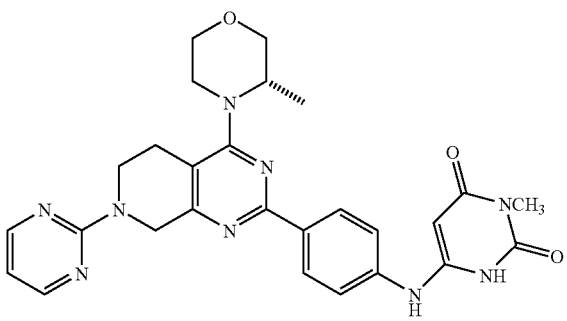

Synthesis of (S)-3-methyl-6-(4-(4-(3-methylmorpholino)-7-(pyrimidin-2-yl)-5,6,7,8-tetrahydropyrido[3,4-d]pyrimidin-2-yl)phenylamino)pyrimidine-2,4(1H,3H)-dione (uj): Compound uj was prepared following a similar procedure as described in Example 387. $^1$H NMR (400 MHz, DMSO) δ 10.85 (s, 1H), 8.71 (s, 1H), 8.44 (d, J=4.7, 2H), 8.32 (d, J=8.7, 2H), 7.31 (d, J=8.7, 2H), 6.69 (t, J=4.7, 1H), 5.04 (s, 1H), 4.91 (d, J=18.7, 1H), 4.76 (d, J=18.8, 1H), 4.21-4.06 (m, 2H), 3.93-3.79 (m, 2H), 3.76-3.55 (m, 4H), 3.49-3.37 (m, 1H), 3.09 (s, 3H), 2.76 (s, 2H), 1.26 (d, J=6.6, 3H). LC/MS-m/z+ 526.3 (M+H)+

Example 397

(uk)

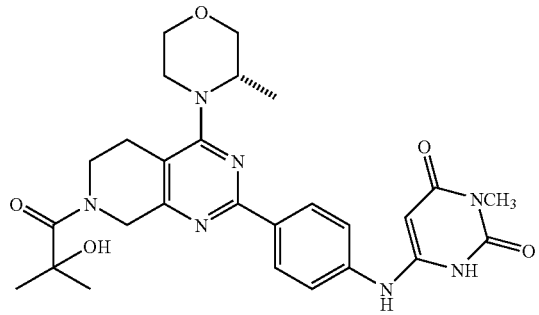

2-Hydroxyisobutyric acid (0.0112 g, 0.000108 mol) (S)-3-methyl-6-(4-(4-(3-methylmorpholino)-5,6,7,8-tetrahydropyrido[3,4-d]pyrimidin-2-yl)phenylamino)pyrimidine-2,4 (1H,3H)-dione (0.0325 g, 0.0000723 mol) 1-Hydroxybenzotriazole (0.0155 g, 0.000115 mol) and N,N-Dimethylformamide (2.00 mL, 0.0258 mol) were combined, stirred for 15 minutes, added N-(3-Dimethylaminopropyl)-N'-ethylcarbodiimide hydrochloride (0.0210 g, 0.000110 mol) followed by N,N-Diisopropylethylamine (0.0314 mL, 0.000180 mol) and stirred overnight. The reaction mixture was concentrated, chromatographed through silica gel (4 g, 0-10% MeOH in dichloromethane), and purified by HPLC. $^1$H NMR (400 MHz, DMSO) δ 8.85 (s, 1H), 8.29 (d, J=8.7, 2H), 7.33 (d, J=8.7, 2H), 5.53 (s, 1H), 5.00 (s, 1H), 4.64 (s, 1H), 4.14 (d, J=6.6, 1H), 3.89 (d, J=11.5, 1H), 3.65 (dt, J=25.6, 12.2, 4H), 3.43 (t, J=12.0, 1H), 3.08 (s, 3H), 2.69 (d, J=13.4, 2H), 1.37 (s, 6H), 1.27 (d, J=6.6, 3H). LC/MS-m/z+536.3 (M+H)+

Example 398

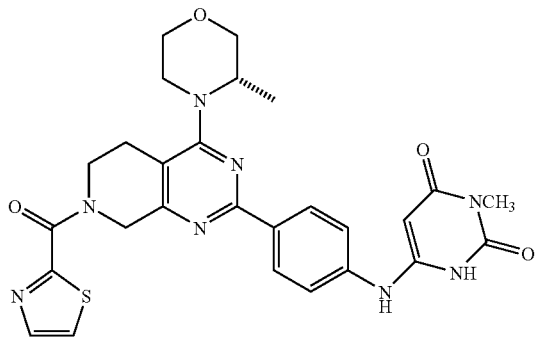

(ul)

Synthesis of (S)-3-methyl-6-(4-(4-(3-methylmorpholino)-7-(thiazole-2-carbonyl)-5,6,7,8-tetrahydropyrido[3,4-d]pyrimidin-2-yl)phenylamino)pyrimidine-2,4(1H,3H)-dione (ul): (S)-3-methyl-6-(4-(4-(3-methylmorpholino)-5,6,7,8-tetrahydropyrido[3,4-d]pyrimidin-2-yl)phenylamino)pyrimidine-2,4(1H,3H)-dione (0.0325 g, 0.0000723 mol) in dry N,N-Dimethylformamide (2.00 mL, 0.0258 mol) was added dry Pyridine (0.030 mL, 0.00037 mol) followed by 1,3-thiazole-2-carbonyl chloride (0.0300 g, 0.000203 mol). The reaction mixture was stirred overnight. The reaction mixture was concentrated, chromatographed through silica gel (4 g, 0-10% MeOH in dichloromethane), and then purifed by HPLC. $^1$H NMR (400 MHz, DMSO) δ 10.74 (s, 1H), 8.69 (s, 1H), 8.32 (t, J=7.8, 2H), 8.13-8.04 (m, 2H), 7.31 (dd, J=8.3, 4.7, 2H), 5.50 (dd, J=75.0, 18.3, 1H), 5.04 (d, J=2.8, 1H), 4.79 (dd, J=47.1, 18.7, 1H), 4.67-4.28 (m, 1H), 4.17 (d, J=6.1, 1H), 4.05-3.73 (m, 2H), 3.73-3.55 (m, 4H), 3.45 (dd, J=17.5, 7.1, 1H), 3.09 (s, 3H), 2.82 (d, J=22.7, 2H), 1.28 (d, J=6.7, 3H). LC/MS-m/z+561.2 (M+H)+

Example 399

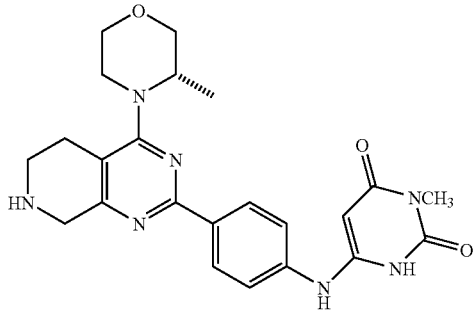

(um)

Synthesis of (S)-3-methyl-6-(4-(4-(3-methylmorpholino)-5,6,7,8-tetrahydropyrido[3,4-d]pyrimidin-2-yl)phenylamino)pyrimidine-2,4(1H,3H)-dione (um)

Step 1—Synthesis of (S)-Tert-butyl 2-(4-(1-methyl-2,6-dioxo-1,2,3,6-tetrahydropyrimidin-4-ylamino)phenyl)-4-(3-methylmorpholino)-5,6-dihydropyrido[3,4-d]pyrimidine-7(8H)-carboxylate: (S)-tert-butyl 2-(4-aminophenyl)-4-(3-methylmorpholino)-5,6-dihydropyrido[3,4-d]pyrimidine-7(8H)-carboxylate (0.231 g, 0.000543 mol), Palladium(II) acetate (0.0242 g, 0.000108 mol) Cesium Carbonate (0.366 g, 0.00112 mol) 4,5-bis(diphenylphosphino)-9,9-dimethylxanthene (0.1208 g, 0.0002088 mol) and 6-chloro-3-methylpyrimidine-2,4(1H,3H)-dione (0.0922 g, 0.000574 mol) were combined, nitrogen purged three times, and then dry 1,4-Dioxane (3.80 mL, 0.0487 mol) was added. The reaction was microwaved on 200 watts, 100° C. for 30 minutes on a CEM microwave. The reaction mixture was concentrated and chromatographed through silica gel (40 g, 0-5% MeOH in dichloromethane). $^1$H NMR (400 MHz, DMSO) δ 8.64 (s, 1H), 8.30 (d, J=8.7, 2H), 7.30 (d, J=8.7, 2H), 5.03 (s, 1H), 4.47 (q, J=18.4, 2H), 4.14 (d, J=6.8, 1H), 3.87 (d, J=11.7, 1H), 3.72-3.56 (m, 5H), 3.50-3.37 (m, 2H), 3.09 (s, 3H), 2.67 (d, J=1.8, 2H), 1.46 (s, 9H), 1.28 (t, J=8.5, 3H). LC/MS-m/z+550.3 (M+H)+

Step 2—Synthesis of compound um: (S)-Tert-butyl 2-(4-(1-methyl-2,6-dioxo-1,2,3,6-tetrahydropyrimidin-4-ylamino)phenyl)-4-(3-methylmorpholino)-5,6-dihydropyrido[3,4-d]pyrimidine-7(8H)-carboxylate (0.196 g, 0.000357 mol) and 4.0 M of Hydrogen chloride in 1,4-Dioxane (5.00 mL) were mixed and stirred for 2 hours. The mixture was concentrated, diluted with sat NaHCO$_3$ and extracted three times with 10% MeOH in dichloromethane. The aqueous layer was lyophilized, slurried in MeOH, vacuum filtered, and purified by HPLC. $^1$H NMR (400 MHz, DMSO) δ 8.95 (s, 1H), 8.28 (d, J=8.7, 2H), 8.23 (s, 1H), 7.28 (d, J=8.7, 2H), 6.52 (s, 1H), 5.02 (s, 1H), 4.11 (d, J=6.4, 1H), 3.88 (d, J=11.1, 3H), 3.71 (dd, J=11.3, 2.8, 1H), 3.65-3.56 (m, 3H), 3.08 (s, 3H), 2.99-2.92 (m, 1H), 2.87-2.80 (m, 1H), 2.58 (s, 2H), 1.24 (d, J=6.6, 3H). LC/MS-m/z+450.2 (M+H)+

Example 400

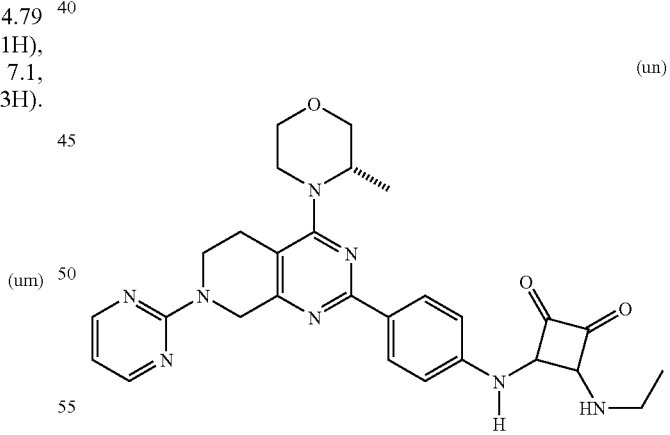

(un)

Synthesis of 3-(ethylamino)-4-(4-(4-((S)-3-methylmorpholino)-7-(pyrimidin-2-yl)-5,6,7,8-tetrahydropyrido[3,4-d]pyrimidin-2-yl)phenylamino)cyclobutane-1,2-dione (un)

Step 1—Synthesis of (S)-3-ethoxy-4-(4-(4-(3-methylmorpholino)-7-(pyrimidin-2-yl)-5,6,7,8-tetrahydropyrido[3,4-d]pyrimidin-2-yl)phenylamino)cyclobut-3-ene-1,2-dione: (S)-4-(4-(3-methylmorpholino)-7-(pyrimidin-2-yl)-5,6,7,8-tetrahydropyrido[3,4-d]pyrimidin-2-yl)aniline (0.0660 g, 0.000164 mol) was suspended in Ethanol (5.00 mL, 0.0856 mol) then added 3,4-Diethoxy-3-cyclobutene-1,2-dione (0.0242 mL, 0.000164 mol) and stirred overnight. Added 3,4-Diethoxy-3-cyclobutene-1,2-dione (0.0242 mL, 0.000164 mol) and Triethylamine (0.0456 mL, 0.000327 mol) and stirred overnight. The reaction mixture was concentrated and chromatographed through silica gel (12 g, 0-5% MeOH in dichloromethane). The reaction mixture was again suspended in Ethanol (5.00 mL, 0.0856 mol) then added 3,4-Diethoxy-3-cyclobutene-1,2-dione (0.0121 mL, 0.0000818 mol) and Triethylamine (0.0228 mL, 0.000164 mol). The reaction mixture was stirred for 3 hours then concentrated and chromatographed through silica gel (12 g, 0-5% MeOH in dichloromethane). The resulting material was used in the next step without further purification. $^1$H NMR (400 MHz, CDCl$_3$) δ 8.43 (d, J=8.7, 2H), 8.37 (t, J=4.8, 2H), 8.00 (d, J=23.9, 1H), 7.40 (d, J=8.5, 2H), 6.55 (dd, J=9.1, 4.3, 1H), 5.09 (dd, J=18.8, 6.9, 1H), 4.99-4.74 (m, 3H), 4.27 (dt, J=12.9, 4.9, 1H), 4.11-4.03 (m, 1H), 3.96 (d, J=11.2, 1H), 3.88-3.80 (m, 2H), 3.75 (td, J=11.0, 2.9, 1H), 3.69 (dd, J=11.3, 1.8, 1H), 3.62 (d, J=13.8, 1H), 3.54 (ddd, J=13.7, 10.7, 3.2, 1H), 2.83-2.65 (m, 2H), 1.55 (t, J=7.1, 3H), 1.34 (t, J=5.2, 3H). LC/MS-m/z+528.3 (M+H)+

Step 2—Synthesis of compound un: (S)-3-ethoxy-4-(4-(4-(3-methylmorpholino)-7-(pyrimidin-2-yl)-5,6,7,8-tetrahydropyrido[3,4-d]pyrimidin-2-yl)phenylamino)cyclobut-3-ene-1,2-dione (0.087 g, 0.00016 mol), Ethylamine Hydrochloride (0.0780 g, 0.000956 mol), and Ethanol (8.00 mL, 0.137 mol) were combined then added Triethylamine (0.230 mL, 0.00165 mol) and stirred overnight. The reaction mixture was concentrated, and chromatographed through silica gel (12 g, 0-5% MeOH in dichloromethane). $^1$H NMR (400 MHz, DMSO) δ 9.83 (s, 1H), 8.44 (d, J=4.7, 2H), 8.31 (d, J=8.7, 2H), 7.72 (s, 1H), 7.53 (d, J=8.5, 2H), 6.69 (t, J=4.7, 1H), 4.90 (d, J=18.7, 1H), 4.75 (d, J=18.6, 1H), 4.14 (t, J=9.3, 2H), 3.85 (dd, J=20.6, 7.2, 2H), 3.74-3.55 (m, 6H), 3.44 (t, J=11.9, 1H), 2.75 (s, 2H), 1.31-1.15 (m, 6H). LC/MS-m/z+ 527.3 (M+H)+.

Example 401

Synthesis of (S)-1-(2-cyanoethyl)-3-(4-(4-(3-methylmorpholino)-7-(pyrimidin-2-yl)-5,6,7,8-tetrahydropyrido[3,4-d]pyrimidin-2-yl)phenyl)urea (uo): (S)-4-(4-(3-methylmorpholino)-7-(pyrimidin-2-yl)-5,6,7,8-tetrahydropyrido[3,4-d]pyrimidin-2-yl)aniline (0.0501 g, 0.000124 mol) in dry 1,4-Dioxane (2.00 mL, 0.0256 mol) was added Triethylamine (0.0190 mL, 0.000136 mol) followed by 20% Phosgene in toluene (1:4, Phosgene:Toluene, 0.080 mL). The reaction mixture was heated at 50° C. for 1 hour. The reaction mixture was cooled to room temperature and then added β-Cyanoethylamine (0.0546 mL, 0.000744 mol). The reaction mixture was stirred for 3 days. The reaction mixture was concentrated and purified by HPLC. $^1$H NMR (400 MHz, DMSO) δ 8.98 (s, 1H), 8.44 (d, J=4.7, 2H), 8.22 (d, J=8.8, 2H), 7.52 (d, J=8.8, 2H), 6.69 (t, J=4.7, 1H), 6.62 (t, J=5.9, 1H), 4.90 (d, J=18.6, 1H), 4.73 (d, J=18.7, 1H), 4.19-4.06 (m, 2H), 3.92-3.77 (m, 2H), 3.73-3.67 (m, 1H), 3.60 (t, J=9.1, 3H), 3.43 (d, J=11.6, 1H), 3.36 (m, 2H), 2.80-2.63 (m, 4H), 1.25 (d, J=6.6, 3H). LC/MS-m/z+500.2 (M+H)+.

Example 402

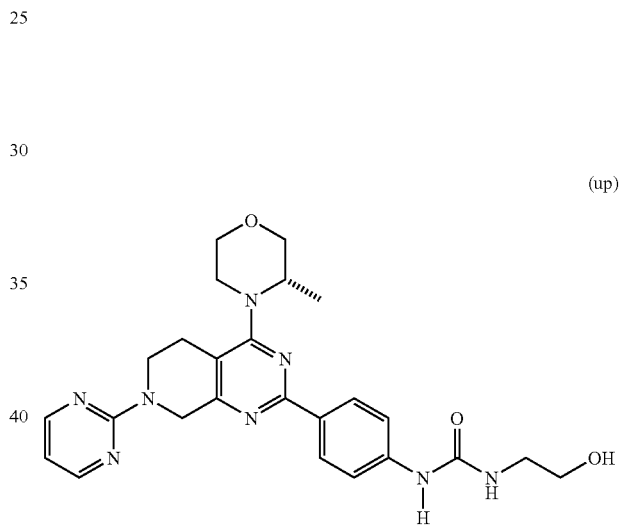

(up)

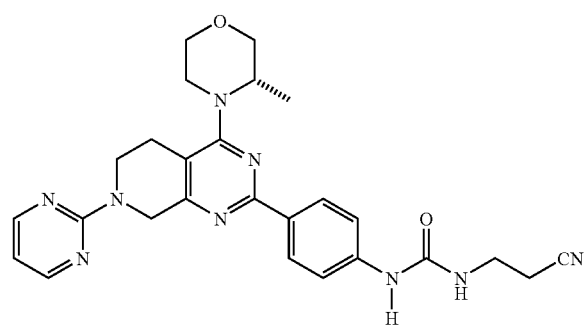

(uo)

Synthesis of (S)-1-(2-hydroxyethyl)-3-(4-(4-(3-methylmorpholino)-7-(pyrimidin-2-yl)-5,6,7,8-tetrahydropyrido[3,4-d]pyrimidin-2-yl)phenyl)urea (up): (S)-4-(4-(3-methylmorpholino)-7-(pyrimidin-2-yl)-5,6,7,8-tetrahydropyrido[3,4-d]pyrimidin-2-yl)aniline (0.0501 g, 0.000124 mol) in dry 1,4-Dioxane (2.00 mL, 0.0256 mol) was added Triethylamine (0.0190 mL, 0.000136 mol) followed by 20% Phosgene in toluene (1:4, Phosgene:Toluene, 0.080 mL). The reaction mixture was heated at 50° C. for 1 hour. The reaction mixture was cooled to room temperature and then added Ethanolamine (0.0450 mL, 0.000745 mol). The reaction mixture was stirred for 3 days. The reaction mixture was concentrated and purified by HPLC. $^1$H NMR (400 MHz, DMSO) δ 8.80 (s, 1H), 8.44 (d, J=4.7, 2H), 8.21 (d, J=8.7, 2H), 7.48 (d, J=8.8, 2H), 6.69 (t, J=4.7, 1H), 6.27 (t, J=5.5, 1H), 4.89 (d, J=18.6, 1H), 4.74 (dd, J=14.1, 8.8, 2H), 4.21-4.06 (m, 2H), 3.93-3.76 (m, 2H), 3.70 (dd, J=11.3, 2.4, 1H), 3.60 (t, J=9.1, 3H), 3.50-3.37 (m, 3H), 3.17 (q, J=5.6, 2H), 2.74 (s, 2H), 1.25 (d, J=6.6, 3H). LC/MS-m/z+491.2 (M+H)+

Example 403

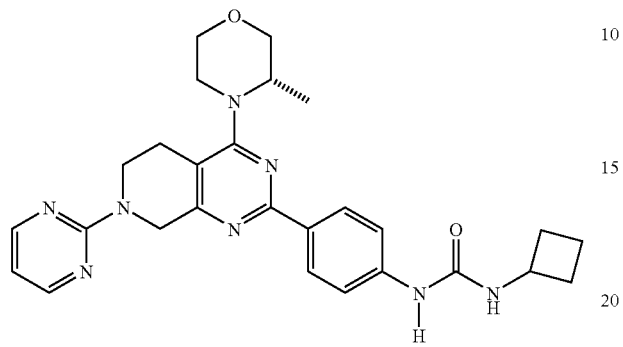

(uq)

Synthesis of (S)-1-cyclobutyl-3-(4-(4-(3-methylmorpholino)-7-(pyrimidin-2-yl)-5,6,7,8-tetrahydropyrido[3,4-d]pyrimidin-2-yl)phenyl)urea (uq): (S)-4-(4-(3-methylmorpholino)-7-(pyrimidin-2-yl)-5,6,7,8-tetrahydropyrido[3,4-d]pyrimidin-2-yl)aniline (0.0501 g, 0.000124 mol) in dry 1,4-Dioxane (2.00 mL, 0.0256 mol) was added Triethylamine (0.0190 mL, 0.000136 mol) followed by 20% Phosgene in toluene (1:4, Phosgene:Toluene, 0.080 mL). The reaction mixture was heated at 50° C. for 1 hour. The reaction mixture was cooled to room temperature and then added aminocyclobutane (0.0638 mL, 0.000745 mol). The reaction mixture was stirred for 3 days. The reaction mixture was concentrated and purified by HPLC. $^1$H NMR (400 MHz, DMSO) δ 8.59 (s, 1H), 8.43 (d, J=4.7, 2H), 8.20 (d, J=8.8, 2H), 7.48 (d, J=8.8, 2H), 6.69 (t, J=4.7, 1H), 6.51 (d, J=8.1, 1H), 4.89 (d, J=18.7, 1H), 4.72 (d, J=18.7, 1H), 4.21-4.03 (m, 3H), 3.91-3.78 (m, 2H), 3.70 (dd, J=11.2, 2.7, 1H), 3.60 (t, J=9.2, 3H), 3.41 (t, J=12.7, 1H), 2.74 (s, 2H), 2.20 (dt, J=14.3, 5.1, 2H), 1.92-1.77 (m, 2H), 1.60 (ddd, J=21.1, 13.6, 8.3, 2H), 1.25 (d, J=6.6, 3H). LC/MS-m/z+501.3 (M+H)+

Example 404

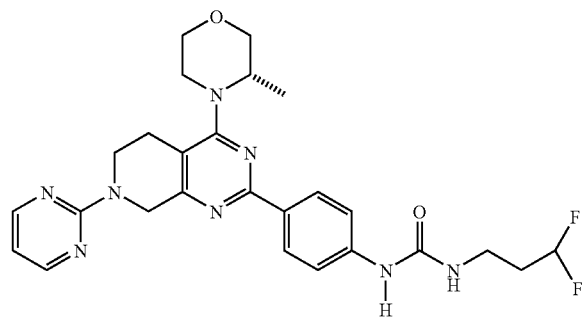

(ur)

Synthesis of (S)-1-(2,2-difluoroethyl)-3-(4-(4-(3-methylmorpholino)-7-(pyrimidin-2-yl)-5,6,7,8-tetrahydropyrido[3,4-d]pyrimidin-2-yl)phenyl)urea (ur): (S)-4-(4-(3-methylmorpholino)-7-(pyrimidin-2-yl)-5,6,7,8-tetrahydropyrido[3,4-d]pyrimidin-2-yl)aniline (0.0501 g, 0.000124 mol) in dry 1,4-Dioxane (2.00 mL, 0.0256 mol) was added Triethylamine (0.0190 mL, 0.000136 mol) followed by 20% Phosgene in toluene (1:4, Phosgene:Toluene, 0.080 mL). The reaction mixture was heated at 50° C. for 1 hour. The reaction mixture was cooled to room temperature and then added 2,2-difluoroethylamine (0.0604 mL, 0.000876 mol). The reaction mixture was stirred for 3 days. The reaction mixture was concentrated and purified by HPLC. $^1$H NMR (400 MHz, DMSO) δ 8.94 (s, 1H), 8.44 (d, J=4.7, 2H), 8.23 (d, J=8.8, 2H), 7.51 (d, J=8.8, 2H), 6.69 (t, J=4.7, 1H), 6.57 (t, J=6.0, 1H), 6.07 (tt, J=56.1, 3.8, 1H), 4.90 (d, J=18.7, 1H), 4.73 (d, J=18.7, 1H), 4.18-4.04 (m, 3H), 3.91-3.78 (m, 2H), 3.70 (dd, J=11.3, 2.5, 1H), 3.65-3.48 (m, 5H), 3.41 (dd, J=17.7, 8.1, 1H), 3.17 (d, J=3.4, 2H), 2.74 (s, 2H), 1.25 (d, J=6.6, 3H). LC/MS-m/z+511.2 (M+H)+

Example 405

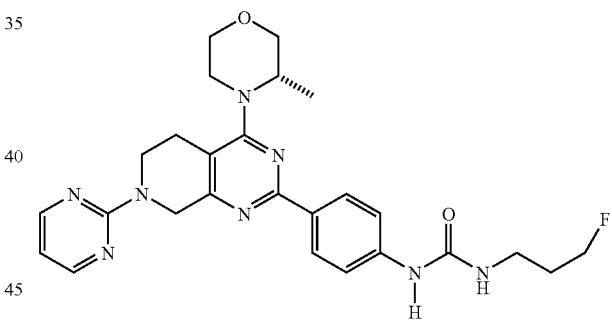

(us)

Synthesis of (S)-1-(2-fluoroethyl)-3-(4-(4-(3-methylmorpholino)-7-(pyrimidin-2-yl)-5,6,7,8-tetrahydropyrido[3,4-d]pyrimidin-2-yl)phenyl)urea (us): (S)-4-(4-(3-methylmorpholino)-7-(pyrimidin-2-yl)-5,6,7,8-tetrahydropyrido[3,4-d]pyrimidin-2-yl)aniline (0.0501 g, 0.000124 mol) in dry 1,4-Dioxane (2.00 mL, 0.0256 mol) was added Triethylamine (0.0190 mL, 0.000136 mol) followed by 20% Phosgene in toluene (1:4, Phosgene:Toluene, 0.080 mL). The reaction mixture was heated at 50° C. for 1 hour. The reaction mixture was cooled to room temperature and then added 2-fluoroethanamine (0.0534 g, 0.000762 mol) followed by Triethylamine (0.1140 mL, 0.0008179 mol). The reaction mixture was stirred for 3 days. The reaction mixture was concentrated and purified by HPLC. LC/MS-m/z+493.2 (M+H)+

Example 406

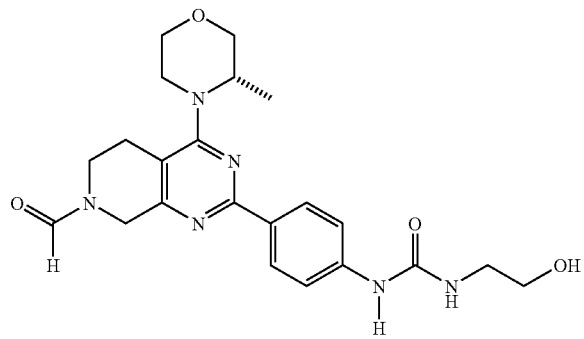

Synthesis of (S)-1-(4-(7-formyl-4-(3-methylmorpholino)-5,6,7,8-tetrahydropyrido[3,4-d]pyrimidin-2-yl)phenyl)-3-(2-hydroxyethyl)urea (ut): (S)-2-(4-aminophenyl)-4-(3-methylmorpholino)-5,6-dihydropyrido[3,4-d]pyrimidine-7(8H)-carbaldehyde (0.100 g, 0.000283 mol) in dry 1,4-Dioxane (2.00 mL, 0.0256 mol) was added Triethylamine (0.0434 mL, 0.000311 mol) followed by 20% Phosgene in toluene (1:4, Phosgene:Toluene, 0.170 mL). The reaction mixture was heated at 50° C. for 1 hour. The reaction mixture was cooled to room temperature and then added ethanolamine (0.1020 mL, 0.001690 mol). The reaction mixture was stirred overnight. The reaction mixture was concentrated and purified by HPLC. LC/MS-m/z+441.2 (M+H)+

Example 407

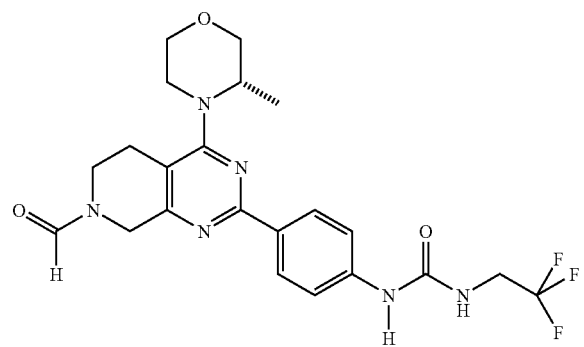

Synthesis of (S)-1-(4-(7-formyl-4-(3-methylmorpholino)-5,6,7,8-tetrahydropyrido[3,4-d]pyrimidin-2-yl)phenyl)-3-(2,2,2-trifluoroethyl)urea (uv)

Step 1—Synthesis of (S)-4-(3-methylmorpholino)-2-(4-nitrophenyl)-5,6-dihydropyrido[3,4-d]pyrimidine-7(8H)-carbaldehyde: (S)-3-methyl-4-(2-(4-nitrophenyl)-5,6,7,8-tetrahydropyrido[3,4-d]pyrimidin-4-yl)morpholine (0.302 g, 0.850 mmol), 2-(1H-benzotriazole-1-yl)-1,1,3,3-tetramethyluronium tetrafluoroborate (0.439 g, 1.37 mmol) and Formic acid (0.0510 mL, 1.35 mmol) were combined then added dry N,N-Dimethylformamide (4.00 mL, 51.6 mmol) followed by N,N-Diisopropylethylamine (0.880 mL, 5.05 mmol). The reaction mixture was heated at 55° C. for 2 hours, concentrated, and chromatographed through silica gel (40 g, 0-5% MeOH in dichloromethane). LC/MS-m/z+384.1 (M+H)+

Step 2—Synthesis of (S)-2-(4-aminophenyl)-4-(3-methylmorpholino)-5,6-dihydropyrido[3,4-d]pyrimidine-7(8H)-carbaldehyde: (S)-4-(3-methylmorpholino)-2-(4-nitrophenyl)-5,6-dihydropyrido[3,4-d]pyrimidine-7(8H)-carbaldehyde (0.313 g, 0.000816 mol) in Tetrahydrofuran (20.0 mL, 0.246 mol) and Methanol (10.0 mL, 0.247 mol) was hydrogenated using the H-Cube and 10% Pd on C at a flow rate of 1mL/min. LC/MS-m/z+354.4 (M+H)+

Step 3—Synthesis of compound uv: (S)-2-(4-aminophenyl)-4-(3-methylmorpholino)-5,6-dihydropyrido[3,4-d]pyrimidine-7(8H)-carbaldehyde (0.100 g, 0.000283 mol) in dry 1,4-Dioxane (2.00 mL, 0.0256 mol) was added Triethylamine (0.0434 mL, 0.000311 mol) followed by 20% Phosgene in toluene (1:4, Phosgene:Toluene, 0.170 mL). The reaction mixture was heated at 50° C. for 1 hour. The reaction mixture was cooled to room temperature and then added 2,2,2-trifluoroethylamine (0.1340 mL, 0.001703 mol). The reaction mixture was stirred overnight. The reaction mixture was concentrated and purified by HPLC. $^1$H NMR (500 MHz, DMSO) δ 9.01 (s, 1H), 8.27-8.17 (m, 3H), 7.52 (d, J=8.8, 2H), 6.81 (d, J=6.5, 1H), 4.66-4.39 (m, 2H), 4.08 (s, 1H), 3.93 (ddd, J=31.8, 19.1, 10.1, 3H), 3.78-3.53 (m, 6H), 3.50-3.40 (m, 2H), 2.73 (s, 1H), 2.64 (s, 1H), 1.25 (t, J=7.4, 3H). LC/MS-m/z+479.2 (M+H)+

Example 408

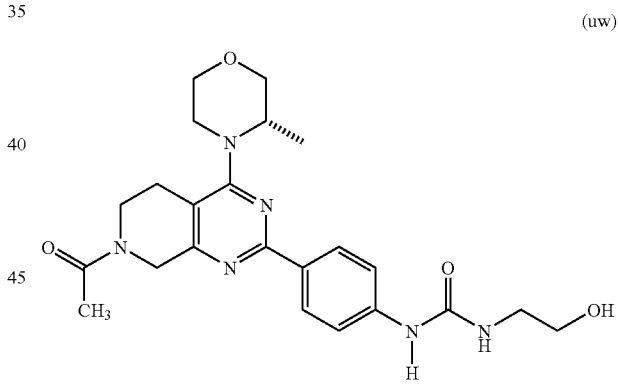

Synthesis of (S)-1-(4-(7-acetyl-4-(3-methylmorpholino)-5,6,7,8-tetrahydropyrido[3,4-d]pyrimidin-2-yl)phenyl)-3-(2-hydroxyethyl)urea (uw): (S)-1-(2-(4-aminophenyl)-4-(3-methylmorpholino)-5,6-dihydropyrido[3,4-d]pyrimidin-7(8H)-yl)ethanone (0.100 g, 0.000272 mol) in dry 1,4-Dioxane (2.00 mL, 0.0256 mol) was added Triethylamine (0.0416 mL, 0.000299 mol) followed by 20% Phosgene in toluene (1:4, Phosgene:Toluene, 0.1580 mL). The reaction mixture was heated at 50° C. for 1 hour. The reaction mixture was cooled to room temperature and then added Ethanolamine (0.0986 mL, 0.00163 mol). The reaction mixture was stirred overnight. The reaction mixture was concentrated and purified by HPLC. $^1$H NMR (500 MHz, DMSO) δ 8.80 (d, J=5.5, 1H), 8.18 (dd, J=8.7, 3.1, 2H), 7.69 (s, 1H), 7.48 (d, J=8.5, 2H), 6.26 (s, 1H), 4.69-4.57 (m, 2H), 4.48 (d, J=18.7, 1H), 4.14 (s, 1H), 3.88 (d, J=9.4, 1H), 3.62 (ddd, J=22.1, 21.5, 8.2, 6H), 3.46 (t, J=5.7, 2H), 3.17 (dd, J=11.1, 5.5, 2H), 2.75 (s, 1H), 2.63 (s, 1H), 2.09 (d, J=27.2, 3H), 1.31-1.21 (m, 3H).

Example 409

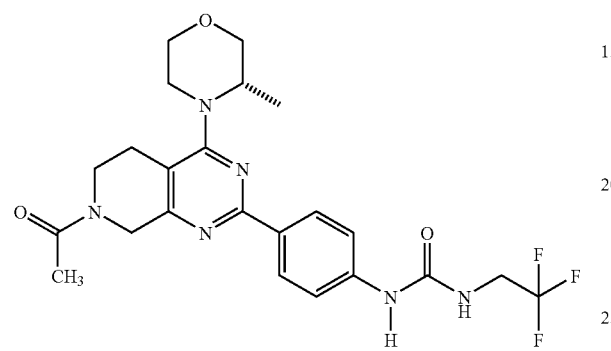

(ux)

Synthesis of (S)-1-(4-(7-acetyl-4-(3-methylmorpholino)-5,6,7,8-tetrahydropyrido[3,4-d]pyrimidin-2-yl)phenyl)-3-(2,2,2-trifluoroethyl)urea (ux)

Step 1—Synthesis of (S)-1-(4-(3-methylmorpholino)-2-(4-nitrophenyl)-5,6-dihydropyrido[3,4-d]pyrimidin-7(8H)-yl)ethanone: (S)-3-methyl-4-(2-(4-nitrophenyl)-5,6,7,8-tetrahydropyrido[3,4-d]pyrimidin-4-yl)morpholine (0.301 g, 0.847 mmol) in dry N,N-Dimethylformamide (4 mL, 50 mmol) was added N,N-Diisopropylethylamine (0.44 mL, 2.5 mmol) followed by Acetyl chloride (0.0900 mL, 1.26 mmol). The reaction mixture was stirred overnight. The reaction mixture was concentrated and was chromatographed through silica gel (40 g, 0-5% MeOH in dichloromethane). $^1$H NMR (400 MHz, CDCl$_3$) δ 8.55 (t, J=8.6, 2H), 8.29 (dd, J=9.0, 2.3, 2H), 4.68 (d, J=8.9, 1H), 4.16-4.02 (m, 1H), 3.97 (dd, J=10.7, 7.5, 2H), 3.86-3.79 (m, 1H), 3.78-3.68 (m, 3H), 3.68-3.50 (m, 3H), 2.74 (dd, J=25.0, 5.1, 2H), 2.23 (s, 3H), 1.40-1.34 (m, 3H). LC/MS-m/z+398.1 (M+H)+

Step 2—Synthesis of (S)-1-(2-(4-aminophenyl)-4-(3-methylmorpholino)-5,6-dihydropyrido[3,4-d]pyrimidin-7(8H)-yl)ethanone: (S)-1-(4-(3-methylmorpholino)-2-(4-nitrophenyl)-5,6-dihydropyrido[3,4-d]pyrimidin-7(8H)-yl)ethanone (0.297 g, 0.000747 mol), Palladium on Carbon 10% (0.1:0.9, Palladium:carbon black, 0.149 g), and Ethanol (10.0 mL, 0.171 mol) were combined under N2 then purged with H$_2$ and stirred for 3 hours then purged with N2, filtered through celite, and concentrated. LC-MS shows incomplete conversion. The reaction mixture was purged with N2, added Palladium on Carbon 10% (0.1:0.9, Palladium:carbon black, 0.147 g) and Ethanol (10.0 mL, 0.171 mol) purged with hydrogen, and stirred overnight under an atmosphere of hydrogen. The reaction mixture was purged with N2, added celite, filtered through celite, filtered through a disc filter, and concentrated. The resulting material was used in the next step without further purification. LC/MS-m/z+368.2 (M+H)+

Step 3—Synthesis of compound ux: (S)-1-(2-(4-aminophenyl)-4-(3-methylmorpholino)-5,6-dihydropyrido[3,4-d]pyrimidin-7(8H)-yl)ethanone (0.100 g, 0.000272 mol) in dry 1,4-Dioxane (2.00 mL, 0.0256 mol) was added Triethylamine (0.0416 mL, 0.000299 mol) followed by 20% Phosgene in toluene (1:4, Phosgene:Toluene, 0.160 mL). The reaction mixture was heated at 50° C. for 1 hour. The reaction mixture was cooled to room temperature and then added 2,2,2-trifluoroethylamine (0.1280 mL, 0.001627 mol). The reaction mixture was stirred overnight. The reaction mixture was concentrated and purified by HPLC. $^1$H NMR (400 MHz, DMSO) δ 9.01 (d, J=5.1, 1H), 8.21 (dd, J=8.8, 2.7, 2H), 7.52 (d, J=8.4, 2H), 6.82 (t, J=6.4, 1H), 4.74-4.43 (m, 2H), 4.16 (s, 1H), 4.00-3.85 (m, 3H), 3.64 (ddd, J=19.4, 16.7, 9.4, 6H), 3.43 (d, J=21.0, 2H), 2.76 (s, 1H), 2.63 (s, 1H), 2.12 (s, 3H), 1.33-1.22 (m, 3H). LC/MS-m/z+493.2 (M+H)+

Example 410

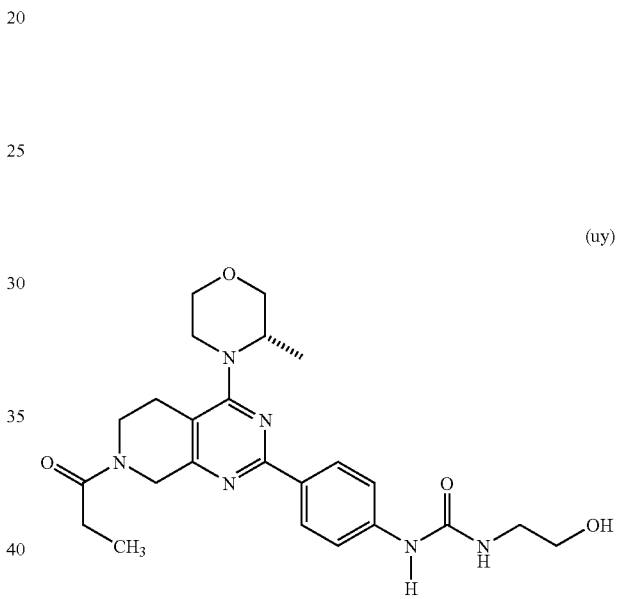

(uy)

Synthesis of (S)-1-(2-hydroxyethyl)-3-(4-(4-(3-methylmorpholino)-7-propionyl-5,6,7,8-tetrahydropyrido[3,4-d]pyrimidin-2-yl)phenyl)urea (uy): (S)-1-(2-(4-aminophenyl)-4-(3-methylmorpholino)-5,6-dihydropyrido[3,4-d]pyrimidin-7(8H)-yl)propan-1-one (0.100 g, 0.000262 mol) in dry 1,4-Dioxane (2.00 mL, 0.0256 mol) was added Triethylamine (0.0402 mL, 0.000288 mol) followed by 20% Phosgene in toluene (1:4, Phosgene:Toluene, 0.150 mL). The reaction mixture was heated at 50° C. for 1 hour. The reaction mixture was cooled to room temperature and then added Ethanolamine (0.0950 mL, 0.00157 mol). The reaction mixture was stirred overnight. The reaction mixture was concentrated and purified by HPLC. $^1$H NMR (500 MHz, DMSO) δ 8.80 (s, 1H), 8.18 (d, J=8.7, 2H), 7.48 (d, J=8.6, 2H), 6.29 (s, 1H), 4.75-4.55 (m, 2H), 4.47 (d, J=18.2, 1H), 4.11 (s, 1H), 3.87 (d, J=12.4, 1H), 3.70 (d, J=11.5, 2H), 3.61 (d, J=11.7, 3H), 3.44 (d, J=16.7, 3H), 3.17 (dd, J=11.3, 5.7, 2H), 2.73 (s, 1H), 2.62 (s, 1H), 2.45 (dd, J=14.7, 7.6, 2H), 1.26 (d, J=6.2, 3H), 1.04 (dd, J=15.4, 7.6, 3H). LC/MS-m/z+469.3 (M+H)+

Example 411

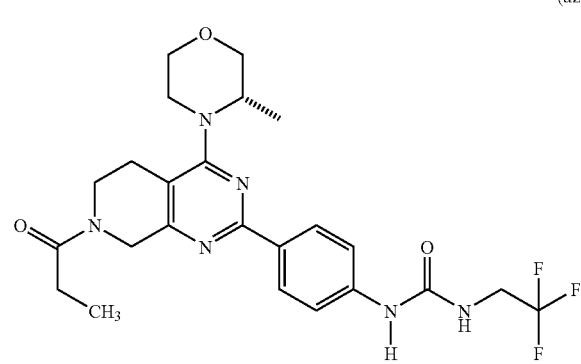

(uz)

Synthesis of (S)-1-(4-(4-(3-methylmorpholino)-7-propionyl-5,6,7,8-tetrahydropyrido[3,4-d]pyrimidin-2-yl)phenyl)-3-(2,2,2-trifluoroethyl)urea (uz): The compound uz was synthesized according to the same route of Example 409. ¹H NMR (500 MHz, DMSO) δ 8.98 (s, 1H), 8.21 (d, J=8.7, 2H), 7.51 (d, J=8.5, 2H), 6.82 (s, 1H), 4.64 (dd, J=18.8, 11.9, 2H), 4.48 (d, J=18.2, 1H), 4.12 (s, 1H), 3.98-3.84 (m, 3H), 3.70 (d, J=10.4, 2H), 3.62 (d, J=11.0, 4H), 3.44 (d, J=14.1, 2H), 2.74 (s, 1H), 2.63 (s, 1H), 2.48-2.42 (m, 2H), 1.26 (d, J=6.5, 3H), 1.04 (dd, J=15.4, 7.6, 3H). LC/MS-m/z+507.3 (M+H)+

Example 412

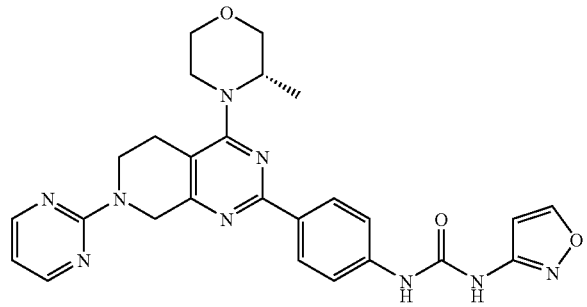

(va)

Synthesis of (S)-1-(isoxazol-3-yl)-3-(4-(4-(3-methylmorpholino)-7-(pyrimidin-2-yl)-5,6,7,8-tetrahydropyrido[3,4-d]pyrimidin-2-yl)phenyl)urea (va): (S)-4-(4-(3-methylmorpholino)-7-(pyrimidin-2-yl)-5,6,7,8-tetrahydropyrido[3,4-d]pyrimidin-2-yl)aniline (0.0795 g, 0.000197 mol) in dry 1,4-Dioxane (1.50 mL, 0.0192 mol) was added Triethylamine (0.0302 mL, 0.000217 mol) followed by 20% Phosgene in toluene (1:4, Phosgene:Toluene, 0.120 mL). The reaction mixture was heated at 50° C. for 1 hour. The reaction mixture was cooled to room temperature and then added 3-aminoisoxazole (0.0874 mL, 0.00118 mol). The reaction mixture was stirred overnight. The reaction mixture was concentrated and purified by HPLC. ¹H NMR (500 MHz, DMSO) δ 9.69 (s, 1H), 9.12 (s, 1H), 8.74 (d, J=1.6, 1H), 8.44 (d, J=4.7, 2H), 8.28 (d, J=8.7, 2H), 7.57 (d, J=8.7, 2H), 6.87 (d, J=1.7, 1H), 6.69 (t, J=4.7, 1H), 4.91 (d, J=18.6, 1H), 4.75 (d, J=18.7, 1H), 4.18-4.09 (m, 2H), 3.86 (dd, J=17.0, 9.4, 2H), 3.73-3.69 (m, 1H), 3.66-3.58 (m, 3H), 3.43 (t, J=10.8, 1H), 2.75 (s, 2H), 1.26 (d, J=6.7, 3H). LC/MS-m/z+514.2 (M+H)+.

Example 413

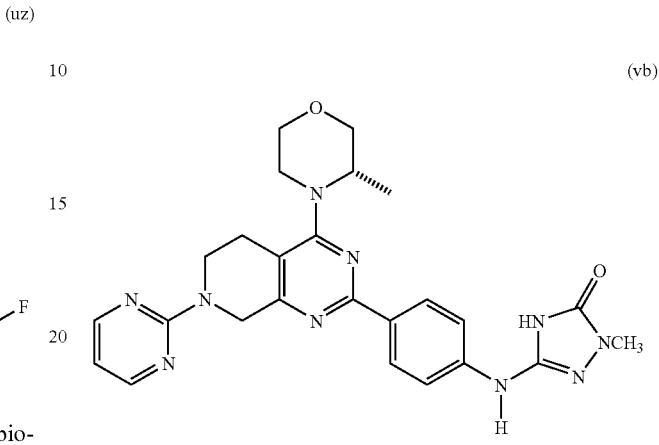

(vb)

Synthesis of (S)-1-methyl-3-(4-(4-(3-methylmorpholino)-7-(pyrimidin-2-yl)-5,6,7,8-tetrahydropyrido[3,4-d]pyrimidin-2-yl)phenylamino)-1H-1,2,4-triazol-5 (4H)-one (vb)

Step 1—Synthesis of (S)-1-phenoxycarbonyl-3-(4-(4-(3-methylmorpholino)-7-(pyrimidin-2-yl)-5,6,7,8-tetrahydropyrido[3,4-d]pyrimidin-2-yl)phenyl)thiourea: Carbonochloridic acid, phenyl ester (0.1450 mL, 0.001156 mol) in Acetone (0.200 mL, 0.00272 mol) was added slowly to Potassium thiocyanate (0.1180 g, 0.001214 mol) in Acetone (0.780 mL, 0.0106 mol). The reaction mixture was heated at 56° C. for 10 minutes then cooled to room temperature, added to (S)-4-(4-(3-methylmorpholino)-7-(pyrimidin-2-yl)-5,6,7,8-tetrahydropyrido[3,4-d]pyrimidin-2-yl)aniline (0.158 g, 0.000392 mol) in Acetone (5.00 mL, 0.0681 mol) and stirred overnight. The reaction mixture was vacuum filtered. The filtrate was concentrated and chromatographed through silica gel (12 g, 0-100% EtOAc in hexanes). The purified fractions was combined with the previously filtered solid. The reaction mixture was used in the next step without further purification. ¹H NMR (400 MHz, DMSO) δ 10.45 (s, 1H), 9.29 (s, 1H), 8.43 (d, J=4.7, 2H), 8.31 (d, J=8.7, 2H), 7.20-7.10 (m, 2H), 7.05 (d, J=8.6, 2H), 6.78-6.72 (m, 2H), 6.69 (t, J=4.7, 1H), 4.90 (d, J=18.6, 1H), 4.74 (d, J=18.6, 1H), 4.15 (s, 2H), 3.85 (t, J=12.5, 2H), 3.64 (dt, J=29.5, 10.2, 4H), 3.44 (d, J=11.6, 2H), 2.75 (s, 2H), 1.25 (d, J=6.6, 3H). LC/MS-m/z+583.2 (M+H)+

Step 2—Synthesis of (S)-1-methyl-N-(4-(4-(3-methylmorpholino)-7-(pyrimidin-2-yl)-5,6,7,8-tetrahydropyrido[3,4-d]pyrimidin-2-yl)phenylcarbamothioyl)hydrazinecarboxamide: The phenyl ester of step 1 (0.265 g, 0.000455 mol) in dry Tetrahydrofuran (3.40 mL, 0.0419 mol) was added N-Methylhydrazine (0.0242 mL, 0.000455 mol) and stirred overnight. Added N-Methylhydrazine (0.0484 mL, 0.000910 mol) and stirred for 4 hours. The reaction mixture was concentrated and chromatographed through silica gel (12 g, 0-10% MeOH in dichloromethane). ¹H NMR (400 MHz, DMSO) δ 12.55 (s, 1H), 9.91 (s, 1H), 8.44 (d, J=4.7, 2H), 8.34 (d, J=8.7, 2H), 7.83 (d, J=8.7, 2H), 6.69 (t, J=4.7, 1H), 5.18 (s, 2H), 4.92 (d, J=18.9, 1H), 4.77 (d, J=18.6, 1H), 4.15 (dd, J=15.6, 10.5, 2H), 3.88 (d, J=7.6, 2H), 3.65 (dt, J=27.2, 10.3, 4H), 3.44 (t, J=10.5, 1H), 3.09 (s, 3H), 2.77 (s, 2H), 1.27 (d, J=6.7, 3H). LC/MS-m/z+535.4 (M+H)+

Step 3—Synthesis of compound vb: (S)-1-methyl-N-(4-(4-(3-methylmorpholino)-7-(pyrimidin-2-yl)-5,6,7,8-tetrahydropyrido[3,4-d]pyrimidin-2-yl)phenylcarbamothioyl)hydrazinecarboxamide (0.113 g, 0.000211 mol) and Ethanol (3.7 mL, 0.063 mol) were combined and the reaction was microwaved on 300 watts, 150° C. for 30 minutes on a CEM microwave. The reaction mixture was chromatographed through silica gel (0-5% MeOH in dichloromethane) and purified by HPLC. $^1$H NMR (400 MHz, DMSO) δ 9.34 (s, 1H), 8.43 (d, J=4.7, 2H), 8.22 (d, J=8.8, 2H), 7.47 (d, J=8.8, 2H), 6.69 (t, J=4.7, 1H), 4.88 (d, J=18.7, 1H), 4.73 (d, J=18.7, 1H), 4.17-4.04 (m, 2H), 3.91-3.79 (m, 2H), 3.70 (dd, J=11.3, 2.6, 1H), 3.61 (dd, J=9.9, 6.5, 3H), 3.43 (d, J=11.3, 1H), 3.23 (s, 3H), 2.73 (s, 2H), 1.25 (d, J=6.6, 3H). LC/MS-m/z+501.2 (M+H)+

Example 414

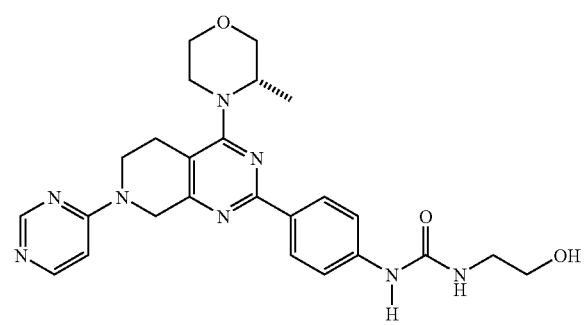

(vc)

Synthesis of (S)-1-(2-hydroxyethyl)-3-(4-(4-(3-methylmorpholino)-7-(pyrimidin-4-yl)-5,6,7,8-tetrahydropyrido[3,4-d]pyrimidin-2-yl)phenyl)urea (vc): (S)-4-(4-(3-methylmorpholino)-7-(pyrimidin-4-yl)-5,6,7,8-tetrahydropyrido[3,4-d]pyrimidin-2-yl)aniline (0.0700 g, 0.000173 mol) in dry 1,4-Dioxane (1.50 mL, 0.0192 mol) was added Triethylamine (0.0266 mL, 0.000191 mol) followed by 20% Phosgene in toluene (1:4, Phosgene:Toluene, 0.100 mL). The reaction mixture was heated at 50° C. for 1 hour. The reaction mixture was cooled to room temperature and then added Ethanolamine (0.0628 mL, 0.00104 mol). The reaction mixture was stirred overnight. The reaction mixture was concentrated and purified by HPLC. $^1$H NMR (400 MHz, DMSO) δ 8.82 (s, 1H), 8.56 (s, 1H), 8.22 (dd, J=13.0, 7.3, 3H), 7.49 (d, J=8.8, 2H), 6.96 (d, J=5.4, 1H), 6.30 (t, J=5.6, 1H), 4.76 (d, J=18.6, 1H), 4.64 (d, J=18.3, 1H), 4.13 (d, J=6.9, 1H), 4.01 (d, J=12.8, 1H), 3.88 (d, J=11.5, 1H), 3.80-3.57 (m, 5H), 3.45 (m, 3H), 3.17 (m, 2H), 2.75 (s, 2H), 1.26 (d, J=6.7, 3H). LC/MS-m/z+ 491.2 (M+H)+

Example 415

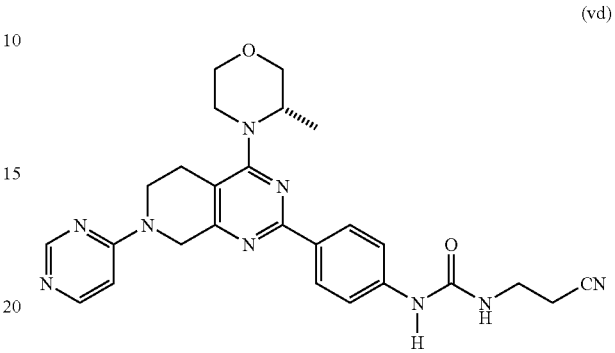

(vd)

Synthesis of (S)-1-(2-cyanoethyl)-3-(4-(4-(3-methylmorpholino)-7-(pyrimidin-4-yl)-5,6,7,8-tetrahydropyrido[3,4-d]pyrimidin-2-yl)phenyl)urea (vd): (S)-4-(4-(3-methylmorpholino)-7-(pyrimidin-4-yl)-5,6,7,8-tetrahydropyrido[3,4-d]pyrimidin-2-yl)aniline (0.0700 g, 0.000173 mol) in dry 1,4-Dioxane (1.50 mL, 0.0192 mol) was added Triethylamine (0.0266 mL, 0.000191 mol) followed by 20% Phosgene in toluene (1:4, Phosgene:Toluene, 0.100 mL). The reaction mixture was heated at 50° C. for 1 hour. The reaction mixture was cooled to room temperature and then added β-Cyanoethylamine (0.0764 mL, 0.00104 mol). The reaction mixture was stirred overnight. The reaction mixture was concentrated and purified by HPLC. $^1$H NMR (400 MHz, DMSO) δ 8.94 (s, 1H), 8.56 (s, 1H), 8.22 (d, J=8.8, 2H), 8.17 (s, 1H), 7.52 (d, J=8.8, 2H), 6.96 (d, J=5.5, 1H), 6.58 (t, J=5.9, 1H), 4.76 (d, J=18.3, 1H), 4.65 (d, J=18.0, 1H), 4.13 (d, J=6.6, 1H), 3.99 (s, 1H), 3.88 (d, J=11.3, 1H), 3.81-3.55 (m, 7H), 3.46-3.32 (m, 1H), 2.74 (d, J=10.3, 2H), 2.70 (t, J=6.4, 2H), 1.26 (d, J=6.6, 3H). LC/MS-m/z+500.3 (M+H)+.

Example 416

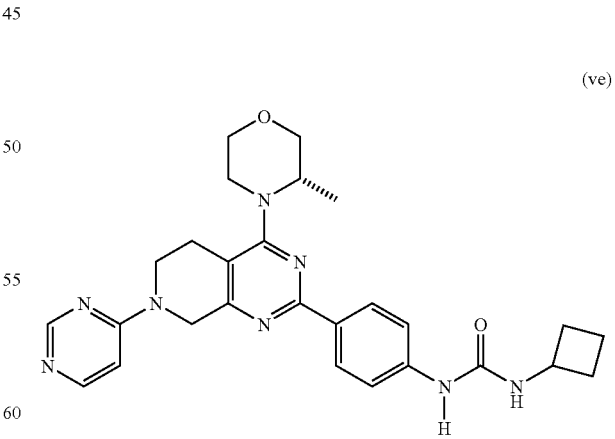

(ve)

Synthesis of (S)-1-cyclobutyl-3-(4-(4-(3-methylmorpholino)-7-(pyrimidin-4-yl)-5,6,7,8-tetrahydropyrido[3,4-d]pyrimidin-2-yl)phenyl)urea (ve): (S)-4-(4-(3-methylmorpholino)-7-(pyrimidin-4-yl)-5,6,7,8-tetrahydropyrido[3,4-d]pyrimidin-2-yl)aniline (0.0700 g, 0.000173 mol) in dry 1,4-

Dioxane (1.50 mL, 0.0192 mol) was added Triethylamine (0.0266 mL, 0.000191 mol) followed by 20% Phosgene in toluene (1:4, Phosgene:Toluene, 0.100 mL). The reaction mixture was heated at 50° C. for 1 hour. The reaction mixture was cooled to room temperature and then added aminocyclobutane (0.0892 mL, 0.00104 mol). The reaction mixture was stirred overnight. LC-MS shows mostly product. The reaction mixture was concentrated purified by HPLC. ¹H NMR (400 MHz, DMSO) δ 8.65 (s, 1H), 8.56 (s, 1H), 8.22 (dd, J=16.1, 7.5, 3H), 7.48 (d, J=8.8, 2H), 6.96 (d, J=6.2, 1H), 6.57 (d, J=7.6, 1H), 4.76 (d, J=18.0, 1H), 4.64 (d, J=18.3, 1H), 4.15 (dt, J=15.6, 7.8, 2H), 4.00 (dd, J=16.4, 8.3, 1H), 3.87 (d, J=11.3, 1H), 3.80-3.57 (m, 5H), 2.75 (s, 2H), 2.20 (dt, J=14.1, 5.0, 2H), 2.10 (ddd, J=10.1, 7.6, 3.6, 1H), 1.93-1.79 (m, 2H), 1.73 (dt, J=11.9, 9.7, 1H), 1.56 (m, 2H), 1.26 (d, J=6.6, 3H). LC/MS-m/z+501.3 (M+H)+

Example 417

Example 418

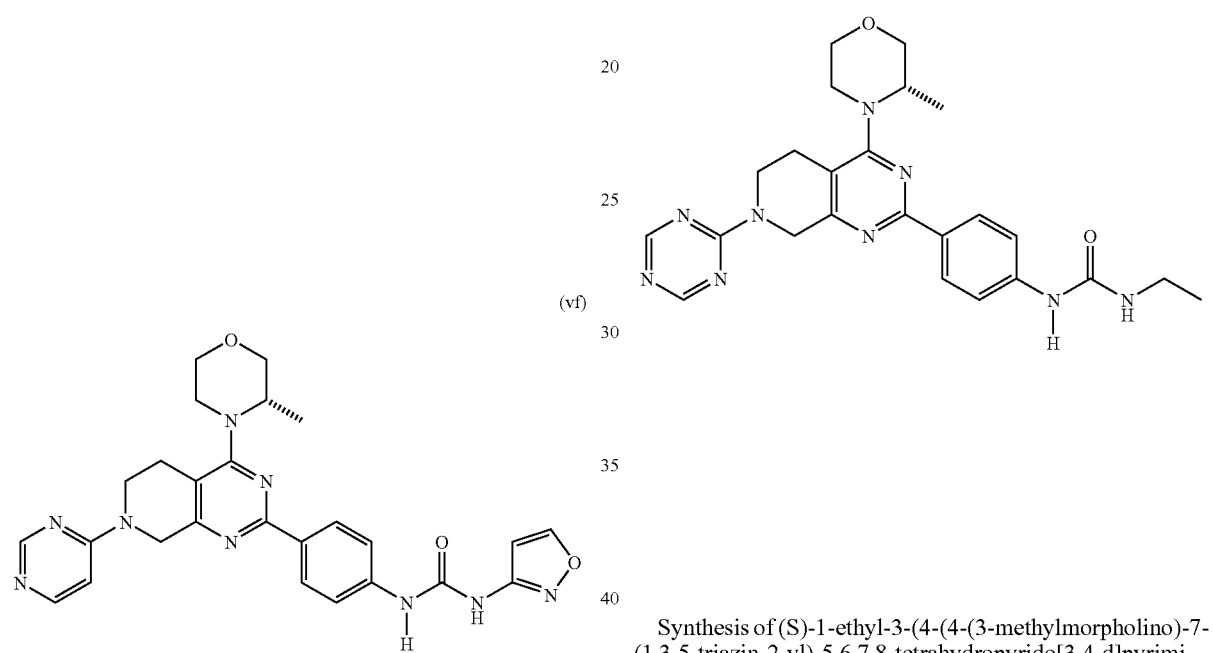

Synthesis of (S)-1-(isoxazol-3-yl)-3-(4-(4-(3-methylmorpholino)-7-(pyrimidin-4-yl)-5,6,7,8-tetrahydropyrido[3,4-d]pyrimidin-2-yl)phenyl)urea (vf): (S)-4-(4-(3-methylmorpholino)-7-(pyrimidin-4-yl)-5,6,7,8-tetrahydropyrido[3,4-d]pyrimidin-2-yl)aniline (0.0700 g, 0.000173 mol) in dry 1,4-Dioxane (1.50 mL, 0.0192 mol) was added Triethylamine (0.0266 mL, 0.000191 mol) followed by 20% Phosgene in toluene (1:4, Phosgene:Toluene, 0.100 mL). The reaction mixture was heated at 50° C. for 1 hour. The reaction mixture was cooled to room temperature and then added 3-aminoisoxazole (0.0770 mL, 0.00104 mol). The reaction mixture was stirred overnight. The reaction mixture was concentrated and purified by HPLC. ¹H NMR (500 MHz, DMSO) δ 9.70 (s, 1H), 9.16 (s, 1H), 8.77 (d, J=1.6, 1H), 8.67 (s, 1H), 8.29 (t, J=7.5, 3H), 7.58 (d, J=8.8, 2H), 7.11 (d, J=6.4, 1H), 6.88 (d, J=1.7, 1H), 4.85 (d, J=18.4, 1H), 4.74 (d, J=18.5, 1H), 4.15 (d, J=6.1, 1H), 4.06 (s, 1H), 3.92-3.82 (m, 3H), 3.76-3.54 (m, 4H), 3.48-3.41 (m, 2H), 2.79 (s, 2H), 1.27 (d, J=6.7, 3H). LC/MS-m/z+514.2 (M+H)+

Synthesis of (S)-1-ethyl-3-(4-(4-(3-methylmorpholino)-7-(1,3,5-triazin-2-yl)-5,6,7,8-tetrahydropyrido[3,4-d]pyrimidin-2-yl)phenyl)urea (vg)

Step 1—Synthesis of (S)-1-(4-(7-(4-chloro-1,3,5-triazin-2-yl)-4-(3-methylmorpholino)-5,6,7,8-tetrahydropyrido[3,4-d]pyrimidin-2-yl)phenyl)-3-ethylurea: (S)-1-ethyl-3-(4-(4-(3-methylmorpholino)-5,6,7,8-tetrahydropyrido[3,4-d]pyrimidin-2-yl)phenyl)urea (0.128 g, 0.245 mmol) and 2,4-dichloro-1,3,5-triazine (0.0596 g, 0.397 mmol) were combined then added N,N-Dimethylformamide (1.60 mL, 20.7 mmol) followed by N,N-Diisopropylethylamine (0.0802 mL, 0.460 mmol). The reaction mixture was stirred for 2 hours. The reaction mixture was concentrated and chromatographed through silica gel (12 g, 0-5% MeOH in dichloromethane). LC/MS-m/z+510.5 (M+H)+

Step 2—Synthesis of vg: (S)-1-(4-(7-(4-chloro-1,3,5-triazin-2-yl)-4-(3-methylmorpholino)-5,6,7,8-tetrahydropyrido[3,4-d]pyrimidin-2-yl)phenyl)-3-ethylurea (0.147 g, 0.000288 mol), Palladium on Carbon 10% (0.1:0.9, Palladium:carbon black, 0.116 g), and Methanol (10.0 mL, 0.247 mol) were combined under N2 then purged with hydrogen, heated at 65° C. and stirred overnight. The reaction mixture was purged with N2, added celite, filtered through celite, filtered through a disc filter, concentrated, and purified by HPLC. ¹H NMR (500 MHz, DMSO) δ 8.71 (s, 1H), 8.67 (d, J=2.0, 2H), 8.20 (d, J=8.8, 2H), 7.49 (d, J=8.8, 2H), 6.21 (t, J=5.6, 1H), 4.91 (d, J=18.6, 1H), 4.77 (d, J=18.6, 1H), 4.20-4.02 (m, 2H), 3.87 (d, J=12.5, 2H), 3.69 (d, J=8.4, 1H), 3.66-3.56 (m, 3H), 3.47-3.36 (m, 1H), 3.17-3.06 (m, 2H), 2.76 (s, 2H), 1.25 (d, J=6.7, 3H), 1.06 (t, J=7.2, 3H). LC/MS-m/z+476.2 (M+H)+.

Example 419

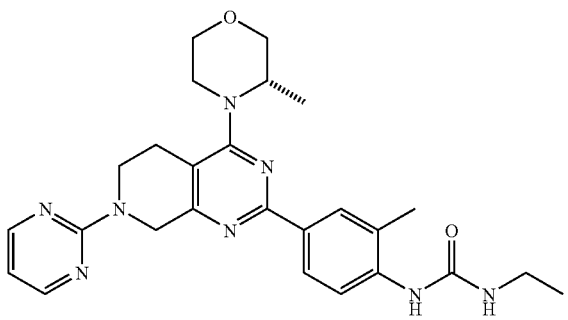

(vh)

Synthesis of (S)-1-ethyl-3-(2-methyl-4-(4-(3-methylmorpholino)-7-(pyrimidin-2-yl)-5,6,7,8-tetrahydropyrido[3,4-d]pyrimidin-2-yl)phenyl)urea (vh)

Step 1—Synthesis of (S)-tert-butyl 2-(4-amino-3-methylphenyl)-4-(3-methylmorpholino)-5,6-dihydropyrido[3,4-d]pyrimidine-7(8H)-carboxylate: (S)-tert-butyl 2-chloro-4-(3-methylmorpholino)-5,6-dihydropyrido[3,4-d]pyrimidine-7(8H)-carboxylate (0.363 g, 0.000983 mol), 2-methyl-4-(4,4,5,5-tetramethyl-1,3,2-dioxaborolan-2-yl) aniline (0.275 g, 0.00118 mol) Tetrakis(triphenylphosphine) palladium(0) (0.05680 g, 4.915E-5 mol) Sodium carbonate (0.1563 g, 0.001474 mol) and Potassium acetate (0.1447 g, 0.001474 mol) were combined, nitrogen purged three times, added dry Acetonitrile (5.29 mL, 0.101 mol) followed by deoxygenated Water (3.04 mL, 0.169 mol) heated at 90° C. and stirred overnight. The reaction mixture was diluted with water, extracted three times with 10% MeOH in CH2Cl2, dried over Magnesium sulfate, filtered, concentrated, and chromatographed through silica gel (120 g, 0-50% EtOAc in hexanes). LC/MS-m/z+440.4 (M+H)+

Step 2—Synthesis of (S)-tert-butyl 2-(4-(3-ethylureido)-3-methylphenyl)-4-(3-methylmorpholino)-5,6-dihydropyrido[3,4-d]pyrimidine-7(8H)-carboxylate: (S)-tert-butyl 2-(4-amino-3-methylphenyl)-4-(3-methylmorpholino)-5,6-dihydropyrido[3,4-d]pyrimidine-7(8H)-carboxylate (0.357 g, 0.812 mmol) in dry N,N-Dimethylformamide (5.50 mL, 71.0 mmol) was added N,N-Diisopropylethylamine (0.212 mL, 1.22 mmol) followed by Ethane, isocyanato- (0.0958 mL, 1.22 mmol) heated at 40° C., and stirred overnight. The reaction mixture was concentrated and chromatographed through silica gel (12 g, 0-100% EtOAc in hexanes). $^1$H NMR (500 MHz, CDCl$_3$) δ 8.20 (d, J=6.6, 2H), 7.57 (d, J=7.3, 1H), 7.27 (s, 1H), 6.17 (s, 1H), 4.84-4.62 (m, 2H), 4.54 (d, J=18.6, 1H), 4.06 (d, J=5.4, 1 H), 3.96 (d, J=11.2, 1H), 3.86-3.66 (m, 4H), 3.64-3.50 (m, 2H), 3.48-3.40 (m, 1H), 3.30 (p, J=6.9, 2H), 2.68 (s, 2H), 2.35 (s, 3H), 1.52 (s, 9H), 1.36 (t, J=12.9, 3H), 1.14 (t, J=7.2, 3H). LC/MS-m/z+511.6 (M+H)+

Step 3—Synthesis of (S)-1-ethyl-3-(2-methyl-4-(4-(3-methylmorpholino)-5,6,7,8-tetrahydropyrido[3,4-d]pyrimidin-2-yl)phenyl)urea: (S)-tert-butyl 2-(4-(3-ethylureido)-3-methylphenyl)-4-(3-methylmorpholino)-5,6-dihydropyrido[3,4-d]pyrimidine-7(8H)-carboxylate (0.115 g, 0.225 mmol) in Methylene chloride (5.0 mL, 78 mmol) was added Trifluoroacetic Acid (5.0 mL, 65 mmol) and stirred for 1 hour. LC-MS shows mostly product and no starting material. The reaction mixture was concentrated and the redissolved in dichloromethane, added PS-Carbonate, and shaken overnight. The reaction mixture was filtered, diluted with sat NaHCO3, extracted 3 with 10% MeOH in dichloromethane, washed three times with sat NaHCO3, dried over Magnesium sulfate, filtered, and concentrated. $^1$H NMR (400 MHz, CDCl$_3$) δ 8.26-8.14 (m, 2H), 7.50 (d, J=8.0, 1H), 6.07 (s, 1H), 4.76-4.56 (m, 1H), 4.17-4.02 (m, 2H), 3.99-3.90 (m, 1H), 3.83 (dd, J=11.2, 2.9, 1H), 3.78-3.65 (m, 2H), 3.61-3.49 (m, 2H), 3.34-3.23 (m, 2H), 3.15 (dt, J=12.0, 5.0, 1H), 3.00 (dt, J=13.7, 7.1, 1H), 2.65 (t, J=5.2, 2H), 2.35 (d, J=4.7, 3H), 1.32 (d, J=6.7, 3H), 1.13 (t, J=7.2, 3H). LC/MS-m/z+411.3 (M+H)+

Step 4—Synthesis of compound vh: (S)-1-ethyl-3-(2-methyl-4-(4-(3-methylmorpholino)-5,6,7,8-tetrahydropyrido[3,4-d]pyrimidin-2-yl)phenyl)urea (0.043 g, 0.10 mmol) and 2-Chloropyrimidine (0.0121 g, 0.106 mmol) were combined, nitrogen purged three times, added N,N-Dimethylformamide (1.50 mL, 19.4 mmol) and N,N-Diisopropylethylamine (0.0730 mL, 0.419 mmol). The reaction was microwaved on 200 watts, 120° C. for 30 minutes on a CEM microwave. The reaction mixture was concentrated and purified by HPLC. $^1$H NMR (400 MHz, DMSO) δ 8.43 (d, J=4.7, 2H), 8.12-7.99 (m, 3H), 7.72 (s, 1H), 6.67 (dt, J=10.9, 5.0, 2H), 4.90 (d, J=18.7, 1H), 4.73 (d, J=18.7, 1H), 4.14 (dd, J=17.9, 5.1, 2H), 3.93-3.77 (m, 2H), 3.71 (dd, J=11.2, 2.5, 1H), 3.61 (d, J=12.1, 3H), 3.43 (dd, J=18.5, 7.5, 1H), 3.18-3.06 (m, 2H), 2.74 (s, 2H), 2.26 (s, 3H), 1.25 (d, J=6.6, 3H), 1.08 (t, J=7.2, 3H). LC/MS-m/z+489.3 (M+H)+

Example 420

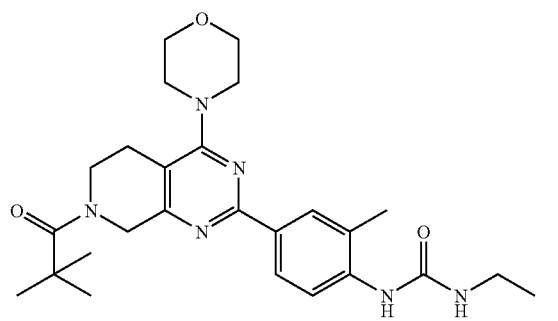

(vi)

Synthesis of 1-ethyl-3-(2-methyl-4-(4-morpholino-7-pivaloyl-5,6,7,8-tetrahydropyrido[3,4-d]pyrimidin-2-yl)phenyl)urea (vi): 1-ethyl-3-(4-(4-morpholino-5,6,7,8-tetrahydropyrido[3,4-d]pyrimidin-2-yl)phenyl)urea (0.042 g, 0.11 mmol) in dry N,N-Dimethylformamide (1.00 mL, 12.9 mmol) was added N,N-Diisopropylethylamine (0.0574 mL, 0.330 mmol) followed by 2,2-Dimethylpropanoyl chloride (0.0204 mL, 0.166 mmol). The reaction mixture was stirred for 3 days. The reaction mixture was concentrated and purified by HPLC. $^1$H NMR (400 MHz, DMSO) δ 8.65 (s, 1H), 8.19 (d, J=8.8, 2H), 7.48 (d, J=8.8, 2H), 6.16 (t, J=5.5, 1H), 4.61 (s, 2H), 3.81-3.68 (m, 6H), 3.49 (d, J=4.5, 4H), 3.19-3.06 (m, 2H), 2.69 (d, J=12.7, 2H), 1.27 (s, 9H), 1.06 (t, J=7.2, 3H). LC/MS-m/z+467.3 (M+H)+

Example 421

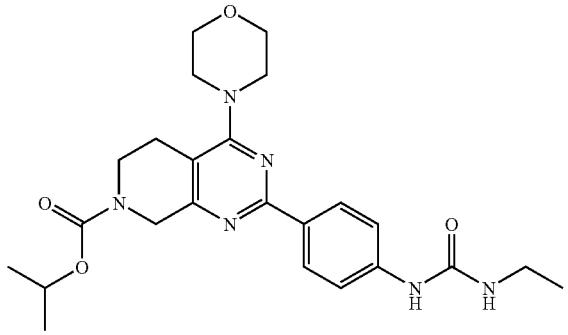

(vj)

Synthesis of isopropyl 2-(4-(3-ethylureido)phenyl)-4-morpholino-5,6-dihydropyrido[3,4-d]pyrimidine-7(8H)-carboxylate (vj): 1-ethyl-3-(4-(4-morpholino-5,6,7,8-tetrahydropyrido[3,4-d]pyrimidin-2-yl)phenyl)urea (0.087 g, 0.23 mmol) in dry N,N-Dimethylformamide (1.00 mL, 12.9 mmol) at 0° C. was added N,N-Diisopropylethylamine (0.1190 mL, 0.6832 mmol) followed by 1.0 M of Isopropyl Chloroformate in Toluene (0.340 mL). The reaction mixture was allowed to warm slowly to room temperature and stirred overnight. The reaction mixture was concentrated and purified by HPLC. $^1$H NMR (400 MHz, DMSO) δ 8.66 (s, 1H), 8.18 (d, J=8.8, 2H), 7.48 (d, J=8.8, 2H), 6.18 (t, J=5.5, 1H), 4.84 (dt, J=12.5, 6.2, 1H), 4.49 (s, 2H), 3.79-3.68 (m, 4H), 3.55 (s, 2H), 3.47 (d, J=4.4, 4H), 3.18-3.05 (m, 2H), 2.68 (t, J=5.0, 2H), 1.24 (d, J=6.2, 6H), 1.06 (t, J=7.2, 3H). LC/MS-m/z+469.3 (M+H)+

Example 422

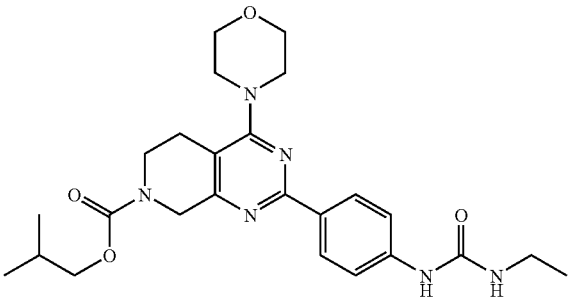

(vk)

Synthesis of isobutyl 2-(4-(3-ethylureido)phenyl)-4-morpholino-5,6-dihydropyrido[3,4-d]pyrimidine-7(8H)-carboxylate (vk): 1-ethyl-3-(4-(4-morpholino-5,6,7,8-tetrahydropyrido[3,4-d]pyrimidin-2-yl) phenyl)urea (0.0867 g, 0.227 mmol) in dry N,N-Dimethylformamide (1.00 mL, 12.9 mmol) at 0° C. was added N,N-Diisopropylethylamine (0.1190 mL, 0.6832 mmol) followed by Isobutyl chloroformate (0.0442 mL, 0.341 mmol). The reaction mixture was allowed to warm slowly to room temperature and stirred overnight. The reaction mixture was concentrated and purified by HPLC. $^1$H NMR (400 MHz, DMSO) δ 8.67 (s, 1H), 8.18 (d, J=8.8, 2H), 7.48 (d, J=8.8, 2H), 6.18 (t, J=5.6, 1H), 4.52 (s, 2H), 3.86 (d, J=6.5, 2H), 3.77-3.68 (m, 4 H), 3.58 (s, 2H), 3.47 (d, J=4.3, 4H), 3.17-3.06 (m, 2H), 2.73-2.62 (m, 2H), 1.92 (dp, J=13.2, 6.6, 1H), 1.06 (t, J=7.2, 3H), 0.93 (d, J=6.7, 6H). LC/MS-m/z+483.3 (M+H)+

Example 423

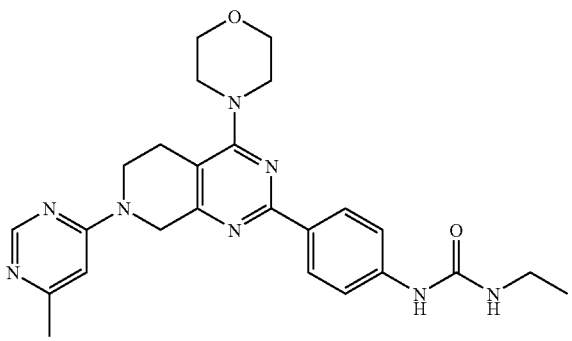

(vl)

Synthesis of 1-ethyl-3-(4-(7-(6-methylpyrimidin-4-yl)-4-morpholino-5,6,7,8-tetrahydropyrido[3,4-d]pyrimidin-2-yl) phenyl)urea (vl): 1-ethyl-3-(4-(4-morpholino-5,6,7,8-tetrahydropyrido[3,4-d]pyrimidin-2-yl)phenyl)urea (0.0499 g, 0.000130 mol) in dry N,N-Dimethylformamide (1.00 mL, 0.0129 mol) was cooled at 0° C. then added sodium hydride, 60% dispension in mineral oil (3:2, Sodium hydride:Mineral Oil, 0.0109 g), warmed to room temperature, stirred for 10 minutes, added 4-Chloro-6-methylpyrimidine (0.0196 g, 0.000152 mol) heated at 60° C. for 3 hours. LC-MS does show some product present but a lot of starting material is still remaining. The reaction mixture was heated at 60° C. and stirred overnight. The reaction mixture was filtered and purified by HPLC. $^1$H NMR (400 MHz, DMSO) δ 8.64 (s, 1H), 8.44 (s, 1H), 8.21 (d, J=8.8, 2H), 7.49 (d, J=8.8, 2H), 6.86 (s, 1H), 6.16 (t, J=5.6, 1H), 4.69 (s, 2H), 3.87 (s, 2H), 3.79-3.68 (m, 4H), 3.48 (d, J=4.4, 4H), 3.20-3.05 (m, 2H), 2.75 (s, 2H), 2.30 (s, 3H), 1.06 (t, J=7.2, 3H). LC/MS-m/z+475.3 (M+H)+

Example 424

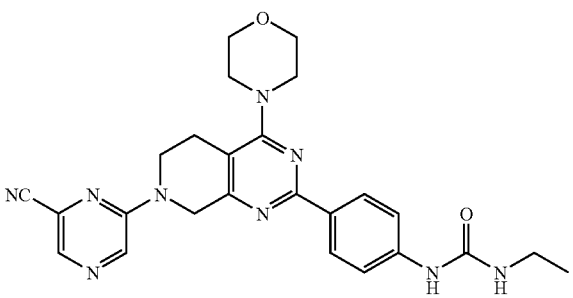

(vm)

Synthesis of 1-(4-(7-(6-cyanopyrazin-2-yl)-4-morpholino-5,6,7,8-tetrahydropyrido[3,4-d]pyrimidin-2-yl)phenyl)-3-ethylurea (vm): 1-Ethyl-3-(4-(4-morpholino-5,6,7,8-tetrahydropyrido[3,4-d]pyrimidin-2-yl)phenyl)urea (0.0513 g, 0.134 mmol) and 6-chloropyrazine-2-carbonitrile (0.0326 g, 0.234 mmol) were combined then added dry N,N-Dimethylformamide (0.910 mL, 11.8 mmol) followed by N,N-Diisopropylethylamine (0.0456 mL, 0.262 mmol). The reaction was microwaved on 300 watts, 120° C. for 30 minutes on the Biotage microwave. The reaction mixture was purified by HPLC. $^1$H NMR (400 MHz, DMSO) δ 8.76 (s, 1H), 8.66 (s, 1H), 8.35 (s, 1H), 8.22 (d, J=8.8, 2H), 7.49 (d, J=8.8, 2H), 6.18 (t, J=5.5, 1H), 4.75 (s, 2H), 3.90 (t, J=5.3, 2H), 3.74 (d, J=4.4, 4H), 3.50 (d, J=4.3, 4H), 3.17-3.06 (m, 2H), 2.81 (s, 2H), 1.06 (t, J=7.2, 3H). LC/MS-m/z+486.2 (M+H)+

Example 425

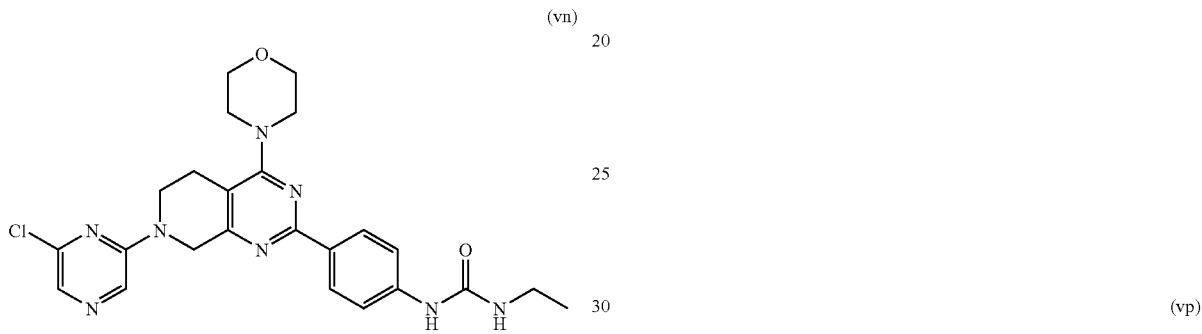

(vn)

Synthesis of 1-(4-(7-(6-chloropyrazin-2-yl)-4-morpholino-5,6,7,8-tetrahydropyrido[3,4-d]pyrimidin-2-yl)phenyl)-3-ethylurea (vn): 1-Ethyl-3-(4-(4-morpholino-5,6,7,8-tetrahydropyrido[3,4-d]pyrimidin-2-yl)phenyl)urea (0.0499 g, 0.130 mmol) and 2,6-Dichloropyrazine (0.0311 g, 0.209 mmol) were combined then added dry N,N-Dimethylformamide (0.911 mL, 11.8 mmol) followed by N,N-Diisopropylethylamine (0.0456 mL, 0.262 mmol). The reaction was microwaved on 200 watts, 120° C. for 30 minutes on a CEM microwave. The reaction mixture was purified by HPLC. $^1$H NMR (400 MHz, DMSO) δ 8.65 (s, 1H), 8.40 (s, 1H), 8.22 (d, J=8.8, 2H), 7.90 (s, 1H), 7.49 (d, J=8.8, 2H), 6.17 (t, J=5.5, 1H), 4.69 (d, J=16.4, 2H), 3.86 (t, J=5.1, 2H), 3.79-3.69 (m, 4H), 3.49 (d, J=4.3, 4H), 3.18-3.06 (m, 2H), 2.80 (s, 2H), 1.06 (t, J=7.2, 3H). LC/MS-m/z+495.2 (M+H)+

Example 426

(vo)

Synthesis of 1-(4-(7-(3-cyanopyrazin-2-yl)-4-morpholino-5,6,7,8-tetrahydropyrido[3,4-d]pyrimidin-2-yl)phenyl)-3-ethylurea (vo): 1-Ethyl-3-(4-(4-morpholino-5,6,7,8-tetrahydropyrido[3,4-d]pyrimidin-2-yl)phenyl)urea (0.0506 g, 0.132 mmol) and 3-chloropyrazine-2-carbonitrile (0.0338 g, 0.242 mmol) were combined then added dry N,N-Dimethylformamide (0.910 mL, 11.8 mmol) followed by N,N-Diisopropylethylamine (0.0456 mL, 0.262 mmol). The reaction was microwaved on 200 watts, 120° C. for 30 minutes on a CEM microwave. The reaction mixture was purified by HPLC. $^1$H NMR (500 MHz, DMSO) δ 8.80 (s, 1H), 8.50 (d, J=2.2, 1H), 8.21 (d, J=8.7, 2H), 8.15 (d, J=2.2, 1H), 7.50 (d, J=8.7, 2H), 6.30 (t, J=5.5, 1H), 4.86 (s, 2H), 4.00 (s, 2H), 3.74 (d, J=4.3, 4H), 3.49 (d, J=4.2, 4H), 3.12 (dt, J=13.8, 7.1, 3H), 2.85 (s, 2H), 1.06 (t, J=7.2, 3H). LC/MS-m/z+486.2 (M+H)+.

Example 427

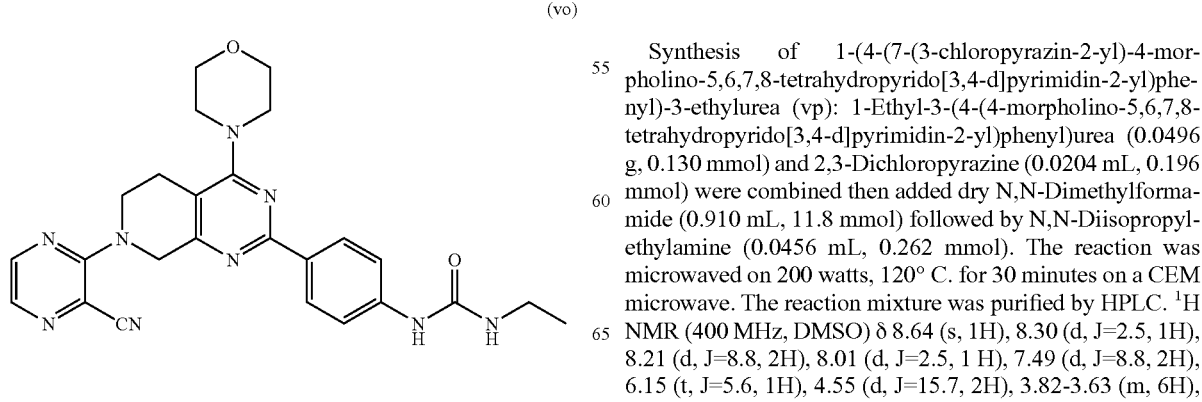

(vp)

Synthesis of 1-(4-(7-(3-chloropyrazin-2-yl)-4-morpholino-5,6,7,8-tetrahydropyrido[3,4-d]pyrimidin-2-yl)phenyl)-3-ethylurea (vp): 1-Ethyl-3-(4-(4-morpholino-5,6,7,8-tetrahydropyrido[3,4-d]pyrimidin-2-yl)phenyl)urea (0.0496 g, 0.130 mmol) and 2,3-Dichloropyrazine (0.0204 mL, 0.196 mmol) were combined then added dry N,N-Dimethylformamide (0.910 mL, 11.8 mmol) followed by N,N-Diisopropylethylamine (0.0456 mL, 0.262 mmol). The reaction was microwaved on 200 watts, 120° C. for 30 minutes on a CEM microwave. The reaction mixture was purified by HPLC. $^1$H NMR (400 MHz, DMSO) δ 8.64 (s, 1H), 8.30 (d, J=2.5, 1H), 8.21 (d, J=8.8, 2H), 8.01 (d, J=2.5, 1H), 7.49 (d, J=8.8, 2H), 6.15 (t, J=5.6, 1H), 4.55 (d, J=15.7, 2H), 3.82-3.63 (m, 6H), 3.56-3.45 (m, 4H), 3.17-3.07 (m, 2H), 2.86 (s, 2H), 1.06 (t, J=7.2, 3H). LC/MS-m/z+495.2 (M+H)+.

Example 428

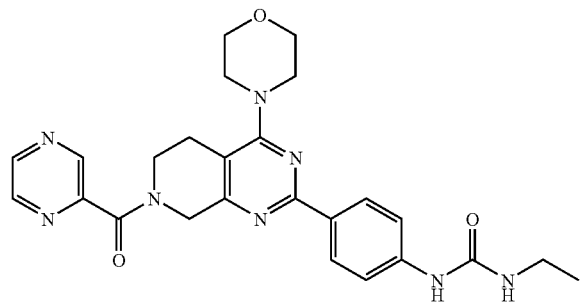

(vq)

Synthesis of 1-ethyl-3-(4-(4-morpholino-7-(pyrazine-2-carbonyl)-5,6,7,8-tetrahydropyrido[3,4-d]pyrimidin-2-yl)phenyl)urea (vq): 1-Ethyl-3-(4-(4-morpholino-5,6,7,8-tetrahydropyrido[3,4-d]pyrimidin-2-yl)phenyl)urea (0.0493 g, 0.000129 mol) in dry N,N-Dimethylformamide (0.610 mL, 0.00788 mol) was added N,N-Diisopropylethylamine (0.0684 mL, 0.000393 mol) cooled at 0° C., added Pyrazine-2-carbonyl chloride (0.0312 g, 0.000219 mol), warmed to room temperature, and stirred overnight. The reaction mixture was purified by HPLC. ¹H NMR (400 MHz, DMSO) δ 8.98-8.91 (m, 1H), 8.80 (dd, J=5.3, 2.6, 1H), 8.74 (d, J=1.4, 1H), 8.64 (d, J=12.3, 1H), 8.18 (dd, J=34.9, 8.7, 2H), 7.47 (dd, J=20.0, 8.8, 2H), 6.20-6.09 (m, 1H), 4.75 (d, J=25.1, 2H), 3.88 (t, J=5.0, 1H), 3.79-3.60 (m, 5H), 3.49 (d, J=4.0, 4H), 3.18-3.02 (m, 2H), 2.77 (s, 2H), 1.06 (dd, J=13.3, 7.0, 3H). LC/MS-m/z+489.2 (M+H)+.

Example 429

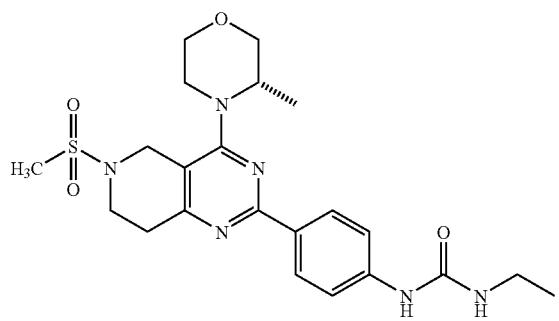

(vr)

Synthesis of (S)-1-ethyl-3-(4-(4-(3-methylmorpholino)-6-(methylsulfonyl)-5,6,7,8-tetrahydropyrido[4,3-d]pyrimidin-2-yl)phenyl)urea (vr): (S)-1-ethyl-3-(4-(4-(3-methylmorpholino)-5,6,7,8-tetrahydropyrido[4,3-d]pyrimidin-2-yl)phenyl)urea hydrochloride (0.1000 g, 0.2310 mmol) in dry N,N-Dimethylformamide (1.60 mL, 20.7 mmol) was added N,N-Diisopropylethylamine (0.161 mL, 0.924 mmol) followed by Methanesulfonyl chloride (0.0268 mL, 0.346 mmol). The reaction mixture was stirred for 2 hours. The reaction mixture was purified by HPLC. ¹H NMR (500 MHz, DMSO) δ 8.69 (s, 1H), 8.19 (d, J=8.7, 2H), 7.49 (d, J=8.8, 2H), 6.18 (t, J=5.5, 1H), 4.23 (dd, J=31.8, 14.8, 2H), 3.97-3.91 (m, 1H), 3.88 (d, J=11.3, 1H), 3.72 (dd, J=11.4, 2.7, 1H), 3.62 (dd, J=10.0, 7.5, 3H), 3.49-3.38 (m, 3H), 3.16-3.08 (m, 2H), 3.03 (s, 3H), 2.99 (t, J=6.3, 2H), 1.22 (d, J=6.6, 3H), 1.06 (t, J=7.2, 3H). LC/MS-m/z+475.2 (M+H)+.

Example 430

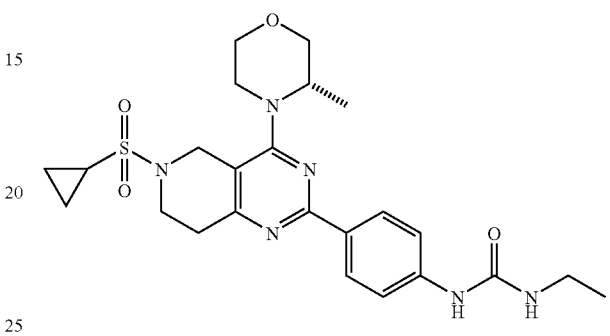

(vs)

Synthesis of (S)-1-(4-(6-(cyclopropylsulfonyl)-4-(3-methylmorpholino)-5,6,7,8-tetrahydropyrido[4,3-d]pyrimidin-2-yl)phenyl)-3-ethylurea (vs): (S)-1-ethyl-3-(4-(4-(3-methylmorpholino)-5,6,7,8-tetrahydropyrido[4,3-d]pyrimidin-2-yl)phenyl)urea hydrochloride (0.1000 g, 0.2310 mmol) in dry N,N-Dimethylformamide (1.60 mL, 20.7 mmol) was added N,N-Diisopropylethylamine (0.161 mL, 0.924 mmol) followed by Cyclopropanesulfonyl chloride (0.0354 mL, 0.347 mmol). The reaction mixture was stirred for 2 hours. The reaction mixture was purified by HPLC. ¹H NMR (500 MHz, DMSO) δ 8.69 (s, 1H), 8.19 (d, J=8.8, 2H), 7.49 (d, J=8.8, 2H), 6.18 (t, J=5.6, 1H), 4.31 (q, J=15.1, 2H), 3.89 (dd, J=12.2, 9.2, 2H), 3.75-3.52 (m, 5H), 3.44 (d, J=5.0, 2H), 3.19-3.05 (m, 2H), 2.99 (d, J=3.7, 2H), 2.75-2.66 (m, 1H), 1.24 (d, J=6.6, 3H), 1.06 (t, J=7.2, 3H), 0.93 (dt, J=13.8, 5.5, 4H). LC/MS-m/z+501.2 (M+H)+.

Example 431

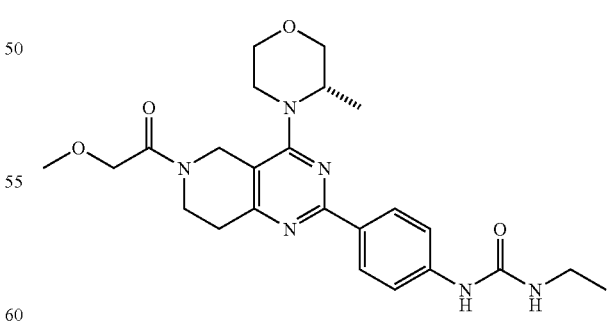

(vt)

Synthesis of (S)-1-ethyl-3-(4-(6-(2-methoxyacetyl)-4-(3-methylmorpholino)-5,6,7,8-tetrahydropyrido[4,3-d]pyrimidin-2-yl)phenyl)urea (vt): (S)-1-ethyl-3-(4-(4-(3-methylmorpholino)-5,6,7,8-tetrahydropyrido[4,3-d]pyrimidin-2-yl)phenyl)urea hydrochloride (0.1000 g, 0.2310 mmol) in dry N,N-Dimethylformamide (1.60 mL, 20.7 mmol) was added N,N-Diisopropylethylamine (0.161 mL, 0.924 mmol) followed by Methoxyacetyl chloride (0.03160 mL, 0.3465 mmol). The reaction mixture was stirred for 2 hours. The reaction mixture was purified by HPLC. LC/MS-m/z+469.2 (M+H)+.

Example 432

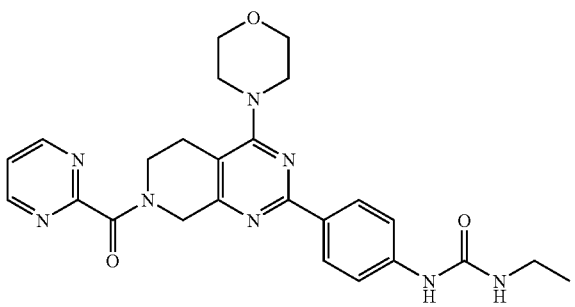

(vu)

Synthesis of 1-ethyl-3-(4-(4-morpholino-7-(pyrimidine-2-carbonyl)-5,6,7,8-tetrahydropyrido[3,4-d]pyrimidin-2-yl)phenyl)urea (vu): Sodium pyrimidine-2-carboxylate (0.0229 g, 0.000157 mol) in dry N,N-Dimethylformamide (0.910 mL, 0.0118 mol) was added 1-Hydroxybenzotriazole (0.0313 g, 0.000232 mol) followed by N-(3-Dimethylaminopropyl)-N'-ethylcarbodiimide hydrochloride (0.0409 g, 0.000213 mol) then followed by N,N-Diisopropylethylamine (0.0570 mL, 0.000327 mol) and then 1-ethyl-3-(4-(4-morpholino-5,6,7,8-tetrahydropyrido[3,4-d]pyrimidin-2-yl)phenyl)urea (0.0493 g, 0.000129 mol). The reaction mixture was stirred overnight. The reaction mixture heated at 40° C. and stirred for 4 days. The reaction mixture was concentrated, chromatographed through silica gel (4 g, 0-10% MeOH in dichloromethane), and purified by HPLC. $^1$H NMR (500 MHz, DMSO) δ 8.99-8.94 (m, 1H), 8.68 (d, J=17.8, 1H), 8.24-8.06 (m, 2H), 7.66 (td, J=5.0, 2.2, 1H), 7.54-7.39 (m, 2H), 6.22-6.11 (m, 1H), 4.77 (s, 1H), 4.38 (s, 1H), 3.89 (d, J=5.2, 1H), 3.72 (dd, J=10.3, 5.7, 4H), 3.49 (dd, J=19.3, 4.3, 4H), 3.40 (d, J=5.3, 1H), 3.20-3.03 (m, 2H), 2.80 (s, 1H), 2.69 (s, 1H), 1.13-0.98 (m, 3H). LC/MS-m/z+489.2 (M+H)+.

Example 433

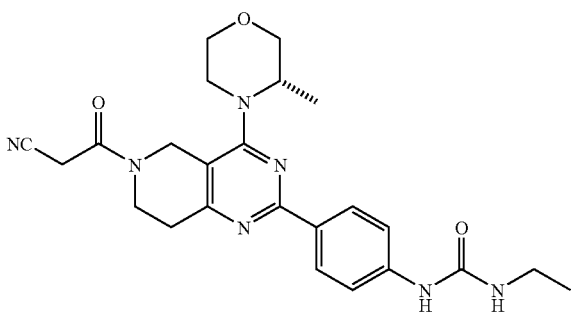

(vv)

Synthesis of (S)-1-(4-(6-(2-cyanoacetyl)-4-(3-methylmorpholino)-5,6,7,8-tetrahydropyrido[4,3-d]pyrimidin-2-yl)phenyl)-3-ethylurea (vv): Cyanoacetic acid (0.0300 g, 0.000353 mol) in dry N,N-Dimethylformamide (1.60 mL, 0.0207 mol) was added 1-Hydroxybenzotriazole (0.0488 g, 0.000361 mol) followed by N-(3-Dimethylaminopropyl)-N'-ethylcarbodiimide hydrochloride (0.0721 g, 0.000376 mol) then followed by N,N-Diisopropylethylamine (0.161 mL, 0.000924 mol) and then (S)-1-ethyl-3-(4-(4-(3-methylmorpholino)-5,6,7,8-tetrahydropyrido[4,3-d]pyrimidin-2-yl)phenyl)urea hydrochloride (0.1000 g, 0.0002310 mol). The reaction mixture heated at 40° C. and was stirred for 4 days. The reaction mixture was concentrated, chromatographed through silica gel again (12 g, 0-10% MeOH in dichloromethane), and purified by HPLC. $^1$H NMR (500 MHz, DMSO) δ 8.69 (s, 1H), 8.18 (d, J=8.8, 2H), 7.48 (d, J=8.8, 2H), 6.18 (t, J=5.6, 1H), 4.65 (d, J=15.7, 1H), 4.51-4.38 (m, 1H), 4.26-4.14 (m, 2H), 3.96-3.84 (m, 2H), 3.80-3.56 (m, 5H), 3.44 (dd, J=19.8, 12.6, 2H), 3.15-3.07 (m, 2H), 3.02-2.94 (m, 1H), 2.84 (s, 1H), 1.25 (t, J=5.4, 3H), 1.06 (t, J=7.2, 3H). LC/MS-m/z+464.2 (M+H)+.

Example 434

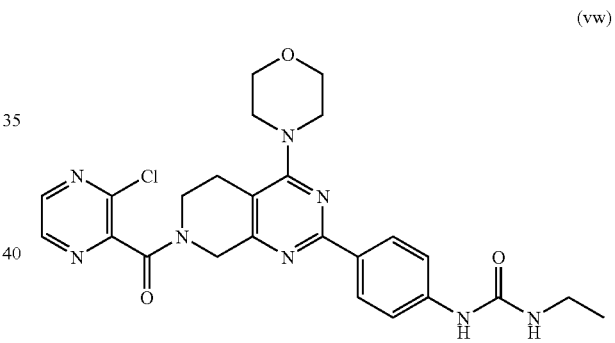

(vw)

Synthesis of 1-(4-(7-(3-chloropyrazine-2-carbonyl)-4-morpholino-5,6,7,8-tetrahydropyrido[3,4-d]pyrimidin-2-yl)phenyl)-3-ethylurea (vw): 3-Chloropyrazine-2-carboxylic acid (0.0648 g, 0.000409 mol) in dry Methylene chloride (1.50 mL, 0.0234 mol) was added N,N-Dimethylformamide (0.00200 mL, 0.0000258 mol) followed by Oxalyl chloride (0.040 mL, 0.00047 mol) dropwise. The reaction mixture was stirred for 3 hours then concentrated, added 1-ethyl-3-(4-(4-morpholino-5,6,7,8-tetrahydropyrido[3,4-d]pyrimidin-2-yl)phenyl)urea (0.102 g, 0.000267 mol), N,N-Dimethylformamide (1.80 mL, 0.0232 mol), and N,N-Diisopropylethylamine (0.180 mL, 0.00103 mol) and stirred overnight. The reaction mixture was filtered and purified by HPLC. $^1$H NMR (400 MHz, DMSO) δ 8.76 (dd, J=5.6, 2.5, 1H), 8.70-8.60 (m, 2H), 8.17 (dd, J=39.6, 8.8, 2H), 7.47 (dd, J=23.6, 8.8, 2H), 6.17 (dd, J=13.2, 5.7, 1H), 4.79 (s, 1H), 4.42 (s, 1H), 3.91 (t, J=5.4, 1H), 3.80-3.66 (m, 4H), 3.54-3.41 (m, 5H), 3.19-3.05 (m, 2H), 2.81 (t, J=5.1, 1H), 2.69 (t, J=5.0, 1H), 1.06 (q, J=7.2, 3H). LC/MS-m/z+523.2 (M+H)+.

Example 435

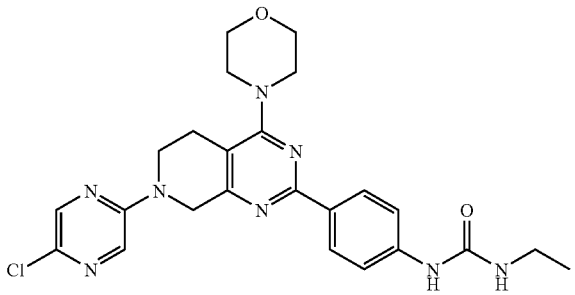
(vx)

Synthesis of 1-(4-(7-(5-chloropyrazin-2-yl)-4-morpholino-5,6,7,8-tetrahydropyrido[3,4-d]pyrimidin-2-yl)phenyl)-3-ethylurea (vx): 1-Ethyl-3-(4-(4-morpholino-5,6,7,8-tetrahydropyrido[3,4-d]pyrimidin-2-yl)phenyl)urea (0.0507 g, 0.132 mmol) and 2,5-dichloropyrazine (0.0320 g, 0.215 mmol) were combined then added dry N,N-Dimethylformamide (0.910 mL, 11.8 mmol) followed by N,N-Diisopropylethylamine (0.0456 mL, 0.262 mmol). The reaction was microwaved on 200 watts, 120° C. for 30 minutes on a CEM microwave. The reaction mixture was purified by HPLC. $^1$H NMR (500 MHz, DMSO) δ 8.67 (s, 1H), 8.30 (d, J=2.5, 1H), 8.21 (d, J=8.7, 2H), 8.02 (d, J=2.5, 1H), 7.49 (d, J=8.8, 2H), 6.17 (t, J=5.6, 1H), 4.57 (s, 2H), 3.79-3.65 (m, 6H), 3.50 (d, J=4.3, 4H), 3.12 (dt, J=14.1, 7.1, 2H), 2.86 (s, 2H), 1.06 (t, J=7.2, 3H). LC/MS-m/z+495.2 (M+H)+

Example 436

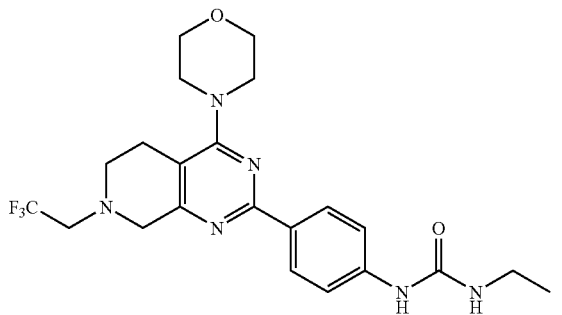
(vy)

Synthesis of 1-ethyl-3-(4-(4-morpholino-7-(2,2,2-trifluoroethyl)-5,6,7,8-tetrahydropyrido[3,4-d]pyrimidin-2-yl)phenyl)urea (vy)

Step 1—Synthesis of 4-(2-(4-Nitrophenyl)-7-(2,2,2-trifluoroethyl)-5,6,7,8-tetrahydropyrido[3,4-d]pyrimidin-4-yl)morpholine: 4-(2-(4-Nitrophenyl)-5,6,7,8-tetrahydropyrido[3,4-d]pyrimidin-4-yl)morpholine (0.101 g, 0.296 mmol), trifluoroethanol triflate (0.169 mL, 1.17 mmol) N,N-Diisopropylethylamine (0.306 mL, 1.76 mmol) dry Acetonitrile (1.50 mL, 28.7 mmol) and dry N,N-Dimethylformamide (1.50 mL, 19.4 mmol) were combined, The reaction was microwaved on 200 watts, 140° C. for 20 minutes on a CEM microwave. The reaction mixture was concentrated and chromatographed through silica gel (12 g, 0-40% EtOAc in hexanes). $^1$H NMR (500 MHz, CDCl$_3$) δ 8.54 (d, J=8.5, 2H), 8.28 (d, J=8.2, 2H), 3.98 (s, 2H), 3.89-3.82 (m, 4H), 3.63-3.53 (m, 4H), 3.23 (dd, J=18.8, 9.2, 2H), 2.95 (d, J=5.1, 2H), 2.80 (s, 2H). LC/MS-m/z+424.2 (M+H)+

Step 2—Synthesis of 4-(4Mmorpholino-7-(2,2,2-trifluoroethyl)-5,6,7,8-tetrahydropyrido[3,4-d]pyrimidin-2-yl)aniline: 4-(2-(4-Nitrophenyl)-7-(2,2,2-trifluoroethyl)-5,6,7,8-tetrahydropyrido[3,4-d]pyrimidin-4-yl)morpholine (0.0800 g, 0.000189 mol) Palladium on Carbon 10% (0.1:0.9, Palladium:carbon black, 0.1038 g), and Methanol (20.0 mL, 0.494 mol) were combined under N2 then purged with hydrogen, heated at 65° C., and stirred overnight. The reaction mixture was purged with N2, added celite, filtered through celite, and concentrated. $^1$H NMR (400 MHz, DMSO) δ 8.00 (d, J=8.6, 2H), 6.58 (d, J=8.6, 2H), 5.48 (s, 2H), 3.78 (s, 2H), 3.75-3.67 (m, 4H), 3.46-3.41 (m, 7H), 2.86 (d, J=5.3, 2H), 2.67 (s, 3H). LC/MS-m/z+394.2 (M+H)+

Step 3—Synthesis of compound vy: 4-(4Mmorpholino-7-(2,2,2-trifluoroethyl)-5,6,7,8-tetrahydropyrido[3,4-d]pyrimidin-2-yl)aniline (0.0743 g, 0.189 mmol) in dry N,N-Dimethylformamide (2.00 mL, 25.8 mmol) was added N,N-Diisopropylethylamine (0.0494 mL, 0.284 mmol) followed by Ethane, isocyanato- (0.0224 mL, 0.285 mmol) heated at 40° C. for 1 hour. The reaction mixture was cooled to room temperature, added N,N-Diisopropylethylamine (0.0494 mL, 0.284 mmol) and Ethane, isocyanato- (0.0224 mL, 0.285 mmol) and stirred overnight at room temperature. The reaction mixture was heated at 40° C. for 6 hours. LC-MS shows no improvement. N,N-Diisopropylethylamine (0.0988 mL, 0.567 mmol) and Ethane, isocyanato- (0.0446 mL, 0.568 mmol) were added to the reaction mixture. The reaction mixture was stirred overnight at 40° C. Added N,N-Diisopropylethylamine (0.0988 mL, 0.567 mmol) and Ethane, isocyanato- (0.0446 mL, 0.568 mmol) and stirred at 40° C. for 6 hours. Added N,N-Diisopropylethylamine (0.0988 mL, 0.567 mmol) and Ethane, isocyanato- (0.0446 mL, 0.568 mmol) and stirred overnight at 40° C. Added N,N-Diisopropylethylamine (0.0988 mL, 0.567 mmol) and Ethane, isocyanato- (0.0446 mL, 0.568 mmol) and stirred at 40° C. for 4 hours. The reaction mixture was concentrated and purified by HPLC. $^1$H NMR (500 MHz, DMSO) δ 8.66 (s, 1H), 8.16 (d, J=8.7, 2H), 7.47 (d, J=8.8, 2H), 6.17 (t, J=5.5, 1H), 3.82 (s, 2H), 3.76-3.69 (m, 4H), 3.45 (dt, J=20.2, 7.3, 6H), 3.18-3.05 (m, 2H), 2.87 (t, J=5.2, 2H), 2.70 (d, J=5.1, 2H), 1.05 (t, 3H). LC/MS-m/z+465.2 (M+H)+.

Example 437

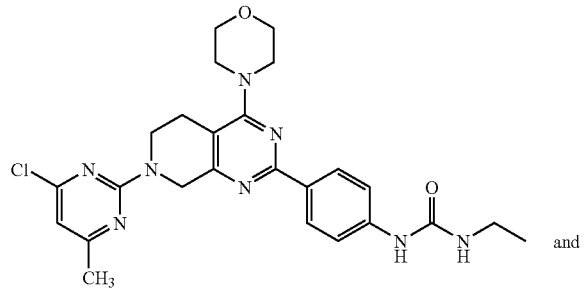
(vz$^1$)

and

-continued

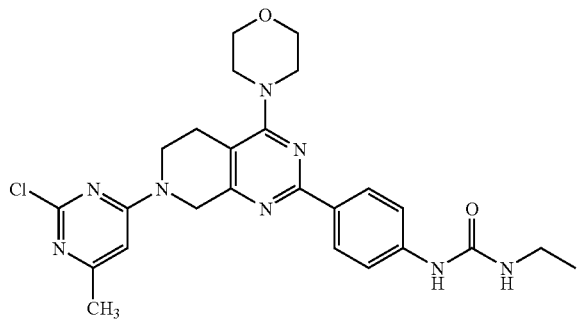

(vz²)

Synthesis of 1-(4-(7-(4-chloro-6-methylpyrimidin-2-yl)-4-morpholino-5,6,7,8-tetrahydropyrido[3,4-d]pyrimidin-2-yl)phenyl)-3-ethylurea (vz¹); and 1-(4-(7-(2-chloro-6-methylpyrimidin-4-yl)-4-morpholino-5,6,7,8-tetrahydropyrido[3,4-d]pyrimidin-2-yl)phenyl)-3-ethylurea (vz²): 1-Ethyl-3-(4-(4-morpholino-5,6,7,8-tetrahydropyrido[3,4-d]pyrimidin-2-yl)phenyl)urea (0.0506 g, 0.132 mmol) and 2,4-Dichloro-6-methylpyrimidine (0.0360 g, 0.221 mmol) were combined then added dry N,N-Dimethylformamide (0.910 mL, 11.8 mmol) followed by N,N-Diisopropylethylamine (0.0456 mL, 0.262 mmol). The reaction was microwaved on 200 watts, 120° C. for 30 minutes on a CEM microwave. The reaction mixture was concentrated, chromatographed through silica gel (4 g, 0-100% EtOAc in heptane), and then purified by HPLC. 1-(4-(7-(4-chloro-6-methylpyrimidin-2-yl)-4-morpholino-5,6,7,8-tetrahydropyrido[3,4-d]pyrimidin-2-yl)phenyl)-3-ethylurea (vz¹): $^1$H NMR (500 MHz, DMSO) δ 8.62 (s, 1H), 8.21 (d, J=8.8, 2H), 7.49 (d, J=8.8, 2H), 6.71 (s, 1H), 6.15 (t, J=5.6, 1H), 4.81 (s, 2H), 3.96 (s, 2H), 3.78-3.68 (m, 4H), 3.53-3.41 (m, 4H), 3.17-3.05 (m, 2H), 2.75 (t, J=5.2, 2H), 2.34 (s, 3H), 1.07 (t, J=7.2, 3H). LC/MS-m/z+509.2 (M+H)+; 1-(4-(7-(2-chloro-6-methylpyrimidin-4-yl)-4-morpholino-5,6,7,8-tetrahydropyrido[3,4-d]pyrimidin-2-yl)phenyl)-3-ethylurea (vz²): $^1$H NMR (500 MHz, DMSO) δ 8.63 (s, 1H), 8.21 (d, J=8.8, 2H), 7.49 (d, J=8.8, 2H), 6.88 (s, 1H), 6.16 (t, J=5.6, 1H), 4.69 (s, 2H), 3.86 (s, 2H), 3.78-3.69 (m, 4H), 3.56-3.43 (m, 4H), 3.18-3.04 (m, 2H), 2.77 (d, J=4.6, 2H), 2.29 (s, 3H), 1.06 (t, J=7.2, 3H). LC/MS-m/z+509.2 (M+H)+

Example 438

(wa)

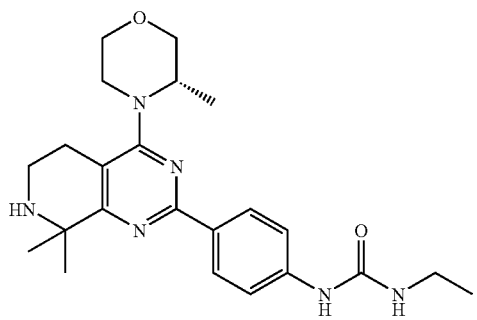

Synthesis of (S)-1-(4-(8,8-dimethyl-4-(3-methylmorpholino)-5,6,7,8-tetrahydropyrido[3,4-d]pyrimidin-2-yl)phenyl)-3-ethylurea (wa)

Step 1—Synthesis of (S)-tert-butyl 2-(4-(3-ethylureido)phenyl)-8,8-dimethyl-4-(3-methylmorpholino)-5,6-dihydropyrido[3,4-d]pyrimidine-7(8H)-carboxylate: (S)-tert-butyl 2-chloro-8,8-dimethyl-4-(3-methylmorpholino)-5,6-dihydropyrido[3,4-d]pyrimidine-7(8H)-carboxylate (0.133 g, 0.000335 mol), [4-Ethylureido)phenyl]boronic acid, pinacol ester (0.1248 g, 0.0004301 mol) Tetrakis(triphenylphosphine)palladium(0) (0.0378 g, 0.0000327 mol) Sodium carbonate (0.05327 g, 0.0005026 mol) and Potassium acetate (0.0548 g, 0.000558 mol) were combined, nitrogen purged three times, added dry Acetonitrile (2.800 mL, 0.05361 mol) followed by deoxygenated Water (1.70 mL, 0.0944 mol), and heated at 90° C. and stirred overnight. The reaction mixture was cooled to room temperature, diluted with water, extracted three times with 10% MeOH in dichloromethane, dried over Magnesium sulfate, filtered, concentrated, chromatographed through silica gel (12 g, 0-10% MeOH in dichloromethane), and purified by HPLC. $^1$H NMR (500 MHz, DMSO) δ 8.68 (s, 1H), 8.19 (d, J=8.8, 2H), 7.49 (d, J=8.8, 2H), 6.17 (t, J=5.6, 1H), 4.11 (d, J=6.7, 1H), 3.87 (d, J=11.5, 1H), 3.69 (dd, J=11.3, 2.6, 1H), 3.63-3.54 (m, 4H), 3.40 (dd, J=18.0, 8.2, 2H), 3.18-3.06 (m, 2H), 2.64 (d, J=4.0, 2H), 1.75 (d, J=1.0, 6H), 1.47 (s, 9H), 1.26 (d, J=6.6, 3H), 1.06 (t, J=7.2, 3H). LC/MS-m/z+525.3 (M+H)+.

Step 2—Synthesis of compound wa: (S)-tert-butyl 2-(4-(3-ethylureido)phenyl)-8,8-dimethyl-4-(3-methylmorpholino)-5,6-dihydropyrido[3,4-d]pyrimidine-7(8H)-carboxylate (0.0861 g, 0.000164 mol) in Methylene chloride (2.00 mL, 0.0312 mol) was added Trifluoroacetic Acid (0.38 mL, 0.0049 mol). The reaction mixture was stirred for 1 hour. The reaction mixture was concentrated, diluted with sat NaHCO3, extracted three times with 10% MeOH in dichloromethane, dried over Magnesium sulfate, filtered, concentrated, and purified by HPLC. $^1$H NMR (400 MHz, DMSO) δ 8.66 (s, 1H), 8.19 (d, J=8.8, 2H), 7.48 (d, J=8.8, 2H), 6.17 (t, J=5.5, 1H), 4.02 (d, J=6.9, 1H), 3.86 (d, J=11.1, 1H), 3.70 (dd, J=11.2, 2.5, 1H), 3.61 (t, J=11.0, 2H), 3.44 (dd, J=22.6, 9.4, 2H), 3.18-3.04 (m, 2H), 2.90-2.77 (m, 2H), 2.55 (t, J=5.1, 2H), 1.40 (d, J=6.9, 6H), 1.22 (d, J=6.6, 3H), 1.06 (t, J=7.2, 3H). LC/MS-m/z+425.2 (M+H)+.

Example 439

(wb¹)

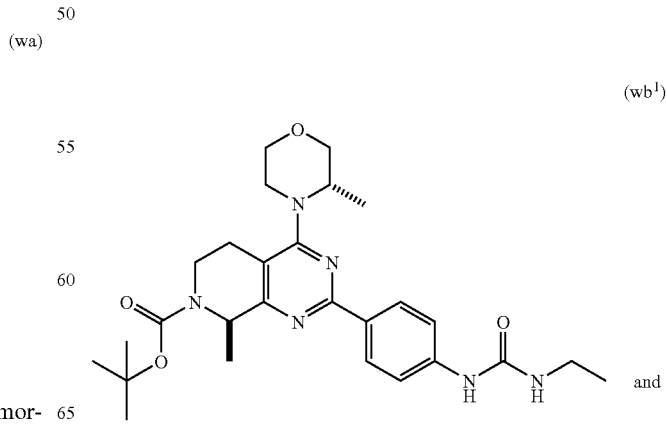

and

-continued (wb²)

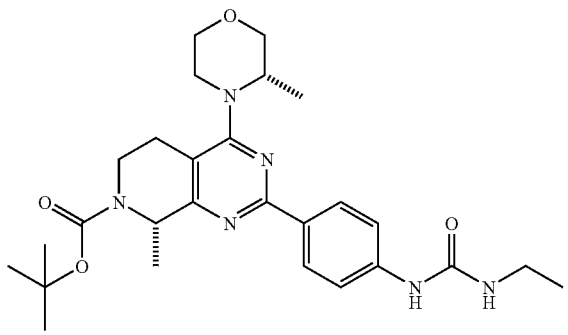

Synthesis of (R)-tert-butyl 2-(4-(3-ethylureido)phenyl)-8-methyl-4-((S)-3-methylmorpholino)-5,6-dihydropyrido[3,4-d]pyrimidine-7(8H)-carboxylate (wb¹); and (S)-tert-butyl 2-(4-(3-ethylureido)phenyl)-8-methyl-4-((S)-3-methylmorpholino)-5,6-dihydropyrido[3,4-d]pyrimidine-7(8H)-carboxylate (wb²)

Step 1—Synthesis of Tert-butyl 2-chloro-8-methyl-4-((S)-3-methylmorpholino)-5,6-dihydropyrido[3,4-d]pyrimidine-7(8H)-carboxylate: (S)-tert-butyl 2-chloro-4-(3-methylmorpholino)-5,6-dihydropyrido[3,4-d]pyrimidine-7(8H)-carboxylate (0.4986 g, 1.352 mmol) in dry Tetrahydrofuran (13.0 mL, 1.60E2 mmol) at −78° C. was added 1.6 M of n-Butyllithium in Hexane (5.00 mL) dropwise. The reaction mixture was stirred at −78° C. for 45 minutes then Methyl iodide (0.500 mL, 8.03 mmol) was added dropwise. The reaction mixture was stirred at −78° C. for 1 hour then added H₂O, extracted three times with CH₂Cl₂, dried over Magnesium sulfate, filtered, concentrated, and was chromatographed through silica gel (40 g, 0-25% EtOAc in hexanes): LC/MS-m/z+383.2 (M+H)+.

Step 2—Synthesis of compounds wb¹ and wb²: Tert-butyl 2-chloro-8-methyl-4-((S)-3-methylmorpholino)-5,6-dihydropyrido[3,4-d]pyrimidine-7(8H)-carboxylate (0.288 g, 0.000752 mol), [4-Ethylureido)phenyl]boronic acid, pinacol ester (0.2685 g, 0.0009253 mol) Tetrakis(triphenylphosphine)palladium(0) (0.0885 g, 0.0000766 mol) Sodium carbonate (0.1236 g, 0.001166 mol) and Potassium acetate (0.1260 g, 0.001284 mol) were combined, nitrogen purged three times, added dry Acetonitrile (6.50 mL, 0.124 mol) followed by deoxygenated Water (3.80 mL, 0.211 mol), and heated at 90° C. and stirred for 1 hour. The reaction mixture was diluted with water, extracted three times with 10% MeOH in dichloromethane, dried over Magnesium sulfate, filtered, concentrated, chromatographed through silica gel (40 g, 0-5% MeOH in dichloromethane), purified by HPLC, and the diastereomers were separated by SFC: R-Diastereomer (wb¹): ¹H NMR (500 MHz, DMSO) δ 8.64 (s, 1H), 8.19 (d, J=8.8, 2H), 7.48 (d, J=8.8, 2H), 6.14 (t, J=5.6, 1H), 4.90 (s, 1H), 4.14 (d, J=6.8, 1H), 4.05 (dd, J=10.6, 5.3, 1H), 3.87 (d, J=10.3, 1H), 3.80 (dd, J=11.2, 2.8, 1H), 3.64-3.57 (m, 1H), 3.51 (dd, J=17.2, 9.2, 2H), 3.36-3.30 (m, 2H), 3.16 (t, J=6.5, 1H), 3.15 (s, 2H), 2.91 (s, 1H), 2.84-2.73 (m, 1H), 2.56-2.45 (m, 2H), 1.52-1.43 (m, 9H), 1.07 (dt, J=15.1, 7.3, 6H). LC/MS-m/z+511.3 (M+H)+; S-Diastereomer (wb²): ¹H NMR (500 MHz, DMSO) δ 8.61 (s, 1H), 8.18 (d, J=8.8, 2H), 7.48 (d, J=8.8, 2H), 6.14 (t, J=5.6, 1H), 4.86 (s, 1H), 4.03 (dt, J=16.0, 6.0, 3H), 3.90-3.76 (m, 2H), 3.70 (dd, J=11.3, 8.8, 1H), 3.57 (dt, J=11.5, 6.7, 2H), 3.17 (d, J=5.2, 2H), 3.15-3.08 (m, 2H), 2.95 (s, 1H), 2.86-2.75 (m, 1H), 2.44 (d, J=15.2, 2H), 1.49 (d, J=6.7, 3H), 1.47-1.44 (m, 9H), 1.06 (t, J=7.2, 3H). LC/MS-m/z+511.3 (M+H)+.

Example 440

(wc)

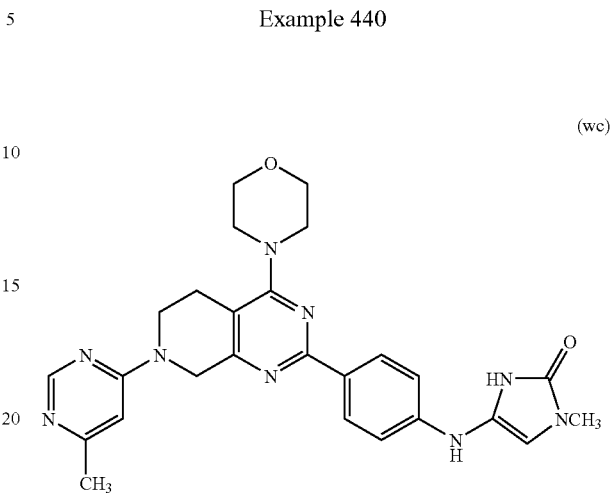

Synthesis of 1-methyl-4-(4-(7-(6-methylpyrimidin-4-yl)-4-morpholino-5,6,7,8-tetrahydropyrido[3,4-d]pyrimidin-2-yl)phenylamino)-1H-imidazol-2(3H)-one (wc): Compound wc was prepared in an analogous manner as described in Example 413: ¹H NMR (500 MHz, DMSO) δ 9.23 (s, 1H), 8.44 (s, 1H), 8.23 (d, J=8.8, 2H), 7.46 (d, J=8.8, 2H), 6.85 (s, 1H), 4.74 (d, J=18.5, 1H), 4.64 (d, J=18.2, 1H), 4.12 (s, 1H), 3.96 (s, 1H), 3.87 (d, J=12.0, 1H), 3.77 (d, J=5.5, 1H), 3.70 (d, J=8.4, 1H), 3.67-3.57 (m, 3H), 3.46-3.39 (m, 2H), 3.23 (s, 3H), 2.74 (d, J=5.1, 2H), 2.30 (s, 3H), 1.27 (d, J=6.7, 3H). LC/MS-m/z+515.2 (M+H)+

Example 441

(wd)

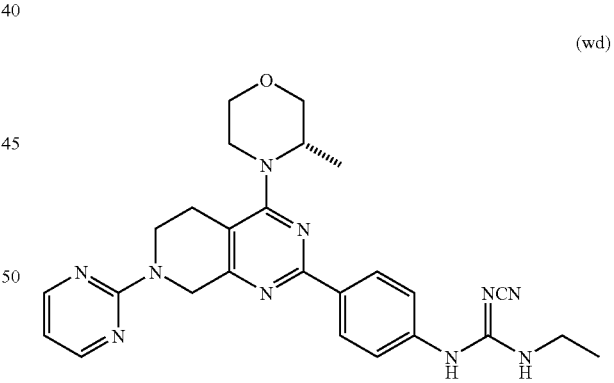

Synthesis of (S)-2-cyano-1-ethyl-3-(4-(4-(3-methylmorpholino)-7-(pyrimidin-2-yl)-5,6,7,8-tetrahydropyrido[3,4-d]pyrimidin-2-yl)phenyl)guanidine (wd): (S)-4-(4-(3-methylmorpholino)-7-(pyrimidin-2-yl)-5,6,7,8-tetrahydropyrido[3,4-d]pyrimidin-2-yl)aniline (0.0328 g, 0.0000813 mol) diphenyl cyanocarbonimidate (0.0643 g, 0.000270 mol) and Isopropyl alcohol (0.560 mL, 0.00732 mol) were combined, heated at 90° C., and stirred for 6 hours. then cooled too room temperature, added Ethylamine Hydrochloride (0.235 g, 0.00288 mol) and N,N-Diisopropylethylamine (0.566 mL, 0.00325 mol), heated at 50° C. and stirred for 3 days. The reaction mixture was concentrated and purified by HPLC. ¹H NMR (500 MHz, DMSO) δ 9.15 (s, 1H), 8.44 (d, J=4.7, 2H), 8.28 (d, J=8.6, 2H), 7.35 (d, J=8.6, 3H), 6.69 (t, J=4.7, 1H), 4.91 (d, J=18.6, 1H), 4.75 (d, J=18.6, 1H), 4.13 (dd, J=12.1, 6.5, 2H), 3.92-3.80 (m, 2H), 3.73-3.57 (m, 4H), 3.49-3.39 (m, 1H), 2.76 (s, 2H), 2.53-2.47 (m, 2H), 1.25 (t, J=7.5, 3H), 1.12 (t, J=7.1, 3H). LC/MS-m/z+499.2 (M+H)+.

Example 442

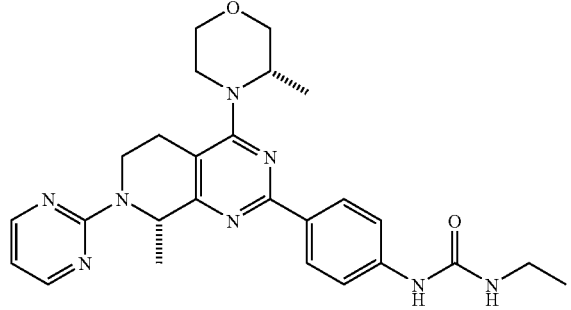

(we)

Synthesis of 1-ethyl-3-(4-((S)-8-methyl-4-((S)-3-methylmorpholino)-7-(pyrimidin-2-yl)-5,6,7,8-tetrahydropyrido[3,4-d]pyrimidin-2-yl)phenyl)urea (we)

Step 1—1-Ethyl-3-(4-((S)-8-methyl-4-((S)-3-methylmorpholino)-5,6,7,8-tetrahydropyrido[3,4-d]pyrimidin-2-yl)phenyl)urea: (S)-tert-butyl 2-(4-(3-ethylureido)phenyl)-8-methyl-4-((S)-3-methylmorpholino)-5,6-dihydropyrido[3,4-d]pyrimidine-7(8H)-carboxylate (0.068 g, 0.00013 mol) in Methylene chloride (1.60 mL, 0.0250 mol) was added Trifluoroacetic Acid (0.31 mL, 0.0040 mol). The reaction mixture was stirred for 1 hour. The reaction mixture was concentrated, diluted with sat NaHCO₃, extracted three times with 10% MeOH in dichloromethane, dried over Magnesium sulfate, filtered, concentrated, and purified by HPLC. LC/MS-m/z+411.3 (M+H)+.

Step 2—Synthesis of compound we: 1-Ethyl-3-(4-((S)-8-methyl-4-((S)-3-methylmorpholino)-5,6,7,8-tetrahydropyrido[3,4-d]pyrimidin-2-yl)phenyl)urea (0.0225 g, 0.0000548 mol) 2-Chloropyrimidine (0.0131 g, 0.000114 mol) N,N-Diisopropylethylamine (0.01910 mL, 0.0001096 mol) and dry N,N-Dimethylformamide (0.600 mL, 0.00775 mol) were combined and the reaction was microwaved on 200 watts, 120° C. for 1 hour on a CEM microwave. The reaction mixture was concentrated, chromatographed through silica gel (4 g, 0-10% MeOH in dichloromethane), and purified by HPLC. LC/MS-m/z+489.3 (M+H)+

Example 443

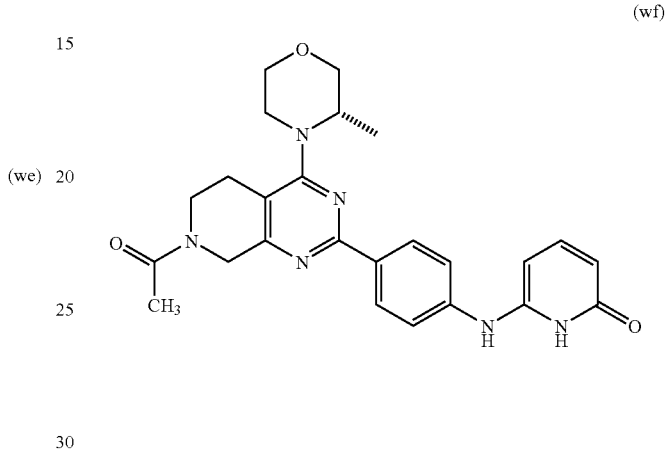

(wf)

Synthesis of (S)-6-(4-(7-acetyl-4-(3-methylmorpholino)-5,6,7,8-tetrahydropyrido[3,4-d]pyrimidin-2-yl)phenylamino)pyridin-2(1H)-one (wf)

Step 1—Synthesis of (S)-1-(2-(4-(6-(benzyloxy)pyridin-2-ylamino)phenyl)-4-(3-methylmorpholino)-5,6-dihydropyrido[3,4-d]pyrimidin-7(8H)-yl)ethanone: (S)-6-(benzyloxy)-N-(4-(4-(3-methylmorpholino)-5,6,7,8-tetrahydropyrido[3,4-d]pyrimidin-2-yl)phenyl)pyridin-2-amine (0.100 g, 0.197 mmol) in dry N,N-Dimethylformamide (1.00 mL, 12.9 mmol) was added N,N-Diisopropylethylamine (0.10 mL, 0.59 mmol) followed by Acetyl chloride (0.0210 mL, 0.295 mmol). The reaction mixture was stirred overnight. The reaction mixture was concentrated and chromatographed through silica gel (4 g, 0-5% MeOH in dichloromethane). ¹H NMR (400 MHz, DMSO) δ 9.33 (s, 1H), 8.20 (dd, J=8.8, 3.5, 2H), 7.68 (dd, J=8.8, 4.6, 2H), 7.54 (t, J=7.8, 1H), 7.47 (d, J=7.3, 2H), 7.39 (t, J=7.3, 2H), 7.33 (d, J=7.1, 1H), 6.47 (d, J=7.8, 1H), 6.27 (d, J=7.8, 1H), 5.39 (s, 2H), 4.74-4.52 (m, 2H), 4.45 (d, J=18.8, 1H), 4.12 (s, 1H), 3.89 (d, J=11.5, 1H), 3.67 (dd, J=33.8, 13.0, 6H), 2.75 (s, 1H), 2.62 (s, 1H), 2.12 (d, J=1.9, 3H), 1.33-1.20 (m, 3H). LC/MS-m/z+551.4 (M+H)+

Step 2—Synthesis of compound wf: (S)-1-(2-(4-(6-(benzyloxy)pyridin-2-ylamino)phenyl)-4-(3-methylmorpholino)-5,6-dihydropyrido[3,4-d]pyrimidin-7(8H)-yl)ethanone (0.098 g, 0.00018 mol), Palladium on Carbon 10% (0.1:0.9, Palladium:carbon black, 0.103 g), dry Methanol (5.00 mL, 0.123 mol) and Acetic acid (0.300 mL, 0.00528 mol) were combined under nitrogen then purged with hydrogen, heated at 65° C., and stirred overnight. The reaction mixture was purged with nitrogen, added celite, filtered through celite, concentrated, and purified by HPLC. ¹H NMR (400 MHz, DMSO) δ 10.23 (s, 1H), 9.13 (s, 1H), 8.21 (d, J=8.6, 2H), 7.78 (s, 2H), 7.42 (t, J=7.9, 1H), 6.32 (s, 1H), 5.99 (s, 1H), 4.71-4.43 (m, 2H), 4.10 (s, 1H), 3.88 (d, J=11.2, 1H), 3.82-3.56 (m, 5H), 3.44 (dd, J=26.9, 16.5, 2H), 2.75 (s, 1H), 2.62 (s, 1H), 2.13 (s, 3H), 1.26 (t, J=5.9, 3H). LC/MS-m/z+461.2 (M+H)+

Example 444

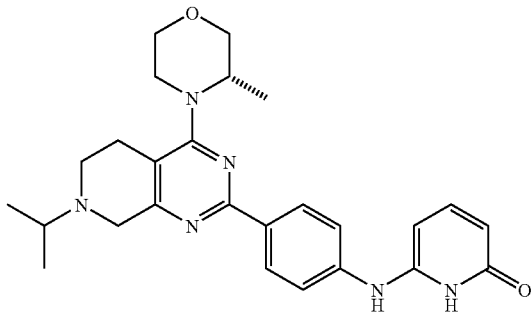
(wg)

Synthesis of (S)-6-(4-(7-isopropyl-4-(3-methylmorpholino)-5,6,7,8-tetrahydropyrido[3,4-d]pyrimidin-2-yl) phenylamino)pyridin-2(1H)-one (wg): The compound wg was synthesized according to the same route of Example 443. $^1$H NMR (400 MHz, DMSO) δ 10.22 (s, 1H), 9.08 (s, 1H), 8.19 (d, J=8.8, 2H), 7.76 (s, 2H), 7.42 (t, J=7.9, 1H), 6.31 (s, 1H), 6.00 (d, J=7.3, 1H), 4.13 (d, J=6.6, 1H), 3.88 (d, J=12.2, 1H), 3.65 (ddd, J=30.6, 14.7, 6.5, 6H), 3.42 (d, J=11.3, 1H), 2.87 (dt, J=12.9, 6.4, 1H), 2.75-2.62 (m, 3H), 2.59-2.53 (m, 1H), 1.24 (d, J=6.4, 3H), 1.08 (d, J=6.5, 6H). LC/MS-m/z+461.3 (M+H)+

Example 445

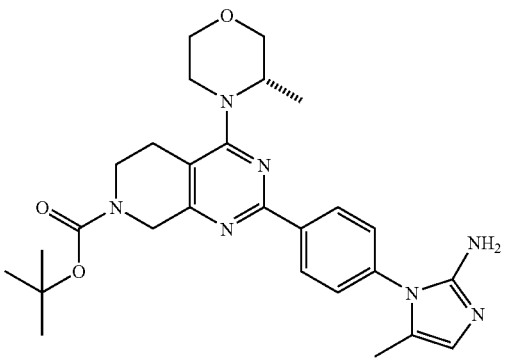
(wh)

Synthesis of (S)-tert-butyl 2-(4-(2-amino-5-methyl-1H-imidazol-1-yl)phenyl)-4-(3-methylmorpholino)-5,6-dihydropyrido[3,4-d]pyrimidine-7(8H)-carboxylate (wh)

Step 1—Synthesis of 1-(4-bromophenyl)-5-methyl-1H-imidazol-2-amine: 1-(4-Bromophenyl)guanidine nitrate (0.992 g, 3.58 mmol) in dry N,N-Dimethylformamide (12 mL, 150 mmol) was cooled at 0° C. then added N,N-Diisopropylethylamine (1.90 mL, 10.9 mmol) followed by Chloroacetone (0.258 mL, 3.24 mmol) in dry N,N-Dimethylformamide (12 mL, 150 mmol) dropwise. The reaction mixture was allowed to warm slowly to room temperature and stirred for 6 days. The reaction mixture was poured into ice, extracted three times with dichloromethane, dried over Magnesium sulfate, filtered, concentrated, and chromatographed through silica gel (12 g, 0-10% MeOH in dichloromethane). $^1$H NMR (400 MHz, CDCl$_3$) δ 7.62-7.56 (m, 2H), 7.29-7.22 (m, 2H), 6.38 (d, J=1.0, 1H), 3.47 (s, 2H), 2.16-2.07 (m, 3H). LC/MS-m/z+252.3 (M+H)+.

Step 2—Synthesis of 5-Methyl-1-(4-(4,4,5,5-tetramethyl-1,3,2-dioxaborolan-2-yl)phenyl)-1H-imidazol-2-amine: Bispinacol ester boronate (0.216 g, 0.850 mmol) [1,1'-Bis (diphenylphosphino)ferrocene]dichloropalladium(II), complex with dichloromethane (1:1) (0.231 g, 0.283 mmol) and Potassium acetate (0.184 g, 1.87 mmol) were combined, nitrogen purged three times, added 1-(4-bromophenyl)-5-methyl-1H-imidazol-2-amine (0.138 g, 0.547 mmol) in dry Dimethyl sulfoxide (2.00 mL, 28.2 mmol) heated at 80° C. and stirred overnight. The reaction mixture was diluted with water and extracted three times with 10% MeOH in dichloromethane. The aqueous layer was lyophilized, slurried with 10% MeOH in dichloromethane, filtered, and concentrated. The resulting material was used in the next step without further purification. LC/MS-m/z+218.0 (M+H)+

Step 3—Synthesis of compound wh: 5-Methyl-1-(4-(4,4,5,5-tetramethyl-1,3,2-dioxaborolan-2-yl)phenyl)-1H-imidazol-2-amine (0.164 g, 0.000548 mol), Tetrakis(triphenylphosphine)palladium(0) (0.0931 g, 0.0000806 mol) Sodium carbonate (0.0887 g, 0.000837 mol) and Potassium acetate (0.1061 g, 0.001081 mol) were combined, nitrogen purged three times, added (S)-tert-butyl 2-chloro-4-(3-methylmorpholino)-5,6-dihydropyrido[3,4-d]pyrimidine-7(8H)-carboxylate (0.219 g, 0.000594 mol) in dry Acetonitrile (4.60 mL, 0.0881 mol) and deoxygenated Water (2.80 mL, 0.155 mol) and the reaction was microwaved on 200 watts, 120° C. for 30 minutes on a CEM microwave. The reaction mixture was cooled to room temperature, diluted with water, extracted three times with 10% MeOH in dichloromethane, dried over Magnesium sulfate, filtered, concentrated, chromatographed through silica gel (120 g, 0-5% MeOH in dichloromethane), and purified by HPLC. $^1$H NMR (400 MHz, DMSO) δ 8.38 (t, J=8.8, 2H), 7.53 (d, J=8.7, 2H), 6.62 (d, J=1.0, 1H), 5.41 (s, 2H), 4.52 (t, J=15.6, 2H), 4.16 (d, J=6.7, 1H), 3.89 (d, J=10.8, 1H), 3.72-3.57 (m, 5H), 3.45 (dd, J=17.3, 7.1, 2H), 2.68 (d, J=6.6, 2H), 1.99 (d, J=0.9, 3H), 1.45 (d, J=7.9, 9H), 1.27 (d, J=6.6, 3H). LC/MS-m/z+506.3 (M+H)+

Example 446

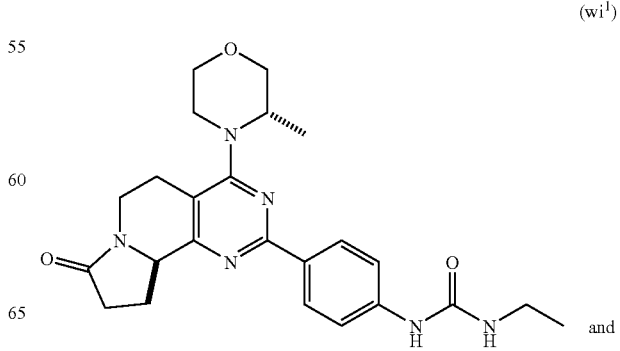
(wi$^1$)

and

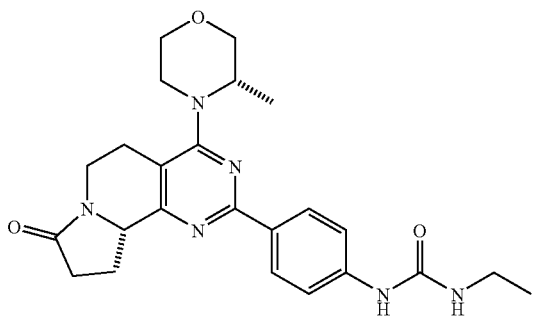

Synthesis of 1-ethyl-3-(4-((R)-4-((S)-3-methylmorpholino)-8-oxo-5,6,8,9,10,10a-hexahydropyrimido[5,4-g]indolizin-2-yl)phenyl)urea (wi¹); and 1-ethyl-3-(4-((S)-4-((S)-3-methylmorpholino)-8-oxo-5,6,8,9,10,10a-hexahydropyrimido[5,4-g]indolizin-2-yl)phenyl)urea (wi²)

Step 1—Synthesis of Tert-butyl 8-allyl-2-chloro-4-((S)-3-methylmorpholino)-5,6-dihydropyrido[3,4-d]pyrimidine-7(8H)-carboxylate: (S)-tert-butyl 2-chloro-4-(3-methylmorpholino)-5,6-dihydropyrido[3,4-d]pyrimidine-7(8H)-carboxylate (0.5037 g, 1.366 mmol) in dry tetrahydrofuran (10.0 mL, 123 mmol) at −78° C. was added 1.6 M of n-Butyllithium in Hexane (1.10 mL) dropwise. The reaction mixture was stirred at −78° C. for 1 hour then added allyl bromide (0.350 mL, 4.04 mmol) dropwise. The mixture was allowed to warm slowly to room temperature and stirred overnight. Water was added slowly and then the mixture was extracted three times with dichloromethane. The combined extract was dried over Magnesium sulfate, filtered, concentrated, and chromatographed through silica gel (12 g, 0-30% EtOAc in heptane). LC/MS-m/z+409.1 (M+H)+

Step 2—Synthesis of Tert-butyl 2-chloro-8-(3-hydroxypropyl)-4-((S)-3-methylmorpholino)-5,6-dihydropyrido[3,4-d]pyrimidine-7(8H)-carboxylate: Tert-butyl 8-allyl-2-chloro-4-((S)-3-methylmorpholino)-5,6-dihydropyrido[3,4-d]pyrimidine-7(8H)-carboxylate (0.504 g, 0.00123 mol) in dry Tetrahydrofuran (10.8 mL, 0.134 mol) at 0° C. was added 1.0 M of Borane-THF complex in Tetrahydrofuran (6.16 mL) dropwise. The reaction mixture was allowed to warm slowly to room temperature and stirred overnight. The reaction mixture cooled at 0° C. then added 1.0 M of Borane-THF complex in Tetrahydrofuran (6.16 mL). The reaction mixture was allowed to warm slowly to room temperature and stirred for 2 hours. Then 10 mL of 50% $H_2O_2$ and 10 mL of 1M NaOH were added and the mixture was stirred for 1 hour then extracted three times with dichloromethane. The combined extract was dried over Magnesium sulfate, filtered, concentrated, and chromatographed through silica gel (12 g, 0-100% EtOAc in heptane). LC/MS-m/z+427.3 (M+H)+

Step 3—Synthesis of Tert-butyl 2-chloro-4-((S)-3-methylmorpholino)-8-(3-oxopropyl)-5,6-dihydropyrido[3,4-d]pyrimidine-7(8H)-carboxylate: Tert-butyl 2-chloro-8-(3-hydroxypropyl)-4-((S)-3-methylmorpholino)-5,6-dihydropyrido[3,4-d]pyrimidine-7(8H)-carboxylate (0.387 g, 0.000906 mol) in dry methylene chloride (10.0 mL, 0.156 mol) was cooled at 0° C. then pyridinium chlorochromate (0.423 g, 0.00196 mol) was added. The reaction mixture was allowed to warm slowly to room temperature and stirred for 4 hours. The reaction mixture was concentrated and chromatographed through silica gel (40 g, 0-50% EtOAc in heptane). LC/MS-m/z+425.1 (M+H)+

Step 4—Synthesis of 3-(7-(Tert-butoxycarbonyl)-2-chloro-4-((S)-3-methylmorpholino)-5,6,7,8-tetrahydropyrido[3,4-d]pyrimidin-8-yl)propanoic acid: Tert-butyl 2-chloro-4-((S)-3-methylmorpholino)-8-(3-oxopropyl)-5,6-dihydropyrido[3,4-d]pyrimidine-7(8H)-carboxylate (0.193 g, 0.000454 mol) in dry tert-Butyl alcohol (10.0 mL, 0.104 mol) was added 2.0 M of 2-Methyl-2-butene in Tetrahydrofuran (11.0 mL) then added Sodium chlorite (0.132 g, 0.00146 mol) in Water (2.00 mL, 0.111 mol) and an equivalent volume of phosphate buffer dropwise. The reaction mixture was stirred overnight. The reaction mixture was acidified to pH3 by adding 1M HCl, extracted three times with 10% MeOH in dichloromethane. The combined extract was dried over Magnesium sulfate, filtered, concentrated, and was chromatographed through silica gel (12 g, 0-10% MeOH in dichloromethane). LC/MS-m/z+441.4 (M+H)+

Step 5—Synthesis of 3-(2-chloro-4-((S)-3-methylmorpholino)-5,6,7,8-tetrahydropyrido[3,4-d]pyrimidin-8-yl)propanoic acid: 3-(7-(Tert-butoxycarbonyl)-2-chloro-4-((S)-3-methylmorpholino)-5,6,7,8-tetrahydropyrido[3,4-d]pyrimidin-8-yl)propanoic acid (0.172 g, 0.000390 mol) in Methylene chloride (5.00 mL, 0.0780 mol) was added Trifluoroacetic Acid (0.90 mL, 0.012 mol) and stirred for 4 hours. LC-MS shows mostly product. The reaction mixture was concentrated and used in the next step without further purification. LC/MS-m/z+341.1 (M+H)+.

Step 6—Synthesis of 2-chloro-4-((S)-3-methylmorpholino)-5,6,10,10a-tetrahydropyrimido[5,4-g]indolizin-8(9H)-one: 3-(2-chloro-4-((S)-3-methylmorpholino)-5,6,7,8-tetrahydropyrido[3,4-d]pyrimidin-8-yl)propanoic acid (0.110 g, 0.000323 mol) in dry N,N-Dimethylformamide (11.0 mL, 0.142 mol) was added PyBOP (0.546 g, 0.00105 mol) followed by N,N-Diisopropylethylamine (0.282 mL, 0.00162 mol). The reaction mixture was stirred overnight. The reaction mixture was concentrated, diluted with 10% MeOH in dichloromethane and water, extracted three times with 10% MeOH in dichloromethane, dried over Magnesium sulfate, filtered, concentrated, and chromatographed through silica gel (12 g, 0-5% MeOH in dichloromethane). LC/MS-m/z+323.3 (M+H)+

Step 7—Synthesis of compounds wi¹ and wi²: [4-Ethylureido)phenyl]boronic acid, pinacol ester (0.1127 g, 0.0003884 mol) Tetrakis(triphenylphosphine)palladium(0) (0.0382 g, 0.0000330 mol) Sodium carbonate (0.0584 g, 0.000551 mol) and Potassium acetate (0.0582 g, 0.000593 mol) were combined, nitrogen purged three times, added 2-chloro-4-((S)-3-methylmorpholino)-5,6,10,10a-tetrahydropyrimido[5,4-g]indolizin-8(9H)-one (0.104 g, 0.000322 mol) in dry Acetonitrile (2.80 mL, 0.0536 mol) followed by deoxygenated Water (1.60 mL, 0.0888 mol), and the reaction was microwaved on 200 watts, 120° C. for 30 minutes on a CEM microwave. The reaction mixture was diluted with water, extracted three times with 10% MeOH in dichloromethane. The combined organic extract was dried over Magnesium sulfate, filtered, concentrated, chromatographed through silica gel (12 g, 0-100% EtOAc in heptane then switching to 10% MeOH in dichloromethane), purified by HPLC, and the diastereomers were separated by SFC. R-Diastereomer (wi¹): ¹H NMR (400 MHz, DMSO) δ 8.65 (s, 1H), 8.19 (d, J=8.7, 2H), 7.49 (d, J=8.7, 2H), 6.15 (t, J=5.6, 1H), 4.68 (t, J=8.2, 1H), 4.11 (dt, J=18.0, 9.1, 2H), 3.90-3.76 (m, 2H), 3.55 (ddd, J=32.3, 16.4, 6.7, 3H), 3.13 (ddd, J=14.1, 10.8, 6.2, 2H), 2.91 (t, J=10.1, 1H), 2.80-2.56 (m, 3H), 2.51 (m, 2H), 2.35-2.23 (m, 1H), 1.88 (dt, J=19.2, 9.7, 1H), 1.10-1.01 (m, 6H). LC/MS-m/z+451.2 (M+H)+; and S-Diastereomer (wi²): ¹H NMR (400 MHz, DMSO) δ 8.69 (s, 1H), 8.18 (d, J=8.7, 2H), 7.49 (d, J=8.8, 2H), 6.19 (t, J=5.6, 1H), 4.66 (t, J=8.1, 1H), 4.09 (dd, J=12.5, 5.2, 1H), 3.97 (d, J=6.5, 1H), 3.85 (d, J=11.2, 2H), 3.70 (t, J=10.2, 1H), 3.64-3.50 (m, 2H), 3.28 (d, J=11.4, 1H), 3.16-3.07 (m, 2H), 2.91 (t, J=10.5, 1H), 2.84-2.72 (m, 1H), 2.63 (dd, J=21.1, 8.9, 1H), 2.56-2.40 (m, 2H), 2.37-2.20 (m, 1H), 1.86 (dt, J=20.1, 9.9, 1H), 1.45 (d, J=6.7, 3H), 1.09-1.03 (m, 3H). LC/MS-m/z+ 451.2 (M+H)+.

Example 447

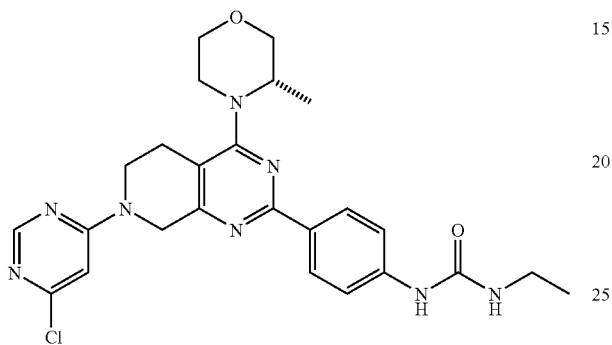

(wj)

Synthesis of (S)-1-(4-(7-(6-chloropyrimidin-4-yl)-4-(3-methylmorpholino)-5,6,7,8-tetrahydropyrido[3,4-d]pyrimidin-2-yl)phenyl)-3-ethylurea (wj): (S)-1-ethyl-3-(4-(4-(3-methylmorpholino)-5,6,7,8-tetrahydropyrido[3,4-d]pyrimidin-2-yl)phenyl)urea (0.196 g, 0.376 mmol), 4,6-dichloropyrimidine (0.112 g, 0.752 mmol) N,N-Diisopropylethylamine (0.150 mL, 0.861 mmol) and dry N,N-Dimethylformamide (1.1 mL, 14 mmol) were combined, The reaction was microwaved on 200 watts, 120° C. for 20 minutes on a CEM microwave. The reaction mixture was concentrated and chromatographed through silica gel (40 g, 0-10% MeOH in dichloromethane), and purified by HPLC. $^1$H NMR (500 MHz, DMSO) δ 8.69 (s, 1H), 8.41 (s, 1H), 8.20 (d, J=8.7, 2H), 7.50 (d, J=8.7, 2H), 7.12 (s, 1H), 6.20 (t, J=5.6, 1H), 4.72 (s, 3H), 4.12 (s, 1H), 4.08-3.92 (m, 1H), 3.88 (d, J=9.4, 1H), 3.80 (s, 1H), 3.64 (dt, J=25.7, 10.3, 4H), 3.43 (t, J=12.6, 1H), 3.17-3.04 (m, 2H), 2.75 (s, 2H), 1.26 (d, J=6.7, 3H), 1.06 (t, J=7.2, 3H). LC/MS-m/z+509.2 (M+H)+.

Example 448

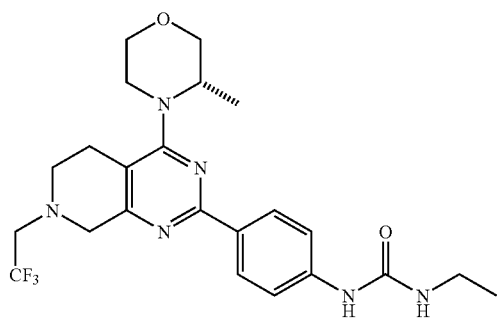

(wl)

Synthesis of (S)-1-ethyl-3-(4-(4-(3-methylmorpholino)-7-(2,2,2-trifluoroethyl)-5,6,7,8-tetrahydropyrido[3,4-d]pyrimidin-2-yl)phenyl)urea (wl): (S)-1-ethyl-3-(4-(4-(3-methylmorpholino)-5,6,7,8-tetrahydropyrido[3,4-d]pyrimidin-2-yl)phenyl)urea (0.139 g, 0.341 mmol) in dry N,N-Dimethylformamide (2.40 mL, 31.0 mmol) was added N,N-Diisopropylethylamine (0.0892 mL, 0.512 mmol) followed by Ethane, isocyanato- (0.0402 mL, 0.512 mmol). The reaction mixture was stirred for 4 hours the added N,N-Diisopropylethylamine (0.0892 mL, 0.512 mmol) and Ethane, isocyanato- (0.0402 mL, 0.512 mmol) and stirred overnight. The reaction mixture was concentrated, chromatographed through silica gel (12 g, 0-5% MeOH in dichloromethane), and purified by HPLC. $^1$H NMR (400 MHz, DMSO) δ 8.62 (s, 1H), 8.15 (d, J=8.7, 2H), 7.47 (d, J=8.8, 2H), 6.14 (t, J=5.6, 1H), 4.14 (d, J=6.5, 1H), 3.90-3.75 (m, 3H), 3.73-3.56 (m, 4H), 3.42 (q, J=10.1, 3H), 3.18-3.06 (m, 2H), 2.92 (dd, J=10.9, 5.3, 1H), 2.82 (dd, J=11.3, 5.9, 1H), 2.69 (s, 2H), 1.24 (d, J=6.6, 3H), 1.06 (t, J=7.2, 3H). LC/MS-m/z+479.2 (M+H)+.

Example 449

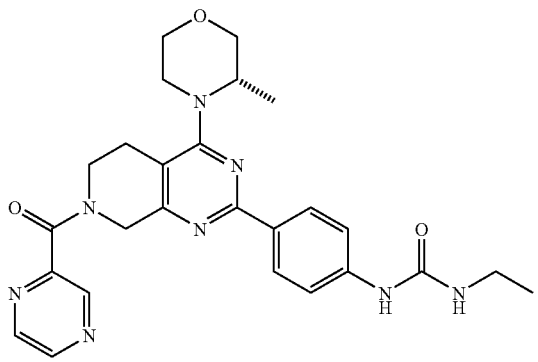

(wm)

Synthesis of (S)-1-ethyl-3-(4-(4-(3-methylmorpholino)-7-(pyrazine-2-carbonyl)-5,6,7,8-tetrahydropyrido[3,4-d]pyrimidin-2-yl)phenyl)urea (wm): (S)-1-ethyl-3-(4-(4-(3-methylmorpholino)-5,6,7,8-tetrahydropyrido[3,4-d]pyrimidin-2-yl)phenyl)urea (0.085 g, 0.00021 mol) in dry N,N-Dimethylformamide (1.00 mL, 0.0129 mol) was added N,N-Diisopropylethylamine (0.1120 mL, 0.0006430 mol) cooled at 0° C., added Pyrazine-2-carbonyl chloride (0.0508 g, 0.000356 mol) stirred at 0° C. for 30 minutes. The reaction mixture was filtered and purified by HPLC. $^1$H NMR (500 MHz, DMSO) δ 8.95 (dd, J=8.4, 1.3, 1H), 8.81 (dd, J=7.1, 2.5, 1H), 8.75 (d, J=3.9, 1H), 8.68 (d, J=15.6, 1H), 8.17 (dd, J=43.7, 8.7, 2H), 7.48 (dd, J=25.1, 8.8, 2H), 6.18 (dt, J=11.1, 5.6, 1H), 4.85 (d, J=18.5, 1H), 4.72 (d, J=7.4, 1H), 4.11 (d, J=5.5, 1H), 3.88 (d, J=9.3, 1H), 3.78-3.54 (m, 6H), 3.43 (t, J=12.3, 1H), 3.11 (dq, J=14.5, 7.2, 2H), 2.76 (s, 2H), 1.26 (d, J=6.6, 3H), 1.06 (q, J=7.3, 3H). LC/MS-m/z+503.2 (M+H)+.

Example 450

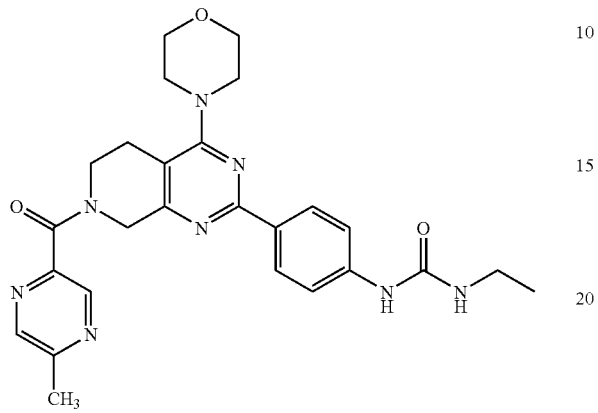

(wn)

Synthesis of 1-ethyl-3-(4-(7-(5-methylpyrazine-2-carbonyl)-4-morpholino-5,6,7,8-tetrahydropyrido[3,4-d]pyrimidin-2-yl)phenyl)urea (wn): 5-Methylpyrazine-2-carboxylic acid (0.0490 g, 0.000355 mol) in dry N,N-Dimethylformamide (1.80 mL, 0.0232 mol) was added 1-Hydroxybenzotriazole (0.0547 g, 0.000405 mol) followed by N-(3-Dimethylaminopropyl)-N'-ethylcarbodiimide hydrochloride (0.0797 g, 0.000416 mol) then followed by N,N-Diisopropylethylamine (0.114 mL, 0.000654 mol) and then 1-ethyl-3-(4-(4-morpholino-5,6,7,8-tetrahydropyrido[3,4-d]pyrimidin-2-yl)phenyl)urea (0.1007 g, 0.0002633 mol). The reaction mixture was stirred overnight. The reaction mixture was vacuum filtered, washed with DMF and then washed with water. $^1$H NMR (400 MHz, DMSO) δ 8.81 (d, J=3.3, 1H), 8.64 (d, J=12.5, 2H), 8.26-8.10 (m, 2H), 7.47 (dd, J=18.5, 8.7, 2H), 6.15 (dd, J=13.1, 5.8, 1H), 4.74 (d, J=15.5, 2H), 3.87 (s, 1H), 3.71 (dd, J=14.7, 4.6, 5H), 3.48 (d, J=3.9, 4H), 3.18-3.03 (m, 2H), 2.75 (d, J=13.1, 2H), 2.59 (s, 3H), 1.06 (dd, J=12.5, 7.1, 3H). LC/MS-m/z+503.2 (M+H)+.

Example 451

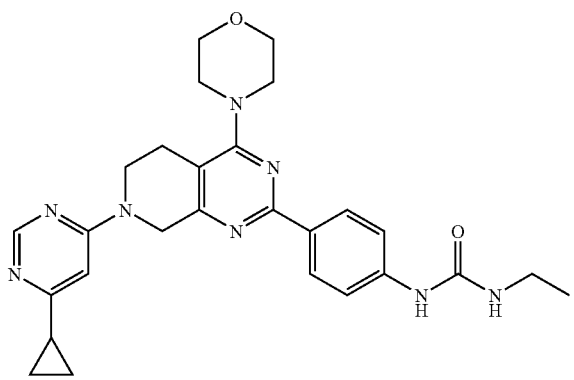

(wo)

Synthesis of 1-(4-(7-(6-cyclopropylpyrimidin-4-yl)-4-morpholino-5,6,7,8-tetrahydropyrido[3,4-d]pyrimidin-2-yl)phenyl)-3-ethylurea (wo): 1-Ethyl-3-(4-(4-morpholino-5,6,7,8-tetrahydropyrido[3,4-d]pyrimidin-2-yl)phenyl)urea (0.0597 g, 0.156 mmol), 4-chloro-6-cyclopropylpyrimidine (0.046 g, 0.30 mmol), N,N-Diisopropylethylamine (0.0570 mL, 0.327 mmol), and dry N,N-Dimethylformamide (0.84 mL, 11 mmol) were combined, the reaction was microwaved on 200 watts, 120° C. for 20 minutes on a CEM microwave. The reaction mixture was purified by HPLC. $^1$H NMR (400 MHz, DMSO) δ 8.70 (s, 1H), 8.37 (s, 1H), 8.21 (d, J=8.8, 2H), 7.50 (d, J=8.8, 2H), 6.91 (s, 1H), 6.21 (t, J=5.5, 1H), 4.70 (s, 2H), 3.88 (s, 2H), 3.73 (d, J=4.5, 4H), 3.48 (d, J=4.3, 4H), 3.16-3.08 (m, 2H), 2.75 (s, 2H), 2.01-1.91 (m, 1H), 1.06 (t, J=7.2, 3H), 1.02-0.88 (m, 4H). LC/MS-m/z+501.2 (M+H)+.

Example 452

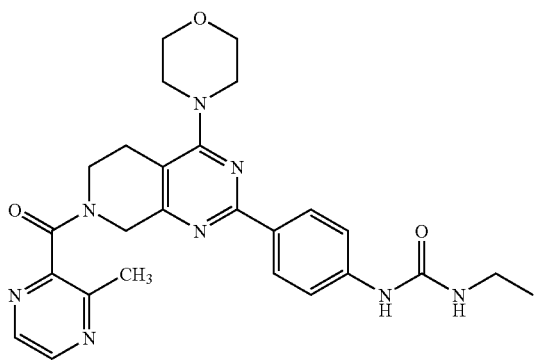

(wp)

Synthesis of 1-ethyl-3-(4-(7-(3-methylpyrazine-2-carbonyl)-4-morpholino-5,6,7,8-tetrahydropyrido[3,4-d]pyrimidin-2-yl)phenyl)urea (wp): 3-Methylpyrazine-2-carboxylic acid (0.0501 g, 0.000363 mol) in dry N,N-Dimethylformamide (1.80 mL, 0.0232 mol) was added 1-Hydroxybenzotriazole (0.0580 g, 0.000429 mol) followed by N-(3-Dimethylaminopropyl)-N'-ethylcarbodiimide hydrochloride (0.0765 g, 0.000399 mol) then followed by N,N-Diisopropylethylamine (0.1150 mL, 0.0006602 mol) and then 1-ethyl-3-(4-(4-morpholino-5,6,7,8-tetrahydropyrido[3,4-d]pyrimidin-2-yl)phenyl)urea (0.1021 g, 0.0002670 mol). The reaction mixture was stirred overnight. The reaction mixture was purified by HPLC. $^1$H NMR (400 MHz, DMSO) δ 8.73-8.60 (m, 2H), 8.55 (s, 1H), 8.17 (dd, J=43.9, 8.8, 2H), 7.47 (dd, J=25.7, 8.8, 2H), 6.22-6.10 (m, 1H), 4.79 (s, 1H), 4.37 (s, 1H), 3.90 (t, J=5.3, 1H), 3.78-3.66 (m, 4H), 3.56-3.37 (m, 6H), 3.21-3.03

(m, 2H), 2.81 (s, 1H), 2.68 (s, 1H), 2.53 (s, 2H), 1.06 (q, J=7.3, 3H). LC/MS-m/z+503.2 (M+H)+

Example 453

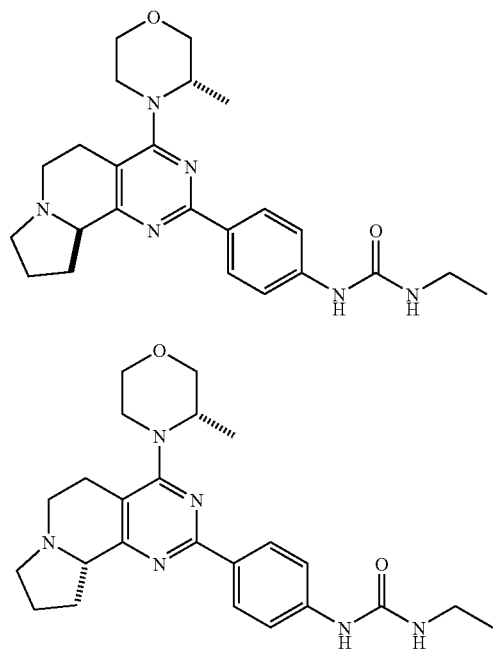

Synthesis of 1-ethyl-3-(4-((R)-4-((S)-3-methylmorpholino)-5,6,8,9,10,10a-hexahydropyrimido[5,4-g]indolizin-2-yl)phenyl)urea (wq¹); and 1-ethyl-3-(4-((S)-4-((S)-3-methylmorpholino)-5,6,8,9,10,10a-hexahydropyrimido[5,4-g]indolizin-2-yl)phenyl)urea (wq²): [4-Ethylureido)phenyl]boronic acid, pinacol ester (0.287 g, 0.000989 mol) (3S)-4-(2-chloro-5,6,8,9,10,10a-hexahydropyrimido[5,4-g]indolizin-4-yl)-3-methylmorpholine (0.251 g, 0.000813 mol), Tetrakis(triphenylphosphine)palladium(0) (0.04696 g, 4.064E-5 mol) Sodium carbonate (0.138 g, 0.00130 mol) and Potassium acetate (0.145 g, 0.00148 mol) were combined, nitrogen purged three times, added dry Acetonitrile (7.00 mL, 0.134 mol) followed by deoxygenated Water (4.00 mL, 0.222 mol), heated at 90° C. and stirred overnight. Added Tetrakis(triphenylphosphine)palladium(0) (0.062 g, 0.000054 mol) Sodium carbonate (0.059 g, 0.00056 mol) Potassium acetate (0.061 g, 0.00062 mol) Acetonitrile (3.50 mL, 0.0670 mol). The reaction mixture was heated at 120° C. for 8 hours. The reaction mixture was cooled to room temperature, diluted with water, extracted three times with 10% MeOH in dichloromethane, dried over Magnesium sulfate, filtered, concentrated, and, chromatographed through silica gel (12 g, 0-10% MeOH in dichloromethane), purified by HPLC, and the diastereomers were separated by SFC. R-Diastereomer (wq¹): ¹H NMR (400 MHz, DMSO) δ 8.66 (s, 1H), 8.16 (t, J=9.2, 2H), 7.47 (d, J=8.8, 2H), 6.18 (t, J=5.5, 1H), 4.16-4.05 (m, 1H), 3.86 (d, J=11.2, 1H), 3.78-3.66 (m, 2H), 3.65-3.54 (m, 2H), 3.49-3.40 (m, 2H), 3.17-3.06 (m, 2H), 3.05-2.89 (m, 3H), 2.87-2.75 (m, 1H), 2.75-2.60 (m, 2H), 2.37 (dd, J=15.5, 7.5, 1H), 1.84-1.71 (m, 3H), 1.17 (d, J=6.6, 3H), 1.12 (t, J=7.2, 2H). LC/MS-m/z+437.2 (M+H)+; S-Diastereomer (wq²): ¹H NMR (400 MHz, DMSO) δ 8.64 (s, 1H), 8.17 (d, J=8.7, 2H), 7.48 (d, J=8.7, 2H), 6.17 (t, J=5.3, 1H), 4.06 (s, 1H), 3.87 (d, J=11.2, 1H), 3.77 (d, J=7.7, 1H), 3.64 (dd, J=19.2, 10.4, 4H), 3.43-3.34 (m, 2H), 3.19-3.07 (m, 2H), 2.90 (dd, J=14.5, 8.1, 2H), 2.84-2.73 (m, 2H), 2.69 (d, J=10.8, 1H), 2.35 (d, J=8.5, 1H), 1.85-1.68 (m, 3H), 1.30 (d, J=6.6, 3H), 1.07 (t, J=7.2, 3H). LC/MS-m/z+437.2 (M+H)+.

Example 454

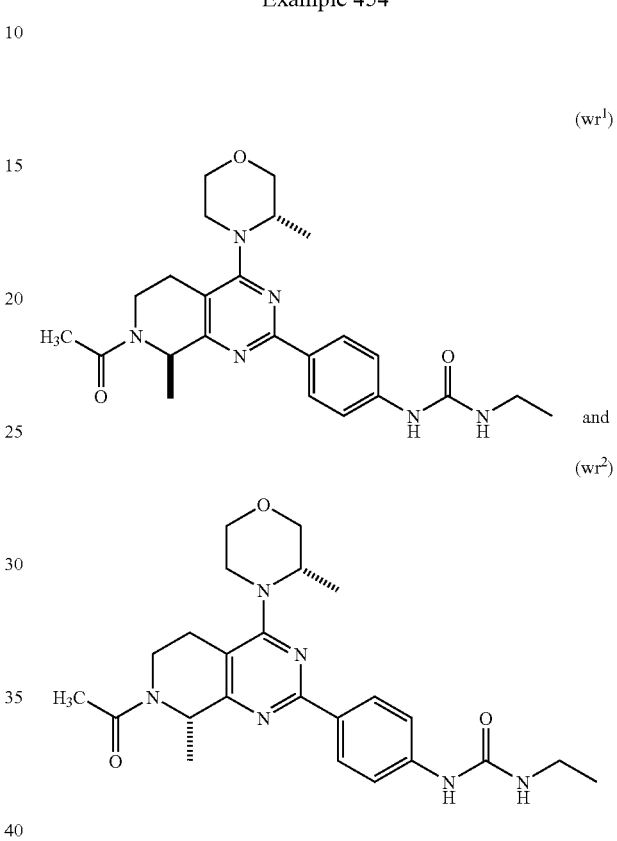

Synthesis of 1-(4-((R)-7-acetyl-8-methyl-4-((S)-3-methylmorpholino)-5,6,7,8-tetrahydropyrido[3,4-d]pyrimidin-2-yl)phenyl)-3-ethylurea (wr¹); and 1-(4-((S)-7-acetyl-8-methyl-4-((S)-3-methylmorpholino)-5,6,7,8-tetrahydropyrido[3,4-d]pyrimidin-2-yl)phenyl)-3-ethylurea (wr²): 1-Ethyl-3-(4-(8-methyl-4-((S)-3-methylmorpholino)-5,6,7,8-tetrahydropyrido[3,4-d]pyrimidin-2-yl)phenyl)urea (0.172 g, 0.419 mmol) in dry N,N-Dimethylformamide (2.00 mL, 25.8 mmol) was added N,N-Diisopropylethylamine (0.219 mL, 1.26 mmol) followed by Acetyl chloride (0.0448 mL, 0.630 mmol). The reaction mixture was stirred for 2 hours. The reaction mixture was purified by HPLC and the diastereomers were separated by SFC. R-Diastereomer (wr¹): ¹H NMR (400 MHz, DMSO) δ 8.69 (s, 1H), 8.18 (d, J=8.6, 2H), 7.48 (d, J=8.6, 2H), 6.21 (s, 1H), 3.99 (s, 1H), 3.88 (d, J=12.3, 2H), 3.71 (d, J=10.8, 1H), 3.58 (dd, J=23.8, 11.1, 2H), 3.13 (dd, J=13.5, 6.4, 2H), 3.06-2.91 (m, 3H), 2.71 (t, J=14.7, 1H), 2.38 (d, J=39.3, 1H), 2.12 (d, J=6.4, 3H), 1.58 (d, J=6.8, 1H), 1.47-1.42 (m, 3H), 1.13 (t, J=7.2, 3H), 1.06 (t, J=7.1, 3H). LC/MS-m/z+453.2 (M+H)+; and S-Diastereomer (wr²): ¹H NMR (400 MHz, DMSO) δ 8.74 (d, J=3.7, 1H), 8.20 (dd, J=8.8, 2.7, 2H), 7.49 (d, J=8.7, 2H), 6.23 (t, J=5.4, 1H), 4.14 (s, 1H), 3.91 (d, J=29.0, 2H), 3.80 (d, J=11.3, 1H), 3.66-3.57 (m, 1H), 3.51 (dd, J=16.3, 7.5, 2H), 3.20-3.08 (m, 5H), 3.03-2.87 (m, 1H), 2.79-2.61 (m, 1H), 2.13 (d, J=9.6, 3H), 1.59 (d, J=6.8, 1H), 1.45 (d, J=6.9, 2H), 1.16 (t, J=7.2, 6H), 1.11-1.00 (m, 6H).

Example 455

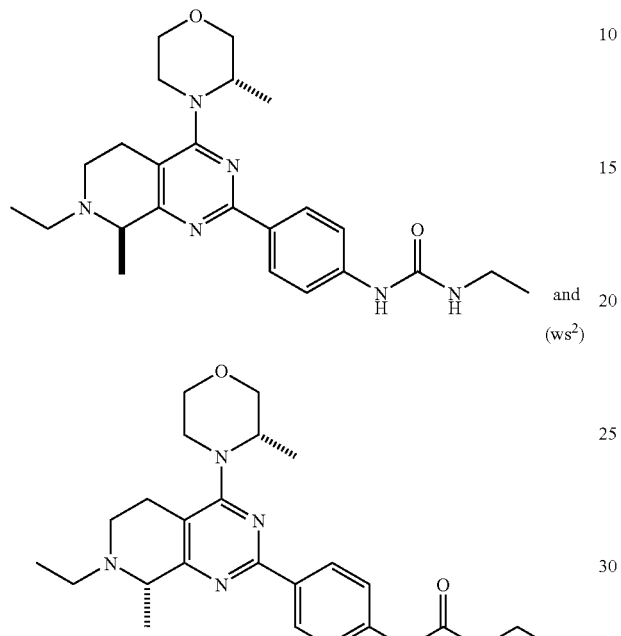

(ws¹)

and (ws²)

Synthesis of 1-ethyl-3-(4-((R)-7-ethyl-8-methyl-4-((S)-3-methylmorpholino)-5,6,7,8-tetrahydropyrido[3,4-d]pyrimidin-2-yl)phenyl)urea (ws¹); and 1-ethyl-3-(4-((S)-7-ethyl-8-methyl-4-((S)-3-methylmorpholino)-5,6,7,8-tetrahydropyrido[3,4-d]pyrimidin-2-yl)phenyl)urea (ws²): (1-Ethyl-3-(4-(8-methyl-4-((S)-3-methylmorpholino)-5,6,7,8-tetrahydropyrido[3,4-d]pyrimidin-2-yl)phenyl)urea (0.172 g, 0.419 mmol) in dry N,N-Dimethylformamide (2.00 mL, 25.8 mmol) at 0° C. was added Acetaldehyde (0.0236 mL, 0.420 mmol). The reaction mixture was stirred at 0° C. for 5 minutes the added Sodium triacetoxyborohydride (0.182 g, 0.859 mmol) followed by Acetic acid (0.0476 mL, 0.838 mmol). The reaction mixture was allowed to warm slowly to room temperature and stirred overnight. The reaction mixture was diluted with 1 M NaOH, extracted three times with 10% MeOH in dichloromethane, dried over Magnesium sulfate, filtered, and concentrated. The reaction mixture was redissovled in dry N,N-Dimethylformamide (2.00 mL, 25.8 mmol) cooled at 0° C., then added Acetaldehyde (0.0236 mL, 0.420 mmol). The reaction mixture was stirred at 0° C. for 5 minutes then added Sodium triacetoxyborohydride (0.181 g, 0.854 mmol) followed by Acetic acid (0.0476 mL, 0.837 mmol). The reaction mixture was stirred for 3 days. The reaction mixture was diluted with 1M NaOH, extracted three times with 10% MeOH in dichloromethane, dried over Magnesium sulfate, filtered, concentrated, purified by HPLC, and the diastereomers were separated by SFC. R Diastereomer (ws¹): ¹H NMR (400 MHz, DMSO) δ 8.66 (s, 1H), 8.17 (d, J=8.7, 2H), 7.47 (d, J=8.8, 2H), 6.19 (t, J=5.6, 1H), 4.12 (d, J=6.7, 1H), 3.87 (d, J=11.1, 1H), 3.73 (dd, J=11.3, 2.7, 1H), 3.64-3.49 (m, 4H), 3.47-3.38 (m, 2H), 3.16-3.09 (m, 2H), 3.01-2.93 (m, 1H), 2.80 (dq, J=14.5, 7.3, 1H), 2.67 (t, J=7.4, 1H), 2.60-2.53 (m, 1H), 2.41-2.31 (m, 1H), 1.42 (d, J=6.6, 3H), 1.18 (d, J=6.6, 3H), 1.14 (t, J=7.2, 3H), 1.06 (t, 3H). LC/MS-m/z+439.3 (M+H)+; and S-Diastereomer (ws²): ¹H NMR (400 MHz, DMSO) δ 8.65 (s, 1H), 8.17 (d, J=8.7, 2H), 7.47 (d, J=8.8, 2H), 6.19 (t, J=5.5, 1H), 4.08 (d, J=6.7, 1H), 3.86 (d, J=11.3, 1H), 3.71-3.55 (m, 5H), 3.39 (d, J=11.4, 1H), 3.16-3.08 (m, 2H), 2.90 (dd, J=11.6, 4.7, 1H), 2.74 (dq, J=14.3, 7.2, 1H), 2.69-2.53 (m, 3H), 2.47-2.40 (m, 1H), 1.38 (d, J=6.6, 3H), 1.29 (d, J=6.6, 3H), 1.13 (t, J=7.2, 3H), 1.07 (t, 3H).

Example 456

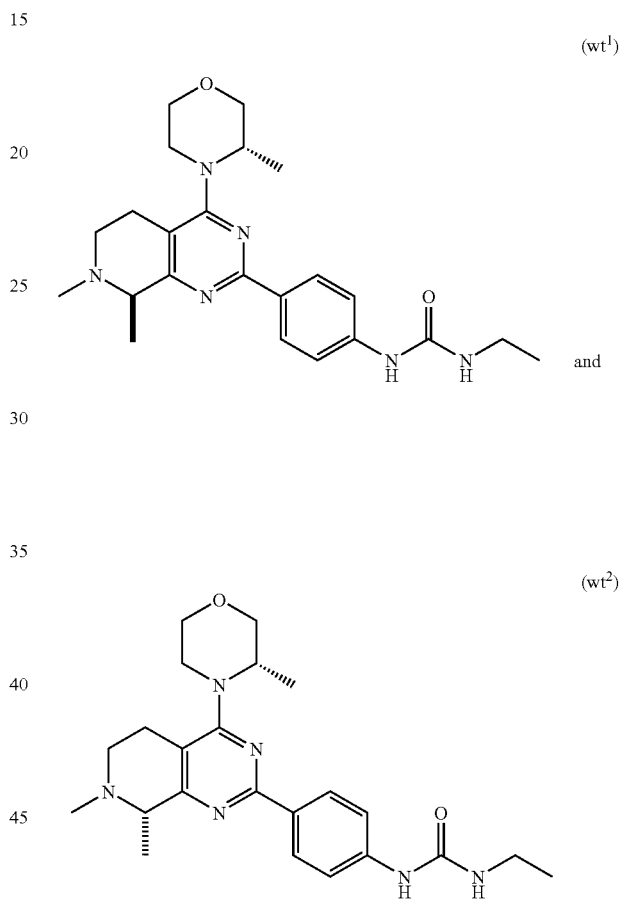

(wt¹)

and (wt²)

Synthesis of 1-(4-((R)-7,8-dimethyl-4-((S)-3-methylmorpholino)-5,6,7,8-tetrahydropyrido[3,4-d]pyrimidin-2-yl)phenyl)-3-ethylurea (wt¹); and 1-(4-((S)-7,8-dimethyl-4-((S)-3-methylmorpholino)-5,6,7,8-tetrahydropyrido[3,4-d]pyrimidin-2-yl)phenyl)-3-ethylurea (wt²): Compounds wt¹ and wt² were prepared in a similar manner as described in Example 455. R-Diastereomer (wt¹): ¹H NMR (400 MHz, DMSO) δ 8.62 (s, 1H), 8.18 (d, J=8.8, 2H), 7.47 (d, J=8.8, 2H), 6.14 (t, J=5.5, 1H), 4.14 (d, J=6.7, 1H), 3.87 (d, J=10.8, 1H), 3.77 (dd, J=11.3, 2.7, 1H), 3.66-3.37 (m, 6H), 3.16-3.07 (m, 2H), 2.92 (d, J=11.1, 1H), 2.82 (t, J=12.6, 1H), 2.38 (d, J=12.9, 3H), 2.34-2.22 (m, 1H), 1.48 (d, J=6.6, 3H), 1.19 (t, J=7.2, 3H), 1.12 (d, J=6.6, 3H). LC/MS-m/z+425.2 (M+H)+; S-Diastereomer (wt²): ¹H NMR (400 MHz, DMSO) δ 8.63 (s, 1H), 8.17 (d, J=8.7, 2H), 7.47 (d, J=8.8, 2H), 6.17 (t, J=5.5, 1H), 4.05 (d, J=6.9, 1H), 3.86 (d, J=10.2, 1H), 3.77 (d, J=13.5, 1H), 3.71-3.59 (m, 3H), 3.50 (s, 1H), 2.95-2.86 (m, 1H), 2.81

(dd, J=15.0, 9.1, 1H), 2.41 (d, J=12.5, 3H), 2.34-2.26 (m, 1H), 1.44 (d, J=6.6, 3H), 1.38 (d, J=6.7, 3H), 1.25-1.12 (m, 7H). LC/MS-m/z+425.2 (M+H)+

Example 457

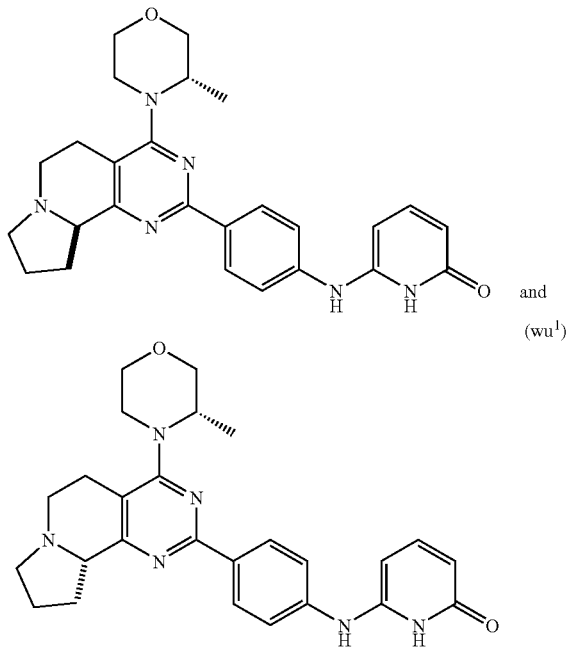

Synthesis of 6-(4-((R)-4-((S)-3-methylmorpholino)-5,6,8,9,10,10a-hexahydropyrimido[5,4-g]indolizin-2-yl)phenylamino)pyridin-2(1H)-one (wu¹); and 6-(4-((S)-4-((S)-3-methylmorpholino)-5,6,8,9,10,10a-hexahydropyrimido[5,4-g]indolizin-2-yl)phenylamino)pyridin-2(1H)-one (wu²)

Step 1—Synthesis of Tert-butyl 2-chloro-8-(3-hydroxypropyl)-4-((S)-3-methylmorpholino)-5,6-dihydropyrido[3,4-d]pyrimidine-7(8H)-carboxylate: Tert-butyl 8-allyl-2-chloro-4-((S)-3-methylmorpholino)-5,6-dihydropyrido[3,4-d]pyrimidine-7(8H)-carboxylate (7.042 g, 0.01722 mol) in dry Tetrahydrofuran (126.0 mL, 1.553 mol) at 0° C. was added Catecholborane (9.00 mL, 0.0844 mol) dropwise. The reaction mixture was allowed to warm slowly to room temperature and stirred overnight. The reaction mixture was cooled at 0° C. then added 1.0 M of Borane-THF complex in Tetrahydrofuran (52.0 mL) dropwise. The reaction mixture was allowed to warm slowly LC-MS shows about 50% conversion. The reaction mixture was cooled at at 0° C., added 1.0 M of Borane-THF complex in Tetrahydrofuran (34.0 mL) dropwise, allowed to warm slowly to room temperature and stirred overnight. The reaction mixture was cooled at 0° C. then added 50% hydrogen peroxide and 100 mL of 1M NaOH, stirred for 1 hour, then extracted three times with 10% MeOH in dichloromethane, dried over Magnesium sulfate, filtered, concentrated, was chromatographed through silica gel (120 g, 0-100% EtOAc in heptane). LC/MS-m/z+427.1 (M+H)+

Step 2—Synthesis of Tert-butyl 2-chloro-4-((S)-3-methylmorpholino)-8-(3-(methylsulfonyloxy)propyl)-5,6-dihydropyrido[3,4-d]pyrimidine-7(8H)-carboxylate Tert-butyl 2-chloro-8-(3-hydroxypropyl)-4-((S)-3-methylmorpholino)-5,6-dihydropyrido[3,4-d]pyrimidine-7(8H)-carboxylate (1.999 g, 0.004682 mol) in dry Methylene chloride (27.0 mL, 0.422 mol) was cooled at 0° C., added Triethylamine (1.30 mL, 0.00933 mol) followed by Methanesulfonyl chloride (0.52 mL, 0.0067 mol) dropwise. The reaction mixture was stirred at 0° C. for 1 hour. The reaction mixture was concentrated and was chromatographed through silica gel (80 g, 0-5% MeOH in dichloromethane). LC/MS-m/z+505.1 (M+H)+

Step 3—Synthesis of (3S)-4-(2-chloro-5,6,8,9,10,10a-hexahydropyrimido[5,4-g]indolizin-4-yl)-3-methylmorpholine: Tert-butyl 2-chloro-4-((S)-3-methylmorpholino)-8-(3-(methylsulfonyloxy)propyl)-5,6-dihydropyrido[3,4-d]pyrimidine-7(8H)-carboxylate (1.915 g, 0.003792 mol) in dry Methylene chloride (22.0 mL, 0.343 mol) at 0° C. was added Trifluoroacetic Acid (9.00 mL, 0.117 mol) dropwise. The reaction mixture was allowed to warm slowly to room temperature and stirred for 2.5 hours. The reaction mixture was concentrated and vacuum pump dried then redissolved in dry Methylene chloride (110.0 mL, 1.716 mol) cooled at 0° C., added Triethylamine (1.80 mL, 0.0129 mol) dropwise, stirred for 1 hour at 0° C. The reaction mixture was allowed to warm slowly to room temperature and stirred overnight. The reaction mixture was cooled at 0° C. then added Triethylamine (1.80 mL, 0.0129 mol) dropwise. The reaction mixture was stirred at 0° C. for 1 hour. The reaction mixture was concentrated and chromatographed through silica gel (80 g, 0-10% MeOH in dichloromethane). The reaction mixture was redissolved with 10% MeOH in dichloromethane and sat NaHCO3, extracted three times with 10% MeOH in dichloromethane, dried over Magnesium sulfate, filtered, and concentrated. LC/MS-m/z+309.3 (M+H)+

Step 4—Synthesis of 6-(Benzyloxy)-N-(4-(4-((S)-3-methylmorpholino)-5,6,8,9,10,10a-hexahydropyrimido[5,4-g]indolizin-2-yl)phenyl)pyridin-2-amine: (3S)-4-(2-chloro-5,6,8,9,10,10a-hexahydropyrimido[5,4-g]indolizin-4-yl)-3-methylmorpholine (0.2513 g, 0.0008138 mol), 6-(benzyloxy)-N-(4-(4,4,5,5-tetramethyl-1,3,2-dioxaborolan-2-yl)phenyl)pyridin-2-amine (0.397 g, 0.000987 mol) Tetrakis(triphenylphosphine)palladium(0) (0.088 g, 0.000076 mol) Sodium carbonate (0.131 g, 0.00124 mol) and Potassium acetate (0.135 g, 0.00138 mol) were combined, nitrogen purged three times, added dry Acetonitrile (7.00 mL, 0.134 mol) followed by deoxygenated Water (4.00 mL, 0.222 mol), heated at 120° C. and stirred overnight. The reaction mixture was diluted with water, extracted three times with 10% MeOH in dichloromethane, dried over Magnesium sulfate, filtered, concentrated, and chromatographed through silica gel (40 g, 0-10% MeOH in dichloromethane). ¹H NMR (400 MHz, CDCl₃) δ 8.34 (d, J=8.6, 2H), 7.47 (dd, J=7.5, 3.7, 3H), 7.44 (s, 1H), 7.40 (dd, J=13.0, 5.9, 3H), 7.32 (t, J=7.2, 1H), 6.51 (s, 1H), 6.47 (d, J=7.8, 1H), 6.31 (d, J=7.9, 1H), 5.39 (s, 2H), 4.14-4.01 (m, 1H), 3.95 (d, J=11.2, 1H), 3.90-3.71 (m, 3H), 3.66 (dd, J=11.2, 2.9, 1H), 3.58-3.41 (m, 2H), 3.16-2.91 (m, 2H), 2.82 (d, J=10.7, 2H), 2.61 (dd, J=29.9, 11.8, 2H), 1.92 (s, 3H), 1.35 (d, J=6.6, 1H), 1.26 (t, J=7.2, 3H). LC/MS-m/z+549.4 (M+H)+

Step 5—Synthesis of compounds wu¹ and wu²: 6-(Benzyloxy)-N-(4-(4-((S)-3-methylmorpholino)-5,6,8,9,10,10a-hexahydropyrimido[5,4-g]indolizin-2-yl)phenyl)pyridin-2-amine was purged under nitrogen then added 20% Palladium hydroxide on carbon (2:8, Palladium hydroxide:carbon black, 0.189 g) followed by dry Methanol (7.00 mL, 173 mmol) Acetic acid (0.70 mL, 12 mmol) and dry Tetrahydrofuran (7.00 mL, 86.3 mmol) purged with hydrogen, heated at 65° C. and stirred overnight under an atmosphere of hydrogen. The reaction mixture was purged with nitrogen, added celite, filtered through celite, concentrated, purified by HPLC and the diastereomers were separated by SFC. R-Diastereomer (wu¹): ¹H NMR (400 MHz, DMSO) δ 10.23 (s, 1H), 9.08 (s, 1H), 8.20 (d, J=8.8, 2H), 7.77 (s, 2H), 7.42 (t, J=7.9, 1H), 6.31 (s, 1H), 5.99 (d, J=7.8, 1H), 4.07 (d, J=6.9, 1H), 3.87 (d, J=11.8, 1H), 3.77 (d, J=7.6, 1H), 3.71-3.57 (m, 4H), 3.44-3.36 (m, 1H), 2.99-2.84 (m, 2H), 2.77 (d, J=6.1, 2H), 2.69 (d, J=7.9, 1H), 2.51 (m, 1H), 2.42-2.29 (m, 1H), 1.85-1.68 (m, 3H), 1.31 (d, J=6.6, 3H). LC/MS-m/z+459.2 (M+H)+; S-Diastereomer (wu²): ¹H NMR (400 MHz, DMSO) δ 10.24 (s, 1H), 9.10 (s, 1H), 8.20 (d, J=8.8, 2H), 7.77 (s, 2H), 7.41 (t, J=7.9, 1H), 6.30 (d, J=6.3, 1H), 5.99 (d, J=7.9, 1H), 4.11 (d, J=6.5, 1H), 3.87 (d, J=11.0, 1H), 3.81-3.66 (m, 2H), 3.66-3.56 (m, 2H), 3.44 (d, J=4.8, 2H), 2.97 (dd, J=14.1, 10.4, 2H), 2.87-2.76 (m, 1H), 2.75-2.59 (m, 2H), 2.51 (m, 1H), 2.36 (dd, J=16.4, 6.9, 1H), 1.77 (s, 3H), 1.20 (t, J=11.0, 3H).

Example 458

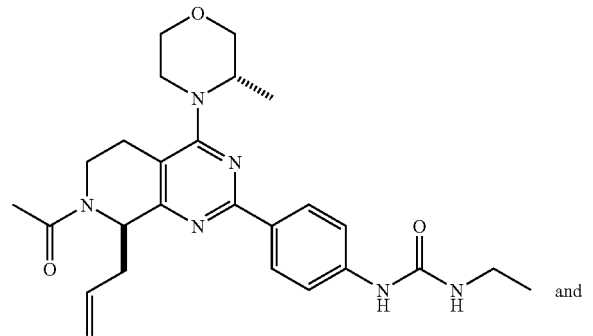

(wv¹)

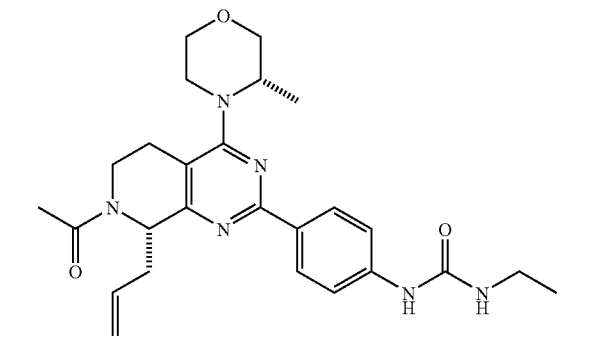

(wv²)

Synthesis of 1-(4-((R)-7-acetyl-8-allyl-4-((S)-3-methylmorpholino)-5,6,7,8-tetrahydropyrido[3,4-d]pyrimidin-2-yl)phenyl)-3-ethylurea (wv¹); and 1-(4-((S)-7-acetyl-8-allyl-4-((S)-3-methylmorpholino)-5,6,7,8-tetrahydropyrido[3,4-d]pyrimidin-2-yl)phenyl)-3-ethylurea (wv²)

Step 1—Tert-butyl 8-allyl-2-(4-(3-ethylureido)phenyl)-4-((S)-3-methylmorpholino)-5,6-dihydropyrido[3,4-d]pyrimidine-7(8H)-carboxylate: Tert-butyl 8-allyl-2-chloro-4-((S)-3-methylmorpholino)-5,6-dihydropyrido[3,4-d]pyrimidine-7(8H)-carboxylate (1.3636 g, 0.0033346 mol) (from Example 446), [4-Ethylureido)phenyl]boronic acid, pinacol ester (1.192 g, 0.004108 mol) Tetrakis(triphenylphosphine)palladium(0) (0.339 g, 0.000293 mol) Sodium carbonate (0.543 g, 0.00512 mol) and Potassium acetate (0.534 g, 0.00544 mol) were combined, nitrogen purged three times, added dry Acetonitrile (29.0 mL, 0.555 mol) followed by deoxygenated Water (16.0 mL, 0.888 mol), heated at 90° C. and stirred overnight. The reaction mixture was diluted with water, extracted three times with 10% MeOH in dichloromethane, dried over Magnesium sulfate, filtered, concentrated, and chromatographed through silica gel (120 g, 0-5% MeOH in dichloromethane) to provide the desired product. LC/MS-m/z+537.4 (M+H)+

Step 2—Synthesis of 1-(4-(8-Allyl-4-((S)-3-methylmorpholino)-5,6,7,8-tetrahydropyrido[3,4-d]pyrimidin-2-yl)phenyl)-3-ethylurea: Tert-butyl 8-allyl-2-(4-(3-ethylureido)phenyl)-4-((S)-3-methylmorpholino)-5,6-dihydropyrido[3,4-d]pyrimidine-7(8H)-carboxylate (1.624 g, 0.003026 mol) in Methylene chloride (18.0 mL, 0.281 mol) was added Trifluoroacetic Acid (7.00 mL, 0.0908 mol) slowly. The reaction mixture was stirred for 2 hours. LC-MS shows reaction is complete. The reaction mixture was concentrated, diluted with sat NaHCO3, extracted three times with sat NaHCO3, dried over Magnesium sulfate, filtered, concentrated, purified by HPLC, and the diastereomers were separated by SFC. R-allyl Diastereomer: ¹H NMR (400 MHz, DMSO) δ 8.66 (s, 1H), 8.18 (d, J=8.7, 2H), 7.48 (d, J=8.8, 2H), 6.16 (t, J=5.6, 1H), 5.91 (td, J=17.2, 7.2, 1H), 5.07 (dd, J=24.7, 13.7, 2H), 4.09 (d, J=7.0, 1H), 3.87 (d, J=11.0, 2H), 3.76 (d, J=8.6, 1H), 3.58 (dd, J=19.7, 9.3, 2H), 3.50-3.38 (m, 2H), 3.12 (dt, J=12.9, 5.6, 3H), 2.91 (s, 1H), 2.73-2.58 (m, 2H), 2.43 (dd, J=15.0, 7.5, 3H), 1.12 (d, J=6.6, 3H), 1.06 (t, J=7.2, 3H), 0.93 (t, J=7.1, 1H). LC/MS-m/z+437.2 (M+H)+; and S allyl Diastereomer ¹H NMR (400 MHz, DMSO) δ 8.65 (s, 1H), 8.18 (d, J=8.8, 2H), 7.47 (d, J=8.8, 2H), 6.16 (t, J=5.5, 1H), 5.92 (td, J=17.1, 7.1, 1H), 5.08 (dd, J=24.0, 13.5, 2H), 4.03 (d, J=6.4, 1H), 3.85 (t, J=10.0, 2H), 3.74-3.57 (m, 4H), 3.19-3.07 (m, 2H), 3.06-2.97 (m, 1H), 2.87 (s, 1H), 2.68 (d, J=4.7, 2H), 2.43 (dd, J=18.9, 11.4, 2H), 1.34 (d, J=6.6, 3H), 1.06 (t, J=7.2, 3H).

Step 4—Synthesis of compounds wv¹ and wv²: 1-(4-(8-Allyl-4-((S)-3-methylmorpholino)-5,6,7,8-tetrahydropyrido[3,4-d]pyrimidin-2-yl)phenyl)-3-ethylurea (1.253 g, 2.870 mmol) in dry N,N-Dimethylformamide (15.0 mL, 194 mmol) was cooled at 0° C. then added N,N-Diisopropylethylamine (1.500 mL, 8.611 mmol) followed by Acetyl chloride (0.31 mL, 4.4 mmol) dropwise. The reaction mixture was stirred overnight. The reaction mixture was concentrated, chromatographed through silica gel (120 g, 0-5% MeOH in dichloromethane), purified by HPLC. The diastereomers were separated by SFC. R-Diastereomer (wv¹): ¹H NMR (400 MHz, DMSO) δ 8.67 (s, 1H), 8.19 (dd, J=8.7, 3.2, 2H), 7.49 (d, J=8.7, 2H), 6.18 (s, 1H), 5.84 (ddd, J=34.3, 17.1, 7.6, 1H), 5.37 (dd, J=9.2, 4.1, 1H), 5.16-4.93 (m, 2H), 4.00 (s, 1H), 3.95-3.81 (m, 2H), 3.70 (t, J=11.1, 1H), 3.65-3.48 (m, 2H), 3.30-3.21 (m, 1H), 3.17-3.06 (m, 2H), 2.92 (dd, J=34.7, 13.2, 2H), 2.68 (ddd, J=23.1, 18.5, 9.0, 2H), 2.42 (dd, J=14.4, 7.2, 2H), 2.09 (d, J=16.1, 3H), 1.45 (d, J=6.6, 3H), 1.06 (t, J=7.2, 3H), 0.93 (t, J=7.1, 2H). LC/MS-m/z+479.2 (M+H)+; and S Diastereomer (wv²): ¹H NMR (400 MHz, DMSO) δ 8.69 (s, 1H), 8.21 (dd, J=8.7, 4.2, 2H), 7.49 (d, J=8.7, 2H), 6.17 (s, 1H), 6.03-5.67 (m, 1H), 5.41 (dd, J=9.1, 4.1, 1H), 5.20-4.93 (m, 2H), 4.14 (s, 1H), 3.91 (dd, J=22.7, 10.4, 2H), 3.80 (d, J=10.7, 1H), 3.62 (d, J=10.3, 1H), 3.58-3.45 (m, 2H), 3.24 (d, J=11.5, 1H), 3.16-3.06 (m, 2H), 2.91 (dd, J=27.1, 12.9, 2H), 2.81-2.57 (m, 2H), 2.54-2.41 (m, 1H), 2.10 (d, J=12.9, 3H), 1.14-1.01 (m, 6H), 0.93 (t, J=7.1, 1H).

Example 459

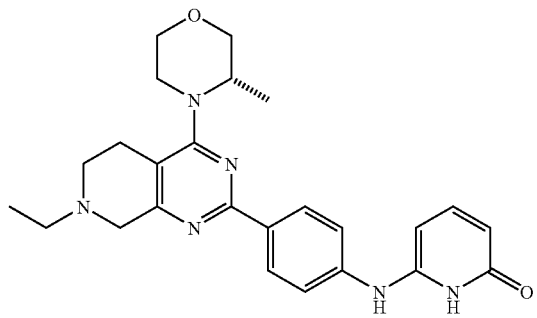

(ww)

Synthesis of (S)-6-(4-(7-ethyl-4-(3-methylmorpholino)-5,6,7,8-tetrahydropyrido[3,4-d]pyrimidin-2-yl)phenylamino)pyridin-2(1H)-one (ww)

Step 1—Synthesis of (S)-1-(2-(4-(6-(benzyloxy)pyridin-2-ylamino)phenyl)-4-(3-methylmorpholino)-5,6-dihydropyrido[3,4-d]pyrimidin-7(8H)-yl)ethanone: (S)-6-(benzyloxy)-N-(4-(4-(3-methylmorpholino)-5,6,7,8-tetrahydropyrido[3,4-d]pyrimidin-2-yl)phenyl)pyridin-2-amine (0.202 g, 0.397 mmol) in dry N,N-Dimethylformamide (2.00 mL, 25.8 mmol) was added N,N-Diisopropylethylamine (0.20 mL, 1.2 mmol) followed by Acetyl chloride (0.0420 mL, 0.591 mmol). The reaction mixture was stirred for 1.5 hours. LC-MS shows mostly product. The reaction mixture was concentrated and chromatographed through silica gel (12 g, 0-5% MeOH in dichloromethane). LC/MS-m/z+549.1 (M+H)+

Step 2-(S)-6-(benzyloxy)-N-(4-(7-ethyl-4-(3-methylmorpholino)-5,6,7,8-tetrahydropyrido[3,4-d]pyrimidin-2-yl)phenyl)pyridin-2-amine: (S)-1-(2-(4-(6-(benzyloxy)pyridin-2-ylamino)phenyl)-4-(3-methylmorpholino)-5,6-dihydropyrido[3,4-d]pyrimidin-7(8H)-yl)ethanone (0.1732 g, 0.0003145 mol) in dry Tetrahydrofuran (2.4 mL, 0.030 mol) at 0° C. was added 1.0 M of Borane-THF complex in Tetrahydrofuran (1.0 mL) dropwise. The reaction mixture was warmed to room temperature and for 2 hours. The reaction mixture was cooled at 0° C. then added 1M HCl until the reaction mixture stops bubbling then added 1M NaOH until pH10. The reaction mixture was extracted three times with 10% MeOH in dichloromethane, dried over Magnesium sulfate, filtered, concentrated, and chromatographed through silica gel (12 g, 0-100% EtOAc in heptane). LC/MS-m/z+ 537.4 (M+H)+.

Step 3—Synthesis of compound ww: (S)-6-(benzyloxy)-N-(4-(7-ethyl-4-(3-methylmorpholino)-5,6,7,8-tetrahydropyrido[3,4-d]pyrimidin-2-yl)phenyl)pyridin-2-amine (0.082 g, 0.15 mmol) was purged under nitrogen then added 20% Palladium hydroxide on carbon (2:8, Palladium hydroxide: carbon black, 0.065 g) followed by dry Methanol (2.20 mL, 54.3 mmol) Acetic acid (0.21 mL, 3.7 mmol) and dry Tetrahydrofuran (2.20 mL, 27.1 mmol) purged with hydrogen, heated at 40° C. and stirred overnight under an atmosphere of hydrogen. The reaction mixture was purged with nitrogen, added celite, filtered through celite, concentrated, chromatographed through silica gel (12 g, 0-10% MeOH in dichloromethane), and purified by HPLC. $^1$H NMR (400 MHz, DMSO) δ 10.21 (s, 1H), 9.06 (s, 1H), 8.20 (d, J=8.8, 2H), 7.74 (s, 2H), 7.42 (t, J=7.9, 1H), 6.30 (s, 1H), 6.00 (d, J=7.1, 1H), 4.14 (d, J=5.9, 1H), 3.89 (d, J=10.8, 1H), 3.72 (d, J=8.7, 1H), 3.63 (d, J=12.3, 4H), 3.45 (dd, J=32.9, 14.4, 2H), 2.69 (s, 3H), 2.58-2.47 (m, 3H), 1.25 (d, J=6.6, 3H), 1.12 (t, J=7.1, 3H). LC/MS-m/z+447.2 (M+H)+

Example 460

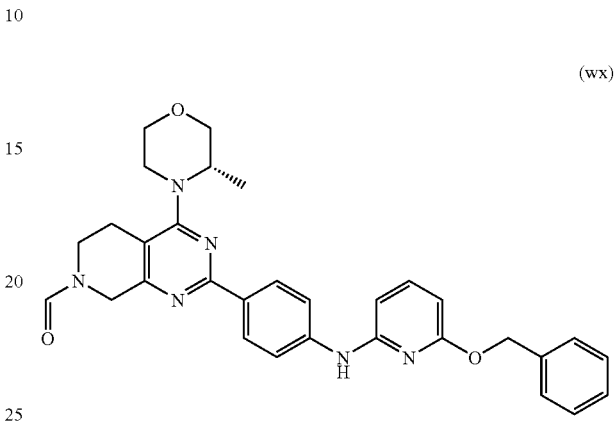

(wx)

Synthesis of (S)-2-(4-(6-(benzyloxy)pyridin-2-ylamino)phenyl)-4-(3-methylmorpholino)-5,6-dihydropyrido[3,4-d]pyrimidine-7(8H)-carbaldehyde (wx): (S)-6-(benzyloxy)-N-(4-(4-(3-methylmorpholino)-5,6,7,8-tetrahydropyrido[3,4-d]pyrimidin-2-yl)phenyl)pyridin-2-amine (0.2684 g, 0.5277 mmol), 2-(1H-benzotriazole-1-yl)-1,1,3,3-tetramethyluronium tetrafluoroborate (0.226 g, 0.704 mmol) and Formic acid (0.0294 mL, 0.779 mmol) were combined then added dry N,N-Dimethylformamide (2.20 mL, 28.4 mmol) followed by N,N-Diisopropylethylamine (0.507 mL, 2.91 mmol). The reaction mixture stirred for 1 hour then concentrated and chromatographed through silica gel (12 g, 0-5% MeOH in dichloromethane). $^1$H NMR (500 MHz, DMSO) δ 9.33 (s, 1H), 8.20 (dd, J=7.4, 5.2, 2H), 7.70-7.65 (m, 2H), 7.54 (t, J=7.9, 1H), 7.47 (d, J=7.7, 2H), 7.39 (t, J=7.5, 2H), 7.32 (t, J=7.2, 1H), 6.47 (d, J=7.9, 1H), 6.27 (d, J=7.7, 1H), 5.39 (s, 2H), 4.58 (dt, J=18.2, 12.9, 2H), 4.41 (d, J=19.0, 1H), 4.08 (s, 1H), 3.89 (d, J=11.5, 1H), 3.80-3.51 (m, 5H), 3.44 (s, 1H), 2.73 (s, 1H), 2.69 (s, 1H), 1.30-1.18 (m, 3H). LC/MS-m/z+ 537.4 (M+H)+.

Example 461

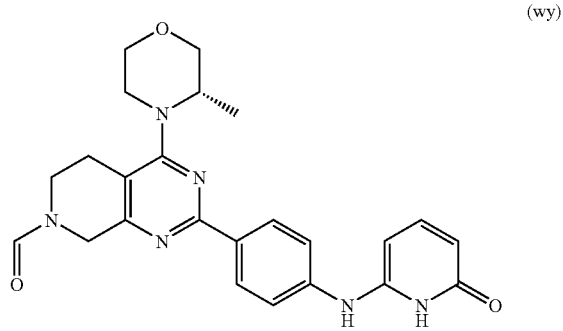

(wy)

Synthesis of (S)-4-(3-methylmorpholino)-2-(4-(6-oxo-1,6-dihydropyridin-2-ylamino)phenyl)-5,6-dihydropyrido[3, 4-d]pyrimidine-7(8H)-carbaldehyde (wy): (S)-2-(4-(6-(benzyloxy)pyridin-2-ylamino)phenyl)-4-(3-methylmorpholino)-5,6-dihydropyrido[3,4-d]pyrimidine-7(8H)-carbaldehyde (0.066 g, 0.00012 mol), Palladium on Carbon 10% (0.1:0.9, Palladium:carbon black, 0.094 g), dry Methanol (3.30 mL, 0.0815 mol) and Acetic acid (0.21 mL, 0.0037 mol) were combined under nitrogen then purged with hydrogen, heated at 40° C., and stirred overnight. The reaction mixture was purged with nitrogen, added celite, filtered through celite, concentrated, and purified by HPLC. $^1$H NMR (400 MHz, DMSO) δ 10.23 (s, 1H), 9.14 (s, 1H), 8.31-8.16 (m, 3H), 7.76 (s, 2H), 7.42 (t, J=7.8, 1H), 6.31 (s, 1H), 6.00 (d, J=8.1, 1H), 4.69-4.39 (m, 2H), 4.07 (d, J=5.4, 2H), 3.89 (d, J=11.1, 1H), 3.75-3.38 (m, 4H), 3.18 (d, J=4.4, 2H), 2.74 (s, 1H), 2.66 (d, J=12.1, 1H), 1.27 (t, J=6.4, 3H). LC/MS-m/z+ 447.2 (M+H)+.

Example 462

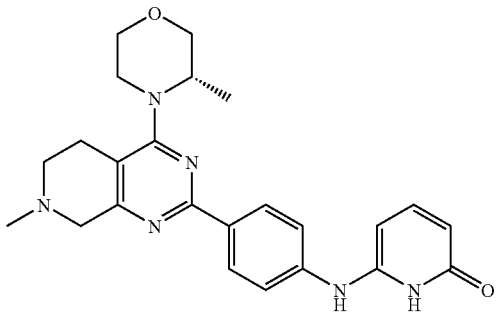

(wz)

Synthesis of (S)-6-(4-(7-methyl-4-(3-methylmorpholino)-5,6,7,8-tetrahydropyrido[3,4-d]pyrimidin-2-yl)phenylamino)pyridin-2(1H)-one (wz)

Step 1—Synthesis of (S)-6-(benzyloxy)-N-(4-(7-methyl-4-(3-methylmorpholino)-5,6,7,8-tetrahydropyrido[3,4-d]pyrimidin-2-yl)phenyl)pyridin-2-amine: (S)-2-(4-(6-(benzyloxy)pyridin-2-ylamino)phenyl)-4-(3-methylmorpholino)-5,6-dihydropyrido[3,4-d]pyrimidine-7(8H)-carbaldehyde (0.183 g, 0.000341 mol) in dry Tetrahydrofuran (2.50 mL, 0.0308 mol) at 0° C. was added 1.0 M of Borane-THF complex in Tetrahydrofuran (1.00 mL) dropwise. The reaction mixture was warmed to room temperature and for 2 hours. The reaction mixture was cooled at 0° C. then added 1M HCl until the reaction mixture stops bubbling then added 1M NaOH until pH10. The reaction mixture was extracted three times with 10% MeOH in dichloromethane, dried over Magnesium sulfate, filtered, concentrated, and chromatographed through silica gel (40 g, 0-50% EtOAc in heptane). LC/MS-m/z+523.4 (M+H)+.

Step 2—Synthesis of compound wz: (S)-6-(benzyloxy)-N-(4-(7-methyl-4-(3-methylmorpholino)-5,6,7,8-tetrahydropyrido[3,4-d]pyrimidin-2-yl)phenyl)pyridin-2-amine (0.099 g, 0.19 mmol) was purged under nitrogen then added 20% Palladium hydroxide on carbon (2:8, Palladium hydroxide:carbon black, 0.0927 g) followed by dry Methanol (2.80 mL, 69.1 mmol) Acetic acid (0.26 mL, 4.6 mmol) and dry Tetrahydrofuran (2.80 mL, 34.5 mmol) purged with hydrogen, heated at 40° C. and stirred overnight under an atmosphere of hydrogen. The reaction mixture was purged with nitrogen, added celite, filtered through celite, concentrated, chromatographed through silica gel (12 g, 0-10% MeOH in dichloromethane), and purified by HPLC. $^1$H NMR (400 MHz, DMSO) δ 10.24 (s, 1H), 9.09 (s, 1H), 8.19 (d, J=8.8, 2H), 7.74 (s, 2H), 7.41 (t, J=7.9, 1H), 6.30 (s, 1H), 5.99 (d, J=7.6, 1H), 4.13 (d, J=6.8, 1H), 3.89 (d, J=11.3, 1H), 3.77-3.68 (m, 1H), 3.60 (dd, J=21.7, 11.0, 4H), 3.44 (d, J=17.4, 2H), 2.74-2.60 (m, 3H), 2.38 (s, 3H), 1.25 (d, J=6.6, 3H). LC/MS-m/z+433.2 (M+H)+.

Example 463

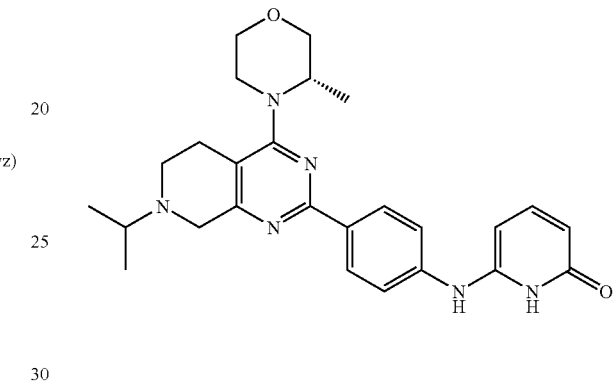

(xa)

Synthesis of (S)-6-(4-(7-isopropyl-4-(3-methylmorpholino)-5,6,7,8-tetrahydropyrido[3,4-d]pyrimidin-2-yl)phenylamino)pyridin-2(1H)-one (xa)

Step 1—Synthesis of (S)-4-(benzyloxy)-N-(4-(7-isopropyl-4-(3-methylmorpholino)-5,6,7,8-tetrahydropyrido[3,4-d]pyrimidin-2-yl)phenyl)pyrimidin-2-amine: (S)-4-(benzyloxy)-N-(4-(4-(3-methylmorpholino)-5,6,7,8-tetrahydropyrido[3,4-d]pyrimidin-2-yl)phenyl)pyrimidin-2-amine (0.193 g, 0.379 mmol) in dry N,N-Dimethylformamide (2.00 mL, 25.8 mmol) was added N,N-Diisopropylethylamine (0.193 mL, 1.11 mmol) followed by Isopropyl iodide (0.0760 mL, 0.760 mmol). The reaction mixture was heated at 50° C. and stirred overnight. The reaction mixture was concentrated and chromatographed through silica gel (40 g, 0-5% MeOH in dichloromethane). LC/MS-m/z+552.4 (M+H)+.

Step 2—Synthesis of compound xa: (S)-4-(benzyloxy)-N-(4-(7-isopropyl-4-(3-methylmorpholino)-5,6,7,8-tetrahydropyrido[3,4-d]pyrimidin-2-yl)phenyl)pyrimidin-2-amine (0.186 g, 0.337 mmol) was purged under nitrogen then added 20% Palladium hydroxide on carbon (2:8, Palladium hydroxide:carbon black, 0.14 g) followed by dry Methanol (4.85 mL, 1.20E2 mmol) Acetic acid (0.46 mL, 8.1 mmol) and dry Tetrahydrofuran (4.85 mL, 59.8 mmol) purged with hydrogen, heated at 40° C. and stirred overnight under an atmosphere of hydrogen. The reaction mixture was purged with nitrogen, added celite, filtered through celite, concentrated, chromatographed through silica gel (12 g, 0-10% MeOH in dichloromethane), and purified by HPLC. $^1$H NMR (400 MHz, DMSO) δ 9.24 (s, 1H), 8.24 (d, J=8.7, 2H), 8.16 (s, 1H), 7.80 (s, 1H), 7.73 (d, J=8.5, 2H), 5.86 (d, J=5.7, 1H), 4.14 (d, J=6.4, 1H), 3.87 (d, J=11.3, 1H), 3.75-3.56 (m, 7H), 3.47-3.39 (m, 2H), 2.88 (dt, J=13.0, 6.5, 1H), 2.74-2.63 (m, 3H), 2.61-2.55 (m, 2H), 2.51 (m, 1H), 1.24 (d, J=6.6, 3H), 1.08 (d, J=6.5, 6H). LC/MS-m/z+462.2 (M+H)+.

Example 464

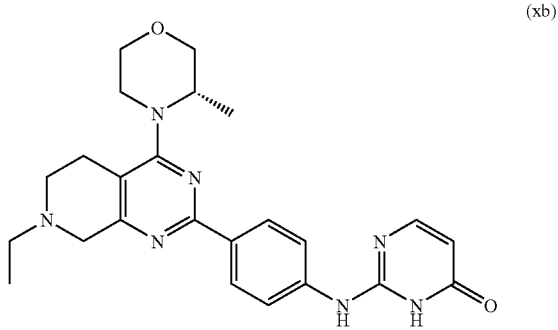

(xb)

Synthesis of (S)-2-(4-(7-ethyl-4-(3-methylmorpholino)-5,6,7,8-tetrahydropyrido[3,4-d]pyrimidin-2-yl)phenylamino)pyrimidin-4(3H)-one (xb)

Step 1—Synthesis of (S)-1-(2-(4-(4-(benzyloxy)pyrimidin-2-ylamino)phenyl)-4-(3-methylmorpholino)-5,6-dihydropyrido[3,4-d]pyrimidin-7(8H)-yl)ethanone: (S)-4-(benzyloxy)-N-(4-(3-methylmorpholino)-5,6,7,8-tetrahydropyrido[3,4-d]pyrimidin-2-yl)phenyl)pyrimidin-2-amine (0.223 g, 0.438 mmol) in dry N,N-Dimethylformamide (2.00 mL, 25.8 mmol) was added N,N-Diisopropylethylamine (0.22 mL, 1.3 mmol) followed by Acetyl chloride (0.0468 mL, 0.658 mmol). The reaction mixture was stirred for 2 hours. The reaction mixture was concentrated and chromatographed through silica gel (40 g, 0-8% MeOH in dichloromethane). ¹H NMR (400 MHz, CDCl₃) δ 8.35 (t, J=9.1, 2H), 8.19 (d, J=5.6, 1H), 7.69 (t, J=7.9, 2H), 7.46 (d, J=7.2, 2H), 7.37 (dt, J=21.2, 6.9, 3H), 7.16 (s, 1H), 6.29 (d, J=5.7, 1H), 5.44 (s, 2H), 4.68-4.63 (m, 1H), 4.00 (dd, J=32.7, 18.4, 3H), 3.87-3.45 (m, 7H), 2.70 (t, J=14.9, 2H), 2.22 (s, 3H), 1.41-1.30 (m, 3H). LC/MS-m/z+552.2 (M+H)+

Step 2—Synthesis of (S)-4-(benzyloxy)-N-(4-(7-ethyl-4-(3-methylmorpholino)-5,6,7,8-tetrahydropyrido[3,4-d]pyrimidin-2-yl)phenyl)pyrimidin-2-amine: (S)-1-(2-(4-(4-(benzyloxy)pyrimidin-2-ylamino)phenyl)-4-(3-methylmorpholino)-5,6-dihydropyrido[3,4-d]pyrimidin-7(8H)-yl)ethanone (0.223 g, 0.000405 mol) in dry Tetrahydrofuran (5.00 mL, 0.0616 mol) at 0° C. was added 1.0 M of Borane-THF complex in Tetrahydrofuran (1.20 mL) dropwise. The reaction mixture was warmed to room temperature and stirred overnight. The reaction mixture was cooled at 0° C. then added 1M HCl until the reaction mixture stops bubbling then added 1M NaOH until pH10. The reaction mixture was extracted three times with 10% MeOH in dichloromethane, dried over Magnesium sulfate, filtered, concentrated, and was chromatographed through silica gel (12 g, 0-50% EtOAc in heptane). LC/MS-m/z+538.1 (M+H)+.

Step 3—Synthesis of compound xb: (S)-4-(benzyloxy)-N-(4-(7-ethyl-4-(3-methylmorpholino)-5,6,7,8-tetrahydropyrido[3,4-d]pyrimidin-2-yl)phenyl)pyrimidin-2-amine (0.066 g, 0.12 mmol) was purged under nitrogen then added 20% Palladium hydroxide on carbon (2:8, Palladium hydroxide: carbon black, 0.101 g) followed by dry Methanol (3.6 mL, 89 mmol), Acetic acid (0.18 mL, 3.2 mmol) and dry Tetrahydrofuran (3.6 mL, 44 mmol) purged with hydrogen, heated at 40° C. and stirred overnight under an atmosphere of hydrogen. The reaction mixture was purged with nitrogen, added celite, filtered through celite, concentrated. chromatographed through silica gel (12 g, 0-10% MeOH in dichloromethane), and purified by HPLC. ¹H NMR (400 MHz, DMSO) δ 8.23 (d, J=8.7, 2H), 7.77 (t, J=9.4, 3H), 5.85 (d, J=5.9, 1H), 4.15 (d, J=6.5, 1H), 3.87 (d, J=10.8, 1H), 3.75-3.68 (m, 1H), 3.62 (dd, J=16.9, 7.9, 4H), 3.55-3.35 (m, 2H), 2.68 (s, 3H), 2.58-2.52 (m, 3H), 1.25 (d, J=6.6, 3H), 1.11 (t, J=7.1, 3H). LC/MS-m/z+448.2 (M+H)+.

Example 465

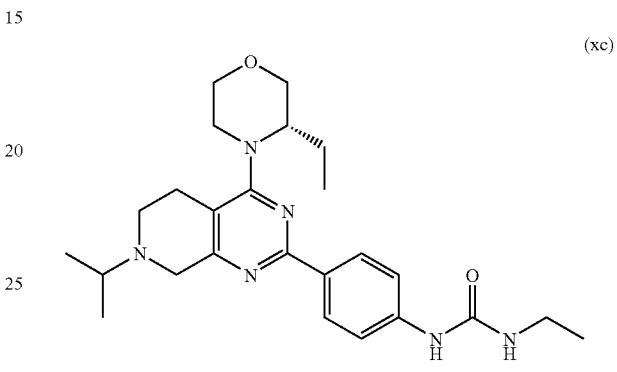

(xc)

Synthesis of (S)-1-ethyl-3-(4-(4-(3-ethylmorpholino)-7-isopropyl-5,6,7,8-tetrahydropyrido[3,4-d]pyrimidin-2-yl)phenyl)urea (xc)

Step 1—Synthesis of (S)-1-ethyl-3-(4-(4-(3-ethylmorpholino)-5,6,7,8-tetrahydropyrido[3,4-d]pyrimidin-2-yl)phenyl)urea: (S)-tert-butyl 4-(3-ethylmorpholino)-2-(4-(3-ethylureido)phenyl)-5,6-dihydropyrido[3,4-d]pyrimidine-7(8H)-carboxylate (1.660 g, 0.003251 mol) in Methylene chloride (20.0 mL, 0.312 mol) was added Trifluoroacetic Acid (5.00 mL, 0.0649 mol). The reaction mixture was stirred for 1.5 hours. The reaction mixture was concentrated, redissolved in 10% MeOH in dichloromethane then added sat NaHCO3, extracted 8 times with 10% MeOH in dichloromethane, dried over Magnesium sulfate, filtered, concentrated, and purified by HPLC. ¹H NMR (400 MHz, DMSO) δ 8.61 (s, 1H), 8.14 (d, J=8.7, 2H), 7.46 (d, J=8.7, 2H), 6.14 (t, J=5.5, 1H), 3.92 (s, 1H), 3.88-3.75 (m, 4H), 3.66 (dd, J=20.5, 8.7, 2H), 3.55 (t, J=11.1, 1H), 3.45-3.36 (m, 1H), 3.17-3.05 (m, 2H), 3.03-2.93 (m, 1H), 2.74 (t, J=8.2, 1H), 2.69-2.56 (m, 1H), 2.48 (m, 1H), 1.86-1.65 (m, 2H), 1.06 (t, J=7.2, 3H), 0.82 (t, J=7.4, 3H). LC/MS-m/z+411.2 (M+H)+

Step 2—Synthesis of compound xc: (S)-1-ethyl-3-(4-(4-(3-ethylmorpholino)-5,6,7,8-tetrahydropyrido[3,4-d]pyrimidin-2-yl)phenyl)urea (0.097 g, 0.24 mmol) in dry N,N-Dimethylformamide (1.30 mL, 16.8 mmol) was added N,N-Diisopropylethylamine (0.1270 mL, 0.7291 mmol) followed by Isopropyl iodide (0.0488 mL, 0.488 mmol). The reaction mixture was heated at 50° C. and stirred overnight. The reaction mixture was purified by HPLC. ¹H NMR (400 MHz, DMSO) δ 8.62 (s, 1H), 8.15 (d, J=8.7, 2H), 7.46 (d, J=8.7, 2H), 6.16 (t, J=5.5, 1H), 3.97 (s, 1H), 3.85 (d, J=10.7, 1H), 3.77 (d, J=11.4, 1H), 3.68 (t, J=13.3, 3H), 3.60-3.49 (m, 2H), 3.40 (t, J=11.0, 1H), 3.18-3.04 (m, 2H), 2.91-2.64 (m, 3H), 2.57 (d, J=15.4, 1H), 1.89-1.63 (m, 2H), 1.06 (t, J=7.5, 9H), 0.94 (t, J=6.3, 1H), 0.82 (t, J=7.4, 3H). LC/MS-m/z+453.2 (M+H)+

Example 466

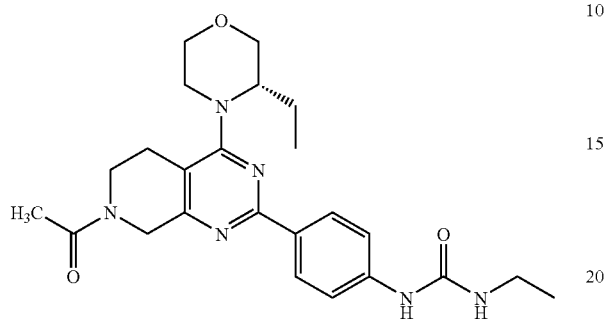

(xd)

Synthesis of (S)-1-(4-(7-acetyl-4-(3-ethylmorpholino)-5,6,7,8-tetrahydropyrido[3,4-d]pyrimidin-2-yl)phenyl)-3-ethylurea (xd): (S)-1-ethyl-3-(4-(4-(3-ethylmorpholino)-5,6,7,8-tetrahydropyrido[3,4-d]pyrimidin-2-yl)phenyl)urea (0.251 g, 0.611 mmol) in dry N,N-Dimethylformamide (3.00 mL, 38.7 mmol) was added N,N-Diisopropylethylamine (0.310 mL, 1.78 mmol) followed by Acetyl chloride (0.0650 mL, 0.913 mmol). The reaction mixture was stirred for overnight. The reaction mixture was purified by HPLC. $^1$H NMR (400 MHz, DMSO) δ 8.68 (s, 1H), 8.17 (d, J=7.6, 2H), 7.48 (d, J=7.9, 2H), 6.22 (d, J=6.1, 1H), 4.78-4.63 (m, 1H), 4.44 (dd, J=82.7, 18.2, 1H), 3.97 (s, 1H), 3.85 (d, J=11.1, 1H), 3.78 (d, J=11.6, 1H), 3.67 (d, J=7.4, 2H), 3.45 (dd, J=38.1, 25.8, 3H), 3.29 (m, 1H), 3.16-3.07 (m, 2H), 2.68 (dd, J=47.0, 37.1, 2H), 2.12 (s, 3H), 1.78 (ddd, J=27.5, 13.8, 7.0, 2H), 1.06 (t, J=7.2, 3H), 0.83 (dd, J=12.0, 7.4, 3H). LC/MS-m/z+453.2 (M+H)+.

Example 467

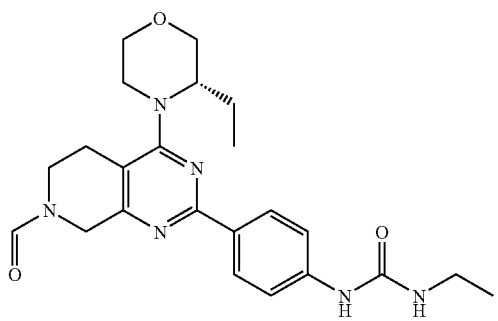

(xe)

Synthesis of (S)-1-ethyl-3-(4-(4-(3-ethylmorpholino)-7-formyl-5,6,7,8-tetrahydropyrido[3,4-d]pyrimidin-2-yl)phenyl)urea (xe): (S)-1-ethyl-3-(4-(4-(3-ethylmorpholino)-5,6,7,8-tetrahydropyrido[3,4-d]pyrimidin-2-yl)phenyl)urea (0.248 g, 0.604 mmol), 2-(1H-benzotriazole-1-yl)-1,1,3,3-tetramethyluronium tetrafluoroborate (0.263 g, 0.819 mmol) and Formic acid (0.0346 mL, 0.917 mmol) were combined then added dry N,N-Dimethylformamide (2.50 mL, 32.3 mmol) followed by N,N-Diisopropylethylamine (0.583 mL, 3.35 mmol). The reaction mixture stirred for overnight. The reaction mixture was purified by HPLC. $^1$H NMR (400 MHz, DMSO) δ 8.64 (s, 1H), 8.23 (d, J=20.5, 1H), 8.17 (d, J=8.7, 2H), 7.48 (d, J=8.7, 2H), 6.16 (t, J=5.1, 1H), 4.64 (dd, J=18.2, 11.9, 1H), 4.41 (dd, J=73.9, 18.2, 1H), 3.91 (d, J=17.0, 1H), 3.84 (d, J=11.1, 1H), 3.76 (dd, J=15.6, 12.5, 2H), 3.70-3.61 (m, 2H), 3.59-3.36 (m, 3H), 3.18-3.05 (m, 2H), 2.85-2.58 (m, 2H), 1.91-1.65 (m, 2H), 1.06 (t, J=7.2, 3H), 0.89-0.77 (m, 3H). LC/MS-m/z+439.2 (M+H)+.

Example 468

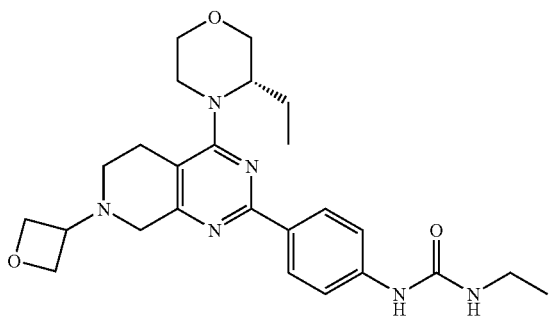

(xf)

Synthesis of (S)-1-ethyl-3-(4-(4-(3-ethylmorpholino)-7-(oxetan-3-yl)-5,6,7,8-tetrahydropyrido[3,4-d]pyrimidin-2-yl)phenyl)urea (xf): (S)-1-ethyl-3-(4-(4-(3-ethylmorpholino)-5,6,7,8-tetrahydropyrido[3,4-d]pyrimidin-2-yl)phenyl)urea (0.0500 g, 0.122 mmol) in dry N,N-Dimethylformamide (0.593 mL, 7.66 mmol) at 0° C. was added 3-oxetanone (0.00881 mL, 0.122 mmol). The reaction mixture was stirred at 50° C. for 10 minutes then cooled at 0° C. and added Sodium triacetoxyborohydride (0.05163 g, 0.2436 mmol). The reaction mixture was allowed to warm slowly to room temperature and stirred overnight. The reaction mixture was filtered through a disc filter and purified by HPLC. $^1$H NMR (400 MHz, DMSO) δ 8.61 (s, 1H), 8.14 (d, J=8.7, 2H), 7.46 (d, J=8.7, 2H), 6.15 (t, J=5.5, 1H), 4.64 (t, J=6.2, 2H), 4.59-4.50 (m, 2H), 3.97 (s, 1H), 3.86 (d, J=10.7, 1H), 3.78 (d, J=11.2, 1H), 3.74-3.60 (m, 4H), 3.55 (t, J=10.9, 1H), 3.43 (d, J=10.4, 1H), 3.35 (d, J=17.0, 1H), 3.18-3.05 (m, 2H), 2.76 (s, 1H), 2.68 (d, J=11.2, 1H), 2.60 (d, J=15.2, 1H), 2.41-2.30 (m, 1H), 1.87-1.67 (m, 2H), 1.06 (t, J=7.2, 3H), 0.83 (t, J=7.4, 3H). LC/MS-m/z+467.2 (M+H)+.

Example 469

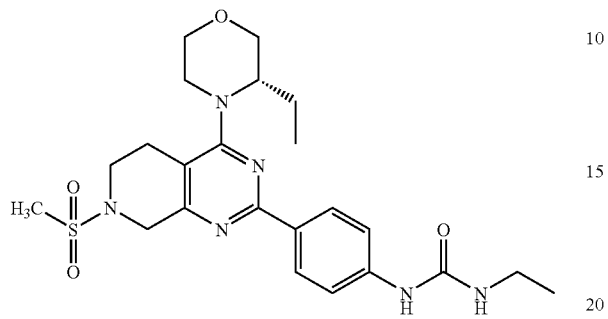

(xg)

Synthesis of (S)-1-ethyl-3-(4-(4-(3-ethylmorpholino)-7-(methylsulfonyl)-5,6,7,8-tetrahydropyrido[3,4-d]pyrimidin-2-yl)phenyl)urea (xg): (S)-1-ethyl-3-(4-(4-(3-ethylmorpholino)-5,6,7,8-tetrahydropyrido[3,4-d]pyrimidin-2-yl)phenyl)urea (0.0499 g, 0.122 mmol) in dry N,N-Dimethylformamide (0.60 mL, 7.7 mmol) was added N,N-Diisopropylethylamine (0.0636 mL, 0.365 mmol) followed by Methanesulfonyl chloride (0.01410 mL, 0.1822 mmol). The reaction mixture was stirred for 1 hour then submitted for purification. ¹H NMR (400 MHz, DMSO) δ 8.65 (s, 1H), 8.16 (d, J=8.7, 2H), 7.48 (d, J=8.8, 2H), 6.18 (t, J=5.5, 1H), 4.32 (dd, J=36.6, 17.0, 2H), 4.01 (s, 1H), 3.85 (d, J=10.7, 1H), 3.79 (d, J=11.4, 1H), 3.68 (dd, J=20.5, 8.8, 2H), 3.59-3.49 (m, 1H), 3.43 (t, J=11.0, 1H), 3.26-3.17 (m, 1H), 3.16-3.06 (m, 2H), 3.02 (s, 3H), 2.94-2.81 (m, 1H), 2.77-2.63 (m, 1H), 1.88-1.69 (m, 2H), 1.06 (t, J=7.2, 3H), 0.83 (t, J=7.4, 3H). LC/MS-m/z+489.2 (M+H)+.

Example 470

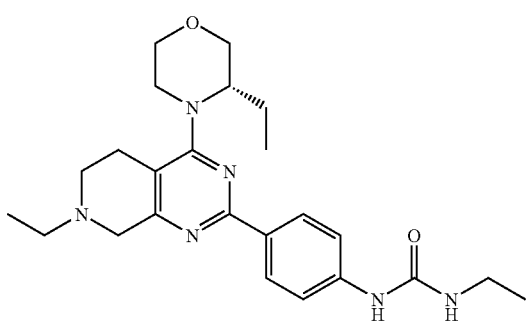

(xh)

Synthesis of (S)-1-ethyl-3-(4-(7-ethyl-4-(3-ethylmorpholino)-5,6,7,8-tetrahydropyrido[3,4-d]pyrimidin-2-yl)phenyl)urea (xh): (S)-1-(4-(7-acetyl-4-(3-ethylmorpholino)-5,6,7,8-tetrahydropyrido[3,4-d]pyrimidin-2-yl)phenyl)-3-ethylurea (0.106 g, 0.000234 mol) in dry Tetrahydrofuran (2.10 mL, 0.0259 mol) at 0° C. was added 1.0 M of Borane-THF complex in Tetrahydrofuran (0.92 mL) dropwise. The reaction mixture was warmed to room temperature and for 1 hour. The reaction mixture was cooled at 0° C. then about 1 mL 1M HCl dropwise then added 1M NaOH until pH10. The reaction mixture was extracted three times with 10% MeOH in dichloromethane, dried over Magnesium sulfate, filtered, concentrated, was chromatographed through silica gel (12 g, 0-5% MeOH on dichloromethane), and submitted for purification. ¹H NMR (400 MHz, DMSO) δ 8.61 (s, 1H), 8.15 (d, J=8.7, 2H), 7.46 (d, J=8.8, 2H), 6.15 (t, J=5.5, 1H), 3.97 (s, 1H), 3.85 (d, J=10.4, 1H), 3.78 (d, J=11.3, 1H), 3.74-3.62 (m, 3H), 3.55 (t, J=11.2, 1H), 3.40 (t, J=13.4, 2H), 3.18-3.05 (m, 2H), 2.85-2.69 (m, 2H), 2.63-2.47 (m, 3H), 2.43 (d, J=9.0, 1H), 1.76 (ddt, J=38.0, 13.8, 7.1, 2H), 1.11 (t, J=7.1, 3H), 1.06 (t, J=7.2, 3H), 0.82 (t, J=7.4, 3H). LC/MS-m/z+439.2 (M+H)+.

Example 471

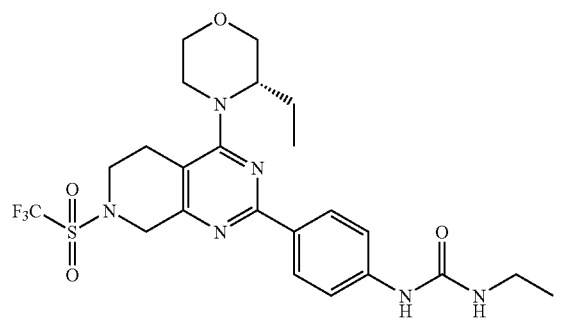

(xi)

Synthesis of (S)-1-ethyl-3-(4-(4-(3-ethylmorpholino)-7-(trifluoromethylsulfonyl)-5,6,7,8-tetrahydropyrido[3,4-d]pyrimidin-2-yl)phenyl)urea (xi): (S)-1-ethyl-3-(4-(4-(3-ethylmorpholino)-5,6,7,8-tetrahydropyrido[3,4-d]pyrimidin-2-yl)phenyl)urea (0.0473 g, 0.115 mmol) in dry N,N-Dimethylformamide (0.60 mL, 7.7 mmol) was added N,N-Diisopropylethylamine (0.0636 mL, 0.365 mmol) followed by Trifluoromethanesulfonyl chloride (0.01940 mL, 0.1822 mmol). The reaction mixture was stirred for overnight. The reaction mixture was concentrated and was chromatographed through silica gel (4 g, 0-100% EtOAc in heptane followed by 10% MeOH in dichloromethane). The trifluoromethanesulfonamide was isolated and purified by HPLC. (S)-1-ethyl-3-(4-(4-(3-ethylmorpholino)-7-(trifluoromethylsulfonyl)-5,6,7,8-tetrahydropyrido[3,4-d]pyrimidin-2-yl)phenyl)urea (xi): ¹H NMR (400 MHz, DMSO) δ 8.66 (s, 1H), 8.16 (d, J=8.7, 2H), 7.48 (d, J=8.8, 2H), 6.18 (t, J=5.6, 1H), 4.68-4.52 (m, 2H), 4.01 (s, 1H), 3.82 (dd, J=26.3, 11.2, 3H), 3.69 (t, J=12.6, 3H), 3.54 (t, J=11.1, 1H), 3.49-3.38 (m, 1H), 3.18-

3.06 (m, 2H), 2.87 (s, 1H), 2.75 (d, J=16.4, 1H), 1.80 (dd, J=11.3, 6.9, 2H), 1.06 (t, J=7.2, 3H), 0.83 (t, J=7.4, 3H). LC/MS-m/z+543.2 (M+H)+

Example 472

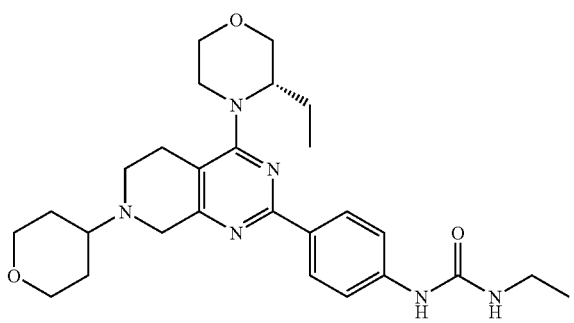

(xj)

Synthesis of (S)-1-ethyl-3-(4-(4-(3-ethylmorpholino)-7-(tetrahydro-2H-pyran-4-yl)-5,6,7,8-tetrahydropyrido[3,4-d]pyrimidin-2-yl)phenyl)urea (xj): (S)-1-ethyl-3-(4-(4-(3-ethylmorpholino)-5,6,7,8-tetrahydropyrido[3,4-d]pyrimidin-2-yl)phenyl)urea (0.0714 g, 0.174 mmol) in dry N,N-Dimethylformamide (0.850 mL, 11.0 mmol) at 0° C. was added Tetrahydro-4H-pyran-4-one (0.0160 mL, 0.174 mmol). The reaction mixture was stirred at 50° C. for 10 minutes then cooled at 0° C. and added Sodium triacetoxyborohydride (0.0788 g, 0.372 mmol). The reaction mixture was allowed to warm slowly to room temperature and stirred overnight. The reaction mixture was filtered through a disc filtered, concentrated, chromatographed through silica gel (40 g, 0-10% MeOH in dichloromethane), and purified by HPLC. LC/MS-m/z+495.3 (M+H)+

Example 473

(xk)

Synthesis of 5-methyl-N-(4-(4-morpholino-7-(pyrimidin-2-yl)-5,6,7,8-tetrahydropyrido[3,4-d]pyrimidin-2-yl)phenyl)-4,5-dihydro-1H-imidazol-2-amine (xk)

Step 1—Synthesis of 1-(2-aminopropyl)-3-(4-(4-morpholino-7-(pyrimidin-2-yl)-5,6,7,8-tetrahydropyrido[3,4-d]pyrimidin-2-yl)phenyl)thiourea: 4-(4-Morpholino-7-(pyrimidin-2-yl)-5,6,7,8-tetrahydropyrido[3,4-d]pyrimidin-2-yl)aniline (0.258 g, 0.000662 mol) in dry 1,4-Dioxane (10.0 mL, 0.128 mol) was added Triethylamine (0.11 mL, 0.00080 mol) followed by Carbonothioic dichloride (0.060 mL, 0.00079 mol). The reaction mixture was heated at 50° C. for 1 hour. The reaction mixture was cooled to room temperature and then added 1,2-Diaminopropane (1.20 mL, 0.0140 mol) very quickly. The reaction mixture was stirred for 1 hour then concentrated and chromatographed through silica gel (40 g, 0-10% MeOH in dichloromethane followed by 6:2:1:1 EtOAc:acetone:MeOH:water). LC/MS-m/z+506.1 (M+H)+

Step 2—Synthesis of compound xk: 1-(2-aminopropyl)-3-(4-(4-morpholino-7-(pyrimidin-2-yl)-5,6,7,8-tetrahydropyrido[3,4-d]pyrimidin-2-yl)phenyl)thiourea (0.293 g, 0.000579 mol) in dry Ethanol (12.0 mL, 0.206 mol) was added Mercury(II) oxide (0.260 g, 0.00120 mol). The reaction mixture was stirred at room temperature for 8 hours. The reaction mixture was heated at 40° C. and stirred overnight. The reaction mixture was heated at 50° C. and stirred overnight. The reaction mixture was heated at 78° C. for 8 hours. The reaction mixture was cooled to room temperature and stirred for 6 days. The reaction mixture was heated at 78° C. for 8 hours. The reaction mixture was cooled to room temperature, filtered through celite, filtered through a disc filter, concentrated, and purified by HPLC. $^1$H NMR (400 MHz, DMSO) δ 8.43 (d, J=4.7, 2H), 8.17 (d, J=8.5, 2H), 7.01 (s, 2H), 6.69 (t, J=4.7, 1H), 6.32 (s, 2H), 4.80 (s, 2H), 3.98 (s, 2H), 3.82-3.70 (m, 5H), 3.46 (s, 5H), 2.92 (s, 1H), 2.75 (s, 2H), 1.15 (d, J=6.1, 3H). LC/MS-m/z+472.2 (M+H)+

Example 474

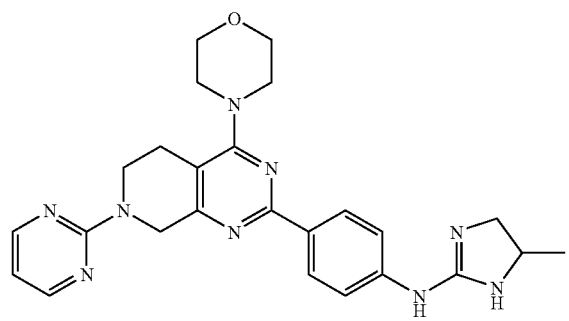

(xl$^1$)

(xl$^2$)

Synthesis of (R)-1-ethyl-3-(4-(4-morpholino-8-oxo-5,6,8,9,10,10a-hexahydropyrimido[5,4-g]indolizin-2-yl)phenyl)urea (xl$^1$); and (S)-1-ethyl-3-(4-(4-morpholino-8-oxo-5,6,8,9,10,10a-hexahydropyrimido[5,4-g]indolizin-2-yl)phenyl)urea (xl$^2$): 2-Chloro-4-morpholino-5,6,10,10a-tetrahydropyrimido[5,4-g]indolizin-8(9H)-one (0.232 g, 0.000751 mol), [4-Ethylureido)phenyl]boronic acid, pinacol ester (0.284 g, 0.000979 mol), Tetrakis(triphenylphosphine) palladium(0) (0.0541 g, 0.0000468 mol) Sodium carbonate (0.122 g, 0.00115 mol) and Potassium acetate (0.118 g, 0.00120 mol) were combined, nitrogen purged three times, added dry Acetonitrile (6.00 mL, 0.115 mol) followed by deoxygenated Water (3.80 mL, 0.211 mol), heated at 90° C. and stirred overnight. The reaction mixture was diluted with water, extracted three times with 10% MeOH in dichloromethane, dried over Magnesium sulfate, filtered, concentrated, chromatographed through silica gel (12 g, 0-50% EtOAc in heptane followed by 5% MeOH in dichloromethane), purified by HPLC, and the enantiomers were separated out by SFC. Enantiomer 1 $^1$H NMR (400 MHz, DMSO) δ 8.65 (s, 1H), 8.20 (d, J=8.7, 2H), 7.49 (d, J=8.8, 2H), 6.15 (t, J=5.5, 1H), 4.68 (t, J=8.2, 1H), 4.11 (dd, J=12.4, 5.0, 1H), 3.78 (dd, J=8.9, 6.2, 2H), 3.71-3.62 (m, 2H), 3.61-3.50 (m, 2H), 3.31 (m, 2H), 3.18-3.05 (m, 2H), 2.91 (t, J=10.2, 1H), 2.84-2.71 (m, 1H), 2.70-2.59 (m, 1H), 2.57-2.43 (m, 2H), 2.35-2.22 (m, 1H), 1.93-1.80 (m, 1H), 1.06 (t, J=7.2, 3H). LC/MS-m/z+437.2 (M+H)+; Enantiomer 2 $^1$H NMR (400 MHz, DMSO) δ 8.65 (s, 1H), 8.20 (d, J=8.7, 2H), 7.49 (d, J=8.7, 2H), 6.15 (t, J=5.4, 1H), 4.68 (t, J=8.0, 1H), 4.11 (dd, J=12.6, 5.3, 1H), 3.78 (dd, J=8.8, 6.3, 2H), 3.73-3.61 (m, 2H), 3.56 (dd, J=11.9, 5.3, 2H), 3.31 (m, 2H), 3.18-3.06 (m, 2H), 2.91 (t, J=12.3, 1H), 2.83-2.71 (m, 1H), 2.70-2.59 (m, 1H), 2.59-2.42 (m, 2H), 2.37-2.21 (m, 1H), 1.94-1.79 (m, 1H), 1.06 (t, J=7.2, 3H). LC/MS-m/z+437.2 (M+H)+.

Example 475

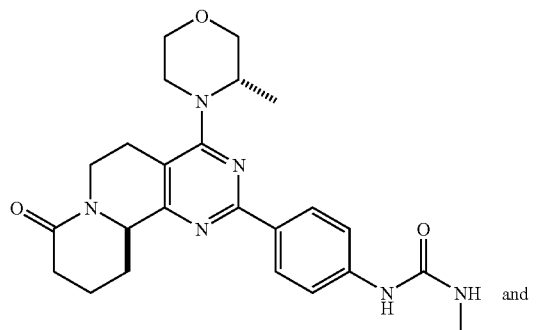

(xm$^1$)

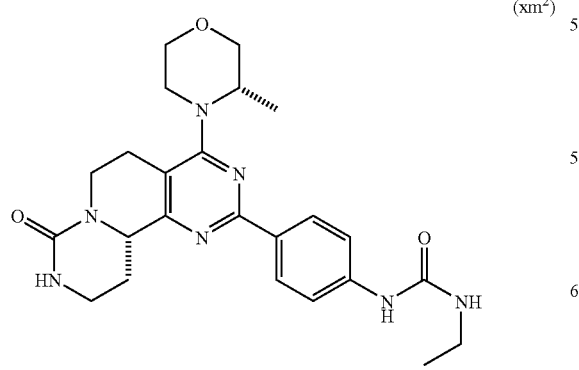

(xm$^2$)

Synthesis of Compounds xm$^1$ and xm$^2$

Step 1—Tert-butyl 8-(2-aminoethyl)-2-(4-(3-ethylureido) phenyl)-4-((S)-3-methylmorpholino)-5,6-dihydropyrido[3, 4-d]pyrimidine-7(8H)-carboxylate: Tert-butyl 8-(cyanomethyl)-2-(4-(3-ethylureido)phenyl)-4-((S)-3-methylmorpholino)-5,6-dihydropyrido[3,4-d]pyrimidine-7 (8H)-carboxylate (0.656 g, 0.00122 mol) in dry Methanol (61.9 mL, 1.53 mol) under nitrogen was added Ammonium hydroxide (1.1 mL, 0.029 mol) and Raney Nickel (2 mL slurry). The reaction mixture was purged with hydrogen, heated at 50° C., and stirred overnight under an atmosphere of hydrogen. The reaction mixture was purged with nitrogen, added celite, filtered through a pad of celite, concentrated, and purified by HPLC. LC/MS-m/z+540.3 (M+H)+

Step 2—Synthesis of compounds xm$^1$ and xm$^2$: Tert-butyl 8-(2-aminoethyl)-2-(4-(3-ethylureido)phenyl)-4-((S)-3-methylmorpholino)-5,6-dihydropyrido[3,4-d]pyrimidine-7 (8H)-carboxylate (0.351 g, 0.000650 mol) and 4.0 M of Hydrogen chloride in 1,4-Dioxane (5.0 mL) were combined and shaken for 3 hours. The reaction mixture was then concentrated. LC-MS shows mostly product but some PPh3O is present. The reaction mixture was vacuum pump dried overnight. To the reaction mixture was added dry Tetrahydrofuran (35.0 mL, 0.432 mol) followed by N,N-Diisopropylethylamine (1.10 mL, 0.00632 mol). The reaction mixture was cooled at 0° C. then added 20% Phosgene in toluene (1:4, Phosgene:Toluene, 0.35 mL) diluted in dry Toluene (3.6 mL, 0.034 mol) dropwise. The reaction mixture was allowed to warm slowly to room temperature and stirred overnight. The reaction mixture was concentrated, chromatographed through silica gel (40 g, 0-10% MeOH in dichloromethane, Note: The reaction mixture streaks on the column), purified by HPLC, and the diastereomers were separated by SFC. R Diastereomer (xm$^1$): $^1$H NMR (400 MHz, DMSO) δ 8.65 (s, 1H), 8.19 (d, J=8.7, 2H), 7.48 (d, J=8.8, 2H), 6.47 (d, J=3.6, 1H), 6.15 (t, J=5.6, 1H), 4.51 (d, J=11.6, 2H), 4.20 (d, J=6.4, 1H), 3.88 (d, J=8.9, 1H), 3.80 (d, J=8.9, 1H), 3.62 (d, J=11.8, 1H), 3.51 (q, J=11.9, 2H), 3.43-3.33 (m, 1H), 3.23-3.06 (m, 3H), 2.66 (dt, J=23.0, 11.1, 3H), 2.56-2.42 (m, 2H), 1.79-1.64 (m, 1H), 1.12-1.02 (m, 6H). LC/MS-m/z+466.2 (M+H)+; S-Diastereomer (xm$^2$): $^1$H NMR (400 MHz, DMSO) δ 8.64 (s, 1H), 8.18 (d, J=8.7, 2H), 7.47 (d, J=8.8, 2H), 6.45 (d, J=3.6, 1H), 6.17 (t, J=5.5, 1H), 4.48 (d, J=11.5, 2H), 4.04 (d, J=6.2, 1H), 3.89 (dd, J=25.8, 11.9, 2H), 3.73-3.52 (m, 3H), 3.21-3.08 (m, 3H), 2.76 (d, J=11.3, 1H), 2.71-2.42 (m, 4H), 2.41-2.31 (m, 1H), 1.78-1.62 (m, 1H), 1.47 (d, J=6.6, 3H), 1.07 (q, J=6.9, 3H). LC/MS-m/z+466.2 (M+H)+

Example 476

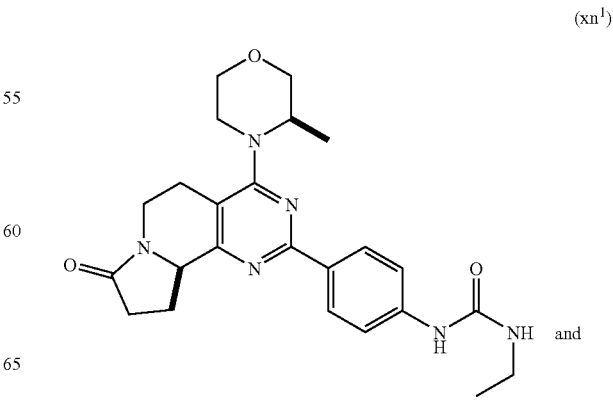

(xn$^1$)

-continued

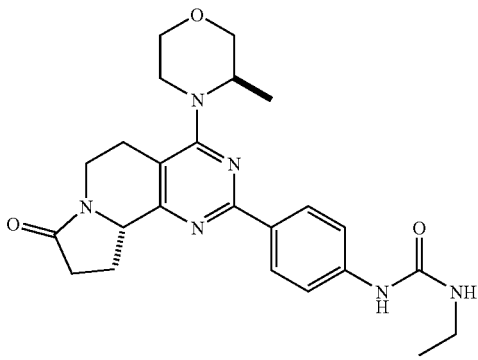

(xn²)

Synthesis of 1 1-ethyl-3-(4-((R)-4-((R)-3-methylmorpholino)-8-oxo-5,6,8,9,10,10a-hexahydropyrimido[5,4-g]indolizin-2-yl)phenyl)urea (xn¹); and 1-ethyl-3-(4-((S)-4-((R)-3-methylmorpholino)-8-oxo-5,6,8,9,10,10a-hexahydropyrimido[5,4-g]indolizin-2-yl)phenyl)urea (xn²): Compounds xn¹ and xn² were prepared analogously to the method described in Example 474. R-Diastereomer (xn¹): ¹H NMR (400 MHz, DMSO) δ 8.64 (s, 1H), 8.18 (d, J=8.7, 2H), 7.48 (d, J=8.7, 2H), 6.16 (t, J=5.5, 1H), 4.66 (t, J=8.0, 1H), 4.09 (dd, J=12.8, 5.1, 1H), 3.97 (d, J=6.2, 1H), 3.84 (d, J=9.5, 2H), 3.70 (t, J=10.3, 1H), 3.63-3.51 (m, 2H), 3.29 (m, 1H), 3.18-3.05 (m, 2H), 2.91 (t, J=10.4, 1H), 2.85-2.71 (m, 1H), 2.63 (dd, J=20.0, 8.0, 1H), 2.57-2.41 (m, 22H), 2.36-2.22 (m, 1H), 1.87 (dt, J=19.6, 9.7, 1H), 1.44 (d, J=6.6, 3H), 1.06 (t, J=7.2, 3H). LC/MS-m/z+451.2 (M+H)+; S-Diastereomer (xn²): ¹H NMR (400 MHz, DMSO) δ 8.66 (s, 1H), 8.19 (d, J=8.7, 2H), 7.49 (d, J=8.8, 2H), 6.15 (t, J=5.5, 1H), 4.68 (t, J=8.1, 1H), 4.12 (dd, J=12.2, 5.5, 2H), 3.91-3.74 (m, 2H), 3.63-3.43 (m, 3H), 3.29 (m, 1H), 3.18-3.06 (m, 2H), 2.91 (t, J=10.4, 1H), 2.81-2.56 (m, 3H), 2.56-2.43 (m, 1H), 2.29 (dd, J=16.6, 8.8, 1H), 1.88 (dt, J=19.4, 9.7, 1H), 1.07 (dd, J=12.7, 6.7, 6H). LC/MS-m/z+451.2 (M+H)+.

Example 477

(xo)

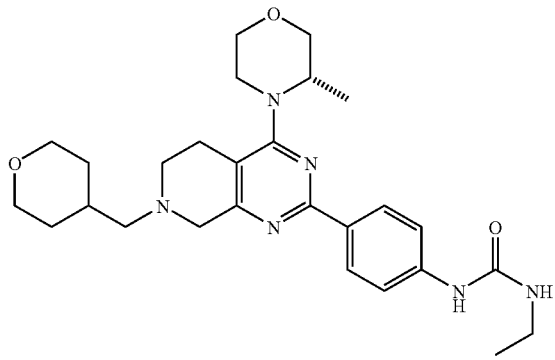

Synthesis of (S)-1-ethyl-3-(4-(4-(3-methylmorpholino)-7-((tetrahydro-2H-pyran-4-yl)methyl)-5,6,7,8-tetrahydropyrido[3,4-d]pyrimidin-2-yl)phenyl)urea (xo): (S)-1-ethyl-3-(4-(4-(3-methylmorpholino)-5,6,7,8-tetrahydropyrido[3,4-d]pyrimidin-2-yl)phenyl)urea (0.100 g, 0.252 mmol) in dry N,N-Dimethylformamide (1.00 mL, 12.9 mmol) at 0° C. was added tetrahydro-2H-pyran-4-carbaldehyde (0.02752 mL, 0.2522 mmol). The reaction mixture was stirred at 50° C. for 15 minutes then cooled at 0° C. and added Sodium triacetoxyborohydride (0.1069 g, 0.5044 mmol). The reaction mixture was allowed to warm slowly to room temperature and stirred for 2 hours. LC-MS shows mostly product. The reaction mixture was concentrated, chromatographed through silica gel (40 g, 0-5% MeOH in dichloromethane), and purified by HPLC. ¹H NMR (400 MHz, DMSO) δ 8.62 (s, 1H), 8.15 (d, J=8.7, 2H), 7.46 (d, J=8.7, 2H), 6.16 (t, J=5.5, 1H), 4.13 (d, J=6.7, 1H), 3.85 (t, J=9.0, 3H), 3.70 (d, J=9.0, 1H), 3.61 (dd, J=12.3, 4.0, 4H), 3.52-3.31 (m, 4H), 3.17-3.07 (m, 2H), 2.67 (s, 3H), 2.51 (m, 1H), 2.34 (d, J=7.3, 2H), 1.90 (d, J=7.3, 1H), 1.66 (d, J=12.6, 2H), 1.28-1.10 (m, 5H), 1.06 (t, J=7.2, 3H). LC/MS-m/z+495.3 (M+H)+.

Example 478

(xp¹)

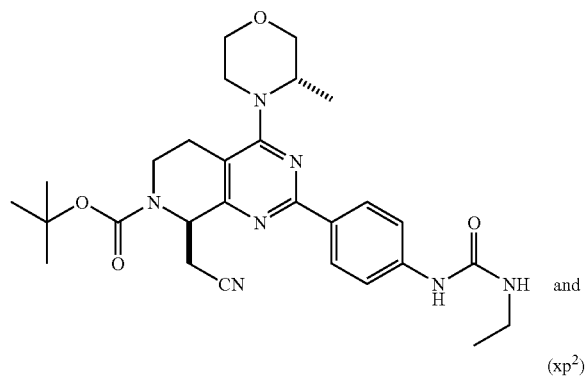

and (xp²)

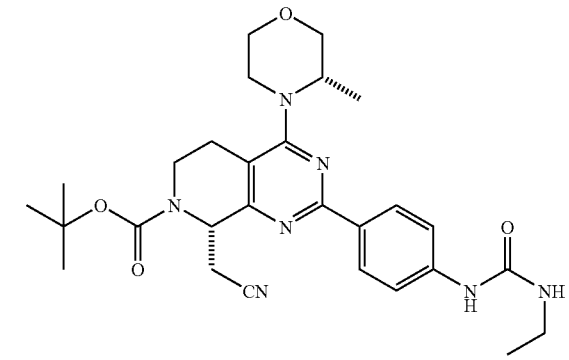

Synthesis of (R)-tert-butyl 8-(cyanomethyl)-2-(4-(3-ethylureido)phenyl)-4-((S)-3-methylmorpholino)-5,6-dihydropyrido[3,4-d]pyrimidine-7(8H)-carboxylate (xp¹); and (S)-tert-butyl 8-(cyanomethyl)-2-(4-(3-ethylureido) phenyl)-4-((S)-3-methylmorpholino)-5,6-dihydropyrido[3,4-d]pyrimidine-7(8H)-carboxylate (xp²)

Step 1—Synthesis of Tert-butyl 2-chloro-8-(cyanomethyl)-4-((S)-3-methylmorpholino)-5,6-dihydropyrido[3,4-d]pyrimidine-7(8H)-carboxylate: (S)-tert-butyl 2-chloro-4-(3-methylmorpholino)-5,6-dihydropyrido[3,4-d]pyrimidine-7(8H)-carboxylate (1.004 g, 2.722 mmol) in dry Tetrahydrofuran (11.0 mL, 136 mmol) at −78° C. was added 1.6 M of n-Butyllithium in Hexane (2.70 mL) dropwise. The reaction mixture was stirred at −78° C. for 1 hour then added Bromoacetonitrile (0.490 mL, 7.03 mmol) dropwise. The reaction mixture was allowed to warm slowly to room temperature and stirred overnight. water was added dropwise to the reaction mixture then extracted three times with dichloromethane, dried over Magnesium sulfate, filtered, concentrated, and chromatographed through silica gel (120 g, 0-50% EtOAc in heptane). LC/MS-m/z+408.4 (M+H)+

Step 2—Synthesis of compounds xp¹ and xp²: Tert-butyl 2-chloro-8-(cyanomethyl)-4-((S)-3-methylmorpholino)-5,6-dihydropyrido[3,4-d]pyrimidine-7(8H)-carboxylate (0.494 g, 0.00121 mol), [4-Ethylureido)phenyl]boronic acid, pinacol ester (0.471 g, 0.00162 mol), Tetrakis(triphenylphosphine)palladium(0) (0.1019 g, 8.818E-5 mol) Sodium carbonate (0.205 g, 0.00193 mol) and Potassium acetate (0.205 g, 0.00209 mol) were combined, nitrogen purged three times, added dry Acetonitrile (10.0 mL, 0.191 mol) followed by deoxygenated Water (6.00 mL, 0.333 mol), heated at 90° C. and stirred overnight. The reaction mixture was cooled to room temperature and stirred for 2 days. The reaction mixture was diluted with water, extracted three times with 10% MeOH in dichloromethane, dried over Magnesium sulfate, filtered, concentrated, chromatographed through silica gel (40 g, 0-100% EtOAc in heptane), purified by HPLC, and the diastereomers were separated out by SFC.

R Diastereomer (xp¹) ¹H NMR (400 MHz, DMSO) δ 8.67 (s, 1H), 8.24 (d, J=8.7, 2H), 7.49 (d, J=8.7, 2H), 6.16 (t, J=5.6, 1H), 5.17 (t, J=6.0, 1H), 4.21 (s, 2H), 3.88 (d, J=9.0, 1H), 3.80 (d, J=9.2, 1H), 3.63 (d, J=11.2, 1H), 3.58-3.46 (m, 2H), 3.41 (d, J=11.5, 1H), 3.13 (dt, J=14.0, 6.3, 3H), 2.99 (s, 1H), 2.80 (s, 1H), 2.52 (d, J=15.1, 2H), 1.48 (s, 9H), 1.12 (d, J=6.6, 3H), 1.06 (t, J=7.2, 3H). LC/MS-m/z+536.3 (M+H)+; S Diastereomer (xp²) ¹H NMR (400 MHz, DMSO) δ 8.65 (s, 1H), 8.22 (d, J=8.7, 2H), 7.49 (d, J=8.7, 2H), 6.16 (t, J=5.5, 1H), 5.13 (t, J=5.8, 1H), 4.15 (s, 1H), 4.05 (d, J=7.1, 1H), 3.94 (d, J=13.3, 1H), 3.87 (d, J=10.7, 1H), 3.69 (t, J=10.3, 1H), 3.61 (d, J=11.2, 1H), 3.54 (d, J=10.6, 1H), 3.32 (m, 2H), 3.18-3.07 (m, 2H), 3.07-2.92 (m, 1H), 2.83 (t, J=10.8, 1H), 2.55-2.39 (m, 2H), 1.47 (d, J=9.1, 12H), 1.06 (t, J=7.2, 3H). LC/MS-m/z+ 536.3 (M+H)+.

Example 479

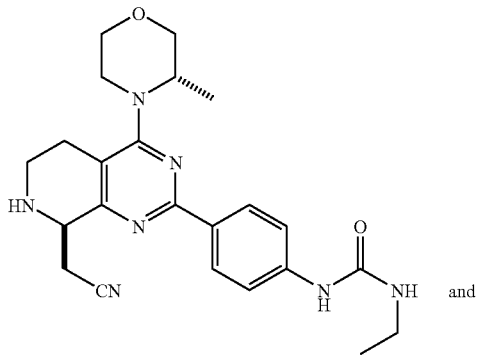

(xq¹)

and

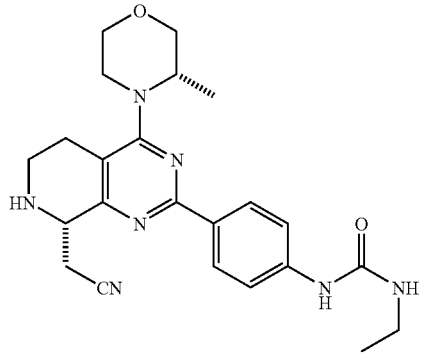

(xq²)

Synthesis of 1-(4-((R)-8-(cyanomethyl)-4-((S)-3-methylmorpholino)-5,6,7,8-tetrahydropyrido[3,4-d]pyrimidin-2-yl)phenyl)-3-ethylurea (xq¹); and 1-(4-((S)-8-(cyanomethyl)-4-((S)-3-methylmorpholino)-5,6,7,8-tetrahydropyrido[3,4-d]pyrimidin-2-yl)phenyl)-3-ethylurea (xq²): Tert-butyl 8-(cyanomethyl)-2-(4-(3-ethylureido)phenyl)-4-((S)-3-methylmorpholino)-5,6-dihydropyrido[3,4-d]pyrimidine-7(8H)-carboxylate (0.599 g, 0.00112 mol) and 4.0 M of Hydrogen chloride in 1,4-Dioxane (8.5 mL) were combined and shaken for 2.5 hours then concentrated, diluted with sat NaHCO3, extracted three times with 10% MeOH in dichloromethane, dried over Magnesium sulfate, filtered, concentrated, purified by HPLC, and the diastereomers were separated by SFC. R Diastereomer (xq¹): ¹H NMR (400 MHz, DMSO) δ 8.65 (s, 1H), 8.21 (d, J=8.7, 2H), 7.48 (d, J=8.7, 2H), 6.16 (t, J=5.6, 1H), 4.21-4.05 (m, 2H), 3.89 (d, J=11.0, 1H), 3.75 (d, J=9.1, 1H), 3.60 (dd, J=20.1, 9.2, 2H), 3.54-3.38 (m, 2H), 3.19-3.02 (m, 5H), 2.83-2.63 (m, 2H), 2.55-2.39 (m, 2H), 1.17 (d, J=6.6, 3H), 1.06 (t, J=7.2, 3H). LC/MS-m/z+436.2 (M+H)+; S Diastereomer (xq²) ¹H NMR (400 MHz, DMSO) δ 8.64 (s, 1H), 8.21 (d, J=8.7, 2H), 7.47 (d, J=8.7, 2H), 6.15 (t, J=5.5, 1H), 4.09 (d, J=5.9, 2H), 3.87 (d, J=10.4, 1H), 3.74-3.57 (m, 4H), 3.38 (t, J=10.6, 1H), 3.16-2.98 (m, 5H), 2.78 (d, J=8.1, 1H), 2.69 (d, J=14.5, 1H), 2.57-2.39 (m, 2H), 1.32 (d, J=6.6, 3H), 1.06 (t, J=7.2, 3H). LC/MS-m/z+436.2 (M+H)+.

Example 480

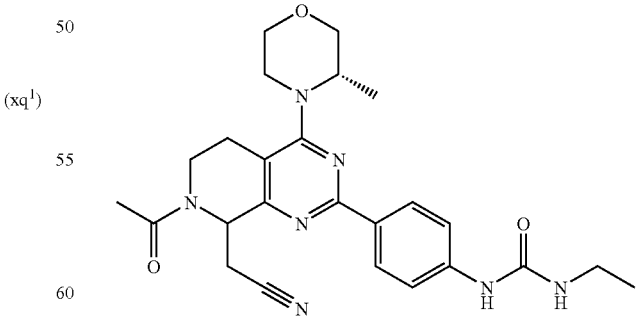

(xr)

Synthesis of 1-(4-(7-acetyl-8-(cyanomethyl)-4-((S)-3-methylmorpholino)-5,6,7,8-tetrahydropyrido[3,4-d]pyrimidin-2-yl)phenyl)-3-ethylurea (xr): 1-(4-(8-(Cyanomethyl)-4-((S)-3-methylmorpholino)-5,6,7,8-tetrahydropyrido[3,4-d] pyrimidin-2-yl)phenyl)-3-ethylurea (0.100 g, 0.230 mmol) in dry N,N-Dimethylformamide (1.00 mL, 12.9 mmol) was added N,N-Diisopropylethylamine (0.120 mL, 0.689 mmol) followed by Acetyl chloride (0.0246 mL, 0.346 mmol). The reaction mixture was stirred for 4 hours. The reaction mixture was concentrated and chromatographed through silica gel (12 g, 0-5% MeOH in dichloromethane). LC/MS-m/z+478.5 (M+H)+.

Example 481

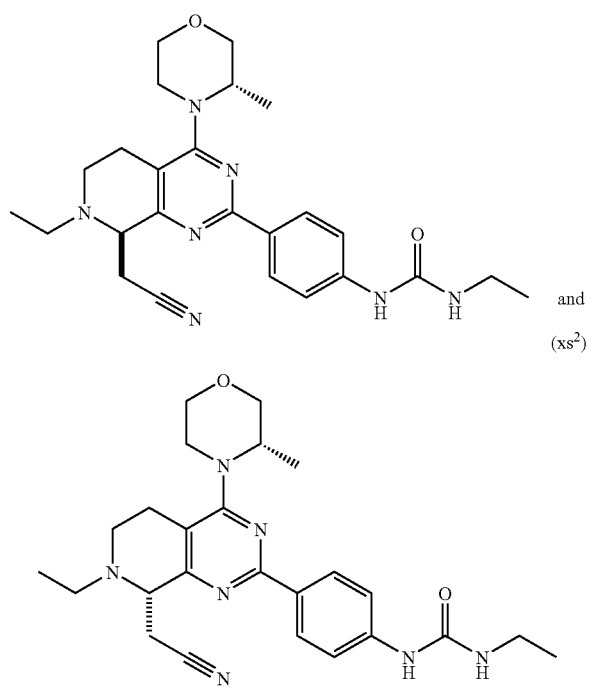

Synthesis of 1-(4-((R)-8-(cyanomethyl)-7-ethyl-4-((S)-3-methylmorpholino)-5,6,7,8-tetrahydropyrido[3,4-d]pyrimidin-2-yl)phenyl)-3-ethylurea (xs$^1$); and 1-(4-((S)-8-(cyanomethyl)-7-ethyl-4-((S)-3-methylmorpholino)-5,6,7,8-tetrahydropyrido[3,4-d]pyrimidin-2-yl)phenyl)-3-ethylurea (xs$^2$): 1-(4-(7-acetyl-8-(cyanomethyl)-4-morpholino-5,6,7,8-tetrahydropyrido[3,4-d]pyrimidin-2-yl)phenyl)-3-ethylurea (0.051 g, 0.00011 mol) in dry Tetrahydrofuran (1.00 mL, 0.0123 mol) at 0° C. was added 1.0 M of Borane-THF complex in Tetrahydrofuran (0.320 mL) dropwise. The reaction mixture was allowed to warm slowly to room temperature and stirred overnight. The reaction mixture was cooled at 0° C. then about 1 mL 1M HCl dropwise then added 1M NaOH until pH10. The reaction mixture was extracted three times with 10% MeOH in dichloromethane, dried over Magnesium sulfate, filtered, concentrated, purified by HPLC, and the diastereomers were separated by SFC. R Diastereomer (xs$^1$): $^1$H NMR (400 MHz, DMSO) δ 8.64 (s, 1H), 8.19 (t, J=11.3, 2H), 7.48 (d, J=8.7, 2H), 6.15 (t, J=5.3, 1H), 4.19 (d, J=6.6, 1H), 3.90 (d, J=11.6, 1H), 3.75 (d, J=12.2, 2H), 3.60 (dd, J=25.9, 11.5, 3H), 3.51-3.38 (m, 1H), 3.23-3.17 (m, 1H), 3.10 (ddd, J=24.6, 15.3, 9.3, 3H), 2.86 (dt, J=14.5, 7.2, 1H), 2.67 (s, 1H), 2.59 (dd, J=13.2, 6.9, 2H), 2.55-2.39 (m, 2H), 1.18 (d, J=6.6, 3H), 1.08 (dt, J=14.3, 7.1, 6H). LC/MS-m/z+ 464.2 (M+H)+; S Diastereomer (xs$^2$) $^1$H NMR (400 MHz, DMSO) δ 8.63 (s, 1H), 8.20 (d, J=8.7, 2H), 7.48 (d, J=8.7, 2H), 6.15 (t, J=5.5, 1H), 4.14 (d, J=6.8, 1H), 3.88 (d, J=10.3, 1H), 3.81-3.70 (m, 2H), 3.70-3.57 (m, 3H), 3.39 (t, J=11.0, 1H), 3.14 (ddd, J=19.9, 12.1, 6.1, 4H), 3.07-2.98 (m, 1H), 2.84 (dq, J=13.9, 7.0, 1H), 2.59 (ddd, J=21.5, 15.3, 8.2, 4H), 1.34 (d, J=6.6, 3H), 1.08 (dt, J=14.3, 7.1, 6H). LC/MS-m/z+ 464.2 (M+H)+.

Example 482

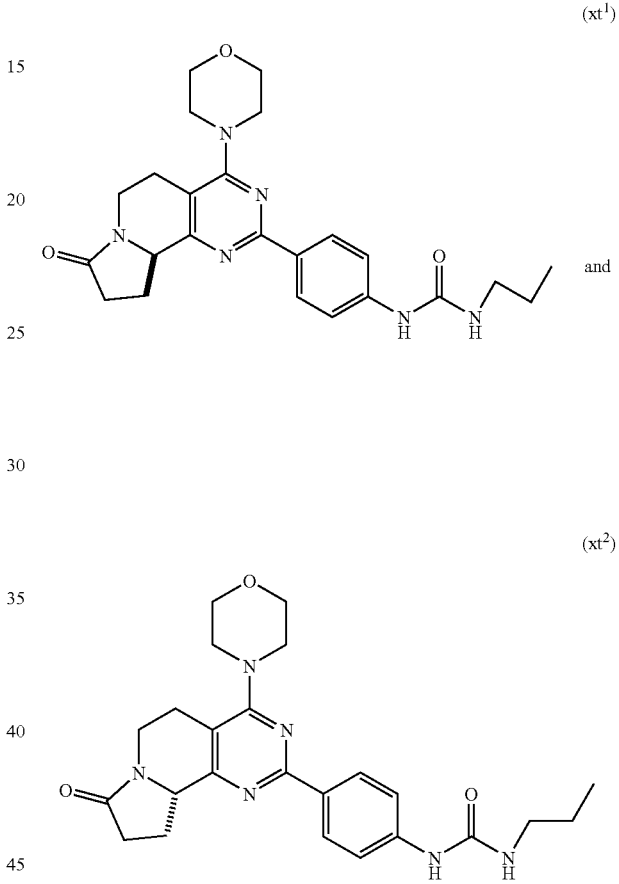

Synthesis of (R)-1-(4-(4-morpholino-8-oxo-5,6,8,9,10,10a-hexahydropyrimido[5,4-g]indolizin-2-yl)phenyl)-3-propylurea (xt$^1$); and (S)-1-(4-(4-morpholino-8-oxo-5,6,8,9,10,10a-hexahydropyrimido[5,4-g]indolizin-2-yl)phenyl)-3-propylurea (xt$^2$): Compounds (xt$^1$) and (xt$^2$) were prepared using similar methods as described in Examples 474 and 476. Enantiomer 1: $^1$H NMR (400 MHz, DMSO) δ 8.64 (s, 1H), 8.20 (d, J=8.7, 2H), 7.48 (d, J=8.7, 2H), 6.19 (t, J=5.7, 1H), 4.68 (t, J=8.2, 1H), 4.11 (dd, J=12.6, 5.2, 1H), 3.78 (dd, J=8.9, 6.4, 2H), 3.73-3.62 (m, 2H), 3.56 (dd, J=17.9, 4.8, 2H), 3.31 (d, J=12.7, 2H), 3.06 (dd, J=13.0, 6.6, 2H), 2.91 (t, J=10.6, 1H), 2.83-2.71 (m, 1H), 2.71-2.58 (m, 1H), 2.58-2.44 (m, 2H), 2.35-2.22 (m, 1H), 1.93-1.79 (m, 1H), 1.52-1.37 (m, 2H), 0.88 (t, J=7.4, 3H). LC/MS-m/z+451.2 (M+H)+; Enantiomer 2: $^1$H NMR (400 MHz, DMSO) δ 8.64 (s, 1H), 8.20 (d, J=8.7, 2H), 7.48 (d, J=8.7, 2H), 6.19 (s, 1H), 4.68 (s, 1H), 4.11 (dd, J=12.4, 5.1, 1H), 3.83-3.74 (m, 2H), 3.67 (s, 2H), 3.59 (s, 2H), 3.31 (d, J=5.5, 2H), 3.06 (d, J=6.2, 2H), 2.91 (t, J=11.7, 1H), 2.85-2.71 (m, 1H), 2.70-2.58 (m, 1H), 2.57-2.45 (m, 2H), 2.35-2.23 (m, 1H), 1.86 (dt, J=19.9, 10.0, 1H), 1.45 (d, J=7.1, 2H), 0.88 (t, J=7.4, 3H). LC/MS-m/z+451.2 (M+H)+ separated out by SFC. Diastereomer 1 LC/MS-m/z+478.3 (M+H)+; Diastereomer 2 LC/MS-m/z+478.2 (M+H)+.

Example 483

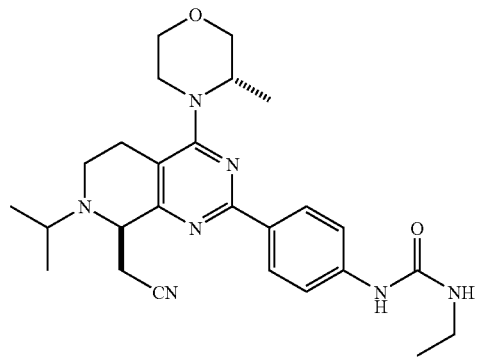

(xu¹)

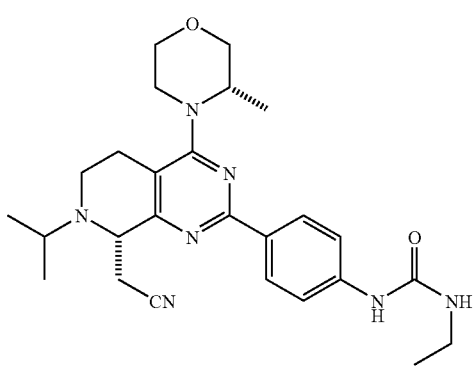

(xu²)

Example 484

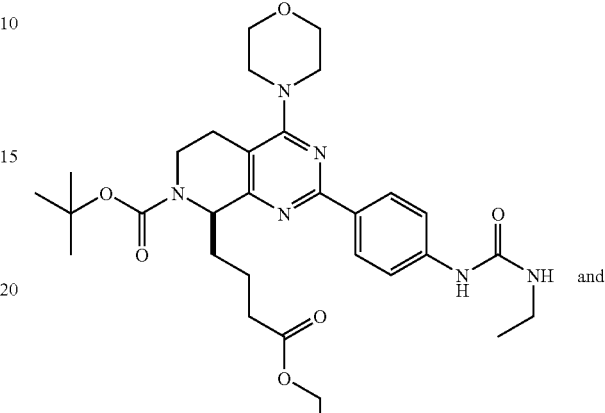

(xv¹)

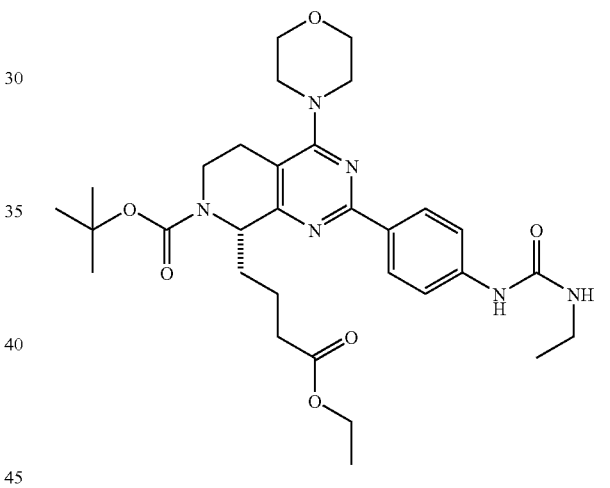

(xv²)

Synthesis of 1-(4-((R)-8-(cyanomethyl)-7-isopropyl-4-((S)-3-methylmorpholino)-5,6,7,8-tetrahydropyrido[3,4-d]pyrimidin-2-yl)phenyl)-3-ethylurea (xu¹); and 1-(4-((S)-8-(cyanomethyl)-7-isopropyl-4-((S)-3-methylmorpholino)-5,6,7,8-tetrahydropyrido[3,4-d]pyrimidin-2-yl)phenyl)-3-ethylurea (xu²): 1-(4-(8-(cyanomethyl)-4-((S)-3-methylmorpholino)-5,6,7,8-tetrahydropyrido[3,4-d]pyrimidin-2-yl)phenyl)-3-ethylurea (0.0947 g, 0.217 mmol) in dry N,N-Dimethylformamide (1.600 mL, 20.66 mmol) was added N,N-Diisopropylethylamine (0.1200 mL, 0.6888 mmol) followed by Isopropyl iodide (0.0460 mL, 0.460 mmol). The reaction mixture was heated at 50° C. and stirred overnight. The reaction mixture was heated at 80° C. and stirred overnight. The reaction mixture was heated at 90° C. overnight. Added Isopropyl iodide (0.1150 mL, 1.150 mmol) and N,N-Diisopropylethylamine (0.1200 mL, 0.6889 mmol). The reaction mixture was heated at 120° C. and stirred for 4 days. The reaction mixture was concentrated and chromatographed through silica gel (40 g, 0-5% MeOH in dichloromethane), purified by HPLC, and the diastereomers were Synthesis of (R)-tert-butyl 8-(4-ethoxy-4-oxobutyl)-2-(4-(3-ethylureido)phenyl)-4-morpholino-5,6-dihydropyrido[3,4-d]pyrimidine-7(8H)-carboxylate (xv¹); and (S)-tert-butyl 8-(4-ethoxy-4-oxobutyl)-2-(4-(3-ethylureido)phenyl)-4-morpholino-5,6-dihydropyrido[3,4-d]pyrimidine-7(8H)-carboxylate (xv²)

Step 1—Synthesis of Tert-butyl 8-allyl-2-chloro-4-morpholino-5,6-dihydropyrido[3,4-d]pyrimidine-7(8H)-carboxylate: Tert-butyl 2-chloro-4-morpholino-5,6-dihydropyrido[3,4-d]pyrimidine-7(8H)-carboxylate (5.00 g, 14.1 mmol) in dry Tetrahydrofuran (55.92 mL, 689.5 mmol) at −78° C. was added 1.6 M of n-Butyllithium in Hexane (14 mL) dropwise. The reaction mixture was stirred at −78° C. for 1 hour then added Allyl bromide (3.20 mL, 36.9 mmol) dropwise. The reaction mixture was stirred allowed to warm slowly to room temperature and stirred overnight. The reaction mixture was diluted with water, extracted three times with CH2Cl2, dried over Magnesium sulfate, filtered, concentrated, and chromatographed through silica gel (120 g, 0-30% EtOAc in heptane). $^1$H NMR (400 MHz, CDCl$_3$) δ 5.83 (td, J=16.8, 7.9, 1H), 5.04 (t, J=14.4, 3H), 4.30 (s, 1H), 3.89-3.79 (m, 2H), 3.78-3.68 (m, 2H), 3.67-3.56 (m, 2H), 3.41-3.31 (m, 2H), 2.91 (s, 2H), 2.74 (s, 1H), 2.57-2.37 (m, 2H), 1.46 (s, 9H). LC/MS-m/z+395.3 (M+H)+.

Step 2 Synthesis of (E)-tert-butyl 2-chloro-8-(4-ethoxy-4-oxobut-2-enyl)-4-morpholino-5,6-dihydropyrido[3,4-d]pyrimidine-7(8H)-carboxylate: Tert-butyl 8-allyl-2-chloro-4-morpholino-5,6-dihydropyrido[3,4-d]pyrimidine-7(8H)-carboxylate (1.000 g, 0.002532 mol) and Grubbs catalyst 2nd generation (0.1202 g, 0.0001416 mol) were combined, nitrogen purged three times, added dry 1,2-Dichloroethane (47.0 mL, 0.596 mol) and Ethyl acrylate (1.50 mL, 0.0138 mol) heated at 80° C. and stirred for 3 days. The reaction mixture was concentrated and and chromatographed through silica gel (120 g, 0-30% EtOAc in heptane). ¹H NMR (400 MHz, CDCl₃) δ 6.96 (dd, J=16.0, 8.1, 1H), 5.84 (d, J=15.9, 1H), 5.14 (s, 1H), 4.32 (s, 1H), 4.17 (q, J=7.1, 2H), 3.88-3.78 (m, 2H), 3.74 (dd, J=9.0, 6.4, 2H), 3.63 (d, J=11.8, 2H), 3.38 (dd, J=13.1, 3.9, 2H), 3.07 (s, 1H), 2.72 (d, J=60.1, 3H), 2.43 (d, J=14.2, 1H), 1.46 (s, 9H), 1.27 (t, J=7.1, 3H). LC/MS-m/z+ 467.4 (M+H)+

Step 3—Synthesis of (E)-tert-butyl 8-(4-ethoxy-4-oxobut-2-enyl)-2-(4-(3-ethylureido)phenyl)-4-morpholino-5,6-dihydropyrido[3,4-d]pyrimidine-7(8H)-carboxylate: [4-Ethylureido)phenyl]boronic acid, pinacol ester (0.621 g, 0.00214 mol), Tetrakis(triphenylphosphine)palladium(0) (0.1081 g, 9.355E-5 mol) Sodium carbonate (0.263 g, 0.00248 mol) and Potassium acetate (0.262 g, 0.00267 mol) were combined, nitrogen purged three times, added (E)-tert-butyl 2-chloro-8-(4-ethoxy-4-oxobut-2-enyl)-4-morpholino-5,6-dihydropyrido[3,4-d]pyrimidine-7(8H)-carboxylate (0.777 g, 0.00166 mol) in dry Acetonitrile (14.0 mL, 0.268 mol) followed by deoxygenated Water (8.50 mL, 0.472 mol), heated at 90° C. and stirred overnight. The reaction mixture was diluted with water, extracted three times with 10% MeOH in dichloromethane, dried over Magnesium sulfate, filtered, concentrated, chromatographed through silica gel (80 g, 0-100% EtOAc in heptane), purified by HPLC, and the enantiomers were separated out by SFC. Enantiomer 1 ¹H NMR (400 MHz, DMSO) δ 8.65 (s, 1H), 8.21 (d, J=8.7, 2H), 7.48 (d, J=8.7, 2H), 7.02 (s, 1H), 6.15 (t, J=5.6, 1H), 5.92 (d, J=13.6, 1H), 5.01 (s, 1H), 4.11 (d, J=6.1, 3H), 3.86-3.74 (m, 2H), 3.72-3.53 (m, 4H), 3.30 (s, 2H), 3.19-3.05 (m, 3H), 2.92 (s, 1H), 2.85-2.64 (m, 3H), 1.42 (s, 9H), 1.21 (t, J=7.1, 3H), 1.06 (t, J=7.2, 3H). LC/MS-m/z+595.3 (M+H)+; and Enantiomer 2 ¹H NMR (400 MHz, DMSO) δ 8.65 (s, 1H), 8.21 (d, J=8.7, 2H), 7.48 (d, J=8.7, 2H), 7.02 (s, 1H), 6.15 (s, 1H), 5.90 (s, 1H), 5.01 (s, 1H), 4.11 (d, J=6.7, 3H), 3.76 (s, 2H), 3.63 (dd, J=22.3, 9.0, 4H), 3.29 (s, 2H), 3.18-3.04 (m, 3H), 2.91 (s, 1H), 2.86-2.67 (m, 3H), 1.42 (s, 9H), 1.21 (t, J=7.0, 3H), 1.06 (t, J=7.1, 3H). LC/MS-m/z+595.3 (M+H)+

Step 4—Synthesis of compounds xv¹ and xv²: (E)-tert-butyl 8-(4-ethoxy-4-oxobut-2-enyl)-2-(4-(3-ethylureido)phenyl)-4-morpholino-5,6-dihydropyrido[3,4-d]pyrimidine-7(8H)-carboxylate (0.841 g, 0.00141 mol), Palladium on Carbon 10% (0.1:0.9, Palladium:carbon black, 0.213 g), and Ethanol (45.0 mL, 0.771 mol) were combined under nitrogen then purged with hydrogen, heated at 65° C., and stirred overnight under an atmosphere of hydrogen. The reaction mixture was purged with nitrogen, added celite, filtered through celite, concentrated, chromatographed through silica gel (12 g, 0-100% EtOAc in heptane), purified by HPLC, and the enantiomers were separated out by SFC. Enantiomer 1 ¹H NMR (400 MHz, DMSO) δ 8.65 (s, 1H), 8.19 (d, J=8.7, 2H), 7.48 (d, J=8.7, 2H), 6.15 (t, J=5.6, 1H), 4.84 (s, 1H), 4.06 (dd, J=14.1, 7.0, 3H), 3.83-3.73 (m, 2H), 3.71-3.62 (m, 2H), 3.57 (d, J=10.7, 2H), 3.30 (s, 2H), 3.18-3.07 (m, 2H), 2.92 (s, 1H), 2.80 (d, J=10.7, 1H), 2.46-2.29 (m, 3H), 2.12 (s, 1H), 1.73 (s, 3H), 1.45 (s, 9H), 1.18 (t, J=7.1, 3H), 1.12-0.99 (m, 3H). LC/MS-m/z+597.3 (M+H)+; Enantiomer 2 ¹H NMR (400 MHz, DMSO) δ 8.64 (s, 1H), 8.19 (d, J=8.7, 2H), 7.48 (d, J=8.7, 2H), 6.14 (t, J=5.6, 1H), 4.85 (s, 1H), 4.06 (q, J=7.1, 3H), 3.78 (dd, J=8.8, 6.3, 2H), 3.73-3.62 (m, 2H), 3.61-3.52 (m, 2H), 3.30 (s, 2H), 3.18-3.05 (m, 2H), 3.03-2.72 (m, 3H), 2.47-2.30 (m, 3H), 2.13 (d, J=12.5, 1H), 1.72 (d, J=8.4, 3H), 1.45 (s, 9H), 1.18 (s, 3H), 1.06 (s, 3H). LC/MS-m/z+597.3 (M+H)+.

Example 485

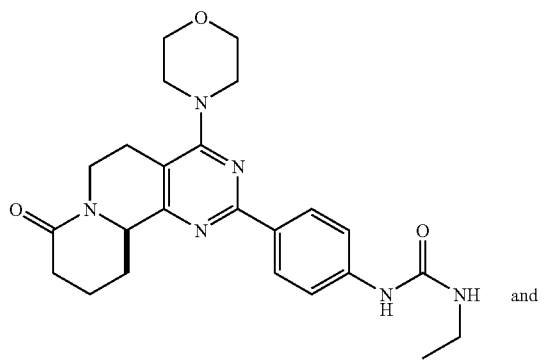

(xw¹)

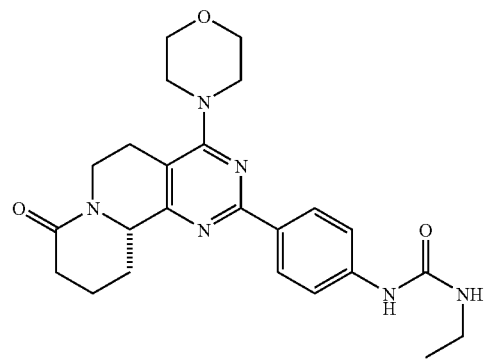

(xw²)

Synthesis of (R)-1-ethyl-3-(4-(4-morpholino-8-oxo-6,8,9,10,11,11a-hexahydro-5H-pyrimido[4,5-a]quinolizin-2-yl)phenyl)urea (xw¹)); and (S)-1-ethyl-3-(4-(4-morpholino-8-oxo-6,8,9,10,11,11a-hexahydro-5H-pyrimido[4,5-a]quinolizin-2-yl)phenyl)urea (xw²): Tert-butyl 8-(4-ethoxy-4-oxobutyl)-2-(4-(3-ethylureido)phenyl)-4-morpholino-5,6-dihydropyrido[3,4-d]pyrimidine-7(8H)-carboxylate (0.847 g, 0.00142 mol) and 4.0 M of Hydrogen chloride in 1,4-Dioxane (11.0 mL) were combined and shaken for 2 hours. LC-MS shows mostly product with a trace of the acid present. The reaction mixture was then concentrated and vacuum pump dried for 30 min. Dry Toluene (68.0 mL, 0.638 mol) and N,N-Diisopropylethylamine (2.50 mL, 0.0144 mol) were then added to the reaction mixture. The reaction mixture was heated at 80° C., and stirred overnight. The reaction mixture was concentrated, chromatographed through silica gel (40 g, 0-5% MeOH in dichloromethane), purified by HPLC, and the enantiomers were separated out by SFC. Enantiomer 1 ¹H NMR (400 MHz, DMSO) δ 8.64 (s, 1H), 8.20 (d, J=8.7, 2H), 7.48 (d, J=8.7, 2H), 6.14 (t, J=5.6, 1H), 4.75 (d, J=8.3, 1H), 4.57 (d, J=6.2, 1H), 3.85-3.73 (m, 2H), 3.71-3.54 (m, 4H), 3.34 (dd, J=12.8, 6.4, 2H), 3.19-3.06 (m, 2H), 2.74 (d, J=10.9, 2H), 2.69-2.43 (m, 2H), 2.42-2.20 (m, 2H), 1.88 (d, J=24.0, 2H), 1.60 (d, J=8.4, 1H), 1.06 (t, J=7.2, 3H). LC/MS-m/z+ 451.2 (M+H)+; Enantiomer 2 $^1$H NMR (400 MHz, DMSO) δ 8.64 (s, 1H), 8.20 (d, J=8.7, 2H), 7.48 (d, J=8.8, 2H), 6.14 (t, J=5.5, 1H), 4.75 (dd, J=12.4, 3.8, 1H), 4.57 (dd, J=10.9, 3.9, 1H), 3.78 (dd, J=8.9, 6.4, 2H), 3.72-3.51 (m, 4H), 3.40-3.30 (m, 2H), 3.19-3.04 (m, 2H), 2.74 (d, J=11.3, 2H), 2.69-2.43 (m, 2H), 2.42-2.20 (m, 2H), 1.88 (d, J=20.4, 2H), 1.69-1.52 (m, 1H), 1.06 (t, J=7.2, 3H). LC/MS-m/z+451.2 (M+H)+.

Example 486

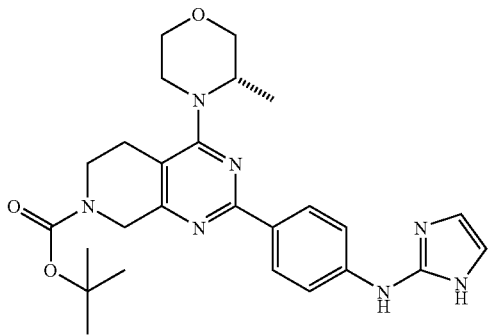

(xx)

Synthesis of (S)-tert-butyl 2-(4-(1H-imidazol-2-ylamino)phenyl)-4-(3-methylmorpholino)-5,6-dihydropyrido[3,4-d]pyrimidine-7(8H)-carboxylate (xx)

Step 1—Synthesis of N-(4-bromophenyl)-1H-imidazol-2-amine: p-Bromoaniline (1.111 g, 0.006458 mol) and 2-chloroimidazole (0.753 g, 0.00734 mol) were combined, nitrogen purged three times added Methanesulfonic acid (0.82 mL, 0.013 mol) and N-Methylpyrrolidinone (11.0 mL, 0.114 mol) heated at 95° C. and stirred overnight. The reaction mixture was heated at 100° C. and stirred for 2 days. The reaction mixture was diluted with water and extracted three times with 10% MeOH in dichloromethane. The aqueous layer was lyophilized, chromatographed through silica gel (120 g, 0-10% MeOH in dichloromethane), and purified by HPLC. $^1$H NMR (400 MHz, DMSO) δ 10.75 (s, 1H), 8.77 (s, 1H), 7.38 (d, J=9.0, 2H), 7.33 (d, J=9.0, 2H), 6.74 (s, 1H), 6.64 (s, 1H). LC/MS-m/z+238.0 (M+H)+.

Step 2—Synthesis of N-(4-(4,4,5,5-tetramethyl-1,3,2-dioxaborolan-2-yl)phenyl)-1H-imidazol-2-amine: N-(4-bromophenyl)-1H-imidazol-2-amine (0.0398 g, 0.167 mmol), Bispinacol ester boronate (0.0805 g, 0.317 mmol) [1,1'-Bis(diphenylphosphino)ferrocene]dichloropalladium(II), complex with dichloromethane (1:1) (0.0238 g, 0.0291 mmol) and Potassium acetate (0.0733 g, 0.747 mmol) were combined, nitrogen purged three times, added dry N,N-Dimethylformamide (2.00 mL, 25.8 mmol) heated at 80° C., and stirred overnight. The reaction mixture was diluted with water and extracted three times with 10% MeOH in dichloromethane, dried over Magnesium sulfate, filtered, and concentrated. The reaction mixture was used in the next step without further purification. LC/MS-m/z+286.3 (M+H)+.

Step 3—Synthesis of compound xx: (S)-tert-butyl 2-chloro-4-(3-methylmorpholino)-5,6-dihydropyrido[3,4-d]pyrimidine-7(8H)-carboxylate (0.0648 g, 0.000176 mol), Tetrakis(triphenylphosphine)palladium(0) (0.014 g, 0.000012 mol) Sodium carbonate (0.0286 g, 0.000270 mol) and Potassium acetate (0.0346 g, 0.000352 mol) were combined, nitrogen purged three times, added N-(4-(4,4,5,5-tetramethyl-1,3,2-dioxaborolan-2-yl)phenyl)-1H-imidazol-2-amine (0.0477 g, 0.000167 mol) in dry Acetonitrile (2.8 mL, 0.054 mol) and deoxygenated Water (1.70 mL, 0.0944 mol) (Note: some of the boronate ester crude material did not completely dissolve), heated at 90° C. and stirred overnight The reaction mixture was diluted with water, extracted three times with 10% MeOH in CH2Cl2, dried over Magnesium sulfate, filtered, concentrated, chromatographed through silica gel (12 g, 0-5% MeOH in dichloromethane), and purified by HPLC. $^1$H NMR (400 MHz, DMSO) δ 10.83 (s, 1H), 8.91 (s, 1H), 8.16 (d, J=8.7, 2H), 7.44 (d, J=8.7, 2H), 6.76 (m, 2H), 4.47 (m, 2H), 4.09 (s, 1H), 3.87 (d, J=10.1, 1H), 3.70 (d, J=8.7, 1H), 3.60 (d, J=11.1, 4H), 3.43 (d, J=11.8, 2H), 2.66 (d, J=6.3, 2H), 1.46 (s, 9H), 1.27 (t, J=10.4, 3H). LC/MS-m/z+ 492.2 (M+H)+

Example 487

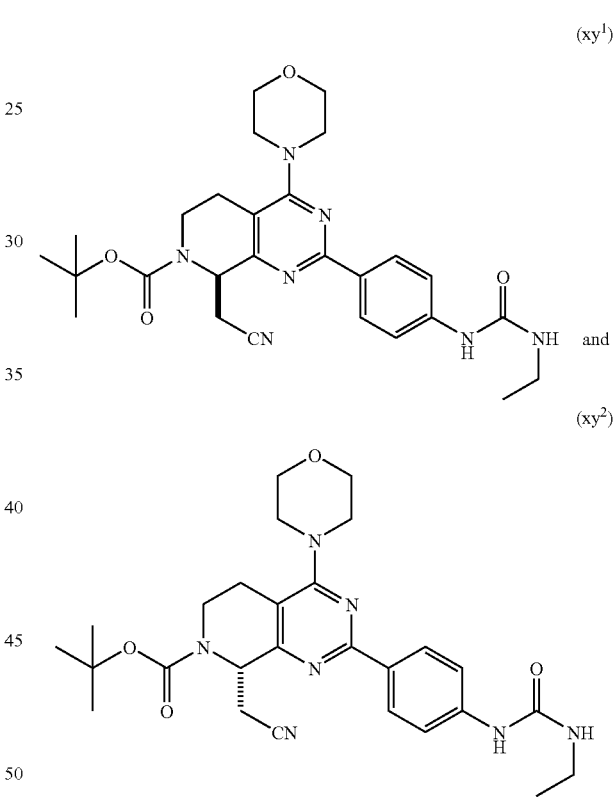

(xy$^1$)

and (xy$^2$)

Synthesis of (R)-tert-butyl 8-(cyanomethyl)-2-(4-(3-ethylureido)phenyl)-4-morpholino-5,6-dihydropyrido[3,4-d]pyrimidine-7(8H)-carboxylate (xy$^1$); and (S)-tert-butyl 8-(cyanomethyl)-2-(4-(3-ethylureido)phenyl)-4-morpholino-5,6-dihydropyrido[3,4-d]pyrimidine-7(8H)-carboxylate (xy$^2$)

Step 1—Synthesis of Tert-butyl 2-chloro-8-(cyanomethyl)-4-morpholino-5,6-dihydropyrido[3,4-d]pyrimidine-7 (8H)-carboxylate: Tert-butyl 2-chloro-4-morpholino-5,6-dihydropyrido[3,4-d]pyrimidine-7(8H)-carboxylate (2.000 g, 5.636 mmol) in dry Tetrahydrofuran (240 mL, 3.0E3 mmol) (Note: The reaction mixture was still not 100% dissolved in solution at this concentration, but most of it was dissolved) at −78° C. was added 1.6 M of n-Butyllithium in Hexane (5.50 mL) dropwise. The reaction mixture was stirred at −78° C. for 1 hour then added Bromoacetonitrile (1.00 mL, 14.4 mmol)

dropwise. The reaction mixture was allowed to warm slowly to room temperature and stirred for 3 days. water was added dropwise to the reaction mixture then extracted three times with dichloromethane, dried over Magnesium sulfate, filtered, concentrated, and chromatographed through silica gel (330 g, 0-30% EtOAc in heptane). $^1$H NMR (500 MHz, CDCl$_3$) δ 5.15 (s, 1H), 3.83 (dd, J=9.0, 6.2, 2H), 3.80-3.71 (m, 2H), 3.64 (s, 2H), 3.49-3.39 (m, 2H), 3.13 (s, 3H), 2.76 (s, 2H), 2.56 (s, 1H), 1.51 (s, 9H). LC/MS-m/z+394.0 (M+H)+

Step 2—Synthesis of compounds xy$^1$ and xy$^2$: Tert-butyl 2-chloro-8-(cyanomethyl)-4-morpholino-5,6-dihydropyrido[3,4-d]pyrimidine-7(8H)-carboxylate (0.803 g, 0.00204 mol), [4-Ethylureido)phenyl]boronic acid, pinacol ester (0.778 g, 0.00268 mol), Tetrakis(triphenylphosphine)palladium(0) (0.148 g, 0.000128 mol) Sodium carbonate (0.334 g, 0.00315 mol) and Potassium acetate (0.330 g, 0.00336 mol) were combined, nitrogen purged three times, added dry Acetonitrile (17.0 mL, 0.325 mol) followed by deoxygenated Water (10.0 mL, 0.555 mol), heated at 90° C. and stirred overnight. The reaction mixture was diluted with water, extracted three times with 10% MeOH in dichloromethane, dried over Magnesium sulfate, filtered, concentrated, chromatographed through silica gel (40 g, 0-100% EtOAc in heptane), purified by HPLC, and the enantiomers were separated by SFC. Enantiomer 1 $^1$H NMR (400 MHz, DMSO) δ 8.71 (s, 1H), 8.24 (d, J=8.8, 2H), 7.49 (d, J=8.8, 2H), 6.19 (t, J=5.5, 1H), 5.16 (t, J=5.9, 1H), 4.22 (s, 1H), 3.84-3.73 (m, 2H), 3.73-3.55 (m, 4H), 3.34 (m, 3H), 3.17-2.90 (m, 4H), 2.82 (s, 1H), 1.48 (s, 9H), 1.13 (t, J=7.2, 1H), 1.06 (t, J=7.2, 3H). LC/MS-m/z+522.2 (M+H)+; Enantiomer 2 $^1$H NMR (400 MHz, DMSO) δ 8.71 (s, 1H), 8.24 (d, J=8.8, 2H), 7.49 (d, J=8.8, 2H), 6.19 (t, J=5.6, 1H), 5.16 (t, J=5.9, 1H), 4.18 (s, 1H), 3.78 (dd, J=8.7, 6.2, 2H), 3.72-3.55 (m, 4H), 3.41-3.25 (m, 3H), 3.17-2.90 (m, 4H), 2.84 (d, J=11.0, 1H), 1.47 (d, J=9.3, 9H), 1.14 (t, J=7.2, 1H), 1.09-1.01 (m, 3H). LC/MS-m/z+522.3 (M+H)+

Example 488

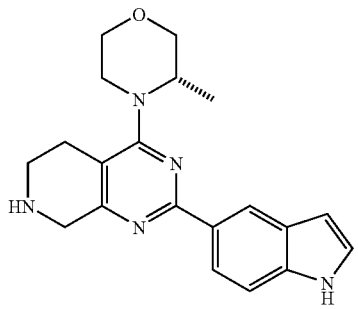

(xz)

Synthesis of (S)-4-(2-(1H-indol-5-yl)-5,6,7,8-tetrahydropyrido[3,4-d]pyrimidin-4-yl)-3-methylmorpholine (xz): Tert-butyl 2-(1H-indol-5-yl)-4-morpholino-5,6-dihydropyrido[3,4-d]pyrimidine-7(8H)-carboxylate (0.199 g, 0.000443 mol) and 4.0 M of Hydrogen chloride in 1,4-Dioxane (3.4 mL) were combined and shaken for 2 hours then concentrated, diluted 10% MeOH in dichloromethane and sat NaHCO3, extracted three times with 10% MeOH in dichloromethane, dried over Magnesium sulfate, filtered, concentrated, and vacuum pump dried overnight, and purified by HPLC. $^1$H NMR (400 MHz, DMSO) δ 11.18 (s, 1H), 8.56 (s, 1H), 8.12 (dd, J=8.6, 1.4, 1H), 7.42 (d, J=8.6, 1H), 7.36 (t, J=2.7, 1H), 6.53 (s, 1H), 4.10 (d, J=6.7, 1H), 3.95-3.78 (m, 3H), 3.74 (dd, J=11.3, 2.8, 1H), 3.68-3.50 (m, 3H), 3.50-3.39 (m, 1H), 3.02-2.90 (m, 1H), 2.87-2.76 (m, 1H), 2.55 (d, J=11.2, 2H), 1.25 (t, J=10.2, 3H). LC/MS-m/z+350.2 (M+H)+

Example 489

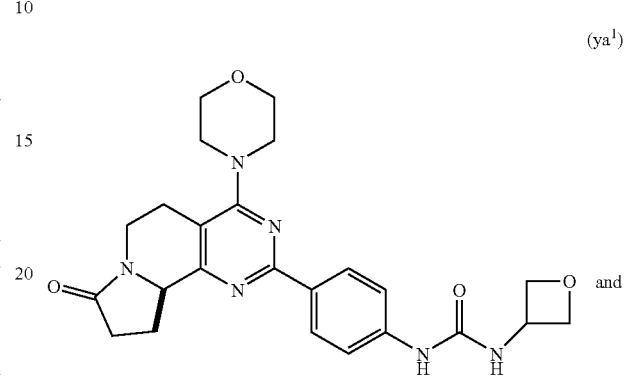

(ya$^1$)

and

(ya$^2$)

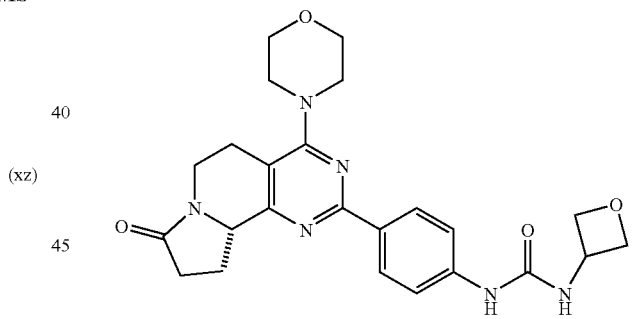

Synthesis of (R)-1-(4-(4-morpholino-8-oxo-5,6,8,9,10,10a-hexahydropyrimido[5,4-g]indolizin-2-yl)phenyl)-3-(oxetan-3-yl)urea (ya$^1$); (S)-1-(4-(4-morpholino-8-oxo-5,6,8,9,10,10a-hexahydropyrimido[5,4-g]indolizin-2-yl)phenyl)-3-(oxetan-3-yl)urea (ya$^2$): and 2-(4-Aminophenyl)-4-morpholino-5,6,10,10a-tetrahydropyrimido[5,4-g]indolizin-8(9H)-one (0.103 g, 0.282 mmol) in dry 1,2-Dichloroethane (3.6 mL, 45 mmol) at 0° C. was added Triethylamine (0.152 mL, 1.09 mmol) followed by Triphosgene (0.0326 g, 0.110 mmol). The reaction mixture was stirred at 0° C. for 5 min then heated at 70° C. for 40 min. The reaction mixture was cooled to room temperature then added oxetan-3-amine hydrochloride (0.0935 g, 0.853 mmol) and stirred overnight at room temperature. The reaction mixture was concentrated, chromatographed through silica gel (40 g, 0-5% MeOH in dichloromethane), purified by HPLC, and the enantiomers were separated out by SFC. Enantiomer 1 $^1$H NMR (400 MHz, DMSO) δ 8.83 (s, 1H), 8.20 (d, J=8.7, 2H), 7.49 (d, J=8.8, 2H), 7.02 (d, J=6.5, 1H), 4.87-4.60 (m, 4H), 4.44 (t, J=5.9, 2H), 4.11 (dd, J=12.7, 5.1, 1H), 3.85-3.73 (m, 2H), 3.73-3.62 (m, 2H), 3.63-3.49 (m, 2H), 2.91 (t, J=10.3, 1H), 2.76 (dt, J=14.2, 6.9, 2H), 2.70-2.59 (m, 1H), 2.59-2.44 (m, 3H), 2.35-2.20 (m, 1H), 1.95-1.75 (m, 1H), 1.08 (t, J=7.2, 1H). LC/MS-m/z+465.2 (M+H)+; Enantiomer 2 ¹H NMR (400 MHz, DMSO) δ 8.89 (s, 1H), 8.20 (d, J=8.8, 2H), 7.49 (d, J=8.8, 2H), 7.08 (d, J=6.6, 1H), 4.84-4.63 (m, 4H), 4.44 (t, J=5.8, 2H), 4.11 (dd, J=12.6, 5.2, 1H), 3.84-3.73 (m, 2H), 3.67 (m, 2H), 3.56 (m, 2H), 2.91 (t, J=10.3, 1H), 2.76 (ddd, J=21.6, 15.3, 6.4, 2H), 2.64 (m, 1H), 2.57-2.41 (m, 3H), 2.36-2.21 (m, 1H), 1.93-1.79 (m, 1H), 1.08 (t, J=7.2, 1H). LC/MS-m/z+465.2 (M+H)+.

Example 490

MeOH in dichloromethane followed by 6:2:1:1 EtOAc:acetone:water:MeOH), and purified by HPLC. ¹H NMR (400 MHz, DMSO) δ 8.61 (s, 1H), 8.49 (d, J=1.7, 1H), 8.46 (dd, J=4.8, 1.6, 1H), 8.15 (d, J=8.8, 2H), 7.71 (d, J=7.8, 1H), 7.46 (d, J=8.8, 2H), 7.36 (dd, J=7.7, 4.8, 1H), 6.15 (t, J=5.6, 1H), 4.12 (d, J=6.5, 1H), 3.91-3.81 (m, 1H), 3.77-3.53 (m, 6H), 3.50 (s, 2H), 3.45-3.34 (m, 1H), 3.17-3.06 (m, 2H), 2.86 (d, J=11.0, 2H), 2.81-2.71 (m, 1H), 2.70-2.56 (m, 3H), 2.39 (t, J=11.3, 1H), 2.01 (t, J=10.8, 2H), 1.83 (s, 2H), 1.60-1.42 (m, 2H), 1.22 (d, J=6.6, 3H), 1.06 (t, J=7.2, 3H). LC/MS-m/z+ 571.3 (M+H)+.

Example 491

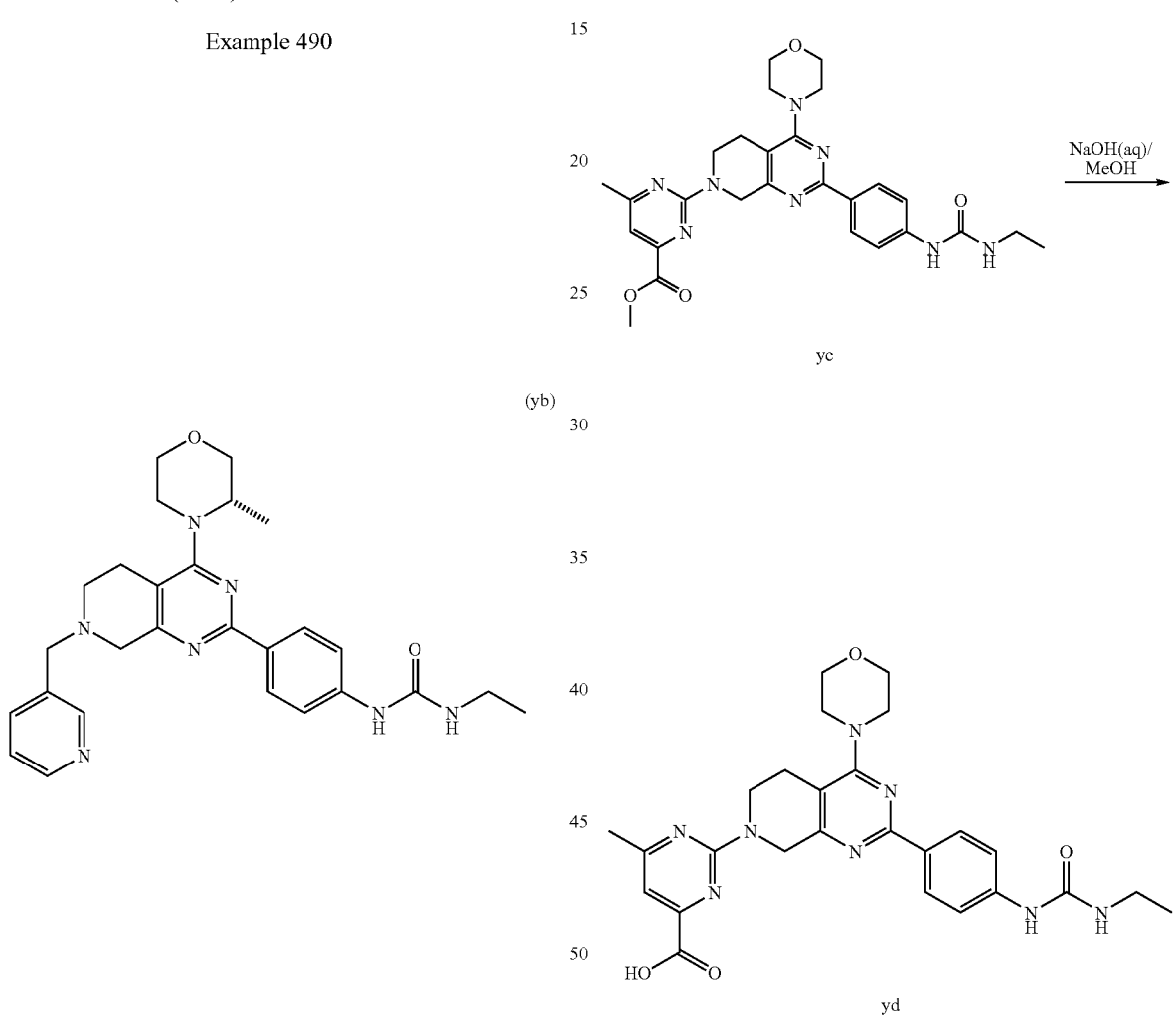

Synthesis of (S)-1-ethyl-3-(4-(4-(3-methylmorpholino)-7-(pyridin-3-ylmethyl)-5,6,7,8-tetrahydropyrido[3,4-d]pyrimidin-2-yl)phenyl)urea (yb): (S)-1-ethyl-3-(4-(4-(3-methylmorpholino)-5,6,7,8-tetrahydropyrido[3,4-d]pyrimidin-2-yl)phenyl)urea (0.0995 g, 0.251 mmol) in dry was added 1-(pyridin-3-ylmethyl)piperidin-4-one (0.0486 g, 0.255 mmol). The reaction mixture was then heated at 70° C. for 40 min. The reaction mixture was then cooled at 0° C. and added Sodium triacetoxyborohydride (0.1118 g, 0.5275 mmol). The reaction mixture was allowed to warm slowly to room temperature and stirred for 3 days. The reaction mixture was diluted with water, extracted three times with 10% MeOH in dichloromethane, dried over Magnesium sulfate, filtered, evaporated, chromatographed through silica gel (12 g, 0-10%

Synthesis of 2-(2-(4-(3-ethyl-ureido)phenyl)-4-morpholino-5,6-dihydropyrido[3,4-d]pyrimidin-7(8H)-yl)-6-methylpyrimidine-4-carboxylic acid (yd): methyl 2-(2-(4-(3-ethylureido)-phenyl)-4-morpholino-5,6-dihydropyrido[3,4-d]pyrimidin-7(8H)-yl)-6-methylpyrimidine-4-carboxylate (yc) (0.25 mmol) in a mixed solvent of NaOH (10%, 5 mL) and MeOH (5 mL) were stirred at room temperature overnight. The mixture was neutralized with diluted HCl to pH=6 and extracted with ethyl acetate thrice. The combined organic phases were dried over Na₂SO₄ and concentrated to give 50.6 mg of 2-(2-(4-(3-ethyl-ureido)phenyl)-4-morpholino-5,6-dihydropyrido[3,4-d]pyrimidin-7(8H)-yl)-6-methylpyrimidine-4-carboxylic acid (yd): ¹H NMR (D₆-DMSO, 400 MHz) δ 8.18 (d, J=8.8, 2H), 7.51 (d, J=8.0, 2H), 6.91 (s, 1H), 4.84 (s, 2H), 3.96 (m, 2H), 3.69 (s, 4H), 3.41 (s, 4H), 3.09 (t, J=7.2, 2H), 2.67 (s, 2H), 2.32 (s, 3H), 1.04 (t, J=7.2, 2H); LC-MS: m/z=+519 (M+H)+.

3.10-3.06 (m, 2H), 2.68-2.65 (m, 4H), 2.40 (s, 1H), 1.90-1.65 (m, 4H), 1.60-1.47 (m, 1H), 1.45-1.28 (m, 2H), 1.25-1.09 (m, 1H), 1.02 (t, J=7.2, 3H). LC-MS: m/z=+481 (M+H)+.

Example 492

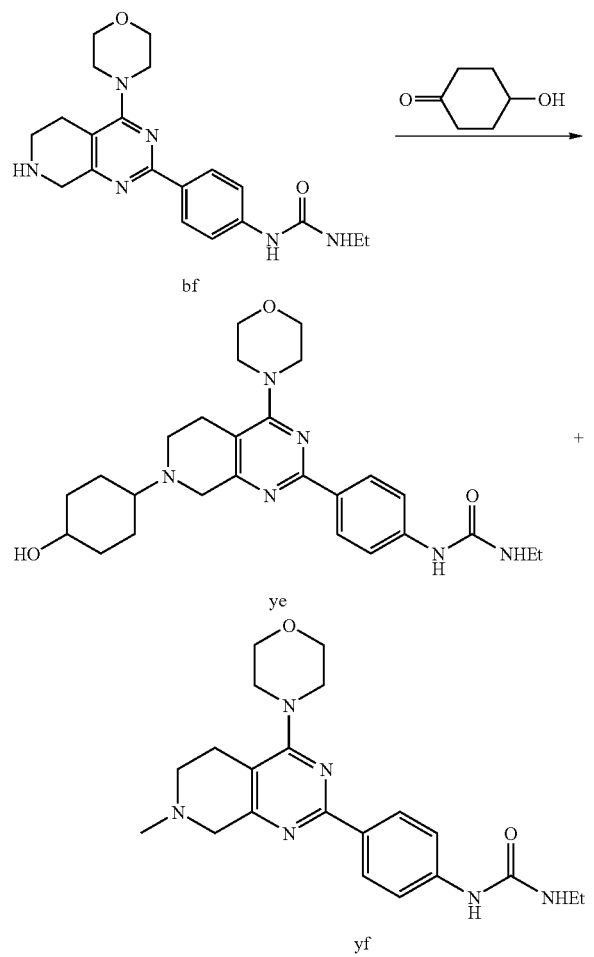

Example 493

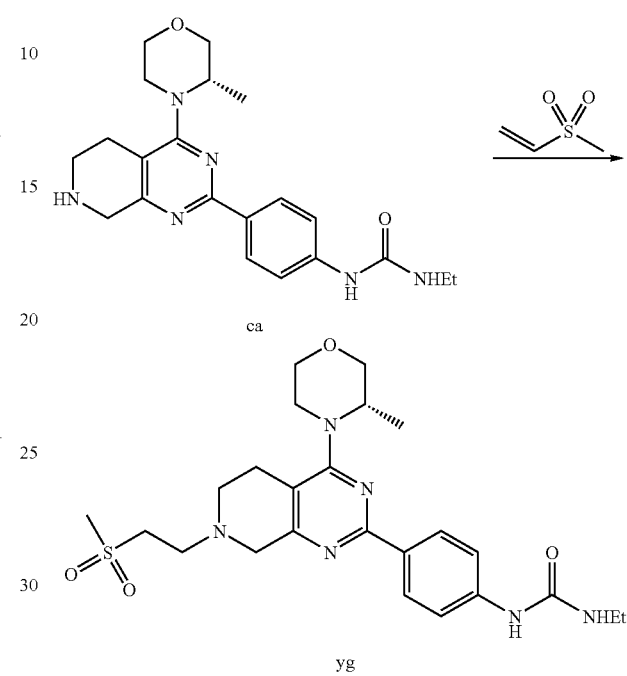

Synthesis of (S)-1-ethyl-3-(4-(4-(3-methylmorpholino)-7-(2-(methylsulfonyl)ethyl)-5,6,7,8-tetrahydropyrido[3,4-d]pyrimidin-2-yl)phenyl)urea (yg): A mixture of (S)-1-ethyl-3-(4-(4-(3-methylmorpholino)-5,6,7,8-tetrahydropyrido[3,4-d]pyrimidin-2-yl)phenyl)urea (ca) (0.35 mmol), methylsulfonylethene (3.5 mmol), DIPEA (1 mL), in a mixed solvent of THF/DMF (30 mL, 10:1) was stirred at 40° C. overnight. The solvent was removed in vacuum and the residue was purified by preparative TLC (Hexanes:ethyl acetate=1:2) to give 48.2 mg (yield: 27%) of (S)-1-ethyl-3-(4-(4-(3-methylmorpholino)-7-(2-(methylsulfonyl)ethyl)-5,6,7,8-tetrahydropyrido[3,4-d]pyrimidin-2-yl)phenyl)urea (yg). $^1$H NMR (D$_6$-DMSO, 400 MHz): δ 8.60 (s, 1H), 8.13 (d, J=7.2, 2H), 7.44 (d, J=7.2, 2H), 6.12 (t, J=2.5, 1H), 4.18-3.33 (m, 11H), 3.19-2.63 (m, 11H), 1.20 (d, J=6.8, 3H), 1.04 (t, J=7.2, 3H). LC-MS: m/z=+503 (M+H)+.

Synthesis of 1-ethyl-3-(4-(7-(4-hydroxy-cyclohexyl)-4-morpholino-5,6,7,8-tetrahydropyrido[3,4-d]pyrimidin-2-yl)phenyl)urea (ye); and 1-ethyl-3-(4-(7-methyl-4-morpholino-5,6,7,8-tetrahydropyrido[3,4-d]pyrimidin-2-yl)phenyl)urea (yf): A mixture of compound 1 (200 mg, 0.52 mmol) and 4-hydroxycyclohexanone (97.9 mg, 0.85 mmol) in a mixed solvent of DCE/DMF (3:5, 10 mL) was stirred at 70-80° C. under N$_2$ for 20 min. The solution was cooled down to 0° C. and NaBH(OAc)$_3$ (366.5 mg, 1.75 mmol) was added and the mixture was stirred at 70-80° C. under N$_2$ for 1 h. The solution was concentrated under high vacuum and the residue was dissolved in DCM (10 mL) and the insoluble solid was filtered off. The mother liquor was dried over anhydrous Na$_2$SO$_4$ and concentrated to give the crude product which was purified by reverse-phase HPLC to give 1-ethyl-3-(4-(7-(4-hydroxy-cyclohexyl)-4-morpholino-5,6,7,8-tetrahydropyrido[3,4-d]pyrimidin-2-yl)phenyl)urea (ye) (55.6 mg, 22%) and 1-ethyl-3-(4-(7-methyl-4-morpholino-5,6,7,8-tetrahydropyrido[3,4-d]pyrimidin-2-yl)phenyl)urea (yf) (67.5 mg). $^1$H NMR of 41 (D$_6$-DMSO, 400 MHz): δ 9.41 (s, 1H), 8.12 (d, J=4, 2H), 7.46 (d, J=8.8, 2H), 6.74-6.70 (m, 1H), 4.55-4.39 (m, 1H), 3.80-3.61 (m, 6H), 3.44-3.36 (m, 4H),

Example 494

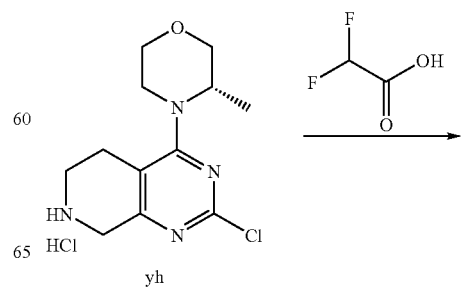

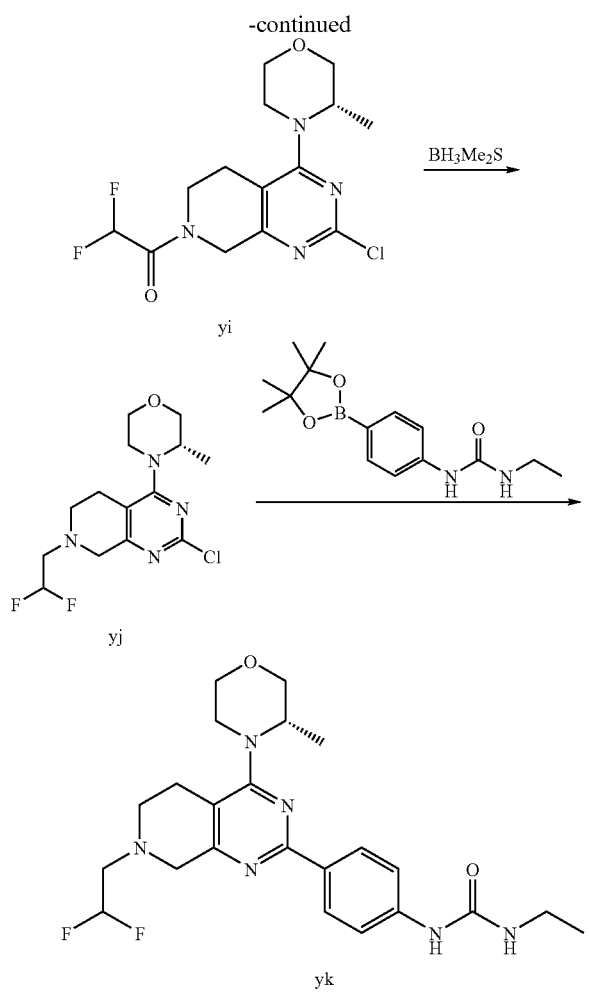

Synthesis of (S)-1-(4-(7-(2,2-difluoroethyl)-4-(3-methylmorpholino)-5,6,7,8-tetrahydropyrido[3,4-d]pyrimidin-2-yl)phenyl)-3-ethylurea (yk)

Step 1—Synthesis of (S)-1-(2-chloro-4-(3-methylmorpholino)-5,6-dihydropyrido[3,4-d]pyrimidin-7(8H)-yl)-2,2-difluoroethanone (yi): A solution of (S)-4-(2-chloro-5,6,7,8-tetrahydropyrido[3,4-d]pyrimidin-4-yl)-3-methylmorpholine hydrochloride (yh) (300 mg, 1.0 mmol), difluoroacetic acid (192 mg, 2.0 mmol), DIPEA (1 mL) and HATU (500 mg, 1.3 mmol) in THF (5 ml) was stirred at r.t. overnight. LC-MS indicated the reaction was completed and the mixture was poured into water, and extracted with EtOAc. The EtOAc layer was dried over anhydrous $Na_2SO_4$ and concentrated to give the crude, which was purified by reverse-phase HPLC to give the desired product (280 mg, 85%). $^1$H NMR ($CDCl_3$, 400 MHz): δ6.23-5.95 (m, 1H), 4.70-4.54 (m, 2H), 4.06-4.04 (m, 1H), 3.90-3.80 (m, 2H), 3.67-3.56 (m, 5H), 3.49-3.35 (m, 1H), 2.66-2.61 (m, 2H), 1.31 (d, J=9.6, 3H). LC-MS: m/z=+496 (M+H)$^+$.

Step 2—Synthesis of (S)-4-(2-chloro-7-(2,2-difluoroethyl)-5,6,7,8-tetrahydropyrido[3,4-d]pyrimidin-4-yl)-3-methylmorpholine (yj): To a solution of (S)-1-(2-chloro-4-(3-methylmorpholino)-5,6-dihydropyrido[3,4-d]pyrimidin-7(8H)-yl)-2,2-difluoroethanone (yi) (270 mg, 0.78 mmol) in THF (30 mL) was added borane-dimethyl sulfide complex (2 M, 3.8 mL) dropwise at 0° C. under $N_2$. The resulting solution was stirred at r.t. for 5h. LC-MS indicated the reaction was completed, HCl (1M) was added to the reaction solution dropwise at 0° C. until pH<2. The reaction mixture was stirred at r.t. overnight, filtered and extracted with EtOAc. Saturated sodium bicarbonate aqueous solution was added to the aqueous until pH>9 and then extracted with EtOAc. The combined EtOAc layers were washed with brine, dried over anhydrous $Na_2SO_4$ and concentrated to give the desired compound yj (160 mg, 58%) which was used for next step without further purification. LC-MS: m/z=+333 (M+H)$^+$.

Step 3—Synthesis of (S)-1-(4-(7-(2,2-difluoroethyl)-4-(3-methylmorpholino)-5,6,7,8-tetrahydropyrido[3,4-d]pyrimidin-2-yl)phenyl)-3-ethylurea (yk): A mixture of compound (S)-4-(2-chloro-7-(2,2-difluoroethyl)-5,6,7,8-tetrahydropyrido[3,4-d]pyrimidin-4-yl)-3-methylmorpholine (yj) (150 mg, 0.45 mmol), 1-ethyl-3-(4-(4,4,5,5-tetramethyl-1,3,2-dioxaborolan-2-yl)phenyl)urea (150 mg, 0.52 mmol), $K_2CO_3$ (124 mg, 0.9 mmol) and Pd(PPh$_3$)$_4$ (40 mg) in MeCN:$H_2O$ (3:1, 4 mL) was subjected to microwave irradiation at 110° C. for 1 h under $N_2$. Then the mixture was cooled down to room temperature, filtered through celite and concentrated. The residue was washed with water and purified by reversed-phase HPLC to give compound yk (143.2 mg, 69%): $^1$H NMR ($D_6$-DMSO, 400 MHz): δ8.64 (s, 1H), 8.15 (d, J=8.8, 2H), 7.45 (d, J=8.8, 2H), 6.25-6.16 (m, 2H), 4.11-4.05 (m, 1H), 3.88-3.56 (m, 8H), 3.12-3.09 (m, 2H), 2.99-2.92 (m, 2H), 2.90-2.82 (m, 1H), 2.71-2.67 (m, 3H), 1.23 (d, J=6.4, 3H), 1.06-1.03 (m, 3H). LC-MS: m/z=+461 (M+H)$^+$.

Example 495

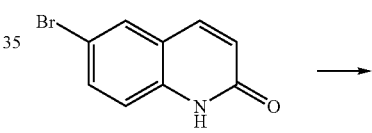

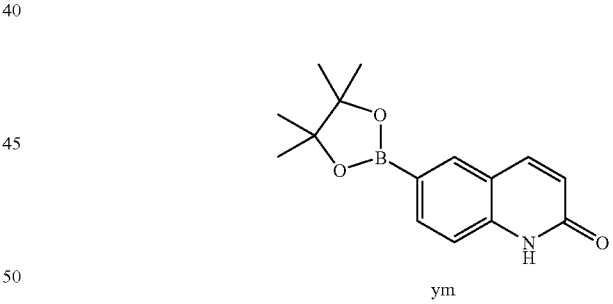

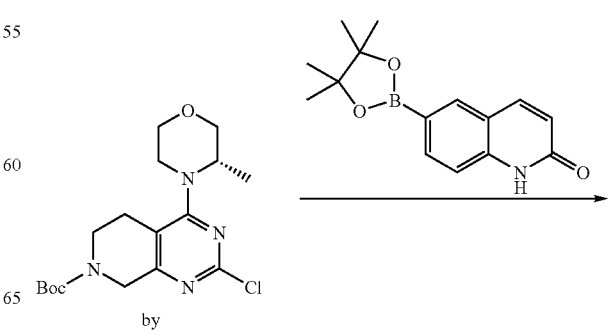

-continued

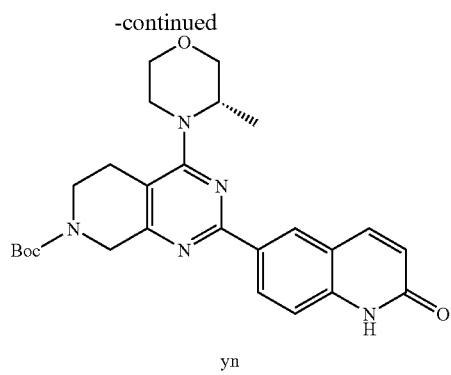

yn

Synthesis of (S)-tert-butyl 4-(3-methylmorpholino)-2-(2-oxo-1,2-dihydroquinolin-6-yl)-5,6-dihydropyrido[3,4-d]pyrimidine-7(8H)-carboxylate (yn)

Step 1—Synthesis of 6-(4,4,5,5-tetramethyl-1,3,2-dioxaborolan-2-yl)quinolin-2(1H)-one (ym): A mixture of 6-bromoquinolin-2(1H)-one (yl) (4.1 g, 18.4 mmol), Bis(pinacolato)diboron (14 g, 55.2 mmol), KOAc (3.6 g, 36.8 mmol) and Pd(dppf)Cl$_2$ (600 mg, 0.82 mmol) in 60 mL of DMF was stirred at 80-90° C. for 3 h under N$_2$. The mixture was cooled down to room temperature, filtered through celite and concentrated. The residue was washed with water, hexanes ether and re-crystallized in EtOAc to give the compound ym (1.8 g, 37%). LC-MS: m/z=+272 (M+H)$^+$.

Step 2—Synthesis of (S)-tert-butyl 4-(3-methylmorpholino)-2-(2-oxo-1,2-dihydroquinolin-6-yl)-5,6-dihydropyrido[3,4-d]pyrimidine-7(8H)-carboxylate (yn): a mixture of compound "by" (880 mg, 2.4 mmol), Compound ym (540 mg, 2.0 mmol), K$_2$CO$_3$ (550 mg, 4 mmol) and Pd(PPh$_3$)$_4$ (75 mg, 0.064 mmol) in MeCN/H$_2$O (3:1, 10 mL) was subjected to microwave at 110° C. for 1 h under N$_2$. The mixture was cooled down to room temperature, filtered through celite and concentrated. The residue was washed with water and MeCN to give the Compound yn (1.0 g, 52%). $^1$H NMR (D$_6$-DMSO, 400 MHz): δ11.87 (s, 1H), 8.54 (d, J=1.6, 1H), 8.40 (d, J=1.6, 1H), 7.33 (d, J=8.4, 1H), 6.48 (d, J=9.6, 1H), 4.58-4.32 (m, 2H), 4.16-4.09 (m, 1H), 3.87-3.81 (m, 1H), 3.70-3.51 (m, 5H), 3.48-3.39 (m, 2H), 2.63 (s, 2H), 1.42 (s, 9H), 1.22 (t, J=6.8, 3H). LC-MS: m/z=+478 (M+H)$^+$.

Example 496

Biological Evaluation of Compounds a. In vitro mTOR Kinase Assay

The kinase activity of mTOR enzyme is assessed by incubating purified recombinant enzyme (mTOR(1360-2549)+GBL, prepared in-house) in a reaction mixture containing ATP, MnCl$_2$, and a fluorescently labeled mTOR substrate, e.g., GFP-4E-BP1 (Invitrogen, product #PR8808A). The reaction is stopped by an addition of a Terbium-labeled phospho-specific antibody, e.g., Tb-labeled anti-p4E-BP1 T37/T46, (Invitrogen, product #PR8835A), EDTA, and TR-FRET buffer solution (Invitrogen, Product #PR3756B). Product formation is detected by way of time-resolved fluorescence resonance energy transfer (TR-FRET), which occurs when the phosphorylated substrate and labeled antibody are in close proximity due to phospho-specific binding. Enzymatic activity is measured as an increase in TR-FRET signal using a Perkin Elmer Envision plate reader. The assay is performed in a 384-well Proxiplate Plus (Perkin Elmer. Product #6008269) using the following protocol:

Compound activity is tested in 10 point dose curves starting at the highest final concentration of 10 uM. They are serially diluted in 100% DMSO prior to further dilution with assay buffer. The reaction mixture (8 uls) containing 0.25 nM mTOR+GBL enzyme, 400 nM GFP-4E-BP1, 8 uM ATP, 50 mM Hepes pH 7.5, 0.01% Tween 20, 10 mM MnCl$_2$, 1 mM EGTA, 1 mM DTT, 1% DMSO (+/−compound) is incubated at room temperature for 30 minutes. 8 μL of solution containing 2 nM Tb-anti-p4E-BP1 antibody & 10 mM EDTA diluted TR-FRET buffer is then added and incubated for 30 minutes to stop the reaction. The plate is scanned with the Envision plate reader. Ki values are calculated in Assay Explorer using the Morrison ATP-competitive tight binding equation for Ki apparent determination.

b. In Vitro Phospho-AKT Serine 473 Cellular Assay

The assay measures a test compound's inhibition of AKT serine-473 phosphorylation in human prostate adenocarcinoma derived PC-3 (ATCC CRL-1435) cells that have been stimulated with epidermal growth factor (EGF).

The PC-3 cell line is maintained in RPMI1640 media supplemented with 10% FBS, 2 mM Glutamine, and 10 mM HEPES pH 7.4 at 37° C. in a 5% CO2 humidified incubator.

Cells are seeded in 384-well plates at 7,000 cells/well in 50 μl growth media. After 24 hours, growth media is removed and replaced with RPMI1640 containing no FBS. Cells are treated with 10 concentrations of test compounds or DMSO alone for controls (final DMSO concentration 0.5%) and incubated at 37° C. for 30 minutes. Cells are then stimulated for 10 minutes with 100 ng/ml EGF (final concentration). One column of controls is not stimulated with EGF to observe the signal ratio between stimulated and non-stimulated cells. After 10 minutes, compounds and stimulation media are removed and replaced with 25 μl lysis buffer containing protease inhibitors and phosphatase inhibitors. This buffer contains detergent to bring about cellular disruption. Following complete cellular disruption, 20 μl lysate is transferred to a MesoScale Discovery 384 well 4-spot plate coated with an antibody to AKT (MesoScale Discovery (MSD) product K211CAD-2) which have been previously blocked with 3% bovine serum albumin in Tris buffered saline. Following the transfer of lysate to the MSD plate, AKT in the lysate is captured on the coated antibody by incubation on a shaker at 4° C. for 16 hours. Following the capture step the plate is washed and then incubated for two hours with an antibody to S473 phosphorylated AKT which is conjugated with a Sulfo-Tag. This tag gives a signal when in proximity to the electrode on the base of the MSD plate. Binding the tagged antibody to the captured protein allow detection on a MSD reader.

The EC$_{50}$ is defined as the concentration at which a given compound achieves 50% decrease of the measured levels of S473 AKT phosphorylation. EC$_{50}$ values are calculated using MDL Assay Explorer 3.0.1.8 fitting a sigmoidal curve with a variable slope.

Example 497

In Table 3, below, is provided the biological activity of certain compounds of the invention against mTOR kinase. Certain compounds of the invention exhibit a Ki value in the mTOR kinase assay (described in Example 90) of ≦100 nM. Examples of compounds having a Ki in the mTOR assay of ≦100 nM are shown in Table 2 as having a mTOR activity level=1. Certain other compounds of the invention exhibit a Ki value in the mTOR kinase assay of >100 nM and ≦5 micromolar. Examples of compounds having a Ki in the mTOR assay of >100 nM and ≦5 micromolar are shown in Table 3 as having a mTOR activity level=2. Certain other compounds of the invention exhibit a Ki value in the mTOR kinase assay of >5 micromolar and ≦10 micromolar.

TABLE 3
| Structure | mTOR Activity Level |
|---|---|
| 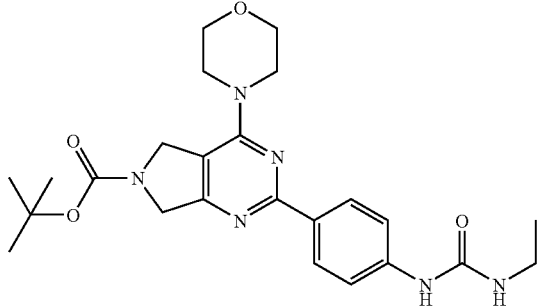 | 1 |
| 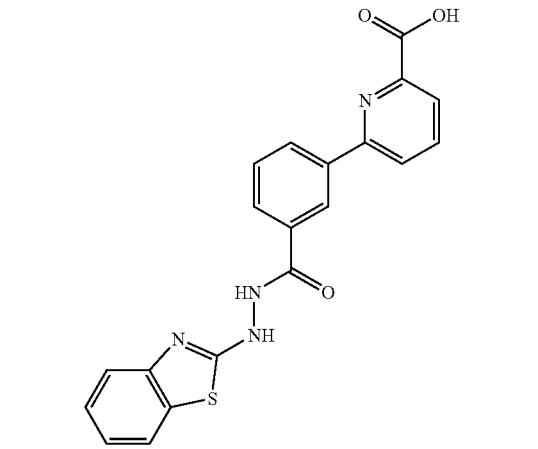 | N/A |
| 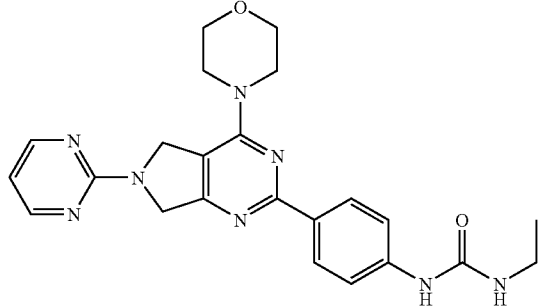 | 1 |
| 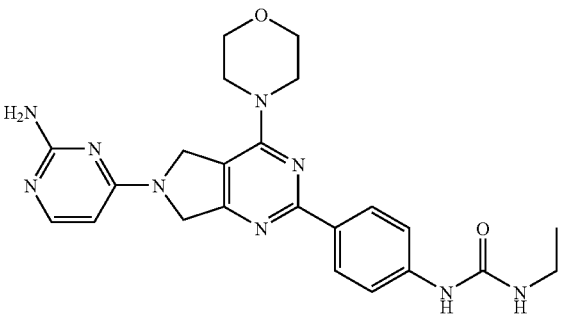 | 1 |

TABLE 3-continued

| Structure | mTOR Activity Level |
|---|---|
| | 1 |
| | 1 |
| | 1 |
| | 1 |

TABLE 3-continued
| Structure | mTOR Activity Level |
|---|---|
| 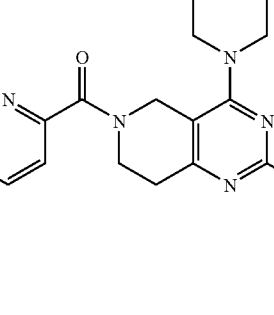 | 1 |
| 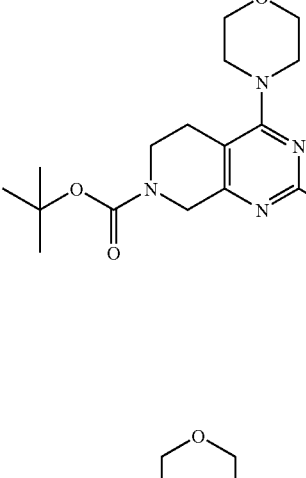 | 1 |
| 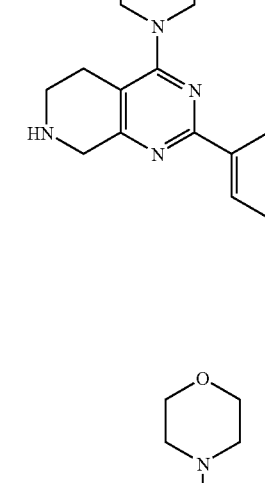 | 2 |
| 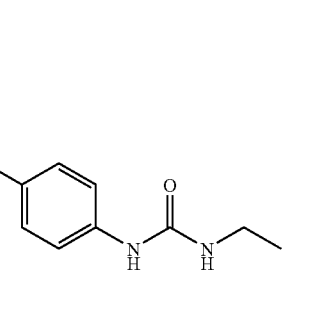 | 1 |

TABLE 3-continued

| Structure | mTOR Activity Level |
|---|---|
| (structure) | 1 |
| (structure) | 1 |
| (structure) | 1 |
| (structure) | 1 |

TABLE 3-continued

| Structure | mTOR Activity Level |
|---|---|
| | 1 |
| | 1 |
| | 1 |
| | 1 |

TABLE 3-continued

| Structure | mTOR Activity Level |
|---|---|
| (structure) | 1 |
| (structure) | 1 |
| (structure) | 1 |
| (structure) | 1 |

TABLE 3-continued

| Structure | mTOR Activity Level |
|---|---|
| | 1 |
| | 1 |
| | 1 |
| | 1 |

TABLE 3-continued

| Structure | mTOR Activity Level |
|---|---|
| | 1 |
| | 1 |
| | 1 |
| | 1 |

TABLE 3-continued

| Structure | mTOR Activity Level |
|---|---|
| | 2 |
| | 2 |
| | 2 |
| 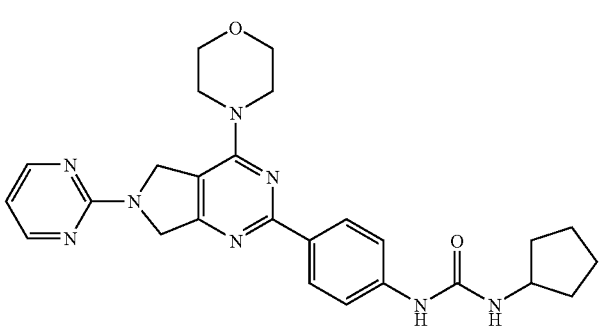 | 1 |

TABLE 3-continued
| Structure | mTOR Activity Level |
|---|---|
| 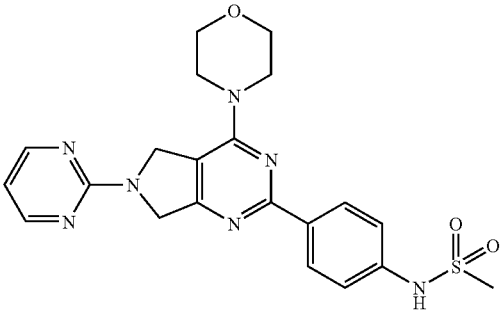 | 2 |
| 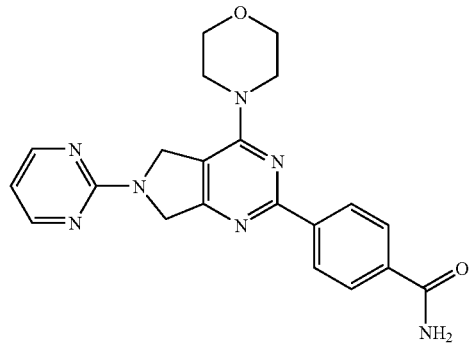 | 2 |
| 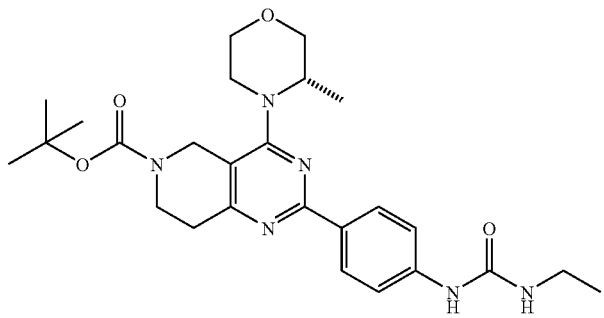 | 1 |
| 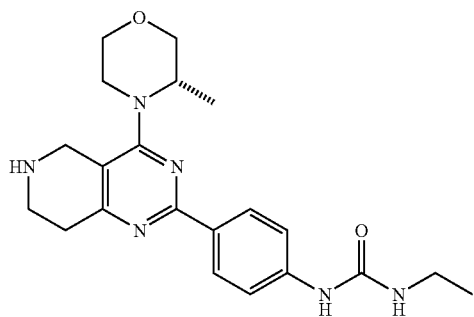 | 1 |

TABLE 3-continued

| Structure | mTOR Activity Level |
|---|---|
| (structure) | 1 |
| (structure) | 1 |
| (structure) | 1 |
| (structure) | 1 |

TABLE 3-continued
| Structure | mTOR Activity Level |
|---|---|
| 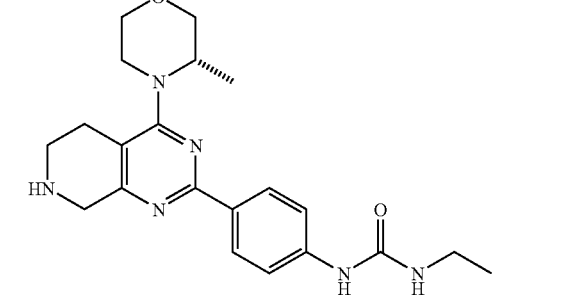 | 1 |
| 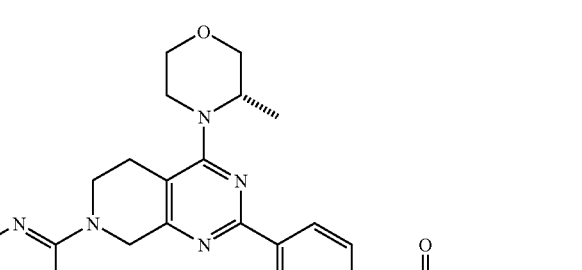 | 1 |
| 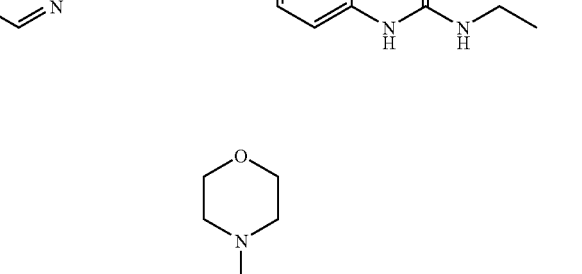 | 2 |
| 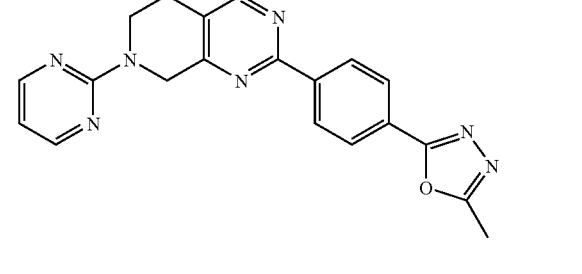 | 2 |

TABLE 3-continued
| Structure | mTOR Activity Level |
|---|---|
| 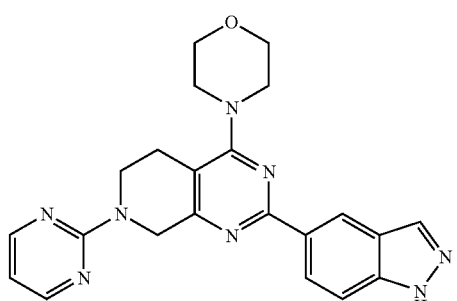 | 2 |
| 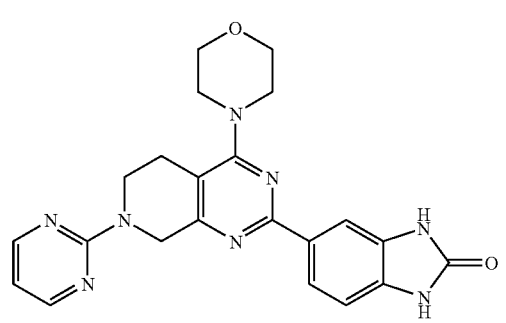 | 2 |
| 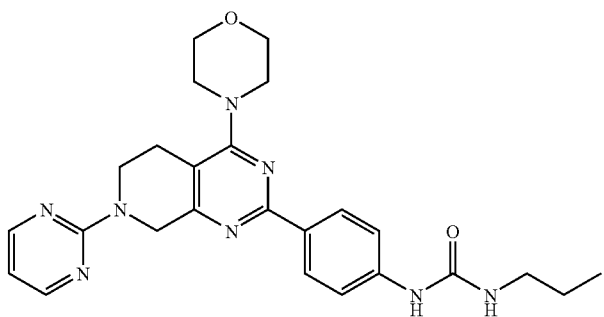 | 2 |
| 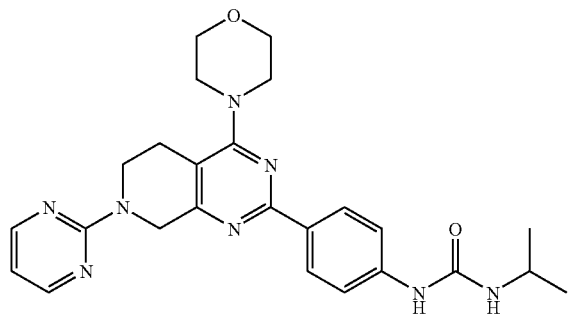 | 2 |

TABLE 3-continued
| Structure | mTOR Activity Level |
|---|---|
| 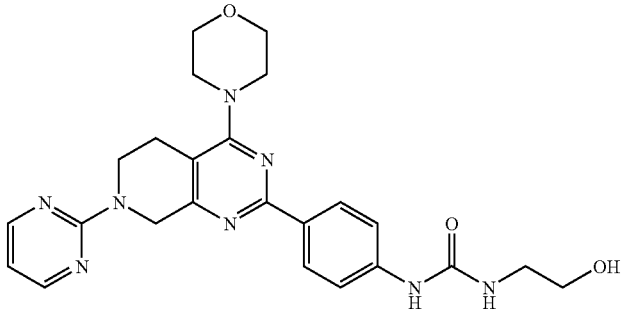 | 2 |
| 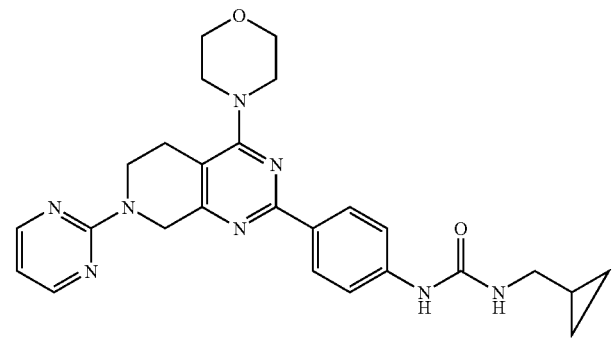 | 1 |
| 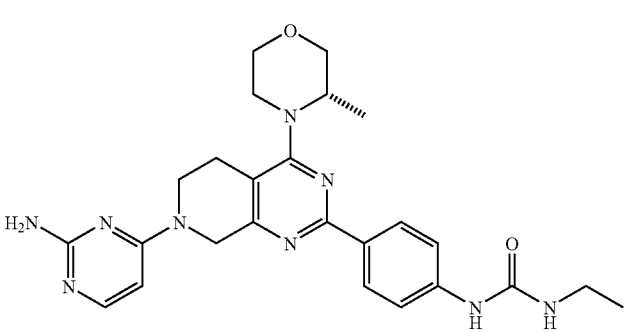 | 1 |
| 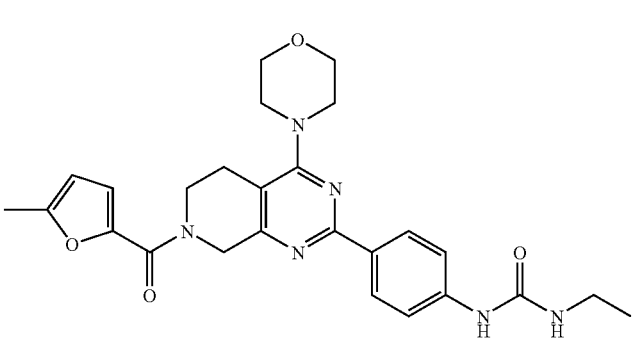 | N/A |

TABLE 3-continued

| Structure | mTOR Activity Level |
|---|---|
| | 1 |
| | 1 |
| | 1 |
| | 1 |

TABLE 3-continued

| Structure | mTOR Activity Level |
|---|---|
| | 1 |
| | 1 |
| | 1 |
| | 1 |

TABLE 3-continued

| Structure | mTOR Activity Level |
|---|---|
| (structure) | 1 |
| (structure) | 1 |
| (structure) | 1 |
| (structure) | 1 |

TABLE 3-continued
| Structure | mTOR Activity Level |
|---|---|
| 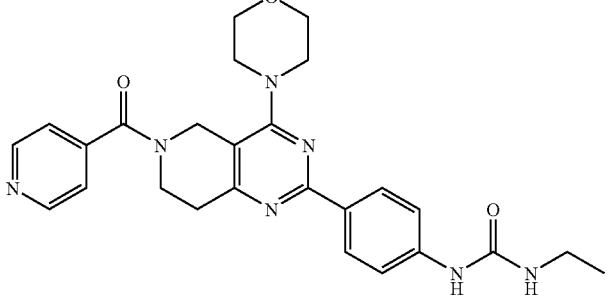 | 1 |
| 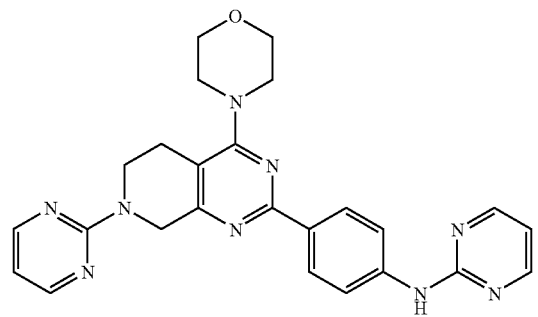 | 1 |
| 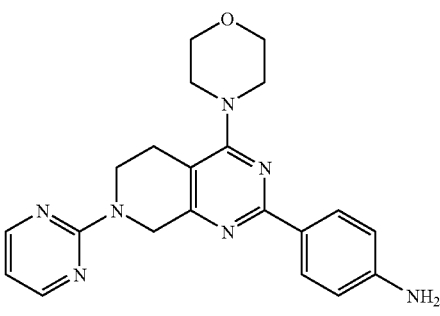 | 2 |
| 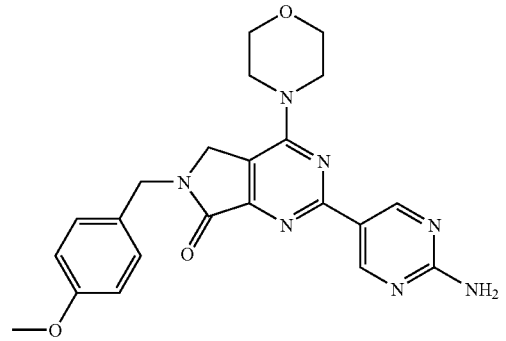 | 2 |

TABLE 3-continued
| Structure | mTOR Activity Level |
|---|---|
| 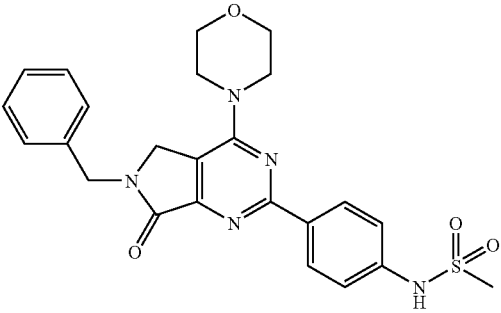 | 2 |
| 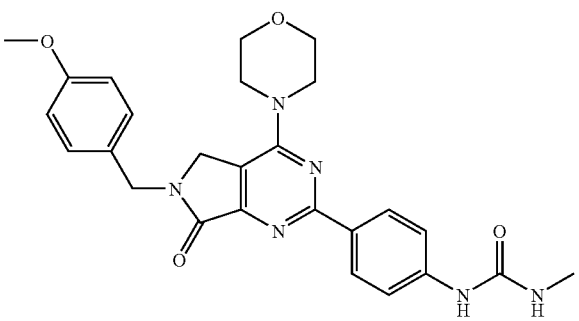 | 1 |
| 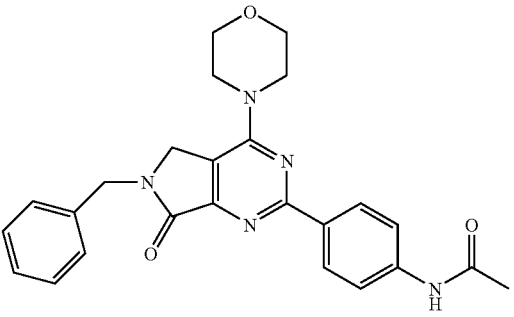 | 2 |
| 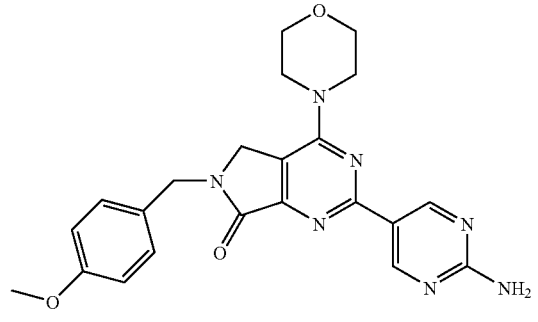 | 2 |

TABLE 3-continued

| Structure | mTOR Activity Level |
|---|---|
| (2-chlorobenzoyl on tetrahydropyrido-pyrimidine with morpholine and phenyl-ethylurea) | 1 |
| (4-chlorobenzoyl on tetrahydropyrido-pyrimidine with morpholine and phenyl-ethylurea) | 1 |
| (cinnamoyl on tetrahydropyrido-pyrimidine with morpholine and phenyl-ethylurea) | 1 |
| (pyrimidin-2-yl on tetrahydropyrido-pyrimidine with morpholine and phenyl-ethylurea) | 1 |

TABLE 3-continued

| Structure | mTOR Activity Level |
|---|---|
| 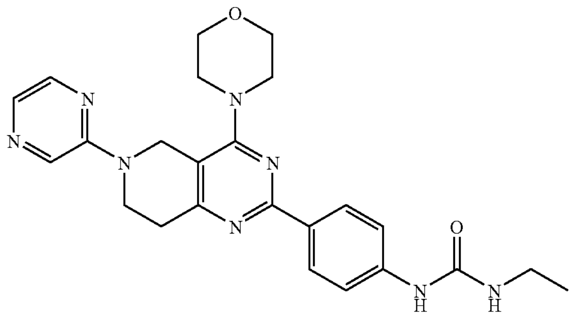 | 1 |
| | 2 |
| | 2 |
| | 2 |

TABLE 3-continued

| Structure | mTOR Activity Level |
|---|---|
| [structure: 4-(tetrahydropyran-4-yl)-7-(pyrimidin-2-yl)-5,6,7,8-tetrahydropyrido[3,4-d]pyrimidin-2-yl phenyl ethylurea] | 2 |
| [structure: 4-(pyridin-3-yl)-7-benzyl-5,6,7,8-tetrahydropyrido[3,4-d]pyrimidin-2-yl phenyl ethylurea] | 2 |
| [structure: 4-morpholino-6-(pyridin-2-ylmethyl)-5,6,7,8-tetrahydropyrrolo[3,4-d]pyrimidin-2-yl phenyl ethylurea] | 1 |

Example 498

In Table 4, below, is provided the biological activity of certain compounds of the invention against mTOR kinase assay described in Example 496.

TABLE 4

| Compound | Ki (uM) |
|---|---|
| (structure) | 0.009 |
| (structure) | 0.002 |
| (structure) | 0.0412 |
| (structure) | 0.252 |

TABLE 4-continued
| Compound | Ki (uM) |
|---|---|
| 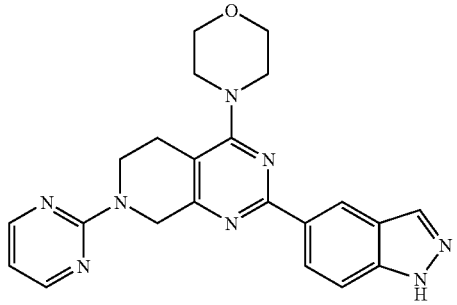 | 0.636 |
| 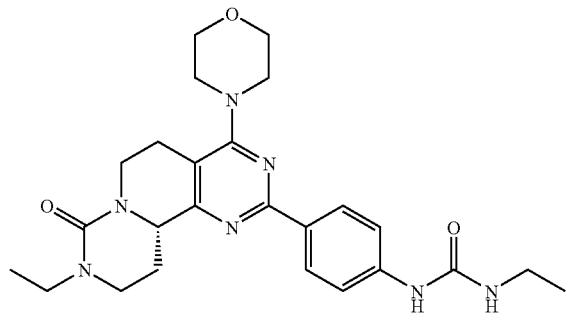 | 0.005 |
| 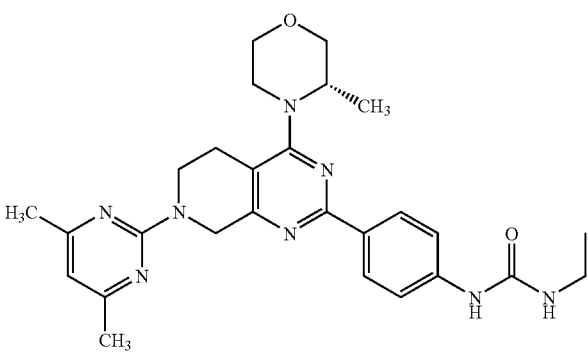 | 0.004 |
| 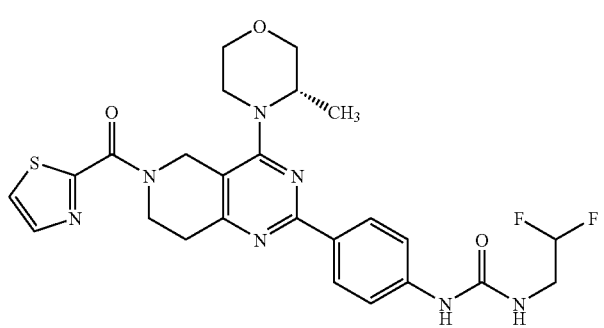 | 0.032 |

TABLE 4-continued

| Compound | Ki (uM) |
|---|---|
| [structure: tetrahydropyran-pyrrolo[3,4-d]pyrimidine with Boc and aminopyrimidine] | 0.753 |
| [structure: morpholine-tetrahydropyrido[3,4-d]pyrimidine with phenylacetyl and phenyl ethylurea] | 0.052 |
| [structure: morpholine-tetrahydropyrido[3,4-d]pyrimidine with pyrimidinyl and phenyl-aminopyrimidine] | 0.022 |
| [structure: methyl-morpholine bridged bicyclic pyrimidine with phenyl ethylurea] | 0.0042 |

The biological activity of exemplary compounds of the invention set forth in Table 2 (the first 468 compounds of Table 2) against the mTOR kinase assay described in Example 496 is provided below (Ki in uM): 0.00655, 0.00565, 0.002, 0.00395, 0.00135, 0.01985, 0.00555, 0.09705, 0.00255, 0.00655, 0.0035, 0.0937, 0.12365, 0.01445, 0.0356, 0.05555, 0.04655, 0.25435, 0.0428, 0.01555, 0.0036, 0.07315, 0.0664, 1.11565, 0.01665, 0.0019, 0.02445, 0.0223, 0.0062, 0.00275, 0.00635, 0.0345, 0.01535, 0.00415, 0.00345, 0.0039, 0.00125, 0.0305, 0.0017, 0.00175, 0.009, 0.0134, 0.00295, 0.0009, 0.0047, 0.00285, 0.0021, 0.03185, 0.00925, 0.00165, 0.00705, 0.0025, 0.02775, 0.1147, 0.01875, 0.0066, 0.01285, 0.00225, 0.0042, 0.00255, 0.0061, 0.0018, 0.0017, 0.00295, 0.0064, 0.00535, 0.0037, 0.0056, 0.0016, 0.00145, 0.00145, 0.00365, 0.0032, 0.00185, 0.00235, 0.00215, 0.0016, 0.00205, 0.0131, 0.06425, 0.00095, 0.00495, 0.00095, 0.0049, 0.0009, 0.0044, 0.0007, 0.05805, 0.0011, 0.0029, 0.0024, 0.0124, 0.0014, 0.00265, 0.00325, 0.01715, 0.00275, 0.0006, 0.0023, 0.0038, 0.0008, 0.0715, 0.0023, 0.00085, 0.00505, 0.03865, 0.00405, 0.002, 0.0004, 0.05395, 0.0023, 0.002, 0.0006, 0.00225, 0.0017, 0.0071, 0.0114, 0.01465, 0.0222, 0.00985, 0.02425, 0.0726, 0.00405, 0.0004, 0.0077, 0.011, 0.0092, 0.00505, 0.0047, 0.0093, 0.01805, 0.0084, 0.0099, 0.00625, 0.0015, 0.0031, 0.003, 0.0462, 0.01195, 0.00365, 0.00575, 0.0197, 0.01015, 0.00345, 0.00315, 0.0013, 0.00245, 0.0031, 0.01575, 0.0149, 0.00205, 0.00645, 0.0026, 0.00505, 0.00375, 0.0015, 0.00505, 0.00655, 0.0091, 0.00445, 0.0029, 0.00405, 0.0109, 0.0068, 0.00665, 0.0243, 0.002, 0.01085, 0.02205, 0.0007, 0.00095, 0.023, 0.02145, 0.0108, 0.07455, 0.01055, 0.0056, 0.0038, 0.0029, 0.0177, 0.00215, 0.0058, 0.0042, 0.01885, 0.0073, 0.0118, 0.0034, 0.0181, 0.0328, 0.00745, 0.00815, 0.00235, 0.00925, 0.0526, 0.0167, 0.00925, 0.0228, 0.031, 0.0058, 0.00665, NA, 0.00685, 0.00525, 0.0054, 0.0045, 0.00245, 0.06335, 0.0339, 0.02485, 0.0315, 0.02025, 0.01975, 0.00075, 0.00505, 0.00525, 0.01995, 0.0338, 0.0736, 0.0149, 0.0384, 0.00245, 0.00075, 0.0021, 0.00285, 0.0013, 0.0084, 0.00865, 0.01745, 0.022, 0.0067, 0.0062, 0.00195, 0.00185, 0.00965, 0.012, 0.0031, 0.00695, 0.00405, 0.01525, 0.02545, 0.02985, 0.03305, NA, 0.01935, 0.56695, 0.00345, 0.0111, 0.00245, 0.00455, 0.00465, 0.00235, 0.0457, 0.3027, 0.02135, 0.0011, NA, 0.00465, 0.0023, 0.0126, 0.05125, 0.00375, 0.00395, 0.0042, 0.0102, 0.00545, 0.00615, 0.0098, 0.0023, NA, 0.0064, 0.0014, 0.0076, 0.00505, 0.0067, 0.00325, 0.0011, 0.01695, 0.0211, 0.0316, NA, 0.01545, 0.0039, 0.0029, 0.00505, 0.00425, 0.02035, 0.00685, 0.0044, 0.0052, 0.00445, 0.0088, 0.00305, 0.00305, 0.00345, 0.00215, 0.00605, 0.0061, 0.00335, 0.00385, 0.0037, 0.00205, 0.0025, 0.0008, 0.0045, 0.0075, 0.0078, 0.00345, 0.00715, 0.00185, 0.0029, 0.005, 0.00225, 0.01365, 0.00475, 0.00175, 0.0986, 0.0054, 0.0339, 0.00365, 0.00325, 0.004, 0.0032, 0.00465, 0.0098, 0.00505, 0.0023, 0.007, 0.00685, 0.0221, 0.0023, 0.00165, 0.00475, 0.0021, 0.00185, 0.0054, 0.00245, 0.00305, 0.00225, 0.0049, 0.00125, 0.0019, 0.00625, 0.00365, 0.0041, 0.1445, 0.0017, 0.1105, 0.08505, 0.076, 0.71805, 0.00435, 0.0038, 4.3262, 0.00215, NA, 0.00145, 0.00275, 0.00185, 0.00275, 0.0019, 0.0046, 0.00375, 0.0012, 0.0009, 0.001, 0.01375, 0.0032, 0.00395, 0.0009, 0.0015, 0.0028, 0.0047, 0.00605, 0.00285, 0.0017, 0.0019, 0.0055, 0.0038, 0.00235, 0.00995, 0.0041, 0.01605, 0.0057, 0.0179, 0.0749, 0.0038, 0.00635, 0.00925, 0.00615, 0.0124, 0.20935, 0.1005, 0.0037, 0.00785, 0.0081, 0.00965, 0.61265, 0.0094, 0.01235, 0.0023, 0.00335, 0.00615, 0.0249, 0.01035, 0.0369, 0.6528, 0.56695, 0.0118, 0.0059, 0.01885, 0.0066, 0.00405, 0.0281, 0.0193, 1.627, 0.00805, 0.0176, 0.009, 0.0033, 0.0046, 0.0014, 0.0107, 0.03685, 0.0067, 0.01145, 0.05255, 0.28655, 0.03755, 0.11915, 0.00615, 0.0128, 0.0089, 0.0081, 0.00585, 0.0044, 0.0061, 0.2272, 0.00305, 0.0043, 0.0154, 0.00235, 0.0089, 0.00865, 0.00675, 0.20495, 0.01235, 0.00875, 0.006, 0.0055, 0.0143, 0.00485, 0.00495, 0.00695, 0.0086, 0.00625, 0.00285, 0.00315, 0.00295, 0.0029, 0.00775, 0.0068, 0.14125, 0.00405, 0.00355, 0.01555, 0.0251, 0.0064, and NA.

What is claimed is:

1. A compound of Formula I-A

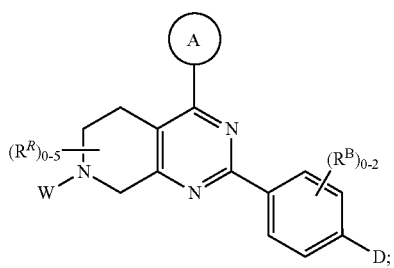

(I-A)

or a pharmaceutically acceptable salt thereof, wherein in Formula I-A,

A is a 5- to 8-membered heterocyclic ring having from 1 to 3 heteroatoms independently selected from N, O and S as ring vertices, and having from 0 to 2 double bonds; optionally fused to the heterocyclic ring of A is a 6-membered aryl ring or a 5- to 6-membered heteroaryl ring having from 1 to 3 heteroatoms selected from N, O and S; and wherein the A ring, and if present, the 6-membered aryl ring or the 5- or 6-membered heteroaryl ring fused thereto, is further substituted with from 0 to 5 $R^A$ substituents selected from the group consisting of —C(O)O$R^a$, —C(O)N$R^a R^b$, —N$R^a R^b$, —OC(O)$R^c$, —O$R^a$, —S$R^a$, —S(O)$_2 R^c$, —S(O)$R^c$, —$R^c$, —(CH$_2$)$_{1-4}$—N$R^a R^b$, —(CH$_2$)$_{1-4}$—N$R^a$C(O)$R^c$, —(CH$_2$)$_{1-4}$—O$R^a$, —(CH$_2$)$_{1-4}$—S$R^a$, —(CH$_2$)$_{1-4}$—S(O)$_2 R^c$, —(CH$_2$)$_{1-4}$—S(O)$R^c$, F, Cl, Br, I, —NO$_2$, —CN and —N$_3$, wherein $R^a$ and $R^b$ are each independently selected from hydrogen, C$_{1-6}$ alkyl, C$_{1-6}$ haloalkyl, C$_{1-6}$ heteroalkyl, C$_{2-6}$ alkenyl, C$_{2-6}$ alkynyl, C$_{3s-6}$ cycloalkyl, phenyl and —(CH$_2$)$_{1-4}$(phenyl), and optionally $R^a$ and $R^b$, together with the nitrogen atom to which each is attached, are combined to form a 3- to 7-membered heterocyclic ring comprising 1 to 2 heteroatoms selected from N, O and S; $R^c$ is selected from C$_{1-6}$ alkyl, C$_{1-6}$ haloalkyl, C$_{2-6}$ alkenyl, C$_{2-6}$ alkynyl, C$_{3-6}$ cycloalkyl, phenyl and —(CH$_2$)$_{1-4}$ (phenyl), and any two substituents attached to the same atom in the 5- to 8-membered heterocyclic ring are optionally combined to form a 3- to 5-membered carbocyclic or a 3 to 5-membered heterocyclic ring substituted with 0-3 $R^A$ substituents;

W is represented by Formula i

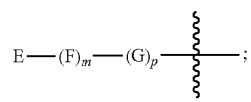

i wherein E is a member selected from the group consisting of hydrogen, C$_{6-10}$ aryl, C$_{5-10}$ heteroaryl, C$_{3-10}$ cycloalkyl, C$_{3-10}$ heterocycloalkyl, C$_{1-6}$ alkyl and C$_{1-6}$ heteroalkyl; and wherein E is optionally substituted with 1 to 5 $R^E$ substituents selected from the group consisting of F, Cl, Br, I, —N$R^d R^e$, —S$R^d$, —O$R^d$, —C(O)O$R^d$, —C(O)N$R^d R^e$, —C(O)$R^d$, —N$R^d$C(O)$R^e$, —OC(O)$R^f$, —N$R^d$C(O)N$R^d R^e$, —OC(O)N$R^d R^e$, —C(=NO$R^d$)N$R^d R^e$, —N$R^d$C(=N—CN)N$R^d R^e$, —N$R^d$S(O)$_2$N$R^d R^e$, —S(O)$_2 R^d$, —S(O)$_2$N$R^d R^e$, —$R^f$, —NO$_2$, —N$_3$, =O, —CN, —(CH$_2$)$_{1-4}$—N$R^d R^e$, —(CH$_2$)$_{1-4}$—S$R^d$, —(CH$_2$)$_{1-4}$—O$R^d$, —(CH$_2$)$_{1-4}$—C(O)O$R^d$, —(CH$_2$)$_{1-4}$—C(O)N$R^d R^e$, —(CH$_2$)$_{1-4}$—C(O)$R^d$, —(CH$_2$)$_{1-4}$—N$R^d$C(O)$R^e$, —(CH$_2$)$_{1-4}$—OC(O)$R^f$, —(CH$_2$)$_{1-4}$—N$R^d$C(O)N$R^d R^e$, —(CH$_2$)$_{1-4}$—OC(O)N$R^d R^e$, —(CH$_2$)$_{1-4}$—C(=NO$R^d$)N$R^d R^e$, —(CH$_2$)$_{1-4}$—N$R^d$C(=N—CN)N$R^d R^e$, —(CH$_2$)$_{1-4}$—N$R^d$S(O)$_2$N$R^d R^e$, —(CH$_2$)$_{1-4}$—S(O)$_2 R^d$, —(CH$_2$)$_{1-4}$—S(O)$_2$N$R^d R^e$, —(CH$_2$)$_{1-4}$—NO$_2$, —(CH$_2$)$_{1-4}$—N$_3$ and —(CH$_2$)$_{1-4}$—CN; wherein $R^d$ and $R^e$ are each independently selected from hydrogen, C$_{1-6}$ alkyl, C$_{1-6}$ haloalkyl, C$_{1-6}$ heteroalkyl, C$_{2-6}$ alkenyl, C$_{2-6}$ alkynyl, C$_{3-7}$ cycloalkyl, C$_{3-7}$ heterocycloalkyl, phenyl and —(CH$_2$)$_{1-4}$-phenyl, and optionally $R^d$ and $R^e$, when attached to the same nitrogen atom are combined to form a 3- to 6-membered heterocyclic ring comprising 1 to 2 heteroatoms selected from N, O and S; $R^f$ is selected from C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ heterocycloalkyl, phenyl and —(CH$_2$)$_{1-4}$-phenyl;

and wherein any two substituents located on adjacent atoms, or located on the same atom of E are optionally combined to form a 5- to 6-membered carbocyclic or heterocyclic ring;

F is a member selected from the group consisting of $C_{1-6}$ alkylene, $C_{2-6}$ alkenylene, $C_{2-6}$ alkynylene and $C_{1-6}$ heteroalkylene; wherein F is independently substituted with from 0 to 3 $R^F$ substituents selected from the group consisting of, F, Cl, Br, I, —$NR^gR^h$, —$SR^g$, —$OR^g$, —$C(O)OR^g$, —$C(O)NR^gR^h$, —$NR^gC(O)R^i$, —$OC(O)R^i$, —$NR^gC(O)NR^gR^h$, —$OC(O)NR^gR^h$, $NR^gS(O)_2NR^gR^h$, —$S(O)_2R^g$, —$S(O)_2NR^gR^h$, —$R^i$, —$NO_2$, $N_3$, =O, —CN, —$(CH_2)_{1-4}$—$NR^gR^h$, —$(CH_2)_{1-4}$—$SR^g$, —$(CH_2)_{1-4}$—$OR^g$, —$(CH_2)_{1-4}$—$C(O)OR^g$, —$(CH_2)_{1-4}$—$C(O)NR^gR^h$, —$(CH_2)_{1-4}$—$C(O)R^g$, —$(CH_2)_{1-4}$—$NR^gC(O)R^h$, —$(CH_2)_{1-4}$—$OC(O)R^i$, —$(CH_2)_{1-4}$—$NR^gC(O)NR^gR^h$, —$(CH_2)_{1-4}$—$OC(O)NR^gR^h$, —$(CH_2)_{1-4}$—$NR^gS(O)_2NR^gR^h$, —$(CH_2)_{1-4}$—$S(O)_2R^g$, —$(CH_2)_{1-4}$—$S(O)_2NR^gR^h$, —$(CH_2)_{1-4}$—$NO_2$, —$(CH_2)_{1-4}$—$N_3$ and —$(CH_2)_{1-4}$—CN; wherein $R^g$ and $R^h$ are each independently selected from hydrogen, $C_{1-6}$ alkyl, $C_{1-6}$ haloalkyl, $C_{1-6}$ heteroalkyl, $C_{3-7}$ cycloalkyl, $C_{3-7}$ heterocycloalkyl, phenyl and —$(CH_2)_{1-4}$-phenyl, and optionally $R^g$ and $R^h$, when attached to the same nitrogen atom are combined to form a 3- to 6-membered heterocyclic ring comprising 1 to 2 heteroatoms selected from N, O and S; $R^i$ is selected from $C_{1-6}$ alkyl, $C_{1-6}$ haloalkyl, $C_{3-7}$ cycloalkyl, $C_{3-7}$ heterocycloalkyl, phenyl and —$(CH_2)_{1-4}$-phenyl;

G is a member selected from the group consisting of —C(O)—, —OC(O)—, —NHC(O)—, —NHC(=NOH)—, —$S(O)_{0-2}$— and —$NHS(O)_2$—;

the subscripts m and p are each independently an integer from 0 to 1;

$R^R$ substituent is selected from the group consisting of F, Cl, Br, I, —$R^m$, —$(CH_2)_{1-4}$—CN, —$(CH_2)_{1-4}$—$CO_2R^j$, —$(CH_2)_{1-4}C(O)NR^jR^k$, —$(CH_2)_{1-4}OR^j$, —$(CH_2)_{1-4}NR^jR^k$, $C_{2-4}$ alkenylene-$CO_2R^j$, $C_{2-4}$ alkenylene-$C(O)NR^jR^k$ and =O, wherein $R^j$ and $R^k$ are each independently selected from hydrogen, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ heterocycloalkyl, phenyl and —$(CH_2)_{1-4}$-(Ph), and $R^j$ and $R^k$, when attached to the same nitrogen atom, are optionally combined to form a 3- to 6-membered heterocyclic ring comprising 1 to 2 heteroatoms selected from N, O and S; and $R^m$ is selected from $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ heterocycloalkyl and —$(CH_2)_{1-4}$-(Ph), and wherein when $R^1$ and $R^2$ are combined to form a monocyclic 5- to 8-membered heterocyclic ring then any two substitutents attached to the same or adjacent atoms in the monocyclic 5- to 8-membered heterocyclic ring are optionally combined to form a 3- to 7-membered cycloalkyl ring, a 3- to 7-membered heterocycloalkyl ring or a 5- to 6-membered heteroaryl ring comprising 1 to 2 heteroatoms selected from N, O and S and is optionally substituted with 1 to 3 $R^R$ substitutents;

$R^B$ substituent is selected from the group consisting of F, Cl, Br, I, CN, $NO_2$ and $R^p$, wherein $R^p$ is selected form $C_{1-6}$ alkyl, $C_{1-6}$ haloalkyl, $C_{2-6}$ alkenyl and $C_{2-6}$ alkynyl;

D is a member selected from the group consisting of —$NR^3C(O)NR^4R^5$, —$NR^4R^5$, —$C(O)NR^4R^5$, —$OC(O)OR^4$, —$OC(O)NR^4R^5$, —$NR^3C(=N—CN)NR^4R^5$, —$NR^3C(=N—OR^4)NR^4R^5$, —$NR^3C(=N—NR^4)NR^4R^5$, —$NR^3C(O)R^4$, —$NR^3C(O)OR^4$, —$NR^3S(O)_2NR^4R^5$ and —$NR^3S(O)_2R^4$, wherein $R^3$ is selected from the group consisting of hydrogen, $C_{1-6}$ alkyl, $C_{1-6}$ haloalkyl and $C_{2-6}$ alkenyl; $R^4$ and $R^5$ are each independently selected from the group consisting of hydrogen, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ heterocycloalkyl, $C_{6-10}$ aryl and $C_{5-10}$ heteroaryl, and $R^4$ and $R^5$, when attached to the same nitrogen atom, are optionally combined to form a 5- to 7-membered heterocyclic or heteroaryl ring comprising 1 to 3 heteroatoms selected from N, O and S as ring vertices and optionally substituted with 1 to 3 $R^D$ substituents; and wherein $R^3$, $R^4$ and $R^5$ are optionally substituted with 1 to 3 $R^D$ substituents independently selected from the group consisting of F, Cl, Br, I, —$NO_2$, —CN, —$NR^qR^r$, —$OR^q$, —$SR^q$, —$C(O)OR^q$, —$C(O)NR^qR^r$, —$NR^qC(O)R^r$, —$NR^qC(O)OR^s$, —$(CH_2)_{1-4}$—$NR^qR^r$, —$(CH_2)_{1-4}$—$OR^q$, —$(CH_2)_{1-4}$—$SR^q$, —$(CH_2)_{1-4}$—$C(O)OR^q$, —$(CH_2)_{1-4}$—$C(O)NR^qR^r$, —$(CH_2)_{1-4}$—$NR^qC(O)R^r$, —$(CH_2)_{1-4}$—$NR^qC(O)OR^r$, —$(CH_2)_{1-4}$—$NO_2$, —$S(O)R^r$, —$S(O)_2R^r$, =O, and —$R^s$; wherein $R^q$ and $R^r$ is selected from hydrogen, $C_{1-6}$ alkyl, $C_{1-6}$ haloalkyl, $C_{2-6}$ alkenyl, $C_{2-6}$ alkynyl, $C_{1-6}$ heteroalkyl, $C_{3-7}$ cycloalkyl, $C_{3-7}$ heterocycloalkyl, $C_{6-10}$ aryl, $C_{5-10}$ heteroaryl; and $R^s$, at each occurrence, is independently selected from $C_{1-6}$ alkyl, $C_{1-6}$ haloalkyl, $C_{3-7}$ cycloalkyl, $C_{3-7}$ heterocycloalkyl, $C_{6-10}$ aryl and $C_{5-10}$ heteroaryl; and wherein the D group and a substituent located on the adjacent phenyl ring are optionally combined to form a 5- to 6-membered heterocyclic or heteroaryl ring comprising 1 to 3 heteroatoms selected from N, O and S as ring vertices and optionally substituted with 1 to 3 $R^D$ substituents.

2. The compound of claim 1, wherein the A ring is a ring selected from the group consisting of morpholin-4-yl, 3-methyl-morpholin-4-yl, 3-ethyl-morpholin-4-yl, 3-iso-propyl-morpholin-4-yl, 3,3-dimethyl-morpholin-4-yl, 3,4-dihydro-2H-pyran-4-yl, 3,6-dihydro-2H-pyran-4-yl, tetrahydro-2H-pyran-4-yl, 1,4-oxazepan-4-yl, piperidin-1-yl, 2-oxa-5-azabicyclo[2.2.1]heptan-5-yl, 3-oxa-8-azabicyclo[3.2.1]octan-8-yl, 3-isopropyl-morpholin-4-yl, 4-methoxy-piperidin-1-yl and is optionally substituted with from 1 to 2 $R^A$ substituents selected from the group consisting of —$C(O)OR^a$, —$C(O)NR^aR^b$, —$NR^aR^b$, —$OR^a$, —$SR^a$, —$S(O)_2R^c$, —$S(O)R^c$, —$R^c$, F, Cl, Br, I, —$NO_2$, —CN and —$N_3$, wherein $R^a$ and $R^b$ are each independently selected from hydrogen, $C_{1-6}$ alkyl, $C_{1-6}$ haloalkyl, $C_{1-6}$ heteroalkyl, $C_{2-6}$ alkenyl and $C_{3-6}$ cycloalkyl, wherein optionally $R^a$ and $R^b$, together with the nitrogen atom to which each is attached, are combined to form a 3- to 6-membered ring, and $R^c$ is selected from $C_{1-6}$ alkyl, $C_{1-6}$ haloalkyl, $C_{2-6}$ alkenyl, $C_{3-6}$ cycloalkyl.

3. The compound of claim 2, wherein the A ring is optionally substituted with 1 to 2 $R^A$ substituents selected from $NR^aR^b$—$OR^a$ and —$R^c$.

4. The compound of claim 1, wherein D is selected from the group consisting of —$NR^3C(O)NR^4R^5$, —$NR^4R^5$, —$C(O)NR^4R^5$, —$NR^3C(=N—CN)NR^4R^5$, —$NR^3C(O)R^4$, —$NR^3C(O)OR^4$, and —$NR^3S(O)R^4$.

5. The compound of claim 1, wherein D is an optionally substituted group selected from —$NR^3C(O)NR^4R^5$ and —$NR^4R^{5-}$, wherein $R^3$ is hydrogen; $R^4$ and $R^5$ are each independently an optionally substituted group selected from the group consisting of hydrogen, $C_{1-6}$ alkyl, $C_{1-6}$ heteroalkyl, $C_{1-6}$ haloalkyl, $C_{3-7}$ cycloalkyl, $C_{3-7}$ heterocycloalkyl, $C_{6-10}$ aryl and $C_{5-10}$ heteroaryl, and $R^4$ and $R^5$, when attached to the same nitrogen atom, are optionally combined to form an optionally substituted 5- to 7-membered heterocyclic or heteroaryl ring.

6. The compound of claim 5, wherein D is —$NR^4R^5$, wherein $R^4$ is hydrogen or $C_{1-3}$ alkyl, and $R^5$ is an optionally substituted group selected from optionally substituted $C_{6-10}$ aryl, $C_{5-10}$ heteroaryl and $C_{3-7}$ heterocyclylalkyl.

7. The compound of claim 6, wherein D is —NR$^4$R$^5$, wherein R$^4$ is hydrogen or $C_{1-3}$ alkyl, and R$^5$ is an optionally substituted $C_{3-7}$ heterocyclylalkyl selected from the group consisting of:

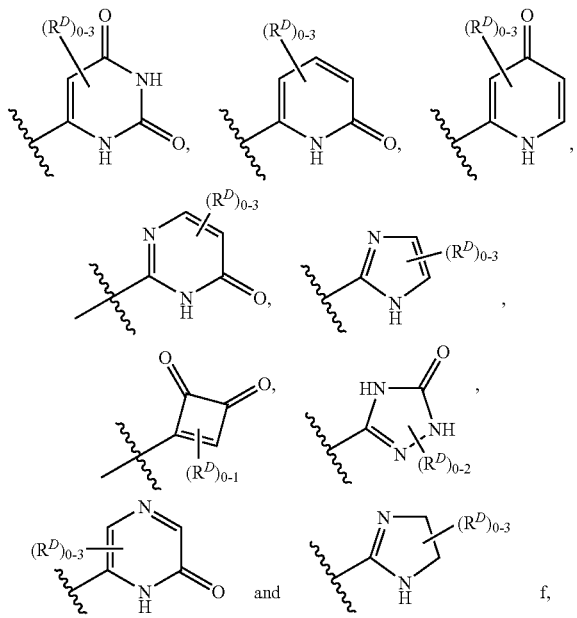

wherein the hydrogen atom attached to one or more nitrogen or carbon ring vertices in the $C_{3-7}$ heterocycloalkyl ring is optionally replace with a R$^D$ substituent selected from the group consisting of F, Cl, Br, I, —NR$^q$R$^r$, —OR$^q$, and R$^s$.

8. The compound of claim 7, wherein R$^5$ is selected from the group consisting of:

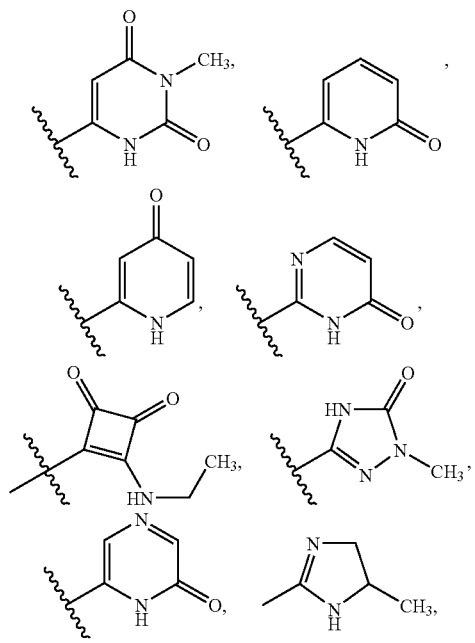

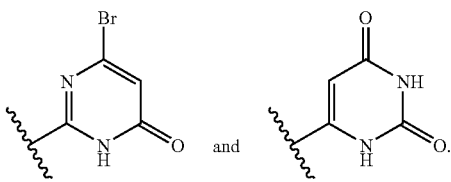

9. The compound of claim 5, wherein D is —NR$^4$R$^5$, wherein R$^4$ and R$^5$ are combined to form an optionally substituted 5-membered heteroaryl ring selected from the group consisting of pyrrolyl, pyrazolyl, imidazolyl and triazolyl.

10. The compound of claim 5, wherein D is —NR$^3$C(O)NR$^4$R$^5$, wherein R$^3$ is hydrogen; R$^4$ and R$^5$ are each independently an optionally substituted group selected from the group consisting of hydrogen, $C_{1-6}$ alkyl, $C_{1-6}$ haloalkyl, $C_{1-6}$ heteroalkyl, $C_{3-7}$ cycloalkyl, $C_{3-7}$ heterocycloalkyl, a 5- to 6-membered heteroaryl, and optionally substituted phenyl.

11. The compound of claim 10, wherein one of R$^4$ and R$^5$ is hydrogen.

12. The compound of claim 11, wherein R$^3$ and R$^4$ are each hydrogen and R$^5$ is an optionally substituted group selected from $C_{1-6}$ alkyl and $C_{1-6}$ haloalkyl.

13. The compound of claim 12, wherein R$^5$ is selected from the group consisting of

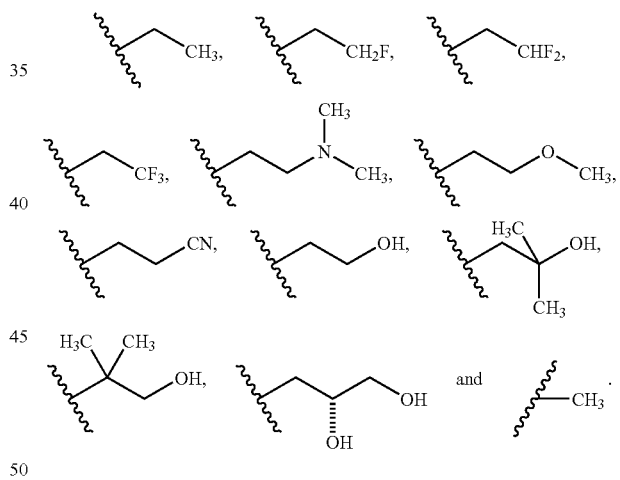

14. The compound of claim 13, wherein R$^5$ is ethyl.

15. The compound of claim 10, wherein R$^3$ and R$^4$ are each hydrogen or $C_{1-4}$ alkyl and R$^5$ is an optionally substituted group selected from the group consisting of optionally substituted isoxazol-3-yl, isoxazol-4-yl isoxazol-5-yl, oxazol-2-yl, oxazol-4-yl, oxazol-5-yl, pyrazol-3-yl, pyrazol-4-yl, pyrazol-5-yl, 1,2,3-oxadiazol-4-yl, 1,2,3-oxadiazol-5-yl, 1,3,4-oxadiazol-2-yl, 1,3,4-oxadiazol-5-yl, 2-pyridyl, 3-pyridyl, 4-pyridyl, 5-pyridyl, cyclobutyl, cyclopentyl, cyclohexyl, 2-oxepanyl, 3-oxepanyl, 2-tetrahydrofuranyl, 3-tetrahydrofuranyl and phenyl.

16. The compound of claim 15, wherein R$^5$ is independently substituted with from 0 to 3 substituents selected from F, Cl, Br, I, —CN, —NR$^q$R$^r$ and —OR$^q$.

17. The compound of claim 16, wherein R⁵ is selected from the group consisting of

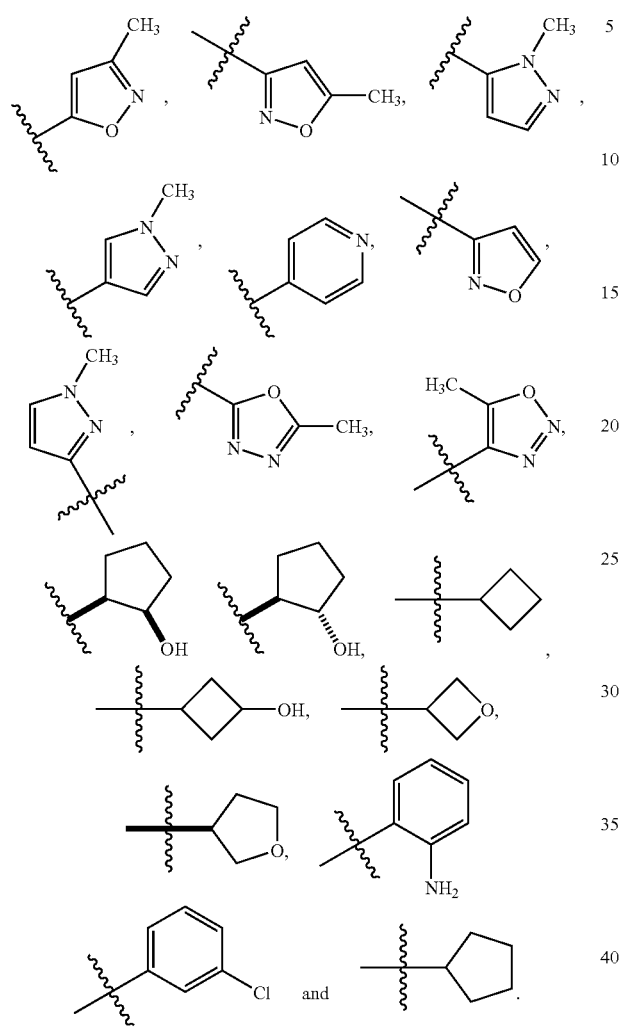

18. The compound of claim 1, wherein in Formula i, E is an optionally substituted group selected from the group consisting of $C_{6-10}$ aryl, $C_{5-10}$ heteroaryl, $C_{3-8}$ heterocycloalkyl, and $C_{3-8}$ cycloalkyl; F is an optionally substituted group selected from the group consisting of $C_{1-4}$ alkylene, $C_{2-4}$ alkenylene, $C_{1-4}$ heteroalkylene, G is selected from the group consisting of —C(O)—, —OC(O)—, —NHC(O)—, —S(O)₂—, —NHS(O)₂—; and the subscripts m and p are each independently an integer from 0 to 1.

19. The compound of claim 18, wherein in Formula i, E is an optionally substituted group selected from the group consisting of optionally substituted pyridyl, pyrimidinyl, quinolinyl, pyrazinyl, pyridazinyl, phenyl, pyrrolyl, pyrazolyl, oxazolyl, thiazolyl, piperidinyl, pyrrolidinyl, morpholinyl, furanyl, triazinyl, thiadiazolyl, imidazolyl, cyclobutyl, cyclopropyl, cyclopentyl, cyclohexyl, pyridonyl, tetrahydrofuranyl, tetrahydropyranyl, dioxolanyl, tetrahydropyrimidinyl and tetrahydropyranyl; F is an optionally substituted group selected from the group consisting of $C_{1-4}$ alkylene, $C_{2-4}$ alkenylene, $C_{1-4}$ heteroalkylene, G is selected from the group consisting of —C(O)—, —OC(O)—, —NHC(O)—, —S(O)₂—, —NHS(O)₂—; and the subscripts m and p are each independently an integer from 0 to 1.

20. The compound of claim 19, wherein E is an $C_{6-10}$ aryl, $C_{5-10}$ heteroaryl, $C_{3-8}$ heterocycloalkyl, and $C_{3-8}$ cycloalkyl selected from the group consisting of

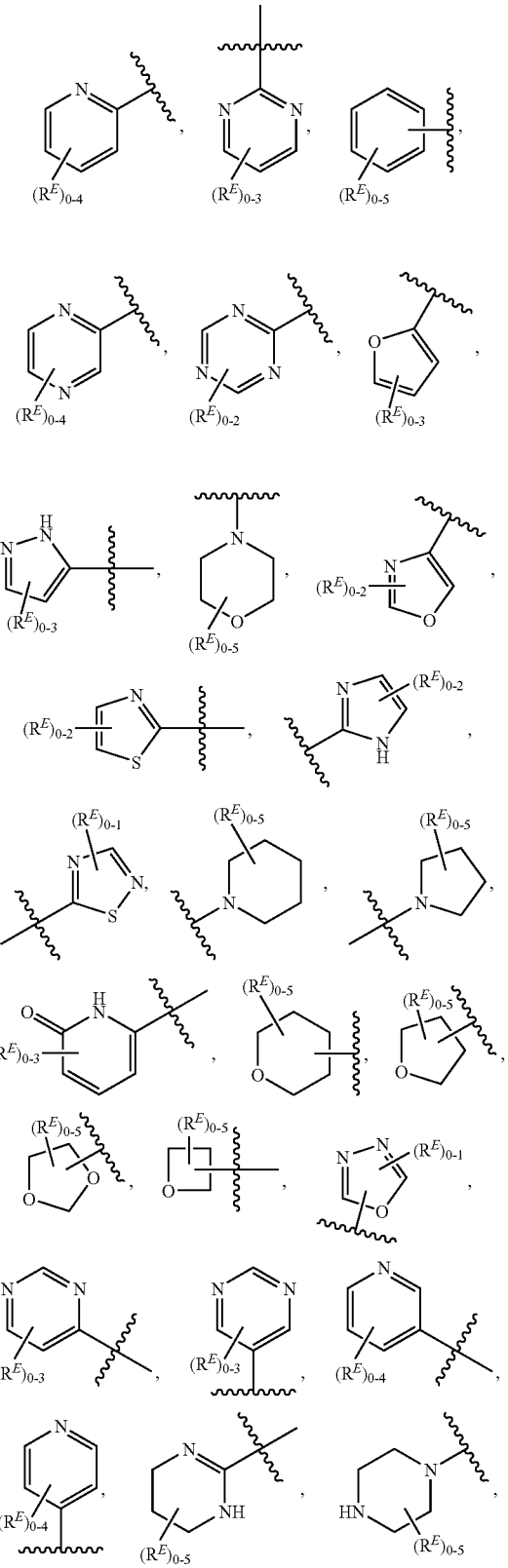

-continued

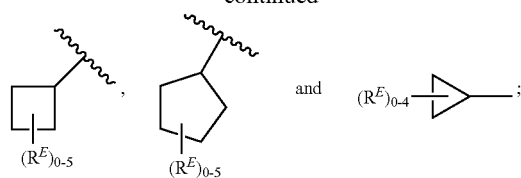 and 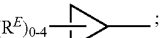;

wherein the hydrogen atom attached to one or more nitrogen or carbon ring vertices in the $C_{6-10}$ aryl, $C_{5-10}$ heteroaryl, $C_{3-8}$ heterocycloalkyl, and $C_{3-8}$ cycloalkyl ring is optionally replaced with a $R^E$ substituent.

21. The compound of claim 18, wherein the subscripts m and p are each 1.

22. The compound of claim 18, wherein the subscript m is 0 and the subscript p is 1.

23. The compound of claim 1, wherein W is selected from the group consisting of

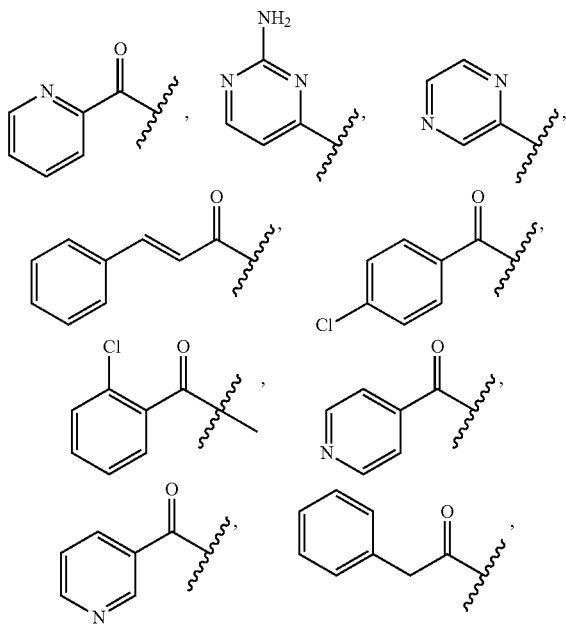

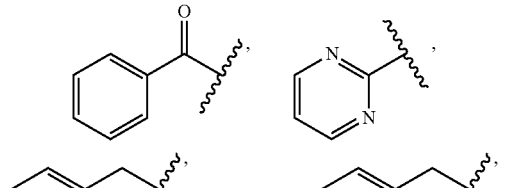

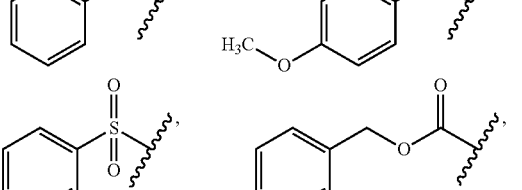

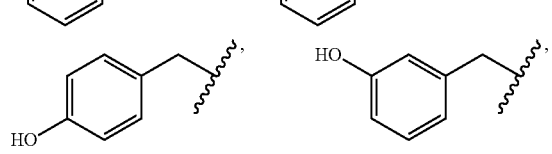

-continued

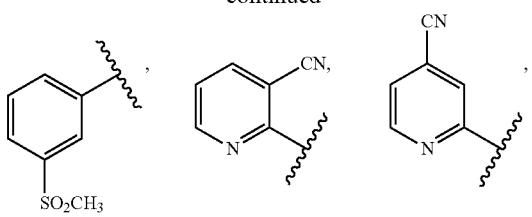

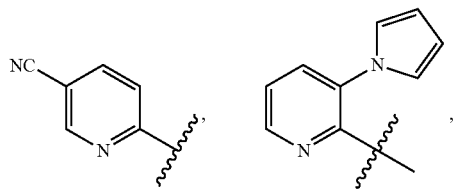

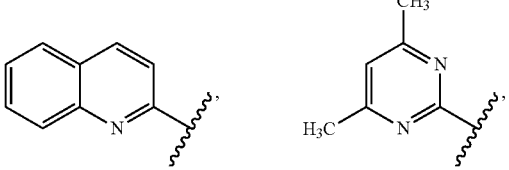

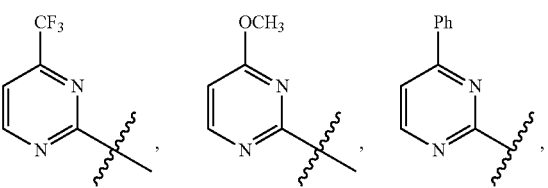

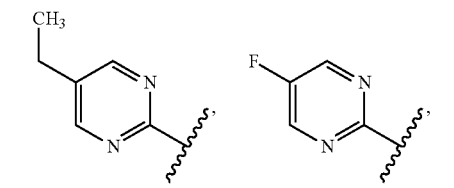

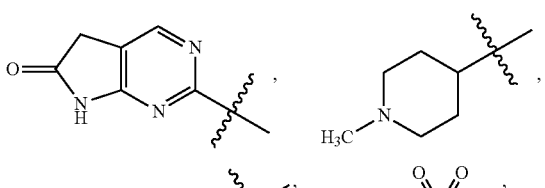

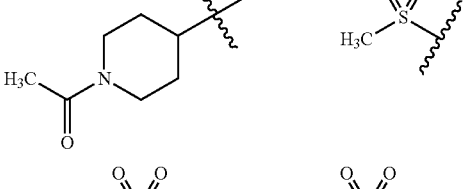

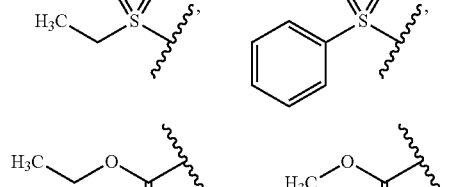

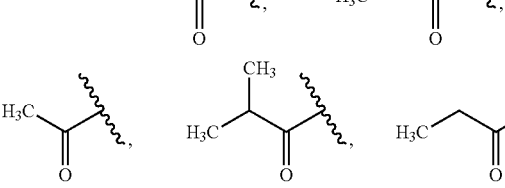

507
-continued
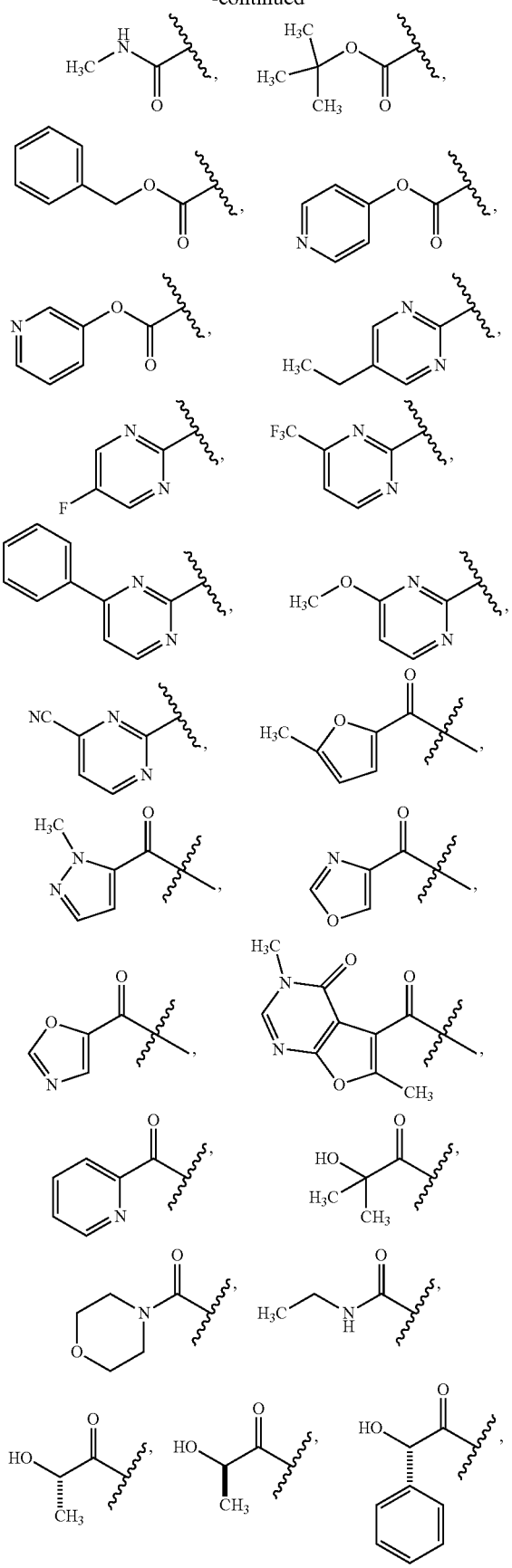
508
-continued
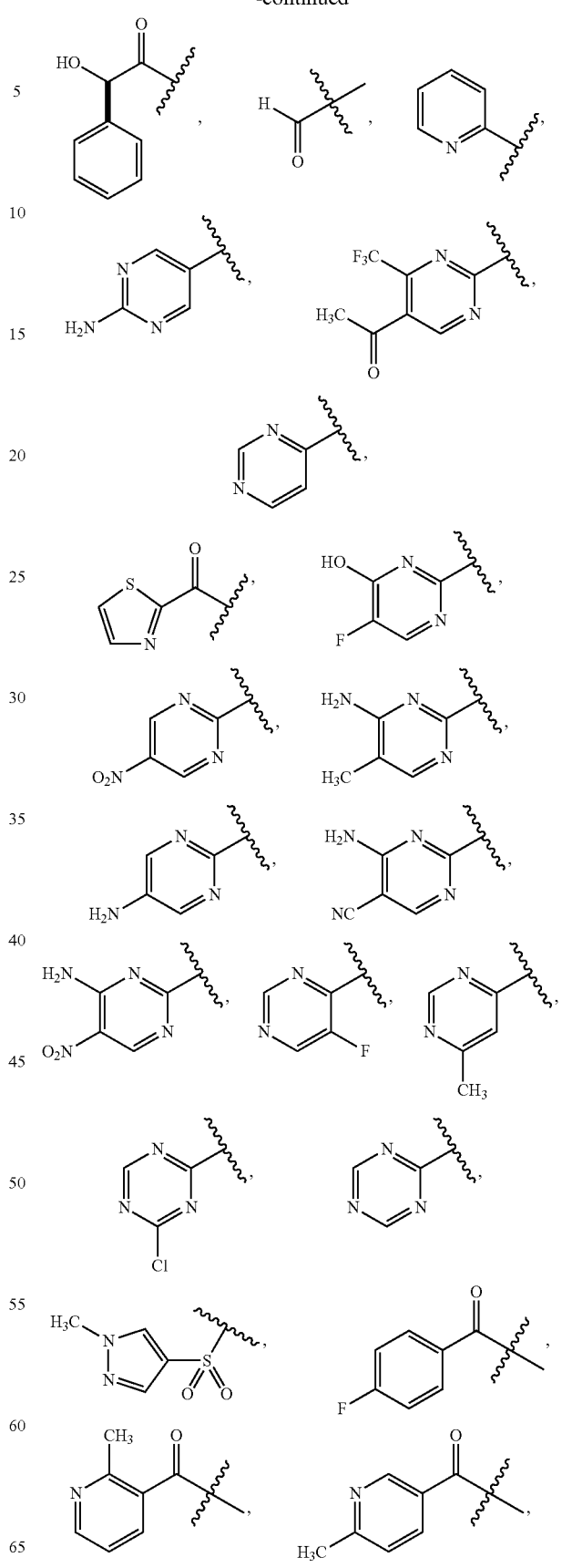

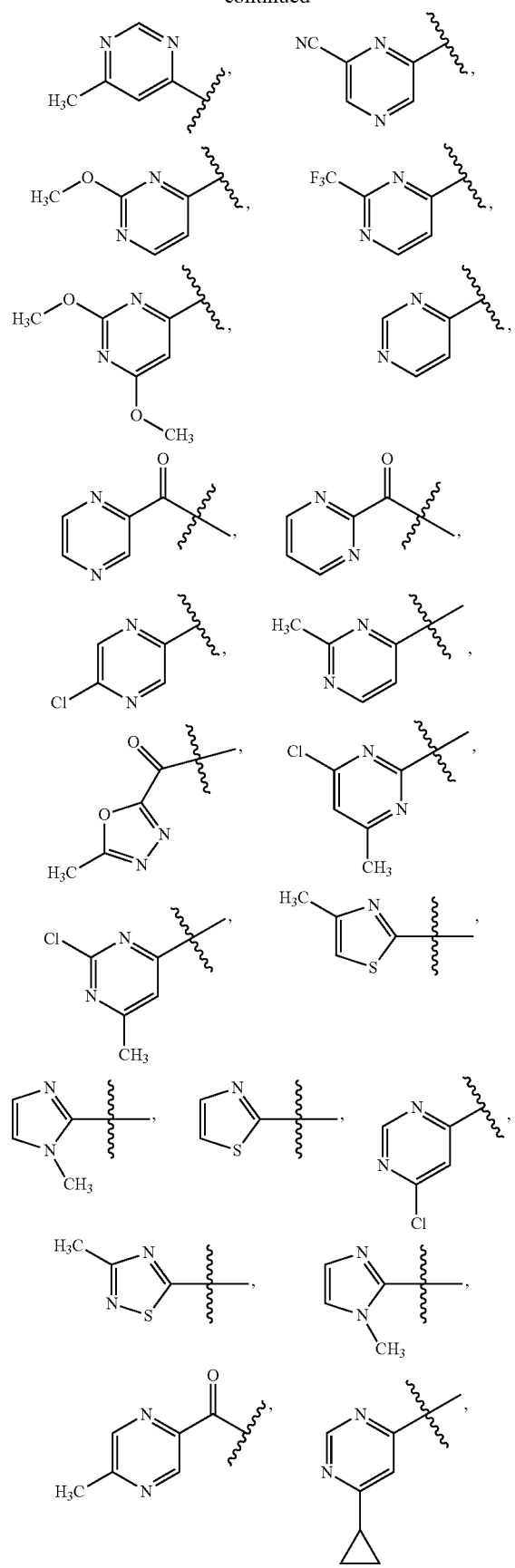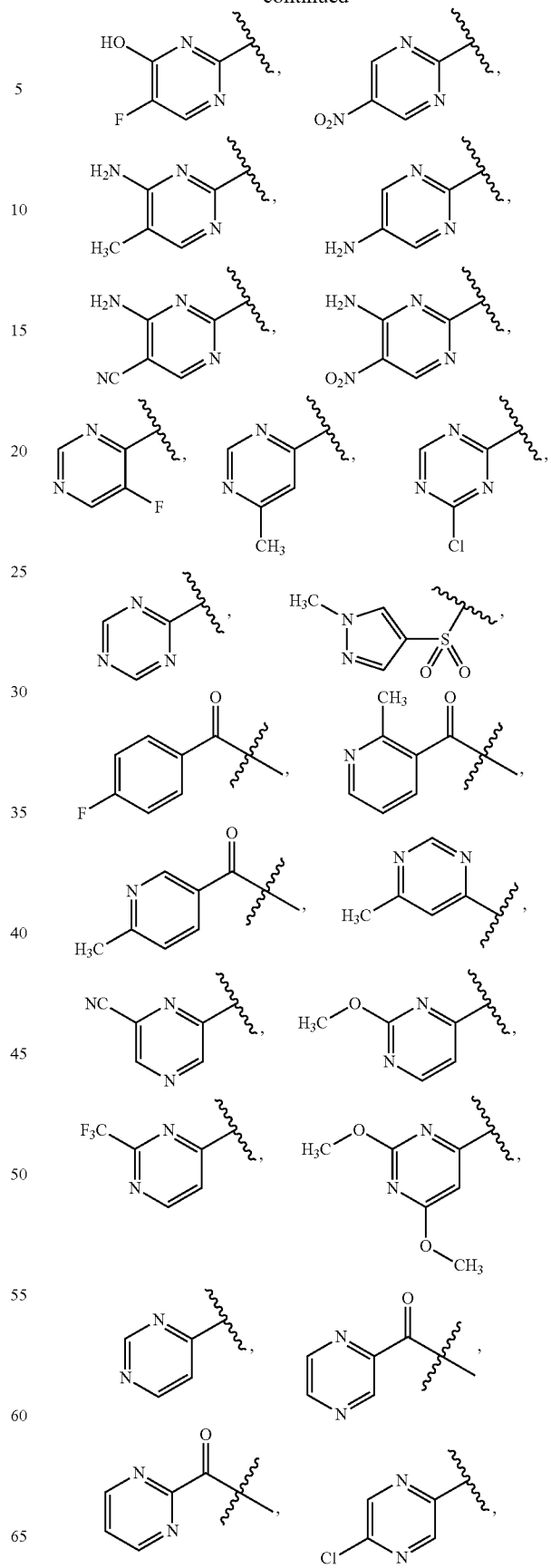

511
-continued
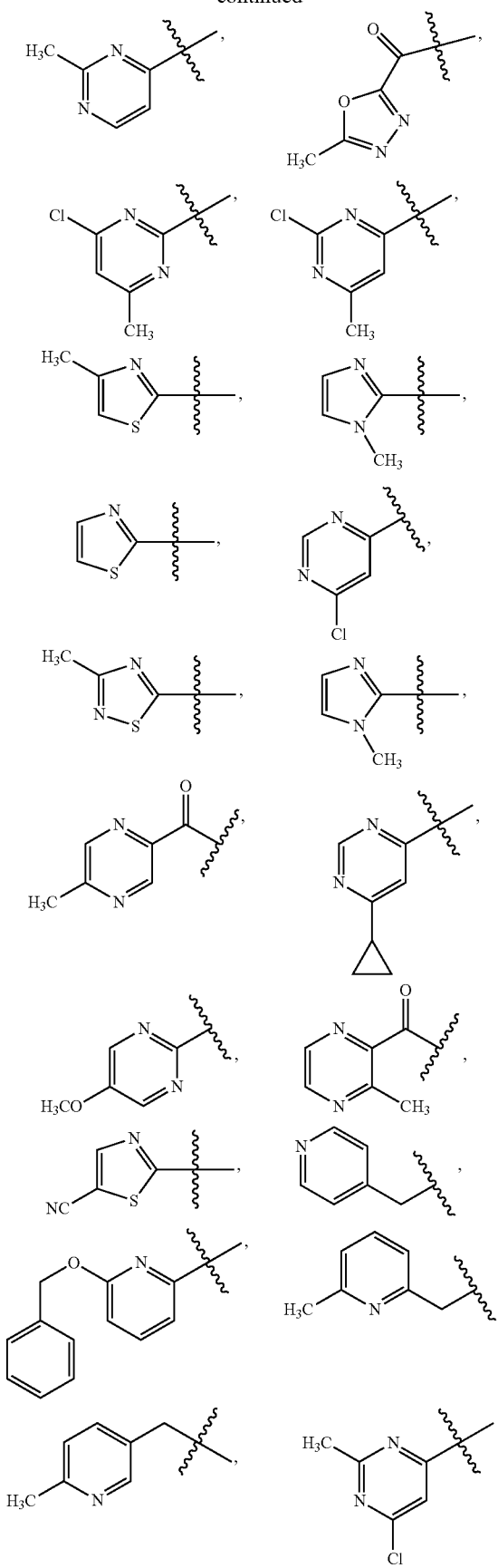
512
-continued
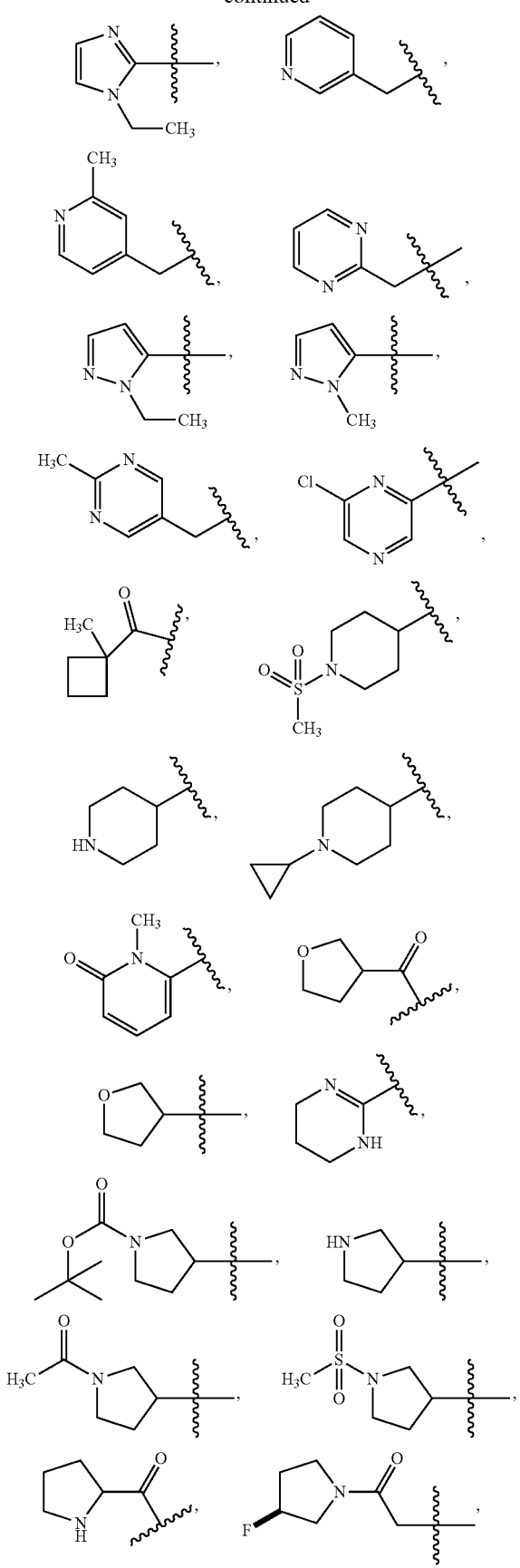

513
-continued
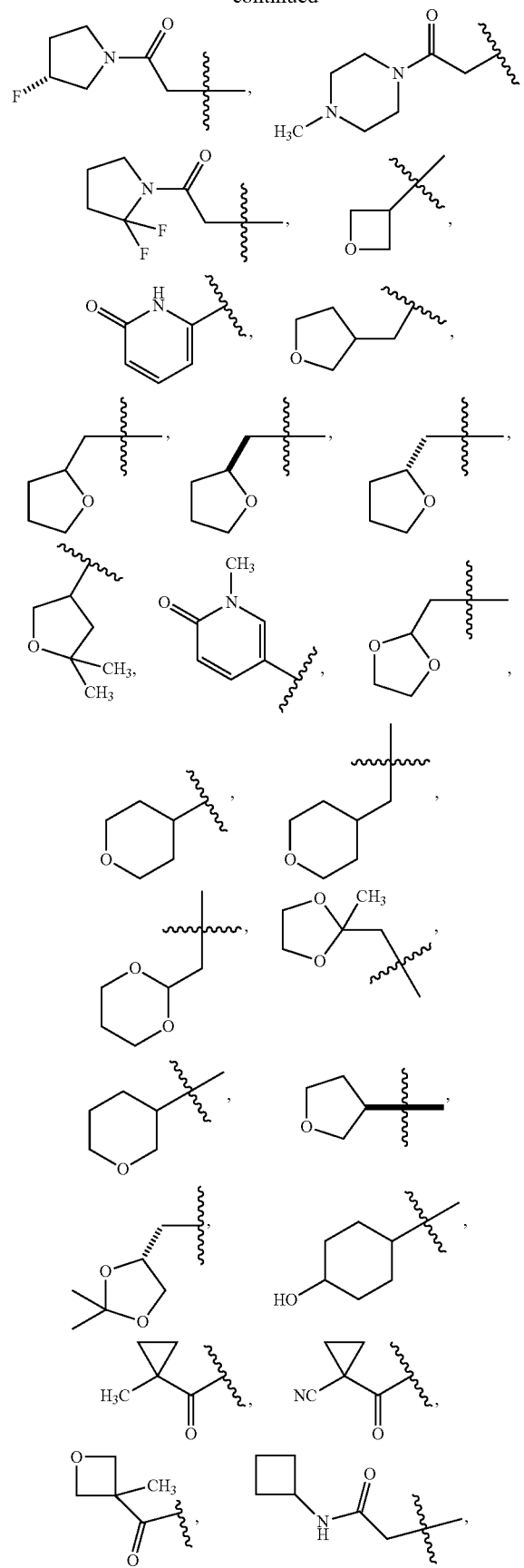
514
-continued
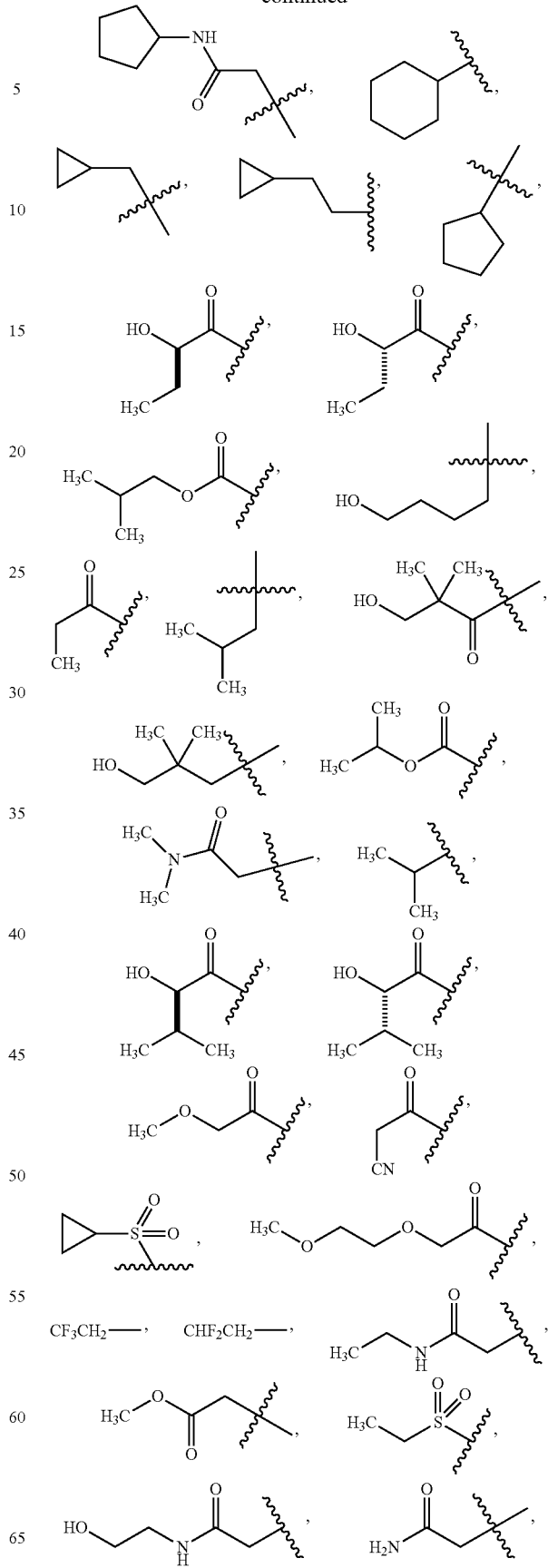

515
-continued
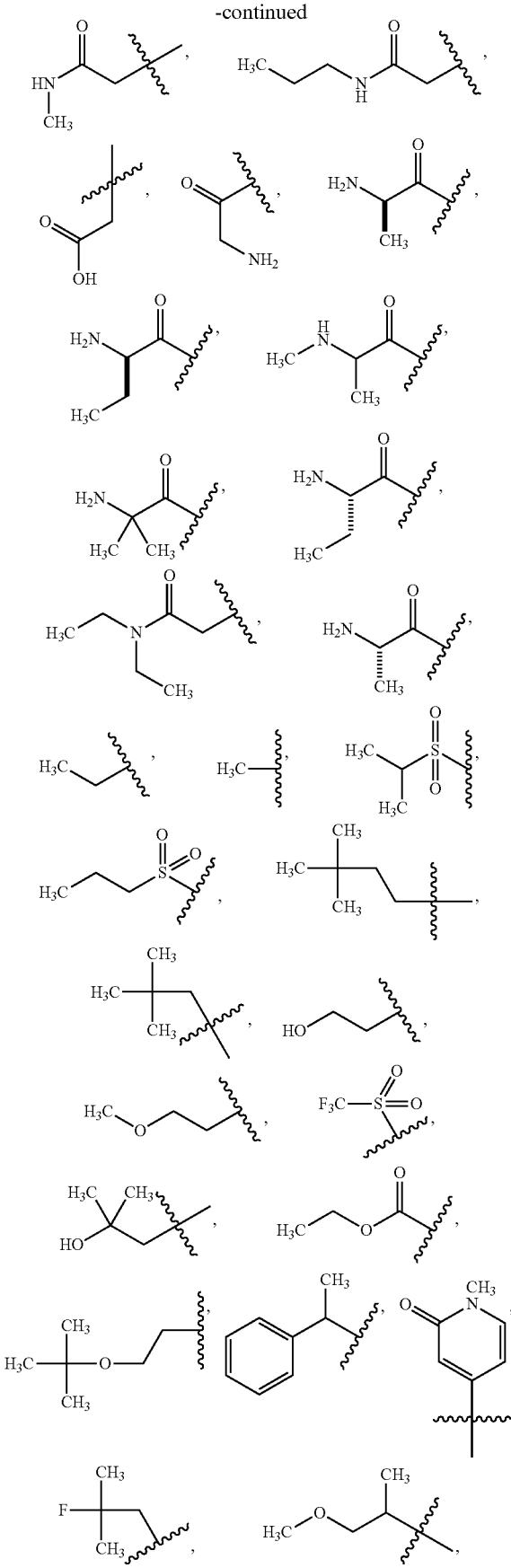
516
-continued
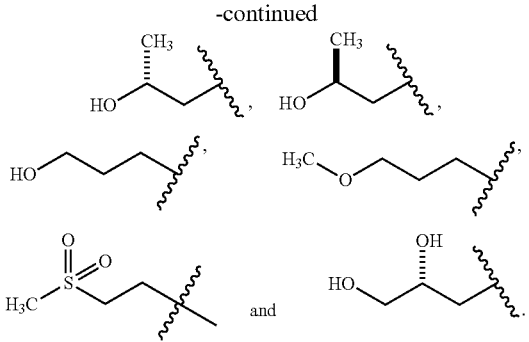
24. The compound of claim 1, wherein D is selected from the group consisting of
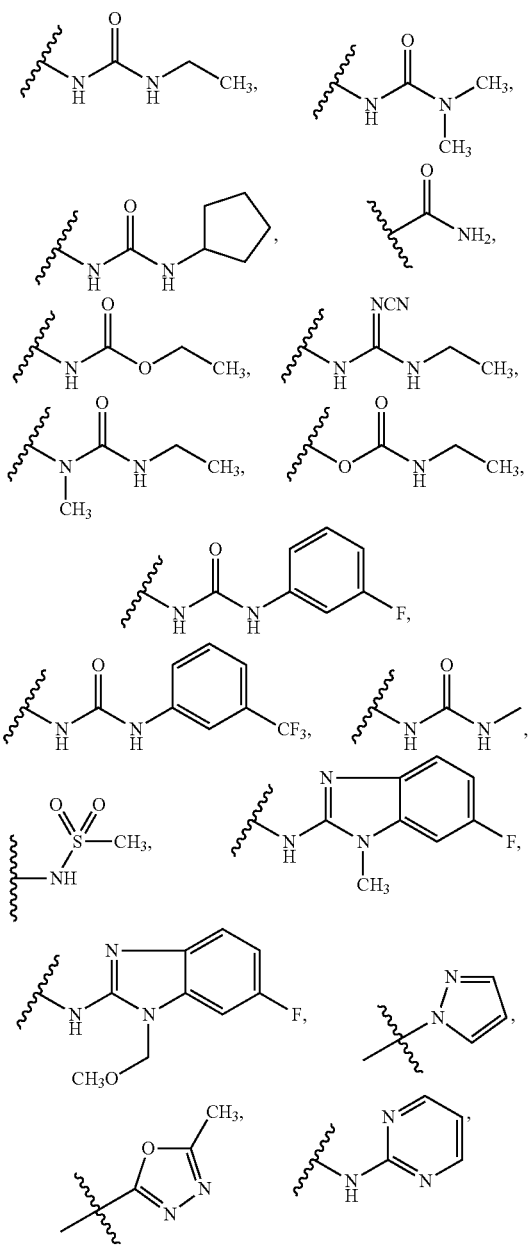

517
-continued
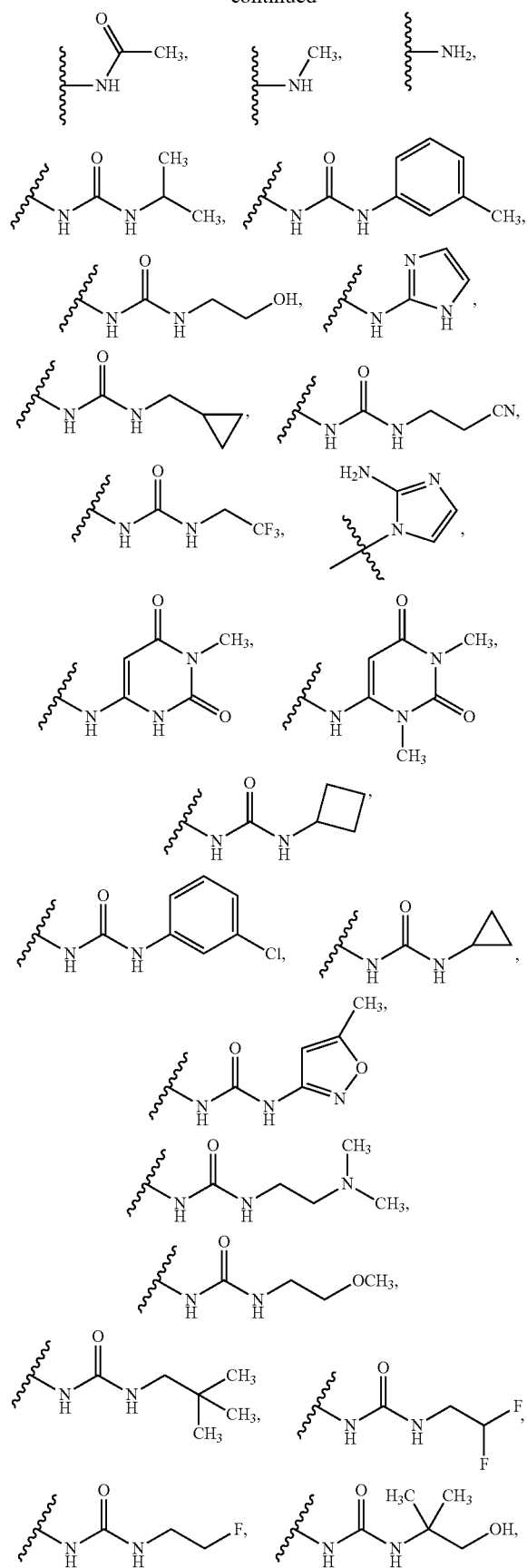
518
-continued
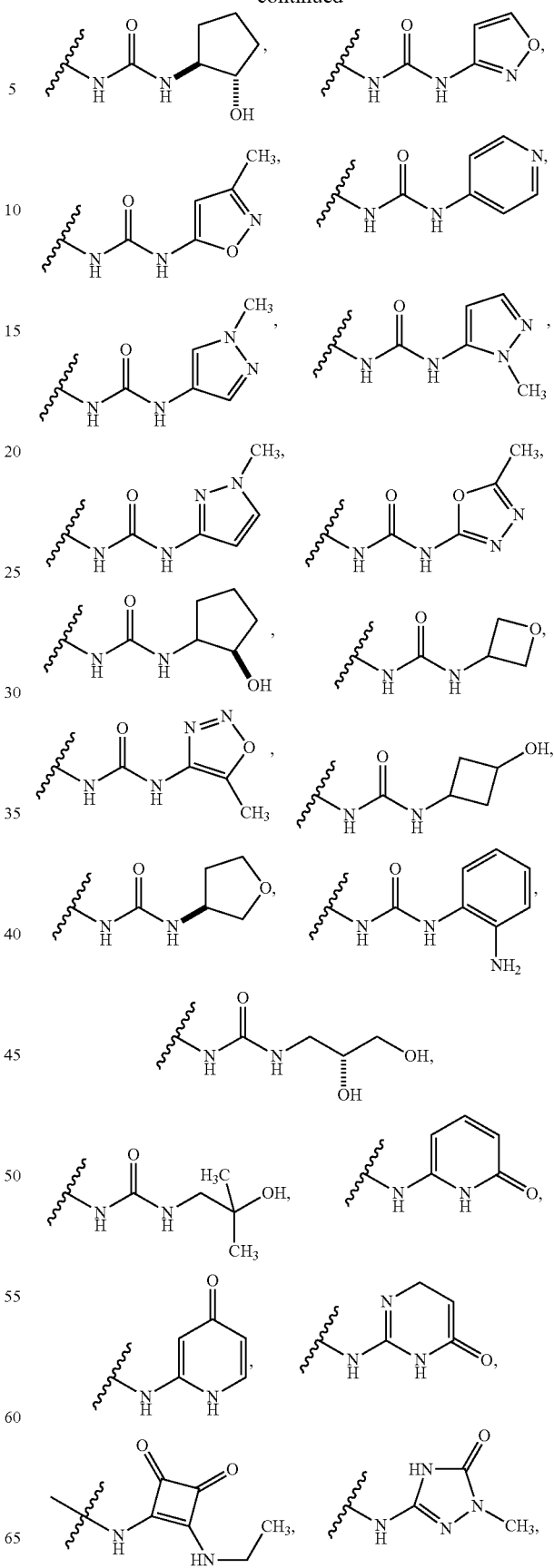

-continued

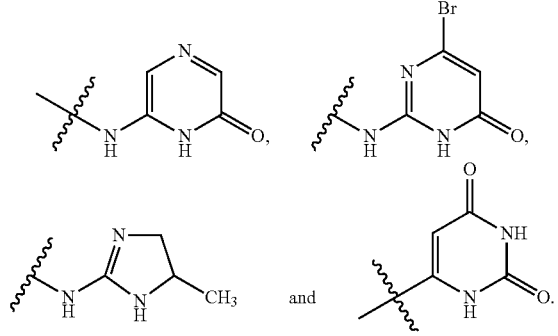

25. The compound of claim 1, wherein said compound has the structure selected from the group consisting of
1-ethyl-3-(4-(4-morpholino-5,6,7,8-tetrahydropyrido[3,4-d]pyrimidin-2-yl)phenyl)urea;
4-(4-morpholino-7-(pyrimidin-2-yl)-5,6,7,8-tetrahydropyrido[3,4-d]pyrimidin-2-yl)aniline;
4-(7-benzyl-4-morpholino-5,6,7,8-tetrahydropyrido[3,4-d]pyrimidin-2-yl)aniline;
tert-butyl 2-(4-aminophenyl)-4-morpholino-5,6-dihydropyrido[3,4-d]pyrimidine-7(8H)-carboxylate;
4-(2-(1H-indazol-5-yl)-7-(pyrimidin-2-yl)-5,6,7,8-tetrahydropyrido[3,4-d]pyrimidin-4-yl)morpholine;
tert-butyl 2-(4-(methylamino)phenyl)-4-morpholino-5,6-dihydropyrido[3,4-d]pyrimidine-7(8H)-carboxylate;
1-(4-(7-acetyl-4-(1,4-oxazepan-4-yl)-5,6,7,8-tetrahydropyrido[3,4-d]pyrimidin-2-yl)phenyl)-3-ethylurea;
4-(2-(4-(1H-pyrazol-1-yl)phenyl)-7-(pyrimidin-2-yl)-5,6,7,8-tetrahydropyrido[3,4-d]pyrimidin-4-yl)morpholine;
(S)-1-ethyl-3-(4-(7-(2-hydroxypropanoyl)-4-morpholino-5,6,7,8-tetrahydropyrido[3,4-d]pyrimidin-2-yl)phenyl)urea;
1-(4-(4-(3,6-dihydro-2H-pyran-4-yl)-7-(pyrimidin-2-yl)-5,6,7,8-tetrahydropyrido[3,4-d]pyrimidin-2-yl)phenyl)-3-ethylurea;
1-ethyl-3-(4-(7-(pyrimidin-2-yl)-4-(tetrahydro-2H-pyran-4-yl)-5,6,7,8-tetrahydropyrido[3,4-d]pyrimidin-2-yl)phenyl)urea;
1-ethyl-3-(4-(4-morpholino-7-(pyrimidin-2-yl)-5,6,7,8-tetrahydropyrido[3,4-d]pyrimidin-2-yl)phenyl)urea;
1,1-dimethyl-3-(4-(4-morpholino-7-(pyrimidin-2-yl)-5,6,7,8-tetrahydropyrido[3,4-d]pyrimidin-2-yl)phenyl)urea;
N-(4-(4-morpholine-7-(pyrimidin-2-yl)-5,6,7,8-tetrahydropyrido[3,4-d]pyrimidin-2-yl)phenyl)pyrimidin-2-amine;
1-ethyl-3-(4-(7-(2-hydroxy-2-methylpropanoyl)-4-morpholino-5,6,7,8-tetrahydropyrido[3,4-d]pyrimidin-2-yl)phenyl)urea;
(Z)-2-cyano-1-methyl-3-(4-(4-morpholino-7-(pyrimidin-2-yl)-5,6,7,8-tetrahydropyrido[3,4-d]pyrimidin-2-yl)phenyl)guanidine;
1-(4-(7-benzyl-4-morpholino-5,6,7,8-tetrahydropyrido[3,4-d]pyrimidin-2-yl)phenyl)-3-ethylurea;
1-(4-(7-benzyl-4-morpholino-5,6,7,8-tetrahydropyrido[3,4-d]pyrimidin-2-yl)phenyl)-3-ethylurea;
1-isopropyl-3-(4-(4-morpholino-7-(pyrimidin-2-yl)-5,6,7,8-tetrahydropyrido[3,4-d]pyrimidin-2-yl)phenyl)urea;
1-(4-(4-(1,4-oxazepan-4-yl)-7-(pyrimidin-2-yl)-5,6,7,8-tetrahydropyrido[3,4-d]pyrimidin-2-yl)phenyl)-3-ethylurea;
1-(4-(7-(2-aminopyrimidin-4-yl)-4-morpholino-5,6,7,8-tetrahydropyrido[3,4-d]pyrimidin-2-yl)phenyl)-3-ethylurea;
1-ethyl-3-(4-(4-morpholino-7-(oxazole-4-carbonyl)-5,6,7,8-tetrahydropyrido[3,4-d]pyrimidin-2-yl)phenyl)urea;
1-ethyl-3-(4-(4-morpholino-7-(oxazole-5-carbonyl)-5,6,7,8-tetrahydropyrido[3,4-d]pyrimidin-2-yl)phenyl)urea;
1-ethyl-3-(4-(7-(1-methylpiperidin-4-yl)-4-morpholino-5,6,7,8-tetrahydropyrido[3,4-d]pyrimidin-2-yl)phenyl)urea;
tert-butyl 2-(4-(3-ethylureido)phenyl)-4-morpholino-5,6-dihydropyrido[3,4-d]pyrimidine-7(8H)-carboxylate;
(E)-2-cyano-1-ethyl-3-(4-(4-morpholino-7-(pyrimidin-2-yl)-5,6,7,8-tetrahydropyrido[3,4-d]pyrimidin-2-yl)phenyl)guanidine;
1-(4-(7-benzoyl-4-morpholino-5,6,7,8-tetrahydropyrido[3,4-d]pyrimidin-2-yl)phenyl-3-ethylurea;
4-(7-benzoyl-4-morpholino-5,6,7,8-tetrahydropyrido[3,4-d]pyrimidin-2-yl)phenyl ethylcarbamate;
ethyl 4-(7-benzoyl-4-morpholino-5,6,7,8-tetrahydropyrido[3,4-d]pyrimidin-2-yl)phenylcarbamate;
1-ethyl-3-(4-(7-isonicotinoyl-4-morpholino-5,6,7,8-tetrahydropyrido[3,4-d]pyrimidin-2-yl)phenyl)urea;
1-ethyl-3-(4-(4-morpholino-7-nicotinoyl-5,6,7,8-tetrahydropyrido[3,4-d]pyrimidin-2-yl)phenyl)urea;
1-ethyl-3-(4-(4-morpholino-7-picolinoyl-5,6,7,8-tetrahydropyrido[3,4-d]pyrimidin-2-yl)phenyl)urea;
1-ethyl-3-(4-(4-morpholino-7-picolinoyl-5,6,7,8-tetrahydropyrido[3,4-d]pyrimidin-2-yl)phenyl)urea;
1-ethyl-3-(4-(7-(5-ethylpyrimidin-2-yl)-4-morpholino-5,6,7,8-tetrahydropyrido[3,4-d]pyrimidin-2-yl)phenyl)urea;
1-ethyl-3-(4-(7-(1-methyl-1H-pyrazole-5-carbonyl)-4-morpholino-5,6,7,8-tetrahydropyrido[3,4-d]pyrimidin-2-yl)phenyl)urea;
1-ethyl-3-(4-(7-(4-methoxypyrimidin-2-yl)-4-morpholino-5,6,7,8-tetrahydropyrido[3,4-d]pyrimidin-2-yl)phenyl)urea;
1-ethyl-3-(4-(4-morpholino-7-(thiazole-2-carbonyl)-5,6,7,8-tetrahydropyrido[3,4-d]pyrimidin-2-yl)phenyl)urea;
tert-butyl 2-(4-(3-ethylureido)phenyl)-4-(3-oxopiperazin-1-yl)-5,6-dihydropyrido[3,4-d]pyrimidine-7(8H)-carboxylate;
1-ethyl-3-(4-(7-(morpholine-4-carbonyl)-4-morpholino-5,6,7,8-tetrahydropyrido[3,4-d]pyrimidin-2-yl)phenyl)urea;
tert-butyl 2-(4-(3-ethyl-1-methylureido)phenyl)-4-morpholino-5,6-dihydropyrido[3,4-d]pyrimidine-7(8H)-carboxylate;
1-cyclopentyl-3-(4-(4-morpholino-7-(pyrimidin-2-yl)-5,6,7,8-tetrahydropyrido[3,4-d]pyrimidin-2-yl)phenyl)urea;
benzyl 2-(4-(3-ethylureido)phenyl)-4-morpholino-5,6-dihydropyrido[3,4-d]pyrimidine-7(8H)-carboxylate;
benzyl 2-(4-(3-ethylureido)phenyl)-4-morpholino-5,6-dihydropyrido[3,4-d]pyrimidine-7(8H)-carboxylate;
(S)-1-ethyl-3-(4-(7-(2-hydroxy-2-phenylacetyl)-4-morpholino-5,6,7,8-tetrahydropyrido[3,4-d]pyrimidin-2-yl)phenyl)urea;
(R)-1-ethyl-3-(4-(7-(2-hydroxy-2-phenylacetyl)-4-morpholino-5,6,7,8-tetrahydropyrido[3,4-d]pyrimidin-2-yl)phenyl)urea;

1-methyl-N-(4-(4-morpholino-7-(pyrimidin-2-yl)-5,6,7,8-tetrahydropyrido[3,4-d]pyrimidin-2-yl)phenyl)-1H-benzo[d]imidazol-2-amine;
1-ethyl-3-(4-(4-morpholino-7-(4-(trifluoromethyl)pyrimidin-2-yl)-5,6,7,8-tetrahydropyrido[3,4-d]pyrimidin-2-yl)phenyl)urea;
benzyl 2-(4-(3-ethylureido)phenyl)-4-(1,4-oxazepan-4-yl)-5,6-dihydropyrido[3,4-d]pyrimidine-7(8H)-carboxylate;
1-ethyl-3-(4-(4-morpholino-7-(4-phenylpyrimidin-2-yl)-5,6,7,8-tetrahydropyrido[3,4-d]pyrimidin-2-yl)phenyl)urea;
1-ethyl-3-(4-(4-morpholino-7-(4-phenylpyrimidin-2-yl)-5,6,7,8-tetrahydropyrido[3,4-d]pyrimidin-2-yl)phenyl)urea;
butyl 4-(4-morpholino-7-(4-phenylpyrimidin-2-yl)-5,6,7,8-tetrahydropyrido[3,4-d]pyrimidin-2-yl)phenylcarbamate;
butyl 4-(4-morpholino-7-(4-phenylpyrimidin-2-yl)-5,6,7,8-tetrahydropyrido[3,4-d]pyrimidin-2-yl)phenylcarbamate;
tert-butyl 4-morpholino-2-(4-(3-(3-(trifluoromethyl)phenyl)ureido)phenyl)-5,6-dihydropyrido[3,4-d]pyrimidine-7(8H)-carboxylate;
4-(2-(1H-indazol-5-yl)-7-(pyrimidin-2-yl)-5,6,7,8-tetrahydropyrido[3,4-d]pyrimidin-4-yl)morpholine;
tert-butyl 4-morpholino-2-(4-(3-(3-(trifluoromethyl)phenyl)ureido)phenyl)-5,6-dihydropyrido[3,4-d]pyrimidine-7(8H)-carboxylate;
tert-butyl 2-(4-(3-ethylureido)phenyl)-4-(2-oxomorpholino)-5,6-dihydropyrido[3,4-d]pyrimidine-7(8H)-carboxylate;
1-ethyl-3-(4-(4-(2-methylmorpholino)-7-(thiazole-5-carbonyl)-5,6,7,8-tetrahydropyrido[3,4-d]pyrimidin-2-yl)phenyl)urea;
1-(4-(7-(4-cyanopyridin-2-yl)-4-morpholino-5,6,7,8-tetrahydropyrido[3,4-d]pyrimidin-2-yl)phenyl)-3-ethylurea;
1-(4-(7-(4,6-dimethylpyrimidin-2-yl)-4-moorpholino-5,6,7,8-tetrahydropyrido[3,4-d]pyrimidin-2-yl)phenyl)-3-ethylurea;
1-ethyl-3-(4-(7-(5-fluoropyrimidin-2-yl)-4-morpholino-5,6,7,8-tetrahydropyrido[3,4-d]pyrimidin-2-yl)phenyl)urea;
1-(4-(7-(4,6-dimethylpyrimidin-2-yl)-4-(1,4-oxazepan-4-yl)-5,6,7,8-tetrahydropyrido[3,4-d]pyrimidin-2-yl)phenyl)-3-ethylurea;
1-ethyl-3-(4-(7-(4-methoxypyrimidin-2-yl)-4-(1,4-oxazepan-4-yl)-5,6,7,8-tetrahydropyrido[3,4-d]pyrimidin-2-yl)phenyl)urea;
1-(4-(4-(1,4-oxazepan-4-yl)-7-(4-(trifluoromethyl)pyrimidin-2-yl)-5,6,7,8-tetrahydropyrido[3,4-d]pyrimidin-2-yl)phenyl)-3-ethylurea;
1-ethyl-3-(4-(7-(5-ethylpyrimidin-2-yl)-4-(1,4-oxazepan-4-yl)-5,6,7,8-tetrahydropyrido[3,4-d]pyrimidin-2-yl)phenyl)urea;
1-ethyl-3-(4-(7-(5-fluoropyrimidin-2-yl)-4-(1,4-oxazepan-4-yl)-5,6,7,8-tetrahydropyrido[3,4-d]pyrimidin-2-yl)phenyl)urea;
5-(4-morpholino-7-(pyrimidin-2-yl)-5,6,7,8-tetrahydropyrido[3,4-d]pyrimidin-2-yl)-1H-benzo[d]imidazol-2(3H)-one;
1-(2-aminophenyl)-3-(4-(4-morpholino-7-(pyrimidin-2-yl)-5,6,7,8-tetrahydropyrido[3,4-d]pyrimidin-2-yl)phenyl)urea;
N-(4-(4-morpholino-7-(pyrimidin-2-yl)-5,6,7,8-tetrahydropyrido[3,4-d]pyrimidin-2-yl)phenyl)-1H-benzo[d]imidazol-2-amine;
1-(2-hydroxyethyl)-3-(4-(4-morpholino-7-(pyrimidin-2-yl)-5,6,7,8-tetrahydropyrido[3,4-d]pyrimidin-2-yl)phenyl)urea;
1-(cyclopropylmethyl)-3-(4-(4-morpholino-7-(pyrimidin-2-yl)-5,6,7,8-tetrahydropyrido[3,4-d]pyrimidin-2-yl)phenyl)urea;
1-(2-cyanoethyl)-3-(4-(4-morpholino-7-(pyrimidin-2-yl)-5,6,7,8-tetrahydropyrido[3,4-d]pyrimidin-2-yl)phenyl)urea;
1-(4-(4-morpholine-7-(pyrimidin-2-yl)-5,6,7,8-tetrahydropyrido[3,4-d]pyrimidin-2-yl)phenyl)-3-(2,2,2-trifluoroethyl)urea;
N-(4-(4-morpholino-7-(pyrimidin-2-yl)-5,6,7,8-tetrahydropyrido[3,4-d]pyrimidin-2-yl)phenyl)-1H-imidazol-2-amine;
1-(4-(4-morpholino-7-(pyrimidin-2-yl)-5,6,7,8-tetrahydropyrido[3,4-d]pyrimidin-2-yl)phenyl)-1H-imidazol-2-amine;
3-methyl-6-(4-(4-morpholino-7-(pyrimidin-2-yl)-5,6,7,8-tetrahydropyrido[3,4-d]pyrimidin-2-yl)phenylamino)pyrimidine-2,4(1H,3H)-dione;
1,3-dimethyl-6-(4-(4-morpholino-7-(pyrimidin-2-yl)-5,6,7,8-tetrahydropyrido[3,4-d]pyrimidin-2-yl)phenylamino)pyrimidine-2,4(1H,3H)-dione;
1-cyclobutyl-3-(4-(4-morpholino-7-(pyrimidin-2-yl)-5,6,7,8-tetrahydropyrido[3,4-d]pyrimidin-2-yl)phenyl)urea;
1-(4-(7-(3-cyanopyridin-2-yl)-4-morpholino-5,6,7,8-tetrahydropyrido[3,4-d]pyrimidin-2-yl)phenyl)-3-ethylurea;
1-(4-(7-(5-cyanopyridin-2-yl)-4-morpholino-5,6,7,8-tetrahydropyrido[3,4-d]pyrimidin-2-yl)phenyl)-3-ethylurea;
1-ethyl-3-(4-(4-morpholino-7-(quinolin-2-yl)-5,6,7,8-tetrahydropyrido[3,4-d]pyrimidin-2-yl)phenyl)urea;
1-ethyl-3-(4-(7-formyl-4-morpholino-5,6,7,8-tetrahydropyrido[3,4-d]pyrimidin-2-yl)phenyl)urea;
1-(4-(7-acetyl-4-morpholino-5,6,7,8-tetrahydropyrido[3,4-d]pyrimidin-2-yl)phenyl)-3-ethylurea;
1-ethyl-3-(4-(4-morpholino-7-propionyl-5,6,7,8-tetrahydropyrido[3,4-d]pyrimidin-2-yl)phenyl)urea;
1-ethyl-3-(4-(7-isobutyryl-4-morpholino-5,6,7,8-tetrahydropyrido[3,4-d]pyrimidin-2-yl)phenyl)urea;
1-ethyl-3-(4-(7-(methylsulfonyl)-4-morpholino-5,6,7,8-tetrahydropyrido[3,4-d]pyrimidin-2-yl)phenyl)urea;
1-ethyl-3-(4-(7-(ethylsulfonyl)-4-morpholino-5,6,7,8-tetrahydropyrido[3,4-d]pyrimidin-2-yl)phenyl)urea;
1-ethyl-3-(4-(4-morpholino-7-(phenylsulfonyl)-5,6,7,8-tetrahydropyrido[3,4-d]pyrimidin-2-yl)phenyl)urea;
methyl 2-(4-(3-ethylureido)phenyl)-4-morpholino-5,6-dihydropyrido[3,4-d]pyrimidine-7(8H)-carboxylate;
tert-butyl 2-(4-(3-ethylureido)phenyl)-4-morpholino-5,6-dihydropyrido[3,4-d]pyrimidine-7(8H)-carboxylate;
(S)-tert-butyl 2-(4-(3-ethylureido)phenyl)-4-(3-methylmorpholino-5,6-dihydropyrido[3,4-d]pyrimidine-7(8H)-carboxylate;
(S)-1-ethyl-3-(4-(4-(3-methylmorpholino)-5,6,7,8-tetrahydropyrido[3,4-d]pyrimidin-2-yl)phenyl)urea;
(S)-1-ethyl-3-(4-(4-(3-methylmorpholino)-7-(pyrimidin-2-yl)-5,6,7,8-tetrahydropyrido[3,4-d]pyrimidin-2-yl)phenyl)urea;
1-cyclopropyl-3-(4-(4-morpholino-7-(pyrimidin-2-yl)-5,6,7,8-tetrahydropyrido[3,4-d]pyrimidin-2-yl)phenyl)urea;

6-(4-(4-morpholino-7-(pyrimidin-2-yl)-5,6,7,8-tetrahydropyrido[3,4-d]pyrimidin-2-yl)phenylamino)pyrimidine-2,4(1H,3H)-dione;

1-ethyl-3-(4-(4-morpholino-7-(pyridin-2-yl)-5,6,7,8-tetrahydropyrido[3,4-d]pyrimidin-2-yl)phenyl)urea;

1-(5-methylisoxazol-3-yl)-3-(4-(4-morpholino-7-(pyrimidin-2-yl)-5,6,7,8-tetrahydropyrido[3,4-d]pyrimidin-2-yl)phenyl)urea;

(S)-1-(4-(7-(2-aminopyrimidin-4-yl)-4-(3-methylmorpholino)-5,6,7,8-tetrahydropyrido[3,4-d]pyrimidin-2-yl)phenyl)-3-ethylurea;

4-(2-(2-chloro-1H-benzo[d]imidazol-5-yl)-7-(pyrimidin-2-yl)-5,6,7,8-tetrahydropyrido[3,4-d]pyrimidin-4-yl)morpholine;

5-(4-morpholino-7-(pyrimidin-2-yl)-5,6,7,8-tetrahydropyrido[3,4-d]pyrimidin-2-yl)indolin-2-one 1-(2-(dimethylamino)ethyl)-3-(4-(4-morpholino-7-(pyrimidin-2-yl)-5,6,7,8-tetrahydropyrido[3,4-d]pyrimidin-2-yl)phenyl)urea;

1-(2-methoxyethyl)-3-(4-(4-morpholino-7-(pyrimidin-2-yl)-5,6,7,8-tetrahydropyrido[3,4-d]pyrimidin-2-yl)phenyl)urea;

1-(4-(4-morpholino-7-(pyrimidin-2-yl)-5,6,7,8-tetrahydropyrido[3,4-d]pyrimidin-2-yl)phenyl)-3-neopentylurea;

1-(2,2-difluoroethyl)-3-(4-(4-morpholino-7-(pyrimidin-2-yl)-5,6,7,8-tetrahydropyrido[3,4-d]pyrimidin-2-yl)phenyl)urea;

1-(2-fluoroethyl)-3-(4-(4-morpholino-7-(pyrimidin-2-yl)-5,6,7,8-tetrahydropyrido[3,4-d]pyrimidin-2-yl)phenyl)urea;

methyl 2-(2-(4-(3-ethylureido)phenyl)-4-morpholino-5,6-dihydropyrido[3,4-d]pyrimidin-7(8H)-yl)-4-(trifluoromethyl)pyrimidine-5-carboxylate;

1-ethyl-3-(4-(4-morpholino-8-oxo-5,6,7,8-tetrahydropyrido[3,4-d]pyrimidin-2-yl)phenyl)urea;

6-(7-benzyl-4-morpholino-5,6,7,8-tetrahydropyrido[3,4-d]pyrimidin-2-yl)quinazolin-2-amine;

1-ethyl-3-(2-fluoro-4-(4-morpholino-7-(pyrimidin-2-yl)-5,6,7,8-tetrahydropyrido[3,4-d]pyrimidin-2-yl)phenyl)urea;

(S)-1-ethyl-3-(4-(7-(2-hydroxy-2-methylpropanoyl)-4-(3-methylmorpholino)-5,6,7,8-tetrahydropyrido[3,4-d]pyrimidin-2-yl)phenyl)urea;

(S)-1-ethyl-3-(4-(7-(1-methyl-1H-pyrazole-5-carbonyl)-4-(3-methylmorpholino)-5,6,7,8-tetrahydropyrido[3,4-d]pyrimidin-2-yl)phenyl)urea;

(S)-1-ethyl-3-(4-(4-(3-methylmorpholino)-7-nicotinoyl-5,6,7,8-tetrahydropyrido[3,4-d]pyrimidin-2-yl)phenyl)urea;

(S)-1-ethyl-3-(4-(4-(3-methylmorpholino)-7-(thiazole-2-carbonyl)-5,6,7,8-tetrahydropyrido[3,4-d]pyrimidin-2-yl)phenyl)urea;

1-(1-hydroxy-2-methylpropan-2-yl)-3-(4-(4-morpholino-7-(pyrimidin-2-yl)-5,6,7,8-tetrahydropyrido[3,4-d]pyrimidin-2-yl)phenyl)urea;

1-((1S,2S)-2-hydroxycyclopentyl)-3-(4-(4-morpholino-7-(pyrimidin-2-yl)-5,6,7,8-tetrahydropyrido[3,4-d]pyrimidin-2-yl)phenyl)urea;

1-(3-methylisoxazol-5-yl)-3-(4-(4-morpholino-7-(pyrimidin-2-yl)-5,6,7,8-tetrahydropyrido[3,4-d]pyrimidin-2-yl)phenyl)urea;

1-(isoxazol-3-yl)-3-(4-(4-morpholino-7-(pyrimidin-2-yl)-5,6,7,8-tetrahydropyrido[3,4-d]pyrimidin-2-yl)phenyl)urea;

N-ethyl-5-(4-morpholino-7-(pyrimidin-2-yl)-5,6,7,8-tetrahydropyrido[3,4-d]pyrimidin-2-yl)-1H-benzo[d]imidazol-2-amine;

(S)-1-(4-(7-(1-acetylpiperidin-4-yl)-4-(3-methylmorpholino)-5,6,7,8-tetrahydropyrido[3,4-d]pyrimidin-2-yl)phenyl)-3-ethylurea;

(S)-1-ethyl-3-(4-(4-(3-methylmorpholino)-7-(1-methylpiperidin-4-yl)-5,6,7,8-tetrahydropyrido[3,4-d]pyrimidin-2-yl)phenyl)urea;

(S)-6-(4-(7-benzyl-4-(3-methylmorpholino)-5,6,7,8-tetrahydropyrido[3,4-d]pyrimidin-2-yl)phenylamino)-3-methylpyrimidine-2,4(1H,3H)-dione;

(R)-tert-butyl 2-(4-(3-ethylureido)phenyl)-4-(3-methylmorpholino)-5,6-dihydropyrido[3,4-d]pyrimidine-7(8H)-carboxylate;

(R)-1-ethyl-3-(4-(4-(3-methylmorpholino)-5,6,7,8-tetrahydropyrido[3,4-d]pyrimidin-2-yl)phenyl)urea;

(R)-1-ethyl-3-(4-(7-(2-hydroxy-2-methylpropanoyl)-4-(3-methylmorpholino)-5,6,7,8-tetrahydropyrido[3,4-d]pyrimidin-2-yl)phenyl)urea;

(R)-1-ethyl-3-(4-(4-(3-methylmorpholino)-7-nicotinoyl-5,6,7,8-tetrahydropyrido[3,4-d]pyrimidin-2-yl)phenyl)urea;

(R)-1-ethyl-3-(4-(4-(3-methylmorpholino)-7-(thiazole-2-carbonyl)-5,6,7,8-tetrahydropyrido[3,4-d]pyrimidin-2-yl)phenyl)urea;

(R)-1-ethyl-3-(4-(4-(3-methylmorpholino)-7-(pyrimidin-2-yl)-5,6,7,8-tetrahydropyrido[3,4-d]pyrimidin-2-yl)phenyl)urea;

(S)-tert-butyl 4-(3-ethylmorpholino)-2-(4-(3-ethylureido)phenyl)-5,6-dihydropyrido[3,4-d]pyrimidine-7(8H)-carboxylate;

(R)-1-ethyl-3-(4-(4-(3-methylmorpholino)-7-(pyrimidin-4-yl)-5,6,7,8-tetrahydropyrido[3,4-d]pyrimidin-2-yl)phenyl)urea;

(S)-tert-butyl 2-(4-(1-methyl-2,6-dioxo-1,2,3,6-tetrahydropyrimidin-4-ylamino)phenyl)-4-(3-methylmorpholino)-5,6-dihydropyrido[3,4-d]pyrimidine-7(8H)-carboxylate;

(S)-1-(4-(7-(3-cyanopyridin-2-)-4-(3-methylmorpholino)-5,6,7,8-tetrahydropyrido[3,4-d]pyrimidin-2-yl)phenyl)-3-ethylurea;

(S)-1-(4-(7-acetyl-4-(3-methylmorpholino)-5,6,7,8-tetrahydropyrido[3,4-d]pyrimidin-2-yl)phenyl)-3-ethylurea;

(S)-1-ethyl-3-(4-(4-(3-methylmorpholino)-7-propionyl-5,6,7,8-tetrahydropyrido[3,4-d]pyrimidin-2-yl)phenyl)urea;

(S)-1-ethyl-3-(4-(7-formyl-4-(3-methylmorpholino)-5,6,7,8-tetrahydropyrido[3,4-d]pyrimidin-2-yl)phenyl)urea;

1-(4-(4-morpholino-7-(pyrimidin-2-yl)-5,6,7,8-tetrahydropyrido[3,4-d]pyrimidin-2-yl)phenyl)-3-(pyridin-4-yl)urea;

(R)-1-ethyl-3-(5-(4-(3-methylmorpholino)-7-(pyrimidin-2-yl)-5,6,7,8-tetrahydropyrido[3,4-d]pyrimidin-2-yl)pyridin-2-yl)urea;

tert-butyl 2-(2-aminopyrimidin-5-yl)-4-morpholino-5,6-dihydropyrido[3,4-d]pyrimidine-7(8H)-carboxylate;

(S)-1-ethyl-3-(4-(7-(1-methyl-1H-pyrazole-5-carbonyl)-4-(3-methylmorpholino)-5,6,7,8-tetrahydropyrido[3,4-d]pyrimidin-2-yl)phenyl)urea;

methyl 2-(2-(4-(3-ethylureido)phenyl)-4-morpholino-5,6-dihydropyrido[3,4-d]pyrimidin-7(8H)-yl)-6-methylpyrimidine-4-carboxylate;

2-(2-(4-(3-ethylureido)phenyl)-4-morpholino-5,6-dihydropyrido[3,4-d]pyrimidin-7(8H)-yl)-6-methylpyrimidine-4-carboxylic acid;

1-ethyl-3-(4-(4-morpholino-7-(4-morpholinopyrimidin-2-yl)-5,6,7,8-tetrahydropyrido[3,4-d]pyrimidin-2-yl)phenyl)urea;

1-(4-(7-(4,6-dimethoxypyrimidin-2-yl)-4-morpholino-5,6,7,8-tetrahydropyrido[3,4-d]pyrimidin-2-yl)phenyl)-3-ethylurea;

2-(2-(4-(3-ethylureido)phenyl)-4-morpholino-5,6-dihydropyrido[3,4-d]pyrimidin-7(8H)-yl)-4-(trifluoromethyl)pyrimidine-5-carboxylic acid;

2-(2-(4-(3-ethylureido)phenyl)-4-morpholino-5,6-dihydropyrido[3,4-d]pyrimidin-7(8H)-yl)-4-(trifluoromethyl)pyrimidine-5-carboxylic acid;

1-(4-(7-(1-cyclopropylpiperidin-4-yl)-4-morpholino-5,6,7,8-tetrahydropyrido[3,4-d]pyrimidin-2-yl)phenyl)-3-ethylurea;

6-(4-(4-morpholino-7-(pyrimidin-2-yl)-5,6,7,8-tetrahydropyrido[3,4-d]pyrimidin-2-yl)phenylamino)pyridin-2(1H)-one;

(S)-1-(4-(7-(4-cyanopyridin-2-yl)-4-(3-methylmorpholino)-5,6,7,8-tetrahydropyrido[3,4-d]pyrimidin-2-yl)phenyl)-3-ethylurea;

(S)-1-(4-(7-(5-cyanopyridin-2-yl)-4-(3-methylmorpholino)-5,6,7,8-tetrahydropyrido[3,4-d]pyrimidin-2-yl)phenyl)-3-ethylurea;

(S)-1-(4-(7-(4,6-dimethylpyrimidin-2-yl)-4-(3-methylmorpholino)-5,6,7,8-tetrahydropyrido[3,4-d]pyrimidin-2-yl)phenyl)-3-ethylurea;

(S)-1-ethyl-3-(4-(7-(5-ethylpyrimidin-2-yl)-4-(3-methylmorpholino)-5,6,7,8-tetrahydropyrido[3,4-d]pyrimidin-2-yl)phenyl)urea;

6-(4-(4-morpholino-7-(pyrimidin-2-yl)-5,6,7,8-tetrahydropyrido[3,4-d]pyrimidin-2-yl)phenylamino)pyridin-2(1H)-one;

1-ethyl-3-(4-(4-morpholino-7-(5-nitropyrimidin-2-yl)-5,6,7,8-tetrahydropyrido[3,4-d]pyrimidin-2-yl)phenyl)urea;

1-(4-(7-(4-amino-5-cyanopyrimidin-2-yl)-4-morpholino-5,6,7,8-tetrahydropyrido[3,4-d]pyrimidin-2-yl)phenyl)-3-ethylurea;

1-ethyl-3-(4-(7-(4-hydroxycyclohexyl)-4-morpholino-5,6,7,8-tetrahydropyrido[3,4-d]pyrimidin-2-yl)phenyl)urea;

(S)-3-methyl-6-(4-(4-(3-methylmorpholino)-7-(pyrimidin-2-yl)-5,6,7,8-tetrahydropyrido[3,4-d]pyrimidin-2-yl)phenylamino)pyrimidine-2,4(1H,3H)-dione;

(S)-6-(4-(7-(2-hydroxy-2-methylpropanoyl)-4-(3-methylmorpholino)-5,6,7,8-tetrahydropyrido[3,4-d]pyrimidin-2-yl)phenylamino)-3-methylpyrimidine-2,4(1H,3H)-dione;

(S)-3-methyl-6-(4-(4-(3-methylmorpholino)-7-(thiazole-2-carbonyl)-5,6,7,8-tetrahydropyrido[3,4-d]pyrimidin-2-yl)phenylamino)pyrimidine-2,4(1H,3H)-dione;

(S)-1-ethyl-3-(4-(4-(3-methylmorpholino)-8-oxo-5,6,7,8-tetrahydropyrido[3,4-d]pyrimidin-2-yl)phenyl)urea;

2-(4-(4-morpholino-7-(pyrimidin-2-yl)-5,6,7,8-tetrahydropyrido[3,4-d]pyrimidin-2-yl)phenylamino)pyridin-4(1H)-one;

1-((1S,2R)-2-hydroxycyclopentyl)-3-(4-(4-morpholino-7-(pyrimidin-2-yl)-5,6,7,8-tetrahydropyrido[3,4-d]pyrimidin-2-yl)phenyl)urea;

tert-butyl 2-(4-(3-ethylureido)phenyl)-4-(pyridin-4-yl)-5,6-dihydropyrido[3,4-d]pyrimidine-7(8H)-carboxylate;

1-ethyl-3-(4-(7-(3-methyloxetane-3-carbonyl)-4-morpholino-5,6,7,8-tetrahydropyrido[3,4-d]pyrimidin-2-yl)phenyl)urea;

2-(4-(4-morpholino-7-(pyrimidin-2-yl)-5,6,7,8-tetrahydropyrido[3,4-d]pyrimidin-2-yl)phenylamino)pyrimidin-4(3H)-one;

(S)-3-methyl-6-(4-(4-(3-methylmorpholino)-5,6,7,8-tetrahydropyrido[3,4-d]pyrimidin-2-yl)phenylamino)pyrimidine-2,4(1H,3H)-dione;

(S)-2-(2-(4-(3-ethylureido)phenyl)-4-(3-methylmorpholino)-5,6-dihydropyrido[3,4-d]pyrimidin-7(8H)-yl)-N,N-dimethylacetamide;

(S)-1-ethyl-3-(4-(4-(3-methylmorpholino)-7-(methylsulfonyl)-5,6,7,8-tetrahydropyrido[3,4-d]pyrimidin-2-yl)phenyl)urea;

(S)-methyl 2-(4-(3-ethylureido)phenyl)-4-(3-methylmorpholino)-5,6-dihydropyrido[3,4-d]pyrimidine-7(8H)-carboxylate;

(S)-ethyl 2-(4-(3-ethylureido)phenyl)-4-(3-methylmorpholino)-5,6-dihydropyrido[3,4-d]pyrimidine-7(8H)-carboxylate;

(S)-1-ethyl-3-(4-(4-(3-ethylmorpholino)-7-(pyrimidin-2-yl)-5,6,7,8-tetrahydropyrido[3,4-d]pyrimidin-2-yl)phenyl)urea;

1-(3-hydroxycyclobutyl)-3-(4-(4-morpholino-7-(pyrimidin-2-yl)-5,6,7,8-tetrahydropyrido[3,4-d]pyrimidin-2-yl)phenyl)urea;

1-ethyl-3-(4-(7-(5-fluoro-4-hydroxypyrimidin-2-yl)-4-morpholino-5,6,7,8-tetrahydropyrido[3,4-d]pyrimidin-2-yl)phenyl)urea;

1-(4-(7-(5-aminopyrimidin-2-yl)-4-morpholino-5,6,7,8-tetrahydropyrido[3,4-d]pyrimidin-2-yl)phenyl)-3-ethylurea;

1-(4-(7-(4-amino-5-nitropyrimidin-2-yl)-4-morpholino-5,6,7,8-tetrahydropyrido[3,4-d]pyrimidin-2-yl)phenyl)-3-ethylurea;

(S)-3-(ethylamino)-4-(4-(4-(3-methylmorpholino)-7-(pyrimidin-2-yl)-5,6,7,8-tetrahydropyrido[3,4-d]pyrimidin-2-yl)phenylamino)cyclobut-3-ene-1,2-dione;

(S)-1-(2-cyanoethyl)-3-(4-(4-(3-methylmorpholino)-7-(pyrimidin-2-yl)-5,6,7,8-tetrahydropyrido[3,4-d]pyrimidin-2-yl)phenyl)urea;

(S)-1-(2-hydroxyethyl)-3-(4-(4-(3-methylmorpholino)-7-(pyrimidin-2-yl)-5,6,7,8-tetrahydropyrido[3,4-d]pyrimidin-2-yl)phenyl)urea;

(S)-1-cyclobutyl-3-(4-(4-(3-methylmorpholino)-7-(pyrimidin-2-yl)-5,6,7,8-tetrahydropyrido[3,4-d]pyrimidin-2-yl)phenyl)urea;

(S)-1-(2,2-difluoroethyl)-3-(4-(4-(3-methylmorpholino)-7-(pyrimidin-2-yl)-5,6,7,8-tetrahydropyrido[3,4-d]pyrimidin-2-yl)phenyl)urea;

(S)-1-(2-fluoroethyl)-3-(4-(4-(3-methylmorpholino)-7-(pyrimidin-2-yl)-5,6,7,8-tetrahydropyrido[3,4-d]pyrimidin-2-yl)phenyl)urea;

(S)-1-(2,2-difluoroethyl)-3-(4-(4-(3-methylmorpholino)-6-(thiazole-2-carbonyl)-5,6,7,8-tetrahydropyrido[4,3-d]pyrimidin-2-yl)phenyl)urea;

(S)-1-ethyl-3-(4-(4-(3-methylmorpholino)-7-(pyrazin-2-yl)-5,6,7,8-tetrahydropyrido[3,4-d]pyrimidin-2-yl)phenyl)urea;

(S)-1-ethyl-3-(4-(4-(3-methylmorpholino)-7-(2-morpholino-2-oxoethyl)-5,6,7,8-tetrahydropyrido[3,4-d]pyrimidin-2-yl)phenyl)urea;

1-(4-(7-(4-amino-5-methylpyrimidin-2-yl)-4-morpholino-5,6,7,8-tetrahydropyrido[3,4-d]pyrimidin-2-yl)phenyl)-3-ethylurea;

1-ethyl-3-(4-(7-(1-(methylsulfonyl)piperidin-4-yl)-4-morpholino-5,6,7,8-tetrahydropyrido[3,4-d]pyrimidin-2-yl)phenyl)urea;

1-ethyl-3-(4-(4-morpholino-7-(piperidin-4-yl)-5,6,7,8-tetrahydropyrido[3,4-d]pyrimidin-2-yl)phenyl)urea;

(S)-1-cyclobutyl-3-(4-(4-(3-methylmorpholino)-5,6,7,8-tetrahydropyrido[3,4-d]pyrimidin-2-yl)phenyl)urea;

1-((1S,2S)-2-hydroxycyclopentyl)-3-(4-(4-((S)-3-methylmorpholino)-5,6,7,8-tetrahydropyrido[3,4-d]pyrimidin-2-yl)phenyl)urea;

(S)-1-(2,2-difluoroethyl)-3-(4-(4-(3-methylmorpholino)-5,6,7,8-tetrahydropyrido[3,4-d]pyrimidin-2-yl)phenyl)urea;

1-(4-(7-(2-hydroxy-2-methylpropanoyl)-4-((S)-3-methylmorpholino)-5,6,7,8-tetrahydropyrido[3,4-d]pyrimidin-2-yl)phenyl)-3-((1S,2S)-2-hydroxycyclopentyl)urea;

(S)-1-(2,2-difluoroethyl)-3-(4-(7-(2-hydroxy-2-methylpropanoyl)-4-(3-methylmorpholino)-5,6,7,8-tetrahydropyrido[3,4-d]pyrimidin-2-yl)phenyl)urea;

(S)-1-(2-fluoroethyl)-3-(4-(7-(2-hydroxy-2-methylpropanoyl)-4-(3-methylmorpholino)-5,6,7,8-tetrahydropyrido[3,4-d]pyrimidin-2-yl)phenyl)urea;

1-((1S,2S)-2-hydroxycyclopentyl)-3-(4-(4-((S)-3-methylmorpholino)-5,6,7,8-tetrahydropyrido[3,4-d]pyrimidin-2-yl)phenyl)urea;

(S)-1-(2,2-difluoroethyl)-3-(4-(4-(3-methylmorpholino)-5,6,7,8-tetrahydropyrido[3,4-d]pyrimidin-2-yl)phenyl)urea;

1-(4-(7-(2-hydroxy-2-methylpropanoyl)-4-((S)-3-methylmorpholino)-5,6,7,8-tetrahydropyrido[3,4-d]pyrimidin-2-yl)phenyl)-3-((1S,2S)-2-hydroxycyclopentyl)urea;

(S)-1-(2,2-difluoroethyl)-3-(4-(7-(2-hydroxy-2-methylpropanoyl)-4-(3-methylmorpholino)-5,6,7,8-tetrahydropyrido[3,4-d]pyrimidin-2-yl)phenyl)urea;

(S)-1-(2-fluoroethyl)-3-(4-(7-(2-hydroxy-2-methylpropanoyl)-4-(3-methylmorpholino)-5,6,7,8-tetrahydropyrido[3,4-d]pyrimidin-2-yl)phenyl)urea;

(S)-1-cyclobutyl-3-(4-(7-(2-hydroxy-2-methylpropanoyl)-4-(3-methylmorpholino)-5,6,7,8-tetrahydropyrido[3,4-d]pyrimidin-2-yl)phenyl)urea;

(S)-1-(2-fluoroethyl)-3-(4-(4-(3-methylmorpholino)-7-nicotinoyl-5,6,7,8-tetrahydropyrido[3,4-d]pyrimidin-2-yl)phenyl)urea;

1-((1S,2S)-2-hydroxycyclopentyl)-3-(4-(4-((S)-3-methylmorpholino)-7-nicotinoyl-5,6,7,8-tetrahydropyrido[3,4-d]pyrimidin-2-yl)phenyl)urea;

(S)-1-(2,2-difluoroethyl)-3-(4-(4-(3-methylmorpholino)-7-nicotinoyl-5,6,7,8-tetrahydropyrido[3,4-d]pyrimidin-2-yl)phenyl)urea;

(S)-1-(2-cyanoethyl)-3-(4-(4-(3-methylmorpholino)-7-nicotinoyl-5,6,7,8-tetrahydropyrido[3,4-d]pyrimidin-2-yl)phenyl)urea;

(S)-1-cyclobutyl-3-(4-(4-(3-methylmorpholino)-7-nicotinoyl-5,6,7,8-tetrahydropyrido[3,4-d]pyrimidin-2-yl)phenyl)urea;

(S)-1-cyclobutyl-3-(4-(4-(3-methylmorpholino)-7-(pyrazin-2-yl)-5,6,7,8-tetrahydropyrido[3,4-d]pyrimidin-2-yl)phenyl)urea;

1-(4-(4-((S)-3-methylmorpholino)-7-(pyrazin-2-yl)-5,6,7,8-tetrahydropyrido[3,4-d]pyrimidin-2-yl)phenyl)-3-((S)-tetrahydrofuran-3-yl)urea;

(S)-1-ethyl-3-(4-(7-(5-fluoropyrimidin-4-yl)-4-(3-methylmorpholino)-5,6,7,8-tetrahydropyrido[3,4-d]pyrimidin-2-yl)phenyl)urea;

(S)-1-(2-fluoroethyl)-3-(4-(4-(3-methylmorpholino)-7-(pyrazin-2-yl)-5,6,7,8-tetrahydropyrido[3,4-d]pyrimidin-2-yl)phenyl)urea;

(S)-2-(4-(4-(3-methylmorpholino)-5,6,7,8-tetrahydropyrido[3,4-d]pyrimidin-2-yl)phenylamino)pyrimidin-4(3H)-one;

1-ethyl-3-(4-(4-morpholino-7-(pyrimidin-4-yl)-5,6,7,8-tetrahydropyrido[3,4-d]pyrimidin-2-yl)phenyl)urea;

(S)-1-(3-methylisoxazol-5-yl)-3-(4-(4-(3-methylmorpholino)-7-(pyrazin-2-yl)-5,6,7,8-tetrahydropyrido[3,4-d]pyrimidin-2-yl)phenyl)urea;

(S)-isopropyl 2-(4-(3-ethylureido)phenyl)-4-(3-methylmorpholino)-5,6-dihydropyrido[3,4-d]pyrimidine-7(8H)-carboxylate;

(S)-isobutyl 2-(4-(3-ethylureido)phenyl)-4-(3-methylmorpholino)-5,6-dihydropyrido[3,4-d]pyrimidine-7(8H)-carboxylate;

(S)-1-ethyl-3-(4-(4-(3-methylmorpholino)-7-(3-methyloxetane-3-carbonyl)-5,6,7,8-tetrahydropyrido[3,4-d]pyrimidin-2-yl)phenyl)urea;

(S)-1-ethyl-3-(4-(4-(3-methylmorpholino)-7-(tetrahydrofuran-3-carbonyl)-5,6,7,8-tetrahydropyrido[3,4-d]pyrimidin-2-yl)phenyl)urea;

(S)-1-ethyl-3-(4-(4-(3-methylmorpholino)-7-(tetrahydrofuran-2-carbonyl)-5,6,7,8-tetrahydropyrido[3,4-d]pyrimidin-2-yl)phen (S)-1-(4-(7-formyl-4-(3-methylmorpholino)-5,6,7,8-tetrahydropyrido[3,4-d]pyrimidin-2-yl)phenyl)-3-(2-hydroxyethyl)urea;

(S)-1-(4-(7-formyl-4-(3-methylmorpholino)-5,6,7,8-tetrahydropyrido[3,4-d]pyrimidin-2-yl)phenyl)-3-(2,2,2-trifluoroethyl)urea;

(S)-1-(4-(7-acetyl-4-(3-methylmorpholino)-5,6,7,8-tetrahydropyrido[3,4-d]pyrimidin-2-yl)phenyl)-3-(2-hydroxyethyl)urea;

(S)-1-(4-(7-acetyl-4-(3-methylmorpholino)-5,6,7,8-tetrahydropyrido[3,4-d]pyrimidin-2-yl)phenyl)-3-(2,2,2-trifluoroethyl)urea;

(S)-1-(2-hydroxyethyl)-3-(4-(4-(3-methylmorpholino)-7-propionyl-5,6,7,8-tetrahydropyrido[3,4-d]pyrimidin-2-yl)phenyl)urea;

(S)-1-(4-(4-(3-methylmorpholino)-7-propionyl-5,6,7,8-tetrahydropyrido[3,4-d]pyrimidin-2-yl)phenyl)-3-(2,2,2-trifluoroethyl)urea;

(S)-1-(isoxazol-3-yl)-3-(4-(4-(3-methylmorpholino)-7-(pyrimidin-2-yl)-5,6,7,8-tetrahydropyrido[3,4-d]pyrimidin-2-yl)phenyl)urea;

(S)-1-(1-methyl-1H-pyrazol-5-yl)-3-(4-(4-(3-methylmorpholino)-7-nicotinoyl-5,6,7,8-tetrahydropyrido[3,4-d]pyrimidin-2-yl)phenyl)urea;

(S)-2-(4-(4-(3-methylmorpholino)-7-nicotinoyl-5,6,7,8-tetrahydropyrido[3,4-d]pyrimidin-2-yl)phenylamino)pyrimidin-4(3H)-one;

(S)-1-methyl-3-(4-(4-(3-methylmorpholino)-7-(pyrimidin-2-yl)-5,6,7,8-tetrahydropyrido[3,4-d]pyrimidin-2-yl)phenylamino)-1H-1,2,4-triazol-5(4H)-one (S)-6-(4-(4-(3-methylmorpholino)-7-nicotinoyl-5,6,7,8-tetrahydropyrido[3,4-d]pyrimidin-2-yl)phenylamino)pyridin-2(1H)-one;

(S)-6-(4-(4-(3-methylmorpholino)-5,6,7,8-tetrahydropyrido[3,4-d]pyrimidin-2-yl)phenylamino)pyridin-2(1H)-one;

(S)-tert-butyl 4-(3-ethylmorpholino)-2-(4-(3-(2-hydroxyethyl)ureido)phenyl)-5,6-dihydropyrido[3,4-d]pyrimidine-7(8H)-carboxylate;

(S)-1-ethyl-3-(4-(4-(3-methylmorpholino)-7-(6-methylpyrimidin-4-yl)-5,6,7,8-tetrahydropyrido[3,4-d]pyrimidin-2-yl)phenyl)urea;
(S)-1-ethyl-3-(4-(7-(5-fluoropyrimidin-2-yl)-4-(3-methylmorpholino)-5,6,7,8-tetrahydropyrido[3,4-d]pyrimidin-2-yl)phenyl)urea;
(S)-1-ethyl-3-(4-(4-(3-methylmorpholino)-7-(4-(trifluoromethyl)pyrimidin-2-yl)-5,6,7,8-tetrahydropyrido[3,4-d]pyrimidin-2-yl)phenyl)urea;
(S)-1-ethyl-3-(4-(7-(4-methoxypyrimidin-2-yl)-4-(3-methylmorpholino)-5,6,7,8-tetrahydropyrido[3,4-d]pyrimidin-2-yl)phenyl)urea;
(S)-1-(2-hydroxyethyl)-3-(4-(4-(3-methylmorpholino)-7-(pyrimidin-4-yl)-5,6,7,8-tetrahydropyrido[3,4-d]pyrimidin-2-yl)phenyl)urea;
(S)-1-(2-cyanoethyl)-3-(4-(4-(3-methylmorpholino)-7-(pyrimidin-4-yl)-5,6,7,8-tetrahydropyrido[3,4-d]pyrimidin-2-yl)phenyl)urea;
(S)-1-cyclobutyl-3-(4-(4-(3-methylmorpholino)-7-(pyrimidin-4-yl)-5,6,7,8-tetrahydropyrido[3,4-d]pyrimidin-2-yl)phenyl)urea;
(S)-1-(isoxazol-3-yl)-3-(4-(4-(3-methylmorpholino)-7-(pyrimidin-4-yl)-5,6,7,8-tetrahydropyrido[3,4-d]pyrimidin-2-yl)phenyl)urea;
(S)-tert-butyl 2-(4-(3-ethylureido)phenyl)-4-(3-isopropylmorpholino)-5,6-dihydropyrido[3,4-d]pyrimidine-7(8H)-carboxylate;
(S)-1-(4-(4-(3-ethylmorpholino)-5,6,7,8-tetrahydropyrido[3,4-d]pyrimidin-2-yl)phenyl)-3-(2-hydroxyethyl)urea;
(S)-2-(4-(7-(2-hydroxy-2-methylpropanoyl)-4-(3-methylmorpholino)-5,6,7,8-tetrahydropyrido[3,4-d]pyrimidin-2-yl)phenylamino)pyrimidin-4(3H)-one;
(S)-2-(4-(4-(3-methylmorpholino)-7-(1,4,5,6-tetrahydropyrimidin-2-yl)-5,6,7,8-tetrahydropyrido[3,4-d]pyrimidin-2-yl)phenylamino)pyrimidin-4(3H)-one;
(S)-1-(1-methyl-1H-pyrazol-5-yl)-3-(4-(4-(3-methylmorpholino)-7-(pyrimidin-2-yl)-5,6,7,8-tetrahydropyrido[3,4-d]pyrimidin-2-yl)phenyl)urea;
(S)-1-(3-methylisoxazol-5-yl)-3-(4-(4-(3-methylmorpholino)-7-(pyrimidin-2-yl)-5,6,7,8-tetrahydropyrido[3,4-d]pyrimidin-2-yl)phenyl)urea;
(S)-1-(1-methyl-1H-pyrazol-3-yl)-3-(4-(4-(3-methylmorpholino)-7-(pyrimidin-2-yl)-5,6,7,8-tetrahydropyrido[3,4-d]pyrimidin-2-yl)phenyl)urea;
(S)-1-(4-(4-(3-ethylmorpholino)-7-(pyrimidin-2-yl)-5,6,7,8-tetrahydropyrido[3,4-d]pyrimidin-2-yl)phenyl)-3-(2-hydroxyethyl)urea;
(S)-1-(4-(7-(2-hydroxy-2-methylpropanoyl)-4-(3-methylmorpholino)-5,6,7,8-tetrahydropyrido[3,4-d]pyrimidin-2-yl)phenyl)-3-(1-methyl-1H-pyrazol-5-yl)urea;
(S)-1-(4-(7-(2-hydroxy-2-methylpropanoyl)-4-(3-methylmorpholino)-5,6,7,8-tetrahydropyrido[3,4-d]pyrimidin-2-yl)phenyl)-3-(3-methylisoxazol-5-yl)urea;
(S)-1-(4-(7-(2-hydroxy-2-methylpropanoyl)-4-(3-methylmorpholino)-5,6,7,8-tetrahydropyrido[3,4-d]pyrimidin-2-yl)phenyl)-3-(1-methyl-1H-pyrazol-3-yl)urea;
(S)-1-(4-(7-(2-hydroxy-2-methylpropanoyl)-4-(3-methylmorpholino)-5,6,7,8-tetrahydropyrido[3,4-d]pyrimidin-2-yl)phenyl)-3-(isoxazol-3-yl)urea;
(S)-1-(4-(7-(4-chloro-1,3,5-triazin-2-yl)-4-(3-methylmorpholino)-5,6,7,8-tetrahydropyrido[3,4-d]pyrimidin-2-yl)phenyl)-3-ethylurea;
(S)-1-ethyl-3-(4-(4-(3-methylmorpholino)-7-(1,3,5-triazin-2-yl)-5,6,7,8-tetrahydropyrido[3,4-d]pyrimidin-2-yl)phenyl)urea;
(S)-1-ethyl-3-(4-(7-isopropyl-4-(3-methylmorpholino)-5,6,7,8-tetrahydropyrido[3,4-d]pyrimidin-2-yl)phenyl)urea;
(S)-1-ethyl-3-(4-(7-isobutyl-4-(3-methylmorpholino)-5,6,7,8-tetrahydropyrido[3,4-d]pyrimidin-2-yl)phenyl)urea;
tert-butyl 3-(2-(4-(3-ethylureido)phenyl)-4-((S)-3-methylmorpholino)-5,6-dihydropyrido[3,4-d]pyrimidin-7(8H)-yl)pyrrolidine-1-carboxylate;
1-ethyl-3-(4-(4-((S)-3-methylmorpholino)-7-(pyrrolidin-3-yl)-5,6,7,8-tetrahydropyrido[3,4-d]pyrimidin-2-yl)phenyl)urea;
(S)-1-ethyl-3-(4-(7-methyl-4-(3-methylmorpholino)-8-oxo-5,6,7,8-tetrahydropyrido[3,4-d]pyrimidin-2-yl)phenyl)urea;
1-ethyl-3-(4-(7-(1-methyl-1H-pyrazol-4-ylsulfonyl)-4-morpholino-5,6,7,8-tetrahydropyrido[3,4-d]pyrimidin-2-yl)phenyl)urea;
(S)-1-ethyl-3-(2-methyl-4-(4-(3-methylmorpholino)-7-(pyrimidin-2-yl)-5,6,7,8-tetrahydropyrido[3,4-d]pyrimidin-2-yl)phenyl)urea;
1-ethyl-3-(4-(4-morpholino-7-pivaloyl-5,6,7,8-tetrahydropyrido[3,4-d]pyrimidin-2-yl)phenyl)urea;
(S)-2-(4-(4-(3-methylmorpholino)-7-(pyrimidin-2-yl)-5,6,7,8-tetrahydropyrido[3,4-d]pyrimidin-2-yl)phenylamino)pyrimidin-4(3H)-one;
1-ethyl-3-(4-(7-(4-fluorobenzoyl)-4-morpholino-5,6,7,8-tetrahydropyrido[3,4-d]pyrimidin-2-yl)phenyl)urea;
1-(4-(7-(4-chlorobenzoyl)-4-morpholino-5,6,7,8-tetrahydropyrido[3,4-d]pyrimidin-2-yl)phenyl)-3-ethylurea;
1-ethyl-3-(4-(7-(2-methylnicotinoyl)-4-morpholino-5,6,7,8-tetrahydropyrido[3,4-d]pyrimidin-2-yl)phenyl)urea;
1-ethyl-3-(4-(7-(6-methylnicotinoyl)-4-morpholino-5,6,7,8-tetrahydropyrido[3,4-d]pyrimidin-2-yl)phenyl)urea;
isopropyl 2-(4-(3-ethylureido)phenyl)-4-morpholino-5,6-dihydropyrido[3,4-d]pyrimidine-7(8H)-carboxylate;
isobutyl 2-(4-(3-ethylureido)phenyl)-4-morpholino-5,6-dihydropyrido[3,4-d]pyrimidine-7(8H)-carboxylate;
1-ethyl-3-(4-(7-(6-methylpyrimidin-4-yl)-4-morpholino-5,6,7,8-tetrahydropyrido[3,4-d]pyrimidin-2-yl)phenyl)urea;
(S)-1-ethyl-3-(4-(7-(1-methylcyclopropanecarbonyl)-4-(3-methylmorpholino)-5,6,7,8-tetrahydropyrido[3,4-d]pyrimidin-2-yl)phenyl)urea;
(S)-1-(4-(7-(1-cyanocyclopropanecarbonyl)-4-(3-methylmorpholino)-5,6,7,8-tetrahydropyrido[3,4-d]pyrimidin-2-yl)phenyl)-3-ethylurea;
(S)-1-ethyl-3-(4-(7-(3-hydroxy-2,2-dimethylpropanoyl)-4-(3-methylmorpholino)-5,6,7,8-tetrahydropyrido[3,4-d]pyrimidin-2-yl)phenyl)urea;
1-(4-(7-(6-cyanopyrazin-2-yl)-4-morpholino-5,6,7,8-tetrahydropyrido[3,4-d]pyrimidin-2-yl)phenyl)-3-ethylurea;
1-(4-(7-(1-acetylpyrrolidin-3-yl)-4-((S)-3-methylmorpholino)-5,6,7,8-tetrahydropyrido[3,4-d]pyrimidin-2-yl)phenyl)-3-ethylurea;
1-ethyl-3-(4-(4-((S)-3-methylmorpholino)-7-(1-(methylsulfonyl)pyrrolidin-3-yl)-5,6,7,8-tetrahydropyrido[3,4-d]pyrimidin-2-yl)phenyl)urea;
(S)-1-(4-(7-(1-cyclopropylpiperidin-4-yl)-4-(3-methylmorpholino)-5,6,7,8-tetrahydropyrido[3,4-d]pyrimidin-2-yl)phenyl)-3-ethylurea;
(S)-1-ethyl-3-(4-(4-(3-methylmorpholino)-7-(tetrahydro-2H-pyran-4-yl)-5,6,7,8-tetrahydropyrido[3,4-d]pyrimidin-2-yl)phenyl)urea;

1-ethyl-3-(4-(7-((R)-2-hydroxypropanoyl)-4-((S)-3-methylmorpholino)-5,6,7,8-tetrahydropyrido[3,4-d]pyrimidin-2-yl)phenyl)urea;

1-ethyl-3-(4-(7-((R)-2-hydroxybutanoyl)-4-((S)-3-methylmorpholino)-5,6,7,8-tetrahydropyrido[3,4-d]pyrimidin-2-yl)phenyl)urea;

1-ethyl-3-(4-(4-((S)-3-methylmorpholino)-7-(1-(methylsulfonyl)pyrrolidin-3-yl)-5,6,7,8-tetrahydropyrido[3,4-d]pyrimidin-2-yl)phenyl)urea;

(S)-1-(4-(7-(1-cyclopropylpiperidin-4-yl)-4-(3-methylmorpholino)-5,6,7,8-tetrahydropyrido[3,4-d]pyrimidin-2-yl)phenyl)-3-ethylurea;

(S)-1-ethyl-3-(4-(4-(3-methylmorpholino)-7-(tetrahydro-2H-pyran-4-yl)-5,6,7,8-tetrahydropyrido[3,4-d]pyrimidin-2-yl)phenyl)urea;

1-ethyl-3-(4-(7-((R)-2-hydroxypropanoyl)-4-((S)-3-methylmorpholino)-5,6,7,8-tetrahydropyrido[3,4-d]pyrimidin-2-yl)phenyl)urea;

1-ethyl-3-(4-(7-((R)-2-hydroxybutanoyl)-4-((S)-3-methylmorpholino)-5,6,7,8-tetrahydropyrido[3,4-d]pyrimidin-2-yl)phenyl)urea;

(S)-1-methyl-3-(4-(4-(3-methylmorpholino)-7-(pyrimidin-2-yl)-5,6,7,8-tetrahydropyrido[3,4-d]pyrimidin-2-yl)phenyl)urea;

1-ethyl-3-(4-(7-((S)-2-hydroxypropanoyl)-4-((S)-3-methylmorpholino)-5,6,7,8-tetrahydropyrido[3,4-d]pyrimidin-2-yl)phenyl)urea;

1-ethyl-3-(4-(7-((S)-2-hydroxybutanoyl)-4-((S)-3-methylmorpholino)-5,6,7,8-tetrahydropyrido[3,4-d]pyrimidin-2-yl)phenyl)urea;

1-(4-(7-(6-chloropyrazin-2-yl)-4-morpholino-5,6,7,8-tetrahydropyrido[3,4-d]pyrimidin-2-yl)phenyl)-3-ethylurea;

(S)-1-ethyl-3-(4-(7-isopropyl-4-(3-methylmorpholino)-8-oxo-5,6,7,8-tetrahydropyrido[3,4-d]pyrimidin-2-yl)phenyl)urea;

(S)-1-ethyl-3-(4-(7-(2-methoxypyrimidin-4-yl)-4-(3-methylmorpholino)-5,6,7,8-tetrahydropyrido[3,4-d]pyrimidin-2-yl)phenyl)urea;

(S)-1-ethyl-3-(4-(4-(3-methylmorpholino)-7-(2-(trifluoromethyl)pyrimidin-4-yl)-5,6,7,8-tetrahydropyrido[3,4-d]pyrimidin-2-yl)phenyl)urea;

(S)-1-(4-(7-(2,6-dimethoxypyrimidin-4-yl)-4-(3-methylmorpholino)-5,6,7,8-tetrahydropyrido[3,4-d]pyrimidin-2-yl)phenyl)-3-ethylurea;

1-(4-(7-(3-cyanopyrazin-2-yl)-4-morpholino-5,6,7,8-tetrahydropyrido[3,4-d]pyrimidin-2-yl)phenyl)-3-ethylurea;

1-ethyl-3-(4-(7-((R)-2-hydroxy-3-methylbutanoyl)-4-((S)-3-methylmorpholino)-5,6,7,8-tetrahydropyrido[3,4-d]pyrimidin-2-yl)phenyl)urea;

(S)-1-methyl-3-(4-(4-(3-methylmorpholino)-7-(pyrimidin-4-yl)-5,6,7,8-tetrahydropyrido[3,4-d]pyrimidin-2-yl)phenyl)urea;

1-(4-(7-(3-chloropyrazin-2-yl)-4-morpholino-5,6,7,8-tetrahydropyrido[3,4-d]pyrimidin-2-yl)phenyl)-3-ethylurea;

1-ethyl-3-(4-(4-morpholino-7-(pyrazine-2-carbonyl)-5,6,7,8-tetrahydropyrido[3,4-d]pyrimidin-2-yl)phenyl)urea;

(S)-1-(5-methyl-1,3,4-oxadiazol-2-yl)-3-(4-(4-(3-methylmorpholino)-7-(pyrimidin-2-yl)-5,6,7,8-tetrahydropyrido[3,4-d]pyrimidin-2-yl)phenyl)urea;

1-ethyl-3-(4-(7-((S)-2-hydroxy-3-methylbutanoyl)-4-((S)-3-methylmorpholino)-5,6,7,8-tetrahydropyrido[3,4-d]pyrimidin-2-yl)phenyl)urea;

(S)-1-ethyl-3-(4-(7-(2-methoxyacetyl)-4-(3-methylmorpholino)-5,6,7,8-tetrahydropyrido[3,4-d]pyrimidin-2-yl)phenyl)urea;

(S)-1-(4-(7-(2-cyanoacetyl)-4-(3-methylmorpholino)-5,6,7,8-tetrahydropyrido[3,4-d]pyrimidin-2-yl)phenyl)-3-ethylurea;

(S)-6-(4-(7-(2-hydroxy-2-methylpropanoyl)-4-(3-methylmorpholino)-5,6,7,8-tetrahydropyrido[3,4-d]pyrimidin-2-yl)phenylamino)pyridin-2(1H)-one;

1-ethyl-3-(4-(4-morpholino-7-(pyrimidine-2-carbonyl)-5,6,7,8-tetrahydropyrido[3,4-d]pyrimidin-2-yl)phenyl)urea;

(S)-1-methyl-3-(4-(4-(3-methylmorpholino)-7-(6-methylpyrimidin-4-yl)-5,6,7,8-tetrahydropyrido[3,4-d]pyrimidin-2-yl)phenyl)urea;

(S)-1-(1-methyl-1H-pyrazol-4-yl)-3-(4-(4-(3-methylmorpholino)-7-(pyrimidin-2-yl)-5,6,7,8-tetrahydropyrido[3,4-d]pyrimidin-2-yl)phenyl)urea;

(S)-6-(4-(4-(3-methylmorpholino)-7-nicotinoyl-5,6,7,8-tetrahydropyrido[3,4-d]pyrimidin-2-yl)phenylamino)pyrazin-2(1H)-one;

(S)-6-(4-(4-(3-methylmorpholino)-7-nicotinoyl-5,6,7,8-tetrahydropyrido[3,4-d]pyrimidin-2-yl)phenylamino)pyrazin-2(1H)-one;

1-ethyl-3-(4-(7-(2-((S)-3-fluoropyrrolidin-1-yl)-2-oxoethyl)-4-((S)-3-methylmorpholino)-5,6,7,8-tetrahydropyrido[3,4-d]pyrimidin-2-yl)phenyl)urea;

(S)-tert-butyl 2-(4-(3-ethylureido)phenyl)-4-(3-(hydroxymethyl)morpholino)-5,6-dihydropyrido[3,4-d]pyrimidine-7(8H)-carboxylate;

1-ethyl-3-(4-(7-(2-((R)-3-fluoropyrrolidin-1-yl)-2-oxoethyl)-4-((S)-3-methylmorpholino)-5,6,7,8-tetrahydropyrido[3,4-d]pyrimidin-2-yl)phenyl)urea;

1-(4-(7-(3-chloropyrazine-2-carbonyl)-4-morpholino-5,6,7,8-tetrahydropyrido[3,4-d]pyrimidin-2-yl)phenyl)-3-ethylurea;

(S)-1-ethyl-3 (4 (7 (2 (2 methoxyethoxy)acetyl)-4-(3-methylmorpholino)-5,6,7,8-tetrahydropyrido[3,4-d]pyrimidin-2-yl)phenyl)urea;

(S)-1-ethyl-3-(4-(7-(5-methyl-1,3,4-oxadiazole-2-carbonyl)-4-(3-methylmorpholino)-5,6,7,8-tetrahydropyrido[3,4-d]pyrimidin-2-yl)phenyl)urea;

(S)-6-(4-(4-(3-methylmorpholino)-7-(2,2,2-trifluoroethyl)-5,6,7,8-tetrahydropyrido[3,4-d]pyrimidin-2-yl)phenylamino)pyridin-2(1H)-one;

(S)—N-ethyl-2-(2-(4-(3-ethylureido)phenyl)-4-(3-methylmorpholino)-5,6-dihydropyrido[3,4-d]pyrimidin-7(8H)-yl)acetamide;

(S)-methyl 2-(2-(4-(3-ethylureido)phenyl)-4-(3-methylmorpholino)-5,6-dihydropyrido[3,4-d]pyrimidin-7(8H)-yl)acetate;

(S)-2-(2-(4-(3-ethylureido)phenyl)-4-(3-methylmorpholino)-5,6-dihydropyrido[3,4-d]pyrimidin-7(8H)-yl)-N-(2-hydroxyethyl)acetamide;

1-(4-(7-(5-chloropyrazin-2-yl)-4-morpholino-5,6,7,8-tetrahydropyrido[3,4-d]pyrimidin-2-yl)phenyl)-3-ethylurea;

(S)-tert-butyl 2-(4-(3-ethylureido)phenyl)-8,8-dimethyl-4-(3-methylmorpholino)-5,6-dihydropyrido[3,4-d]pyrimidine-7(8H)-carboxylate;

1-ethyl-3-(4-(4-morpholino-7-(2,2,2-trifluoroethyl)-5,6,7,8-tetrahydropyrido[3,4-d]pyrimidin-2-yl)phenyl)urea;

tert-butyl 2-(4-(3-ethylureido)phenyl)-8-methyl-4-((S)-3-methylmorpholino)-5,6-dihydropyrido[3,4-d]pyrimidine-7(8H)-carboxylate;

(S)-1-ethyl-3-(4-(4-(3-methylmorpholino)-7-(2-methylpyrimidin-4-yl)-5,6,7,8-tetrahydropyrido[3,4-d]pyrimidin-2-yl)phenyl)urea;

1-(4-(7-(4-chloro-6-methylpyrimidin-2-yl)-4-morpholino-5,6,7,8-tetrahydropyrido[3,4-d]pyrimidin-2-yl)phenyl)-3-ethylurea;

1-(4-(7-(2-chloro-6-methylpyrimidin-4-yl)-4-morpholino-5,6,7,8-tetrahydropyrido[3,4-d]pyrimidin-2-yl)phenyl)-3-ethylurea;

tert-butyl 2-(4-(3-ethylureido)phenyl)-8-methyl-4-morpholino-5,6-dihydropyrido[3,4-d]pyrimidine-7(8H)-carboxylate;

(S)-1-(4-(8,8-dimethyl-4-(3-methylmorpholino)-5,6,7,8-tetrahydropyrido[3,4-d]pyrimidin-2-yl)phenyl)-3-ethylurea;

(R)-tert-butyl 2-(4-(3-ethylureido)phenyl)-8-methyl-4-((S)-3-methylmorpholino)-5,6-dihydropyrido[3,4-d]pyrimidine-7(8H)-carboxylate;

(S)-tert-butyl 2-(4-(3-ethylureido)phenyl)-8-methyl-4-((S)-3-methylmorpholino)-5,6-dihydropyrido[3,4-d]pyrimidine-7(8H)-carboxylate;

(S)-2-(2-(4-(3-ethylureido)phenyl)-4-(3-methylmorpholino)-5,6-dihydropyrido[3,4-d]pyrimidin-7(8H)-yl)acetamide;

(S)-2-(2-(4-(3-ethylureido)phenyl)-4-(3-methylmorpholino)-5,6-dihydropyrido[3,4-d]pyrimidin-7(8H)-yl)-N-methylacetamide;

(S)-2-(2-(4-(3-ethylureido)phenyl)-4-(3-methylmorpholino)-5,6-dihydropyrido[3,4-d]pyrimidin-7(8H)-yl)-N-propylacetamide;

(S)—N-cyclobutyl-2-(2-(4-(3-ethylureido)phenyl)-4-(3-methylmorpholino)-5,6-dihydropyrido[3,4-d]pyrimidin-7(8H)-yl)acetamide;

(S)—N-cyclopentyl-2-(2-(4-(3-ethylureido)phenyl)-4-(3-methylmorpholino)-5,6-dihydropyrido[3,4-d]pyrimidin-7(8H)-yl)acetamide;

(S)-1-ethyl-3-(4-(4-(3-methylmorpholino)-7-(2-oxo-2-(pyrrolidin-1-yl)ethyl)-5,6,7,8-tetrahydropyrido[3,4-d]pyrimidin-2-yl)phenyl)urea;

(S)-2-(2-(4-(3-ethylureido)phenyl)-4-(3-methylmorpholino)-5,6-dihydropyrido[3,4-d]pyrimidin-7(8H)-yl) acetic acid;

(S)-1-(4-(7-(2-aminoacetyl)-4-(3-methylmorpholino)-5,6,7,8-tetrahydropyrido[3,4-d]pyrimidin-2-yl)phenyl)-3-ethylurea;

1-(4-(7-((R)-2-aminopropanoyl)-4-((S)-3-methylmorpholino)-5,6,7,8-tetrahydropyrido[3,4-d]pyrimidin-2-yl)phenyl)-3-ethylurea;

1-(4-(7-((R)-2-aminopropanoyl)-4-((S)-3-methylmorpholino)-5,6,7,8-tetrahydropyrido[3,4-d]pyrimidin-2-yl)phenyl)-3-ethylurea;

1-ethyl-3-(4-(4-((S)-3-methylmorpholino)-7-(pyrrolidine-2-carbonyl)-5,6,7,8-tetrahydropyrido[3,4-d]pyrimidin-2-yl)phenyl)urea;

1-ethyl-3-(4-(7-(2-(methylamino)propanoyl)-4-((S)-3-methylmorpholino)-5,6,7,8-tetrahydropyrido[3,4-d]pyrimidin-2-yl)phenyl)urea;

(S)-1-(4-(7-(2-amino-2-methylpropanoyl)-4-(3-methylmorpholino)-5,6,7,8-tetrahydropyrido[3,4-d]pyrimidin-2-yl)phenyl)-3-ethylurea;

(S)-2-(4-(4-(3-methylmorpholino)-7-(6-methylpyrimidin-4-yl)-5,6,7,8-tetrahydropyrido[3,4-d]pyrimidin-2-yl)phenylamino)pyrimidin-4(3H)-one;

(S)-6-bromo-2-(4-(4-(3-ethylmorpholino)-7-(pyrimidin-2-yl)-5,6,7,8-tetrahydropyrido[3,4-d]pyrimidin-2-yl)phenylamino)pyrimidin-4(3H)-one;

(S)-1-methyl-3-(4-(4-(3-methylmorpholino)-7-(6-methylpyrimidin-4-yl)-5,6,7,8-tetrahydropyrido[3,4-d]pyrimidin-2-yl)phenylamino)-1H-1,2,4-triazol-5(4H)-one;

1-(4-(7-((S)-2-aminobutanoyl)-4-((S)-3-methylmorpholino)-5,6,7,8-tetrahydropyrido[3,4-d]pyrimidin-2-yl)phenyl)-3-ethylurea;

(S,E)-2-cyano-1-ethyl-3-(4-(4-(3-methylmorpholino)-7-(pyrimidin-2-yl)-5,6,7,8-tetrahydropyrido[3,4-d]pyrimidin-2-yl)phenyl)guanidine;

1-ethyl-3-(4-((S)-8-methyl-4-((S)-3-methylmorpholino)-5,6,7,8-tetrahydropyrido[3,4-d]pyrimidin-2-yl)phenyl)urea;

tert-butyl 2-(4-(3-ethylureido)phenyl)-8,8-dimethyl-4-morpholino-5,6-dihydropyrido[3,4-d]pyrimidine-7(8H)-carboxylate;

1-(4-(7-((S)-2-aminopropanoyl)-4-((S)-3-methylmorpholino)-5,6,7,8-tetrahydropyrido[3,4-d]pyrimidin-2-yl)phenyl)-3-ethylurea;

(S)-2-(4-(4-(3-ethylmorpholino)-7-(pyrimidin-2-yl)-5,6,7,8-tetrahydropyrido[3,4-d]pyrimidin-2-yl)phenylamino)pyrimidin-4(3H)-one;

1-ethyl-3-(4-((S)-8-methyl-4-((S)-3-methylmorpholino)-7-(pyrimidin-2-yl)-5,6,7,8-tetrahydropyrido[3,4-d]pyrimidin-2-yl)phenyl)urea;

1-ethyl-3-(4-(7-(1-methyl-1H-imidazol-2-yl)-4-morpholino-5,6,7,8-tetrahydropyrido[3,4-d]pyrimidin-2-yl)phenyl)urea;

(S)-6-(4-(4-(3-methylmorpholino)-7-(6-methylpyrimidin-4-yl)-5,6,7,8-tetrahydropyrido[3,4-d]pyrimidin-2-yl)phenylamino)pyridin-2(1H)-one;

(S)-1-(4-(7-(cyclopropylsulfonyl)-4-(3-methylmorpholino)-5,6,7,8-tetrahydropyrido[3,4-d]pyrimidin-2-yl)phenyl)-3-ethylurea;

1-(4-(4-morpholino-7-(pyrimidin-2-yl)-5,6,7,8-tetrahydropyrido[3,4-d]pyrimidin-2-yl)phenyl)urea;

(S)-1-ethyl-3-(4-(4-(3-methylmorpholino)-7-(2-(4-methylpiperazin-1-yl)-2-oxoethyl)-5,6,7,8-tetrahydropyrido[3,4-d]pyrimidin-2-yl)phenyl)urea;

(S)-1-ethyl-3-(4-(7-ethyl-4-(3-methylmorpholino)-8-oxo-5,6,7,8-tetrahydropyrido[3,4-d]pyrimidin-2-yl)phenyl)urea;

1-ethyl-3-(4-(8-methyl-4-morpholino-7-(pyrimidin-2-yl)-5,6,7,8-tetrahydropyrido[3,4-d]pyrimidin-2-yl)phenyl)urea;

(S)-6-(4-(7-acetyl-4-(3-methylmorpholino)-5,6,7,8-tetrahydropyrido[3,4-d]pyrimidin-2-yl)phenylamino)pyridin-2(1H)-one;

(S)—N,N-diethyl-2-(2-(4-(3-ethylureido)phenyl)-4-(3-methylmorpholino)-5,6-dihydropyrido[3,4-d]pyrimidin-7(8H)-yl)acetamide;

(S)-1-(4-(7-(2-(3,3-difluoropyrrolidin-1-yl)-2-oxoethyl)-4-(3-methylmorpholino)-5,6,7,8-tetrahydropyrido[3,4-d]pyrimidin-2-yl)phenyl)-3-ethylurea;

(S)-1-(4-(4-(3-methylmorpholino)-7-(pyrimidin-2-yl)-5,6,7,8-tetrahydropyrido[3,4-d]pyrimidin-2-yl)phenyl)urea;

(S)-6-(4-(7-isopropyl-4-(3-methylmorpholino)-5,6,7,8-tetrahydropyrido[3,4-d]pyrimidin-2-yl)phenylamino)pyridin-2(1H)-one;

(S)-tert-butyl 8-allyl-2-(4-(3-ethylureido)phenyl)-4-((S)-3-methylmorpholino)-5,6-dihydropyrido[3,4-d]pyrimidine-7(8H)-carboxylate;

(R)-tert-butyl 8-allyl-2-(4-(3-ethylureido)phenyl)-4-((S)-3-methylmorpholino)-5,6-dihydropyrido[3,4-d]pyrimidine-7(8H)-carboxylate;

(S)-1-ethyl-3-(5-(4-(3-methylmorpholino)-7-(pyrimidin-2-yl)-5,6,7,8-tetrahydropyrido[3,4-d]pyrimidin-2-yl)pyridin-2-yl)urea;

(S)-1-ethyl-3-(5-(4-(3-methylmorpholino)-7-(6-methylpyrimidin-4-yl)-5,6,7,8-tetrahydropyrido[3,4-d]pyrimidin-2-yl)pyridin-2-yl)urea;

(S)-2-(5-(4-(3-methylmorpholino)-7-(6-methylpyrimidin-4-yl)-5,6,7,8-tetrahydropyrido[3,4-d]pyrimidin-2-yl)pyridin-2-ylamino)pyrimidin-4(3H)-one;

(S)-6-(5-(4-(3-methylmorpholino)-7-(6-methylpyrimidin-4-yl)-5,6,7,8-tetrahydropyrido[3,4-d]pyrimidin-2-yl)-pyridin-2-ylamino)pyridin-2(1H)-one;

(S)-tert-butyl 2-(4-(2-amino-5-methyl-1H-imidazol-1-yl)phenyl)-4-(3-methylmorpholino)-5,6-dihydropyrido[3,4-d]pyrimidine-7(8H)-carboxylate;

(S)-1-(4-(4-(3-ethylmorpholino)-7-(pyrimidin-2-yl)-5,6,7,8-tetrahydropyrido[3,4-d]pyrimidin-2-yl)phenyl)-3-(isoxazol-3-yl)urea;

(S)-1-(4-(4-(3-ethylmorpholino)-7-(pyrimidin-2-yl)-5,6,7,8-tetrahydropyrido[3,4-d]pyrimidin-2-yl)phenyl)-3-(5-methyl-1,2,3-oxadiazol-4-yl)urea;

(S)-2-(4-(4-(3-methylmorpholino)-6-(6-methylpyrimidin-4-yl)-5,6,7,8-tetrahydropyrido[4,3-d]pyrimidin-2-yl)phenylamino)pyrimidin-4(3H)-one;

1-ethyl-3-(4-(7-(1-methylcyclopropanecarbonyl)-4-morpholino-5,6,7,8-tetrahydropyrido[3,4-d]pyrimidin-2-yl)phenyl)urea;

1-(4-(7-(1-cyanocyclopropanecarbonyl)-4-morpholino-5,6,7,8-tetrahydropyrido[3,4-d]pyrimidin-2-yl)phenyl)-3-ethylurea;

(S)-1-(4-(4-(3-ethylmorpholino)-7-(pyrimidin-2-yl)-5,6,7,8-tetrahydropyrido[3,4-d]pyrimidin-2-yl)phenyl)-3-(oxetan-3-yl)urea;

(S)-6-(5-(7-methyl-4-(3-methylmorpholino)-5,6,7,8-tetrahydropyrido[3,4-d]pyrimidin-2-yl)pyridin-2-ylamino)pyridin-2(1H)-one;

(S)-6-(5-(7-methyl-4-(3-methylmorpholino)-5,6,7,8-tetrahydropyrido[3,4-d]pyrimidin-2-yl)pyridin-2-ylamino)pyridin-2(1H)-one;

(S)-6-(5-(7-methyl-4-(3-methylmorpholino)-5,6,7,8-tetrahydropyrido[3,4-d]pyrimidin-2-yl)pyridin-2-ylamino)pyridin-2(1H)-one;

(S)-1-ethyl-3-(4-(4-(3-methylmorpholino)-7-(thiazol-2-yl)-5,6,7,8-tetrahydropyrido[3,4-d]pyrimidin-2-yl)phenyl)urea;

(S)-1-(4-(7-cyclopentyl-4-(3-methylmorpholino)-5,6,7,8-tetrahydropyrido[3,4-d]pyrimidin-2-yl)phenyl)-3-ethylurea;

(S)-1-ethyl-3-(4-(4-(3-methylmorpholino)-7-(4-methylthiazol-2-yl)-5,6,7,8-tetrahydropyrido[3,4-d]pyrimidin-2-yl)phenyl)urea;

(S)-1-ethyl-3-(4-(4-(3-ethylmorpholino)-7-methyl-8-oxo-5,6,7,8-tetrahydropyrido[3,4-d]pyrimidin-2-yl)phenyl)urea;

(S)-1-(4-(7-cyclohexyl-4-(3-methylmorpholino)-5,6,7,8-tetrahydropyrido[3,4-d]pyrimidin-2-yl)phenyl)-3-ethylurea;

(S)-1-(4-(7-(6-chloropyrimidin-4-yl)-4-(3-methylmorpholino)-5,6,7,8-tetrahydropyrido[3,4-d]pyrimidin-2-yl)phenyl)-3-ethylurea;

(S)-1-isopropyl-3-(4-(4-(3-methylmorpholino)-7-(pyrimidin-2-yl)-5,6,7,8-tetrahydropyrido[3,4-d]pyrimidin-2-yl)phenyl)urea;

1-ethyl-3-(4-(7-(2-methylpyrimidin-4-yl)-4-morpholino-5,6,7,8-tetrahydropyrido[3,4-d]pyrimidin-2-yl)phenyl)urea;

(S)-1-ethyl-3-(4-(4-(3-methylmorpholino)-7-(2,2,2-trifluoroethyl)-5,6,7,8-tetrahydropyrido[3,4-d]pyrimidin-2-yl)phenyl)urea;

1-(4-(4-(((1S,4S)-2-oxa-5-azabicyclo[2.2.1]heptan-5-yl)-7-pyrimidin-2-yl)-5,6,7,8-tetrahydropyrido[3,4-d]pyrimidin-2-yl)phenyl)-3-ethylurea;

(S)-1-ethyl-3-(4-(4-(3-methylmorpholino)-7-(pyrazine-2-carbonyl)-5,6,7,8-tetrahydropyrido[3,4-d]pyrimidin-2-yl)phenyl)urea;

(S)-6-(5-(7-isopropyl-4-(3-methylmorpholino)-5,6,7,8-tetrahydropyrido[3,4-d]pyrimidin-2-yl)pyridin-2-ylamino)pyridin-2(1H)-one;

1-ethyl-3-(4-(7-(3-methyl-1,2,4-thiadiazol-5-yl)-4-morpholino-5,6,7,8-tetrahydropyrido[3,4-d]pyrimidin-2-yl)phenyl)urea;

(S)-1-ethyl-3-(4-(7-(1-methyl-1H-imidazol-2-yl)-4-(3-methylmorpholino)-5,6,7,8-tetrahydropyrido[3,4-d]pyrimidin-2-yl)phenyl)urea;

1-ethyl-3-(4-(7-(5-methylpyrazine-2-carbonyl)-4-morpholino-5,6,7,8-tetrahydropyrido[3,4-d]pyrimidin-2-yl)phenyl)urea;

1-(4-(7-(6-cyclopropylpyrimidin-4-yl)-4-morpholino-5,6,7,8-tetrahydropyrido[3,4-d]pyrimidin-2-yl)phenyl)-3-ethylurea;

1-ethyl-3-(4-(7-(1-methyl-6-oxo-1,6-dihydropyridin-2-yl)-4-morpholino-5,6,7,8-tetrahydropyrido[3,4-d]pyrimidin-2-yl)phenyl)urea;

(S)-1-ethyl-3-(4-(4-(3-methylmorpholino)-7-(5-methylpyrimidin-2-yl)-5,6,7,8-tetrahydropyrido[3,4-d]pyrimidin-2-yl)phenyl)urea;

1-(4-(4-(((1S,4S)-2-oxa-5-azabicyclo[2.2.1]heptan-5-yl)-7-(6-methylpyrimidin-4-yl)-5,6,7,8-tetrahydropyrido[3,4-d]pyrimidin-2-yl)phenyl)-3-ethylurea;

1-(4-(4-(((1S,4S)-2-oxa-5-azabicyclo[2.2.1]heptan-5-yl)-7-(5-fluoropyrimidin-2-yl)-5,6,7,8-tetrahydropyrido[3,4-d]pyrimidin-2-yl)phenyl)-3-ethylurea;

1-(4-(4-(((1S,4S)-2-oxa-5-azabicyclo[2.2.1]heptan-5-yl)-7-(2-methylpyrimidin-4-yl)-5,6,7,8-tetrahydropyrido[3,4-d]pyrimidin-2-yl)phenyl)-3-ethylurea;

1-ethyl-3-(4-(7-(3-methylpyrazine-2-carbonyl)-4-morpholino-5,6,7,8-tetrahydropyrido[3,4-d]pyrimidin-2-yl)phenyl)urea;

(S)-1-cyclobutyl-3-(4-(4-(3-ethylmorpholino)-7-(2-methylpyrimidin-4-yl)-5,6,7,8-tetrahydropyrido[3,4-d]pyrimidin-2-yl)phenyl)urea;

(S)-1-ethyl-3-(4-(4-(3-ethylmorpholino)-7-(5-fluoropyrimidin-2-yl)-5,6,7,8-tetrahydropyrido[3,4-d]pyrimidin-2-yl)phenyl)urea;

(S)-1-ethyl-3-(4-(4-(3-methylmorpholino)-7-(oxetan-3-yl)-5,6,7,8-tetrahydropyrido[3,4-d]pyrimidin-2-yl)phenyl)urea;

(S)-1-ethyl-3-(4-(7-(ethylsulfonyl)-4-(3-methylmorpholino)-5,6,7,8-tetrahydropyrido[3,4-d]pyrimidin-2-yl)phenyl)urea;

(S)-1-ethyl-3-(4-(7-(isopropylsulfonyl)-4-(3-methylmorpholino)-5,6,7,8-tetrahydropyrido[3,4-d]pyrimidin-2-yl)phenyl)urea;

(S)-1-ethyl-3-(4-(7-methyl-4-(3-methylmorpholino)-5,6,7,8-tetrahydropyrido[3,4-d]pyrimidin-2-yl)phenyl)urea;

(S)-1-ethyl-3-(4-(7-(5-methyl-1,3,4-oxadiazol-2-yl)-4-(3-methylmorpholino)-5,6,7,8-tetrahydropyrido[3,4-d]pyrimidin-2-yl)phenyl)urea;

(S)-1-(4-(7-(5-cyanothiazol-2-yl)-4-(3-methylmorpholino)-5,6,7,8-tetrahydropyrido[3,4-d]pyrimidin-2-yl)phenyl)-3-ethylurea;

1-ethyl-3-(4-(4-((S)-3-methylmorpholino)-7-(tetrahydrofuran-3-yl)-5,6,7,8-tetrahydropyrido[3,4-d]pyrimidin-2-yl)phenyl)urea;

(S)-1-ethyl-3-(4-(7-(isobutylsulfonyl)-4-(3-methylmorpholino)-5,6,7,8-tetrahydropyrido[3,4-d]pyrimidin-2-yl)phenyl)urea;

(S)-1-ethyl-3-(4-(7-(3-methyl-1,2,4-thiadiazol-5-yl)-4-(3-methylmorpholino)-5,6,7,8-tetrahydropyrido[3,4-d]pyrimidin-2-yl)phenyl)urea;

(S)-6-(4-(7-(1-methyl-1H-imidazol-2-yl)-4-(3-methylmorpholino)-5,6,7,8-tetrahydropyrido[3,4-d]pyrimidin-2-yl)phenylamino)pyridin-2(1H)-one;

(S)-1-ethyl-3-(4-(4-(3-ethylmorpholino)-7-(2,2,2-trifluoroethyl)-5,6,7,8-tetrahydropyrido[3,4-d]pyrimidin-2-yl)phenyl)urea;

(S)-1-(4-(7-(cyclopropylmethyl)-4-(3-methylmorpholino)-5,6,7,8-tetrahydropyrido[3,4-d]pyrimidin-2-yl)phenyl)-3-ethylurea;

(S)-1-ethyl-3-(4-(4-(3-methylmorpholino)-7-(pyridin-4-ylmethyl)-5,6,7,8-tetrahydropyrido[3,4-d]pyrimidin-2-yl)phenyl)urea;

(S)-1-ethyl-3-(4-(7-ethyl-4-(3-ethylmorpholino)-8-oxo-5,6,7,8-tetrahydropyrido[3,4-d]pyrimidin-2-yl)phenyl)urea;

(S)-1-ethyl-3-(4-(7-(3-hydroxy-2,2-dimethylpropyl)-4-(3-methylmorpholino)-5,6,7,8-tetrahydropyrido[3,4-d]pyrimidin-2-yl)phenyl)urea;

(S)-7-ethyl-4-(3-ethylmorpholino)-2-(4-(6-oxo-1,6-dihydropyridin-2-ylamino)phenyl)-6,7-dihydropyrido[3,4-d]pyrimidin-8(5H)-one;

1-(4-((R)-7-acetyl-8-methyl-4-((S)-3-methylmorpholino)-5,6,7,8-tetrahydropyrido[3,4-d]pyrimidin-2-yl)phenyl)-3-ethylurea;

1-ethyl-3-(4-((R)-7-ethyl-8-methyl-4-((S)-3-methylmorpholino)-5,6,7,8-tetrahydropyrido[3,4-d]pyrimidin-2-yl)phenyl)urea;

1-ethyl-3-(4-((S)-7-ethyl-8-methyl-4-((S)-3-methylmorpholino)-5,6,7,8-tetrahydropyrido[3,4-d]pyrimidin-2-yl)phenyl)urea;

1-(4-((R)-7,8-dimethyl-4-((S)-3-methylmorpholino)-5,6,7,8-tetrahydropyrido[3,4-d]pyrimidin-2-yl)phenyl)-3-ethylurea;

1-(4-((S)-7,8-dimethyl-4-((S)-3-methylmorpholino)-5,6,7,8-tetrahydropyrido[3,4-d]pyrimidin-2-yl)phenyl)-3-ethylurea;

(S)-1-ethyl-3-(4-(7-ethyl-4-(3-methylmorpholino)-5,6,7,8-tetrahydropyrido[3,4-d]pyrimidin-2-yl)phenyl)urea;

(S)-1-ethyl-3-(4-(4-(3-methylmorpholino)-7-(propylsulfonyl)-5,6,7,8-tetrahydropyrido[3,4-d]pyrimidin-2-yl)phenyl)urea;

(R)-1-ethyl-3-(4-(8-methyl-7-(2-methylpyrimidin-4-yl)-4-morpholino-5,6,7,8-tetrahydropyrido[3,4-d]pyrimidin-2-yl)phenyl)urea;

(S)-1-ethyl-3-(4-(8-methyl-7-(2-methylpyrimidin-4-yl)-4-morpholino-5,6,7,8-tetrahydropyrido[3,4-d]pyrimidin-2-yl)phenyl)urea;

1-ethyl-3-(4-(8-methyl-7-(2-methylpyrimidin-4-yl)-4-morpholino-5,6,7,8-tetrahydropyrido[3,4-d]pyrimidin-2-yl)phenyl)urea;

(S)-1-ethyl-3-(4-(7-(1-methyl-6-oxo-1,6-dihydropyridin-2-yl)-4-(3-methylmorpholino)-5,6,7,8-tetrahydropyrido[3,4-d]pyrimidin-2-yl)phenyl)urea;

1-(4-(7-(6-(benzyloxy)pyridin-2-yl)-4-morpholino-5,6,7,8-tetrahydropyrido[3,4-d]pyrimidin-2-yl)phenyl)-3-ethylurea;

(S)-1-(4-(7-(3,3-dimethylbutyl)-4-(3-methylmorpholino)-5,6,7,8-tetrahydropyrido[3,4-d]pyrimidin-2-yl)phenyl)-3-ethylurea;

(S)-1-(4-(7-(5-fluoropyrimidin-2-yl)-4-(3-methylmorpholino)-5,6,7,8-tetrahydropyrido[3,4-d]pyrimidin-2-yl)phenyl)-3-methylurea;

(S)-1-(4-(7-(6-chloro-2-methylpyrimidin-4-yl)-4-(3-methylmorpholino)-5,6,7,8-tetrahydropyrido[3,4-d]pyrimidin-2-yl)phenyl)-3-methylurea;

1-ethyl-3-(4-(4-morpholino-7-(6-oxo-1,6-dihydropyridin-2-yl)-5,6,7,8-tetrahydropyrido[3,4-d]pyrimidin-2-yl)phenyl)urea;

1-ethyl-3-(4-(4-((S)-3-methylmorpholino)-7-((tetrahydrofuran-3-yl)methyl)-5,6,7,8-tetrahydropyrido[3,4-d]pyrimidin-2-yl)phenyl)urea;

1-(4-((S)-7-acetyl-8-methyl-4-((S)-3-methylmorpholino)-5,6,7,8-tetrahydropyrido[3,4-d]pyrimidin-2-yl)phenyl)-3-ethylurea;

(S)-1-ethyl-3-(4-(4-(3-methylmorpholino)-7-((6-methylpyridin-2-yl)methyl)-5,6,7,8-tetrahydropyrido[3,4-d]pyrimidin-2-yl)phenyl)urea;

(S)-1-methyl-3-(4-(4-(3-methylmorpholino)-7-(2-methylpyrimidin-4-yl)-5,6,7,8-tetrahydropyrido[3,4-d]pyrimidin-2-yl)phenyl)urea;

1-(4-((R)-8-allyl-4-((S)-3-methylmorpholino)-5,6,7,8-tetrahydropyrido[3,4-d]pyrimidin-2-yl)phenyl)-3-ethylurea;

1-(4-((S)-8-allyl-4-((S)-3-methylmorpholino)-5,6,7,8-tetrahydropyrido[3,4-d]pyrimidin-2-yl)phenyl)-3-ethylurea;

1-(4-((R)-7-acetyl-8-allyl-4-((S)-3-methylmorpholino)-5,6,7,8-tetrahydropyrido[3,4-d]pyrimidin-2-yl)phenyl)-3-ethylurea;

1-(4-((S)-7-acetyl-8-allyl-4-((S)-3-methylmorpholino)-5,6,7,8-tetrahydropyrido[3,4-d]pyrimidin-2-yl)phenyl)-3-ethylurea;

1-ethyl-3-(4-(4-((S)-3-methylmorpholino)-7-((R)-tetrahydrofuran-3-yl)methyl)-5,6,7,8-tetrahydropyrido[3,4-d]pyrimidin-2-yl)phenyl)urea;

(S)-1-ethyl-3-(4-(4-(3-methylmorpholino)-7-((6-methylpyridin-3-yl)methyl)-5,6,7,8-tetrahydropyrido[3,4-d]pyrimidin-2-yl)phenyl)urea;

(S)-4-(3-methylmorpholino)-2-(4-(6-oxo-1,6-dihydropyridin-2-ylamino)phenyl)-5,6-dihydropyrido[3,4-d]pyrimidine-7(8H)-carbaldehyde;

(S)-6-(4-(7-ethyl-4-(3-methylmorpholino)-5,6,7,8-tetrahydropyrido[3,4-d]pyrimidin-2-yl)phenylamino)pyridin-2(1H)-one;

(S)-6-(4-(7-ethyl-4-(3-methylmorpholino)-5,6,7,8-tetrahydropyrido[3,4-d]pyrimidin-2-yl)phenylamino)pyridin-2(1H)-one;

1-ethyl-3-(4-(4-((S)-3-methylmorpholino)-7-((tetrahydrofuran-2-yl)methyl)-5,6,7,8-tetrahydropyrido[3,4-d]pyrimidin-2-yl)phenyl)urea;

(S)—N-ethyl-4-(3-methylmorpholino)-2-(4-(6-oxo-1,6-dihydropyridin-2-ylamino)phen yl)-5,6-dihydropyrido[3,4-d]pyrimidine-7(8H)-carboxamide;

(S)-1-ethyl-3-(4-(7-(1-ethyl-1H-imidazol-2-yl)-4-(3-methylmorpholino)-5,6,7,8-tetrahydropyrido[3,4-d]pyrimidin-2-yl)phenyl)urea;

(S)-1-ethyl-3-(4-(4-(3-methylmorpholino)-7-(trifluoromethylsulfonyl)-5,6,7,8-tetrahydropyrido[3,4-d]pyrimidin-2-yl)phenyl)urea;

1-ethyl-3-(4-(4-((S)-3-methylmorpholino)-7-(((S)-tetrahydrofuran-2-yl)methyl)-5,6,7,8-tetrahydropyrido[3,4-d]pyrimidin-2-yl)phenyl)urea;

1-ethyl-3-(4-(4-((S)-3-methylmorpholino)-7-(((R)-tetrahydrofuran-2-yl)methyl)-5,6,7,8-tetrahydropyrido[3,4-d]pyrimidin-2-yl)phenyl)urea;

(S)-1-ethyl-3-(4-(4-(3-methylmorpholino)-7-neopentyl-5,6,7,8-tetrahydropyrido[3,4-d]pyrimidin-2-yl)phenyl)urea;

(S)-6-(4-(7-(1-ethyl-1H-imidazol-2-yl)-4-(3-methylmorpholino)-5,6,7,8-tetrahydropyrido[3,4-d]pyrimidin-2-yl)phenylamino)pyridin-2(1H)-one;

(S)-tert-butyl 2-(2-aminopyrimidin-5-yl)-4-(3-methylmorpholino)-5,6-dihydropyrido[3,4-d]pyrimidine-7(8H)-carboxylate;

(S)-5-(4-(3-methylmorpholino)-7-(2-methylpyrimidin-4-yl)-5,6,7,8-tetrahydropyrido[3,4-d]pyrimidin-2-yl)pyrimidin-2-amine;

(S)-5-(7-(5-fluoropyrimidin-2-yl)-4-(3-methylmorpholino)-5,6,7,8-tetrahydropyrido[3,4-d]pyrimidin-2-yl)pyrimidin-2-amine;

(S)-5-(7-isopropyl-4-(3-methylmorpholino)-5,6,7,8-tetrahydropyrido[3,4-d]pyrimidin-2-yl)pyrimidin-2-amine;

(S)-2-(4-(7-isopropyl-4-(3-methylmorpholino)-5,6,7,8-tetrahydropyrido[3,4-d]pyrimidin-2-yl)phenylamino)pyrimidin-4(3H)-one;

1-ethyl-3-(4-(7-(5-fluoropyrimidin-2-yl)-4-(4-methoxypiperidin-1-yl)-5,6,7,8-tetrahydropyrido[3,4-d]pyrimidin-2-yl)phenyl)urea;

(S)-2-(4-(7-ethyl-4-(3-methylmorpholino)-5,6,7,8-tetrahydropyrido[3,4-d]pyrimidin-2-yl)phenylamino)pyrimidin-4(3H)-one;

1-ethyl-3-(4-(7-(1-methyl-6-oxo-1,6-dihydropyridin-3-yl)-4-morpholino-5,6,7,8-tetrahydropyrido[3,4-d]pyrimidin-2-yl)phenyl)urea;

(S)-6-(4-(4-(3-methylmorpholino)-7-(2-methylpyrimidin-4-yl)-5,6,7,8-tetrahydropyrido[3,4-d]pyrimidin-2-yl)phenylamino)pyridin-2(1H)-one;

(S)-6-(4-(7-(5-fluoropyrimidin-2-yl)-4-(3-methylmorpholino)-5,6,7,8-tetrahydropyrido[3,4-d]pyrimidin-2-yl)phenylamino)pyridin-2(1H)-one;

(S)-6-(4-(7-(2-hydroxyethyl)-4-(3-methylmorpholino)-5,6,7,8-tetrahydropyrido[3,4-d]pyrimidin-2-yl)phenylamino)pyridin-2(1H)-one;

(S)-1-ethyl-3-(4-(4-(3-methylmorpholino)-7-(pyridin-3-ylmethyl)-5,6,7,8-tetrahydropyrido[3,4-d]pyrimidin-2-yl)phenyl)urea;

(S)-1-(4-(7-((1,3-dioxolan-2-yl)methyl)-4-(3-methylmorpholino)-5,6,7,8-tetrahydropyrido[3,4-d]pyrimidin-2-yl)phenyl)-3-ethylurea;

(S)-1-ethyl-3-(4-(4-(3-ethylmorpholino)-5,6,7,8-tetrahydropyrido[3,4-d]pyrimidin-2-yl)phenyl)urea;

(S)-1-ethyl-3-(4-(4-(3-ethylmorpholino)-7-isopropyl-5,6,7,8-tetrahydropyrido[3,4-d]pyrimidin-2-yl)phenyl)urea;

(S)-1-(4-(7-acetyl-4-(3-ethylmorpholino)-5,6,7,8-tetrahydropyrido[3,4-d]pyrimidin-2-yl)phenyl)-3-ethylurea;

(S)-1-ethyl-3-(4-(4-(3-ethylmorpholino)-7-formyl-5,6,7,8-tetrahydropyrido[3,4-d]pyrimidin-2-yl)phenyl)urea;

(S)-1-ethyl-3-(4-(4-(3-ethylmorpholino)-7-(oxetan-3-yl)-5,6,7,8-tetrahydropyrido[3,4-d]pyrimidin-2-yl)phenyl)urea;

1-ethyl-3-(4-(7-(2-methoxyethyl)-4-morpholino-5,6,7,8-tetrahydropyrido[3,4-d]pyrimidin-2-yl)phenyl)urea;

(S)-1-ethyl-3-(4-(7-(2-methoxyethyl)-4-(3-methylmorpholino)-5,6,7,8-tetrahydropyrido[3,4-d]pyrimidin-2-yl)phenyl)urea;

(S)-1-ethyl-3-(4-(4-(3-methylmorpholino)-7-((2-methylpyridin-4-yl)methyl)-5,6,7,8-tetrahydropyrido[3,4-d]pyrimidin-2-yl)phenyl)urea;

(S)-1-(4-(7-ethyl-4-(3-ethylmorpholino)-8-oxo-5,6,7,8-tetrahydropyrido[3,4-d]pyrimidin-2-yl)phenyl)-3-(isoxazol-3-yl)urea;

(S)-1-ethyl-3-(4-(4-(3-ethylmorpholino)-7-(methylsulfonyl)-5,6,7,8-tetrahydropyrido[3,4-d]pyrimidin-2-yl)phenyl)urea;

(S)-6-(4-(7-(2-methoxyethyl)-4-(3-methylmorpholino)-5,6,7,8-tetrahydropyrido[3,4-d]pyrimidin-2-yl)phenylamino)pyridin-2(1H)-one;

1-(4-(7-(5,5-dimethyltetrahydrofuran-3-yl)-4-((S)-3-methylmorpholino)-5,6,7,8-tetrahydropyrido[3,4-d]pyrimidin-2-yl)phenyl)-3-ethylurea;

1-(4-(7-(5,5-dimethyltetrahydrofuran-3-yl)-4-((S)-3-methylmorpholino)-5,6,7,8-tetrahydropyrido[3,4-d]pyrimidin-2-yl)phenyl)-3-ethylurea;

(S)-1-ethyl-3-(4-(7-ethyl-4-(3-ethylmorpholino)-5,6,7,8-tetrahydropyrido[3,4-d]pyrimidin-2-yl)phenyl)urea;

(S)-1-ethyl-3-(4-(4-(3-ethylmorpholino)-7-(trifluoromethylsulfonyl)-5,6,7,8-tetrahydropyrido[3,4-d]pyrimidin-2-yl)phenyl)urea;

(S)-tert-butyl 8-(cyanomethyl)-2-(4-(3-ethylureido)phenyl)-4-((S)-3-methylmorpholino)-5,6-dihydropyrido[3,4-d]pyrimidine-7(8H)-carboxylate;

(S)-1-ethyl-3-(4-(4-(3-methylmorpholino)-6-(oxetan-3-yl)-5,6,7,8-tetrahydropyrido[4,3-d]pyrimidin-2-yl)phenyl)urea;

tert-butyl 8-(2-aminoethyl)-2-(4-(3-ethylureido)phenyl)-4-((S)-3-methylmorpholino)-5,6-dihydropyrido[3,4-d]pyrimidine-7(8H)-carboxylate;

(S)-1-ethyl-3-(4-(4-(3-ethylmorpholino)-7-(tetrahydro-2H-pyran-4-yl)-5,6,7,8-tetrahydropyrido[3,4-d]pyrimidin-2-yl)phenyl)urea;

(S)-1-ethyl-3-(4-(7-(2-hydroxy-2-methylpropyl)-4-(3-methylmorpholino)-5,6,7,8-tetrahydropyrido[3,4-d]pyrimidin-2-yl)phenyl)urea;

(S)-1-ethyl-3-(4-(4-(3-methylmorpholino)-7-(pyrimidin-2-ylmethyl)-5,6,7,8-tetrahydropyrido[3,4-d]pyrimidin-2-yl)phenyl)urea;

(S)-1-(4-(7-(2,2-difluoroethyl)-4-(3-methylmorpholino)-5,6,7,8-tetrahydropyrido[3,4-d]pyrimidin-2-yl)phenyl)-3-ethylurea;

(S)-tert-butyl 4-(3-methylmorpholino)-2-(4-(3-oxetan-3-ylureido)phenyl)-5,6-dihydropyrido[3,4-d]pyrimidine-7(8H)-carboxylate;

5-methyl-N-(4-(4-morpholino-7-(pyrimidin-2-yl)-5,6,7,8-tetrahydropyrido[3,4-d]pyrimidin-2-yl)phenyl)-4,5-dihydro-1H-imidazol-2-amine;

(S)-1-(4-(7-(2-tert-butoxyethyl)-4-(3-methylmorpholino)-5,6,7,8-tetrahydropyrido[3,4-d]pyrimidin-2-yl)phenyl)-3-ethylurea;

1-ethyl-3-(4-(4-((S)-3-methylmorpholino)-7-(1-(pyridin-3-yl)ethyl)-5,6,7,8-tetrahydropyrido[3,4-d]pyrimidin-2-yl)phenyl)urea;

1-ethyl-3-(4-(7-(2-methoxyethyl)-8-methyl-4-morpholino-5,6,7,8-tetrahydropyrido[3,4-d]pyrimidin-2-yl)phenyl)urea;

(S)-1-(isoxazol-3-yl)-3-(4-(7-methyl-4-(3-methylmorpholino)-5,6,7,8-tetrahydropyrido[3,4-d]pyrimidin-2-yl)phenyl)urea;

(S)-1-(4-(7-ethyl-4-(3-methylmorpholino)-5,6,7,8-tetrahydropyrido[3,4-d]pyrimidin-2-yl)phenyl)-3-(isoxazol-3-yl)urea;

(S)-1-(1-methyl-1H-pyrazol-4-yl)-3-(4-(7-methyl-4-(3-methylmorpholino)-5,6,7,8-tetrahydropyrido[3,4-d]pyrimidin-2-yl)phenyl)urea;

(S)-1-(5-methyl-1,3,4-oxadiazol-2-yl)-3-(4-(7-methyl-4-(3-methylmorpholino)-5,6,7,8-tetrahydropyrido[3,4-d]pyrimidin-2-yl)phenyl)urea;

(S)-1-(4-(7-ethyl-4-(3-methylmorpholino)-5,6,7,8-tetrahydropyrido[3,4-d]pyrimidin-2-yl)phenyl)-3-(1-methyl-1H-pyrazol-4-yl)urea;

(S)-1-(4-(7-ethyl-4-(3-methylmorpholino)-5,6,7,8-tetrahydropyrido[3,4-d]pyrimidin-2-yl)phenyl)-3-(5-methyl-1,3,4-oxadiazol-2-yl)urea;

(S)-tert-butyl 4-(3-methylmorpholino)-2-(2-oxo-1,2-dihydroquinolin-6-yl)-5,6-dihydropyrido[3,4-d]pyrimidine-7(8H)-carboxylate;

(S)-6-(7-isopropyl-4-(3-methylmorpholino)-5,6,7,8-tetrahydropyrido[3,4-d]pyrimidin-2-yl)quinolin-2(1H)-one;

(S)-1-ethyl-3-(4-(4-(3-methylmorpholino)-7-((tetrahydro-2H-pyran-4-yl)methyl)-5,6,7,8-tetrahydropyrido[3,4-d]pyrimidin-2-yl)phenyl)urea;

1-(4-((S)-8-(cyanomethyl)-4-((S)-3-methylmorpholino)-5,6,7,8-tetrahydropyrido[3,4-d]pyrimidin-2-yl)phenyl)-3-ethylurea;

1-(4-((R)-8-(cyanomethyl)-4-((S)-3-methylmorpholino)-5,6,7,8-tetrahydropyrido[3,4-d]pyrimidin-2-yl)phenyl)-3-ethylurea;

1-(4-((R)-8-(cyanomethyl)-7-ethyl-4-((S)-3-methylmorpholino)-5,6,7,8-tetrahydropyrido[3,4-d]pyrimidin-2-yl)phenyl)-3-ethylurea;

1-(4-((S)-8-(cyanomethyl)-7-ethyl-4-((S)-3-methylmorpholino)-5,6,7,8-tetrahydropyrido[3,4-d]pyrimidin-2-yl)phenyl)-3-ethylurea;

(S)-1-ethyl-3-(4-(7-(2-methoxyethyl)-8-methyl-4-morpholino-5,6,7,8-tetrahydropyrido[3,4-d]pyrimidin-2-yl)phenyl)urea;

(R)-1-ethyl-3-(4-(7-(2-methoxyethyl)-8-methyl-4-morpholino-5,6,7,8-tetrahydropyrido[3,4-d]pyrimidin-2-yl)phenyl)urea;

(R)-1-ethyl-3-(4-(7-(2-methoxyethyl)-8-methyl-4-morpholino-5,6,7,8-tetrahydropyrido[3,4-d]pyrimidin-2-yl)phenyl)urea;

(S)-1-(4-(7-(2-cyclopropylethyl)-4-(3-methylmorpholino)-5,6,7,8-tetrahydropyrido[3,4-d]pyrimidin-2-yl)phenyl)-3-ethylurea;

1-(4-((R)-8-(cyanomethyl)-7-isopropyl-4-((S)-3-methylmorpholino)-5,6,7,8-tetrahydropyrido[3,4-d]pyrimidin-2-yl)phenyl)-3-ethylurea;

1-(4-((S)-8-(cyanomethyl)-7-isopropyl-4-((S)-3-methylmorpholino)-5,6,7,8-tetrahydropyrido[3,4-d]pyrimidin-2-yl)phenyl)-3-ethylurea;

(S)-1-ethyl-3-(4-(7-(1-methyl-2-oxo-1,2-dihydropyridin-4-yl)-4-(3-methylmorpholino)-5,6,7,8-tetrahydropyrido[3,4-d]pyrimidin-2-yl)phenyl)urea;

(S)-1-(4-(7-isopropyl-4-(3-methylmorpholino)-5,6,7,8-tetrahydropyrido[3,4-d]pyrimidin-2-yl)phenyl)-3-(1-methyl-1H-pyrazol-4-yl)urea;

(S)-1-(4-(7-isopropyl-4-(3-methylmorpholino)-5,6,7,8-tetrahydropyrido[3,4-d]pyrimidin-2-yl)phenyl)-3-(5-methyl-1,3,4-oxadiazol-2-yl)urea;

(S)-1-(4-(7-isopropyl-4-(3-methylmorpholino)-5,6,7,8-tetrahydropyrido[3,4-d]pyrimidin-2-yl)phenyl)-3-(5-methyl isoxazol-3-yl)urea;

(S,E)-tert-butyl 8-(4-ethoxy-4-oxobut-2-enyl)-2-(4-(3-ethylureido)phenyl)-4-morpholino-5,6-dihydropyrido[3,4-d]pyrimidine-7(8H)-carboxylate;

(R,E)-tert-butyl 8-(4-ethoxy-4-oxobut-2-enyl)-2-(4-(3-ethylureido)phenyl)-4-morpholino-5,6-dihydropyrido[3,4-d]pyrimidine-7(8H)-carboxylate;

(S)-tert-butyl 8-(4-ethoxy-4-oxobutyl)-2-(4-(3-ethylureido)phenyl)-4-morpholino-5,6-dihydropyrido[3,4-d]pyrimidine-7(8H)-carboxylate;

(R)-tert-butyl 8-(4-ethoxy-4-oxobutyl)-2-(4-(3-ethylureido)phenyl)-4-morpholino-5,6-dihydropyrido[3,4-d]pyrimidine-7(8H)-carboxylate;

(S)-1-(4-(7-((1,3-dioxan-2-yl)methyl)-4-(3-methylmorpholino)-5,6,7,8-tetrahydropyrido[3,4-d]pyrimidin-2-yl)phenyl)-3-ethylurea;

1-(4-(7-((1,3-dioxolan-2-yl)methyl)-8-methyl-4-morpholino-5,6,7,8-tetrahydropyrido[3,4-d]pyrimidin-2-yl)phenyl)-3-ethylurea;

(S)-1-ethyl-3-(4-(7-(2-fluoro-2-methylpropyl)-4-(3-methylmorpholino)-5,6,7,8-tetrahydropyrido[3,4-d]pyrimidin-2-yl)phenyl)urea;

(S)-1-ethyl-3-(4-(4-(3-methylmorpholino)-7-((2-methylpyrimidin-5-yl)methyl)-5,6,7,8-tetrahydropyrido[3,4-d]pyrimidin-2-yl)phenyl)urea;

(S)-1-ethyl-3-(4-(7-((1-methyl-1H-pyrazol-5-yl)methyl)-4-(3-methylmorpholino)-5,6,7,8-tetrahydropyrido[3,4-d]pyrimidin-2-yl)phenyl)urea;

(S)-1-(4-(7-isopropyl-4-(3-methylmorpholino)-5,6,7,8-tetrahydropyrido[3,4-d]pyrimidin-2-yl)phenyl)-3-(isoxazol-3-yl)urea;

(S)-1-(4-(7-(5-fluoropyrimidin-2-yl)-4-(3-methylmorpholino)-5,6,7,8-tetrahydropyrido[3,4-d]pyrimidin-2-yl)phenyl)-3-(isoxazol-3-yl)urea;

(S)-tert-butyl 2-(3-(hydroxymethyl)-4-methoxyphenyl)-4-(3-methylmorpholino)-5,6-dihydropyrido[3,4-d]pyrimidine-7(8H)-carboxylate;

(S)-1-(4-(7-methyl-4-(3-methylmorpholino)-5,6,7,8-tetrahydropyrido[3,4-d]pyrimidin-2-yl)phenyl)-3-(5-methylisoxazol-3-yl)urea;

(S)-1-(4-(7-ethyl-4-(3-methylmorpholino)-5,6,7,8-tetrahydropyrido[3,4-d]pyrimidin-2-yl)phenyl)-3-(5-methylisoxazol-3-yl)urea;

1-ethyl-3-(4-(7-(1-methoxypropan-2-yl)-4-((S)-3-methylmorpholino)-5,6,7,8-tetrahydropyrido[3,4-d]pyrimidin-2-yl)phenyl)urea;

1-ethyl-3-(4-(4-((S)-3-methylmorpholino)-7-(tetrahydro-2H-pyran-3-yl)-5,6,7,8-tetrahydropyrido[3,4-d]pyrimidin-2-yl)phenyl)urea;

1-ethyl-3-(4-(4-((S)-3-methylmorpholino)-7-(tetrahydro-2H-pyran-3-yl)-5,6,7,8-tetrahydropyrido[3,4-d]pyrimidin-2-yl)phenyl)urea;

1-(4-(4-(3,3-dimethylmorpholino)-7-(2-methoxyethyl)-5,6,7,8-tetrahydropyrido[3,4-d]pyrimidin-2-yl)phenyl)-3-ethylurea;

(S)-tert-butyl 2-(4-(1H-imidazol-2-ylamino)phenyl)-4-(3-methylmorpholino)-5,6-dihydropyrido[3,4-d]pyrimidine-7(8H)-carboxylate;

(S)-1-ethyl-3-(4-(7-((1-ethyl-1H-pyrazol-5-yl)methyl)-4-(3-methylmorpholino)-5,6,7,8-tetrahydropyrido[3,4-d]pyrimidin-2-yl)phenyl)urea;

1-ethyl-3-(4-(7-((R)-2-hydroxypropyl)-4-((S)-3-methylmorpholino)-5,6,7,8-tetrahydropyrido[3,4-d]pyrimidin-2-yl)phenyl)urea;

(S)-1-(4-(7-(2-ethoxyethyl)-4-(3-methylmorpholino)-5,6,7,8-tetrahydropyrido[3,4-d]pyrimidin-2-yl)phenyl)-3-ethylurea;

(S)-1-ethyl-3-(4-(7-(3-hydroxy-3-methylbutyl)-4-(3-methylmorpholino)-5,6,7,8-tetrahydropyrido[3,4-d]pyrimidin-2-yl)phenyl)urea;

1-ethyl-3-(4-(7-((S)-2-hydroxypropyl)-4-((S)-3-methylmorpholino)-5,6,7,8-tetrahydropyrido[3,4-d]pyrimidin-2-yl)phenyl)urea;

1-ethyl-3-(4-(4-((S)-3-methylmorpholino)-7-((R)-tetrahydrofuran-3-yl)-5,6,7,8-tetrahydropyrido[3,4-d]pyrimidin-2-yl)phenyl)urea;

1-(4-(7-(((R)-2,2-dimethyl-1,3-dioxolan-4-yl)methyl)-4-((S)-3-methylmorpholino)-5,6,7,8-tetrahydropyrido[3,4-d]pyrimidin-2-yl)phenyl)-3-ethylurea;

(S)-tert-butyl 8-(cyanomethyl)-2-(4-(3-ethylureido)phenyl)-4-morpholino-5,6-dihydropyrido[3,4-d]pyrimidine-7(8H)-carboxylate;

(R)-tert-butyl 8-(cyanomethyl)-2-(4-(3-ethylureido)phenyl)-4-morpholino-5,6-dihydropyrido[3,4-d]pyrimidine-7(8H)-carboxylate;

(S)-1-ethyl-3-(4-(7-((2-methyl-1,3-dioxolan-2-yl)methyl)-4-(3-methylmorpholino)-5,6,7,8-tetrahydropyrido[3,4-d]pyrimidin-2-yl)phenyl)urea;

(S)-1-ethyl-3-(4-(7-(2-hydroxyethyl)-4-(3-methylmorpholino)-5,6,7,8-tetrahydropyrido[3,4-d]pyrimidin-2-yl)phenyl)urea;

(S)-1-ethyl-3-(4-(7-(3-hydroxypropyl)-4-(3-methylmorpholino)-5,6,7,8-tetrahydropyrido[3,4-d]pyrimidin-2-yl)phenyl)urea;

(S)-1-ethyl-3-(4-(7-(3-methoxypropyl)-4-(3-methylmorpholino)-5,6,7,8-tetrahydropyrido[3,4-d]pyrimidin-2-yl)phenyl)urea;

(R)-1-(4-(7-((1,3-dioxolan-2-yl)methyl)-8-methyl-4-morpholino-5,6,7,8-tetrahydropyrido[3,4-d]pyrimidin-2-yl)phenyl)-3-ethylurea;

(S)-1-(4-(7-((1,3-dioxolan-2-yl)methyl)-8-methyl-4-morpholino-5,6,7,8-tetrahydropyrido[3,4-d]pyrimidin-2-yl)phenyl)-3-ethylurea;

(S)-4-(2-(1H-indol-5-yl)-5,6,7,8-tetrahydropyrido[3,4-d]pyrimidin-4-yl)-3-methylmorpholine;

(S)-1-ethyl-3-(4-(4-(3-methylmorpholino)-7-(2-(methylsulfonyl)ethyl)-5,6,7,8-tetrahydropyrido[3,4-d]pyrimidin-2-yl)phenyl)urea;

(S)-1-(4-(4-(3-methylmorpholino)-7-(6-methylpyrimidin-4-yl)-5,6,7,8-tetrahydropyrido[3,4-d]pyrimidin-2-yl)phenyl)-3-(oxetan-3-yl)urea;

1-(4-(4-((1R,5S)-3-oxa-8-azabicyclo[3.2.1]octan-8-yl)-7-(oxetan-3-yl)-5,6,7,8-tetrahydropyrido[3,4-d]pyrimidin-2-yl)phenyl)-3-ethylurea;

(S)-1-(4-(7-(2-cyanoethyl)-4-(3-methylmorpholino)-5,6,7,8-tetrahydropyrido[3,4-d]pyrimidin-2-yl)phenyl)-3-ethylurea;

(S)-tert-butyl 2-(1H-indol-5-yl)-4-(3-methylmorpholino)-5,6-dihydropyrido[3,4-d]pyrimidine-7(8H)-carboxylate;

1-ethyl-3-(4-(7-(2-methoxypyrimidin-4-yl)-4-morpholino-5,6,7,8-tetrahydropyrido[3,4-d]pyrimidin-2-yl)phenyl)urea;

1-ethyl-3-(4-(4-morpholino-7-(oxetan-3-yl)-5,6,7,8-tetrahydropyrido[3,4-d]pyrimidin-2-yl)phenyl)urea;

1-(4-(7-((R)-2,3-dihydroxypropyl)-4-((S)-3-methylmorpholino)-5,6,7,8-tetrahydropyrido[3,4-d]pyrimidin-2-yl)phenyl)-3-ethylurea;

1-(4-(4-((1R,5S)-3-oxa-8-azabicyclo[3.2.1]octan-8-yl)-7-(6-methylpyrimidin-4-yl)-5,6,7,8-tetrahydropyrido[3,4-d]pyrimidin-2-yl)phenyl)-3-ethylurea;

(S)—N-(4-(7-isopropyl-4-(3-methylmorpholino)-5,6,7,8-tetrahydropyrido[3,4-d]pyrimidin-2-yl)phenyl)-1H-imidazol-2-amine;

(S)—N-(4-(4-(3-methylmorpholino)-7-(oxetan-3-yl)-5,6,7,8-tetrahydropyrido[3,4-d]pyrimidin-2-yl)phenyl)-1H-imidazol-2-amine;

(S)-1-ethyl-3-(4-(7-(3-fluoropropyl)-4-(3-methylmorpholino)-5,6,7,8-tetrahydropyrido[3,4-d]pyrimidin-2-yl)phenyl)urea;

(S)-methyl 3-(2-(4-(3-ethylureido)phenyl)-4-(3-methylmorpholino)-5,6-dihydropyrido[3,4-d]pyrimidin-7(8H)-yl)propanoate;

1-(4-(4-((1R,5S)-8-oxa-3-azabicyclo[3.2.1]octan-3-yl)-7-(pyrimidin-2-yl)-5,6,7,8-tetrahydropyrido[3,4-d]pyrimidin-2-yl)phenyl)-3-ethylurea;

1-(4-(4-((1R,5S)-8-oxa-3-azabicyclo[3.2.1]octan-3-yl)-7-(6-methylpyrimidin-4-yl)-5,6,7,8-tetrahydropyrido[3,4-d]pyrimidin-2-yl)phenyl)-3-ethylurea;

1-(4-(4-((1R,5S)-8-oxa-3-azabicyclo[3.2.1]octan-3-yl)-7-(oxetan-3-yl)-5,6,7,8-tetrahydropyrido[3,4-d]pyrimidin-2-yl)phenyl)-3-ethylurea;

1-(4-(4-((1R,5S)-8-oxa-3-azabicyclo[3.2.1]octan-3-yl)-7-isopropyl-5,6,7,8-tetrahydropyrido[3,4-d]pyrimidin-2-yl)phenyl)-3-ethylurea;

1-ethyl-3-(4-(8-methyl-4-morpholino-7-(oxetan-3-yl)-5,6,7,8-tetrahydropyrido[3,4-d]pyrimidin-2-yl)phenyl)urea;

(S)-1-ethyl-3-(4-(8-methyl-4-morpholino-7-(oxetan-3-yl)-5,6,7,8-tetrahydropyrido[3,4-d]pyrimidin-2-yl)phenyl)urea;

(R)-1-ethyl-3-(4-(8-methyl-4-morpholino-7-(oxetan-3-yl)-5,6,7,8-tetrahydropyrido[3,4-d]pyrimidin-2-yl)phenyl)urea;

1-ethyl-3-(4-(4-(2-methylmorpholino)-7-(oxetan-3-yl)-5,6,7,8-tetrahydropyrido[3,4-d]pyrimidin-2-yl)phenyl)urea;

tert-butyl 4-((1R,5S)-8-oxa-3-azabicyclo[3.2.1]octan-3-yl)-2-(4-(3-ethylureido)phenyl)-5,6-dihydropyrido[3,4-d]pyrimidine-7(8H)-carboxylate;

(S)-4-(2-(1H-indol-5-yl)-7-(1-(pyridin-3-ylmethyl)piperidin-4-yl)-5,6,7,8-tetrahydropyrido[3,4-d]pyrimidin-4-yl)-3-methylmorpholine;

1-(4-(4-((1R,5S)-3-oxa-8-azabicyclo[3.2.1]octan-8-yl)-7-isopropyl-5,6,7,8-tetrahydropyrido[3,4-d]pyrimidin-2-yl)phenyl)-3-ethylurea;

1-ethyl-3-(4-(4'-morpholino-6',8'-dihydro-5'H-spiro[oxetane-3,7'-pyrido[4,3-d]pyrimidine]-2'-yl)phenyl)urea;

allyl 2'-(4-(3-ethylureido)phenyl)-4'-morpholino-5'H-spiro[oxetane-3,7'-pyrido[4,3-d]pyrimidine]-6'(8'H)-carboxylate;

1-ethyl-3-(4-(6'-methyl-4'-morpholino-6',8'-dihydro-5'H-spiro[oxetane-3,7'-pyrido[4,3-d]pyrimidine]-2'-yl)phenyl)urea;

(S)-1-(4-(7-(6-chloro-2-methylpyrimidin-4-yl)-4-(3-methylmorpholino)-5,6,7,8-tetrahydropyrido[3,4-d]pyrimidin-2-yl)phenyl)-3-(isoxazol-3-yl)urea;

(S)-1-(4-(7-(2-chloro-6-methylpyrimidin-4-yl)-4-(3-methylmorpholino)-5,6,7,8-tetrahydropyrido[3,4-d]pyrimidin-2-yl)phenyl)-3-(isoxazol-3-yl)urea;

(S)-1-ethyl-3-(4-(4-(3-methylmorpholino)-7-((3-methyloxetan-3-yl)methyl)-5,6,7,8-tetrahydropyrido[3,4-d]pyrimidin-2-yl)phenyl)urea;

(S)-tert-butyl 2-(4-(3-ethylureido)phenyl)-8-(2-hydroxyethyl)-4-morpholino-5,6-dihydropyrido[3,4-d]pyrimidine-7(8H)-carboxylate;

(S)-tert-butyl 2-(4-(3-ethylureido)phenyl)-8-(2-hydroxyethyl)-4-morpholino-5,6-dihydropyrido[3,4-d]pyrimidine-7(8H)-carboxylate;

(R)-tert-butyl 2-(4-(3-ethylureido)phenyl)-8-(2-hydroxyethyl)-4-morpholino-5,6-dihydropyrido[3,4-d]pyrimidine-7(8H)-carboxylate;

(S)-1-ethyl-3-(4-(8-(2-hydroxyethyl)-4-morpholino-5,6,7,8-tetrahydropyrido[3,4-d]pyrimidin-2-yl)phenyl)urea;
(R)-1-ethyl-3-(4-(8-(2-hydroxyethyl)-4-morpholino-5,6,7,8-tetrahydropyrido[3,4-d]pyrimidin-2-yl)phenyl)urea;
(S)-1-(4-(7-(2-(dimethylamino)pyrimidin-4-yl)-4-(3-methylmorpholino)-5,6,7,8-tetrahydropyrido[3,4-d]pyrimidin-2-yl)phenyl)-3-ethylurea;
(S)-1-(4-(7-(2,6-dimethoxypyrimidin-4-yl)-8-methyl-4-morpholino-5,6,7,8-tetrahydropyrido[3,4-d]pyrimidin-2-yl)phenyl)-3-ethylurea;
(R)-1-(4-(7-(2,6-dimethoxypyrimidin-4-yl)-8-methyl-4-morpholino-5,6,7,8-tetrahydropyrido[3,4-d]pyrimidin-2-yl)phenyl)-3-ethylurea;
(S)-1-(4-(7-(2-chloro-6-methylpyrimidin-4-yl)-8-methyl-4-morpholino-5,6,7,8-tetrahydropyrido[3,4-d]pyrimidin-2-yl)phenyl)-3-ethylurea;
(R)-1-(4-(7-(2-chloro-6-methylpyrimidin-4-yl)-8-methyl-4-morpholino-5,6,7,8-tetrahydropyrido[3,4-d]pyrimidin-2-yl)phenyl)-3-ethylurea;
1-(4-(7-(2,6-dimethylpyrimidin-4-yl)-4-morpholino-5,6,7,8-tetrahydropyrido[3,4-d]pyrimidin-2-yl)phenyl)-3-ethylurea;
(R)-1-(4-(7-(2,6-dimethylpyrimidin-4-yl)-8-methyl-4-morpholino-5,6,7,8-tetrahydropyrido[3,4-d]pyrimidin-2-yl)phenyl)-3-ethylurea;
(S)-1-(4-(7-(2,6-dimethylpyrimidin-4-yl)-8-methyl-4-morpholino-5,6,7,8-tetrahydropyrido[3,4-d]pyrimidin-2-yl)phenyl)-3-ethylurea;
(S)-1-(4-(7-(4-chloro-6-methylpyrimidin-2-yl)-8-methyl-4-morpholino-5,6,7,8-tetrahydropyrido[3,4-d]pyrimidin-2-yl)phenyl)-3-ethylurea;
(R)-1-(4-(7-(4-chloro-6-methylpyrimidin-2-yl)-8-methyl-4-morpholino-5,6,7,8-tetrahydropyrido[3,4-d]pyrimidin-2-yl)phenyl)-3-ethylurea;
(S)-1-(isoxazol-3-yl)-3-(4-(4-(3-methylmorpholino)-7-(2-methylpyrimidin-4-yl)-5,6,7,8-tetrahydropyrido[3,4-d]pyrimidin-2-yl)phenyl)urea;
(S)-1-isopropyl-3-(4-(4-(3-methylmorpholino)-7-(oxetan-3-yl)-5,6,7,8-tetrahydropyrido[3,4-d]pyrimidin-2-yl)phenyl)urea;
(S)-1-(3-fluoropropyl)-3-(4-(4-(3-methylmorpholino)-7-(oxetan-3-yl)-5,6,7,8-tetrahydropyrido[3,4-d]pyrimidin-2-yl)phenyl)urea;
(S)-1-(isoxazol-3-yl)-3-(4-(4-(3-methylmorpholino)-7-(oxetan-3-yl)-5,6,7,8-tetrahydropyrido[3,4-d]pyrimidin-2-yl)phenyl)urea;
(S)-1-ethyl-3-(4-(8-(2-hydroxyethyl)-7-(2-methylpyrimidin-4-yl)-4-morpholino-5,6,7,8-tetrahydropyrido[3,4-d]pyrimidin-2-yl)phenyl)urea;
(R)-1-ethyl-3-(4-(8-(2-hydroxyethyl)-7-(2-methylpyrimidin-4-yl)-4-morpholino-5,6,7,8-tetrahydropyrido[3,4-d]pyrimidin-2-yl)phenyl)urea;
(S)-1-ethyl-3-(4-(8-(2-hydroxyethyl)-7-(2-methoxyethyl)-4-morpholino-5,6,7,8-tetrahydropyrido[3,4-d]pyrimidin-2-yl)phenyl)urea;
(R)-1-ethyl-3-(4-(8-(2-hydroxyethyl)-7-(2-methoxyethyl)-4-morpholino-5,6,7,8-tetrahydropyrido[3,4-d]pyrimidin-2-yl)phenyl)urea;
1-ethyl-3-(4-(8-(2-hydroxyethyl)-7-(6-methylpyrimidin-4-yl)-4-morpholino-5,6,7,8-tetrahydropyrido[3,4-d]pyrimidin-2-yl)phenyl)urea;
(S)-1-ethyl-3-(4-(8-methyl-7-(6-methylpyrimidin-4-yl)-4-morpholino-5,6,7,8-tetrahydropyrido[3,4-d]pyrimidin-2-yl)phenyl)urea;
(R)-1-ethyl-3-(4-(8-methyl-7-(6-methylpyrimidin-4-yl)-4-morpholino-5,6,7,8-tetrahydropyrido[3,4-d]pyrimidin-2-yl)phenyl)urea;
(S)-1-ethyl-3-(4-(7-(5-fluoropyrimidin-2-yl)-8-methyl-4-morpholino-5,6,7,8-tetrahydropyrido[3,4-d]pyrimidin-2-yl)phenyl)urea;
(R)-1-ethyl-3-(4-(7-(5-fluoropyrimidin-2-yl)-8-methyl-4-morpholino-5,6,7,8-tetrahydropyrido[3,4-d]pyrimidin-2-yl)phenyl)urea;
(S)-1-(5-methyl-1,3,4-oxadiazol-2-yl)-3-(4-(4-(3-methylmorpholino)-7-(oxetan-3-yl)-5,6,7,8-tetrahydropyrido[3,4-d]pyrimidin-2-yl)phenyl)urea;
(S)-1-(5-methylisoxazol-3-yl)-3-(4-(4-(3-methylmorpholino)-7-(oxetan-3-yl)-5,6,7,8-tetrahydropyrido[3,4-d]pyrimidin-2-yl)phenyl)urea;
(S)-1-(1-methyl-1H-pyrazol-4-yl)-3-(4-(4-(3-methylmorpholino)-7-(oxetan-3-yl)-5,6,7,8-tetrahydropyrido[3,4-d]pyrimidin-2-yl)phenyl)urea;
(S)-1-ethyl-3-(4-(8-methyl-4-morpholino-7-(pyrimidin-2-ylmethyl)-5,6,7,8-tetrahydropyrido[3,4-d]pyrimidin-2-yl)phenyl)urea;
(R)-1-ethyl-3-(4-(8-methyl-4-morpholino-7-(pyrimidin-2-ylmethyl)-5,6,7,8-tetrahydropyrido[3,4-d]pyrimidin-2-yl)phenyl)urea;
(R)-1-(4-(7-(5-cyanopyridin-2-yl)-8-methyl-4-morpholino-5,6,7,8-tetrahydropyrido[3,4-d]pyrimidin-2-yl)phenyl)-3-ethylurea;
1-ethyl-3-(4-(4-((S)-3-methylmorpholino)-7-((S)-tetrahydrofuran-3-yl)-5,6,7,8-tetrahydropyrido[3,4-d]pyrimidin-2-yl)phenyl)urea;
1-ethyl-3-(4-(4-((S)-3-methylmorpholino)-7-((S)-tetrahydrofuran-3-yl)-5,6,7,8-tetrahydropyrido[3,4-d]pyrimidin-2-yl)phenyl)urea;
(S)-1-ethyl-3-(4-(4-(3-methylmorpholino)-7-(3-oxocyclohex-1-enyl)-5,6,7,8-tetrahydropyrido[3,4-d]pyrimidin-2-yl)phenyl)urea;
(S)-1-ethyl-3-(4-(4-(3-methylmorpholino)-7-(6-methylpyridazin-3-yl)-5,6,7,8-tetrahydropyrido[3,4-d]pyrimidin-2-yl)phenyl)urea;
(S)-1-(4-(4-(3-methylmorpholino)-7-(oxetan-3-yl)-5,6,7,8-tetrahydropyrido[3,4-d]pyrimidin-2-yl)phenyl)-3-(oxetan-3-yl)urea;
1-ethyl-3-(4-(4-(2-(methoxymethyl)morpholino)-7-methyl-5,6,7,8-tetrahydropyrido[3,4-d]pyrimidin-2-yl)phenyl)urea;
(S)-1-(4-(7-(2,6-dimethylpyrimidin-4-yl)-4-(3-methylmorpholino)-5,6,7,8-tetrahydropyrido[3,4-d]pyrimidin-2-yl)phenyl)-3-ethylurea;
(S)-1-ethyl-3-(4-(7-(1-methylazetidin-3-yl)-4-(3-methylmorpholino)-5,6,7,8-tetrahydropyrido[3,4-d]pyrimidin-2-yl)phenyl)urea;
(S)-1-ethyl-3-(4-(7-(1-methyl-6-oxo-1,6-dihydropyridin-3-yl)-4-(3-methylmorpholino)-5,6,7,8-tetrahydropyrido[3,4-d]pyrimidin-2-yl)phenyl)urea;
(S)-1-ethyl-3-(4-(4-(3-methylmorpholino)-7-(3-oxocyclopent-1-enyl)-5,6,7,8-tetrahydropyrido[3,4-d]pyrimidin-2-yl)phenyl)urea;
1-ethyl-3-(4-(7-((S)-2-methoxypropyl)-4-((S)-3-methylmorpholino)-5,6,7,8-tetrahydropyrido[3,4-d]pyrimidin-2-yl)phenyl)urea;
(S)-1-methyl-3-(4-(4-(3-methylmorpholino)-7-(oxetan-3-yl)-5,6,7,8-tetrahydropyrido[3,4-d]pyrimidin-2-yl)phenyl)urea;
(S)-1-ethyl-3-(4-(4-(3-methylmorpholino)-7-(5-oxo-2,5-dihydrofuran-3-yl)-5,6,7,8-tetrahydropyrido[3,4-d]pyrimidin-2-yl)phenyl)urea;

(R)-tert-butyl 8-ethyl-2-(4-(3-ethylureido)phenyl)-4-morpholino-5,6-dihydropyrido[3,4-d]pyrimidine-7(8H)-carboxylate;

(S)-tert-butyl 8-ethyl-2-(4-(3-ethylureido)phenyl)-4-morpholino-5,6-dihydropyrido[3,4-d]pyrimidine-7(8H)-carboxylate;

(S)-1-ethyl-3-(4-(4-(3-methylmorpholino)-7-(pyridazin-3-yl)-5,6,7,8-tetrahydropyrido[3,4-d]pyrimidin-2-yl)phenyl)urea;

(S)-1-(4-(7-(6-chloropyridazin-3-yl)-4-(3-methylmorpholino)-5,6,7,8-tetrahydropyrido[3,4-d]pyrimidin-2-yl)phenyl)-3-ethylurea;

(S)-1-(4-(7-(azetidin-3-yl)-4-(3-methylmorpholino)-5,6,7,8-tetrahydropyrido[3,4-d]pyrimidin-2-yl)phenyl)-3-ethylurea;

(S)-1-(3,4-difluorophenyl)-3-(4-(4-(3-methylmorpholino)-7-(oxetan-3-yl)-5,6,7,8-tetrahydropyrido[3,4-d]pyrimidin-2-yl)phenyl)urea;

(S)-1-ethyl-3-(4-(7-(6-methoxypyridazin-3-yl)-4-(3-methylmorpholino)-5,6,7,8-tetrahydropyrido[3,4-d]pyrimidin-2-yl)phenyl)urea; and (S)-1-(isoxazol-3-yl)-3-(4-(4-(3-methylmorpholino)-7-(6-methylpyrimidin-4-yl)-5,6,7,8-tetrahydropyrido[3,4-d]pyrimidin-2-yl)phenyl)urea.

26. A pharmaceutical composition comprising a compound of claim 1, and a pharmaceutically acceptable carrier, diluent or excipient.

27. The compound 1-ethyl-3-(4-(4-morpholino-7-(pyrimidin-2-yl)-5,6,7,8-tetrahydropyrido[3,4-d]pyrimidin-2-yl)phenyl)urea.

28. The compound (S)-1-ethyl-3-(4-(4-(3-methylmorpholino)-7-(pyrimidin-2-yl)-5,6,7,8-tetrahydropyrido[3,4-d]pyrimidin-2-yl)phenyl)urea.

29. The compound (S)-1-ethyl-3-(4-(4-(3-methylmorpholino)-7-(tetrahydro-2H-pyran-4-yl)-5,6,7,8-tetrahydropyrido[3,4-d]pyrimidin-2-yl)phenyl)urea.

30. The compound (S)-1-ethyl-3-(4-(4-(3-methylmorpholino)-7-(oxetan-3-yl)-5,6,7,8-tetrahydropyrido[3,4-d]pyrimidin-2-yl)phenyl)urea.

31. The compound (S)-1-ethyl-3-(4-(4-(3-ethylmorpholino)-7-(tetrahydro-2H-pyran-4-yl)-5,6,7,8-tetrahydropyrido[3,4-d]pyrimidin-2-yl)phenyl)urea.

32. The compound 1-ethyl-3-(4-(4-((S)-3-methylmorpholino)-7-((R)-tetrahydrofuran-3-yl)-5,6,7,8-tetrahydropyrido[3,4-d]pyrimidin-2-yl)phenyl)urea.

33. The compound 1-ethyl-3-(4-(4-morpholino-7-(oxetan-3-yl)-5,6,7,8-tetrahydropyrido[3,4-d]pyrimidin-2-yl)phenyl)urea.

* * * * *

UNITED STATES PATENT AND TRADEMARK OFFICE
CERTIFICATE OF CORRECTION

PATENT NO. : 8,163,763 B2
APPLICATION NO. : 12/533935
DATED : April 24, 2012
INVENTOR(S) : Bergeron et al.

Page 1 of 1

It is certified that error appears in the above-identified patent and that said Letters Patent is hereby corrected as shown below:

Under Column 500, line 18, claim 1, please insert -the group -- -$(CH_2)_{1-4}$-CN -- before the group –$(CH_2)_{1-4}$-$NO_2$.

Under Column 517, line 10, claim 24, please delete the chemical structure " 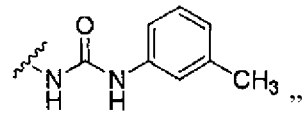 "
and replace with -- 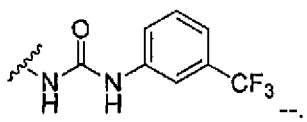 --.

Under Column 528, lines 25-27, claim 25, please delete "(S)-1-ethyl-3-(4-(4-(3-methylmorpholino)-7-(tetrahydrofuran-2-carbonyl)-5,6,7,8-tetrahydropyrido[3,4-d]pyrimidin-2-yl)phen" and replace with -- (S)-1-ethyl-3-(4-(4-(3-methylmorpholino)-7-(tetrahydrofuran-2-carbonyl)-5,6,7,8-tetrahydropyrido[3,4-d]pyrimidin-2-yl)phenyl)urea --.

Signed and Sealed this
Fifth Day of June, 2012

David J. Kappos
*Director of the United States Patent and Trademark Office*